US008461328B2

(12) United States Patent
Babu et al.

(10) Patent No.: US 8,461,328 B2
(45) Date of Patent: Jun. 11, 2013

(54) TRICYCLIC HETEROCYCLIC COMPOUNDS, COMPOSITIONS AND METHODS OF USE THEREOF

(75) Inventors: Srinivasan Babu, San Diego, CA (US); Phillippe Bergeron, Oakland, CA (US); Peter Dragovich, San Diego, CA (US); Hazel Joan Dyke, Storrington (GB); Paul Gibbons, San Francisco, CA (US); Stefan Gradl, Princeton, NJ (US); Emily Hanan, Redwood City, CA (US); Christopher Hurley, Welwyn Garden City (GB); Tony Johnson, Soham (GB); Michael Koehler, Palo Alto, CA (US); Janusz Kulagowski, Sawbridgeworth (GB); Sharada Labadie, Sunnyvale, CA (US); Joseph Lyssikatos, Piedmont, CA (US); Rohan Mendonca, Pleasanton, CA (US); Rebecca Pulk, San Francisco, CA (US); Stuart Ward, Royston (GB); Bohdan Waszkowycz, Macclesfield (GB); Mark Zak, San Mateo, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 13/004,808

(22) Filed: Jan. 11, 2011

(65) Prior Publication Data

US 2011/0201593 A1 Aug. 18, 2011

Related U.S. Application Data

(60) Provisional application No. 61/366,785, filed on Jul. 22, 2010, provisional application No. 61/294,404, filed on Jan. 12, 2010.

(51) Int. Cl.

| | |
|---|---|
| *A61P 11/06* | (2006.01) |
| *A61P 17/06* | (2006.01) |
| *A61P 19/02* | (2006.01) |
| *A61P 37/06* | (2006.01) |
| *C07D 413/14* | (2006.01) |
| *C07D 471/14* | (2006.01) |

(52) U.S. Cl.
USPC ........... 540/597; 544/126; 544/133; 544/361; 546/82

(58) Field of Classification Search
None
See application file for complete search history.

(56) References Cited

U.S. PATENT DOCUMENTS

| | | | |
|---|---|---|---|
| 5,461,062 | A | 10/1995 | Takada et al. |
| 5,658,791 | A | 8/1997 | Wilks et al. |
| 5,716,818 | A | 2/1998 | Wilks et al. |
| 5,728,536 | A | 3/1998 | Ihle et al. |
| 5,821,069 | A | 10/1998 | Wilks et al. |
| 5,852,184 | A | 12/1998 | Wilks et al. |
| 5,910,426 | A | 6/1999 | Wilks et al. |
| 6,136,595 | A | 10/2000 | Ihle et al. |
| 6,210,654 | B1 | 4/2001 | Ihle et al. |
| 6,627,754 | B2 | 9/2003 | Blumenkopf et al. |
| 6,653,471 | B2 | 11/2003 | Yohannes et al. |
| 6,894,165 | B2 | 5/2005 | Gerster et al. |
| 6,927,221 | B2 | 8/2005 | Hibi et al. |
| 6,949,562 | B2 | 9/2005 | Yohannes et al. |
| 6,969,027 | B2 | 11/2005 | Flanagan et al. |
| 7,091,208 | B2 | 8/2006 | Blumenkopf et al. |
| 7,169,926 | B1 | 1/2007 | Burgess et al. |
| 7,301,023 | B2 | 11/2007 | Flanagan et al. |
| 7,335,773 | B2 | 2/2008 | Gerster et al. |
| 7,737,279 | B2 | 6/2010 | Pitts et al. |
| 2004/0167157 | A1 | 8/2004 | Masui et al. |
| 2006/0270654 | A1 | 11/2006 | Pitts et al. |
| 2007/0287724 | A1 | 12/2007 | Stoermer et al. |
| 2007/0287725 | A1 | 12/2007 | Miser et al. |
| 2009/0030031 | A1 | 1/2009 | Kshirsagar et al. |
| 2009/0105295 | A1 | 4/2009 | Kshirsagar et al. |
| 2009/0124609 | A1 | 5/2009 | Albrecht et al. |
| 2009/0240055 | A1 | 9/2009 | Krepski et al. |
| 2009/0312338 | A1 | 12/2009 | Wishart et al. |
| 2010/0105661 | A1 | 4/2010 | Shirakami et al. |
| 2010/0311714 | A1 | 12/2010 | Furet et al. |
| 2011/0021425 | A1 | 1/2011 | Billedeau |

FOREIGN PATENT DOCUMENTS

| | | | |
|---|---|---|---|
| WO | 2005/082367 | A1 | 9/2005 |
| WO | 2005/105788 | A1 | 11/2005 |
| WO | 2007/007919 | A2 | 1/2007 |
| WO | 2007/012953 | A2 | 2/2007 |

(Continued)

OTHER PUBLICATIONS

Vippagunta et al., Crystalline Solids, 48 Adv. Drug Delivery Rev. 3-26 (2001).*
Rautio et al., Prodrugs: Design and Clinical Applications, 7 Nat. Rev. Drug Dis. 255-70 (2008).*
PCT "Written Opinion of the International Searching Authority for PCT/EP2011/050239" pp. 7 pages. (Jun. 6, 2011).
Baslund et al., "Targeting interleukin-15 in patients with rheumatoid arthritis: a proof-of-concept study" *Arthritis Rheum.* 52(9):2688-92 (Sep. 2005).

(Continued)

*Primary Examiner* — Janet Andres
*Assistant Examiner* — Timothy R Rozof
(74) *Attorney, Agent, or Firm* — Genentech, Inc.

(57) ABSTRACT

The invention provides novel compounds of formula I having the general formula:

I

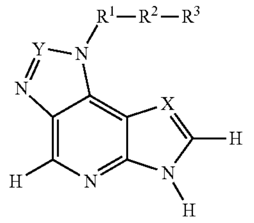

wherein $R_1$, $R_2$, $R_3$, X and Y are as described herein. Accordingly, the compounds may be provided in pharmaceutically acceptable compositions and used for the treatment of immunological or hyperproliferative disorders.

18 Claims, No Drawings

FOREIGN PATENT DOCUMENTS

| | | | |
|---|---|---|---|
| WO | 2007/075468 A1 | | 7/2007 |
| WO | 2007/077949 A1 | | 7/2007 |
| WO | 2008/029237 A2 | | 3/2008 |
| WO | WO2008/084861 | * | 7/2008 |
| WO | 2009/070657 A1 | | 6/2009 |
| WO | 2009/111337 A1 | | 9/2009 |
| WO | 2010/003133 A2 | | 1/2010 |
| WO | 2010/038165 A1 | | 4/2010 |
| WO | 2011/012540 A1 | | 2/2011 |
| WO | 2011/068881 | | 6/2011 |

OTHER PUBLICATIONS

Changelian et al., "Prevention of organ allograft rejection by a specific Janus kinase 3 inhibitor" *Science* 302:875-8 (Oct. 2003).

Kisseleva et al., "Signaling through the JAK/STAT pathway, recent advances and future challenges" *Gene* 285:1-24 (2002).

Krueger et al., "A human interleukin-12/23 monoclonal antibody for the treatment of psoriasis" *N Engl J Med.* 356(6):580-92 (Feb. 2007).

Levy et al., "Stats: transcriptional control and biological impact" *Nat Rev Mol Cell Biol.* 3:651-62 (Sep. 2002)

Mannon et al., "Anti-interleukin-12 antibody for active Crohn's disease" *N Engl J Med.* 351(20):2069-79 (Nov. 2004).

Muller et al., "The protein tyrosine kinase JAK1 complements defects in interferon-$\alpha/\beta$ and -$\gamma$ signal transduction" *Nature* 366:129-35 (Nov. 1993).

O'Shea et al., "Cytokine Signaling in 2002: New Surprises in the Jak/Stat Pathway" *Cell* 109:S121-S131 (Apr. 2002).

Reich et al., "Ustekinumab" *Nat Rev Drug Discov.* 8(5):355-6 (May 2009).

Scheinecker et al., "Tocilizumab" *Nat Rev Drug Discov.* 8(4):273-4 (Apr. 2009).

Schindler et al., "JAK-STAT signaling: from interferons to cytokines" *J Biol Chem.* 282(28) :20059-63 (Jul. 2007).

Watford and O'Shea, "Human tyk2 kinase deficiency: another primary immunodeficiency syndrome" *Immunity* 25:695-7 (Nov. 2006).

Wilks et al., "Two nove protein-tyrosine kinases, each with a second phosphotransferase-related catalytic domain, define a new class of protein kinase" *Molecular & Cellular Biology* 11:2057-2065 (1991).

Wilks, "Two putative protein-tyrosine kinases identified by application of the polymerase chain reaction" *Proc. Natl. Acad. Sci. USA* 86:1603-1607 (1989).

* cited by examiner

TRICYCLIC HETEROCYCLIC COMPOUNDS, COMPOSITIONS AND METHODS OF USE THEREOF

CROSS-REFERENCE TO RELATED APPLICATIONS

This application, filed under 35 U.S.C. §111(a), claims the benefit under 35 U.S.C. §119(e) of U.S. Provisional Patent Application Ser. No. 61/294,404, filed Jan. 12, 2010, and U.S. Provisional Patent Application Ser. No. 61/366,785, filed Jul. 22, 2010, which are each incorporated herein by reference in their entirety for all purposes.

FIELD OF THE INVENTION

Compounds of formula I, which are inhibitors of a Janus kinase, as well as compositions containing these compounds, and methods of use including, but not limited to, in vitro, in situ and in vivo diagnosis or treatment of mammalian cells.

BACKGROUND OF INVENTION

Cytokine pathways mediate a broad range of biological functions, including many aspects of inflammation and immunity. Janus kinases (JAK), including JAK1, JAK2, JAK3 and TYK2 are cytoplasmic protein kinases that associate with type I and type II cytokine receptors and regulate cytokine signal transduction. Cytokine engagement with cognate receptors triggers activation of receptor associated JAKs and this leads to JAK-mediated tyrosine phosphorylation of signal transducer and activator of transcription (STAT) proteins and ultimately transcriptional activation of specific gene sets (Schindler et al., 2007, J. Biol. Chem. 282: 20059-63). JAK1, JAK2 and TYK2 exhibit broad patterns of gene expression, while JAK3 expression is limited to leukocytes. Cytokine receptors are typically functional as heterodimers, and as a result, more than one type of JAK kinase is usually associated with cytokine receptor complexes. The specific JAKs associated with different cytokine receptor complexes have been determined in many cases through genetic studies and corroborated by other experimental evidence.

JAK1 was initially identified in a screen for novel kinases (Wilks A. F., 1989, Proc. Natl. Acad. Sci. U.S.A. 86:1603-1607). Genetic and biochemical studies have shown that JAK1 is functionally and physically associated with the type I interferon (e.g., IFNalpha), type II interferon (e.g., IFN-gamma), IL-2 and IL-6 cytokine receptor complexes (Kisseleva et al., 2002, gene 285:1-24; Levy et al., 2005, Nat. Rev. Mol. Cell. Biol. 3:651-662; O'Shea et al., 2002, Cell, 109 (suppl.): S121-S131). JAK1 knockout mice die perinatally due to defects in LIF receptor signaling (Kisseleva et al., 2002, gene 285:1-24; O'Shea et al., 2002, Cell, 109 (suppl.): S121-S131). Characterization of tissues derived from JAK1 knockout mice demonstrated critical roles for this kinase in the IFN, IL-10, IL-2/IL-4, and IL-6 pathways. A humanized monoclonal antibody targeting the IL-6 pathway (Tocilizumab) was recently approved by the European Commission for the treatment of moderate-to-severe rheumatoid arthritis (Scheinecker et al., 2009, Nat. Rev. Drug Discov. 8:273-274).

Biochemical and genetic studies have shown an association between JAK2 and single-chain (e.g., EPO), IL-3 and interferon gamma cytokine receptor families (Kisseleva et al., 2002, gene 285:1-24; Levy et al., 2005, Nat. Rev. Mol. Cell. Biol. 3:651-662; O'Shea et al., 2002, Cell, 109 (suppl.): S121-S131). Consistent with this, JAK2 knockout mice die of anemia (O'Shea et al., 2002, Cell, 109 (suppl.): S121-S131).

Kinase activating mutations in JAK2 (e.g., JAK2 V617F) are associated with myeloproliferative disorders (MPDS) in humans.

JAK3 associates exclusively with the gamma common cytokine receptor chain, which is present in the IL-2, IL-4, IL-7, IL-9, IL-15 and IL-21 cytokine receptor complexes. JAK3 is critical for lymphoid cell development and proliferation and mutations in JAK3 result in severe combined immunodeficiency (SCID) (O'Shea et al., 2002, Cell, 109 (suppl.): S121-S131). Based on its role in regulating lymphocytes, JAK3 and JAK3-mediated pathways have been targeted for immunosuppressive indications (e.g., transplantation rejection and rheumatoid arthritis) (Baslund et al., 2005, Arthritis & Rheumatism 52:2686-2692; Changelian et al., 2003, Science 302: 875-878).

TYK2 associates with the type I interferon (e.g., IFNalpha), IL-6, IL-10, IL-12 and IL-23 cytokine receptor complexes (Kisseleva et al., 2002, gene 285:1-24; Watford, W. T. & O'Shea, J. J., 2006, Immunity 25:695-697). Consistent with this, primary cells derived from a TYK2 deficient human are defective in type I interferon, IL-6, IL-10, IL-12 and IL-23 signaling. A fully human monoclonal antibody targeting the shared p40 subunit of the IL-12 and 11-23 cytokines (Ustekinumab) was recently approved by the European Commission for the treatment of moderate-to-severe plaque psoriasis (Krueger et al., 2007, N. Engl. J. Med. 356:580-92; Reich et al., 2009, Nat. Rev. Drug Discov. 8:355-356). In addition, an antibody targeting the IL-12 and IL-23 pathways underwent clinical trials for treating Crohn's Disease (Mannon et al., 2004, N. Engl. J. Med. 351:2069-79).

SUMMARY OF INVENTION

One aspect includes a compound of formula I:

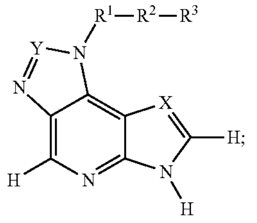

stereoisomers, tautomers, solvates, metabolites, pharmaceutically acceptable salts and prodrugs thereof, wherein X, Y, $R^1$, $R^2$ and $R^3$ are defined herein.

Another aspect includes a pharmaceutical composition that includes a compound of formula I and a pharmaceutically acceptable carrier, adjuvant or vehicle.

Another aspect includes a method of treating or lessening the severity of a disease or condition responsive to the inhibition of JAK1 kinase activity in a patient. The method includes administering to the patient a therapeutically effective amount of a compound of formula I.

Another aspect includes a compound of formula I, a stereoisomer, tautomer, prodrug or pharmaceutically acceptable salt thereof, for use in therapy.

Another aspect includes the use of a compound of formula I, a stereoisomer, tautomer, prodrug or pharmaceutically acceptable salt thereof, in the manufacture of a medicament for the treatment of a disease responsive to the inhibition of JAK1 kinase activity.

Another aspect includes a kit for treating a disease or disorder responsive to the inhibition of JAK1 kinase. The kit includes a first pharmaceutical composition comprising a compound of formula I and instructions for use

DETAILED DESCRIPTION OF THE INVENTION

Definitions

"Acyl" means a carbonyl containing substituent represented by the formula —C(O)—R in which R is hydrogen, alkyl, a cycloalkyl, a heterocyclyl, cycloalkyl-substituted alkyl or heterocyclyl-substituted alkyl wherein the alkyl, alkoxy, cycloalkyl and heterocyclyl are as defined herein. Acyl groups include alkanoyl (e.g. acetyl), aroyl (e.g. benzoyl), and heteroaroyl (e.g. pyridinoyl).

The term "alkyl" refers to a saturated linear or branched-chain monovalent hydrocarbon radical, wherein the alkyl radical may be optionally substituted independently with one or more substituents described herein. In one example, the alkyl radical is one to eighteen carbon atoms ($C_1$-$C_{18}$). In other examples, the alkyl radical is $C_0$-$C_6$, $C_0$-$C_5$, $C_0$-$C_3$, $C_1$-$C_{12}$, $C_1$-$C_{10}$, $C_1$-$C_8$, $C_1$-$C_6$, $C_1$-$C_5$, $C_1$-$C_4$, or $C_1$-$C_3$. $C_0$ alkyl refers to a bond. Examples of alkyl groups include methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —CH$(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$, 1-heptyl and 1-octyl.

The term "alkenyl" refers to linear or branched-chain monovalent hydrocarbon radical with at least one site of unsaturation, i.e., a carbon-carbon double bond, wherein the alkenyl radical may be optionally substituted independently with one or more substituents described herein, and includes radicals having "cis" and "trans" orientations, or alternatively, "E" and "Z" orientations. In one example, the alkenyl radical is two to eighteen carbon atoms ($C_2$-$C_{18}$). In other examples, the alkenyl radical is $C_2$-$C_{12}$, $C_2$-$C_{10}$, $C_2$-$C_8$, $C_2$-$C_6$ or $C_2$-$C_3$. Examples include, but are not limited to, ethenyl or vinyl (—$CH{=}CH_2$), prop-1-enyl (—$CH{=}CHCH_3$), prop-2-enyl (—$CH_2CH{=}CH_2$), 2-methylprop-1-enyl, but-1-enyl, but-2-enyl, but-3-enyl, buta-1,3-dienyl, 2-methylbuta-1,3-diene, hex-1-enyl, hex-2-enyl, hex-3-enyl, hex-4-enyl and hexa-1,3-dienyl.

The term "alkoxy" refers to a linear or branched monovalent radical represented by the formula —OR in which R is alkyl, alkenyl, alkynyl or cycloalkyl, which can be further optionally substituted as defined herein. Alkoxy groups include methoxy, ethoxy, propoxy, isopropoxy, mono-, di- and tri-fluoromethoxy and cyclopropoxy.

The term "alkynyl" refers to a linear or branched monovalent hydrocarbon radical with at least one site of unsaturation, i.e., a carbon-carbon, triple bond, wherein the alkynyl radical may be optionally substituted independently with one or more substituents described herein. In one example, the alkynyl radical is two to eighteen carbon atoms ($C_2$-$C_{18}$). In other examples, the alkynyl radical is $C_2$-$C_{12}$, $C_2$-$C_{10}$, $C_2$-$C_8$, $C_2$-$C_6$ or $C_2$-$C_3$. Examples include, but are not limited to, ethynyl (—$C{\equiv}CH$), prop-1-ynyl (—$C{\equiv}CH_3$), prop-2-ynyl (propargyl, —$CH_2C{\equiv}CH$), but-1-ynyl, but-2-ynyl and but-3-ynyl.

"Alkylene" refers to a saturated, branched or straight chain hydrocarbon group having two monovalent radical centers derived by the removal of two hydrogen atoms from the same or two different carbon atoms of a parent alkane. In one example, the divalent alkylene group is one to eighteen carbon atoms ($C_1$-$C_{18}$). In other examples, the divalent alkylene group is $C_0$-$C_6$, $C_0$-$C_5$, $C_0$-$C_3$, $C_1$-$C_{12}$, $C_1$-$C_{10}$, $C_1$-$C_8$, $C_1$-$C_6$, $C_1$-$C_5$, $C_1$-$C_4$, or $C_1$-$C_3$. The group $C_0$ alkylene refers to a bond. Example alkylene groups include methylene (—$CH_2$—), 1,1-ethyl (—$CH(CH_3)$—), (1,2-ethyl (—$CH_2CH_2$—), 1,1-propyl (—$CH(CH_2CH_3)$—), 2,2-propyl (—$C(CH_3)_2$—), 1,2-propyl (—$CH(CH_3)CH_2$—), 1,3-propyl (—$CH_2CH_2CH_2$—), 1,1-dimethyleth-1,2-yl (—$C(CH_3)_2CH_2$—), 1,4-butyl (—$CH_2CH_2CH_2CH_2$—), and the like.

"Alkenylene" refers to an unsaturated, branched or straight chain hydrocarbon group having two monovalent radical centers derived by the removal of two hydrogen atoms from the same or two different carbon atoms of a parent alkene. In one example, the alkenylene group is two to eighteen carbon atoms ($C_2$-$C_{18}$). In other examples, the alkenylene group is $C_2$-$C_{12}$, $C_2$-$C_{10}$, $C_2$-$C_8$, $C_2$-$C_6$ or $C_2$-$C_3$. Example alkenylene groups include: 1,2-ethylene (—$CH{=}CH$—).

"Alkynylene" refers to an unsaturated, branched or straight chain hydrocarbon group having two monovalent radical centers derived by the removal of two hydrogen atoms from the same or two different carbon atoms of a parent alkyne. In one example, the alkynylene radical is two to eighteen carbon atoms ($C_2$-$C_{18}$). In other examples, the alkynylene radical is $C_2$-$C_{12}$, $C_2$-$C_{10}$, $C_2$-$C_8$, $C_2$-$C_6$ or $C_2$-$C_3$. Example alkynylene radicals include: acetylene (—$C{\equiv}C$—), propargyl (—$CH_2C{\equiv}C$—), and 4-pentynyl (—$CH_2CH_2CH_2C{\equiv}C$—).

"Amidine" means the group —C(NH)—NHR in which R is hydrogen, alkyl, a cycloalkyl, a heterocyclyl, cycloalkyl-substituted alkyl or heterocyclyl-substituted alkyl wherein the alkyl, alkoxy, cycloalkyl and heterocyclyl are as defined herein. A particular amidine is the group —NH—C(NH)—$NH_2$.

"Amino" means primary (i.e., —$NH_2$), secondary (i.e., —NRH) and tertiary (i.e., —NRR) amines, that are optionally substituted, in which R is alkyl, alkoxy, a cycloalkyl, a heterocyclyl, cycloalkyl-substituted alkyl or heterocyclyl-substituted alkyl wherein the alkyl, alkoxy, cycloalkyl and heterocyclyl are as defined herein Particular secondary and tertiary amines are alkylamine, dialkylamine, arylamine, diarylamine, aralkylamine and diaralkylamine wherein the alkyl is as herein defined and optionally substituted. Particular secondary and tertiary amines are methylamine, ethylamine, propylamine, isopropylamine, phenylamine, benzylamine dimethylamine, diethylamine, dipropylamine and diisopropylamine.

"Amino-protecting group" as used herein refers to a derivative of the groups commonly employed to block or protect an amino group while reactions are carried out on other functional groups on the compound. Examples of such protecting groups include carbamates, amides, alkyl and aryl groups, imines, as well as many N-heteroatom derivatives which can be removed to regenerate the desired amine group. Particular amino protecting groups are Pmb (p-Methoxybenzyl), Boc (tert-Butyloxycarbonyl), Fmoc (9-Fluorenylmethyloxycarbonyl) and Cbz (Carbobenzyloxy). Further examples of these groups are found in T. W. Greene and P. G. M. Wuts, "Protective Groups in Organic Synthesis", 2nd ed., John Wiley & Sons, Inc., New York, N.Y., 1991, chapter 7; E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981. The term "protected amino" refers to an amino group substituted with one of the above amino-protecting groups.

"Aryl" when used alone, or as part of another term, means a carbocyclic aromatic group, whether or not fused to one or more groups, having the number of carbon atoms designated, or if no number is designated, up to 14 carbon atoms. One example includes aryl groups having 6-14 carbon atoms. Another example includes aryl groups having 6-10 carbon atoms. Examples of aryl groups include phenyl, naphthyl, biphenyl, phenanthrenyl, naphthacenyl, 1,2,3,4-tetrahydronaphthalenyl, 1H-indenyl, 2,3-dihydro-1H-indenyl, and the like (see e.g. *Lang's Handbook of Chemistry* (Dean, J. A., ed) 13th ed. Table 7-2 [1985]). A particular aryl is phenyl. Substituted phenyl or substituted aryl means a phenyl group or aryl group substituted with one, two, three, four or five, for example 1-2, 1-3 or 1-4 substituents chosen from groups specified herein. In one example, optional substituents on aryl are selected from halogen (F, Cl, Br, I), hydroxy, protected hydroxy, cyano, nitro, alkyl (for example $C_1$-$C_6$ alkyl), alkoxy (for example $C_1$-$C_6$ alkoxy), benzyloxy, carboxy, protected carboxy, carboxymethyl, protected carboxymethyl, hydroxymethyl, protected hydroxymethyl, aminomethyl, protected aminomethyl, trifluoromethyl, alkylsulfonylamino, alkylsulfonylaminoalkyl, arylsulfonylamino, arylsulfonylamino alkyl, heterocyclylsulfonylamino, heterocyclylsulfonylaminoalkyl, heterocyclyl, aryl, or other groups specified. One or more methyne (CH) and/or methylene ($CH_2$) groups in these substituents may in turn be substituted with a similar group as those denoted above. Examples of the term "substituted phenyl" include a mono- or di(halo)phenyl group such as 2-chlorophenyl, 2-bromophenyl, 4-chlorophenyl, 2,6-dichlorophenyl, 2,5-dichlorophenyl, 3,4-dichlorophenyl, 3-chlorophenyl, 3-bromophenyl, 4-bromophenyl, 3,4-dibromophenyl, 3-chloro-4-fluorophenyl, 2-fluorophenyl and the like; a mono- or di(hydroxy)phenyl group such as 4-hydroxyphenyl, 3-hydroxyphenyl, 2,4-dihydroxyphenyl, the protected-hydroxy derivatives thereof and the like; a nitrophenyl group such as 3- or 4-nitrophenyl; a cyanophenyl group, for example, 4-cyanophenyl; a mono- or di(lower alkyl)phenyl group such as 4-methylphenyl, 2,4-dimethylphenyl, 2-methylphenyl, 4-(isopropyl)phenyl, 4-ethylphenyl, 3-(n-propyl) phenyl and the like; a mono or di(alkoxy)phenyl group, for example, 3,4-dimethoxyphenyl, 3-methoxy-4-benzyloxyphenyl, 3-ethoxyphenyl, 4-(isopropoxy)phenyl, 4-(t-butoxy)phenyl, 3-ethoxy-4-methoxyphenyl and the like; 3- or 4-trifluoromethylphenyl; a mono- or dicarboxyphenyl or (protected carboxy)phenyl group such 4-carboxyphenyl, a mono- or di(hydroxymethyl)phenyl or (protected hydroxymethyl)phenyl such as 3-(protected hydroxymethyl)phenyl or 3,4-di(hydroxymethyl)phenyl; a mono- or di(aminomethyl) phenyl or (protected aminomethyl)phenyl such as 2-(aminomethyl)phenyl or 2,4-(protected aminomethyl)phenyl; or a mono- or di(N-(methylsulfonylamino))phenyl such as 3-(N-methylsulfonylamino))phenyl. Also, the term "substituted phenyl" represents disubstituted phenyl groups where the substituents are different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy-4-chlorophenyl, and the like, as well as trisubstituted phenyl groups where the substituents are different, for example 3-methoxy-4-benzyloxy-6-methyl sulfonylamino, 3-methoxy-4-benzyloxy-6-phenyl sulfonylamino, and tetrasubstituted phenyl groups where the substituents are different such as 3-methoxy-4-benzyloxy-5-methyl-6-phenyl sulfonylamino. Particular substituted phenyl groups include the 2-chlorophenyl, 2-aminophenyl, 2-bromophenyl, 3-methoxyphenyl, 3-ethoxy-phenyl, 4-benzyloxyphenyl, 4-methoxyphenyl, 3-ethoxy-4-benzyloxyphenyl, 3,4-diethoxyphenyl, 3-methoxy-4-benzyloxyphenyl, 3-methoxy-4-(1-chloromethyl)benzyloxy-6-methylsulfonyl aminophenyl groups. Fused aryl rings may also be substituted with any, for example 1, 2 or 3, of the substituents specified herein in the same manner as substituted alkyl groups.

The terms "cancer" and "cancerous", "neoplasm", "tumor" refer to or describe the physiological condition in mammals that is typically characterized by unregulated cell growth. A "tumor" comprises one or more cancerous cells. Examples of cancer include carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, melanoma, multiple myeloma and B-cell lymphoma, brain, as well as head and neck cancer, and associated metastases.

A "chemotherapeutic agent" is an agent useful in the treatment of a given disorder, for example, cancer or inflammatory disorders. Examples of chemotherapeutic agents include NSAIDs; hormones such as glucocorticoids; corticosteroids such as hydrocortisone, hydrocortisone acetate, cortisone acetate, tixocortol pivalate, prednisolone, methylprednisolone, prednisone, triamcinolone acetonide, triamcinolone alcohol, mometasone, amcinonide, budesonide, desonide, fluocinonide, fluocinolone acetonide, halcinonide, betamethasone, betamethasone sodium phosphate, dexamethasone, dexamethasone sodium phosphate, fluocortolone, hydrocortisone-17-butyrate, hydrocortisone-17-valerate, aclometasone dipropionate, betamethasone valerate, betamethasone dipropionate, prednicarbate, clobetasone-17-butyrate, clobetasol-17-propionate, fluocortolone caproate, fluocortolone pivalate and fluprednidene acetate; immune selective anti-inflammatory peptides (ImSAIDs) such as phenylalanine-glutamine-glycine (FEG) and its D-isomeric form (feG) (IMULAN BioTherapeutics, LLC); anti-rheumatic drugs such as azathioprine, ciclosporin (cyclosporine A), D-penicillamine, gold salts, hydroxychloroquine, leflunomide, methotrexate (MTX), minocycline, sulfasalazine, cyclophosphamide, tumor necrosis factor alpha (TNFα) blockers such as etanercept (Enbrel), infliximab (Remicade), adalimumab (Humira), certolizumab pegol (Cimzia), golimumab (Simponi), Interleukin 1 (IL-1) blockers such as anakinra (Kineret), monoclonal antibodies against B cells such as rituximab (RITUXAN®), T cell costimulation blockers such as abatacept (Orencia), Interleukin 6 (IL-6) blockers such as tocilizumab (ACTEMERA®); Interleukin 13 (IL-13) blockers such as lebrikizumab; Interferon alpha (IFN) blockers such as Rontalizumab; Beta 7 integrin blockers such as rhuMAb Beta7; IgE pathway blockers such as Anti-M1 prime; Secreted homotrimeric LTa3 and membrane bound heterotrimer LTa1/β2 blockers such as Anti-lymphotoxin alpha (LTa); hormone antagonists, such as tamoxifen, finasteride or LHRH antagonists; radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); miscellaneous investigational agents such as thioplatin, PS-341, phenylbutyrate, ET-18-$OCH_3$, or farnesyl transferase inhibitors (L-739749, L-744832); polyphenols such as quercetin, resveratrol, piceatannol, epigallocatechine gallate, theaflavins, flavanols, procyanidins, betulinic acid and derivatives thereof; autophagy inhibitors such as chloroquine; alkylating agents such as thiotepa and cyclosphosphamide (CYTOXAN®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omegaI1 (see, e.g., Nicolaou et al., *Angew. Chem. Intl. Ed. Engl.,* 33: 183-186 (1994)); CDP323, an oral alpha-4 integrin inhibitor; dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycins, dactinomycin, daunorubicin, detorubicin, 6-diazo-5-oxo-L-norleucine, doxorubicin (including ADRIAMYCIN®, morpholino-doxorubicin, cyanomorpholino-doxorubicin, 2-pyrrolino-doxorubicin, doxorubicin HCl liposome injection (DOXIL®), liposomal doxorubicin TLC D-99 (MYOCET®), peglylated liposomal doxorubicin (CAELYX®), and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate, gemcitabine (GEMZAR®), tegafur (UFTORAL®), capecitabine (XELODA®), an epothilone, and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2'-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoid, e.g., paclitaxel (TAXOL®), albumin-engineered nanoparticle formulation of paclitaxel (ABRAXANE™), and docetaxel (TAXOTERE®); chloranbucil; 6-thioguanine; mercaptopurine; methotrexate; platinum agents such as cisplatin, oxaliplatin (e.g., ELOXATIN®), and carboplatin; vincas, which prevent tubulin polymerization from forming microtubules, including vinblastine (VELBAN®), vincristine (ONCOVIN®), vindesine (ELDISINE®, FILDESIN®), and vinorelbine (NAVELBINE®); etoposide (VP-16); ifosfamide; mitoxantrone; leucovorin; novantrone; edatrexate; daunomycin; aminopterin; ibandronate; topoisomerase inhibitor RFS 2000; difluoromethylornithine (DMFO); retinoids such as fenretinide, retinoic acid, including bexarotene (TARGRETIN®); bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); troxacitabine (a 1,3-dioxolane nucleoside cytosine analog); antisense oligonucleotides, particularly those that inhibit expression of genes in signaling pathways implicated in aberrant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; topoisomerase 1 inhibitor (e.g., LURTOTECAN®); rmRH (e.g., ABARELIX®); BAY439006 (sorafenib; Bayer); SU-11248 (sunitinib, SUTENT®, Pfizer); perifosine, COX-2 inhibitor (e.g. celecoxib or etoricoxib), proteosome inhibitor (e.g. PS341); bortezomib (VELCADE®); CCI-779; tipifarnib (R11577); orafenib, ABT510; Bcl-2 inhibitor such as oblimersen sodium (GENASENSE®); pixantrone; EGFR inhibitors (see definition below); farnesyltransferase inhibitors such as lonafarnib (SCH 6636, SARASAR™); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone; and FOLFOX, an abbreviation for a treatment regimen with oxaliplatin (ELOXATIN™) combined with 5-FU and leucovorin.

Additional chemotherapeutic agents as defined herein include "anti-hormonal agents" or "endocrine therapeutics" which act to regulate, reduce, block, or inhibit the effects of hormones that can promote the growth of cancer. They may be hormones themselves, including, but not limited to: anti-estrogens with mixed agonist/antagonist profile, including, tamoxifen (NOLVADEX®), 4-hydroxytamoxifen, toremifene (FARESTON®), idoxifene, droloxifene, raloxifene (EVISTA®), trioxifene, keoxifene, and selective estrogen receptor modulators (SERMs) such as SERM3; pure anti-estrogens without agonist properties, such as fulvestrant (FASLODEX®), and EM800 (such agents may block estrogen receptor (ER) dimerization, inhibit DNA binding, increase ER turnover, and/or suppress ER levels); aromatase inhibitors, including steroidal aromatase inhibitors such as formestane and exemestane (AROMASIN®), and nonsteroidal aromatase inhibitors such as anastrazole (ARIMIDEX®), letrozole (FEMARA®) and aminoglutethimide, and other aromatase inhibitors include vorozole (RIVISOR®), megestrol acetate (MEGASE®), fadrozole, and 4(5)-imidazoles; lutenizing hormone-releasing hormone agonists, including leuprolide (LUPRON® and ELIGARD®), goserelin, buserelin, and tripterelin; sex steroids, including progestines such as megestrol acetate and medroxyprogesterone acetate, estrogens such as diethylstilbestrol and premarin, and androgens/retinoids such as fluoxymesterone, all transretionic acid and fenretinide; onapristone; anti-progesterones; estrogen receptor down-regulators (ERDs); anti-androgens such as flutamide, nilutamide and bicalutamide.

Additional chemotherapeutic agents include therapeutic antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (OMNITARG®, 2C4, Genentech), trastuzumab (HERCEPTIN®, Genentech), tositumomab (Bexxar, Corixia), and the antibody drug conjugate, gemtuzumab ozogamicin (MYLOTARG®, Wyeth). Additional humanized monoclonal antibodies with therapeutic potential as agents in combination with the compounds of the invention include: apolizumab, aselizumab, atlizumab, bapineuzumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, tucotuzumab celmoleukin, tucusituzumab, umavizumab, urtoxazumab, ustekinumab, visilizumab, and the anti-interleukin-12 (ABT-874/J695, Wyeth Research and Abbott Laboratories) which is a recombinant exclusively human-sequence, full-length $IgG_1\lambda$ antibody genetically modified to recognize interleukin-12 p40 protein.

Chemotherapeutic agents also include "EGFR inhibitors," which refers to compounds that bind to or otherwise interact directly with EGFR and prevent or reduce its signaling activity, and is alternatively referred to as an "EGFR antagonist." Examples of such agents include antibodies and small molecules that bind to EGFR. Examples of antibodies which bind to EGFR include MAb 579 (ATCC CRL HB 8506), MAb 455 (ATCC CRL HB8507), MAb 225 (ATCC CRL 8508), MAb 528 (ATCC CRL 8509) (see, U.S. Pat. No. 4,943,533, Mendelsohn et al.) and variants thereof, such as chimerized 225 (C225 or Cetuximab; ERBUTIX®) and reshaped human 225 (H225) (see, WO 96/40210, Imclone Systems Inc.); IMC-11F8, a fully human, EGFR-targeted antibody (Imclone); antibodies that bind type II mutant EGFR (U.S. Pat. No. 5,212,290); humanized and chimeric antibodies that bind EGFR as described in U.S. Pat. No. 5,891,996; and human antibodies that bind EGFR, such as ABX-EGF or Panitumumab (see WO98/50433, Abgenix/Amgen); EMD 55900 (Stragliotto et al. Eur. J. Cancer 32A:636-640 (1996)); EMD7200 (matuzumab) a humanized EGFR antibody directed against EGFR that competes with both EGF and TGF-alpha for EGFR binding (EMD/Merck); human EGFR antibody, HuMax-EGFR (GenMab); fully human antibodies known as E1.1, E2.4, E2.5, E6.2, E6.4, E2.11, E6.3 and E7.6.3 and described in U.S. Pat. No. 6,235,883; MDX-447 (Medarex Inc); and mAb 806 or humanized mAb 806 (Johns et al., *J. Biol. Chem.* 279(29):30375-30384 (2004)). The anti-EGFR antibody may be conjugated with a cytotoxic agent, thus generating an immunoconjugate (see, e.g., EP659, 439A2, Merck Patent GmbH). EGFR antagonists include small molecules such as compounds described in U.S. Pat. Nos. 5,616,582, 5,457,105, 5,475,001, 5,654,307, 5,679,683, 6,084,095, 6,265,410, 6,455,534, 6,521,620, 6,596,726, 6,713,484, 5,770,599, 6,140,332, 5,866,572, 6,399,602, 6,344,459, 6,602,863, 6,391,874, 6,344,455, 5,760,041, 6,002,008, and 5,747,498, as well as the following PCT publications: WO98/14451, WO98/50038, WO99/09016, and WO99/24037. Particular small molecule EGFR antagonists include OSI-774 (CP-358774, erlotinib, TARCEVA® Genentech/OSI Pharmaceuticals); PD 183805 (CI 1033, 2-prop enamide, N-[4-[(3-chloro-4-fluorophenyl)amino]-7-[3-(4-morpholinyl)propoxy]-6-quinazolinyl]-, dihydrochloride, Pfizer Inc.); ZD1839, gefitinib (IRESSA™) 4-(3'-Chloro-4'-fluoro anilino)-7-methoxy-6-(3-morpholinopropoxy)quinazoline, AstraZeneca); ZM 105180 ((6-amino-4-(3-methylphenyl-amino)-quinazoline, Zeneca); BIBX-1382 (N-8-(3-chloro-4-fluoro-phenyl)-N2-(1-methyl-piperidin-4-yl)-pyrimido[5,4-d]pyrimidine-2,8-diamine, Boehringer Ingelheim); PKI-166 ((R)-4-[4-[(1-phenylethyl)amino]-1H-pyrrolo[2,3-d]pyrimidin-6-yl]-phenol); (R)-6-(4-hydroxyphenyl)-4-[(1-phenylethyl)amino]-7H-pyrrolo[2,3-d]pyrimidine); CL-387785 (N-[4-[(3-bromophenyl)amino]-6-quinazolinyl]-2-butynamide); EKB-569 (N-[4-[(3-chloro-4-fluorophenyl)amino]-3-cyano-7-ethoxy-6-quinolinyl]-4-(dimethylamino)-2-butenamide) (Wyeth); AG1478 (Pfizer); AG1571 (SU 5271; Pfizer); dual EGFR/HER2 tyrosine kinase inhibitors such as lapatinib (TYKERB®, GSK572016 or N-[3-chloro-4-[(3 fluorophenyl)methoxy]phenyl]-6 [5 [[[2-methylsulfonyl)ethyl]amino]methyl]-2-furanyl]-4-quinazolinamine).

Chemotherapeutic agents also include "tyrosine kinase inhibitors" including the EGFR-targeted drugs noted in the preceding paragraph; small molecule HER2 tyrosine kinase inhibitor such as TAK165 available from Takeda; CP-724,714, an oral selective inhibitor of the ErbB2 receptor tyrosine kinase (Pfizer and OSI); dual-HER inhibitors such as EKB-569 (available from Wyeth) which preferentially binds EGFR but inhibits both HER2 and EGFR-overexpressing cells; lapatinib (GSK572016; available from Glaxo-SmithKline), an oral HER2 and EGFR tyrosine kinase inhibitor; PKI-166 (available from Novartis); pan-HER inhibitors such as canertinib (CI-1033; Pharmacia); Raf-1 inhibitors such as antisense agent ISIS-5132 available from ISIS Pharmaceuticals which inhibit Raf-1 signaling; non-HER targeted TK inhibitors such as imatinib mesylate (GLEEVEC™, available from Glaxo SmithKline); multi-targeted tyrosine kinase inhibitors such as sunitinib (SUTENT®, available from Pfizer); VEGF receptor tyrosine kinase inhibitors such as vatalanib (PTK787/ZK222584, available from Novartis/Schering AG); MAPK extracellular regulated kinase I inhibitor CI-1040 (available from Pharmacia); quinazolines, such as PD 153035,4-(3-chloro anilino) quinazoline; pyridopyrimidines; pyrimidopyrimidines; pyrrolopyrimidines, such as CGP 59326, CGP 60261 and CGP 62706; pyrazolopyrimidines, 4-(phenylamino)-7H-pyrrolo[2,3-d]pyrimidines; curcumin (diferuloyl methane, 4,5-bis(4-fluoroanilino)phthalimide); tyrphostines containing nitrothiophene moieties; PD-0183805 (Warner-Lamber); antisense molecules (e.g. those that bind to HER-encoding nucleic acid); quinoxalines (U.S. Pat. No. 5,804,396); tryphostins (U.S. Pat. No. 5,804, 396); ZD6474 (Astra Zeneca); PTK-787 (Novartis/Schering AG); pan-HER inhibitors such as CI-1033 (Pfizer); Affinitac (ISIS 3521; Isis/Lilly); imatinib mesylate (GLEEVEC™); PKI 166 (Novartis); GW2016 (Glaxo SmithKline); CI-1033 (Pfizer); EKB-569 (Wyeth); Semaxinib (Pfizer); ZD6474 (AstraZeneca); PTK-787 (Novartis/Schering AG); INC-1C11 (Imclone), rapamycin (sirolimus, RAPAMUNE®); or as described in any of the following patent publications: U.S. Pat. No. 5,804,396; WO 1999/09016 (American Cyanamid); WO 1998/43960 (American Cyanamid); WO 1997/38983 (Warner Lambert); WO 1999/06378 (Warner Lambert); WO 1999/06396 (Warner Lambert); WO 1996/30347 (Pfizer, Inc); WO 1996/33978 (Zeneca); WO 1996/3397 (Zeneca) and WO 1996/33980 (Zeneca).

The term "NSAID" and the terms "non-steroidal anti-inflammatory drug" refer to therapeutic agents with analgesic, antipyretic and anti-inflammatory effects. NSAIDs include non-selective inhibitors of the enzyme cyclooxygenase. Specific examples of NSAIDs include aspirin, propionic acid derivatives such as ibuprofen, fenoprofen, ketoprofen, flurbiprofen, oxaprozin and naproxen, acetic acid derivatives such as indomethacin, sulindac, etodolac, diclofenac, enolic acid derivatives such as piroxicam, meloxicam, tenoxicam, droxicam, lornoxicam and isoxicam, fenamic acid derivatives such as mefenamic acid, meclofenamic acid, flufenamic acid, tolfenamic acid, and COX-2 inhibitors such as celecoxib, etoricoxib, lumiracoxib, parecoxib, rofecoxib, rofecoxib, and valdecoxib. NSAIDs can be indicated for the symptomatic relief of conditions such as rheumatoid arthritis, osteoarthritis, inflammatory arthropathies, ankylosing spondylitis, psoriatic arthritis, Reiter's syndrome, acute gout, dysmenorrhoea, metastatic bone pain, headache and migraine, postoperative pain, mild-to-moderate pain due to inflammation and tissue injury, pyrexia, ileus, and renal colic.

Additionally, chemotherapeutic agents include pharmaceutically acceptable salts, acids or derivatives of any of chemotherapeutic agents, described herein, as well as combinations of two or more of them.

"Cycloalkyl" refers to a non-aromatic, saturated or partially unsaturated hydrocarbon ring group wherein the cycloalkyl group may be optionally substituted independently with one or more substituents described herein. In one example, the cycloalkyl group is 3 to 12 carbon atoms ($C_3$-$C_{12}$). In other examples, cycloalkyl is $C_3$-$C_8$, $C_3$-$C_{10}$ or $C_5$-$C_{10}$. In other examples, the cycloalkyl group, as a monocycle, is $C_3$-$C_8$, $C_3$-$C_6$ or $C_5$-$C_6$. In another example, the cycloalkyl group, as a bicycle, is $C_7$-$C_{12}$. In another example, the cycloalkyl group, as a spiro system, is $C_5$-$C_{12}$. Examples of monocyclic cycloalkyl include cyclopropyl, cyclobutyl, cyclopentyl, 1-cyclopent-1-enyl, 1-cyclopent-2-enyl, 1-cyclopent-3-enyl, cyclohexyl, perdeuteriocyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl and cyclododecyl. Exemplary arrangements of bicyclic cycloalkyls having 7 to 12 ring atoms include, but are not limited to, [4,4], [4,5], [5,5], [5,6] or [6,6] ring systems. Exemplary bridged bicyclic cycloalkyls include, but are not limited to, bicyclo[2.2.1]heptane, bicyclo[2.2.2]octane and bicyclo[3.2.2]nonane. Examples of spiro cycloalkyl include, spiro[2.2]pentane, spiro[2.3]hexane, spiro[2.4]heptane, spiro [2.5]octane and spiro[4.5]decane.

"Carboxy-protecting group" as used herein refers to those groups that are stable to the conditions of subsequent reaction (s) at other positions of the molecule, which may be removed at the appropriate point without disrupting the remainder of the molecule, to give the unprotected carboxy-group. Examples of carboxy protecting groups include, ester groups and heterocyclyl groups. Ester derivatives of the carboxylic acid group may be employed to block or protect the carboxylic acid group while reactions are carried out on other functional groups on the compound. Examples of such ester groups include substituted arylalkyl, including substituted benzyls, such as 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxybenzhydryl, 2,2',4,4'-tetramethoxybenzhydryl, alkyl or substituted alkyl esters such as methyl, ethyl, t-butyl allyl or t-amyl, triphenylmethyl (trityl), 4-methoxytrityl, 4,4'-dimethoxytrityl, 4,4',4"-trimethoxytrityl, 2-phenylprop-2-yl, thioesters such as t-butyl thioester, silyl esters such as trimethylsilyl, t-butyldimethylsilyl esters, phenacyl, 2,2,2-trichloroethyl, b eta-(trimethylsilyl)ethyl, beta-(di(n-butyl)methylsilyl)ethyl, p-toluenesulfonylethyl, 4-nitrobenzylsulfonylethyl, allyl, cinnamyl, 1-(trimethylsilylmethyl)prop-1-en-3-yl, and like moieties. Another example of carboxy-protecting groups are heterocyclyl groups such as 1,3-oxazolinyl. Further examples of these groups are found in T. W. Greene and P. G. M. Wuts, "Protective Groups in Organic Synthesis", $2^{nd}$ ed., John Wiley & Sons, Inc., New York, N.Y., 1991, chapter 5; E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981, Chapter 5. The term "protected carboxy" refers to a carboxy group substituted with one of the above carboxy-protecting groups.

"Guanidine" means the group —NH—C(NH)—NHR in which R is hydrogen, alkyl, alkoxy, a cycloalkyl, a heterocyclyl, cycloalkyl-substituted alkyl or heterocyclyl-substituted alkyl wherein the alkyl, alkoxy, cycloalkyl and heterocyclyl are as defined herein. A particular guanidine is the group $—NH—C(NH)—NH_2$.

"Hydroxy-protecting group" as used herein refers to a derivative of the hydroxy group commonly employed to block or protect the hydroxy group while reactions are carried out on other functional groups on the compound. Examples of such protecting groups include tetrahydropyranyloxy, benzoyl, acetoxy, carbamoyloxy, benzyl, and silylethers (e.g. TBS, TBDPS) groups. Further examples of these groups are found in T. W. Greene and P. G. M. Wuts, "Protective Groups in Organic Synthesis", $2^{nd}$ ed., John Wiley & Sons, Inc., New York, N.Y., 1991, chapters 2-3; E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981. The term "protected hydroxy" refers to a hydroxy group substituted with one of the above hydroxy-protecting groups.

"Heterocyclic group", "heterocyclic", "heterocycle", "heterocyclyl", or "heterocyclo" alone, and when used as a moiety in a complex group such as a heterocycloalkyl group, are used interchangeably and refer to any mono-, bi-, tricyclic or spiro, saturated or unsaturated, aromatic (heteroaryl) or non-aromatic, ring system, having 3 to 20 ring atoms, where the ring atoms are carbon, and at least one atom in the ring or ring system is a heteroatom selected from nitrogen, sulfur or oxygen. In one example, heterocyclyl includes 3-12 ring atoms and includes monocycles, bicycles, tricycles and spiro ring systems, wherein the ring atoms are carbon, and at least one atom in the ring or ring system is a heteroatom selected from nitrogen, sulfur or oxygen. In one example, heterocyclyl includes 1 to 4 heteroatoms. In another example, heterocyclyl includes 3- to 7-membered monocycles having one or more heteroatoms selected from nitrogen, sulfur or oxygen. In another example, heterocyclyl includes 4- to 6-membered monocycles having one or more heteroatoms selected from nitrogen, sulfur or oxygen. In another example, heterocyclyl includes 3-membered monocycles. In another example, heterocyclyl includes 4-membered monocycles. In another example, heterocyclyl includes 5-6-membered monocycles. In one example, the heterocyclyl group includes 0 to 3 double bonds. Any nitrogen or sulfur heteroatom may optionally be oxidized (e.g. NO, SO, $SO_2$), and any nitrogen heteroatom may optionally be quaternized (e.g. $[NR_4]^+Cl^-$, $[NR_4]^+OH^-$). Example heterocycles are oxiranyl, aziridinyl, thiiranyl, azetidinyl, oxetanyl, thietanyl, 1,2-dithietanyl, 1,3-dithietanyl, pyrrolidinyl, dihydro-1H-pyrrolyl, dihydrofuranyl, tetrahydrofuranyl, dihydrothienyl, tetrahydrothienyl, imidazolidinyl, piperidinyl, piperazinyl, morpholinyl, thiomorpholinyl, 1,1-dioxo-thiomorpholinyl, dihydropyranyl, tetrahydropyranyl, hexahydrothiopyranyl, hexahydropyrimidinyl, oxazinanyl, thiazinanyl, thioxanyl, homopiperazinyl, homopiperidinyl, azepanyl, oxepanyl, thiepanyl, oxazepinyl, oxazepanyl, diazepanyl, 1,4-diazepanyl, diazepinyl, thiazepinyl, thiazepanyl, tetrahydrothiopyranyl, oxazolidinyl, thiazolidinyl, isothiazolidinyl, 1,1-dioxoisothiazolidinonyl, oxazolidinonyl, imidazolidinonyl, 4,5,6,7-tetrahydro[2H]indazolyl, tetrahydrobenzoimidazolyl, 4,5,6,7-tetrahydrobenzo[d]imidazolyl, 1,6-dihydroimidazol[4,5-d]pyrrolo[2,3-b]pyridinyl, thiazinyl, oxazinyl, thiadiazinyl, oxadiazinyl, dithiazinyl, dioxazinyl, oxathiazinyl, thiatriazinyl, oxatriazinyl, dithiadiazinyl, imidazolinyl, dihydropyrimidyl, tetrahydropyrimidyl, 1-pyrrolinyl, 2-pyrrolinyl, 3-pyrrolinyl, indolinyl, thiapyranyl, 2H-pyranyl, 4H-pyranyl, dioxanyl, 1,3-dioxolanyl, pyrazolinyl, pyrazolidinyl, dithianyl, dithiolanyl, pyrimidinonyl, pyrimidindionyl, pyrimidin-2,4-dionyl, piperazinonyl, piperazindionyl, pyrazolidinylimidazolinyl, 3-azabicyclo[3.1.0]hexanyl, 3,6-diazabicyclo[3.1.1]heptanyl, 6-azabicyclo[3.1.1]heptanyl, 3-azabicyclo[3.1.1]heptanyl, 3-azabicyclo[4.1.0]heptanyl, azabicyclo[2.2.2]hexanyl, 2-azabicyclo[3.2.1]octanyl, 8-azabicyclo[3.2.1]octanyl, 2-azabicyclo[2.2.2]octanyl, 8-azabicyclo[2.2.2]octanyl, 7-oxabicyclo[2.2.1]heptane, azaspiro[3.5]nonanyl, azaspiro[2.5]octanyl, azaspiro[4.5]decanyl, 1-azaspiro[4.5]decan-2-only, azaspiro[5.5]undecanyl, tetrahydroindolyl, octahydroindolyl, tetrahydroisoindolyl, tetrahydroindazolyl, 1,1-dioxohexahydrothiopyranyl. Examples of 5-membered heterocycles containing a sulfur or oxygen atom and one to three nitrogen atoms are thiazolyl, including thiazol-2-yl and thiazol-2-yl N-oxide, thiadiazolyl, including 1,3,4-thiadiazol-5-yl and 1,2,4-thiadiazol-5-yl, oxazolyl, for example oxazol-2-yl, and oxadiazolyl, such as 1,3,4-oxadiazol-5-yl, and 1,2,4-oxadiazol-5-yl. Example 5-membered ring heterocycles containing 2 to 4 nitrogen atoms include imidazolyl, such as imidazol-2-yl; triazolyl, such as 1,3,4-triazol-5-yl; 1,2,3-triazol-5-yl, 1,2,4-triazol-5-yl, and tetrazolyl, such as 1H-tetrazol-5-yl. Example benzo-fused 5-membered heterocycles are benzoxazol-2-yl, benzthiazol-2-yl and benzimidazol-2-yl. Example 6-membered heterocycles contain one to three nitrogen atoms and optionally a sulfur or oxygen atom, for example pyridyl, such as pyrid-2-yl, pyrid-3-yl, and pyrid-4-yl; pyrimidyl, such as pyrimid-2-yl and pyrimid-4-yl; triazinyl, such as 1,3,4-triazin-2-yl and 1,3,5-triazin-4-yl; pyridazinyl, in particular pyridazin-3-yl, and pyrazinyl. The pyridine N-oxides and pyridazine N-oxides and the pyridyl, pyrimid-2-yl, pyrimid-4-yl, pyridazinyl and the 1,3,4-triazin-2-yl groups, are other example heterocycle groups. Substituents for "optionally substituted heterocycles" include hydroxyl, alkyl, alkoxy, acyl, halogen, mercapto, oxo, carboxyl, halo-substituted alkyl, amino, cyano, nitro, amidino, guanidino.

"Heteroaryl" alone and when used as a moiety in a complex group such as a heteroaralkyl group, refers to any mono-, bi-, or tricyclic ring system where at least one ring is a 5- or, 6-membered aromatic ring containing from 1 to 4 heteroatoms selected from nitrogen, oxygen, and sulfur, and in an example embodiment, at least one heteroatom is nitrogen. See, for example, *Lang's Handbook of Chemistry*, supra. Included in the definition are any bicyclic groups where any of the above heteroaryl rings are fused to an aryl ring. In one embodiment, heteroaryl includes 4-6 membered monocyclic aromatic groups where one or more ring atoms is nitrogen, sulfur or oxygen. In another embodiment, heteroaryl includes 5-6 membered monocyclic aromatic groups where one or more ring atoms is nitrogen, sulfur or oxygen. Example heteroaryl groups (whether substituted or unsubstituted) include thienyl, furyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, triazinyl, tetrazinyl, tetrazolo[1,5-b]pyridazinyl, imidazol[1,2-a]pyrimidinyl and purinyl, as well as benzo-fused derivatives, for example benzoxazolyl, benzofuryl, benzothiazolyl, benzothiadiazolyl, benzotriazolyl, benzoimidazolyl and indolyl. Additional examples of "heteroaryl" groups are: 1,3-thiazol-2-yl, 4-(carboxymethyl)-5-methyl-1,3-thiazol-2-yl, 4-(carboxymethyl)-5-methyl-1,3-thiazol-2-yl sodium salt, 1,2,4-thiadiazol-5-yl, 3-methyl-1,2,4-thiadiazol-5-yl, 1,3,4-triazol-5-yl, 2-methyl-1,3,4-triazol-5-yl, 2-hydroxy-1,3,4-triazol-5-yl, 2-carboxy-4-methyl-1,3,4-triazol-5-yl sodium salt, 2-carboxy-4-methyl-1,3,4-triazol-5-yl, 1,3-oxazol-2-yl, 1,3,4-oxadiazol-5-yl, 2-methyl-1,3,4-oxadiazol-5-yl, 2-(hydroxymethyl)-1,3,4-oxadiazol-5-yl, 1,2,4-oxadiazol-5-yl, 1,3,4-thiadiazol-5-yl, 2-thiol-1,3,4-thiadiazol-5-yl, 2-(methylthio)-1,3,4-thiadiazol-5-yl, 2-amino-1,3,4-thiadiazol-5-yl, 1H-tetrazol-5-yl, 1-methyl-1H-tetrazol-5-yl, 1-(1-(dimethylamino)eth-2-yl)-1H-tetrazol-5-yl, 1-(carboxymethyl)-1H-tetrazol-5-yl, 1-(carboxymethyl)-1H-tetrazol-5-yl sodium salt, 1-(methylsulfonic acid)-1H-tetrazol-5-yl, 1-(methylsulfonic acid)-1H-tetrazol-5-yl sodium salt, 2-methyl-1H-tetrazol-5-yl, 1,2,3-triazol-5-yl, 1-methyl-1,2,3-triazol-5-yl, 2-methyl-1,2,3-triazol-5-yl, 4-methyl-1,2,3-triazol-5-yl, pyrid-2-yl N-oxide, 6-methoxy-2-(n-oxide)-pyridaz-3-yl, 6-hydroxypyridaz-3-yl, 1-methylpyrid-2-yl, 1-methylpyrid-4-yl, 2-hydroxypyrimid-4-yl, 1,4,5,6-tetrahydro-5,6-dioxo-4-methyl-as-triazin-3-yl, 1,4,5,6-tetrahydro-4-(formylmethyl)-5,6-dioxo-as-triazin-3-yl, 2,5-dihydro-5-oxo-6-hydroxy-astriazin-3-yl, 2,5-dihydro-5-oxo-6-hydroxy-as-triazin-3-yl sodium salt, 2,5-dihydro-5-oxo-6-hydroxy-2-methyl-astriazin-3-yl sodium salt, 2,5-dihydro-5-oxo-6-hydroxy-2-methyl-as-triazin-3-yl, 2,5-dihydro-5-oxo-6-methoxy-2-methyl-as-triazin-3-yl, 2,5-dihydro-5-oxo-as-triazin-3-yl, 2,5-dihydro-5-oxo-2-methyl-as-triazin-3-yl, 2,5-dihydro-5-oxo-2,6-dimethyl-as-triazin-3-yl, tetrazolo[1,5-b]pyridazin-6-yl and 8-aminotetrazolo[1,5-b]-pyridazin-6-yl. Heteroaryl groups are optionally substituted as described for heterocycles.

In particular embodiments, a heterocyclyl group is attached at a carbon atom of the heterocyclyl group. By way of example, carbon bonded heterocyclyl groups include bonding arrangements at position 2, 3, 4, 5, or 6 of a pyridine ring, position 3, 4, 5, or 6 of a pyridazine, position 2, 4, 5, or 6 of a pyrimidine ring, position 2, 3, 5, or 6 of a pyrazine ring, position 2, 3, 4, or 5 of a furan, tetrahydrofuran, thiofuran, thiophene, pyrrole or tetrahydropyrrole ring, position 2, 4, or 5 of an oxazole, imidazole or thiazole ring, position 3, 4, or 5 of an isoxazole, pyrazole, or isothiazole ring, position 2 or 3 of an aziridine ring, position 2, 3, or 4 of an azetidine ring, position 2, 3, 4, 5, 6, 7, or 8 of a quinoline ring or position 1, 3, 4, 5, 6, 7, or 8 of an isoquinoline ring.

In certain embodiments, the heterocyclyl group is N-attached. By way of example, the nitrogen bonded heterocyclyl or heteroaryl group include bonding arrangements at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline.

"Leaving group" refers to a portion of a first reactant in a chemical reaction that is displaced from the first reactant in the chemical reaction. Examples of leaving groups include, but are not limited to, halogen atoms, alkoxy and sulfonyloxy groups. Example sulfonyloxy groups include, but are not limited to, alkylsulfonyloxy groups (for example methylsulfonyloxy (mesylate group) and trifluoromethylsulfonyloxy (triflate group)) and arylsulfonyloxy groups (for example p-toluenesulfonyloxy (tosylate group) and p-nitrosulfonyloxy (nosylate group)).

"Optionally substituted" unless otherwise specified means that a group may be unsubstituted or substituted by one or more (e.g. 0, 1, 2, 3 or 4) of the substituents listed for that group in which said substituents may be the same or different. In an embodiment an optionally substituted group has 1 substituent. In another embodiment an optionally substituted group has 2 substituents. In another embodiment an optionally substituted group has 3 substituents.

In certain embodiments, divalent groups are described generically without specific bonding configurations, for example in the group $—CH_2C(O)—$. It is understood that the generic description is meant to include both bonding configurations, unless specified otherwise. For example, in the group $R^1$-$R^2$-$R^3$, if the group $R^2$ is described as $—CH_2C(O)—$, then it is understood that this group can be bonded both as $R^1—CH_2C(O)—R^3$, and as $R^1—C(O)CH_2$-$R^3$, unless specified otherwise.

"Package insert" is used to refer to instructions customarily included in commercial packages of therapeutic products that contain information about the indications, usage, dosage, administration, contraindications and/or warnings concerning the use of such therapeutic products.

"Pharmaceutically acceptable salts" include both acid and base addition salts. "Pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric acid, carbonic acid, phosphoric acid and the like, and organic acids may be selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, maloneic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, benzenesulfonic acid, p-toluenesulfonic acid, salicyclic acid and the like.

"Pharmaceutically acceptable base addition salts" include those derived from inorganic bases such as sodium, potassium, lithium, ammonium, calcium, magnesium, iron, zinc, copper, manganese, aluminum salts and the like. Particularly base addition salts are the ammonium, potassium, sodium, calcium and magnesium salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, tromethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, polyamine resins and the like. Particularly organic non-toxic bases are isopropylamine, diethylamine, ethanolamine, tromethamine, dicyclohexylamine, choline, and caffeine.

A "sterile" formulation is aseptic or free from all living microorganisms and their spores.

"Stereoisomers" refers to compounds which have identical chemical constitution, but differ with regard to the arrangement of the atoms or groups in space. Stereoisomers include diastereomers, enantiomers, conformers and the like.

"Chiral" refers to molecules which have the property of non-superimposability of the mirror image partner, while the term "achiral" refers to molecules which are superimposable on their mirror image partner.

"Diastereomer" refers to a stereoisomer with two or more centers of chirality and whose molecules are not mirror images of one another. Diastereomers have different physical properties, e.g. melting points, boiling points, spectral properties or biological activities. Mixtures of diastereomers may separate under high resolution analytical procedures such as electrophoresis and chromatography such as HPLC.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., "Stereochemistry of Organic Compounds", John Wiley & Sons, Inc., New York, 1994. Many organic compounds exist in optically active forms, i.e., they have the ability to rotate the plane of plane-polarized light. In describing an optically active compound, the prefixes D and L, or R and S, are used to denote the absolute configuration of the molecule about its chiral center (s). The prefixes d and l or (+) and (−) are employed to designate the sign of rotation of plane-polarized light by the compound, with (−) or 1 meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

A "solvate" refers to an association or complex of one or more solvent molecules and a compound of the present invention. Examples of solvents that form solvates include water, isopropanol, ethanol, methanol, DMSO, ethyl acetate, acetic acid, and ethanolamine. The term "hydrate" refers to the complex where the solvent molecule is water.

A "subject," "individual," or "patient" is a vertebrate. In certain embodiments, the vertebrate is a mammal. Mammals include, but are not limited to, farm animals (such as cows), sport animals, pets (such as cats, dogs, and horses), primates, mice and rats. In certain embodiments, a mammal is a human.

"Therapeutically effective amount" means an amount of a compound of the present invention that (i) treats or prevents the particular disease, condition or disorder, (ii) attenuates, ameliorates or eliminates one or more symptoms of the particular disease, condition, or disorder, or (iii) prevents or delays the onset of one or more symptoms of the particular disease, condition or disorder described herein. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can, for example, be measured by assessing the time to disease progression (TTP) and/or determining the response rate (RR). In the case of immunological disorders, the therapeutic effective amount is an amount sufficient to decrease or alleviate an allergic disorder, the symptoms of an autoimmune and/or inflammatory disease, or the symptoms of an acute inflammatory reaction (e.g. asthma). In some embodiments, a therapeutically effective amount is an amount of a chemical entity described herein sufficient to significantly decrease the activity or number of B-cells.

"Treatment" (and variations such as "treat" or "treating") refers to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, diminishment of any direct or indirect pathological consequences of the disease, stabilized (i.e., not worsening) state of disease, preventing metastasis, decreasing the rate of disease progression, amelioration or palliation of the disease state, prolonging survival as compared to expected survival if not receiving treatment and remission or improved prognosis. In some embodiments, compounds of the invention are used to delay development of a disease or disorder or to slow the progression of a disease or disorder. Those in need of treatment include those already with the condition or disorder as well as those prone to have the condition or disorder, (for example, through a genetic mutation) or those in which the condition or disorder is to be prevented.

The terms "compound(s) of this invention," and "compound(s) of the present invention", unless otherwise indicated, include compounds of formula I and stereoisomers, tautomers, solvates, metabolites, salts (e.g., pharmaceutically acceptable salts), and prodrugs thereof. Unless otherwise stated, structures depicted herein are also meant to include compounds that differ only in the presence of one or more isotopically enriched atoms. For example, compounds of formulas I, II and III, wherein one or more hydrogen atoms are replaced by deuterium or tritium, or one or more carbon atoms are replaced by $^{13}C$- or $^{14}C$-enriched carbon are within the scope of this invention.

Inhibitors of JAK1 Kinase

One aspect of the invention provides compounds of formula I:

I

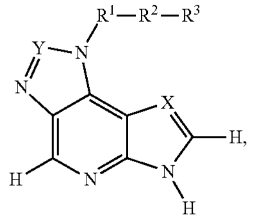

stereoisomers, tautomers, solvates, metabolites, pharmaceutically acceptable salts and prodrugs thereof, wherein X is N or $CR^4$;

Y is N or $CR^5$;

$R^1$ is absent, $C_{1-12}$ alkyl, $C_{1-12}$ alkenyl, $C_{1-12}$ alkynyl, $C_{3-12}$ cycloalkyl, $C_{6-14}$ aryl or 3-20 membered heterocyclyl, wherein $R^1$ is independently optionally substituted by halogen, oxo, —CN, —$OR^a$, —$SR^a$, —$NR^aR^b$, $C_{1-3}$ alkylene or $C_{1-6}$ alkyl optionally substituted by oxo, —CN or halogen;

$R^2$ is absent, $C_{1-6}$ alkyl, $C_{2-6}$ alkenyl, $C_{2-6}$ alkynyl, —($C_{1-6}$ alkylene)-, —($C_{2-6}$ alkenylene)-, —($C_{2-6}$ alkynylene)-, —($C_{0-6}$ alkylene)CN, —($C_{0-3}$ alkylene)$NR^a$($C_{0-3}$ alkylene)-, —($C_{0-3}$ alkylene)O($C_{0-3}$ alkylene)-, —($C_{0-3}$ alkylene)C(O)($C_{0-3}$ alkylene)-, —($C_{0-3}$ alkylene)$NR^a$C(O)($C_{0-3}$ alkylene)-, —($C_{0-3}$ alkylene)C(O)$NR^a$($C_{0-3}$ alkylene)-, —($C_{0-3}$ alkylene)C(O)O($C_{0-3}$ alkylene)-, —($C_{0-3}$ alkylene)OC(O)($C_{0-3}$ alkylene)-, —($C_{0-3}$ alkylene)$NR^a$C(O)$NR^b$($C_{0-3}$ alkylene)-, —($C_{0-3}$ alkylene)OC(O)$NR^a$($C_{0-3}$ alkylene)-, —($C_{0-3}$ alkylene)$NR^a$C(O)O($C_{0-3}$ alkylene)-, —($C_{0-3}$ alkylene)$S(O)_{1-2}$($C_{0-3}$ alkylene)-, —($C_{0-3}$ alkylene)$NR^aS(O)_{1-2}$($C_{0-3}$ alkylene)-, —($C_{0-3}$ alkylene)$S(O)_{1-2}NR^a$($C_{0-3}$ alkylene)- or —($C_{0-3}$ alkylene)$NR^aS(O)_{1-2}NR^b$($C_{0-3}$ alkylene)-, wherein said alkyl, alkyenyl, alkynyl, alkylene, alkenylene and alkynylene are independently optionally substituted by halogen, oxo, —CN, —$OR^c$, —$SR^c$, —$NR^cR^d$ or $C_{1-3}$ alkyl optionally substituted by halogen;

$R^3$ is absent, hydrogen, $C_{1-6}$ alkyl, $C_{2-6}$ alkenyl, $C_{2-6}$ alkynyl, $C_{3-7}$ cycloalkyl, $C_{6-14}$ aryl or 3-20 membered heterocyclyl, wherein $R^3$ is independently optionally substituted by $R^6$;

$R^4$ is hydrogen, halogen or $C_{1-3}$ alkyl;

$R^5$ is hydrogen, halogen, $C_{1-12}$ alkyl, $C_{2-12}$ alkenyl, $C_{2-12}$ alkynyl, —($C_{0-3}$ alkylene)CN, —($C_{0-3}$ alkylene)$NR^aR^b$, —($C_{0-3}$ alkylene)$OR^a$, —($C_{0-3}$ alkylene)$SR^a$, —($C_{0-3}$ alkylene)C(O)$R^a$, —($C_{0-3}$ alkylene)$NR^a$C(O)$R^b$, —($C_{0-3}$ alkylene)C(O)$NR^aR^b$, —($C_{0-3}$ alkylene)C(O)$OR^a$, —($C_{0-3}$ alkylene)OC(O)$R^a$, —($C_{0-3}$ alkylene)$NR^a$C(O)$NR^aR^b$, —($C_{0-3}$ alkylene)OC(O)$NR^aR^b$, —($C_{0-3}$ alkylene)$NR^a$C(O)$OR^b$, —($C_{0-3}$ alkylene)$S(O)_{1-2}R^a$, —($C_{0-3}$ alkylene)$NR^aS(O)_{1-2}R^b$, —($C_{0-3}$ alkylene)$S(O)_{1-2}NR^aR^b$, —($C_{0-3}$ alkylene)$NR^aS(O)_{1-2}NR^aR^b$, —($C_{0-3}$ alkylene)$C_{3-12}$ cycloalkyl, —($C_{0-3}$ alkylene)$C_{6-14}$ aryl, —($C_{0-3}$ alkylene)3-12 membered heterocyclyl or —($C_{0-3}$alkylene)C(O)3-12 membered heterocyclyl, wherein said alkyl, alkenyl, alkynyl, alkylene, cycloalkyl, aryl and heterocyclyl are independently optionally substituted by halogen, oxo, —($C_{0-3}$ alkylene)CN, —($C_{0-3}$ alkylene)$OR^c$, —($C_{0-3}$ alkylene)$NR^cR^d$, —($C_{0-3}$ alkylene)C(O)$R^c$, —($C_{0-3}$ alkylene)C(O)$OR^c$, —($C_{0-3}$ alkylene)C(O)$NR^cR^d$, —($C_{0-3}$ alkylene)$NR^cR^d$, (O)$R^d$, —($C_{0-3}$ alkylene)OC(O)$NR^cR^d$, —($C_{0-3}$ alkylene)$NR^c$C(O)$NR^cR^d$, —($C_{0-3}$ alkylene)$NR^c$C(O)$OR^d$, —($C_{0-3}$ alkylene)$S(O)_{0-2}R^c$, —($C_{0-3}$ alkylene)$NR^cS(O)_{1-2}R^d$, —($C_{0-3}$ alkylene)$S(O)_{1-2}NR^cR^d$, —($C_{0-3}$ alkylene)$NR^cS(O)_{1-2}NR^cR^d$ or $C_{1-6}$ alkyl optionally substituted by oxo, —CN or halogen;

$R^6$ is independently oxo, halogen, —CN, —C(O)$R^a$, —C(O)$OR^a$, —$NR^a$C(O)$R^b$, —C(O)$NR^aR^b$, —$NR^a$C(O)$NR^aR^b$, —OC(O)$NR^aR^b$, —$NR^a$C(O)$OR^b$, —$S(O)_{1-2}R^a$, —$NR^aS(O)_2R^b$, —$S(O)_2NR^aR^b$, —$OR^a$, —$SR^a$, —$NR^aR^b$, $C_{1-6}$ alkyl, $C_{3-6}$ cycloalkyl, $C_{2-6}$ alkenyl, $C_{2-6}$ alkynyl, 3-7 membered heterocycyl or $C_{6-14}$ aryl, and wherein said alkyl, alkenyl, alkynyl, cycloalkyl, heterocyclyl and aryl are independently optionally substituted by halogen, oxo, —CN, —$OR^c$, —$SR^c$, —$NR^cR^d$ or $C_{1-6}$ alkyl optionally substituted by oxo or halogen;

each $R^a$ and $R^b$ are independently hydrogen, $C_{1-6}$ alkyl, $C_{2-6}$ alkenyl, $C_{2-6}$ alkynyl, —($C_{0-3}$ alkylene)$C_{3-6}$ cycloalkyl, —($C_{0-3}$ alkylene)3-12 membered heterocyclyl, —($C_{0-3}$ alkylene)C(O)3-12 membered heterocyclyl or —($C_{0-3}$ alkylene) $C_{6-14}$ aryl, wherein said alkyl, cycloalkyl, heterocyclyl and aryl are independently optionally substituted by halogen, oxo, —CN, —$OR^e$, —$NR^eR^f$, —C(O)$R^g$, —C(O)$OR^g$, —C(O)$NR^gR^h$, —$NR^g$C(O)$R^h$, —OC(O)$NR^gR^h$, —$NR^g$C(O)$NR^gR^h$, —$NR^g$C(O)$OR^h$, —$S(O)_{1-2}R^g$, —$NR^gS(O)_{1-2}R^h$, —$S(O)_{1-2}NR^gR^h$, —$NR^gS(O)_{1-2}NR^gR^h$, $C_{3-6}$ cycloalkyl, 3-6 membered heterocyclyl, phenyl or $C_{1-3}$ alkyl optionally substituted by oxo or halogen, or taken together with the atom to which they are attached to form a 3-6 membered heterocyclyl optionally substituted by oxo, halogen, —C(O)$C_{1-6}$ alkyl or $C_{1-6}$ alkyl optionally substituted by oxo, halogen, $OR^g$ or $NR^gNR^h$;

each $R^c$ and $R^d$ are independently hydrogen, $C_{1-6}$ alkyl, $C_{2-6}$ alkenyl, $C_{2-6}$ alkynyl, —($C_{0-3}$ alkylene)$C_{3-6}$ cycloalkyl, —($C_{0-3}$ alkylene)3-12 membered heterocyclyl, —($C_{0-3}$ alkylene)C(O)3-12 membered heterocyclyl or —($C_{0-3}$ alkylene) $C_{6-14}$ aryl, wherein said alkyl, alkenyl, alkynyl, cycloalkyl, heterocyclyl and aryl are independently optionally substituted by halogen, oxo, —CN, —$OR^g$, —$NR^gR^h$, —C(O)$R^g$, —C(O)$OR^g$, —C(O)$NR^gR^h$, —$NR^g$C(O)$R^h$, —OC(O)$NR^gR^h$, —$NR^g$C(O)$NR^gR^h$, —$NR^g$C(O)$OR^h$, —$S(O)_{1-2}R^g$, —$NR^gS(O)_{1-2}R^h$, —$S(O)_{1-2}NR^gR^h$, —$NR^gS(O)_{1-2}NR^gR^h$, $C_{3-6}$ cycloalkyl, 3-6 membered heterocyclyl, phenyl or $C_{1-6}$ alkyl optionally substituted by oxo or halogen, or taken together with the atom to which they are attached to form a 3-6 membered heterocyclyl optionally substituted by oxo, halogen, —C(O)$C_{1-6}$ alkyl or $C_{1-6}$ alkyl optionally substituted by oxo or halogen; and each $R^e$, $R^f$, $R^g$, $R^h$ are independently hydrogen or $C_{1-6}$ alkyl optionally substituted by halogen or oxo.

In certain embodiments, when $R^1$ and $R^2$ are absent, one of $R^3$, $R^4$ and $R^5$ is other than hydrogen.

In certain embodiments, $R^1$, $R^2$ and $R^3$ are not absent at the same time.

In certain embodiments, when $R^2$ and $R^3$ are absent, $R^1$ is other than $C_{1-12}$ alkyl, $C_{1-12}$ alkenyl and $C_{1-12}$ alkynyl. In certain embodiments, when $R^2$ and $R^3$ are absent, $R^5$ is other than OH.

Certain embodiments include compounds of formula I, stereoisomers, tautomers and pharmaceutically acceptable salts thereof, wherein X is N or $CR^4$;

Y is N or $CR^5$;

$R^1$ is absent, $C_{1-12}$ alkyl, $C_{1-12}$ alkenyl, $C_{1-12}$ alkynyl, $C_{3-12}$ cycloalkyl, phenyl, 5-6 membered heteroaryl or 3-20 membered heterocyclyl, wherein $R^1$ is independently optionally substituted by halogen, oxo, —CN, —$OR^a$, —$NR^aR^b$, $C_{1-3}$ alkylene or $C_{1-6}$ alkyl optionally substituted by oxo, —CN or halogen;

$R^2$ is absent, $C_{1-6}$ alkyl, $C_{2-6}$ alkenyl, $C_{2-6}$ alkynyl, —($C_{1-6}$ alkylene)-, —($C_{2-6}$ alkenylene)-, —($C_{2-6}$ alkynylene)-, —($C_{1-6}$ alkylene)CN, —($C_{0-3}$ alkylene)$NR^a$($C_{0-3}$ alkylene)-, —($C_{0-3}$ alkylene)O($C_{0-3}$ alkylene)-, —($C_{0-3}$ alkylene)C(O)($C_{0-3}$ alkylene)-, —($C_{0-3}$ alkylene)$NR^a$C(O)($C_{0-3}$ alkylene)-, —($C_{0-3}$ alkylene)C(O)$NR^a$($C_{0-3}$ alkylene)-, —($C_{0-3}$ alkylene)C(O)O($C_{0-3}$ alkylene)-, —($C_{0-3}$ alkylene)OC(O)($C_{0-3}$ alkylene)-, —($C_{0-3}$ alkylene)$NR^a$C(O)$NR^b$($C_{0-3}$ alkylene)-, —($C_{0-3}$ alkylene)OC(O)$NR^a$($C_{0-3}$ alkylene)-, —($C_{0-3}$ alkylene)$NR^a$C(O)O($C_{0-3}$ alkylene)-, —($C_{0-3}$ alkylene)$S(O)_{1-2}$($C_{0-3}$ alkylene)-, —($C_{0-3}$ alkylene)$NR^aS(O)_{1-2}$($C_{0-3}$ alkylene)-, —($C_{0-3}$ alkylene)$S(O)_{1-2}NR^a$($C_{0-3}$ alkylene)- or —($C_{0-3}$ alkylene)$NR^aS(O)_{1-2}NR^b$($C_{0-3}$ alkylene)-, wherein said alkyl, alkyenyl, alkynyl, alkylene, alkenylene and alkynylene are independently optionally substituted by halogen, oxo, —CN, —$OR^c$, —$NR^cR^d$ or $C_{1-3}$ alkyl optionally substituted by halogen;

$R^3$ is absent, hydrogen, $C_{1-6}$ alkyl, $C_{2-6}$ alkenyl, $C_{2-6}$ alkynyl, $C_{3-7}$ cycloalkyl, phenyl, 3-12 membered heterocyclyl or 5-6 membered heteroaryl, wherein said alkyl, alkenyl, alkynyl, cycloalkyl, phenyl, heterocyclyl and heteroaryl are independently optionally substituted by 1 to 4 $R^6$;

$R^4$ is hydrogen, halogen or $C_{1-3}$ alkyl;

$R^5$ is hydrogen, halogen, $C_{1-6}$ alkyl, $C_{2-6}$ alkenyl, $C_{2-6}$ alkynyl, —($C_{1-6}$ alkylene)CN, —($C_{0-3}$ alkylene)$NR^aR^b$, —($C_{0-3}$ alkylene)$OR^a$, —($C_{0-3}$ alkylene)C(O)$R^a$, —($C_{0-3}$ alkylene) $NR^a$C(O)$R^b$, —($C_{0-3}$ alkylene)C(O)$NR^aR^b$, —($C_{0-3}$ alkylene)C(O)$OR^a$, —($C_{0-3}$ alkylene)OC(O)$R^a$, —($C_{0-3}$ alkylene) $NR^a$C(O)$NR^aR^b$, —($C_{0-3}$ alkylene)OC(O)$NR^aR^b$, —($C_{0-3}$ alkylene)$NR^a$C(O)$OR^b$, —($C_{0-3}$ alkylene)$S(O)_{1-2}R^a$, —($C_{0-3}$ alkylene)$NR^aS(O)_{1-2}R^b$, —($C_{0-3}$ alkylene)$S(O)_{1-2}NR^aR^b$, —($C_{0-3}$ alkylene)$NR^aS(O)_{1-2}NR^aR^b$, —($C_{0-3}$ alkylene)$C_{3-6}$ cycloalkyl, —($C_{0-3}$ alkylene)phenyl, —($C_{0-3}$ alkylene)$_{3-7}$ membered heterocyclyl, —($C_{0-3}$ alkylene)$_{5-6}$ membered heteroaryl, wherein said alkyl, alkenyl, alkynyl, alkylene, cycloalkyl, phenyl, heterocyclyl and heteroaryl are independently optionally substituted by halogen, oxo, —CN, —$OR^c$, —$NR^cR^d$, —C(O)$OR^c$, or $C_{1-6}$ alkyl optionally substituted by oxo, —CN or halogen;

$R^6$ is independently oxo, halogen, —CN, —C(O)$R^a$, —C(O)$OR^a$, —$NR^a$C(O)$R^b$, —C(O)$NR^aR^b$, —$NR^a$C(O)$NR^aR^b$, —OC(O)$NR^aR^b$, —$NR^a$C(O)$OR^b$, —$S(O)_2R^a$, —$NR^aS(O)_2R^a$, —$S(O)_2NR^aR^b$, —$OR^a$, —$NR^aR^b$, $C_{1-6}$ alkyl, $C_{3-6}$ cycloalkyl, $C_{2-6}$ alkenyl, $C_{2-6}$ alkynyl, 3-7 membered heterocyclyl, 5-6 membered heteroaryl or phenyl, and wherein said alkyl, alkenyl, alkynyl, cycloalkyl, heterocyclyl, heteroaryl and phenyl are independently optionally substituted by halogen, oxo, —CN, —$OR^c$, —$NR^cR^d$ or $C_{1-6}$ alkyl optionally substituted by halogen;

each $R^a$ and $R^b$ are independently hydrogen, $C_{1-6}$ alkyl, $C_{3-6}$ cycloalkyl, 3-6 membered heterocyclyl, 5-6 membered heteroaryl or phenyl, wherein said alkyl, cycloalkyl, heterocyclyl, heteroaryl and phenyl are independently optionally substituted by halogen, oxo, —CN, —$OR^e$, —$NR^eR^f$ or $C_{1-3}$ alkyl optionally substituted by halogen, or taken together with the atom to which they are attached to form a 3-6 membered heterocyclyl optionally substituted by oxo, halogen, —C(O)$C_{1-6}$ alkyl or $C_{1-6}$ alkyl optionally substituted by halogen;

each $R^c$ and $R^d$ are independently hydrogen, $C_{1-6}$ alkyl, $C_{3-6}$ cycloalkyl, 3-6 membered heterocyclyl, 5-6 membered heteroaryl or phenyl, wherein said alkyl, cycloalkyl, heterocyclyl, heteroaryl and phenyl are independently optionally substituted by halogen, oxo, —CN, —$OR^g$, —$NR^gR^h$ or $C_{1-6}$ alkyl optionally substituted by halogen, or taken together with the atom to which they are attached to form a 3-6 membered heterocyclyl optionally substituted by oxo, halogen, —C(O)$C_{1-6}$ alkyl or $C_{1-6}$ alkyl optionally substituted by halogen; and each $R^e$, $R^f$, $R^g$, $R^h$ are independently hydrogen or $C_{1-6}$ alkyl optionally substituted by halogen or oxo.

In certain embodiments, when $R^1$ and $R^2$ are absent, one of $R^3$, $R^4$ and $R^5$ is other than hydrogen.

In certain embodiments, $R^1$, $R^2$ and $R^3$ are not absent at the same time.

Certain embodiments include compounds of formula I, stereoisomers, tautomers and pharmaceutically acceptable salts thereof, wherein:

X is N or $CR^4$;

Y is N or $CR^5$;

$R^1$ is a $C_{4-7}$ cycloalkyl or 4-7 membered heterocyclyl, wherein said cycloalkyl and heterocyclyl are independently optionally substituted by halogen, oxo, $C_{1-3}$ alkylene or $C_{1-6}$ alkyl optionally substituted by halogen;

$R^2$ is absent, —($C_{1-6}$ alkylene)-, —($C_{0-3}$ alkylene)$NR^a$($C_{0-3}$ alkylene)-, —($C_{0-3}$ alkylene)O($C_{0-3}$ alkylene)-, —($C_{0-3}$ alkylene)C(O)($C_{0-3}$ alkylene)-, —($C_{0-3}$ alkylene)$NR^a$C(O)($C_{0-3}$ alkylene)-, —($C_{0-3}$ alkylene)C(O)$NR^a$($C_{0-3}$ alkylene)-, —($C_{0-3}$ alkylene)C(O)O($C_{0-3}$ alkylene)-, —($C_{0-3}$ alkylene)OC(O)($C_{0-3}$ alkylene)-, —($C_{0-3}$ alkylene)$NR^a$C(O)$NR^b$($C_{0-3}$ alkylene)-, —($C_{0-3}$ alkylene)OC(O)$NR^a$($C_{0-3}$ alkylene)-, —($C_{0-3}$ alkylene)$NR^a$C(O)O($C_{0-3}$ alkylene)-, —($C_{0-3}$ alkylene)$S(O)_{1-2}$ ($C_{0-3}$ alkylene)-, —($C_{0-3}$ alkylene)$NR^a$$S(O)_{1-2}$ ($C_{0-3}$ alkylene)- or —($C_{0-3}$ alkylene)$S(O)_{1-2}$$NR^a$($C_{0-3}$ alkylene)-, wherein said alkylene is optionally substituted by halogen, oxo, —CN or $C_{1-3}$ alkyl;

$R^3$ is absent, hydrogen, $C_{1-6}$ alkyl, $C_{2-6}$ alkenyl, $C_{2-6}$ alkynyl, $C_{3-7}$ cycloalkyl, phenyl, 4-7 membered heterocyclyl or 5-6 membered heteroaryl, wherein said alkyl, alkenyl, alkynyl, cycloalkyl, phenyl, heterocyclyl and heteroaryl are independently optionally substituted by 1 to 4 $R^6$;

$R^4$ is hydrogen, halogen or $C_{1-3}$ alkyl;

$R^5$ is hydrogen, —CN, $C_{1-6}$ alkyl, $C_{2-6}$ alkenyl or $C_{2-6}$ alkynyl, —($C_{0-3}$ alkylene)$C_{3-7}$ cycloalkyl, —($C_{0-3}$ alkylene) phenyl, —($C_{0-3}$ alkylene)4-6 membered heteroaryl, —($C_{0-3}$ alkylene)4-6 membered heterocyclyl, —($C_{0-3}$ alkylene)C(O) 4-6 membered heterocyclyl or —($C_{0-3}$ alkylene)C(O)$NR^aR^b$, wherein said alkylene is optionally substituted by oxo or halogen, said alkyl, alkenyl or alkynyl are optionally substituted by halogen, oxo, —CN, —$OR^a$ or —$NR^aR^b$, and said cycloalkyl, phenyl, heteroaryl and heterocyclyl are independently optionally substituted by oxo, halogen, $C_{1-3}$ alkyl, —$OR^c$ or —$NR^cR^d$;

$R^6$ is independently oxo, halogen, —CN, —C(O)($C_{1-6}$ alkyl), —$S(O)_2$($C_{1-6}$ alkyl), —$OR^a$, —$NR^aR^b$, $C_{1-6}$ alkyl, $C_{3-6}$ cycloalkyl, $C_{2-6}$ alkenyl, or $C_{2-6}$ alkynyl, and wherein said alkyl, alkenyl and alkynyl are independently optionally substituted by halogen, oxo, —CN, —$OR^c$ or —$NR^cR^d$;

each $R^a$ and $R^b$ are independently hydrogen, $C_{1-6}$ alkyl, $C_{3-6}$ cycloalkyl, 4-6 membered heterocyclyl, wherein said alkyl, cycloalkyl and heterocyclyl are independently optionally substituted by halogen, oxo, —CN, —$OR^e$ or —$NR^eR^f$, or taken together with the atom to which they are attached to form a 3-6 membered heterocyclyl optionally substituted by oxo, halogen, —C(O)$C_{1-6}$ alkyl or $C_{1-6}$ alkyl;

each $R^c$ and $R^d$ are independently hydrogen, $C_{1-6}$ alkyl optionally substituted by halogen, oxo, —CN, —$OR^g$ or —$NR^gR^h$, or taken together with the atom to which they are attached to form a 3-6 membered heterocyclyl optionally substituted by oxo, halogen, —C(O)$C_{1-6}$ alkyl or $C_{1-6}$ alkyl; and each $R^e$, $R^f$, $R^g$, $R^h$ are independently hydrogen or $C_{1-6}$ alkyl optionally substituted by halogen or oxo.

In one embodiment, X is $CR^4$, Y is N, $R^1$ and $R^2$ are absent, and $R^3$ and $R^4$ are hydrogen.

In one embodiment, X is $CR^4$, Y is $CR^5$, $R^1$ and $R^2$ are absent, and $R^3$ and $R^4$ are hydrogen.

In one embodiment, X is $CR^4$, Y is $CR^5$, $R^1$ and $R^2$ are absent, and $R^3$, $R^4$ and $R^5$ are hydrogen.

In one embodiment, X is $CR^4$. In another embodiment, X is N.

In one embodiment, Y is $CR^5$. In another embodiment, Y is N.

In one embodiment, X is $CR^4$ and Y is $CR^5$.

In another embodiment, X is $CR^4$ and Y is N.

In another embodiment, X is N and Y is $CR^5$.

In another embodiment, X is N and Y is N.

In one embodiment, $R^1$ is absent. In one embodiment, $R^1$ is absent with the proviso that $R^1$, $R^2$ and $R^3$ are not all absent at the same time.

In one embodiment $R^1$ is $C_1$-$C_6$ alkyl optionally substituted by halogen, oxo, —CN, —$OR^a$, —$SR^a$, or —$NR^aR^b$. In one embodiment $R^1$ is $C_1$-$C_6$ alkyl optionally substituted by halogen, oxo, —CN, —$OR^a$ or —$NR^aR^b$. In one embodiment, $R^1$ is selected from methyl, ethyl, propyl, butyl,

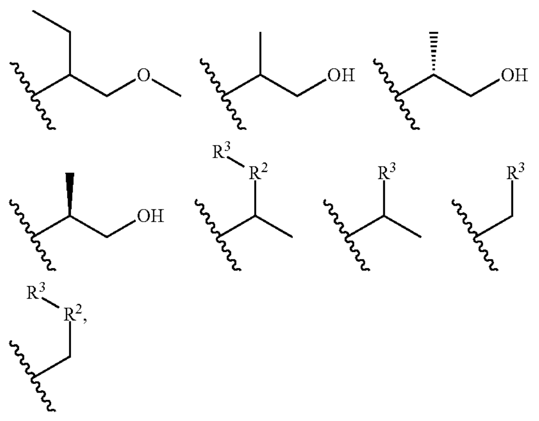

wherein the wavy line represents the point of attachment in formula I. In one embodiment, $R^1$ is selected from methyl, ethyl, propyl, butyl,

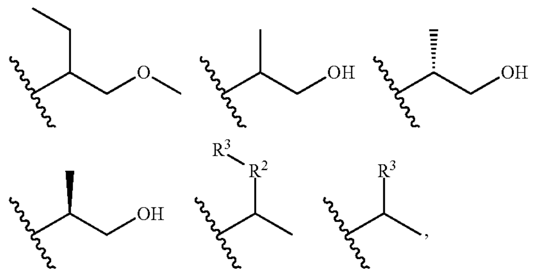

wherein the wavy line represents the point of attachment in formula I.

In one embodiment $R^1$ is a 3-20 membered heterocyclyl, wherein $R^1$ is independently optionally substituted by halogen, oxo, —CN, —$OR^a$, —$SR^a$, —$NR^aR^b$, $C_{1-3}$ alkylene or $C_{1-6}$ alkyl optionally substituted by oxo, —CN or halogen. In one embodiment $R^1$ is a 3-12 membered heterocyclyl optionally substituted by halogen, oxo, —CN, —$OR^a$, —$NR^aR^b$, $C_{1-3}$ alkylene or $C_{1-6}$ alkyl optionally substituted by halogen. In one embodiment $R^1$ is a 4-7 membered heterocyclyl optionally substituted by halogen, oxo, $C_{1-3}$ alkylene or $C_{1-6}$ alkyl optionally substituted by halogen, wherein said heterocyclyl is selected from oxetanyl, azetidinyl, thietanyl, tetrahydrofuranyl, 2,3-dihydrofuranyl, tetrahydrothienyl, 2,3-dihydrothienyl, pyrrolidinyl, 2,3-dihydro-1H-pyrrolyl, imidazolidinyl, 2H-pyranyl, tetrahydropyranyl, morpholinyl, piperazinyl, hexahydropyrimidinyl, oxazinanyl, thiazinanyl, piperidinyl, 8-azabicyclo[3.2.1]octanyl, 2-azabicyclo[2.2.2]octanyl, oxepanyl and azepanyl. In another embodiment, $R^1$ is azetidinyl, pyrrolidinyl, imidazolidinyl, morpholinyl, piperazinyl, hexahydropyrimidinyl, or piperidinyl, wherein $R^1$ is optionally substituted by halogen, oxo, $C_{1-3}$ alkylene or $C_{1-6}$ alkyl optionally substituted by halogen. In another embodiment, $R^1$ is 4,5,6,7-tetrahydrobenzoimidazolyl, 4,5,6,7-tetrahydro[2H]indazolyl, oxazolidinyl, thiazolidinyl, isothiazolidinyl, 1,1-dioxoisothiazolidinyl, oxazolidinonyl, 3-azabicyclo[3.1.0]hexanyl or imidazolidinonyl, wherein $R^1$ is independently optionally substituted by halogen, oxo, —CN, —$OR^a$, —$SR^a$, —$NR^aR^b$, $C_{1-3}$ alkylene or $C_{1-6}$ alkyl optionally substituted by oxo, —CN or halogen. In another embodiment, $R^1$ is piperidinyl or tetrahydropyranyl wherein $R^1$ is independently optionally substituted by halogen, oxo, —CN, —$OR^a$, —$SR^a$, —$NR^aR^b$, $C_{1-3}$ alkylene or $C_{1-6}$ alkyl optionally substituted by oxo, —CN or halogen.

In one embodiment $R^1$ is a 3-20 membered heterocyclyl, wherein $R^1$ is independently optionally substituted by halogen, oxo, —CN, —$OR^a$, —$SR^a$, —$NR^aR^b$, $C_{1-3}$ alkylene or $C_{1-6}$ alkyl optionally substituted by oxo, —CN or halogen, with the proviso that $R^5$ is other than hydrogen or —OH.

In another embodiment, $R^1$ is a 3-12 membered heterocyclyl, wherein $R^1$ is independently optionally substituted by halogen, oxo, —CN, —$OR^a$, —$SR^a$, —$NR^aR^b$, $C_{1-3}$ alkylene or $C_{1-6}$ alkyl optionally substituted by oxo, —CN or halogen. In another embodiment, $R^1$ is a 3-12 membered heterocyclyl optionally substituted by halogen, oxo, —CN, —$OR^a$, —$NR^aR^b$, $C_{1-3}$ alkylene or $C_{1-6}$ alkyl, wherein said heterocyclyl is selected from oxetanyl, azetidinyl, thietanyl, tetrahydrofuranyl, 2,3-dihydrofuranyl, tetrahydrothienyl, 2,3-dihydrothienyl, pyrrolidinyl, 2,3-dihydro-1H-pyrrolyl, imidazolidinyl, 2H-pyranyl, tetrahydropyranyl, morpholinyl, piperazinyl, hexahydropyrimidinyl, oxazinanyl, thiazinanyl, piperidinyl, 8-azabicyclo[3.2.1]octanyl, 2-azabicyclo[2.2.2]octanyl, oxepanyl, azepanyl, 7-oxabicyclo[2.2.1]heptane, octahydro-1H-indolyl, 1-azaspiro[4.5]decanyl,

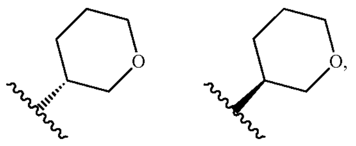 [SMILES: *[C@@H]1CCCOC1 ; *[C@H]1CCCOC1]

wherein the wavy line represents the point of attachment in formula I. In one embodiment, $R^1$ is

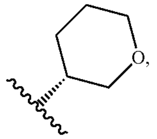 [SMILES: *[C@@H]1CCCOC1]

wherein the wavy line represents the point of attachment in formula I. In one embodiment, $R^1$ is

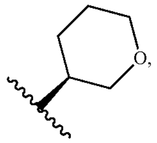 [SMILES: *[C@H]1CCCOC1]

wherein the wavy line represents the point of attachment in formula I.

In another embodiment, $R^1$ is azetidinyl, pyrrolidinyl or piperidinyl, optionally substituted by 1 or 2 halogen, oxo, $C_{1-3}$ alkylene or $C_{1-6}$ alkyl optionally substituted by halogen. In another embodiment, $R^1$ is azetidinyl, pyrrolidinyl or piperidinyl, optionally substituted by 1 or 2 halogen, oxo, —CN, —$OR^a$, —$NR^aR^b$, $C_{1-3}$ alkylene or $C_{1-6}$ alkyl optionally substituted by halogen halogen, oxo, —CN, —$OR^a$, —$NR^aR^b$, $C_{1-3}$ alkylene or $C_{1-6}$ alkyl optionally substituted by halogen In another embodiment, $R^1$ is morpholinyl, piperazinyl, 2-azabicyclo[2.2.2]octanyl, 8-azabicyclo[3.2.1]octanyl or piperidinyl, optionally substituted by 1 or 2 halogen, oxo, —CN, —$OR^a$, —$SR^a$, —$NR^aR^b$, $C_{1-3}$ alkylene or $C_{1-6}$ alkyl optionally substituted by oxo, —CN or halogen. In another embodiment, $R^1$ is morpholinyl, piperazinyl, 2-azabicyclo[2.2.2]octanyl, 8-azabicyclo[3.2.1]octanyl or piperidinyl, optionally substituted by 1 or 2 halogen, oxo or $C_{1-6}$ alkyl optionally substituted by halogen.

In another embodiment, $R^1$ is piperidinyl optionally substituted by halogen, oxo, —CN, —$OR^a$, —$SR^a$, —$NR^aR^b$, $C_{1-3}$ alkylene or $C_{1-6}$ alkyl optionally substituted by oxo, —CN or halogen. In another embodiment, $R^1$ is piperidinyl optionally substituted by 1 or 2 halogen, oxo, —CN, —$OR^a$, —$NR^aR^b$, $C_{1-3}$ alkylene or $C_{1-6}$ alkyl optionally substituted by halogen. In another embodiment, $R^1$ is piperidinyl optionally substituted by 1 or 2 halogen, oxo or $C_{1-6}$ alkyl. In another embodiment, $R^1$ is piperidinyl optionally substituted by methyl, oxo, fluoro or methoxy. In another embodiment, $R^1$ is piperidin-3-yl, piperidin-4-yl, 2-methylpiperidin-3-yl or 2-methylpiperidin-4-yl. In another embodiment, $R^1$ is (R)-piperidin-3-yl. In another embodiment, $R^1$ is (S)-piperidin-3-yl. In another embodiment, $R^1$ is substituted (R)-piperidin-4-yl, wherein said piperidinyl is substituted by 1-3 groups selected from oxo, $C_{1-3}$ alkyl, halogen or —$OR^a$. In another embodiment, $R^1$ is substituted (S)-piperidin-4-yl, wherein said piperidinyl is substituted by 1-3 groups selected from oxo, $C_{1-3}$ alkyl, halogen or —$OR^a$. In another embodiment, $R^1$ is (R)—(R)-2-methylpiperidin-4-yl, (R)—(S)-2-methylpiperidin-4-yl, (S)—(R)-2-methylpiperidin-4-yl or (S)—(S)-2-methylpiperidin-4-yl. In another embodiment, $R^1$ is (R)—(R)-3-fluoropiperidin-4-yl, (R)—(S)-3-fluoropiperidin-4-yl, (S)—(R)-3-fluoropiperidin-4-yl or (S)—(S)-3-fluoropiperidin-4-yl. In another embodiment, $R^1$ is piperidinonyl, 2-methylpiperidin-4-yl, 3-methylpiperidin-4-yl, 4-methylpiperidin-4-yl, 2-fluoropiperidinyl, 3-fluoropiperidin-4-yl, 3,3-difluoropiperidin-4-yl, 3-methoxypiperidin-4-yl or

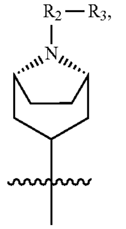

wherein the wavy line represents the point of attachment in formula I.

In another embodiment, $R^1$ is piperidinyl optionally substituted by halogen, oxo, —CN, —$OR^a$, —$SR^a$, —$NR^aR^b$, $C_{1-3}$ alkylene or $C_{1-6}$ alkyl optionally substituted by oxo, —CN or halogen, with the proviso that $R^5$ is other than hydrogen or —OH.

In another embodiment, $R^1$ is tetrahydropyranyl optionally substituted by halogen, oxo, —CN, —$OR^a$, —$SR^a$, —$NR^aR^b$, $C_{1-3}$ alkylene or $C_{1-6}$ alkyl optionally substituted by oxo, —CN or halogen, with the proviso that $R^5$ is other than hydrogen or —OH. In another embodiment, $R^1$ is tetrahydropyranyl optionally substituted by halogen, oxo, —CN, —$OR^a$, —$SR^a$, —$NR^aR^b$, $C_{1-3}$ alkylene or $C_{1-6}$ alkyl optionally substituted by oxo, —CN or halogen, and $R^2$ and $R^3$ are both absent, with the proviso that $R^5$ is other than hydrogen or —OH.

In another embodiment, $R^1$ is (R)-pyrrolidin-3-yl. In another embodiment, $R^1$ is (S)-pyrrolidin-3-yl.

In one embodiment $R^1$ is a $C_{4-7}$ cycloalkyl, wherein $R^1$ is independently optionally substituted by halogen, oxo, —CN, —$OR^a$, —$SR^a$, —$NR^aR^b$, $C_{1-3}$ alkylene or $C_{1-6}$ alkyl optionally substituted by oxo, —CN or halogen. In one embodiment $R^1$ is a $C_{4-7}$ cycloalkyl optionally substituted by halogen, oxo, —CN, —$OR^a$, —$NR^aR^b$, $C_{1-3}$ alkylene or $C_{1-6}$ alkyl optionally substituted by halogen. In one embodiment $R^1$ is a $C_{4-7}$ cycloalkyl optionally substituted by halogen, oxo, $C_{1-3}$ alkylene or $C_{1-6}$ alkyl optionally substituted by halogen. In one embodiment, said cycloalkyl is cyclopropyl, cyclobutyl, cyclopentyl or cyclohexyl. In one embodiment, $R^1$ is selected from

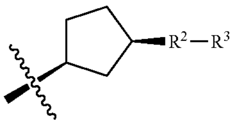
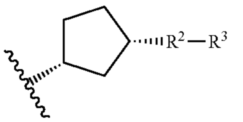
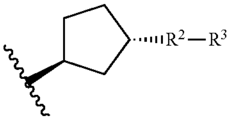
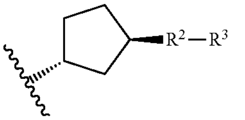
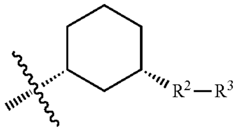
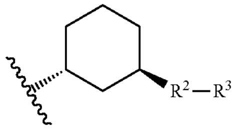
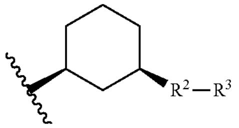
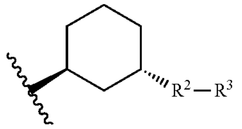

-continued

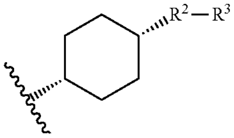
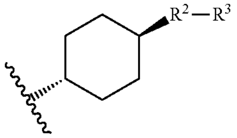
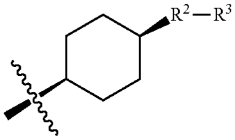
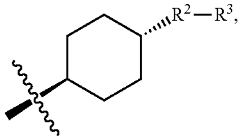

wherein the wavy line represents the point of attachment in formula I.

In another embodiment, $R^1$ is cyclohexyl optionally substituted by halogen, oxo, —CN, —$OR^a$, —$SR^a$, —$NR^aR^b$, $C_{1-3}$ alkylene or $C_{1-6}$ alkyl optionally substituted by oxo, —CN or halogen. In another embodiment, $R^1$ is cyclohexyl optionally substituted by halogen, oxo, —CN, —$OR^a$, —$NR^aR^b$, $C_{1-3}$ alkylene or $C_{1-6}$ alkyl optionally substituted by halogen. In another embodiment, $R^1$ is cyclohexyl optionally substituted by halogen, oxo, $C_{1-3}$ alkylene or $C_{1-6}$ alkyl optionally substituted by halogen. In another embodiment, $R^1$ is cyclohexyl. In one embodiment, $R^1$ is selected from cyclohexyl, 2-hydroxycyclohexyl, 3-hydroxycyclohexyl, 4-hydroxycyclohexyl, bicyclo[2.2.1]heptanyl, 2-methylcyclohexyl or 4,4-difluorocyclohexyl,

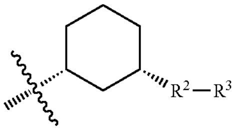
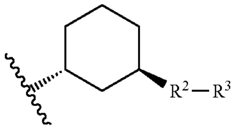
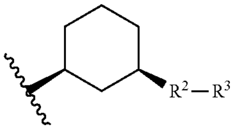
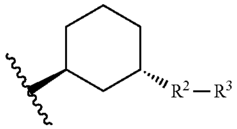
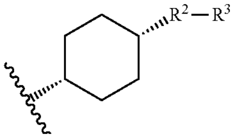
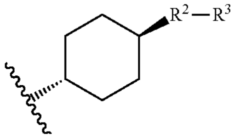
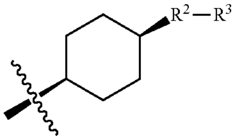
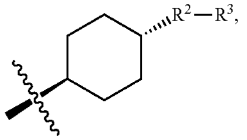

wherein $R^1$ is optionally substituted by halogen, oxo, —CN, —$OR^a$, —$NR^aR^b$, $C_{1-3}$ alkylene or $C_{1-6}$ alkyl optionally substituted by halogen, and wherein the wavy line represents the point of attachment in formula I.

In one embodiment, $R^1$ is selected from

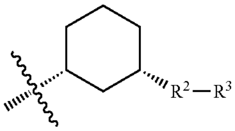
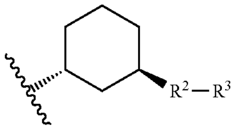

-continued

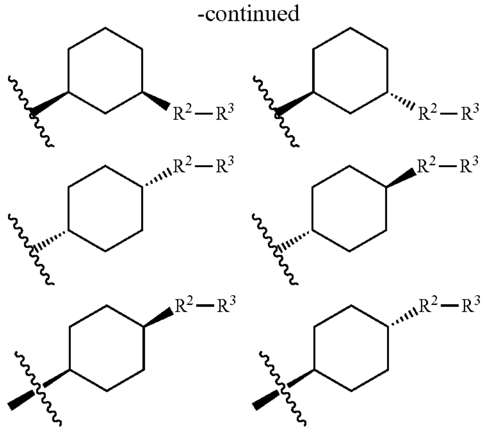

and $R^2$-$R^3$ is selected from

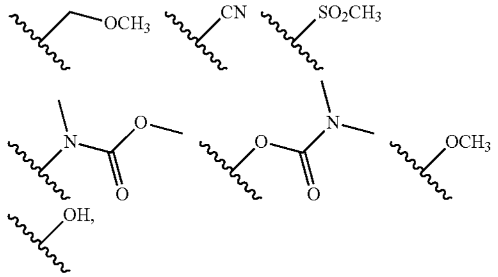

wherein the wavy line represents the point of attachment in formula I.

In one embodiment, $R^1$ is selected from

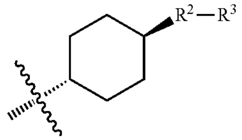

and

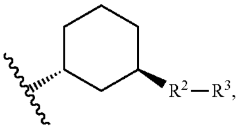

wherein the wavy line represents the point of attachment in formula I.

In certain embodiments, $R^2$ and $R^3$ are absent, and $R^1$ is selected from

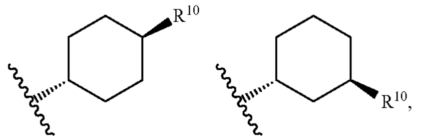

wherein $R^{10}$ is halogen, oxo, —CN, —$OR^a$, —$SR^a$, —$NR^aR^b$, $C_{1-3}$ alkylene or $C_{1-6}$ alkyl optionally substituted by oxo, —CN or halogen, and wherein the wavy line represents the point of attachment in formula I. In another embodiment of this paragraph, $R^5$ is other than hydrogen or —OH.

In certain embodiments, $R^2$ and $R^3$ are absent, and $R^1$ is selected from

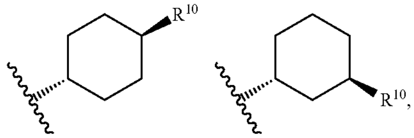

wherein $R^{10}$ is OH, —$NH(CH_2CF_3)$, —CN, —$CH_2CN$, —$CH_2CH_2CN$ or halogen, and wherein the wavy line represents the point of attachment in formula I. In another embodiment of this paragraph, $R^5$ is other than hydrogen or —OH.

In another embodiment, $R^1$ is cyclopentyl optionally substituted by halogen, oxo, —CN, —$OR^a$, —$SR^a$, —$NR^aR^b$, $C_{1-3}$ alkylene or $C_{1-6}$ alkyl optionally substituted by oxo, —CN or halogen. In another embodiment, $R^1$ is cyclopentyl optionally substituted by halogen, oxo, —CN, —OR %—$NR^aR^b$, $C_{1-3}$ alkylene or $C_{1-6}$ alkyl optionally substituted by halogen. In another embodiment, $R^1$ is cyclopentyl.

In another embodiment, $R^1$ is $C_{6-14}$ aryl optionally substituted by halogen, oxo, —CN, —$OR^a$, —$SR^a$, —$NR^aR^b$, $C_{1-3}$ alkylene or $C_{1-6}$ alkyl optionally substituted by oxo, —CN or halogen. In another embodiment, $R^1$ is phenyl optionally substituted by halogen, oxo, —CN, —$OR^a$, —$SR^a$, —$NR^aR^b$, $C_{1-3}$ alkylene or $C_{1-6}$ alkyl optionally substituted by oxo, —CN or halogen. In another embodiment, $R^1$ is phenyl optionally substituted by halogen, oxo, —CN, —$OR^a$, —$NR^aR^b$ or $C_{1-6}$ alkyl optionally substituted by halogen. In one embodiment, $R^1$ is 4-cyanophenyl.

In another embodiment, $R^1$ is selected from methyl, ethyl, propyl, butyl, phenyl, 4-cyanophenyl, cyclopropyl, cyclobutyl, cyclopentyl, cyclohexyl, 2-methylcyclohexyl, 2-hydroxycyclohexyl, 3-hydroxycyclohexyl, 4-hydroxycyclohexyl, bicyclo[2.2.1]heptanyl, pyrrolidinyl, piperidinyl, piperidinonyl, 2-methylpiperidin-4-yl, 3-methylpiperidin-4-yl, 4-methylpiperidin-4-yl, 2-fluoropiperidinyl, 3-fluoropiperidin-4-yl, 3,3-difluoropiperidin-4-yl, 3-methoxypiperidin-4-yl, 2,2-dimethyltetrahydropyranyl, tetrahydropyranyl, azepanyl, octahydro-1H-indol-2-onyl, 1-azaspiro[4.5]decan-2-only, 8-azabicyclo[3.2.1]octanyl, 4,5,6,7-tetrahydro-1H-indazoloyl, 1,1-dioxohexahydrothiopyranyl, (1R,5S)-8-azabicyclo[3.2.1]octane,

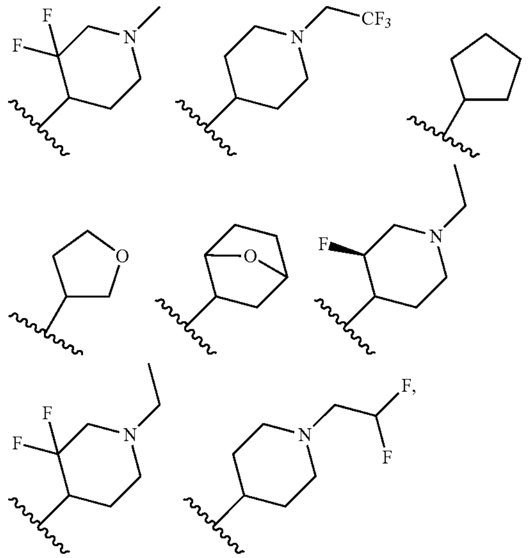

and wherein the wavy line represents the point of attachment in formula I.

In another embodiment, $R^1$ is selected from methyl, methylene, ethyl, propyl, butyl, phenyl, 4-cyanophenyl, cyclopropyl, cyclobutyl, cyclopentyl, cyclohexyl, 2-methylcyclohex-1-yl, 2-hydroxycyclohex-1-yl, 3-hydroxycyclohex-1-yl, 4-hydroxycyclohex-1-yl, bicyclo[2.2.1]heptanyl, pyrrolidinyl, piperidinyl, piperidinonyl, 2-methylpiperidin-4-yl, 3-methylpiperidin-4-yl, 4-methylpiperidin-4-yl, 2-fluoropiperidinyl, 3-fluoropiperidin-4-yl, 3,3-difluoropiperidin-4-yl, 3-methoxypiperidin-4-yl, 2,2-dimethyltetrahydropyranyl, tetrahydropyranyl, tetrahydropyran-2-yl, tetrahydropyran-3-yl, tetrahydropyran-4-yl, azepanyl, octahydro-1H-indol-2-onyl, 1-azaspiro[4.5]decan-2-only, 8-azabicyclo[3.2.1]octanyl, 4,5,6,7-tetrahydrobenzoimdazoloyl, 4,5,6,7-tetrahydro-1H-indazoloyl, 1,1-dioxohexahydrothiopyranyl, (1R,5S)-8-azabicyclo[3.2.1]octane,

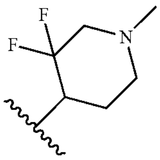
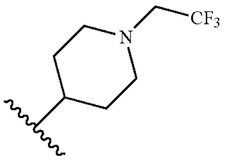
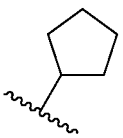
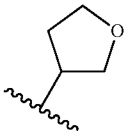
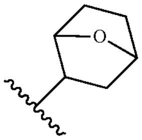
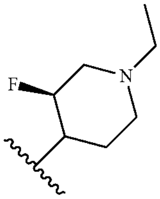
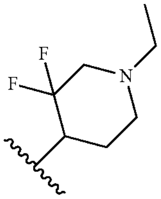
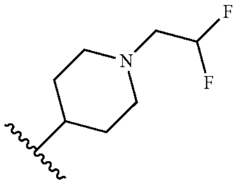
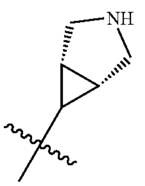
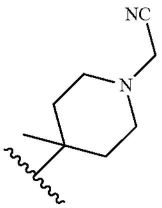
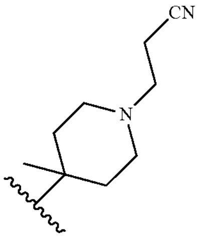
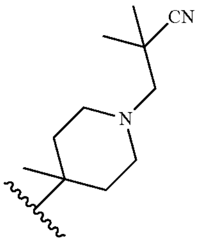
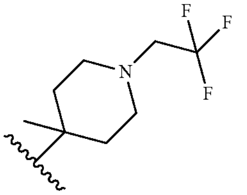
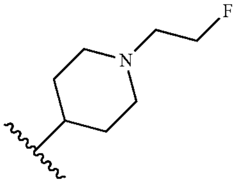
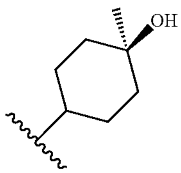

-continued

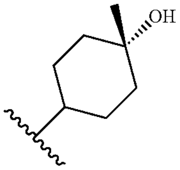
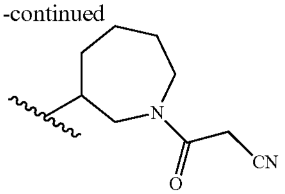
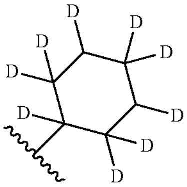
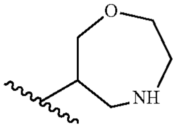
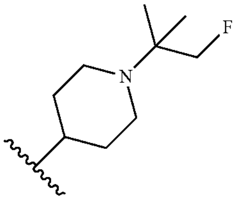
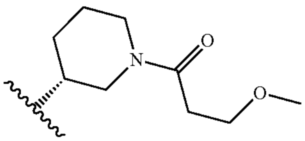
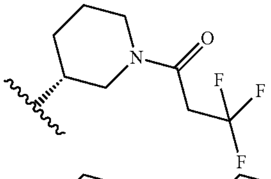
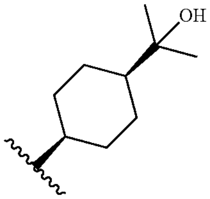
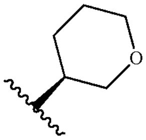
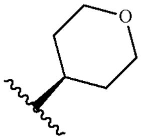
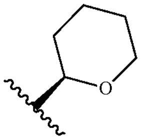
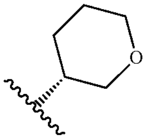
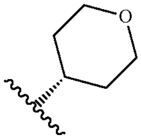
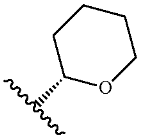
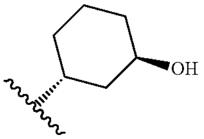
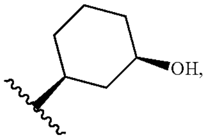

and wherein the wavy line represents the point of attachment in formula I.

In one embodiment, $R^2$ is absent. In one embodiment, $R^2$ is absent with the proviso that $R^1$, $R^2$ and $R^3$ are not all absent at the same time.

In one embodiment, $R^2$ and $R^3$ are absent. In one embodiment, $R^2$ and $R^3$ are absent with the proviso that $R^1$, $R^2$ and $R^3$ are not all absent at the same time.

In one embodiment, $R^2$ is $C_{1-6}$ alkyl, $C_{2-6}$ alkenyl, $C_{2-6}$ alkynyl, wherein said alkyl, alkenyl or alkynyl are independently optionally substituted by halogen, oxo, —CN, —$OR^c$, —$SR^c$, —$NR^cR^d$ or $C_{1-3}$ alkyl optionally substituted by halogen, and $R^3$ is absent. In one embodiment, $R^2$ is $C_{1-6}$ alkyl, $C_{2-6}$ alkenyl, $C_{2-6}$ alkynyl, wherein said alkyl, alkenyl or alkynyl are independently optionally substituted by halogen, oxo, —CN, —$OR^c$, —$NR^cR^d$ or $C_{1-3}$ alkyl optionally substituted by halogen, and $R^3$ is absent. In one embodiment, $R^2$ is selected from —$CH_2CF_3$, —$CH_2CH_2CF_3$, —$CH_2CH_2F$, —$C(CH_3)_2OH$, —$CH_2C(CH_3)_2OH$, —$CH_2CH_2OH$, —$CH_2CH_2OCH_3$ and

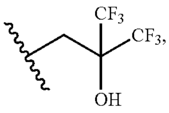 [SMILES: *CC(O)(C(F)(F)F)C(F)(F)F]

wherein the wavy line represents the point of attachment in formula I.

In one embodiment, $R^2$ is —($C_{1-6}$ alkylene)-, wherein said alkylene is optionally substituted by halogen, oxo, —CN, —$OR^c$, —$SR^c$, —$NR^cR^d$ or $C_{1-3}$ alkyl optionally substituted by halogen. In one embodiment, $R^2$ is —($C_{1-6}$ alkylene)-, wherein said alkylene is optionally substituted by halogen, oxo, —CN, —$OR^c$, —$NR^cR^d$ or $C_{1-3}$ alkyl optionally substituted by halogen. In one embodiment, $R^2$ is —($C_{1-6}$ alkylene)-, wherein said alkylene is optionally substituted by halogen, oxo, —CN or $C_{1-3}$ alkyl. In another embodiment, $R^2$ is methylene, ethylene, —$CH(CH_3)$—, —$C(CH_3)_2$—, propylene or butylene, optionally substituted by halogen, oxo, —CN, —$OR^c$, —$NR^cR^d$ or $C_{1-3}$ alkyl. In another embodiment, $R^2$ is selected from methylene, ethylene, —$C(CH_3)_2$— and

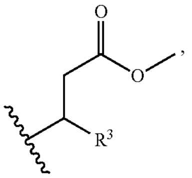

wherein the wavy line represents the point of attachment in formula I.

In one embodiment, $R^2$ is —($C_{0-6}$ alkylene)CN, wherein said alkylene is optionally substituted by halogen, oxo, —CN, —$OR^c$, —$SR^c$, —$NR^cR^d$ or $C_{1-3}$ alkyl optionally substituted by halogen, and $R^3$ is absent. In one embodiment, $R^2$ is —($C_{1-6}$ alkylene)CN, wherein said alkylene is optionally substituted by halogen, oxo, —CN, —$OR^c$, —$NR^cR^d$ or $C_{1-3}$ alkyl optionally substituted by halogen, and $R^3$ is absent. In another embodiment, $R^2$ is —$CH_2CN$, —$CH_2CH_2CN$, —$CH(CH_3)CN$ or —$CH(CH_3)CH_2CN$ and $R^3$ is absent.

In another embodiment, $R^1$ is a 3-20 membered heterocyclyl or $C_{3-12}$ cycloalkyl, wherein $R^1$ is independently optionally substituted by halogen, oxo, —CN, —$OR^a$, —$SR^a$, —$NR^aR^b$, $C_{1-3}$ alkylene or $C_{1-6}$ alkyl optionally substituted by oxo, —CN or halogen, $R^2$ is —CN, —$CH_2CN$, —$CH_2CH_2CN$, —$CH(CH_3)CN$ or —$CH(CH_3)CH_2CN$, and $R^3$ is absent, with the proviso that $R^5$ is other than hydrogen or —OH.

In one embodiment, $R^2$ is —($C_{0-3}$ alkylene)$NR^a$($C_{0-3}$ alkylene)-, wherein said alkylene is optionally substituted by halogen, oxo, —CN, —$OR^a$, —SR', —$NR^cR^d$ or $C_{1-3}$ alkyl optionally substituted by halogen. In one embodiment, $R^2$ is —($C_{0-3}$ alkylene)$NR^a$($C_{0-3}$ alkylene)-, wherein said alkylene is optionally substituted by halogen, oxo, —CN, —$OR^a$, —$NR^cR^d$ or $C_{1-3}$ alkyl optionally substituted by halogen. In one embodiment, $R^2$ is —($C_{0-3}$ alkylene)$NR^a$($C_{0-3}$ alkylene)-, wherein said alkylene is optionally substituted by halogen, oxo, —CN or $C_{1-3}$ alkyl. In another embodiment, $R^2$ is —NH—, —$NHCH_2$— or —$NHCH_2CH_2$—.

In one embodiment, $R^2$ is —($C_{0-3}$ alkylene)O($C_{0-3}$ alkylene)-, wherein said alkylene is optionally substituted by halogen, oxo, —CN, —$OR^c$, —$SR^c$, —$NR^cR^d$ or $C_{1-3}$ alkyl optionally substituted by halogen. In one embodiment, $R^2$ is —($C_{0-3}$ alkylene)O($C_{0-3}$ alkylene)-, wherein said alkylene is optionally substituted by halogen, oxo, —CN, —$OR^c$, —$NR^cR^d$ or $C_{1-3}$ alkyl optionally substituted by halogen. In one embodiment, $R^2$ is —($C_{0-3}$ alkylene)O($C_{0-3}$ alkylene)-, wherein said alkylene is optionally substituted by halogen, oxo, —CN or $C_{1-3}$ alkyl. In another embodiment, $R^2$ is —$CH_2O$—, —$CH_2C(CH_2)_2O$— or —$(CH_2)_2O$—.

In one embodiment, $R^2$ is —($C_{0-3}$ alkylene)$NR^aC(O)$($C_{0-3}$ alkylene)- or —($C_{0-3}$ alkylene)$C(O)NR^a$($C_{0-3}$ alkylene)-, wherein said alkylene is optionally substituted by halogen, oxo, —CN, —$OR^c$, —$SR^c$, —$NR^cR^d$ or $C_{1-3}$ alkyl optionally substituted by halogen. In one embodiment, $R^2$ is —($C_{0-3}$ alkylene)$NR^aC(O)$($C_{0-3}$ alkylene)- or —($C_{0-3}$ alkylene)$C(O)NR^a$($C_{0-3}$ alkylene)-, wherein said alkylene is optionally substituted by halogen, oxo, —CN, —$OR^c$, —$NR^cR^d$ or $C_{1-3}$ alkyl optionally substituted by halogen. In one embodiment, $R^2$ is —($C_{0-3}$ alkylene)$NR^aC(O)$($C_{0-3}$ alkylene)- or —($C_{0-3}$ alkylene)$C(O)NR^a$($C_{0-3}$ alkylene)-, wherein said alkylene is optionally substituted by halogen, oxo, —CN or $C_{1-3}$ alkyl. In another embodiment, $R^2$ is —C(O)NH—, —$CH_2C(O)NH$— or —$CH_2C(O)N(CH_3)$—. In another embodiment, $R^2$ is —NHC(O)— or —$NHC(O)CH_2$—.

In one embodiment $R^2$ is —($C_{0-3}$ alkylene)$OC(O)NR^a$($C_{0-3}$ alkylene)- or —($C_{0-3}$ alkylene)$NR^aC(O)O$($C_{0-3}$ alkylene)-, wherein said alkylene is optionally substituted by halogen, oxo, —CN, —$OR^c$, —$SR^c$, —$NR^cR^d$ or $C_{1-3}$ alkyl optionally substituted by halogen. In one embodiment $R^2$ is —($C_{0-3}$ alkylene)$OC(O)NR^a$($C_{0-3}$ alkylene)- or —($C_{0-3}$ alkylene)$NR^aC(O)O$($C_{0-3}$ alkylene)-, wherein said alkylene is optionally substituted by halogen, oxo, —CN, —$OR^c$, —$NR^cR^d$ or $C_{1-3}$ alkyl optionally substituted by halogen. In one embodiment $R^2$ is —($C_{0-3}$ alkylene)$OC(O)NR^a$($C_{0-3}$ alkylene)- or —($C_{0-3}$ alkylene)$NR^aC(O)O$($C_{0-3}$ alkylene)-, wherein said alkylene is optionally substituted by halogen, oxo, —CN or $C_{1-3}$ alkyl. In another embodiment, $R^2$ is —NHC(O)O—, —$N(CH_3)C(O)O$—, —$NHC(O)OCH_2$— or —$NHC(O)OCH_2CH_2$—.

In one embodiment $R^2$ is —($C_{0-3}$ alkylene)C(O)($C_{0-3}$ alkylene)-, wherein said alkylene is optionally substituted by halogen, oxo, —CN, —$OR^c$, —$SR^c$, —$NR^cR^d$ or $C_{1-3}$ alkyl optionally substituted by halogen. In one embodiment $R^2$ is —($C_{0-3}$ alkylene)C(O)($C_{0-3}$ alkylene)-, wherein said alkylene is optionally substituted by halogen, oxo, —CN, —$OR^c$, —$NR^cR^d$ or $C_{1-3}$ alkyl optionally substituted by halogen. In one embodiment $R^2$ is —($C_{0-3}$ alkylene)C(O)($C_{0-3}$ alkylene)-, wherein said alkylene is optionally substituted by halogen, oxo, —CN or $C_{1-3}$ alkyl. In another embodiment, $R^2$ is selected from:

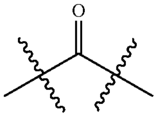
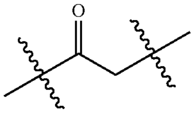
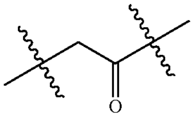
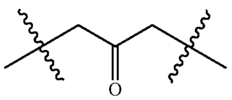

-continued

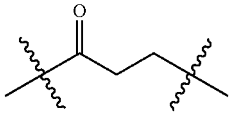

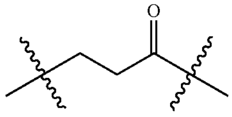

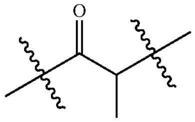

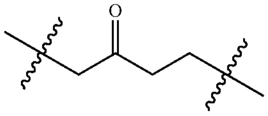

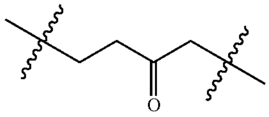

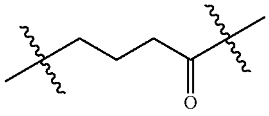

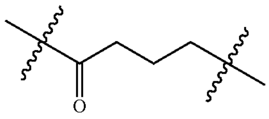

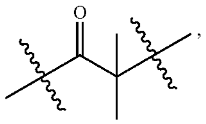, wherein the wavy lines represent points of attachment.

In one embodiment $R^2$ is —($C_{0-3}$ alkylene)C(O)O($C_{0-3}$ alkylene)- or —($C_{0-3}$ alkylene)OC(O)($C_{0-3}$ alkylene)-, wherein said alkylene is optionally substituted by halogen, oxo, —CN, —$OR^c$, —$SR^c$, —$NR^cR^d$ or $C_{1-3}$ alkyl optionally substituted by halogen. In one embodiment $R^2$ is —($C_{0-3}$ alkylene)C(O)O($C_{0-3}$ alkylene)- or —($C_{0-3}$ alkylene)OC(O)($C_{0-3}$ alkylene)-, wherein said alkylene is optionally substituted by halogen, oxo, —CN, —$OR^c$, —$NR^cR^d$ or $C_{1-3}$ alkyl optionally substituted by halogen. In one embodiment $R^2$ is —($C_{0-3}$ alkylene)C(O)O($C_{0-3}$ alkylene)- or —($C_{0-3}$ alkylene)OC(O)($C_{0-3}$ alkylene)-, wherein said alkylene is optionally substituted by halogen, oxo, —CN or $C_{1-3}$ alkyl. In another embodiment, $R^2$ is selected from —C(O)O—.

In one embodiment $R^2$ is —($C_{0-3}$ alkylene)$S(O)_{1-2}$($C_{0-3}$ alkylene)-, wherein said alkylene is optionally substituted by halogen, oxo, —CN, —$OR^c$, —$SR^c$, —$NR^cR^d$ or $C_{1-3}$ alkyl optionally substituted by halogen. In one embodiment $R^2$ is —($C_{0-3}$ alkylene)$S(O)_{1-2}$($C_{0-3}$ alkylene)-, wherein said alkylene is optionally substituted by halogen, oxo, —CN, —$OR^c$, —$NR^cR^d$ or $C_{1-3}$ alkyl optionally substituted by halogen. In one embodiment $R^2$ is —($C_{0-3}$ alkylene)$S(O)_{1-2}$($C_{0-3}$ alkylene)-, wherein said alkylene is optionally substituted by halogen, oxo, —CN or $C_{1-3}$ alkyl. In another embodiment, $R^2$ is selected from —$C(O)CH_2S(O)_2$,

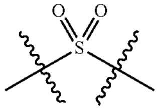

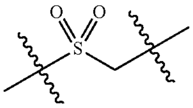

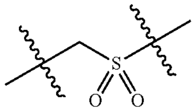

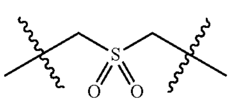

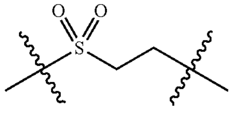

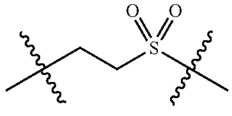

-continued

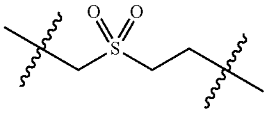

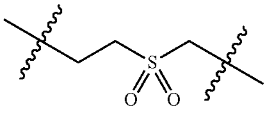

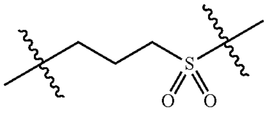

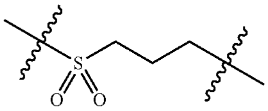, wherein the wavy lines represent points of attachment.

In one embodiment, $R^2$ is —($C_{0-3}$ alkylene)$NR^aS(O)_{1-2}$($C_{0-3}$ alkylene)- or —($C_{0-3}$-alkylene)$S(O)_{1-2}NR^a$($C_{0-3}$ alkylene)-, wherein said alkylene is optionally substituted by halogen, oxo, —CN, —$OR^c$, —$SR^c$, —$NR^cR^d$ or $C_{1-3}$ alkyl optionally substituted by halogen. In one embodiment, $R^2$ is —($C_{0-3}$ alkylene)$NR^aS(O)_{1-2}$($C_{0-3}$ alkylene)- or —($C_{0-3}$ alkylene)$S(O)_{1-2}NR^a$($C_{0-3}$ alkylene)-, wherein said alkylene is optionally substituted by halogen, oxo, —CN, —$OR^c$, —$NR^cR^d$ or $C_{1-3}$ alkyl optionally substituted by halogen. In one embodiment, $R^2$ is —($C_{0-3}$ alkylene)$NR^aS(O)_{1-2}$($C_{0-3}$ alkylene)- or —($C_{0-3}$ alkylene)$S(O)_{1-2}NR^a$($C_{0-3}$ alkylene)-, wherein said alkylene is optionally substituted by halogen, oxo, —CN or $C_{1-3}$ alkyl. In another embodiment, $R^2$ is —$NHS(O)_2$—, —$N(CH_3)S(O)_2$— or —$NHS(O)_2CH_2$—.

In one embodiment, $R^2$ is selected from absent, —$NHS(O)_2$—, —$N(CH_3)S(O)_2$—, —$NHS(O)_2CH_2$—, —$C(O)CH_2S(O)_2$, —C(O)O—, —NHC(O)O—, —$N(CH_3)C(O)O$—, —$NHC(O)OCH_2$—, —$NHC(O)OCH_2CH_2$—, —C(O)NH—, —$CH_2C(O)NH$—, —$CH_2C(O)N(CH_3)$—, —NHC(O)—, —$NHC(O)CH_2$—, —$CH_2O$—, —$CH_2C(CH_2)_2O$—, —$(CH_2)_2O$—, —NH—, —$NHCH_2$—, —$NHCH_2CH_2$—, —$CH_2CN$, —$CH_2CH_2CN$, —$CH(CH_3)CN$, —$CH(CH_3)CH_2CN$, methylene, ethylene, —$C(CH_3)_2$—, —$CH_2CF_3$, —$CH_2CH_2CF_3$, —$CH_2CH_2F$, —$CH_2C(CH_3)_2OH$, —$CH_2CH_2OH$, —$CH_2CH_2OCH_3$,

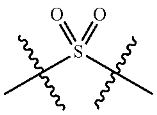

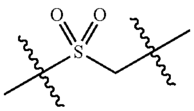

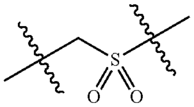

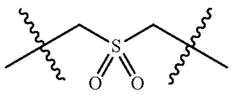

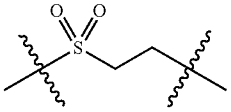

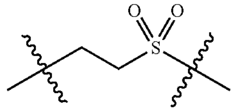

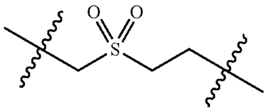

-continued

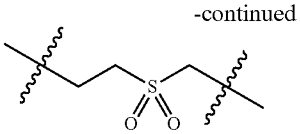

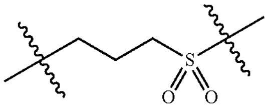

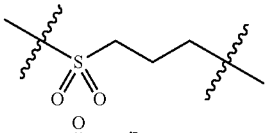

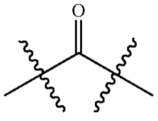

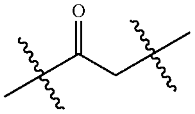

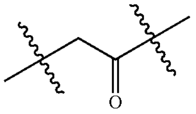

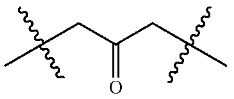

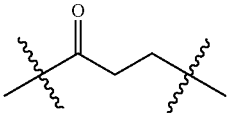

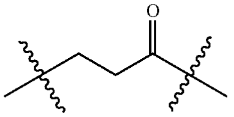

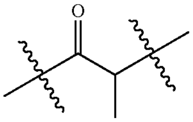

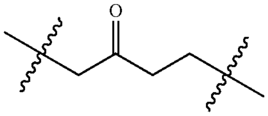

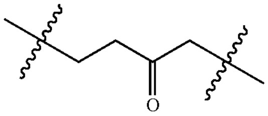

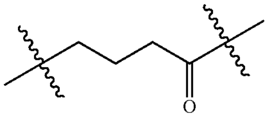

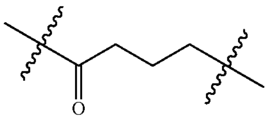

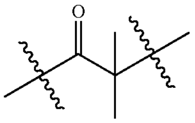

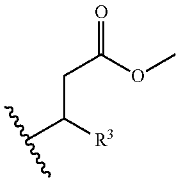

and

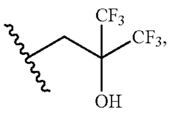

wherein the wavy line represents the point of attachment in formula I.

In one embodiment, $R^2$ is absent, methylene, ethylene, —$CH(CH_3)$—, —NH—, —$NHCH_2$—, —$(CH_2)_2O$—, —C(O)O—, —C(O)NH—, —NHC(O)O—, —$CH_2C(O)N(CH_3)$—, —$NHS(O)_2$—,

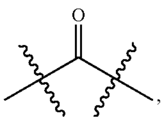

,

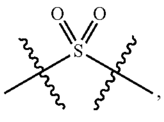

,

-continued

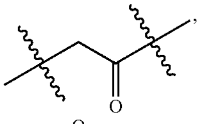

,

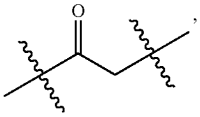

,

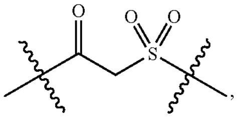

, or

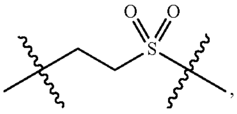

, wherein the wavy line represents the point of attachment in formula I.

In one embodiment, $R^2$ is absent, methylene, ethylene,

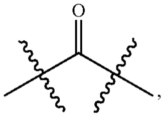

,

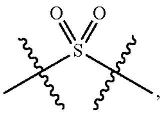

,

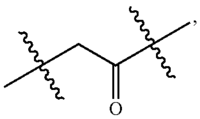

, or

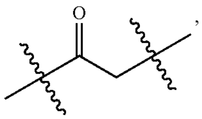

, wherein the wavy line represents the point of attachment in formula I.

In one embodiment, $R^3$ is absent.

In one embodiment, $R^3$ is hydrogen.

In one embodiment, —$R^2$-$R^3$ is —CHO.

In one embodiment, $R^2$ is absent and $R^3$ is hydrogen.

In one embodiment, $R^1$ and $R^2$ are absent.

In one embodiment, $R^3$ is $C_{1-6}$ alkyl optionally substituted by 1 to 3 $R^6$. In another embodiment, $R^3$ is $C_{1-6}$ alkyl optionally substituted by 1 to 3 oxo, $C_{1-6}$ alkyl, halogen, —CN, —$S(O)_{1-2}(C_{1-6}$ alkyl), —$OR^a$, —$SR^a$ or —$NR^aR^b$. In another embodiment, $R^3$ is $C_{1-6}$ alkyl optionally substituted by 1 to 3 oxo, $C_{1-6}$ alkyl, halogen, —CN, —$S(O)_2(C_{1-6}$ alkyl), —$OR^a$ or —$NR^aR^b$. In another embodiment, $R^3$ is methyl, ethyl, propyl, isopropyl, butyl, isobutyl or t-butyl optionally substituted by oxo, $C_{1-6}$ alkyl, halogen, —CN, —$S(O)_2(C_{1-6}$ alkyl), —$OR^a$ or —$NR^aR^b$. In another embodiment, $R^3$ is selected from methyl, ethyl, n-butyl, sec-butyl, t-butyl, —$CF_3$, —$CH_2CF_3$, —$CH_2CH_2F$, —$CH_2CH_2CF_3$, —$CH_2OCH_3$, —$CH_2CH_2OCH_3$, —$CH(CH_2CH_3)CH_2OCH_3$, —$CH(CH_3)CH_2CH_2OH$, —$CH_2C(CH_3)_2OH$, —$CH_2C(CF_3)_2OH$, —$CH_2CH_2OH$, —$C(CH_3)_2OH$, —$CH_2CN$, —$(CH_2)_2CN$, —$(CH_2)_3CN$, —$CH(CH_3)CH_2CN$, —$C(CH_3)_2CN$, —$CH(CH_3)CN$, —$CH_2NH_2$, —$CH(CH_3)N(CH_3)_2$ and —$CH_2CH_2N(CH_3)_2$.

In one embodiment, $R^3$ is $C_{3-7}$ cycloalkyl optionally substituted by 1 to 3 $R^6$. In one embodiment, $R^3$ is $C_{3-7}$ cycloalkyl optionally substituted by 1 to 3 oxo, halogen, —CN, —$S(O)_{1-2}(C_{1-6}$ alkyl), —$OR^a$, —$SR^a$, —$NR^aR^b$ or $C_{1-6}$ alkyl optionally substituted by oxo or halogen. In one embodiment, $R^3$ is $C_{3-7}$ cycloalkyl optionally substituted by 1 to 3 oxo, halogen, —CN, —$S(O)_2(C_{1-6}$ alkyl), —$OR^a$, —$NR^aR^b$ or $C_{1-6}$ alkyl optionally substituted by halogen. In another embodiment, $R^3$ is cyclopropyl optionally substituted by 1 to 3 oxo, halogen, —CN, —$S(O)_2(C_{1-6}$ alkyl), —$OR^a$, —$NR^aR^b$ or $C_{1-6}$ alkyl optionally substituted by halogen. In another embodiment, $R^3$ is selected from cyclopropyl, 1-cyanocycloprop-1-yl, 1-trifluoromethylcycloprop-1-yl, 1-methylcycloprop-1-yl, 2-fluorocyclopyrop-1-yl, 2,2-dimethylcycloprop-1-yl, 2-cyanocyclopropyl, cyclobutyl, 4-carboxyclobutyl, 1-cyanocyclobut- 1-yl, 4-aminocyclobutyl, cyclopentyl, 3-aminocyclohexyl, 4-aminocyclohexyl, 2-hydroxycyclohexyl, 3-hydroxycyclohexyl, 4-hydroxycyclohexyl and 2-hydroxycyclohexyl.

In one embodiment, $R^3$ is $C_{6-14}$ aryl optionally substituted by 1 to 3 $R^6$. In one embodiment, $R^3$ is $C_{6-14}$ aryl optionally substituted by 1 to 3 $C_{1-6}$ alkyl, $C_{2-6}$ alkenyl, $C_{2-6}$ alkynyl, halogen, —CN, —$S(O)_{1-2}(C_{1-6}$ alkyl), —$OR^a$, —$SR^a$ or —$NR^aR^b$. In one embodiment, $R^3$ is phenyl optionally substituted by 1 to 3 $R^6$. In one embodiment, $R^3$ is phenyl optionally substituted by 1 to 3 $C_{1-6}$ alkyl, $C_{2-6}$ alkenyl, $C_{2-6}$ alkynyl, halogen, —CN, —$S(O)_2(C_{1-6}$ alkyl), —$OR^a$ or —$NR^aR^b$. In another embodiment, $R^3$ is phenyl, 2-chloro-4-cyanophenyl, 2-cyanophenyl, 3-cyanophenyl, 4-cyanophenyl, 3-methylsulfonylphenyl, 3-fluorophenyl or 4-methoxyphenyl.

In one embodiment, $R^3$ is 5-6 membered heteroaryl optionally substituted by 1 to 3 $R^6$. In one embodiment, $R^3$ is 5-6 membered heteroaryl optionally substituted by 1 to 3 oxo, $C_{1-6}$ alkyl, $C_{2-6}$ alkenyl, $C_{2-6}$ alkynyl, halogen, —CN, —$S(O)_{1-2}(C_{1-6}$ alkyl), —$OR^a$, —$SR^a$ or —$NR^aR^b$. In one embodiment, $R^3$ is 5-6 membered heteroaryl optionally substituted by 1 to 3 oxo, $C_{1-6}$ alkyl, $C_{2-6}$ alkenyl, $C_{2-6}$ alkynyl, halogen, —CN, —$S(O)_2(C_{1-6}$ alkyl), —$OR^a$ or —$NR^aR^b$. In one embodiment, $R^3$ is pyridinyl, thiazolyl, pyrimidinyl, pyrazinyl, oxazolyl, pyrazolyl, imidazolyl, optionally substituted by 1 to 3 oxo, $C_{1-6}$ alkyl, $C_{2-6}$ alkenyl, $C_{2-6}$ alkynyl, halogen, —CN, —$S(O)_2(C_{1-6}$ alkyl), —$OR^a$ or —$NR^aR^b$. In one embodiment, $R^3$ is selected from pyridinyl, pyridin-3-yl, 6-cyanopyridinyl, 6-trifluoromethylpyridinyl, 2-cyanopyridin-4-yl, 4-cyanopyridin-2-yl, 5-cyanopyridin-2-yl, 3-fluoropyridin-5-yl, thiazol-5-yl, pyrimidin-2-yl, pyrimidin-4-yl, pyrimidin-5-yl, pyrazin-2-yl, oxazol-2-yl, oxazol-4-yl, 1-methylpyrazol-5-yl, 1-methylpyrazol-4-yl, 1-methylimidazol-2-yl

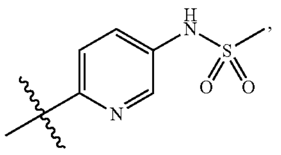
,
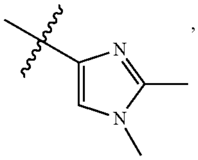
,
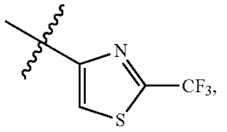
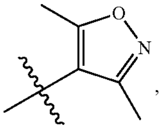
,
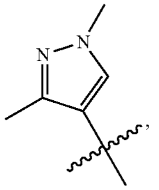
,
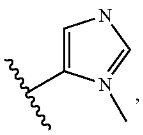
, wherein the wavy line represents the point of attachment in formula I. In one embodiment, $R^3$ is selected from thiazol-5-yl and isothiazol-5-yl.

In one embodiment, $R^3$ is 3-12 membered heterocyclyl optionally substituted by 1 to 3 $R^6$. In one embodiment, $R^3$ is 4-7 membered heterocyclyl optionally substituted by 1 to 3 $R^6$. In one embodiment, $R^3$ is 4-7 membered heterocyclyl optionally substituted by 1 to 3 oxo, $C_{1-6}$ alkyl, $C_{2-6}$ alkenyl, $C_{2-6}$ alkynyl, halogen, —CN, —$S(O)_{1-2}R^a$, —$C(O)OR^a$, —$OR^a$, —$SR^a$ or —$NR^aR^b$, wherein said alkyl, alkenyl and alkynyl are optionally substituted by oxo, halogen, —CN, —$OR^c$ or —$NR^cR^d$. In one embodiment, $R^3$ is 4-7 membered heterocyclyl optionally substituted by 1 to 3 oxo, $C_{1-6}$ alkyl, $C_{2-6}$ alkenyl, $C_{2-6}$ alkynyl, halogen, —CN, —$S(O)_2R^a$, —$C(O)OR^a$, —$OR^a$ or —$NR^aR^b$, wherein said alkyl, alkenyl and alkynyl are optionally substituted by oxo, halogen, —CN, —$OR^c$ or —$NR^cR^d$. In one embodiment, $R^3$ is oxetanyl, tetrahydrofuranyl, pyrrolidinyl, piperidinyl, piperazinyl, pyranyl, tetrahydropyranyl, morpholinyl optionally substituted by 1 to 3 oxo, $C_{1-6}$ alkyl, $C_{2-6}$ alkenyl, $C_{2-6}$ alkynyl, halogen, —CN, —$S(O)_2R^a$, —$C(O)OR^a$, —$OR^a$ or —$NR^aR^b$, wherein said alkyl, alkenyl and alkynyl are optionally substituted by oxo, halogen, —CN, —$OR^c$ or —$NR^cR^d$. In one embodiment, $R^3$ is selected from oxetan-3-yl, piperidin-3-yl, piperidin-4-yl, N-methylpiperidin-2-yl, N-methylmorpholin-2-yl, 1-methylpyrrolidin-2-yl, pyrrolidinyl, pyrrolidinonyl, piperidinonyl, 3,3-difluoropyrrolidin-2-yl, 1-isopropylpyrrolidin-2-yl, 2-methylpyrrolidin-2-yl, 1-methylcyanopyrrolidin-2-yl, 1-cyclobutylpyrrolidin-2-yl, morpholinyl, pyran-4-yl, N-methylpiperazinyl,

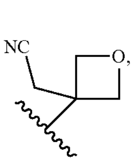
,
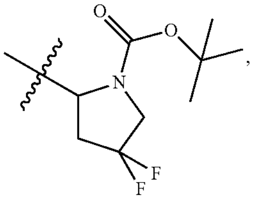
,
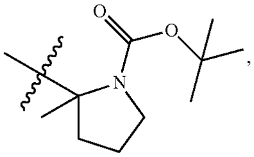
,
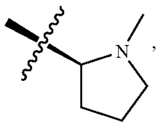
,
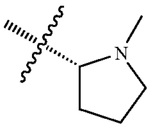
or
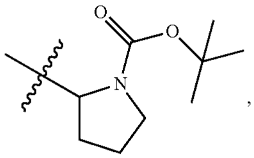
,
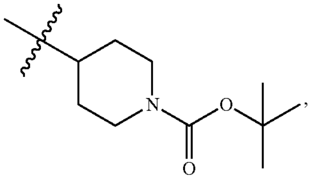
,
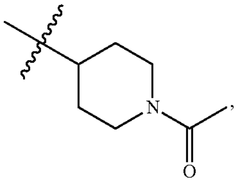
,
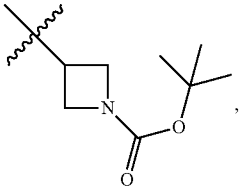
,
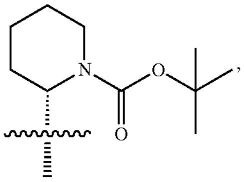
,
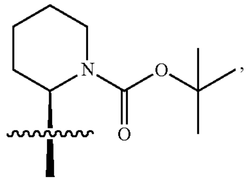
,
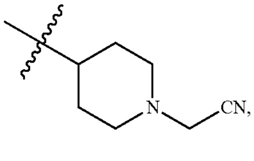
, wherein the wavy line represents the point of attachment in formula I. In one embodiment, $R^3$ is (S)-1-methylpyrrolidin-2-yl. In one embodiment, $R^3$ is selected from N-ethylpiperidin-2-yl, N-(2-methoxyethyl)piperidin-2-yl, N-methylazepan-2-yl,

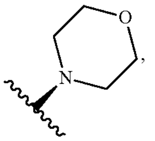

wherein the wavy line represents the point of attachment in formula I.

In one embodiment, $R^3$ is absent, hydrogen, methyl, ethyl, propyl, isopropyl, butyl, isobutyl, t-butyl, cyclopropyl, phenyl, pyridinyl, thiazolyl, pyrimidinyl, pyrazinyl, oxazolyl, pyrazolyl, imidazolyl, oxetanyl, pyrrolidinyl, piperidinyl, pyranyl or morpholinyl, optionally substituted by oxo, $C_{1-6}$ alkyl, halogen, —CN, —$S(O)_2(C_{1-6}$ alkyl), —$OR^a$ or —$NR^aR^b$.

In one embodiment, $R^3$ is absent, hydrogen, methyl, —$CF_3$, —$CH_2CN$, —$(CH_2)_2CN$, 1-cyanocycloprop-1-yl, cyclopropyl, phenyl, 3-cyanophenyl, 4-cyanophenyl, 3-methylsulfonylphenyl, 3-fluorophenyl, 6-cyanopyridinyl, 4-cyanopyridin-2-yl, pyridin-3-yl, pyrazin-2-yl, pyrimidin-5-yl, thiazol-5-yl or oxazol-4-yl.

In one embodiment, $R^3$ is selected from absent, hydrogen, methyl, ethyl, n-butyl, sec-butyl, t-butyl, —$CF_3$, —$CH_2CF_3$, —$CH_2CH_2F$, —$CH_2CH_2CF_3$, —$CH_2OCH_3$, —$CH_2CH_2OCH_3$, —$CH(CH_2CH_3)CH_2OCH_3$, —$CH(CH_3)CH_2CH_2OH$, —$CH_2C(CH_3)_2OH$, —$CH_2C(CF_3)_2OH$, —$CH_2CH_2OH$, —$C(CH_3)_2OH$, —$CH_2CN$, —$(CH_2)_2CN$, —$(CH_2)_3CN$, —$CH(CH_3)CH_2CN$, —$C(CH_3)_2CN$, —$CH(CH_3)CN$, —$CH_2NH_2$, —$CH(CH_3)N(CH_3)_2$, —$CH_2CH_2N(CH_3)_2$, cyclopropyl, 1-cyano cycloprop-1-yl, 1-trifluoromethylcycloprop-1-yl, 1-methylcycloprop-1-yl, 2-fluorocyclopyrop-1-yl, 2,2-dimethyl cycloprop-1-yl, 2-cyano cyclopropyl, cyclobutyl, 4-carboxyclobutyl, 1-cyanocyclobut-1-yl, 4-aminocyclobutyl, cyclopentyl, 3-aminocyclohexyl, 4-aminocyclohexyl, 2-hydroxycyclohexyl, 3-hydroxycyclohexyl, 4-hydroxycyclohexyl, 2-hydroxycyclohexyl, phenyl, 2-chloro-4-cyanophenyl, 2-cyanophenyl, 3-cyanophenyl, 4-cyanophenyl, 3-methylsulfonylphenyl, 3-fluorophenyl, 4-methoxyphenyl, pyridinyl, pyridin-3-yl, 6-cyanopyridinyl, 6-trifluoromethylpyridinyl, 2-cyanopyridin-4-yl, 4-cyanopyridin-2-yl, 5-cyanopyridin-2-yl, 3-fluoropyridin-5-yl, thiazol-5-yl, pyrimidin-2-yl, pyrimidin-4-yl, pyrimidin-5-yl, pyrazin-2-yl, oxazol-2-yl, oxazol-4-yl, 1-methylpyrazol-5-yl, 1-methylpyrazol-4-yl, 1-methylimidazol-2-yl

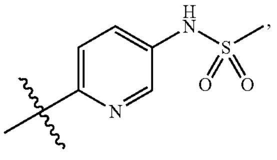

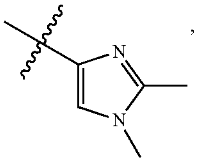

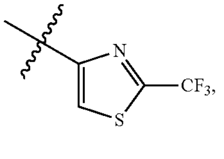

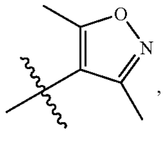

-continued

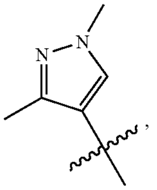

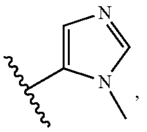

oxetan-3-yl, piperidin-3-yl, piperidin-4-yl, N-methylpiperidin-2-yl, N-methylmorpholin-2-yl, 1-methylpyrrolidin-2-yl, pyrrolidinyl, pyrrolidinonyl, piperidinonyl, 3,3-difluoropyrrolidin-2-yl, 1-isopropylpyrrolidin-2-yl, 2-methylpyrrolidin-2-yl, 1-methylcyanopyrrolidin-2-yl, 1-cyclobutylpyrrolidin-2-yl, morpholinyl, pyran-4-yl, N-methylpiperazinyl,

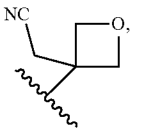

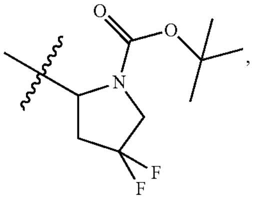

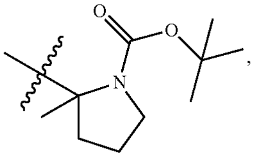

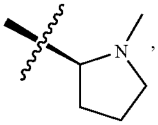

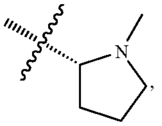

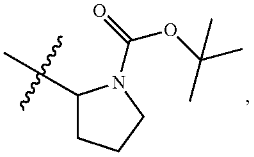

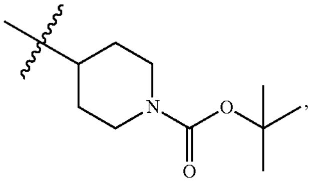

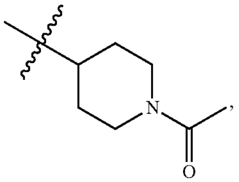

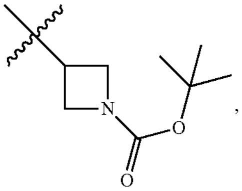

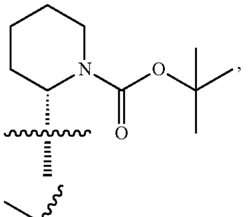

and

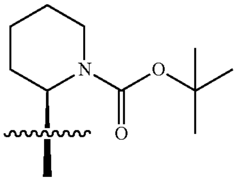

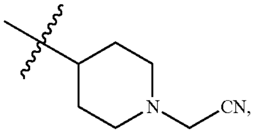

wherein the wavy line represents the point of attachment in formula I.

In one embodiment, $R^4$ is hydrogen, methyl or F. In another embodiment, $R^4$ is hydrogen. In certain embodiments, $R^4$ is hydrogen, methyl, chloro or bromo.

In one embodiment, $R^5$ is hydrogen.

In certain embodiments, $R^5$ is hydrogen, halogen, $C_{1-12}$ alkyl, $C_{2-12}$ alkenyl, $C_{2-12}$ alkynyl, —($C_{0-6}$ alkylene)CN, —($C_{0-3}$ alkylene)$NR^aR^b$, —($C_{0-3}$ alkylene)$OR^a$, —($C_{0-3}$ alkylene)$SR^a$, —($C_{0-3}$ alkylene)C(O)$R^a$, —($C_{0-3}$ alkylene) $NR^aC(O)R^b$, —($C_{0-3}$ alkylene)C(O)$NR^aR^b$, —($C_{0-3}$ alkylene)C(O)$OR^a$, —($C_{0-3}$ alkylene)OC(O)$R^a$, —($C_{0-3}$ alkylene) $NR^aC(O)NR^aR^b$, —($C_{0-3}$ alkylene)OC(O)$NR^aR^b$, —($C_{0-3}$ alkylene)$NR^aC(O)OR^b$, —($C_{0-3}$ alkylene)$S(O)_{1-2}R^a$, —($C_{0-3}$ alkylene)$NR^aS(O)_{1-2}R^b$, —($C_{0-3}$ alkylene)$S(O)_{1-2}$ $NR^aR^b$, —($C_{0-3}$ alkylene)$NR^aS(O)_{1-2}NR^aR^b$, —($C_{0-3}$ alkylene)$C_{3-6}$ cycloalkyl, —($C_{0-3}$ alkylene)$C_{6-14}$ aryl, —($C_{0-3}$ alkylene)$_{3-12}$ membered heterocyclyl or —($C_{0-3}$ alkylene)C(O)$_{3-12}$ membered heterocyclyl, wherein said alkyl, alkenyl, alkynyl, alkylene, cycloalkyl, aryl and heterocyclyl are independently optionally substituted by halogen, oxo, —($C_{0-3}$ alkylene)CN, —($C_{0-3}$ alkylene)$OR^c$, —($C_{0-3}$ alkylene)$NR^c$ $R^d$, —($C_{0-3}$ alkylene)C(O)$R^c$, —($C_{0-3}$ alkylene)C(O)$OR^c$, —($C_{0-3}$ alkylene)C(O)$NR^cR^d$, —($C_{0-3}$ alkylene)$NR^cC(O)$ $R^d$, —($C_{0-3}$ alkylene)OC(O)$NR^cR^d$, —($C_{0-3}$ alkylene)$NR^cC$ (O)$NR^cR^d$, —($C_{0-3}$ alkylene)$NR^cC(O)OR^d$, —($C_{0-3}$ alkylene)$S(O)_{0-2}R^c$, —($C_{0-3}$ alkylene)$NR^cS(O)_{1-2}R^d$, —($C_{0-3}$ alkylene)$S(O)_{1-2}NR^cR^d$, —($C_{0-3}$ alkylene)$NR^cS(O)_{1-2}NR^c$ $R^d$ or $C_{1-6}$ alkyl optionally substituted by oxo, —CN or halogen, with the proviso that $R^5$ is other than OH.

In certain embodiments, $R^5$ is halogen, $C_{1-12}$ alkyl, $C_{2-12}$ alkenyl, $C_{2-12}$ alkynyl, —($C_{0-6}$ alkylene)CN, —($C_{0-3}$ alkylene)$NR^aR^b$, —($C_{0-3}$ alkylene)$OR^a$, —($C_{0-3}$ alkylene)$SR^a$, —($C_{0-3}$ alkylene)C(O)$R^a$, —($C_{0-3}$ alkylene)$NR^aC(O)R^b$, —($C_{0-3}$ alkylene)C(O)$NR^aR^b$, —($C_{0-3}$ alkylene)C(O)$OR^a$, —($C_{0-3}$ alkylene)OC(O)$R^a$, —($C_{0-3}$ alkylene)$NR^aC(O)$ $NR^aR^b$, —($C_{0-3}$ alkylene)OC(O)$NR^aR^b$, —($C_{0-3}$ alkylene) $NR^aC(O)OR^b$, —($C_{0-3}$ alkylene) $S(O)_{1-2}R^a$, —($C_{0-3}$ alkylene)$NR^aS(O)_{1-2}R^b$, —($C_{0-3}$ alkylene)$S(O)_{1-2}NR^aR^b$, —($C_{0-3}$ alkylene)$NR^aS(O)_{1-2}NR^aR^b$, —($C_{0-3}$ alkylene)$C_{3-6}$ cycloalkyl, —($C_{0-3}$ alkylene)$C_{6-14}$ aryl, —($C_{0-3}$ alkylene)$_{3-12}$ membered heterocyclyl or —($C_{0-3}$ alkylene)C(O)$_{3-12}$ membered heterocyclyl, wherein said alkyl, alkenyl, alkynyl, alkylene, cycloalkyl, aryl and heterocyclyl are independently optionally substituted by halogen, oxo, —($C_{0-3}$ alkylene)CN, —($C_{0-3}$ alkylene)$OR^c$, —($C_{0-3}$ alkylene)$NR^cR^d$, —($C_{0-3}$ alkylene)C(O)$R^c$, —($C_{0-3}$ alkylene)C(O)$OR^c$, —($C_{0-3}$ alkylene)C(O)$NR^cR^d$, —($C_{0-3}$ alkylene)$NR^cC(O)R^d$, —($C_{0-3}$ alkylene)OC(O)$NR^cR^d$, —($C_{0-3}$ alkylene)$NR^cC(O)NR^cR^d$, —($C_{0-3}$ alkylene)$NR^cC(O)OR^d$, —($C_{0-3}$ alkylene)$S(O)_{0-2}R^c$, —($C_{0-3}$ alkylene)$NR^cS(O)_{1-2}R^d$, —($C_{0-3}$ alkylene)$S(O)_{1-2}$ $NR^cR^d$, —($C_{0-3}$ alkylene)$NR^cS(O)_{1-2}NR^cR^d$ or $C_{1-6}$ alkyl optionally substituted by oxo, —CN or halogen, with the proviso that $R^5$ is other than OH.

In one embodiment, $R^5$ is halogen. In one embodiment, $R^5$ is F.

In one embodiment, $R^5$ is $C_{1-12}$ alkyl, $C_{2-12}$ alkenyl, $C_{2-12}$ alkynyl, wherein said alkyl, alkenyl and alkynyl are independently optionally substituted by halogen, oxo, —($C_{0-3}$ alkylene)CN, —($C_{0-3}$ alkylene)$OR^c$, —($C_{0-3}$ alkylene)$NR^cR^d$, —($C_{0-3}$ alkylene)C(O)$R^c$, —($C_{0-3}$ alkylene)C(O)$OR^c$, —($C_{0-3}$ alkylene)C(O)$NR^cR^d$, —($C_{0-3}$ alkylene)$NR^cC(O)$ $R^d$, —($C_{0-3}$ alkylene)OC(O)$NR^cR^d$, —($C_{0-3}$ alkylene)$NR^cC$ (O)$NR^cR^d$, —($C_{0-3}$ alkylene)$NR^cC(O)OR^d$, —($C_{0-3}$ alkylene)$S(O)_{0-2}R^c$, —($C_{0-3}$ alkylene)$NR^cS(O)_{1-2}R^d$, —($C_{0-3}$ alkylene)$S(O)_{1-2}NR^cR^d$, —($C_{0-3}$ alkylene)$NR^cS(O)_{1-2}NR^c$ $R^d$ or $C_{1-6}$ alkyl optionally substituted by oxo, —CN or halogen. In one embodiment, $R^5$ is $C_{1-6}$ alkyl, $C_{2-6}$ alkenyl, $C_{2-6}$ alkynyl, wherein said alkyl, alkenyl and alkynyl are independently optionally substituted by halogen, oxo, —CN, —$OR^c$, —$NR^cR^d$, —C(O)$OR^c$, or $C_{1-6}$ alkyl optionally substituted by oxo, —CN or halogen. In one embodiment, $R^5$ is selected from methyl, ethyl, 1-hydroxyethyl, 2-hydroxyethyl, propyl, isopropyl, butyl, 2-methylbutyl, 3,3-difluorobut-1-yl, isobutyl, —$CH_2F$, —$CHF_2$, —$CF_3$, —$CH_2OH$, —$C(CH_3)_2OH$,

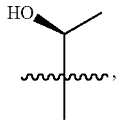,
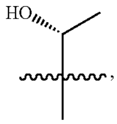, wherein the wavy line represents the point of attachment in formula I.

In one embodiment, $R^5$ is $C_{1-12}$ alkyl independently optionally substituted by halogen, oxo, —($C_{0-3}$ alkylene)CN, —($C_{0-3}$ alkylene)$OR^c$, —($C_{0-3}$ alkylene)$NR^cR^d$, —($C_{0-3}$ alkylene)C(O)$R^c$, —($C_{0-3}$ alkylene)C(O)$OR^c$, —($C_{0-3}$ alkylene)C(O)$NR^cR^d$, —($C_{0-3}$ alkylene)$NR^cC(O)R^d$, —($C_{0-3}$ alkylene)OC(O)$NR^cR^d$, —($C_{0-3}$ alkylene)$NR^cC(O)NR^cR^d$, —($C_{0-3}$ alkylene)$NR^cC(O)OR^d$, —($C_{0-3}$ alkylene)$S(O)_{0-2}R^c$, —($C_{0-3}$ alkylene)$NR^cS(O)_{1-2}R^d$, —($C_{0-3}$ alkylene)$S(O)_{1-2}$ $NR^cR^d$, —($C_{0-3}$ alkylene)$NR^cS(O)_{1-2}NR^cR^d$ or $C_{1-6}$ alkyl optionally substituted by oxo, —CN or halogen. In one embodiment, $R^5$ is $C_{1-6}$ alkyl optionally substituted by halogen, oxo, —CN, —$OR^a$ or —$NR^aR^b$. In another embodiment, $R^5$ is methyl, ethyl, propyl, isopropyl or 2-methylpropyl, optionally substituted by halogen, oxo, —CN, —$OR^a$ or —$NR^aR^b$, wherein $R^a$ and $R^b$ are independently hydrogen, $C_{1-6}$ alkyl, $C_{3-6}$ cycloalkyl, 4-6 membered heterocyclyl or taken together with the atom to which they are attached to form a pyrrolidinyl, piperidinyl, piperazinyl or morpholinyl group. In another embodiment, $R^5$ is methyl, hydroxymethyl, 1-hydroxyethyl, 2-hydroxyethyl, isopropyl or 2-methylpropyl.

In one embodiment, $R^5$ is —($C_{0-3}$ alkylene)CN, wherein said alkylene is independently optionally substituted by halogen, oxo, —($C_{0-3}$ alkylene)CN, —($C_{0-3}$ alkylene)$OR^c$, —($C_{0-3}$ alkylene)$NR^cR^d$, —($C_{0-3}$ alkylene)C(O)$R^c$, —($C_{0-3}$ alkylene)C(O)$OR^c$, —($C_{0-3}$ alkylene)C(O)$NR^cR^d$, —($C_{0-3}$ alkylene)$NR^cC(O)R^d$, —($C_{0-3}$ alkylene)OC(O)$NR^cR^d$, —($C_{0-3}$ alkylene)$NR^cC(O)NR^cR^d$, —($C_{0-3}$ alkylene)$NR^cC$ (O)$OR^d$, —($C_{0-3}$ alkylene)$S(O)_{0-2}R^c$, —($C_{0-3}$ alkylene)$NR^cS$ $(O)_{1-2}R^d$, —($C_{0-3}$ alkylene)$S(O)_{1-2}NR^cR^d$, —($C_{0-3}$ alkylene) $NR^cS(O)_{1-2}NR^cR^d$ or $C_{1-6}$ alkyl optionally substituted by oxo, —CN or halogen. In one embodiment, $R^5$ is —($C_{0-3}$ alkylene)CN, wherein said alkylene is optionally substituted by halogen, oxo, —CN, —$OR^c$, —$NR^cR^d$, —C(O)$OR^c$, or $C_{1-6}$ alkyl optionally substituted by oxo, —CN or halogen. In one embodiment, $R^5$ is —($C_{1-6}$ alkylene)CN, wherein said alkylene is optionally substituted by halogen, oxo, —CN, —$OR^c$, —$NR^cR^d$, —C(O)$OR^c$, or $C_{1-6}$ alkyl optionally substituted by oxo, —CN or halogen. In one embodiment, $R^5$ is selected from —CN, —$C(CH_3)_2CN$.

In one embodiment, $R^5$ is —CN.

In one embodiment, $R^5$ is —($C_{0-3}$ alkylene)$OR^a$ or —($C_{0-3}$ alkylene)$SR^a$, wherein said alkylene is independently optionally substituted by halogen, oxo, —($C_{0-3}$ alkylene)CN, —($C_{0-3}$ alkylene)$OR^c$, —($C_{0-3}$ alkylene)$NR^cR^d$, —($C_{0-3}$ alkylene)C(O)$R^c$, —($C_{0-3}$ alkylene)C(O)$OR^c$, —($C_{0-3}$ alkylene)C(O)$NR^cR^d$, —($C_{0-3}$ alkylene)$NR^cC(O)R^d$, —($C_{0-3}$ alkylene)OC(O)$NR^cR^d$, —($C_{0-3}$ alkylene)$NR^cC(O)NR^cR^d$, —($C_{0-3}$ alkylene)$NR^cC(O)OR^d$, —($C_{0-3}$ alkylene)$S(O)_{0-2}R^c$, —($C_{0-3}$ alkylene)$NR^cS(O)_{1-2}R^d$, —($C_{0-3}$ alkylene)$S(O)_{1-2}$ $NR^cR^d$, —($C_{0-3}$ alkylene)$NR^cS(O)_{1-2}NR^cR^d$ or $C_{1-6}$ alkyl optionally substituted by oxo, —CN or halogen. In one embodiment, $R^5$ is —($C_{0-3}$ alkylene)$OR^a$, wherein said alkylene is independently optionally substituted by halogen, oxo, —($C_{0-3}$ alkylene)CN, —($C_{0-3}$ alkylene)$OR^c$, —($C_{0-3}$ alkylene)$NR^cR^d$, —($C_{0-3}$ alkylene)C(O)$OR^c$, —($C_{0-3}$ alkylene)C(O)$NR^cR^d$, —($C_{0-3}$ alkylene)$NR^c$C(O)$R^d$, —($C_{0-3}$ alkylene)OC(O)$NR^cR^d$, —($C_{0-3}$ alkylene)$NR^c$C(O)$NR^cR^d$, —($C_{0-3}$ alkylene)$NR^c$C(O)$OR^d$, —($C_{0-3}$ alkylene)$S(O)_{0-2}R^c$, —($C_{0-3}$ alkylene)$NR^cS(O)_{1-2}R^d$, —($C_{0-3}$ alkylene)$S(O)_{1-2}NR^cR^d$, —($C_{0-3}$ alkylene)$NR^cS(O)_{1-2}NR^cR^d$ or $C_{1-6}$ alkyl optionally substituted by oxo, —CN or halogen. In one embodiment, $R^5$ is —($C_{0-3}$ alkylene)$OR^a$, wherein said alkylene is optionally substituted by halogen, oxo, —CN, —$OR^c$, —$NR^cR^d$, —C(O)$OR^c$, or $C_{1-6}$ alkyl optionally substituted by oxo, —CN or halogen. In one embodiment, $R^5$ is selected from —$CH_2OH$, —$CH_2CH_2OH$, —$C(CH_3)_2OH$, —$CH_2C(CH_3)_2OH$, —$CH_2OCH_2CH(CH_3)_2$, —$CH_2OCH_2C(CH_3)_3$,

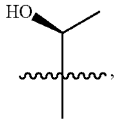, 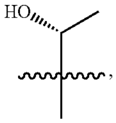, 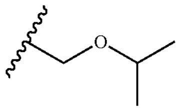

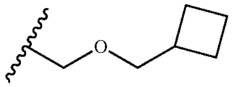 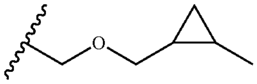

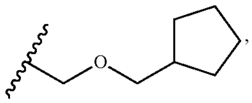, wherein the wavy line represents the point of attachment in formula I.

In one embodiment, $R^5$ is —($C_{0-3}$ alkylene)$NR^aR^b$, wherein said alkylene is independently optionally substituted by halogen, oxo, —($C_{0-3}$ alkylene)CN, —($C_{0-3}$ alkylene)$OR^c$, —($C_{0-3}$ alkylene)$NR^cR^d$, —($C_{0-3}$ alkylene)C(O)$R^c$, —($C_{0-3}$ alkylene)C(O)$OR^c$, —($C_{0-3}$ alkylene)C(O)$NR^cR^d$, —($C_{0-3}$ alkylene)$NR^c$C(O)$R^d$, —($C_{0-3}$ alkylene)OC(O)$NR^cR^d$, —($C_{0-3}$ alkylene)$NR^c$C(O)$NR^cR^d$, —($C_{0-3}$ alkylene)$NR^c$C(O)$OR^d$, —($C_{0-3}$ alkylene)$S(O)_{0-2}R^c$, —($C_{0-3}$ alkylene)$NR^cS(O)_{1-2}R^d$, —($C_{0-3}$ alkylene)$S(O)_{1-2}NR^cR^d$, —($C_{0-3}$ alkylene)$NR^cS(O)_{1-2}NR^cR^d$ or $C_{1-6}$ alkyl optionally substituted by oxo, —CN or halogen. In one embodiment, $R^5$ is —($C_{0-3}$ alkylene)$NR^aR^b$, wherein said alkylene is optionally substituted by halogen, oxo, —CN, —$OR^c$, —$NR^cR^d$, —C(O)$OR^c$, or $C_{1-6}$ alkyl optionally substituted by oxo, —CN or halogen. In one embodiment, $R^5$ is selected from —$NHCH_2CH_2OH$, —$CF_2CH_2NH_2$, —$CH_2C(O)NH_2$,

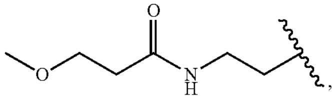,

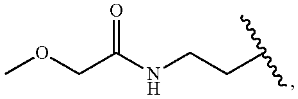, 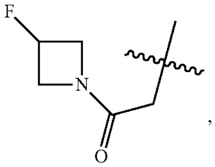,

-continued

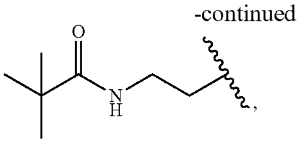,

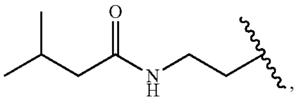, wherein the wavy line represents the point of attachment in formula I.

In one embodiment, $R^5$ is —($C_{0-3}$ alkylene)$C_{3-12}$ cycloalkyl, wherein said alkylene and cycloalkyl are independently optionally substituted by halogen, oxo, —($C_{0-3}$ alkylene)CN, —($C_{0-3}$ alkylene)$OR^c$, —($C_{0-3}$ alkylene)$NR^cR^d$, —($C_{0-3}$ alkylene)C(O)$R^c$, —($C_{0-3}$ alkylene)C(O)$OR^c$, —($C_{0-3}$ alkylene)C(O)$NR^cR^d$, —($C_{0-3}$ alkylene)$NR^c$C(O)$R^d$, —($C_{0-3}$ alkylene)OC(O)$NR^cR^d$, —($C_{0-3}$ alkylene)$NR^c$C(O)$NR^cR^d$, —($C_{0-3}$ alkylene)$NR^c$C(O)$OR^d$, —($C_{0-3}$ alkylene)$S(O)_{0-2}R^c$, —($C_{0-3}$ alkylene)$NR^cS(O)_{1-2}R^d$, —($C_{0-3}$ alkylene)$S(O)_{1-2}NR^cR^d$, —($C_{0-3}$ alkylene)$NR^cS(O)_{1-2}NR^cR^d$ or $C_{1-6}$ alkyl optionally substituted by oxo, —CN or halogen. In one embodiment, $R^5$ is —($C_{0-3}$ alkylene)$C_{3-6}$ cycloalkyl, wherein said alkylene and cycloalkyl are independently optionally substituted by halogen, oxo, —CN, —$OR^c$, —$NR^cR^d$, —C(O)$OR^c$, or $C_{1-6}$ alkyl optionally substituted by oxo, —CN or halogen. In one embodiment, $R^5$ is selected from —$CH_2$cyclopentyl, —$CH_2$cyclopropyl, —$CH_2CH_2$cyclopropyl, cyclopropyl, 2,2-difluorocyclopropyl and cyclobutyl.

In one embodiment, $R^5$ is —($C_{0-3}$ alkylene)$C_{3-7}$ cycloalkyl. In another embodiment, $R^5$ is cyclopropyl or cyclobutyl.

In one embodiment, $R^5$ is —($C_{0-3}$ alkylene)C(O)$NR^aR^b$, wherein said alkylene is independently optionally substituted by halogen, oxo, —($C_{0-3}$ alkylene)CN, —($C_{0-3}$ alkylene)$OR^c$, —($C_{0-3}$ alkylene)$NR^cR^d$, —($C_{0-3}$ alkylene)C(O)$R^c$, —($C_{0-3}$ alkylene)C(O)$OR^c$, —($C_{0-3}$ alkylene)C(O)$NR^cR^d$, —($C_{0-3}$ alkylene)$NR^c$C(O)$R^d$, —($C_{0-3}$ alkylene)OC(O)$NR^cR^d$, —($C_{0-3}$ alkylene)$NR^c$C(O)$NR^cR^d$, —($C_{0-3}$ alkylene)$NR^c$C(O)$OR^d$, —($C_{0-3}$ alkylene)$S(O)_{0-2}R^c$, —($C_{0-3}$ alkylene)$NR^cS(O)_{1-2}R^d$, —($C_{0-3}$ alkylene)$S(O)_{1-2}NR^cR^d$, —($C_{0-3}$ alkylene)$NR^cS(O)_{1-2}NR^cR^d$ or $C_{1-6}$ alkyl optionally substituted by oxo, —CN or halogen. In one embodiment, $R^5$ is —($C_{0-3}$ alkylene)C(O)$NR^aR^b$, wherein said alkylene is optionally substituted by halogen, oxo, —CN, —$OR^c$, —$NR^cR^d$, —C(O)$OR^c$, or $C_{1-6}$ alkyl optionally substituted by oxo, —CN or halogen. In one embodiment, $R^5$ is selected from —$CH_2C(O)NH_2$, —$CH_2C(O)NH$cyclopentyl, —$CH_2C(O)N(CH_3)$(cyclopentyl), —$CH_2C(O)NHCH_3$, —$CH(CH_3)C(O)NHCH(CH_3)_2$, —$CH_2C(O)$(pyrrolidin-1-yl), —$CH_2C(O)$(4,4-difluorpiperidin-1-yl), —$CH_2C(O)$(morpholinyl) and

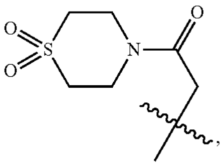 [SMILES: *CC(=O)N1CCS(=O)(=O)CC1], wherein the wavy line represents the point of attachment in formula I.

In one embodiment, $R^5$ is —($C_{0-3}$ alkylene)C(O)$NR^aR^b$, wherein said alkylene is independently optionally substituted by halogen, oxo, —($C_{0-3}$ alkylene)CN, —($C_{0-3}$ alkylene)$OR^c$, —($C_{0-3}$ alkylene)$NR^cR^d$, —($C_{0-3}$ alkylene)C(O)$R^c$, —($C_{0-3}$ alkylene)C(O)$OR^c$, —($C_{0-3}$ alkylene)C(O)$NR^cR^d$, —($C_{0-3}$ alkylene)$NR^c$C(O)$R^d$, —($C_{0-3}$ alkylene)OC(O)$NR^cR^d$, —($C_{0-3}$ alkylene)$NR^c$C(O)$NR^cR^d$, —($C_{0-3}$ alkylene)N$R^c$C(O)$OR^d$, —($C_{0-3}$ alkylene)$S(O)_{0-2}R^c$, —($C_{0-3}$ alkylene)$NR^cS(O)_{1-2}R^d$, —($C_{0-3}$ alkylene)$S(O)_{1-2}NR^cR^d$, —($C_{0-3}$ alkylene)$NR^cS(O)_{1-2}NR^cR^d$ or $C_{1-6}$ alkyl optionally substituted by oxo, —CN or halogen. In one embodiment, $R^5$ is —($C_{0-3}$ alkylene)C(O)$NR^aR^b$, wherein said alkylene is optionally substituted by oxo or halogen; and $R^a$ and $R^b$ are independently hydrogen, $C_{1-6}$ alkyl, $C_{3-6}$ cycloalkyl, 4-6 membered heterocyclyl, wherein said alkyl, cycloalkyl and heterocyclyl are independently optionally substituted by halogen, oxo, —CN, —$OR^e$ or —$NR^eR^f$, or taken together with the atom to which they are attached to form a 3-6 membered heterocyclyl optionally substituted by oxo, halogen, —C(O)$C_{1-6}$ alkyl or $C_{1-6}$ alkyl. In another embodiment, $R^5$ is —$CH_2C(O)NR^aR^b$, —$CH_2C(O)NHR^a$, and $R^a$ and $R^b$ are independently hydrogen, $C_{1-6}$ alkyl, $C_{3-6}$ cycloalkyl, 4-6 membered heterocyclyl, wherein said alkyl, cycloalkyl and heterocyclyl are independently optionally substituted by halogen, oxo, —CN, —$OR^e$ or $NR^eR^f$, or taken together with the atom to which they are attached to form a 3-6 membered heterocyclyl optionally substituted by oxo, halogen, —C(O)$C_{1-6}$ alkyl or $C_{1-6}$ alkyl. In another embodiment, $R^5$ is —$CH_2C(O)NHCH_3$, —$CH_2C(O)N(CH_3)$(cyclopentyl), —$CH_2C(O)$NH(cyclopentyl), —$CH_2C(O)$NH(isopropyl), —$CH_2C(O)$(pyrrolidin-1-yl), —$CH_2C(O)$(4,4-difluorpiperidin-1-yl), —$CH_2C(O)$(morpholinyl) or

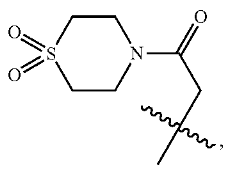 [SMILES: *CC(=O)N1CCS(=O)(=O)CC1]

wherein the wavy line represents the point of attachment in formula I.

In one embodiment, $R^5$ is —($C_{0-3}$ alkylene)$NR^a$C(O)$R^b$, wherein said alkylene is independently optionally substituted by halogen, oxo, —($C_{0-3}$ alkylene)CN, —($C_{0-3}$ alkylene)$OR^c$, —($C_{0-3}$ alkylene)$NR^cR^d$, —($C_{0-3}$ alkylene)C(O)$R^c$, —($C_{0-3}$ alkylene)C(O)$OR^c$, —($C_{0-3}$ alkylene)C(O)$NR^cR^d$, —($C_{0-3}$ alkylene)$NR^c$C(O)$R^d$, —($C_{0-3}$ alkylene)OC(O)$NR^cR^d$, —($C_{0-3}$ alkylene)$NR^c$C(O)$NR^cR^d$, —($C_{0-3}$ alkylene)N$R^c$C(O)$OR^d$, —($C_{0-3}$ alkylene)$S(O)_{0-2}R^c$, —($C_{0-3}$ alkylene)$NR^cS(O)_{1-2}R^d$, —($C_{0-3}$ alkylene)$S(O)_{1-2}NR^cR^d$, —($C_{0-3}$ alkylene)$NR^cS(O)_{1-2}NR^cR^d$ or $C_{1-6}$ alkyl optionally substituted by oxo, —CN or halogen. In one embodiment, $R^5$ is —($C_{0-3}$ alkylene)$NR^a$C(O)$R^b$, wherein said alkylene is optionally substituted by halogen, oxo, —CN, —$OR^c$, —$NR^cR^d$, —C(O)$OR^c$, or $C_{1-6}$ alkyl optionally substituted by oxo, —CN or halogen. In one embodiment, $R^5$ is selected from —$CH_2NHC(O)CH_3$, —$CH_2NHC(O)CH(CH_3)_2$, —$CH_2NHC(O)CH_2CH_3$, —$CH_2NHC(O)CH_2OCH_3$, —$CH_2NHC(O)$pyridin-3-yl, —$CH_2NHC(O)$pyridin-4-yl,

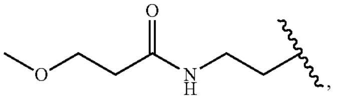

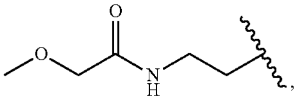

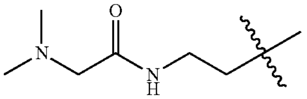

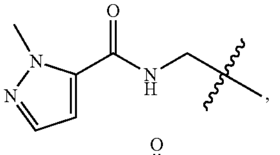

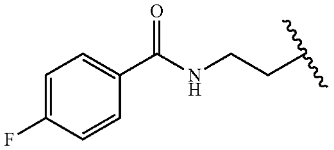

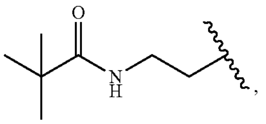

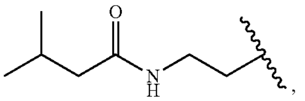

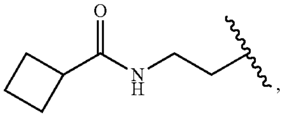

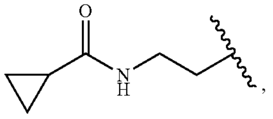

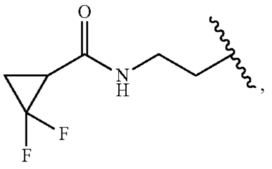

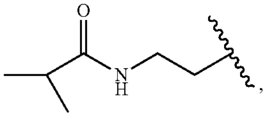

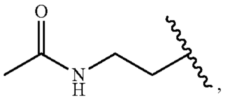

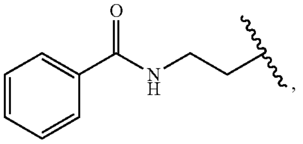

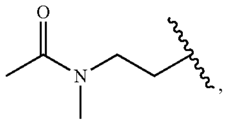

wherein the wavy line represents the point of attachment in formula I.

In one embodiment, $R^5$ is —($C_{0-3}$ alkylene)$NR^aS(O)_{1-2}R^b$, wherein said alkylene is independently optionally substituted by halogen, oxo, —($C_{0-3}$ alkylene)CN, —($C_{0-3}$ alkylene)$OR^c$, —($C_{0-3}$ alkylene)$NR^cR^d$, —($C_{0-3}$ alkylene)C(O)$R^c$, —($C_{0-3}$ alkylene)C(O)$OR^c$, —($C_{0-3}$ alkylene)C(O)$NR^cR^d$, —($C_{0-3}$ alkylene)$NR^c$C(O)$R^d$, —($C_{0-3}$ alkylene)OC(O)$NR^cR^d$, —($C_{0-3}$ alkylene)$NR^c$C(O)$NR^cR^d$, —($C_{0-3}$ alkylene)N$R^c$C(O)$OR^d$, —($C_{0-3}$ alkylene)$S(O)_{0-2}R^c$, —($C_{0-3}$ alkylene)$NR^cS(O)_{1-2}R^d$, —($C_{0-3}$ alkylene)$S(O)_{1-2}NR^cR^d$, —($C_{0-3}$ alkylene)$NR^cS(O)_{1-2}NR^cR^d$ or $C_{1-6}$ alkyl optionally substituted by oxo, —CN or halogen. In one embodiment, $R^5$ is —($C_{0-3}$ alkylene)$NR^aS(O)_{1-2}R^b$, wherein said alkylene is optionally substituted by halogen, oxo, —CN, —$OR^c$, —$NR^cR^d$, —$C(O)OR^c$, or $C_{1-6}$ alkyl optionally substituted by oxo, —CN or halogen. In one embodiment, $R^5$ is selected from —$CH_2NHS(O)_2CH_3$, —$CH_2NHS(O)_2CH_2CH_3$, —$CH_2NHS(O)_2CH_2CH(CH_3)_2$, —$CH_2NHS(O)_2CH(CH_3)_2$, —$CH_2NHS(O)_2CH(CH_3)CH_2CH_3$, —$CH_2NHS(O)_2$cyclopropyl, —$CH_2NHS(O)_2$cyclopentyl, —$CH_2N(CH_3)_2S(O)_2CH_3$, —$CH_2CH_2NHS(O)_2CH_3$, —$CH_2CH_2NHS(O)_2CH_2CH_3$,

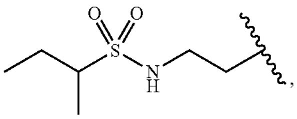,

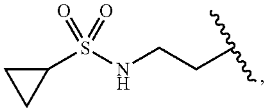,

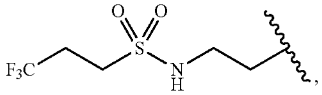,

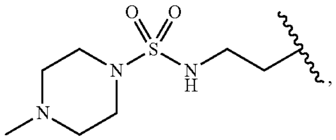, wherein the wavy line represents the point of attachment in formula I.

In one embodiment, $R^5$ is —($C_{0-3}$ alkylene)$_{5-12}$ membered heteroaryl, wherein said alkylene and heteroaryl are independently optionally substituted by halogen, oxo, —($C_{0-3}$ alkylene)CN, —($C_{0-3}$ alkylene)$OR^c$, —($C_{0-3}$ alkylene)$NR^cR^d$, —($C_{0-3}$ alkylene)$C(O)R^c$, —($C_{0-3}$ alkylene)$C(O)OR^c$, —($C_{0-3}$ alkylene)$C(O)NR^cR^d$, —($C_{0-3}$ alkylene)$NR^cC(O)R^d$, —($C_{0-3}$ alkylene)$OC(O)NR^cR^d$, —($C_{0-3}$ alkylene)$NR^cC(O)NR^cR^d$, —($C_{0-3}$ alkylene)$NR^cC(O)OR^d$, —($C_{0-3}$ alkylene)$S(O)_{0-2}R^c$, —($C_{0-3}$ alkylene)$NR^cS(O)_{1-2}R^d$, —($C_{0-3}$ alkylene)$S(O)_{1-2}NR^cR^d$, —($C_{0-3}$ alkylene)$NR^cS(O)_{1-2}NR^cR^d$ or $C_{1-6}$ alkyl optionally substituted by oxo, —CN or halogen. In one embodiment, $R^5$ is —($C_{0-3}$ alkylene)$_{5-6}$ membered heteroaryl, wherein said alkylene and heteroaryl are independently optionally substituted by halogen, oxo, —CN, —$OR^c$, —$NR^cR^d$, —$C(O)OR^c$, or $C_{1-6}$ alkyl optionally substituted by oxo, —CN or halogen. In one embodiment, $R^5$ is selected from —$CH_2CH_2$-triazolyl, triazolyl, pyridinyl, —$CH_2$pyrazolyl, —$CH_2$pyridinyl,

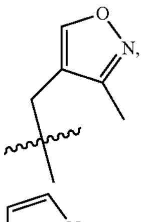,

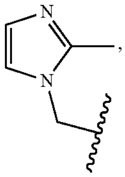,

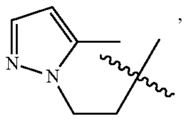,

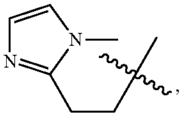,

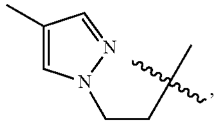,

-continued

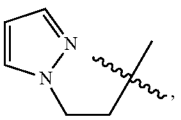,

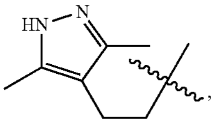,

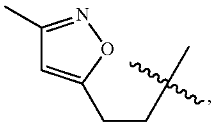, wherein the wavy line represents the point of attachment in formula I.

In one embodiment, $R^5$ is —($C_{0-3}$ alkylene)$_{4-6}$ membered heteroaryl, wherein said alkylene is independently optionally substituted by halogen, oxo, —($C_{0-3}$ alkylene)CN, —($C_{0-3}$ alkylene)$OR^c$, —($C_{0-3}$ alkylene)$NR^cR^d$, —($C_{0-3}$ alkylene)$C(O)R^c$, —($C_{0-3}$ alkylene)$C(O)OR^c$, —($C_{0-3}$ alkylene)$C(O)NR^cR^d$, —($C_{0-3}$ alkylene)$NR^cC(O)R^d$, —($C_{0-3}$ alkylene)$OC(O)NR^cR^d$, —($C_{0-3}$ alkylene)$NR^cC(O)NR^cR^d$, —($C_{0-3}$ alkylene)$NR^cC(O)OR^d$, —($C_{0-3}$ alkylene)$S(O)_{0-2}R^c$, —($C_{0-3}$ alkylene)$NR^cS(O)_{1-2}R^d$, —($C_{0-3}$ alkylene)$S(O)_{1-2}NR^cR^d$, —($C_{0-3}$ alkylene)$NR^cS(O)_{1-2}NR^cR^d$ or $C_{1-6}$ alkyl optionally substituted by oxo, —CN or halogen. In one embodiment, $R^5$ is —($C_{0-3}$ alkylene)$_{4-6}$ membered heteroaryl, wherein said alkylene is optionally substituted by oxo or halogen, and said heteroaryl is optionally substituted by oxo, halogen, $C_{1-3}$ alkyl, —$OR^c$ or —$NR^cR^d$. In one embodiment, $R^5$ is pyridinyl.

In one embodiment, $R^5$ is —($C_{0-3}$ alkylene)$_{3-12}$ membered heterocyclyl, wherein said alkylene and heterocyclyl are independently optionally substituted by halogen, oxo, —($C_{0-3}$ alkylene)CN, —($C_{0-3}$ alkylene)$OR^c$, —($C_{0-3}$ alkylene)$NR^cR^d$, —($C_{0-3}$ alkylene)$C(O)R^c$, —($C_{0-3}$ alkylene)$C(O)OR^c$, —($C_{0-3}$ alkylene)$C(O)NR^cR^d$, —($C_{0-3}$ alkylene)$NR^cC(O)R^d$, —($C_{0-3}$ alkylene)$OC(O)NR^cR^d$, —($C_{0-3}$ alkylene)$NR^cC(O)NR^cR^d$, —($C_{0-3}$ alkylene)$NR^cC(O)OR^d$, —($C_{0-3}$ alkylene)$S(O)_{0-2}R^c$, —($C_{0-3}$ alkylene)$NR^cS(O)_{1-2}R^d$, —($C_{0-3}$ alkylene)$S(O)_{1-2}NR^cR^d$, —($C_{0-3}$ alkylene)$NR^cS(O)_{1-2}NR^cR^d$ or $C_{1-6}$ alkyl optionally substituted by oxo, —CN or halogen. In one embodiment, $R^5$ is —($C_{0-3}$ alkylene)$_{3-7}$ membered heterocyclyl, wherein said alkylene and heterocyclyl are independently optionally substituted by halogen, oxo, —CN, —$OR^c$, —$NR^cR^d$, —$C(O)OR^c$, or $C_{1-6}$ alkyl optionally substituted by oxo, —CN or halogen. In one embodiment, $R^5$ is selected from oxetanyl, 1,1-dioxothiomorpholinyl, —$CH_2CH_2$(1,1-dioxothiomorpholinyl), —$CH_2CH_2$-triazolyl, triazolyl, —$CH_2$pyrazolyl, —$CH_2$pyridinyl, pyridinyl, pyrrolidinyl, piperidinyl, —$CH_2$(4-hydroxypiperidin-1-yl), morpholinyl, azetidinyl, 2-acetylpyrrolidin-3-yl, —$CH_2$tetrahydropyranyl, —$CH_2$tetrahydropyran-4-yl, tetrahydropyranyl, tetrahydrofuranyl, —$CH_2$tetrahydrofuran-2-yl, —$CH_2CH_2$tetrahydrofuranyl, —$CH_2$-morpholinyl, 1-acetylpiperidin-4-yl, —C(O)morpholinyl, —$CH_2C(O)$morpholinyl, —$CH_2C(O)$(1,1-dioxothiomorpholin-4-yl), —$CH_2C(O)$pyrrolidinyl,

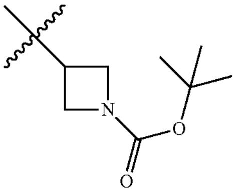,
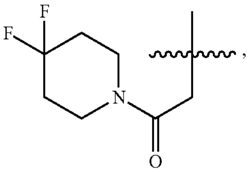,
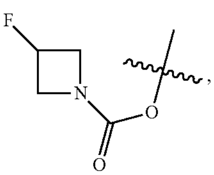,
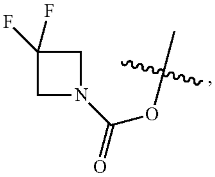,
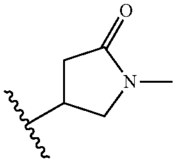,
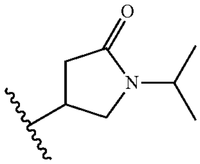,
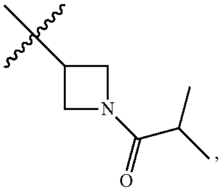,
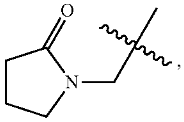,
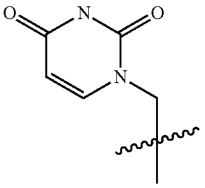,
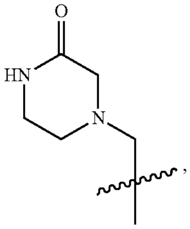,
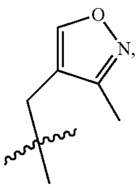
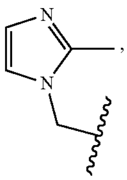,
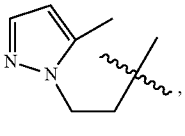,
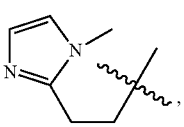,
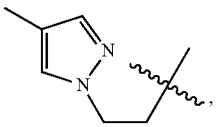,
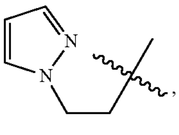,
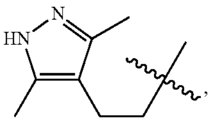,
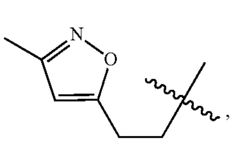,
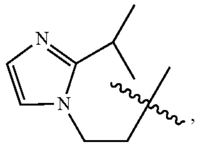, -continued

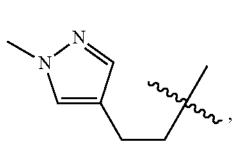,
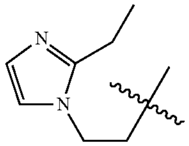

wherein the wavy line represents the point of attachment in formula I.

In one embodiment, $R^5$ is —($C_{0-3}$ alkylene)$_{4-6}$ membered heterocyclyl, wherein said alkylene is independently optionally substituted by halogen, oxo, —($C_{0-3}$ alkylene)CN, —($C_{0-3}$ alkylene)$OR^c$, —($C_{0-3}$ alkylene)$NR^cR^d$, —($C_{0-3}$ alkylene)C(O)$R^c$, —($C_{0-3}$ alkylene)C(O)$OR^c$, —($C_{0-3}$ alkylene)C(O)$NR^cR^d$, —($C_{0-3}$ alkylene)$NR^c$C(O)$R^d$, —($C_{0-3}$ alkylene)OC(O)$NR^cR^d$, —($C_{0-3}$ alkylene)$NR^c$C(O)$NR^cR^d$, —($C_{0-3}$ alkylene)$NR^c$C(O)$OR^d$, —($C_{0-3}$ alkylene)S(O)$_{0-2}R^c$, —($C_{0-3}$ alkylene)$NR^c$S(O)$_{1-2}R^d$, —($C_{0-3}$ alkylene)S(O)$_{1-2}$ $NR^cR^d$, —($C_{0-3}$ alkylene)$NR^c$S(O)$_{1-2}NR^cR^d$ or $C_{1-6}$ alkyl optionally substituted by oxo, —CN or halogen. In one embodiment, $R^5$ is —($C_{0-3}$ alkylene)$_{4-6}$ membered heterocyclyl, wherein said alkylene is optionally substituted by oxo or halogen, and said heterocyclyl is optionally substituted by oxo, halogen, $C_{1-3}$ alkyl, —$OR^c$ or —$NR^cR^d$. In one embodiment, $R^5$ is —$CH_2$C(O)(4-6 membered heterocyclyl) or —$CH_2$(4-6 membered heterocyclyl), wherein said heterocyclyl is optionally substituted by oxo, halogen, $C_{1-3}$ alkyl, —$OR^c$ or —$NR^cR^d$. In another embodiment, said heterocyclyl is oxetanyl, pyridinyl, pyrrolindinyl, pyranyl, piperidinyl, morpholinyl or

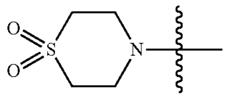, wherein the wavy line represents the point of attachment in formula I. In another embodiment, $R^5$ is pyridin-3-yl, pyrrolidin-1-yl, pyran-4-yl, —$CH_2$C(O)(pyrrolidin-1-yl), —$CH_2$C(O)(4,4-difluorpiperidin-1-yl), —$CH_2$ (morpholinyl), —$CH_2$C(O)(morpholinyl), —$CH_2$(pyrrolidin-2-on-1-yl) or

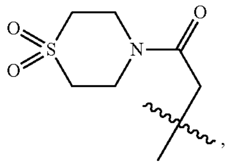 [SMILES: *CC(=O)N1CCS(=O)(=O)CC1], wherein the wavy line represents the point of attachment in formula I.

In one embodiment, $R^5$ is —($C_{0-3}$ alkylene)S(O)$_{1-2}R^a$, wherein said alkylene is independently optionally substituted by halogen, oxo, —($C_{0-3}$ alkylene)CN, —($C_{0-3}$ alkylene) $OR^c$, —($C_{0-3}$ alkylene)$NR^cR^d$, —($C_{0-3}$ alkylene)C(O)$R^c$, —($C_{0-3}$ alkylene)C(O)$OR^c$, —($C_{0-3}$ alkylene)C(O)$NR^cR^d$, —($C_{0-3}$ alkylene)$NR^c$C(O)$R^d$, —($C_{0-3}$ alkylene)OC(O)$NR^c$ $R^d$, —($C_{0-3}$ alkylene)$NR^c$C(O)$NR^cR^d$, —($C_{0-3}$ alkylene)N-$R^c$C(O)$OR^d$, —($C_{0-3}$ alkylene)S(O)$_{0-2}R^c$, —($C_{0-3}$ alkylene) $NR^c$S(O)$_{1-2}R^d$, —($C_{0-3}$ alkylene)S(O)$_{1-2}NR^cR^d$, —($C_{0-3}$ alkylene)$NR^c$S(O)$_{1-2}NR^cR^d$ or $C_{1-6}$ alkyl optionally substituted by oxo, —CN or halogen. In one embodiment, $R^5$ is —($C_{0-3}$ alkylene)$S(O)_{1-2}R^a$, wherein said alkylene is optionally substituted by halogen, oxo, —CN, —$OR^c$, —$NR^cR^d$, —$C(O)OR^c$, or $C_{1-6}$ alkyl optionally substituted by oxo, —CN or halogen. In one embodiment, $R^5$ is selected from —$CH_2S(O)_2CH_3$.

In one embodiment, $R^5$ is —($C_{0-3}$ alkylene)$C_{6-42}$ aryl, wherein said alkylene and aryl are independently optionally substituted by halogen, oxo, —($C_{0-3}$ alkylene)CN, —($C_{0-3}$ alkylene)$OR^c$, —($C_{0-3}$ alkylene)$NR^cR^d$, —($C_{0-3}$ alkylene)C(O)$R^c$, —($C_{0-3}$ alkylene)C(O)$OR^c$, —($C_{0-3}$ alkylene)C(O)N-$R^cR^d$, —($C_{0-3}$ alkylene)$NR^cC(O)R^d$, —($C_{0-3}$ alkylene)OC(O)$NR^cR^d$, —($C_{0-3}$ alkylene)$NR^cC(O)NR^cR^d$, —($C_{0-3}$ alkylene)$NR^cC(O)OR^d$, —($C_{0-3}$ alkylene)$S(O)_{0-2}R^c$, —($C_{0-3}$ alkylene)$NR^cS(O)_{1-2}R^d$, —($C_{0-3}$ alkylene)$S(O)_{1-2}NR^cR^d$, —($C_{0-3}$ alkylene)$NR^cS(O)_{1-2}NR^cR^d$ or $C_{1-6}$ alkyl optionally substituted by oxo, —CN or halogen. In one embodiment, $R^5$ is —($C_{0-3}$ alkylene)phenyl, wherein said alkylene and phenyl are independently optionally substituted by halogen, oxo, —CN, —$OR^c$, —$NR^cR^d$, —$C(O)OR^c$, or $C_{1-6}$ alkyl optionally substituted by oxo, —CN or halogen. In one embodiment, $R^5$ is selected from —$CH_2$-phenyl, phenyl,

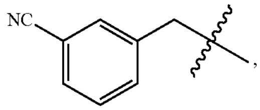,

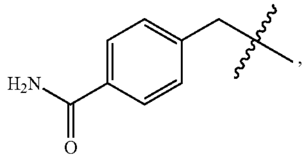, 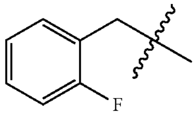,

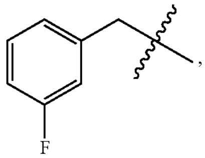, wherein the wavy line represents the point of attachment in formula I.

In one embodiment, $R^5$ is —($C_{0-3}$ alkylene)phenyl, wherein said alkylene is optionally substituted by oxo or halogen, and said phenyl is optionally substituted by halogen, $C_{1-3}$ alkyl, —$OR^c$ or —$NR^cR^d$.

In one embodiment, $R^5$ is —($C_{0-3}$ alkylene)$NR^aC(O)OR^b$, wherein said alkylene is independently optionally substituted by halogen, oxo, —($C_{0-3}$ alkylene)CN, —($C_{0-3}$ alkylene)$OR^c$, alkylene)$NR^cR^d$, alkylene)C(O)$R^c$, alkylene)C(O)$OR^c$, —($C_{0-3}$ alkylene)C(O)$NR^cR^d$, alkylene)$NR^cC(O)R^d$, —($C_{0-3}$ alkylene)OC(O)$NR^cR^d$, —($C_{0-3}$ alkylene)$NR^cC(O)NR^cR^d$, —($C_{0-3}$ alkylene)$NR^cC(O)OR^d$, —($C_{0-3}$ alkylene)$S(O)_{0-2}R^c$, —($C_{0-3}$ alkylene)$NR^cS(O)_{1-2}R^d$, —($C_{0-3}$ alkylene)$S(O)_{1-2}NR^cR^d$, —($C_{0-3}$ alkylene)$NR^cS(O)_{1-2}NR^cR^d$ or $C_{1-6}$ alkyl optionally substituted by oxo, —CN or halogen. In one embodiment, $R^5$ is —($C_{0-3}$ alkylene)$NR^aC(O)OR^b$, wherein said alkylene is optionally substituted by halogen, oxo, —CN, —$OR^c$, —$NR^cR^d$, —$C(O)OR^c$, or $C_{1-6}$ alkyl optionally substituted by oxo, —CN or halogen. In one embodiment, $R^5$ is selected from —$CH_2NHC(O)OCH_2CH_3$ and —$CH_2NHC(O)OCH_3$.

In one embodiment, $R^5$ is selected from hydrogen, fluoro, methyl, ethyl, 1-hydroxyethyl, 2-hydroxyethyl, propyl, isopropyl, butyl, 2-methylbutyl, isobutyl, —$CH_2F$, —$CHF_2$, —$CF_3$, —$CH_2OH$, —$C(CH_3)_2OH$, —CN, —$C(CH_3)_2CN$, —$CH_2CH_2OH$, —$CH_2C(CH_3)_2OH$, —$CH_2OCH_2CH(CH_3)_2$,

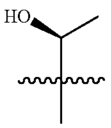, 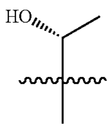,

—$CF_2CH_2NH_2$, —$CH_2C(O)NH_2$,

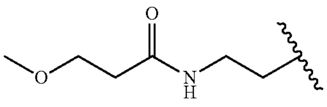,

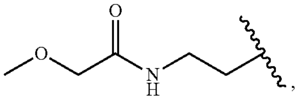, 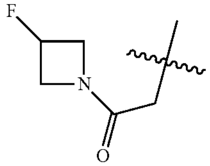,

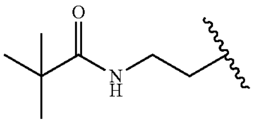,

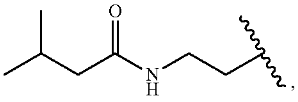,

—$CH_2$cyclopentyl, —$CH_2$cyclopropyl, —$CH_2CH_2$cyclopropyl, cyclopropyl, 2,2-difluorocyclopropyl, cyclobutyl, —$CH_2C(O)NH_2$, —$CH_2C(O)NH$cyclopentyl, —$CH_2C(O)N(CH_3)$(cyclopentyl), —$CH_2C(O)NHCH_3$, —$CH(CH_3)C(O)NHCH(CH_3)_2$, —$CH_2C(O)$(pyrrolidin-1-yl), —$CH_2C(O)$(4,4-difluorpiperidin-1-yl), —$CH_2C(O)$(morpholinyl),

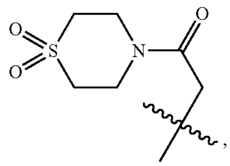 [SMILES: *CC(=O)N1CCS(=O)(=O)CC1],

—$CH_2NHC(O)CH_3$, —$CH_2NHC(O)CH(CH_3)_2$, —$CH_2NHC(O)CH_2CH_3$, —$CH_2NHC(O)CH_2OCH_3$, —$CH_2NHC(O)$pyridin-3-yl, —$CH_2NHC(O)$pyridin-4-yl,

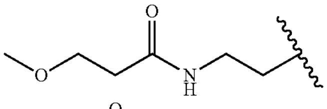,

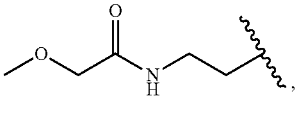,

-continued

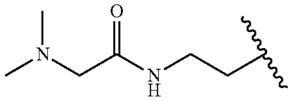

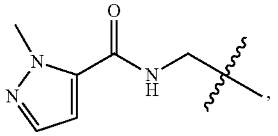

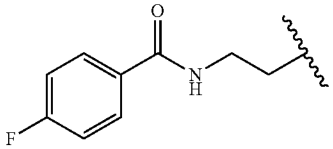

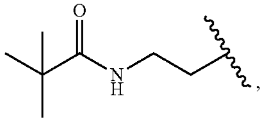

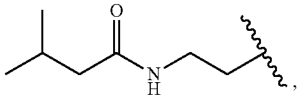

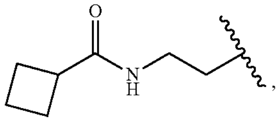

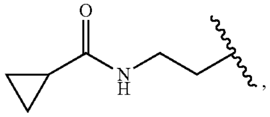

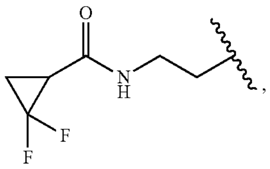

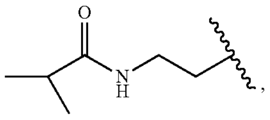 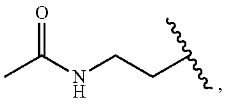

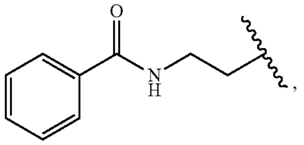

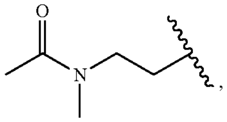

—$CH_2NHS(O)_2CH_3$, —$CH_2NHS(O)_2CH_2CH_3$, —$CH_2NHS(O)_2CH_2CH(CH_3)_2$, —$CH_2NHS(O)_2CH(CH_3)_2$, —$CH_2NHS(O)_2CH(CH_3)CH_2CH_3$, —$CH_2NHS(O)_2$cyclopropyl, —$CH_2NHS(O)_2$cyclopentyl, —$CH_2N(CH_3)_2S(O)_2CH_3$, —$CH_2CH_2NHS(O)_2CH_3$, —$CH_2CH_2NHS(O)_2CH_2CH_3$,

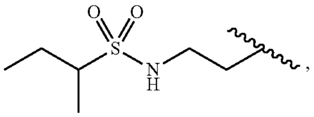

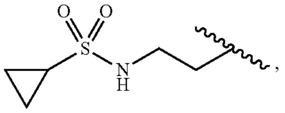

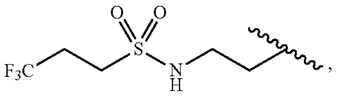

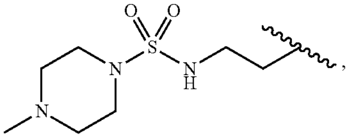

oxetanyl, 1,1-dioxothiomorpholinyl, —$CH_2CH_2$ (1,1-dioxothiomorpholinyl), —$CH_2CH_2$-triazolyl, triazolyl, —$CH_2$pyrazolyl, —$CH_2$pyridinyl, pyridinyl, pyrrolidinyl, piperidinyl, morpholinyl, azetidinyl, 2-acetylpyrrolidin-3-yl, —$CH_2$tetrahydropyranyl, tetrahydropyranyl, tetrahydrofuranyl, —$CH_2CH_2$tetrahydrofuranyl, —$CH_2$-morpholinyl, 1-acetylpiperidin-4-yl, —C(O)morpholinyl, —$CH_2C(O)$morpholinyl, —$CH_2C(O)$(1,1-dioxothiomorpholin-4-yl), —$CH_2C(O)$pyrrolidinyl,

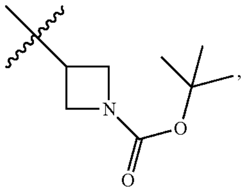 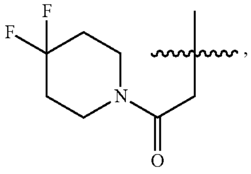

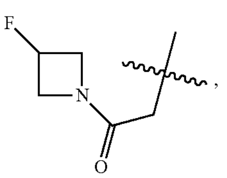 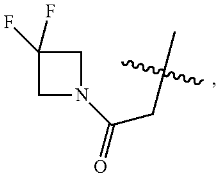

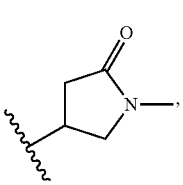 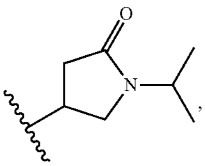

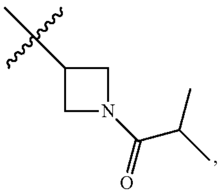 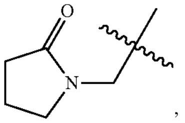

-continued

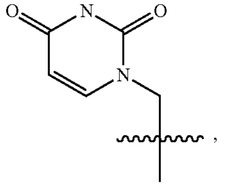, 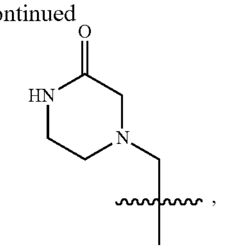,

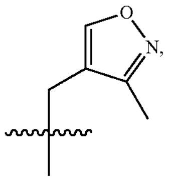, 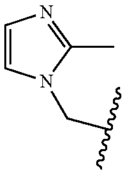, 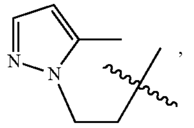,

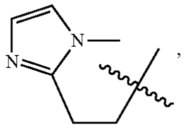, 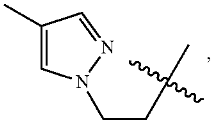,

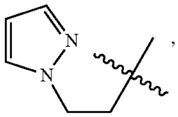, 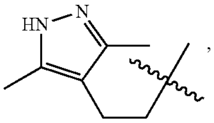,

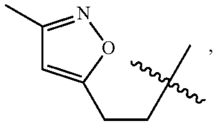, $-CH_2S(O)_2CH_3$, $-CH_2NHC(O)OCH_2CH_3$, $-CH_7NHC(O)OCH_3$, $-CH_2$-phenyl, phenyl,

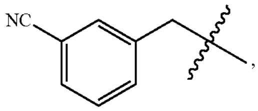,

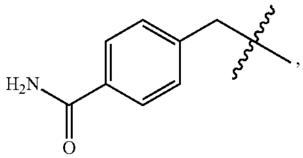,

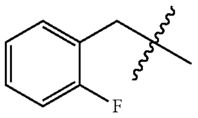 and 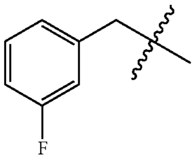, wherein the wavy line represents the point of attachment in formula I.

In certain embodiments, Y is $CR^5$ and $R^5$ is hydrogen, methyl, ethyl, propyl, isopropyl, cyclopropyl, cyclobutyl, cyano, 2-methylbutyl, N-(2-hydroxyethyl)amino, N-(2-methoxyethyl)amino, methylsulfonylaminomethyl, 2-(methylsulfonylamino)ethyl, cyclopropylmethyl, 2-[N-(2-propylsulfonyl)amino]ethyl, 2-[N-(cyclopropylsulfonyl)-amino]ethyl, 2-(cyclopropylcarbonylamino)ethyl, 2-(acetylamino)ethyl, 2-(methoxymethyl-carbonylamino)ethyl, cyclopentoxymethyl, cyclopropylmethoxymethyl, 2,2,2-trifluoroethoxymethyl, cyclohexyl, methylamino, 2-(N,N-dimethylaminocarbonyl)ethyl, 2-(N-acetyl-N-methylamino)ethyl, 2-(ethoxycarbonylamino)ethyl, 1-hydroxyethyl, N-acylaminomethyl, 2-amino-1,1-difluoroethyl, N,N-dimethylamino, hydroxymethyl, methoxy, N-methylamino, N,N-dimethylamino, N-(2,2,2-trifluoroethyl)aminomethyl, (2-carboxycyclopropyl)(hydroxy)methyl, 2-hydroxyethyl, amino carb onylmethyl, methylaminocarbonylmethyl, ethylaminocarbonylmethyl, 1-hydroxypropyl, 1,2-dihydroxyethyl, N-(2-methylpropyl)aminocarbonylmethyl, cyclopentylaminocarbonylmethyl, 2-(methoxycarbonylamino)ethyl, 2,2,2-trifluoro-1-hydroxyethyl, tert-butylaminocarbonylmethyl, cyclobutylaminocarbonylmethyl, 2-hydroxyethoxy, isopropylaminocarbonylmethyl, N—(N'N'-diemthylaminocarbonylmethyl)aminocarbonylmethyl, 4,4-difluoro cyclohexyl-aminocarbonylmethyl, 2,2-difluoroethylaminocarbonylmethyl, N-(2-hydroxyethyl)-N-methylaminocarbonylmethyl, cyclopentylmethyl, N-cyclopentyl-N-methylaminocarbonylmethyl, 2-amino-1,1-difluoroethyl, 3-pyridyl, morpholinomethyl, morpholinocarbonylmethyl, 2-cyano-2-methylethyl, trifluoromethyl, 1-hydroxy-1-methylethyl, 1-(N-isopropylaminocarbonyl)ethyl, 2-hydroxy-2-methylpropyl, N-(methylsulfonyl)-N-methylaminomethyl, difluoromethyl, 2-(2-butyl sulfonylamino)ethyl, 2-(4-fluorophenylcarbonylamino)ethyl, 2-(cyclobutylcarbonylamino)ethyl, 2-(2-methylbutanoylamino)ethyl, 2-(benzoylamino)ethyl, 2,2-difluorocyclopropyl, 3-cyanobenzyl, 2-methylpropoxymethyl, 2-cyclopropylethyl, 3-pyridylmethyl, methylsulfonylmethyl, ethoxycarbonylaminomethyl, 3-pyridylcarbonylaminomethyl, isopropylsulfonylaminomethyl, 2-pyridylcarbonylaminomethyl, cyclopropylsulfonylaminomethyl, cyclopentylsulfonylaminomethyl, 2-methylpropanoylaminomethyl, cyclopropylcarbonylaminomethyl, 2-fluorobenzoylaminomethyl, 3-fluorobenzoylaminomethyl, 1-methylpropylsulfonylaminomethyl, 2-methylpropylsulfonylaminomethyl, methoxyacetylaminomethyl, ethylsylfonylaminomethyl, 2-(3,3,3-trifluoropropylsulfonyl-amino)ethyl, 2-(2,2-difluorocyclopropylcarbonylamino)ethyl, fluoromethyl, 2-hydroxyethylamino, 2-methoxyethylamino, 1-aminoethyl, 2-(ethylsulfonylamino)ethyl, 2,2-dimethylpropoxymethyl, 1-methoxyethyl, tert-butylsulfonylaminomethyl, 2,2,2-trifluoroethylaminomethyl,

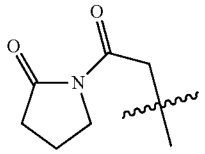 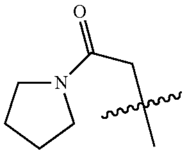

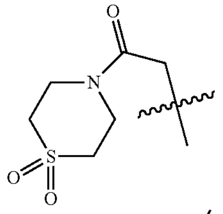 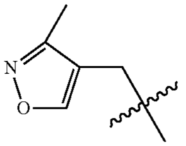

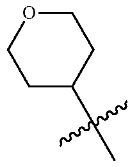 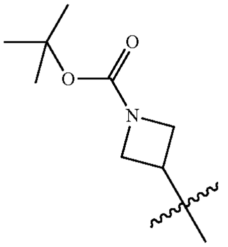 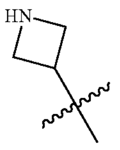

-continued
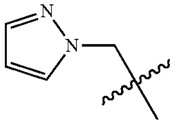
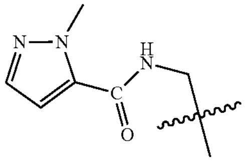
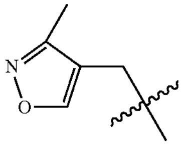
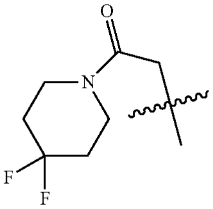
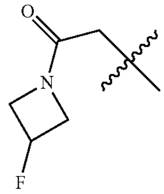
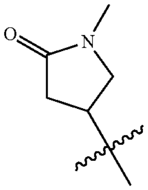
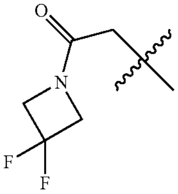
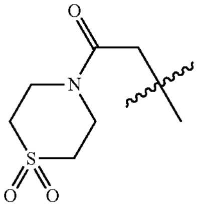
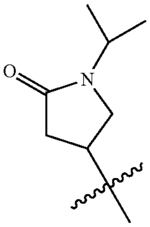
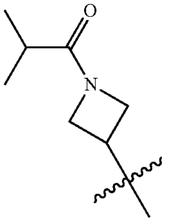
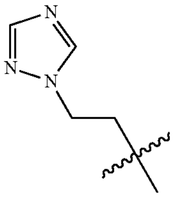
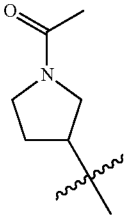
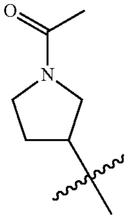
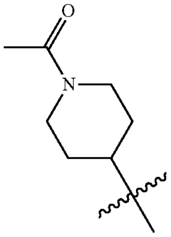
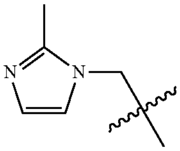
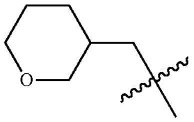
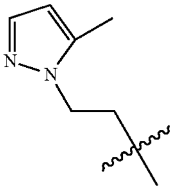
-continued
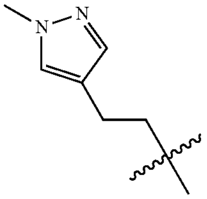
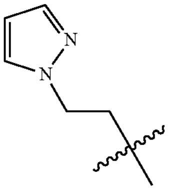
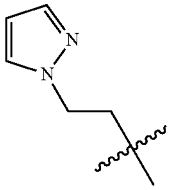
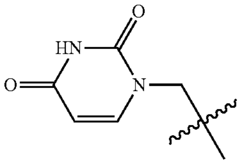
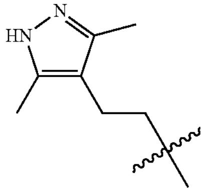
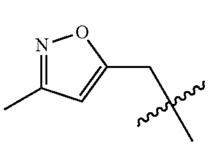
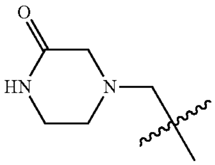
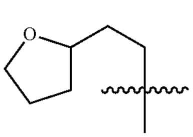
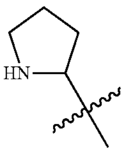
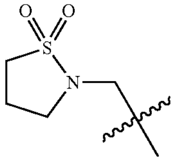
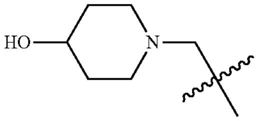
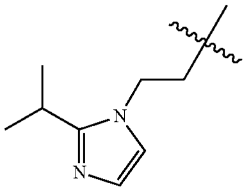
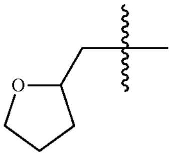
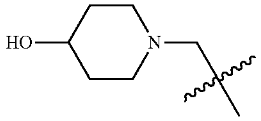
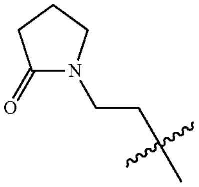
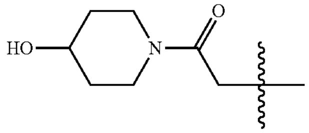
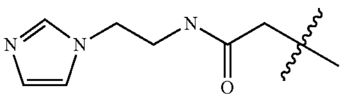

-continued

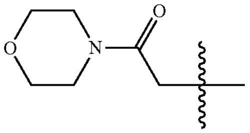
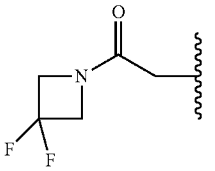
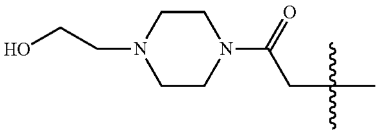
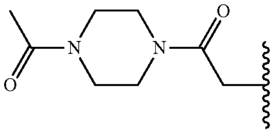
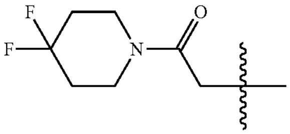
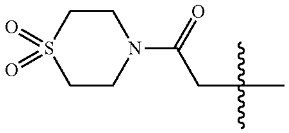
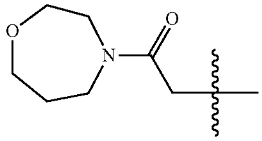
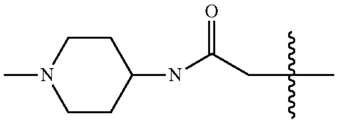
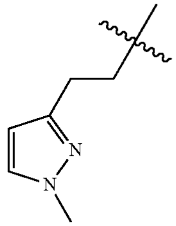
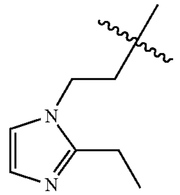
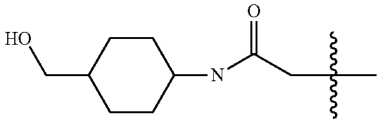
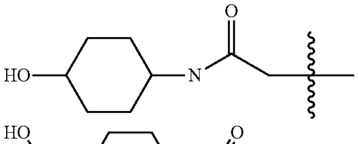
or
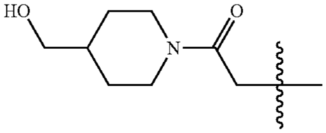
, wherein the wavy line represents the point of attachment in formula I.

In certain embodiments, $R^6$ is independently oxo, halogen, —CN, —C(O)$R^a$, —C(O)O$R^a$, —N$R^a$C(O)$R^b$, —C(O)N$R^aR^b$, —N$R^a$C(O)N$R^aR^b$, —OC(O)N$R^aR^b$, —N$R^a$C(O)O$R^b$, —S(O)$_{1-2}R^a$, —NR'S(O)$_2R^b$, —S(O)$_2$N$R^aR^b$, —O$R^a$, —S$R^a$, —N$R^aR^b$, $C_{1-6}$ alkyl, $C_{3-6}$ cycloalkyl, $C_{2-6}$ alkenyl, $C_{2-6}$ alkynyl, 3-7 membered heterocyclyl or $C_{6-14}$ aryl, and wherein said alkyl, alkenyl, alkynyl, cycloalkyl, heterocyclyl and aryl are independently optionally substituted by halogen, oxo, —CN, —O$R^c$, —S$R^c$, —N$R^cR^d$ or $C_{1-6}$ alkyl optionally substituted by oxo or halogen.

In one embodiment, $R^6$ is independently oxo, halogen, —CN, —C(O)($C_{1-6}$ alkyl), —C(O)O($C_{1-6}$ alkyl), —S(O)$_2$ ($C_{1-6}$ alkyl), —N$R^a$S(O)$_2$($C_{1-6}$ alkyl), —O($C_{1-6}$ alkyl), $C_{1-6}$ alkyl, $C_{3-6}$ cycloalkyl or 3-7 membered heterocyclyl, wherein said alkyl, cycloalkyl and heterocyclyl are independently optionally substituted by halogen, oxo, —CN, —O$R^c$, —N$R^c$ $R^d$ or $C_{1-6}$ alkyl optionally substituted by halogen. In one embodiment, $R^6$ is independently oxo, F, Cl, —CN, —OH, —C(O)$CH_3$, —$CH_2$CN, —$CH_2CH_2$CN, cyclopropyl, cyclobutyl, —$CF_3$, —NHS(O)$_2CH_3$, —S(O)$_2CH_3$, —C(O) O$CH_3$, pyrrolidinyl or pyrrolidinonyl.

In one embodiment, $R^6$ is independently oxo, halogen, —CN, —C(O)($C_{1-6}$ alkyl), —S(O)$_2$($C_{1-6}$ alkyl), —O$R^a$, —N$R^aR^b$, $C_{1-6}$ alkyl or $C_{3-6}$ cycloalkyl, and wherein said alkyl, alkenyl and alkynyl are independently optionally substituted by halogen, oxo, —CN, —O$R^c$ or —N$R^cR^d$. In one embodiment, $R^6$ is halogen, —S(O)$_2CH_3$ or —CN.

In one embodiment, $R^3$ is optionally substituted by 1 to 3 $R^6$ independently selected from oxo, halogen, —CN, —S(O)$_2$ ($C_{1-6}$ alkyl), —O$R^a$, —N$R^aR^b$ and $C_{1-6}$ alkyl, and wherein said alkyl, alkenyl and alkynyl are independently optionally substituted by halogen, oxo, —CN, —O$R^c$ or —N$R^cR^d$.

In one embodiment, $R^3$ is optionally substituted by 1 to 3 $R^6$ independently selected from oxo, halogen, —CN, —C(O) ($C_{1-6}$ alkyl), —C(O)O($C_{1-6}$ alkyl), —S(O)$_2$($C_{1-6}$ alkyl), —N$R^a$S(O)$_2$($C_{1-6}$ alkyl), —O($C_{1-6}$ alkyl), $C_{1-6}$ alkyl, $C_{3-6}$ cycloalkyl or 3-7 membered heterocyclyl, wherein said alkyl, cycloalkyl and heterocyclyl are independently optionally substituted by halogen, oxo, —CN, —O$R^c$, —N$R^cR^d$ or $C_{1-6}$ alkyl optionally substituted by halogen.

In certain embodiments, each $R^a$ and $R^b$ are independently hydrogen, $C_{1-6}$ alkyl, $C_{2-6}$ alkenyl, $C_{2-6}$ alkynyl, —$C_{3-6}$ cycloalkyl, -3-12 membered heterocyclyl, —C(O)$_{3-12}$ membered heterocyclyl or —$C_{6-14}$ aryl, wherein said alkyl, cycloalkyl, heterocyclyl and aryl are independently optionally substituted by halogen, oxo, —CN, —O$R^e$, —N$R^eR^f$, —C(O)$R^g$, —C(O)O$R^g$, —C(O)N$R^gR^h$, —N$R^g$C(O)$R^h$, —OC(O)N$R^gR^h$, —N$R^g$C(O)N$R^gR^h$, —N$R^g$C(O)O$R^h$, —S(O)$_{1-2}R^g$, —N$R^g$S(O)$_{1-2}R^h$, —S(O)$_{1-2}$N$R^gR^h$, —N$R^g$S (O)$_{1-2}$N$R^gR^h$, $C_{3-6}$ cycloalkyl, 3-6 membered heterocyclyl, phenyl or $C_{1-3}$ alkyl optionally substituted by oxo or halogen, or taken together with the atom to which they are attached to form a 3-6 membered heterocyclyl optionally substituted by oxo, halogen, —C(O)$C_{1-6}$ alkyl or $C_{1-6}$ alkyl optionally substituted by oxo, halogen, O$R^g$ or N$R^g$N$R^h$.

In certain embodiments, each $R^a$ and $R^b$ are independently hydrogen, $C_{1-6}$ alkyl, $C_{3-6}$ cycloalkyl, 3-6 membered heterocyclyl, —C(O)$_{3-6}$ membered heterocyclyl or phenyl, wherein said alkyl, cycloalkyl, heterocyclyl and phenyl are independently optionally substituted by halogen, oxo, —CN, —O$R^e$, —N$R^eR^f$, —C(O)$R^g$, —C(O)O$R^g$, —C(O)N$R^gR^h$, —N$R^g$C (O)$R^h$, —OC(O)N$R^gR^h$, —N$R^g$C(O)N$R^gR^h$, —N$R^g$C(O) O$R^h$, —S(O)$_{1-2}R^g$, —N$R^g$S(O)$_{1-2}R^h$, —S(O)$_{1-2}$N$R^gR^h$, —N$R^g$S(O)$_{1-2}$N$R^gR^h$, $C_{3-6}$ cycloalkyl, 3-6 membered heterocyclyl, phenyl or $C_{1-3}$ alkyl optionally substituted by oxo or halogen.

In one embodiment, each $R^a$ and $R^b$ are independently hydrogen, $C_{1-6}$ alkyl, $C_{3-6}$ cycloalkyl, 3-6 membered heterocyclyl, 5-6 membered heteroaryl or phenyl, wherein said alkyl, cycloalkyl, heterocyclyl, heteroaryl and phenyl are independently optionally substituted by halogen, oxo, —CN, —O$R^e$, —N$R^eR^f$ or $C_{1-3}$ alkyl optionally substituted by halogen.

In one embodiment, each $R^a$ and $R^b$ are independently selected from hydrogen, methyl, ethyl, propyl, isopropyl, butyl, t-butyl, sec-butyl, —$CF_3$, —$CH_2CF_3$, —$CH_2$F, —$CHF_2$, —$CH_2$OH, —$CH_2CH_2$OH, —$CH_2NH_2$, —$CH_2CH_2NH_2$, —$CH_2CH_2N(CH_3)_2$, —$CH_2N(CH_3)_2$, cyclopropyl, 2,2-difluorocyclopropyl, 2-fluorocyclopropyl, 2-methylcyclopropyl, cyclobutyl, cyclopentyl, cyclohexyl, piperidinyl, morpholinyl, piperazinyl, N-methylpiperazinyl, pyrazolyl, N-methylpyrazolyl, azetidinyl, 1,1-dioxothiomorpholinyl, pyrrolidinyl, pyrrolidinonyl, pyridinyl, cyanopyridinyl, phenyl and fluorophenyl.

In certain embodiments, a $R^a$ and a $R^b$ are independently taken together with the atom to which they are attached to form a 3-6 membered heterocyclyl optionally substituted by oxo, halogen, —C(O)$C_{1-6}$ alkyl or $C_{1-6}$ alkyl optionally substituted by oxo, halogen, $OR^g$ or $NR^gNR^h$.

In one embodiment, a $R^a$ and a $R^b$ are independently taken together with the atom to which they are attached to form a 3-6 membered heterocyclyl optionally substituted by oxo, halogen, —C(O)$C_{1-6}$ alkyl or $C_{1-6}$ alkyl optionally substituted by halogen. In one embodiment, said heterocyclyl is azetidinyl, pyrrolidinyl, piperidinyl, piperazinyl, piperidinonyl, morpholinyl and 1,1-dioxomorpholinyl.

In one embodiment, $R^a$ and $R^b$ are taken together with the atom to which they are attached to form a 4-6 membered heterocyclyl selected from azetidinyl, pyrrolidinyl, piperidinyl, piperazinyl and morpholinyl, optionally substituted by oxo, halogen, —C(O)$C_{1-6}$ alkyl or $C_{1-6}$ alkyl.

In one embodiment, $R^a$ and $R^b$ are independently hydrogen, methyl, isopropyl, cyclopropyl or cyclopentyl.

In one embodiment, $R^a$ and $R^b$ are taken together with the atom to which they are attached to form a 4-6 membered heterocyclyl selected from azetidinyl, pyrrolidinyl, piperidinyl, piperazinyl and morpholinyl, optionally substituted by oxo, halogen, —C(O)$C_{1-6}$ alkyl or $C_{1-6}$ alkyl.

In certain embodiments, each $R^c$ and $R^d$ are independently hydrogen, $C_{1-6}$ alkyl, $C_{2-6}$ alkenyl, $C_{2-6}$ alkynyl, —$C_{3-6}$ cycloalkyl, -3-12 membered heterocyclyl, —$C(O)_{3-12}$ membered heterocyclyl or —$C_{6-14}$ aryl, wherein said alkyl, alkenyl, alkynyl, cycloalkyl, heterocyclyl and aryl are independently optionally substituted by halogen, oxo, —CN, —$OR^g$, —$NR^gR^h$, —C(O)$R^g$, —C(O)$OR^g$, —C(O)$NR^gR^h$, —$NR^g$C(O)$R^h$, —OC(O)$NR^gR^h$, —$NR^g$C(O)$NR^gR^h$, —$NR^g$C(O)$OR^h$, —$S(O)_{1-2}R^g$, —$NR^gS(O)_{1-2}R^h$, —$S(O)_{1-2}NR^gR^h$, —$NR^gS(O)_{1-2}NR^gR^h$, $C_{3-6}$ cycloalkyl, 3-6 membered heterocyclyl, phenyl or $C_{1-6}$ alkyl optionally substituted by oxo or halogen, or taken together with the atom to which they are attached to form a 3-6 membered heterocyclyl optionally substituted by oxo, halogen, —C(O)$C_{1-6}$ alkyl or $C_{1-6}$ alkyl optionally substituted by oxo or halogen.

In certain embodiments, each $R^c$ and $R^d$ are independently hydrogen, $C_{1-6}$ alkyl, $C_{2-6}$ alkenyl, $C_{2-6}$ alkynyl, —$C_{3-6}$ cycloalkyl, -3-6 membered heterocyclyl, —$C(O)_{3-6}$ membered heterocyclyl or phenyll, wherein said alkyl, alkenyl, alkynyl, cycloalkyl, heterocyclyl and phenyl are independently optionally substituted by halogen, oxo, —CN, —$OR^g$, —$NR^gR^h$, —C(O)$R^g$, —C(O)$OR^g$, —C(O)$NR^gR^h$, —$NR^g$C(O)$R^h$, —OC(O)$NR^gR^h$, —$NR^g$C(O)$NR^gR^h$, —$NR^g$C(O)$OR^h$, —$S(O)_{1-2}R^g$, —$NR^gS(O)_{1-2}R^h$, —$S(O)_{1-2}NR^gR^h$, —$NR^gS(O)_{1-2}NR^gR^h$, $C_{3-6}$ cycloalkyl, 3-6 membered heterocyclyl, phenyl or $C_{1-6}$ alkyl optionally substituted by oxo or halogen.

In one embodiment, each $R^c$ and $R^d$ are independently hydrogen, $C_{1-6}$ alkyl, $C_{3-6}$ cycloalkyl, 3-6 membered heterocyclyl, 5-6 membered heteroaryl or phenyl, wherein said alkyl, cycloalkyl, heterocyclyl, heteroaryl and phenyl are independently optionally substituted by halogen, oxo, —CN, —$OR^g$, —$NR^gR^h$ or $C_{1-6}$ alkyl optionally substituted by halogen.

In one embodiment, each $R^c$ and $R^d$ are independently hydrogen, methyl, ethyl, isopropyl, butyl, t-butyl, sec-butyl, —$CF_3$, —$CH_2CF_3$, —$CH_2F$, —$CHF_2$, —$CH_2OH$, —$CH_2CH_2OH$, —$CH_2NH_2$, —$CH_2CH_2NH_2$, —$CH_2CH_2N(CH_3)_2$, —$CH_2N(CH_3)_2$, cyclopropyl, 2,2-difluorocyclopropyl, 2-fluorocyclopropyl, 2-methylcyclopropyl, cyclobutyl, cyclopentyl, cyclohexyl, piperidinyl, morpholinyl, piperazinyl, N-methylpiperazinyl, pyrazolyl, N-methylpyrazolyl, azetidinyl, 1,1-dioxothiomorpholinyl, pyrrolidinyl, pyrrolidinonyl, pyridinyl, cyanopyridinyl, phenyl and fluorophenyl.

In certain embodiments, a $R^c$ and a $R^d$ are independently taken together with the atom to which they are attached to form a 3-6 membered heterocyclyl optionally substituted by oxo, halogen, —C(O)$C_{1-6}$ alkyl or $C_{1-6}$ alkyl optionally substituted by oxo or halogen.

In one embodiment, each $R^c$ and $R^d$ are independently hydrogen, methyl or ethyl, optionally substituted by fluoro or oxo. In one embodiment, each $R^c$ and $R^d$ are independently hydrogen, methyl or ethyl.

In one embodiment, a $R^c$ and a $R^d$ are taken together with the atom to which they are attached to form a 3-6 membered heterocyclyl optionally substituted by oxo, halogen, —C(O)$C_{1-6}$ alkyl or $C_{1-6}$ alkyl optionally substituted by halogen. In one embodiment, said heterocyclyl is azetidinyl, pyrrolidinyl, piperidinyl, piperazinyl, piperidinonyl, morpholinyl and 1,1-dioxomorpholinyl.

In one embodiment, $R^c$, $R^d$, $R^e$, $R^f$, $R^g$ and $R^h$ are independently hydrogen or methyl.

In one embodiment, each $R^e$, $R^f$, $R^g$, $R^h$ are independently hydrogen, methyl, ethyl, propyl or isopropyl, optionally substituted by halogen or oxo. In one embodiment, each $R^e$, $R^f$, $R^g$, $R^h$ are independently hydrogen, methyl or ethyl.

In another embodiment, X is $CR^4$;

Y is N or $CR^5$;

$R^1$ is azetidinyl, piperidinyl, pyrrolidinyl or cyclohexyl, optionally substituted by $C_{1-3}$ alkylene or $C_{1-3}$ alkyl;

$R^2$ is absent, $C_{1-3}$ alkyl, —NH—, —$NHCH_2$—, —$CH_2O$—, —$(CH_2)_2O$—, —C(O)NH—, —$CH_2$C(O)NH—, —$CH_2C(O)N(CH_3)$—, —NHC(O)$CH_2$—, —NHC(O)O—, —C(O)O—, —C(O)$CH_2S(O)_2$, —$NHS(O)_2$—, —$NHS(O)_2CH_2$—, —$CH_2$C(O)—, —$(CH_2)_2$C(O)—, —$S(O)_2$—, —$CH_2S(O)_2$—, —$S(O)_2(CH_2)_2$—;

$R^3$ is absent, $C_{1-6}$ alkyl optionally substituted by oxo, halogen, —CN, —$S(O)_2(C_{1-6}$ alkyl), —$OR^a$ or —$NR^aR^b$;

$C_{3-7}$ cycloalkyl optionally substituted by oxo, halogen, —CN, —$S(O)_2(C_{1-6}$ alkyl), —$OR^a$, —$NR^aR^b$ or $C_{1-6}$ alkyl optionally substituted by halogen, phenyl optionally substituted by $C_{1-6}$ alkyl, $C_{2-6}$ alkenyl, $C_{2-6}$ alkynyl, halogen, —$CF_3$, —CN, —$S(O)_2(C_{1-6}$ alkyl), —$OR^a$ or —$NR^aR^b$, 5-6 membered heteroaryl optionally substituted by oxo, $C_{1-6}$ alkyl, $C_{2-6}$ alkenyl, $C_{2-6}$ alkynyl, —$CF_3$, halogen, —CN, —$S(O)_2(C_{1-6}$ alkyl), —$OR^a$ or —$NR^aR^b$, or 4-7 membered heterocyclyl optionally substituted by oxo, $C_{1-6}$ alkyl, $C_{2-6}$ alkenyl, $C_{2-6}$ alkynyl, —$CF_3$, halogen, —CN, —$S(O)_2(C_{1-6}$ alkyl), —$OR^a$ or —$NR^aR^b$;

$R^4$ is hydrogen, F or methyl;

$R^5$ is hydrogen, $C_{1-6}$ alkyl or $C_{3-6}$ cycloalkyl optionally substituted by halogen, oxo, —CN, —$OR^a$ or —$NR^aR^b$, —$CH_2C(O)NR^aR^b$, —$CH_2C(O)NHR^a$, —$CH_2$C(O)(4-6 membered heterocyclyl), —$CH_2$(4-6 membered heterocyclyl), —$(C_{0-3}$ alkylene$)_{4-6}$ membered heteroaryl or —($C_{0-3}$ alkylene)phenyl, wherein said alkylene is optionally substituted by oxo or halogen, and said heterocyclyl, heteroaryl and phenyl are independently optionally substituted by oxo, halogen, $C_{1-3}$ alkyl, —$OR^c$ or —$NR^cR^d$;

each $R^a$ and $R^b$ are independently hydrogen, $C_{1-3}$ alkyl or $C_{3-6}$ cycloalkyl, wherein said alkyl and cycloalkyl are independently optionally substituted by oxo or halogen; or are taken together with the atom to which they are attached to form a 3-6 membered heterocyclyl optionally substituted by oxo, halogen or $C_{1-3}$ alkyl; and each $R^c$ and $R^d$ are independently hydrogen or $C_{1-6}$ alkyl; or are taken together with the atom to which they are attached to form a 3-6 membered heterocyclyl optionally substituted by oxo, halogen, or $C_{1-3}$-alkyl.

In another embodiment, X is $CR^4$; Y is N or $CR^5$; $R^1$ is azetidinyl, piperidinyl, pyrrolidinyl, tetrahydropyranyl, cyclopentyl or cyclohexyl, optionally substituted by $C_{1-3}$ alkylene, —CN, —$OR^a$ or $C_{1-3}$ alkyl; $R^2$ is absent, $C_{1-3}$ alkyl, —NH—, —$NHCH_2$—, —$CH_2O$—, —$(CH_2)_2O$—, —C(O)NH—, —$CH_2C(O)NH$—, —$CH_2C(O)N(CH_3)$—, —NHC(O)$CH_2$—, —NHC(O)O—, —C(O)O—, —C(O)$CH_2S(O)_2$, —$NHS(O)_2$—, —$NHS(O)_2CH_2$—, —$CH_2C(O)$—, —$(CH_2)_2$ C(O)—, —$S(O)_2$—, —$CH_2S(O)_2$—, —$S(O)_2(CH_2)_2$;

$R^3$ is absent, hydrogen, $C_{1-6}$ alkyl optionally substituted by oxo, halogen, —CN, —$S(O)_2(C_{1-6}$ alkyl), —$OR^a$ or —$NR^aR^b$;

$C_{3-7}$ cycloalkyl optionally substituted by oxo, halogen, —CN, —$S(O)_2(C_{1-6}$ alkyl), —$OR^a$, —$NR^aR^b$ or $C_{1-6}$ alkyl optionally substituted by halogen, phenyl optionally substituted by $C_{1-6}$ alkyl, $C_{2-6}$ alkenyl, $C_{2-6}$ alkynyl, halogen, —$CF_3$, —CN, —$S(O)_2(C_{1-6}$ alkyl), —$OR^a$ or —$NR^aR^b$, 5-6 membered heteroaryl optionally substituted by oxo, $C_{1-6}$ alkyl, $C_{2-6}$ alkenyl, $C_{2-6}$ alkynyl, —$CF_3$, halogen, —CN, —$S(O)_2(C_{1-6}$ alkyl), —$OR^a$ or —$NR^aR^b$, or 4-7 membered heterocyclyl optionally substituted by oxo, $C_{1-6}$ alkyl, $C_{2-6}$ alkenyl, $C_{2-6}$ alkynyl, —$CF_3$, halogen, —CN, —$S(O)_2(C_{1-6}$ alkyl), —$OR^a$ or —$NR^aR^b$;

$R^4$ is hydrogen, F or methyl;

$R^5$ is hydrogen, $C_{1-12}$ alkyl or $C_{3-12}$ cycloalkyl optionally substituted by halogen, oxo, —CN, —$OR^a$ or —$NR^aR^b$, —$CH_2C(O)NR^aR^b$, —$CH_2C(O)NHR^a$, —$CH_2C(O)$(4-6 membered heterocyclyl), —$CH_2$(4-6 membered heterocyclyl), —($C_{0-3}$ alkylene)$_{4-6}$ membered heteroaryl or —($C_{0-3}$ alkylene)phenyl, wherein said alkylene is optionally substituted by oxo or halogen, and said heterocyclyl, heteroaryl and phenyl are independently optionally substituted by oxo, halogen, $C_{1-3}$ alkyl, —$OR^c$ or —$NR^cR^d$;

each $R^a$ and $R^b$ are independently hydrogen, $C_{1-3}$ alkyl or $C_{3-6}$ cycloalkyl, wherein said alkyl and cycloalkyl are independently optionally substituted by oxo or halogen; or are taken together with the atom to which they are attached to form a 3-6 membered heterocyclyl optionally substituted by oxo, halogen or $C_{1-3}$ alkyl; and each $R^c$ and $R^d$ are independently hydrogen or $C_{1-6}$ alkyl; or are taken together with the atom to which they are attached to form a 3-6 membered heterocyclyl optionally substituted by oxo, halogen, or $C_{1-3}$-alkyl.

In another embodiment, $R^1$ is azetidinyl, piperidinyl, pyrrolidinyl or cyclohexyl, optionally substituted by $C_{1-3}$ alkylene or $C_{1-3}$ alkyl; $R^2$ is absent; and $R^3$ is hydrogen. In another embodiment, $R^1$ is azetidinyl, piperidinyl, pyrrolidinyl or cyclohexyl, optionally substituted by $C_{1-3}$ alkylene or $C_{1-3}$ alkyl; $R^2$ is absent; $R^3$ is hydrogen; and $R^5$ is —CN or $C_{1-3}$ alkyl optionally substituted by halogen or oxo.

In another embodiment, X is CH; Y is $CR^5$; $R^1$ is piperidinyl, tetrahydropyranyl, cyclopentyl or cyclohexyl, wherein $R^1$ is optionally substituted by $C_{1-3}$ alkylene, halogen, —$OR^a$, —CN, —$NR^aR^b$ or $C_{1-6}$ alkyl optionally substituted by oxo, —$OR^a$, —CN, —$NR^aR^b$ or halogen; $R^2$ is absent; $R^3$ is absent; $R^5$ is $C_{1-12}$ alkyl optionally substituted by halogen, oxo, —CN, —OH, —$OCH_3$, —$NH_2$ or —$N(CH_3)_2$; and each $R^a$ and $R^b$ are independently selected from $C_{1-3}$ alkyl optionally substituted by oxo or halogen.

In another embodiment, X is CH; Y is $CR^5$; $R^1$ is piperidinyl, tetrahydropyranyl or cyclohexyl, wherein $R^1$ is optionally substituted by $C_{1-3}$ alkylene, halogen, —OH, —$NH_2$ or $C_{1-3}$ alkyl optionally substituted by oxo, —CN or halogen; $R^2$ is absent; $R^3$ is absent; and $R^5$ is $C_{1-6}$ alkyl optionally substituted by halogen, oxo, —CN, —OH, —$OCH_3$, —$NH_2$ or —$N(CH_3)_2$.

In another embodiment, X is CH; Y is $CR^5$; $R^1$ is piperidinyl, tetrahydrofuranyl, tetrahydropyranyl, cyclopentyl or cyclohexyl, wherein $R^1$ is optionally substituted by $C_{1-3}$ alkylene, halogen, —OH, —$NH_2$ or $C_{1-3}$ alkyl optionally substituted by oxo, —CN or halogen; $R^2$ is absent; $R^3$ is absent; and $R^5$ is selected from

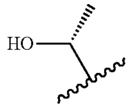
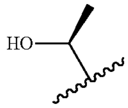
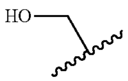
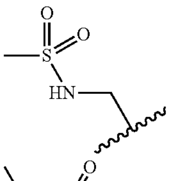
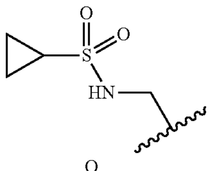
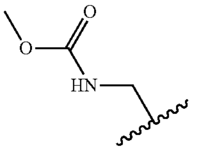
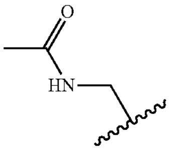
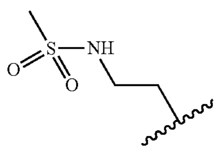
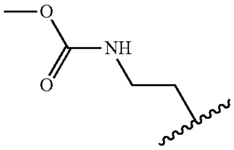
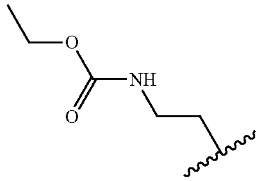
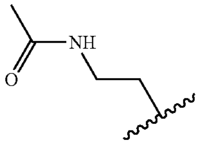
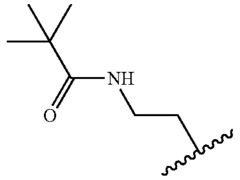
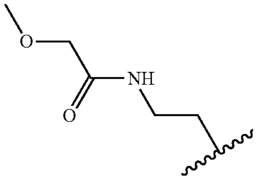
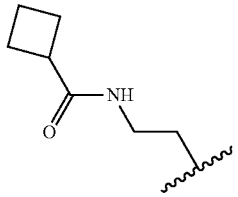
, wherein the wavy line represents the point of attachment in formula I.

In another embodiment, $R^1$ is piperidinyl optionally substituted by $C_{1-3}$ alkylene or $C_{1-3}$ alkyl; $R^2$ is $C_{1-3}$ alkyl optionally substituted by oxo; $R^3$ is $C_{1-6}$ alkyl optionally substituted by oxo, halogen or —CN, phenyl or pyridinyl, wherein said phenyl and pyridinyl are independently optionally substituted by halogen or —CN.

Another embodiment includes compounds of formulas IIa-IIc:

IIa

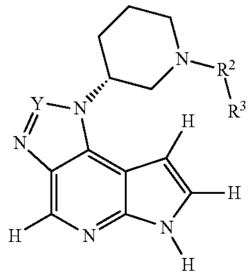

IIb

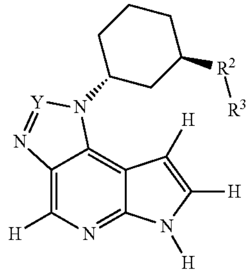

IIc

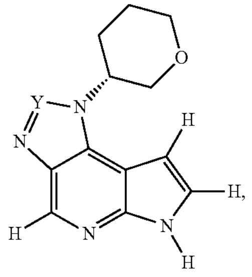

stereoisomers, tautomers, solvates, metabolites, pharmaceutically acceptable salts and prodrugs thereof.

Another embodiment includes compounds of formulas IIa-IIf:

IId

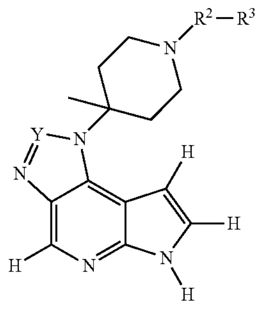

-continued

IIe

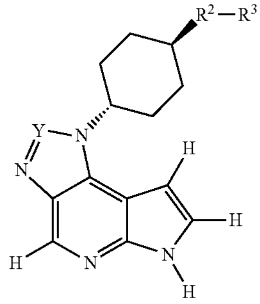

IIf

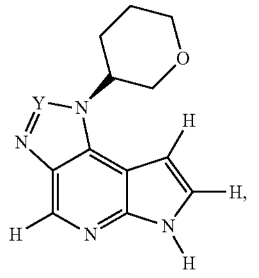

stereoisomers, tautomers, solvates, metabolites, pharmaceutically acceptable salts and prodrugs thereof.

In another embodiment, in formula II, $R^2$ is absent, C(O) or $S(O)_2$; and $R^3$ is hydrogen or $C_{1-6}$ alkyl optionally substituted by halogen, oxo, —CN, —$OR^c$ or —$NR^cR^d$; or taken together —$R^2$-$R^3$ is —CN, —OH or —$NH_2$.

In another embodiment, in formula II, $R^2$ is absent; and $R^3$ is hydrogen, —$OR^a$, —$NR^aR^b$ or $C_{1-6}$ alkyl optionally substituted by halogen, oxo, —CN, —$OR^c$ or —$NR^cR^d$; or taken together —$R^2$-$R^3$ is —CN, —OH or —$NH_2$.

In another embodiment, in formulas IIa-IIf, Y is $CR^5$; $R^5$ is halogen, $C_{1-12}$ alkyl, $C_{2-12}$ alkenyl, $C_{2-12}$ alkynyl, —($C_{0-3}$ alkylene)CN, —($C_{0-3}$ alkylene)$NR^aR^b$, —($C_{0-3}$ alkylene)$OR^a$, —($C_{0-3}$ alkylene)$SR^a$, —($C_{0-3}$ alkylene)C(O)$R^a$, —($C_{0-3}$ alkylene)$NR^a$C(O)$R^b$, —($C_{0-3}$ alkylene)C(O)$NR^aR^b$, —($C_{0-3}$ alkylene)C(O)$OR^a$, —($C_{0-3}$ alkylene)OC(O)$R^a$, —($C_{0-3}$ alkylene)$NR^a$C(O)$NR^aR^b$, —($C_{0-3}$ alkylene)OC(O)$NR^aR^b$, —($C_{0-3}$ alkylene)$NR^a$C(O)$OR^b$, —($C_{0-3}$ alkylene)$S(O)_{1-2}R^a$, —($C_{0-3}$ alkylene)$NR^aS(O)_{1-2}R^b$, —($C_{0-3}$ alkylene)$S(O)_{1-2}NR^aR^b$, —($C_{0-3}$ alkylene)$NR^aS(O)_{1-2}NR^aR^b$, —($C_{0-3}$ alkylene)$C_{3-6}$ cycloalkyl, —($C_{0-3}$ alkylene)$C_{6-44}$ aryl, —($C_{0-3}$ alkylene)$_{3-12}$ membered heterocyclyl or —($C_{0-3}$ alkylene)C(O)$_{3-12}$ membered heterocyclyl, wherein said alkyl, alkenyl, alkynyl, alkylene, cycloalkyl, aryl and heterocyclyl are independently optionally substituted by halogen, oxo, —($C_{0-3}$ alkylene)CN, —($C_{0-3}$ alkylene)$OR^c$, —($C_{0-3}$ alkylene)$NR^cR^d$, —($C_{0-3}$ alkylene)C(O)$OR^c$, —($C_{0-3}$ alkylene)C(O)$NR^cR^d$, —($C_{0-3}$ alkylene)$NR^c$C(O)$R^d$, —($C_{0-3}$ alkylene)OC(O)$NR^cR^d$, —($C_{0-3}$ alkylene)$NR^c$C(O)$NR^cR^d$, —($C_{0-3}$ alkylene)$NR^c$C(O)$OR^d$, —($C_{0-3}$ alkylene)$S(O)_{0-2}R^c$, —($C_{0-3}$ alkylene)$NR^cS(O)_{1-2}R^d$, —($C_{0-3}$ alkylene)$S(O)_{1-2}NR^cR^d$, —($C_{0-3}$ alkylene)$NR^cS(O)_{1-2}NR^cR^d$ or $C_{1-6}$ alkyl optionally substituted by oxo, —CN or halogen, with the proviso that $R^5$ is other than —OH.

In another embodiment, in formula II, Y is $CR^5$; $R^5$ is $C_{1-6}$ alkyl optionally substituted by halogen, oxo, —CN, —$OR^a$ or —$NR^aR^b$, and each $R^a$ and $R^b$ are independently hydrogen or $C_{1-3}$ alkyl optionally substituted by halogen, oxo or —CN, or are taken together with the atom to which they are attached to form a 3-6 membered heterocyclyl optionally substituted by oxo, halogen or $C_{1-3}$ alkyl.

Another embodiment includes compounds of formula II:

II

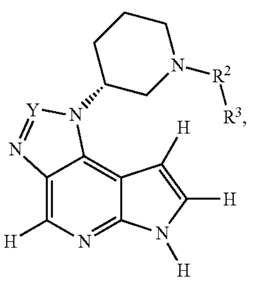

stereoisomers, tautomers and pharmaceutically acceptable salts thereof.

In another embodiment, in formula II, $R^2$ is absent; and $R^3$ is hydrogen.

In another embodiment, in formula II, $R^2$ is —C(O)—; and $R^3$ is $C_{1-6}$ alkyl or $C_{3-6}$ cycloalkyl, wherein said alkyl and cycloalkyl are independently optionally substituted by $C_{1-3}$ alkyl, oxo, halogen or —CN.

In another embodiment, in formula II, Y is $CR^5$; $R^5$ is $C_{1-6}$ alkyl optionally substituted by halogen, oxo, —CN, —$OR^a$ or —$NR^aR^b$, and $R^a$ and $R^b$ are independently hydrogen or $C_{1-3}$ alkyl, or are taken together with the atom to which they are attached to form a 3-6 membered heterocyclyl optionally substituted by oxo, halogen or $C_{1-3}$ alkyl.

In another embodiment, in formula II, Y is N.

Another embodiment includes compounds of formula III:

III

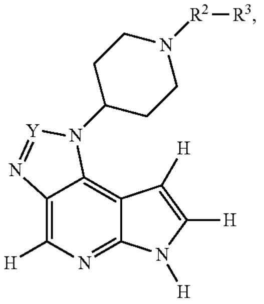

stereoisomers, tautomers and pharmaceutically acceptable salts thereof.

Another embodiment includes compounds of formulas III-IIIa:

IIIa

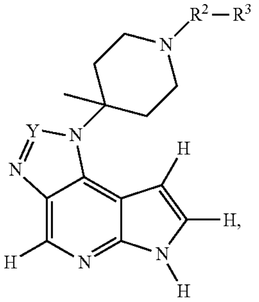

stereoisomers, tautomers, solvates, metabolites, pharmaceutically acceptable salts and prodrugs thereof.

In another embodiment, in formula III, $R^2$ is absent; and $R^3$ is hydrogen.

In another embodiment, in formula III, $R^2$ is —$CH_2$— or —$CH_2CH_2$—; and $R^3$ is phenyl, pyridinyl or pyrimidinyl, wherein said $R^3$ is independently optionally substituted by $C_{1-3}$ alkyl, halogen, —$CF_3$, —CN or —$S(O)_2(C_{1-3}$ alkyl).

In another embodiment, in formula III, $R^2$ is —$S(O)_2$—; and $R^3$ is $C_{1-6}$ alkyl, $C_{3-6}$ cycloalkyl, phenyl, pyridinyl or pyrimidinyl, wherein said alkyl and cycloalkyl are independently optionally substituted by $C_{1-3}$ alkyl, oxo, halogen or —CN, and wherein said phenyl, pyridinyl and pyrimidinyl are independently optionally substituted by $C_{1-3}$ alkyl, halogen, —$CF_3$, —CN or —$S(O)_2(C_{1-6}$ alkyl).

In another embodiment, in formula III, $R^2$ is absent; $R^3$ is $C_{1-6}$ alkyl optionally substituted by oxo, halogen, —CN, —$S(O)_2(C_{1-6}$ alkyl), —$OR^a$ or —$NR^aR^b$; and $R^a$ and $R^b$ are independently hydrogen or $C_{1-3}$ alkyl.

In another embodiment, in formula III, $R^2$ is absent; $R^3$ is 4-7 membered heterocyclyl optionally substituted by oxo, $C_{1-3}$ alkyl, halogen, —CN, —$S(O)_2(C_{1-3}$ alkyl), —$OR^a$ or —$NR^aR^b$, wherein said alkyl is optionally substituted by halogen or —CN; and $R^a$ and $R^b$ are independently hydrogen or $C_{1-3}$ alkyl.

In another embodiment, in formula III, $R^2$ is —C(O)—; $R^3$ is phenyl, 4-6 membered heteroaryl or 4-6 membered heterocyclyl, wherein said heterocyclyl, heteroaryl and phenyl are independently optionally substituted by oxo, $C_{1-6}$ alkyl, halogen, —CN, —$S(O)_2(C_{1-6}$ alkyl), —$OR^a$ or —$NR^aR^b$, wherein said alkyl is optionally substituted by halogen or —CN; and $R^a$ and $R^b$ are independently hydrogen or $C_{1-3}$ alkyl.

In another embodiment, in formula II, $R^2$ is —$CH_2$—, —$CH_2CH_2$—, —C(O)—, —$CH_2C(O)$—, —$C(O)CH_2$—; and $R^3$ is 5-6 membered heterocyclyl or 5-6 membered heteroaryl, wherein said $R^3$ is independently optionally substituted by $C_{1-3}$ alkyl, halogen, —$CF_3$, —CN or —$S(O)_2(C_{1-3}$ alkyl).

In another embodiment, in formulas III-IIIa, $R^2$ is —S(O)$_2$—, $R^3$ is $C_{1-6}$ alkyl, $C_{3-6}$ cycloalkyl, phenyl, pyridinyl or pyrimidinyl, wherein said alkyl and cycloalkyl are independently optionally substituted by $C_{1-3}$ alkyl, oxo, halogen or —CN, and wherein said phenyl, pyridinyl and pyrimidinyl are independently optionally substituted by $C_{1-3}$ alkyl, halogen, —$CF_3$, —CN or $S(O)_2(C_{1-6}$ alkyl). Y is $CR^5$, and $R^5$ is halogen, $C_{1-6}$ alkyl, $C_{2-6}$ alkenyl, $C_{2-6}$ alkynyl, ($C_{0-6}$ alkylene)CN, —($C_{0-3}$ alkylene)$NR^aR^b$, —($C_{0-3}$ alkylene)$OR^a$, —($C_{0-3}$ alkylene)$SR^a$, —($C_{0-3}$ alkylene)$C(O)R^a$, —($C_{0-3}$ alkylene)$NR^aC(O)R^b$, —($C_{0-3}$ alkylene)$C(O)NR^aR^b$, —($C_{0-3}$ alkylene)$C(O)OR^a$, —($C_{0-3}$ alkylene)$OC(O)R^a$, —($C_{0-3}$ alkylene)$NR^aC(O)NR^aR^b$, —($C_{0-3}$ alkylene)$OC(O)NR^aR^b$, —($C_{0-3}$ alkylene)$NR^aC(O)OR^b$, —($C_{0-3}$ alkylene)$S(O)_{1-2}R^a$, —($C_{0-3}$ alkylene)$NR^aS(O)_{1-2}R^b$, —($C_{0-3}$ alkylene)$S(O)_{1-2}NR^aR^b$, —($C_{0-3}$ alkylene)$NR^aS(O)_{1-2}NR^aR^b$, —($C_{0-3}$ alkylene)$C_{3-6}$ cycloalkyl, —($C_{0-3}$ alkylene)$C_{6-14}$ aryl, —($C_{0-3}$ alkylene)$_{3-12}$ membered heterocyclyl or —($C_{0-3}$ alkylene)C(O)$_{3-12}$ membered heterocyclyl, wherein said alkyl, alkenyl, alkynyl, alkylene, cycloalkyl, aryl and heterocyclyl are independently optionally substituted by halogen, oxo, —($C_{0-3}$ alkylene)CN, —($C_{0-3}$ alkylene)$OR^c$, —($C_{0-3}$ alkylene)$NR^cR^d$, —($C_{0-3}$ alkylene)$C(O)OR^c$, —($C_{0-3}$ alkylene)$C(O)NR^cR^d$, —($C_{0-3}$ alkylene)$NR^cC(O)R^d$, —($C_{0-3}$ alkylene)$OC(O)NR^cR^d$, —($C_{0-3}$ alkylene)$NR^cC(O)NR^cR^d$, —($C_{0-3}$ alkylene)$NR^cC(O)OR^d$, —($C_{0-3}$ alkylene)$S(O)_{0-2}R^c$, —($C_{0-3}$ alkylene)$NR^cS(O)_{1-2}R^d$, —($C_{0-3}$ alkylene)$S(O)_{1-2}NR^cR^d$, —($C_{0-3}$ alkylene)$NR^cS(O)_{1-2}NR^cR^d$ or $C_{1-6}$ alkyl optionally substituted by oxo, —CN or halogen, with the proviso that $R^5$ is other than —OH.

In another embodiment, in formula III, Y is $CR^5$; $R^5$ is $C_{1-6}$ alkyl optionally substituted by halogen, oxo, —CN, —$OR^c$ or —$NR^aR^b$, and $R^a$ and $R^b$ are independently hydrogen or $C_{1-3}$ alkyl, or are taken together with the atom to which they are attached to form a 3-6 membered heterocyclyl optionally substituted by oxo, halogen or $C_{1-3}$ alkyl.

In another embodiment, in formula III, Y is N.

In certain embodiments, —$R^1$-$R^2$-$R^3$ taken together are:

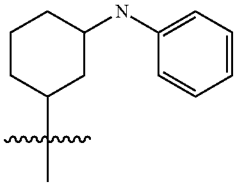
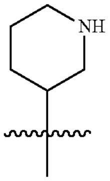
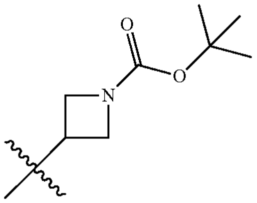
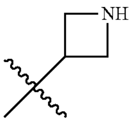
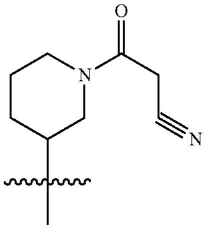
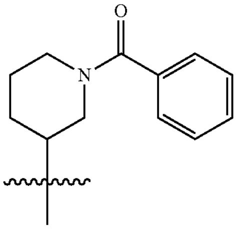
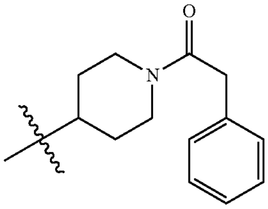
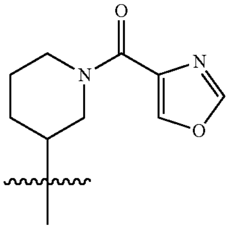
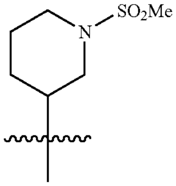
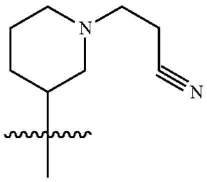
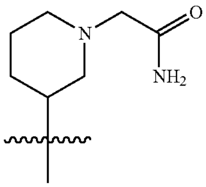
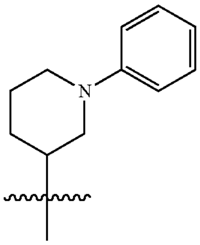

-continued

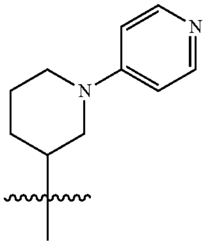
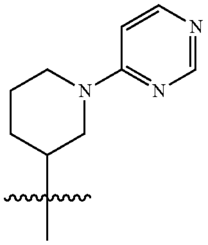
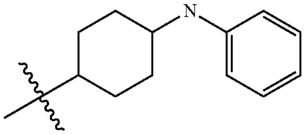
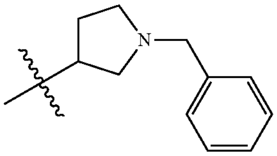
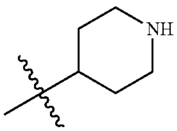
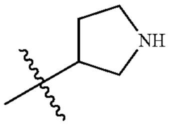
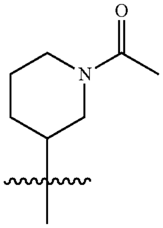
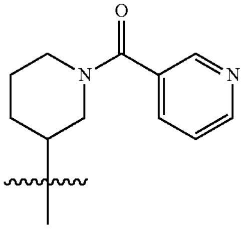
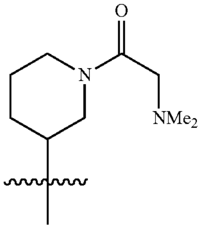
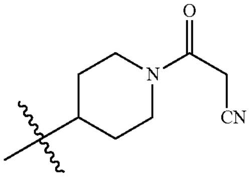
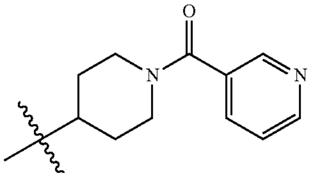
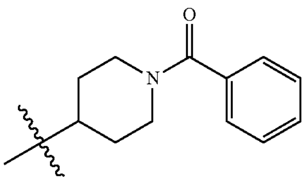
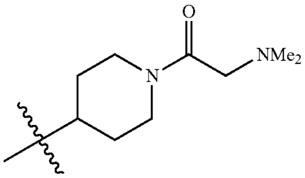
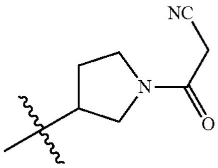

-continued
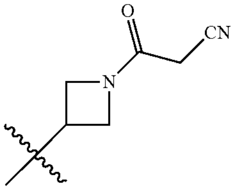
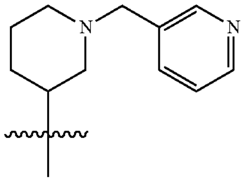
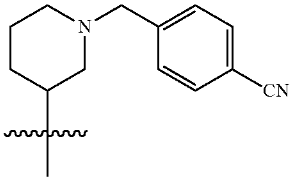
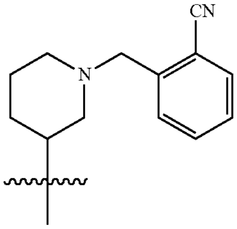
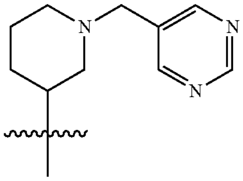
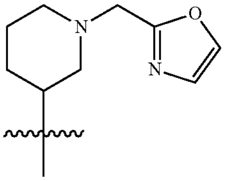
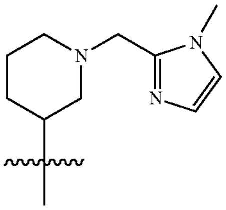
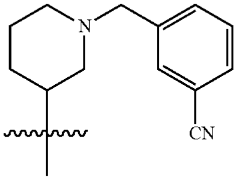
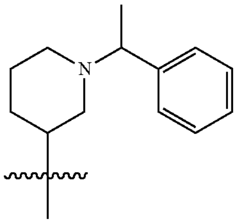
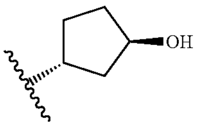
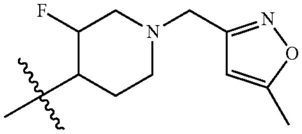
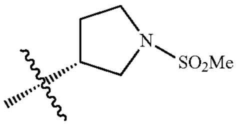
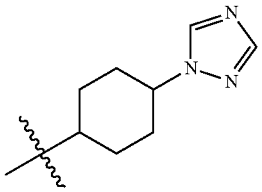
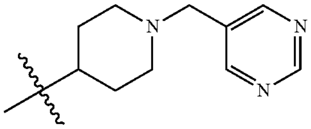
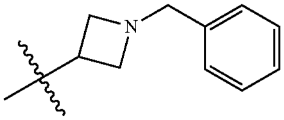
-continued
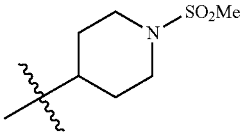
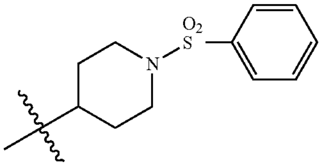
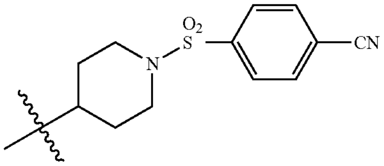
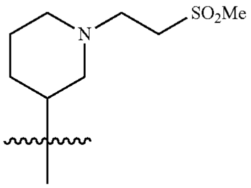
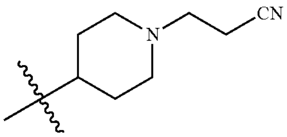
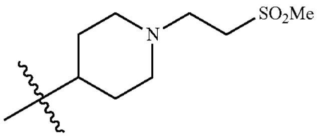
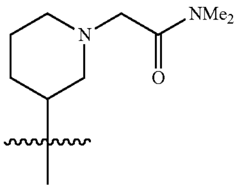
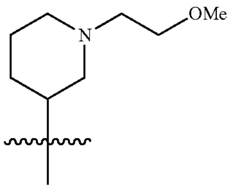
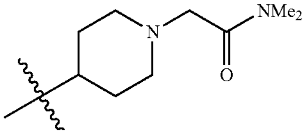
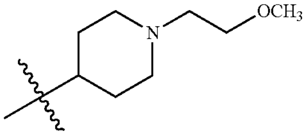
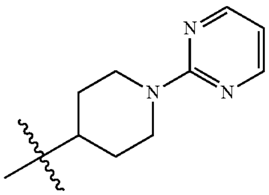
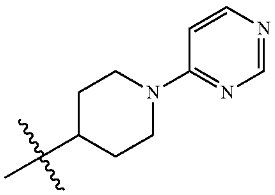
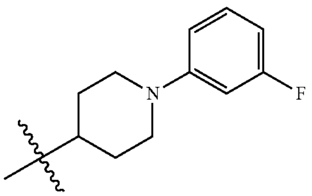

-continued
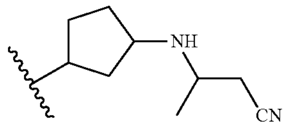
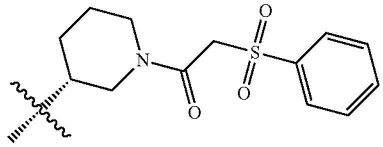
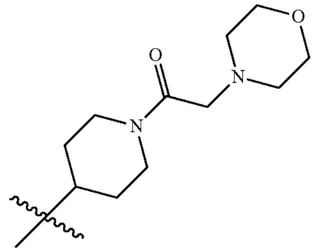
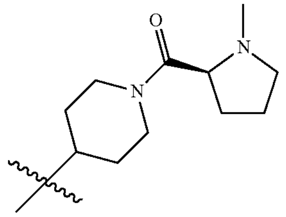
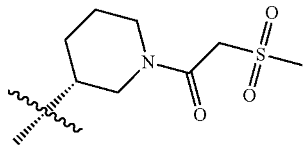
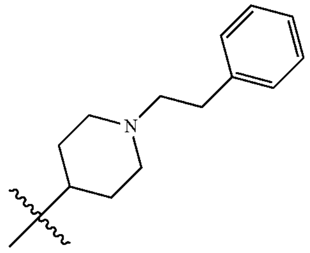
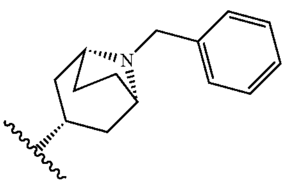
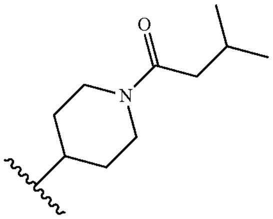
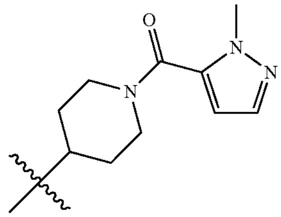
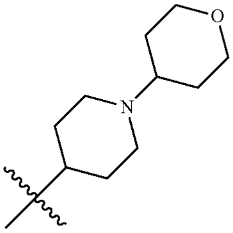
-continued
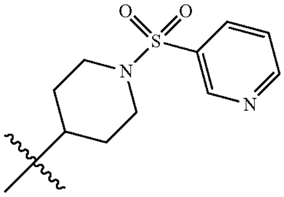
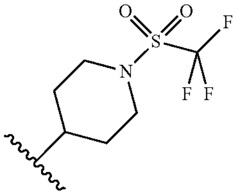
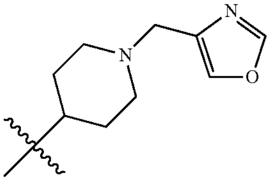
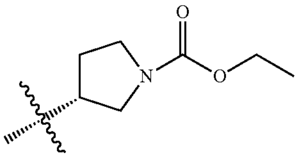
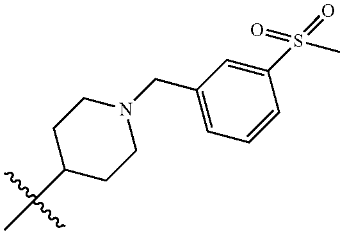
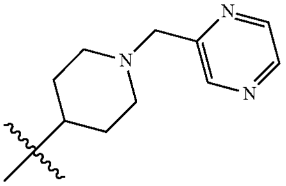
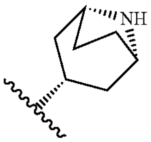
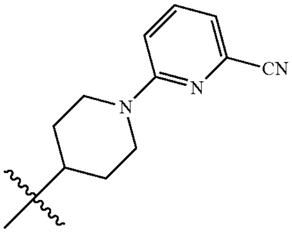
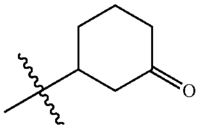
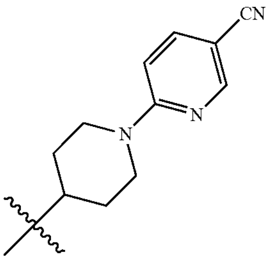
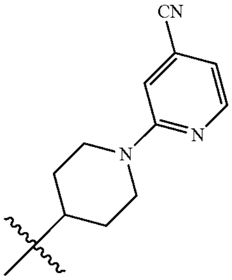
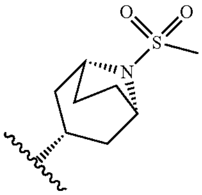
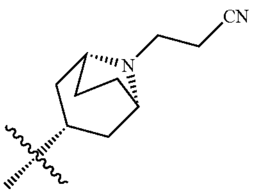

-continued
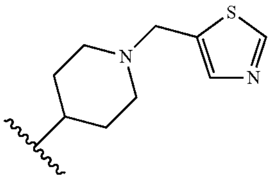
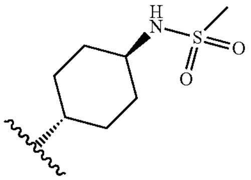
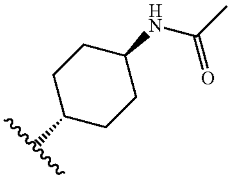
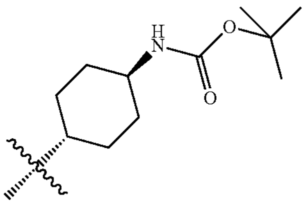
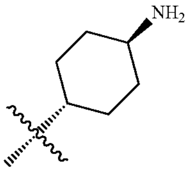
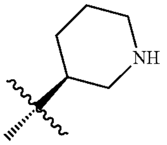
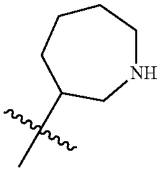
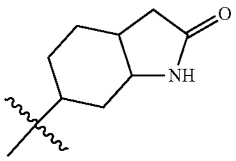
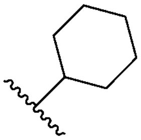
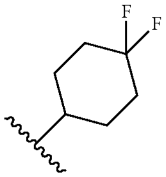
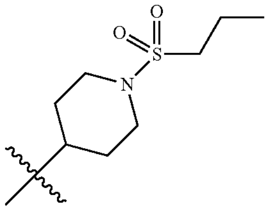
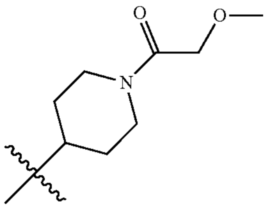
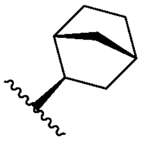
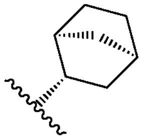
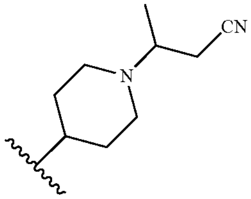
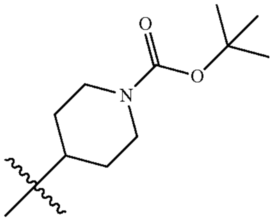
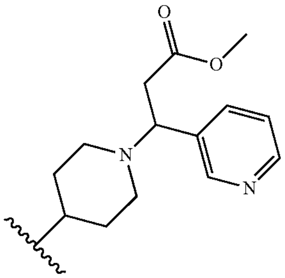
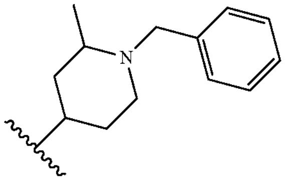
-continued
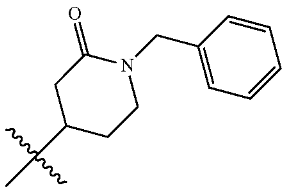
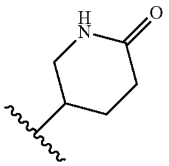
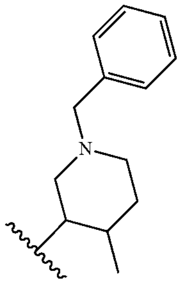
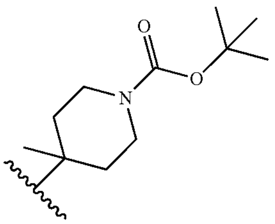
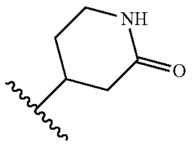
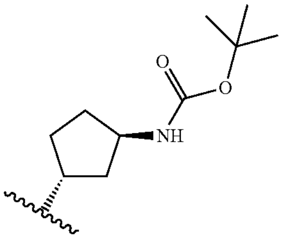
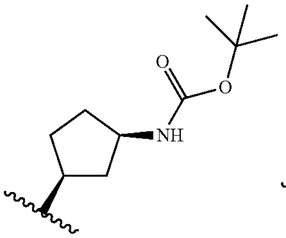
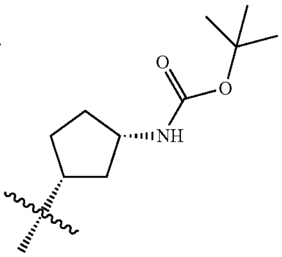
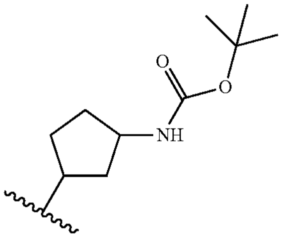
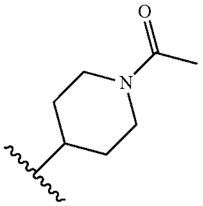
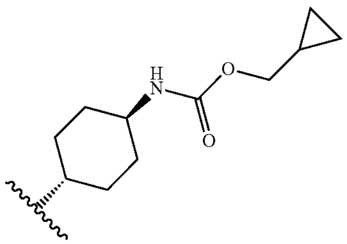
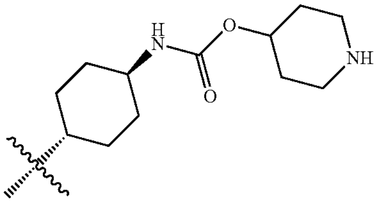

-continued
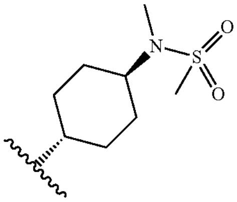
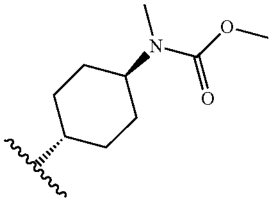
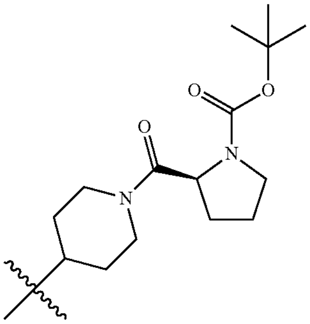
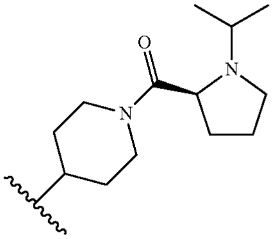
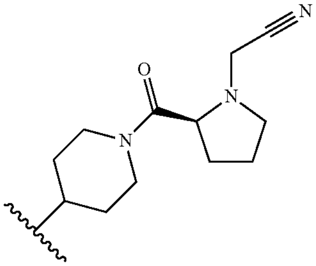
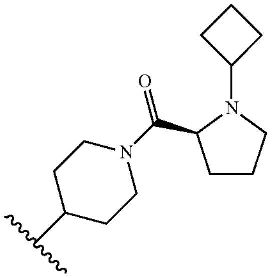
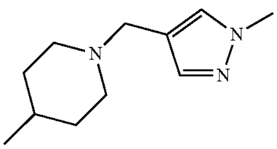
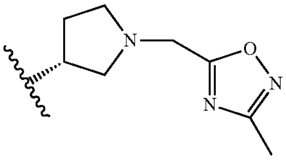
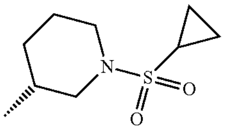
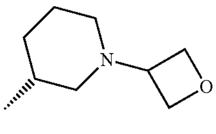
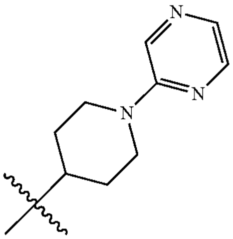
-continued
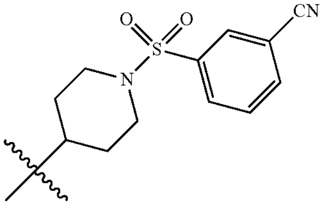
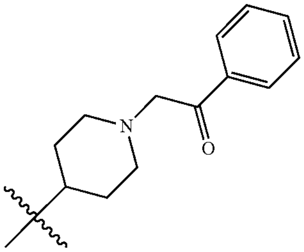
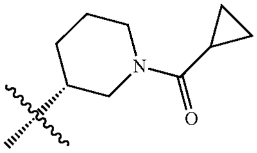
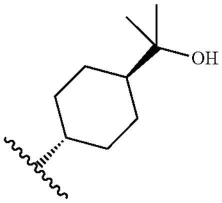
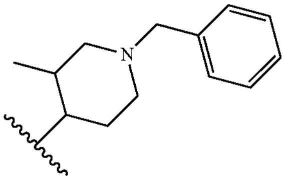
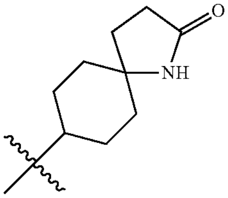
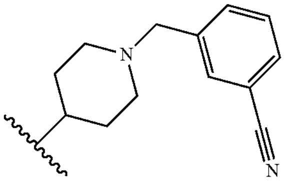
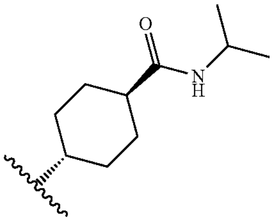
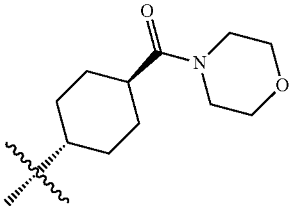
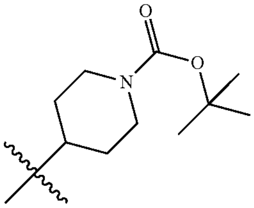
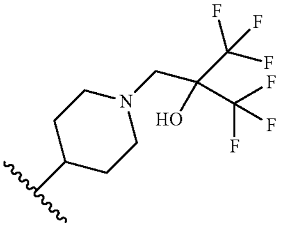
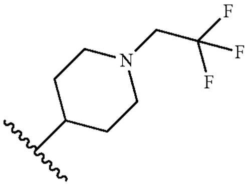
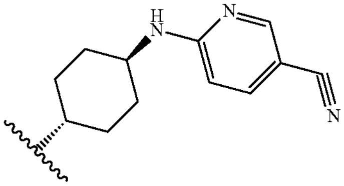

-continued
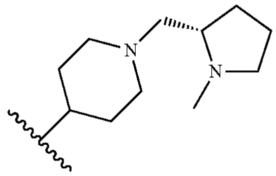
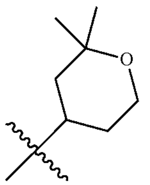
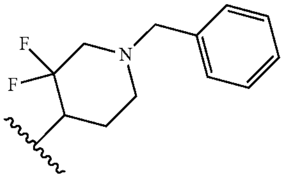
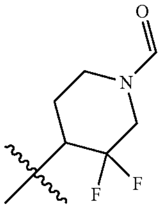
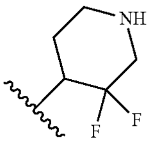
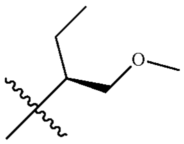
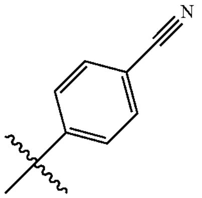
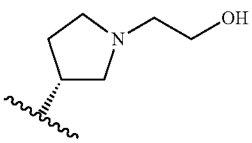
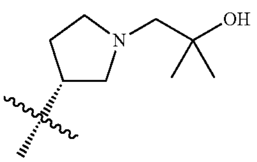
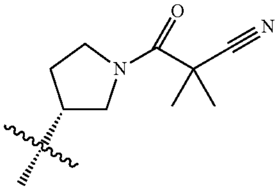
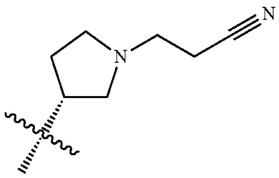
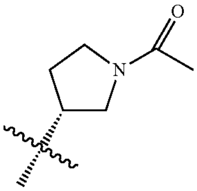
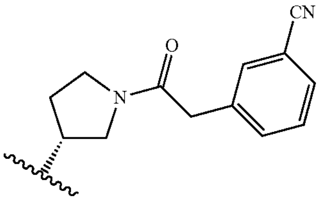
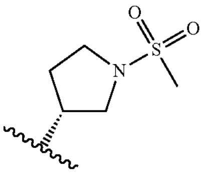
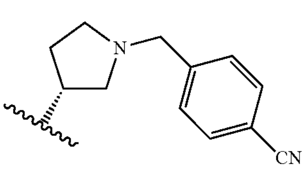
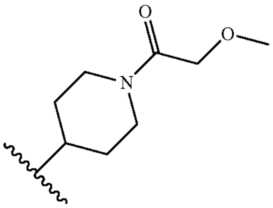
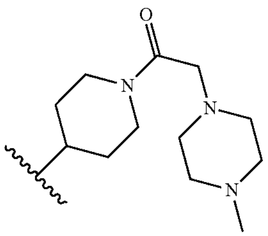
-continued
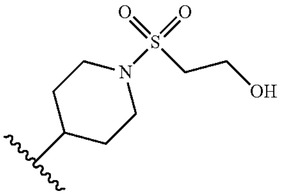
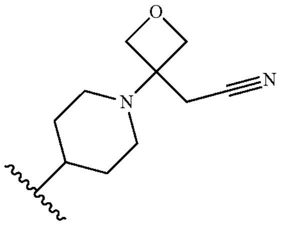
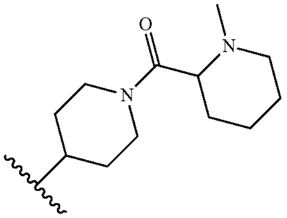
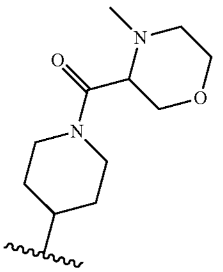
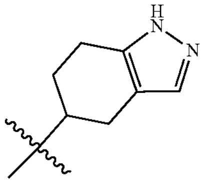
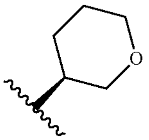
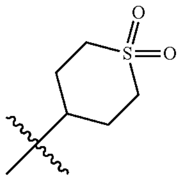
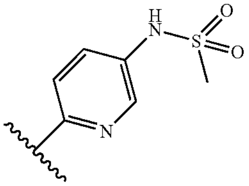
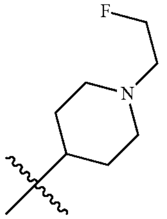
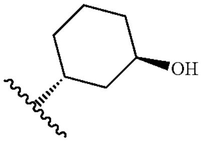
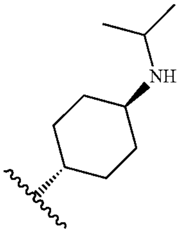
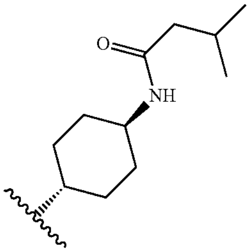
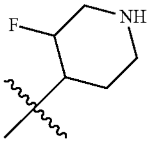
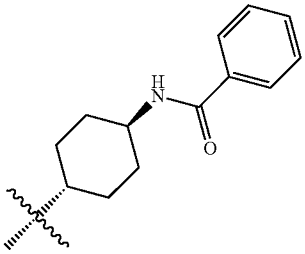

-continued
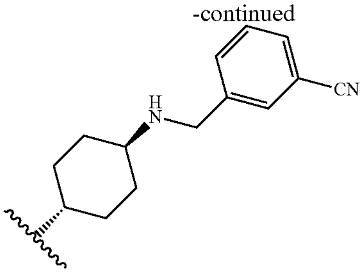
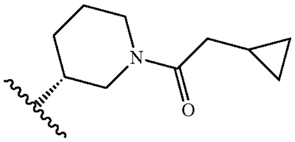
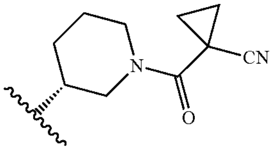
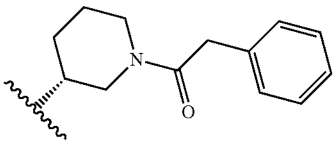
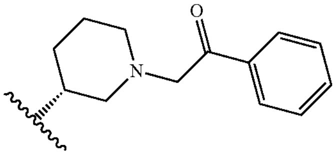
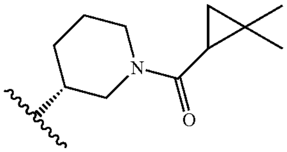
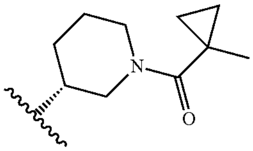
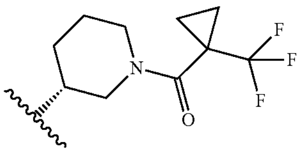
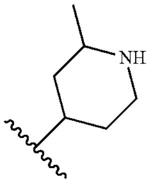
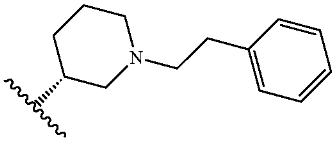
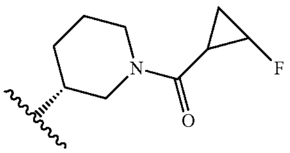
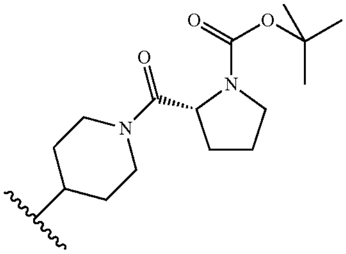
-continued
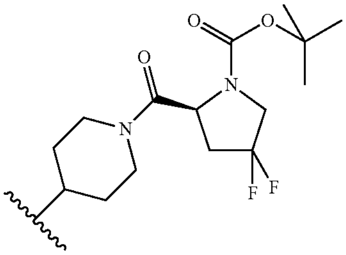
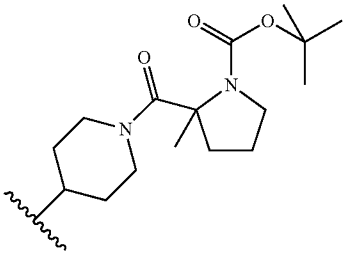
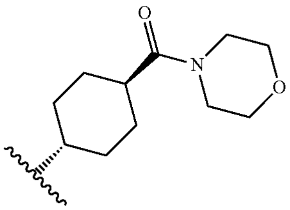
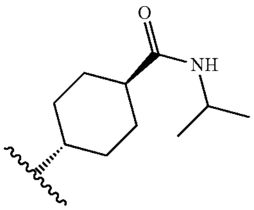
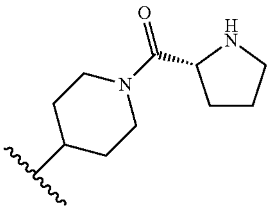
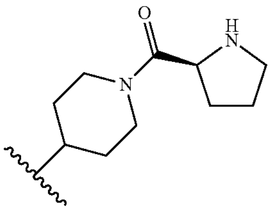
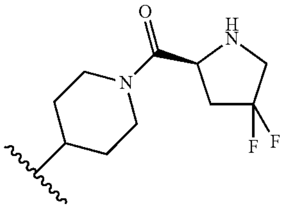
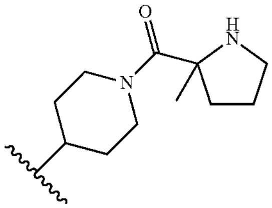
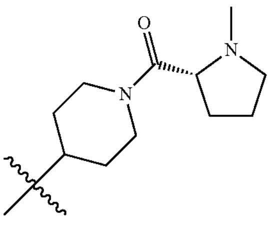
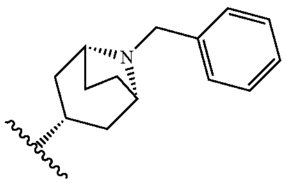
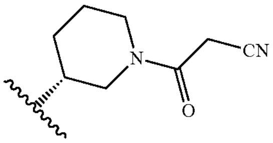

-continued
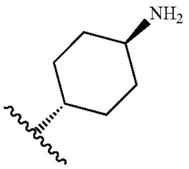
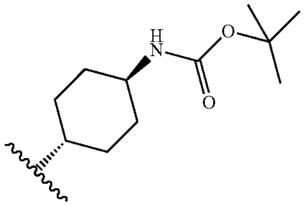
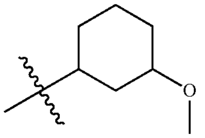
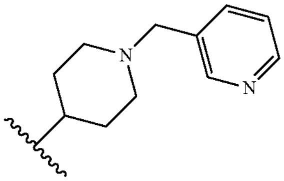
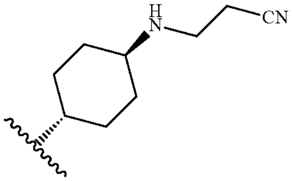
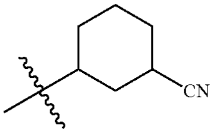
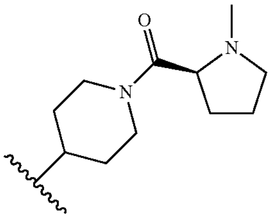
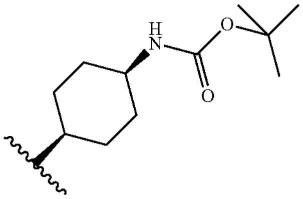
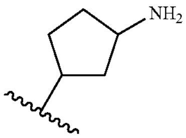
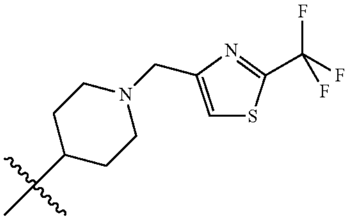
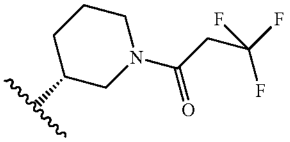
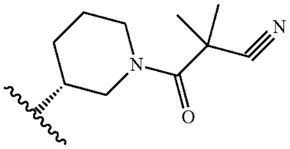
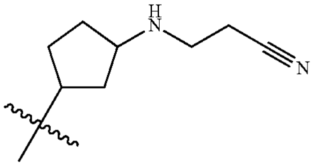
-continued
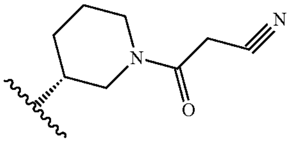
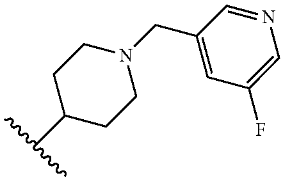
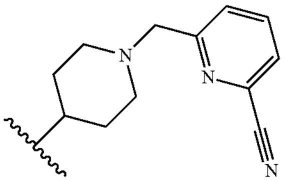
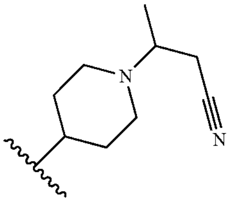
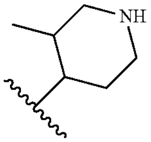
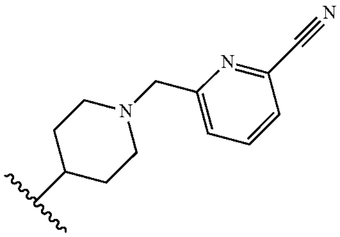
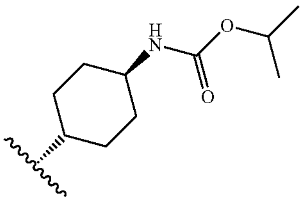
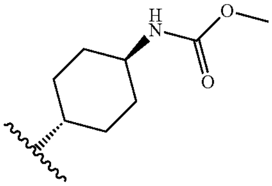
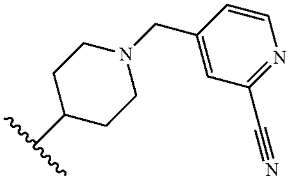
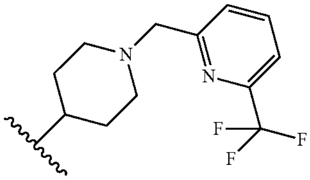
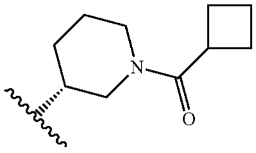
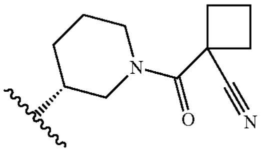

-continued
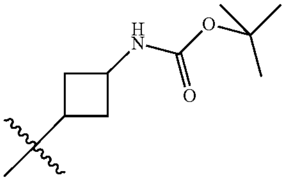
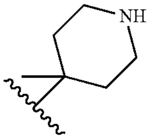
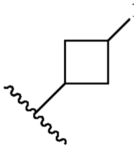
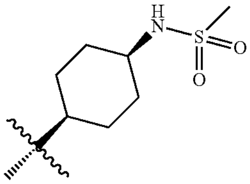
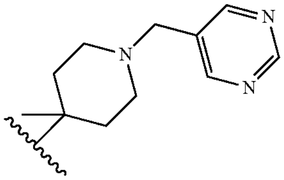
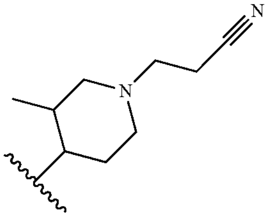
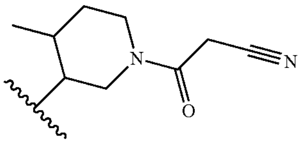
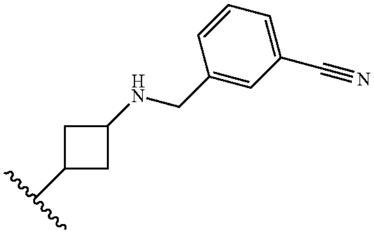
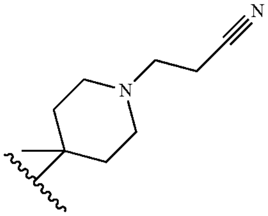
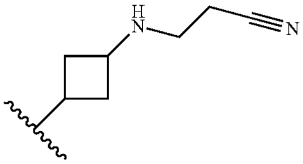
-continued
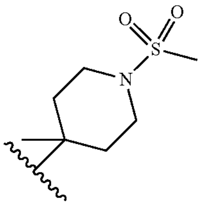
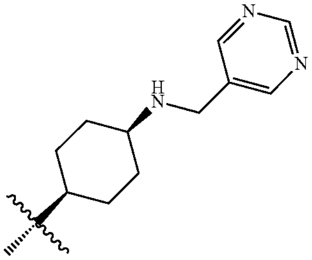
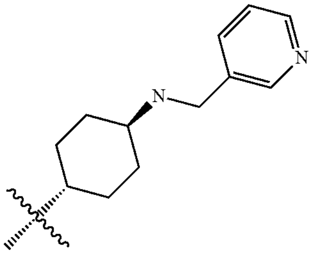
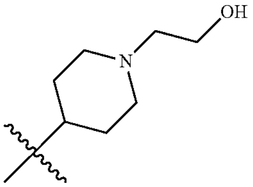
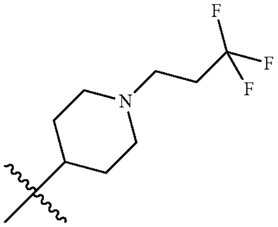
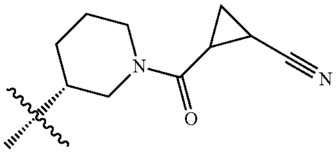
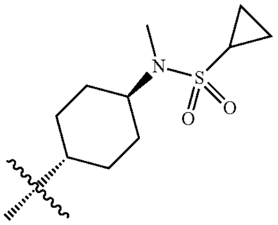
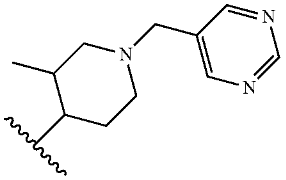
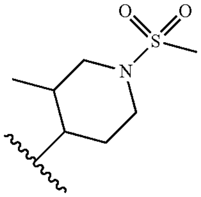
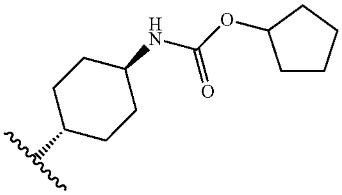

-continued
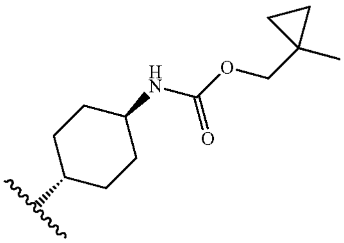
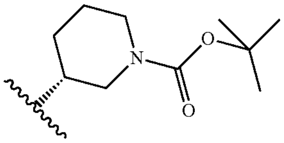
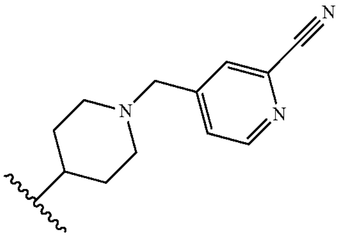
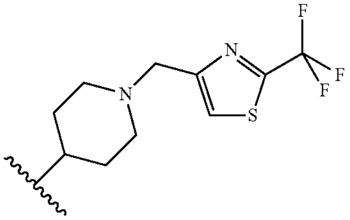
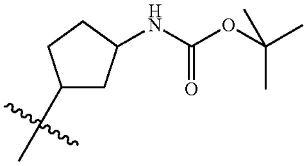
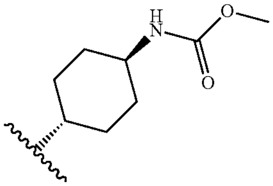
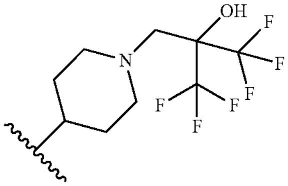
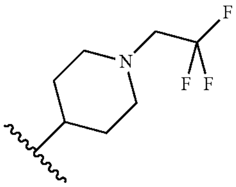
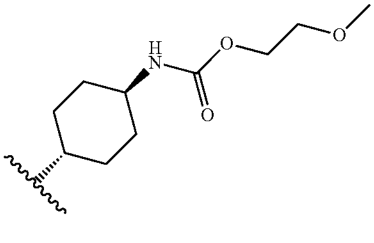
-continued
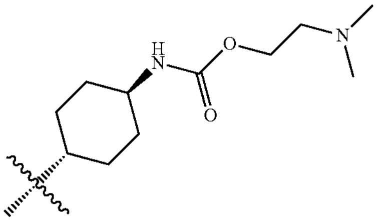
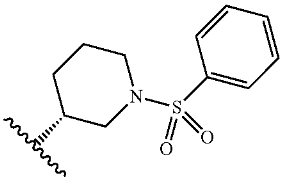
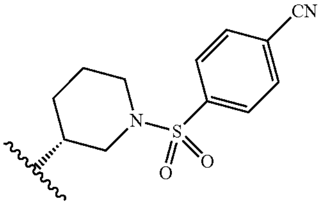
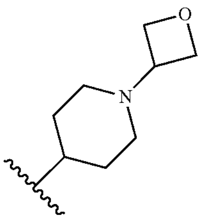
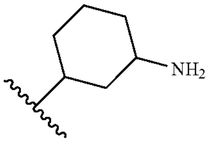
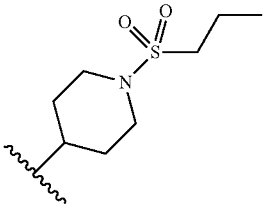
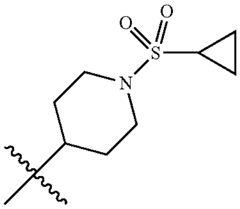
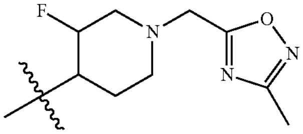
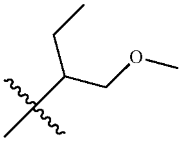
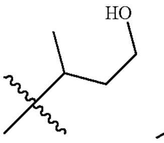
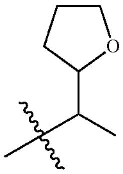
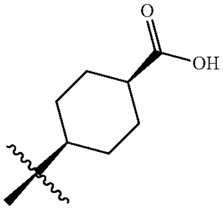
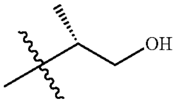
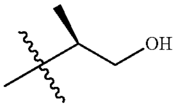
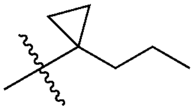
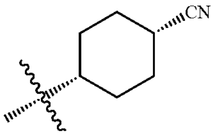
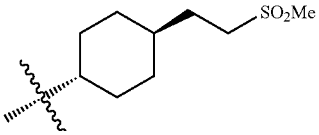

-continued
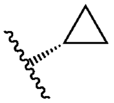
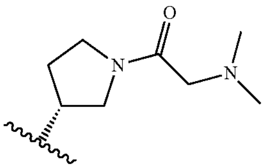
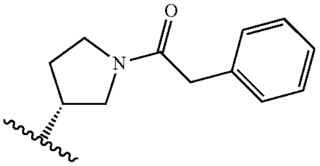
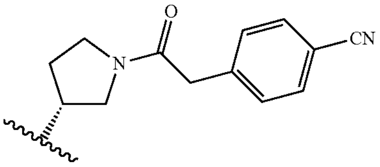
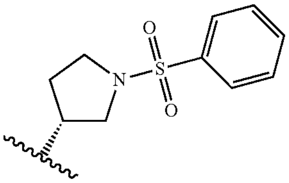
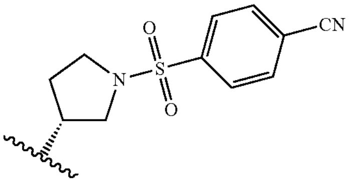
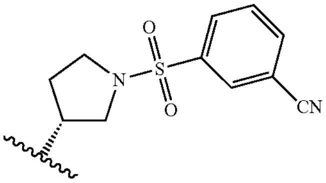
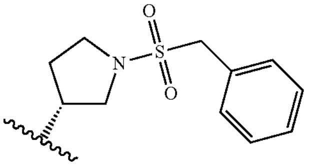
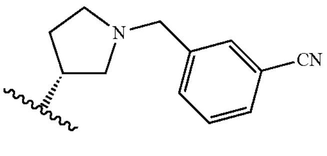
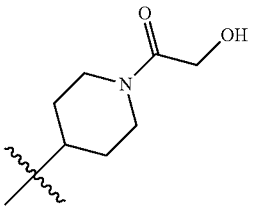
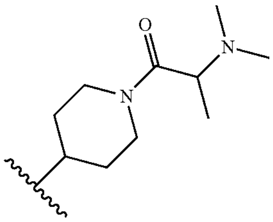
-continued
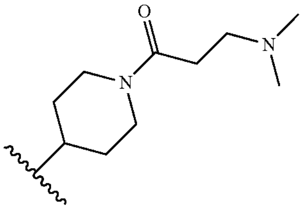
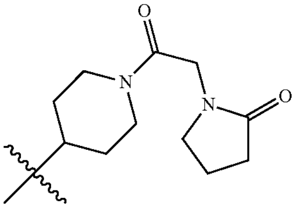
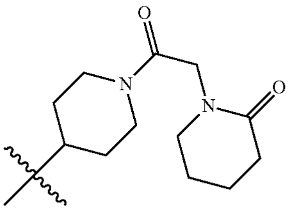
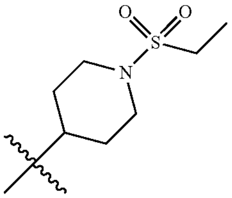
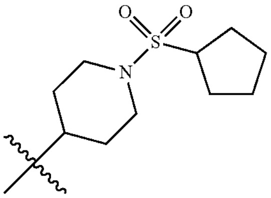
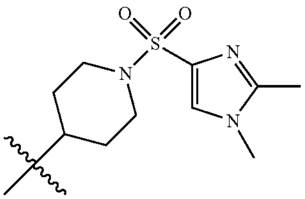
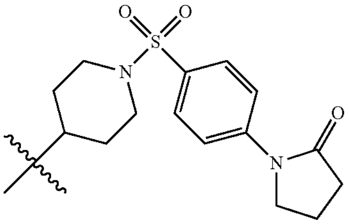
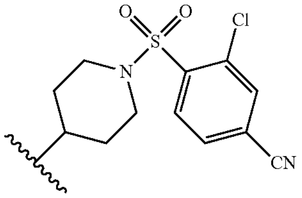
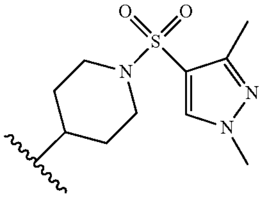
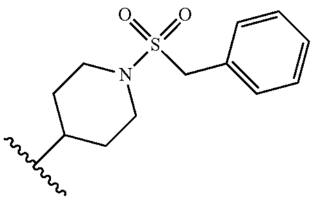

-continued
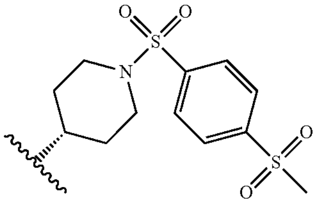
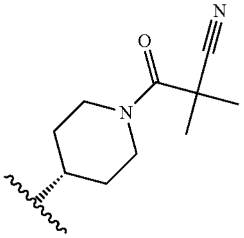
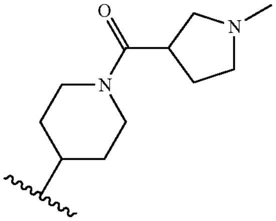
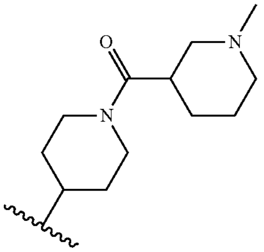
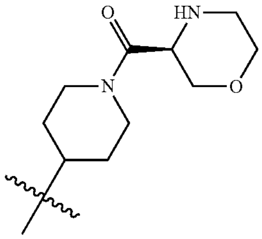
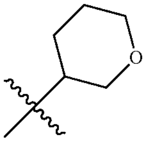
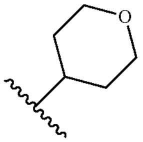
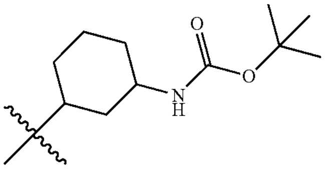
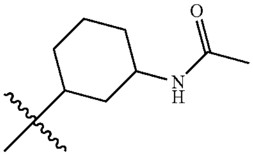
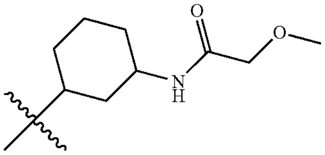
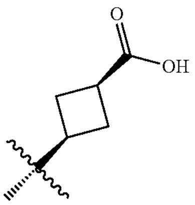
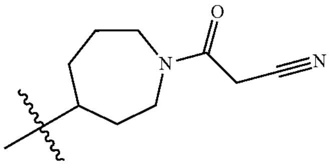
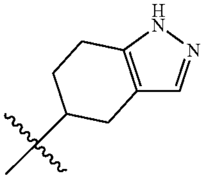
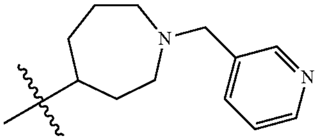
-continued
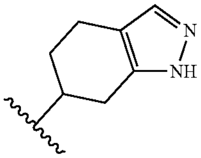
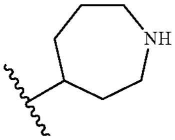
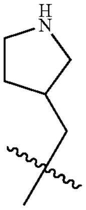
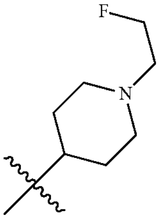
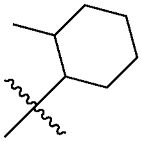
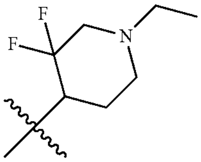
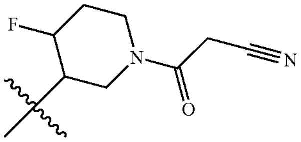
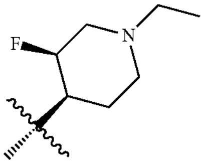
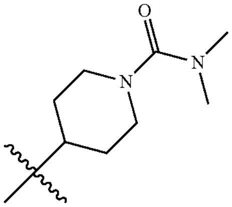
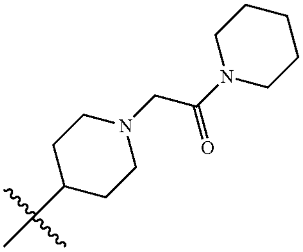
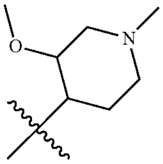
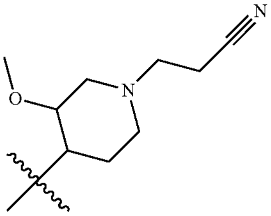
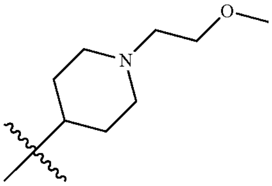
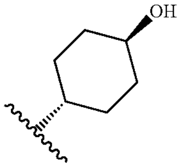
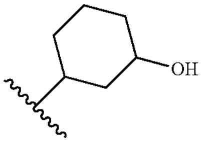
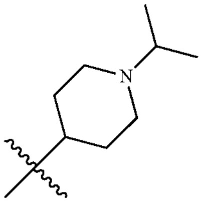

-continued
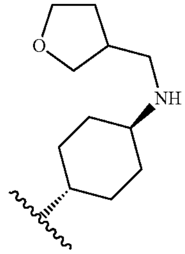
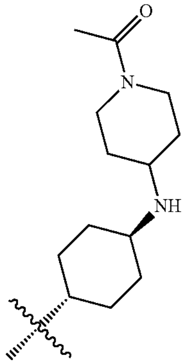
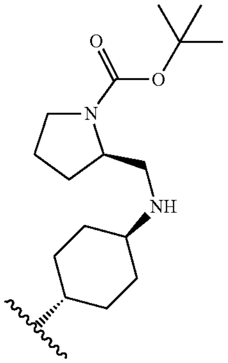
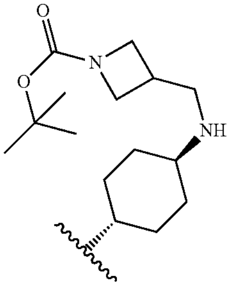
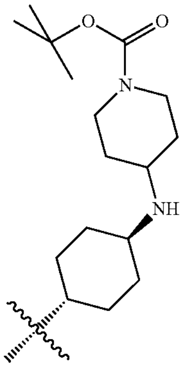
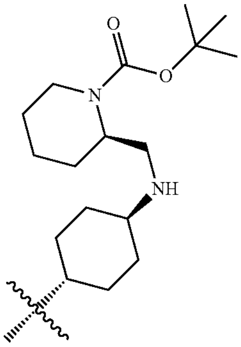
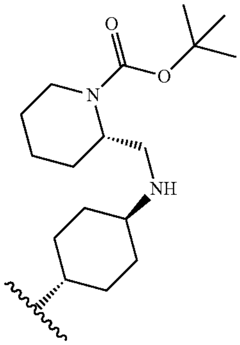
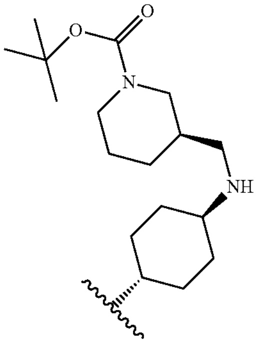
-continued
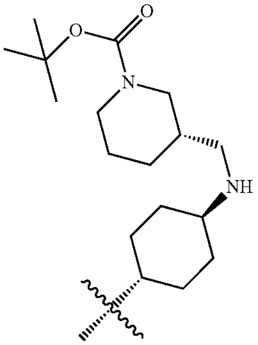
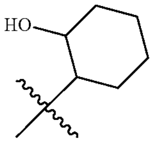
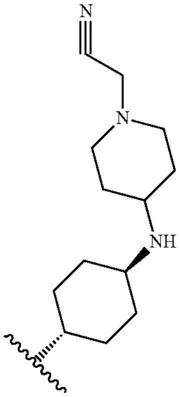
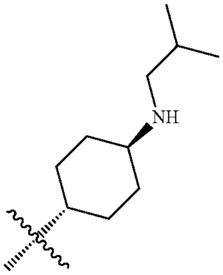
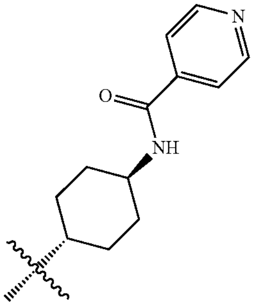
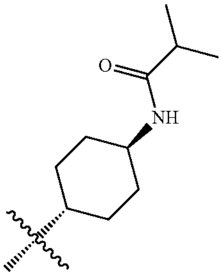
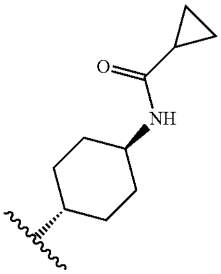
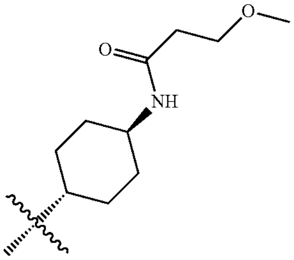
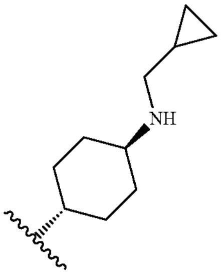
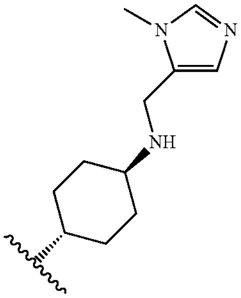

-continued
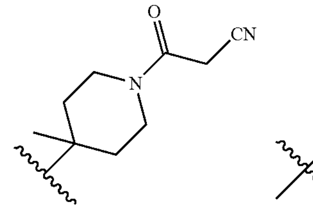
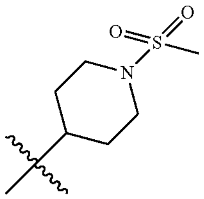
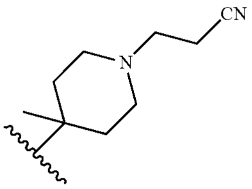
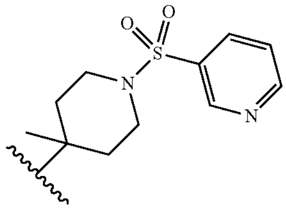
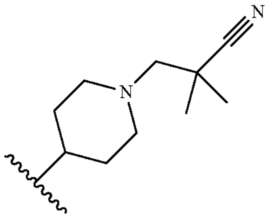
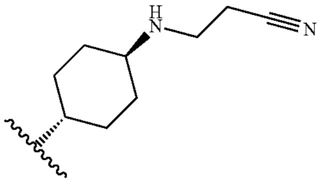
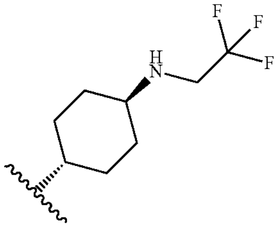
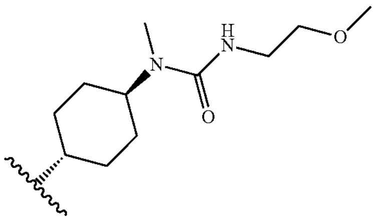
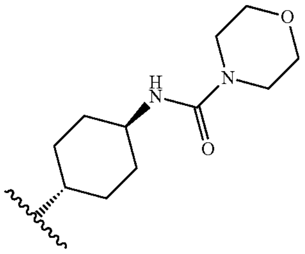
-continued
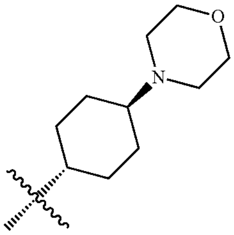
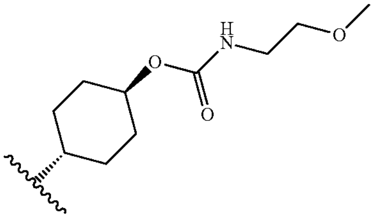
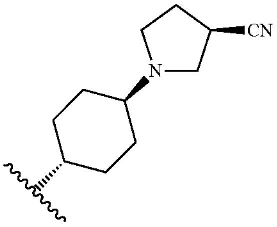
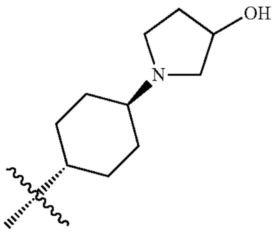
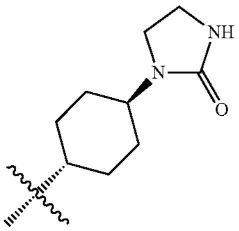
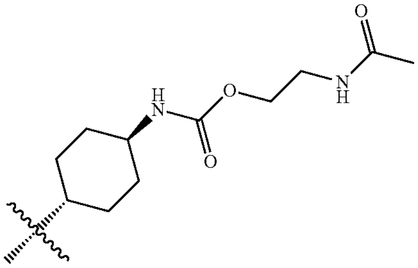
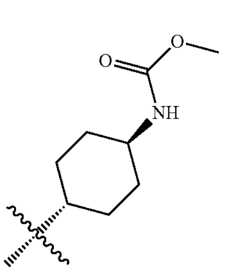
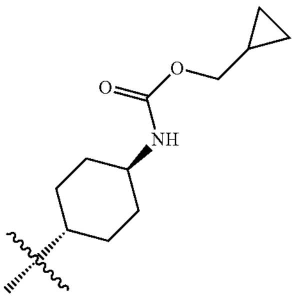

-continued
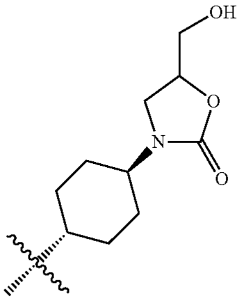
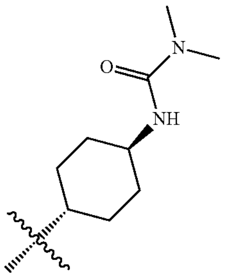
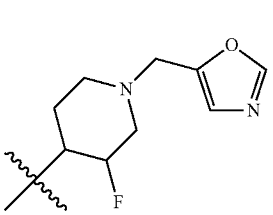
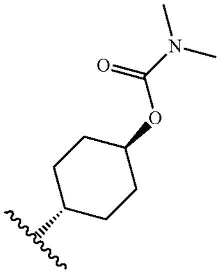
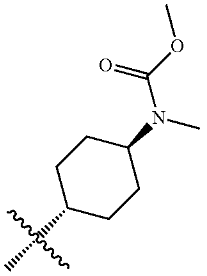
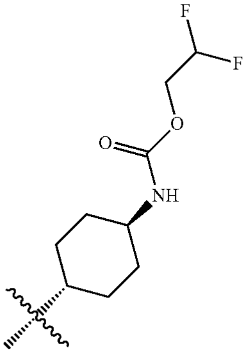
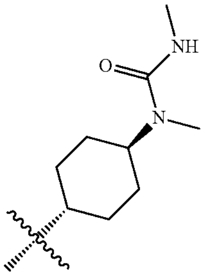
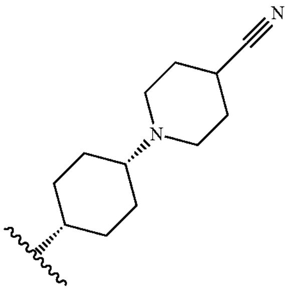
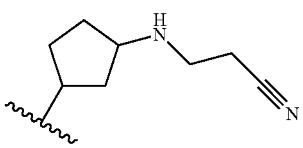
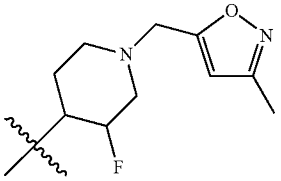
-continued
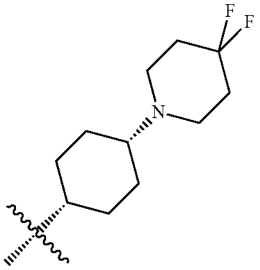
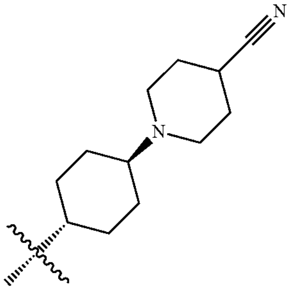
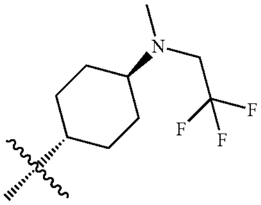
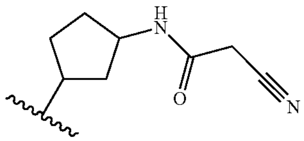
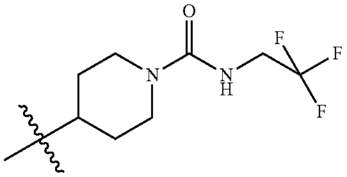
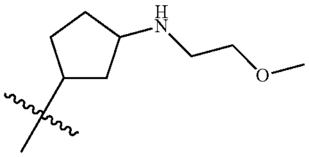
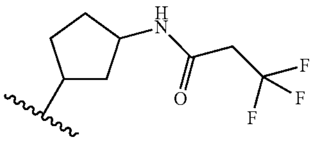
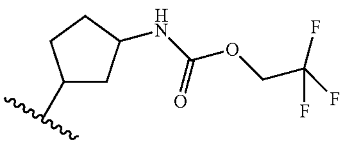
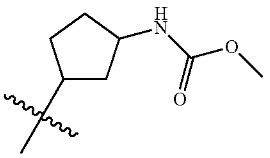
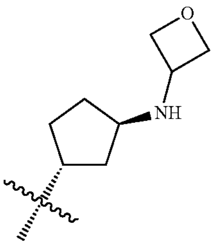

-continued
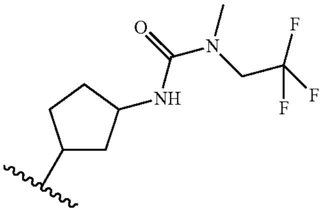
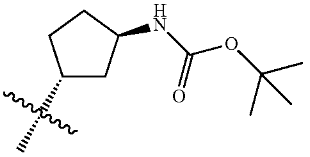
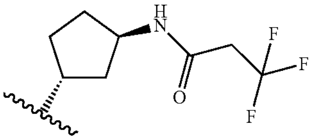
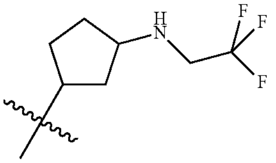
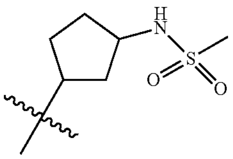
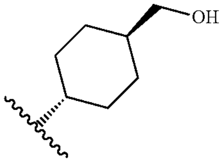
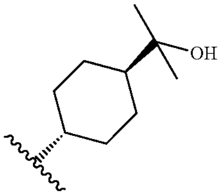
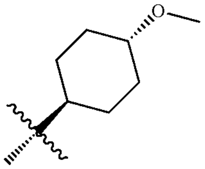
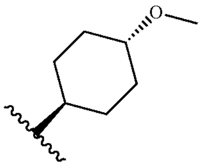
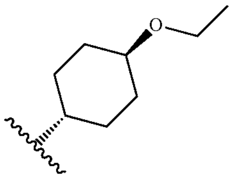
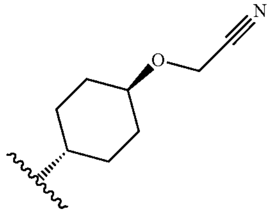
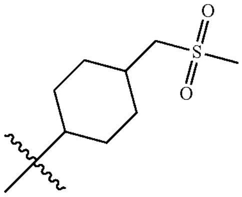
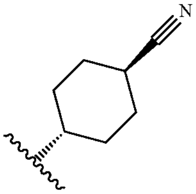
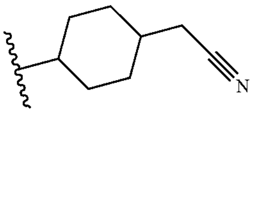
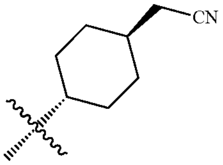
-continued
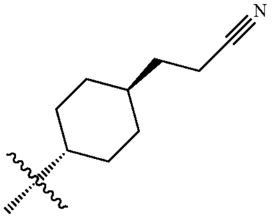
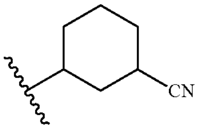
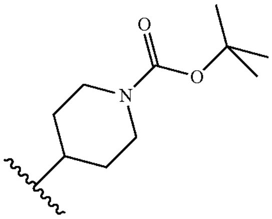
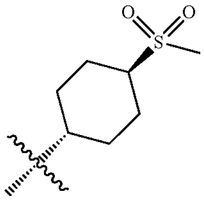
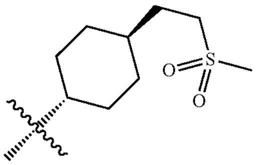
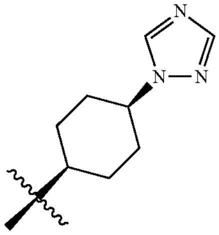
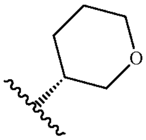
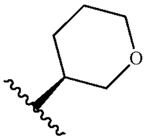
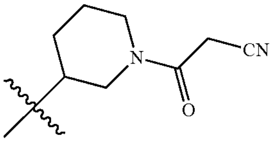
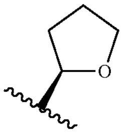
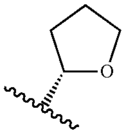
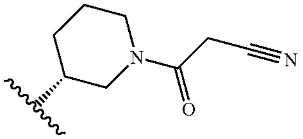
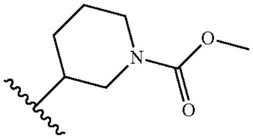
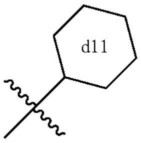
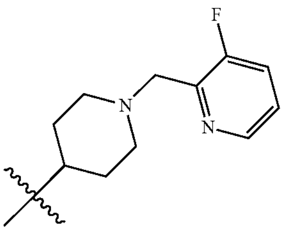
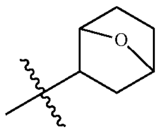
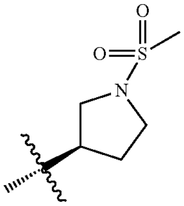
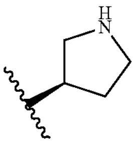
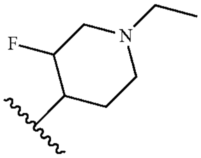

-continued
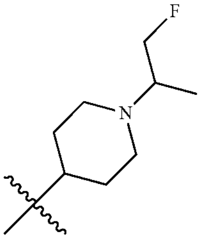
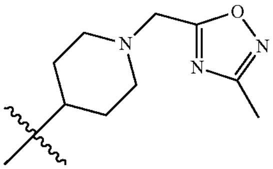
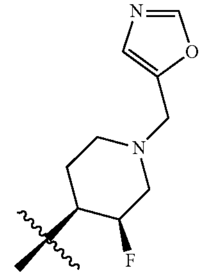
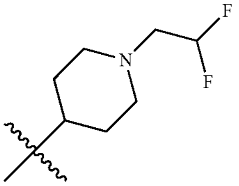
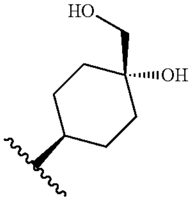
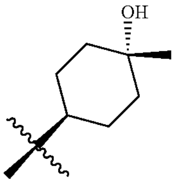
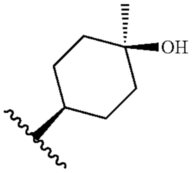
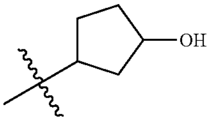
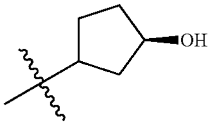
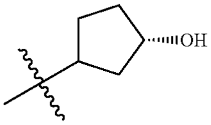
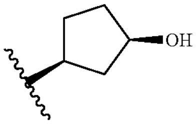
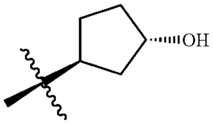
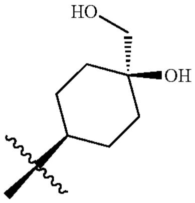
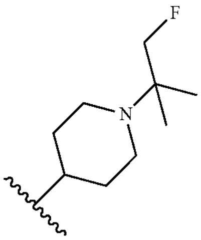
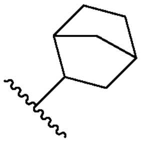
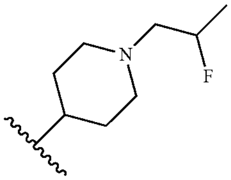
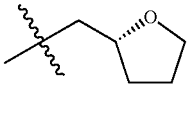
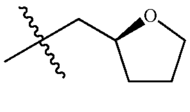
-continued
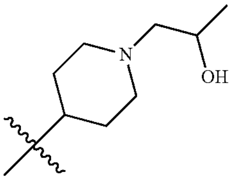
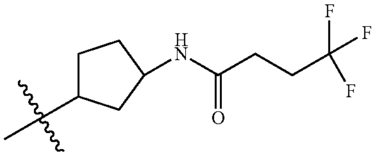
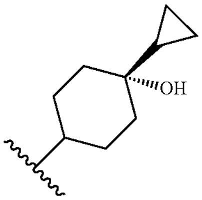
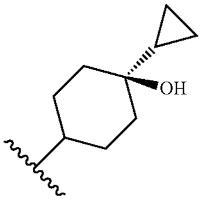
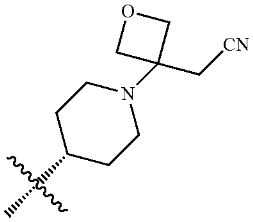
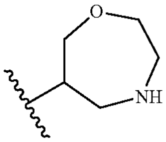
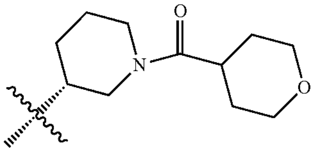
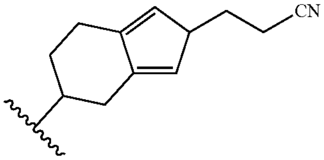
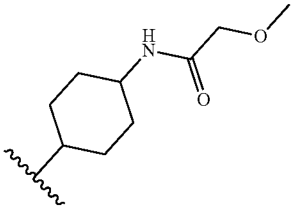
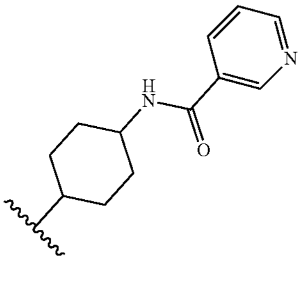

-continued
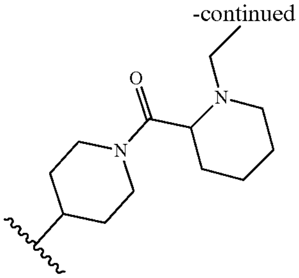
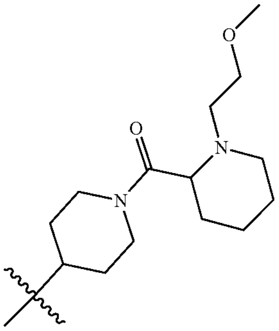
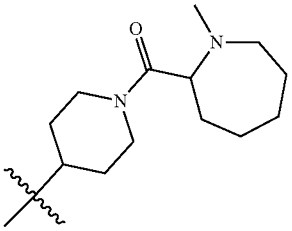
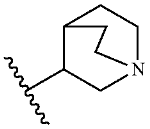
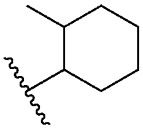
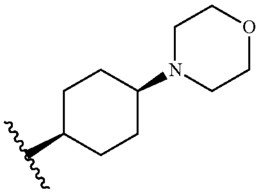
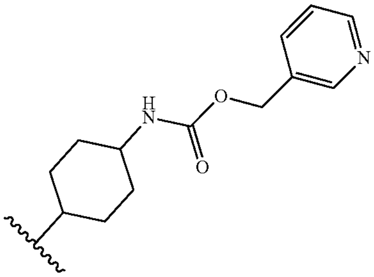
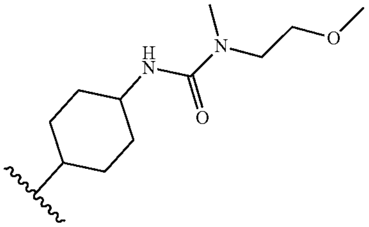
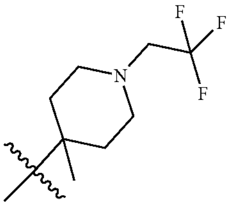
-continued
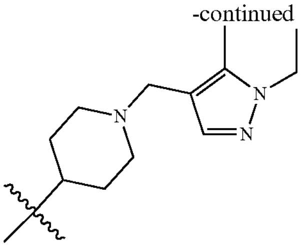
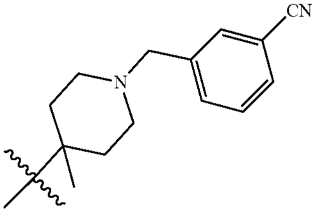
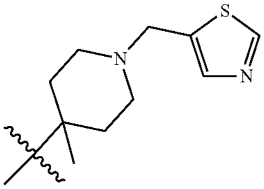
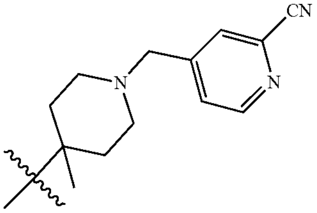
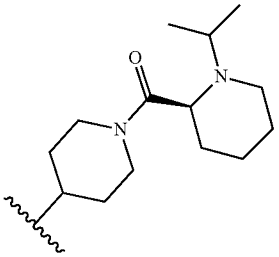
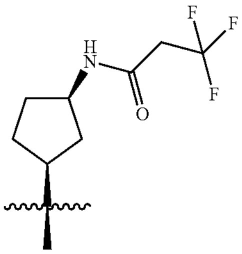
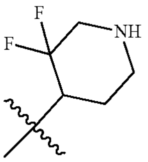
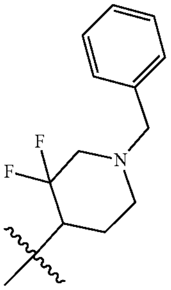
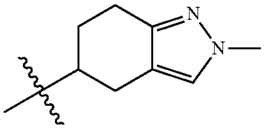
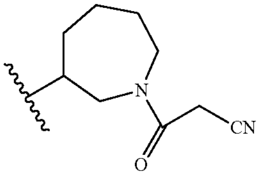
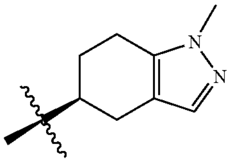
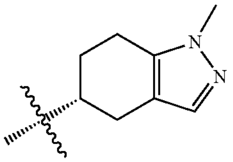

-continued
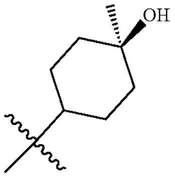
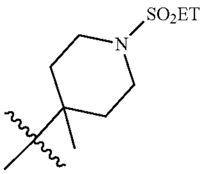
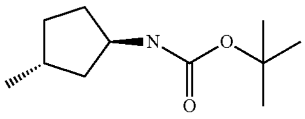
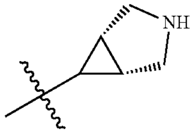
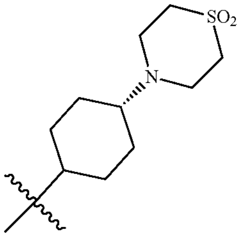
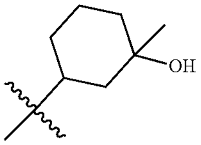
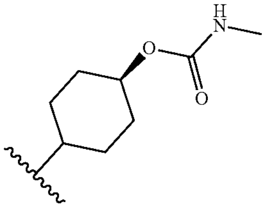
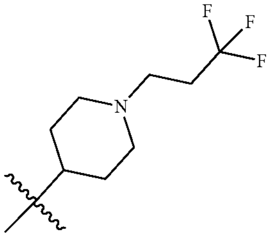
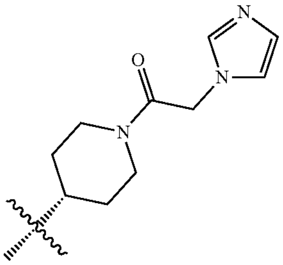
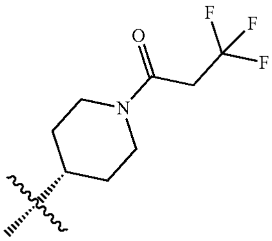
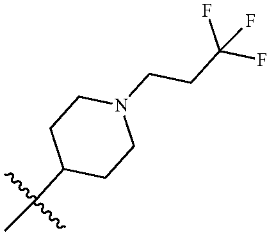
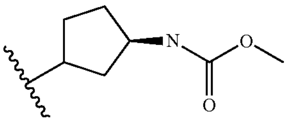
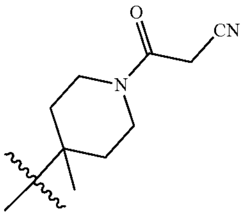
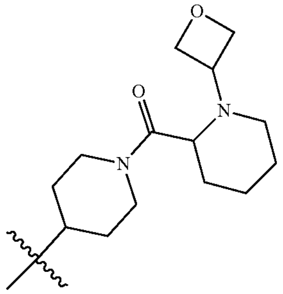
-continued
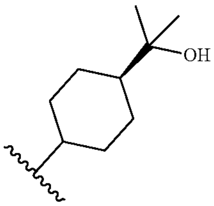
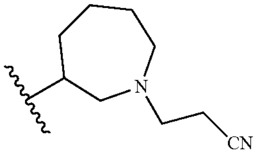
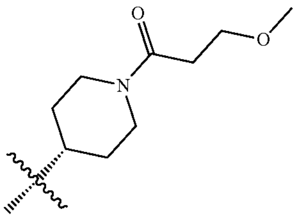
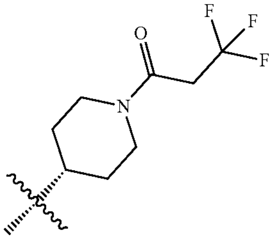
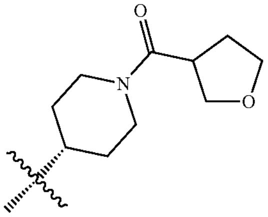
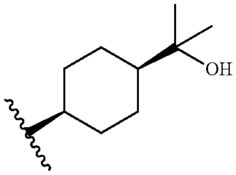
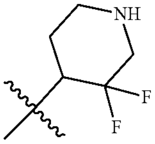
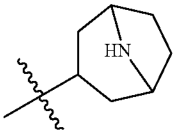
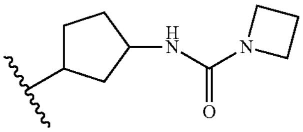
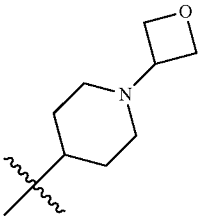
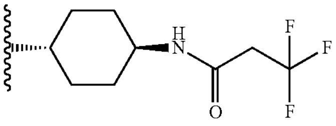
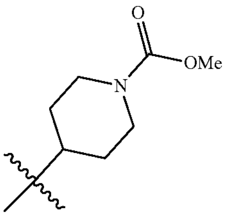
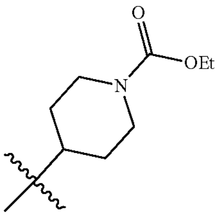

-continued
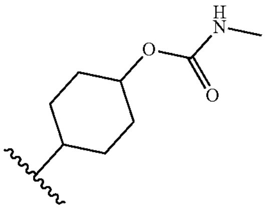
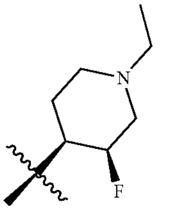
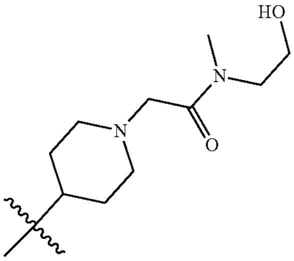
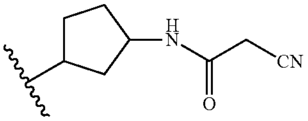
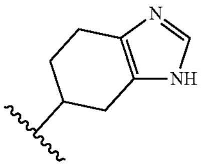
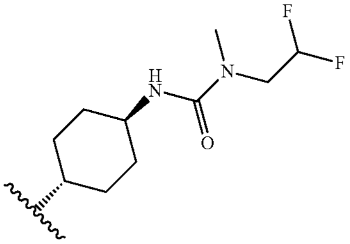
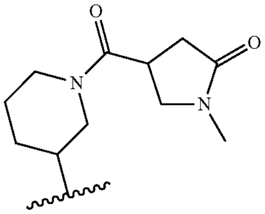
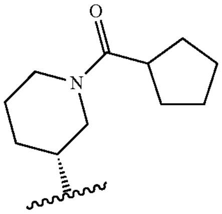
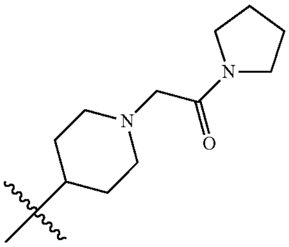
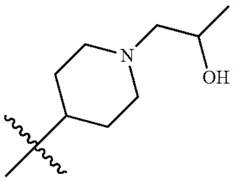
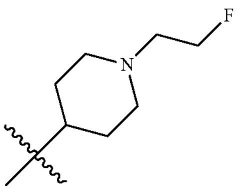
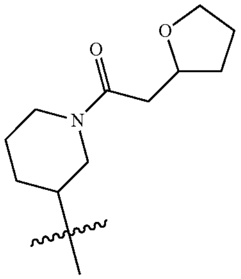
-continued
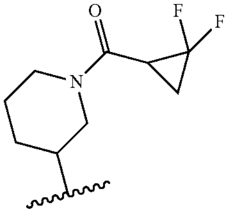
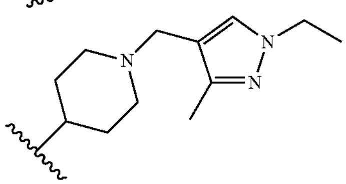
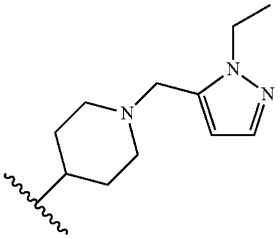
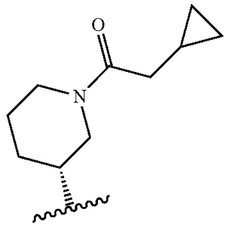
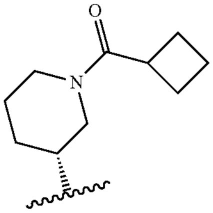
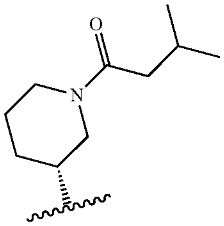
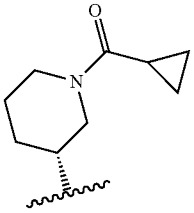
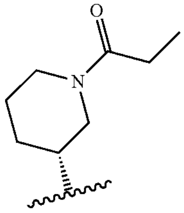
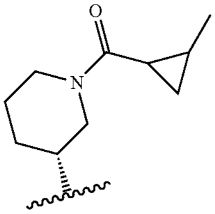
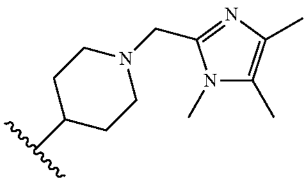
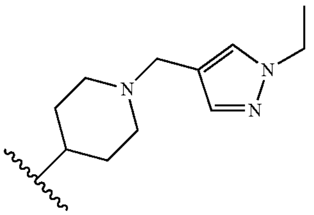
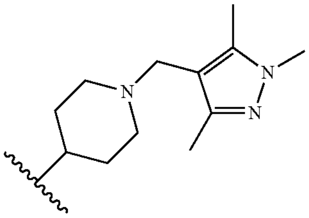

-continued
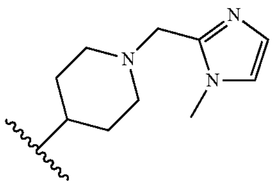
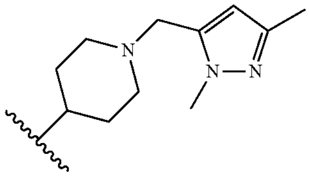
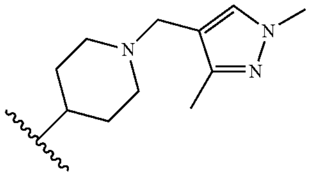
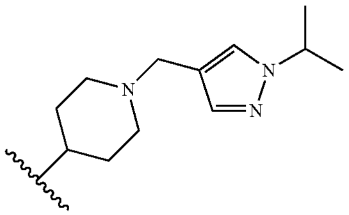
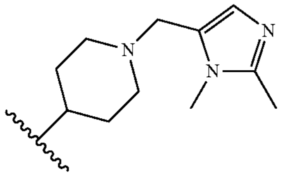
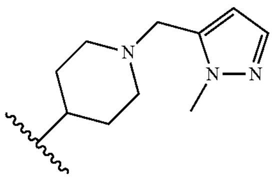
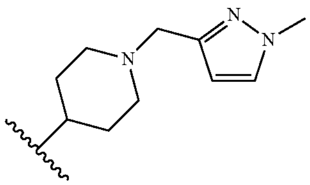
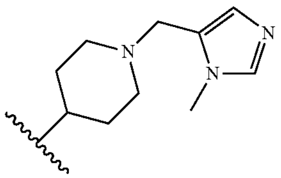
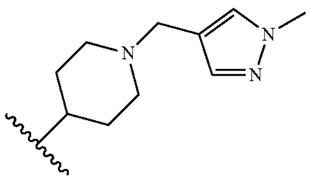
-continued
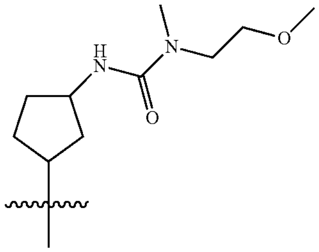
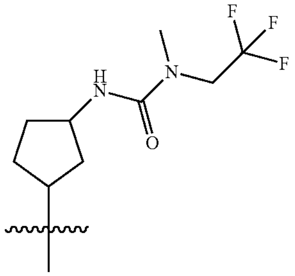
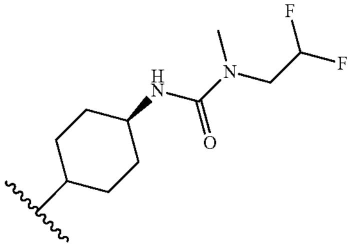
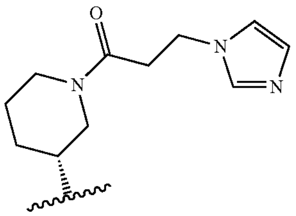
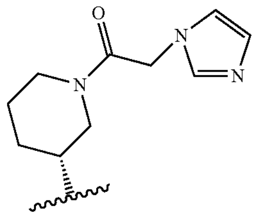
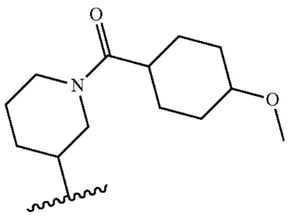
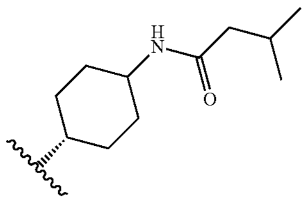
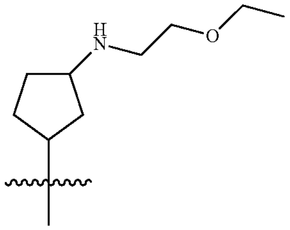

-continued

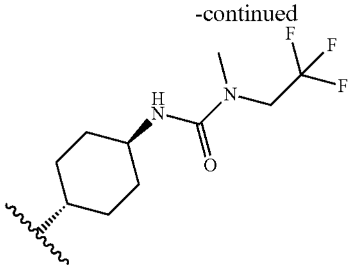

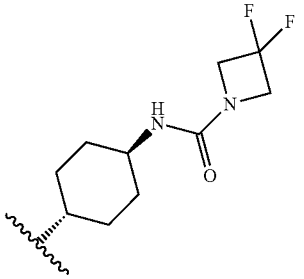

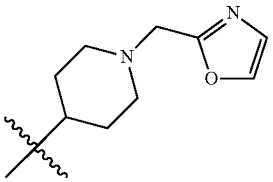

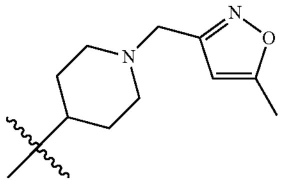

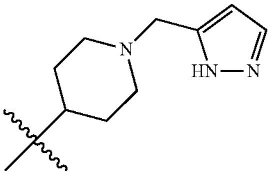

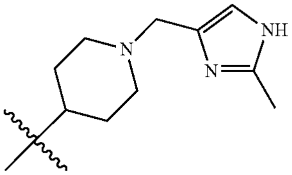

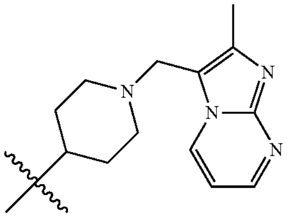

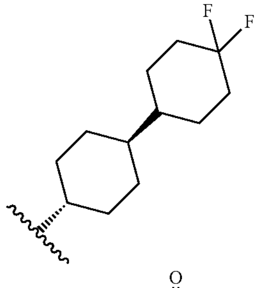

or

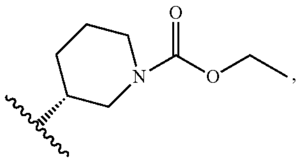

, wherein the wavy line represents the point of attachment in formula I.

Another embodiment includes a compound selected from Examples 1-108.

Another embodiment includes a compound selected from Examples 1-578.

Another embodiment includes a compound selected from Examples 1-1014.

Another embodiment includes a compound selected from:

1-[4-(2-Hydroxy-ethyl)-piperazin-1-yl]-2-[1-(tetrahydro-pyran-3-yl)-1,6-dihydro-1,2,3,5,6-tetraaza-as-indacen-2-yl]-ethanone;

N-tert-Butyl-2-[1-(tetrahydro-pyran-3-yl)-1,6-dihydro-1,2,3,5,6-tetraaza-as-indacen-2-yl]-acetamide;

((S)-1-Oxetan-3-yl-piperidin-2-yl)-[4-(6H-1,2,3,5,6-tetraaza-as-indacen-1-yl)-piperidin-1-yl]-methanone;

(1R,5S,6S)-1-(3-Aza-bicyclo[3.1.0]hex-6-yl)-1,6-dihydro-1,2,3,5,6-tetraaza-as-indacene;

(1-Cyclohexyl-1,6-dihydro-1,2,3,5,6-tetraaza-as-indacen-2-yl)-methanol-d11;

trans[3-(2-Methyl-6H-1,2,3,5,6-tetraaza-as-indacen-1-yl)-cyclopentyl]-(2,2,2-trifluoro-ethyl)-amine;

Isopropyl-[4-(6H-1,2,3,5,6-tetraaza-as-indacen-1-yl)-cyclohexyl]-amine;

(1R,3R)-3-(2-Methyl-6H-1,2,3,5,6-tetraaza-as-indacen-1-yl)-cyclohexanol; and

N-[4-(6H-1,2,3,5,6-Tetraaza-as-indacen-1-yl)-3,4,5,6-tetrahydro-2H-[1,2]bipyridinyl-5'-yl]-methanesulfonamide.

Another embodiment includes a compound selected from:

Cis 4-[2-((R)-1-Hydroxy-ethyl)-6H-1,2,3,5,6-tetraaza-as-indacen-1-yl]-cyclohexanecarbonitrile;

Trans (R)-1-{1-[4-(2,2,2-trifluoro-ethylamino)-cyclohexyl]-1,6-dihydro-1,2,3,5,6-tetraaza-as-indacen-2-yl}-ethanol;

Trans {4-[2-((R)-1-Hydroxy-ethyl)-6H-1,2,3,5,6-tetraaza-as-indacen-1-yl]-cyclohexyl}-acetonitrile;

(1R,3R)-3-[2-((R)-1-Hydroxy-ethyl)-6H-1,2,3,5,6-tetraaza-as-indacen-1-yl]-cyclohexanol;

Trans 3-{4-[2-((R)-1-Hydroxy-ethyl)-6H-1,2,3,5,6-tetraaza-as-indacen-1-yl]-cyclohexyl}-propionitrile;

trans 4-[2-((R)-1-Hydroxy-ethyl)-6H-1,2,3,5,6-tetraaza-as-indacen-1-yl]-cyclohexanecarbonitrile;

1-(1-Methanesulfonyl-4-methyl-piperidin-4-yl)-2-methyl-1,6-dihydro-1,2,3,5,6-tetraaza-as-indacene;

(R)-1-[(S)-1-(Tetrahydro-pyran-3-yl)-1,6-dihydro-1,2,3,5,6-tetraaza-as-indacen-2-yl]-ethanol; and (1R,3R)-3-(2-Methyl-6H-1,2,3,5,6-tetraaza-as-indacen-1-yl)-cyclohexanol.

Another embodiment includes a compound selected from:

1-(1-Benzyl-3,3-difluoro-piperidin-4-yl)-1,6-dihydro-1,2,3,5,6-tetraaza-as-indacene;

2-[(R)-3-(6H-1,2,3,5,6-Tetraaza-as-indacen-1-yl)-pyrrolidin-1-yl]-ethanol;

3-[(R)-3-(6H-1,2,3,5,6-Tetraaza-as-indacen-1-yl)-pyrrolidin-1-yl]-propionitrile;

N-(1-Piperidin-4-yl-1,6-dihydro-1,2,3,5,6-tetraaza-as-indacen-2-ylmethyl)-methanesulfonamide;

Isopropyl-[4-(6H-1,2,3,5,6-tetraaza-as-indacen-1-yl)-cyclohexyl]-amine;

Trans 3-{[4-(6H-1,2,3,5,6-Tetraaza-as-indacen-1-yl)-cyclohexylamino]-methyl}-benzonitrile;

1-Phenyl-2-[(R)-3-(6H-1,2,3,5,6-tetraaza-as-indacen-1-yl)-piperidin-1-yl]-ethanone;

1-(8-Benzyl-8-aza-bicyclo[3.2.1]oct-3-yl)-2-methyl-1,6-dihydro-1,2,3,5,6-tetraaza-as-indacene; and 3-[4-(2-Isopropyl-6H-1,2,3,5,6-tetraaza-as-indacen-1-yl)-piperidin-1-yl]-propionitrile.

Another embodiment includes a compound selected from:

[4-(2-Hydroxymethyl-6H-1,2,3,5,6-tetraaza-as-indacen-1-yl)-cyclohexyl]-acetonitrile;

3-[4-(2-hydroxymethyl-6H-1,2,3,5,6-tetraaza-as-indacen-1-yl)-cyclohexyl]-propionitrile;

(R)-1-[1-(4-Methanesulfonylmethyl-cyclohexyl)-1,6-dihydro-1,2,3,5,6-tetraaza-as-indacen-2-yl]-ethanol;

N-[2-(1-Cyclohexyl-1,6-dihydro-1,2,3,5,6-tetraaza-as-indacen-2-yl)-ethyl]-acetamide;

1-Cyclohexyl-2-((R)-1-methoxy-ethyl)-1,6-dihydro-1,2,3,5,6-tetraaza-as-indacene;

(R)-1-(1-Cyclopentyl-1,6-dihydro-1,2,3,5,6-tetraaza-as-indacen-2-yl)-ethanol;

(R)-1-[1-(1-But-3-ynyl-piperidin-4-yl)-1,6-dihydro-1,2,3,5,6-tetraaza-as-indacen-2-yl]-ethanol;

2-[1-(1-Benzyl-piperidin-4-yl)-2-methyl-1,6-dihydro-1,2,3,5,6-tetraaza-as-indacen-2-yl]ethanol; and 2-Methyl-1-piperidin-4-yl-1,6-dihydro-1,2,3,5,6-tetraaza-as-indacene.

Compounds of the invention may contain one or more asymmetric carbon atoms. Accordingly, the compounds may exist as diastereomers, enantiomers or mixtures thereof. The syntheses of the compounds may employ racemates, diastereomers or enantiomers as starting materials or as intermediates. Mixtures of particular diastereomeric compounds may be separated, or enriched in one or more particular diastereomers, by chromatographic or crystallization methods. Similarly, enantiomeric mixtures may be separated, or enantiomerically enriched, using the same techniques or others known in the art. Each of the asymmetric carbon or nitrogen atoms may be in the R or S configuration and both of these configurations are within the scope of the invention.

Another aspect includes prodrugs of the compounds of formula I, including known amino-protecting and carboxy-protecting groups which are released, for example hydrolyzed, to yield the compound of formula I under physiologic conditions. A particular class of prodrugs are compounds in which a nitrogen atom in an amino, amidino, aminoalkyleneamino, iminoalkyleneamino or guanidino group is substituted with a hydroxy (OH) group, an alkylcarbonyl (—CO—R) group, an alkoxycarbonyl (—CO—OR), an acyloxyalkyl-alkoxycarbonyl (—CO—O—R—O—CO—R) group where R is a monovalent or divalent group, for example alkyl, alkylene or aryl, or a group having the formula —C(O)—O—CP1P2-haloalkyl, where P1 and P2 are the same or different and are hydrogen, alkyl, alkoxy, cyano, halogen, alkyl or aryl. In a particular embodiment, the nitrogen atom is one of the nitrogen atoms of the amidino group of the compounds of formula I. Prodrugs may be prepared by reacting a compound of formula I with an activated group, such as acyl groups, to bond, for example, a nitrogen atom in the compound of formula I to the exemplary carbonyl of the activated acyl group. Examples of activated carbonyl compounds are those containing a leaving group bonded to the carbonyl group, and include, for example, acyl halides, acyl amines, acyl pyridinium salts, acyl alkoxides, acyl phenoxides such as p-nitrophenoxy acyl, dinitrophenoxy acyl, fluorophenoxy acyl, and difluorophenoxy acyl. The reactions are generally carried out in inert solvents at reduced temperatures such as −78 to about 50° C. The reactions may also be carried out in the presence of an inorganic base, for example potassium carbonate or sodium bicarbonate, or an organic base such as an amine, including pyridine, trimethylamine, triethylamine, triethanolamine, or the like.

Synthesis of JAK1 Inhibitor Compounds

Compounds of formula I may be synthesized by synthetic routes described herein. In certain embodiments, processes well-known in the chemical arts can be used, in addition to, or in light of, the description contained herein. The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, *Reagents for Organic Synthesis*, v. 1-19, Wiley, N.Y. (1967-1999 ed.), Beilsteins Handbuch der organischen Chemie, 4, Aufl. ed. Springer-Verlag, Berlin, including supplements (also available via the Beilstein online database)), or *Comprehensive Heterocyclic Chemistry, Editors Katrizky and Rees, Pergamon Press,* 1984.

Compounds of formula I may be prepared singly or as compound libraries comprising at least 2, for example 5 to 1,000 compounds, or 10 to 100 compounds of formula I. Libraries of compounds of formula I may be prepared by a combinatorial 'split and mix' approach or by multiple parallel syntheses using either solution phase or solid phase chemistry, by procedures known to those skilled in the art. Thus according to a further aspect of the invention there is provided a compound library comprising at least 2 compounds of formula I, enantiomers, diastereomers, tautomers or pharmaceutically acceptable salts thereof.

For illustrative purposes, reaction schemes 1-22 depicted below provide routes for synthesizing the compounds of the present invention as well as key intermediates. For a more detailed description of the individual reaction steps, see the Examples section below. Those skilled in the art will appreciate that other synthetic routes may be used to synthesize the inventive compounds. Although specific starting materials and reagents are depicted in the Schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

In the preparation of compounds of the present invention, protection of remote functionality (e.g., primary or secondary amine) of intermediates may be necessary. The need for such protection will vary depending on the nature of the remote functionality and the conditions of the preparation methods. Suitable amino-protecting groups (NH-Pg) include acetyl, trifluoroacetyl, benzyl, phenylsulfonyl, t-butoxycarbonyl (BOC), benzyloxycarbonyl (CBz) and 9-fluorenylmethyleneoxycarbonyl (Fmoc). The need for such protection is readily determined by one skilled in the art. For a general description of protecting groups and their use, see T. W. Greene, Protective Groups in Organic Synthesis, John Wiley & Sons, New York, 1991.

Compounds of the invention may be prepared from readily available starting materials using the general methods illustrated in Reaction Schemes 1-22 below.

Reaction Scheme 1

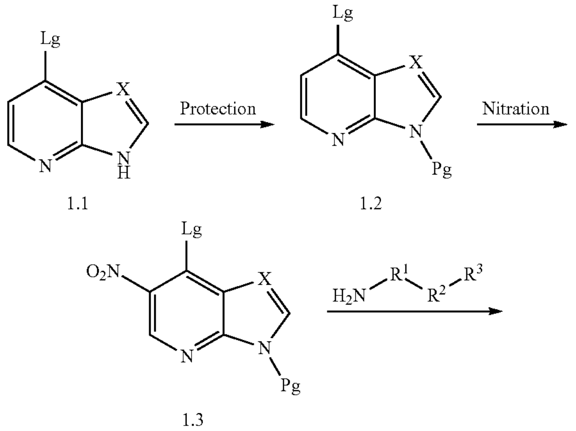

1.1 1.2 1.3

-continued

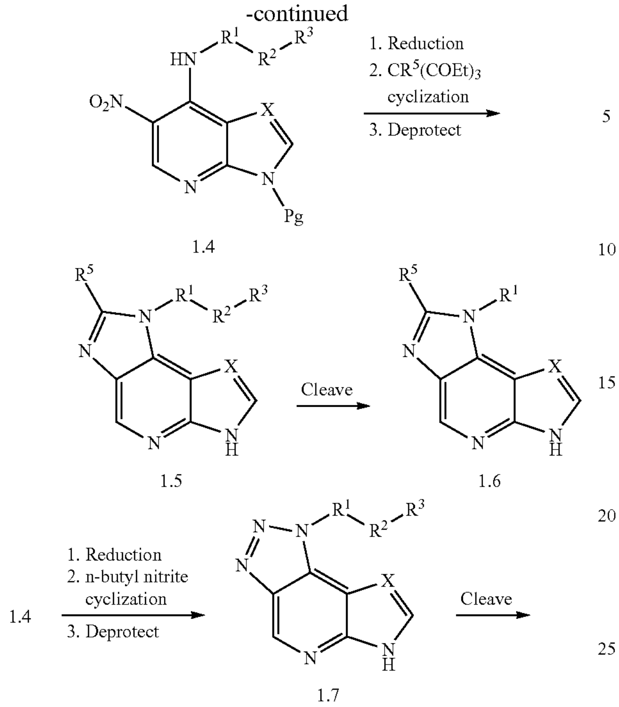

1.4

1.5

1.6

1.7

-continued

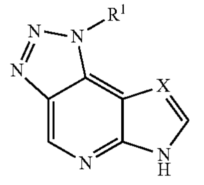

1.8

Compounds of formula I can be synthesized as shown in Reaction Scheme 1. For example, commercially available 4-substituted azaindole (where X is $CR^4$) or imidazopyridine (where X is N) (Lg is a leaving group, for example chloro) can be protected with an appropriate amino protecting group (Pg), to give amino-protected 1.2. Nitration of 1.2 gives nitro compound 1.3. Compound 1.4 can be prepared by treatment of compound 1.3 with a suitably substituted amine (wherein $R^1$, $R^2$ and $R^3$ are defined herein) in the presence of base. Compound 1.4 can be cyclized via two different routes to obtain tricyclic derivatives. In one route, reduction of compounds 1.4, cyclization with triethyl ortho formyl derivative (where $R^5$ is defined herein), and deprotection gives compounds 1.5. In another route, reduction of compounds 1.4, cyclization with n-butyl nitrite, and deprotection gives compounds 1.7. Independent treatment of compounds 1.5 or 1.7 with suitable cleavage conditions provides compounds 1.6 or 1.8.

Reaction Scheme 2

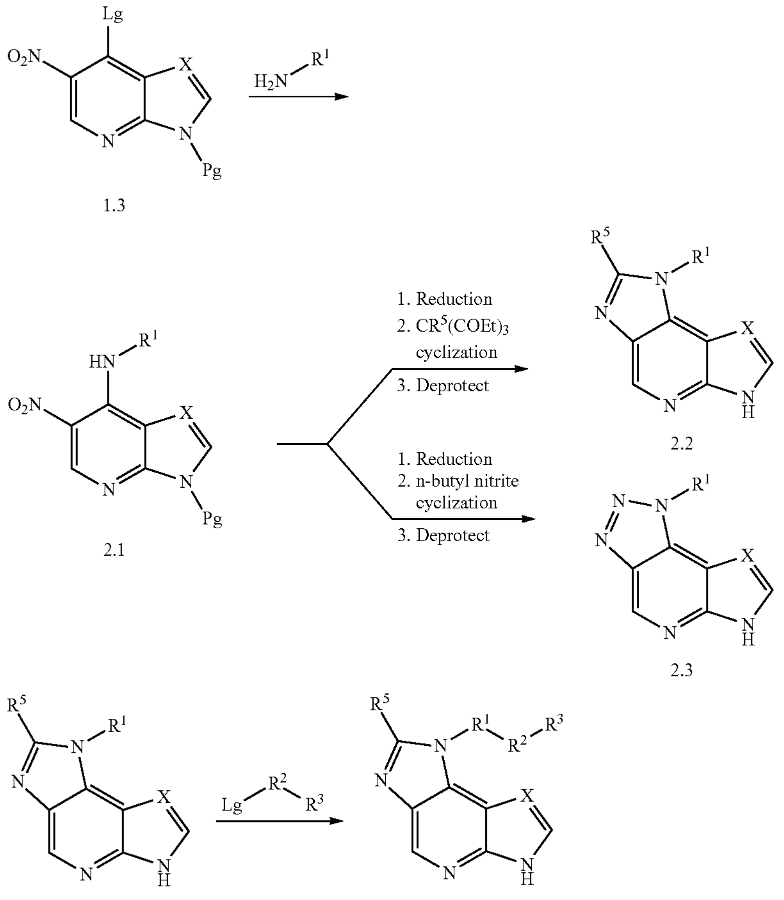

1.3

2.1

2.2

2.3

2.2

2.4

-continued

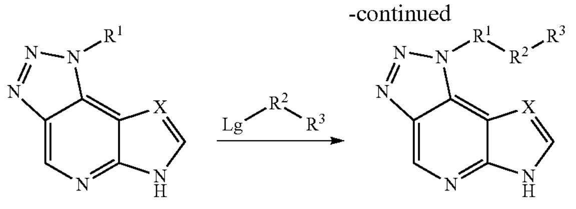

Compounds of formula I can also be synthesized as shown in Reaction Scheme 2. For example, azaindole (where X is $CR^4$) or imidazopyridine (where X is N) 1.3 can be reacted with a substituted amine, for example $—NH_2R^1$, in the presence of base to give compound 2.1. Independent reduction, cyclization and deprotection separately gives compounds 2.2 or 2.3. Further independent derivatization of compounds 2.2 or 2.3 gives compounds 2.4 or 2.5.

with a substituted amine, for example $—NH_2R^1$, in the presence of base to give compound 2.1a. After reduction, imidazole formation can be achieved using two general methods. i) Amide bond formation by treatment with an acid chloride or a carboxylic acid in the presence of a suitable coupling reagent such as EDCI or HATU will give an amide which can then be dehydratively cyclized by treating with a reagent such as glacial acetic acid. Deprotection will give compound 2.3a.

Reaction Scheme 2a

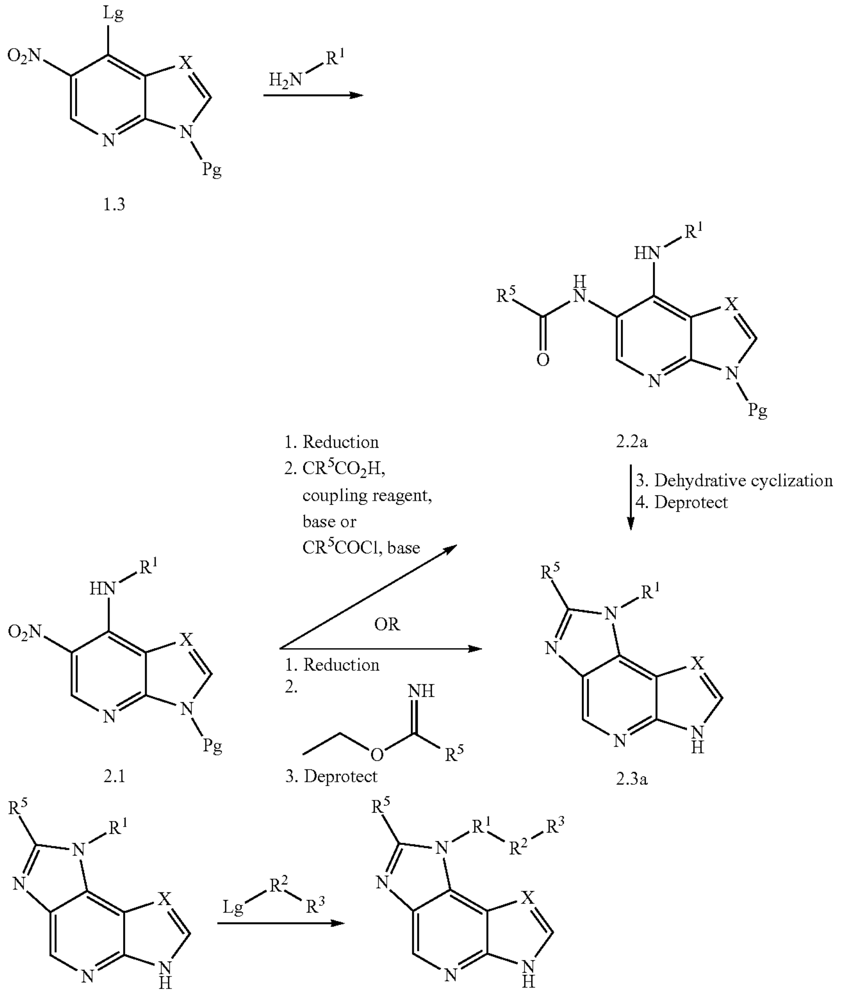

Compounds of formula I can also be synthesized as shown in Reaction Scheme 2a. For example, azaindole (where X is $CR^4$) or imidazopyridine (where X is N) 1.3 can be reacted ii) Treatment with an imidate, followed by deprotection will give compound 2.3a. Further independent derivatization of compound 2.3a gives compound 2.4a.

Reaction Scheme 3

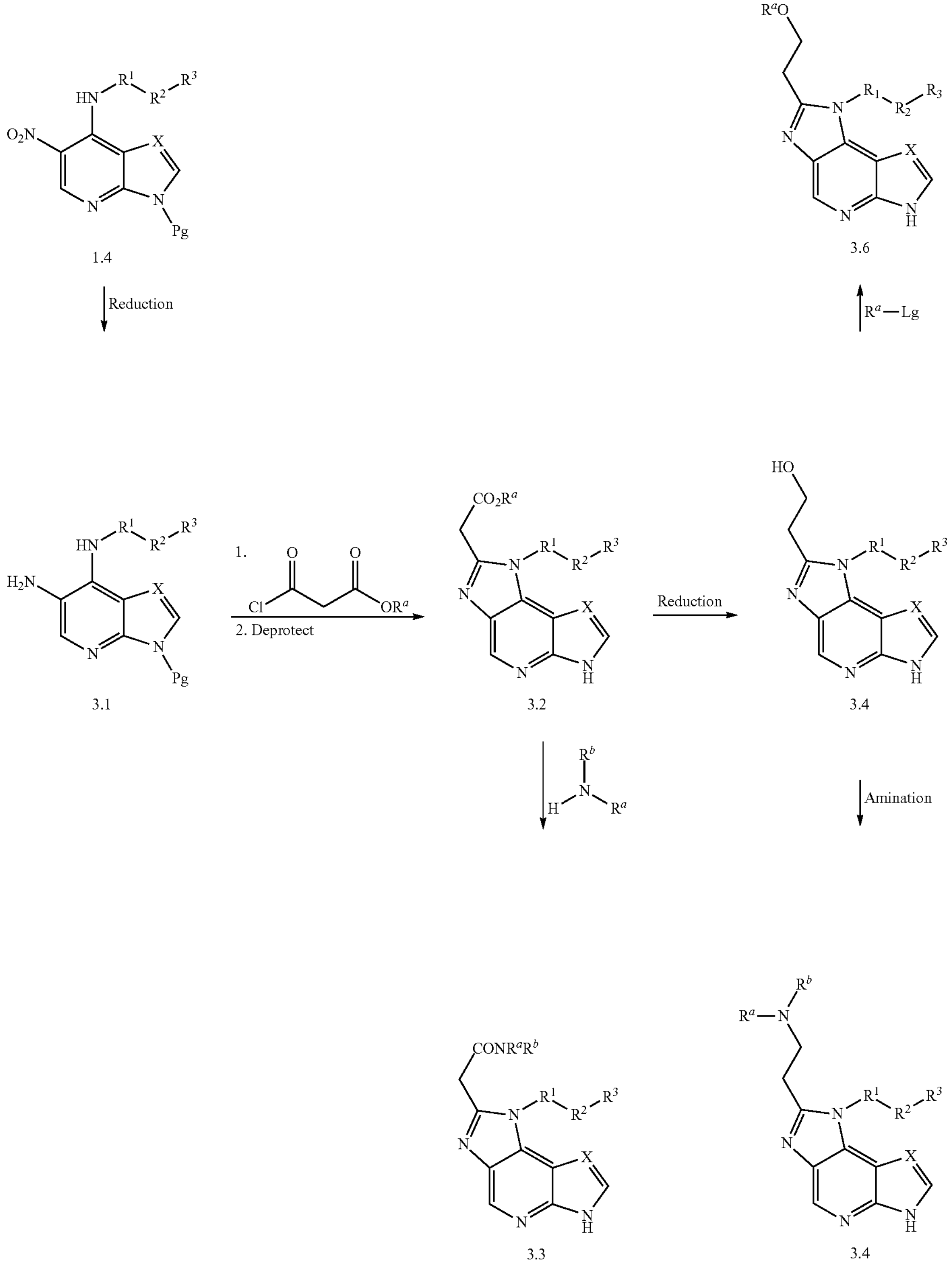

Compounds of formula I can also be synthesized as shown in Reaction Scheme 3. For example, azaindole (where X is $CR^4$) or imidazopyridine (where X is N) 1.4 can undergo reduction to produce the amine 3.1. Compound 3.1 can be cyclized, for example with malonyl chlorides, and deprotected to give compounds 3.2. Amidation of 3.2 with substituted amines (wherein $R^a$ and $R^b$ are defined herein) gives compounds 3.3. Reduction of 3.2 gives the alcohol 3.4. Alcohols 3.4 can undergo amination to give compounds 3.5, or further derivatized with $R^a$-Lg (where Lg is a leaving group) to give compounds 3.6.

Reaction Scheme 4

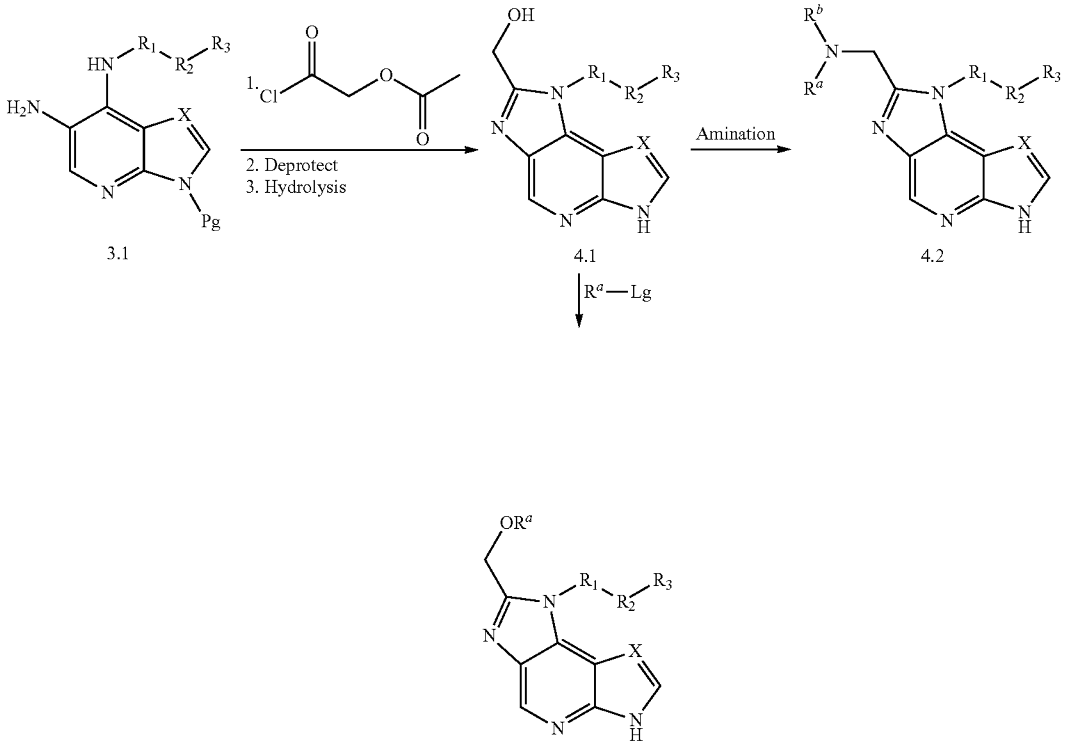

3.1 4.1 4.2 4.3

Compounds of formula I can also be synthesized as shown in Reaction Scheme 4. For example, compound 3.1 can be cyclized, for example with 2-chloro-2-oxoethyl acetate, deprotected and hydrolyzed to give tricyclic alcohol compounds 4.1. Alcohols 4.1 can undergo amination to give compounds 4.2, or further derivatized with $R^a$-Lg (where Lg is a leaving group) to give compounds 4.3.

Reaction Scheme 5

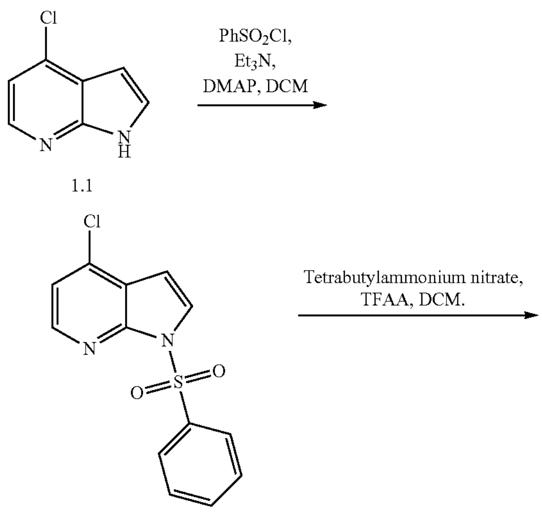

1.1 5.1

-continued

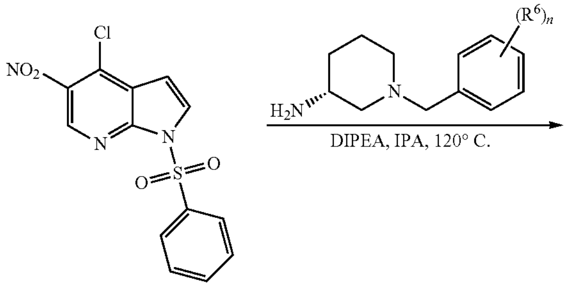

5.2

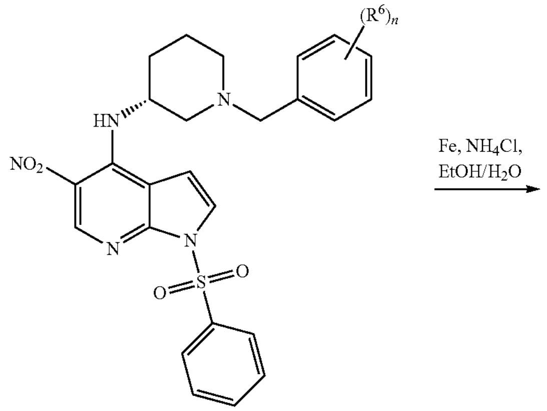

5.3

-continued

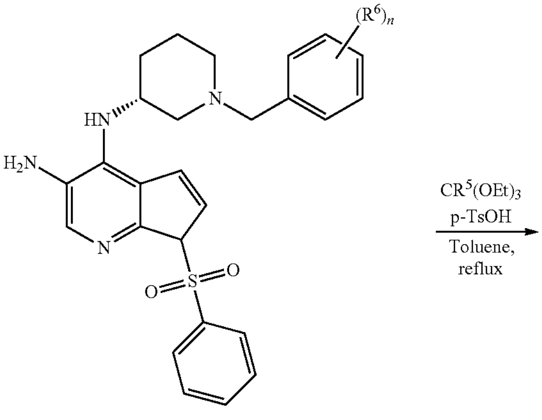

5.4

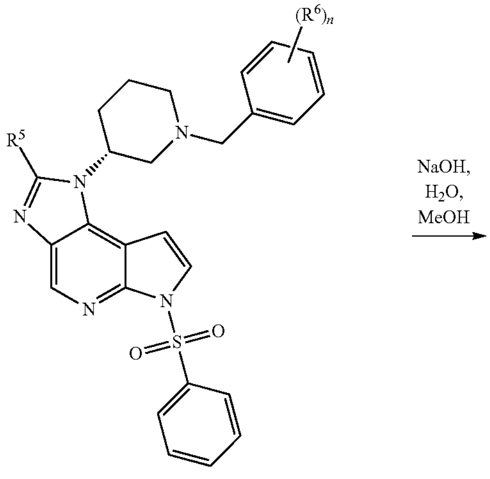

5.5

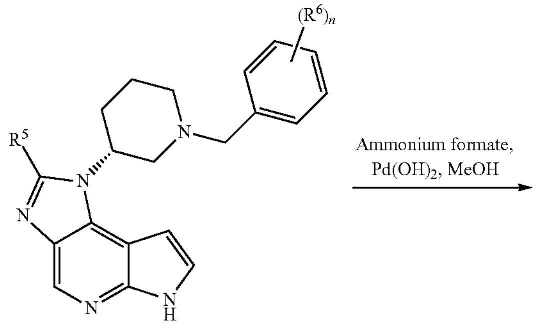

5.6

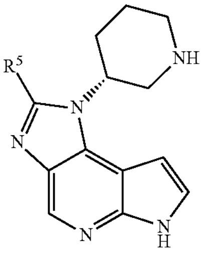

5.7

Compounds of formula I, for example 5.7, can be synthesized as shown in Reaction Scheme 5. For example, commercially available 4-chloroazaindole can be protected with phenylsulfonyl chloride in the presence of 4-(dimethylamino)pyridine (DMAP) and triethylamine to give sulfonamide 5.1. Compound 5.1 can be nitrated with tetrabutylammonium nitrate and trifluoroacetic anhydride (TFAA) to give nitro compound 5.2. Compound 5.2 can be derivatized with an amine having the formula $H_2N[R^1\text{-}R^2—(R^3—(R^6)_n)]$, where n is 0 to 4, for example with commercially available (R)-1-benzyl-3-aminopiperidine (wherein $R^1$ is piperidinyl, $R^2$ is methylene, $R^3$ is phenyl and n is 0), in the presence of base such as diisopropylethylamine. Reduction of compound 5.3, with iron in the presence of ammonium chloride, affords diamine compound 5.4. Cyclization of compound 5.4 with $R^5$-substituted orthoformate, for example triethyl orthoformate (where $R^5$ is hydrogen), in presence of p-toluenesulfonic acid gives 1,6-dihydroimidazo[4,5-d]pyrrolo[2,3-b]pyridine compound 5.5. Hydrolysis of compound 5.5 with aqueous sodium hydroxide in methanol provides compound 5.6. Treatment of compound 5.6 with a suitable hydrogen source such as ammonium formate in the presence of a suitable catalyst such as palladium (II) hydroxide in refluxing methanol provides compound 5.7.

Reaction Scheme 6

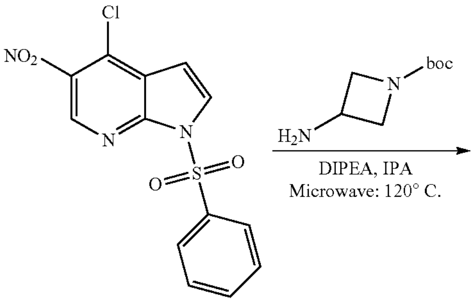

5.2

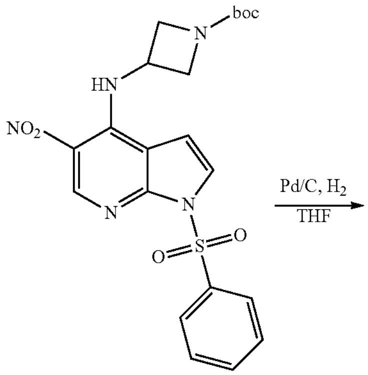

6.1

-continued

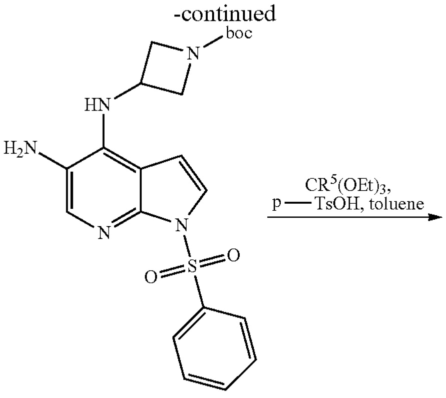

6.2

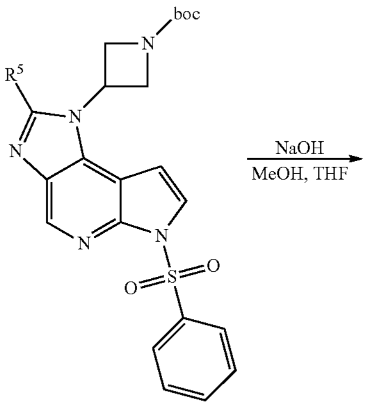

6.3

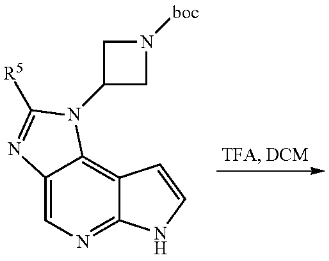

6.4

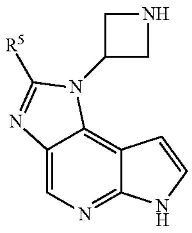

6.5

Reaction Scheme 6 illustrates the synthesis of compounds of formula I, for example compounds 6.5. Compound 6.1 can be prepared by treatment of compound 5.2 with a suitably protected diamine, for example commercially available 1-Boc-3-aminoazetidine, in the presence of base such as diisopropylethylamine. Reduction of compound 6.1 with hydrogen in the presence of palladium on carbon gives diamine compound 6.2. Cyclization of compound 6.2 with $R^5$-substituted orthoformate, for example triethyl orthoformate (where $R^5$ is hydrogen), in presence of p-toluenesulfonic acid gives tricyclic compound 6.3. Hydrolysis of compound 6.3 with aqueous sodium hydroxide in methanol/tetrahydrofuran (THF) provides compound 6.4.

Deprotection of 6.4 with an acid, such as trifluoroacetic acid, gives compound 6.5.

Reaction Scheme 7

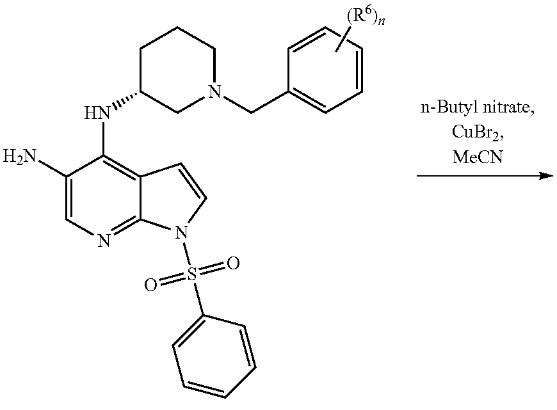

5.4

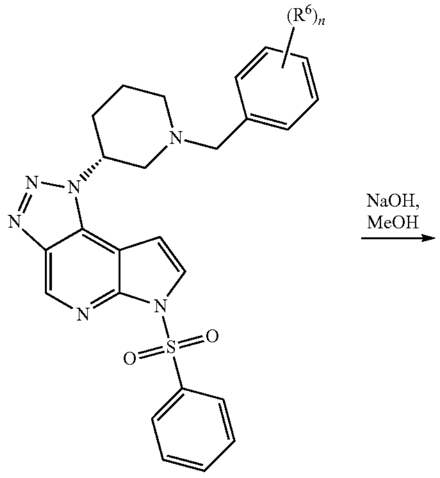

7.1

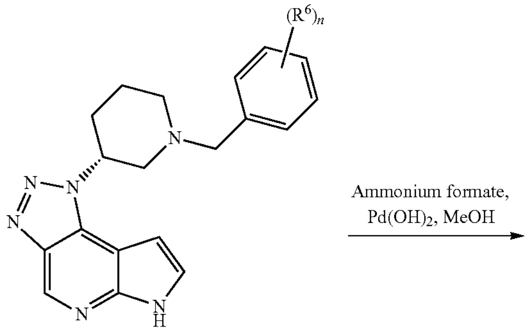

7.2

-continued

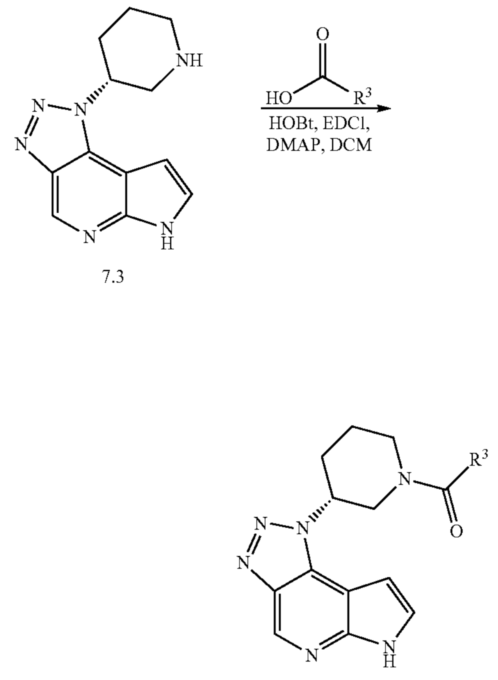

7.3

7.4

Reaction Scheme 7 illustrates the synthesis of compounds of formula I, for example compounds 7.4. Protected 3,4-diaminoazaindole 5.4 can be cyclised using n-butyl nitrite in the presence of copper (II) bromide to give 1,6-dihydropyrrolo[2,3-b][1,2,3]triazolo[4,5-d]pyridine compound 7.1. Deprotection of compound 7.1 using aqueous sodium hydroxide in methanol provides compounds 7.2. Treatment of compound 7.2 with ammonium formate and palladium (II) hydroxide in refluxing methanol provides compounds 7.3. Compounds 7.3 can be derivatized by reacting with compounds of the formula Lg-$R^2$-$R^3$ (where Lg is a leaving group), for example, carboxylic acids of the formula $R^3CO_2H$ (where $R^2$ is —C(O)—) in the presence of suitable coupling reagents such as N-hydroxybenzotriazole (HOBt), 1-ethyl-3-(3-dimethylaminopropyl)carbodiimide hydrochloride (EDCI) and DMAP in dichloromethane (DCM).

Reaction Scheme 8

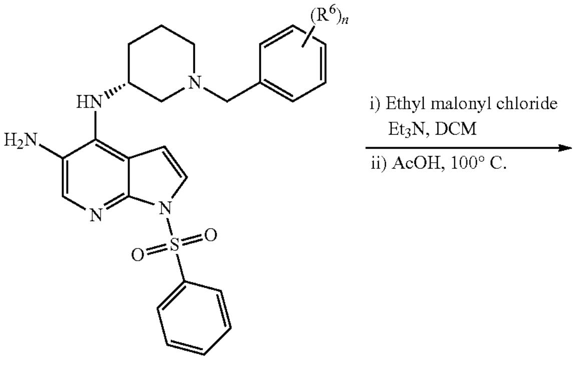

5.4

-continued

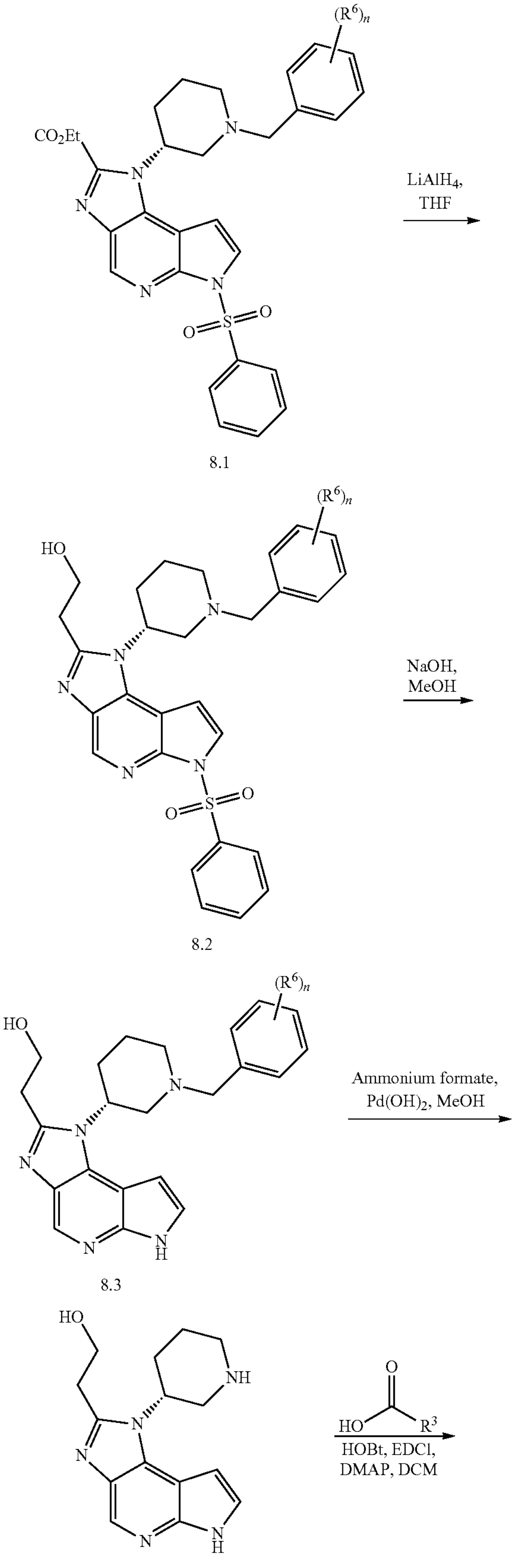

8.1

8.2

8.3

8.4

-continued

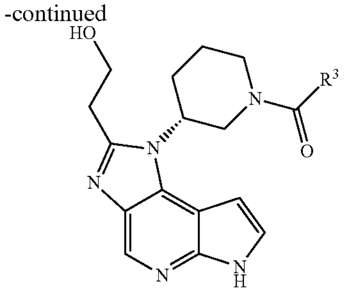

8.5

Reaction Scheme 8 illustrates the synthesis of compounds 8.5. For example, protected 3,4-diaminoazaindole 5.4 can be treated with ethyl malonyl chloride in the presence of base such as triethylamine and then cyclized in the presence of acetic acid to give imidazolo compound 8.1. Compound 8.1 can be reduced with a reducing agent, such as lithium aluminium hydride, to provide alcohol 8.2. Deprotection of compound 8.2 using aqueous sodium hydroxide in methanol provides compounds 8.3. Treatment of compound 8.3 with ammonium formate and palladium (II) hydroxide in refluxing methanol provides compounds 8.4. Compounds 8.4 can be converted using, for example, carboxylic acids in the presence of suitable coupling reagents such as HOBt and EDCI in DCM, to provide compounds 8.5.

Reaction Scheme 9

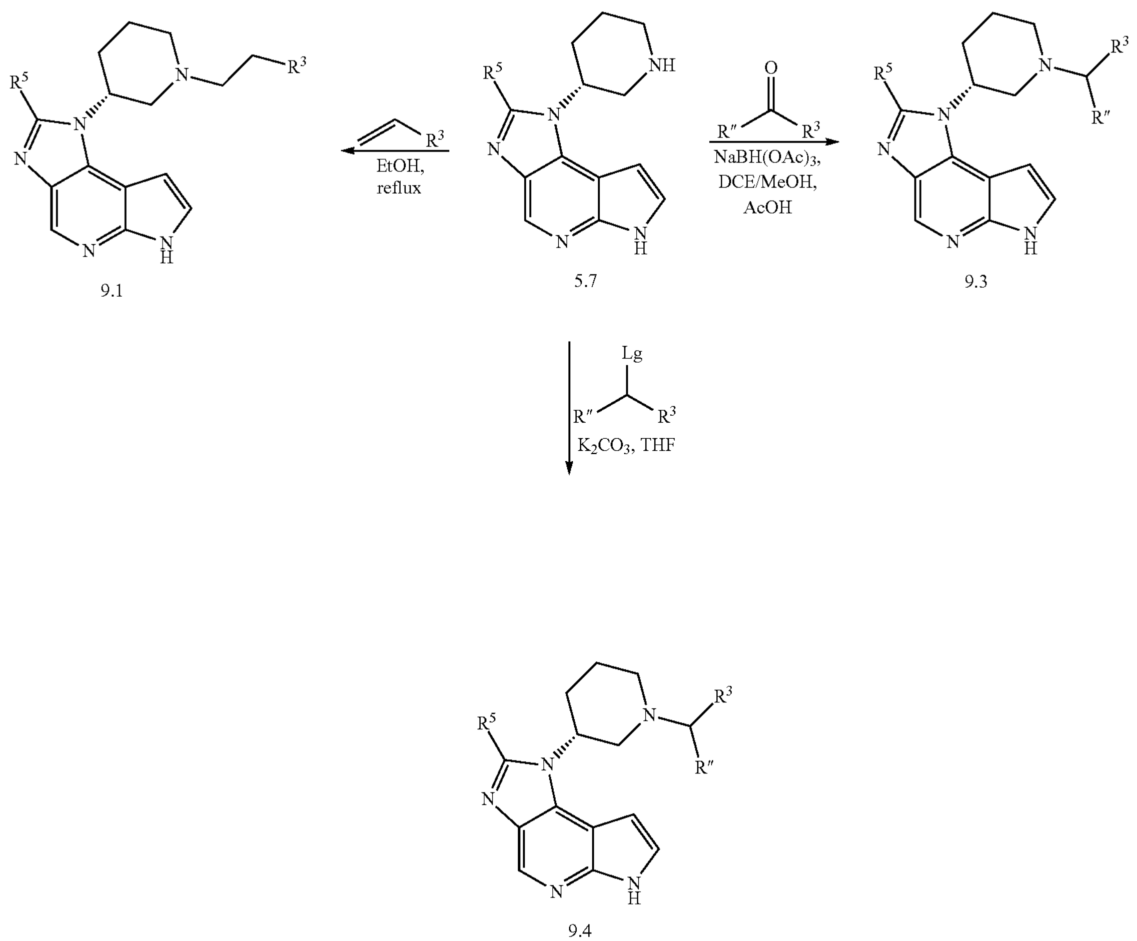

9.1 5.7 9.3 9.4

Reaction Scheme 9 illustrates the synthesis of compounds 9.4. Amino compounds such as 5.7 can be alkylated to give compounds 9.1 using a 2-substituted ethene in ethanol heated under reflux. Compounds 5.7 can be alkylated to give compounds 9.3 using an appropriate aldehyde (where R" is hydrogen) or ketone (where R" is $C_{1-3}$ alkyl), or an oxo-substituted compound such as $0{=}R^2{-}R^3$, in the presence of a suitable reducing agent such as sodium triacetoxyborohydride either in the presence or absence of acetic acid. Alternatively compounds 5.7 can be alkylated with a suitable haloalkane (where Lg is a leaving group such as a halogen) in the presence of base such as potassium carbonate in THF to provide compounds of 9.4.

Reaction Scheme 10

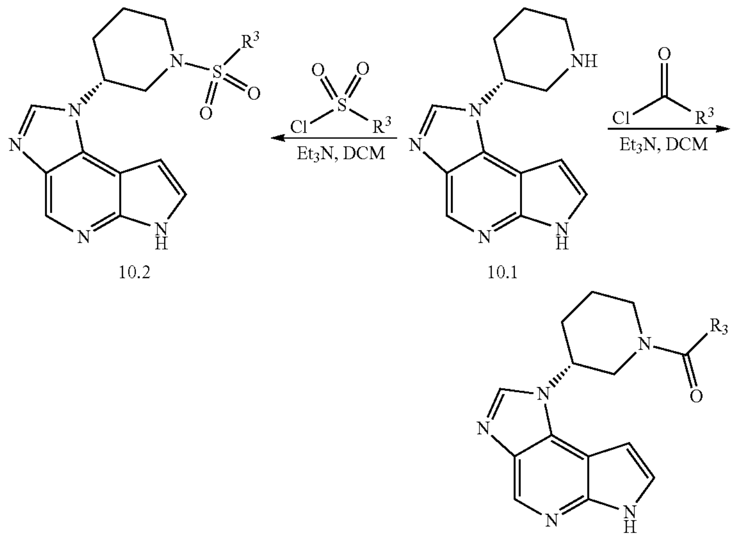

10.2

10.1

10.3

Reaction Scheme 10 illustrates the synthesis of compounds 10.2 and 10.3. For example, amino compounds 10.1 can be treated with various functionalized sulfonyl chlorides in presence of base such as triethylamine to give compounds 10.2. Compounds 10.1 can be coupled to various acid chlorides in the presence of base such as triethylamine to give compounds 10.3.

Reaction Scheme 11

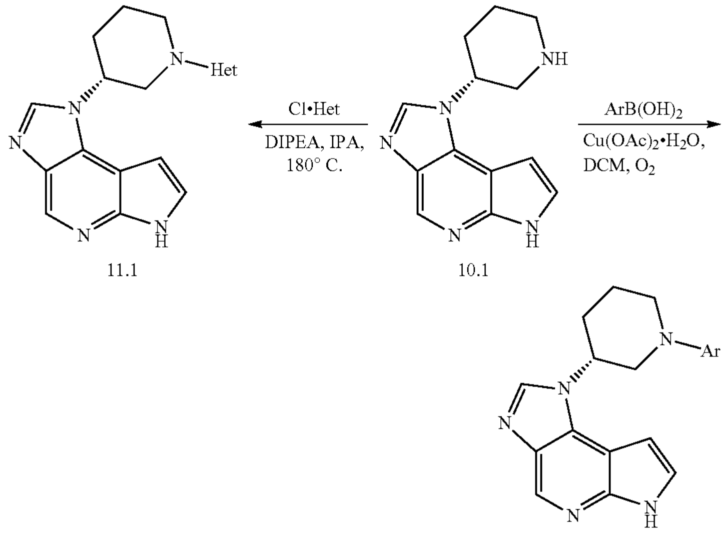

11.1

10.1

11.2

Reaction Scheme 11 illustrates the synthesis of compounds 11.1 and 11.2. Amino compounds 10.1 can be treated with a suitable heteroaryl chloride, such as 4-chloropyridine, in presence of base, such as diisopropylethylamine, to provide compounds 11.1. Compounds 10.1 can be coupled to aryl or heteroaryl boronic acids in the presence of copper (II) acetate, either in the presence or absence of an oxygen atmosphere, using a suitable solvent, such as dichloromethane, to give compounds 11.2.

Reaction Scheme 12

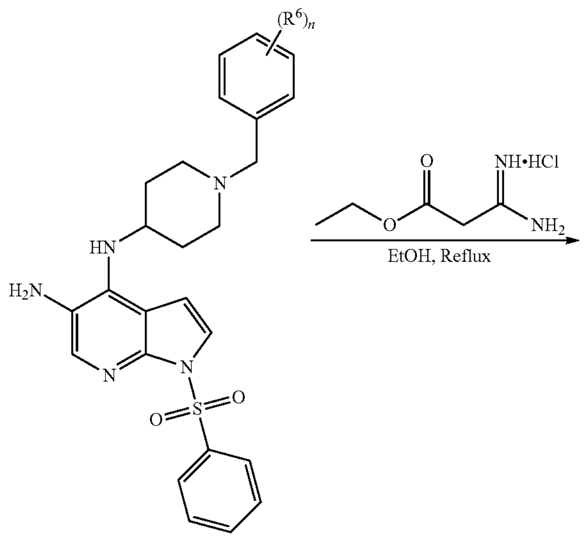

12.1

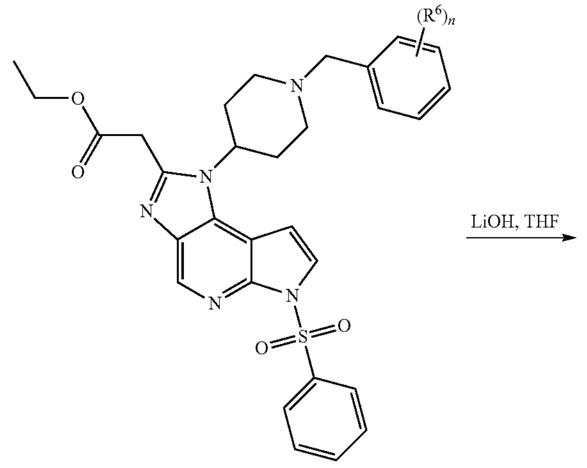

12.2

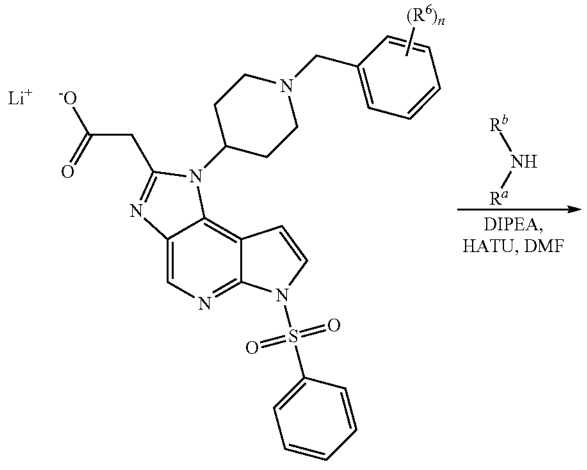

12.3

-continued

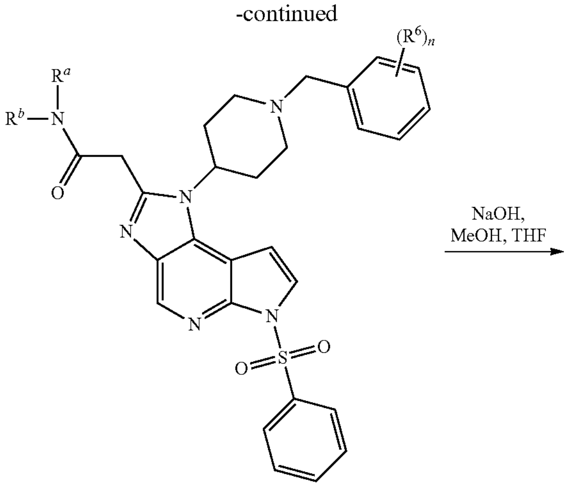

12.4

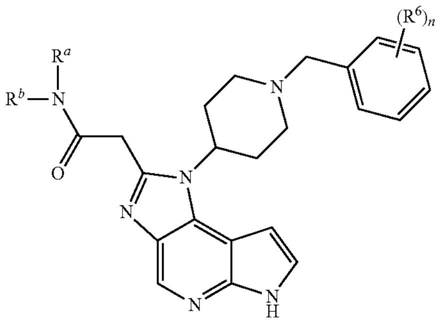

12.5

Reaction Scheme 12 illustrates the synthesis of compounds 12.5. A suitably protected 3,4-diaminoazaindole, such as compound 12.1, can be cyclised with a suitable amidine in the presence of a suitable solvent, such as ethanol, to give substituted imidazolo compound 12.2. Compound 12.2 can be hydrolysed using an aqueous base such as lithium hydroxide in a compatible solvent, such as THF, to provide acid salt compound 12.3. Compound 12.4 can be prepared from compound 12.3 using suitable primary or secondary amines in the presence of a suitable coupling reagent, such as HATU, in a compatible solvent, such as DMF. Compound 12.4 can be hydrolysed using aqueous sodium hydroxide to give compounds 12.5.

Reaction Scheme 13

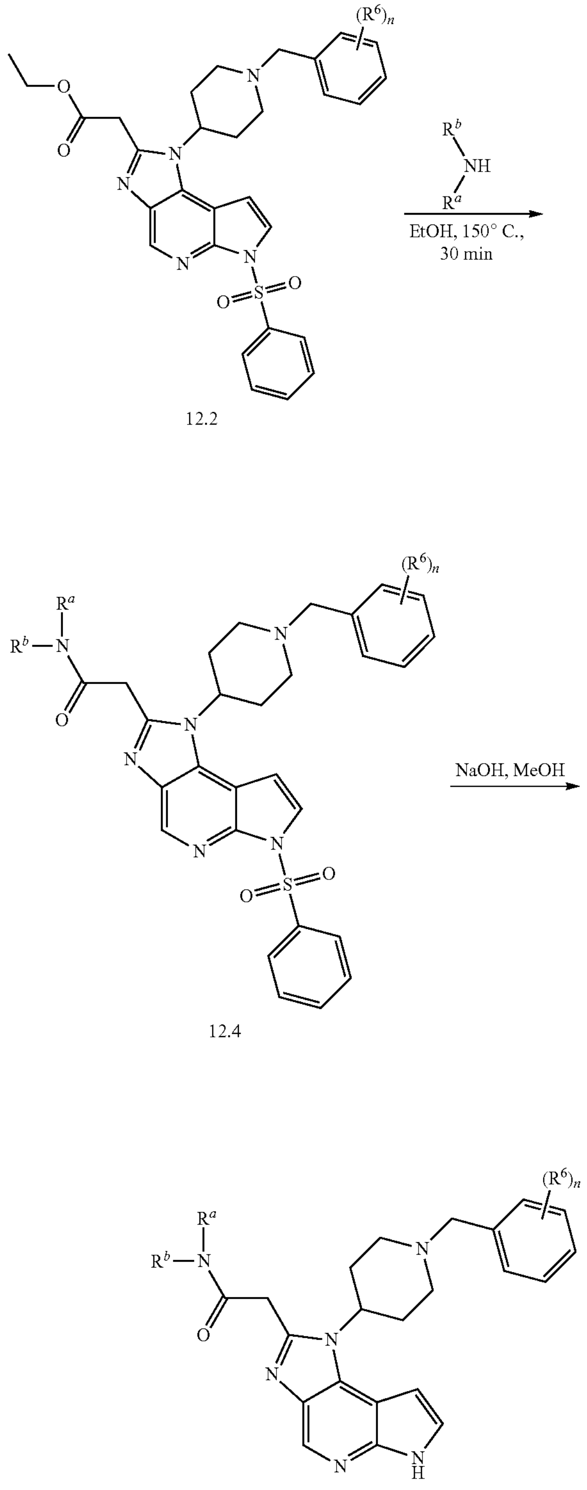

12.2 12.4 12.5

Reaction Scheme 13 illustrates an alternative synthesis of compounds 12.5. Compound 14 can be treated with suitable amines, such as methylamine, in a compatible solvent, such as ethanol, at elevated temperatures to directly provide amide compound 12.4. Compound 12.4 can be hydrolysed using aqueous sodium hydroxide to give compound 12.5.

Reaction Scheme 14

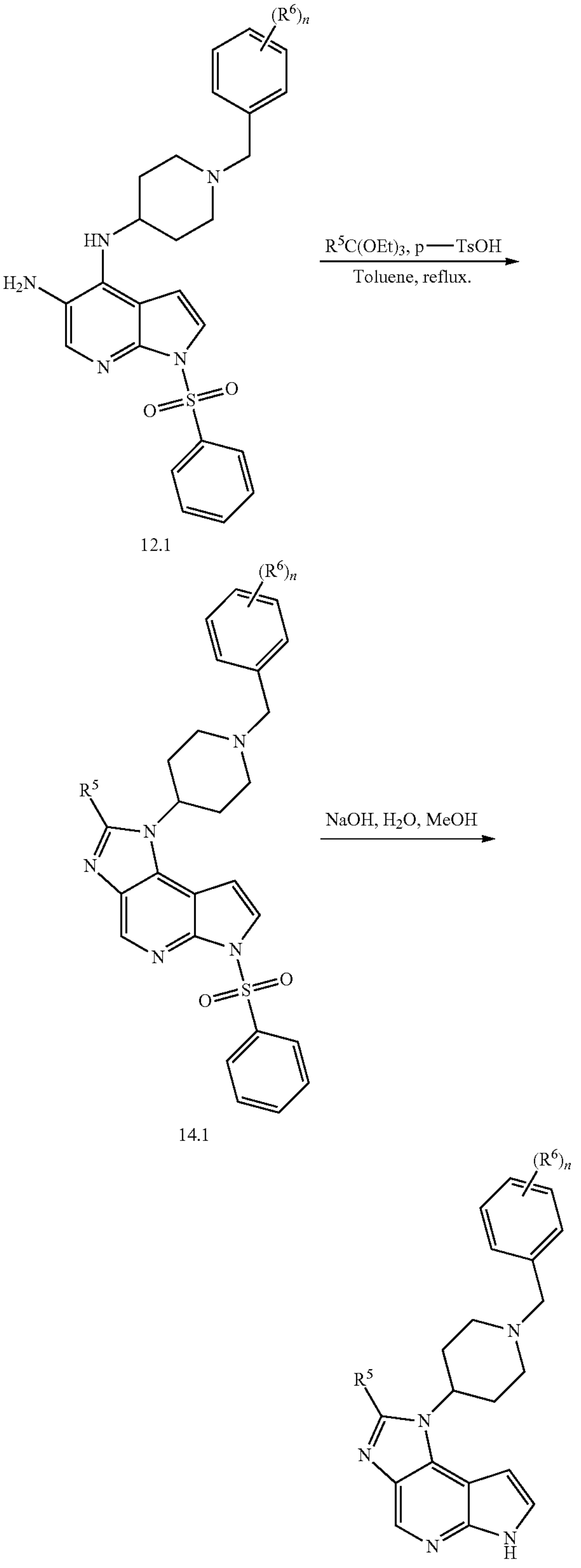

12.1 14.1 14.2

Reaction Scheme 14 illustrates the synthesis of compounds 14.2. A protected 3,4-diaminoazaindole, such as compound 12.1, can be cyclised with a triethyl orthoalkane, such as triethyl orthoacetate, in the presence of catalytic p-toluenesulfonic acid with prolonged heating to give substituted imidazolo compound 14.1. Hydrolysis of compound 14.1 with aqueous sodium hydroxide in methanol provides compounds 14.2.

Reaction Scheme 15

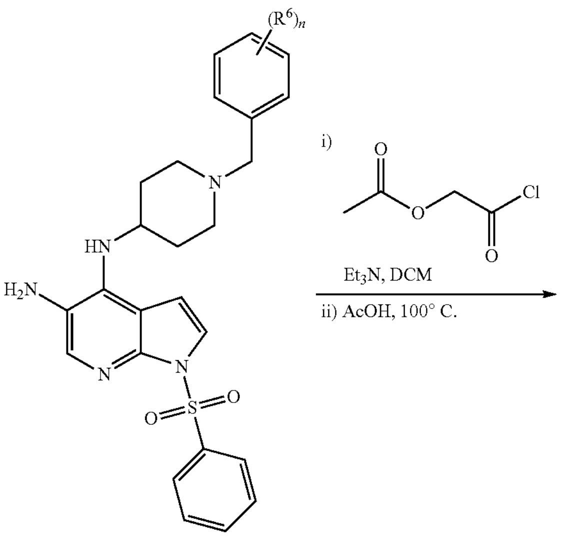

12.1

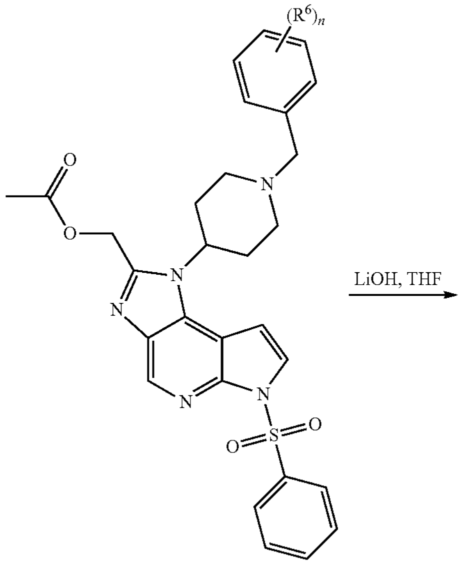

15.1

-continued

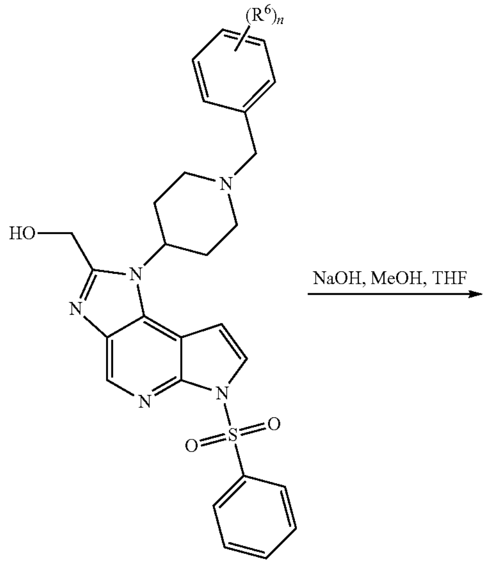

15.2

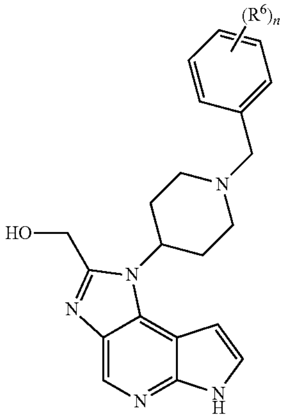

15.3

Reaction Scheme 15 illustrates the synthesis of compounds 15.3. A suitably protected 3,4-diaminoazaindole, such as compound 12.1, can be treated with acetoxyacetyl chloride in the presence of base, such as triethylamine, and then cyclized in the presence of acetic acid to give substituted imidazolo compound 15.1. Compound 15.1 can be hydrolysed using an aqueous base such as lithium hydroxide in a compatible solvent, such as THF, to provide alcohol compound 15.2. Hydrolysis of compound 15.2 with aqueous sodium hydroxide in methanol provides compounds 15.3.

Reaction Scheme 16

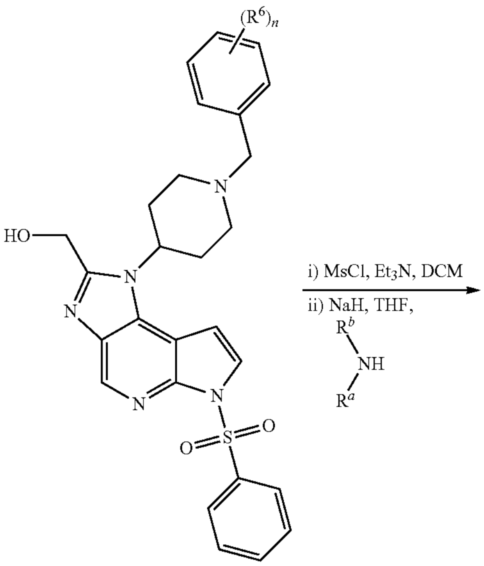

15.2

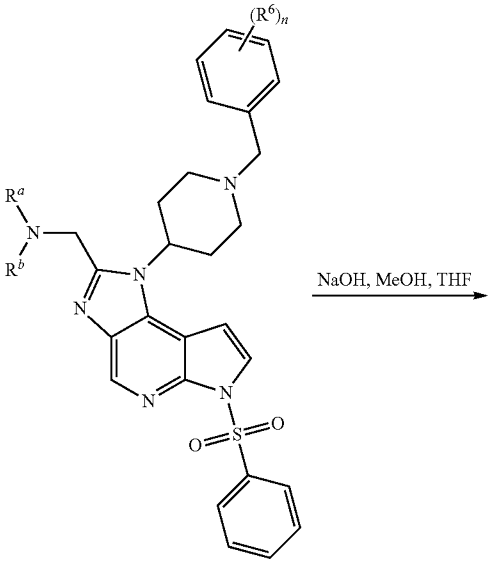

16.1

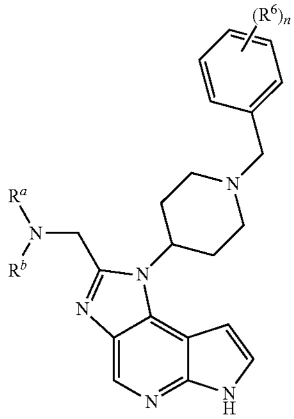

16.2

Reaction Scheme 16 illustrates the synthesis of compounds 16.2. For example, alcohol compound 15.2 can be treated with methanesulfonyl chloride in the presence of a suitable base, such as triethylamine, and the resulting product can be reacted with a compatible amine or lactam, such as 2-pyrrolidinone, in the presence of a suitable base, such as sodium hydride, to provide compound 16.1. Hydrolysis of compound 16.1 with aqueous sodium hydroxide provides compounds 16.2.

Reaction Scheme 17

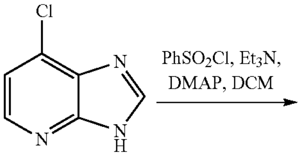

17.1

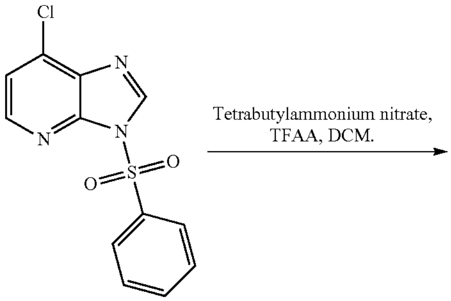

17.2

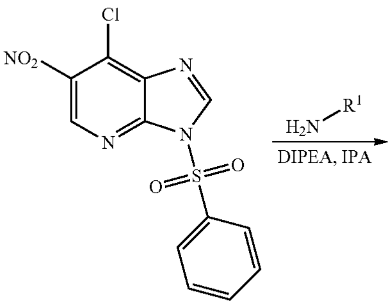

17.3

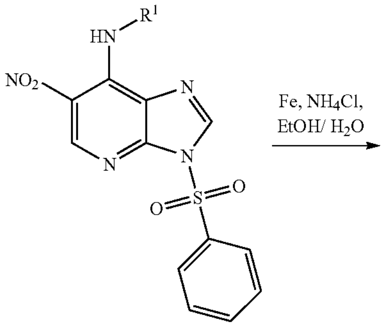

17.4

-continued

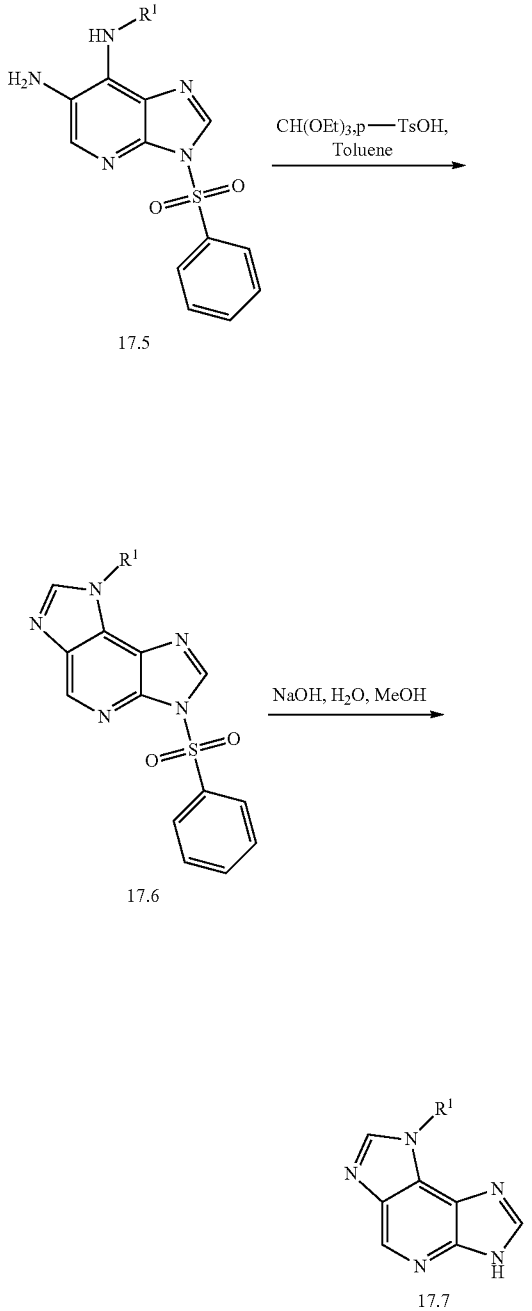

17.5

17.6

17.7

Reaction Scheme 17 illustrates the synthesis of compounds 17.7. The preparation of compound 17.1 has been previously described (see: Itoh et. al., *J. Heterocyclic Chem.,* 19, 513-517 (1982)). Compound 17.1 can be treated with methanesulfonyl chloride in the presence of a suitable base, such as triethylamine, to give compound 17.2. Nitration of 17.2 using tetrabutylammonium nitrate in the presence of trifluoroacetic anhydride gives compound 17.3. Compound 17.3 can be reacted with an appropriate primary amine to give compound 17.4, which can then be treated with a reducing reagent, such as iron, in the presence of ammonium chloride to give aniline 17.5. Compound 17.5 can be cyclized to give imidazole 17.6, which can then be hydrolyzed with aqueous sodium hydroxide to give compound 17.7.

Reaction Scheme 18

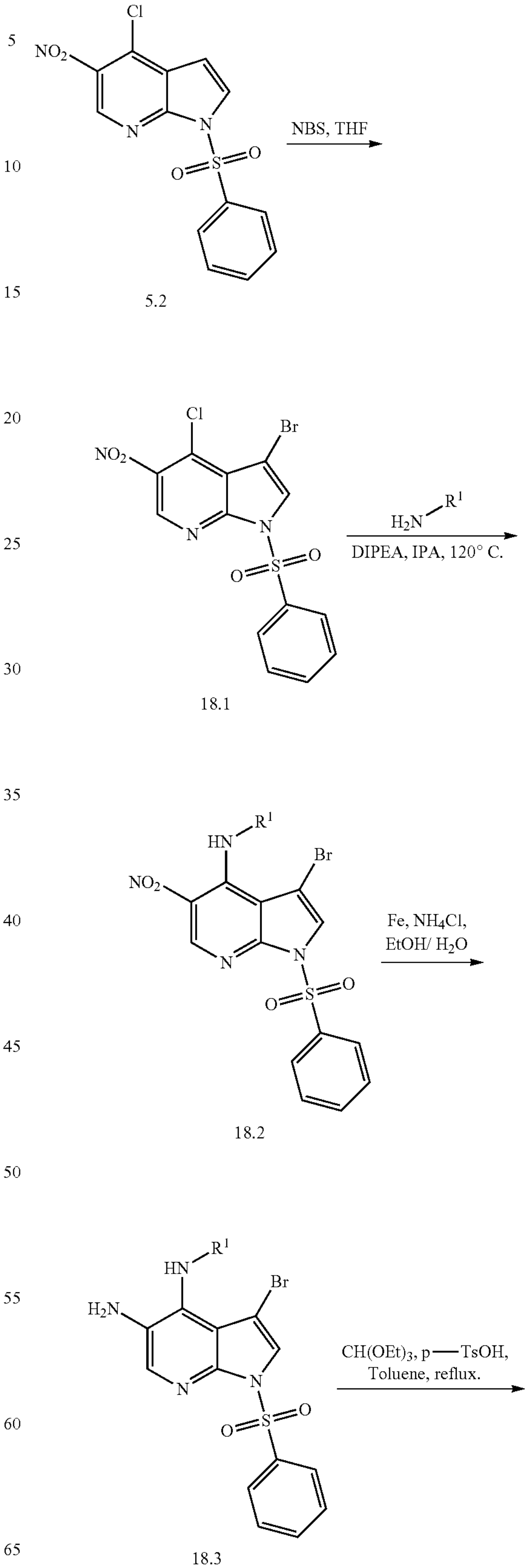

5.2

18.1

18.2

18.3

-continued

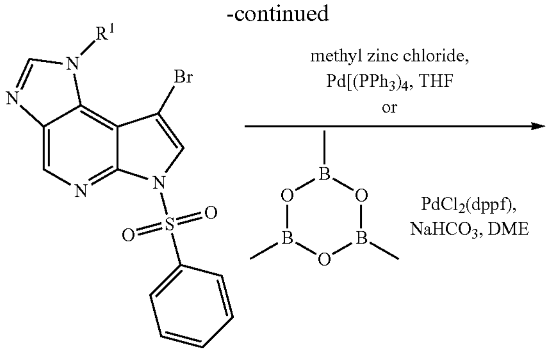

18.4

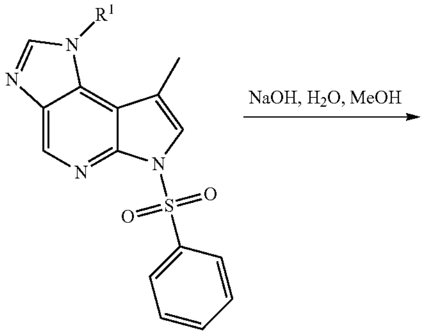

18.5

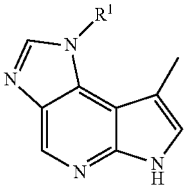

18.6

Reaction Scheme 18 illustrates the synthesis of compound 18.6. Compound 5.2 can be treated with a brominating reagent such as N-bromosuccinimide to give compound 18.1, which can then be treated with an appropriate primary amine to give intermediate 18.2. Compound 18.2 can be treated with a reducing agent, such as iron, in the presence of ammonium chloride to give aniline 18.3, which then can be cyclized to give imidazole 18.4. Compound 18.4 can be treated with alkylating reagents, such as methyl zinc chloride and tetrakis (triphenylphosphine)palladium(0), or trimethylboroxine in the presence of [1,1'-Bis(diphenylphosphino)ferrocene] dichloropalladium(II) and sodium hydrogen carbonate, to give alkylated compound 18.5. Compound 18.5 can then be hydrolyzed with aqueous sodium hydroxide to give compounds 18.6.

Reaction Scheme 19

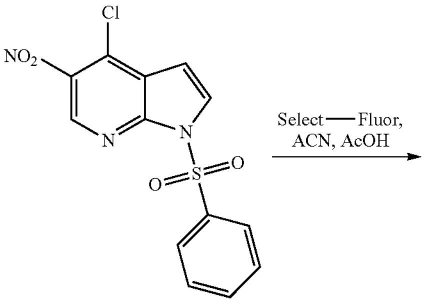

5.2

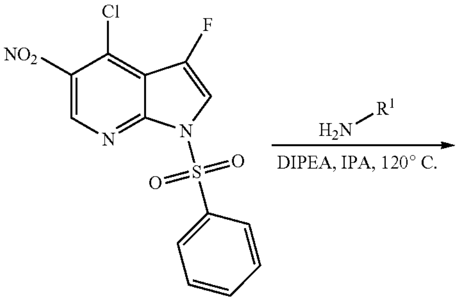

19.1

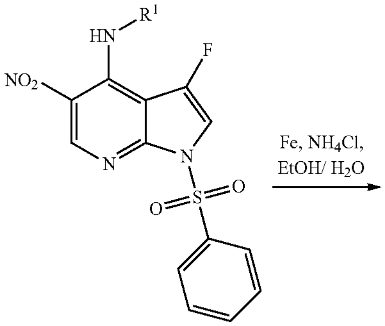

19.2

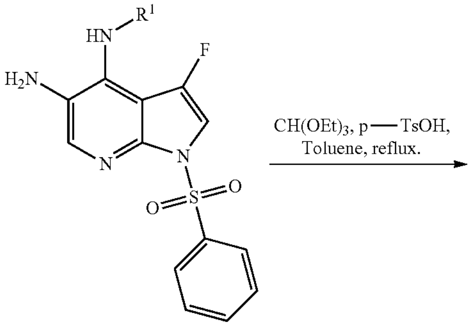

19.3

-continued

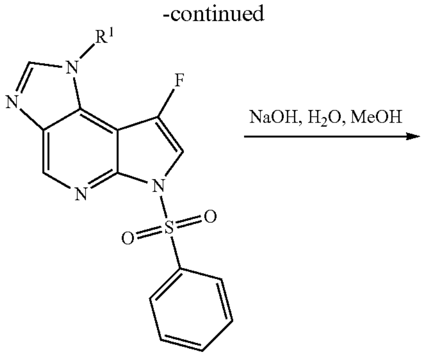

19.4

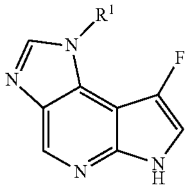

19.5

Reaction Scheme 19 illustrates the synthesis of compounds 19.5. Compound 5.2 can be treated with a fluorinating reagent, such as Select-Fluor, to give compound 19.1, which can then be treated with an appropriate primary amine to give intermediate 19.2. Compound 19.2 can then be treated with a reducing agent, such as iron in the presence of ammonium chloride, to give aniline 19.3, which then can be cyclized to give imidazole 19.4. Compound 19.4 can be hydrolyzed with aqueous sodium hydroxide to give compounds 19.5.

Reaction Scheme 20

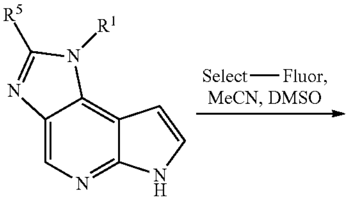

20.1

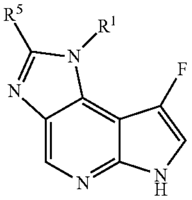

20.2

Reaction Scheme 20 illustrates the synthesis of compounds 20.2. For example, compound 20.1 can be treated with a fluorinating agent, such as Select-Fluor, to directly provide compounds 20.2.

Reaction Scheme 21

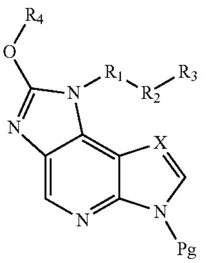

21.4

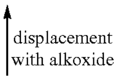

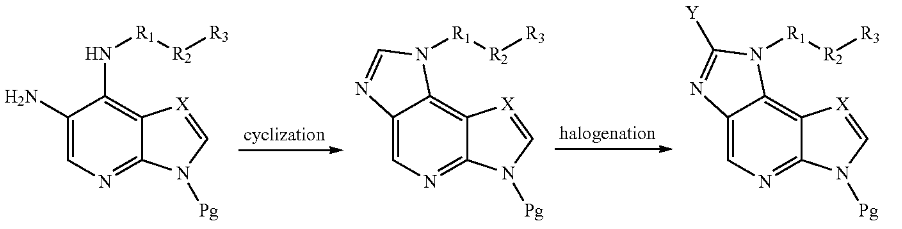

21.1 21.2 21.3

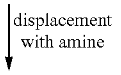

-continued

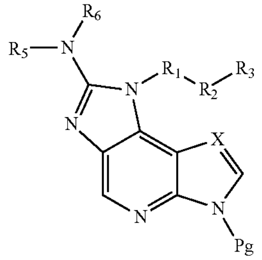

21.5

Compounds of type 21.4 and 21.5 can be synthesized from compounds of type 21.1 by cyclization for example with triethyl orthoformate. Halogenenation of 21.2 can be achieved for example by treating 21.2 with a suitable base such as lithium diisopropylamide then quenching with a suitable halogen source such as an N-halosuccinimide. Compounds of type 21.4 can be prepared by displacing the halogen in 21.3 with a suitable nucleophile such as sodium methoxide. Compounds of type 21.5 can similarly be prepared by displacement of the halogen in 21.3 with a suitable amine such as ethanolamine.

Reaction Scheme 22

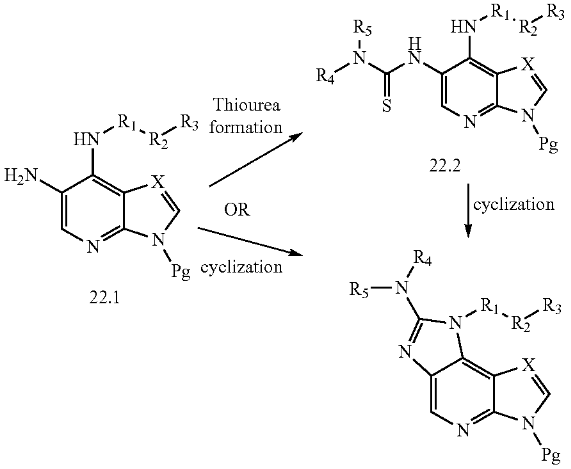

22.1 22.2 22.3

Compounds of type 22.3 can be prepared directly from compounds of type 22.1 by reaction with a reagent such as dichloromethylene-dimethyliminium chloride. Alternatively, compounds of type 22.3 can be prepared by first reacting compounds of type 22.1 with a reagent such as an alkyl isothiocyanate. Compounds of type 22.3 may be prepared by cyclisation of a compound of type 22.2 by reaction with a reagent such as 1-(3-dimethylaminopropyl)-3-ethylcarbodiimide hydrochloride.

It will be appreciated that where appropriate functional groups exist, compounds of various formulae or any intermediates used in their preparation may be further derivatized by one or more standard synthetic methods employing condensation, substitution, oxidation, reduction, or cleavage reactions. Particular substitution approaches include conventional alkylation, arylation, heteroarylation, acylation, sulfonylation, halogenation, nitration, formylation and coupling procedures.

In a further example, primary amine or secondary amine groups may be converted into amide groups (—NHCOR' or —NRCOR') by acylation. Acylation may be achieved by reaction with an appropriate acid chloride in the presence of a base, such as triethylamine, in a suitable solvent, such as dichloromethane, or by reaction with an appropriate carboxylic acid in the presence of a suitable coupling agent such HATU (O-(7-azabenzotriazol-1-yl)-N,N,N',N'-tetramethyluronium hexafluorophosphate) in a suitable solvent such as dichloromethane. Similarly, amine groups may be converted into sulfonamide groups (—$NHSO_2R'$ or —$NR''SO_2R'$) groups by reaction with an appropriate sulfonyl chloride in the presence of a suitable base, such as triethylamine, in a suitable solvent such as dichloromethane. Primary or secondary amine groups can be converted into urea groups (—NHCONR'R" or —NRCONR'R") by reaction with an appropriate isocyanate in the presence or absence of a suitable base such as triethylamine, in a suitable solvent, such as dichloromethane.

An amine (—$NH_2$) may be obtained by reduction of a nitro (—$NO_2$) group, for example by catalytic hydrogenation, using for example hydrogen in the presence of a metal catalyst, for example palladium on a support such as carbon in a solvent such as ethyl acetate or an alcohol e.g. methanol. Alternatively, the transformation may be carried out by chemical reduction using for example a metal, e.g. tin or iron, in the presence of an acid such as hydrochloric acid.

In a further example, amine (—$CH_2NH_2$) groups may be obtained by reduction of nitriles (—CN), for example by catalytic hydrogenation using for example hydrogen in the presence of a metal catalyst, for example palladium on a support such as carbon, or Raney nickel, in a solvent such as an ether e.g. a cyclic ether such as tetrahydrofuran, at an appropriate temperature, for example from about −78° C. to the reflux temperature of the solvent.

In a further example, amine (—$NH_2$) groups may be obtained from carboxylic acid groups (—$CO_2H$) by conversion to the corresponding acyl azide (—$CON_3$), Curtius rearrangement and hydrolysis of the resultant isocyanate (—N═C═O).

Aldehyde groups (—CHO) may be converted to amine groups (—$CH_2NR'R''$)) by reductive amination employing an amine and a borohydride, for example sodium triacetoxyborohydride or sodium cyanoborohydride, in a solvent such as a halogenated hydrocarbon, for example dichloromethane, or an alcohol such as methanol, where necessary in the presence of an acid such as acetic acid at around ambient temperature.

In a further example, aldehyde groups may be converted into alkenyl groups (—CH═CHR') by the use of a Wittig or Wadsworth-Emmons reaction using an appropriate phosphorane or phosphonate under standard conditions known to those skilled in the art.

Aldehyde groups may be obtained by reduction of ester groups (such as —$CO_2Et$) or nitriles (—CN) using diisobutylaluminum hydride in a suitable solvent such as toluene. Alternatively, aldehyde groups may be obtained by the oxidation of alcohol groups using any suitable oxidising agent known to those skilled in the art.

Ester groups (—$CO_2R'$) may be converted into the corresponding acid group (—$CO_2H$) by acid- or base-catalysed hydrolysis, depending on the nature of R. If R is t-butyl, acid-catalysed hydrolysis can be achieved for example by treatment with an organic acid such as trifluoroacetic acid in an aqueous solvent, or by treatment with an inorganic acid such as hydrochloric acid in an aqueous solvent.

Carboxylic acid groups (—$CO_2H$) may be converted into amides (CONHR' or —CONR'R") by reaction with an appropriate amine in the presence of a suitable coupling agent, such as HATU, in a suitable solvent such as dichloromethane.

In a further example, carboxylic acids may be homologated by one carbon (i.e. —$CO_2H$ to —$CH_2CO_2H$) by conversion to the corresponding acid chloride (—COCl) followed by Arndt-Eistert synthesis.

In a further example, —OH groups may be generated from the corresponding ester (e.g. —$CO_2R'$), or aldehyde (—CHO) by reduction, using for example a complex metal hydride such as lithium aluminium hydride in diethyl ether or tetrahydrofuran, or sodium borohydride in a solvent such as methanol. Alternatively, an alcohol may be prepared by reduction of the corresponding acid (—$CO_2H$), using for example lithium aluminium hydride in a solvent such as tetrahydrofuran, or by using borane in a solvent such as tetrahydrofuran.

Alcohol groups may be converted into leaving groups, such as halogen atoms or sulfonyloxy groups such as an alkylsulfonyloxy, e.g. trifluoromethylsulfonyloxy or arylsulfonyloxy, e.g. p-toluenesulfonyloxy group using conditions known to those skilled in the art. For example, an alcohol may be reacted with thionyl chloride in a halogenated hydrocarbon (e.g. dichloromethane) to yield the corresponding chloride. A base (e.g. triethylamine) may also be used in the reaction.

In another example, alcohol, phenol or amide groups may be alkylated by coupling a phenol or amide with an alcohol in a solvent such as tetrahydrofuran in the presence of a phosphine, e.g. triphenylphosphine and an activator such as diethyl-, diisopropyl, or dimethylazodicarboxylate. Alternatively alkylation may be achieved by deprotonation using a suitable base e.g. sodium hydride followed by subsequent addition of an alkylating agent, such as an alkyl halide.

Aromatic halogen substituents in the compounds may be subjected to halogen-metal exchange by treatment with a base, for example a lithium base such as n-butyl or t-butyl lithium, optionally at a low temperature, e.g. around −78° C., in a solvent such as tetrahydrofuran, and then quenched with an electrophile to introduce a desired substituent. Thus, for example, a formyl group may be introduced by using N,N-dimethylformamide as the electrophile. Aromatic halogen substituents may alternatively be subjected to metal (e.g. palladium or copper) catalysed reactions, to introduce, for example, acid, ester, cyano, amide, aryl, heteroaryl, alkenyl, alkynyl, thio- or amino substituents. Suitable procedures which may be employed include those described by Heck, Suzuki, Stille, Buchwald or Hartwig.

Aromatic halogen substituents may also undergo nucleophilic displacement following reaction with an appropriate nucleophile such as an amine or an alcohol. Advantageously, such a reaction may be carried out at elevated temperature in the presence of microwave irradiation.

Methods of Separation

In each of the exemplary Schemes it may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization or trituration from a solvent or solvent mixture, distillation, sublimation, or chromatography. Chromatography can involve any number of methods including, for example: reverse-phase and normal phase; size exclusion; ion exchange; supercritical fluid; high, medium, and low pressure liquid chromatography methods and apparatus; small scale analytical; simulated moving bed (SMB) and preparative thin or thick layer chromatography, as well as techniques of small scale thin layer and flash chromatography.

Another class of separation methods involves treatment of a mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like.

Selection of appropriate methods of separation depends on the nature of the materials involved. Example separation methods include boiling point, and molecular weight in distillation and sublimation, presence or absence of polar functional groups in chromatography, stability of materials in acidic and basic media in multiphase extraction, and the like. One skilled in the art will apply techniques most likely to achieve the desired separation.

Diastereomeric mixtures can be separated into their individual diastereoisomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereoisomers and converting (e.g., hydrolyzing) the individual diastereoisomers to the corresponding pure enantiomers. Also, some of the compounds of the present invention may be atropisomers (e.g., substituted biaryls) and are considered as part of this invention. Enantiomers can also be separated by use of a chiral HPLC column or supercritical fluid chromatography.

A single stereoisomer, e.g. an enantiomer, substantially free of its stereoisomer may be obtained by resolution of the racemic mixture using a method such as formation of diastereomers using optically active resolving agents (Eliel, E. and Wilen, S., *Stereochemistry of Organic Compounds*, John Wiley & Sons, Inc., New York, 1994; Lochmuller, C. H., *J. Chromatogr.,* 113(3):283-302 (1975)). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: *Drug Stereochemistry, Analytical Methods and Pharmacology*, Irving W. Wainer, Ed., Marcel Dekker, Inc., New York (1993).

Diastereomeric salts can be formed by reaction of enantiomerically pure chiral bases such as brucine, quinine, ephedrine, strychnine, α-methyl-β-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, the substrate to be resolved is reacted with one enantiomer of a chiral compound to form a diastereomeric pair (Eliel, E. and Wilen, S., *Stereochemistry of Organic Compounds*, John Wiley & Sons, Inc., New York, 1994, p. 322). Diastereomeric compounds can be formed by reacting asymmetric compounds with enantiomerically pure chiral derivatizing reagents, such as menthyl derivatives, followed by separation of the diastereomers and hydrolysis to yield the pure or enriched enantiomer. A method of determining optical purity involves making chiral esters, such as a menthyl ester, e.g. (−) menthyl chloroformate in the presence of base, or Mosher ester, α-methoxy-α-(trifluoromethyl)phenyl acetate (Jacob, *J. Org. Chem.* 47:4165 (1982)), of the racemic mixture, and analyzing the NMR spectrum for the presence of the two atropisomeric enantiomers or diastereomers. Stable diastereomers of atropisomeric compounds can be separated and isolated by normal- and reverse-phase chromatography following methods for separation of atropisomeric naphthyl-isoquinolines (WO 96/15111). By method (3), a racemic mixture of two enantiomers can be separated by chromatography using a chiral stationary phase (*Chiral Liquid Chromatography* W. J. Lough, Ed., Chapman and Hall, New York, (1989); Okamoto, *J. of Chromatogr.* 513:375-378 (1990)). Enriched or purified enantiomers can be distinguished by methods used to distinguish other chiral molecules with asymmetric carbon atoms, such as optical rotation and circular dichroism. The absolute stereochemistry of chiral centers and enantiomers can be determined by x-ray crystallography.

Positional isomers, for example E and Z forms, of compounds of formula I, and intermediates for their synthesis, may be observed by characterization methods such as NMR and analytical HPLC. For certain compounds where the energy barrier for interconversion is sufficiently high, the E and Z isomers may be separated, for example by preparatory HPLC.

Pharmaceutical Compositions and Administration

Another embodiment provides pharmaceutical compositions or medicaments containing the compounds of the invention and a therapeutically inert carrier, diluent or excipient, as well as methods of using the compounds of the invention to prepare such compositions and medicaments. In one example, compounds of formula I may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of formula I is formulated in an acetate buffer, at pH 5. In another embodiment, the compounds of formula I are sterile. The compound may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

In one example, the therapeutically effective amount of the compound of the invention administered parenterally per dose will be in the range of about 0.01-100 mg/kg, alternatively about 0.1 to 20 mg/kg of patient body weight per day, with the typical initial range of compound used being 0.3 to 15 mg/kg/day. In another embodiment, oral unit dosage forms, such as tablets and capsules, contain from about 5 to about 100 mg of the compound of the invention.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal, inhaled and epidural and intranasal, and, if desired for local treatment, intralesional administration. Parenteral infusions include intramuscular, intravenous, intraarterial, intraperitoneal, or subcutaneous administration.

The compounds of the present invention may be administered in any convenient administrative form, e.g., tablets, powders, capsules, solutions, dispersions, suspensions, syrups, sprays, vapors, suppositories, gels, emulsions, patches, etc. Such compositions may contain components conventional in pharmaceutical preparations, e.g., diluents, carriers, pH modifiers, sweeteners, bulking agents, and further active agents.

A typical formulation is prepared by mixing a compound of the present invention and a carrier or excipient. Suitable carriers and excipients are well known to those skilled in the art and are described in detail in, e.g., Ansel, Howard C., et al., Ansel's Pharmaceutical Dosage Forms and Drug Delivery Systems. Philadelphia: Lippincott, Williams & Wilkins, 2004; Gennaro, Alfonso R., et al. Remington: The Science and Practice of Pharmacy. Philadelphia: Lippincott, Williams & Wilkins, 2000; and Rowe, Raymond C. Handbook of Pharmaceutical Excipients. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

An example of a suitable oral dosage form is a tablet containing about 2 mg, 5 mg, 25 mg, 50 mg, 100 mg, 250 mg, or 500 mg of the compound of the present invention compounded with about 95-30 mg anhydrous lactose, about 5-40 mg sodium croscarmellose, about 5-30 mg polyvinylpyrrolidone (PVP) K30, and about e.g., 1-10 mg magnesium stearate. The powdered ingredients are first mixed together and then mixed with a solution of the PVP. The resulting composition can be dried, granulated, mixed with the magnesium stearate and compressed to tablet form using conventional equipment. An example of an aerosol formulation can be prepared by dissolving the compound of the present invention, for example 5-400 mg, in a suitable buffer solution, e.g. a phosphate buffer, adding a tonicifier, e.g. a salt such sodium chloride, if desired. The solution may be filtered, e.g. using a 0.2 micron filter, to remove impurities and contaminants.

An embodiment, therefore, includes a pharmaceutical composition comprising a compound of formula I, stereoisomers, tautomers, solvates, metabolites, pharmaceutically acceptable salts and prodrugs thereof. In a further embodiment includes a pharmaceutical composition comprising a compound of formula I, stereoisomers, tautomers, solvates, metabolites, pharmaceutically acceptable salts and prodrugs thereof, together with a pharmaceutically acceptable carrier or excipient.

Another embodiment includes a pharmaceutical composition comprising a compound of formula I stereoisomers, tautomers, solvates, metabolites, pharmaceutically acceptable salts and prodrugs thereof, for use in the treatment of a hyperproliferative disease. Another embodiment includes a pharmaceutical composition comprising a compound of formula I stereoisomers, tautomers, solvates, metabolites, pharmaceutically acceptable salts and prodrugs thereof, for use in the treatment of cancer. Another embodiment includes a pharmaceutical composition comprising a compound of formula I stereoisomers, tautomers, solvates, metabolites, pharmaceutically acceptable salts and prodrugs thereof, for use in the treatment of an immunological disorder. Another embodiment includes a pharmaceutical composition comprising a compound of formula I stereoisomers, tautomers, solvates, metabolites, pharmaceutically acceptable salts and prodrugs thereof, for use in the treatment of rheumatoid arthritis, psoriasis, inflammatory bowel disease (IBD) or asthma. Another embodiment includes a pharmaceutical composition comprising a compound of formula I stereoisomers, tautomers, solvates, metabolites, pharmaceutically acceptable salts and prodrugs thereof, for use in the treatment of rheumatoid arthritis, asthma, systemic lupus erythematosus, psoriasis, IBD and transplant rejection.

Methods of Treatment with and Uses of JAK1 Inhibitors

The compounds of Formula I inhibit the activity of JAK1 kinase. Accordingly, the compounds of Formula I inhibit the phosphorylation of signal transducers and activators of transcription (STATs) by JAK1 kinase as well as STAT mediated cytokine production. Compounds of Formula I are useful for inhibiting JAK1 kinase activity in cells through cytokine pathways, such as IL-6, IL-15, IL-7, IL-2, IL-4, IL-9, IL-10, IL-13, IL-21, G-CSF, IFNalpha, IFNbeta or IFNgamma pathways. The compounds of Formula I can be used for the treatment of immunological disorders driven by aberrant IL-6, IL-15, IL-7, IL-2, IL-4, IL9, IL-10, IL-13, IL-21, G-CSF, IFNalpha, IFNbeta or IFNgamma cytokine signaling.

Another embodiment includes a method of treating or lessening the severity of a disease or condition responsive to the inhibition of JAK1 kinase activity in a patient. The method includes the step of administering to a patient a therapeutically effective amount of a compound of the present invention.

In one embodiment, the disease or condition is cancer, stroke, diabetes, hepatomegaly, cardiovascular disease, multiple sclerosis, Alzheimer's disease, cystic fibrosis, viral disease, autoimmune diseases, atherosclerosis, restenosis, psoriasis, rheumatoid arthritis, inflammatory bowel disease, asthma, allergic disorders, inflammation, neurological disorders, a hormone-related disease, conditions associated with organ transplantation, immunodeficiency disorders, destructive bone disorders, proliferative disorders, infectious diseases, conditions associated with cell death, thrombin-induced platelet aggregation, liver disease, pathologic immune conditions involving T cell activation, CNS disorders or a myeloproliferative disorder.

In one embodiment, the disease or condition is cancer.

In one embodiment, the disease is a myeloproliferative disorder.

In one embodiment, the myeloproliferative disorder is polycythemia vera, essential thrombocytosis, myelofibrosis or chronic myelogenous leukemia (CML).

In one embodiment, the cancer is breast, ovary, cervix, prostate, testis, penile, genitourinary tract, seminoma, esophagus, larynx, gastric, stomach, gastrointestinal, skin, keratoacanthoma, follicular carcinoma, melanoma, lung, small cell lung carcinoma, non-small cell lung carcinoma (NSCLC), lung adenocarcinoma, squamous carcinoma of the lung, colon, pancreas, thyroid, papillary, bladder, liver, biliary passage, kidney, bone, myeloid disorders, lymphoid disorders, hairy cells, buccal cavity and pharynx (oral), lip, tongue, mouth, salivary gland, pharynx, small intestine, colon, rectum, anal, renal, prostate, vulval, thyroid, large intestine, endometrial, uterine, brain, central nervous system, cancer of the peritoneum, hepatocellular cancer, head cancer, neck cancer, Hodgkin's or leukemia.

In one embodiment, the cardiovascular disease is restenosis, cardiomegaly, atherosclerosis, myocardial infarction or congestive heart failure.

In one embodiment, the neurodegenerative disease is Alzheimer's disease, Parkinson's disease, amyotrophic lateral sclerosis, Huntington's disease, and cerebral ischemia, and neurodegenerative disease caused by traumatic injury, glutamate neurotoxicity or hypoxia.

In one embodiment, the inflammatory diseases is rheumatoid arthritis, psoriasis, asthma, inflammatory bowel disease, contact dermatitis or delayed hypersensitivity reactions.

In one embodiment, the autoimmune disease is lupus or multiple sclerosis.

In one embodiment, the disease or condition responsive to the inhibition of JAK1 kinase is rheumatoid arthritis.

In one embodiment, the disease or condition responsive to the inhibition of JAK1 kinase is rheumatoid arthritis, asthma, systemic lupus erythematosus, psoriasis, IBD or transplant rejection.

Another embodiment includes a method of treating cancer in a mammal in need of such treatment, wherein the method comprises administering to said mammal a therapeutically effective amount of a compound of formula I, a stereoisomer, tautomer, prodrug or pharmaceutically acceptable salt thereof.

Another embodiment includes compounds of formula I, a stereoisomer, tautomer, prodrug or pharmaceutically acceptable salt thereof, for use in therapy. In another embodiment, the therapy is the treatment of an immunological disorder, for example rheumatoid arthritis. In another embodiment, the therapy is the treatment of cancer.

Another embodiment includes compounds of formula I, a stereoisomer, tautomer, prodrug or pharmaceutically acceptable salt thereof, for use in treating a disease selected from rheumatoid arthritis, asthma, systemic lupus erythematosus, psoriasis, IBD and transplant rejection.

Another embodiment includes the use of a compound of formulas I, a stereoisomer, tautomer, prodrug or pharmaceutically acceptable salt thereof, in the manufacture of a medicament for the treatment of a disease described herein (e.g., cancer or immunological disorder).

Combination Therapy

The compounds of formula I may be employed alone or in combination with other chemotherapeutic agents for treatment. The compounds of the present invention can be used in combination with one or more additional drugs, for example an anti-hyperproliferative, anti-cancer, cytostatic, cytotoxic, anti-inflammatory or chemotherapeutic agent. The second compound of the pharmaceutical combination formulation or dosing regimen preferably has complementary activities to the compound of this invention such that they do not adversely affect each other. Such agents are suitably present in combination in amounts that are effective for the purpose intended. The compounds may be administered together in a unitary pharmaceutical composition or separately and, when administered separately this may occur simultaneously or sequentially. Such sequential administration may be close or remote in time. In one embodiment, compounds of the present invention are coadministered with a cytostatic compound selected from the group consisting of cisplatin, doxorubicin, taxol, taxotere and mitomycin C. In another embodiment, the cytostatic compound is doxorubicin. In another embodiment, compounds of the present invention are coadministered with an anti-inflammatory agent selected from a NSAID and corticosteroid. In another embodiment, compounds of the present invention are coadministered with an anti-rheumatoid agent, in one example, RITUXAN®. In another embodiment, compounds of the present invention are coadministered with a chemotherapeutic agent selected from etanercept (Enbrel), infliximab (Remicade), adalimumab (Humira), certolizumab pegol (Cimzia), golimumab (Simponi), Interleukin 1 (IL-1) blockers such as anakinra (Kineret), monoclonal antibodies against B cells such as rituximab (RITUXAN®), T cell costimulation blockers such as abatacept (Orencia), Interleukin 6 (IL-6) blockers such as tocilizumab (ACTEMERA®); Interleukin 13 (IL-13) blockers such as lebrikizumab; Interferon alpha (IFN) blockers such as Rontalizumab; Beta 7 integrin blockers such as rhuMAb Beta7; IgE pathway blockers such as Anti-M1 prime; Secreted homotrimeric LTa3 and membrane bound heterotrimer LTa1/β2 blockers such as Anti-lymphotoxin alpha (LTa)

The compounds of the present invention can be also used in combination with radiation therapy. The phrase "radiation therapy" refers to the use of electromagnetic or particulate radiation in the treatment of neoplasia. Radiation therapy delivers doses of radiation sufficiently high to a target area to cause death of reproducing cells, in both tumor and normal tissues. The radiation dosage regimen is generally defined in terms of radiation absorbed dose (rad), time and fractionation, and must be carefully defined by the oncologist. The amount of radiation a patient receives will depend on various considerations but two of the most important considerations are the location of the tumor in relation to other critical structures or organs of the body, and the extent to which the tumor has spread. Examples of radiotherapeutic agents are provided in Hellman, Principles of Radiation Therapy, Cancer, in Principles I and Practice of Oncology, 24875 (Devita et al., 4th ed., vol 1, 1993). Alternative forms of radiation therapy include three-dimensional conformal external beam radiation, intensity modulated radiation therapy (IMRT), stereotactic radiosurgery and brachytherapy (interstitial radiation therapy), the latter placing the source of radiation directly into the tumor as implanted "seeds". These alternative treatment modalities deliver greater doses of radiation to the tumor, which accounts for their increased effectiveness when compared to standard external beam radiation therapy.

Articles of Manufacture

Another embodiment includes a method of manufacturing a compound of formula I. The method includes: (a) reacting a compound of formula i:

i

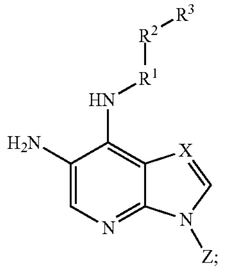

wherein $R^1$, $R^2$, $R^3$ and X are as defined in formula I, and Z is hydrogen or an amino protecting group, with a compound of formula ii:

$CR^5(Lg)_3$, ii;

wherein $R^5$ is defined in formula I and Lg is a leaving group, under conditions sufficient to form a compound of formula iii:

iii

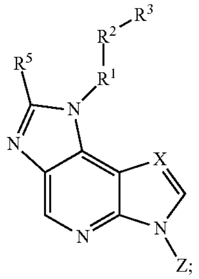

and (b) optionally deprotecting said amino protecting group to form a compound of formula I.

Another embodiment includes a method of manufacturing a compound of formula I. The method includes: (a) contacting a compound of formula iv:

iv

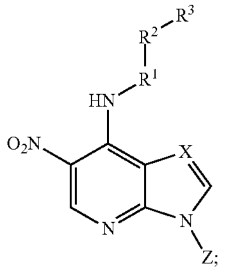

wherein $R^1$, $R^2$, $R^3$ and X are as defined in formula I, and Z is hydrogen or an amino protecting group, with iron powder, formic acid and a halide salt to form a compound of formula v:

v

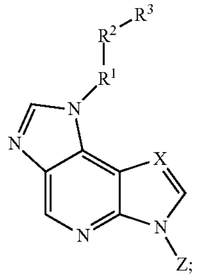

; and (b) optionally deprotecting said amino protecting group to form a compound of formula I. In one embodiment, said contacting step is free of mineral acids, for example HBr, HCl and $H_2SO_4$. In one embodiment, said contacting step further comprises heating the reaction to a temperature in the range of about 50-120° C. In another embodiment, said contacting step further comprises solvent, for example a protic solvent, selected from ethanol, isopropanol, butanol, hexanol or cyclohexanol. In one embodiment, said alcohol is isopropanol. In one embodiment, said alcohol is 1-butanol. In one embodiment, said halide salt is selected from NaI, LiBr, LiCl, NaCl and $NH_4Cl$. In one embodiment, said halide salt is $NH_4Cl$. In one embodiment, said contacting step further comprises 10 equivalents of said iron powder, 10 equivalents of said halide salt, for example $NH_4Cl$, a 1:1 mixture of formic acid:solvent, for example formic acid:isopropanol, alternatively formic acid:1-butanol, and heating the reaction to a temperature in the range of about 60-80° C., alternatively 80-120° C.

Another embodiment includes a method of manufacturing a compound of formulas vi-i or vi-ii:

vi-i

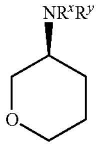

vi-ii

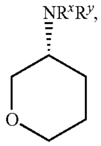

, and salts thereof, wherein $R^x$ and $R^y$ are independently selected from amino protecting group, hydrogen, $C_{1-6}$ alkyl, $C_{2-6}$ alkenyl, $C_{2-6}$ alkynyl, —C(O)$R^a$, —C(O)O$R^a$, —C(O)N$R^aR^b$, —S(O)$_{1-2}R^a$, —S(O)$_{1-2}$N$R^aR^b$, $C_{3-6}$ cycloalkyl, 3-12 membered heterocyclyl or $C_{6-10}$ aryl, wherein said alkyl, alkenyl, alkynyl, cycloalkyl, heterocyclyl and aryl are optionally independently substituted by halogen, oxo, —CN, —O$R^g$, —N$R^gR^h$, —C(O)$R^g$, —C(O)O$R^g$, —C(O)N$R^gR^h$, —N$R^g$C(O)$R^h$, —OC(O)N$R^gR^h$, —N$R^g$C(O)N$R^gR^h$, —N$R^g$C(O)O$R^h$, —S(O)$_{1-2}R^g$, —N$R^g$S(O)$_{1-2}R^h$, —S(O)$_{1-2}$N$R^gR^h$, —N$R^g$S(O)$_{1-2}$N$R^gR^h$, $C_{3-6}$ cycloalkyl, 3-6 membered heterocyclyl, phenyl or $C_{1-6}$ alkyl optionally substituted by oxo or halogen; and $R^a$, $R^b$, $R^g$ and $R^h$ are as defined in formula I. In one embodiment, $R^x$ and $R^y$ are independently hydrogen, methyl or amino protecting group. In one embodiment, the group —N$R^xR^y$ is —NHC(O)Otert-butyl. In one embodiment, the group —N$R^xR^y$ is —$NH_2$.

The method includes reacting a compound of formulas vii-i or vii-ii under ether forming conditions to form a compound of formulas vi-i or vi-ii.

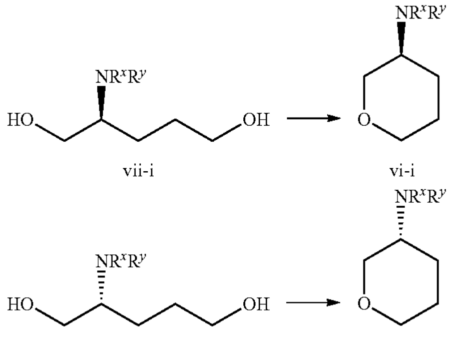

vii-i vi-i vii-ii vi-ii

In one embodiment, said ether forming conditions comprise (a) contacting a compound of the formula $P(R^v)_3$, with a compound of formula $R^w$N═N$R^z$, wherein $R^v$, $R^w$ and $R^z$ are independently selected from hydrogen, halogen, —O$R^g$, —S$R^g$, —N$R^gR^h$, $C_{1-6}$ alkyl, $C_{1-6}$ alkoxy, $C_{2-6}$ alkenyl, $C_{2-6}$ alkynyl, $C_{3-12}$ cycloalkyl, 3-12 membered heterocyclyl or $C_{6-14}$ aryl, wherein said alkyl, alkoxy, alkenyl, alkynyl, cycloalkyl, heterocyclyl and aryl are optionally independently substituted by halogen, oxo, —CN, —O$R^g$, —N$R^gR^h$, —C(O)$R^g$, —C(O)O$R^g$, —C(O)N$R^gR^h$, —N$R^g$C(O)$R^h$, —OC(O)N$R^gR^h$, —N$R^g$C(O)N$R^gR^h$, —N$R^g$C(O)O$R^h$, —S(O)$_{1-2}R^g$, —N$R^g$S(O)$_{1-2}R^h$, —S(O)$_{1-2}$N$R^gR^h$, —N$R^g$S(O)$_{1-2}$N$R^gR^h$, $C_{3-6}$ cycloalkyl, 3-6 membered heterocyclyl, phenyl or $C_{1-6}$ alkyl optionally substituted by oxo or halogen; and $R^a$, $R^{b}$, $R^g$ and $R^h$ are as defined in formula I, and a compound selected from formula vii-i or vii-ii, under conditions sufficient to form a compound of vi-i or vi-ii.

In one embodiment, the compound of the formula $P(R^v)_3$ is selected from: phosphine, methyldiphenylphosphine, trifluorophosphine, trimethylphosphite, triethylphosphite, tripropylphosphite, tricyclopentylphosphine, tricyclohexylphosphine, triphenylphosine, tritolylphosphine, trimethylphosphine, triethylphosphine, tripropylphosphine and tributylphosphine.

In one embodiment, the compound of the formula $R^w$N═N$R^z$ is selected from di-p-chlorobenzyl azodicarboxylate, Diisopropylazodicarboxylate, Diethylazocarboxylate, Azodicarbonyldipiperidine, Dibenzyl azodicarboxylate, N,N,N',N"-Tetramethylazodicarboxamide, Tetraisopropylazodicarboxamide and 4,4'-azopyridine, In one embodiment, the conditions sufficient include a solvent, for example a solvent selected from acetonitrile, dichloromethane, tetrahydrofuran, toluene and diethylether.

In one embodiment, said ether forming conditions comprise contacting a compound of formula vii-i, wherein $R^x$ is hydrogen and $R^y$ is an amino protecting group, with triphenylphosphine and diisopropylazodicarboxylate to form a compound of formula vi-i. In one embodiment, the compound of formula vi-i, wherein $R^x$ or $R^y$ is an amino protecting group, is further reacted under conditions sufficient to remove said amino protecting group and form a compound of formula vi-i, wherein $R^x$ and $R^y$ are hydrogen.

Another embodiment includes a kit for treating a disease or disorder responsive to the inhibition of JAK1 kinase. The kit includes:

(a) a first pharmaceutical composition comprising a compound of formula I; and (b) instructions for use.

In another embodiment, the kit further includes:

(c) a second pharmaceutical composition, which includes a chemotherapeutic agent.

In one embodiment, the instructions describe the simultaneous, sequential or separate administration of said first and second pharmaceutical compositions to a patient in need thereof.

In one embodiment, the first and second compositions are contained in separate containers.

In one embodiment, the first and second compositions are contained in the same container.

Containers for use include, for example, bottles, vials, syringes, blister pack, etc. The containers may be formed from a variety of materials such as glass or plastic. The container includes a compound of formula I or formulation thereof which is effective for treating the condition and may have a sterile access port (for example the container may be an intravenous solution bag or a vial having a stopper pierceable by a hypodermic injection needle). The container includes a composition comprising at least one compound of formula I. The label or package insert indicates that the composition is used for treating the condition of choice, such as cancer. In one embodiment, the label or package inserts indicates that the composition comprising the compound of formula I can be used to treat a disorder. In addition, the label or package insert may indicate that the patient to be treated is one having a disorder characterized by overactive or irregular kinase activity. The label or package insert may also indicate that the composition can be used to treat other disorders.

The article of manufacture may comprise (a) a first container with a compound of formula I contained therein; and (b) a second container with a second pharmaceutical formulation contained therein, wherein the second pharmaceutical formulation comprises a chemotherapeutic agent. The article of manufacture in this embodiment of the invention may further comprise a package insert indicating that the first and second compounds can be used to treat patients at risk of stroke, thrombus or thrombosis disorder. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In order to illustrate the invention, the following examples are included. However, it is to be understood that these examples do not limit the invention and are only meant to suggest a method of practicing the invention. Persons skilled in the art will recognize that the chemical reactions described may be readily adapted to prepare other compounds of formula I, and alternative methods for preparing the compounds of formula I are within the scope of this invention. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds of the invention.

EXAMPLES

The invention will be more fully understood by reference to the following examples. They should not, however, be construed as limiting the scope of the invention. Abbreviations used herein are as follows:

Abbreviations:

aq. Aqueous
Bn Benzyl
$Boc_2O$ Di-tert-butyl dicarbonate
$CDCl_3$ Deuterated chloroform
DCM Dichloromethane
DIAD Diisopropyl azodicarboxylate
DIPEA Diisopropylethylamine
DMAP 4-(Dimethylamino)pyridine
DMAW 90 DCM/MeOH/AcOH/$H_2O$ (90:18:3:2)
DMAW 240 DCM/MeOH/AcOH/$H_2O$ (240:20:3:2)
DMSO Dimethylsulfoxide
DMSO-d6 Deuterated DMSO
DME 1,2-Dimethoxyethane
DMF Dimethylformamide
EDCl 1-Ethyl-3-(3-dimethylaminopropyl) carbodiimide hydrochloride
eq equivalents
ESI Electrospray
Et Ethyl
EtOAc Ethyl acetate
EtOH Ethanol
$Et_3N$ Triethylamine
$Et_2O$ Diethyl ether
h Hour
hr Hour
HATU 2-(7-aza-1H-benzotriazole-1-yl)-1,1,3,3-tetramethyluronium hexafluorophosphate
HCl Hydrochloric acid
HM-N Isolute® HM-N is a modified form of diatomaceous earth
HOBt Hydroxybenzotriazole
HPLC High performance liquid chromatography
IMS Industrial methylated spirit
IPA Isopropyl alcohol
LDA Lithium diisopropylamide
LiOH Lithium Hydroxide
min minutes
MeOH Methanol
MeOD Deuterated methanol
$MgSO_4$ Magnesium sulfate
NaH Sodium Hydride
NaOH Sodium Hydroxide
$Na_2SO_4$ Sodium sulfate
$NaHCO_3$ Sodium bicarbonate/Sodium hydrogen carbonate
NaOH Sodium hydroxide
$NEt_3$ Triethylamine
$NH_3$ Ammonia
NH4Cl Ammonium chloride
p-TsOH para-toluenesulfonic acid
RT Retention time in minutes
SCX-2 Pre-packed Isolute® silica-based sorbent with a chemically bonded propylsulfonic acid functional group
SFC Supercritical fluid chromatography
Si-SPE Pre-packed Isolute® silica flash chromatography cartridge
Si-ISCO Pre-packed ISCO® silica flash chromatography cartridge
TBAF Tetrabutylammonium fluoride
TBS tert-butyl dimethylsilyl
TBDMS-OTf Trifluoromethanesulfonic acid tert-butyldimethylsilyl ester
TEA Triethylamine
TFA Trifluoroacetic acid TFAA Trifluoroacetic anhydride THF Tetrahydrofuran TLC Thin layer chromatography TMSCl Trimethylsilyl chloride General Experimental Conditions:

All temperatures are in degrees Celsius (° C.). Unless otherwise stated, operations were carried out at room or ambient temperature (18-25° C.).

Unless otherwise noted, the solvents used in preparing the example compounds were commercial anhydrous grade and were used without further drying or purification.

$^1$H NMR spectra were recorded at ambient temperature or at 80° C. where indicated using one of the following machines: Varian Unity Inova (400 MHz) spectrometer with a triple resonance 5 mm probe, Bruker Avance DRX 400 (400 MHz) spectrometer with a triple resonance 5 mm probe, a Bruker Avance DPX 300 (300 MHz) equipped with a standard 5 mm dual frequency probe for detection of $^1$H and $^{13}$C, a Bruker AVIII (400 MHz) using a BBI Broad Band Inverse 5 mm probe, or a Bruker AVIII (500 MHz) using a QNP (Quad Nucleus detect) 5 mm probe. Chemical shifts are expressed in ppm relative to an internal standard; tetramethylsilane (ppm=0.00). The following abbreviations have been used: br=broad signal, s=singlet, d=doublet, dd=double doublet, t=triplet, q=quartet, m=multiplet.

High Pressure Liquid Chromatography—Mass Spectrometry (LCMS) experiments to determine retention times (RT) and associated mass ions (m+H) were performed using one of the following methods:

Method A: Experiments performed on a Waters Micromass ZQ2000 quadrupole mass spectrometer linked to a Waters Acquity HPLC system with a PDA UV detector. The spectrometer has an electrospray source operating in positive and negative ion mode. This system uses an Acquity BEH C18 1.7 um 100×2.1 mm column, maintained at 40° C. or an Acquity BEH Shield RP18 1.7 μm 100×2.1 mm column, maintained at 40° C. and a 0.4 ml/minute flow rate. The initial solvent system was 95% water containing 0.1% formic acid (solvent A) and 5% acetonitrile containing 0.1% formic acid (solvent B) for the first 0.4 minute followed by a gradient up to 5% solvent A and 95% solvent B over the next 5.6 minutes. This was maintained for 0.8 minute before returning to 95% solvent A and 5% solvent B over the next 1.2 minutes. Total run time was 8 minutes.

Method B: Experiments performed on a Finnigan AQA single quadrupole mass spectrometer linked to a Hewlett Packard 1050 LC system with UV diode array detector and autosampler. The spectrometer has an electrospray source operating in positive ion mode. Additional detection is achieved using a Sedex 65 evaporative light scattering detector. This system uses a Luna 3 micron C18(2) 30×4.6 mm column at ambient temperature and a 2.0 ml/minute flow rate. The initial solvent system was 95% water containing 0.1% formic acid (solvent A) and 5% methanol containing 0.1% formic acid (solvent B) for the first 0.5 minute followed by a gradient up to 5% solvent A and 95% solvent B over the next 4.0 minutes. This was maintained for 1.0 minute before returning to 95% solvent A and 5% solvent B over the next 0.5 minute. Total run time was 6 minutes.

| Method C: HPLC-Agilent 1200 | |
|---|---|
| Mobile phase A | $H_2O$ with 0.05% TFA |
| Mobile phase B | Acetonitrile with 0.05% TFA |

-continued

| | |
|---|---|
| Column | Agilent SD-C18, 1.8 um, 2.1 * 30 mm |
| Column temperature | 40° C. |
| LC gradient | 3-95% B in 8.5 min, 95% in 2.5 min |
| LC Flowrate | 700 uL/min |
| UV wavelength | 220 nm and 254 nm |
| Mass Spec - Agilent quadrupole 6140 | |
| Ionization | ESI+ |
| Scan range | 110-800 amu |

| Method D: HPLC-Agilent 1200 | |
|---|---|
| Mobile phase A | $H_2O$ with 0.05% TFA |
| Mobile phase B | Acetonitrile with 0.05% TFA |
| Column | Agilent SD-C18, 3.5 μm, 3.0 * 100 mm |
| Column temperature | 40° C. |
| LC gradient | 2-98% B in 25.5 min, hold for 4.5 min |
| LC Flowrate | 700 μL/min |
| UV wavelength | 220 nm and 254 nm |
| Mass Spec - Agilent quadrupole 6140 | |
| Ionization | ESI+ |
| Scan range | 110-800 amu |

| Method E: HPLC-Agilent 1200 | |
|---|---|
| Mobile phase A | H2O with 0.1% Formic Acid |
| Mobile phase B | Acetonitrile with 0.1% Formic Acid |
| Column | XBridge C18 2.5 μm 3.0 * 30 mm |
| Column temperature | 40° C. |
| LC gradient | 2-95% B in 2.2 min, 95% in 0.3 min |
| LC Flowrate | 2 mL/min |
| UV wavelength | 220 nm and 254 nm |
| Mass Spec - Agilent quadrupole 6140 | |
| Ionization | ESI+ |
| Scan range | 110-800 amu |

| Method F: Waters Acquity UPLC | |
|---|---|
| Mobile phase A | $H_2O$ with 0.1% Formic Acid |
| Mobile phase B | Acetonitrile with 0.1% Formic Acid |
| Column | Acquity UPLC BEH C18, 1.7 μm, 2.1 * 30 mm |
| Column temperature | 40 degree C. |
| LC gradient | 5-95% B in 1.4 min, 95% in 0.3 min |
| LC Flowrate | 800 uL/min |
| UV wavelength | 220 nm and 254 nm |
| Mass Spec - Waters SQ Detector | |
| Ionization | ESI+ |
| Scan range | 100-800 amu |

Method G: HPLC instrument: Waters Acquity UPLC; mobile phase A: $H_2O$ with 0.1% formic acid; mobile phase B: $CH_3CN$ with 0.1% formic acid; column: Acquity UPLC BEH C18, 1.7 um, 2.1×30 mm; column temperature: 80° C.; LC gradient: 5-95% B in 1.4 min, 95% in 0.3 min; LC flowrate: 800 uL/min; UV wavelength: 220 nm and 254 nm; mass spectrometer: Waters SQ detector; ionization: ESI+; scan range: 100-800 amu.

Method H: Experiments were performed on a Waters Platform LC quadrupole mass spectrometer linked to a Hewlett Packard HP1100 LC system with diode array detector and 100 position autosampler. The spectrometer has an electrospray source operating in positive and negative ion mode. Additional detection is achieved using a Sedex 85 evaporative light scattering detector. This system uses an Phenomenex Luna 3 micron C18(2) 30×4.6 mm column at ambient temperature, and a 2.0 ml/minute flow rate. The initial solvent system was 95% water containing 0.1% formic acid (solvent A) and 5% acetonitrile containing 0.1% formic acid (solvent B) for the first 0.5 minute followed by a gradient up to 5% solvent A and 95% solvent B over the next 4 minutes. This was maintained for 1 minute before returning to 95% solvent A and 5% solvent B over the next 0.5 minute. Total run time was 6 minutes.

Method I: Experiments were performed on a Waters ZMD quadrupole mass spectrometer linked to a Waters 1525 LC system with Waters 996 diode array detector. The spectrometer has an electrospray source operating in positive and negative ion mode. Additional detection is achieved using a Sedex 85 evaporative light scattering detector. This system uses an Luna 3 micron C18(2) 30×4.6 mm column at ambient temperature, and a 2.0 ml/minute flow rate. The initial solvent system was 95% water containing 0.1% formic acid (solvent A) and 5% acetonitrile containing 0.1% formic acid (solvent B) for the first 0.5 minute followed by a gradient up to 5% solvent A and 95% solvent B over the next 4 minutes. This was maintained for 1 minute before returning to 95% solvent A and 5% solvent B over the next 0.5 minute. Total run time was 6 minutes.

| Method J: | |
|---|---|
| LCMS | SHIMADZU LC/20A or Agilent 1200 Series |
| Mobile phase A | $H_2O$ with 0.375% TFA |
| Mobile phase B | Acetonitrile with 0.187% TFA |
| Column | Shimpack ODS XR-ODS, 3 * 30 mm or Xtimate 3 μm, 2.1 * 30 mm SN:3u410901511 |
| Column temperature | 50° C. |
| LC gradient | 10-80% B in 2 min, 80% in 0.9 min |
| LC Flowrate | 1200 μL/min |
| UV wavelength | 220 nm |
| Mass Spec - SHIMADZU 2010MSD or Agilent MSD VL | |
| Ionization | ESI+ |
| Scan range | 100-1000 amu |
| Method K: | |
| LCMS | SHIMADZU LC/20A or Agilent 1200 Series |
| Mobile phase A | $H_2O$ with 0.375% TFA |
| Mobile phase B | Acetonitrile with 0.187% TFA |
| Column | Shimpack ODS XR-ODS, 3 * 30 mm or Xtimate 3 μm, 2.1 * 30 mm SN:3u410901511 |
| Column temperature | 50° C. |
| LC gradient | 0-60% B in 2 min, 60% in 0.9 min |
| LC Flowrate | 1200 μL/min |
| UV wavelength | 220 nm |
| Mass Spec - SHIMADZU 2010MSD or Agilent MSD VL | |
| Ionization | ESI+ |
| Scan range | 100-1000 amu |
| Method L: | |
| LCMS | SHIMADZU LC/20A or Agilent 1200 Series |
| Mobile phase A | $H_2O$ with 0.375% TFA |
| Mobile phase B | Acetonitrile with 0.187% TFA |
| Column | Shimpack ODS XR-ODS, 3 * 30 mm or Xtimate 3 μm, 2.1 * 30 mm SN:3u410901511 |
| Column temperature | 50° C. |
| LC gradient | 0-30% B in 2 min, 30% in 0.9 min |
| LC Flowrate | 1200 μL/min |
| UV wavelength | 220 nm |
| Mass Spec - SHIMADZU 2010MSD or Agilent MSD VL | |
| Ionization | ESI+ |
| Scan range | 100-1000 amu |
| Method M: | |
| System | Shimadzu HPLC |
| Mobile phase A | $H_2O$ with 0.05% TFA |
| Mobile phase B | Acetonitrile with 0.0375% TFA |
| Column | Phenomenex Onyx Monolithic C18 4.6 * 50 mm |
| Column temperature | Room temperature |
| LC gradient | 5-85% B in 4.0 min, 85% in 0.5 min |
| LC Flowrate | 3000 μL/min |
| UV wavelength | 214 nm and 254 nm |

-continued

| Mass Spec - Waters SQ Detector | |
|---|---|
| Ionization | ESI+ |
| Scan range | 150-1250 amu |
| Method N: | |
| System | Waters Acquity UPLC |
| Mobile phase A | Waters with 0.05% TFA |
| Mobile phase B | Acetonitrile with 0.05% TFA |
| Column | Acquity UPLC BEH C18, 1.7 μm, 2.1 * 50 mm |
| Column temperature | 40° C. |
| LC gradient | 2-98% B in 17.0 min, 98% in 1.5 min |
| LC Flowrate | 600 μL/min |
| UV wavelength | 254 nm |
| Mass Spec - Waters LCT Premier XE | |
| Ionization | ESI positive |
| Scan range | 100-800 amu |
| Method O: | |
| System | HPLC-Agilent 1200 |
| Mobile phase A | Water with 0.05% TFA |
| Mobile phase B | Acetonitrile with 0.05% TFA |
| Column | Agilent ZORBAX SD-C18, 1.8 μm, 2.1 * 30 mm |
| Column temperature | 40° C. |
| LC gradient | 3-95% B in 8.5 min, 95% in 2.5 min |
| LC Flowrate | 400 μL/min |
| UV wavelength | 220 nm and 254 nm |
| Mass Spec - Agilent quadrupole 6140 | |
| Ionization | ESI positive |
| Scan range | 110-800amu |
| Method P: | |
| System | HPLC-Agilent 1200 |
| Mobile phase A | $H_2O$ with 0.05% TFA |
| Mobile phase B | Acetonitrile with 0.05% TFA |
| Column | Onyx-C18, 2.0 * 50 mm |
| Column temprature | 35° C. |
| LC gradient | 5-65% B in 4 min |
| LC Flowrate | 785 μL/min |
| UV wavelength | 220 nm and 254 nm |
| Mass Spec - Agilent quadrupole 6140 | |
| Ionization | ESI+ |
| Scan range | 60-1000 amu |

Method Q: Compounds were analysed using the following conditions: Experiments were performed on a The system consists of a Waters ZMD single quadrupole mass spectrometer linked to a Hewlett Packard HP1100 LC system with UV diode array detector and 100 position autosampler. The spectrometer has an electrospray source operating in positive and negative ion mode. This system uses an Phenomenex Luna 3 micron C18(2) 30×4.6 mm column at ambient temperature, and a 2.0 ml/minute flow rate. The initial solvent system was 95% water containing 0.1% formic acid (solvent A) and 5% acetonitrile containing 0.1% formic acid (solvent B) for the first 0.5 minute followed by a gradient up to 5% solvent A and 95% solvent B over the next 4 minutes. This was maintained for 1 minute before returning to 95% solvent A and 5% solvent B over the next 0.5 minute. Total run time was 6 minutes.

Method R: Compounds were analysed using the following conditions: Experiments were performed on a VG Platform II quadrupole spectrometer is linked to a Hewlett Packard HP1050 LC system with diode array detector and 100 position autosampler. The spectrometer has an electrospray source operating in positive and negative ion mode. Additional detection is achieved using a Sedex 85 evaporative light scattering detector. This system uses an Luna 3 micron C18

(2) 30×4.6 mm column at ambient temperature, and a 2.0 ml/minute flow rate. The initial solvent system was 95% water containing 0.1% formic acid (solvent A) and 5% acetonitrile containing 0.1% formic acid (solvent B) for the first 0.5 minute followed by a gradient up to 5% solvent A and 95% solvent B over the next 4 minutes. This was maintained for 1 minute before returning to 95% solvent A and 5% solvent B over the next 0.5 minute. Total run time was 6 minutes.

Analytical chiral supercritical fluid chromatography (SFC) experiments to determine retention times (RT) were performed using one of the following methods, unless specified otherwise:

Method A1:

System: Berger Analytical SFC
Column: 4.6 × 100 mm, 5 μm, Chiralpak AD from Chiral Technologies
Flowrate: 5 mL/min
Solvent A: $CO_2$
Solvent B: Methanol
Method: 35% B over 3 minutes
Pressure: 120 Bar
Temperature: 40° C.
Detection: UV at 230 nm Method A2:

| | |
|---|---|
| System | Mettler-Toledo MGII |
| Mobile phase A | Methanol with 0.1% Diethylamine |
| Mobile phase B | Super-critical $CO_2$ |
| Column | Chiral Technologies Chiralpak IC, 5 μm |
| Column temperature | 40° C. |
| LC gradient | Isocratic 30% B, 3 min |
| LC Flowrate | 50 g/min |
| UV wavelength | 230 nm |

Method A3:

Instrument: Berger analytical and Waters ZQ
Column: Phenomenex Lux Cellulose-2, 4.6 × 100 mm, 5 μm
Detection: UV 220 nm
Mobile Phase: 30% EtOH containing 0.1% TEA, 70% $CO_2$
Flowrate: 5 g/min
Runtime: 3 minutes
Back pressure setting: 120 bar
Temperature: 40° C.

Method A4:

Mobile Phase A: $CO_2$
Mobile phase B: Methanol with 0.1% dimethylamine
Isocratic conditions with 30% Mobile phase B
Flow Rate: 200 mL/min
Column: Lux Cellulose-1, 3 × 25 cm, 5 μM
Outlet pressure: 100 Bar
Temperatuer: 40° C.
System: Thar 350
Uv: 230 nm
Runtime: 5.2 minutes Reverse Phase High Performance Liquid Chromatography (HPLC) was used to purify compounds where indicated. Unless otherwise indicated, the conditions were: elution on a Phenomenex Gemini C18 column (250×21.2 mm, 5 micron) as stationary phase and using mobile phase indicated, operating at a 18 ml/min flow rate using a Gilson UV/Vis −155 dual channel detector and Gilson GX-271 automated liquid handler.

Microwave experiments were carried out using a Biotage Initiator 2.0 (400 W MAGNETRON®) which uses a single-mode resonator and dynamic field tuning Temperature from 40-250° C. can be achieved, and pressures of up to 20 bar can be reached.

BIOLOGICAL EXAMPLES

Previous studies have shown that the isolated kinase domains of human JAK1, JAK2, JAK3 or TYK2 phosphorylate peptide substrates in in vitro kinase assays (Saltzman et al., Biochem. Biophys. Res. Commun. 246:627-633 (2004)). The catalytically active kinase domain of human JAK1, JAK2, JAK3 or TYK2 was purified from extracts of SF9 insect cells infected with a recombinant baculovirus expression vector encoding the human JAK1, JAK2, JAK3 or TYK2 kinase domains (JAK1 amino acid residues N852-D1154 according to the numbering of GenBank sequence accession number P23458, JAK2 amino acid residues D812-G1132 according to the numbering of GenBank sequence accession number NP 004963.1; JAK3 amino acid residues S783-S1124 according to the numbering of GenBank sequence accession number P52333, and TYK2 amino acid residues N873-C1187 according to the numbering of GenBank sequence accession number P29597). The activity of the JAK1, JAK2, JAK3 or TYK2 kinase domains can be measured by a number of direct and indirect methods, including quantification of phosphorylation of peptide substrates derived from the human JAK3 protein (Saltzman et al., Biochem. Biophys. Res. Commun. 246:627-633 (2004)). The activity of the JAK1, JAK2, JAK3 or TYK2 kinase domains was measured in vitro by monitoring phosphorylation of JAK3 derived peptides using the Caliper LabChip technology.

Example A

JAK2 Inhibition Assay Protocol

The activity of the isolated JAK2 kinase domain was measured by monitoring phosphorylation of a peptide derived from JAK3 (Val-Ala-Leu-Val-Asp-Gly-Tyr-Phe-Arg-Leu-Thr-Thr) fluorescently labelled on the N-terminus with 5-carboxyfluorescein using the Caliper LabChip technology (Caliper Life Sciences, Hopkinton, Mass.). To determine the inhibition constants ($K_i$), compounds were diluted serially in DMSO and added to 50 μL kinase reactions containing 0.2 nM purified JAK2 enzyme, 100 mM Hepes pH7.2, 0.015% Brij-35, 1.5 μM peptide substrate, 25 μM ATP, 10 mM $MgCl_2$, 4 mM DTT at a final DMSO concentration of 2%. Reactions were incubated at 22° C. in 384-well polypropylene microtiter plates for 30 minutes and then stopped by addition of 25 μL of an EDTA containing solution (100 mM Hepes pH 7.2, 0.015% Brij-35, 150 mM EDTA), resulting in a final EDTA concentration of 50 mM. After termination of the kinase reaction, the proportion of phosphorylated product was determined as a fraction of total peptide substrate using the Caliper LabChip 3000 according to the manufacturer's specifications. $K_i$ values were then determined using the Morrison tight binding model. Morrison, J. F., *Biochim. Biophys. Acta.* 185:269-296 (1969); William, J. W. and Morrison, J. F., *Meth. Enzymol.,* 63:437-467 (1979).

Example B

JAK1 and TYK2 Inhibition Assay Protocol

The activity of the isolated JAK1 or TYK2 kinase domain was measured by monitoring phosphorylation of a peptide derived from JAK3 (Val-Ala-Leu-Val-Asp-Gly-Tyr-Phe-Arg-Leu-Thr-Thr) fluorescently labelled on the N-terminus with 5-carboxyfluorescein using the Caliper LabChip technology (Caliper Life Sciences, Hopkinton, Mass.). To determine inhibition constants ($K_i$), compounds were diluted serially in DMSO and added to 50 uL kinase reactions containing 1.5 nM JAK1 or 1 nM purified TYK2 enzyme, 100 mM Hepes pH7.2, 0.015% Brij-35, 1.5 μM peptide substrate, 25 μM ATP, 10 mM MgCl2, 4 mM DTT at a final DMSO concentration of 2%. Reactions were incubated at 22° C. in 384-well polypropylene microtiter plates for 30 minutes and then stopped by addition of 25 uL of an EDTA containing solution (100 mM Hepes pH 7.2, 0.015% Brij-35, 150 mM EDTA), resulting in a final EDTA concentration of 50 mM. After termination of the kinase reaction, the proportion of phosphorylated product was determined as a fraction of total peptide substrate using the Caliper LabChip 3000 according to the manufacturer's specifications. $K_i$ values were then determined using the Morrison tight binding model (Morrison, J. F., Biochim. Biophys. Acta. 185:269-296 (1969); William, J. W. and Morrison, J. F., Meth. Enzymol., 63:437-467 (1979)).

Example C

JAK3 Inhibition Assay Protocol

The activity of the isolated JAK3 kinase domain was measured by monitoring phosphorylation of a peptide derived from JAK3 (Leu-Pro-Leu-Asp-Lys-Asp-Tyr-Tyr-Val-Val-Arg) fluorescently labelled on the N-terminus with 5-carboxyfluorescein using the Caliper LabChip technology (Caliper Life Sciences, Hopkinton, Mass.). To determine inhibition constants ($K_i$), compounds were diluted serially in DMSO and added to 50 uL kinase reactions containing 5 nM purified JAK3 enzyme, 100 mM Hepes pH7.2, 0.015% Brij-35, 1.5 μM peptide substrate, 5 μM ATP, 10 mM MgCl2, 4 mM DTT at a final DMSO concentration of 2%. Reactions were incubated at 22° C. in 384-well polypropylene microtiter plates for 30 minutes and then stopped by addition of 25 uL of an EDTA containing solution (100 mM Hepes pH 7.2, 0.015% Brij-35, 150 mM EDTA), resulting in a final EDTA concentration of 50 mM. After termination of the kinase reaction, the proportion of phosphorylated product was determined as a fraction of total peptide substrate using the Caliper LabChip 3000 according to the manufacturer's specifications. $K_i$ values were then determined using the Morrison tight binding model (Morrison, J. F., Biochim. Biophys. Acta. 185:269-296 (1969); William, J. W. and Morrison, J. F., Meth. Enzymol., 63:437-467 (1979)).

Example D

Cell-Based Pharmacology Assays

The activities of compounds were determined in cell-based assays that are designed to measure JAK2-dependent signaling or proliferation. Compounds were serially diluted in DMSO and incubated with Set-2 cells (German Collection of Microorganisms and Cell Cultures (DSMZ); Braunschweig, Germany), which express the JAK2V617F mutant protein, in 96-well microtiter plates for 1 hr at 37° C. in RPMI medium at a final cell density of 100,000 cells per well and a final DMSO concentration of 0.57%. Compound-mediated effects on STATS phosphorylation were then measured in the lysates of incubated cells using the Meso Scale Discovery (MSD) technology (Gaithersburg, Md.) according to the manufacturer's protocol and EC50 values were determined. Alternatively, serially diluted compounds were added to 384-well microtiter plates in RPMI medium with 10% fetal bovine serum (Invitrogen Corp.; Carlsbad, Calif.) at a final cell density of 2500 cells per well and a final DMSO concentration of 0.3% and incubated at 37° C. for 72 hours. Cell viability was then determined using the CellTiter-Glo® Luminescent Cell Viability Assay according to the manufacturer's protocol (Promega; Madison, Wis.) and EC50 values were determined.

The activities of compounds were determined in cell-based assays that are designed to measure TYK2-dependent signaling. Compounds were serially diluted in DMSO and incubated with NK92 cells (American Type Culture Collection (ATCC); Manassas, Va.) in 96-well microtiter plates in RPMI medium at a final cell density of 100,000 cells per well and a final DMSO concentration of 0.57%. Human recombinant IL-12 (R&D systems; Minneapolis, Minn.) was then added at a final concentration of 10 ng/mL to the microtiter plates containing the NK92 cells and compound and the plates were incubated for 1 hr at 37° C. Compound-mediated effects on STAT4 phosphorylation were then measured in the lysates of incubated cells using the Meso Scale Discovery (MSD) technology (Gaithersburg, Md.) according to the manufacturer's protocol and EC50 values were determined.

The activities of compounds were determined in cell-based assays that are designed to measure JAK1 or JAK2-dependent signaling. Compounds were serially diluted in DMSO and incubated with TF-1 cells (American Type Culture Collection (ATCC); Manassas, Va.) in 384-well microtiter plates in Opti-MEM medium without phenol red, 1% Charcoal/Dextran stripped FBS, 0.1 mM NEAA, 1 mM sodium pyruvate (Invitrogen Corp.; Carlsbad, Calif.) at a final cell density of 100,000 cells per well and a final DMSO concentration of 0.2%. Human recombinant IL-6 (R&D systems; Minneapolis, Minn.) or EPO (Invitrogen Corp.; Carlsbad, Calif.) was then added at a final concentration of 30 ng/mL or 10 Units/mL, respectively, to the microtiter plates containing the TF-1 cells and compound and the plates were incubated for 30 min at 37° C. Compound-mediated effects on STAT3 or STATS phosphorylation were then measured in the lysates of cells incubated in the presence of IL-6 or EPO, respectively, using the Meso Scale Discovery (MSD) technology (Gaithersburg, Md.) according to the manufacturer's protocol and EC50 values were determined.

Example E

Alternative Cell-Based Pharmacology Assay

The activities of compounds were determined in cell-based assays that are designed to measure TYK2-dependent signaling. Compounds were serially diluted in DMSO and incubated with NK92 cells (American Type Culture Collection (ATCC); Manassas, Va.) in 384-well microtiter plates in RPMI medium at a final cell density of 50,000 cells per well and a final DMSO concentration of 0.2%. Human recombinant IL-12 (R&D systems; Minneapolis, Minn.) was then added at a final concentration of 30 ng/ml to the microtiter plates containing the NK92 cells and compound and the plates were incubated for 45 min at 37° C. Compound-mediated effects on STAT4 phosphorylation were then measured in the lysates of incubated cells using the Meso Scale Discovery (MSD) technology (Gaithersburg, Md.) according to the manufacturer's protocol and EC50 values were determined.

The compounds of Examples 1-3, 5-28 and 30-1014 were tested for their capacity to inhibit JAK1 kinase activity. The compounds of Examples 1-3, 5-28 and 30-1014 were found to have a $K_i$ of less than about 500 nM in a JAK1 kinase activity assay (Example B). The compounds of Examples 1, 5-12, 14, 17-23, 25, 26, 28-32, 34-38, 40-54, 57-65 and 67-108 were found to have a $K_i$ of less than about 100 nM in a JAK1 kinase activity assay (Example B). The compounds of the present invention are therefore useful as inhibitors of JAK1 kinase.

PREPARATIVE EXAMPLES

Example F

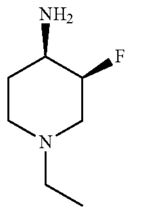

(3S,4R)-1-Ethyl-3-fluoro-piperidin-4-ylamine

N-(3-Fluoro-pyridin-4-yl)-benzamide

A solution of 3-fluoropyridin-4-amine (2.20 kg, 19.6 mol) in anhydrous tetrahydrofuran (25 L) was cooled to −5° C. and flushed with nitrogen. This solution was charged with triethylamine (3.99 kg/5.5 L, 39.4 mol). Benzoylchloride (3.173 kg/2.62 l, 22.57 mol) was added drop-wise via an addition funnel over two hours while the internal temperature was maintained between −5° C. to 5° C. and the reaction mixture was left to stand for an additional two hours. The reaction mixture was then filtered and washed with dry tetrahydrofuran (5×20 L). The tetrahydrofuran solution was concentrated under vacuum to give crude product which was recrystallized from ethyl acetate and hexane, filtered and dried to afford N-(3-fluoro-pyridin-4-yl)-benzamide, 3.90 kg, (92%). $^{1}$H NMR (400 MHz, $CDCl_3$): δ 8.51 (1H, t, J=5.46 Hz), 8.45 (1H, d, J=2.34 Hz), 8.39 (1H, d, J=5.46 Hz), 8.30 (1H, s), 7.89 (2H, d, J=8.20 Hz), 7.62 (1H, t, J=7.03 Hz), 7.53 (2H, t, J=7.81 Hz).

4-benzamido-1-ethyl-3-fluoro-pyridinium iodide

A solution of N-(3-fluoro-pyridin-4-yl)-benzamide (1.95 kg, 9.0 mol) in anhydrous dimethylformamide (10 L) was placed under nitrogen atmosphere and heated at 70° C. The heated solution was charged with iodoethane via dropwise addition (1.55 kg/0.795 L, 9.9 mol) with temperature monitoring. The addition caused an exoterm that raised the internal reactor temperature to 110° C. for the duration of the addition. A temperature of 100° C. was maintained for a further two hours before the reaction was cooled to room temperature. The reaction mixture was poured into ethyl acetate (50 L, pre-cooled to 5° C.) and stirred for one hour. The precipitated solid was collected by filtration and washed with ethyl acetate (3×10 L). The yellowish solid 4-benzamido-1-ethyl-3-fluoro-pyridinium iodide was dried in a tray vacuum oven at 50° C., yielding 3.25 kg. (97%). $^{1}$H NMR (400 MHz, DMSO): δ 11.37 (1H, s), 9.41 (1H, dd, J=5.86, 1.56 Hz), 8.88 (1H, dd, J=7.03, 1.56 Hz), 8.73 (1H, t, J=7.42 Hz), 7.99 (2H, d, J=8.20 Hz), 7.72 (1H, t, J=7.42 Hz), 7.61 (2H, t, J=8.20 Hz), 4.52 (2H, q, J=7.42 Hz), 1.54 (3H, t, J=7.42 Hz).

N-(1-ethyl-3-fluoro-1,2,5,6-tetrahydro-pyridin-4-yl)benzamide

A solution of 4-benzamido-1-ethyl-3-fluoro-pyridinium iodide (6.45 kg, 17.3 mol) in methanol (40 L) was charged with sodium borohydride (1.82 kg, 43.3 mol) via portion-wise addition over five to six hours maintaining an internal reaction temperature between −5° C. and 10° C. Following this addition saturated aqueous ammonium chloride (10 L) was added and the reaction mixture stirred for 1 h, and then saturated aqueous sodium bicarbonate (12 L) was added and the mixture was left to stand overnight. Methanol was removed under vacuum and the resulting aqueous solution was extracted with ethyl acetate (3×30 L), washed with water, brine and dried over sodium sulfate. The concentrated organic layer yielded 3.36 kg of N-(1-ethyl-3-fluoro-1,2,5,6-tetrahydro-pyridin-4-yl)benzamide (78%). $^{1}$H NMR (400 MHz, $CDCl_3$) δ 7.78 (2H, d, J=7.7 Hz), 7.48 (4H, dq, J=14.9, 7.4 Hz), 3.17 (2H, s), 2.89 (2H, s), 2.65 (2H, t, J=5.6 Hz), 2.55 (2H, q, J=7.1 Hz), 1.13 (3H t, J=7.2 Hz).

N-((3S,4R)-1-ethyl-3-fluoropiperidin-4-yl)benzamide

A 10 L Schlenck flask was charged with [Ru(COD)($CF_3CO_2$)$_2$] (52.6 g, 121 mmol) and (R)-(−)-1-[(S)-2-DIPHENYLPHOSPHINO)FERROCENYL]ETHYLDI-TERT-BUTYLPHOSPHINE (CAS #: 155830-69-6, 68.8 g, 127 mmol) and taken through five vacuum—argon fill cycles. Dried and degassed methanol (4.0 L) and dichloromethane (2.5 L) were added to the reaction via cannula and the resulting suspension was stirred for 45 min at 40° C. before being cooled to room temperature.

A 50 L autoclave was purged with nitrogen. N-(1-ethyl-3-fluoro-1,2,5,6-tetrahydro-pyridin-4-yl)benzamide (6.00 kg, 24.16 mol) was dissolved in methanol (19 L) and dichloromethane (1 L) and transferred to the inert autoclave. After four high vacuum—nitrogen fill cycles the prepared catalyst solution (6.5 L) was added to the autoclave. The reaction was pressurized with hydrogen gas to 20 bar and left to stand at 1000 rpm for 20 h at room temperature, was heated to 40° C. for 7 h, and then cooled to 25° C. Following a nitrogen purge the contents of autoclave were transferred into a 60 L reactor with methanol (2.0 L). Deloxan THPII (2.4 kg, 40 mass %) was added, and stirred at 500 rpm for 3 days at room temperature. The suspension was filtered over Arbocel (0.7 kg) applying high vacuum, the filter cake was washed with methanol (5.0 L), and solvent evaporated at 20 mbar and 45° C. Obtained 6.58 kg of N-((3S,4R)-1-ethyl-3-fluoropiperidin-4-yl)benzamide which was used without further purification. $^{1}$H NMR (400 MHz, MeOD) δ 7.83 (2H, t, J=9.1 Hz), 7.53 (1H, t, J=7.3 Hz), 7.45 (2H, t, J=7.6 Hz), 4.84 (1H, d, J=49.28 Hz), 4.25-3.91 (1H, m), 3.37-3.22 (2H, m), 3.10-2.95 (1H, m), 2.60-2.39 (2H, m), 2.32-2.02 (3H, m), 1.79 (1H, d, J=12.3 Hz), 1.11 (3H, t, J=7.2 Hz).

(3S,4R)-1-ethyl-3-fluoropiperidin-4-amine dihydrochloride

A solution of N-((3S,4R)-1-ethyl-3-fluoropiperidin-4-yl)benzamide (6.58 kg, 24.16 mol) in aqueous hydrochloric acid (35 L, 209 mol) was heated to 130° C. external temperature for 10 hours then was allowed to stand overnight at room temperature. The precipitated solid was filtered off and washed with water (2 L). The filtrate was concentrated, and ethanol (20 L) was added at 60° C. The solution was slowly cooled to room temperature overnight, crystallization occurred, and the yellow suspension was cooled to 0° C. for 1 h, filtered over a glass frit, washed with chilled ethanol (10 L, 0° C.), and diethyl ether (5 L). The tan solid was removed from the filter and dried in vacuum oven to yield 4.70 kg of (3S,4R)-1-ethyl-3-fluoropiperidin-4-amine dihydrochloride (85%). $^1$H NMR (400 MHz, MeOD) δ 5.35 (d, J=47.2 Hz, 1H), 4.32-3.43 (m, 4H), 3.32 (s, 3H), 2.32 (s, 2H), 1.40 (s, 3H), 1.16 (d, J=6.1 Hz, 2H).

Example G

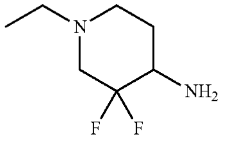

1-Ethyl-3,3-difluoro-piperidin-4-ylamine

A solution of 1-benzyl-5,5-difluoro-4-hydroxy-1,2,5,6-tetrahydro-pyridine-3-carboxylic acid ethyl ester was (59.46 g, 0.2 mol, prepared according to EP2123651 A1) in ethyl acetate (600 ml) was degassed and charged with acetaldehyde (13.22 g, 0.3 mol) and 10% palladium on activated carbon (6 g). This mixture was allowed to stir for three hours under an atmosphere then filtered through Celite, washed with copious methanol and concentrated under vacuum to give 1-ethyl-5,5-difluoro-4-hydroxy-1,2,5,6-tetrahydro-pyridine-3-carboxylic acid ethyl ester that was immediately taken up into a 3N solution of hydrochloric acid (470 ml) and heated to reflux for four hours. Upon completion, the reaction was cooled to room temperature and concentrated under vacuum to yield 43.5 g 1-ethyl-3,3-difluoro-4,4-dihydroxy-piperidinium as a pale yellow powder (100%) LCMS (Method F): RT=0.13 min, m+H=182.0 $^1$H NMR (400 MHz, DMSO) δ 10.84 (s, 1H), 6.93 (s, 2H), 3.82 (s, 1H), 3.60-3.32 (m, 2H), 3.15 (d, J=41.5, 2H), 3.09 (s, 1H), 2.07 (dd, J=30.7, 17.4, 2H), 1.25 (t, J=7.2, 3H).

1-Ethyl-3,3-difluoro-piperidin-4-one oxime

A suspension of 1-ethyl-3,3-difluoro-4,4-dihydroxy-piperidinium (10.213 g, 46.93 mmol) in ethanol (80 ml) was charged with aqueous hydroxylamine solution (50% by weight, 3.58 ml, 58.4 mmol) and left to stand overnight. The thick precipitate was dissolved with the addition of ethanol (20 ml) and heating. The solution was then cooled to room temperature before being place over ice. The precipitated solid was then collected by filtration and dried over vacuum to yield 8.27 g 1-ethyl-3,3-difluoro-piperidin-4-one oxime (99%) LCMS (Method F): RT=0.14 min, m+H=179.0 $^1$H NMR (400 MHz, D2O) δ 4.07-3.82 (m, 2H), 3.53 (s, 2H), 3.38 (q, J=7.3 Hz, 2H), 3.13 (s, 2H), 1.38 (t, J=7.3 Hz, 3H).

1-ethyl-3,3-difluoro-piperidin-4-ylamine

A solution of 1-ethyl-3,3-difluoro-piperidin-4-one oxime (6.186 g, 34.72 mmol) in tetrahydrofuran (300 ml) was cooled to 0° C. over an ice bath and charged with 1M lithium tetrahydroaluminate in tetrahydrofuran (69.4 ml, 69.4 mmol) and left to stand overnight gradually warming to room temperature. The reaction was quenched with the addition of 1 N aqueous solution of sodium potassium tartrate (70 ml) and left to stir for an additional night. The white slurry was extracted twice with ethyl acetate (50 ml) and twice with dichloromethane (50 ml) and dried over sodium sulfate and concentrated under vacuum to yield 4.71 g 1-ethyl-3,3-difluoro-piperidin-4-ylamine (83%) LCMS (Method F): RT=0.14 min, m+H=179.0 $^1$H NMR (400 MHz, D2O) δ 4.07-3.82 (m, 2H), 3.53 (s, 2H), 3.38 (q, J=7.3 Hz, 2H), 3.13 (s, 2H), 1.38 (t, J=7.3 Hz, 3H).

Example H

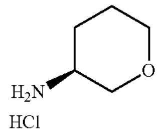

(S)-(Tetrahydro-pyran-3-yl)amine hydrochloride (S)-dimethyl 2-(tert-butoxycarbonylamino)pentanedioate To MeOH (7 L) was added TMSCl slowly at 0° C., and the mixture was stirred for 30 min, then L-Glutamic acid (700 g, 4.76 mol) was added to the mixture. The mixture was stirred at room temperature until complete reaction was observed (monitored by TLC). After cooling to 0° C., $Et_3N$ (3130 g, 3 μmol) and $Boc_2O$ (1142 g, 5.23 mol) were added slowly to the reaction solution successively while keeping the internal temperature below 25° C., and the resultant solution was stirred for 16 h. After concentration, the residue was poured into 5 L of water and extracted with ethyl acetate (10 L). The organic phase was washed with 4 L of 20% citric acid and brine, and dried over $Na_2SO_4$. After filtration and concentration, the crude (S)-dimethyl 2-(tert-butoxycarbonylamino)pentanedioate (1300 g) was obtained as pale yellow oil.

(S)-tert-butyl 1,5-dihydroxypentan-2-ylcarbamate

A 20 L reactor was charged with 10 L of dry THF and $LiBH_4$ (400 g) and cooled to 0° C. A THF solution of (S)-dimethyl 2-(tert-butoxycarbonylamino)pentanedioate (1000 g/3.63 mol, dissolved in 2 L of dry THF) was then added dropwise while keeping the internal temp. below 15° C. The mixture was slowly warmed to room temperature and stirred for 16 h. Cooled to 0° C., then MeOH (10 L) was added dropwise to the reaction mixture to quench the excess amount of reducing reagent. Concentrated, and the residue was poured into 5 L water. After extraction with ethyl acetate, the combined organic phase was dried over $Na_2SO_4$. After filtration the solvent was removed in vacuo to give 730 g of crude (S)-tert-butyl 1,5-dihydroxypentan-2-ylcarbamate as a pale yellow oil.

(S)-tert-butyl tetrahydro-2H-pyran-3-ylcarbamate

A 20-L reactor equipped with a mechanical stirrer was charged with (S)-tert-butyl 1,5-dihydroxypentan-2-ylcarbamate (950 g, 4.33 mol), $Ph_3P$ (2272 g, 8.66 mol) and DCM (10 L). Then DIAD (1751 g, 8.66 mol) was added dropwise to the reaction solution. The solution was stirred for 48 h at room temperature until the reaction was complete. After filtration and concentration in vacuo, the residue was purified by column chromatography with petroleum ether as eluent to give 550 g of (S)-tert-butyl tetrahydro-2H-pyran-3-ylcarbamate as white solid. $^1$H NMR (400 MHz, $CDCl_3$) δ 4.77 (m, 1H), 3.78 (d, J=11.1 Hz, 1H), 3.63 (d, J=8.8 Hz, 3H), 3.38 (m, 1H), 1.88

(td, J=8.4, 3.8 Hz, 1H), 1.74 (ddd, J=10.4, 9.1, 4.9 Hz, 1H), 1.65-1.51 (m, 2H), 1.45 (s, 9H).

(S)-(Tetrahydro-pyran-3-yl)amine hydrochloride

Intermediate (S)-tert-butyl tetrahydro-2H-pyran-3-ylcarbamate (414 g, 2.06 mol) was added to a 6N HCl solution of MeOH (4 L) at room temperature, and the reaction mixture was stirred until it was complete (monitored by TLC). After concentration in vacuo, 283 g of (S)-(Tetrahydro-pyran-3-yl) amine hydrochloride was obtained as a white solid (yield, 99.8%, enantiomeric excess >99%). $^{1}$H NMR (400 MHz, DMSO-d6) δ 8.37 (s, 3H), 3.87-3.72 (m, 1H), 3.70-3.57 (m, 1H), 3.54-3.38 (m, 2H), 3.12 (d, J=2.1 Hz, 1H), 2.05-1.89 (m, 1H), 1.81-1.60 (m, 2H), 1.49 (dtd, J=12.5, 8.3, 4.3 Hz, 1H).

The above procedures were also used to synthesize (R)-(Tetrahydro-pyran-3-yl)amine hydrochloride by substituting D-Glutamic acid for L-Glutamic acid.

The enantiomeric excess of the products was determined as described below.

(S)—N-(tetrahydro-2H-pyran-3-yl)cinnamamide

To a solution of (S)-(Tetrahydro-pyran-3-yl)amine hydrochloride (0.65 g, 4.7 mmol, 1.0 eq) in 30 ml of DCM, acid chloride 6 (1.2 g, 7.2 mmol. 1.5 eq) and $Et_3N$ (1.43 g, 14.4 mmol, 3.0 eq) were added dropwise at 0° C. successively, and the mixture was stirred for 2 h at room temperature. The reaction mixture was then washed with brine, and the organic phase was dried over $Na_2SO_4$. After filtration and concentration, the residue was purified by column chromatography (Petroleum ether/ethyl acetate=10/1) giving 1.0 g of (S)—N-(tetrahydro-2H-pyran-3-yl)cinnamamide (yield, 90%) as a white solid. $^{1}$H NMR (400 MHz, $CDCl_3$) δ 7.63 (d, J=15.6 Hz, 1H), 7.50 (dd, J=7.4, 1.9 Hz, 2H), 7.42-7.30 (m, 3H), 6.41 (d, J=15.6 Hz, 1H), 5.99 (m, 1H), 4.22-4.08 (m, 1H), 3.84-3.70 (m, 2H), 3.68-3.51 (m, 2H), 1.98-1.70 (m, 4H), 1.68-1.52 (m, 1H).

Chiral HPLC conditions for e.e. analysis of (R)— and (S)—N-(tetrahydro-2H-pyran-3-yl)cinnamamide:

Column: CHIRALPAK IA 0.46 cm×25 cm, 5 μm

Mobile Phase: n-heptane/EtOH=80/20 v/v %

Detector: UV 214 nm

Flow Rate: 0.7 mL/min

Column Temp. ambient temperature

Retention time for (S) isomer: 10.2 minutes

Retention time for (R) isomer: 13.4 minutes

Example 1

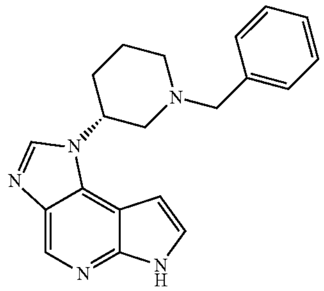 [SMILES: c1ccc(CN2CCC[C@@H](n3cnc4cnc5[nH]ccc5c43)C2)cc1]

1-((R)-1-Benzyl-piperidin-3-yl)-1,6-dihydro-1,2,3,5,6-tetraaza-as-indacene

1-Benzenesulfonyl-4-chloro-1H-pyrrolo[2,3-b]pyridine

A stirred suspension of 4-chloro-7-azaindole (1.00 g, 6.55 mmol) in dichloromethane (DCM) (50 ml) was treated with 4-(dimethylamino)pyridine (80.0 mg, 0.66 mmol), triethylamine (1.36 ml, 9.83 mmol) and benzenesulfonyl chloride (0.93 ml, 7.21 mmol) at ambient temperature. The mixture was left to stand overnight and then diluted with DCM and washed with 1M aqueous HCl solution, saturated sodium hydrogen carbonate solution, water, and brine, dried with sodium sulfate and concentrated under vacuum to give crude product. Trituration (diethyl ether) afforded 1.59 g (83%) of 1-benzenesulfonyl-4-chloro-1H-pyrrolo[2,3-b]pyridine. LCMS (Method B, ESI): RT=4.48 min, m+H=293.3; $^{1}$H NMR (400 MHz, $CDCl_3$) δ: 8.31 (d, 1H), 8.18 (m, 2H), 7.78 (m, 1H), 7.62-7.56 (m, 1H), 7.52-7.45 (m, 2H), 7.20 (m, 1H), 6.72 (m, 1H).

1-Benzenesulfonyl-4-chloro-5-nitro-1H-pyrrolo[2,3-b]pyridine

Tetrabutylammonium nitrate (381 mg, 1.25 mmol) dissolved in DCM (5 ml) was added dropwise to a stirred solution of 1-benzenesulfonyl-4-chloro-1H-pyrrolo[2,3-b]pyridine (293 mg, 1.00 mmol) in DCM (5 ml) at −5° C. Trifluoroacetic anhydride (180 μl, 1.29 mmol) was added while maintaining the reaction temperature below 0° C. The mixture was then stirred at −5° C. for 30 minutes at ambient temperature for 5 hours, after which 0.25 eq of tetrabutylammonium nitrate and trifluoroacetic anhydride were added and the resulting mixture left to stand for 18 hours at ambient temperature. DCM was added and the mixture washed with water, dried with sodium sulfate and concentrated under vacuum. Purification by column chromatography on silica gel (gradient: 0 to 25% ethyl acetate in cyclohexane) gave 266 mg (79%) of 1-benzenesulfonyl-4-chloro-5-nitro-1H-pyrrolo[2,3-b]pyridine. LCMS (Method B, ESI): RT=4.57 min, m+H=338.4; $^{1}$H NMR (400 MHz, $CDCl_3$) δ: 9.00 (s, 1H), 8.23-8.17 (m, 2H), 7.94 (dd, 1H), 7.68-7.62 (m, 1H), 7.58-7.52 (m, 2H), 6.88-6.85 (m, 1H).

(1-Benzenesulfonyl-5-nitro-1H-pyrrolo[2,3-b]pyridin-4-yl)-((R)-1-benzyl-piperidin-3-yl)amine A mixture of 1-benzenesulfonyl-4-chloro-5-nitro-1H-pyrrolo[2,3-b]pyridine (260 mg, 0.77 mmol), (R)-1-benzyl-3-aminopiperidine (175 mg, 0.92 mmol), diisopropylethylamine (197 μl, 1.16 mmol) in propan-2-ol (5 ml) was heated in a microwave reactor at 120° C. for 10 minutes. The mixture was diluted with DCM and then purified by column chromatography on silica gel (gradient: 0 to 40% ethyl acetate in cyclohexane) affording 429 mg of (1-benzenesulfonyl-5-nitro-1H-pyrrolo[2,3-b]pyridin-4-yl)-((R)-1-benzyl-piperidin-3-yl)amine, which was used for the next step without further purification. LCMS (Method B, ESI): RT=3.58 min, m+H=492.5; $^{1}$H NMR (400 MHz, $CDCl_3$) δ: 9.53 (br s, 1H), 9.10 (s, 1H), 8.19-8.15 (m, 2H), 7.69-7.33 (m, 9H), 6.68-6.61 (m, 1H), 4.24-4.15 (br m, 1H), 3.54 (s, 2H), 2.77-2.27 (br m, 4H), 1.88-1.74 (br m, 3H), 1.69-1.52 (br m, 1H).

1-Benzenesulfonyl-N*4*-((R)-1-benzyl-piperidin-3-yl)-1H-pyrrolo[2,3-b]pyridine-4,5-diamine A mixture of (1-benzenesulfonyl-5-nitro-1H-pyrrolo[2,3-b]pyridin-4-yl)-((R)-1-benzyl-piperidin-3-yl)amine (about 0.77 mmol), iron powder (129 mg, 2.31 mmol) and ammonium chloride (206 mg, 3.85 mmol) in ethanol/water (8 ml, 3:1) was heated to reflux for 4 hours. After cooling the mixture was filtered through CELITE®, thoroughly washing the filter cake with ethanol. The filtrate and washings were combined and concentrated under vacuum. The resulting residue was partitioned between ethyl acetate and water, and the organic layer dried with sodium sulfate and concentrated under vacuum. Purification by column chromatography on silica gel (gradient: 0 to 10% methanol in DCM) gave a residue, which was purified by column chromatography on silica gel (gradient: 0 to 5% methanol in ethyl acetate) affording 303 mg (84%) of 1-benzenesulfonyl-N*4*-((R)-1-benzyl-piperidin-3-yl)-1H-pyrrolo[2,3-b]pyridine-4,5-diamine. LCMS (Method B, ESI): RT=2.48-2.68 min, m+H=462.6; $^1$H NMR (400 MHz, $CDCl_3$) δ: 8.12-8.08 (m, 2H), 7.79 (s, 1H), 7.55-7.49 (m, 1H), 7.46-7.38 (m, 3H), 7.37-7.22 (m, 5H), 6.47 (s, 1H), 5.32-5.26 (br m, 1H), 4.00-3.87 (br m, 1H), 3.58-3.46 (br m, 2H), 2.94-2.28 (br m, 6H), 1.82-1.67 (br m, 2H).

6-Benzenesulfonyl-1-((R)-1-benzyl-piperidin-3-yl)-1,6-dihydro-1,2,3,5,6-tetraaza-as-indacene A mixture of 1-benzenesulfonyl-N*4*-((R)-1-benzyl-piperidin-3-yl)-1H-pyrrolo[2,3-b]pyridine-4,5-diamine (50.0 mg, 108 μmol), triethyl orthoformate (45.0 μl, 271 μmol) and p-toluenesulfonic acid monohydrate (catalytic) in toluene (1 ml) was heated to reflux for 18 hours. After cooling, ethyl acetate was added and the mixture washed with water and brine, dried with sodium sulfate and concentrated under vacuum. Purification by column chromatography on silica gel (gradient: 0 to 100% ethyl acetate in DCM) gave 45.0 mg (88%) of 6-benzenesulfonyl-1-((R)-1-benzyl-piperidin-3-yl)-1,6-dihydro-1,2,3,5,6-tetraaza-as-indacene. LC MS (Method B, ESI): RT=3.22 min, m+H=472.6; $^1$H NMR (400 MHz, $CDCl_3$) δ: 8.88 (s, 1H), 8.31 (br s, 1H), 8.22-8.18 (m, 2H), 7.72 (d, 1H), 7.56-7.51 (m, 1H), 7.48-7.43 (m, 2H), 7.35-7.26 (m, 5H), 6.62 (d, 1H), 4.65 (br s, 1H), 3.68-3.48 (br m, 2H), 3.12-3.03 (br m, 1H), 2.79-2.69 (br m, 1H), 2.63-2.43 (br m, 2H), 2.23-2.12 (br m, 1H), 2.03-1.90 (br m, 1H), 1.88-1.69 (br m, 2H).

1-((R)-1-Benzyl-piperidin-3-yl)-1,6-dihydro-1,2,3,5,6-tetraaza-as-indacene

6-Benzenesulfonyl-1-((R)-1-benzyl-piperidin-3-yl)-1,6-dihydro-1,2,3,5,6-tetraaza-as-indacene (40.0 mg, 85.0 μmol) was treated with sodium hydroxide (6.80 mg, 170 μmol) in methanol (1 ml) at ambient temperature followed after 2 hours by addition of 1M aqueous sodium hydroxide (1 ml) and stirring for an additional 5 hours. The mixture was partially concentrated under vacuum and the resulting suspension was extracted with ethyl acetate (2×). The combined organic extracts were dried with sodium sulfate and concentrated under vacuum to leave a residue. Purification by column chromatography on silica gel (eluting with 2.5 to 5% methanol in DCM) afforded 22.0 mg (78%) of 1-((R)-1-benzyl-piperidin-3-yl)-1,6-dihydro-1,2,3,5,6-tetraaza-as-indacene. LCMS (Method A, ESI): RT=1.92 min, m+H=332.2; $^1$H NMR (400 MHz, $CDCl_3$) δ: 9.95 (s, 1H), 8.81 (s, 1H), 8.29 (s, 1H), 7.39-7.31 (m, 5H), 7.31-7.22 (m, 1H), 6.63 (d, 1H), 4.86-4.77 (m, 1H), 3.65 (dd, 2H), 3.20 (m, 1H), 2.78 (m, 1H), 2.66 (m, 1H), 2.50 (m, 1H), 2.25 (m, 1H), 2.15-1.94 (m, 1H), 1.92-1.80 (m, 2H).

Example 2

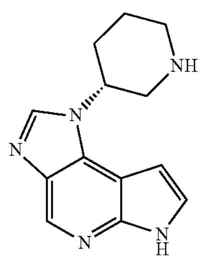 [SMILES: c1cc2c(ncc3ncn([C@@H]4CCCNC4)c32)[nH]1]

(R)-1-Piperidin-3-yl-1,6-dihydro-1,2,3,5,6-tetraaza-as-indacene

A mixture of 1-((R)-1-benzyl-piperidin-3-yl)-1,6-dihydro-1,2,3,5,6-tetraaza-as-indacene (125 mg, 0.38 mmol), palladium hydroxide (20 wt % on carbon, 26.0 mg, 40.0 μmol) and ammonium formate (239 mg, 3.80 mmol) in methanol (10 ml) was heated to reflux for 1½ hours. After cooling the mixture was filtered through Celite®, washing the filter cake with methanol, and concentrated under vacuum. Purification by column chromatography on silica gel (eluting with 5 to 10% 2M $NH_3$ in methanol solution in DCM) afforded 70.0 mg (76%) of (R)-1-piperidin-3-yl-1,6-dihydro-1,2,3,5,6-tetraaza-as-indacene. LCMS (Method A, ESI): RT=0.86 min, m+H=242.2; $^1$H NMR (400 MHz, DMSO-$d_6$) δ: 11.84 (s, 1H), 8.57 (s, 1H), 8.34 (s, 1H), 7.48-7.45 (m, 1H), 6.79 (m, 1H), 4.64-4.54 (m, 1H), 3.27 (m, 1H), 2.95 (m, 1H), 2.87 (dd, 1H), 2.58 (m, 1H), 2.23 (m, 1H), 2.09 (m, 1H), 1.81-1.74 (m, 1H), 1.72-1.60 (m, 1H).

Example 3

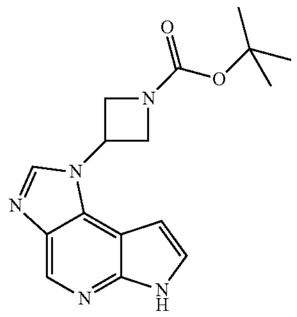 [SMILES: CC(C)(C)OC(=O)N1CC(n2cnc3cnc4[nH]ccc4c32)C1]

3-(6H-1,2,3,5,6-Tetraaza-as-indacen-1-yl)-azetidine-1-carboxylic acid tert-butyl ester 3-(1-Benzenesulfonyl-5-nitro-1H-pyrrolo[2,3-b]pyridin-4-ylamino)-azetidine-1-carboxylic acid tert-butyl ester 431 mg (88%) of the title compound was made by following the procedure described for the preparation of (1-benzenesulfonyl-5-nitro-1H-pyrrolo[2,3-b]pyridin-4-yl)-((R)-1-benzyl-piperidin-3-yl)-amine but substituting 1-Boc-3-aminoazetidine for (R)-1-benzyl-3-aminopiperidine. LCMS (Method B, ESI): RT=4.79 min, m+H=474.6; $^1$H NMR (400 MHz, $CDCl_3$) δ: 9.23 (d, 1H), 9.12 (s, 1H), 8.20 (m, 2H), 7.66-7.60 (m, 2H), 7.56-7.50 (m, 2H), 6.58 (d, 1H), 4.75 (m, 1H), 4.42 (dd, 2H), 3.91 (dd, 2H), 1.45 (s, 9H).

3-(5-Amino-1-benzenesulfonyl-1H-pyrrolo[2,3-b]pyridin-4-ylamino)-azetidine-1-carboxylic acid tert-butyl ester A solution of 3-(1-benzenesulfonyl-5-nitro-1H-pyrrolo[2,3-b]pyridin-4-ylamino)-azetidine-1-carboxylic acid tert-butyl ester (425 mg, 898 μmol) in THF (15 ml) containing palladium (10% on carbon, 95.0 mg, 90.0 μmol) was stirred at ambient temperature under a hydrogen atmosphere for 24 hours. The mixture was filtered through Celite®, the filter cake thoroughly washed with THF, and the combined filtrates concentrated under vacuum to give 498 mg of 3-(5-amino-1-benzenesulfonyl-1H-pyrrolo[2,3-b]pyridin-4-ylamino)-azetidine-1-carboxylic acid tert-butyl ester, which was used without further purification. LCMS (Method B, ESI): RT=4.04 min, m+H=444.4.

3-(6-Benzenesulfonyl-6H-1,2,3,5,6-tetraaza-as-indacen-1-yl)-azetidine-1-carboxylic acid tert-butyl ester A mixture of 3-(5-amino-1-benzenesulfonyl-1H-pyrrolo[2,3-b]pyridin-4-ylamino)-azetidine-1-carboxylic acid tert-butyl ester (assumed to be 898 μmol), triethyl orthoformate (373 μl, 2.25 mmol) and p-toluenesulfonic acid monohydrate (17.0 mg, 90.0 μmol) in toluene (10 ml) was heated at 110° C. in a sealed tube for 2 hours. After cooling, ethyl acetate was added and the resulting solid isolated by filtration, washed with ethyl acetate and dried under vacuum at 50° C. to give 292 mg (72%) of 3-(6-benzenesulfonyl-6H-1,2,3,5,6-tetraaza-as-indacen-1-yl)-azetidine-1-carboxylic acid tert-butyl ester. An additional 76 mg of the title compound was also isolated by chromatographic purification of the filtrate residues on silica gel (gradient: 0 to 100% ethyl acetate in DCM) of the filtrate. LCMS (Method B, ESI): RT=4.45 min, m+H=454.4; $^1$H NMR (400 MHz, DMSO-$d_6$) δ: 8.75 (s, 1H), 8.66 (s, 1H), 8.15-8.11 (m, 2H), 8.00 (d, 1H), 7.71-7.67 (m, 1H), 7.62-7.57 (m, 2H), 7.16 (d, 1H), 5.67 (m, 1H), 4.48 (m, 2H), 4.29 (m, 2H), 1.43 (s, 9H).

3-(6H-1,2,3,5,6-Tetraaza-as-indacen-1-yl)-azetidine-1-carboxylic acid tert-butyl ester A suspension of 3-(6-benzenesulfonyl-6H-1,2,3,5,6-tetraaza-as-indacen-1-yl)-azetidine-1-carboxylic acid tert-butyl ester (355 mg, 0.78 mmol) in methanol (10 ml) and THF (10 ml) was treated with 1M aqueous NaOH solution (10 ml) at ambient temperature for 90 hours. The mixture was partially concentrated under vacuum and the resulting aqueous residue was extracted with ethyl acetate (2×). The combined organic extract was dried with sodium sulfate, concentrated under vacuum and purified by column chromatography on silica gel (gradient: 0 to 10% methanol in DCM) to leave 215 mg (88%) of 3-(6H-1,2,3,5,6-tetraaza-as-indacen-1-yl)-azetidine-1-carboxylic acid tert-butyl ester. LCMS (Method A, ESI): RT=3.00 min, m+H=314.1; $^1$H NMR (400 MHz, DMSO-$d_6$) δ: 11.91 (s, 1H), 8.60 (s, 1H), 8.43 (s, 1H), 7.49 (t, 1H), 6.72 (dd, 1H), 5.68 (m, 1H), 4.50 (m, 2H), 4.35 (m, 2H), 1.45 (s, 9H).

Example 4

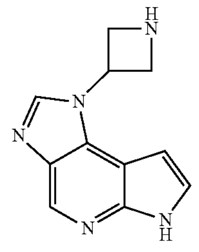 [SMILES: c1cc2c(ncc3ncn(C4CNC4)c32)[nH]1]

1-Azetidin-3-yl-1,6-dihydro-1,2,3,5,6-tetraaza-as-indacene 3-(6H-1,2,3,5,6-Tetraaza-as-indacen-1-yl)-azetidine-1-carboxylic acid tert-butyl ester (185 mg, 0.59 mmol) in DCM (5 ml) was treated with TFA (5 ml) at ambient temperature for 1 hour. The solvent was removed under vacuum and the residue purified using an Isolute® SCX-2 column (gradient: methanol to 2M $NH_3$ in methanol) affording 118 mg (94%) of 1-azetidin-3-yl-1,6-dihydro-1,2,3,5,6-tetraaza-as-indacene. LCMS (Method B, ESI): RT=0.36 min, m+H=214.2; $^1$H NMR (400 MHz, DMSO-$d_6$) δ: 11.84 (s, 1H), 8.58 (s, 1H), 8.36 (s, 1H), 7.46 (t, 1H), 6.94 (dd, 1H), 5.61-5.54 (m, 1H), 4.00 (m, 4H).

Example 5

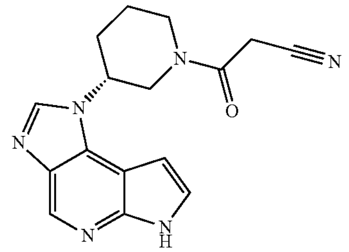 [SMILES: N#CCC(=O)N1CCC[C@@H](n2cnc3cnc4[nH]ccc4c32)C1]

3-Oxo-3-[(R)-3-(6H-1,2,3,5,6-tetraaza-as-indacen-1-yl)-piperidin-1-yl]-propionitrile To a stirred solution of (R)-1-piperidin-3-yl-1,6-dihydro-1,2,3,5,6-tetraaza-as-indacene (34.0 mg, 140 μmol) in DCM (8 ml) at 0° C., cyanoacetic acid (13.0 mg, 150 μmol), N-hydroxybenzotriazole (23.0 mg, 170 μmol), 4-(dimethylamino)pyridine (26.0 mg, 210 μmol) and 1-ethyl-3-(3-dimethylaminopropyl)carbodiimide hydrochloride (41.0 mg, 210 μmol) were added. The mixture was then stirred at ambient temperature for 24 hours. The resulting suspension was filtered and the isolated solid triturated (DCM) to afford 27.0 mg (63%) of 3-oxo-3-[(R)-3-(6H-1,2,3,5,6-tetraaza-as-indacen-1-yl)-piperidin-1-yl]-propionitrile. LCMS (Method A, ESI): RT=1.93 min, m+H=309.1; $^1$H NMR (400 MHz, DMSO-$d_6$) δ: 11.87 (s, 1H), 8.60 (s, 1H), 8.30 (d, 1H), 7.51-7.47 (m, 1H), 6.95-

6.82 (m, 1H), 4.90-4.38 (m, 2H), 4.17 (s, 1H), 4.07-3.94 (m, 1H), 3.77-3.57 (m, 1H), 3.23-2.67 (m, 2H), 2.36-2.05 (m, 2H), 1.93-1.63 (m, 2H).

Example 6

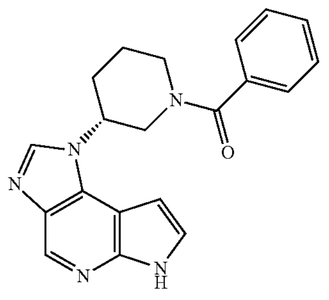 [SMILES: O=C(c1ccccc1)N1CCC[C@@H](n2cnc3cnc4[nH]ccc4c32)C1]

Phenyl-[(R)-3-(6H-1,2,3,5,6-tetraaza-as-indacen-1-yl)-piperidin-1-yl]-methanone

Benzoyl chloride (26.0 μl, 0.22 mmol) was added to a stirred suspension of (R)-1-piperidin-3-yl-1,6-dihydro-1,2,3,5,6-tetraaza-as-indacene (50.0 mg, 0.21 mmol) and triethylamine (57.0 μl, 0.41 mmol) in DCM (1 ml) at ambient temperature. The mixture was then stirred for 30 minutes at which time the solvent was removed under vacuum. The residue was suspended in cyclohexane for 18 hours and the solvent was decanted. The remaining solid was purified by column chromatography on silica gel (gradient: 0 to 5% methanol in DCM) to afford a yellow solid. Trituration (water) yielded a sticky gum which was dissolved in DCM, dried with magnesium sulfate and concentrated to give 12.8 mg (18%) of phenyl-[(R)-3-(6H-1,2,3,5,6-tetraaza-as-indacen-1-yl)-piperidin-1-yl]-methanone. LCMS (Method A, ESI): RT=2.62 min, m+H=346.1; $^1$H NMR (400 MHz, 80° C., DMSO-$d_6$) δ: 11.44 (s, 1H), 8.55 (s, 1H), 8.20 (s, 1H), 7.44-7.32 (m, 6H), 6.75 (s, 1H), 4.77-4.70 (m, 1H), 4.46 (m, 1H), 3.95 (m, 1H), 3.48 (t, 1H), 3.26-3.17 (m, 1H), 2.37-2.28 (m, 2H), 1.90-1.75 (m, 2H).

Example 7

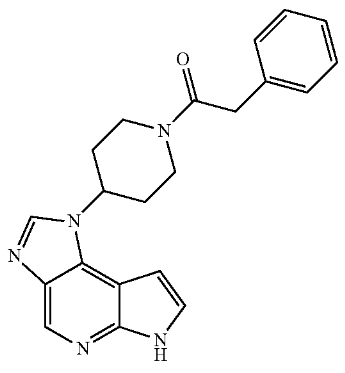 [SMILES: O=C(Cc1ccccc1)N1CCC(n2cnc3cnc4[nH]ccc4c32)CC1]

2-Phenyl-1-[4-(6H-1,2,3,5,6-tetraaza-as-indacen-1-yl)-piperidin-1-yl]-ethanone

1-Piperidin-4-yl-1,6-dihydro-1,2,3,5,6-tetraaza-as-indacene (48.0 mg, 0.20 mmol) was added to a stirred solution of phenylacetic acid (33.0 mg, 0.24 mmol), HATU (91.0 mg, 0.24 mmol) and diisopropylethylamine (75.0 μl, 0.44 mmol) in DMF (1 ml). The resulting mixture was stirred at ambient temperature for 60 hours. The solvent was evaporated under vacuum and the residue purified by column chromatography on silica gel (gradient: 0 to 5% 2M $NH_3$ in methanol solution in DCM) affording 47.5 mg (66%) of 2-phenyl-1-[4-(6H-1,2,3,5,6-tetraaza-as-indacen-1-yl)-piperidin-1-yl]-ethanone. LCMS (Method A, ESI): RT=2.73 min, m+H=360.1; $^1$H NMR (400 MHz, DMSO-$d_6$) δ: 11.85 (s, 1H), 8.57 (s, 1H), 8.24 (s, 1H), 7.46 (t, 1H), 7.36-7.21 (m, 5H), 6.71 (dd, 1H), 4.91-4.80 (m, 1H), 4.64 (m, 1H), 4.19 (m, 1H), 3.81 (dd, 2H), 3.37 (m, 1H), 2.92 (m, 1H), 2.12 (m, 2H), 2.04-1.77 (m, 2H).

Example 8

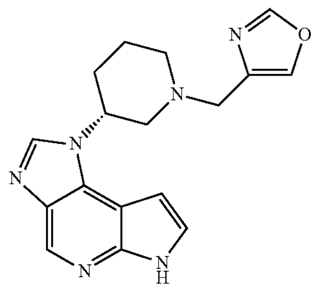 [SMILES: c1cc2c(ncc3ncn([C@@H]4CCCN(Cc5cocn5)C4)c32)[nH]1]

1-((R)-1-Oxazol-4-ylmethyl-piperidin-3-yl)-1,6-dihydro-1,2,3,5,6-tetraaza-as-indacene A mixture of (R)-1-piperidin-3-yl-1,6-dihydro-1,2,3,5,6-tetraaza-as-indacene (50.0 mg, 210 mmol), oxazole-4-carboxaldehyde (40.0 mg, 414 μmol) and sodium triacetoxyborohydride (88 mg, 414 μmol) in 1,2-dichloroethane/methanol (5 ml, 4:1) was stirred at ambient temperature overnight. The mixture was loaded on to an Isolute® SCX-2 column (gradient: methanol to 2M $NH_3$ in methanol) and the basic products combined and concentrated under vacuum. The resulting residue was purified by column chromatography on silica gel (gradient: 5 to 10% methanol in DCM) affording 32.0 mg (48%) of 1-((R)-1-oxazol-4-ylmethyl-piperidin-3-yl)-1,6-dihydro-1,2,3,5,6-tetraaza-as-indacene. LCMS (Method A, ESI): RT=1.26 min, m+H=323.1; $^1$H NMR (400 MHz, DMSO-$d_6$) δ: 11.83 (s, 1H), 8.57 (s, 1H), 8.43 (s, 1H), 8.32 (s, 1H), 8.01 (s, 1H), 7.44 (t, 1H), 6.58 (m, 1H), 4.76-4.69 (m, 1H), 3.61-3.48 (q, 2H), 3.11 (m, 1H), 2.77

(m, 1H), 2.60 (m, 1H), 2.43 (m, 1H), 2.17-2.10 (m, 1H), 2.05-1.94 (m, 1H), 1.74 (m, 2H).

Example 9

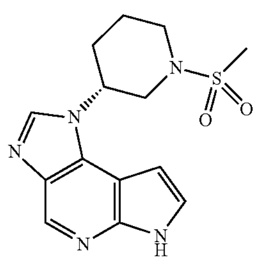 [SMILES: CS(=O)(=O)N1CCC[C@@H](n2cnc3cnc4[nH]ccc4c32)C1]

1-((R)-1-Methanesulfonyl-piperidin-3-yl)-1,6-dihydro-1,2,3,5,6-tetraaza-as-indacene Methanesulfonyl chloride (17.0 μl, 220 μmol) was added to a stirred suspension of (R)-1-piperidin-3-yl-1,6-dihydro-1,2,3,5,6-tetraaza-as-indacene (50.0 mg, 210 μmol) and triethylamine (57.0 μl, 410 μmol) in DCM (1 ml) at ambient temperature. Stirring was continued for 30 minutes and then the solvent was removed under vacuum. The residue was purified by column chromatography on silica gel (gradient: 0 to 5% methanol in DCM) affording a crude solid. Trituration (water) afforded 42.7 mg (64%) of 1-((R)-1-methanesulfonyl-piperidin-3-yl)-1,6-dihydro-1,2,3,5,6-tetraaza-as-indacene. LCMS (Method A, ESI): RT=2.18 min, m+H=320.1; $^{1}$H NMR (400 MHz, DMSO-$d_6$) δ: 11.89 (s, 1H), 8.60 (s, 1H), 8.34 (s, 1H), 7.50-7.47 (t, 1H), 6.75 (dd, 1H), 4.85-4.76 (m, 1H), 3.96 (m, 1H), 3.59 (m, 1H), 3.19 (dd, 1H), 3.02-2.91 (m+s, 4H), 2.34-2.14 (m, 2H), 1.97-1.78 (m, 2H).

Example 10

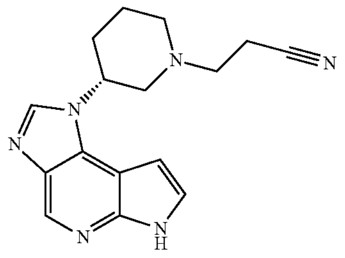 [SMILES: N#CCCN1CCC[C@@H](n2cnc3cnc4[nH]ccc4c32)C1]

3-[(R)-3-(6H-1,2,3,5,6-Tetraaza-as-indacen-1-yl)-piperidin-1-yl]-propionitrile

A mixture of acrylonitrile (12.5 μl, 208 μmol) and (R)-1-piperidin-3-yl-1,6-dihydro-1,2,3,5,6-tetraaza-as-indacene (10.0 mg, 41.0 μmol) in ethanol (1 ml) was heated at 80° C. for 5 hours. After cooling, the solvent was removed under vacuum and the residue was purified by column chromatography on silica gel (gradient: 0 to 10% 2M $NH_3$ in methanol solution in DCM) affording 10.0 mg (83%) of 3-[(R)-3-(6H-1,2,3,5,6-tetraaza-as-indacen-1-yl)-piperidin-1-yl]propionitrile. LCMS (Method A, ESI): RT=1.80 min, m+H=295.2; $^{1}$H NMR (400 MHz, $CDCl_3$) δ: 10.06 (s, 1H), 8.84-8.79 (m, 1H), 8.31 (s, 1H), 7.45 (d, 1H), 6.80 (d, 1H), 4.88-4.80 (m, 1H), 3.31 (m, 1H), 2.89-2.74 (m, 3H), 2.68 (m, 1H), 2.61-2.49 (m, 3H), 2.32 (m, 1H), 2.14-1.85 (m, 3H).

Example 11

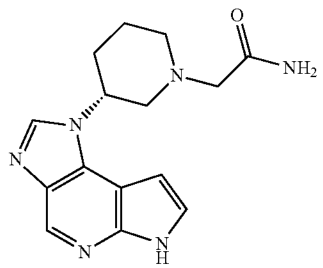 [SMILES: NC(=O)CN1CCC[C@@H](n2cnc3cnc4[nH]ccc4c32)C1]

2-[(R)-3-(6H-1,2,3,5,6-Tetraaza-as-indacen-1-yl)-piperidin-1-yl]acetamide

To a stirred solution of (R)-1-piperidin-3-yl-1,6-dihydro-1,2,3,5,6-tetraaza-as-indacene (50.0 mg, 210 μmol) in THF (3 ml) was added 2-bromoacetamide (32.0 mg, 220 μmol) and potassium carbonate (86.0 mg, 620 μmol). The mixture was stirred at ambient temperature for 18 hours and then heated to 50° C. for 24 hours. The solution was diluted with THF, filtered, and concentrated under vacuum. Purification of the residue by column chromatography on silica gel (gradient: 0 to 20% methanol in ethyl acetate) and subsequent drying of the isolated product under vacuum at 45° C. gave 7.50 mg (12%) of 2-[(R)-3-(6H-1,2,3,5,6-tetraaza-as-indacen-1-yl)-piperidin-1-yl]-acetamide. LCMS (Method A, ESI): RT=1.09 min, m+H=299.1; $^{1}$H NMR (400 MHz, DMSO-$d_6$) δ: 11.83 (s, 1H), 8.58 (s, 1H), 8.50 (s, 1H), 7.46 (m, 2H), 7.13 (s, 1H), 6.80 (dd, 1H), 4.88-4.79 (m, 1H), 3.10 (m, 1H), 2.99 (s, 2H), 2.74 (m, 2H), 2.42 (m, 1H), 2.14 (m, 1H), 2.09-1.89 (m, 1H), 1.84-1.73 (m, 2H).

Example 12

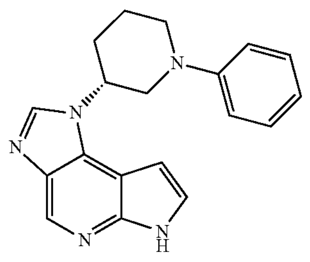 [SMILES: c1ccc(N2CCC[C@@H](n3cnc4cnc5[nH]ccc5c43)C2)cc1]

1-((R)-1-Phenyl-piperidin-3-yl)-1,6-dihydro-1,2,3,5,6-tetraaza-as-indacene

A suspension of phenylboronic acid (50.0 mg, 414 μmol), copper (II) acetate monohydrate (4.00 mg, 20.7 μmol) and 4 Å molecular sieves in DCM (3 ml) was stirred for 5 minutes in a sealed vial. (R)-1-Piperidin-3-yl-1,6-dihydro-1,2,3,5,6-tetraaza-as-indacene (50.0 mg, 210 μmol) was added and the mixture heated at 40° C. under an oxygen atmosphere for 78 hours. After cooling, DCM was added and the mixture washed with saturated sodium hydrogen carbonate solution, water and brine, dried with sodium sulfate and concentrated under vacuum to leave a residue. Purification by column chromatography on silica gel (gradient: 0 to 10% methanol in DCM) gave 6.00 mg (9%) of 1-((R)-1-phenyl-piperidin-3-yl)-1,6-dihydro-1,2,3,5,6-tetraaza-as-indacene. LCMS (Method A, ESI): RT=3.34 min, m+H=318.1; $^1$H NMR (400 MHz, DMSO-$d_6$) δ: 11.88 (s, 1H), 8.60 (s, 1H), 8.38 (s, 1H), 7.48-7.45 (m, 1H), 7.25-7.19 (m, 2H), 7.02 (d, 2H), 6.84-6.78 (t, 1H), 6.68 (dd, 1H), 4.89-4.81 (m, 1H), 3.96 (m, 1 H), 3.66 (m, 1H), 3.29-3.24 (m, 1H), 3.01-2.92 (m, 1H), 2.33-2.15 (m, 2H), 1.98-1.86 (m, 2H).

Example 13

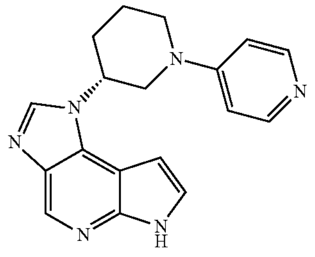 [SMILES: c1cc(N2CCC[C@@H](n3cnc4cnc5[nH]ccc5c43)C2)ccn1]

(R)-1-(3,4,5,6-Tetrahydro-2H-[1,4]bipyridinyl-3-yl)-1,6-dihydro-1,2,3,5,6-tetraaza-as-indacene A 5 ml microwave vial was charged with (R)-1-piperidin-3-yl-1,6-dihydro-1,2,3,5,6-tetraaza-as-indacene (50.0 mg, 210 μmol), 4-chloropyridine hydrochloride (39.0 mg, 259 μmol), diisopropylethylamine (89.0 μl, 518 μmol) and propan-2-ol (4 ml). The mixture was heated in a microwave reactor at 150° C. for 20 minutes followed by 180° C. for 1 hour. Additional 4-chloropyridine hydrochloride (0.5 eq) and diisopropylethylamine (0.5 eq) were added and the mixture was heated in a microwave reactor at 180° C. for 1 hour. The solvent was removed under vacuum and the isolated residue partitioned between DCM and water. The organic phase was dried with sodium sulfate and concentrated to dryness. Purification by column chromatography on silica gel (gradient: 0 to 10% 2M $NH_3$ in methanol solution in DCM) gave a residue which was triturated (diethyl ether) to afford 28.0 mg (42%) of (R)-1-(3,4,5,6-tetrahydro-2H-[1,4]bipyridinyl-3-yl)-1,6-dihydro-1,2,3,5,6-tetraaza-as-indacene. LCMS (Method A, ESI): RT=1.70 min, m+H=319.1; $^1$H NMR (400 MHz, DMSO-$d_6$) δ: 11.88 (s, 1H), 8.60 (s, 1H), 8.33 (s, 1H), 8.17 (m, 2H), 7.46 (t, 1H), 6.90 (m, 2H), 6.68 (dd, 1H), 4.82-4.72 (m, 1H), 4.23 (m, 1H), 3.96 (m, 1H), 3.47 (dd, 1H), 3.14-3.05 (m, 1H), 2.32-2.21 (m, 2H), 1.94-1.81 (m, 2H).

Example 14

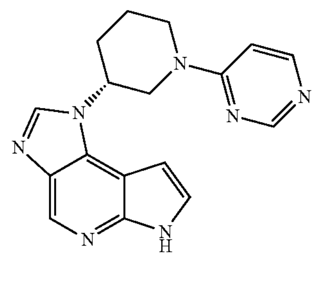 [SMILES: c1cc(N2CCC[C@@H](n3cnc4cnc5[nH]ccc5c43)C2)ncn1]

1-((R)-1-Pyrimidin-4-yl-piperidin-3-yl)-1,6-dihydro-1,2,3,5,6-tetraaza-as-indacene 1-[(R)-1-(6-Chloro-pyrimidin-4-yl)-piperidin-3-yl]-1,6-dihydro-1,2,3,5,6-tetraaza-as-indacene A mixture of (R)-1-piperidin-3-yl-1,6-dihydro-1,2,3,5,6-tetraaza-as-indacene (50.0 mg, 210 μmol), 4,6-dichloropyrimidine (39.0 mg, 259 μmol) and triethylamine (43.0 μl, 311 μmol) in DCM (5 ml) was stirred at ambient temperature for 6 hours and left to stand for 72 hours. DCM was added and the mixture washed with water and brine, dried with sodium sulfate and concentrated under vacuum to leave a yellow solid. Purification by column chromatography on silica gel (gradient: 0 to 10% methanol in DCM) gave 65.0 mg (89%) of 1-[(R)-1-(6-chloro-pyrimidin-4-yl)-piperidin-3-yl]-1,6-dihydro-1,2,3,5,6-tetraaza-as-indacene. LCMS (Method B, ESI): RT=3.31 min, m+H=354.3; $^1$H NMR (400 MHz, $CDCl_3$) δ: 10.10 (s, 1H), 8.84 (s, 1H), 8.45 (s, 1H), 8.09 (s, 1H), 7.45 (d, 1H), 6.83 (d, 1H), 6.65 (s, 1H), 4.99 (m, 1H), 4.75-4.69 (m, 1H), 4.24 (m, 1H), 3.45 (dd, 1H), 3.25 (m, 1H), 2.56 (m, 1H), 2.41-2.31 (m, 1H), 2.11 (m, 1H), 1.91-1.85 (m, 1H).

1-((R)-1-Pyrimidin-4-yl-piperidin-3-yl)-1,6-dihydro-1,2,3,5,6-tetraaza-as-indacene A solution of 1-[(R)-1-(6-chloro-pyrimidin-4-yl)-piperidin-3-yl]-1,6-dihydro-1,2,3,5,6-tetraaza-as-indacene (62.0 mg, 175 μmol) in ethanol (6 ml) containing palladium (10% on carbon, 19.0 mg, 18.0 μmol) was stirred at ambient temperature under a hydrogen atmosphere for 18 hours. The mixture was re-charged with palladium (10% on carbon, 19.0 mg, 18.0 μmol) and stirring was continued for 24 hours. The mixture was filtered through Celite® and concentrated under vacuum. Purification by column chromatography on silica gel (gradient: 0 to 10% methanol in DCM) gave 23.0 mg (41%) of 1-((R)-1-pyrimidin-4-yl-piperidin-3-yl)-1,6-dihydro-1,2,3,5,6-tetraaza-as-indacene. LCMS (Method A, ESI): RT=1.64 min, m+H=320.1; $^1$H NMR (400 MHz, DMSO-$d_6$) δ: 11.87 (s, 1H), 8.61 (s, 1H), 8.54 (s, 1H), 8.34 (s, 1H), 8.24 (s, 1H), 7.47 (t, 1H), 6.96 (d, 1H), 6.83 (dd, 1H), 4.84 (m, 1H), 4.77-4.67 (m, 1H), 4.36 (m, 1H), 3.47 (dd, 1H), 3.22-3.12 (m, 1H), 2.36 (m, 2H), 1.93 (m, 1H), 1.85-1.74 (m, 1H).

Example 15

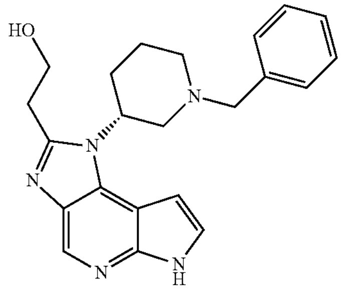 [SMILES: OCCc1nc2cnc3[nH]ccc3c2n1[C@@H]1CCCN(Cc2ccccc2)C1]

2-[1-((R)-1-Benzyl-piperidin-3-yl)-1,6-dihydro-1,2,3,5,6-tetraaza-as-indacen-2-yl]ethanol

[6-Benzenesulfonyl-1-((R)-1-benzyl-piperidin-3-yl)-1,6-dihydro-1,2,3,5,6-tetraaza-as-indacen-2-yl]acetic acid ethyl ester To a stirred solution of 1-benzenesulfonyl-N*4*-((R)-1-benzyl-piperidin-3-yl)-1H-pyrrolo[2,3-b]pyridine-4,5-diamine (350 mg, 0.76 mmol) in DCM (20 ml), triethylamine (126 μl, 0.91 mmol) followed by ethyl malonyl chloride (100 μl, 0.80 mmol) was added dropwise at 0° C. The mixture was stirred for 1 hour and the solvent removed under vacuum. The resulting residue was dissolved in acetic acid (10 ml) and heated to 110° C. for 22 hours. After removal of solvent, the residue was basified with saturated sodium hydrogen carbonate solution and extracted with DCM (3×). The combined organic extracts were dried with sodium sulfate, concentrated to dryness and purified by column chromatography on silica gel (eluting with 40% ethyl acetate in DCM) affording 310 mg (73%) of [6-benzenesulfonyl-14R)-1-benzyl-piperidin-3-yl)-1,6-dihydro-1,2,3,5,6-tetraaza-as-indacen-2-yl]-acetic acid ethyl ester. LCMS (Method B, ESI): RT=3.64 min, m+H=558.5; $^{1}$H NMR (400 MHz, $CDCl_3$) δ: 8.83 (s, 1H), 8.23 (d, 2H), 7.80 (d, 1H), 7.59-7.45 (m, 3H), 7.36-7.27 (m, 5H), 6.97 (s, 1H), 4.63-4.42 (m, 1H), 4.17-4.04 (m, 5H), 3.74-3.51 (m, 2H), 3.16-2.67 (m, 3H), 2.40-2.15 (m, 2H), 2.12-1.69 (m, 2H), 1.29-1.18 (m, 3H).

2-[6-Benzenesulfonyl-1-((R)-1-benzyl-piperidin-3-yl)-1,6-dihydro-1,2,3,5,6-tetraaza-as-indacen-2-yl]ethanol Lithium aluminium hydride (1M solution in THF, 404 μl, 404 μmol) was added to a stirred solution of [6-benzenesulfonyl-1-((R)-1-benzyl-piperidin-3-yl)-1,6-dihydro-1,2,3,5,6-tetraaza-as-indacen-2-yl]-acetic acid ethyl ester (300 mg, 538 μmol) in THF (10 ml) at −10° C. The mixture was allowed to warm to ambient temperature over 3 hours. TLC indicated incomplete conversion, therefore the mixture was re-cooled to −10° C. and treated with additional lithium aluminium hydride (269 μl, 269 μmol) and stirred for a further 1 hour. The reaction was carefully quenched by the addition of water (ca. 0.5 ml), ethyl acetate and saturated sodium hydrogen carbonate solution added and the resulting mixture filtered and concentrated to dryness. Purification by column chromatography on silica gel (gradient: 0 to 10% methanol in DCM) afforded 110 mg (40%) of 2-[6-benzenesulfonyl-1-((R)-1-benzyl-piperidin-3-yl)-1,6-dihydro-1,2,3,5,6-tetraaza-as-indacen-2-yl]ethanol. LCMS (Method B, ESI): RT=3.13-3.27 min, m+H=516.4; $^{1}$H NMR (400 MHz, $CDCl_3$) δ: 8.79 (s, 1H), 8.22 (d, 2H), 7.79 (d, 1H), 7.58-7.52 (m, 1H), 7.50-7.43 (m, 2H), 7.30 (m, 5H), 6.90 (m, 1H), 4.81-4.48 (m, 1H), 4.21-3.89 (m, 3H), 3.78-3.43 (m, 2H), 3.20-2.58 (m, 4H), 2.45-1.80 (m, 5H).

2-[1-((R)-1-Benzyl-piperidin-3-yl)-1,6-dihydro-1,2,3,5,6-tetraaza-as-indacen-2-yl]ethanol A solution of 2-[6-benzenesulfonyl-1-((R)-1-benzyl-piperidin-3-yl)-1,6-dihydro-1,2,3,5,6-tetraaza-as-indacen-2-yl]ethanol (105 mg, 204 μmol) in methanol (5 ml) was treated with 2M aqueous NaOH solution (3 ml) at ambient temperature for 2½ hours. The mixture was partially concentrated under vacuum and the aqueous residue was diluted with water and extracted with ethyl acetate (2×). The combined organic extracts were dried with sodium sulfate, concentrated under vacuum and purified by column chromatography on silica gel (gradient: 0 to 10% methanol in DCM) affording 61 mg (80%) of 2-[1-((R)-1-benzyl-piperidin-3-yl)-1,6-dihydro-1,2,3,5,6-tetraaza-as-indacen-2-yl]ethanol. LCMS (Method A, ESI): RT=1.91 min, m+H=376.2; $^{1}$H NMR (400 MHz, $CDCl_3$) δ: 9.91 (s, 1H), 8.70 (s, 1H), 7.40-7.20 (m, 6H), 6.82 (s, 1H), 4.84-4.26 (m, 2H), 4.25-4.16 (m, 2H), 3.74-3.59 (m, 2H), 3.23-3.02 (m, 5H), 2.37 (m, 2H), 2.09-1.81 (m, 3H).

Example 16

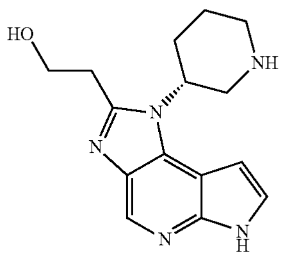 [SMILES: OCCc1nc2cnc3[nH]ccc3c2n1[C@@H]1CCCNC1]

2-((R)-1-Piperidin-3-yl-1,6-dihydro-1,2,3,5,6-tetraaza-as-indacen-2-yl)ethanol 93 mg (71%) of the title compound was made by following the procedure described for the preparation of (R)-1-piperidin-3-yl-1,6-dihydro-1,2,3,5,6-tetraaza-as-indacene but using 2-[1-((R)-1-benzyl-piperidin-3-yl)-1,6-dihydro-1,2,3,5,6-tetraaza-as-indacen-2-yl]ethano 1. LCMS (Method A, ESI): RT=0.93 min, m+H=286.1; $^{1}$H NMR (400 MHz, DMSO-$d_6$) δ: 11.84 (s, 1H), 8.53 (s, 1H), 7.52-7.49 (m, 1H), 6.87 (dd, 1H), 4.95-4.89 (m, 1H), 4.59 (s, 1H), 3.91 (dd, 2H), 3.22-3.14 (m, 2H), 3.11-3.00 (m, 2H), 2.82-2.68 (m, 1H), 2.60-2.52 (m, 1H), 2.03 (d, 1H), 1.91 (d, 1H), 1.77-1.66 (m, 1H).

Example 17

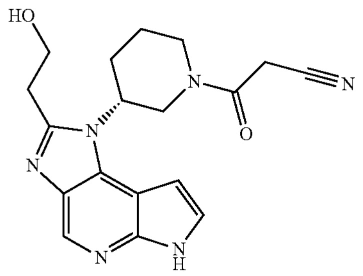 [SMILES: N#CCC(=O)N1CCC[C@@H](n2c(CCO)nc3cnc4[nH]ccc4c32)C1]

3-{(R)-3-[2-(2-Hydroxy-ethyl)-6H-1,2,3,5,6-tetraaza-as-indacen-1-yl]-piperidin-1-yl}-3-oxopropionitrile To a stirred solution of (2-((R)-1-piperidin-3-yl-1,6-dihydro-1,2,3,5,6-tetraaza-as-indacen-2-yl)ethanol (48.0 mg, 168 μmol) in DCM (10 ml) at 0° C., cyanoacetic acid (16.0 mg, 185 μmol), N-hydroxybenzotriazole (27.0 mg, 202 μmol), 4-(dimethylamino)pyridine (27.0 mg, 210 μmol), and 1-ethyl-3-(3-dimethylaminopropyl)carbodiimide hydrochloride (41.0 mg, 210 μmol) were added. The mixture was stirred at ambient temperature for 18 hours. The crude reaction mixture was purified by column chromatography on silica gel (gradient: 0 to 10% methanol in DCM) and re-purified using an Isolute® SCX-2 column (gradient: methanol to 2M $NH_3$ in methanol) affording 39.0 mg (66%) of 3-{(R)-3-[2-(2-hydroxy-ethyl)-6H-1,2,3,5,6-tetraaza-as-indacen-1-yl]-piperidin-1-yl}-3-oxopropionitrile. LCMS (Method A, ESI): RT=1.92 min, m+H=353.1; $^1$H NMR (400 MHz, DMSO-$d_6$) δ: 11.86 (s, 1H), 8.52 (d, 1H), 7.48 (d, 1H), 6.78 (d, 1H), 5.01-4.81 (m, 1H), 4.81-4.47 (m, 2H), 4.24-3.74 (m, 6H), 3.45-2.85 (m, 4H), 2.12-1.58 (m, 3H).

Example 18

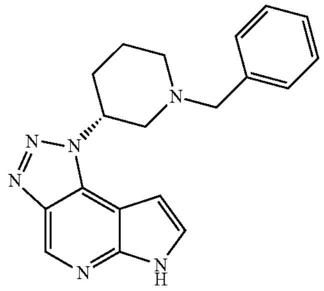 [SMILES: c1ccc(CN2CCC[C@@H](n3nnc4cnc5[nH]ccc5c43)C2)cc1]

1-((R)-1-Benzyl-piperidin-3-yl)-1,6-dihydro-1,2,3,5,6-pentaaza-as-indacene

6-Benzenesulfonyl-1-((R)-1-benzyl-piperidin-3-yl)-1,6-dihydro-1,2,3,5,6-pentaaza-as-indacene A stirred solution of 1-benzenesulfonyl-N*4*-((R)-1-benzyl-piperidin-3-yl)-1H-pyrrolo[2,3-b]pyridine-4,5-diamine (300 mg, 0.65 mmol) in acetonitrile (6 ml) was treated with copper (II) bromide (174 mg, 0.78 mmol) and n-butyl nitrite (114 μl, 0.97 mmol) and then heated to 70° C. for 2 hours. After cooling, the reaction was quenched by the addition of 1M aqueous HCl solution (ca. 5 ml) and stirred for 5 minutes. The mixture was basified with saturated sodium hydrogen carbonate solution and extracted with ethyl acetate (3×). The combined extracts were washed with brine, dried with sodium sulfate and concentrated under vacuum to leave a brown residue. Purification by column chromatography on silica gel (gradient: 0 to 60% ethyl acetate in cyclohexane) gave 200 mg (65%) of 6-benzenesulfonyl-1-((R)-1-benzyl-piperidin-3-yl)-1,6-dihydro-1,2,3,5,6-pentaaza-as-indacene as a brown residue. LCMS (Method B, ESI): RT=3.38 min, m+H=473.5; $^1$H NMR (400 MHz, $CDCl_3$) δ: 9.18 (s, 1H), 8.21 (m, 2H), 7.82 (d, 1H), 7.57 (m, 1H), 7.53-7.46 (m, 2H), 7.30 (s, 5H), 6.75 (d, 1H), 4.88 (m, 1H), 3.61 (dd, 2H), 3.25 (m, 1H), 3.03 (m, 1H), 2.57 (m, 1H), 2.39-2.17 (m, 3H), 2.10-1.87 (m, 2H).

1-((R)-1-Benzyl-piperidin-3-yl)-1,6-dihydro-1,2,3,5,6-pentaaza-as-indacene

6-Benzenesulfonyl-1-((R)-1-benzyl-piperidin-3-yl)-1,6-dihydro-1,2,3,5,6-pentaaza-as-indacene (195 mg, 0.41 mmol) was treated with 1M aqueous NaOH solution (5 ml) and methanol (5 ml) at ambient temperature for 4 hours. The mixture was partially concentrated under vacuum and the aqueous residue was extracted with ethyl acetate (3×). The combined extracts were washed with brine, dried with sodium sulfate and concentrated under vacuum to leave an orange residue. Purification by column chromatography on silica gel (eluting with 50 to 80% ethyl acetate in DCM) afforded a glass (78 mg). Subsequent trituration (diethyl ether) afforded 31 mg (23%) of 1-((R)-1-benzyl-piperidin-3-yl)-1,6-dihydro-1,2,3,5,6-pentaaza-as-indacene. LC MS (Method A, ESI): RT=2.42 min, m+H=333.2; $^1$H NMR (400 MHz, DMSO-$d_6$) δ: 12.34 (s, 1H), 8.99 (s, 1H), 7.55 (t, 1H), 7.34-7.17 (m, 5H), 6.78 (dd, 1H), 5.10-5.00 (m, 1H), 3.72-3.49 (m, 2H), 3.22 (m, 1H), 2.95 (m, 1H), 2.57-2.50 (m, 1H), 2.32 (m, 1H), 2.26-2.09 (m, 2H), 1.98-1.83 (m, 2H).

Example 19

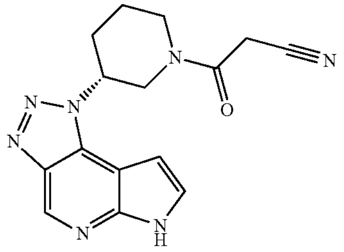 [SMILES: N#CCC(=O)N1CCC[C@@H](n2nnc3cnc4[nH]ccc4c32)C1]

3-Oxo-3-[(R)-3-(6H-1,2,3,5,6-pentaaza-as-indacen-1-yl)-piperidin-1-yl]propionitrile

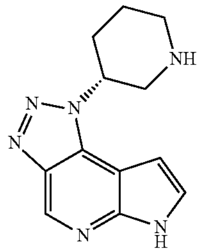 [SMILES: c1cc2c(ncc3nnn([C@@H]4CCCNC4)c32)[nH]1]

(R)-1-Piperidin-3-yl-1,6-dihydro-1,2,3,5,6-pentaaza-as-indacene 77 mg (76%) of the title compound was made by following the procedure described for the preparation of (R)-1-piperidin-3-yl-1,6-dihydro-1,2,3,5,6-tetraaza-as-indacene but using 1-((R)-1-benzyl-piperidin-3-yl)-1,6-dihydro-1,2,3,5,6-pentaaza-as-indacene. LCMS (Method B, E SI): RT=0.39 min, m+H=243.3; $^1$H NMR (400 MHz, $CDCl_3$) δ: 10.18 (s, 1H), 9.11 (m, 1H), 7.45 (m, 1H), 6.90 (m, 1H), 4.96 (m, 1H), 3.55 (m, 1H), 3.44 (dd, 1H), 3.20-3.13 (m, 1H), 2.88 (m, 1H), 2.48-2.40 (m, 2H), 2.02-1.94 (m, 1H), 1.86-1.71 (m, 1H).

3-Oxo-3-[(R)-3-(6H-1,2,3,5,6-pentaaza-as-indacen-1-yl)-piperidin-1-yl]propionitrile To a stirred solution of (R)-1-piperidin-3-yl-1,6-dihydro-1,2,3,5,6-pentaaza-as-indacene (72 mg, 297 μmol) in DCM (15 ml) at 0° C., cyanoacetic acid (30.0 mg, 357 μmol), N-hydroxybenzotriazole (56.0 mg, 416 μmol), 4-(dimethylamino)pyridine (58.0 mg, 475 μmol) and 1-ethyl-3-(3-dimethylaminopropyl)carbodiimide hydrochloride (91.0 mg, 475 μmol) were added. The mixture was then stirred at ambient temperature for 18 hours. The crude reaction mixture was purified by column chromatography on silica gel (gradient: 0 to 6% methanol in DCM) affording 82 mg (92%) of 3-oxo-3-[(R)-3-(6H-1,2,3,5,6-pentaaza-as-indacen-1-yl)-piperidin-1-yl]propionitrile. LCMS (Method A, ESI): RT=2.73 min, m+H=310.1; $^1$H NMR (400 MHz, DMSO-$d_6$) δ: 12.38 (s, 1H), 9.02 (s, 1H), 7.64-7.59 (m, 1H), 7.12 (m, 1H), 5.28-4.96 (m, 1H), 4.81-4.31 (m, 1H), 4.20-3.70 (m, 3H), 3.36-2.96 (m, 2H), 2.44-1.68 (m, 4H).

Example 20

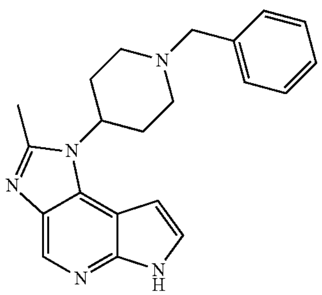 [SMILES: Cc1nc2cnc3[nH]ccc3c2n1C1CCN(Cc2ccccc2)CC1]

1-(1-Benzyl-piperidin-4-yl)-2-methyl-1,6-dihydro-1,2,3,5,6-tetraaza-as-indacene

6-Benzenesulfonyl-1-(1-benzyl-piperidin-4-yl)-2-ethoxy-2-methyl-1,2,3,6-tetrahydro-1,2,3,5,6-tetraaza-as-indacene A mixture of 1-benzenesulfonyl-N*4*-(1-benzyl-piperidin-4-yl)-1H-pyrrolo[2,3-b]pyridine-4,5-diamine (500 mg, 1.08 mmol), triethyl orthoacetate (394 μl, 2.16 mmol) and p-toluenesulfonic acid monohydrate (20.0 mg, 108 μmol) in toluene (10 ml) was heated to reflux for 2 hours. After cooling, ethyl acetate was added and the mixture washed with a saturated sodium hydrogen carbonate solution, water and brine, dried with sodium sulfate and concentrated under vacuum. Purification by column chromatography on silica gel (gradient: 0 to 50% ethyl acetate in DCM) gave 481 mg (88%) of 6-benzenesulfonyl-1-(1-benzyl-piperidin-4-yl)-2-ethoxy-2-methyl-1,2,3,6-tetrahydro-1,2,3,5,6-tetraaza-as-indacene. LCMS (Method B, ESI): RT=3.30 min, m+H=532.4.

6-Benzenesulfonyl-1-(1-benzyl-piperidin-4-yl)-2-methyl-1,6-dihydro-1,2,3,5,6-tetraaza-as-indacene A mixture of 6-benzene sulfonyl-1-(1-benzyl-piperidin-4-yl)-2-ethoxy-2-methyl-1,2,3,6-tetrahydro-1,2,3,5,6-tetraaza-as-indacene (375 mg, 705 μmol) and p-toluenesulfonic acid monohydrate (catalytic) in toluene (10 ml) was heated to reflux for 18 hours. After cooling, ethyl acetate was added and the mixture washed with a saturated sodium hydrogen carbonate solution, water, and brine, dried with sodium sulfate and concentrated under vacuum. Purification by column chromatography on silica gel (gradient: 0 to 7.5% methanol in DCM) afforded 282 mg (82%) of 6-benzenesulfonyl-1-(1-benzyl-piperidin-4-yl)-2-methyl-1,6-dihydro-1,2,3,5,6-tetraaza-as-indacene. LCMS (Method B, ESI): RT=3.16 min, m+H=486.4; $^1$H NMR (400 MHz, $CDCl_3$) δ: 8.79 (s, 1H), 8.23 (d, 2H), 7.85 (d, 1H), 7.42-7.39 (m, 9H), 4.48-4.28 (m, 1H), 3.62 (s, 2H), 3.24-3.03 (m, 2H), 2.75-2.48 (m, 5H), 2.29-2.15 (m, 2H), 1.93-1.76 (m, 2H).

1-(1-Benzyl-piperidin-4-yl)-2-methyl-1,6-dihydro-1,2,3,5,6-tetraaza-as-indacene

A mixture of 6-benzenesulfonyl-1-(1-benzyl-piperidin-4-yl)-2-methyl-1,6-dihydro-1,2,3,5,6-tetraaza-as-indacene (275 mg, 566 μmol) in methanol (20 ml) was treated with 1M aqueous NaOH solution (5 ml) and left to stand at ambient temperature for 18 hours. The mixture was partially concentrated under vacuum and the resulting suspension was extracted with ethyl acetate (3×). The combined organic extracts were washed with water and brine, dried with sodium sulfate and concentrated under vacuum. Purification by column chromatography on silica gel (gradient: 0 to 10% methanol in DCM) afforded a residue which was triturated (diethyl ether) to give 137 mg (70%) of 1-(1-benzyl-piperidin-4-yl)-2-methyl-1,6-dihydro-1,2,3,5,6-tetraaza-as-indacene. LCMS (Method A, ESI): RT=1.83 min, m+H=346.1; $^1$H NMR (400 MHz, DMSO-$d_6$) δ: 11.78 (s, 1H), 8.46 (s, 1H), 7.51 (t, 1H), 7.40-7.40 (m, 4H), 7.28-7.27 (m, 1H), 6.96 (s, 1H), 4.48 (s, 1H), 3.62 (s, 2H), 3.04 (d, 2H), 2.62 (s, 3H), 2.57 (d, 2H), 2.23 (t, 2H), 1.88 (d, 2H).

Example 21

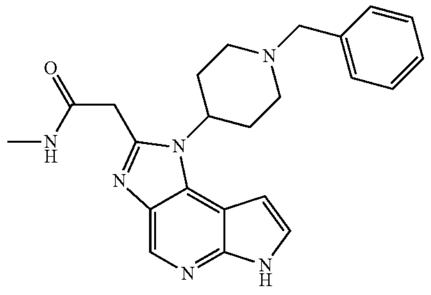 [SMILES: CNC(=O)Cc1nc2cnc3[nH]ccc3c2n1C1CCN(Cc2ccccc2)CC1]

2-[1-(1-Benzyl-piperidin-4-yl)-1,6-dihydro-1,2,3,5,6-tetraaza-as-indacen-2-yl]-N-methyl acetamide 2-[6-Benzenesulfonyl-1-(1-benzyl-piperidin-4-yl)-1,6-dihydro-1,2,3,5,6-tetraaza-as-indacen-2-yl]-N-methyl acetamide A 25 ml microwave vial was charged with [6-benzenesulfonyl-1-(1-benzyl-piperidin-4-yl)-1,6-dihydro-1,2,3,5,6-tetraaza-as-indacen-2-yl]-acetic acid ethyl ester (250 mg, 448 μmol) and methylamine (33% wt in ethanol, 5 ml). The mixture was heated in a microwave reactor at 150° C. for 30 minutes and concentrated under vacuum. Purification by column chromatography on silica gel (gradient: 0 to 10% methanol in DCM) afforded 231 mg (quantitative yield) of 2-[6-benzenesulfonyl-1-(1-benzyl-piperidin-4-yl)-1,6-dihydro-1,2,3,5,6-tetraaza-as-indacen-2-yl]-N-methyl acetamide. LCMS (Method B, ESI): RT=3.19 min, m+H=543.4; $^1$H NMR (400 MHz, $CDCl_3$) δ: 8.83 (s, 1H), 8.23 (d, 2H), 7.89 (d, 1H), 7.57-7.27 (m, 9H), 7.00 (br s, 1H), 4.62-4.49 (m, 1H), 3.93 (s, 2H), 3.61 (s, 2H), 3.16-3.06 (m, 2H), 2.83-2.77 (d, 3H), 2.66-2.50 (m, 2H), 2.29-2.16 (m, 2H), 1.89-1.79 (m, 2H).

2-[1-(1-Benzyl-piperidin-4-yl)-1,6-dihydro-1,2,3,5,6-tetraaza-as-indacen-2-yl]-N-methyl acetamide A mixture of 2-[6-benzenesulfonyl-1-(1-benzyl-piperidin-4-yl)-1,6-dihydro-1,2,3,5,6-tetraaza-as-indacen-2-yl]-N-methyl acetamide (250 mg, 460 μmol) in methanol (10 ml) was treated with 1M aqueous NaOH solution (5 ml) and left to stand at ambient temperature for 8 hours. The mixture was partially concentrated under vacuum and the resulting suspension was extracted with ethyl acetate (2×). The combined organic extracts were washed with water and brine, dried with sodium sulfate and concentrated under vacuum. Purification by column chromatography on silica gel (gradient: 0 to 12% methanol in DCM) afforded a residue which was triturated (diethyl ether) to give 163 mg (88%) of 2-[1-(1-benzyl-piperidin-4-yl)-1,6-dihydro-1,2,3,5,6-tetraaza-as-indacen-2-yl]-N-methyl acetamide. LCMS (Method A, ESI): RT=1.92 min, m+H=403.1; $^1$H NMR (400 MHz, DMSO-$d_6$) δ: 11.82 (s, 1H), 8.49 (s, 1H), 8.19 (d, 1H), 7.53 (t, 1H), 7.41-7.39 (m, 4H), 7.28 (t, 1H), 7.01 (s, 1H), 4.56-4.54 (m, 1H), 3.95 (s, 2H), 3.61 (s, 2H), 3.04 (d, 2H), 2.66-2.52 (m, 5H), 2.17 (t, 2H), 1.91 (d, 2H).

Example 22

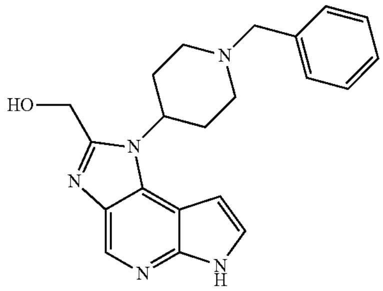 [SMILES: OCc1nc2cnc3[nH]ccc3c2n1C1CCN(Cc2ccccc2)CC1]

[1-(1-Benzyl-piperidin-4-yl)-1,6-dihydro-1,2,3,5,6-tetraaza-as-indacen-2-yl]methanol Acetic acid 6-benzenesulfonyl-1-(1-benzyl-piperidin-4-yl)-1,6-dihydro-1,2,3,5,6-tetraaza-as-indacen-2-ylmethyl ester A mixture of 1-benzenesulfonyl-N*4*-(1-benzyl-piperidin-4-yl)-1H-pyrrolo[2,3-b]pyridine-4,5-diamine (250 mg, 540 μmol) and triethylamine (97.0 μl, 700 μmol) in DCM (6 ml) was treated dropwise with acetoxyacetyl chloride (64.0 μl, 596 μmol) and stirred at ambient temperature for 1 hour. The mixture was concentrated under vacuum, taken up in acetic acid (3 ml) and heated at 100° C. in a sealed tube for 18 hours. After cooling, the acetic acid was removed under vacuum and the residue partitioned between ethyl acetate and a saturated sodium hydrogen carbonate solution. The organic phase was washed with water and brine, dried with sodium sulfate and concentrated under vacuum. Purification by column chromatography on silica gel (gradient: 0 to 100% ethyl acetate in DCM) afforded 219 mg (75%) of acetic acid 6-benzenesulfonyl-1-(1-benzyl-piperidin-4-yl)-1,6-dihydro-1,2,3,5,6-tetraaza-as-indacen-2-ylmethyl ester. LCMS (Method B, ESI): RT=3.30 min, m+H=544.4; $^1$H NMR (400 MHz, $CDCl_3$) δ: 8.90 (s, 1H), 8.23 (d, 2H), 7.89 (d, 1H), 7.58-7.27 (m, 9H), 5.40 (s, 2H), 4.50-4.37 (m, 1H), 3.62 (s, 2H), 3.13 (d, 2H), 2.68-2.52 (m, 2H), 2.26-2.16 (m, 2H), 2.11 (s, 3H), 1.92-1.82 (m, 2H).

[6-Benzenesulfonyl-1-(1-benzyl-piperidin-4-yl)-1,6-dihydro-1,2,3,5,6-tetraaza-as-indacen-2-yl]methanol A solution of acetic acid 6-benzenesulfonyl-1-(1-benzyl-piperidin-4-yl)-1,6-dihydro-1,2,3,5,6-tetraaza-as-indacen-2-ylmethyl ester (215 mg, 395 μmol) in THF (4 ml) was treated with 1M aqueous LiOH solution (514 μl, 514 μmol) and vigorously stirred at ambient temperature for 45 minutes. The mixture was diluted with water and extracted into ethyl acetate (2×). The combined extracts were dried with sodium sulfate and concentrated under vacuum. Purification by column chromatography on silica gel (gradient: 0 to 10% methanol in DCM) afforded 158 mg (80%) of [6-benzenesulfonyl-1-(1-benzyl-piperidin-4-yl)-1,6-dihydro-1,2,3,5,6-tetraaza-as-indacen-2-yl]methanol. LCMS (Method B, ESI): RT=3.11 min, m+H=502.4; $^1$H NMR (400 MHz, DMSO-$d_6$) δ: 8.69 (s, 1H), 8.20-8.09 (m, 3H), 7.76-7.57 (m, 3H), 7.44-7.33 (m, 6H), 5.74 (t, 1H), 4.83-4.67 (m, 3H), 3.62 (s, 2H), 3.04 (d, 2H), 2.46-2.30 (m, 2H), 2.27-2.12 (m, 2H), 1.99-1.86 (m, 2H).

[1-(1-Benzyl-piperidin-4-yl)-1,6-dihydro-1,2,3,5,6-tetraaza-as-indacen-2-yl]methanol A mixture of [6-benzenesulfonyl-1-(1-benzyl-piperidin-4-yl)-1,6-dihydro-1,2,3,5,6-tetraaza-as-indacen-2-yl]methanol (75.0 mg, 150 μmol) in methanol/THF (1:1, 10 ml) was treated with 1M aqueous NaOH solution (5 ml) and left to stand at ambient temperature for 8 hours. The mixture was partially concentrated under vacuum and the resulting suspension was extracted with ethyl acetate (2×). The combined organic extracts were washed with water and brine, dried with sodium sulfate and concentrated under vacuum. Purification by column chromatography on silica gel (gradient: 0 to 10% methanol in DCM) afforded a residue which was triturated (diethyl ether) to give 34 mg (63%) of [1-(1-benzyl-piperidin-4-yl)-1,6-dihydro-1,2,3,5,6-tetraaza-as-indacen-2-yl]methanol. LCMS (Method A, ESI): RT=1.85 min, m+H=362.1; $^{1}$H NMR (400 MHz, DMSO-$d_6$) δ: 11.86 (s, 1H), 8.54 (s, 1H), 7.54 (t, 1H), 7.41-7.39 (m, 4H), 7.29-7.27 (m, 1H), 6.99 (s, 1H), 5.65 (t, 1H), 4.80-4.67 (m, 3H), 3.62 (s, 2H), 3.06 (d, 2H), 2.71-2.49 (m, 2H), 2.21-2.18 (m, 2H), 1.95-1.85 (m, 2H).

Example 23

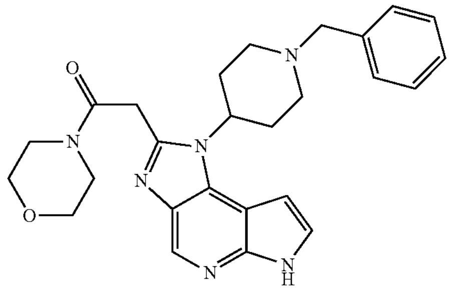 [SMILES: O=C(Cc1nc2cnc3[nH]ccc3c2n1C1CCN(Cc2ccccc2)CC1)N1CCOCC1]

2-[1-(1-Benzyl-piperidin-4-yl)-1,6-dihydro-1,2,3,5,6-tetraaza-as-indacen-2-yl]-1-morpholin-4-yl-ethanone

[6-Benzenesulfonyl-1-(1-benzyl-piperidin-4-yl)-1,6-dihydro-1,2,3,5,6-tetraaza-as-indacen-2-yl]-acetic acid ethyl ester A mixture of 1-benzenesulfonyl-N*4*-(1-benzyl-piperidin-4-yl)-1H-pyrrolo[2,3-b]pyridine-4,5-diamine (2.00 g, 4.33 mmol) and ethyl-3-ethoxy-imino propionate hydrochloride (2.54 g, 13.0 mmol) in ethanol (30 ml) was heated to reflux for 18 hours. After cooling, the solvent was removed under vacuum and the resulting residue partitioned between ethyl acetate and a saturated sodium hydrogen carbonate solution. The organic phase was washed with water and brine, dried with sodium sulfate and concentrated under vacuum. Purification by column chromatography on silica gel (gradient: 0 to 100% ethyl acetate in DCM) afforded 2.08 g (86%) of [6-benzene sulfonyl-1-(1-benzyl-piperidin-4-yl)-1,6-dihydro-1,2,3,5,6-tetraaza-as-indacen-2-yl]-acetic acid ethyl ester. LCMS (Method B, ESI): RT=3.48 min, m+H=558.4; $^{1}$H NMR (400 MHz, $CDCl_3$) δ: 8.84 (s, 1H), 8.23 (d, 2H), 7.88 (s, 1H), 7.60-7.35 (m, 9H), 4.42-4.23 (m, 1H), 4.18 (q, 2H), 4.07 (s, 2H), 3.61 (s, 2H), 3.18-3.07 (m, 2H), 2.71-2.52 (m, 2H), 2.27-2.11 (m, 2H), 1.98-1.84 (m, 2H), 1.25 (t, 3H).

Lithium; [6-benzenesulfonyl-1-(1-benzyl-piperidin-4-yl)-1,6-dihydro-1,2,3,5,6-tetraaza-as-indacen-2-yl] acetate A solution of [6-benzenesulfonyl-1-(1-benzyl-piperidin-4-yl)-1,6-dihydro-1,2,3,5,6-tetraaza-as-indacen-2-yl]-acetic acid ethyl ester (200 mg, 360 μmol) in THF (5 ml) was treated with 1M aqueous lithium hydroxide (430 μl, 430 μmol) and vigorously stirred at ambient temperature for 45 minutes. The mixture was concentrated under vacuum and the residue azeotroped with toluene (2×) to afford 205 mg (quantitative yield) of lithium; [6-benzenesulfonyl-1-(1-benzyl-piperidin-4-yl)-1,6-dihydro-1,2,3,5,6-tetraaza-as-indacen-2-yl]acetate. LCMS (Method B, ESI): RT=3.34 min, m+H=530.3; $^{1}$H NMR (400 MHz, DMSO-$d_6$) δ: 8.55 (s, 1H), 8.16-8.00 (m, 3H), 7.71-7.64 (m, 1H), 7.63-7.54 (m, 2H), 7.49-7.27 (m, 6H), 4.62-4.42 (m, 1H), 3.64-3.53 (m, 4H), 3.06-2.90 (m, 2H), 2.40-2.23 (m, 2H), 2.18-2.06 (m, 2H), 2.05-1.94 (m, 2H).

2-[6-Benzenesulfonyl-1-(1-benzyl-piperidin-4-yl)-1,6-dihydro-1,2,3,5,6-tetraaza-as-indacen-2-yl]-1-morpholin-4-yl-ethanone A solution of lithium; [6-benzenesulfonyl-1-(1-benzyl-piperidin-4-yl)-1,6-dihydro-1,2,3,5,6-tetraaza-as-indacen-2-yl]-acetate (193 mg, 360 μmol) in DMF (5 ml) was treated with morpholine (47.0 μl, 540 μmol), DIPEA (277 μl, 1.62 mmol) and HATU (205 mg, 540 μmol) and stirred at ambient temperature for 2 hours. The mixture was diluted with water and extracted into ethyl acetate (3×). The combined organic extracts were washed with water and brine, dried with sodium sulfate and concentrated under vacuum. Purification by column chromatography on silica gel (gradient: 0 to 10% methanol in DCM) afforded 231 mg (quantitative yield) of 2-[6-benzenesulfonyl-1-(1-benzyl-piperidin-4-yl)-1,6-dihydro-1,2,3,5,6-tetraaza-as-indacen-2-yl]-1-morpholin-4-yl-ethanone. LCMS (Method B, ESI): RT=3.23 min, m+H=599.4; $^{1}$H NMR (400 MHz, $CDCl_3$) δ: 8.81 (s, 1H), 8.24 (d, 2H), 7.88 (d, 1H), 7.60-7.26 (m, 9H), 4.81-4.68 (m, 1H), 4.10 (s, 2H), 3.80-3.74 (m, 2H), 3.63-3.51 (m, 8H), 3.15-3.05 (m, 2H), 2.67-2.50 (m, 2H), 2.32-2.18 (m, 2H), 1.93-1.80 (m, 2H).

2-[1-(1-Benzyl-piperidin-4-yl)-1,6-dihydro-1,2,3,5,6-tetraaza-as-indacen-2-yl]-1-morpholin-4-yl-ethanone A mixture of 2-[6-benzenesulfonyl-1-(1-benzyl-piperidin-4-yl)-1,6-dihydro-1,2,3,5,6-tetraaza-as-indacen-2-yl]-1-morpholin-4-yl-ethanone (216 mg, 360 μmol) in methanol/THF (4:1, 8 ml) was treated with 2M aqueous NaOH solution (5 ml) and left to stand at ambient temperature for 3 hours. The mixture was partially concentrated under vacuum and the resulting suspension was extracted with ethyl acetate (3×). The combined organic extracts were washed with water and brine, dried with sodium sulfate and concentrated under vacuum to leave an orange residue. Purification by column chromatography on silica gel (gradient: 0 to 10% methanol in DCM) afforded a residue which was triturated (diethyl ether) to give 109 mg (66%) of 2-[1-(1-benzyl-piperidin-4-yl)-1,6-dihydro-1,2,3,5,6-tetraaza-as-indacen-2-yl]-1-morpholin-4-yl-ethanone. LCMS (Method A, ESI): RT=2.08 min, m+H=459.1; $^1$H NMR (400 MHz, DMSO-$d_6$) δ: 11.82 (s, 1H), 8.50 (s, 1H), 7.54 (t, 1H), 7.41-7.39 (m, 4H), 7.28-7.27 (m, 1H), 7.01 (s, 1H), 4.48-4.33 (m, 1H), 4.25 (s, 2H), 3.67-3.52 (m, 8H), 3.51-3.44 (m, 2H), 3.08-2.99 (m, 2H), 2.64-2.52 (m, 2H), 2.21-2.11 (m, 2H), 1.95-1.84 (m, 2H).

Example 24

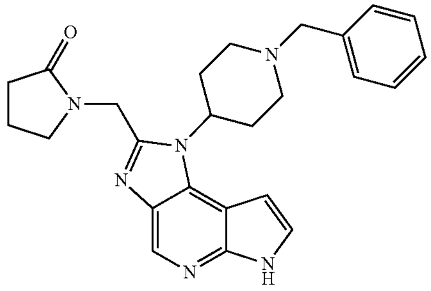 [SMILES: O=C1CCCN1Cc1nc2cnc3[nH]ccc3c2n1C1CCN(Cc2ccccc2)CC1]

1-[1-(1-Benzyl-piperidin-4-yl)-1,6-dihydro-1,2,3,5,6-tetraaza-as-indacen-2-ylmethyl]-pyrrolidin-2-one Methanesulfonic acid 6-benzenesulfonyl-1-(1-benzyl-piperidin-4-yl)-1,6-dihydro-1,2,3,5,6-tetraaza-as-indacen-2-ylmethyl ester A mixture [6-benzenesulfonyl-1-(1-benzyl-piperidin-4-yl)-1,6-dihydro-1,2,3,5,6-tetraaza-as-indacen-2-yl]-methanol (70.0 mg, 140 μmol) and triethylamine (48.0 μl, 350 μmol) at 0° C. was treated with methanesulfonyl chloride (22.0 μl, 280 μmol). After 1 hour the mixture was diluted with DCM, washed with a saturated sodium hydrogen carbonate solution, water and brine, dried with sodium sulfate and concentrated under vacuum to leave 87 mg (quant. yield) of methanesulfonic acid 6-benzenesulfonyl-1-(1-benzyl-piperidin-4-yl)-1,6-dihydro-1,2,3,5,6-tetraaza-as-indacen-2-ylmethyl ester, which was used for the next step without purification. LCMS (Method B, ESI): RT=3.42 min, m+H=580.3.

1-[6-Benzenesulfonyl-1-(1-benzyl-piperidin-4-yl)-1,6-dihydro-1,2,3,5,6-tetraaza-as-indacen-2-ylmethyl]-pyrrolidin-2-one A solution of 2-pyrrolidinone (18.0 mg, 212 μmol) in THF (1 ml) was treated with sodium hydride (60% dispersion in mineral oil, 8.00 mg, 212 μmol) and stirred at ambient temperature for 30 minutes. A solution containing methanesulfonic acid 6-benzenesulfonyl-1-(1-benzyl-piperidin-4-yl)-1,6-dihydro-1,2,3,5,6-tetraaza-as-indacen-2-ylmethyl ester (82.0 mg, 141 mmol) in THF (4 ml) was added and then stirred for 2 hours. The mixture was diluted with ethyl acetate, washed water and brine, dried with sodium sulfate and concentrated under vacuum. Purification by column chromatography on silica gel (gradient: 0 to 10% methanol in DCM) afforded 53 mg (66%) of 1-[6-benzenesulfonyl-1-(1-benzyl-piperidin-4-yl)-1,6-dihydro-1,2,3,5,6-tetraaza-as-indacen-2-ylmethyl]-pyrrolidin-2-one. LCMS (Method B, ESI): RT=3.26 min, m+H=569.4; $^1$H NMR (400 MHz, $CDCl_3$) δ: 8.86 (s, 1H), 8.24 (d, 2H), 7.89 (d, 1H), 7.56-7.27 (m, 9H), 4.82-70 (m, 3H), 3.59 (s, 2H), 3.33 (t, 2H), 3.10-3.03 (m, 2H), 2.63-2.50 (m, 2H), 2.40 (t, 2H), 2.30-2.21 (m, 2H), 2.02-1.90 (m, 2H), 1.73-1.64 (m, 2H).

1-[1-(1-Benzyl-piperidin-4-yl)-1,6-dihydro-1,2,3,5,6-tetraaza-as-indacen-2-ylmethyl]-pyrrolidin-2-one A mixture of 1-[6-benzenesulfonyl-1-(1-benzyl-piperidin-4-yl)-1,6-dihydro-1,2,3,5,6-tetraaza-as-indacen-2-ylmethyl]-pyrrolidin-2-one (50.0 mg, 88.0 μmol) in methanol/THF (3:1, 6 ml) was treated with 2M aqueous NaOH solution (5 ml) and left to stand at ambient temperature for 3 hours. The mixture was partially concentrated under vacuum and the resulting suspension was extracted with ethyl acetate (3×). The combined organic extracts were washed with water and brine, dried with sodium sulfate and concentrated under vacuum. Purification by column chromatography on silica gel (gradient: 0 to 10% methanol in DCM) afforded a residue which was triturated (diethyl ether) to give 15.0 mg (40%) of 1-[1-(1-benzyl-piperidin-4-yl)-1,6-dihydro-1,2,3,5,6-tetraaza-as-indacen-2-ylmethyl]-pyrrolidin-2-one as an off-white solid. LCMS (Method A, ESI): RT=2.18 min, m+H=429.1; $^1$H NMR (400 MHz, $CDCl_3$) δ: 9.49 (s, 1H), 8.77 (s, 1H), 7.45 (d, 3H), 7.37 (t, 2H), 7.32-7.27 (m, 1H), 7.22 (br s, 1H), 4.86 (s, 2H), 4.81-4.69 (m, 1H), 3.63 (s, 2H), 3.37 (t, 2H), 3.16-3.07 (m, 2H), 2.88-2.71 (m, 2H), 2.43 (t, 2H), 2.37-2.24 (m, 2H), 2.03-1.92 (m, 2H), 1.77-1.67 (m, 2H).

Examples 25-108 shown in Table 1 were prepared generally following the above-described Examples and making non-critical variations where necessary. The general synthetic method used for each compound is indicated.

TABLE 1

| Ex | Structure | Name | Synthetic Method | LCMS RT (min)/Method | LCMS (ESI) m/z |
|---|---|---|---|---|---|
| 25 | 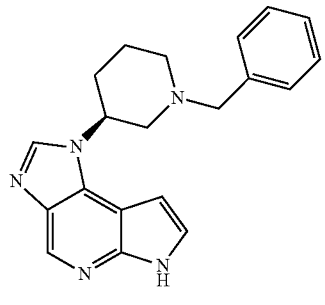 [SMILES: c1ccc(CN2CCC[C@H](n3cnc4cnc5[nH]ccc5c43)C2)cc1] | 1-((S)-1-Benzyl-piperidin-3-yl)-1,6-dihydro-1,3,5,6-tetraaza-as-indacene | 1 | 1.91/A | 332.2 |

TABLE 1-continued
| Ex | Structure | Name | Synthetic Method | LCMS RT (min)/Method | LCMS (ESI) m/z |
|---|---|---|---|---|---|
| 26 | 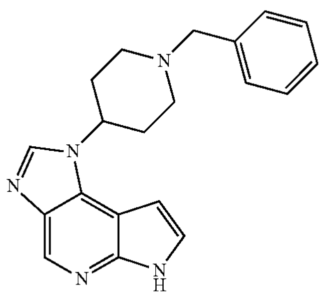 [SMILES: c1ccc(CN2CCC(n3cnc4cnc5[nH]ccc5c43)CC2)cc1] | 1-(1-Benzyl-piperidin-4-yl)-1,6-dihydro-1,3,5,6-tetraaza-as-indacene | 1 | 1.92/A | 332.2 |
| 27 | 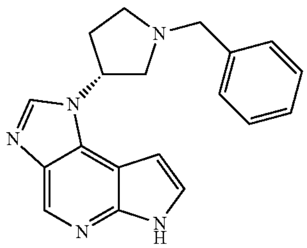 [SMILES: c1ccc(CN2CC[C@@H](n3cnc4cnc5[nH]ccc5c43)C2)cc1] | 1-((R)-1-Benzyl-pyrrolidin-3-yl)-1,6-dihydro-1,3,5,6-tetraaza-as-indacene | 1 | 1.89/A | 318.1 |
| 28 | 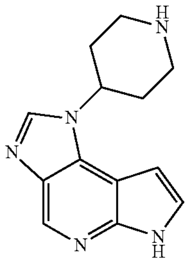 [SMILES: c1cc2c(ncc3ncn(C4CCNCC4)c32)[nH]1] | 1-Piperidin-4-yl-1,6-dihydro-1,3,5,6-tetraaza-as-indacene | 2 | 0.69/A | 242.2 |
| 29 | 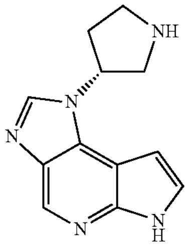 [SMILES: c1cc2c(ncc3ncn([C@@H]4CCNC4)c32)[nH]1] | (R)-1-Pyrrolidin-3-yl-1,6-dihydro-1,3,5,6-tetraaza-as-indacene | 2 | 0.39/B | 228.3 |
| 30 | 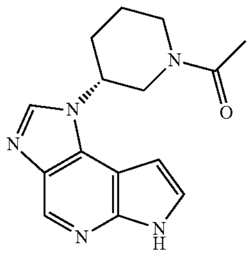 [SMILES: CC(=O)N1CCC[C@@H](n2cnc3cnc4[nH]ccc4c32)C1] | 1-[(R)-3-(6H-1,3,5,6-Tetraaza-as-indacen-1-yl)-piperidin-1-yl]ethanone | 6 | 1.98/A | 284.2 |

TABLE 1-continued

| Ex | Structure | Name | Synthetic Method | LCMS RT (min)/Method | LCMS (ESI) m/z |
|---|---|---|---|---|---|
| 31 | 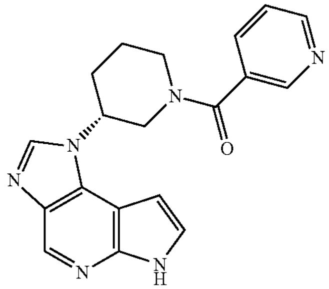 [SMILES: O=C(c1cccnc1)N1CCC[C@@H](n2cnc3cnc4[nH]ccc4c32)C1] | Pyridin-3-yl-[(R)-3-(6H-1,3,5,6-tetraaza-as-indacen-1-yl)-piperidin-1-yl]methanone | 6 | 1.96/A | 347.1 |
| 32 | 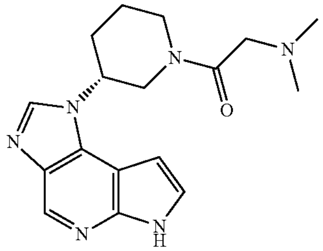 [SMILES: CN(C)CC(=O)N1CCC[C@@H](n2cnc3cnc4[nH]ccc4c32)C1] | 2-Dimethylamino-1-[(R)-3-(6H-1,3,5,6-tetraaza-as-indacen-1-yl)-piperidin-1-yl]ethanone | 7 | 1.17/A | 327.1 |
| 33 | 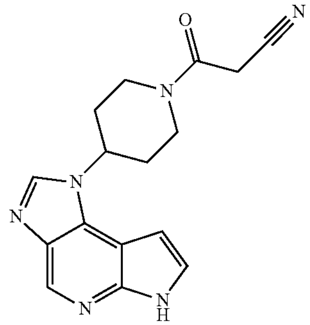 [SMILES: N#CCC(=O)N1CCC(n2cnc3cnc4[nH]ccc4c32)CC1] | 3-Oxo-3-[4-(6H-1,3,5,6-tetraaza-as-indacen-1-yl)-piperidin-1-yl]propionitrile | 5 | 1.80/A | 309.1 |
| 34 | 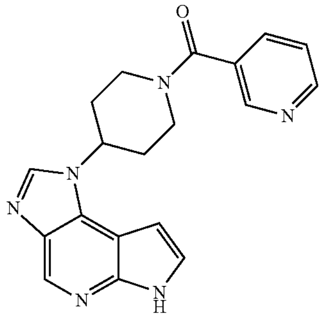 [SMILES: O=C(c1cccnc1)N1CCC(n2cnc3cnc4[nH]ccc4c32)CC1] | Pyridin-3-yl-[4-(6H-1,3,5,6-tetraaza-as-indacen-1-yl)-piperidin-1-yl]methanone | 6 | 1.86/A | 347.1 |
| 35 | 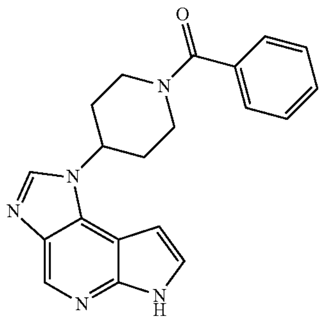 [SMILES: O=C(c1ccccc1)N1CCC(n2cnc3cnc4[nH]ccc4c32)CC1] | Phenyl-[4-(6H-1,3,5,6-tetraaza-as-indacen-1-yl)-piperidin-1-yl]methanone | 6 | 2.60/A | 346.1 |

TABLE 1-continued

| Ex | Structure | Name | Synthetic Method | LCMS RT (min)/Method | LCMS (ESI) m/z |
|---|---|---|---|---|---|
| 36 | 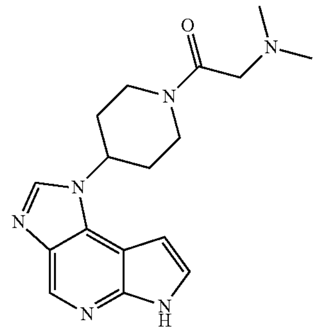 [SMILES: CN(C)CC(=O)N1CCC(n2cnc3cnc4[nH]ccc4c32)CC1] | 2-Dimethylamino-1-[4-(6H-1,3,5,6-tetraaza-as-indacen-1-yl)-piperidin-1-yl]ethanone | 7 | 0.92/A | 327.1 |
| 37 | 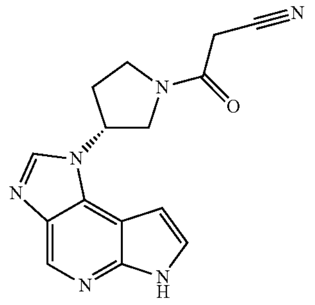 [SMILES: N#CCC(=O)N1CC[C@@H](n2cnc3cnc4[nH]ccc4c32)C1] | 3-Oxo-3-[(R)-3-(6H-1,3,5,6-tetraaza-as-indacen-1-yl)-pyrrolidin-1-yl]propionitrile | 5 | 1.66/A | 295.1 |
| 38 | 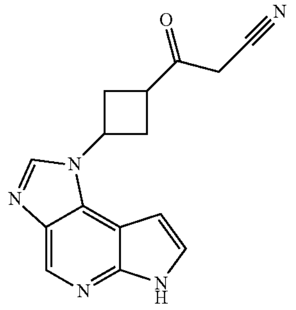 [SMILES: N#CCC(=O)C1CC(n2cnc3cnc4[nH]ccc4c32)C1] | 3-Oxo-3-[3-(6H-1,3,5,6-tetraaza-as-indacen-1-yl)-azetidin-1-yl]propionitrile | 5 | 1.54/A | 281.1 |
| 39 | 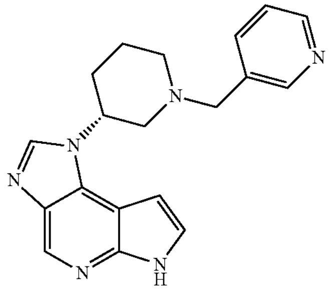 [SMILES: c1cncc(CN2CCC[C@@H](n3cnc4cnc5[nH]ccc5c43)C2)c1] | 1-((R)-1-Pyridin-3-ylmethyl-piperidin-3-yl)-1,6-dihydro-1,3,5,6-tetraaza-as-indacene | 8 | 1.65/A | 333.2 |
| 40 | 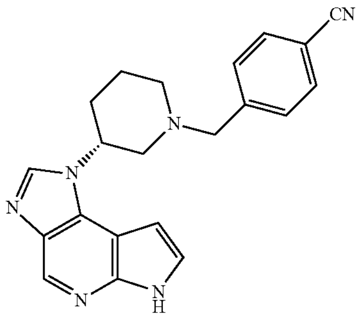 [SMILES: N#Cc1ccc(CN2CCC[C@@H](n3cnc4cnc5[nH]ccc5c43)C2)cc1] | 4-[(R)-3-(6H-1,3,5,6-Tetraaza-as-indacen-1-yl)-piperidin-1-ylmethyl]benzonitrile | 8 | 2.17/A | 357.2 |

TABLE 1-continued

| Ex | Structure | Name | Synthetic Method | LCMS RT (min)/Method | LCMS (ESI) m/z |
|---|---|---|---|---|---|
| 41 | 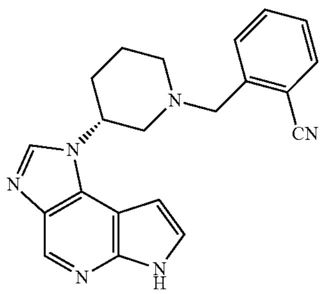 [SMILES: N#Cc1ccccc1CN1CCC[C@@H](n2cnc3cnc4[nH]ccc4c32)C1] | 2-[(R)-3-(6H-1,3,5,6-Tetraaza-as-indacen-1-yl)-piperidin-1-ylmethyl]benzonitrile | 8 | 2.62/A | 357.2 |
| 42 | 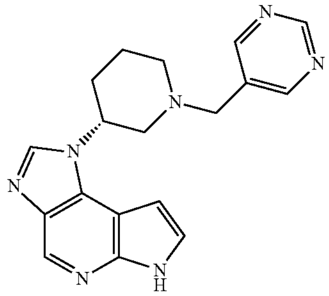 [SMILES: c1ncc(CN2CCC[C@@H](n3cnc4cnc5[nH]ccc5c43)C2)cn1] | 1-((R)-1-Pyrimidin-5-ylmethyl-piperidin-3-yl)-1,6-dihydro-1,3,5,6-tetraaza-as-indacene | 8 | 1.75/A | 334.2 |
| 43 | 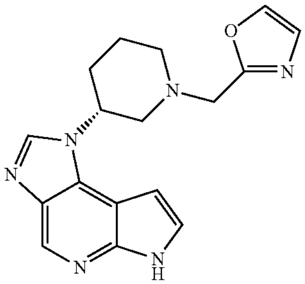 [SMILES: c1coc(CN2CCC[C@@H](n3cnc4cnc5[nH]ccc5c43)C2)n1] | 1-((R)-1-Oxazol-2-ylmethyl-piperidin-3-yl)-1,6-dihydro-1,3,5,6-tetraaza-as-indacene | 8 | 2.02/A | 323.1 |
| 44 | 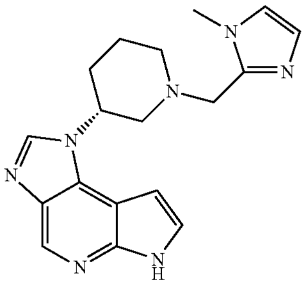 [SMILES: Cn1ccnc1CN1CCC[C@@H](n2cnc3cnc4[nH]ccc4c32)C1] | 1-[(R)-1-(1-Methyl-1H-imidazol-2-ylmethyl)-piperidin-3-yl]-1,6-dihdyro-1,3,5,6-tetraaza-as-indacene | 8 | 1.69/A | 336.1 |
| 45 | 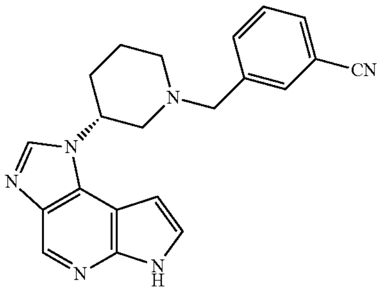 [SMILES: N#Cc1cccc(CN2CCC[C@@H](n3cnc4cnc5[nH]ccc5c43)C2)c1] | 3-[(R)-3-(6H-1,3,5,6-Tetraaza-as-indacen-1-yl)-piperidin-1-ylmethyl]benzonitrile | 8 | 2.13/A | 357.1 |

TABLE 1-continued

| Ex | Structure | Name | Synthetic Method | LCMS RT (min)/Method | LCMS (ESI) m/z |
|---|---|---|---|---|---|
| 46 | 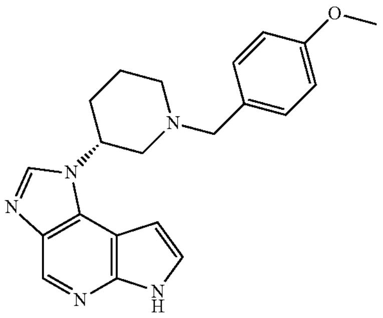 [SMILES: COc1ccc(CN2CCC[C@@H](n3cnc4cnc5[nH]ccc5c43)C2)cc1] | 1-[(R)-1-(4-Methoxy-benzyl)-piperidin-3-yl]-1,6-dihydro-1,3,5,6-tetraaza-as-indacene | 8 | 1.98/A | 362.1 |
| 47 | 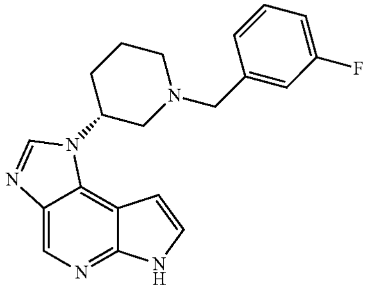 [SMILES: Fc1cccc(CN2CCC[C@@H](n3cnc4cnc5[nH]ccc5c43)C2)c1] | 1-[(R)-1-(3-Fluoro-benzyl)-piperidin-3-yl]-1,6-dihydro-1,3,5,6-tetraaza-as-indacene | 8 | 2.11/A | 350.1 |
| 48 | 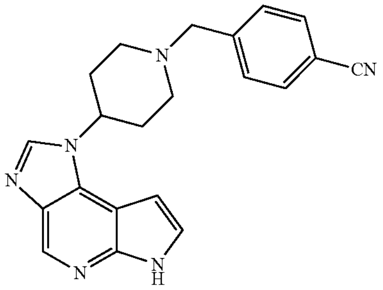 [SMILES: N#Cc1ccc(CN2CCC(n3cnc4cnc5[nH]ccc5c43)CC2)cc1] | 4-[4-(6H-1,3,5,6-Tetraaza-as-indacen-1-yl)-piperidin-1-ylmethyl]benzonitrile | 8 | 1.77/A | 357.1 |
| 49 | 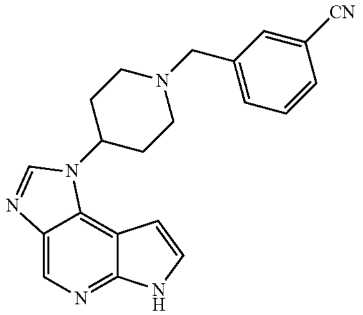 [SMILES: N#Cc1cccc(CN2CCC(n3cnc4cnc5[nH]ccc5c43)CC2)c1] | 3-[4-(6H-1,3,5,6-Tetraaza-as-indacen-1-yl)-piperidin-1-ylmethyl]benzonitrile | 8 | 1.77/A | 357.1 |
| 50 | 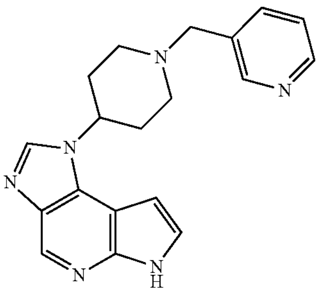 [SMILES: c1cncc(CN2CCC(n3cnc4cnc5[nH]ccc5c43)CC2)c1] | 1-(1-Pyridin-3-ylmethyl-piperidin-4-yl)-1,6-dihydro-1,3,5,6-tetraaza-as-indacene | 8 | 0.98/A | 333.1 |

TABLE 1-continued

| Ex | Structure | Name | Synthetic Method | LCMS RT (min)/Method | LCMS (ESI) m/z |
|---|---|---|---|---|---|
| 51 | 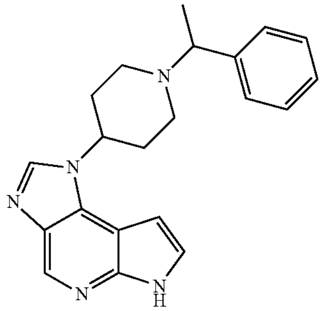 [SMILES: CC(c1ccccc1)N1CCC(n2cnc3cnc4[nH]ccc4c32)CC1] | 1-[1-(1-Phenyl-ethyl)-piperidin-4-yl]-1,6-dihydro-1,3,5,6-tetraaza-as-indacene | 11 | 2.05/A | 346.1 |
| 52 | 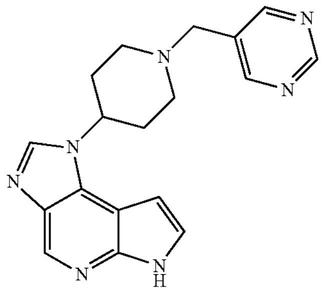 [SMILES: c1ncc(CN2CCC(n3cnc4cnc5[nH]ccc5c43)CC2)cn1] | 1-(1-Pyrimidin-5-ylmethyl-piperidin-4-yl)-1,6-dihydro-1,3,5,6-tetraaza-as-indacene | 8 | 0.94/A | 334.1 |
| 53 | 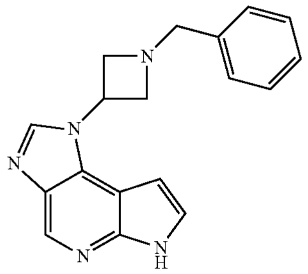 [SMILES: c1ccc(CN2CC(n3cnc4cnc5[nH]ccc5c43)C2)cc1] | 1-(1-Benzyl-azetidin-3-yl)-1,6-dihydro-1,3,5,6-tetraaza-as-indacene | 8 | 1.84/A | 304.1 |
| 54 | 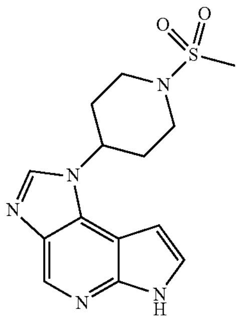 [SMILES: CS(=O)(=O)N1CCC(n2cnc3cnc4[nH]ccc4c32)CC1] | 1-(1-Methanesulfonyl-piperidin-4-yl)-1,6-dihydro-1,3,5,6-tetraaza-as-indacene | 9 | 2.02/A | 320.1 |
| 55 | 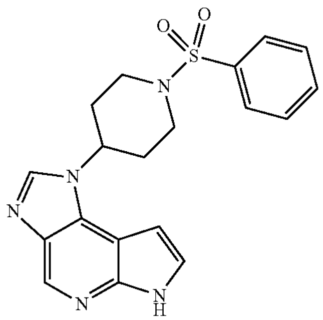 [SMILES: O=S(=O)(c1ccccc1)N1CCC(n2cnc3cnc4[nH]ccc4c32)CC1] | 1-(1-Benzenesulfonyl-piperidin-4-yl)-1,6-dihydro-1,3,5,6-tetraaza-as-indacene | 9 | 3.08/A | 382.1 |

TABLE 1-continued

| Ex | Structure | Name | Synthetic Method | LCMS RT (min)/Method | LCMS (ESI) m/z |
|---|---|---|---|---|---|
| 56 | 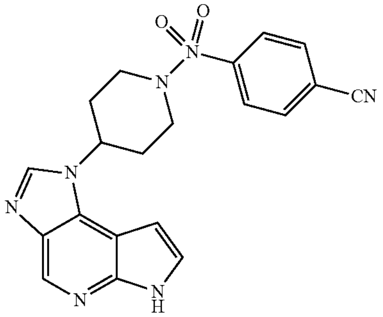 | 4-[4-(6H-1,3,5,6-Tetraaza-as-indacen-1-yl)-piperidine-1-sulfonyl]benzonitrile | 9 | 3.09/A | 407.1 |
| 57 | 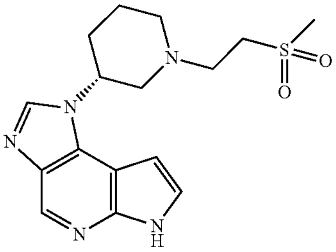 [SMILES: CS(=O)(=O)CCN1CCC[C@@H](n2cnc3cnc4[nH]ccc4c32)C1] | 1-[(R)-1-(2-Methanesulfonyl-ethyl)-piperidin-3-yl]-1,6-dihydro-1,3,5,6-tetraaza-as-indacene | 10 | 1.72/A | 348.1 |
| 58 | 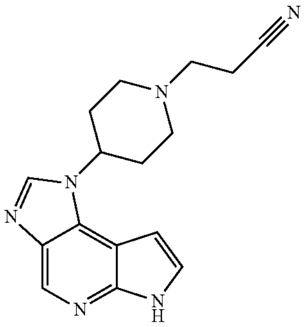 [SMILES: N#CCCN1CCC(n2cnc3cnc4[nH]ccc4c32)CC1] | 3-[4-(6H-1,3,5,6-Tetraaza-as-indacen-1-yl)-piperidin-1-yl]propionitrile | 10 | 0.87/A | 295.1 |
| 59 | 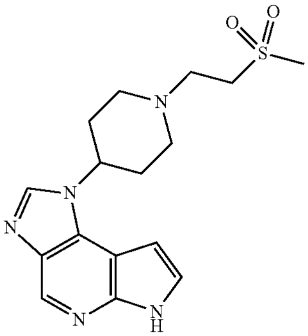 [SMILES: CS(=O)(=O)CCN1CCC(n2cnc3cnc4[nH]ccc4c32)CC1] | 1-[1-(2-Methanesulfonyl-ethyl)-piperidin-4-yl]-1,6-dihydro-1,3,5,6-tetraaza-as-indacene | 10 | 0.90/A | 348.1 |
| 60 | 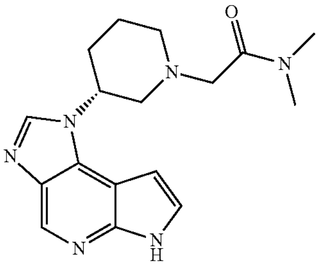 [SMILES: CN(C)C(=O)CN1CCC[C@@H](n2cnc3cnc4[nH]ccc4c32)C1] | N,N-Dimethyl-2-[(R)-3-(6H-1,3,5,6-tetraaza-as-indacen-1-yl)-piperidin-1-yl]acetamide | 11 | 1.23/A | 327.1 |

TABLE 1-continued
| Ex | Structure | Name | Synthetic Method | LCMS RT (min)/Method | LCMS (ESI) m/z |
|---|---|---|---|---|---|
| 61 | 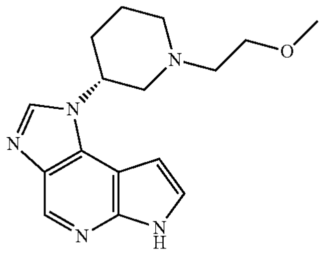 [SMILES: COCCN1CCC[C@@H](n2cnc3cnc4[nH]ccc4c32)C1] | 1-[(R)-1-(2-Methoxy-ethyl)-piperidin-3-yl]-1,6-dihydro-1,3,5,6-tetraaza-as-indacene | 11 | 1.06/A | 300.1 |
| 62 | 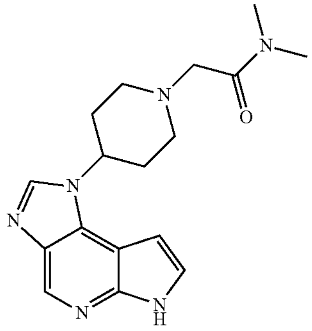 [SMILES: CN(C)C(=O)CN1CCC(n2cnc3cnc4[nH]ccc4c32)CC1] | N,N-Dimethyl-2-[4-(6H-1,3,5,6-tetraaza-as-indacen-1-yl)-piperidin-1-yl]acetamide | 11 | 0.96/A | 327.1 |
| 63 | 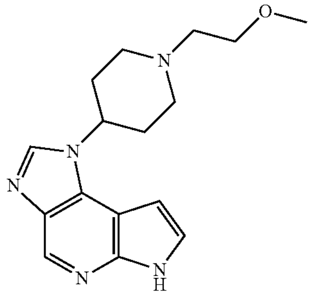 [SMILES: COCCN1CCC(n2cnc3cnc4[nH]ccc4c32)CC1] | 1-[1-(2-Methoxy-ethyl)-piperidin-4-yl]-1,6-dihydro-1,3,5,6-tetraaza-as-indacene | 11 | 0.96/A | 300.1 |
| 64 | 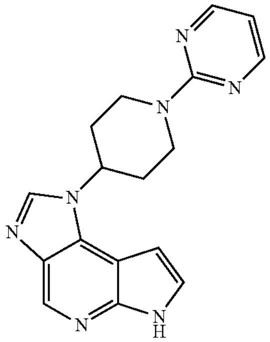 [SMILES: c1cnc(N2CCC(n3cnc4cnc5[nH]ccc5c43)CC2)nc1] | 1-(1-Pyrimidin-2-yl-piperidin-4-yl)-1,6-dihydro-1,3,5,6-tetraaza-as-indacene | 13 | 2.52/A | 320.1 |

TABLE 1-continued

| Ex | Structure | Name | Synthetic Method | LCMS RT (min)/Method | LCMS (ESI) m/z |
|---|---|---|---|---|---|
| 65 | 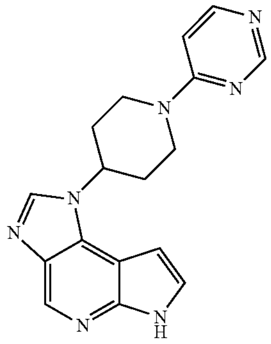 [SMILES: c1cc(N2CCC(n3cnc4cnc5[nH]ccc5c43)CC2)ncn1] | 1-(1-Pyrimidin-4-yl-piperidin-4-yl)-1,6-dihydro-1,3,5,6-tetraaza-as-indacene | 14 | 1.47/A | 320.1 |
| 66 | 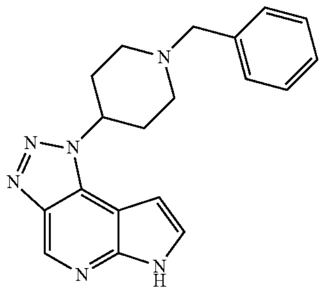 [SMILES: c1ccc(CN2CCC(n3nnc4cnc5[nH]ccc5c43)CC2)cc1] | 1-(1-Benzyl-piperidin-4-yl)-1,6-dihydro-1,2,3,5,6-pentaaza-as-indacene | 18 | 2.39/A | 333.1 |
| 67 | 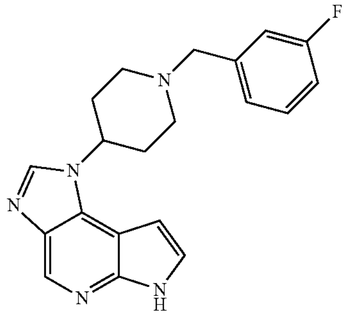 [SMILES: Fc1cccc(CN2CCC(n3cnc4cnc5[nH]ccc5c43)CC2)c1] | 1-[1-(3-Fluoro-benzyl)-piperidin-4-yl]-1,6-dihydro-1,3,5,6-tetraaza-as-indacene | 8 | 1.98/A | 350.0 |
| 68 | 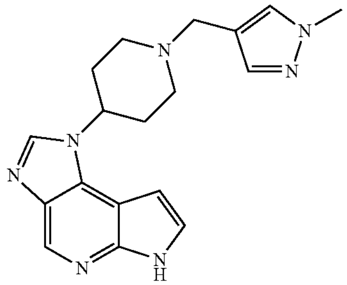 [SMILES: Cn1cc(CN2CCC(n3cnc4cnc5[nH]ccc5c43)CC2)cn1] | 1-[1-(1-Methyl-1H-pyrazol-4-yl)-piperidin-4-yl]-1,6-dihydro-1,3,5,6-tetraaza-as-indacene | 8 | 1.00/A | 336.1 |
| 69 | 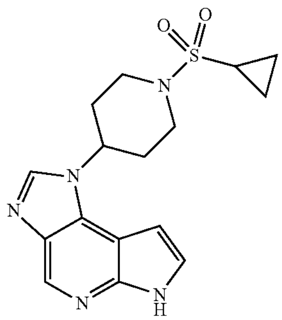 [SMILES: O=S(=O)(C1CC1)N1CCC(n2cnc3cnc4[nH]ccc4c32)CC1] | 1-(1-Cyclopropanesulfonyl-piperidin-4-yl]-1,6-dihydro-1,3,5,6-tetraaza-as-indacene | 9 | 2.41/A | 346.1 |

TABLE 1-continued
| Ex | Structure | Name | Synthetic Method | LCMS RT (min)/Method | LCMS (ESI) m/z |
|---|---|---|---|---|---|
| 70 | 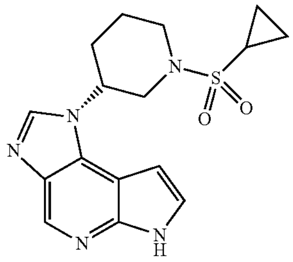 | (R)-1-(1-Cyclopropanesulfonyl-piperidin-3-yl]-1,6-dihydro-1,3,5,6-tetraaza-as-indacene | 9 | 2.50/A | 346.1 |
| 71 | 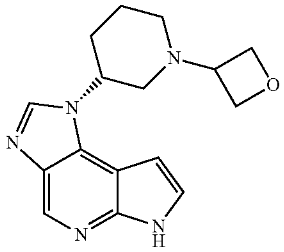 | (R)-1-(1-Oxetan-3-yl-piperidin-3-yl]-1,6-dihydro-1,3,5,6-tetraaza-as-indacene | 8 | 1.62/A | 298.1 |
| 72 | 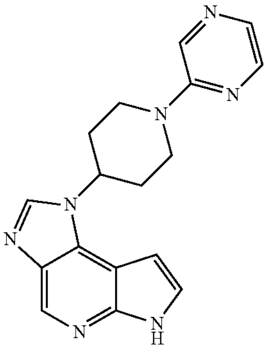 [SMILES: c1cnc(N2CCC(n3cnc4cnc5[nH]ccc5c43)CC2)cn1] | 1-(1-Pyrazin-2-yl-piperidin-4-yl]-1,6-dihydro-1,3,5,6-tetraaza-as-indacene | 13 | 2.39/A | 320.1 |
| 73 | 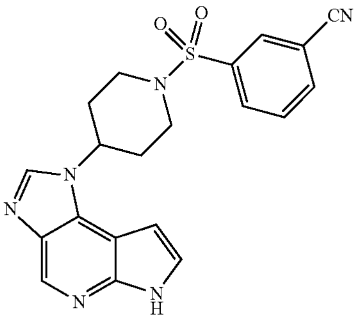 [SMILES: N#Cc1cccc(S(=O)(=O)N2CCC(n3cnc4cnc5[nH]ccc5c43)CC2)c1] | 3-[4-(6H-1,3,5,6-Tetraaza-as-indacen-1-yl)-piperidine-1-sulfonyl]benzonitrile | 9 | 3.06/A | 407.1 |

TABLE 1-continued
| Ex | Structure | Name | Synthetic Method | LCMS RT (min)/Method | LCMS (ESI) m/z |
| --- | --- | --- | --- | --- | --- |
| 74 | 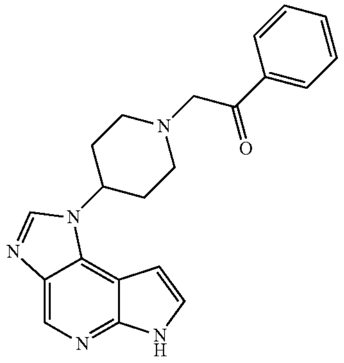 [SMILES: O=C(CN1CCC(n2cnc3cnc4[nH]ccc4c32)CC1)c1ccccc1] | 1-Phenyl-2-[4-(6H-1,3,5,6-tetraaza-as-indacen-1-y])-piperidin-1-yl]ethanone | 11 | 1.91/A | 360.1 |
| 75 | 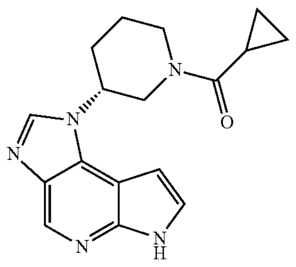 [SMILES: O=C(C1CC1)N1CCC[C@@H](n2cnc3cnc4[nH]ccc4c32)C1] | Cyclopropyl-[(R)-3-(6H-1,3,5,6-tetraaza-as-indacen-1-yl)-piperidin-1-yl]methanone | 7 | 2.33/A | 310.1 |
| 76 | 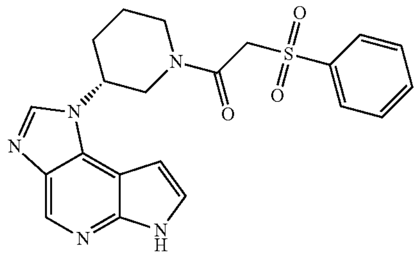 [SMILES: O=C(CS(=O)(=O)c1ccccc1)N1CCC[C@@H](n2cnc3cnc4[nH]ccc4c32)C1] | 2-Benzenesulfonyl-1-[(R)-3-(6H-1,3,5,6-tetraaza-as-indacen-1-yl)-piperidin-1-yl]ethanone | 7 | 2.63/A | 424.1 |
| 77 | 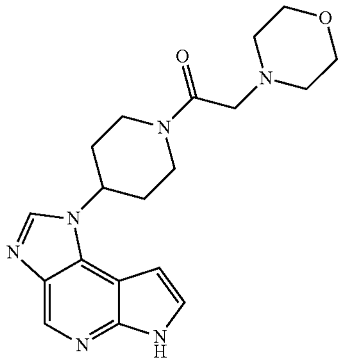 [SMILES: O=C(CN1CCOCC1)N1CCC(n2cnc3cnc4[nH]ccc4c32)CC1] | 2-Morpholin-4-yl-1-[4-(6H-1,3,5,6-tetraaza-as-indacen-1-yl)-piperidin-1-yl]ethanone | 7 | 1.06/A | 369.1 |

TABLE 1-continued

| Ex | Structure | Name | Synthetic Method | LCMS RT (min)/Method | LCMS (ESI) m/z |
|---|---|---|---|---|---|
| 78 | 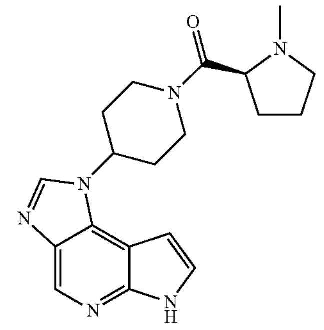 [SMILES: CN1CCC[C@H]1C(=O)N1CCC(n2cnc3cnc4[nH]ccc4c32)CC1] | ((S)-1-Methyl-pyrrolidin-2-yl)-[4-(6H-1,3,5,6-tetraaza-as-indacen-1-yl)-piperidin-1-yl]methanone | 7 | 1.16/A | 353.1 |
| 79 | 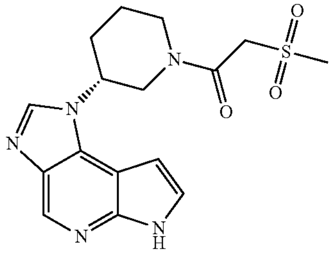 [SMILES: CS(=O)(=O)CC(=O)N1CCC[C@@H](n2cnc3cnc4[nH]ccc4c32)C1] | 2-Methanesulfonyl-1-[(R)-3-(6H-1,3,5,6-tetraaza-as-indacen-1-yl)-piperidin-1-yl]ethanone | 7 | 1.91/A | 362.0 |
| 80 | 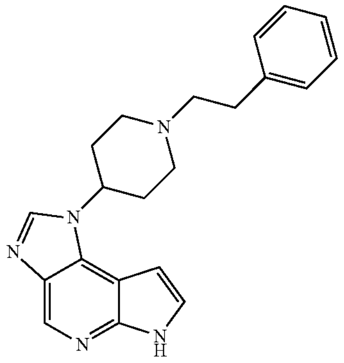 [SMILES: c1ccc(CCN2CCC(n3cnc4cnc5[nH]ccc5c43)CC2)cc1] | 1-(1-Phenethyl-piperidin-4-yl)-1,6-dihydro-1,3,5,6-tetraaza-as-indacene | 8 | 2.10/A | 346.1 |
| 81 | 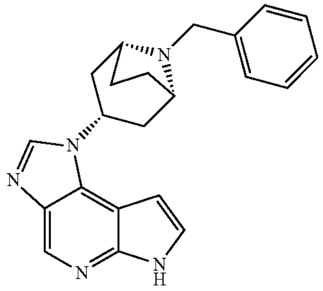 [SMILES: c1ccc(CN2[C@@H]3CC[C@H]2C[C@H](n2cnc4cnc5[nH]ccc5c42)C3)cc1] | 1-((1S),3(S),5(R))-8-Benzyl-8-aza-bicyclo[3.2.1]oct-3-yl)-1,6-dihydro-1,3,5,6-tetraaza-as-indacene | 1 | 2.03/A | 358.1 |
| 82 | 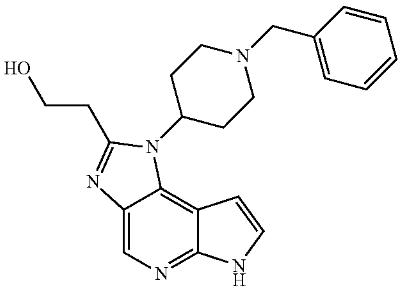 [SMILES: OCCc1nc2cnc3[nH]ccc3c2n1C1CCN(Cc2ccccc2)CC1] | 2-[1-(1-Benzyl-piperidin-4-yl)-2-methyl-1,6-dihydro-1,3,5,6-tetraaza-as-indacen-2-yl]ethanol | 15 | 1.81/A | 376.1 |

TABLE 1-continued
| Ex | Structure | Name | Synthetic Method | LCMS RT (min)/Method | LCMS (ESI) m/z |
|---|---|---|---|---|---|
| 83 | 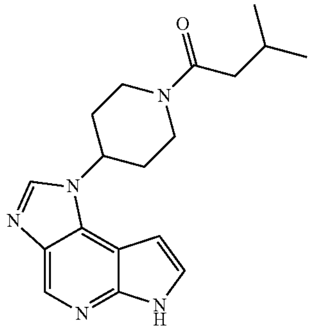 [SMILES: CC(C)CC(=O)N1CCC(n2cnc3cnc4[nH]ccc4c32)CC1] | 3-Methyl-1-[4-(6H-1,3.5,6-tetraaza-as-indacen-1-yl)-piperidin-1-yl]-butan-1-one | 6 | 2.59/A | 326.1 |
| 84 | 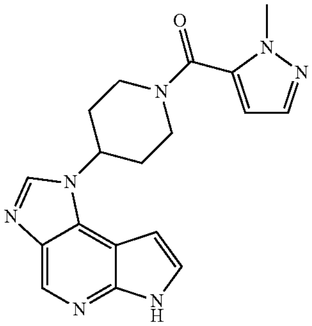 [SMILES: Cn1nccc1C(=O)N1CCC(n2cnc3cnc4[nH]ccc4c32)CC1] | (2-Methyl-2H-pyrazol-3-yl)-[4-(6H-1,3,5,6-tetraaza-as-indacen-1-yl)-piperidin-1-yl]methanone | 6 | 2.11/A | 350.1 |
| 85 | 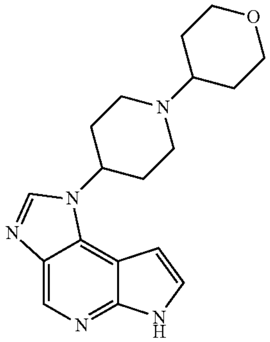 [SMILES: c1cc2c(ncc3ncn(C4CCN(C5CCOCC5)CC4)c32)[nH]1] | 1-[-(Tetrahydro-pyran-4-yl)-piperidin-4-yl]-1,6-dihydro-1,3,5,6-tetraaza-as-indacene | 8 | 0.91/A | 326.1 |
| 86 | 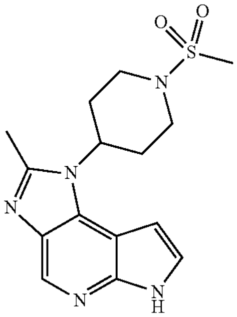 | 1-(1-Methanesulfonyl-piperidin-4-yl)-2-methyl-1,6-dihydro-1,3,5,6-tetraaza-as-indacene | 9 | 1.97/A | 334.1 |

TABLE 1-continued

| Ex | Structure | Name | Synthetic Method | LCMS RT (min)/Method | LCMS (ESI) m/z |
|---|---|---|---|---|---|
| 87 | 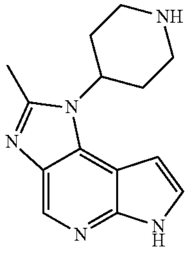 [SMILES: Cc1nc2cnc3[nH]ccc3c2n1C1CCNCC1] | 2-Methyl-1-piperidin-4-yl-1,6-dihydro-1,3,5,6-tetraaza-as-indacene | 2 | 0.68/A | 256.1 |
| 88 | 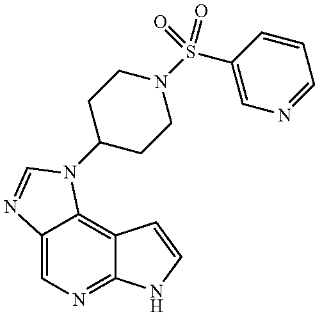 [SMILES: O=S(=O)(c1cccnc1)N1CCC(n2cnc3cnc4[nH]ccc4c32)CC1] | 1-[1-(Pyridine-3-sulfonyl)-piperidin-4-yl]-1,6-dihydro-1,3,5,6-tetraaza-as-indacene | 9 | 2.49/A | 383.1 |
| 89 | 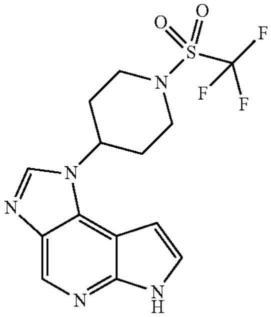 [SMILES: O=S(=O)(N1CCC(n2cnc3cnc4[nH]ccc4c32)CC1)C(F)(F)F] | 1-(1-Trifluoromethanesulfonyl-piperidin-4-yl)-1,6-dihydro-1,3,5,6-tetraaza-as-indacene | 9 | 3.30/A | 374.0 |
| 90 | 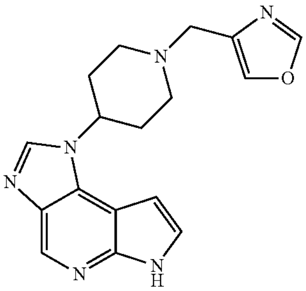 [SMILES: c1cc2c(ncc3ncn(C4CCN(Cc5cocn5)CC4)c32)[nH]1] | 1-(1-Oxazol-4-ylmethyl-piperidin-4-yl)-1,6-dihydro-1,3,5,6-tetraaza-as-indacene | 8 | 0.89/A | 323.0 |
| 91 | 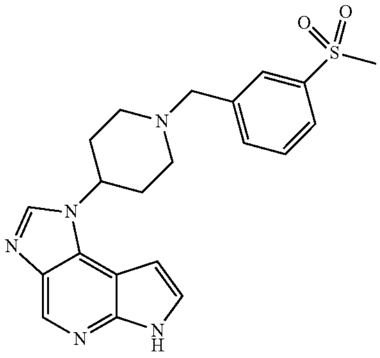 [SMILES: CS(=O)(=O)c1cccc(CN2CCC(n3cnc4cnc5[nH]ccc5c43)CC2)c1] | 1-[1-(3-Methanesulfonyl-benzyl)-piperidin-4-yl]-1,6-dihydro-1,3,5,6-tetraaza-as-indacene | 8 | 1.65/A | 410.0 |

TABLE 1-continued
| Ex | Structure | Name | Synthetic Method | LCMS RT (min)/Method | LCMS (ESI) m/z |
|---|---|---|---|---|---|
| 92 | 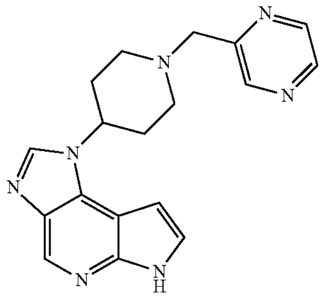 [SMILES: c1cnc(CN2CCC(n3cnc4cnc5[nH]ccc5c43)CC2)cn1] | 1-(1-Pyrazin-2-ylmethyl-piperidin-4-yl)-1,6-dihydro-1,3,5,6-tetraaza-as-indacene | 8 | 1.03/A | 334.1 |
| 93 | 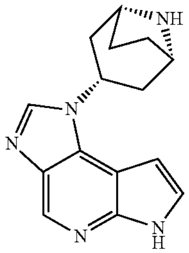 [SMILES: c1cc2c(ncc3ncn([C@@H]4C[C@H]5CC[C@@H](C4)N5)c32)[nH]1] | (1S,3S,5R)-1-(8-aza-bicyclo[3.2.1]oct-3-yl)-1,6-dihydro-1,3,5,6-tetraaza-as-indacene | 2 | 0.86/A | 268.1 |
| 94 | 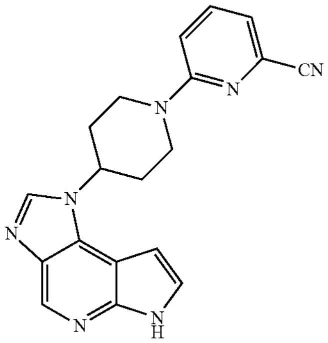 [SMILES: N#Cc1cccc(N2CCC(n3cnc4cnc5[nH]ccc5c43)CC2)n1] | 4-(6H-1,3,5,6-Tetraaza-as-indacen-1-yl)-3,4,5,6-tetrahydro-2H-[1,2']bipyridinyl-6'-carbonitrile | 13 | 3.07/A | 334.1 |
| 95 | 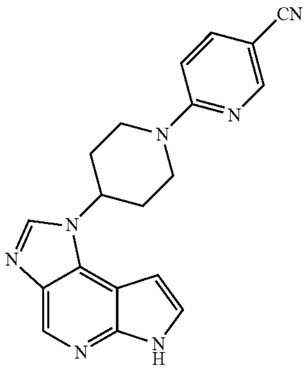 [SMILES: N#Cc1ccc(N2CCC(n3cnc4cnc5[nH]ccc5c43)CC2)nc1] | 4-(6H-1,3,5,6-Tetraaza-as-indacen-1-yl)-3,4,5,6-tetrahydro-2H-[1,2']bipyridinyl-5'-carbonitrile | 13 | 2.85/A | 334.1 |

TABLE 1-continued

| Ex | Structure | Name | Synthetic Method | LCMS RT (min)/Method | LCMS (ESI) m/z |
|---|---|---|---|---|---|
| 96 | 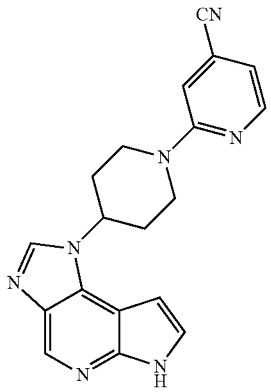 [SMILES: N#Cc1ccnc(N2CCC(n3cnc4cnc5[nH]ccc5c43)CC2)c1] | 4-(6H-1,3,5,6-Tetraaza-as-indacen-1-yl)-3,4,5,6-tetrahydro-2H-[1,2']bipyridinyl-4'-carbonitrile | 13 | 2.97/A | 334.1 |
| 97 | 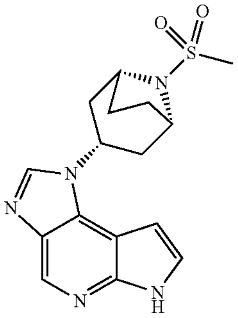 [SMILES: CS(=O)(=O)N1[C@@H]2CC[C@H]1C[C@H](n1cnc3cnc4[nH]ccc4c31)C2] | 1-((1S,3S,5R)-8-Methanesulfonyl-8-aza-bicyclo[3.2.1]oct-3-yl)-1,6-dihydro-1,3,5,6-tetraaza-as-indacene | 9 | 2.21/A | 346.1 |
| 98 | 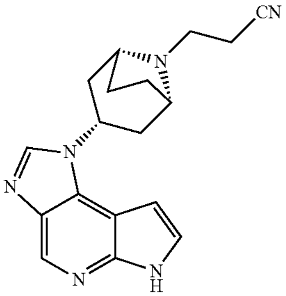 [SMILES: N#CCCN1[C@@H]2CC[C@H]1C[C@H](n1cnc3cnc4[nH]ccc4c31)C2] | 3-[(1S,3S,5R)-3-(6H-1,3,5,6-Tetraaza-as-indacen-1-yl)-8-aza-bicyclo[3.2.1]oct-8-yl]propionitrile | 10 | 1.02/A | 321.1 |
| 99 | 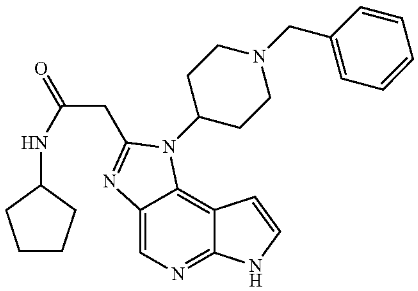 [SMILES: O=C(Cc1nc2cnc3[nH]ccc3c2n1C1CCN(Cc2ccccc2)CC1)NC1CCCC1] | 2-[1-(1-Benzyl-piperidin-4-yl)-1,6-dihydro-1,3,5,6-tetraaza-as-indacen-2-yl]-N-cyclopentyl-acetamide | 23 | 2.54/A | 457.2 |

TABLE 1-continued

| Ex | Structure | Name | Synthetic Method | LCMS RT (min)/Method | LCMS (ESI) m/z |
|---|---|---|---|---|---|
| 100 | 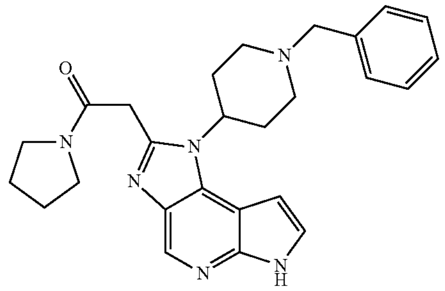 [SMILES: O=C(Cc1nc2cnc3[nH]ccc3c2n1C1CCN(Cc2ccccc2)CC1)N1CCCC1] | 2-[1-(1-Benzyl-piperidin-4-yl)-1,6-dihydro-1,3,5,6-tetraaza-as-indacen-2-yl]-1-pyrrolidin-1-yl-ethanone | 23 | 2.21/A | 443.1 |
| 101 | 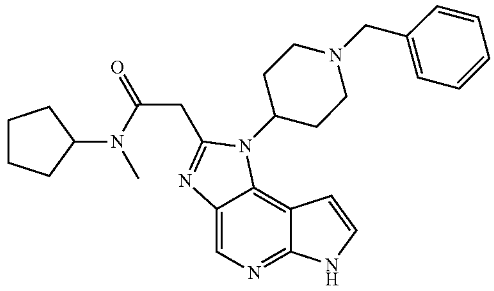 [SMILES: CN(C(=O)Cc1nc2cnc3[nH]ccc3c2n1C1CCN(Cc2ccccc2)CC1)C1CCCC1] | 2-[1-(1-Benzyl-piperidin-4-yl)-1,6-dihydro-1,3,5,6-tetraaza-as-indacen-2-yl]-N-cyclopentyl-N-methyl-acetamide | 23 | 2.67/A | 471.1 |
| 102 | 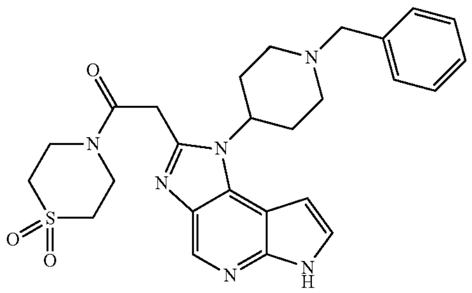 [SMILES: O=C(Cc1nc2cnc3[nH]ccc3c2n1C1CCN(Cc2ccccc2)CC1)N1CCS(=O)(=O)CC1] | 2-[1-(1-Benzyl-piperidin-4-yl)-1,6-dihydro-1,3,5,6-tetraaza-as-indacen-2-yl]-1-(1,1-dioxo-1λ*6*thiomorpholin-4-yl)ethanone | 23 | 2.09/A | 507.1 |
| 103 | 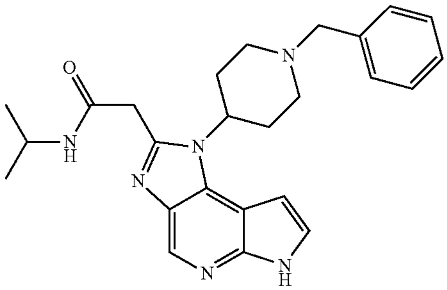 [SMILES: CC(C)NC(=O)Cc1nc2cnc3[nH]ccc3c2n1C1CCN(Cc2ccccc2)CC1] | 2-[1-(1-Benzyl-piperidin-4-yl)-1,6-dihydro-1,3,5,6-tetraaza-as-indacen-2-yl]-N-isopropylacetamide | 23 | 2.30/A | 431.1 |
| 104 | 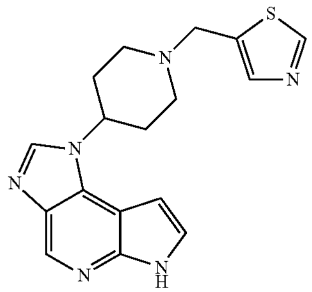 [SMILES: c1cc2c(ncc3ncn(C4CCN(Cc5cncs5)CC4)c32)[nH]1] | 1-(1-Thiazol-5-ylmethyl-piperidin-4-yl)-1,6-dihydro-1,3,5,6-tetraaza-as-indacene | 8 | 1.04/A | 339.1 |

TABLE 1-continued
| Ex | Structure | Name | Synthetic Method | LCMS RT (min)/Method | LCMS (ESI) m/z |
|---|---|---|---|---|---|
| 105 | 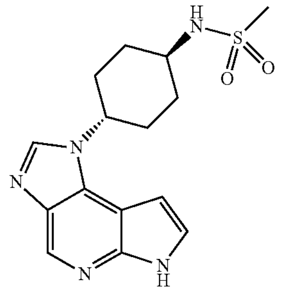 [SMILES: CS(=O)(=O)N[C@H]1CC[C@H](n2cnc3cnc4[nH]ccc4c32)CC1] | Trans N-[4-(6H-1,3,5,6-tetraaza-as-indacen-1-yl)-cyclohexyl]-methanesulfonamide | 9 | 1.95/A | 334.0 |
| 106 | 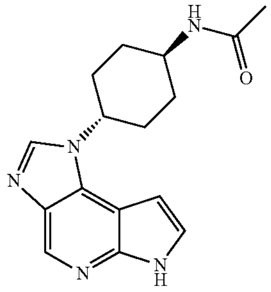 [SMILES: CC(=O)N[C@H]1CC[C@H](n2cnc3cnc4[nH]ccc4c32)CC1] | Trans N-[4-(6H-1,3,5,6-tetraaza-as-indacen-1-yl)-cyclohexyl]acetamide | 6 | 1.85/A | 298.1 |
| 107 | 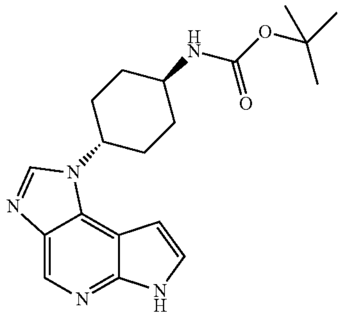 [SMILES: CC(C)(C)OC(=O)N[C@H]1CC[C@H](n2cnc3cnc4[nH]ccc4c32)CC1] | Trans [4-(6H-1,3,5,6-tetraaza-as-indacen-1-yl)-cyclohexyl] -carbamic acid tert-butyl ester | 3 | 3.06/A | 356.1 |
| 108 | 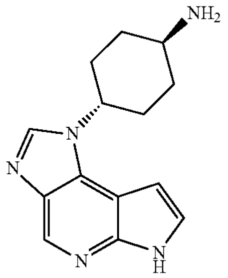 [SMILES: N[C@H]1CC[C@H](n2cnc3cnc4[nH]ccc4c32)CC1] | Trans 4-(6H-1,3,5,6-tetraaza-as-indacen-1-yl)-cyclohexylamine | 4 | 0.75/A | 256.1 |

Example 109

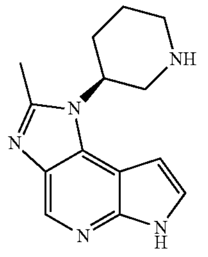 [SMILES: Cc1nc2cnc3[nH]ccc3c2n1[C@H]1CCCNC1]

2-Methyl-1-(S)-piperidin-3-yl-1,6-dihydro-1,2,3,5,6-tetraaza-as-indacene (S)-3-(1-Benzenesulfonyl-5-nitro-1H-pyrrolo[2,3-b]pyridin-4-ylamino)-piperidine-1-carboxylic acid tert-butyl ester A mixture of 1-benzenesulfonyl-4-chloro-5-nitro-1H-pyrrolo[2,3-b]pyridine (0.6769 g, 2.004 mmol), (S)-3-amino-1-Boc-piperidine (0.4269 g, 2.132 mmol), and diisopropylethylamine (0.45 mL, 2.6 mmol) in propan-2-ol (12 ml) was heated in a microwave reactor at 110° C. for 20 minutes. The solvent was evaporated in vacuo and then purified by column chromatography on silica gel (gradient: 0 to 30% ethyl acetate in heptanes) affording 853.7 mg (85%) of (S)-3-(1-Benzenesulfonyl-5-nitro-1H-pyrrolo[2,3-b]pyridin-4-ylamino)-piperidine-1-carboxylic acid tert-butyl ester. LCMS (Method F, ESI): RT=1.19 min, m+H=502.3.

6-Benzenesulfonyl-2-methyl-1-(S)-piperidin-3-yl-1,6-dihydro-1,2,3,5,6-tetraaza-as-indacene To a mixture of (S)-3-(1-Benzenesulfonyl-5-nitro-1H-pyrrolo[2,3-b]pyridin-4-ylamino)-piperidine-1-carboxylic acid tert-butyl ester (0.3036 g, 0.6053 mmol) and iron powder (0.3399 g, 6.086 mmol) was added acetic acid (4 mL) and 4.0M of Hydrogen chloride in 1,4-dioxane (0.80 mL, 3.2 mmol). The reaction was stirred in a sealed vial at 100° C. for 20 hours. The solids were collected by filtration, and then re-dissolved in concentrated aqueous HCl (2 mL) and acetic acid (2 mL). This mixture was heated in a microwave reactor at 120° C. for 30 minutes and then kept at 100° C. in an oil bath for 15 hours. The reaction mixture was neutralized with saturated aqueous sodium bicarbonate, and extracted three times with dichloromethane. The combined organic extracts were dried over magnesium sulphate, filtered, and evaporated in vacuo to yield 68.5 mg (29%) of 6-Benzenesulfonyl-2-methyl-1-(S)-piperidin-3-yl-1,6-dihydro-1,2,3,5,6-tetraaza-as-indacene, which was carried forward without purification. LCMS (Method F, ESI): RT=0.53 min, m+H=396.2.

2-Methyl-1-(S)-piperidin-3-yl-1,6-dihydro-1,2,3,5,6-tetraaza-as-indacene

To a solution of 6-Benzenesulfonyl-2-methyl-1-(S)-piperidin-3-yl-1,6-dihydro-1,2,3,5,6-tetraaza-as-indacene (68.5 mg, 0.173 mmol) in methanol (2 mL) was added 5.0 M of sodium hydroxide in water (0.20 mL, 1.0 mmol). The reaction mixture was stirred at 50° C. for 1.5 hours, and then the solvent evaporated in vacuo. The crude residue was partitioned between dichloromethane and saturated aqueous sodium bicarbonate, and the aqueous layer extracted four times with dichloromethane. The combined organic extracts were dried over magnesium sulphate, filtered, and evaporated in vacuo. Purification by preparative HPLC yielded 6.4 mg (14%) of 2-Methyl-1-(S)-piperidin-3-yl-1,6-dihydro-1,2,3,5,6-tetraaza-as-indacene. LCMS (Method C, ESI): RT=2.05 min, m+H=256.1; $^1$H NMR (400 MHz, DMSO-$d_6$) δ: 11.76 (s, 1H), 8.45 (s, 1H), 7.45 (t, J=3.0 Hz, 1H), 6.86-6.76 (m, 1H), 4.49 (s, 1H), 3.10-2.92 (m, 2H), 2.74-2.65 (m, 1H), 2.63 (s, 3H), 2.45-2.30 (m, 2H), 2.01 (d, J=12.1 Hz, 1H), 1.85 (d, J=12.3 Hz, 1H), 1.77-1.60 (m, 1H).

Example 110 and 110a

Single Enantiomers

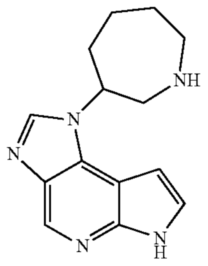 [SMILES: c1cc2c(ncc3ncn(C4CCCCNC4)c32)[nH]1]

1-Azepan-3-yl-1,6-dihydro-1,2,3,5,6-tetraaza-as-indacene 3-(1-Benzenesulfonyl-5-nitro-1H-pyrrolo[2,3-b]pyridin-4-ylamino)-azepane-1-carboxylic acid tert-butyl ester A mixture of 1-benzenesulfonyl-4-chloro-5-nitro-1H-pyrrolo[2,3-b]pyridine (0.6981 g, 2.067 mmol), 3-Amino-azepane-1-carboxylic acid tert-butyl ester (0.4752 g, 2.217 mmol), and diisopropylethylamine (0.50 mL, 2.9 mmol) in propan-2-ol (12 mL) was heated in a microwave reactor at 120° C. for 20 minutes. The solvent was evaporated in vacuo and then purified by column chromatography on silica gel (gradient: 0 to 30% ethyl acetate in heptanes) affording 0.8869 g (83%) of 3-(1-Benzenesulfonyl-5-nitro-1H-pyrrolo[2,3-b]pyridin-4-ylamino)-azepane-1-carboxylic acid tert-butyl ester. LCMS (Method E, ESI): RT=2.07 min, m+H=516.2.

3-(6-Benzenesulfonyl-6H-1,2,3,5,6-tetraaza-as-indacen-1-yl)-azepane-1-carbaldehyde A mixture of 3-(1-Benzenesulfonyl-5-nitro-1H-pyrrolo[2,3-b]pyridin-4-ylamino)-azepane-1-carboxylic acid tert-butyl ester (470.9 mg, 0.9133 mmol), iron powder (0.5187 g, 9.288 mmol), ammonium chloride (0.4985 g, 9.319 mmol), formic acid (8 mL, 200 mmol) and 1-butanol (8 mL, 90 mmol) was stirred at 100° C. for two hours. After cooling to room temperature, the reaction mixture was filtered through Celite® to remove iron and inorganic solids, rinsing with ethanol. The filtrate was neutralized with saturated aqueous sodium bicarbonate, and extracted three times with dichloromethane. The combined organic extracts were dried over magnesium sulphate, filtered, and evaporated in vacuo to yield 371.3 mg of 3-(6-Benzenesulfonyl-6H-1,2,3,5,6-tetraaza-as-indacen-1- yl)-azepane-1-carb aldehyde which was carried forward without purification. LCMS (Method F, ESI): RT=0.56 min, m+H=396.2.

1-Azepan-3-yl-1,6-dihydro-1,2,3,5,6-tetraaza-as-indacene

To a solution of 3-(6-Benzenesulfonyl-6H-1,2,3,5,6-tetraaza-as-indacen-1-yl)-azepane-1-carbaldehyde (0.913 mmol) in methanol (8 mL) was added 10.0M of sodium hydroxide in water (1.0 mL, 10 mmol). The reaction mixture was stirred at 50° C. for 20 hours. The methanol was evaporated under vacuum, and the crude residue partitioned between dichloromethane and saturated aqueous sodium bicarbonate, and the aqueous layer extracted four times with dichloromethane. The combined organic extracts were dried over magnesium sulphate, filtered, and evaporated in vacuo. Purification by preparative HPLC followed by chiral SFC yielded the separated enantiomers of 1-Azepan-3-yl-1,6-dihydro-1,2,3,5,6-tetraaza-as-indacene (13.5 mg and 15.7 mg). First eluting enantiomer: LCMS (Method C, ESI): RT=2.13 min, m+H=256.1; $^1$H NMR (400 MHz, DMSO-$d_6$) δ: 11.79 (s, 1H), 8.55 (s, 1H), 8.35 (s, 1H), 7.44 (t, J=3.0 Hz, 1H), 6.79 (dd, J=3.3, 1.9 Hz, 1H), 4.80 (dq, J=10.1, 5.2 Hz, 1H), 3.26-3.22 (m, 1H), 3.22-3.11 (m, 2H), 2.98 (dt, J=8.9, 4.7 Hz, 1H), 2.85-2.71 (m, 1H), 2.21 (dd, J=13.6, 6.6 Hz, 1H), 2.12 (t, J=10.4 Hz, 1H), 1.86-1.73 (m, 2H), 1.73-1.60 (m, 2H).
Second eluting enantiomer: LCMS (Method C, ESI): RT=2.17 min, m+H=256.1; $^1$H NMR (400 MHz, DMSO-$d_6$) δ: 11.79 (s, 1H), 8.55 (s, 1H), 8.35 (s, 1H), 7.44 (t, J=3.0 Hz, 1H), 6.79 (dd, J=3.3, 1.9 Hz, 1H), 4.79 (dq, J=10.1, 5.2 Hz, 1H), 3.24 (d, J=4.9 Hz, 1H), 3.22-3.12 (m, 2H), 2.98 (dt, J=12.2, 4.6 Hz, 1H), 2.87-2.73 (m, 1H), 2.29-2.16 (m, 1H), 2.10 (dd, J=21.5, 11.0 Hz, 1H), 1.79 (d, J=6.8 Hz, 2H), 1.72-1.60 (m, 2H).

Example 111

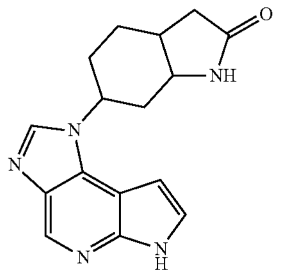

racemic, cis 6-(6H-1,2,3,5,6-Tetraaza-as-indacen-1-yl)-octahydro-indol-2-one

N-(2,4-Dimethoxy-benzyl)-2-chloro-acetamide

To a solution of 2,4-dimethoxybenzylamine (1.50 mL, 10.0 mmol) and triethylamine (2.00 mL, 14.3 mmol) in tetrahydrofuran (20 mL) at 0° C. was added chloroacetyl chloride (0.80 mL, 10 mmol). The reaction was then stirred at 0° C. for three hours. The crude reaction mixture was partitioned between ethyl acetate and water, and the organic layer dried over brine and magnesium sulfate, filtered, and evaporated in vacuo to yield 2.2074 g (91%) of N-(2,4-Dimethoxy-benzyl)-2-chloro-acetamide which was carried forward without purification. LCMS (Method E, ESI): RT=1.43 min, m+H=244.2

N-(2,4-Dimethoxy-benzyl)-2-iodo-acetamide

To a solution of N-(2,4-Dimethoxy-benzyl)-2-chloro-acetamide (2.2074 g, 9.0584 mmol) in acetone (20 mL) was added sodium iodide (4.121 g, 27.49 mmol). The reaction mixture was stirred at 50° C. for two hours, and then filtered to remove inorganic salts. The filtrate was evaporated in vacuo, re-suspended in ethyl acetate, and filtered again. The filtrate was evaporated in vacuo to provide 4.01 g of N-(2,4-Dimethoxy-benzyl)-2-iodo-acetamide, which was carried forward without purification. LCMS (Method E, ESI): RT=1.46 min, m+H=336.2; $^1$H NMR (400 MHz, $CDCl_3$) δ: 7.17 (d, J=8.2, 1H), 6.55 (s, 1H), 6.47 (d, J=2.2, 1H), 6.44 (dd, J=8.2, 2.3, 1H), 4.36 (d, J=5.8, 2H), 3.85 (s, 3H), 3.80 (s, 3H), 3.68 (s, 2H).

N-(2,4-Dimethoxy-benzyl)-2-(4-ethoxy-2-oxo-cyclohex-3-enyl)-acetamide

To a −78° C. solution of 1.0 M lithium hexamethyldisilazide in THF (0.90 mL) in 4.0 mL THF was added 3-ethoxy-2-cyclohexen-1-one (0.100 mL, 0.687 mmol). After stirring at −78° C. for 40 minutes, 1,3-dimethyl-3,4,5,6-tetrahydro-2(1H)-pyrimidinone (1.0 mL, 8.3 mmol) was added. After 5 minutes, N-(2,4-Dimethoxy-benzyl)-2-iodo-acetamide (0.342 g, 1.02 mmol) was added as a solution in 2.0 mL THF. The reaction was kept at −78° C. for one hour, and then quenched with water and partitioned between ethyl acetate and water. The organic layer was dried over magnesium sulfate, filtered, and evaporated in vacuo. Purification by column chromatography on silica gel (gradient: 0 to 100% ethyl acetate in dichloromethane) yielded 133.5 mg (56%) of N-(2,4-dimethoxy-benzyl)-2-(4-ethoxy-2-oxo-cyclohex-3-enyl)-acetamide. LCMS (Method E, ESI): RT=1.57 min, m+H=336.2; $^1$H NMR (400 MHz, $CDCl_3$) δ: 7.17 (d, J=8.1 Hz, 1H), 6.47-6.39 (m, 2H), 6.35 (s, 1H), 5.32 (s, 1H), 4.38-4.30 (m, 2H), 3.90 (dd, J=13.5, 6.5 Hz, 2H), 3.82 (s, 3H), 3.79 (s, 3H), 2.77 (dd, J=14.3, 5.6 Hz, 1H), 2.68 (dt, J=10.6, 5.5 Hz, 1H), 2.59-2.48 (m, 1H), 2.37 (ddd, J=12.0, 6.3, 2.9 Hz, 1H), 2.17 (ddd, J=13.1, 11.2, 4.6 Hz, 2H), 1.72 (ddd, J=25.0, 12.6, 4.9 Hz, 1H), 1.36 (t, J=7.0 Hz, 3H).

N-(2,4-Dimethoxy-benzyl)-2-(4-oxo-cyclohex-2-enyl)-acetamide

To a solution of N-(2,4-Dimethoxy-benzyl)-2-(4-ethoxy-2-oxo-cyclohex-3-enyl)-acetamide (549 mg, 1.58 mmol) in THF (10 mL) at −78° C. was added 1.0M of diisobutylaluminum hydride in heptane (2.0 mL). The reaction mixture was then stirred at 0° C. for one hour. 5 M of hydrogen chloride in water (2.0 mL) was added and the reaction mixture stirred at room temperature for 30 minutes. The reaction mixture was then partitioned between water and ethyl acetate, and the organic layer dried with brine and magnesium sulfate, filtered, and evaporated in vacuo to yield 471.8 mg (98%) of N-(2,4-Dimethoxy-benzyl)-2-(4-oxo-cyclohex-2-enyl)-acetamide which was carried forward without purification. LCMS (Method E, ESI): RT=1.23 min, m+H=304.2; $^1$H NMR (400 MHz, $CDCl_3$) δ: 7.19 (d, J=8.1 Hz, 1H), 6.84 (ddd, J=10.2, 2.6, 1.3 Hz, 1H), 6.45 (dt, J=8.2, 2.2 Hz, 2H), 5.97 (dd, J=10.2, 2.1 Hz, 1H), 5.88 (s, 1H), 4.38 (d, J=5.7 Hz, 2H), 3.83 (s, 3H), 3.80 (s, 3H), 3.02 (s, 1H), 2.51-2.36 (m, 2H), 2.36-2.27 (m, 1H), 2.23 (dd, J=14.5, 7.6 Hz, 1H), 2.19-2.08 (m, 1H), 1.76-1.62 (m, 1H).

1-(2,4-Dimethoxy-benzyl)-hexahydro-indole-2,6-dione

To a solution of N-(2,4-Dimethoxy-benzyl)-2-(4-oxo-cyclohex-2-enyl)-acetamide (469.8 mg, 1.549 mmol) in THF (15 mL) was added sodium hydride (60 wt % on mineral oil, 245 mg, 6.12 mmol). The reaction mixture was stirred at room temperature for one hour and then quenched with saturated aqueous ammonium chloride. The mixture was then extracted twice with dichloromethane, and the combined extracts dried over magnesium sulfate, filtered, and evaporated in vacuo. Purification by column chromatography on silica gel (gradient: 0 to 10% methanol in dichloromethane) yielded 365.0 mg (78%) of 1-(2,4-Dimethoxy-benzyl)-hexahydro-indole-2,6-dione. LCMS (Method E, ESI): RT=1.22 min, m+H=304.2; $^{1}$H NMR (400 MHz, $CD_3OD$) δ: 7.11 (d, J=8.3 Hz, 1H), 6.53 (d, J=1.8 Hz, 1H), 6.48 (dd, J=8.3, 2.1 Hz, 1H), 4.72 (d, J=14.8 Hz, 1H), 4.04 (d, J=14.8 Hz, 1H), 3.88 (dd, J=13.3, 6.7 Hz, 1H), 3.81 (s, 3H), 3.78 (s, 3H), 2.77-2.59 (m, 4H), 2.38-2.21 (m, 3H), 2.10 (dd, J=13.8, 7.8 Hz, 1H), 1.82 (dd, J=13.3, 6.2 Hz, 1H).

6-Amino-1-(2,4-dimethoxy-benzyl)-octahydro-indol-2-one

To a solution of 1-(2,4-Dimethoxy-benzyl)-hexahydro-indole-2,6-dione (47 mg, 0.15 mmol) in 7.0 M of ammonia in methanol (10 mL) was added palladium (10 wt % on activated carbon, 26 mg). The reaction mixture was stirred at room temperature under 1 atm of hydrogen gas for 20 hours. The reaction mixture was then filtered through celite and evaporated in vacuo. Purification by column chromatography on silica gel (gradient: 0 to 5% methanol in dichloromethane containing 2% triethylamine) yielded 28.7 mg (61%) of 6-Amino-1-(2,4-dimethoxy-benzyl)-octahydro-indol-2-one. LCMS (Method E, ESI): RT=0.94 min, m+H=305.2; $^{1}$H NMR (400 MHz, $CD_3OD$) δ: 7.11 (d, J=8.3, 1H), 6.52 (d, J=1.7, 1H), 6.50-6.44 (m, 1H), 4.73 (d, J=15.1, 1H), 4.13 (d, J=15.1, 1H), 3.81 (s, 3H), 3.77 (s, 3H), 3.64 (d, J=3.2, 1H), 2.56-2.52 (m, 1H), 2.49 (dd, J=16.5, 6.9, 1H), 2.25 (d, J=14.5, 1H), 2.19 (td, J=11.4, 5.7, 1H), 2.01 (d, J=16.2, 1H), 1.83-1.69 (m, 2H), 1.25 (s, 2H), 1.14 (s, 1H).

6-(1-Benzenesulfonyl-5-nitro-1H-pyrrolo[2,3-b]pyridin-4-ylamino)-1-(2,4-dimethoxy-benzyl)-octahydro-indol-2-one A mixture of 1-benzenesulfonyl-4-chloro-5-nitro-1H-pyrrolo[2,3-b]pyridine (137.2 mg, 0.4062 mmol), 6-amino-1-(2,4-dimethoxy-benzyl)-octahydro-indol-2-one (107.8 mg, 0.3542 mmol), and diisopropylethylamine (0.10 mL, 0.57 mmol) in propan-2-ol (1.5 ml) was heated in a microwave reactor at 120° C. for 20 minutes. The solvent was evaporated in vacuo and then purified by column chromatography on silica gel (gradient: 0 to 100% ethyl acetate in dichloromethane) affording 152.3 mg (71%) of 6-(1-benzenesulfonyl-5-nitro-1H-pyrrolo[2,3-b]pyridin-4-ylamino)-1-(2,4-dimethoxy-benzyl)-octahydro-indol-2-one. LCMS (Method E, ESI): RT=1.81 min, m+H=606.0.

6-(6-Benzenesulfonyl-6H-1,2,3,5,6-tetraaza-as-indacen-1-yl)-1-(2,4-dimethoxy-benzyl)-octahydro-indol-2-one A mixture of 6-(1-benzenesulfonyl-5-nitro-1H-pyrrolo[2,3-b]pyridin-4-ylamino)-1-(2,4-dimethoxy-benzyl)-octahydro-indol-2-one (122 mg, 0.201 mmol), iron powder (67.2 mg, 1.20 mmol), ammonium chloride (92.2 mg, 1.72 mmol), 1-butanol (4.0 mL), and formic acid (1.0 mL) was heated at 100° C. for 6 hours. Formic acid (2 mL), iron powder (131 mg), and ammonium chloride (144 mg) were added, and the reaction mixture heated at 100° C. for an additional two hours. After cooling to room temperature, the reaction mixture was filtered through celite to remove iron and inorganic solids, rinsing with ethanol. The filtrate was neutralized with saturated aqueous sodium bicarbonate, and extracted three times with dichloromethane. The combined organic extracts were dried over magnesium sulphate, filtered, and evaporated in vacuo. Purification by column chromatography on silica gel (gradient: 0 to 10% methanol in dichloromethane) yielded 81.0 mg (69%) of 6-(6-benzenesulfonyl-6H-1,2,3,5,6-tetraaza-as-indacen-1-yl)-1-(2,4-dimethoxy-benzyl)-octahydro-indol-2-one. LCMS (Method E, ESI): RT=1.58 min, m+H=586.2.

6-(6H-1,2,3,5,6-Tetraaza-as-indacen-1-yl)-octahydro-indol-2-one

To a solution of 6-(6-benzenesulfonyl-6H-1,2,3,5,6-tetraaza-as-indacen-1-yl)-1-(2,4-dimethoxy-benzyl)-octahydro-indol-2-one (81.0 mg, 0.138 mmol) in anisole (2 mL, 20 mmol) was added trifluoroacetic acid (0.5 mL, 6 mmol). The reaction mixture was sealed in a heavy-walled reaction vessel and heated at 110° C. for 20 hours. The crude reaction mixture was evaporate in vacuo, and then redissolved in methanol (3 mL) with 0.4 mL of 1 M sodium hydroxide in water. The reaction mixture was stirred at 50° C. for 2.5 hours, and then evaporated in vacuo. Purification by preparative HPLC yielded 11.5 mg (28%) of 6-(6H-1,2,3,5,6-Tetraaza-as-indacen-1-yl)-octahydro-indol-2-one, as a racemic mixture (cis). LCMS (Method C, ESI): RT=2.53 min, m+H=296.1; $^{1}$H NMR (400 MHz, DMSO-$d_6$) δ: 11.82 (s, 1H), 8.57 (s, 1H), 8.30 (s, 1H), 7.79 (s, 1H), 7.46 (d, J=3.4 Hz, 1H), 6.78 (d, J=3.4 Hz, 1H), 4.57 (t, J=11.8 Hz, 1H), 3.90-3.74 (m, 1H), 2.58 (m, 1H), 2.31 (d, J=15.2 Hz, 1H), 2.12-1.81 (m, 7H).

Examples 112 and 112a

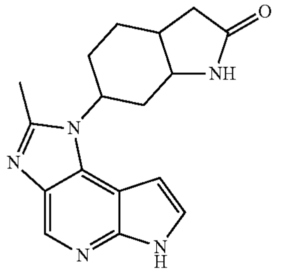

cis, single enantiomers 6-(2-Methyl-6H-1,2,3,5,6-tetraaza-as-indacen-1-yl)-octahydro-indol-2-one 6-(5-Amino-1-benzenesulfonyl-1H-pyrrolo[2,3-b]pyridin-4-ylamino)-1-(2,4-dimethoxy-benzyl)-octahydro-indol-2-one To a solution of 6-(1-Benzenesulfonyl-5-nitro-1H-pyrrolo[2,3-b]pyridin-4-ylamino)-1-(2,4-dimethoxy-benzyl)-octahydro-indol-2-one (prepared as in Example 111) (152.3 mg, 0.2515 mmol) in ethanol (3 mL) was added ammonium chloride (59.0 mg, 1.10 mmol), iron powder (70.4 mg, 1.26 mmol), and water (5 mL). The reaction mixture was stirred at 70° C. for 1.5 hours. After cooling to room temperature, the reaction mixture was filtered through celite to remove iron and inorganic solids, rinsing with ethanol. The filtrate was neutralized with saturated aqueous sodium bicarbonate, and extracted twice with dichloromethane. The combined organic extracts were dried over magnesium sulphate, filtered, and evaporated in vacuo to yield 134.5 mg (93%) of 6-(5-amino-1-benzenesulfonyl-1H-pyrrolo[2,3-b]pyridin-4-ylamino)-1-(2,4-dimethoxy-benzyl)-octahydro-indol-2-one, which was carried forward without purification. LCMS (Method E, ESI): RT=1.43 min, m+H=576.2.

6-(6-Benzenesulfonyl-2-methyl-6H-1,2,3,5,6-tetraaza-as-indacen-1-yl)-1-(2,4-dimethoxy-benzyl)-octahydro-indol-2-one To a solution of 6-(5-amino-1-benzenesulfonyl-1H-pyrrolo[2,3-b]pyridin-4-ylamino)-1-(2,4-dimethoxy-benzyl)-octahydro-indol-2-one (134.5 mg, 0.2336 mmol) in acetic acid (1.5 mL) was added iron powder (98.6 mg, 1.76 mmol). The reaction mixture was heated at 100° C. for 22 hours. The reaction mixture was diluted with methanol and filtered through celite. The filtrate was neutralized with saturated aqueous sodium bicarbonate, and extracted twice with dichloromethane. The combined organic extracts were dried over magnesium sulphate, filtered, and evaporated in vacuo. Purification by column chromatography on silica gel (gradient: 0 to 10% methanol in dichloromethane) yielded 55.9 mg (40%) of 6-(6-benzenesulfonyl-2-methyl-6H-1,2,3,5,6-tetraaza-as-indacen-1-yl)-1-(2,4-dimethoxy-benzyl)-octahydro-indol-2-one. LCMS (Method E, ESI): RT=1.53 min, m+H=600.2.

6-(2-Methyl-6H-1,2,3,5,6-tetraaza-as-indacen-1-yl)-octahydro-indol-2-one

Using 6-(6-benzenesulfonyl-2-methyl-6H-1,2,3,5,6-tetraaza-as-indacen-1-yl)-1-(2,4-dimethoxy-benzyl)-octahydro-indol-2-one and following the procedures described for Example 111, the title compound was obtained in 56.5% yield as a mixture of stereoisomers LCMS (Method C, ESI): RT=2.55 min, m+H=310.1; $^1$H NMR (400 MHz, DMSO-$d_6$) δ: 11.78 (s, 1H), 8.45 (s, 1H), 7.84 (s, 1H), 7.47 (s, 1H), 6.60 (s, 1H), 4.50 (s, 1H), 3.83 (dd, J=16.1, 7.5 Hz, 1H), 2.62 (m, 4H), 2.33 (m, 2H), 2.07 (m, 3H), 1.95 (m, 2H), 1.85 (m, 1H).

Purification by chiral SFC yielded the separated enantiomers of 6-(2-Methyl-6H-1,2,3,5,6-tetraaza-as-indacen-1-yl)-octahydro-indol-2-one.

Example 113

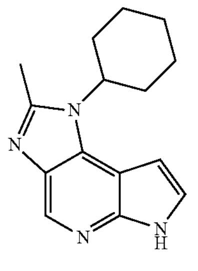 [SMILES: Cc1nc2cnc3[nH]ccc3c2n1C1CCCCC1]

1-Cyclohexyl-2-methyl-1,6-dihydro-1,2,3,5,6-tetraaza-as-indacene (1-Benzenesulfonyl-5-nitro-1H-pyrrolo[2,3-b]pyridin-4-yl)-cyclohexyl-amine A mixture of 1-benzenesulfonyl-4-chloro-5-nitro-1H-pyrrolo[2,3-b]pyridine (10 g, 29.6 mmol), cyclohexyl amine (3.4 ml, 30.0 mmol), diisopropylethylamine (11 ml, 65.0 mmol) in propan-2-ol (150 ml) was heated at 80° C. for 14 h. The mixture was then cooled to 25° C. and stirred for 6 h. The resulting yellow solid was collected by vacuum filtration, washed with propan-2-ol (1×30 ml), and was air-dried to afford (1-benzenesulfonyl-5-nitro-1H-pyrrolo[2,3-b]pyridin-4-yl)-cyclohexyl-amine (10.45 g, 90%). LCMS (Method G, ESI): RT=1.33 min, m+H=401.2; $^1$H NMR (400 MHz, DMSO) δ 8.93 (s, 1H), 8.91 (s, 1H), 8.13 (d, J=7.6 Hz, 2H), 7.82 (d, J=4.1 Hz, 1H), 7.77 (t, J=7.4 Hz, 1H), 7.66 (t, J=7.8 Hz, 2H), 6.99 (d, J=4.2 Hz, 1H), 4.12-4.01 (m, 1H), 2.02-1.93 (m, 2H), 1.76-1.54 (m, 3H), 1.55-1.38 (m, 4H), 1.33-1.20 (m, 1H).

1-Benzenesulfonyl-N-4-cyclohexyl-1H-pyrrolo[2,3-b]pyridine-4,5-diamine

A suspension of (1-benzenesulfonyl-5-nitro-1H-pyrrolo[2,3-b]pyridin-4-yl)-cyclohexyl-amine (10 g, 25.0 mmol) and palladium on carbon (2.7 g, 10%, wet, Degussa, E101 NE/W) in a 3:1 mixture of THF and ethanol (200 ml) was stirred under a hydrogen atmosphere (2-3 balloons) at 50° C. for 13 h. The reaction mixture was cooled to 25° C. then was filtered through Celite. The filtrate was concentrated under reduced pressure to afford crude 1-benzenesulfonyl-N-4-cyclohexyl-1H-pyrrolo[2,3-b]pyridine-4,5-diamine (9.61 g, 100%) as a rose foam. LCMS (Method G, ESI): RT=0.83 min, m+H=371.2. This material was used in subsequent reactions without additional purification or characterization.

6-Benzenesulfonyl-1-cyclohexyl-2-methyl-1,6-dihydro-1,2,3,5,6-tetraaza-as-indacene p-Toluenesulfonic acid monohydrate (0.429 g, 2.26 mmol) was added to a solution of 1-benzenesulfonyl-N-4-cyclohexyl-1H-pyrrolo[2,3-b]pyridine-4,5-diamine (1.04 g, 2.82 mmol) and triethyl orthoacetate (1.29 ml, 7.05 mmol) in toluene (10 ml) at 25° C. The reaction mixture was heated at 105° C. for 13 h, then was cooled to 25° C. and partitioned between half-saturated $NaHCO_3$ (100 ml) and a 1:1 mixture of EtOAc and heptane (2×125 ml). The organic layers were dried over $MgSO_4$, filtered, and the filtrate was concentrated under reduced pressure. Purification of the resulting solid by column chromatography on silica gel (gradient: 0 to 8% $CH_3OH$ in $CH_2Cl_2$) afforded 6-benzenesulfonyl-1-cyclohexyl-2-methyl-1,6-dihydro-1,2,3,5,6-tetraaza-as-indacene (0.57 g, 52%) as a beige solid. LCMS (Method G, ESI): RT=0.99 min, m+H=395.2; $^1$H NMR (400 MHz, $CDCl_3$) δ 8.80 (s, 1H), 8.23 (d, J=7.8 Hz, 2H), 7.80 (d, J=4.0 Hz, 1H), 7.55 (t, J=7.4 Hz, 1H), 7.47 (t, J=7.7 Hz, 2H), 7.26 (s, 1H), 6.90 (br s, 1H), 4.43-4.25 (m, 1H), 2.67 (s, 3H), 2.30-2.11 (m, 2H), 2.11-1.99 (m, 3H), 1.99-1.81 (m, 2H), 1.57-1.41 (m, 2H).

1-Cyclohexyl-2-methyl-1,6-dihydro-1,2,3,5,6-tetraaza-as-indacene

Sodium hydroxide (10 ml of a 1.0 M solution in water, 10 mmol) was added to a solution of 6-benzenesulfonyl-1-cyclohexyl-2-methyl-1,6-dihydro-1,2,3,5,6-tetraaza-as-indacene (0.574 g, 1.46 mmol) in $CH_3OH$ (20 ml) at 25° C. The reaction mixture was stirred at 50° C. for 14 h, then was cooled to 25° C. and was concentrated under reduced pressure to approximately 15 ml volume. This material was then partitioned between water (100 ml) and EtOAc (2×200 ml). The combined organic layers were dried over $MgSO_4$, filtered, and the filtrate was concentrated under reduced pressure. Purification of the residue by preparative HPLC (column: Gemini-NX, 5×10 cm, 10 um; detection: UV 254 nm, mobile phase A: water containing 0.1% $NH_4OH$; mobile phase B: $CH_3CN$; flowrate: 120 mL/min; gradient 5-95% B over 15 min) afforded 1-cyclohexyl-2-methyl-1,6-dihydro-1,2,3,5,6-tetraaza-as-indacene (0.181 g, 49%) as an off-white solid. LCMS (Method C, ESI): RT=3.26 min, m+H=255.1; $^1$H NMR (400 MHz, DMSO) δ 11.77 (s, 1H), 8.45 (s, 1H), 7.45 (t, J=2.9 Hz, 1H), 6.71 (s, 1H), 4.53-4.35 (m, 1H), 2.62 (s, 3H), 2.34-2.18 (m, 2H), 1.92 (t, J=13.8 Hz, 4H), 1.78 (d, J=11.3 Hz, 1H), 1.64-1.36 (m, 3H).

Example 114

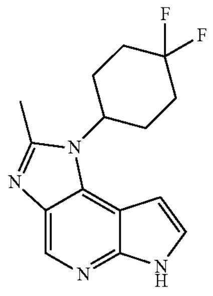 [SMILES: Cc1nc2cnc3[nH]ccc3c2n1C1CCC(F)(F)CC1]

1-(4,4-Difluoro-cyclohexyl)-2-methyl-1,6-dihydro-1,2,3,5,6-tetraaza-as-indacene (1-Benzenesulfonyl-5-nitro-1H-pyrrolo[2,3-b]pyridin-4-yl)-(4,4-difluoro-cyclohexyl)-amine A mixture of 1-benzenesulfonyl-4-chloro-5-nitro-1H-pyrrolo[2,3-b]pyridine (0.433 g, 1.28 mmol), 4,4-difluorocyclohexyl amine hydrochloride (0.242 g, 1.41 mmol), diisopropylethylamine (0.491 ml, 2.82 mmol) in propan-2-ol (10 ml) was heated at 110° C. in a microwave reactor for 20 min. The mixture was then cooled to 25° C. and was partitioned between water (50 ml) and $CH_2Cl_2$ (2×100 ml). The combined organic layers were dried over $MgSO_4$, filtered, and the filtrate was concentrated under reduced pressure. Purification of the resulting yellow solid by column chromatography on silica gel (gradient: 0 to 60% EtOAc in heptanes) afforded (1-benzenesulfonyl-5-nitro-1H-pyrrolo[2,3-b]pyridin-4-yl)-(4,4-di fluoro-cyclohexyl)-amine (0.46 g, 82%) as a yellow solid. LCMS (Method G, ESI): RT=1.21 min, m+H=437; $^1$H NMR (400 MHz, DMSO) δ 8.91 (s, 1H), 8.83 (d, J=8.1 Hz, 1H), 8.13 (d, J=7.5 Hz, 2H), 7.84 (d, J=4.2 Hz, 1H), 7.77 (t, J=7.4 Hz, 1H), 7.66 (t, J=7.8 Hz, 2H), 7.17 (d, J=4.3 Hz, 1H), 4.39-4.26 (m, 1H), 2.29-1.98 (m, 6H), 1.83-1.68 (m, 2H).

1-Benzenesulfonyl-N-4-(4,4-difluoro-cyclohexyl)-1H-pyrrolo[2,3-b]pyridine-4,5-diamine A suspension of (1-benzenesulfonyl-5-nitro-1H-pyrrolo[2,3-b]pyridin-4-yl)-(4,4-difluoro-cyclohexyl)-amine (0.46 g, 1.46 mmol) and palladium on carbon (0.300 g, 10%, wet, Degussa, E101 NE/W) in a 2:1 mixture of THF and ethanol (60 ml) was stirred under a hydrogen atmosphere (2 balloons) at 50° C. for 13 h. The reaction mixture was cooled to 25° C. then was filtered through Celite. The filtrate was concentrated under reduced pressure to afford crude 1-benzenesulfonyl-N-4-(4,4-difluoro-cyclohexyl)-1H-pyrrolo[2,3-b]pyridine-4,5-diamine as light pink oil. TLC: 40% EtOAc in heptanes, Rf=0.10. This material was used in the next step below without additional purification or characterization.

6-Benzenesulfonyl-1-(4,4-difluoro-cyclohexyl)-2-methyl-1,6-dihydro-1,2,3,5,6-tetraaza-as-indacene p-Toluenesulfonic acid monohydrate (0.240 g, 1.30 mmol) was added to a solution of the crude material obtained in the previous step and triethyl orthoacetate (0.73 ml, 4.00 mmol) in toluene (70 ml) at 25° C. The reaction mixture was heated at 100° C. for 4.5 h, then was cooled to 25° C. and partitioned between half-saturated $NaHCO_3$ (100 ml) and EtOAc (2×100 ml). The organic layers were dried over $MgSO_4$, filtered, and the filtrate was concentrated under reduced pressure. Purification of the resulting solid by column chromatography on silica gel (gradient: 0 to 10% $CH_3OH$ in $CH_2Cl_2$) afforded 6-benzenesulfonyl-1-(4,4-difluoro-cyclohexyl)-2-methyl-1,6-dihydro-1,2,3,5,6-tetraaza-as-indacene (0.29 g, 42% over two steps) as an off-white solid. LCMS (Method G, ESI): RT=0.92 min, m+H=431.3; $^1$H NMR (400 MHz, $CDCl_3$) δ 8.81 (s, 1H), 8.23 (d, J=7.6 Hz, 2H), 7.83 (d, J=4.1 Hz, 1H), 7.55 (t, J=7.4 Hz, 1H), 7.47 (t, J=7.6 Hz, 2H), 7.26 (s, 1H), 6.93 (s, 1H), 4.52-4.37 (m, 1H), 2.68 (s, 3H), 2.66-2.56 (m, 1H), 2.46-2.33 (m, 2H), 2.13-1.90 (m, 4H).

1-(4,4-Difluoro-cyclohexyl)-2-methyl-1,6-dihydro-1,2,3,5,6-tetraaza-as-indacene

Sodium hydroxide (10 ml of a 1.0 M solution in water, 10 mmol) was added to a solution of 6-benzenesulfonyl-1-(4,4-difluoro-cyclohexyl)-2-methyl-1,6-dihydro-1,2,3,5,6-tetraaza-as-indacene (0.286 g, 0.664 mmol) in $CH_3OH$ (20 ml) at 25° C. The reaction mixture was stirred at 50° C. for 3 h, then was cooled to 25° C. and was concentrated under reduced pressure to approximately 15 ml volume. This material was then partitioned between water (100 ml) and EtOAc (2×200 ml). The combined organic layers were dried over $MgSO_4$, filtered, and the filtrate was concentrated under reduced pressure. Purification of the residue by preparative HPLC afforded 1-(4,4-difluoro-cyclohexyl)-2-methyl-1,6-dihydro-1,2,3,5,6-tetraaza-as-indacene (0.125 g, 65%) as an off-white solid. LCMS (Method C, ESI): RT=3.23 min, m+H=291.1; $^1$H NMR (400 MHz, DMSO) δ 11.81 (s, 1H), 8.47 (s, 1H), 7.48 (t, J=3.0 Hz, 1H), 6.65 (s, 1H), 4.78-4.66 (m, 1H), 2.64 (s, 3H), 2.59-2.52 (m, 1H), 2.35-2.13 (m, 5H), 2.06-1.94 (m, 2H).

Example 115

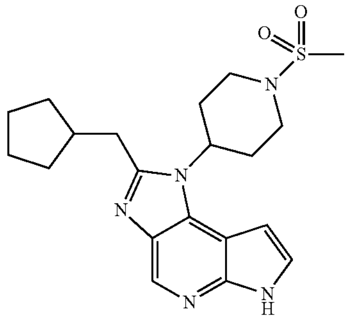 [SMILES: CS(=O)(=O)N1CCC(n2c(CC3CCCC3)nc3cnc4[nH]ccc4c32)CC1]

2-Cyclopentylmethyl-1-(1-methanesulfonyl-piperidin-4-yl)-1,6-dihydro-1,2,3,5,6-tetraaza-as-indacene 4-(1-Benzenesulfonyl-5-nitro-1H-pyrrolo[2,3-b]pyridin-4-ylamino)-piperidine-1-carboxylic acid tert-butyl ester A mixture of 1-benzenesulfonyl-4-chloro-5-nitro-1H-pyrrolo[2,3-b]pyridine (15.6 g, 46.2 mmol), 4-amino-1-Boc-piperidine (10.18 g, 50.8 mmol), diisopropylethylamine (20.9 ml, 120 mmol) in propan-2-ol (200 ml) was heated at 80° C. for 11 h. The mixture was then cooled to 25° C. and was concentrated under reduced pressure. The yellow-orange residue was partitioned between water (150 ml) and $CH_2Cl_2$ (2×200 ml). The combined organic layers were dried over $MgSO_4$, filtered, and the filtrate was concentrated under reduced pressure to afford crude 4-(1-benzenesulfonyl-5-nitro-1H-pyrrolo[2,3-b]pyridin-4-ylamino)-piperidine-1-carboxylic acid tert-butyl ester (26.4 g, 114%) as a yellow-orange foam. A portion of this material (11.2 g) was used in the next step below. The remaining material was purified by column chromatography on silica gel (gradient: 0 to 70% EtOAc in heptanes) to give the title compound (13.49 g) as a yellow solid. LCMS (Method G, ESI): RT=1.24 min, m+H=502.3; $^1$H NMR (400 MHz, $CDCl_3$) δ 9.10 (s, 1H), 9.08 (s, 1H), 8.19 (d, J=8.0 Hz, 2H), 7.63 (dd, J=8.1, 5.9 Hz, 2H), 7.52 (t, J=7.8 Hz, 2H), 6.70 (d, J=4.2 Hz, 1H), 4.22-4.07 (m, 1H), 4.01 (d, J=13.3 Hz, 2H), 3.12 (t, J=11.3 Hz, 2H), 2.17-2.04 (m, 2H), 1.69-1.58 (m, 2H), 1.47 (s, 9H).

4-(5-Amino-1-benzenesulfonyl-1H-pyrrolo[2,3-b]pyridin-4-ylamino)-piperidine-1-carboxylic acid tert-butyl ester A suspension of 4-(1-benzenesulfonyl-5-nitro-1H-pyrrolo[2,3-b]pyridin-4-ylamino)-piperidine-1-carboxylic acid tert-butyl ester (11.2 g, 22.4 mmol) and palladium on carbon (1.45 g, 10%, wet, Degussa, E101 NE/W) in a 2:1 mixture of THF and ethanol (150 ml) was stirred under a hydrogen atmosphere (2-3 balloons) at 50° C. for 18 h. The reaction mixture was cooled to 25° C. then was filtered through Celite. The filtrate was concentrated under reduced pressure and the red-orange residue was purified by column chromatography on silica gel (gradient: 0 to 7% $CH_3OH$ in $CH_2Cl_2$) to give a dark red oil. This material was dissolved in $CH_2Cl_2$ (40 ml) and $Et_2O$ (200 ml) was added. Concentration of this mixture to approximately 60 ml volume under reduced pressure afforded a pink solid. This material was collected by vacuum filtration, was washed with $Et_2O$ (2×30 ml), and was air-dried to afford 4-(5-amino-1-benzenesulfonyl-1H-pyrrolo[2,3-b]pyridin-4-ylamino)-piperidine-1-carboxylic acid tert-butyl ester (7.23 g, 69%). LCMS (Method G, ESI): RT=0.87 min, m+H=472.3; $^1$H NMR (400 MHz, DMSO) δ 8.04-7.99 (m, 2H), 7.70-7.65 (m, 1H), 7.61-7.55 (m, 3H), 7.49 (d, J=4.2 Hz, 1H), 6.78 (d, J=4.3 Hz, 1H), 5.11 (d, J=8.7 Hz, 1H), 4.37 (s, 1H), 3.94-3.86 (m, 2H), 2.95 (s, 1H), 2.54-2.48 (m, 2H), 1.92-1.79 (m, 3H), 1.40 (s, 9H), 1.38-1.27 (m, 2H).

4-[1-Benzenesulfonyl-5-(2-cyclopentyl-acetylamino)-1H-pyrrolo[2,3-b]pyridin-4-ylamino]-piperidine-1-carboxylic acid tert-butyl ester Cyclopentylacetic acid (0.532 ml, 4.24 mmol), diisopropylethylamine (1.5 ml, 8.50 mmol) and N-(3-dimethylaminopropyl)-N'-ethylcarbodiimide hydrochloride (0.89 g, 4.70 mmol) were added sequentially to a solution of 4-(5-amino-1-benzenesulfonyl-1H-pyrrolo[2,3-b]pyridin-4-ylamino)-piperidine-1-carboxylic acid tert-butyl ester (2.00 g, 4.00 mmol) in $CH_2Cl_2$ (60 ml) at 25° C. The reaction mixture was stirred for 9 h at 25° C., then was partitioned between 1.0 M HCl (125 ml) and $CH_2Cl_2$ (125 ml). The organic layer was dried over $MgSO_4$, filtered, and the filtrate was concentrated under reduced pressure. Purification of the residue by column chromatography on silica gel (gradient: 0 to 8% $CH_3OH$ in $CH_2Cl_2$) afforded 4-[1-benzenesulfonyl-5-(2-cyclopentyl-acetylamino)-1H-pyrrolo[2,3-b]pyridin-4-ylamino]-piperidine-1-carboxylic acid tert-butyl ester (1.05 g, 40%) as an off-white solid. LCMS (Method G, ESI): RT=1.15 min, m+H=582.5. This material was used in the next step below without additional characterization.

N-[1-Benzenesulfonyl-4-(piperidin-4-ylamino)-1H-pyrrolo[2,3-b]pyridin-5-yl]-2-cyclopentyl-acetamide (hydrochloride salt)

A 4.0 M solution of HCl in 1,4-dioxane (10 ml) was added to a solution of 4-[1-benzenesulfonyl-5-(2-cyclopentyl-acetylamino)-1H-pyrrolo[2,3-b]pyridin-4-ylamino]-piperidine-1-carboxylic acid tert-butyl ester (0.222 g, 0.382 mmol) in 1,4-dioxane (10 ml) at 25° C. The reaction mixture was stirred at 25° C. for 1 h, then was concentrated under reduced pressure to afford crude N-[1-benzenesulfonyl-4-(piperidin-4-ylamino)-1H-pyrrolo[2,3-b]pyridin-5-yl]-2-cyclopentyl-acetamide (hydrochloride salt) as a white solid. This material was used in the next step below without additional purification or characterization.

N-[1-Benzenesulfonyl-4-(1-methanesulfonyl-piperidin-4-ylamino)-1H-pyrrolo[2,3-b]pyridin-5-yl]-2-cyclopentyl-acetamide Diisopropylethylamine (0.166 ml, 0.954 mmol) and methanesulfonyl chloride (0.027 ml, 0.350 mmol), were added sequentially to a solution of crude N-[1-benzenesulfonyl-4-

(piperidin-4-ylamino)-1H-pyrrolo[2,3-b]pyridin-5-yl]-2-cyclopentyl-acetamide (hydrochloride salt) (0.382 mmol, obtained in preceding step) in $CH_2Cl_2$ (10 ml) at 25° C. The reaction mixture was stirred for 30 min at 25° C., then was partitioned between half-saturated $NaHCO_3$ (75 ml) and $CH_2Cl_2$ (100 ml). The organic layer was dried over $MgSO_4$, filtered, and the filtrate was concentrated under reduced pressure to afford N-[1-benzenesulfonyl-4-(1-methanesulfonyl-piperidin-4-ylamino)-1H-pyrrolo[2,3-b]pyridin-5-yl]-2-cyclopentyl-acetamide as a white foam. LCMS (Method G, ESI): RT=0.93 min, m+H=560.3. This material was used in the next step below without additional purification or characterization.

6-Benzenesulfonyl-2-cyclopentylmethyl-1-(1-methanesulfonyl-piperidin-4-yl)-1,6-dihydro-1,2,3,5,6-tetraaza-as-indacene A solution of crude N-[1-benzenesulfonyl-4-(1-methanesulfonyl-piperidin-4-ylamino)-1H-pyrrolo[2,3-b]pyridin-5-yl]-2-cyclopentyl-acetamide (0.382 mmol, obtained in preceding step) in glacial HOAc (6 ml) was heated at 105° C. for 8 h. The reaction mixture was then cooled to 25° C., was stirred overnight at that temperature, and was concentrated under reduced pressure to afford crude 6-benzenesulfonyl-2-cyclopentylmethyl-1-(1-methanesulfonyl-piperidin-4-yl)-1,6-dihydro-1,2,3,5,6-tetraaza-as-indacene as a brown oil. LCMS (Method G, ESI): RT=0.98 min, m+H=542.3. This material was used in the next step below without additional purification or characterization.

2-Cyclopentylmethyl-1-(1-methanesulfonyl-piperidin-4-yl)-1,6-dihydro-1,2,3,5,6-tetraaza-as-indacene Sodium hydroxide (5 ml of a 1.0 M solution in water, 10 mmol) was added to a solution of crude 6-benzenesulfonyl-2-cyclopentylmethyl-1-(1-methanesulfonyl-piperidin-4-yl)-1,6-dihydro-1,2,3,5,6-tetraaza-as-indacene (0.382 mmol, obtained in the preceding step) in EtOH (10 ml) at 25° C. The reaction mixture was stirred at 50° C. for 4 h, then was cooled to 25° C. and was concentrated under reduced pressure to approximately 7 ml volume. This material was then partitioned between water (100 ml) and EtOAc (2×100 ml). The combined organic layers were dried over $MgSO_4$, filtered, and the filtrate was concentrated under reduced pressure. Purification of the residue by column chromatography on silica gel (gradient: 7 to 15% $CH_3OH$ in $CH_2Cl_2$) afforded an off-white solid. This material was subjected to additional purification via preparative HPLC (column: Gemini-NX, 3×10 cm, 10 um; detection: UV 254 nm, mobile phase A: water containing 0.1% $NH_4OH$; mobile phase B: $CH_3CN$; flowrate: 60 mL/min; gradient 5-95% B over 15 min) to afford 2-cyclopentylmethyl-1-(1-methanesulfonyl-piperidin-4-yl)-1,6-dihydro-1,2,3,5,6-tetraaza-as-indacene (0.023 g, 15% over 4 steps) as an off-white solid. LCMS (Method C, ESI): RT=3.54 min, m+H=402.1; $^1H$ NMR (400 MHz, DMSO) δ 11.82 (s, 1H), 8.51 (s, 1H), 7.50 (t, J=2.9 Hz, 1H), 6.70 (s, 1H), 4.79-4.63 (m, 1H), 3.81 (d, J=11.7 Hz, 2H), 3.06 (t, J=11.4 Hz, 2H), 2.99 (s, 3H), 2.66-2.53 (m, 2H), 2.46-2.31 (m, 1H), 1.98 (d, J=10.2 Hz, 2H), 1.86-1.74 (m, 2H), 1.72-1.60 (m, 3H), 1.60-1.48 (m, 3H), 1.36-1.23 (m, 2H).

Example 116

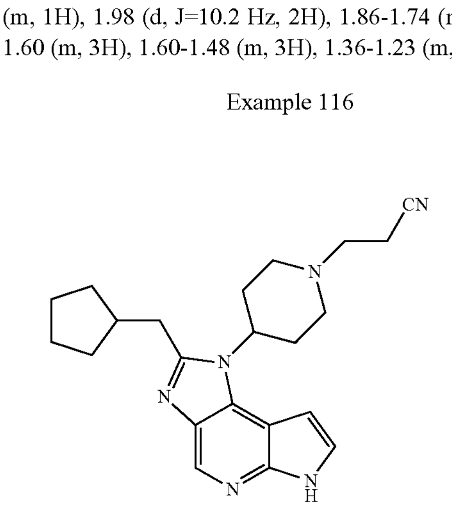

3-[4-(2-Cyclopentylmethyl-6H-1,2,3,5,6-tetraaza-as-indacen-1-yl)-piperidin-1-yl]-propionitrile N-{1-Benzenesulfonyl-4-[1-(2-cyano-ethyl)-piperidin-4-ylamino]-1H-pyrrolo[2,3-b]pyridin-5-yl}-2-cyclopentyl-acetamide Trifluoroacetic acid (2 ml) was added to a solution of 4-[1-benzenesulfonyl-5-(2-cyclopentyl-acetylamino)-1H-pyrrolo[2,3-b]pyridin-4-ylamino]-piperidine-1-carboxylic acid tert-butyl ester (0.421 g, 0.724 mmol) in $CH_2Cl_2$ (10 ml) at 25° C. The reaction mixture was stirred at 25° C. for 30 min, then was concentrated under reduced pressure. The residue was partitioned between half-saturated $NaHCO_3$ (100 ml) and EtOAc (2×100 ml) and the combined organic layers were dried over $MgSO_4$ and filtered. The filtrate was concentrated under reduced pressure and the residue was dissolved in DMF (8 ml) at 25° C. Acrylonitrile (1.0 ml, 0.200 mmol) was added and the reaction mixture was stirred at 25° C. for 18 h, then was concentrated under reduced pressure. The residue was partitioned between water (100 ml) and EtOAc (2×100 ml). The combined organic layers were dried over $MgSO_4$, filtered, and the filtrate was concentrated under reduced pressure. Purification of the residue by column chromatography on silica gel (gradient: 0 to 7% $CH_3OH$ in $CH_2Cl_2$) afforded N-{1-benzenesulfonyl-4-[1-(2-cyano-ethyl)-piperidin-4-ylamino]-1H-pyrrolo[2,3-b]pyridin-5-yl}-2-cyclopentyl-acetamide (0.169 g, 63%) as a white foam. LCMS (Method G, ESI): RT=0.70 min, m+H=535.4. This material was used in the next step below without additional characterization.

3-[4-(6-Benzenesulfonyl-2-cyclopentylmethyl-6H-1,2,3,5,6-tetraaza-as-indacen-1-yl)-piperidin-1-yl]-propionitrile A solution of N-{1-benzenesulfonyl-4-[1-(2-cyano-ethyl)-piperidin-4-ylamino]-1H-pyrrolo[2,3-b]pyridin-5-yl}-2-cyclopentyl-acetamide (0.316 mmol, obtained in preceding step) in glacial HOAc (6 ml) was heated at 100° C. for 13 h. The reaction mixture was cooled to 25° C., and was concentrated under reduced pressure to afford crude 3-[4-(6-benzenesulfonyl-2-cyclopentylmethyl-6H-1,2,3,5,6-tetraaza-as-indacen-1-yl)-piperidin-1-yl]-propionitrile as a brown oil.

LCMS (Method G, ESI): RT=0.82 min, m+H=517.4. This material was used in the next step below without additional purification or characterization.

3-[4-(2-Cyclopentylmethyl-6H-1,2,3,5,6-tetraaza-as-indacen-1-yl)-piperidin-1-yl]-propionitrile Sodium hydroxide (5 ml of a 1.0 M solution in water, 10 mmol) was added to a solution of crude 3-[4-(6-benzenesulfonyl-2-cyclopentylmethyl-6H-1,2,3,5,6-tetraaza-as-indacen-1-yl)-piperidin-1-yl]-propionitrile (0.316 mmol, obtained in the preceding step) in EtOH (10 ml) at 25° C. The reaction mixture was stirred at 50° C. for 3 h, then was cooled to 25° C. and was stirred overnight. The reaction mixture was then partitioned between water (100 ml) and EtOAc (2×100 ml). The combined organic layers were dried over $MgSO_4$, filtered, and the filtrate was concentrated under reduced pressure. Purification of the residue by preparative HPLC (column: Gemini-NX, 3×10 cm, 10 um; detection: UV 230 nm, mobile phase A: water containing 0.1% $NH_4OH$; mobile phase B: $CH_3CN$; flowrate: 60 mL/min; gradient 5-95% B over 15 min) afforded 3-[4-(2-cyclopentylmethyl-6H-1,2,3,5,6-tetraaza-as-indacen-1-yl)-piperidin-1-yl]-propionitrile (0.023 g, 19% over 4 steps) as an off-white solid. LCMS (Method C, ESI): RT=2.95 min, m+H=377.2; $^1$H NMR (400 MHz, DMSO) δ 11.75 (s, 1H), 8.49 (s, 1H), 7.39 (t, J=3.0 Hz, 1H), 6.98 (s, 1H), 4.57-4.45 (m, 1H), 3.12 (d, J=11.3 Hz, 2H), 2.96 (d, J=7.5 Hz, 2H), 2.78 (t, J=6.2 Hz, 2H), 2.75-2.55 (m, 4H), 2.43-2.24 (m, 3H), 1.92-1.71 (m, 4H), 1.72-1.59 (m, 2H), 1.60-1.45 (m, 2H), 1.38-1.20 (m, 2H).

Example 117

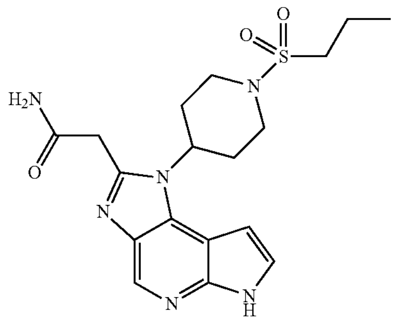 [SMILES: CCCS(=O)(=O)N1CCC(n2c(CC(N)=O)nc3cnc4[nH]ccc4c32)CC1]

2-{1-[1-(Propane-1-sulfonyl)-piperidin-4-yl]-1,6-dihydro-1,2,3,5,6-tetraaza-as-indacen-2-yl}-acetamide 4-[1-Benzenesulfonyl-5-(2-cyano-acetylamino)-1H-pyrrolo[2,3-b]pyridin-4-ylamino]-piperidine-1-carboxylic acid tert-butyl ester Cyanoacetic acid (0.134 g, 1.58 mmol), HATU (0.600 g, 1.58 mmol), and diisopropylethylamine (0.300 ml, 1.72 mmol) were added sequentially to a solution of 4-(5-amino-1-benzenesulfonyl-1H-pyrrolo[2,3-b]pyridin-4-ylamino)-piperidine-1-carboxylic acid tert-butyl ester (0.677 g, 1.44 mmol, prepared as described in Example 115) in a 6:1 mixture of $CH_2Cl_2$ and DMF (7 ml) at 25° C. The reaction mixture was stirred for 14 h at 25° C., then saturated $NaHCO_3$ (7 ml) was added and the mixture was vigorously shaken by hand for 1 min. The phases were separated using a phase separation column (Biotage) and the organic layer was concentrated under reduced pressure to give crude 4-[1-benzenesulfonyl-5-(2-cyano-acetylamino)-1H-pyrrolo[2,3-b]pyridin-4-ylamino]-piperidine-1-carboxylic acid tert-butyl ester as a brown oil. LCMS (Method G, ESI): RT=0.99 min, m+H=539.3. This material was used in the next step below without additional purification or characterization.

N-[1-Benzenesulfonyl-4-(piperidin-4-ylamino)-1H-pyrrolo[2,3-b]pyridin-5-yl]-2-cyano-acetamide (hydrochloride salt)

A 4.0 M solution of HCl in 1,4-dioxane (4 ml) was added to a solution of 4-[1-benzenesulfonyl-5-(2-cyano-acetylamino)-1H-pyrrolo[2,3-b]pyridin-4-ylamino]-piperidine-1-carboxylic acid tert-butyl ester (1.44 mmol) in 1,4-dioxane (2 ml) at 25° C. The reaction mixture was stirred at 25° C. for 1 h, then was concentrated under reduced pressure to afford crude N-[1-benzenesulfonyl-4-(piperidin-4-ylamino)-1H-pyrrolo[2,3-b]pyridin-5-yl]-2-cyano-acetamide (hydrochloride salt) as a brown solid. This material was used in the next step below without additional purification or characterization.

N-{1-Benzenesulfonyl-4-[1-(propane-1-sulfonyl)-piperidin-4-ylamino]-1H-pyrrolo[2,3-b]pyridin-5-yl}-2-cyano-acetamide Diisopropylethylamine (0.107 ml, 0.615 mmol) and 1-propanesulfonyl chloride (0.035 ml, 0.308 mmol) were added sequentially to a solution of N-[1-benzenesulfonyl-4-(piperidin-4-ylamino)-1H-pyrrolo[2,3-b]pyridin-5-yl]-2-cyano-acetamide (hydrochloride salt) (0.205 mmol) in $CH_2Cl_2$ (2 ml) at 25° C. The reaction mixture was stirred for 3 h at 25° C., then was partitioned between saturated $NaHCO_3$ (6 ml) and $CH_2Cl_2$ (2 ml). The phases were separated using a phase separation column (Biotage) and the organic layer was concentrated under reduced pressure to give crude N-{1-benzenesulfonyl-4-[1-(propane-1-sulfonyl)-piperidin-4-ylamino]-1H-pyrrolo[2,3-b]pyridin-5-yl}-2-cyano-acetamide as a brown oil/solid. LCMS (Method G, ESI): RT=0.88 min, m+H=545.3. This material was used in the next step below without additional purification or characterization.

{6-Benzenesulfonyl-1-[1-(propane-1-sulfonyl)-piperidin-4-yl]-1,6-dihydro-1,2,3,5,6-tetraaza-as-indacen-2-yl}-acetonitrile A solution of N-{1-benzenesulfonyl-4-[1-(propane-1-sulfonyl)-piperidin-4-ylamino]-1H-pyrrolo[2,3-b]pyridin-5-yl}-2-cyano-acetamide (0.205 mmol) in glacial HOAc (3 ml) was heated at 100° C. for 6 h. The reaction mixture was cooled to 25° C., and was concentrated under reduced pressure to afford crude {6-benzenesulfonyl-1-[1-(propane-1-sulfonyl)-piperidin-4-yl]-1,6-dihydro-1,2,3,5,6-tetraaza-as-indacen-2-yl}-acetonitrile as a brown oil. LCMS (Method G, ESI): RT=0.93 min, m+H=527.3. This material was used in the next step below without additional purification or characterization.

2-{1-[1-(Propane-1-sulfonyl)-piperidin-4-yl]-1,6-dihydro-1,2,3,5,6-tetraaza-as-indacen-2-yl}-acetamide Sodium hydroxide (1 ml of a 1.0 M solution in water, 1 mmol) was added to a solution of {6-benzenesulfonyl-1-[1-(propane-1-sulfonyl)-piperidin-4-yl]-1,6-dihydro-1,2,3,5,6- tetraaza-as-indacen-2-yl}-acetonitrile (0.205 mmol) in EtOH (2 ml) at 25° C. The reaction mixture was stirred at 50° C. for 5 h, then was concentrated under reduced pressure. Purification of the residue by preparative HPLC (column: Gemini-NX, 3×10 cm, 10 um; detection: UV 230 nm, mobile phase A: water containing 0.1% $NH_4OH$; mobile phase B: $CH_3CN$; flowrate: 60 mL/min; gradient 5-95% B over 15 min) afforded 2-{1-[1-(propane-1-sulfonyl)-piperidin-4-yl]-1,6-dihydro-1,2,3,5,6-tetraaza-as-indacen-2-yl}-acetamide (0.011 g, 13% over 4 steps) as an off-white solid. LCMS (Method C, ESI): RT=2.92 min, m+H=405.1; $^1H$ NMR (400 MHz, DMSO) δ 11.83 (s, 1H), 8.51 (s, 1H), 7.71 (s, 1H), 7.50 (d, J=2.6 Hz, 1H), 7.12 (s, 1H), 6.73 (d, J=2.8 Hz, 1H), 4.70 (s, 1H), 3.99 (s, 2H), 3.86 (d, J=11.5 Hz, 2H), 3.18-3.10 (m, 2H), 3.04 (t, J=11.8 Hz, 2H), 2.06 (d, J=8.9 Hz, 2H), 1.83-1.69 (m, 2H), 1.04 (t, J=7.4 Hz, 3H).

Example 118

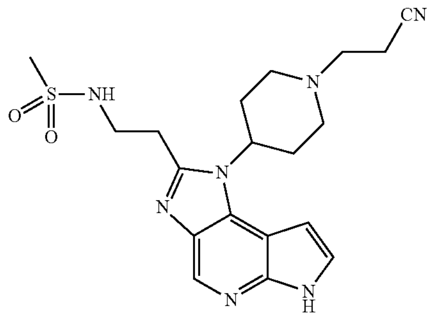 [SMILES: CS(=O)(=O)NCCc1nc2cnc3[nH]ccc3c2n1C1CCN(CCC#N)CC1]

N-(2-{1-[1-(2-Cyano-ethyl)-piperidin-4-yl]-1,6-dihydro-1,2,3,5,6-tetraaza-as-indacen-2-yl}-ethyl)-methanesulfonamide

[1-(2-Cyano-ethyl)-piperidin-4-yl]-carbamic acid tert-butyl ester

Acrylonitrile (3.6 ml, 55.0 mmol) and triethylamine (2 drops) were added sequentially to a solution of piperidin-4-yl-carbamic acid tert-butyl ester (10 g, 50.0 mmol) in ethanol (100 ml) at 25° C. The reaction mixture was stirred at 25° C. for 3.5 h, then was concentrated under reduced pressure to afford crude [1-(2-cyano-ethyl)-piperidin-4-yl]-carbamic acid tert-butyl ester as a white solid. TLC: 5% $CH_3OH$ in $CH_2Cl_2$, Rf=0.56; $^1H$ NMR (400 MHz, $CDCl_3$) δ 4.42 (s, 1H), 3.45 (s, 1H), 2.82 (d, J=11.8 Hz, 2H), 2.67 (t, J=7.0 Hz, 2H), 2.49 (t, J=7.0 Hz, 2H), 2.18 (td, J=11.5, 2.3 Hz, 2H), 1.94 (d, J=12.1 Hz, 3H), 1.51-1.36 (m, 1H), 1.44 (s, 9H). This material was used in the next step below without additional purification or characterization.

3-(4-Amino-piperidin-1-yl)-propionitrile (hydrochloride salt)

A 4.0 M solution of HCl in 1,4-dioxane (100 ml) was added to a solution of [1-(2-cyano-ethyl)-piperidin-4-yl]-carbamic acid tert-butyl ester (50.0 mmol) in 1,4-dioxane (50 ml) at 25° C. The reaction mixture was stirred at 50° C. for 5 h, then was concentrated under reduced pressure to afford crude 3-(4-amino-piperidin-1-yl)-propionitrile (hydrochloride salt) as a white solid. $^1H$ NMR (400 MHz, DMSO) δ 11.43 (s, 1H), 8.48 (s, 2H), 3.58-3.50 (m, 2H), 3.46-3.32 (m, 2H), 3.31-3.21 (m, 1H), 3.17 (t, J=7.2 Hz, 2H), 3.13-2.95 (m, 2H), 2.15 (d, J=13.5 Hz, 2H), 2.04-1.86 (m, 2H). This material was used in the next step below without additional purification or characterization.

3-[4-(1-Benzenesulfonyl-5-nitro-1H-pyrrolo[2,3-b]pyridin-4-ylamino)-piperidin-1-yl]-propionitrile A mixture of 1-benzenesulfonyl-4-chloro-5-nitro-1H-pyrrolo[2,3-b]pyridine (15.35 g, 45.5 mmol), 3-(4-amino-piperidin-1-yl)-propionitrile (hydrochloride salt) (9.48 g, 50.0 mmol), diisopropylethylamine (24.5 ml, 141 mmol) in propan-2-ol (200 ml) was heated at 80° C. for 18 h. The mixture was cooled to 25° C. and was concentrated to approximately 40 ml volume. This material was partitioned between water (2000 ml) and $CH_2Cl_2$ (3×2000 ml). The combined organic layers were dried over $MgSO_4$, filtered, and the filtrate was concentrated under reduced pressure. Purification of the residue by column chromatography on silica gel (gradient: 0 to 6% $CH_3OH$ in $CH_2Cl_2$) afforded 3-[4-(1-benzenesulfonyl-5-nitro-1H-pyrrolo[2,3-b]pyridin-4-ylamino)-piperidin-1-yl]-propionitrile (19.3 g, 93% over 3 steps) as a yellow-orange foam. LCMS (Method G, ESI): RT=0.69 min, m+H=455.3. This material was used in the next step below without additional characterization.

3-[4-(5-Amino-1-benzenesulfonyl-1H-pyrrolo[2,3-b]pyridin-4-ylamino)-piperidin-1-yl]-propionitrile A suspension of 3-[4-(1-benzenesulfonyl-5-nitro-1H-pyrrolo[2,3-b]pyridin-4-ylamino)-piperidin-1-yl]-propionitrile (19.3 g, 4.25 mmol) and palladium on carbon (3.7 g, 10%, wet, Degussa, E101 NE/W) in EtOAc (150 ml) was stirred under a hydrogen atmosphere (2-3 balloons) at 50° C. for 24 h. The reaction mixture was cooled to 25° C. then was filtered through Celite and the Celite washed with EtOAc (2×20 ml). The filtrate and washings were concentrated under reduced pressure. Purification of the residue by column chromatography on silica gel (gradient: 0 to 6% $CH_3OH$ in $CH_2Cl_2$) afforded 3-[4-(5-amino-1-benzenesulfonyl-1H-pyrrolo[2,3-b]pyridin-4-ylamino)-piperidin-1-yl]-propionitrile (13.6 g, 75%) as a grey foam. $^1H$ NMR (400 MHz, $CDCl_3$) δ 8.17-8.09 (m, 2H), 7.83 (s, 1H), 7.54 (t, J=7.4 Hz, 1H), 7.49-7.41 (m, 3H), 6.52 (d, J=4.2 Hz, 1H), 4.76 (d, J=8.4 Hz, 1H), 3.79-3.66 (m, 1H), 2.94-2.82 (m, 3H), 2.72 (t, J=6.9 Hz, 2H), 2.51 (t, J=6.9 Hz, 2H), 2.29 (td, J=11.5, 2.1 Hz, 2H), 2.12-2.00 (m, 2H), 1.58 (qd, J=10.9, 3.6 Hz, 2H). This material was used in the next step below without additional characterization.

(2-{1-Benzenesulfonyl-4-[1-(2-cyano-ethyl)-piperidin-4-ylamino]-1H-pyrrolo[2,3-b]pyridin-5-ylcarbamoyl}-ethyl)-carbamic acid 9H-fluoren-9-ylmethyl ester Fmoc-beta-Alanine (3.1 g, 9.90 mmol), HATU (3.8 g, 9.90 mmol), and diisopropylethylamine (2.1 ml, 12.0 mmol) were added sequentially to a solution of 3-[4-(5-amino-1-benzenesulfonyl-1H-pyrrolo[2,3-b]pyridin-4-ylamino)-piperidin-1-yl]-propionitrile (4.2 g, 9.90 mmol) in DMF (100 ml) at 25° C. The reaction mixture was stirred for 14 h at 25° C., then was concentrated under reduced pressure. The residue was partitioned between half-saturated $NaHCO_3$ (200 ml) and EtOAc (2×200 ml). the combined organic layers were dried over $Mg_2SO_4$, filtered, and the filtrate was concentrated under reduced pressure. Purification of the residue by column chromatography on silica gel (gradient: 0 to 7% $CH_3OH$ in $CH_2Cl_2$) afforded (2-{1-benzenesulfonyl-4-[1-(2-cyano-ethyl)-piperidin-4-ylamino]-1H-pyrrolo[2,3-b]pyridin-5-yl-carbamoyl}-ethyl)-carbamic acid 9H-fluoren-9-ylmethyl ester (6.89 g, 97%) as a white foam. LCMS (Method G, ESI): RT=0.85 min, m+H=718.5. $^1$H NMR (400 MHz, $CDCl_3$, mixture of rotamers) δ 8.14 (t, J=10.3 Hz), 7.84 (s), 7.75 (dd, J=15.2, 7.5 Hz), 7.60-7.54 (m), 7.50 (d, J=4.1 Hz), 7.44 (t, J=7.8 Hz), 7.37 (t, J=7.4 Hz), 7.28 (t, J=5.8 Hz), 6.52 (t, J=4.7 Hz), 5.50 (d, J=11.4 Hz), 4.70 (s), 4.40 (s), 4.33 (d, J=7.1 Hz), 4.19 (t, J=6.6 Hz), 3.64 (td, J=13.3, 6.7 Hz), 3.51 (d, J=21.9 Hz), 3.39 (d, J=5.4 Hz), 2.80-2.47 (m), 2.35 (s), 2.30-2.07 (m), 1.93 (d, J=12.0 Hz), 1.51 (dt, J=13.5, 6.8 Hz).

(2-{6-Benzenesulfonyl-1-[1-(2-cyano-ethyl)-piperidin-4-yl]-1,6-dihydro-1,2,3,5,6-tetraaza-as-indacen-2-yl}-ethyl)-carbamic acid 9H-fluoren-9-ylmethyl ester A solution of (2-{1-benzenesulfonyl-4-[1-(2-cyano-ethyl)-piperidin-4-yl amino]-1H-pyrrolo[2,3-b]pyridin-5-yl carbamoyl}-ethyl)-carbamic acid 9H-fluoren-9-ylmethyl ester (6.89 g, 9.60 mmol) in glacial HOAc (90 ml) was heated at 95° C. for 14 h. The reaction mixture was cooled to 25° C. and was concentrated under reduced pressure. Purification of the residue by column chromatography on silica gel (gradient: 0 to 8% $CH_3OH$ in $CH_2Cl_2$) afforded (2-{6-benzenesulfonyl-1-[1-(2-cyano-ethyl)-piperidin-4-yl]-1,6-dihydro-1,2,3,5,6-tetraaza-as-indacen-2-yl}-ethyl)-carbamic acid 9H-fluoren-9-ylmethyl ester (3.00 g, 45%) as a white foam. LCMS (Method G, ESI): RT=0.94 min, m+H=700.4. This material was used in the next step below without additional characterization.

3-{4-[2-(2-Amino-ethyl)-6-benzenesulfonyl-6H-1,2,3,5,6-tetraaza-as-indacen-1-yl]-piperidin-1-yl}-propionitrile Piperidine (2 ml, 20 mmol) was added to a solution of (2-{6-benzenesulfonyl-1-[1-(2-cyano-ethyl)-piperidin-4-yl]-1,6-dihydro-1,2,3,5,6-tetraaza-as-indacen-2-yl}-ethyl)-carbamic acid 9H-fluoren-9-ylmethyl ester (3.00 g, 4.29 mmol) in DMF (40 ml) at 25° C. The reaction mixture was stirred at 25° C. for 1 h, then was concentrated under reduced pressure. Purification of the residue by column chromatography on silica gel (5% $CH_3OH$ in $CH_2Cl_2$, then 5% $CH_3OH$ in $CH_2Cl_2$+2.0 M $NH_3$) afforded 3-{4-[2-(2-amino-ethyl)-6-benzenesulfonyl-6H-1,2,3,5,6-tetraaza-as-indacen-1-yl]-piperidin-1-yl}-propionitrile (1.23 g, 6%) as a white foam. LCMS (Method G, ESI): RT=0.47 min, m+H=478.3; $^1$H NMR (400 MHz, $CDCl_3$) δ 8.84 (s, 1H), 8.27-8.14 (m, 2H), 7.83 (d, J=4.1 Hz, 1H), 7.57-7.50 (m, 1H), 7.45 (t, J=7.6 Hz, 2H), 7.33 (s, 1H), 4.48-4.35 (m, 1H), 3.27 (t, J=6.4 Hz, 2H), 3.20-3.10 (m, 3H), 3.05 (t, J=6.4 Hz, 2H), 2.79 (t, J=6.6 Hz, 2H), 2.73-2.65 (m, 2H), 2.61 (t, J=6.6 Hz, 2H), 2.35 (td, J=12.0, 2.2 Hz, 2H), 1.94-1.83 (m, 2H).

N-(2-{6-Benzenesulfonyl-1-[1-(2-cyano-ethyl)-piperidin-4-yl]-1,6-dihydro-1,2,3,5,6-tetraaza-as-indacen-2-yl}-ethyl)-methanesulfonamide Diisopropylethylamine (0.084 ml, 0.483 mmol) and methanesulfonyl chloride (0.022 ml, 0.290 mmol) were added sequentially to a solution of 3-{4-[2-(2-amino-ethyl)-6-benzenesulfonyl-6H-1,2,3,5,6-tetraaza-as-indacen-1-yl]-piperidin-1-yl}-propionitrile (0.161 mmol) in $CH_2Cl_2$ (2 ml) at 25° C. The reaction mixture was stirred for 1.5 h at 25° C., then was partitioned between half-saturated $NaHCO_3$ (6 ml) and $CH_2Cl_2$ (3 ml). The phases were separated using a phase separation column (Biotage) and the organic layer was concentrated under reduced pressure to give crude N-(2-{6-benzenesulfonyl-1-[1-(2-cyano-ethyl)-piperidin-4-yl]-1,6-dihydro-1,2,3,5,6-tetraaza-as-indacen-2-yl}-ethyl)-methanesulfonamide as a beige solid. This material was used in the next step below without additional purification or characterization.

N-(2-{1-[1-(2-Cyano-ethyl)-piperidin-4-yl]-1,6-dihydro-1,2,3,5,6-tetraaza-as-indacen-2-yl}-ethyl)-methanesulfonamide Sodium hydroxide (0.5 ml of a 1.0 M solution in water, 0.5 mmol) was added to a solution of N-(2-{6-benzenesulfonyl-1-[1-(2-cyano-ethyl)-piperidin-4-yl]-1,6-dihydro-1,2,3,5,6-tetraaza-as-indacen-2-yl}-ethyl)-methanesulfonamide (0.161 mmol) in EtOH (2 ml) at 25° C. The reaction mixture was stirred at 50° C. for 3.5 h, then was cooled to 25° C. Aqueous 1.0 M hydrochloric acid (0.5 ml) was then added and the mixture was concentrated under reduced pressure. The residue was suspended in DMF (2 ml) and was passed through a 0.45 μM syringe filter. Purification of the resulting solution by preparative HPLC (column: Gemini-NX, 21.2×100 mm, 10 um; detection: UV 220 nm and mass, mobile phase A: water containing 0.1% $NH_4OH$; mobile phase B: $CH_3CN$; flowrate: 35 mL/min; gradient 5-85% B over 10 min) afforded N-(2-{1-[1-(2-cyano-ethyl)-piperidin-4-yl]-1,6-dihydro-1,2,3,5,6-tetraaza-as-indacen-2-yl}-ethyl)-methanesulfonamide (0.031 g, 46% over 2 steps) as an off-white solid. LCMS (Method C, ESI): RT=2.18 min, m+H=416.1; $^1$H NMR (400 MHz, DMSO) δ 11.77 (s, 1H), 8.51 (s, 1H), 7.40 (s, 1H), 7.18 (t, J=5.6 Hz, 1H), 6.97 (s, 1H), 4.58-4.45 (m, 1H), 3.47 (dd, J=12.9, 6.4 Hz, 2H), 3.19 (t, J=7.0 Hz, 2H), 3.13 (d, J=10.5 Hz, 2H), 2.94 (s, 3H), 2.78 (t, J=6.5 Hz, 2H), 2.70 (t, J=6.3 Hz, 2H), 2.60 (d, J=10.2 Hz, 2H), 2.29 (t, J=11.5 Hz, 2H), 1.91 (d, J=9.8 Hz, 2H).

Example 119

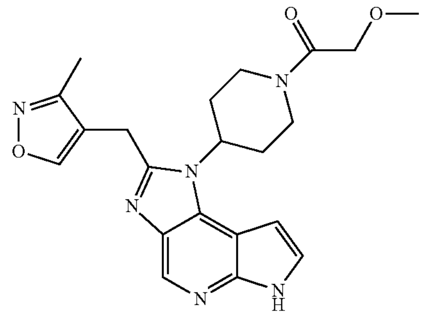 [SMILES: COCC(=O)N1CCC(n2c(Cc3conc3C)nc3cnc4[nH]ccc4c32)CC1]

2-Methoxy-1-{4-[2-(3-methyl-isoxazol-4-ylmethyl)-6H-1,2,3,5,6-tetraaza-as-indacen-1-yl]-piperidin-1-yl}-ethanone 4-{1-Benzenesulfonyl-5-[2-(3-methyl-isoxazol-4-yl)-acetylamino]-1H-pyrrolo[2,3-b]pyridin-4-ylamino}-piperidine-1-carboxylic acid tert-butyl ester 2-(3-Methylisoxazol-4-yl)acetic acid (0.223 g, 1.58 mmol), HATU (0.600 g, 1.58 mmol), and diisopropylethylamine (0.300 ml, 1.72 mmol) were added sequentially to a solution of 4-(5-amino-1-benzenesulfonyl-1H-pyrrolo[2,3-b]pyridin-4-yl amino)-piperidine-1-carboxylic acid tert-butyl ester (0.677 g, 1.44 mmol, prepared as described in Example 115) in a 6:1 mixture of $CH_2Cl_2$ and DMF (7 ml) at 25° C. The reaction mixture was stirred for 14 h at 25° C., then saturated $NaHCO_3$ (7 ml) was added and the mixture was vigorously shaken by hand for 1 min. The phases were separated using a phase separation column (Biotage) and the organic layer was concentrated under reduced pressure to give crude 4-{1-benzenesulfonyl-5-[2-(3-methyl-isoxazol-4-yl)-acetylamino]-1H-pyrrolo[2,3-b]pyridin-4-ylamino}-piperidine-1-carboxylic acid tert-butyl ester as a brown oil. LCMS (Method G, ESI): RT=0.99 min, m+H=595.4. This material was used in the next step below without additional purification or characterization.

N-[1-Benzenesulfonyl-4-(piperidin-4-ylamino)-1H-pyrrolo[2,3-b]pyridin-5-yl]-2-(3-methyl-isoxazol-4-yl)-acetamide (hydrochloride salt)

A 4.0 M solution of HCl in 1,4-dioxane (4 ml) was added to a solution of 4-{1-benzenesulfonyl-5-[2-(3-methyl-isoxazol-4-yl)-acetylamino]-1H-pyrrolo[2,3-b]pyridin-4-ylamino}-piperidine-1-carboxylic acid tert-butyl (1.44 mmol) in 1,4-dioxane (2 ml) at 25° C. The reaction mixture was stirred at 25° C. for 1 h, then was concentrated under reduced pressure to afford crude N-[1-benzenesulfonyl-4-(piperidin-4-ylamino)-1H-pyrrolo[2,3-b]pyridin-5-yl]-2-(3-methyl-isoxazol-4-yl)-acetamide (hydrochloride salt) as a brown solid. This material was used in the next step below without additional purification or characterization.

N-{1-Benzenesulfonyl-4-[1-(2-methoxy-acetyl)-piperidin-4-ylamino]-1H-pyrrolo[2,3-b]pyridin-5-yl}-2-(3-methyl-isoxazol-4-yl)-acetamide Diisopropylethylamine (0.107 ml, 0.615 mmol) and methoxyacetyl chloride (0.028 ml, 0.308 mmol) were added sequentially to a solution of N-[1-benzenesulfonyl-4-(piperidin-4-ylamino)-1H-pyrrolo[2,3-b]pyridin-5-yl]-2-(3-methyl-isoxazol-4-yl)-acetamide (hydrochloride salt) (0.205 mmol) in $CH_2Cl_2$ (2 ml) at 25° C. The reaction mixture was stirred for 3 h at 25° C., then was partitioned between saturated $NaHCO_3$ (6 ml) and $CH_2Cl_2$ (2 ml). The phases were separated using a phase separation column (Biotage) and the organic layer was concentrated under reduced pressure to give crude N-{1-benzenesulfonyl-4-[1-(2-methoxy-acetyl)-piperidin-4-ylamino]-1H-pyrrolo[2,3-b]pyridin-5-yl}-2-(3-methyl-isoxazol-4-yl)-acetamide as a brown oil/solid. LCMS (Method G, ESI): RT=0.73 min, m+H=567.3. This material was used in the next step below without additional purification or characterization.

1-{-4-[6-Benzenesulfonyl-2-(3-methyl-isoxazol-4-ylmethyl)-6H-1,2,3,5,6-tetraaza-as-indacen-1-yl]-piperidin-1-yl}-2-methoxy-ethanone A solution of N-{1-benzenesulfonyl-4-[1-(2-methoxy-acetyl)-piperidin-4-ylamino]-1H-pyrrolo[2,3-b]pyridin-5-yl}-2-(3-methyl-isoxazol-4-yl)-acetamide (0.205 mmol) in glacial HOAc (3 ml) was heated at 100° C. for 6 h. The reaction mixture was cooled to 25° C., and was concentrated under reduced pressure to afford crude 1-{-4-[6-benzenesulfonyl-2-(3-methyl-isoxazol-4-ylmethyl)-6H-1,2,3,5,6-tetraaza-as-indacen-1-yl]-piperidin-1-yl}-2-methoxy-ethanone as a brown oil. LCMS (Method G, ESI): RT=0.77 min, m+H=549.3. This material was used in the next step below without additional purification or characterization.

2-Methoxy-1-{4-[2-(3-methyl-isoxazol-4-ylmethyl)-6H-1,2,3,5,6-tetraaza-as-indacen-1-yl]-piperidin-1-yl}-ethanone Sodium hydroxide (1 ml of a 1.0 M solution in water, 1 mmol) was added to a solution of 1-{4-[6-benzenesulfonyl-2-(3-methyl-isoxazol-4-ylmethyl)-6H-1,2,3,5,6-tetraaza-as-indacen-1-yl]-piperidin-1-yl}-2-methoxy-ethanone (0.205 mmol) in EtOH (2 ml) at 25° C. The reaction mixture was stirred at 50° C. for 5 h, then was concentrated under reduced pressure. Purification of the residue by preparative HPLC (column: Gemini-NX, 21.2×100 mm, 10 um; detection: UV 254 nm and mass, mobile phase A: water containing 0.1% $NH_4OH$; mobile phase B: $CH_3CN$; flowrate: 35 mL/min; gradient 10-90% B over 23 min) afforded 2-methoxy-1-{4-[2-(3-methyl-isoxazol-4-ylmethyl)-6H-1,2,3,5,6-tetraaza-as-indacen-1-yl]-piperidin-1-yl}-ethanone (0.0079 g, 9.4% over 4 steps) as an off-white solid. LCMS (Method C, ESI): RT=2.87 min, m+H=409.1; $^1$H NMR (400 MHz, DMSO) δ 11.88 (s, 1H), 8.53 (s, 1H), 7.46 (s, J=11.1 Hz, 1H), 6.43 (s, 1H), 6.31 (s, 1H), 4.95-4.79 (m, 1H), 4.68 (s, 2H), 4.60 (t, J=14.6 Hz, 1H), 4.22 (dd, J=46.2, 14.1 Hz, 2H), 4.02 (d, J=16.0 Hz, 1H), 3.39 (s, 3H), 2.85-2.73 (m, 1H), 2.44-2.33 (m, 3H), 2.21 (s, 3H), 1.84 (d, J=10.4 Hz, 2H).

Example 120

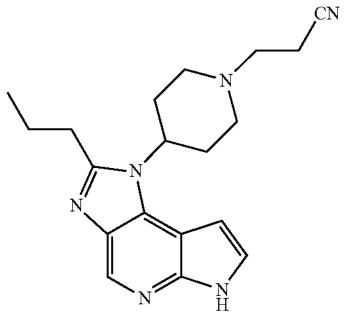 [SMILES: CCCc1nc2cnc3[nH]ccc3c2n1C1CCN(CCC#N)CC1]

3-[4-(2-Propyl-6H-1,2,3,5,6-tetraaza-as-indacen-1-yl)-piperidin-1-yl]-propionitrile N-{1-Benzenesulfonyl-4-[1-(2-cyano-ethyl)-piperidin-4-ylamino]-1H-pyrrolo[2,3-b]pyridin-5-yl}-butyramide Butyric acid (0.029 ml, 0.321 mmol), diisopropylethylamine (0.065 ml, 0.375 mmol), and HATU (0.122 g, 0.321 mmol) were added sequentially to a solution of 3-[4-(5-amino-1-benzenesulfonyl-1H-pyrrolo[2,3-b]pyridin-4-ylamino)-piperidin-1-yl]-propionitrile (0.130 g, 0.306 mmol, prepared as described in Example 118) in a 4:1 mixture of $CH_2Cl_2$ and DMF (5 ml) at 25° C. The reaction mixture was stirred for 15 h at 25° C., then was partitioned between saturated $NaHCO_3$ (6 ml) and $CH_2Cl_2$ (2 ml). The phases were separated using a phase separation column (Biotage) and the organic layer was concentrated under reduced pressure to give crude N-{1-benzenesulfonyl-4-[1-(2-cyano-ethyl)-piperidin-4-ylamino]-1H-pyrrolo[2,3-b]pyridin-5-yl}-butyramide as a brown oil. LCMS (Method G, ESI): RT=0.59 min, m+H=495.3. This material was used in the next step below without additional purification or characterization.

3-[4-(6-Benzenesulfonyl-2-propyl-6H-1,2,3,5,6-tetraaza-as-indacen-1-yl)-piperidin-1-yl]-propionitrile A solution of N-{1-benzenesulfonyl-4-[1-(2-cyano-ethyl)-piperidin-4-ylamino]-1H-pyrrolo[2,3-b]pyridin-5-yl}-butyramide (0.306 mmol) in glacial HOAc (3 ml) was heated at 95° C. for 13 h. The reaction mixture was cooled to 25° C., and was concentrated under reduced pressure to afford crude 3-[4-(6-benzenesulfonyl-2-propyl-6H-1,2,3,5,6-tetraaza-as-indacen-1-yl)-piperidin-1-yl]-propionitrile as a brown oil. LCMS (Method G, ESI): RT=0.66 min, m+H=477.3. This material was used in the next step below without additional purification or characterization.

3-[4-(2-Propyl-6H-1,2,3,5,6-tetraaza-as-indacen-1-yl)-piperidin-1-yl]-propionitrile Sodium hydroxide (3 ml of a 1.0 M solution in water, 3 mmol) was added to a solution of crude 3-[4-(6-benzenesulfonyl-2-propyl-6H-1,2,3,5,6-tetraaza-as-indacen-1-yl)-piperidin-1-yl]-propionitrile (0.306 mmol) in EtOH (2 ml) at 25° C. The reaction mixture was stirred at 50° C. for 5 h, then was cooled to 25° C. and stirred overnight. The mixture was concentrated under reduced pressure and the residue was purified by preparative HPLC (column: Gemini-NX, 21.2×100 mm, 10 um; detection: UV 254 nm and mass, mobile phase A: water containing 0.1% $NH_4OH$; mobile phase B: $CH_3CN$; flowrate: 35 mL/min; gradient 5-85% B over 10 min) to give 3-[4-(2-propyl-6H-1,2,3,5,6-tetraaza-as-indacen-1-yl)-piperidin-1-yl]-propionitrile (0.015 g, 14.5% over 3 steps) as an off-white solid. LCMS (Method C, ESI): RT=2.45 min, m+H=337.1; $^1$H NMR (400 MHz, DMSO) δ 11.73 (s, 1H), 8.49 (s, J=13.7 Hz, 1H), 7.38 (s, 1H), 6.97 (s, 1H), 4.55-4.44 (m, 1H), 3.12 (d, J=11.0 Hz, 2H), 2.94 (t, J=7.5 Hz, 2H), 2.78 (t, J=6.4 Hz, 2H), 2.71 (t, J=6.2 Hz, 2H), 2.66-2.55 (m, 2H), 2.31 (t, J=11.2 Hz, 2H), 1.90-1.76 (m, 4H), 1.02 (t, J=7.4 Hz, 3H).

Example 121 and 121a

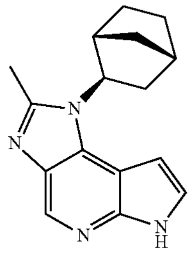

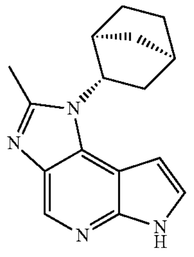

1-Bicyclo[2.2.1]hept-2-yl-2-methyl-1,6-dihydro-1,2,3,5,6-tetraaza-as-indacene (1-Benzenesulfonyl-5-nitro-1H-pyrrolo[2,3-b]pyridin-4-yl)-bicyclo[2.2.1]hept-2-yl-amine A mixture of 1-benzenesulfonyl-4-chloro-5-nitro-1H-pyrrolo[2,3-b]pyridine (0.92 g, 2.7 mmol), bicyclo[2.2.1]hept-2-ylamine (0.36 ml, 3.0 mmol), diisopropylethylamine (0.62 ml, 3.5 mmol) in propan-2-ol (12 ml) was heated at 110° C. in a microwave reactor for 20 min. The mixture was then cooled to 25° C. and was partitioned between water (200 ml) and EtOAc (2×200 ml). The combined organic layers were dried over $MgSO_4$, filtered, and the filtrate was concentrated under reduced pressure. Purification of the resulting yellow oil by column chromatography on silica gel (gradient: 0 to 60% EtOAc in heptanes) afforded (1-benzenesulfonyl-5-nitro-1H-pyrrolo[2,3-b]pyridin-4-yl)-bicyclo[2.2.1]hept-2-yl-amine (1.1 g, 98%) as a yellow solid. TLC: 50% EtOAc in heptanes; Rf=0.66). This material was used in the next step below without additional characterization.

1-Benzenesulfonyl-N-4-bicyclo[2.2.1]hept-2-yl-1H-pyrrolo[2,3-b]pyridine-4,5-diamine A suspension of (1-benzenesulfonyl-5-nitro-1H-pyrrolo[2,3-b]pyridin-4-yl)-bicyclo[2.2.1]hept-2-yl-amine (1.1 g, 2.7 mmol) and palladium on carbon (0.30 g, 10%, wet, Degussa, E101 NE/W) in a 2:1 mixture of THF and ethanol (60 ml) was stirred under a hydrogen atmosphere (2 balloons) at 50° C. for 24 h. The reaction mixture was cooled to 25° C., filtered through Celite, and the Celite was washed with THF (2×20 ml). The filtrate and washings were concentrated under reduced pressure to afford crude 1-benzenesulfonyl-N-4-bicyclo[2.2.1]hept-2-yl-1H-pyrrolo[2,3-b]pyridine-4,5-diamine as an orange-brown oil. This material was used in the next step below without further purification or characterization.

6-Benzenesulfonyl-1-bicyclo[2.2.1]hept-2-yl-2-methyl-1,6-dihydro-1,2,3,5,6-tetraaza-as-indacene p-Toluenesulfonic acid monohydrate (0.56 g, 3.0 mmol) was added to a solution of the crude material obtained in the previous step and triethyl orthoacetate (1.2 ml, 6.7 mmol) in toluene (100 ml) at 25° C. The reaction mixture was heated at 100° C. for 7 h, then was cooled to 25° C. and partitioned between half-saturated $NaHCO_3$ (100 ml) and EtOAc (2×100 ml). The organic layers were dried over $MgSO_4$, filtered, and the filtrate was concentrated under reduced pressure. Purification of the resulting solid by column chromatography on silica gel (gradient: 0 to 6% $CH_3OH$ in $CH_2Cl_2$) afforded 6-benzenesulfonyl-1-bicyclo[2.2.1]hept-2-yl-2-methyl-1,6-dihydro-1,2,3,5,6-tetraaza-as-indacene (0.71 g, 65% over two steps) as an off-white solid. LCMS (Method G, ESI): RT=1.02 min, m+H=407.3. This material was used in the next step below without further characterization.

1-Bicyclo[2.2.1]hept-2-yl-2-methyl-1,6-dihydro-1,2,3,5,6-tetraaza-as-indacene

Sodium hydroxide (10 ml of a 1.0 M solution in water, 10 mmol) was added to a solution of 6-benzenesulfonyl-1-bicyclo[2.2.1]hept-2-yl-2-methyl-1,6-dihydro-1,2,3,5,6-tetraaza-as-indacene (0.71 g, 1.75 mmol) in a 1:1 mixture of THF and EtOH (30 ml) at 25° C. The reaction mixture was stirred at 50° C. for 2 h, then was cooled to 25° C. and partitioned between 0.5 M aqueous HCl (100 ml) and EtOAc (2×200 ml). The aqueous phase was subsequently partitioned between saturated $NaHCO_3$ (120 ml) and EtOAc (2×200 ml). The organic layers were dried over $MgSO_4$, filtered, and the filtrate was concentrated under reduced pressure to afford a white solid (0.470 g). Half of this material was triturated with DMF (2 ml), filtered, and the collected solid was washed with $Et_2O$ (2×4 ml) and air dried to afford racemic 1-bicyclo[2.2.1]hept-2-yl-2-methyl-1,6-dihydro-1,2,3,5,6-tetraaza-as-indacene (0.053 g, 23%). LCMS (Method G, ESI): RT=0.62 min, m+H=267.1 (68275-121); $^1$H NMR (400 MHz, DMSO) δ 11.75 (s, 1H), 8.45 (s, 1H), 7.42 (t, J=2.9 Hz, 1H), 6.60-6.56 (m, 1H), 4.66 (dd, J=8.7, 3.9 Hz, 1H), 2.67 (s, 3H), 2.62-2.54 (m, 2H), 2.49-2.41 (m, 1H), 2.10-2.00 (m, 1H), 1.91 (d, J=10.2 Hz, 1H), 1.74-1.56 (m, 2H), 1.51 (t, J=10.1 Hz, 1H), 1.37 (dd, J=19.1, 9.7 Hz, 2H). Purification of the other half of the collected solid by chiral SFC (column: Phenomenex Lux Cellulose-1, 21.2×250 mm, 5 um; detection: UV 230 nm, mobile phase: 1:3 $CH_3OH$:$CO_2$; flowrate: 60 g/min; runtime: 6 min) afforded separate pure enantiomers of the title compound.

Example 122

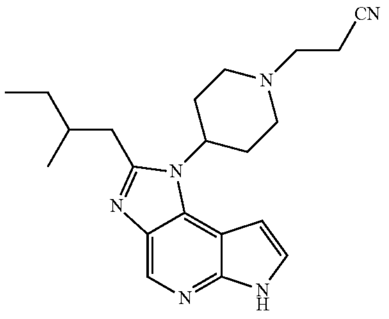 [SMILES: CCC(C)Cc1nc2cnc3[nH]ccc3c2n1C1CCN(CCC#N)CC1]

Racemic

3-{4-[2-(2-Methyl-butyl)-6H-1,2,3,5,6-tetraaza-as-indacen-1-yl]-piperidin-1-yl}-propionitrile 3-Methyl-pentanoic acid {1-benzenesulfonyl-4-[1-(2-cyano-ethyl)-piperidin-4-ylamino]-1H-pyrrolo[2,3-b]pyridin-5-yl}-amide Racemic 3-methylpentanoic acid (0.180 ml, 1.4 mmol), HATU (0.53 g, 1.4 mmol), and diisopropylethylamine (0.46 ml, 2.7 mmol), were added sequentially to a solution of 3-[4-(5-amino-1-benzenesulfonyl-1H-pyrrolo[2,3-b]pyridin-4-ylamino)-piperidin-1-yl]-propionitrile (0.54 g, 1.3 mmol, prepared as described in Example 118) in DMF (20 ml) at 25° C. The reaction mixture was stirred for 4 h at 25° C., then was concentrated under reduced pressure. The residue was partitioned between half-saturated $NaHCO_3$ (100 ml) and EtOAc (2×200 ml). The organic layers were dried over $MgSO_4$, filtered, and the filtrate was concentrated under reduced pressure. Purification of the residue by column chromatography on silica gel (gradient: 0 to 8% $CH_3OH$ in $CH_2Cl_2$) afforded 3-methyl-pentanoic acid {1-benzenesulfonyl-4-[1-(2-cyano-ethyl)-piperidin-4-ylamino]-1H-pyrrolo[2,3-b]pyridin-5-yl}-amide (0.706 g, 110%) as an off-white solid. LCMS (Method G, ESI): RT=0.73 min, m+H=523.4. This material was used in the next step below without further characterization.

3-{-4-[6-Benzenesulfonyl-2-(2-methyl-butyl)-6H-1,2,3,5,6-tetraaza-as-indacen-1-yl]-piperidin-1-yl}-propionitrile A solution of {1-benzenesulfonyl-4-[1-(2-cyano-ethyl)-piperidin-4-ylamino]-1H-pyrrolo[2,3-b]pyridin-5-yl}-amide (0.300 g, 0.574 mmol) in glacial HOAc (8 ml) was heated at 95° C. for 14 h. The reaction mixture was cooled to 25° C., and was concentrated under reduced pressure. The residue was partitioned between half-saturated $NaHCO_3$ (100 ml) and EtOAc (2×100 ml). The organic layers were dried over $MgSO_4$, filtered, and the filtrate was concentrated under reduced pressure. Purification of the residue by column chromatography on silica gel (gradient: 0 to 6% $CH_3OH$ in $CH_2Cl_2$) afforded 3-{-4-[6-benzenesulfonyl-2-(2-methyl-butyl)-6H-1,2,3,5,6-tetraaza-as-indacen-1-yl]-piperidin-1-yl}-propionitrile (0.051 g, 18%) as colorless foam. LCMS (Method G, ESI): RT=0.83 min, m+H=505.3. This material was used in the next step below without further characterization.

3-{4-[2-(2-Methyl-butyl)-6H-1,2,3,5,6-tetraaza-as-indacen-1-yl]-piperidin-1-yl}-propionitrile Sodium hydroxide (1.5 ml of a 1.0 M solution in water, 1.5 mmol) was added to a solution of 3-{4-[6-benzenesulfonyl-2-(2-methyl-butyl)-6H-1,2,3,5,6-tetraaza-as-indacen-1-yl]-piperidin-1-yl}-propionitrile (0.051 g, 1.0 mmol) in a 1:1 mixture of THF and EtOH (4 ml) at 25° C. The reaction mixture was stirred at 50° C. for 2 h, then was cooled to 25° C. and concentrated under reduced pressure. $CH_3OH$ (20 ml) was added to the resulting solid and the mixture was concentrated under reduced pressure. The solid thus obtained was suspended in DMF (1.5 ml) and the resulting mixture was filtered through a 0.45 μM syringe filter. The filtrate was purified by preparative HPLC (column: Gemini-NX, 21.2×100 mm, 10 um; detection: UV 254 nm and mass, mobile phase A: water containing 0.1% formic acid; mobile phase B: $CH_3CN$; flowrate: 35 mL/min; gradient 5-85% B over 9.5 min) to give 3-{4-[2-(2-methyl-butyl)-6H-1,2,3,5,6-tetraaza-as-indacen-1-yl]-piperidin-1-yl}-propionitrile (0.0087 g, 23% over 2 steps) as an off-white solid. LCMS (Method C, ESI): RT=2.85 min, m+H=365.2; $^1$H NMR (400 MHz, DMSO) δ 11.73 (s, 1H), 8.49 (s, 1H), 8.17 (s, 1H), 7.39 (t, J=2.9 Hz, 1H), 6.98 (s, 1H), 4.56-4.42 (m, 1H), 3.13 (d, J=10.6 Hz, 3H), 2.96 (dd, J=15.0, 6.4 Hz, 1H), 2.78 (t, J=7.2 Hz, 3H), 2.74-2.57 (m, 4H), 2.30 (t, J=11.4 Hz, 2H), 1.98-1.88 (m, 1H), 1.83 (d, J=11.3 Hz, 2H), 1.52-1.41 (m, 1H), 1.33-1.22 (m, 1H), 0.92 (dd, J=14.6, 7.1 Hz, 6H).

Example 123

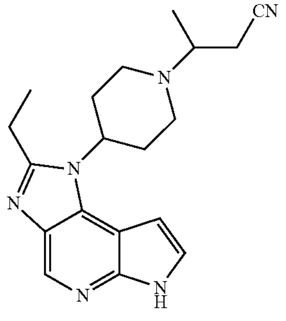

racemic

3-[4-(2-Ethyl-6H-1,2,3,5,6-tetraaza-as-indacen-1-yl)-piperidin-1-yl]-butyronitrile

[1-(2-Cyano-1-methyl-ethyl)-piperidin-4-yl]-carbamic acid tert-butyl ester (E)-but-2-enenitrile (4.5 ml, 55.0 mmol) and triethylamine (2 drops) were added sequentially to a solution of piperidin- 4-yl-carbamic acid tert-butyl ester (10 g, 50.0 mmol) in ethanol (120 ml) at 25° C. The reaction mixture was stirred at 60° C. for 1 week, then was cooled to 25° C. and concentrated under reduced pressure to afford crude [1-(2-cyano-1-methyl-ethyl)-piperidin-4-yl]-carbamic acid tert-butyl ester as tan oil. $^1$H NMR (400 MHz, $CDCl_3$) δ 4.48 (s, 1H), 3.42 (s, 1H), 3.09-2.95 (m, 1H), 2.81-2.61 (m, 3H), 2.49 (dd, J=16.7, 6.0 Hz, 2H), 2.39-2.23 (m, 3H), 1.94 (d, J=11.6 Hz, 2H), 1.44 (s, 9H), 1.18 (d, J=6.7 Hz, 3H). This material was used in the next step below without additional purification or characterization.

3-(4-Amino-piperidin-1-yl)-butyronitrile (hydrochloride salt)

A 4.0 M solution of HCl in 1,4-dioxane (100 ml) was added to a solution of [1-(2-cyano-1-methyl-ethyl)-piperidin-4-yl]-carbamic acid tert-butyl ester (50.0 mmol) in 1,4-dioxane (50 ml) at 25° C. The reaction mixture was stirred at 45° C. for 3.5 h, then was cooled to 25° C. and concentrated under reduced pressure to afford crude 3-(4-amino-piperidin-1-yl)-butyronitrile (hydrochloride salt) as a beige solid. $^1$H NMR (400 MHz, DMSO) δ 8.52 (s, 2H), 4.21 (s, 2H), 3.83-3.68 (m, 1H), 3.49-3.25 (m, 2H), 3.17 (dd, J=16.9, 8.0 Hz, 1H), 2.23-1.99 (m, 2H), 1.42 (d, J=6.7 Hz, 1H). This material was used in the next step below without additional purification or characterization.

3-[4-(1-Benzenesulfonyl-5-nitro-1H-pyrrolo[2,3-b]pyridin-4-ylamino)-piperidin-1-yl]-butyronitrile A mixture of 1-benzenesulfonyl-4-chloro-5-nitro-1H-pyrrolo[2,3-b]pyridine (15.33 g, 45.4 mmol), 3-(4-amino-piperidin-1-yl)-butyronitrile (hydrochloride salt) (50.0 mmol), diisopropylethylamine (24.5 ml, 141 mmol) in propan-2-ol (200 ml) was heated at 80° C. for 18 h. The mixture was cooled to 25° C. and was concentrated to approximately 25 ml volume. This material was partitioned between water (200 ml) and $CH_2Cl_2$ (2×200 ml). The combined organic layers were dried over $MgSO_4$, filtered, and the filtrate was concentrated under reduced pressure. Purification of the residue by column chromatography on silica gel (gradient: 0 to 6% $CH_3OH$ in $CH_2Cl_2$) afforded 3-[4-(1-benzenesulfonyl-5-nitro-1H-pyrrolo[2,3-b]pyridin-4-ylamino)-piperidin-1-yl]-butyronitrile (11.3 g, 53% over 3 steps) as a yellow-orange foam. LCMS (Method G, ESI): RT=0.70 min, m+H=469.3. This material was used in the next step below without additional characterization.

3-[4-(5-Amino-1-benzenesulfonyl-1H-pyrrolo[2,3-b]pyridin-4-ylamino)-piperidin-1-yl]-butyronitrile A suspension of 3-[4-(1-benzenesulfonyl-5-nitro-1H-pyrrolo[2,3-b]pyridin-4-ylamino)-piperidin-1-yl]-butyronitrile (11.3 g, 24.1 mmol) and palladium on carbon (3.2 g, 10%, wet, Degussa, E101 NE/W) in EtOAc (150 ml) was stirred under a hydrogen atmosphere (2-3 balloons) at 50° C. for 14 h. The reaction mixture was cooled to 25° C. then was filtered through Celite and the Celite was washed with EtOAc (2×20 ml). The filtrate and washings were concentrated under reduced pressure. Purification of the residue by column chromatography on silica gel (gradient: 0 to 8% $CH_3OH$ in $CH_2Cl_2$) afforded 3-[4-(5-amino-1-benzenesulfonyl-1H-pyrrolo[2,3-b]pyridin-4-ylamino)-piperidin-1-yl]-butyronitrile (6.51 g, 61%) as a grey foam. TLC: 5% $CH_3OH$ in $CH_2Cl_2$, Rf=0.40; $^1$H NMR (400 MHz, $CDCl_3$) δ 8.12 (d, J=7.8 Hz, 2H), 7.81 (s, 1H), 7.56-7.49 (m, 1H), 7.48-7.39 (m, 3H), 6.52 (d, J=4.2 Hz, 1H), 4.74 (d, J=8.5 Hz, 1H), 3.75-3.63 (m, 1H), 3.13-3.00 (m, 1H), 2.90-2.69 (m, 3H), 2.51 (dd, J=16.7, 6.3 Hz, 1H), 2.45-2.32 (m, 3H), 2.06 (d, J=10.9 Hz, 2H), 1.61-1.46 (m, 2H), 1.19 (d, J=6.7 Hz, 3H).

N-{1-Benzenesulfonyl-4-[1-(2-cyano-1-methyl-ethyl)-piperidin-4-ylamino]-1H-pyrrolo[2,3-b]pyridin-5-yl}-propionamide Propionic acid (0.0176 ml, 0.320 mmol), HATU (0.122 g, 0.320 mmol), and diisopropylethylamine (0.062 ml, 0.358 mmol) were added sequentially to a solution of 3-[4-(5-amino-1-benzenesulfonyl-1H-pyrrolo[2,3-b]pyridin-4-ylamino)-piperidin-1-yl]-butyronitrile (0.134 g, 0.305 mmol) in a 4:1 mixture of $CH_2Cl_2$ and DMF (5 ml) at 25° C. The reaction mixture was stirred for 14 h at 25° C., then was partitioned between saturated $NaHCO_3$ (4 ml) and $CH_2Cl_2$ (3 ml). The phases were separated using a phase separator column (Biotage) and the organic layer was concentrated under reduced pressure to afford crude N-{1-benzenesulfonyl-4-[1-(2-cyano-1-methyl-ethyl)-piperidin-4-ylamino]-1H-pyrrolo[2,3-b]pyridin-5-yl}-propionamide as a brown oil. LCMS (Method G, ESI): RT=0.60 min, m+H=495.3. This material was used in the next step below without additional purification or characterization.

3-[4-(6-Benzenesulfonyl-2-ethyl-6H-1,2,3,5,6-tetraaza-as-indacen-1-yl)-piperidin-1-yl]-butyronitrile A solution of N-{1-benzenesulfonyl-4-[1-(2-cyano-1-methyl-ethyl)-piperidin-4-ylamino]-1H-pyrrolo[2,3-b]pyridin-5-yl}-propionamide (0.305 mmol) in glacial HOAc (3 ml) was heated at 95° C. for 14 h. The reaction mixture was cooled to 25° C., and was concentrated under reduced pressure to afford crude 3-[4-(6-benzenesulfonyl-2-ethyl-6H-1,2,3,5,6-tetraaza-as-indacen-1-yl)-piperidin-1-yl]-butyronitrile as a brown oil. LCMS (Method G, ESI): RT=0.69 min, m+H=477.3. This material was used in the next step below without additional purification or characterization.

3-[4-(2-Ethyl-6H-1,2,3,5,6-tetraaza-as-indacen-1-yl)-piperidin-1-yl]-butyronitrile Sodium hydroxide (3 ml of a 1.0 M solution in water, 2 mmol) was added to a solution of 3-[4-(6-benzene sulfonyl-2-ethyl-6H-1,2,3,5,6-tetraaza-as-indacen-1-yl)-piperidin-1-yl]-butyronitrile (0.305 mmol) in EtOH (2 ml) at 25° C. The reaction mixture was stirred at 50° C. for 5 h, then was cooled to 25° C. 1.0 M Aqueous hydrochloric acid (2 ml) and saturated $NaHCO_3$ (0.5 ml) were added sequentially and the mixture was concentrated under reduced pressure. The solid thus obtained was suspended in DMF (2 ml) and the resulting mixture was filtered through a 0.45 μM syringe filter. The filtrate was purified by preparative HPLC (column: Gemini-NX, 21.2×100 mm, 10 um; detection: UV 220 nm and mass, mobile phase A: water containing 0.1% $NH_4OH$; mobile phase B: $CH_3CN$; flowrate: 35 mL/min; gradient 5-85% B over 9.5 min) to give 3-[4-(2-ethyl-6H-1,2,3,5,6-tetraaza-as-indacen-1-yl)-piperidin-1-yl]-butyronitrile (0.015 g, 15% over 4 steps) as an off-white solid. LCMS (Method C, ESI): RT=2.39 min, m+H=337.1; $^1$H NMR (400 MHz, DMSO) δ 11.74 (s, 1H), 8.49 (s, 1H), 7.36-7.34 (m, 1H), 7.05 (s, 1H), 4.53-4.39 (m, 1H), 3.21-3.11 (m, 1H), 3.07-2.93 (m, 3H), 2.78 (dd, J=16.9, 8.1 Hz, 1H), 2.68 (dd, J=16.9, 6.1 Hz, 1H), 2.63-2.55 (m, 2H), 2.46-2.36 (m, 1H), 1.90-1.83 (m, 1H), 1.34 (t, J=7.4 Hz, 2H), 1.10 (t, J=6.6 Hz, 3H).

Example 124

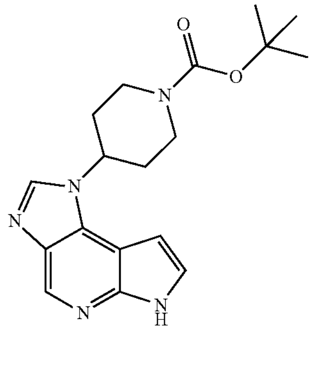 [SMILES: CC(C)(C)OC(=O)N1CCC(n2cnc3cnc4[nH]ccc4c32)CC1]

4-(6H-1,2,3,5,6-Tetraaza-as-indacen-1-yl)-piperidine-1-carboxylic acid tert-butyl ester A mixture of 1-piperidin-4-yl-1,6-dihydro-1,2,3,5,6-tetraaza-as-indacene (100 mg, 0.41 mmol), BOC anhydride (91 mg, 0.41 mmol) and triethylamine (42 μL, 0.41 mmol) in DCE (5 mL) and DMF (5 drops) was stirred at ambient temperature for 16 hours. The reaction mixture was concentrated under vacuum and purified by column chromatography on silica gel (gradient: 0 to 10% 2M $NH_3$ in methanol solution in DCM) to afford 106 mg (75%) of 4-(6H-1,2,3,5,6-tetraaza-as-indacen-1-yl)-piperidine-1-carboxylic acid tert-butyl ester. LCMS (Method A, ESI): RT=3.12 min, m+H=342.2; $^1$H NMR (400 MHz, DMSO-d6) δ: 11.86 (s, 1H), 8.58 (s, 1H), 8.31 (s, 1H), 7.47 (t, 1H), 6.76 (dd, 1H), 4.84-4.74 (m, 1H), 4.11 (m, 2H), 3.11 (br s, 2H) 2.12 (d, 2H), 1.99 (qd, 2H), 1.45 (s, 9H).

Example 125

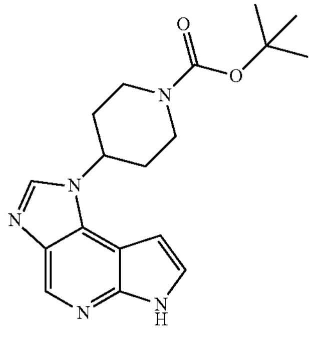 [SMILES: CC(C)(C)OC(=O)N1CCC(n2cnc3cnc4[nH]ccc4c32)CC1]

4-(6H-1,2,3,5,6-Tetraaza-as-indacen-1-yl)-piperidine-1-carboxylic acid tert-butyl ester 4-(1-Benzenesulfonyl-5-nitro-1H-pyrrolo[2,3-b]pyridine-4-ylamino)-piperidine-1-carboxylic acid tert-butyl ester A stirred mixture of 1-benzenesulfonyl-4-chloro-5-nitro-1H-pyrrolo[2,3-b]pyridine (23.8 g, 70.5 mmol), 1-BOC-4-aminopiperidine (15.5 g, 77.5 mmol) and diisopropylethylamine (17.0 mL, 98.7 mmol) in propan-2-ol (250 mL) was heated to reflux for approximately 2 hours. After cooling, the resulting suspension was filtered and the solid washed with propan-2-ol and diethyl ether, then air dried to afford 33.6 g (95%) of 4-(1-benzenesulfonyl-5-nitro-1H-pyrrolo[2,3-b]pyridine-4-ylamino)-piperidine-1-carboxylic acid tert-butyl ester as a yellow solid. $^1$H NMR (400 MHz, $CDCl_3$) δ: 9.12 (br d, 1H), 9.09 (s, 1H), 8.21 (m, 2H), 7.66 (m, 2H), 7.53 (t, 2H), 6.69 (d, 1H), 4.14 (m, 1H), 4.01 (d, 2H), 3.12 (t, 2H), 2.11-2.08 (m, 2H), 1.65-1.64 (m, 2H), 1.48 (s, 9H).

4-(5-Amino-1-benzenesulfonyl-1H-pyrrolo[2,3-b]pyridine-4-ylamino)-piperidine-1-carboxylic acid tert-butyl ester Palladium hydroxide (20% wt on carbon, 2.2 g) was added to a solution of 4-(1-benzenesulfonyl-5-nitro-1H-pyrrolo[2,3-b]pyridine-4-ylamino)-piperidine-1-carboxylic acid tert-butyl ester (22.0 g, 43.9 mmol) in acetic acid (220 mL) under nitrogen. The reaction was evacuated and purged with hydrogen and the reaction warmed to 50° C. for 8 hours. The reaction vessel was recharged with hydrogen gas and stirred at room temperature for 18 hours. The mixture was then filtered through Celite® and the filtrate concentrated to dryness under vacuum. The resulting residue was partitioned between DCM and sodium hydrogen carbonate (sat. aq.), the organic layer dried with sodium sulphate and concentrated under vacuum. The residues were triturated with methanol, filtered, washed with diethyl ether and air dried to afford 16.9 g (82%) of 4-(5-amino-1-benzenesulfonyl-1H-pyrrolo[2,3-b]pyridine-4-ylamino)-piperidine-1-carboxylic acid tert-butyl ester. $^1$H NMR (400 MHz, $CDCl_3$) δ: 8.14 (dd, 2H), 7.85 (s, 1H), 7.54 (m, 1H), 7.49 (d, 1H), 7.45 (m, 2H), 6.52 (d, 1H), 4.80 (br s, 1H), 4.05 (s, 2H), 3.86 (m, 1H), 2.97 (t, 2H), 2.61 (m, 2H), 2.03 (d, 2H), 1.46 (s, 9H).

4-(6-Benzenesulfonyl-6H-1,2,3,5,6-tetraaza-as-indacen-1-yl)-piperidine-1-carboxylic acid tert-butyl ester A solution of 4-(5-amino-1-benzenesulfonyl-1H-pyrrolo[2,3-b]pyridin-4-ylamino)-piperidine-1-carboxylic acid tert-butyl ester (8.00 g, 17.0 mmol) and triethyl orthoformate (10.0 g, 67.8 mmol) in acetic acid (75 mL) was heated to 120° C. for 2 hours. After cooling, the mixture was concentrated in vacuo and the resulting residue dissolved in ethyl acetate and washed with sodium hydrogen carbonate (sat. aq.). The aqueous layer was then extracted with ethyl acetate to recover any remaining product. The combined organic extracts were dried with sodium sulfate and concentrated under vacuum. The residue was triturated (MeOH) affording 6.80 g (83%) of 4-(6-benzenesulfonyl-6H-1,2,3,5,6-tetraaza-as-indacen-1-yl)-piperidine-1-carboxylic acid tert-butyl ester as a white solid. $^1$H NMR (400 MHz, $CDCl_3$) δ: 8.93 (s, 1H), 8.24 (m, 2H), 8.01 (s, 1H), 7.77 (d, 1H), 7.59-7.45 (m, 3H), 6.74 (d, 1H), 4.56 (m, 1H), 4.40 (br s, 2H), 2.98 (br m, 2H), 2.23 (m, 2H), 2.05 (m, 2H), 1.51 (s, 9H).

4-(6H-1,2,3,5,6-Tetraaza-as-indacen-1-yl)-piperidine-1-carboxylic acid tert-butyl ester A suspension of 4-(6-benzenesulfonyl-6H-1,2,3,5,6-tetraaza-as-indacen-1-yl)-piperidine-1-carboxylic acid tert-butyl ester (7.00 g, 14.5 mmol) in methanol (35 mL) was treated with sodium hydroxide (2.90 g, 72.5 mmol) in water (10 mL). The mixture was stirred at 50° C. for 2 hours. After cooling, the mixture was concentrated in vacuo and then triturated (water) to provide a solid which was air dried and then dried in vacuo at 60° C. for 18 h. Providing 4.43 g (89%) of 4-(6H-1,2,3,5,6-tetraaza-as-indacen-1-yl)-piperidine-1-carboxylic acid tert-butyl ester as a cream solid. LCMS (Method A, ESI): RT=3.12 min, m+H=342.2, $^1$H NMR (400 MHz, $CDCl_3$) δ: 10.48 (s, 1H), 8.85 (s, 1H), 7.97 (s, 1H), 7.43 (m, 1H), 6.66 (m, 1H), 4.66 (m, 1H), 4.43 (br s, 2H), 3.02 (m, 2H), 2.31 (m, 2H), 2.10 (m, 2H), 1.52 (s, 9H).

Example 126

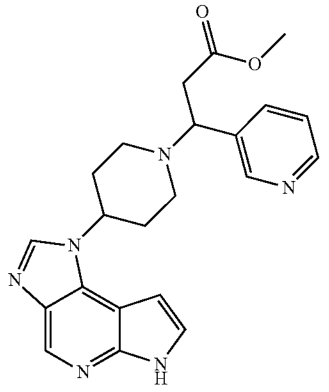 [SMILES: COC(=O)CC(c1cccnc1)N1CCC(n2cnc3cnc4[nH]ccc4c32)CC1]

Racemic 3-pyridin-3-yl-3-[4-(6H-1,2,3,5,6-tetraaza-as-indacen-1-yl)-piperidin-1-yl]-propionic acid methyl ester 1-Piperidin-4-yl-1,6-dihydro-1,2,3,5,6-tetraaza-as-indacene 4-(6H-1,2,3,5,6-Tetraaza-as-indacen-1-yl)-piperidine-1-carboxylic acid tert-butyl ester (4.40 g, 12.9 mmol) was treated with trifluoroacetic acid (50 mL) at ambient temperature for 1 hour. The mixture was concentrated in vacuo and the residue was purified by flash chromatography (SCX-2, eluting with 2M $NH_3$ in MeOH solution). The crude product was triturated ($MeOH/Et_2O$) then air dried to give 2.56 g (83%) of 1-piperidin-4-yl-1,6-dihydro-1,2,3,5,6-tetraaza-as-indacene as a cream solid. $^1$H NMR (400 MHz, DMSO) δ: 11.85 (s, 1H), 8.58 (s, 1H), 8.27 (s, 1H), 7.47 (t, 1H), 6.78 (dd, 1H), 4.61 (m, 1H), 3.12 (m, 2H), 2.77 (td, 2H), 2.27 (br s, 1H), 2.10-1.95 (m, 4H).

Racemic 3-pyridin-3-yl-3-[4-(6H-1,2,3,5,6-tetraaza-as-indacen-1-yl)-piperidin-1-yl]-propionic acid methyl ester A mixture of 1-piperidin-4-yl-1,6-dihydro-1,2,3,5,6-tetraaza-as-indacene (500 mg, 2.07 mmol), 3-pyridine carboxaldehyde (195 μL, 2.07 mmol), 1-(tert-butyldimethylsilyloxy)-1-methoxyethene (904 μL, 4.14 mmol) and triphenylborane (26 mg, 5 mol %) in DMSO (4 mL) was heated to 60° C. in a sealed tube for 24 hours. The cooled reaction mixture was purified using an Isolute® SCX-2 column (gradient: methanol to 2M $NH_3$ in methanol). The resulting residue was further purified by column chromatography on silica gel (gradient: 0 to 5% methanol in DCM) then preparative HPLC (gradient: 5 to 70% MeCN in water containing 0.1% $NH_4OH$) to afford 21 mg (13%) of racemic 3-pyridin-3-yl-3-[4-(6H-1,2,3,5,6-tetraaza-as-indacen-1-yl)-piperidin-1-yl]-propionic acid methyl ester. LCMS (Method A, ESI): RT=1.82 min, m+H=405.2; $^1$H NMR (400 MHz, DMSO) δ: 11.82 (s, 1H), 8.54 (m, 3H), 8.23 (s, 1H), 7.80 (dt, 1H), 7.42 (m, 2H), 6.67 (dd, 1H), 4.41 (s, 1H), 4.23 (t, 1H), 3.61 (s, 3H), 3.17-3.03 (m, 3H), 2.89 (dd, 1H), 2.33-1.97 (m, 6H).

Example 127

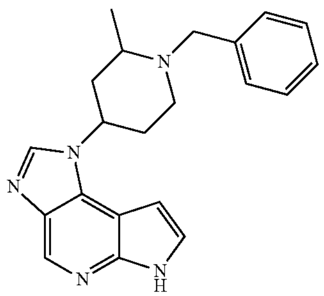 [SMILES: CC1CC(n2cnc3cnc4[nH]ccc4c32)CCN1Cc1ccccc1]

Racemic cis, 1-(1-Benzyl-2-methyl-piperidin-4-yl)-1,6-dihydro-1,2,3,5,6-tetraaza-as-indacene Racemic cis and racemic trans, (1-Benzenesulfonyl-5-nitro-1H-pyrrolo[2,3-b]pyridin-4-yl)-(1-benzyl-2-methyl-piperidin-4-yl)-amine A mixture of 1-benzenesulfonyl-4-chloro-5-nitro-1H-pyrrolo[2,3-b]pyridine (1.01 g, 3.00 mmol), 1-benzyl-2-methyl-piperidin-4-ylamine (674 mg, 3.30 mmol) and diisopropylethylamine (1.83 mL, 10.5 mmol) in propan-2-ol (30 mL) was heated to reflux for 1 hour. The mixture was filtered through Celite® and the filtrate concentrated under vacuum. Purification by column chromatography on silica gel (gradient: 0 to 30% ethyl acetate in toluene) afforded 990 mg (65%) of racemic cis (1-benzenesulfonyl-5-nitro-1H-pyrrolo[2,3-b]pyridin-4-yl)-(1-benzyl-2-methyl-piperidin-4-yl)-amine as a yellow foam and 320 mg (21%) of racemic trans (1-benzenesulfonyl-5-nitro-1H-pyrrolo[2,3-b]pyridin-4-yl)-(1-benzyl-2-methyl-piperidin-4-yl)-amine as a yellow foam.

Analysis for racemic cis: LCMS (Method I, ESI): RT=2.53 min, m+H=506.4; $^1$H NMR (400 MHz, $CDCl_3$) δ: 9.09 (s, 1H), 8.98 (d, 1H), 8.19 (dd, 2H), 7.61 (m, 2H), 7.54-7.49 (m, 2H), 7.35 (br s, 4H), 7.17 (m, 1H), 6.67 (s, 1H), 4.18 (br s, 1H), 3.94 (br s, 1H), 3.18 (br s, 1H), 2.97 (br s, 1H), 2.36 (s, 1H), 2.21-1.98 (m, 5H), 1.41-1.20 (m, 3H).

Analysis for racemic trans: LCMS (Method I, ESI): RT=2.56 min, m+H=506.4; $^1$H NMR (400 MHz, DMSO) δ: 9.07 (d, 1H), 8.92 (s, 1H), 8.15-8.10 (m, 2H), 7.80 (m, 2H), 7.66 (t, 2H), 7.38-7.19 (m, 4H), 7.02 (d, 1H), 4.42 (s, 1H), 3.89 (d, 1H), 2.80-2.57 (m, 2H), 2.34-2.24 (m, 1H), 1.93-1.58 (m, 4H), 1.15 (d, 3H).

Racemic cis, 1-Benzenesulfonyl-N*4*-(1-benzyl-2-methyl-piperidin-4-yl)-1H-pyrrolo[2,3-b]pyridine-4,5-diamine Following the procedure for 1-benzenesulfonyl-N*4*-((R)-1-benzyl-piperidin-3-yl)-1H-pyrrolo[2,3-b]pyridine-4,5-diamine the title compound was prepared from racemic cis (1-benzenesulfonyl-5-nitro-1H-pyrrolo[2,3-b]pyridin-4-yl)-(1-benzyl-2-methyl-piperidin-4-yl)-amine with further purification by column chromatography on silica gel (gradient: 0 to 5% 2M $NH_3$ in methanol solution in DCM) to afford 820 mg (88%) of racemic cis 1-benzenesulfonyl-N*4*-(1-benzyl-2-methyl-piperidin-4-yl)-1H-pyrrolo[2,3-b]pyridine-4,5-diamine. LCMS (Method H, ESI): RT=2.05 min, m+H=476.2; $^1$H NMR (400 MHz, $CDCl_3$) δ: 8.13 (m, 2H), 7.82 (s, 1H), 7.47 (m, 5H), 7.37-7.32 (m, 5H), 6.50 (d, 1H), 4.67 (d, 1H), 4.20 (d, 1H), 3.77-3.66 (m, 1H), 3.31-3.22 (m, 1H), 2.95 (d, 1H), 2.81 (s, 1H), 2.50 (br s, 1H), 2.06-2.02 (m, 2H), 1.33 (d, 3H).

Racemic cis, 6-Benzenesulfonyl-1-(1-benzyl-2-methyl-piperidin-4-yl)-1,6-dihydro-1,2,3,5,6-tetraaza-as-indacene Following the procedure for 6-benzenesulfonyl-1-((R)-1-benzyl-piperidin-3-yl)-1,6-dihydro-1,2,3,5,6-tetraaza-as-indacene the title compound was prepared from racemic cis 1-benzenesulfonyl-N*4*-(1-benzyl-2-methyl-piperidin-4-yl)-1H-pyrrolo[2,3-b]pyridine-4,5-diamine with further purification by column chromatography on silica gel (gradient: 0 to 5% 2M $NH_3$ in methanol solution in DCM) to afford 665 mg (80%) racemic cis 6-Benzenesulfonyl-1-(1-benzyl-2-methyl-piperidin-4-yl)-1,6-dihydro-1,2,3,5,6-tetraaza-as-indacene. LCMS (Method H, ESI): RT=2.34 min m+H=486.2; $^1$H NMR (400 MHz, DMSO) δ: 8.73 (s, 1H), 8.49 (s, 1H), 8.13 (m, 2H), 7.98 (d, 1H), 7.68 (m, 1H), 7.60 (m, 2H), 7.35 (m, 5H), 7.18 (d, 1H), 4.71-4.59 (m, 1H), 4.13 (d, 1H), 3.17 (d, 1H), 2.87 (m, 1H), 2.67-2.57 (m, 1H), 2.32-2.22 (m, 1H), 2.11-1.97 (m, 3H), 1.87 (q, 1H), 1.22 (d, 3H).

Racemic cis, 1-(1-Benzyl-2-methyl-piperidin-4-yl)-1,6-dihydro-1,2,3,5,6-tetraaza-as-indacene Racemic cis, 6-benzenesulfonyl-1-(1-benzyl-2-methyl-piperidin-4-yl)-1,6-dihydro-1,2,3,5,6-tetraaza-as-indacene (665 mg, 1.37 mmol) in a mixture of methanol (15 mL) and THF (18 mL) was treated with 1M aqueous sodium hydroxide (6.9 mL) at ambient temperature and stirred for 18 hours. The mixture was partially concentrated under vacuum and the resulting residue partitioned between ethyl acetate and water. The organic layer was washed with brine then dried with sodium sulfate and concentrated under vacuum affording 471 mg (99%) of racemic cis, 1-(1-benzyl-2-methyl-piperidin-4-yl)-1,6-dihydro-1,2,3,5,6-tetraaza-as-indacene. LCMS (Method A, ESI): RT=1.94 min m+H=346.1; $^1$H NMR (400 MHz, DMSO) δ: 11.84 (s, 1H), 8.57 (s, 1H), 8.30 (s, 1H), 7.47 (t, 1H), 7.37 (m, 4H), 7.26 (m, 1H), 6.75 (dd, 1H), 4.63 (m, 1H), 4.16 (d, 1H), 3.17 (d, 1H), 2.93-2.87 (m, 1H), 2.67-2.57 (m, 1H), 2.28 (m, 1H), 2.19-2.01 (m, 3H), 1.95 (m, 1H), 1.25 (d, 3H).

Example 128

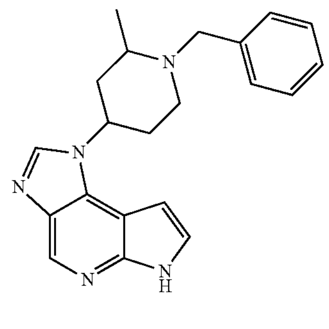 [SMILES: CC1CC(n2cnc3cnc4[nH]ccc4c32)CCN1Cc1ccccc1]

Racemic trans, 1-(1-Benzyl-2-methyl-piperidin-4-yl)-1,6-dihydro-1,2,3,5,6-tetraaza-as-indacene Racemic trans, 1-Benzenesulfonyl-N*4*-(1-benzyl-2-methyl-piperidin-4-yl)-1H-pyrrolo[2,3-b]pyridine-4,5-diamine Following the procedure for 1-benzenesulfonyl-N*4*-((R)-1-benzyl-piperidin-3-yl)-1H-pyrrolo[2,3-b]pyridine-4,5-diamine the title compound was prepared from racemic trans (1-benzenesulfonyl-5-nitro-1H-pyrrolo[2,3-b]pyridin-4-yl)-(1-benzyl-2-methyl-piperidin-4-yl)-amine with further purification by column chromatography on silica gel (gradient: 0 to 4% 2M $NH_3$ in methanol solution in DCM) to afford 256 mg (85%) of racemic trans 1-benzenesulfonyl-N*4*-(1-benzyl-2-methyl-piperidin-4-yl)-1H-pyrrolo[2,3-b]pyridine-4,5-diamine. LCMS (Method I, ESI): RT=2.03 min, m+H=476.3; $^1$H NMR (400 MHz, DMSO) δ: 8.00 (m, 2H), 7.69-7.61 (m, 1H), 7.59 (m, 3H), 7.47 (d, 1H), 7.30 (m, 4H), 7.26-7.17 (m, 1H), 6.69 (d, 1H), 5.03 (d, 1H), 4.35 (s, 2H), 3.69 (d, 1H), 3.44 (d, 1H), 2.99-2.90 (m, 1H), 2.55 (d, 1H), 2.41 (s, 2H), 1.72 (d, 3H), 1.09 (m, 3H).

Racemic trans, 6-Benzenesulfonyl-1-(1-benzyl-2-methyl-piperidin-4-yl)-1,6-dihydro-1,2,3,5,6-tetraaza-as-indacene Following the procedure for 6-benzenesulfonyl-1-((R)-1-benzyl-piperidin-3-yl)-1,6-dihydro-1,2,3,5,6-tetraaza-as-indacene the title compound was prepared from racemic trans 1-benzenesulfonyl-N*4*-(1-benzyl-2-methyl-piperidin-4-yl)-1H-pyrrolo[2,3-b]pyridine-4,5-diamine with further purification by column chromatography on silica gel (gradient: 0 to 5% 2M $NH_3$ in methanol solution in DCM) to afford 236 mg (90%) of racemic trans 6-benzenesulfonyl-1-(1-benzyl-2-methyl-piperidin-4-yl)-1,6-dihydro-1,2,3,5,6-tetraaza-as-indacene. LCMS (Method H, ESI): RT=2.34 min, m+H=486.2; $^1$H NMR (400 MHz, DMSO) δ: 8.74 (s, 1H), 8.53 (s, 1H), 8.15-8.10 (m, 2H), 8.01 (d, 1H), 7.72-7.66 (m, 1H), 7.60 (m, 2H), 7.36 (m, 4H), 7.28-7.22 (m, 1H), 7.12 (d, 1H), 4.96-4.83 (m, 1H), 3.66 (q, 2H), 3.27-3.19 (m, 1H), 2.82 (m, 1H), 2.67-2.58 (m, 1H), 2.28-2.20 (m, 1H), 2.14 (m, 1H), 1.98 (m, 2H), 1.23 (d, 3H).

Racemic trans, 1-(1-Benzyl-2-methyl-piperidin-4-yl)-1,6-dihydro-1,2,3,5,6-tetraaza-as-indacene Following the procedure for racemic cis 1-(1-benzyl-2-methyl-piperidin-4-yl)-1,6-dihydro-1,2,3,5,6-tetraaza-as-indacene the title compound was prepared from racemic trans 6-benzenesulfonyl-1-(1-benzyl-2-methyl-piperidin-4-yl)-1,6-dihydro-1,2,3,5,6-tetraaza-as-indacene to afford 169 mg (99%) of racemic trans 1-(1-benzyl-2-methyl-piperidin-4-yl)-1,6-dihydro-1,2,3,5,6-tetraaza-as-indacene as an off-white foam. LCMS (Method A, ESI): RT1.94 min, m+H=346.1; $^1$H NMR (400 MHz, DMSO) δ: 11.86 (s, 1H), 8.58 (s, 1H), 8.34 (s, 1H), 7.49 (t, 1H), 7.37 (m, 4H), 7.27 (m, 1H), 6.75 (dd, 1H), 4.95-4.85 (m, 1H), 3.70-3.66 (m, 1H), 3.30-3.22 (m, 1H), 3.27 (s, 1H), 2.83 (td, 1H), 2.70-2.64 (m, 1H), 2.27 (m, 2H), 2.02 (m, 2H), 1.25 (d, 3H).

Example 129

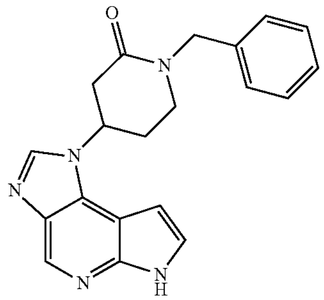 [SMILES: O=C1CC(n2cnc3cnc4[nH]ccc4c32)CCN1Cc1ccccc1]

Racemic, 1-Benzyl-4-(6H-1,2,3,5,6-tetraaza-as-indacen-1-yl)-piperidin-2-one

3-Benzylamino-propionic acid ethyl ester

To a mixture of β-alanine ethyl ester hydrochloride (2.69 g, 17.5 mmol), benzaldehyde (1.68 mL, 16.6 mmol) and sodium sulfate in DCM (30 mL) was added diisopropylethylamine (3.35 mL, 19.3 mmol) and the resulting mixture stirred at ambient temperature for 4 hours. The reaction mixture was filtered and the filtrate concentrated under vacuum to a clear oil. The oil was re-dissolved in methanol (30 mL) and cooled to 0° C., and then sodium borohydride (662 mg, 17.5 mmol) was added. The resulting mixture was warmed to ambient temperature and stirred for 16 hours. The reaction mixture was concentrated under vacuum and the resulting residue dissolved in DCM and washed with 10% aqueous citric acid, then dried over sodium sulfate and concentrated under vacuum to afford 2.45 g (71%) of 3-benzylamino-propionic acid ethyl ester as a clear oil. LCMS (Method I, ESI): RT=1.49 and 0.31 min, m+H=208.3; $^1$H NMR (400 MHz, $CDCl_3$) δ: 7.32 (s, 3H), 7.25 (m, 2H), 4.14 (q, 2H), 3.68 (s, 2H), 2.90 (t, 2H), 2.55 (m, 2H), 1.25 (t, 3H).

N-Benzyl-N-(2-ethoxycarbonyl-ethyl)-malonamic acid ethyl ester

To a mixture of 3-benzylamino-propionic acid (2.45 g, 11.8 mmol) and ethyl malonyl chloride (1.89 mL, 14.8 mmol) in DCM (30 mL) was added diisopropylethylamine (3.09 mL, 17.7 mmol) and the resulting mixture stirred at ambient temperature for 60 hours. The reaction mixture was diluted with DCM and washed with 10% aqueous citric acid, saturated aqueous sodium bicarbonate and brine, then dried over sodium sulfate and concentrated under vacuum. The resulting residue was purified by column chromatography on silica gel (gradient: 0 to 50% ethyl acetate in cyclohexane) to afford 3.63 g (96%) of a mixture of N-benzyl-N-(2-ethoxycarbonyl-ethyl)-malonamic acid ethyl ester and N-benzyl-N-(2-ethoxycarbonyl-ethyl)-malonamic acid methyl ester which was used directly in the next step.

1-Benzyl-2,4-dioxo-piperidine-3-carboxylic acid methyl ester

The generated mixture of N-benzyl-N-(2-ethoxycarbonyl-ethyl)-malonamic acid ethyl ester and N-benzyl-N-(2-ethoxycarbonyl-ethyl)-malonamic acid methyl ester was treated with sodium methoxide (2.97 mL, 13.0 mmol, 25% solution) in toluene at reflux for 18 hours. The cooled reaction mixture was acidified with 10% sulfuric acid and concentrated under vacuum. The resulting residue was dissolved in DCM and washed with water and brine, then dried over sodium sulfate and concentrated under vacuum. The resulting residue was purified by column chromatography on silica gel (gradient: 0 to 2% methanol in DCM) to afford 2.09 g (68%) of 1-benzyl-2,4-dioxo-piperidine-3-carboxylic acid methyl ester. $^1$H NMR (400 MHz, $CDCl_3$) δ: 7.29 (m, 5H), 4.70 (s, 1H), 4.64 (s, 2H), 3.93 (s, 3H), 3.34 (t, 2H), 2.59 (t, 2H).

1-Benzyl-piperidine-2,4-dione

A solution of 1-benzyl-2,4-dioxo-piperidine-3-carboxylic acid methyl ester (2.09 g, 8.0 mmol) in MeCN (250 mL) and water (20 mL) was heated at reflux for 76 hours. The cooled reaction mixture was concentrated under vacuum to afford 1.60 g (98%) of 1-benzyl-piperidine-2,4-dione as a yellow oil. $^1$H NMR (400 MHz, $CDCl_3$) δ: 7.36-7.24 (m, 5H), 4.69 (s, 2H), 3.48 (t, 2H), 3.43 (s, 2H), 2.54 (t, 2H).

Racemic 4-Allylamino-1-benzyl-piperidin-2-one

A mixture of 1-benzyl-piperidine-2,4-dione (508 mg, 0.25 mmol), allylamine (188 μL, 2.50 mmol) and 4 Å molecular sieves (500 mg) in DCE (5 mL) was stirred at ambient temperature for 5 hours, then sodium triacetoxyborohydride (106 mg, 0.50 mmol) was added. The resulting mixture was stirred for 16 hours, filtered through Celite®, and concentrated under vacuum. The resulting residue was dissolved in methanol (4 mL) and sodium borohydride (114 mg, 3.00 mmol) was added. The mixture was stirred for 40 hours and then concentrated under vacuum. The residue was dissolved in DCM and washed with 5% aqueous sodium bicarbonate, and dried over sodium sulfate and concentrated under vacuum. The residue was purified by column chromatography on silica gel (gradient: 0 to 80% methanol in DCM then 0 to 60% 2M $NH_3$ in methanol solution in DCM) to afford 430 mg (70%) of racemic 4-allylamino-1-benzyl-piperidin-2-one. $^1$H NMR (400 MHz, $CDCl_3$) δ: 7.29 (m, 5H), 5.89-5.85 (m, 1H), 5.20 (m, 2H), 4.85 (s, 1H), 4.61 (m, 2H), 3.95 (s, 1H), 3.68 (m, 1H), 3.29-3.25 (m, 2H), 3.10 (m, 1H), 2.75 (ddd, 1H), 2.33 (t, 1H), 1.99 (m, 1H), 1.70-1.57 (m, 1H).

Racemic, 4-Amino-1-benzyl-piperidin-2-one

A mixture of racemic 4-allylamino-1-benzyl-piperidin-2-one (430 mg, 1.76 mmol), 1,3-dimethyl barbituric acid (824 mg 5.28 mmol) and $Pd(PPh_3)_4$ (204 mg, 0.18 mmol) in DCM (20 mL) was stirred at ambient temperature for 2 hours then concentrated under vacuum. The resulting residue was purified by Isolute® SCX-2 column (gradient: DCM to 5 to 60% 2M $NH_3$ in methanol solution in DCM) to afford 260 mg (72%) of racemic 4-amino-1-benzyl-piperidin-2-one. LCMS (Method H, ESI): RT=0.35 min, m+H=204.9; $^1$H NMR (400 MHz, $CDCl_3$) δ: 7.29 (m, 5H), 4.60 (m, 2H), 3.34-3.13 (m, 3H), 2.74 (ddd, 1H), 2.37-2.23 (m, 1H), 2.01 (m, 3H), 1.64 (m, 1H).

Racemic, 4-(1-Benzenesulfonyl-5-nitro-1H-pyrrolo[2,3-b]pyridin-4-ylamino)-1-benzyl-piperidin-2-one Following the procedure for racemic (1-benzenesulfonyl-5-nitro-1H-pyrrolo[2,3-b]pyridin-4-yl)-(1-benzyl-2-methyl-piperidin-4-yl)-amine the title compound was prepared using racemic 4-amino-1-benzyl-piperidin-2-one with further purification by column chromatography on silica gel (gradient: 0 to 25% ethyl acetate in DCM) to afford 350 mg (57%) of racemic 4-(1-benzenesulfonyl-5-nitro-1H-pyrrolo[2,3-b]pyridin-4-ylamino)-1-benzyl-piperidin-2-one. LC MS (Method I, ESI): RT 3.68 min, m+H=506.2; $^1$H NMR (400 MHz, $CDCl_3$) δ: 9.11 (s, 1H), 8.19 (dd, 2H), 7.64 (m, 2H), 7.55-7.50 (m, 2H), 7.31 (m, 5H), 6.66 (d, 1H), 4.77 (d, 1H), 4.57-4.46 (m, 2H), 3.37 (m, 2H), 3.02 (dd, 1H), 2.64 (dd, 1H), 2.34-2.22 (m, 2H), 2.07-1.94 (m, 1H).

Racemic, 4-(5-Amino-1-benzenesulfonyl-1H-pyrrolo[2,3-b]pyridin-4-ylamino)-1-benzyl-piperidin-2-one Following the procedure for 1-benzenesulfonyl-N*4*-((R)-1-benzyl-piperidin-3-yl)-1H-pyrrolo[2,3-b]pyridine-4,5-diamine the title compound was prepared from racemic 4-(1-benzenesulfonyl-5-nitro-1H-pyrrolo[2,3-b]pyridin-4-ylamino)-1-benzyl-piperidin-2-one with further purification by column chromatography on silica gel (gradient: 0 to 5% 2M $NH_3$ in methanol solution in DCM) to afford 280 mg (85%) of racemic 4-(5-amino-1-benzenesulfonyl-1H-pyrrolo[2,3-b]pyridin-4-ylamino)-1-benzyl-piperidin-2-one as an off-white foam. LC MS (Method H, ESI): RT=2.62 min, m+H=476.2; $^1$H NMR (400 MHz, DMSO) δ: 8.01 (m, 2H), 7.66 (m, 1H), 7.58 (m, 3H), 7.49 (d, 1H), 7.34 (m, 2H), 7.26 (m, 3H), 6.76 (d, 1H), 5.25 (d, 1H), 4.60 (d, 1H), 4.43 (m, 3H), 3.29-3.19 (m, 2H), 2.72 (dd, 1H), 2.42 (dd, 1H), 2.06-1.97 (m, 1H), 1.72-1.65 (m, 1H).

Racemic, 4-(6-Benzenesulfonyl-6H-1,2,3,5,6-tetraaza-as-indacen-1-yl)-1-benzyl-piperidin-2-one Following the procedure for 6-benzenesulfonyl-1-((R)-1-benzyl-piperidin-3-yl)-1,6-dihydro-1,2,3,5,6-tetraaza-as-indacene the title compound was prepared from racemic 4-(5-amino-1-benzenesulfonyl-1H-pyrrolo[2,3-b]pyridin-4-ylamino)-1-benzyl-piperidin-2-one with further purification by column chromatography on silica gel (gradient: 0 to 5% 2M $NH_3$ in methanol solution in DCM) to afford 240 mg (84%) of racemic 4-(6-benzenesulfonyl-6H-1,2,3,5,6-tetraaza-as-indacen-1-yl)-1-benzyl-piperidin-2-one as an off-white foam. LCMS (Method H, ESI): RT=3.15 min, m+H=486.1; $^1$H NMR (400 MHz, DMSO) δ: 8.74 (s, 1H), 8.48 (s, 1H), 8.13 (m, 2H), 7.99 (d, 1H), 7.69 (m, 1H), 7.61 (m, 2H), 7.40-7.28 (m, 6H), 5.26 (m, 1H), 4.83 (d, 1H), 4.37 (d, 1H), 3.52 (m, 1H), 3.27 (m, 1H), 3.02-2.95 (m, 2H), 2.32 (s, 2H).

Racemic, 1-Benzyl-4-(6H-1,2,3,5,6-tetraaza-as-indacen-1-yl)-piperidin-2-one

Following the procedure for racemic cis 1-(1-benzyl-2-methyl-piperidin-4-yl)-1,6-dihydro-1,2,3,5,6-tetraaza-as-indacene the title compound was prepared from racemic 4-(6-benzenesulfonyl-6H-1,2,3,5,6-tetraaza-as-indacen-1-yl)-1-benzyl-piperidin-2-one with further purification by column chromatography on silica gel (gradient: 0 to 6% 2M $NH_3$ in methanol solution in DCM) followed by preparative HPLC (gradient: 25 to 75% MeCN in water) to afford 29 mg (17%) of racemic 1-benzyl-4-(6H-1,2,3,5,6-tetraaza-as-indacen-1-yl)-piperidin-2-one. LCMS (Method A, ESI): RT 2.79 min, m+H=346.1; $^1$H NMR (400 MHz, $CDCl_3$) δ: 11.86 (s, 1H), 8.59 (s, 1H), 8.28 (s, 1H), 7.47 (t, 1H), 7.40-7.27 (m, 5H), 6.83 (dd, 1H), 5.27-5.18 (m, 1H), 4.82 (d, 1H), 4.41 (d, 1H), 3.55 (m, 2H), 3.05 (m, 2H), 2.36 (m, 2H).

Example 130

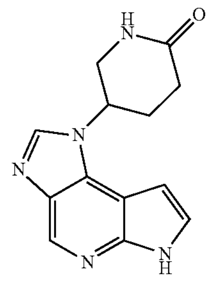 [SMILES: O=C1CCC(n2cnc3cnc4[nH]ccc4c32)CN1]

Racemic, 5-(6H-1,2,3,5,6-Tetraaza-as-indacen-1-yl)-piperidin-2-one

Racemic, 5-(1-Benzenesulfonyl-5-nitro-1H-pyrrolo[2,3-b]pyridin-4-ylamino)-1-benzyl-piperidin-2-one Following the procedure for racemic (1-benzenesulfonyl-5-nitro-1H-pyrrolo[2,3-b]pyridin-4-yl)-(1-benzyl-2-methyl-piperidin-4-yl)-amine the title compound was prepared using 5-amino-1-benzyl-piperidin-2-one with further purification by column chromatography on silica gel (gradient: 0 to 70% ethyl acetate in DCM) to afford 680 mg (90%) of racemic 5-(1-benzenesulfonyl-5-nitro-1H-pyrrolo[2,3-b]pyridin-4-ylamino)-1-benzyl-piperidin-2-one. LC MS (Method H, ESI): RT=3.57 min, m+H=506.2; $^1$H NMR (400 MHz, $CDCl_3$) δ: 9.07 (s, 1H), 9.02 (d, 1H), 8.18 (m, 2H), 7.66-7.61 (m, 1H), 7.55-7.50 (m, 2H), 7.47 (d, 1H), 7.27 (m, 4H), 6.31 (d, 1H), 4.71 (d, 1H), 4.48 (d, 1H), 4.32 (m, 1H), 3.59 (m, 1H), 3.29 (dd, 1H), 2.77-2.64 (m, 2H), 2.29 (s, 1H), 2.10 (m, 1H).

Racemic, 5-(5-Amino-1-benzenesulfonyl-1H-pyrrolo[2,3-b]pyridin-4-ylamino)-1-benzyl-piperidin-2-one Following the procedure for 1-benzenesulfonyl-N*4*-((R)-1-benzyl-piperidin-3-yl)-1H-pyrrolo[2,3-b]pyridine-4,5-diamine the title compound was prepared from racemic 5-(1-benzenesulfonyl-5-nitro-1H-pyrrolo[2,3-b]pyridin-4-ylamino)-1-benzyl-piperidin-2-one with further purification by column chromatography on silica gel (gradient: 0 to 5% 2M $NH_3$ in methanol solution in DCM) to afford 570 mg (89%) of racemic 5-(5-amino-1-benzenesulfonyl-1H-pyrrolo

[2,3-b]pyridin-4-ylamino)-1-benzyl-piperidin-2-one of as an off-white foam. LCMS (Method H, ESI): RT=2.51 min, m+H=476.1; $^1$H NMR (400 MHz, $CDCl_3$) δ: 7.99 (m, 2H), 7.66 (m, 1H), 7.57 (m, 3H), 7.29 (m, 6H), 6.59 (d, 1H), 5.24 (d, 1H), 4.56 (d, 1H), 4.41 (d, 1H), 4.37 (s, 2H), 4.28-4.18 (m, 1H), 3.37 (m, 1H), 3.11 (dd, 1H), 2.50 (m, 2H) 2.07-1.97 (m, 1H), 1.89-1.77 (m, 1H).

Racemic, 5-(6-Benzenesulfonyl-6H-1,2,3,5,6-tetraaza-as-indacen-1-yl)-1-benzyl-piperidin-2-one Following the procedure for 6-benzenesulfonyl-1-((R)-1-benzyl-piperidin-3-yl)-1,6-dihydro-1,2,3,5,6-tetraaza-as-indacene the title compound was prepared from racemic 5-(5-amino-1-benzenesulfonyl-1H-pyrrolo[2,3-b]pyridin-4-ylamino)-1-benzyl-piperidin-2-one with further purification by column chromatography on silica gel (gradient: 0 to 6% methanol in DCM) to afford 560 mg (97%) of racemic 5-(6-benzenesulfonyl-6H-1,2,3,5,6-tetraaza-as-indacen-1-yl)-1-benzyl-piperidin-2-one as an off-white foam. LCMS (Method H, ESI): RT=3.00 min, m+H=486.1; $^1$H NMR (400 MHz, $CDCl_3$) δ: 8.88 (s, 1H), 8.24-8.19 (m, 2H), 7.80 (s, 1H), 7.67 (d, 1H), 7.51 (m, 3H), 7.33 (m, 5H), 6.25 (d, 1H), 4.84 (m, 2H), 4.49 (d, 1H), 3.80-3.73 (m, 1H), 3.53 (dd, 1H), 2.73 (m, 2H), 2.57-2.45 (m, 2H).

Racemic, 1-Benzyl-5-(6H-1,2,3,5,6-tetraaza-as-indacen-1-yl)-piperidin-2-one

Following the procedure for racemic cis 1-(1-benzyl-2-methyl-piperidin-4-yl)-1,6-dihydro-1,2,3,5,6-tetraaza-as-indacene the title compound was prepared from racemic 5-(6-benzenesulfonyl-6H-1,2,3,5,6-tetraaza-as-indacen-1-yl)-1-benzyl-piperidin-2-one to afford 357 mg (90%) of racemic 1-benzyl-5-(6H-1,2,3,5,6-tetraaza-as-indacen-1-yl)-piperidin-2-one. LCMS (Method A, ESI): RT 2.49 min, m+H=346.2; $^1$H NMR (400 MHz, DMSO) δ: 11.84 (s, 1H), 8.57 (s, 1H), 8.18 (s, 1H), 7.37-7.27 (m, 6H), 6.53 (dd, 1H), 5.21-5.12 (m, 1H), 4.72 (d, 1H), 4.43 (d, 1H), 3.74-3.58 (m, 2H), 2.76 (m, 1H), 2.67-2.30 (m, 3H).

Racemic, 5-(6H-1,2,3,5,6-Tetraaza-as-indacen-1-yl)-piperidin-2-one

A suspension of racemic 1-benzyl-5-(6H-1,2,3,5,6-tetraaza-as-indacen-1-yl)-piperidin-2-one (69.0 mg, 0.20 mmol) in THF (2 mL) was added to liquid ammonia at −40° C. Sodium was added until a persistent blue color remained and the mixture was stirred at −40° C. for 5 minutes, then quenched by the addition of solid ammonium chloride. The resulting mixture was stirred at ambient temperature for 4 hours then diluted with sodium hydrogen carbonate (sat. aq.) and extracted with DCM. The aqueous layer was filtered to collect 24 mg (47%) of 5-(6H-1,2,3,5,6-tetraaza-as-indacen-1-yl)-piperidin-2-one. LCMS (Method A, ESI): RT 0.81 min, m+H=256.1; $^1$H NMR (400 MHz, DMSO) δ: 11.89 (s, 1H), 8.59 (s, 1H), 8.27 (s, 1H), 7.71 (s, 1H), 7.49 (d, 1H), 6.83 (d, 1H), 5.16-5.07 (m, 1H), 3.64 (m, 2H), 2.50 (m, 2H), 2.30 (m, 2H).

Example 131

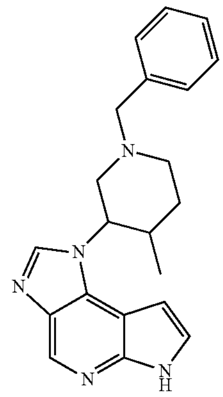 [SMILES: CC1CCN(Cc2ccccc2)CC1n1cnc2cnc3[nH]ccc3c21]

Racemic cis 1-(1-benzyl-4-methyl-piperidin-3-yl)-1,6-dihydro-1,2,3,5,6-tetraaza-as-indacene (4-Methyl-pyridin-3-yl)-carbamic acid methyl ester A solution of potassium tert-butoxide (32.8 g, 277 mmol) in THF (250 mL) at 0° C. was treated with 3-amino-4-methylpyridine (10.0 g, 92.5 mmol) and the resulting mixture stirred for 30 minutes before dimethyl carbonate (11.7 mL, 139 mmol) was added. The mixture was stirred for 30 minutes then quenched with water and extracted with ethyl acetate. The combined organic phases were washed with brine then dried over sodium sulfate and concentrated under vacuum. The resulting residue was purified by column chromatography on silica gel (DCM) then triturated with diethyl ether to afford 9.42 g (62%) of (4-methyl-pyridin-3-yl)-carbamic acid methyl ester. LCMS (Method B, ESI): RT=0.40 min, m+H=167.4; $^1$H NMR (400 MHz, $CDCl_3$) δ: 8.86 (s, 1H), 8.28 (d, 1H), 7.12-7.12 (m, 1H), 6.45 (s, 1H), 3.80 (s, 3H), 2.28 (s, 3H).

Racemic cis 3-Methoxycarbonylamino-4-methyl-piperidine-1-carboxylic acid tert-butyl ester A mixture of (4-methyl-pyridin-3-yl)-carbamic acid methyl ester (10.0 g, 60.2 mmol) and Rh/alumina (5.00 g, 5 mol %)) in ethanol (250 mL) was heated at 70° C. under hydrogen at 4 bar 3.5 days. The cooled reaction mixture was filtered through Celite® and the filtrate concentrated under vacuum. The resulting residue was dissolved in DCM (250 mL) and treated with BOC anhydride (14.5 g, 66.2 mmol) and diisopropylethylamine (15.5 mL, 90.3 mmol) and stirred at ambient temperature for 18 hours. The reaction mixture was diluted with DCM and washed with 1M aqueous HCl, water and brine, then dried over sodium sulfate and concentrated under vacuum. The resulting residue was purified by column chromatography on silica gel (gradient: 0 to 50% ethyl acetate in cyclohexane) to afford 3.43 g (20%) of racemic cis 3-methoxycarbonylamino-4-methyl-piperidine-1-carboxylic acid tert-butyl ester. LCMS (Method B, ESI): RT=4.02 min, m+H=287; $^1$H NMR (300 MHz, $CDCl_3$) δ: 4.75 (s, 1H), 4.17-4.01 (m, 2H), 3.83-3.73 (m, 1H), 3.68 (s, 3H), 2.86 (dd, 1H), 2.76-2.65 (m, 1H), 1.86-1.71 (m, 2H), 1.44 (s, 9H), 1.25 (d, 1H), 0.93 (d, 3H).

Racemic cis, (4-Methyl-piperidin-3-yl)-carbamic acid methyl ester hydrochloride A solution of racemic cis 3-methoxycarbonylamino-4-methyl-piperidine-1-carboxylic acid tert-butyl ester (2.00 g, 7.35 mmol) in 4 M HCl in dioxane (40 mL) was stirred at ambient temperature for 1 hour then concentrated under vacuum. The resulting residue was azeotroped with DCM to afford 1.7 g (quant.) of racemic cis (4-methyl-piperidin-3-yl)-carbamic acid methyl ester hydrochloride. LCMS (Method I, ESI): RT=0.34 min, m+H=173.4.

Racemic cis (1-Benzyl-4-methyl-piperidin-3-yl)-carbamic acid methyl ester

A mixture of racemic cis (4-methyl-piperidin-3-yl)-carbamic acid methyl ester hydrochloride (7.35 mmol), benzaldehyde (818 μL, 8.09 mmol), diisopropylethylamine (3.9 mL, 22.1 mmol) and 4 Å molecular sieves (7 g) in DCE (50 mL) was stirred at ambient temperature for 5 hours before the addition of sodium triacetoxyborohydride (2.34 g, 11.03 mmol). The resulting mixture was stirred for 60 hours then filtered through Celite® and the filtrate concentrated under vacuum. The resulting residue was purified by Isolute® SCX-2 (gradient: DCM to 2M $NH_3$ in methanol solution) then column chromatography on silica gel (gradient: 0 to 5% 2M $NH_3$ in methanol solution in DCM) to afford 1.56 g (81%) of racemic cis (1-benzyl-4-methyl-piperidin-3-yl)-carbamic acid methyl ester as a clear oil. LCMS (Method H, ESI): RT=1.53 and 0.35 min, m+H=263.9; $^1H$ NMR (400 MHz, $CDCl_3$) δ: 7.31-7.23 (m, 5H), 5.42 (d, 1H), 3.78 (d, 1H), 3.66 (s, 3H), 3.45 (s, 2H), 2.80-2.77 (m, 2H), 2.20-2.12 (m, 1H), 1.94 (td, 1H), 1.72-1.48 (m, 1H), 1.38 (m, 2H), 0.90 (d, 3H).

Racemic cis 1-Benzyl-4-methyl-piperidin-3-ylamine

A mixture of racemic cis (1-benzyl-4-methyl-piperidin-3-yl)-carbamic acid methyl ester (1.56 g, 5.95 mmol) and potassium hydroxide (9.90 mL, 59.5 mmol, 6M solution) in methanol (50 mL) was heated at reflux for 48 hours. The cooled reaction mixture was diluted with water and extracted with ethyl acetate. The combined organic phases were washed with brine then dried over sodium sulfate and concentrated under vacuum. The resulting residue was purified by column chromatography on silica gel (gradient: 0 to 7% 2M $NH_3$ in methanol solution in DCM) to afford 460 mg (38%) of racemic cis 1-benzyl-4-methyl-piperidin-3-ylamine. LCMS (Method H, ESI): RT=0.35 min, m+H=204.9; $^1H$ NMR (400 MHz, $CDCl_3$) δ: 7.29-7.28 (m, 5H), 3.45 (s, 2H), 2.76-2.72 (m, 3H), 2.20-2.11 (m, 1H), 1.97 (td, 1H), 1.42 (m, 5H), 0.91 (d, 3H).

Racemic cis (1-benzenesulfonyl-5-nitro-1H-pyrrolo[2,3-b]pyridin-4-yl)-(1-benzyl-4-methyl-piperidin-3-yl)-amine A mixture of 1-benzenesulfonyl-4-chloro-5-nitro-1H-pyrrolo[2,3-b]pyridine (692 mg, 2.10 mmol), racemic cis 1-benzyl-4-methyl-piperidin-3-ylamine (460 mg, 2.30 mmol) and diisopropylethylamine (1.25 mL, 7.20 mmol) in propan-2-ol (30 mL) was heated to reflux for 2 hours. The cooled reaction mixture was filtered and the yellow solid dried under vacuum to afford 940 mg (90%) of racemic cis (1-benzenesulfonyl-5-nitro-1H-pyrrolo[2,3-b]pyridin-4-yl)-(1-benzyl-4-methyl-piperidin-3-yl)-amine. LCMS (Method H, ESI): RT=2.61 min, m+H=506.2; $^1H$ NMR (400 MHz, DMSO) δ: 9.67 (d, 1H), 8.94 (s, 1H), 8.13 (dd, 2H), 7.75 (m, 2H), 7.66 (m, 2H), 7.30-7.10 (m, 6H), 4.54 (d, 1H), 3.49 (m, 2H) 2.83 (t, 2H), 2.27 (d, 1H), 2.07 (m, 1H), 1.91 (br s, 1H), 1.47 (m, 2H), 0.81 (d, 3H).

Racemic cis 1-benzenesulfonyl-N*4*-(1-benzyl-4-methyl-piperidin-3-yl)-1H-pyrrolo[2,3-b]pyridine-4,5-diamine Following the procedure for 1-benzenesulfonyl-N*4*-((R)-1-benzyl-piperidin-3-yl)-1H-pyrrolo[2,3-b]pyridine-4,5-diamine the title compound was prepared from racemic cis (1-benzenesulfonyl-5-nitro-1H-pyrrolo[2,3-b]pyridin-4-yl)-(1-benzyl-4-methyl-piperidin-3-yl)-amine with further purification by column chromatography on silica gel (gradient: 0 to 5% 2M $NH_3$ in methanol solution in DCM) to afford 820 mg (93%) racemic cis 1-benzenesulfonyl-N*4*-(1-benzyl-4-methyl-piperidin-3-yl)-1H-pyrrolo[2,3-b]pyridine-4,5-diamine of as an off-white foam. LCMS (Method I, ESI): RT=2.16 min, m+H=476.1; $^1H$ NMR (400 MHz, DMSO) δ: 8.02 (m, 2H), 7.67 (m, 2H), 7.58 (m, 2H), 7.43 (d, 1H), 7.31-7.25 (m, 2H), 7.18 (m, 3H), 6.73 (d, 1H), 5.30 (d, 1H), 4.26 (s, 2H), 4.07-3.98 (m, 1H), 3.46 (d, 2H), 2.74-2.55 (m, 1H), 2.25-2.06 (m, 1H), 1.83 (br s, 1H), 1.71-1.46 (m, 1H), 0.89 (d, 3H).

Racemic cis 6-benzenesulfonyl-1-(1-benzyl-4-methyl-piperidin-3-yl)-1,6-dihydro-1,2,3,5,6-tetraaza-as-indacene Following the procedure for 6-benzenesulfonyl-1-((R)-1-benzyl-piperidin-3-yl)-1,6-dihydro-1,2,3,5,6-tetraaza-as-indacene the title compound was prepared from racemic cis 1-benzenesulfonyl-N*4*-(1-benzyl-4-methyl-piperidin-3-yl)-1H-pyrrolo[2,3-b]pyridine-4,5-diamine with further purification by column chromatography on silica gel (gradient: 0 to 4% 2M $NH_3$ solution in methanol in DCM) to afford 356 mg (81%) of racemic cis 6-benzenesulfonyl-1-(1-benzyl-4-methyl-piperidin-3-yl)-1,6-dihydro-1,2,3,5,6-tetraaza-as-indacene as a white foam. LCMS (Method H, ESI): RT=2.61 min, m+H=486.1; $^1H$ NMR (400 MHz, DMSO) δ: 9.08 (s, 1H), 8.72 (s, 1H), 8.16-8.10 (m, 2H), 7.94 (d, 1H), 7.71-7.66 (m, 1H), 7.60 (m, 2H), 7.37 (d, 1H), 7.30 (m, 5H), 5.03 (d, 1H), 3.59 (d, 1H), 3.49 (d, 1H), 3.09-2.99 (m, 2H), 2.57 (m, 1H), 2.25-2.08 (m, 2H), 1.63-1.43 (m, 2H), 0.48 (d, 3H).

Racemic cis 1-(1-benzyl-4-methyl-piperidin-3-yl)-1,6-dihydro-1,2,3,5,6-tetraaza-as-indacene Following the procedure for racemic cis 1-(1-benzyl-2-methyl-piperidin-4-yl)-1,6-dihydro-1,2,3,5,6-tetraaza-as-indacene the title compound was prepared from racemic cis 6-benzenesulfonyl-1-(1-benzyl-4-methyl-piperidin-3-yl)-1,6-dihydro-1,2,3,5,6-tetraaza-as-indacene to afford 273 mg (quant.) of racemic cis 1-(1-benzyl-4-methyl-piperidin-3-yl)-1,6-dihydro-1,2,3,5,6-tetraaza-as-indacene. LCMS (Method A, ESI): RT=2.39 min, m+H=346.3; $^1H$ NMR (400 MHz, DMSO) δ: 11.78 (s, 1H), 8.91 (s, 1H), 8.57 (s, 1H), 7.42 (t, 1H), 7.35-7.30 (m, 4H), 7.23 (m, 1H), 6.87 (dd, 1H), 5.04 (m, 1H), 3.61 (d, 1H), 3.53 (d, 1H), 3.04 (m, 2H), 2.63 (dd, 1H), 2.20 (m, 2H), 1.56 (m, 2H), 0.54 (d, 3H).

Example 132

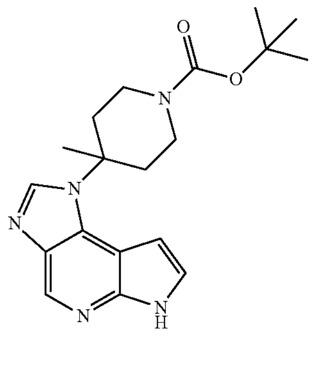 [SMILES: CC(C)(C)OC(=O)N1CCC(C)(n2cnc3cnc4[nH]ccc4c32)CC1]

4-Methyl-4-(6H-1,2,3,5,6-tetraaza-as-indacen-1-yl)-piperidine-1-carboxylic acid tert-butyl ester 4-(1-Benzenesulfonyl-5-nitro-1H-pyrrolo[2,3-b]pyridin-4-ylamino)-4-methyl-piperidine-1-carboxylic acid tert-butyl ester A mixture of 1-benzenesulfonyl-4-chloro-5-nitro-1H-pyrrolo[2,3-b]pyridine (750 mg, 2.20 mmol), 4-amino-4-methyl-piperidine-1-carboxylic acid tert-butyl ester (525 mg, 2.50 mmol) and diisopropylethylamine (1.36 mL, 7.80 mmol) in propan-2-ol (30 mL) was heated to reflux for 65 hours. The cooled reaction mixture was filtered and the yellow solid further purified by column chromatography on silica gel (gradient: 0 to 30% ethyl acetate in cyclohexane) to afford 910 mg (79%) of 4-(1-benzenesulfonyl-5-nitro-1H-pyrrolo[2,3-b]pyridin-4-ylamino)-4-methyl-piperidine-1-carboxylic acid tert-butyl ester. LCMS (Method H, ESI): RT=4.35 min, m+H=516.2; $^1$H NMR (400 MHz, DMSO) δ: 9.42 (s, 1H), 8.95 (s, 1H), 8.15 (dd, 2H), 7.84-7.76 (m, 2H), 7.66 (m, 2H), 7.06 (d, 1H), 3.57 (m, 2H), 3.23-3.08 (m, 1H), 2.09 (d, 2H), 1.80 (m, 2H), 1.57 (s, 3H), 1.39 (s, 9H).

4-(5-Amino-1-benzenesulfonyl-1H-pyrrolo[2,3-b]pyridin-4-ylamino)-4-methyl-piperidine-1-carboxylic acid tert-butyl ester Following the procedure for 1-benzenesulfonyl-N*4*-((R)-1-benzyl-piperidin-3-yl)-1H-pyrrolo[2,3-b]pyridine-4,5-diamine the title compound was prepared from 4-(1-benzenesulfonyl-5-nitro-1H-pyrrolo[2,3-b]pyridin-4-ylamino)-4-methyl-piperidine-1-carboxylic acid tert-butyl ester with further purification by column chromatography on silica gel (gradient: 0 to 4% 2M $NH_3$ in methanol solution in DCM) to afford 720 mg (84%) 4-(5-amino-1-benzenesulfonyl-1H-pyrrolo[2,3-b]pyridin-4-ylamino)-4-methyl-piperidine-1-carboxylic acid tert-butyl ester of as an off-white foam. LCMS (Method I, ESI): RT=3.21 min, m+H=486.3; $^1$H NMR (400 MHz, $CDCl_3$) δ: 8.03 (m, 2H), 7.75 (s, 1H), 7.67 (m, 1H), 7.57 (m, 3H), 6.68 (d, 1H), 3.41 (m, 2H), 3.22 (s, 2H), 1.77 (m, 2H), 1.56-1.49 (m, 2H), 1.36 (s, 9H), 1.24 (s, 3H).

4-(6-Benzenesulfonyl-6H-1,2,3,5,6-tetraaza-as-indacen-1-yl)-4-methyl-piperidine-1-carboxylic acid tert-butyl ester Following the procedure for 6-benzenesulfonyl-1-((R)-1-benzyl-piperidin-3-yl)-1,6-dihydro-1,2,3,5,6-tetraaza-as-indacene the title compound was prepared from 4-(5-amino-1-benzenesulfonyl-1H-pyrrolo[2,3-b]pyridin-4-ylamino)-4-methyl-piperidine-1-carboxyli c acid tert-butyl ester with further purification by column chromatography on silica gel (gradient: 0 to 4% 2M $NH_3$ in methanol solution in DCM) to afford 630 mg (86%) of 4-(6-benzenesulfonyl-6H-1,2,3,5,6-tetraaza-as-indacen-1-yl)-4-methyl-piperidine-1-carboxylic acid tert-butyl ester as a white foam. LCMS (Method H, ESI): RT=3.54 min, m+H=496.2; $^1$H NMR (400 MHz, DMSO) δ: 8.78 (s, 1H), 8.50 (s, 1H), 8.17 (m, 2H), 7.97 (d, 1H), 7.70 (m, 1H), 7.62 (m, 2H), 7.04 (d, 1H), 3.66 (m, 2H), 2.57-2.48 (m, 2H), 2.38-2.29 (m, 2H), 2.13-2.03 (m, 2H), 1.77 (s, 3H), 1.43 (s, 9H).

4-Methyl-4-(6H-1,2,3,5,6-tetraaza-as-indacen-1-yl)-piperidine-1-carboxylic acid tert-butyl ester Following the procedure for racemic cis 1-(1-benzyl-2-methyl-piperidin-4-yl)-1,6-dihydro-1,2,3,5,6-tetraaza-as-indacene the title compound was prepared from 4-(6-benzenesulfonyl-6H-1,2,3,5,6-tetraaza-as-indacen-1-yl)-4-methyl-piperidine-1-carboxylic acid tert-butyl ester to afford 440 mg (98%) of 4-methyl-4-(6H-1,2,3,5,6-tetraaza-as-indacen-1-yl)-piperidine-1-carboxylic acid tert-butyl ester. LCMS (Method A, ESI): RT=3.27 min, m+H=356.2; $^1$H NMR (400 MHz, DMSO) δ: 11.92 (s, 1H), 8.62 (s, 1H), 8.34 (s, 1H), 7.44 (m, 1H), 6.62 (dd, 1H), 5.76 (s, 1H), 3.76-3.66 (m, 3H), 3.43-3.31 (m, 1H), 2.58-2.46 (m, 1H), 2.09-1.98 (m, 2H), 1.85 (s, 3H), 1.45 (s, 9H).

Example 133

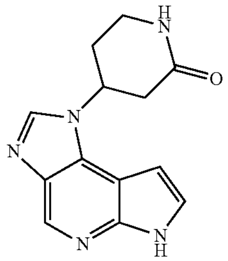 [SMILES: O=C1CC(n2cnc3cnc4[nH]ccc4c32)CCN1]

Racemic, 4-(6H-1,2,3,5,6-Tetraaza-as-indacen-1-yl)-piperidin-2-one 3-(2,4-Dimethoxy-benzylamino)-propionic acid ethyl ester Following the procedure for 3-benzylamino-propionic acid ethyl ester the title compound was prepared from 2,4-dimethoxybenzaldehyde to afford 9.57 g (76%) of 3-(2,4-dimethoxy-benzylamino)-propionic acid ethyl ester as a clear oil. $^1$H NMR (400 MHz) δ: 7.13 (d, 1H), 6.44 (m, 2H), 4.13 (q, 2H), 3.81 (s, 3H), 3.80 (s, 3H), 3.73 (s, 2H), 2.85 (t, 2H), 2.53 (m, 2H), 1.25 (t, 3H).

N-(2,4-Dimethoxy-benzyl)-N-(2-ethoxycarbonyl-ethyl)-malonamic acid ethyl ester

Following the procedure for N-benzyl-N-(2-ethoxycarbonyl-ethyl)-malonamic acid ethyl ester the title compound was prepared from 3-(2,4-dimethoxy-benzylamino)-propionic acid ethyl ester with further purification by column chromatography on silica gel (gradient: 0 to 60% ethyl acetate in cyclohexane) to afford 13.8 g (quant.) of N-(2,4-dimethoxy-benzyl)-N-(2-ethoxycarbonyl-ethyl)-malonamic acid ethyl ester. $^1$H NMR (400 MHz, $CDCl_3$) δ: 7.04 (d, 1H), 6.46 (m, 2H), 4.42 (s, 2H), 4.19 (m, 4H), 3.81 (s, 6H), 3.65 (s, 2H), 3.56 (s, 2H), 2.58 (m, 2H), 1.28 (t, 6H).

1-(2,4-Dimethoxy-benzyl)-2,4-dioxo-piperidine-3-carboxylic acid methyl ester Following the procedure for 1-benzyl-2,4-dioxo-piperidine-3-carboxylic acid methyl ester the title compound was prepared from N-(2,4-dimethoxy-benzyl)-N-(2-ethoxycarbonyl-ethyl)-malonamic acid ethyl ester with further purification by column chromatography on silica gel (gradient: 0 to 5% methanol in DCM) to afford 9.35 g (81%) of 1-(2,4-dimethoxy-benzyl)-2,4-dioxo-piperidine-3-carboxylic acid methyl ester as a pale brown oil. $^1$H NMR (400 MHz) δ: 7.27 (m, 1H), 6.48-6.42 (m, 2H), 4.57 (s, 2H), 3.91 (s, 3H), 3.90 (s, 1H), 3.82-3.77 (m, 6H), 3.40 (m, 2H), 2.58 (t, 2H).

1-(2,4-Dimethoxy-benzyl)-piperidine-2,4-dione

Following the procedure for 1-benzyl-piperidine-2,4-dione the title compound was prepared from 1-(2,4-dimethoxy-benzyl)-2,4-dioxo-piperidine-3-carboxylic acid methyl ester with further purification by column chromatography on silica gel (gradient: 0 to 2.5% methanol in DCM) to afford 7.66 g (quant.) of 1-(2,4-dimethoxy-benzyl)-piperidine-2,4-dione as a yellow liquid. $^1$H NMR (400 MHz, $CDCl_3$) δ: 7.22 (m, 1H), 6.46 (m, 2H), 4.63 (s, 2H), 3.81 (s, 3H), 3.80 (s, 3H), 3.54 (t, 2H), 3.36 (s, 2H), 2.51 (t, 2H).

Racemic, 4-(Benzhydryl-amino)-1-(2,4-dimethoxy-benzyl)-piperidin-2-one

A mixture of 1-(2,4-dimethoxy-benzyl)-piperidine-2,4-dione (2.63 g, 10.0 mmol), benzhydrylamine (1.72 mL, 10.0 mmol) and sodium sulfate (5 g) in acetic acid (2.29 mL, 40.0 mmol) and DCM (40 mL) was stirred at ambient temperature for 6 hours before the addition of sodium triacetoxyborohydride (3.18 g, 15.0 mmol). The resulting mixture was stirred for 18 hours then filtered through Celite®, the filtrate washed with brine then dried over sodium sulfate and concentrated under vacuum. The resulting residue was purified by column chromatography on silica gel (gradient: 0 to 2.5% methanol in DCM). The residue was re-dissolved in acetic acid (300 μL) and methanol (30 mL) and treated with sodium cyanoborohydride (1.46 g, 23.2 mmol) and the resulting mixture stirred at ambient temperature for 18 hours. The mixture was concentrated under vacuum, the residue dissolved in DCM and washed with saturated aqueous sodium bicarbonate. The organic phase was dried over sodium sulfate and concentrated under vacuum to afford 3.3 g (77%) of racemic 4-(benzhydryl-amino)-1-(2,4-dimethoxy-benzyl)-piperidin-2-one as an oil. LCMS (Method H, ESI): RT=2.47 min, m+H=431.3; $^1$H NMR (400 MHz, $CDCl_3$) δ: 7.31 (m, 13H), 6.41 (s, 2H), 4.64 (d, 1H), 4.40 (d, 1H), 3.78 (s, 3H), 3.74 (s, 3H), 3.32 (m, 1H), 3.13-3.05 (m, 1H), 2.95 (m, 1H), 2.72 (dd, 1H), 2.30 (dd, 1H), 2.02-1.92 (m, 1H), 1.74-1.57 (m, 1H).

Racemic, 4-Amino-1-(2,4-dimethoxy-benzyl)-piperidin-2-one

A mixture of racemic 4-(benzhydryl-amino)-1-(2,4-dimethoxy-benzyl)-piperidin-2-one (3.30 g, 7.80 mmol), 10% Pd on carbon (410 mg, 0.39 mmol) and 2M aqueous HCl (4 mL, 8.15 mmol) in ethanol (150 mL) was stirred at ambient temperature under an atmosphere of hydrogen for 23 hours. The reaction mixture was filtered through Celite® which was washed with ethanol, and the filtrate concentrated under vacuum. The resulting residue was purified by column chromatography on silica gel (gradient: 2M $NH_3$ in methanol solution in DCM) to afford 1.53 g (75%) of 4-amino-1-(2,4-dimethoxy-benzyl)-piperidin-2-one as an oil. LCMS (Method I, ESI): RT=1.57 min, m+H=265.3; $^1$H NMR (400 MHz, $CDCl_3$) δ: 7.15 (d, 1H), 6.46-6.42 (m, 2H), 4.56 (m, 2H), 3.80 (m, 6H), 3.33 (dt, 1H), 3.22 (m, 2H), 2.69 (ddd, 1H), 2.21 (dd, 1H), 1.94 (m, 1H), 1.59 (dtd, 1H).

Racemic, 4-(1-Benzenesulfonyl-5-nitro-1H-pyrrolo[2,3-b]pyridin-4-ylamino)-1-(2,4-dimethoxy-benzyl)-piperidin-2-one Following the procedure for racemic (1-benzenesulfonyl-5-nitro-1H-pyrrolo[2,3-b]pyridin-4-yl)-(1-benzyl-4-methyl-piperidin-3-yl)-amine the title compound was prepared from racemic 4-amino-1-(2,4-dimethoxy-benzyl)-piperidin-2-one to afford 1.1 g (88%) of racemic 4-(1-benzenesulfonyl-5-nitro-1H-pyrrolo[2,3-b]pyridin-4-ylamino)-1-(2,4-dimethoxy-benzyl)-piperidin-2-one. LCMS (Method H, ESI): RT=3.77 min, m+H=566.2; $^1$H NMR (400 MHz, DMSO) δ: 8.91 (s, 1H), 8.86 (d, 1H), 8.14-8.09 (m, 2H), 7.85 (d, 1H), 7.79-7.73 (m, 1H), 7.68-7.61 (m, 2H), 7.11 (m, 1H), 7.02 (d, 1H), 6.57 (d, 1H), 6.47 (dd, 1H), 4.58 (m, 2H), 4.25 (d, 1H), 3.79 (s, 3H), 3.75 (s, 3H), 3.41-3.32 (m, 1H), 3.24 (m, 1H), 2.79 (dd, 1H), 2.61 (dd, 1H), 2.15 (m, 1H), 2.00 (m, 1H).

Racemic, 4-(5-Amino-1-benzenesulfonyl-1H-pyrrolo[2,3-b]pyridin-4-ylamino)-1-(2,4-dimethoxy-benzyl)-piperidin-2-one Following the procedure for 1-benzenesulfonyl-N*4*-((R)-1-benzyl-piperidin-3-yl)-1H-pyrrolo[2,3-b]pyridine-4,5-diamine the title compound was prepared from racemic 4-(1-benzenesulfonyl-5-nitro-1H-pyrrolo[2,3-b]pyridin-4-ylamino)-1-(2,4-dimethoxy-benzyl)-piperidin-2-one with further purification by column chromatography on silica gel (gradient: 0 to 4% methanol in DCM) to afford 930 mg (89%) racemic 4-(5-amino-1-benzenesulfonyl-1H-pyrrolo[2,3-b]pyridin-4-ylamino)-1-(2,4-dimethoxy-benzyl)-piperidin-2-one of as a cream foam. LCMS (Method I, ESI): RT=2.76 min, m+H=536.4; $^1$H NMR (400 MHz, DMSO) δ: 8.01 (m, 2H), 7.68-7.63 (m, 1H), 7.61-7.55 (m, 3H), 7.49 (d, 1H), 7.01 (d, 1H), 6.76 (d, 1H), 6.56 (d, 1H), 6.49 (dd, 1H), 5.25 (d, 1H), 4.50-4.29 (m, 5H), 3.78 (s, 3H), 3.75 (s, 3H), 3.24 (m, 2H), 2.69 (dd, 1H), 2.39 (dd, 1H), 2.01 (m, 1H), 1.69 (m, 1H).

Racemic, 4-(6-Benzenesulfonyl-6H-1,2,3,5,6-tetraaza-as-indacen-1-yl)-1-(2,4-dimethoxy-benzyl)-piperidin-2-one Following the procedure for 6-benzenesulfonyl-1-((R)-1-benzyl-piperidin-3-yl)-1,6-dihydro-1,2,3,5,6-tetraaza-as-indacene the title compound was prepared from racemic 4-(5-amino-1-benzenesulfonyl-1H-pyrrolo[2,3-b]pyridin-4-ylamino)-1-(2,4-dimethoxy-benzyl)-piperidin-2-one with further purification by column chromatography on silica gel (gradient: 0 to 5% methanol in DCM) to afford 840 mg (88%) of racemic 4-(6-benzenesulfonyl-6H-1,2,3,5,6-tetraaza-as-indacen-1-yl)-1-(2,4-dimethoxy-benzyl)-piperidin-2-one as a white foam. LCMS (Method H, ESI): RT=3.20 min, m+H=545.8; $^{1}$H NMR (400 MHz, DMSO) δ: 8.74 (s, 1H), 8.46 (s, 1H), 8.14-8.09 (m, 2H), 7.99 (d, 1H), 7.69 (m, 1H), 7.63-7.56 (m, 2H), 7.34 (d, 1H), 7.12 (d, 1H), 6.59 (d, 1H), 6.51 (dd, 1H), 5.25 (m, 1H), 4.71 (d, 1H), 4.24 (d, 1H), 3.81 (s, 3H), 3.76 (s, 3H), 3.51 (d, 1H), 3.26-3.17 (m, 1H), 2.95 (m, 2H), 2.30 (m, 2H).

Racemic, 4-(6-Benzenesulfonyl-6H-1,2,3,5,6-tetraaza-as-indacen-1-yl)-piperidin-2-one A mixture of racemic 4-(6-benzenesulfonyl-6H-1,2,3,5,6-tetraaza-as-indacen-1-yl)-1-(2,4-dimethoxy-benzyl)-piperidin-2-one (790 mg, 1.45 mmol), TFA (30 mL) and triisopropylsilane (300 μL) was heated at 60° C. for 7 hours. The cooled reaction mixture concentrated under vacuum and azeotroped with DCM. The resulting residue was purified using an Isolute® SCX-2 column (gradient: methanol to 2M $NH_3$ in methanol) then by column chromatography on silica gel (gradient: 0 to 12% methanol in DCM) to afford 398 mg (70%) of racemic 4-(6-benzenesulfonyl-6H-1,2,3,5,6-tetraaza-as-indacen-1-yl)-piperidin-2-one as a white solid. LCMS (Method H, ESI): RT=2.46 min, m+H=396.2; $^{1}$H NMR (400 MHz, DMSO) δ: 8.74 (s, 1H), 8.49 (s, 1H), 8.15-8.10 (m, 2H), 7.98 (d, 1H), 7.81 (s, 1H), 7.69 (m, 1H), 7.61 (m, 2H), 7.35 (d, 1H), 5.18 (m, 1H), 3.44 (m, 1H), 3.19-3.14 (m, 1H), 2.85-2.72 (m, 2H), 2.23 (m, 2H).

Racemic, 4-(6H-1,2,3,5,6-etraaza-as-indacen-1-yl)-piperidin-2-one

A suspension of lithium (154 mg, 5.50 mmol) and naphthalene (775 mg, 6.05 mmol) in THF (4 mL) was sonicated for 1 hour to form a green solution. An aliquot (1 mL, 1.35 mmol) of this solution was added to a suspension of racemic 4-(6-benzenesulfonyl-6H-1,2,3,5,6-tetraaza-as-indacen-1-yl)-piperidin-2-one (59.0 mg, 0.15 mmol) in THF (3 mL) at −78° C. The resulting mixture was stirred at −78° C. for 30 minutes then room temperature for 30 minutes. The solution was re-cooled to −78° C. before a further aliquot (1 mL, 1.35 mmol) of the lithium solution was added. The resulting mixture was stirred at −78° C. for 30 minutes then room temperature for 30 minutes. The mixture was quenched with saturated aqueous ammonium chloride and extracted with DCM. The combined organic layers were dried with sodium sulfate and concentrated under vacuum. The resulting residue was purified by column chromatography on silica gel (gradient: 2M $NH_3$ in methanol solution in DCM) to afford 18 mg (47%) of racemic 4-(6H-1,2,3,5,6-tetraaza-as-indacen-1-yl)-piperidin-2-one as a white powder. LCMS (Method A, ESI): RT=1.18 min, m+H=256.2; $^{1}$H NMR (400 MHz, DMSO) δ: 11.86 (s, 1H), 8.59 (s, 1H), 8.28 (s, 1H), 7.83 (s, 1H), 7.47 (t, 1H), 6.83 (dd, 1H), 5.16 (m, 1H), 3.45 (m, 1H), 3.23 (m, 1H), 2.90-2.81 (m, 2H), 2.30-2.23 (m, 2H).

Example 134

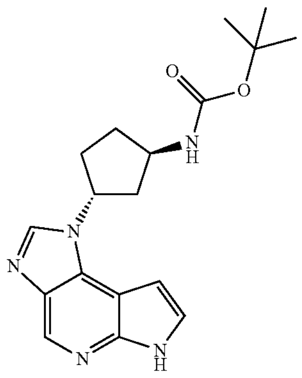 [SMILES: CC(C)(C)OC(=O)N[C@@H]1CC[C@@H](n2cnc3cnc4[nH]ccc4c32)C1]

[(1R,3R)-3-(6H-1,2,3,5,6-Tetraaza-as-indacen-1-yl)-cyclopentyl]-carbamic acid tert-butyl ester ((1R,3R)-3-Allyloxycarbonylamino-cyclopentyl)-carbamic acid tert-butyl ester A mixture of (1R,3R)-3-tert-butoxycarbonylamino-cyclopentanecarboxylic acid (1.00 g, 4.36 mmol), diphenylphosphoryl azide (1.41 mL, 6.54 mmol) and triethylamine (1.21 mL, 8.72 mmol) in toluene (15 mL) was heated at 90° C. for 2 hours then cooled to ambient temperature. Allyl alcohol (1.63 mL, 24.0 mmol) and DMAP (54.0 mg, 0.44 mmol) were added and the resulting mixture heated at 90° C. for 18 hours. The cooled reaction mixture was concentrated under vacuum and the resulting residue was dissolved in ethyl acetate. The mixture was washed with 10% aqueous citric acid, saturated aqueous sodium carbonate and brine and the combined aqueous layers were back-extracted with ethyl acetate. The combined organic layers were dried over sodium sulfate and concentrated under vacuum. The resulting residue was purified by column chromatography on silica gel (gradient: 0 to 12% ethyl acetate in cyclohexane) to afford 890 mg (72%) of ((1R,3R)-3-allyloxycarbonylamino-cyclopentyl)-carbamic acid tert-butyl ester. $^{1}$H NMR (400 MHz, DMSO) δ: 7.23 (d, 1H), 6.85 (d, 1H), 5.90 (m, 1H), 5.26 (dq, 1H), 5.16 (dq, 1H), 4.46-4.41 (m, 2H), 3.93-3.83 (m, 2H), 1.88 (m, 2H), 1.65 (t, 2H), 1.37 (s, 9H).

((1R,3R)-3-Amino-cyclopentyl)-carbamic acid tert-butyl ester

A mixture of ((1R,3R)-3-allyloxycarbonylamino-cyclopentyl)-carbamic acid tert-butyl ester (890 mg, 3.13 mmol), 1,3-dimethylbarbituric acid (1.47 g, 9.39 mmol) and $Pd(PPh_3)_4$ (181 mg, 0.15 mmol) in DCM (30 mL) was stirred at ambient temperature for 90 minutes. The reaction mixture was concentrated under vacuum and purified by column chromatography on silica gel (gradient: 2M $NH_3$ in methanol solution in DCM) to afford 350 mg (56%) ((1R,3R)-3-amino-cyclopentyl)-carbamic acid tert-butyl ester. LCMS (Method H, ESI): RT=0.36 min, m+H=200.9; $^1$H NMR (400 MHz, DMSO) δ: 6.77 (s, 1H), 3.90 (m, 1H), 3.31 (m, 1H), 1.87 (m, 2H), 1.54 (m, 2H), 1.37 (s, 10H), 1.18 (m, 1H).

[(1R,3R)-3-(1-Benzenesulfonyl-5-nitro-1H-pyrrolo[2,3-b]pyridin-4-ylamino)-cyclopentyl]-carbamic acid tert-butyl ester Following the procedure for racemic (1-benzenesulfonyl-5-nitro-1H-pyrrolo[2,3-b]pyridin-4-yl)-(1-benzyl-4-methyl-piperidin-3-yl)-amine the title compound was prepared from ((1R,3R)-3-amino-cyclopentyl)-carbamic acid tert-butyl ester to afford 700 mg (88%) of [(1R,3R)-3-(1-benzenesulfonyl-5-nitro-1H-pyrrolo[2,3-b]pyridin-4-ylamino)-cyclopentyl]-carb amic acid tert-butyl ester. LCMS (Method I, ESI): RT=4.08 min, m+H=502.1; $^1$H NMR (400 MHz, DMSO) δ: 8.89 (s, 1H), 8.12 (m, 2H), 7.83 (d, 1H), 7.76 (m, 1H), 7.66 (m, 2H), 7.17 (d, 1H), 7.05 (m, 1H), 4.61 (m, 1H), 4.07-3.98 (m, 1H), 2.28-2.20 (m, 1H), 1.99 (s, 3H), 1.55 (m, 2H), 1.39 (s, 9H).

[(1R,3R)-3-(5-Amino-1-benzenesulfonyl-1H-pyrrolo[2,3-b]pyridin-4-ylamino)-cyclopentyl]-carbamic acid tert-butyl ester Following the procedure for 1-benzenesulfonyl-N*4*-((R)-1-benzyl-piperidin-3-yl)-1H-pyrrolo[2,3-b]pyridine-4,5-diamine the title compound was prepared from [(1R,3R)-3-(1-benzenesulfonyl-5-nitro-1H-pyrrolo[2,3-b]pyridin-4-ylamino)-cyclopentyl]-carb amic acid tert-butyl ester to afford 700 mg (quant.) of [(1R,3R)-3-(5-amino-1-benzenesulfonyl-1H-pyrrolo[2,3-b]pyridin-4-ylamino)-cyclopentyl]-carbamic acid tert-butyl ester of as a foam. LCMS (Method I, ESI): RT=2.67 min, m+H=472.3; $^1$H NMR (400 MHz, DMSO) δ: 8.02-7.97 (m, 2H), 7.66 (m, 1H), 7.61-7.51 (m, 3H), 7.45 (d, 1H), 6.97 (d, 1H), 6.82 (d, 1H), 5.21 (d, 1H), 4.36 (m, 3H), 3.96 (m, 1H), 2.03 (m, 2H), 1.80 (m, 2H), 1.45 (m, 2H), 1.38 (s, 9H).

[(1R,3R)-3-(6-Benzenesulfonyl-6H-1,2,3,5,6-tetraaza-as-indacen-1-yl)-cyclopentyl]-carbamic acid tert-butyl ester Following the procedure for 6-benzenesulfonyl-1-((R)-1-benzyl-piperidin-3-yl)-1,6-dihydro-1,2,3,5,6-tetraaza-as-indacene the title compound was prepared from [(1R,3R)-3-(5-amino-1-benzenesulfonyl-1H-pyrrolo[2,3-b]pyridin-4-ylamino)-cyclopentyl]-carb amic acid tert-butyl ester with further purification by column chromatography on silica gel (gradient: 0 to 5% 2M $NH_3$ in methanol solution in DCM) to afford 243 mg (63%) of [(1R,3R)-3-(6-benzenesulfonyl-6H-1,2,3,5,6-tetraaza-as-indacen-1-yl)-cyclopentyl]-carbamic acid tert-butyl ester as a white foam. LCMS (Method I, ESI): RT=3.38 min, m+H=482.4; $^1$H NMR (400 MHz, DMSO) δ: 8.73 (s, 1H), 8.49 (s, 1H), 8.13 (m, 2H), 8.01 (d, 1H), 7.69 (m, 1H), 7.62 (m, 2H), 7.29 (d, 1H), 7.19 (d, 1H), 5.23 (m, 1H), 4.11 (s, 1H), 2.25 (m, 4H), 1.96 (m, 1H), 1.64 (m, 1H), 1.40 (s, 9H).

[(1R,3R)-3-(6H-1,2,3,5,6-Tetraaza-as-indacen-1-yl)-cyclopentyl]-carbamic acid tert-butyl ester Following the procedure for racemic cis 1-(1-benzyl-2-methyl-piperidin-4-yl)-1,6-dihydro-1,2,3,5,6-tetraaza-as-indacene the title compound was prepared from [(1R,3R)-3-(6-benzenesulfonyl-6H-1,2,3,5,6-tetraaza-as-indacen-1-yl)-cyclopentyl]-carb amic acid tert-butyl ester to afford 165 mg (96%) of [(1R,3R)-3-(6H-1,2,3,5,6-tetraaza-as-indacen-1-yl)-cyclopentyl]-carb amic acid tert-butyl ester. LCMS (Method A, ESI): RT=2.92 min, m+H=342.3; $^1$H NMR (400 MHz, DMSO) δ: 11.83 (s, 1H), 8.57 (s, 1H), 8.30 (s, 1H), 7.47 (t, 1H), 7.20 (d, 1H), 6.83 (dd, 1H), 5.24 (t, 1H), 4.13 (s, 1H), 2.26 (m, 4H), 2.03 (m, 1H), 1.68 (m, 1H), 1.40 (s, 9H).

Example 135

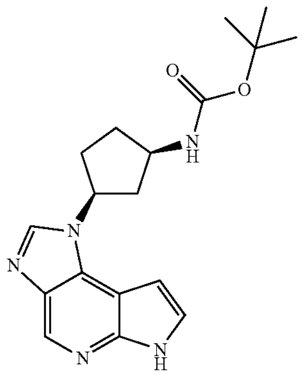 [SMILES: CC(C)(C)OC(=O)N[C@@H]1CC[C@H](n2cnc3cnc4[nH]ccc4c32)C1]

[(1R,3S)-3-(6H-1,2,3,5,6-Tetraaza-as-indacen-1-yl)-cyclopentyl]-carbamic acid tert-butyl ester ((1R,3S)-3-Allyloxycarbonylamino-cyclopentyl)-carbamic acid tert-butyl ester Following the procedure for ((1R,3R)-3-allyloxycarbonylamino-cyclopentyl)-carbamic acid tert-butyl ester the title compound was prepared from (1R,3S)-3-tert-butoxycarbonylamino-cyclopentanecarboxylic acid to afford 760 mg (61%) of ((1R,3S)-3-allyloxycarbonylamino-cyclopentyl)-carbamic acid tert-butyl ester as a white solid. $^1$H NMR (400 MHz, DMSO) δ: 7.22 (d, 1H), 6.84 (d, 1H), 5.90 (m, 1H), 5.27 (dq, 1H), 5.16 (dq, 1H), 4.47-4.42 (m, 2H), 3.76 (m, 2H), 2.14 (m, 1H), 1.78-1.71 (m, 2H), 1.50-1.44 (m, 2H), 1.37 (s, 9H), 1.27 (m, 1H).

((1R,3S)-3-Amino-cyclopentyl)-carbamic acid tert-butyl ester

Following the procedure for ((1R,3R)-3-amino-cyclopentyl)-carbamic acid tert-butyl ester the title compound was prepared from ((1R,3S)-3-allyloxycarbonylamino-cyclopentyl)-carbamic acid tert-butyl ester with further purification by column chromatography on silica gel (gradient: 0 to 5% methanol in DCM then 0 to 10% 2M $NH_3$ in methanol solution in DCM) to afford 300 mg (56%) of ((1R,3S)-3-aminocyclopentyl)-carbamic acid tert-butyl ester. LCMS (Method I, ESI): RT=0.32 min, m+H-Boc=101.2; $^1$H NMR (400 MHz, DMSO) δ: 6.84 (s, 1H), 3.77-3.69 (m, 1H), 3.21 (m, 2H), 2.00 (m, 1H), 1.78-1.63 (m, 2H), 1.50 (m, 1H), 1.37 (s, 9H), 1.17 (m, 1H).

[(1R,3S)-3-(1-Benzenesulfonyl-5-nitro-1H-pyrrolo[2,3-b]pyridin-4-ylamino)-cyclopentyl]-carbamic acid tert-butyl ester Following the procedure for racemic (1-benzenesulfonyl-5-nitro-1H-pyrrolo[2,3-b]pyridin-4-yl)-(1-benzyl-4-methyl-piperidin-3-yl)-amine the title compound was prepared from ((1R,3S)-3-amino-cyclopentyl)-carbamic acid tert-butyl ester to afford 347 mg (69%) of [(1R,3S)-3-(1-benzenesulfonyl-5-nitro-1H-pyrrolo[2,3-b]pyridin-4-ylamino)-cyclopentyl]-carb amic acid tert-butyl ester. LCMS (Method H, ESI): RT=4.06 min, m+H=502.2; $^1$H NMR (400 MHz, DMSO) δ: 8.97 (d, 1H), 8.90 (s, 1H), 8.13 (dd, 2H), 7.82-7.75 (m, 2H), 7.65 (t, 2H), 7.14 (d, 1H), 7.04 (s, 1H), 4.52 (d, 1H), 3.88 (s, 1H), 2.43 (m, 1H), 2.08 (m, 1H), 1.88 (m, 1H), 1.75 (m, 1H), 1.67-1.51 (m, 2H), 1.36 (s, 9H).

[(1R,3S)-3-(6-Benzenesulfonyl-6H-1,2,3,5,6-tetraaza-as-indacen-1-yl)-cyclopentyl]-carbamic acid tert-butyl ester A mixture of [(1R,3S)-3-(1-benzenesulfonyl-5-nitro-1H-pyrrolo[2,3-b]pyridin-4-ylamino)-cyclopentyl]-carbamic acid tert-butyl ester (347 mg, 0.69 mmol), iron powder (308 mg, 5.52 mmol) and triethylorthoformate (287 μL, 1.73 mmol) in acetic acid (5 mL) was stirred at 100° C. for 1 hour. The cooled reaction mixture was filtered through Celite® which was washed with acetic acid, and the combined filtrate concentrated under vacuum. The residue was dissolved in ethyl acetate and the organic layer washed with saturated aqueous sodium bicarbonate then brine and the combined aqueous layers back-extracted with DCM. The combined organic layers were dried over sodium sulfate and concentrated under vacuum. The resulting residue was purified by column chromatography on silica gel (gradient: 0 to 5% 2M $NH_3$ in methanol solution in DCM) to afford 102 mg (31%) of [(1R,3S)-3-(6-benzenesulfonyl-6H-1,2,3,5,6-tetraaza-as-indacen-1-yl)-cyclopentyl]-carbamic acid tert-butyl ester as a yellow foam. LCMS (Method H, ESI): RT=3.40 min, m+H=482.2; $^1$H NMR (400 MHz, DMSO) δ: 8.73 (s, 1H), 8.49 (s, 1H), 8.13 (m, 2H), 7.97 (d, 1H), 7.68 (m, 1H), 7.61 (m, 2H), 7.29 (d, 1H), 7.12 (m, 1H), 5.11 (m, 1H), 4.02 (s, 1H), 2.65-2.55 (m, 1H), 2.21 (m, 1H), 2.09-1.98 (m, 2H), 1.88 (m, 1H), 1.74 (m, 1H), 1.38 (s, 9H).

[(1R,3S)-3-(6H-1,2,3,5,6-Tetraaza-as-indacen-1-yl)-cyclopentyl]-carbamic acid tert-butyl ester Following the procedure for racemic cis 1-(1-benzyl-2-methyl-piperidin-4-yl)-1,6-dihydro-1,2,3,5,6-tetraaza-as-indacene the title compound was prepared from [(1R,3S)-3-(6-benzenesulfonyl-6H-1,2,3,5,6-tetraaza-as-indacen-1-yl)-cyclopentyl]-carbamic acid tert-butyl ester to afford 71 mg (98%) of [(1R,3S)-3-(6H-1,2,3,5,6-tetraaza-as-indacen-1-yl)-cyclopentyl]-carbamic acid tert-butyl ester. LCMS (Method A, ESI): RT=2.94 min, m+H=342.3; $^1$H NMR (400 MHz, DMSO) δ: 11.82 (s, 1H), 8.56 (s, 1H), 8.31 (s, 1H), 7.45 (t, 1H), 7.16 (d, 1H), 6.83 (dd, 1H), 5.15-5.06 (m, 1H), 4.04 (m, 1H), 2.61 (m, 1H), 2.24 (m, 1H), 2.00 (m, 3H), 1.76 (m, 1H), 1.39 (s, 9H).

Example 136

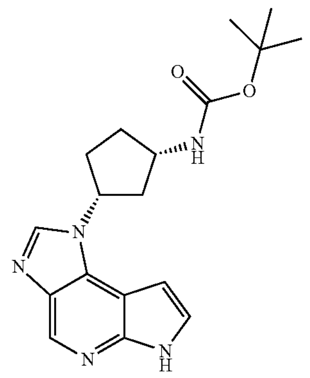 [SMILES: CC(C)(C)OC(=O)N[C@H]1CC[C@@H](n2cnc3cnc4[nH]ccc4c32)C1]

[(1S,3R)-3-(6H-1,2,3,5,6-Tetraaza-as-indacen-1-yl)-cyclopentyl]-carbamic acid tert-butyl ester ((1S,3R)-3-Benzyloxycarbonylamino-cyclopentyl)-carbamic acid tert-butyl ester A mixture of (1R,3S)-3-tert-butoxycarbonylamino-cyclopentanecarboxylic acid (1.0 g, 4.36 mmol), diphenylphosphoryl azide (1.41 mL, 6.54 mmol) and triethylamine (1.21 mL, 8.72 mmol) in toluene (15 mL) was heated at 90° C. for 3 hours then cooled to ambient temperature. Benzyl alcohol (2.48 mL, 23.98 mmol) and DMAP (54 mg, 0.44 mmol) were added and the resulting mixture heated at 90° C. for 16 hours. The cooled reaction mixture was concentrated under vacuum and the resulting residue was dissolved in ethyl acetate. The organic layer was washed with 10% aqueous citric acid and brine and the organic layer dried over sodium sulfate and concentrated under vacuum. The resulting residue was purified by column chromatography on silica gel (gradient: 0 to 30% ethyl acetate in cyclohexane) to afford 635 mg (43%) of ((1S,3R)-3-benzyloxycarbonylamino-cyclopentyl)-carbamic acid tert-butyl ester. $^1$H NMR (400 MHz, DMSO) δ: 7.36 (m, 5H), 6.84 (d, 1H), 5.00 (s, 2H), 3.78 (m, 2H), 2.14 (m, 1H), 1.76 (m, 2H), 1.53-1.43 (m, 2H), 1.37 (s, 9H), 1.32-1.20 (m, 1H).

((1S,3R)-3-Amino-cyclopentyl)-carbamic acid tert-butyl ester

A mixture of ((1S,3R)-3-benzyloxycarbonylamino-cyclopentyl)-carbamic acid tert-butyl ester (635 mg, 1.90 mmol) and 10% Pd on carbon (202 mg, 0.19 mmol) in ethanol (15 mL) was stirred at ambient temperature under an atmosphere of hydrogen for 16 hours. The reaction mixture was filtered through Celite® which was washed with ethanol and the filtrate concentrated under vacuum to afford 390 mg (quant.) of ((1S,3R)-3-amino-cyclopentyl)-carbamic acid tert-butyl ester as a colorless oil. LCMS (Method H, ESI): RT=0.38 min, m+H=200.9; $^1$H NMR (400 MHz, DMSO) δ: 6.82 (d, 1H), 3.75-3.66 (m, 1H), 3.17 (m, 2H), 1.98 (m, 1H), 1.70 (m, 3H), 1.49 (m, 1H), 1.37 (s, 9H), 1.31 (m, 1H), 1.14 (m, 1H).

[(1S,3R)-3-(1-Benzenesulfonyl-5-nitro-1H-pyrrolo[2,3-b]pyridin-4-ylamino)-cyclopentyl]-carbamic acid tert-butyl ester Following the procedure for racemic (1-benzenesulfonyl-5-nitro-1H-pyrrolo[2,3-b]pyridin-4-yl)-(1-benzyl-4-methyl-piperidin-3-yl)-amine the title compound was prepared from ((1S,3R)-3-amino-cyclopentyl)-carbamic acid tert-butyl ester to afford 860 mg (97%) of [(1S,3R)-3-(1-benzenesulfonyl-5-nitro-1H-pyrrolo[2,3-b]pyridin-4-ylamino)-cyclopentyl]-carb amic acid tert-butyl ester. LCMS (Method H, ESI): RT=4.05 min, m+H=502.1; $^1$H NMR (400 MHz, DMSO) δ: 8.97 (d, 1H), 8.90 (s, 1H), 8.13 (m, 2H), 7.78 (m, 2H), 7.68-7.62 (m, 2H), 7.13 (d, 1H), 7.04 (d, 1H), 4.52 (m, 1H), 3.88 (s, 1H), 2.43 (m, 1H), 2.07 (m, 1H), 1.91-1.71 (m, 2H), 1.59 (m, 2H), 1.36 (s, 9H).

[(1S,3R)-3-(5-Amino-1-benzenesulfonyl-1H-pyrrolo[2,3-b]pyridin-4-ylamino)-cyclopentyl]-carbamic acid tert-butyl ester Following the procedure for 1-benzenesulfonyl-N*4*-((R)-1-benzyl-piperidin-3-yl)-1H-pyrrolo[2,3-b]pyridine-4,5-diamine the title compound was prepared from [(1S,3R)-3-(1-benzenesulfonyl-5-nitro-1H-pyrrolo[2,3-b]pyridin-4-ylamino)-cyclopentyl]-carb amic acid tert-butyl ester to afford 783 mg (97%) of [(1S,3R)-3-(5-amino-1-benzenesulfonyl-1H-pyrrolo[2,3-b]pyridin-4-ylamino)-cyclopentyl]-carbamic acid tert-butyl ester of as a foam. LCMS (Method H, ESI): RT=2.72 min, m+H=472.2; $^1$H NMR (400 MHz, DMSO) δ: 8.00 (m, 2H), 7.65 (m, 1H), 7.57 (m, 3H), 7.45 (d, 1H), 6.92 (d, 1H), 6.78 (d, 1H), 5.23 (d, 1H), 4.32 (s, 2H), 4.26-4.18 (m, 1H), 3.87-3.77 (m, 1H), 2.31 (m, 1H), 1.94-1.80 (m, 2H), 1.61-1.50 (m, 2H), 1.37 (s, 9H).

[(1S,3R)-3-(6-Benzenesulfonyl-6H-1,2,3,5,6-tetraaza-as-indacen-1-yl)-cyclopentyl]-carbamic acid tert-butyl ester Following the procedure for 6-benzenesulfonyl-1-((R)-1-benzyl-piperidin-3-yl)-1,6-dihydro-1,2,3,5,6-tetraaza-as-indacene the title compound was prepared from [(1S,3R)-3-(5-amino-1-benzenesulfonyl-1H-pyrrolo[2,3-b]pyridin-4-ylamino)-cyclopentyl]-carb amic acid tert-butyl ester with further purification by column chromatography on silica gel (gradient: 0 to 4% 2M $NH_3$ in methanol solution in DCM) to afford 800 mg (quant.) of [(1S,3R)-3-(6-benzenesulfonyl-6H-1,2,3,5,6-tetraaza-as-indacen-1-yl)-cyclopentyl]-carbamic acid tert-butyl ester as a white foam. LCMS (Method I, ESI): RT=3.37 min, m+H=482.3; $^1$H NMR (400 MHz, $CDCl_3$) δ: 8.73 (s, 1H), 8.49 (s, 1H), 8.13 (m, 2H), 7.97 (d, 1H), 7.69 (m, 1H), 7.61 (m, 2H), 7.29 (d, 1H), 7.16-7.09 (m, 1H), 5.14-5.07 (m, 1H), 4.08-3.97 (m, 1H), 2.59 (m, 1H), 2.12 (m, 3H), 1.88 (m, 1H), 1.74-1.72 (m, 1H), 1.38 (s, 9H).

[(1S,3R)-3-(6H-1,2,3,5,6-Tetraaza-as-indacen-1-yl)-cyclopentyl]-carbamic acid tert-butyl ester Following the procedure for racemic cis 1-(1-benzyl-2-methyl-piperidin-4-yl)-1,6-dihydro-1,2,3,5,6-tetraaza-as-indacene the title compound was prepared from [(1S,3R)-3-(6-benzenesulfonyl-6H-1,2,3,5,6-tetraaza-as-indacen-1-yl)-cyclopentyl]-carbamic acid tert-butyl ester to afford 97 mg (95%) of [(1S,3R)-3-(6H-1,2,3,5,6-tetraaza-as-indacen-1-yl)-cyclopentyl]-carb amic acid tert-butyl ester. LCMS (Method A, ESI): RT=2.94 min, m+H=342.3; $^1$H NMR (400 MHz, $CDCl_3$) δ: 11.82 (s, 1H), 8.57 (s, 1H), 8.31 (s, 1H), 7.45 (t, 1H), 7.16 (s, 1H), 6.84 (dd, 1H), 5.15-5.06 (m, 1H), 4.03 (m, 1H), 2.62 (m, 1H), 2.24 (m, 1H), 2.03 (m, 3H), 1.78 (m, 1H), 1.40 (s, 9H).

Example 137

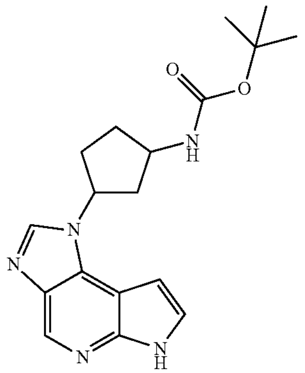 [SMILES: CC(C)(C)OC(=O)NC1CCC(n2cnc3cnc4[nH]ccc4c32)C1]

Racemic trans [3-(6H-1,2,3,5,6-Tetraaza-as-indacen-1-yl)-cyclopentyl]-carbamic acid tert-butyl ester The title compound was prepared according to the methods used for the preparation of [(1R,3R)-3-(6H-1,2,3,5,6-tetraaza-as-indacen-1-yl)-cyclopentyl]-carb amic acid tert-butyl ester using racemic trans 3-amino-cyclopentyl)-carbamic acid tert-butyl ester that was prepared following the methods of J. Org. Chem. 2004, 69(13), 4538; Tetrahedron 1997, 53(9), 3347; WO94/17090 and Org. Lett. 2000, 2, 4169. LCMS (Method A, ESI): RT=2.92 min, m+H=342.3; $^1$H NMR (400 MHz, DMSO) δ: 11.83 (s, 1H), 8.57 (s, 1H), 8.30 (s, 1H), 7.47 (t, 1H), 7.20 (d, 1H), 6.83 (dd, 1H), 5.24 (t, 1H), 4.13 (s, 1H), 2.27 (m, 4H), 2.03 (m, 1H), 1.68 (m, 1H), 1.40 (s, 9H).

Example 138

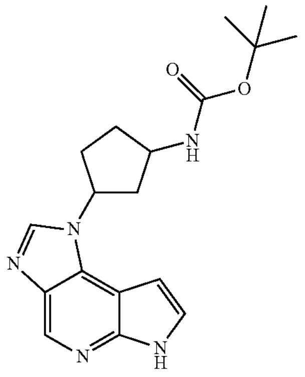 [SMILES: CC(C)(C)OC(=O)NC1CCC(n2cnc3cnc4[nH]ccc4c32)C1]

Racemic cis[3-(6H-1,2,3,5,6-Tetraaza-as-indacen-1-yl)-cyclopentyl]-carbamic acid tert-butyl ester The title compound was prepared according to the methods used for the preparation of [(1R,3S)-3-(6H-1,2,3,5,6-tetraaza-as-indacen-1-yl)-cyclopentyl]-carb amic acid tert-butyl ester using racemic cis 3-amino-cyclopentyl)-carbamic acid tert-butyl ester that was prepared following the methods of J. Org. Chem. 2004, 69, 4538; Tetrahedron 1997, 53, 3347; WO2008/065021; WO94/17090; and Org Lett 2000, 2, 4169. LCMS (Method A, ESI): RT=2.94 min, m+H=342.3; $^1$H NMR (400 MHz, DMSO) δ: 11.82 (s, 1H), 8.56 (s, 1H), 8.31 (s, 1H), 7.45 (t, 1H), 7.16 (d, 1H), 6.83 (dd, 1H), 5.15-5.06 (m, 1H), 4.03 (m, 1H), 2.61 (m, 1H), 2.23 (m, 1H), 2.01 (m, 3H), 1.77 (m, 1H), 1.39 (s, 9H).

Example 139

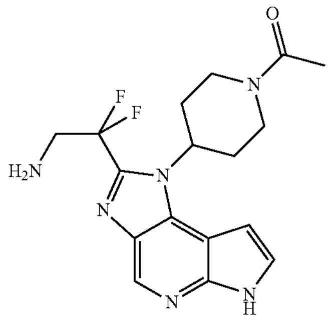 [SMILES: CC(=O)N1CCC(n2c(C(F)(F)CN)nc3cnc4[nH]ccc4c32)CC1]

1-{4-[2-(2-Amino-1,1-difluoro-ethyl)-6H-1,2,3,5,6-tetraaza-as-indacen-1-yl]-piperidin-1-yl}-ethanone 4-[1-Benzenesulfonyl-5-(3-benzyloxycarbonylamino-2,2-difluoro-propionylamino)-1H-pyrrolo[2,3-b]pyridin-4-ylamino]-piperidine-1-carboxylic acid tert-butyl ester A mixture of 4-(5-amino-1-benzenesulfonyl-1H-pyrrolo[2,3-b]pyridin-4-ylamino)-piperidine-1-carboxylic acid tert-butyl ester (500 mg, 1.06 mmol), 3-benzyloxycarbonylamino-2,2-difluoro-propionic acid (300 mg, 1.15 mmol), diisopropylethylamine (363 μL, 2.12 mmol) and HATU (440 mg, 1.15 mmol) in DCM (10 mL) was stirred at ambient temperature for 3.5 hours. The reaction mixture was concentrated under vacuum and the residue purified by column chromatography on silica gel (gradient: 0 to 5% methanol in DCM then 0 to 10% 2M $NH_3$ in methanol solution in DCM) to afford 1.20 g of 4-[1-benzenesulfonyl-5-(3-benzyloxycarbonylamino-2,2-difluoro-propionylamino)-1H-pyrrolo[2,3-b]pyridin-4-ylamino]-piperidine-1-carboxylic acid tert-butyl ester. LCMS (Method B, ESI): RT=3.91 min, m+H=713.

{2-[1-(1-Acetyl-piperidin-4-yl)-6-benzenesulfonyl-1,6-dihydro-1,2,3,5,6-tetraaza-as-indacen-2-yl]-2,2-difluoro-ethyl}-carbamic acid benzyl ester A solution of 4-[1-benzenesulfonyl-5-(3-benzyloxycarbonylamino-2,2-difluoro-propionylamino)-1H-pyrrolo[2,3-b]pyridin-4-ylamino]-piperidine-1-carboxylic acid tert-butyl ester (1.20 g) in acetic acid (10 mL) was stirred at 100° C. for 2 hours. The cooled reaction mixture was concentrated under vacuum then purified by column chromatography on silica gel (gradient: 0 to 10% methanol in DCM then 10% 2M $NH_3$ in methanol solution in DCM). The resulting residue was further purified by Isolute® SCX-2 column (gradient: methanol to 2M $NH_3$ in methanol solution) to afford {2-[1-(1-acetyl-piperidin-4-yl)-6-benzenesulfonyl-1,6-dihydro-1,2,3,5,6-tetraaza-as-indacen-2-yl]-2,2-difluoro-ethyl}-carbamic acid benzyl ester. $^1$H NMR (400 MHz, $CDCl_3$) δ: 8.89 (s, 1H), 8.22-8.18 (m, 2H), 7.87 (d, 1H), 7.57-7.53 (m, 1H), 7.47 (m, 2H), 7.39-7.27 (m, 5H), 6.66 (d, 1H), 5.87-5.78 (m, 1H), 5.12 (s, 2H), 5.10-4.90 (m, 2H), 4.37-4.24 (m, 2H), 4.13-4.04 (m, 1H), 3.36-3.24 (m, 1H), 2.75-2.68 (m, 1H), 2.42 (m, 2H), 2.26 (s, 3H), 2.09-1.97 (m, 2H).

{2-[1-(1-Acetyl-piperidin-4-yl)-1,6-dihydro-1,2,3,5,6-tetraaza-as-indacen-2-yl]-2,2-difluoro-ethyl}-carbamic acid benzyl ester Following the procedure for racemic cis 1-(1-benzyl-2-methyl-piperidin-4-yl)-1,6-dihydro-1,2,3,5,6-tetraaza-as-indacene the title compound was prepared from {2-[1-(1-acetyl-piperidin-4-yl)-6-benzenesulfonyl-1,6-dihydro-1,2,3,5,6-tetraaza-as-indacen-2-yl]-2,2-difluoro-ethyl}-carbamic acid benzyl ester with further purification by preparative HPLC (gradient: 5 to 75% MeCN in water containing 0.1% $NH_4OH$) to afford 50 mg of {2-[1-(1-acetyl-piperidin-4-yl)-1,6-dihydro-1,2,3,5,6-tetraaza-as-indacen-2-yl]-2,2-difluoro-ethyl}-carbamic acid benzyl ester. LCMS (Method A, ESI): RT=3.68 min, m+H=497.3; $^1$H NMR (400 MHz, DMSO) δ: 8.72 (s, 1H), 7.93 (s, 1H), 7.60 (d, 1H), 7.40-7.26 (m, 5H), 6.41 (s, 1H), 5.06 (s, 3H), 4.65 (d, 1H), 4.23 (td, 2H), 4.10 (d, 1H), 3.41-3.23 (m, 1H), 2.81 (t, 1H), 2.48-2.35 (m, 1H), 2.17 (s, 3H), 2.03-1.91 (m, 3H).

1-{4-[2-(2-Amino-1,1-difluoro-ethyl)-6H-1,2,3,5,6-tetraaza-as-indacen-1-yl]-piperidin-1-yl}-ethanone A solution of {2-[1-(1-acetyl-piperidin-4-yl)-1,6-dihydro-1,2,3,5,6-tetraaza-as-indacen-2-yl]-2,2-difluoro-ethyl}-carbamic acid benzyl ester (30.0 mg, 60.0 μmol) in TFA (2 mL) was stirred at 80° C. in a sealed tube for 1 hour. The cooled reaction mixture was concentrated under vacuum and the resulting residue was dissolved in 1M aqueous lithium hydroxide (250 μL) and MeCN in water containing 0.1% $NH_4OH$. The residue was purified by preparative HPLC (gradient: 5 to 70% MeCN in water containing 0.1% $NH_4OH$) to afford 16 mg (55%) of 1-{4-[2-(2-amino-1,1-difluoro-ethyl)-6H-1,2,3,5,6-tetraaza-as-indacen-1-yl]-piperidin-1-yl}-ethanone. LCMS (Method A, ESI): RT=1.86 min, m+H=363.2; $^1$H NMR (400 MHz, DMSO) δ: 12.14 (s, 1H), 7.58 (s, 2H), 6.41 (s, 1H), 5.20-5.02 (m, 1H), 4.66 (d, 1H), 4.10 (d, 1H), 3.55 (t, 2H), 3.41-3.23 (m, 1H), 2.82 (t, 2H), 2.58-2.34 (m, 1H), 2.17 (s, 3H), 1.94 (s, 4H).

Example 140

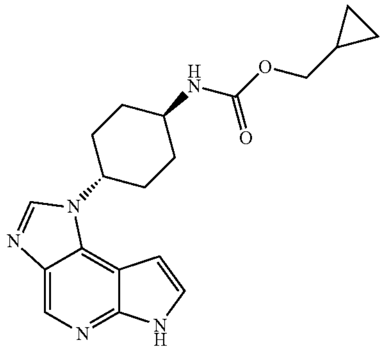 [SMILES: O=C(N[C@H]1CC[C@H](n2cnc3cnc4[nH]ccc4c32)CC1)OCC1CC1]

Trans[4-(6H-1,2,3,5,6-Tetraaza-as-indacen-1-yl)-cyclohexyl]-carbamic acid cyclopropylmethyl ester Trans[4-(6-Benzenesulfonyl-6H-1,2,3,5,6-tetraaza-as-indacen-1-yl)-cyclohexyl]-carbamic acid tert-butyl ester A mixture of trans[4-(5-amino-1-benzenesulfonyl-1H-pyrrolo[2,3-b]pyridin-4-ylamino)-cyclohexyl]-carbamic acid tert-butyl ester (4.22 g, 8.70 mmol), triethyl orthoformate (5.8 mL, 34.8 mmol) and p-toluenesulfonic acid monohydrate (catalytic) in toluene (60 mL) was stirred at 110° C. for 90 minutes. The cooled reaction mixture was filtered and the resulting solid precipitate washed with diethyl ether and methanol and dried under vacuum to afford 3.85 g (81%) of trans[4-(6-benzenesulfonyl-6H-1,2,3,5,6-tetraaza-as-indacen-1-yl)-cyclohexyl]-carb amic acid tert-butyl ester as an off-white solid. LCMS (Method B, ESI): RT=3.65 min, m+H=496.4.

Trans 4-(6-Benzenesulfonyl-6H-1,2,3,5,6-tetraaza-as-indacen-1-yl)-cyclohexylamine A solution of trans[4-(6-benzenesulfonyl-6H-1,2,3,5,6-tetraaza-as-indacen-1-yl)-cyclohexyl]-carbamic acid tert-butyl ester (2.85 g, 7.77 mmol) in water (4 mL) and TFA (12 mL) was stirred at ambient temperature for 2 hours. The reaction mixture was concentrated under vacuum and the resulting residue purified by Isolute® SCX-2 column (gradient: methanol to 2M $NH_3$ in methanol) to afford 3.25 g of trans 4-(6-benzenesulfonyl-6H-1,2,3,5,6-tetraaza-as-indacen-1-yl)-cyclohexylamine. LCMS (Method B, ESI): RT=2.14 min, m+H=396.2.

Trans[4-(6-Benzenesulfonyl-6H-1,2,3,5,6-tetraaza-as-indacen-1-yl)-cyclohexyl]-carbamic acid 4-nitro-phenyl ester To a suspension of trans 4-(6-benzenesulfonyl-6H-1,2,3,5,6-tetraaza-as-indacen-1-yl)-cyclohexylamine (900 mg, 2.28 mmol) in pyridine (10 mL) at 0° C. was added p-nitrophenyl chloroformate (733 mg, 3.65 mmol) and the resulting mixture stirred for 90 minutes. Further p-nitrophenyl chloroformate (229 mg, 1.14 mmol) was added and the mixture stirred for 45 minutes then concentrated under vacuum. The residue was triturated with diethyl ether and the resulting precipitate collected by filtration. The filtrate was washed with water then dried over sodium sulfate and concentrated under vacuum. The resulting residue was purified by column chromatography on silica gel (gradient: 25 to 100% ethyl acetate in cyclohexane) to afford 740 mg (58%) of trans[4-(6-benzenesulfonyl-6H-1,2,3,5,6-tetraaza-as-indacen-1-yl)-cyclohexyl]-carbamic acid 4-nitro-phenyl ester. LCMS (Method B, ESI): RT=3.72 min, m+H=561.3.

Trans[4-(6H-1,2,3,5,6-Tetraaza-as-indacen-1-yl)-cyclohexyl]-carbamic acid cyclopropylmethyl ester To a suspension of trans[4-(6-benzenesulfonyl-6H-1,2,3,5,6-tetraaza-as-indacen-1-yl)-cyclohexyl]-carbamic acid 4-nitro-phenyl ester (167 mg, 0.30 mmol) in cyclopropyl methanol (4 mL) was added sodium hydride (119 mg, 3.0 mmol) and the resulting mixture heated in a microwave reactor at 100° C. for 10 minutes. 1M aqueous HCl (2 mL) was added and the mixture concentrated under vacuum. The resulting residue was partitioned between water and DCM, the organic layer dried over sodium sulfate and concentrated under vacuum. The resulting residue was purified by column chromatography on silica gel (gradient: 0 to 10% methanol in DCM) to afford 70 mg (66%) of trans[4-(6H-1,2,3,5,6-tetraaza-as-indacen-1-yl)-cyclohexyl]-carbamic acid cyclopropylmethyl ester as a white solid. LCMS (Method A, ESI): RT=2.86 min, m+H=354.3; $^1H$ NMR (400 MHz, DMSO) δ: 11.84 (s, 1H), 8.57 (s, 1H), 8.28 (s, 1H), 7.47 (t, 1H), 7.25 (d, 1H), 6.70 (dd, 1H), 4.56-4.53 (m, 1H), 3.80 (d, 2H), 3.53-3.41 (m, 1H), 2.22-2.12 (m, 2H), 2.06-1.96 (m, 4H), 1.58 (m, 2H), 1.08 (m, 1H), 0.50 (m, 2H), 0.25 (m, 2H).

Example 141

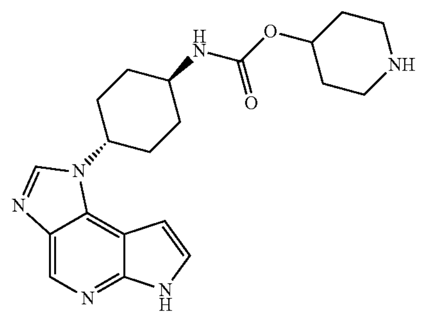 [SMILES: O=C(N[C@H]1CC[C@H](n2cnc3cnc4[nH]ccc4c32)CC1)OC1CCNCC1]

Trans[4-(6H-1,2,3,5,6-Tetraaza-as-indacen-1-yl)-cyclohexyl]-carbamic acid piperidin-4-yl ester Trans 4-[4-(6H-1,2,3,5,6-Tetraaza-as-indacen-1-yl)-cyclohexylcarbamoyloxy]-piperidine-1-carboxylic acid tert-butyl ester To a suspension of trans[4-(6-benzenesulfonyl-6H-1,2,3,5,6-tetraaza-as-indacen-1-yl)-cyclohexyl]-carbamic acid 4-nitro-phenyl ester (250 mg, 0.45 mmol) in MeCN (4 mL) was added 4-hydroxy-piperidine-1-carboxylic acid tert-butyl ester (280 mg, 1.40 mmol) and sodium hydride (54 mg, 1.35 mmol) and the resulting mixture heated in a microwave reactor at 120° C. for 15 minutes. 2M aqueous NaOH (1.5 mL) and methanol (2 mL) were added and the resulting mixture stirred at ambient temperature for 16 hours. The reaction mixture was concentrated under vacuum and the resulting residue partitioned between water and DCM. The organic layer was dried over sodium sulfate and concentrated under vacuum. The resulting residue was triturated with ethyl acetate and diethyl ether to afford 92 mg (42%) of trans 4-[4-(6H-1,2,3,5,6-tetraaza-as-indacen-1-yl)-cyclohexylcarbamoyloxy]-piperidine-1-carboxylic acid tert-butyl ester as a pale yellow solid. LCMS (Method B, ESI): RT=2.72 min, m+H=483.4.

Trans[4-(6H-1,2,3,5,6-Tetraaza-as-indacen-1-yl)-cyclohexyl]-carbamic acid piperidin-4-yl ester A suspension of trans 4-[4-(6H-1,2,3,5,6-tetraaza-as-indacen-1-yl)-cyclohexylcarbamoyloxy]-piperidine-1-carboxylic acid tert-butyl ester (90 mg, 0.19 mmol) in 4M HCl in dioxane was stirred at ambient temperature for 90 minutes then diluted with methanol and purified by Isolute® SCX-2 column (gradient: methanol to 2M $NH_3$ in methanol). The resulting residue was purified by column chromatography on silica gel (gradient: 10 to 20% methanol in DCM) then Isolute® SCX-2 column (gradient: methanol to 2M $NH_3$ in methanol) to afford 34 mg (51%) of trans[4-(6H-1,2,3,5,6-tetraaza-as-indacen-1-yl)-cyclohexyl]-carbamic acid piperidin-4-yl ester. LCMS (Method A, ESI): RT=1.71 min, m+H=383.3; $^1$H NMR (400 MHz, DMSO) δ: 11.84 (s, 1H), 8.57 (s, 1H), 8.28 (s, 1H), 7.47 (t, 1H), 7.16 (d, 1H), 6.69 (dd, 1H), 4.54 (s, 2H), 3.46 (s, 1H), 3.17 (s, 2H), 2.97-2.85 (m, 2H), 2.21-1.96 (m, 6H), 1.87-1.75 (m, 2H), 1.59-1.54 (m, 2H), 1.44-1.28 (s, 2H).

Example 142

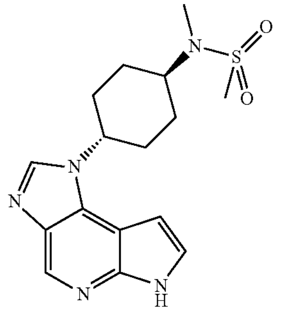 [SMILES: CN([C@H]1CC[C@H](n2cnc3cnc4[nH]ccc4c32)CC1)S(C)(=O)=O]

Trans N-Methyl-N-[4-(6H-1,2,3,5,6-tetraaza-as-indacen-1-yl)-cyclohexyl]-methanesulfonamide Trans N-[4-(6-Benzenesulfonyl-6H-1,2,3,5,6-tetraaza-as-indacen-1-yl)-cyclohexyl]-formamide A mixture of acetic anhydride (359 μL, 3.78 mmol) and formic acid (713 μL, 18.9 mmol) was heated to 50° C. for 5 minutes then cooled to 0° C. before trans 4-(6-benzenesulfonyl-6H-1,2,3,5,6-tetraaza-as-indacen-1-yl)-cyclohexylamine (500 mg, 1.26 mmol) and THF (2 mL) were added and the resulting mixture stirred for 30 minutes. The reaction mixture was quenched with saturated aqueous sodium bicarbonate and extracted with DCM. The combined organic layers were dried over sodium sulfate and concentrated under vacuum. The aqueous layer was filtered and an insoluble solid collected and washed with water. This was combined with the concentrated organic layers to afford 550 mg (quant.) of trans N-[4-(6-benzenesulfonyl-6H-1,2,3,5,6-tetraaza-as-indacen-1-yl)-cyclohexyl]-formamide. LCMS (Method B, ESI): RT=2.79 min, m+H=424.3; $^1$H NMR (400 MHz, DMSO) δ: 8.73 (s, 1H), 8.48 (s, 1H), 8.11-8.10 (m, 3H), 7.98-7.97 (m, 2H), 7.69-7.66 (m, 1H), 7.61-7.60 (m, 2H), 7.23 (d, 1H), 4.70-4.58 (m, 1H), 3.82-3.69 (m, 1H), 2.02-1.99 (m, 6H) 1.67-1.53 (m, 2H).

Trans[4-(6-Benzenesulfonyl-6H-1,2,3,5,6-tetraaza-as-indacen-1-yl)-cyclohexyl]-methyl-amine A mixture of trans N-[4-(6-benzenesulfonyl-6H-1,2,3,5,6-tetraaza-as-indacen-1-yl)-cyclohexyl]-formamide (550 mg, 1.29 mmol) and 1M borane in THF (1.94 mL, 1.94 mmol) in THF was stirred at ambient temperature for 75 minutes then heated to 60° C. for 2 hours. Further 1M borane in THF (6.45 mL, 6.45 mmol) was added and heated to 80° C. for 1 hour. The reaction mixture was quenched with methanol then concentrated under vacuum. The resulting residue was dissolved in water (10 mL) and concentrated HCl (2 mL) and the mixture heated at 100° C. for 30 minutes. The mixture was diluted with methanol and purified by Isolute® SCX-2 column (gradient: methanol to 2M $NH_3$ in methanol) to afford 454 mg (86%) of trans[4-(6-benzenesulfonyl-6H-1,2,3,5,6-tetraaza-as-indacen-1-yl)-cyclohexyl]-methyl-amine. LCMS (Method B, ESI): RT=2.12, m+H=410.3, $^1$H NMR (400 MHz, DMSO) δ: 8.73 (s, 1H), 8.47 (s, 1H), 8.13 (dd, 2H), 7.97 (d, 1H), 7.72-7.68 (m, 1H), 7.61-7.60 (m, 2H), 7.19 (d, 1H), 4.64-4.54 (m, 1H), 2.73-2.58 (m, 1H), 2.33 (s, 3H), 2.10-1.86 (m, 6H), 1.42-1.36 (m, 2H).

Trans N-[4-(6-Benzenesulfonyl-6H-1,2,3,5,6-tetraaza-as-indacen-1-yl)-cyclohexyl]-N-methyl-methanesulfonamide A mixture of trans[4-(6-benzenesulfonyl-6H-1,2,3,5,6-tetraaza-as-indacen-1-yl)-cyclohexyl]-methyl-amine (100 mg, 0.24 mmol), methanesulfonyl chloride (20 μL, 0.26 mmol) and diisopropylethylamine (50 μL, 0.29 mmol) in MeCN (2 mL) was stirred at ambient temperature for 16 hours. Further methanesulfonyl chloride (7 μL, 0.10 mmol) and diisopropylethylamine (21 μL, 0.12 mmol) were added and the mixture stirred for 30 minutes. The reaction mixture was concentrated under vacuum the purified by column chromatography on silica gel (gradient: 0 to 3% methanol in chloroform) to afford 98 mg (84%) of trans N-[4-(6-benzenesulfonyl-6H-1,2,3,5,6-tetraaza-as-indacen-1-yl)-cyclohexyl]-N-methyl-methanesulfonamide. LCMS (Method B, ESI): RT=3.22 min, m+H=488.3.

Trans N-Methyl-N-[4-(6H-1,2,3,5,6-tetraaza-as-indacen-1-yl)-cyclohexyl]-methanesulfonamide Following the procedure for racemic cis 1-(1-benzyl-2-methyl-piperidin-4-yl)-1,6-dihydro-1,2,3,5,6-tetraaza-as-indacene the title compound was prepared from trans N-[4-(6-benzenesulfonyl-6H-1,2,3,5,6-tetraaza-as-indacen-1-yl)-cyclohexyl]-N-methyl-methanesulfonamide with further purification by Isolute® SCX-2 column (gradient: methanol to 2M $NH_3$ in methanol) and trituration with methanol to afford 66 mg (50%) of trans N-methyl-N-[4-(6H-1,2,3,5,6-tetraaza-as-indacen-1-yl)-cyclohexyl]-methanesulfonamide. LCMS (Method A, ESI): RT=2.31 min, m+H=348.2; $^1$H NMR (400 MHz, DMSO) δ: 11.83 (s, 1H), 8.56 (s, 1H), 8.28 (s, 1H), 7.47 (t, 1H), 6.85 (dd, 1H), 4.61 (s, 1H), 3.81 (s, 1H), 2.94 (s, 3H), 2.80 (s, 3H), 2.20 (s, 2H), 2.06-2.02 (m, 4H), 1.84 (s, 2H).

Example 143

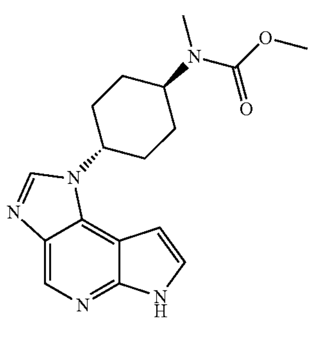 [SMILES: COC(=O)N(C)[C@H]1CC[C@H](n2cnc3cnc4[nH]ccc4c32)CC1]

Trans Methyl-[4-(6H-1,2,3,5,6-tetraaza-as-indacen-1-yl)-cyclohexyl]-carbamic acid methyl ester Trans[4-(6-Benzenesulfonyl-6H-1,2,3,5,6-tetraaza-as-indacen-1-yl)-cyclohexyl]-methyl-carbamic acid methyl ester A mixture of trans[4-(6-benzenesulfonyl-6H-1,2,3,5,6-tetraaza-as-indacen-1-yl)-cyclohexyl]-methyl-amine (100 mg, 0.24 mmol), methyl chloroformate (28 μL, 0.36 mmol) and diisopropylethylamine (125 μL, 0.72 mmol) in DCM (3 mL) was stirred at ambient temperature for 1 hour. The reaction mixture was concentrated under vacuum the purified by column chromatography on silica gel (gradient: 0 to 2% methanol in DCM) to afford 125 mg (quant.) of trans[4-(6-benzenesulfonyl-6H-1,2,3,5,6-tetraaza-as-indacen-1-yl)-cyclohexyl]-methyl-carbamic acid methyl ester. LCMS (Method B, ESI): RT=3.37 min, m+H=468.3.

Trans Methyl-[4-(6H-1,2,3,5,6-tetraaza-as-indacen-1-yl)-cyclohexyl]-carbamic acid methyl ester Following the procedure for racemic cis 1-(1-benzyl-2-methyl-piperidin-4-yl)-1,6-dihydro-1,2,3,5,6-tetraaza-as-indacene the title compound was prepared from trans[4-(6-benzenesulfonyl-6H-1,2,3,5,6-tetraaza-as-indacen-1-yl)-cyclohexyl]-methyl-carbamic acid methyl ester with further purification by column chromatography on silica gel (gradient: 50% DCM in pentane then 1 to 5% methanol in DCM) and trituration with ethyl acetate to afford 41 mg (55%) of trans methyl-[4-(6H-1,2,3,5,6-tetraaza-as-indacen-1-yl)-cyclohexyl]-carbamic acid methyl ester. LCMS (Method A, ESI): RT=2.59 min, m+H=328.3; $^1$H NMR (400 MHz, $CDCl_3$) δ: 11.83 (s, 1H), 8.57 (s, 1H), 8.30 (s, 1H), 7.47 (t, 1H), 6.85 (dd, 1H), 4.70-4.56 (m, 1H), 4.18-3.95 (m, 1H), 3.62 (s, 3H), 2.82 (s, 3H), 2.21 (d, 2H), 2.03 (m, 4H), 1.79-1.70 (m, 2H).

Example 144

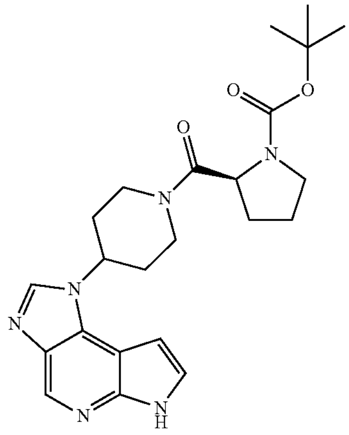 [SMILES: CC(C)(C)OC(=O)N1CCC[C@H]1C(=O)N1CCC(n2cnc3cnc4[nH]ccc4c32)CC1]

(S)-2-[4-(6H-1,2,3,5,6-Tetraaza-as-indacen-1-yl)-piperidine-1-carbonyl]-pyrrolidine-1-carboxylic acid tert-butyl ester A mixture of 1-piperidin-4-yl-1,6-dihydro-1,2,3,5,6-tetraaza-as-indacene (60 mg, 0.25 mmol), (S)-pyrrolidine-1,2-dicarboxylic acid 1-tert-butyl ester (65 mg, 0.30 mmol), diisopropylethylamine (60 μL, 0.37 mmol) and HATU (115 mg, 0.30 mmol) in DMF (2 mL) was stirred at ambient temperature for 1 hour. The reaction mixture was concentrated under vacuum and purified by column chromatography on silica gel (gradient: 0 to 10% 2M $NH_3$ in methanol solution in DCM) to afford 85 mg (78%) of (S)-2-[4-(6H-1,2,3,5,6-tetraaza-as-indacen-1-yl)-piperidine-1-carbonyl]-pyrrolidine-1-carboxylic acid tert-butyl ester. LCMS (Method A, ESI): RT=2.88 min, m+H=439.1; $^1$H NMR (400 MHz, MeOD) δ: 8.59 (s, 1H), 8.34 (d, 1H), 7.47 (t, 1H), 6.94 (d, 1H), 6.86 (m, 1H), 5.05-4.94 (m, 2H), 4.88-4.73 (m, 1H), 4.38-4.23 (m, 2H), 3.51 (m, 3H), 3.22-2.99 (m, 2H), 2.74-2.63 (m, 1H), 2.25-2.21 (m, 5H), 1.49-1.45 (m, 5H), 1.11 (d, 4H).

Example 145

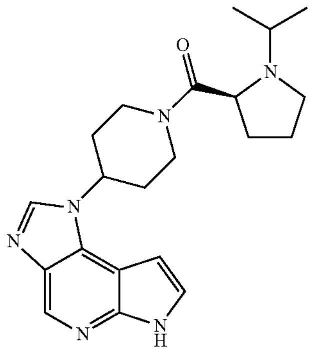 [SMILES: CC(C)N1CCC[C@H]1C(=O)N1CCC(n2cnc3cnc4[nH]ccc4c32)CC1]

((S)-1-Isopropyl-pyrrolidin-2-yl)-[4-(6H-1,2,3,5,6-tetraaza-as-indacen-1-yl)-piperidin-1-yl]-methanone Following the procedure for (S)-2-[4-(6H-1,2,3,5,6-tetraaza-as-indacen-1-yl)-piperidine-1-carbonyl]-pyrrolidine-1-carboxylic acid tert-butyl ester the title compound was prepared from (S)-1-isopropyl-pyrrolidine-2-carboxylic acid to afford 55 mg (88%) of ((S)-1-isopropyl-pyrrolidin-2-yl)-[4-(6H-1,2,3,5,6-tetraaza-as-indacen-1-yl)-piperidin-1-yl]-methanone. LCMS (Method A, ESI): RT=1.57 min, m+H=381.2; $^1$H NMR (400 MHz, DMSO) δ: 11.85 (s, 1H), 8.57 (s, 1H), 8.30 (s, 1H), 7.47 (s, 1H), 6.77 (s, 1H), 4.89 (s, 1H), 4.86-4.83 (m, 1H), 4.60 (s, 3H), 3.70 (s, 1H), 3.08-2.76 (m, 4H), 2.28-1.64 (m, 8H), 1.02 (m, 5H).

Example 146

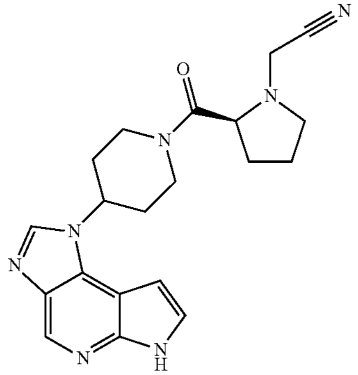 [SMILES: N#CCN1CCC[C@H]1C(=O)N1CCC(n2cnc3cnc4[nH]ccc4c32)CC1]

{(S)-2-[4-(6H-1,2,3,5,6-Tetraaza-as-indacen-1-yl)-piperidine-1-carbonyl]-pyrrolidin-1-yl}-acetonitrile (S)-1-Cyanomethyl-pyrrolidine-2-carboxylic acid methyl ester To a solution of (S)-pyrrolidine-2-carboxylic acid methyl ester hydrochloride salt (1.0 g, 7.75 mmol) in water (5 mL) was added a mixture of formaldehyde (780 μL, 10.0 mmol, 37% aqueous solution) and potassium cyanide (390 mg) in water (5 mL) and the resulting mixture was stirred at ambient temperature for 20 hours. The reaction mixture was extracted with chloroform and the combined organics washed with water then dried over sodium sulfate and concentrated under vacuum to afford 350 mg (27%) of (S)-1-cyanomethyl-pyrrolidine-2-carboxylic acid methyl ester. $^1$H NMR (400 MHz, $CDCl_3$) δ: 3.92 (d, 1H), 3.75 (m, 4H), 3.39 (dd, 1H), 3.12 (m, 1H), 2.73 (q, 1H), 2.24 (m, 1H), 1.97 (m, 3H).

(S)-1-Cyanomethyl-pyrrolidine-2-carboxylic acid

A mixture of (S)-1-cyanomethyl-pyrrolidine-2-carboxylic acid methyl ester (100 mg, 0.60 mmol) and lithium hydroxide (16 mg, 0.66 mmol) in THF (2 mL) was stirred at ambient temperature for 16 hours. The reaction mixture was concentrated under vacuum and the resulting residue dissolved in water (5 mL) and neutralized with 1M aqueous HCl. The resulting solution was freeze-dried to afford (S)-1-cyanomethyl-pyrrolidine-2-carboxylic acid. $^1$H NMR (300 MHz, $CDCl_3$) δ: 3.80 (d, 2H), 3.53 (dd, 1H), 3.25 (m, 1H), 2.85 (m, 1H), 2.40-1.94 (m, 4H).

{(S)-2-[4-(6H-1,2,3,5,6-Tetraaza-as-indacen-1-yl)-piperidine-1-carbonyl]-pyrrolidin-1-yl}-acetonitrile Following the procedure for (S)-2-[4-(6H-1,2,3,5,6-tetraaza-as-indacen-1-yl)-piperidine-1-carbonyl]-pyrrolidine-1-carboxylic acid tert-butyl ester the title compound was prepared from (S)-1-cyanomethyl-pyrrolidine-2-carboxylic acid to afford 25 mg (79%) of {(S)-2-[4-(6H-1,2,3,5,6-tetraaza-as-indacen-1-yl)-piperidine-1-carbonyl]-pyrrolidin-1-yl}-acetonitrile. LCMS (Method A, ESI): RT=2.04 min, m+H=378.2; $^1$H NMR (400 MHz, DMSO) δ: 11.85 (s, 1H), 8.57 (s, 1H), 8.29 (d, 1H), 7.47 (s, 1H), 6.79 (s, 1H), 4.92-4.84 (m, 1H), 4.61 (s, 1H), 4.23 (d, 1H), 3.86 (m, 1H), 3.60-3.35 (m, 1H), 3.09-2.86 (m, 2H), 2.60-2.41 (m, 2H), 2.39-1.85 (m, 8H), 1.32-1.16 (m, 1H).

Example 147

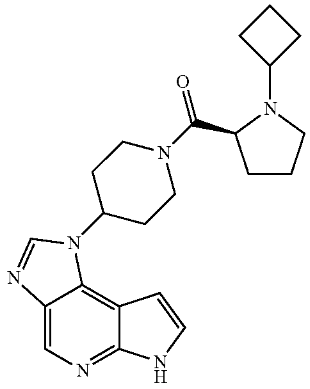 [SMILES: O=C([C@@H]1CCCN1C1CCC1)N1CCC(n2cnc3cnc4[nH]ccc4c32)CC1]

((S)-1-Cyclobutyl-pyrrolidin-2-yl)-[4-(6H-1,2,3,5,6-tetraaza-as-indacen-1-yl)-piperidin-1-yl]-methanone (S)-1-Cyclobutyl-pyrrolidine-2-carboxylic acid A mixture of (S)-pyrrolidine-2-carboxylic acid (1.0 g, 8.69 mmol), cyclobutanone (671 mg, 9.56 mmol) and 10% Pd/C (44 mg) in MeOH (10 mL) was stirred under an atmosphere of hydrogen for 20 hours. The reaction mixture was filtered through Celite® and the filtrate concentrated under vacuum. The resulting residue was triturated with diethyl ether to afford (S)-1-cyclobutyl-pyrrolidine-2-carboxylic acid. $^1$H NMR (300 MHz, $CDCl_3$) δ: 4.41 (s, 1H), 3.86 (dt, 1H), 3.78-3.63 (m, 2H), 2.78 (m, 1H), 2.55 (m, 1H), 2.57-2.09 (m, 4H), 1.91 (m, 4H).

((S)-1-Cyclobutyl-pyrrolidin-2-yl)-[4-(6H-1,2,3,5,6-tetraaza-as-indacen-1-yl)-piperidin-1-yl]-methanone Following the procedure for (S)-2-[4-(6H-1,2,3,5,6-tetraaza-as-indacen-1-yl)-piperidine-1-carbonyl]-pyrrolidine-1-carboxylic acid tert-butyl ester the title compound was prepared from (S)-1-cyclobutyl-pyrrolidine-2-carboxylic acid to afford 40 mg (43%) of ((S)-1-cyclobutyl-pyrrolidin-2-yl)-[4-(6H-1,2,3,5,6-tetraaza-as-indacen-1-yl)-piperidin-1-yl]-methanone. LCMS (Method A, ESI): RT=1.68 min, m+H=393.2; $^1$H NMR (400 MHz, MeOD) δ: 8.59 (s, 1H), 8.32 (s, 1H), 7.47 (s, 1H), 6.83 (d, 1H), 4.98 (m, 1H), 4.47 (d, 1H), 3.60-3.35 (m, 3H), 3.06 (m, 3H), 2.05 (m, 16H).

Example 148

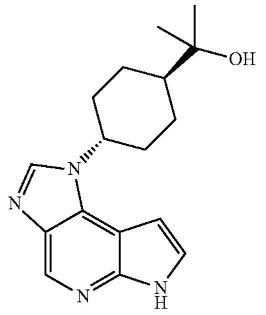 [SMILES: CC(C)(O)[C@H]1CC[C@H](n2cnc3cnc4[nH]ccc4c32)CC1]

Trans 2-[4-(6H-1,2,3,5,6-Tetraaza-as-indacen-1-yl)-cyclohexyl]-propan-2-ol

Trans 4-(1-Benzenesulfonyl-5-nitro-1H-pyrrolo[2,3-b]pyridin-4-ylamino)-cyclohexanecarboxylic acid ethyl ester A stirred mixture of 1-benzenesulfonyl-4-chloro-5-nitro-1H-pyrrolo[2,3-b]pyridine (15.0 g, 44.4 mmol), trans-4-aminocyclohexane ethyl ester (8.36 g, 48.8 mmol) and diisopropylethylamine (10.8 mL, 62.2 mmol) in propan-2-ol (150 mL) was heated to reflux for approximately 2 hours. After cooling, the solvent was removed in vacuo and the residue partitioned between DCM and water. The pH of the aqueous phase adjusted to 7.0 and the mixture separated. The organic extract was dried over sodium sulfate and concentrated to afford 22.4 g (quantitative yield) of trans 4-(1-benzenesulfonyl-5-nitro-1H-pyrrolo[2,3-b]pyridin-4-ylamino)-cyclohex anecarboxylic acid ethyl ester as an orange foam. $^1$H NMR (400 MHz, $CDCl_3$) δ: 9.10 (s, 1H), 9.01 (br d, 1H), 8.19 (dd, 2H), 7.61 (m, 2H), 7.52 (m, 2H), 6.69 (d, 1H), 4.16 (q, 2H), 3.91 (m, 1H), 2.38 (m, 1H), 2.26 (m, 2H), 2.15 (m, 2H), 1.64 (m, 2H), 1.50 (m, 2H), 1.28 (t, 3H).

Trans 4-(5-Amino-1-benzenesulfonyl-1H-pyrrolo[2,3-b]pyridin-4-ylamino)-cyclohexanecarboxylic acid ethyl ester Palladium hydroxide (20% wt on carbon, 2.5 g) was added to a solution of trans 4-(1-benzenesulfonyl-5-nitro-1H-pyrrolo[2,3-b]pyridin-4-ylamino)-cyclohexane carboxylic acid ethyl ester (assumed to be 44.4 mmol) in acetic acid (150 mL) under nitrogen. The reaction was evacuated and purged with hydrogen and the reaction warmed to 50° C. for 8 hours. The reaction vessel was recharged with hydrogen gas and stirred at room temperature for 18 hours. The mixture was then filtered through Celite® and the filtrate concentrated to dryness under vacuum. The resulting residue was partitioned between DCM and sodium hydrogen carbonate (sat. aq.), the organic layer dried with sodium sulphate and concentrated under vacuum. The residue was purified by column chromatography on silica gel (eluting: ethyl acetate) to give 16.2 g (83%) of trans 4-(5-amino-1-benzenesulfonyl-1H-pyrrolo[2,3-b]pyridin-4-ylamino)-cyclohexanecarboxylic acid ethyl ester as a purple solid. $^1$H NMR (400 MHz, $CDCl_3$) δ: 8.13 (m, 2H), 7.83 (s, 1H), 7.53 (m, 1H), 7.45 (m, 3H), 6.54 (d, 1H), 4.75 (br s, 1H), 4.14 (q, 2H), 3.68 (m, 1H), 2.65 (br s, 2H), 2.32 (m, 1H), 2.20 (m, 2H), 2.09 (m, 2H), 1.63 (m, 2H), 1.33-1.20 (m, 5H).

Trans 4-(6-Benzenesulfonyl-6H-1,2,3,5,6-tetraaza-as-indacen-1-yl)-cyclohexanecarboxylic acid ethyl ester A mixture of trans 4-(5-amino-1-benzenesulfonyl-1H-pyrrolo[2,3-b]pyridin-4-ylamino)-cyclohexanecarboxylic acid ethyl ester (16.0 g, 36.1 mmol) and triethyl orthoformate (21.4 g, 144 mmol) in acetic acid (50 mL) was heated to 110° C. for 15 minutes. After cooling, the mixture was concentrated in vacuo and the resulting residue dissolved in DCM and washed with saturated sodium hydrogencarbonate solution. The organic extract was dried with sodium sulfate and concentrated under vacuum. The residue was triturated (MeOH), washed (diethyl ether) and air dried to afford 14.1 g (86%) of trans 4-(6-benzenesulfonyl-6H-1,2,3,5,6-tetraaza-as-indacen-1-yl)-cyclohexanecarboxylic acid ethyl ester as a grey solid. $^1$H NMR (400 MHz, $CDCl_3$) δ: 8.92 (s, 1H), 8.23 (m, 2H), 8.04 (s, 1H), 7.83 (d, 1H), 7.55 (m, 1H), 7.47 (m, 2H), 6.76 (d, 1H), 4.44 (m, 1H), 4.19 (q, 2H), 2.47 (m, 1H), 2.39 (m, 2H), 2.30 (m, 2H), 1.93-1.72 (m, 4H), 1.30 (t, 3H).

Trans 2-[4-(6-Benzenesulfonyl-6H-1,2,3,5,6-tetraaza-as-indacen-1-yl)-cyclohexyl]-propan-2-ol A solution of trans 4-(6-benzenesulfonyl-6H-1,2,3,5,6-tetraaza-as-indacen-1-yl)-cyclohexanecarboxylic acid ethyl ester (200 mg, 0.44 mmol) in THF (3 mL) was treated with methyl magnesium bromide (714 μL, 0.71 mmol, 1M solution in toluene) and the resulting mixture stirred at ambient temperature for 16 hours. The reaction mixture was concentrated under vacuum and the resulting residue dissolved in DCM. The organic phase was washed with water then dried over sodium sulfate and concentrated under vacuum. The resulting residue was purified by column chromatography on silica gel (gradient: 0 to 2% methanol in DCM) to afford 167 mg (86%) of trans 2-[4-(6-benzenesulfonyl-6H-1,2,3,5,6-tetraaza-as-indacen-1-yl)-cyclohexyl]-propan-2-ol. LCMS (Method H, ESI): RT=3.00 min, m+H=439.2; $^1$H NMR (400 MHz, $CDCl_3$) δ: 8.91 (s, 1H), 8.23 (m, 2H), 7.99 (s, 1H), 7.82 (d, 1H), 7.55 (d, 1H), 7.47 (t, 2H), 6.78 (d, 1H), 4.38 (m, 1H), 2.38 (d, 2H), 2.16 (d, 2H), 1.85 (d, 2H), 1.47-1.40 (m, 3H), 1.27 (s, 6H).

Trans 2-[4-(6H-1,2,3,5,6-Tetraaza-as-indacen-1-yl)-cyclohexyl]-propan-2-ol

Following the procedure for racemic cis 1-(1-benzyl-2-methyl-piperidin-4-yl)-1,6-dihydro-1,2,3,5,6-tetraaza-as-indacene the title compound was prepared from trans 2-[4-(6-benzenesulfonyl-6H-1,2,3,5,6-tetraaza-as-indacen-1-yl)-cyclohexyl]-propan-2-ol to afford 81 mg (75%) of trans 2-[4-(6H-1,2,3,5,6-tetraaza-as-indacen-1-yl)-cyclohexyl]-propan-2-ol. LCMS (Method A, ESI): RT=2.37 min, m+H=299.1; $^1$H NMR (400 MHz, DMSO) δ: 11.83 (s, 1H), 8.58 (s, 1H), 8.28 (s, 1H), 7.47 (t, 1H), 6.74 (dd, 1H), 4.52 (m, 1H), 4.19 (s, 1H), 2.23 (d, 2H), 1.96 (m, 5H), 1.41 (s, 2H), 1.12 (s, 6H).

Example 149

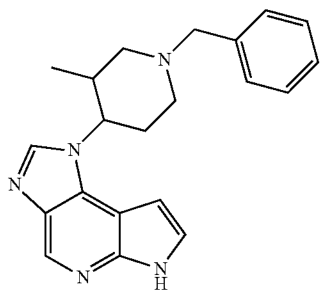 [SMILES: CC1CN(Cc2ccccc2)CCC1n1cnc2cnc3[nH]ccc3c21]

Racemic cis 1-(1-Benzyl-3-methyl-piperidin-4-yl)-1,6-dihydro-1,2,3,5,6-tetraaza-as-indacene Racemic (1-benzenesulfonyl-5-nitro-1H-pyrrolo[2,3-b]pyridin-4-yl)-(1-benzyl-3-methyl-piperidin-4-yl)-amine Following the procedure for (1-benzenesulfonyl-5-nitro-1H-pyrrolo[2,3-b]pyridin-4-yl)-((R)-1-benzyl-piperidin-3-yl) amine the title compound was prepared from racemic 1-benzyl-3-methyl-piperidin-4-ylamine with further purification by column chromatography on silica gel (gradient: 0 to 50% ethyl acetate in DCM) to afford 2.05 g (quant.) of racemic (1-benzenesulfonyl-5-nitro-1H-pyrrolo[2,3-b]pyridin-4-yl)-(1-benzyl-3-methyl-piperidin-4-yl)-amine. $^1$H NMR (400 MHz, $CDCl_3$) 6: Mixture of diastereoisomers: 9.30 and 9.03 (m, 1H), 9.11 (d, 1H), 8.19 (m, 2H), 7.60 (m, 2H), 7.52 (t, 2H), 7.36-7.22 (m, 5H), 6.71 (dd, 1H), 4.18 (m) 3.57-3.49 (m), 2.93 (m), 2.64-2.10 (m), 1.98-1.86 (m), 1.75-1.63 (m) combined integration of 10H, 0.99 (dd, 3H).

Racemic cis 6-benzenesulfonyl-1-(1-benzyl-3-methyl-piperidin-4-yl)-1,6-dihydro-1,2,3,5,6-tetraaza-as-indacene Racemic trans 6-benzenesulfonyl-1-(1-benzyl-3-methyl-piperidin-4-yl)-1,6-dihydro-1,2,3,5,6-tetraaza-as-indacene N-[1-Benzenesulfonyl-4-(1-benzyl-3-methyl-piperidin-4-ylamino)-1H-pyrrolo[2,3-b]pyridin-5-yl]-acetamide A mixture of racemic (1-benzenesulfonyl-5-nitro-1H-pyrrolo[2,3-b]pyridin-4-yl)-(1-benzyl-3-methyl-piperidin-4-yl)-amine (1.88 g, 3.7 mmol), iron powder (1.68 g, 30.0 mmol) and triethyl orthoformate (1.66 mL, 10.0 mmol) in acetic acid (20 mL) were heated at 100° C. for 1 hour. The cooled reaction mixture was filtered through Celite® and the filtrate concentrated under vacuum. The resulting residue was dissolved in ethyl acetate and the organic phase washed with saturated aqueous sodium bicarbonate, dried over sodium sulfate and concentrated under vacuum. The resulting residue was purified by column chromatography on silica gel (gradient: 0 to 3% methanol in DCM) to afford 822 mg (46%) of racemic cis 6-benzenesulfonyl-1-(1-benzyl-3-methyl-piperidin-4-yl)-1,6-dihydro-1,2,3,5,6-tetraaza-as-indacene, 523 mg (29%) of racemic trans 6-benzenesulfonyl-1-(1-benzyl-3-methyl-piperidin-4-yl)-1,6-dihydro-1,2,3,5,6-tetraaza-as-indacene and 203 mg (10%) of N-[1-benzenesulfonyl-4-(1-benzyl-3-methyl-piperidin-4-yl amino)-1H-pyrrolo[2,3-b]pyridin-5-yl]-acetamide.

Analysis for racemic cis 6-benzenesulfonyl-1-(1-benzyl-3-methyl-piperidin-4-yl)-1,6-dihydro-1,2,3,5,6-tetraaza-as-indacene: LCMS (Method I, ESI): RT=2.33 min, m+H=486.3; $^1$H NMR (400 MHz, $CDCl_3$) δ: 8.92 (s, 1H), 8.26-8.21 (m, 2H), 7.96 (s, 1H), 7.80 (d, 1H), 7.56-7.44 (m, 3H), 7.35-7.32 (m, 4H), 7.29-7.24 (m, 1H), 6.70 (d, 1H), 4.64 (dt, 1H), 3.62 (d, 1H), 3.52 (d, 1H), 3.20-3.09 (m, 1H), 2.88 (m, 1H), 2.60 (m, 1H), 2.48-2.38 (m, 2H), 2.27 (td, 1H), 2.04 (s, 1H), 0.83 (d, 3H).

Analysis for racemic trans 6-benzenesulfonyl-1-(1-benzyl-3-methyl-piperidin-4-yl)-1,6-dihydro-1,2,3,5,6-tetraaza-as-indacene: LCMS (Method I, ESI): RT=2.37 min, m+H=486.3; $^1$H NMR (400 MHz, $CDCl_3$) δ: 8.91 (s, 1H), 8.26 (m, 2H), 8.05-7.96 (br s, 1H), 7.87-7.77 (br s, 1H), 7.50 (m, 3H), 7.35 (m, 4H), 7.30 (m, 1H), 6.79 (br s, 1H), 4.05 (br s, 1H), 3.60 (s, 2H), 3.14-3.04 (m, 3H), 2.40-1.85 (m, 3H), 1.63-1.54 (m, 1H), 0.78-0.66 (m, 3H).

Analysis for N-[1-Benzenesulfonyl-4-(1-benzyl-3-methyl-piperidin-4-ylamino)-1H-pyrrolo[2,3-b]pyridin-5-yl]-acetamide: LCMS (Method I, ESI): RT=2.26 min, m+H=518.3; $^1$H NMR (400 MHz, $CDCl_3$) δ: 8.19-8.12 (m, 1H), 8.08 (d, 2H), 7.84 (s, 1H), 7.79 (s, 1H), 7.59-7.37 (m, 5H), 7.33-7.26 (m, 3H), 6.52 (d, 1H), 3.89 (s, 1H), 3.56 (m, 2H), 2.48-2.37 (m, 3H), 2.20 (s, 3H), 2.04 (s, 3H), 1.82-1.77 (m, 2H), 0.95-0.89 (m, 3H).

Racemic cis 1-(1-Benzyl-3-methyl-piperidin-4-yl)-1,6-dihydro-1,2,3,5,6-tetraaza-as-indacene Following the procedure for racemic cis 1-(1-benzyl-2-methyl-piperidin-4-yl)-1,6-dihydro-1,2,3,5,6-tetraaza-as-indacene the title compound was prepared from racemic cis 6-benzenesulfonyl-1-(1-benzyl-3-methyl-piperidin-4-yl)-1,6-dihydro-1,2,3,5,6-tetraaza-as-indacene with further purification by Isolute® SCX-2 column (gradient: methanol to 2M $NH_3$ in methanol solution) and recrystallization from propan-2ol to afford 248 mg (50%) of racemic cis 1-(1-benzyl-3-methyl-piperidin-4-yl)-1,6-dihydro-1,2,3,5,6-tetraaza-as-indacene. LCMS (Method A, ESI): RT=2.00 min, m+H=346.2; $^1$H NMR (400 MHz, DMSO) δ: 11.84 (s, 1H), 8.59 (s, 1H), 8.28 (s, 1H), 7.45 (t, 1H), 7.35 (m, 4H), 7.26 (m, 1H), 6.66 (dd, 1H), 4.79 (dt, 1H), 3.60 (d, 1H), 3.50 (d, 1H), 3.04 (d, 1H), 2.83-2.73 (m, 1H), 2.67 (m, 1H), 2.55-2.47 (m, 1H), 2.39 (s, 1H), 2.36-2.24 (m, 1H), 1.99 (m, 1H), 0.72 (d, 3H).

Example 150

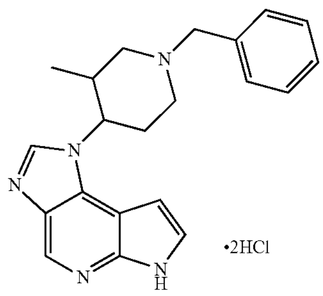 [SMILES: CC1CN(Cc2ccccc2)CCC1n1cnc2cnc3[nH]ccc3c21]

Racemic trans 1-(1-Benzyl-3-methyl-piperidin-4-yl)-1,6-dihydro-1,2,3,5,6-tetraaza-as-indacene dihydrochloride Following the procedure for racemic cis 1-(1-benzyl-2-methyl-piperidin-4-yl)-1,6-dihydro-1,2,3,5,6-tetraaza-as-indacene the title compound was prepared from racemic trans 6-benzenesulfonyl-1-(1-benzyl-3-methyl-piperidin-4-yl)-1,6-dihydro-1,2,3,5,6-tetraaza-as-indacene with further purification by Isolute® SCX-2 column (gradient: methanol to 2M $NH_3$ in methanol solution) and column chromatography on silica gel (gradient: 0 to 20% methanol in ethyl acetate) to afford 240 mg (85%) of racemic trans 1-(1-Benzyl-3-methyl-piperidin-4-yl)-1,6-dihydro-1,2,3,5,6-tetraaza-as-indacene. A small sample of this was converted to the dihydrochloride salt which was recrystallized from methanol and diethyl ether. LCMS (Method A, ESI): RT=2.06 min, m+H=346.2; $^1$H NMR (400 MHz, MeOD) δ: 8.98 (s, 1H), 8.92 (s, 1H), 7.75 (d, 1H), 7.66 (s, 2H), 7.54 (m, 3H), 7.38 (s, 1H), 4.48 (m, 2H), 3.72-3.65 (m, 2H), 3.57-3.46 (m, 1H), 3.34 (s, 3H), 2.82 (br s, 1H), 2.56 (s, 1H), 0.89 (d, 3H).

Example 151

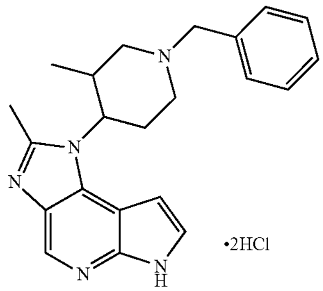 [SMILES: Cc1nc2cnc3[nH]ccc3c2n1C1CCN(Cc2ccccc2)CC1C]

Racemic 1-(1-benzyl-3-methyl-piperidin-4-yl)-2-methyl-1,6-dihydro-1,2,3,5,6-tetraaza-as-indacene dihydrochloride salt Racemic 6-benzenesulfonyl-1-(1-benzyl-3-methyl-piperidin-4-yl)-2-methyl-1,6-dihydro-1,2,3,5,6-tetraaza-as-indacene A mixture of N-[1-benzenesulfonyl-4-(1-benzyl-3-methyl-piperidin-4-ylamino)-1H-pyrrolo[2,3-b]pyridin-5-yl]-acetamide (160 mg, 0.31 mmol) and $POCl_3$ (1 mL, 10.4 mmol) in DCE (5 mL) was heated at reflux for 3 hours. The cooled reaction mixture was concentrated under vacuum and the residue purified by Isolute® SCX-2 column (gradient: methanol to 2M $NH_3$ in methanol solution). The resulting residue was further purified by column chromatography on silica gel (gradient: 0 to 5% methanol in ethyl acetate) to afford 89 mg (59%) of racemic 6-benzenesulfonyl-1-(1-benzyl-3-methyl-piperidin-4-yl)-2-methyl-1,6-dihydro-1,2,3,5,6-tetraaza-as-indacene. $^1$H NMR (400 MHz, $CDCl_3$) δ: 8.78 (s, 1H), 8.22 (m, 2H), 7.78 (d, 1H), 7.54 (m, 1H), 7.47 (m, 2H), 7.35 (m, 4H), 7.31-7.27 (m, 1H), 6.72 (d, 1H), 4.78-4.70 (m, 1H), 3.63 (d, 1H), 3.52 (d, 1H), 3.21-3.15 (s, 1H), 2.93-2.86 (m, 3H), 2.75 (s, 3H), 2.44 (dd, 1H), 2.34 (br s, 1H), 2.24-2.17 (m, 1H), 2.01-1.94 (m, 1H), 1.03 (d, 3H).

Racemic 1-(1-benzyl-3-methyl-piperidin-4-yl)-2-methyl-1,6-dihydro-1,2,3,5,6-tetraaza-as-indacene dihydrochloride salt Following the procedure for racemic cis 1-(1-benzyl-2-methyl-piperidin-4-yl)-1,6-dihydro-1,2,3,5,6-tetraaza-as-indacene the title compound was prepared from racemic 6-benzenesulfonyl-1-(1-benzyl-3-methyl-piperidin-4-yl)-2-methyl-1,6-dihydro-1,2,3,5,6-tetraaza-as-indacene with further purification by Isolute® SCX-2 column (gradient: methanol to 2M $NH_3$ in methanol solution) and column chromatography on silica gel (gradient: 0 to 20% methanol in ethyl acetate). The residue was converted to the dihydrochloride salt by treatment with HCl in diethyl ether. The resulting solid was recrystallized from methanol and diethyl ether to afford 25 mg (41%) of racemic 1-(1-benzyl-3-methyl-piperidin-4-yl)-2-methyl-1,6-dihydro-1,2,3,5,6-tetraaza-as-indacene dihydrochloride salt. LCMS (Method A, ESI): RT=1.95 min, m+H=360.2; $^1$H NMR (400 MHz, MeOD) δ: 8.75 (s, 1H), 7.76 (d, 1H), 7.67 (m, 2H), 7.55 (m, 3H), 7.17 (s, 1H), 4.57 (d, 1H), 4.41 (d, 1H), 3.91-3.73 (m, 2H), 3.57-3.46 (m, 3H), 3.35-3.28 (m, 1H), 2.96 (s, 3H), 2.90 (br s, 1H), 2.63-2.53 (s, 1H), 1.17 (d, 3H).

Example 152

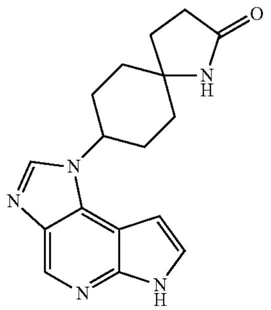 [SMILES: O=C1CCC2(CCC(n3cnc4cnc5[nH]ccc5c43)CC2)N1]

8-(6H-1,2,3,5,6-Tetraaza-as-indacen-1-yl)-1-aza-spiro[4.5]decan-2-one

1-Aza-spiro[4.5]decane-2,8-dione

A suspension of 1,4-dioxa-9-aza-dispiro[4.2.4.2]tetradecan-10-one (prepared according to *J. Org. Chem.* 2004, 69, 2755) (500 mg, 2.4 mmol) in THF (7 mL) was treated with 1M aqueous HCl (7 mL) and the resulting mixture stirred at ambient temperature for 20 hours. The reaction mixture was quenched with 1M aqueous NaOH (7 mL) and the mixture concentrated under vacuum. The resulting solid was purified by column chromatography on silica gel (gradient: DCM then 2 to 10% methanol in ethyl acetate) to afford 398 mg (quant.) of 1-aza-spiro[4.5]decane-2,8-dione. LCMS (Method B, ESI): RT=1.63 min, 168; $^1$H NMR (400 MHz, $CDCl_3$) δ: 3.95 (s, 1H), 3.77-3.71 (m, 1H), 2.46-2.44 (m, 3H), 2.05-2.03 (m, 3H), 1.81-1.65 (m, 4H).

8-Amino-1-aza-spiro[4.5]decan-2-one

A mixture of 1-aza-spiro[4.5]decane-2,8-dione (390 mg, 2.30 mmol) and $NH_4OAc$ (540 mg, 7.0 mmol) in THF (10 mL) and acetic acid (1 drop) was stirred at ambient temperature for 5 minutes before sodium triacetoxyborohydride (1.49 g, 7.0 mmol) was added. The resulting mixture was stirred for 3.5 hours before further $NH_4OAc$ (180 mg, 2.3 mmol), sodium triacetoxyborohydride (500 mg, 2.4 mmol) and acetic acid (3 mL) were added. The resulting mixture was stirred for 16 hours then concentrated under vacuum and azeotroped with toluene. The resulting residue was purified by Isolute® SCX-2 column (gradient: methanol to 2M $NH_3$ in methanol solution) to afford 125 mg (32%) of 8-amino-1-aza-spiro[4.5] decan-2-one. LCMS (Method B, ESI): RT=0.38 min, m+H=169.

8-(1-Benzenesulfonyl-5-nitro-1H-pyrrolo[2,3-b]pyridin-4-ylamino)-1-aza-spiro[4.5]decan-2-one Following the procedure for (1-benzenesulfonyl-5-nitro-1H-pyrrolo[2,3-b]pyridin-4-yl)-((R)-1-benzyl-piperidin-3-yl) amine the title compound was prepared from 8-amino-1-aza-spiro[4.5]decan-2-one with further purification by column chromatography on silica gel (gradient: 0 to 7% methanol in DCM) to afford 88 mg (29%) of 8-(1-benzenesulfonyl-5-nitro-1H-pyrrolo[2,3-b]pyridin-4-ylamino)-1-aza-spiro[4.5] decan-2-one. LCMS (Method B, ESI): RT=3.46 and 3.51 min, m+H=470; $^1$H NMR (400 MHz, $CDCl_3$) δ: 9.11 (s, 1H), 8.19 (m, 2H), 7.62 (m, 2H), 7.52 (t, 2H), 6.68 (d, 1H), 4.03 (br s, 1H), 2.45 (m, 2H), 2.01 (m, 4H), 1.93-1.80 (m, 2H), 1.76-1.64 (m, 4H).

8-(5-Amino-1-benzenesulfonyl-1H-pyrrolo[2,3-b]pyridin-4-ylamino)-1-aza-spiro[4.5]decan-2-one Following the procedure for 1-benzenesulfonyl-N*4*-((R)-1-benzyl-piperidin-3-yl)-1H-pyrrolo[2,3-b]pyridine-4,5-diamine the title compound was prepared from 8-(1-benzenesulfonyl-5-nitro-1H-pyrrolo[2,3-b]pyridin-4-ylamino)-1-aza-spiro[4.5]decan-2-one to afford 72 mg (92%) of 8-(5-amino-1-benz ene sulfonyl-1H-pyrrolo[2,3-b]pyridin-4-ylamino)-1-aza-spiro[4.5]decan-2-one. LCMS (Method B, ESI): 2.16, 2.26 and 2.44 min, m+H=440; $^1$H NMR (400 MHz, DMSO): δ 8.67 (s, 1H), 8.39 (s, 1H), 8.10 (m, 1H), 8.00 (m, 1H), 7.88 (d, 1H), 7.57 (m, 3H), 7.44 (m, 1H), 7.20 (m, 1H), 6.69 (d, 1H), 5.64 (s, 1H), 4.81 (d, 1H), 4.69-4.49 (m, 1H), 4.13-3.89 (m, 1H), 3.80-3.60 (m, 1H), 2.20 (m, 2H), 2.04 (m, 1H), 1.85 (m, 3H), 1.60 (m, 2H).

8-(6-Benzenesulfonyl-6H-1,2,3,5,6-tetraaza-as-indacen-1-yl)-1-aza-spiro[4.5]decan-2-one Following the procedure of 6-benzenesulfonyl-1-((R)-1-benzyl-piperidin-3-yl)-1,6-dihydro-1,2,3,5,6-tetraaza-as-indacene the title compound was prepared from 8-(5-amino-1-benzenesulfonyl-1H-pyrrolo[2,3-b]pyridin-4-ylamino)-1-aza-spiro[4.5]decan-2-one with further purification by preparative HPLC (gradient: 5 to 95% MeCN in water with 0.1% formic acid) to afford 19 mg (33%) of 8-(6-benzenesulfonyl-6H-1,2,3,5,6-tetraaza-as-indacen-1-yl)-1-aza-spiro [4.5]decan-2-one. LCMS (Method B, ESI): RT=2.78 and 2.97 min, m+H=450; $^1$H NMR (400 MHz, DMSO): δ 8.72 (s, 1H), 8.46 (s, 1H), 8.43 (s, 1H), 8.12 (m, 2H), 7.97 (d, 1H), 7.70-7.65 (m, 1H), 7.60 (t, 2H), 7.30 (d, 1H), 4.73-4.62 (m, 1H), 2.29-2.21 (m, 2H), 2.03 (m, 4H), 1.85 (m, 3H), 1.79-1.67 (m, 3H).

8-(6H-1,2,3,5,6-Tetraaza-as-indacen-1-yl)-1-aza-spiro[4.5]decan-2-one

Following the procedure for racemic cis 1-(1-benzyl-2-methyl-piperidin-4-yl)-1,6-dihydro-1,2,3,5,6-tetraaza-as-indacene the title compound was prepared from 8-(5-amino-1-benzenesulfonyl-1H-pyrrolo[2,3-b]pyridin-4-ylamino)-1-aza-spiro[4.5]decan-2-one with further purification by preparative HPLC (gradient: 5 to 50% MeCN in water with 0.1% formic acid) to afford 5 mg (43%) of 8-(6H-1,2,3,5,6-tetraaza-as-indacen-1-yl)-1-aza-spiro[4.5]decan-2-one. LCMS (Method A, ESI): RT=1.88 and 2.14 min, m+H=310; $^1$H NMR (400 MHz, DMSO) δ: 11.80 (s, 1H), 8.55 (s, 1H), 8.46 (s, 1H), 8.28 (s, 1H), 7.73 (s, 1H), 7.44 (t, 1H), 6.81 (dd, 1H), 6.66 (d, 1H), 2.25 (m, 2H), 2.09 (m, 4H), 1.84 (m, 5H).

Example 153

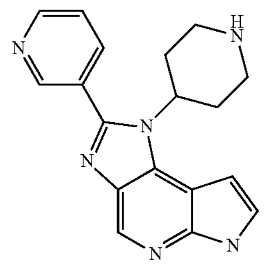 [SMILES: c1cncc(-c2nc3cnc4[nH]ccc4c3n2C2CCNCC2)c1]

1-Piperidin-4-yl-2-pyridin-3-yl-1,6-dihydro-1,2,3,5,6-tetraaza-as-indacene (1-Benzenesulfonyl-5-nitro-1H-pyrrolo[2,3-b]pyridin-4-yl)-(1-benzyl-piperidin-4-yl)amine A mixture of 1-benzenesulfonyl-4-chloro-5-nitro-1H-pyrrolo[2,3-b]pyridine (34.5 g, 102 mmol), 4-amino-1-benzyl piperidine (21.4 g, 112 mmol), diisopropylethylamine (245 ml, 143 mmol) in propan-2-ol (1 L) was heated at reflux for 2 hours. The mixture was concentrated under vacuum and the residues partitioned between ethyl acetate and water. The organics were washed with water, dried with sodium sulfate and concentrated under vacuum affording 52.1 g of (1-benzenesulfonyl-5-nitro-1H-pyrrolo[2,3-b]pyridin-4-yl)-(1-benzyl-piperidin-4-yl)amine as an orange residue which was used for the next step without further purification. $^1$H NMR (400 MHz, DMSO) δ: 9.10 (s, 1H), 8.19 (m, 2H), 7.63-7.58 (m, 2H), 7.51 (t, 3H), 7.33 (d, 4H), 6.69 (d, 1H), 4.00 (s, 1H), 3.57 (br s, 2H), 2.84 (br s, 2H), 2.31 (br s, 2H), 2.11 (s, 3H), 2.04 (s, 1H).

1-Benzenesulfonyl-N*4*-(1-benzyl-piperidin-4-yl)-1H-pyrrolo[2,3-b]pyridine-4,5-diamine The title compound was made by following the procedure described for the preparation of 1-benzenesulfonyl-N*4*-

((R)-1-benzyl-piperidin-3-yl)-1H-pyrrolo[2,3-b]pyridine-4,5-diamine but using (1-benzenesulfonyl-5-nitro-1H-pyrrolo[2,3-b]pyridin-4-yl)-(1-benzyl-piperidin-4-yl)amine. LCMS (Method B, ESI): RT=2.63 min, m+H=462.33.

6-Benzenesulfonyl-1-(1-benzyl-piperidin-4-yl)-2-pyridin-3-yl-1,6-dihydro-1,2,3,5,6-tetraaza-as-indacene 258 mg (87%) of the title compound was made by following the procedure described for the preparation of acetic acid 6-benzenesulfonyl-1-(1-benzyl-piperidin-4-yl)-1,6-dihydro-1,2,3,5,6-tetraaza-as-indacen-2-ylmethyl ester but using 1-benzenesulfonyl-N*4*-(1-benzyl-piperidin-4-yl)-1H-pyrrolo[2,3-b]pyridine-4,5-diamine and nicotinoyl chloride. LCMS (Method B, ESI): RT=3.27 min, m+H=549.38; $^{1}$H NMR (400 MHz, $CDCl_3$) δ: 8.96 (s, 1H), 8.85 (s, 1H), 8.80 (dd, 1H), 8.25 (d, 2H), 8.01 (d, 1H), 7.93 (d, 1H), 7.44-7.41 (m, 10H), 4.53-4.37 (m, 1H), 3.72-3.52 (m, 2H), 3.37-3.05 (m, 2H), 2.82-2.64 (m, 2H), 2.18-2.06 (m, 2H), 1.93-1.82 (m, 2H).

1-(1-Benzyl-piperidin-4-yl)-2-pyridin-3-yl-1,6-dihydro-1,2,3,5,6-tetraaza-as-indacene The title compound was made by following the procedure described for the preparation of 2-[1-((R)-1-benzyl-piperidin-3-yl)-1,6-dihydro-1,2,3,5,6-tetraaza-as-indacen-2-yl]ethano 1 but using 6-benzenesulfonyl-1-(1-benzyl-piperidin-4-yl)-2-pyridin-3-yl-1,6-dihydro-1,2,3,5,6-tetraaza-as-indacene. LCMS (Method A, ESI): RT=2.02 min, m+H=409.1; $^{1}$H NMR (400 MHz, DMSO) δ: 12.00 (s, 1H), 8.90 (m, 1H), 8.78 (dd, 1H), 8.68 (s, 1H), 8.12 (dt, 1H), 7.66-7.60 (m, 2H), 7.42-7.33 (m, 4H), 7.27 (t, 1H), 7.09 (t, 1H), 4.40 (m, 1H), 3.58 (s, 2H), 3.01 (d, 2H), 2.76-2.62 (m, 2H), 2.09 (t, 2H), 1.98 (d, 2H).

1-Piperidin-4-yl-2-pyridin-3-yl-1,6-dihydro-1,2,3,5,6-tetraaza-as-indacene 25 mg (44%) of the title compound was made by following the procedure described for the preparation of (R)-1-piperidin-3-yl-1,6-dihydro-1,2,3,5,6-tetraaza-as-indacene but using 1-(1-benzyl-piperidin-4-yl)-2-pyridin-3-yl-1,6-dihydro-1,2,3,5,6-tetraaza-as-indacene. LCMS (Method A, ESI): RT=1.31 min, m+H=319.05; $^{1}$H NMR (400 MHz, DMSO) δ: 11.95 (s, 1H), 8.89 (dd, 1H), 8.78 (dd, 1H), 8.66 (s, 1H), 8.12 (dt, 1H), 7.64 (m, 1H), 7.53 (t, 1H), 7.08 (dd, 1H), 4.39 (m, 1H), 3.14 (m, 2H), 2.56-2.54 (m, 4H), 1.89 (m, 2H).

Example 154

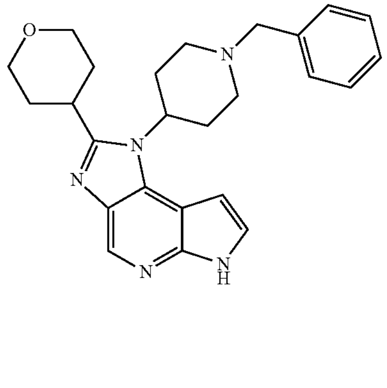 [SMILES: c1ccc(CN2CCC(n3c(C4CCOCC4)nc4cnc5[nH]ccc5c43)CC2)cc1]

1-(1-Benzyl-piperidin-4-yl)-2-(tetrahydro-pyran-4-yl)-1,6-dihydro-1,2,3,5,6-tetraaza-as-indacene Tetrahydro-pyran-4-carbonyl chloride Oxalyl chloride (170 μL, 1.94 mmol) and DMF (2 drops) were added to a solution of tetrahydro-2H-pyran-4-carboxylic acid (84 mg, 0.64 mmol) in DCM (4 mL) and stirred for 1.5 hours. The reaction was concentrated under vacuum affording tetrahydro-pyran-4-carbonyl chloride. This was used with no further purification or analysis.

6-Benzenesulfonyl-1-(1-benzyl-piperidin-4-yl)-2-(tetrahydro-pyran-4-yl)-1,6-dihydro-1,2,3,5,6-tetraaza-as-indacene 71 mg (24%) of the title compound was made by following the procedure described for the preparation of acetic acid 6-benzenesulfonyl-1-(1-benzyl-piperidin-4-yl)-1,6-dihydro-1,2,3,5,6-tetraaza-as-indacen-2-ylmethyl ester but using 1-benzenesulfonyl-N*4*-(1-benzyl-piperidin-4-yl)-1H-pyrrolo[2,3-b]pyridine-4,5-diamine and tetrahydro-pyran-4-carbonyl chloride. LCMS (Method B, ESI): RT=3.28 min, m+H=556.37; $^{1}$H NMR (400 MHz, DMSO) δ: 8.67 (s, 1H), 8.12 (m, 3H), 7.68 (m, 1H), 7.62-7.57 (m, 2H), 7.42 (m, 5H), 7.33-7.28 (m, 1H), 4.66 (m, 1H), 3.93 (m, 3H), 3.62 (s, 2H), 3.54 (td, 3H), 3.45 (m, 1H), 3.02 (m, 2H), 2.43 (m, 1H), 2.29-2.22 (m, 2H), 1.90-1.78 (m, 6H).

1-(1-Benzyl-piperidin-4-yl)-2-(tetrahydro-pyran-4-yl)-1,6-dihydro-1,2,3,5,6-tetraaza-as-indacene 40 mg (81%) of the title compound was made by following the procedure described for the preparation of (R)-1-piperidin-3-yl-1,6-dihydro-1,2,3,5,6-tetraaza-as-indacene but using 6-benzenesulfonyl-1-(1-benzyl-piperidin-4-yl)-2-(tetrahydro-pyran-4-yl)-1,6-dihydro-1,2,3,5,6-tetraaza-as-indacene. LCMS (Method A, ESI): RT=2.16 min, m+H=416.10; $^{1}$H NMR (400 MHz, DMSO) δ: 11.80 (s, 1H), 8.52 (s, 1H), 7.53 (t, 1H), 7.46-7.36 (m, 4H), 7.31-7.25 (m, 1H), 7.06 (s, 1H), 4.60 (s, 1H), 3.96 (d, 2H), 3.64 (s, 2H), 3.57 (m, 2H), 3.47-3.36 (m, 1H), 3.04 (d, 2H), 2.72-2.60 (m, 2H), 2.28 (t, 2H), 1.87-1.84 (m, 6H).

Example 155

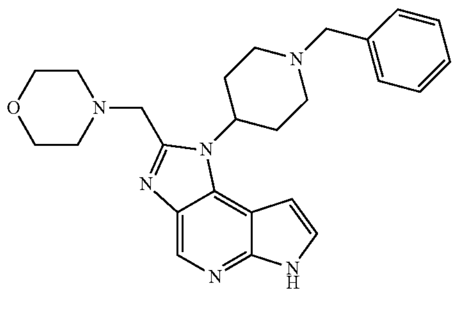 [SMILES: c1ccc(CN2CCC(n3c(CN4CCOCC4)nc4cnc5[nH]ccc5c43)CC2)cc1]

1-(1-Benzyl-piperidin-4-yl)-2-morpholin-4-ylmethyl-1,6-dihydro-1,2,3,5,6-tetraaza-as-indacene 6-Benzenesulfonyl-1-(1-benzyl-piperidin-4-yl)-1,6-dihydro-1,2,3,5,6-tetraaza-as-indacene-2-carbaldehyde A mixture [6-benzenesulfonyl-1-(1-benzyl-piperidin-4-yl)-1,6-dihydro-1,2,3,5,6-tetraaza-as-indacen-2-yl]-methanol (100 mg, 200 μmol) and triethylamine (111 μl, 800 μmol) in DMSO (2 ml) was treated with sulfur trioxide pyridine complex (127 mg, 800 μmol) and stirred at ambient temperature for 4 hours. A further portion of triethylamine (55 μl, 400 μmol) and sulfur trioxide pyridine complex (64 mg, 400 μmol) were added. After 3 hours the reaction was quenched with water and extracted into ethyl acetate. The organics were washed with water, dried with sodium sulfate and concentrated under vacuum to leave a colorless residue. Purification by column chromatography on silica gel (gradient: 0 to 6% methanol in DCM) afforded 89 mg (89%) of 6-benzenesulfonyl-1-(1-benzyl-piperidin-4-yl)-1,6-dihydro-1,2,3,5,6-tetraaza-as-indacene-2-carbaldehyde as a colorless residue. LCMS (Method B, ESI): RT=3.31 min, m+H=500.31; $^1$H NMR (400 MHz, DMSO) δ: 10.01 (s, 1H), 8.98 (s, 1H), 8.23 (d, 1H), 8.24-8.09 (m, 2H), 7.77-7.60 (m, 1H), 7.64 (t, 2H), 7.55-7.28 (m, 5H), 7.33-7.25 (m, 1H), 5.61-5.44 (m, 1H), 3.61 (s, 2H), 3.08-2.99 (m, 2H), 2.48-2.36 (m, 2H), 2.24-2.14 (m, 2H), 1.98-1.88 (m, 2H).

6-Benzenesulfonyl-1-(1-benzyl-piperidin-4-yl)-2-morpholin-4-ylmethyl-1,6-dihydro-1,2,3,5,6-tetraaza-as-indacene A mixture of 6-benz ene sulfonyl-1-(1-benzyl-piperidin-4-yl)-1,6-dihydro-1,2,3,5,6-tetraaza-as-indacene-2-carbaldehyde (85.0 mg, 170 μmol) and morpholine (22.0 μl, 255 μmol) in DCE (3 ml) was treated with sodium triacetoxyborohydride (54.0 mg, 255 μmol) and stirred at ambient temperature for 5 hours. The mixture was diluted with DCM, washed with a saturated sodium hydrogen carbonate solution, water and brine, dried with sodium sulfate and concentrated under vacuum to leave a colorless residue. Purification by column chromatography on silica gel (gradient: 0 to 7% methanol in DCM) afforded 89 mg (92%) of 6-benzenesulfonyl-1-(1-benzyl-piperidin-4-yl)-2-morpholin-4-ylmethyl-1,6-dihydro-1,2,3,5,6-tetraaza-as-indacene as a colorless residue. LCMS (Method B, ESI): RT=3.28 min, m+H=571.34; $^1$H NMR (400 MHz, DMSO) δ: 8.67 (s, 1H), 8.14 (m, 3H), 7.71-7.67 (m, 1H), 7.61 (m, 2H), 7.41 (m, 4H), 7.31 (m, 2H), 4.79 (m, 1H), 3.87 (s, 2H), 3.61 (s, 2H), 3.50 (s, 5H), 3.05 (m, 2H), 2.38 (s, 5H), 2.18 (m, 2H), 1.91 (m, 2H).

1-(1-Benzyl-piperidin-4-yl)-2-morpholin-4-ylmethyl-1,6-dihydro-1,2,3,5,6-tetraaza-as-indacene 33 mg (53%) of the title compound was made by following the procedure described for the preparation of (R)-1-piperidin-3-yl-1,6-dihydro-1,2,3,5,6-tetraaza-as-indacene but using 6-benzenesulfonyl-1-(1-benzyl-piperidin-4-yl)-2-morpholin-4-ylmethyl-1,6-dihydro-1,2,3,5,6-tetraaza-as-indacene. LCMS (Method A, ESI): RT=2.03 min, m+H=431.14; $^1$H NMR (400 MHz, DMSO) δ: 11.84 (s, 1H), 8.52 (s, 1H), 7.54 (t, 1H), 7.41-7.40 (m, 4H), 7.28 (t, 1H), 6.98 (s, 1H), 4.77 (s, 1H), 3.85 (s, 2H), 3.62 (s, 2H), 3.53 (s, 5H), 3.08 (d, 2H), 2.40 (s, 5H), 2.20 (t, 2H), 1.89 (d, 2H).

Example 156

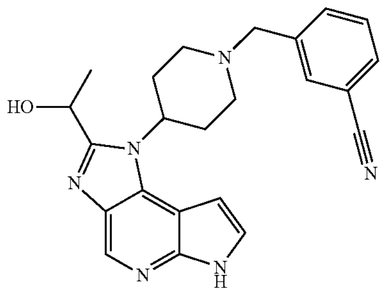 [SMILES: CC(O)c1nc2cnc3[nH]ccc3c2n1C1CCN(Cc2cccc(C#N)c2)CC1]

Racemic 3-{4-[2-(1-Hydroxy-ethyl)-6H-1,2,3,5,6-tetraaza-as-indacen-1-yl]-piperidin-1-ylmethyl}-benzonitrile Racemic Acetic acid 1-[6-benzenesulfonyl-1-(1-benzyl-piperidin-4-yl)-1,6-dihydro-1,2,3,5,6-tetraaza-as-indacen-2-yl]-ethyl ester A mixture of 1-benzenesulfonyl-N*4*-(1-benzyl-piperidin-4-yl)-1H-pyrrolo[2,3-b]pyridine-4,5-diamine (4.0 g, 8.7 mmol), 2-acetoxypropionyl chloride (1.32 mL, 10.44 mmol) and triethylamine (1.81 mL, 13.05 mmol) in DCM (100 mL) was stirred at ambient temperature for 2 hours. The reaction mixture was concentrated under vacuum and the resulting residue dissolved in acetic acid (40 mL) and heated to 120° C. for 16 hours. The cooled reaction mixture was concentrated under vacuum and the residue dissolved in DCM. The organic layer was washed with saturated aqueous sodium bicarbonate, water and brine, then dried over sodium sulfate and concentrated under vacuum. The resulting residue was purified by column chromatography on silica gel (gradient: 0 to 100% ethyl acetate in cyclohexane) to afford 2.5 g (52%) of racemic acetic acid 1-[6-benzenesulfonyl-1-(1-benzyl-piperidin-4-yl)-1,6-dihydro-1,2,3,5,6-tetraaza-as-indacen-2-yl]-ethyl ester. LCMS (Method I, ESI): RT=2.38, m+H=558.3.

Racemic 1-[1-(1-Benzyl-piperidin-4-yl)-1,6-dihydro-1,2,3,5,6-tetraaza-as-indacen-2-yl]-ethanol Following the procedure for racemic cis 1-(1-benzyl-2-methyl-piperidin-4-yl)-1,6-dihydro-1,2,3,5,6-tetraaza-as-indacene the title compound was prepared from racemic acetic acid 1-[6-benzenesulfonyl-1-(1-benzyl-piperidin-4-yl)-1,6-dihydro-1,2,3,5,6-tetraaza-as-indacen-2-yl]-ethyl ester to afford 1.20 g (81%) of racemic 1-[1-(1-benzyl-piperidin-4-yl)-1,6-dihydro-1,2,3,5,6-tetraaza-as-indacen-2-yl]-ethanol. LCMS (Method I, ESI): RT=1.57 min, m+H=376.1; $^1$H NMR (300 MHz, DMSO) δ: 11.81 (s, 1H), 8.54 (s, 1H), 7.52 (t, 1H), 7.39 (m, 4H), 7.27 (s, 1H), 7.02 (s, 1H), 5.66 (d, 1H), 5.11 (t, 1H), 4.86 (s, 1H), 3.61 (s, 2H), 3.05 (d, 2H), 2.61 (d, 2H), 2.17 (t, 2H), 1.87 (d, 2H), 1.61 (d, 3H).

Racemic 1-(1-Piperidin-4-yl-1,6-dihydro-1,2,3,5,6-tetraaza-as-indacen-2-yl)-ethanol A mixture of racemic 1-[1-(1-benzyl-piperidin-4-yl)-1,6-dihydro-1,2,3,5,6-tetraaza-as-indacen-2-yl]-ethanol (1.2 g, 3.14 mmol), 20% $Pd(OH)_2$ on carbon (220 mg) and ammonium formate (2.0 g, 31.4 mmol) in methanol (70 mL) was heated to reflux for 2 hours. The cooled reaction mixture was filtered through Celite® and the filtrate concentrated under vacuum. The resulting residue was purified by column chromatography on silica gel (gradient: 0 to 20% 2M $NH_3$ in methanol solution in DCM) to afford 600 mg (67%) of racemic 1-(1-piperidin-4-yl-1,6-dihydro-1,2,3,5,6-tetraaza-as-indacen-2-yl)-ethanol. LCMS (Method H, ESI): RT=0.56 min, m+H=286.2; $^1$H NMR (400 MHz, DMSO) δ: 11.79 (s, 1H), 8.54 (s, 1H), 7.44 (d, 1H), 7.02 (s, 1H), 5.66 (d, 1H), 5.13 (m, 1H), 4.88 (s, 1H), 3.17 (m, 2H), 2.67 (m, 2H), 2.42 (m, 2H), 1.80 (m, 2H), 1.63 (d, 3H).

Racemic 3-{4-[2-(1-Hydroxy-ethyl)-6H-1,2,3,5,6-tetraaza-as-indacen-1-yl]-piperidin-1-ylmethyl}-benzonitrile A mixture of racemic 1-(1-piperidin-4-yl-1,6-dihydro-1,2,3,5,6-tetraaza-as-indacen-2-yl)-ethanol (50 mg, 0.18 mmol), 3-formyl benzonitrile (26 mg, 0.19 mmol), acetic acid (22 μL, 0.35 mmol) and 4 Å molecular sieves (200 mg) in DCE (5 mL) was stirred at ambient temperature for 4 hours before sodium triacetoxyborohydride (57 mg, 0.26 mmol) was added. The resulting mixture was stirred for 16 hours then filtered through Celite® and the filtrate concentrated under vacuum. The resulting residue was purified by column chromatography on silica gel (gradient: 0 to 10% 2M $NH_3$ in methanol solution in DCM) to afford 15 mg (21%) of racemic 3-{4-[2-(1-hydroxy-ethyl)-6H-1,2,3,5,6-tetraaza-as-indacen-1-yl]-piperidin-1-ylmethyl}-benzonitrile. LCMS (Method A, ESI): RT=1.98 min, 401.2; $^1$H NMR (400 MHz, MeOD) δ: 8.56 (s, 1H), 7.86 (s, 1H), 7.76 (d, 1H), 7.67-7.62 (m, 1H), 7.54-7.53 (m, 2H), 7.26 (s, 1H), 5.24 (q, 1H), 5.00-4.98 (m, 1H), 3.69 (s, 2H), 3.16-3.05 (m, 2H), 2.91-2.75 (m, 2H), 2.37-2.33 (m, 2H), 1.97-1.95 (m, 3H), 1.74 (d, 3H).

Example 157

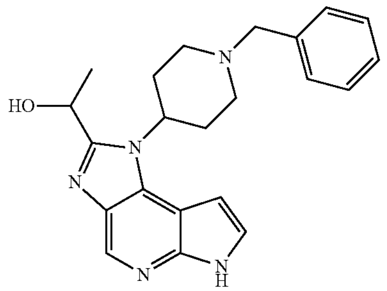

Racemic 1-[1-(1-Benzyl-piperidin-4-yl)-1,6-dihydro-1,2,3,5,6-tetraaza-as-indacen-2-yl]-ethanol Racemic 1-[6-Benzenesulfonyl-1-(1-benzyl-piperidin-4-yl)-1,6-dihydro-1,2,3,5,6-tetraaza-as-indacen-2-yl]-ethanol Methyl magnesium chloride (3.0 M, 90 μL, 0.27 mmol) was slowly added to a solution of 6-benzenesulfonyl-1-(1-benzyl-piperidin-4-yl)-1,6-dihydro-1,2,3,5,6-tetraaza-as-indacene-2-carbaldehyde (100 mg, 0.20 mmol) in THF (2.5 ml), under argon at 0° C. and stirred for 30 minutes before a further methyl magnesium chloride (3.0 M, 180 μL, 0.54 mmol) was added. This was stirred at 0° C. for 2 hours before warming to ambient temperature. 1M HCl was added before the mixture was basified with sodium hydrogen carbonate (sat. aq.) and extracted into ethyl acetate. The organics were washed with water and brine, dried with sodium sulfate and concentrated under vacuum. Purification by column chromatography on silica gel (gradient: 0 to 7% methanol in DCM) afforded 67 mg (65%) of racemic 1-[6-benzenesulfonyl-1-(1-benzyl-piperidin-4-yl)-1,6-dihydro-1,2,3,5,6-tetraaza-as-indacen-2-yl]-ethanol as a colorless residue. LCMS (Method B, ESI): RT=2.44 min, m+H=516.22; $^1$H NMR (400 MHz, DMSO) δ: 8.70 (s, 1H), 8.13 (m, 3H), 7.69 (m, 1H), 7.63-7.58 (m, 2H), 7.43-7.38 (m, 5H), 7.29 (m, 1H), 5.75 (d, 1H), 4.90 (m, 1H), 3.61 (s, 2H), 3.07-3.00 (m, 2H), 2.40 (m, 2H), 2.22-2.15 (m, 2H), 1.89 (m, 2H), 1.59 (d, 3H).

Racemic 1-[1-(1-Benzyl-piperidin-4-yl)-1,6-dihydro-1,2,3,5,6-tetraaza-as-indacen-2-yl]-ethanol 30 mg (66%) of the title compound was made by following the procedure described for the preparation of (R)-1-piperidin-3-yl-1,6-dihydro-1,2,3,5,6-tetraaza-as-indacene but using racemic 1-[6-benzenesulfonyl-1-(1-benzyl-piperidin-4-yl)-1,6-dihydro-1,2,3,5,6-tetraaza-as-indacen-2-yl]-ethanol. LCMS (Method A, ESI): RT=1.98 min, m+H=376.10; $^1$H NMR (400 MHz, DMSO) δ: 11.83 (s, 1H), 8.55 (s, 1H), 7.53 (t, 1H), 7.40 (m, 4H), 7.28 (t, 1H), 7.03 (s, 1H), 5.67 (d, 1H), 4.87 (s, 1H), 3.62 (s, 2H), 3.06 (d, 2H), 2.64 (m, 2H), 2.19 (t, 2H), 1.88 (d, 2H), 1.62 (d, 3H).

Example 158

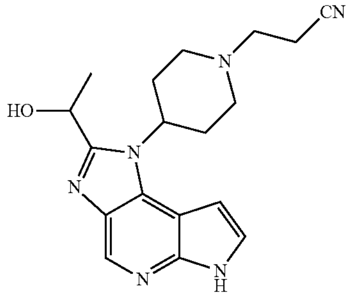 [SMILES: CC(O)c1nc2cnc3[nH]ccc3c2n1C1CCN(CCC#N)CC1]

Racemic 3-{4-[2-(1-Hydroxy-ethyl)-6H-1,2,3,5,6-tetraaza-as-indacen-1-yl]-piperidin-1-yl}-propionitrile Racemic 1-(1-Piperidin-4-yl-1,6-dihydro-1,2,3,5,6-tetraaza-as-indacen-2-yl)-ethanol A stirred solution of racemic 1-[1-(1-benzyl-piperidin-4-yl)-1,6-dihydro-1,2,3,5,6-tetraaza-as-indacen-2-yl]-ethanol (137 mg, 0.36 mmol), palladium hydroxide (20 wt % on carbon, 26.0 mg) and ammonium formate (230 mg, 3.65 mmol) in methanol (15 mL) was heated at reflux for 1 hour. After cooling, the mixture was filtered through Celite® and the filtrate was concentrated on to HMN and purified by column chromatography on silica gel (gradient: 0 to 20% [2M $NH_3$ in MeOH] in DCM) to leave a white solid. Trituration (diethyl ether) and subsequent drying in vacuo at 45° C. afforded 79.0 mg (76%) of racemic 1-(1-piperidin-4-yl-1,6-dihydro-1,2,3,5,6-tetraaza-as-indacen-2-yl)-ethanol as a white solid. LCMS (Method A, ESI): RT=1.00 min, m+H=286.2; $^1$H NMR (400 MHz, DMSO) δ: 11.75 (s, 1H), 8.49 (s, 1H), 7.41 (t, 1H), 6.98 (s, 1H), 5.62 (d, 1H), 5.08 (m, 1H), 4.85 (m, 1H), 3.14 (m, 3H), 2.64 (t, 2H), 2.39 (m, 2H), 1.77 (m, 2H), 1.58 (d, 3H).

Racemic 3-{4-[2-(1-Hydroxy-ethyl)-6H-1,2,3,5,6-tetraaza-as-indacen-1-yl]-piperidin-1-yl}-propionitrile A stirred solution of racemic 1-(1-piperidin-4-yl-1,6-dihydro-1,2,3,5,6-tetraaza-as-indacen-2-yl)-ethanol (28.0 mg, 98.0 μmol) and acrylonitrile (19.0 μL, 294 μmol) in ethanol (5 mL) was heated to 80° C. in a sealed tube for 2 hours. The mixture was concentrated under vacuum and then purified by column chromatography on silica gel (gradient: 0 to 15% methanol in DCM) to leave a colorless residue. Trituration (diethyl ethyl) and drying in vacuo at 40° C. afforded 20.0 mg (61%) of racemic 3-{4-[2-(1-hydroxy-ethyl)-6H-1,2,3,5,6-tetraaza-as-indacen-1-yl]-piperidin-1-yl}-propionitrile as an off white solid. LCMS (Method A, ESI): RT=1.38 min, m+H=339.2; $^1$H NMR (400 MHz, DMSO) δ: 11.75 (s, 1H), 8.50 (s, 1H), 7.35 (t, 1H), 6.95 (s, 1H), 5.64 (d, 1H), 5.08 (m, 1H), 4.84 (m, 1H), 3.09 (m, 2H), 2.74 (t, 2H), 2.66 (t, 2H), 2.57 (m, 2H), 2.20 (br t, 2H), 1.85 (m, 2H), 1.58 (d, 3H).

Example 159

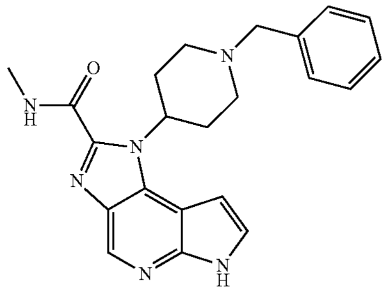 [SMILES: CNC(=O)c1nc2cnc3[nH]ccc3c2n1C1CCN(Cc2ccccc2)CC1]

1-(1-Benzyl-piperidin-4-yl)-1,6-dihydro-1,2,3,5,6-tetraaza-as-indacene-2-carboxylic acid methylamide 6-Benzenesulfonyl-1-(1-benzyl-piperidin-4-yl)-1,6-dihydro-1,2,3,5,6-tetraaza-as-indacene-2-carboxylic acid ethyl ester Ethyl glyoxylate (50% in toluene, 161 μL, 0.81 mmol) was added to a solution of 1-benzenesulfonyl-N*4*-(1-benzyl-piperidin-4-yl)-1H-pyrrolo[2,3-b]pyridine-4,5-diamine (250 mg, 0.54 mmol) in ethanol/THF (1:1.5 mL) and stirred for 30 minutes. A solution of iodine (69 mg, 0.27 mmol) in ethanol/THF (1:1.1 mL) was added and stirred for 18 hours before refluxing for 2 hours. Ethyl acetate was added to the cooled reaction, the organics were washed with sodium thiosulphate, water and brine, dried with sodium sulfate and concentrated under vacuum. Purification by column chromatography on silica gel (gradient: 0 to 10% methanol in DCM) afforded 203 mg (69%) of 6-benzenesulfonyl-1-(1-benzyl-piperidin-4-yl)-1,6-dihydro-1,2,3,5,6-tetraaza-as-indacene-2-carboxylic acid ethyl ester as an orange residue. LCMS (Method B, ESI): RT=2.72 min, m+H=544.25.

6-Benzenesulfonyl-1-(1-benzyl-piperidin-4-yl)-1,6-dihydro-1,2,3,5,6-tetraaza-as-indacene-2-carboxylic acid methylamide A 5 ml microwave vial was charged with 6-benzenesulfonyl-1-(1-benzyl-piperidin-4-yl)-1,6-dihydro-1,2,3,5,6-tetraaza-as-indacene-2-carboxylic acid ethyl ester (196 mg, 0.36 mmol) and methylamine (33% in ethanol, 5 mL). The mixture was heated in a microwave reactor at 150° C. for 8 minutes. The solvent was removed under vacuum and the isolated residue purified by column chromatography on silica gel (gradient: 0 to 100% ethyl acetate in DCM) afforded 76 mg (40%) of 6-benzenesulfonyl-1-(1-benzyl-piperidin-4-yl)-1,6-dihydro-1,2,3,5,6-tetraaza-as-indacene-2-carboxylic acid methylamide as a yellow residue. LCMS (Method B, ESI): RT=2.63 min, m+H=529.27; $^1$H NMR (400 MHz, DMSO) δ: 9.08 (m, 1H), 8.83 (s, 1H), 8.20 (d, 1H), 8.16 (m, 2H), 7.71 (m, 1H), 7.63 (dd, 2H), 7.45-7.38 (m, 4H), 7.29 (m, 1H), 5.74 (m, 1H), 3.60 (s, 2H), 3.04 (m, 2H), 2.82 (d, 3H), 2.46 (m, 2H), 2.19-2.12 (m, 2H), 1.89 (m, 2H).

1-(1-Benzyl-piperidin-4-yl)-1,6-dihydro-1,2,3,5,6-tetraaza-as-indacene-2-carboxylic acid methylamide 21 mg (40%) of the title compound was made by following the procedure described for the preparation of (R)-1-piperidin-3-yl-1,6-dihydro-1,2,3,5,6-tetraaza-as-indacene but using 6-benzenesulfonyl-1-(1-benzyl-piperidin-4-yl)-1,6-dihydro-1,2,3,5,6-tetraaza-as-indacene-2-carboxylic acid methylamide. LCMS (Method A, ESI): RT=2.40 min, m+H=389.13; $^1$H NMR (400 MHz, DMSO) δ: 12.08 (s, 1H), 8.98 (m, 1H), 8.67 (s, 1H), 7.62 (t, 1H), 7.46-7.36 (m, 3H), 7.28 (t, 1H), 7.10 (m, 1H), 5.81 (m, 1H), 3.61 (s, 2H), 3.06 (d, 2H), 2.83 (d, 3H), 2.68-2.65 (m, 2H), 2.17 (t, 2H), 1.88-1.85 (m, 2H).

Example 160

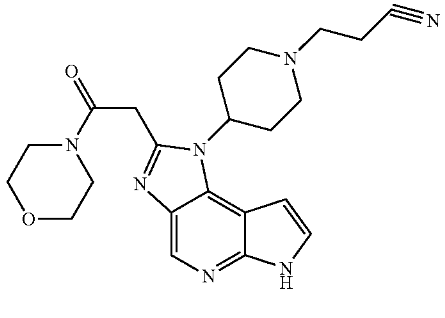 [SMILES: N#CCCN1CCC(n2c(CC(=O)N3CCOCC3)nc3cnc4[nH]ccc4c32)CC1]

3-{4-[2-(2-Morpholin-4-yl-2-oxo-ethyl)-6H-1,2,3,5,6-tetraaza-as-indacen-1-yl]-piperidin-1-yl}-propionitrile 1-Morpholin-4-yl-2-(1-piperidin-4-yl-1,6-dihydro-1,2,3,5,6-tetraaza-as-indacen-2-yl)-ethanone 57 mg (99%) of the title compound was made by following the procedure described for the preparation of (R)-1-piperidin-3-yl-1,6-dihydro-1,2,3,5,6-tetraaza-as-indacene but using 2-[1-(1-benzyl-piperidin-4-yl)-1,6-dihydro-1,2,3,5,6-tetraaza-as-indacen-2-yl]-1-morpholin-4-yl-ethanone. LCMS (Method B, ESI): RT=0.41 min, m+H=369.24; $^1$H NMR (400 MHz, DMSO) δ: 11.78 (s, 1H), 8.49 (s, 1H), 7.45 (t, 1H), 7.01 (s, 1H), 4.40 (m, 1H), 4.25 (s, 2H), 3.63 (s, 4H), 3.57 (m, 2H), 3.48 (m, 2H), 3.20-3.12 (m, 3H), 2.64 (t, 2H), 2.39 (m, 2H), 1.81 (d, 2H).

3-{4-[2-(2-Morpholin-4-yl-2-oxo-ethyl)-6H-1,2,3,5,6-tetraaza-as-indacen-1-yl]-piperidin-1-yl}-propionitrile 47 mg (71%) of the title compound was made by following the procedure described for the preparation of 3-[(R)-3-(6H-1,2,3,5,6-tetraaza-as-indacen-1-yl)-piperidin-1-yl]-propionitrile but using 1-morpholin-4-yl-2-(1-piperidin-4-yl-1,6-dihydro-1,2,3,5,6-tetraaza-as-indacen-2-yl)-ethanone. LCMS (Method A, ESI): RT=1.56 min, m+H=422.15; $^1$H NMR (400 MHz, DMSO) δ: 11.75 (s, 1H), 8.45 (s, 1H), 7.36 (t, 1H), 6.93 (s, 1H), 4.35 (s, 1H), 4.22 (s, 2H), 3.59 (s, 4H), 3.52 (t, 2H), 3.44 (d, 2H), 3.07 (d, 2H), 2.73 (t, 2H), 2.64 (t, 2H), 2.53 (d, 2H), 2.17 (t, 2H), 1.87 (d, 2H).

Example 161

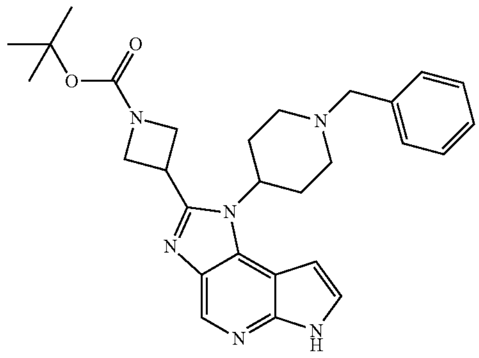 [SMILES: CC(C)(C)OC(=O)N1CC(c2nc3cnc4[nH]ccc4c3n2C2CCN(Cc3ccccc3)CC2)C1]

3-[1-(1-Benzyl-piperidin-4-yl)-1,6-dihydro-1,2,3,5,6-tetraaza-as-indacen-2-yl]azetidine-1-carboxylic acid tert-butyl ester 3-[6-Benzenesulfonyl-1-(1-benzyl-piperidin-4-yl)-1,6-dihydro-1,2,3,5,6-tetraaza-as-indacen-2-yl]azetidine-carboxylic acid tert-butyl ester 149 mg (44%) of the title compound was made by following the procedure described for the preparation of 6-benzenesulfonyl-1-(1-benzyl-piperidin-4-yl)-1,6-dihydro-1,2,3,5,6-tetraaza-as-indacene-2-carboxylic acid ethyl ester but using N-boc-azetidine-3-carboxaldehyde. LCMS (Method B, ESI): RT=2.91 min, m+H=627.38; $^1$H NMR (400 MHz, $CDCl_3$) δ: 8.88 (s, 1H), 8.22 (m, 2H), 7.87 (m, 1H), 7.49 (m, 4H), 7.39 (m, 4H), 7.30 (m, 1H), 4.35 (t, 3H), 4.05 (m, 1H), 3.61 (s, 2H), 3.15-3.06 (m, 3H), 2.59 (m, 2H), 2.21-2.13 (m, 2H), 1.79-1.72 (m, 3H), 1.44 (s, 9H).

3-[1-(1-Benzyl-piperidin-4-yl)-1,6-dihydro-1,2,3,5,6-tetraaza-as-indacen-2-yl]azetidine-1-carboxylic acid tert-butyl ester 49 mg (44%) of the title compound was made by following the procedure described for the preparation of 1-((R)-1-benzyl-piperidin-3-yl)-1,6-dihydro-1,2,3,5,6-tetraaza-as-indacene but using 3-[6-benzenesulfonyl-1-(1-benzyl-piperidin-4-yl)-1,6-dihydro-1,2,3,5,6-tetraaza-as-indacen-2-yl]azetidine-1-carboxylic acid tert-butyl ester. LCMS (Method A, ESI): RT=2.90 min, m+H=487.24; $^1$H NMR (400 MHz, DMSO) δ: 11.86 (s, 1H), 8.57 (s, 1H), 7.54 (t, 1H), 7.40 (m, 4H), 7.28 (t, 1H), 6.98 (s, 1H), 4.38-4.16 (m, 6H), 3.62 (s, 2H), 3.02 (d, 2H), 2.55 (m, 2H), 2.23 (t, 2H), 1.82 (d, 2H), 1.40 (s, 9H).

Example 162

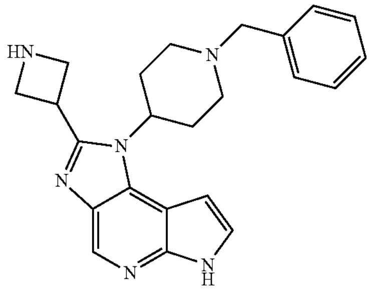 [SMILES: c1ccc(CN2CCC(n3c(C4CNC4)nc4cnc5[nH]ccc5c43)CC2)cc1]

2-Azetidin-3-yl-1-(1-benzyl-piperidin-4-yl)-1,6-dihydro-1,2,3,5,6-tetraaza-as-indacene 3-[1-(1-Benzyl-piperidin-4-yl)-1,6-dihydro-1,2,3,5,6-tetraaza-as-indacen-2-yl]azetidine-carboxylic acid tert-butyl ester (40 mg, 0.08 mmol) in DCM (2 ml) was treated with TFA (2 ml) at ambient temperature for 1 hour. The solvent was removed under vacuum and the residue purified by HPLC (gradient: 0 to 75% acetonitrile in water with 0.1% ammonium hydroxide) affording 2-azetidin-3-yl-1-(1-benzyl-piperidin-4-yl)-1,6-dihydro-1,2,3,5,6-tetraaza-as-indacene as a white solid. LCMS (Method A, ESI): RT=1.55 min, m+H=387.2, $^1$H NMR (400 MHz, DMSO) δ: 11.78 (s; 1H); 8.49 (s; 1H); 7.48 (t; 1H); 7.40-7.30 (m; 4H); 7.26-7.20 (m; 1H); 6.91 (s; 1H); 4.31 (m; 1H); 4.18 (s; 1H); 3.92 (t; 2H); 3.72 (t; 2H); 3.57 (s; 2H); 2.98 (d; 2H); 2.56-2.46 (m; 1H); 2.17 (t; 2H); 1.78-1.68 (m; 2H).

Example 163

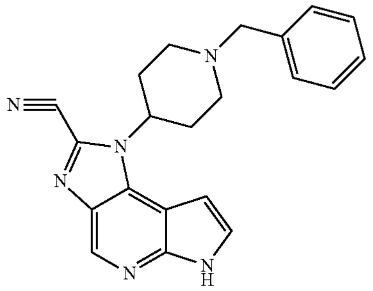 [SMILES: N#Cc1nc2cnc3[nH]ccc3c2n1C1CCN(Cc2ccccc2)CC1]

1-(1-Benzyl-piperidin-4-yl)-1,6-dihydro-1,2,3,5,6-tetraaza-as-indacene-2-carbonitrile 6-Benzenesulfonyl-1-(1-benzyl-piperidin-4-yl)-1,6-dihydro-1,2,3,5,6-tetraaza-as-indacene-2-carbaldehyde oxime Hydroxylamine (150 mg, 2.16 mmol) and sodium acetate (177 mg, 2.16 mmol) were added to a solution of 6-benzene sulfonyl-1-(1-benzyl-piperidin-4-yl)-1,6-dihydro-1,2,3,5,6-tetraaza-as-indacene-2-carbaldehyde (830 mg, 1.66 mmol) in ethanol/water (8:2, 10 mL) and THF (5 mL) and stirred for 4 hours. The solvent was removed under vacuum and the isolated residue partitioned between ethyl acetate and water. The organic phase was dried with sodium sulphate and concentrated under vacuum. Purification by column chromatography on silica gel (gradient: 0 to 5% methanol in DCM) afforded 996 mg (99%) of 1-(1-benzyl-piperidin-4-yl)-1,6-dihydro-1,2,3,5,6-tetraaza-as-indacene-2-carbaldehyde oxime as an orange residue. LCMS (Method B, ESI): RT=2.61 min, m+H=515.27; $^1$H NMR (400 MHz, DMSO) δ: 12.20 (s, 1H), 8.77 (s, 1H), 8.38 (s, 1H), 8.16 (m, 3H), 7.70 (m, 1H), 7.63 (m, 2H), 7.43 (m, 4H), 7.30 (m, 1H), 5.42 (m, 1H), 3.61 (s, 2H), 3.17 (d, 2H), 3.08-2.99 (m, 2H), 2.46 (m, 2H), 2.14 (m, 2H), 1.90 (s, 1H).

6-Benzenesulfonyl-1-(1-benzyl-piperidin-4-yl)-1,6-dihydro-1,2,3,5,6-tetraaza-as-indacene-2-carbonitrile A 5 ml microwave vial was charged 6-benzenesulfonyl-1-(1-benzyl-piperidin-4-yl)-1,6-dihydro-1,2,3,5,6-tetraaza-as-indacene-2-carbaldehyde oxime (100 mg, 0.19 mmol) and acetic anhydride (1 mL). The mixture was heated in a microwave reactor at 100° C. for 6 hours. Ethyl acetate was added to the cooled reaction, the organics were washed with sodium hydrogen carbonate (sat. aq.), water and brine, dried with sodium sulfate and concentrated under vacuum. Purification by column chromatography on silica gel (gradient: 0 to 50% ethyl acetate in cyclohexane) afforded 87 mg (90%) of 6-benzenesulfonyl-1-(1-benzyl-piperidin-4-yl)-1,6-dihydro-1,2,3,5,6-tetraaza-as-indacene-2-carbonitrile as a white solid. LCMS (Method B, ESI): RT=2.72 min, m+H=497.37.

1-(1-Benzyl-piperidin-4-yl)-1,6-dihydro-1,2,3,5,6-tetraaza-as-indacene-2-carbonitrile 49 mg (44%) of the title compound was made by following the procedure described for the preparation of 4-[2-(cyano-dimethyl-methyl)-6H-1,2,3,5,6-tetraaza-as-indacen-1-yl]-piperidine-1-carboxylic acid tert-butyl ester but using 6-benzenesulfonyl-1-(1-benzyl-piperidin-4-yl)-1,6-dihydro-1,2,3,5,6-tetraaza-as-indacene-2-carbonitrile. LCMS (Method A, ESI): RT=2.57 min, m+H=357.11; $^1$H NMR (400 MHz, DMSO) δ: 12.25 (br s, 1H), 8.71 (s, 1H), 7.62 (d, 1H), 7.36-7.31 (m, 4H), 7.24 (m, 1H), 6.97 (d, 1H), 4.75-4.66 (m, 1H), 3.58 (s, 2H), 3.01 (d, 2H), 2.50 (m, 2H), 2.26 (t, 2H), 2.05 (m, 2H).

Example 164

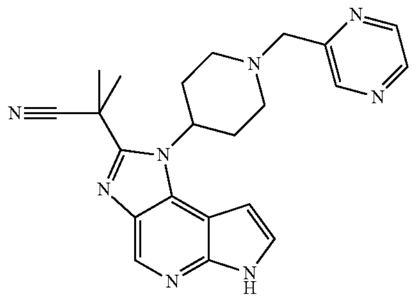 [SMILES: CC(C)(C#N)c1nc2cnc3[nH]ccc3c2n1C1CCN(Cc2cnccn2)CC1]

2-Methyl-2-[1-(1-pyrazin-2-ylmethyl-piperidin-4-yl)-1,6-dihydro-1,2,3,5,6-tetraaza-as-indacen-2-yl]-propionitrile

2-Cyano-acetimidic acid methyl ester hydrochloride salt

A solution of malonitrile (6.60 g, 100 mmol) in diethyl ether (50 mL) was treated with methanol (4.40 g, 138 mmol) and cooled to 0° C. before HCl (gas) was bubbled through for 5 minutes. The resulting suspension was stirred for 30 minutes before the solid was collected by filtration, washed with diethyl ether and dried under vacuum to afford 10.0 g of 2-cyano-acetimidic acid methyl ester hydrochloride salt.

3,3,3-Trimethoxy-propionitrile

A solution of 2-cyano-acetimidic acid methyl ester hydrochloride salt (2.00 g, 15.0 mmol) in methanol (15 mL) was stirred at ambient temperature for 16 hours. The suspension was filtered and the filtrated concentrated under vacuum. The resulting residue was partitioned between ethyl acetate and 2M aqueous sodium carbonate, the organic layer further washed with brine then dried over sodium sulfate and concentrated under vacuum to afford 1.47 g (68%) of 3,3,3-trimethoxy-propionitrile. $^1$H NMR (400 MHz, $CDCl_3$) δ: 3.36 (s, 9H), 2.85 (s, 2H).

4-(6-Benzenesulfonyl-2-cyanomethyl-6H-1,2,3,5,6-tetraaza-as-indacen-1-yl)-piperidine-1-carboxylic acid tert-butyl ester A mixture of 4-(5-amino-1-benzenesulfonyl-1H-pyrrolo[2,3-b]pyridin-4-ylamino)-piperidine-1-carboxylic acid tert-butyl ester (300 mg, 0.64 mmol), 3,3,3-trimethoxy-propionitrile (277 mg, 1.91 mmol) and p-toluenesulfonic acid monohydrate (catalytic) in toluene (5 mL) was heated at 100° C. for 90 minutes in a sealed tube. The cooled reaction mixture was diluted with ethyl acetate and the organic layer washed with saturated aqueous sodium bicarbonate, water and brine, then dried over sodium sulfate and concentrated under vacuum. The resulting residue was purified by column chromatography on silica gel (gradient: 0 to 100% ethyl acetate in DCM) to afford 297 mg (89%) of 4-(6-benzenesulfonyl-2-cyanomethyl-6H-1,2,3,5,6-tetraaza-as-indacen-1-yl)-piperidine-1-carboxylic acid tert-butyl ester. LCMS (Method B, ESI): RT=3.69 min, m+H=521.3; $^1$H NMR (400 MHz, $CDCl_3$) δ: 8.88 (s, 1H), 8.23 (m, 2H), 7.82 (d, 1H), 7.57 (m, 1H), 7.52-7.46 (m, 2H), 6.73 (d, 1H), 4.62-4.33 (m, 3H), 4.18 (s, 2H) 2.97 (s, 2H), 2.54-2.40 (m, 2H), 2.03-1.94 (m, 2H), 1.58 (s, 9H).

4-[6-Benzenesulfonyl-2-(cyano-dimethyl-methyl)-6H-1,2,3,5,6-tetraaza-as-indacen-1-yl]-piperidine-1-carboxylic acid tert-butyl ester A mixture of 4-(6-benzenesulfonyl-2-cyanomethyl-6H-1,2,3,5,6-tetraaza-as-indacen-1-yl)-piperidine-1-carboxylic acid tert-butyl ester (100 mg, 0.19 mmol), methyl iodide (76 μL, 1.16 mmol) and cesium carbonate (250 mg, 0.77 mmol) in DMF (2 mL) was heated at 100° C. for 90 minutes. The reaction mixture was diluted with ethyl acetate and the organic layer washed with water and brine, then dried over sodium sulfate and concentrated under vacuum. The resulting residue was purified by column chromatography on silica gel (gradient: 0 to 100% ethyl acetate in cyclohexane) to afford 35 mg (33%) of 4-[6-benzenesulfonyl-2-(cyano-dimethylmethyl)-6H-1,2,3,5,6-tetraaza-as-indacen-1-yl]-piperidine-1-carboxylic acid tert-butyl ester. LCMS (Method B, ESI): RT=4.21 min, m+H=549.4; $^{1}$H NMR (400 MHz, $CDCl_3$) δ: 8.89 (s, 1H), 8.21 (d, 2H), 7.79 (d, 1H), 7.55 (d, 1H), 7.47 (t, 2H), 6.75 (d, 1H), 5.03 (m, 1H), 4.43 (m, 2H), 2.98 (m, 2H), 2.52 (m, 2H), 2.01 (m, 2H), 1.96 (s, 6H), 1.58 (s, 9H).

4-[2-(Cyano-dimethyl-methyl)-6H-1,2,3,5,6-tetraaza-as-indacen-1-yl]-piperidine-1-carboxylic acid tert-butyl ester A mixture of 4-[6-benzenesulfonyl-2-(cyano-dimethyl-methyl)-6H-1,2,3,5,6-tetraaza-as-indacen-1-yl]-piperidine-1-carboxylic acid tert-butyl ester (220 mg, 0.40 mmol) and TBAF (1.2 mL, 1.20 mmol, 1M solution in THF) in THF (5 mL) was heated at reflux for 6 hours. The cooled reaction mixture was diluted with ethyl acetate and the organic layer washed with water and brine, then dried over sodium sulfate and concentrated under vacuum. The resulting residue was purified by column chromatography on silica gel (gradient: 0 to 10% methanol in DCM) to afford 142 mg (87%) of 4-[2-(cyano-dimethyl-methyl)-6H-1,2,3,5,6-tetraaza-as-indacen-1-yl]-piperidine-1-carboxylic acid tert-butyl ester. LCMS (Method B, ESI): RT=3.27 min, m+H=409.4.

2-Methyl-2-(1-piperidin-4-yl-1,6-dihydro-1,2,3,5,6-tetraaza-as-indacen-2-yl)-propionitrile A solution of 4-[2-(cyano-dimethyl-methyl)-6H-1,2,3,5,6-tetraaza-as-indacen-1-yl]-piperidine-1-carboxylic acid tert-butyl ester (135 mg, 0.33 mmol) in DCM (5 mL) was treated with TFA (2 mL) and the resulting mixture stirred at ambient temperature for 1 hour. The reaction mixture was concentrated under vacuum and purified by column chromatography on silica gel (gradient: 0 to 10% 2M $NH_3$ in methanol solution in DCM) to afford 65 mg (64%) of 2-methyl-2-(1-piperidin-4-yl-1,6-dihydro-1,2,3,5,6-tetraaza-as-indacen-2-yl)-propionitrile as a white solid. LCMS (Method B, ESI): RT=1.69 min, m+H=309.3; $^{1}$H NMR (400 MHz, DMSO) δ: 11.95 (s, 1H), 8.60 (d, 1H), 7.52 (t, 1H), 7.12 (dd, 1H), 4.82 (m, 1H), 3.23 (d, 2H), 2.72 (t, 2H), 2.59-2.57 (m, 2H), 1.91-1.86 (m, 8H).

2-Methyl-2-[1-(1-pyrazin-2-ylmethyl-piperidin-4-yl)-1,6-dihydro-1,2,3,5,6-tetraaza-as-indacen-2-yl]-propionitrile A mixture of 2-methyl-2-(1-piperidin-4-yl-1,6-dihydro-1,2,3,5,6-tetraaza-as-indacen-2-yl)-propionitrile (60 mg, 0.20 mmol), pyrazine-2-carboxaldehyde (32 mg, 0.29 mmol) and sodium triacetoxyborohydride (62 mg, 0.29 mmol) in methanol (1 mL) and DCE (4 mL) was stirred at ambient temperature for 16 hours. Further pyrazine-2-carboxaldehyde (32 mg, 0.29 mmol) and sodium triacetoxyborohydride (62 mg, 0.29 mmol) were added and the mixture stirred for 48 hours then purified by column chromatography on silica gel (gradient: DMAW 240). The resulting residue was further purified by Isolute® SCX-2 column (gradient: methanol to 2M $NH_3$ in methanol) then triturated with diethyl ether. The resulting solid was slurried with hot MeCN for 30 minutes, collected by filtration, then slurried with water and collected by filtration and air dried under vacuum to afford 27 mg (35%) of 2-methyl-2-[1-(1-pyrazin-2-ylmethyl-piperidin-4-yl)-1,6-dihydro-1,2,3,5,6-tetraaza-as-indacen-2-yl]-propionitrile as an off-white solid. LCMS (Method A, ESI): RT=2.16 min, m+H=401.2; $^{1}$H NMR (400 MHz, DMSO) δ: 12.00 (s, 1H), 8.86 (d, 1H), 8.62 (m, 3H), 7.61 (t, 1H), 7.10 (m, 1H), 4.84 (m, 1H), 3.86 (s, 2H), 3.15 (m, 2H), 2.76 (m, 2H), 2.40 (t, 2H), 2.02-1.92 (m, 2H), 1.92 (s, 6H).

Example 165

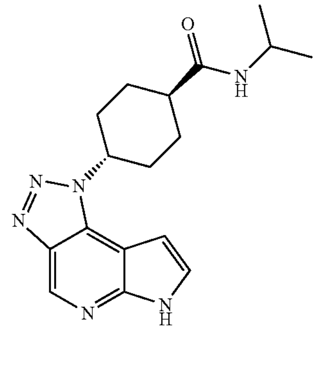 [SMILES: CC(C)NC(=O)[C@H]1CC[C@H](n2nnc3cnc4[nH]ccc4c32)CC1]

Trans 4-(6H-1,2,3,5,6-Pentaaza-as-indacen-1-yl)-cyclohexanecarboxylic acid isopropylamide Trans 4-tert-Butoxycarbonylamino-cyclohexanecarboxylic acid Di-tert-butyl dicarbonate (4.57 g, 20.95 mmol) was added to a solution of trans-4-aminocyclohexylcarboxylic acid (2.5 g, 17.46 mmol), sodium hydroxide (1M solution, 34.9 mL, 34.9 mmol) in 1,4-dioxane (35 mL) and stirred for 18 hours. The mixture was basified with 1M sodium hydroxide, extracted with ethyl acetate and the aqueous layer acidified with conc. HCl. The resulting acidic layer was extracted with ethyl acetate. The organic extracts were separated and washed with water, dried with magnesium sulfate and concentrated under vacuum affording 2.64 g of trans 4-tert-butoxycarbonylamino-cyclohexanecarboxylic acid as a white solid. LCMS (Method H, ESI): RT=2.73 min, m-H=242.1; $^{1}$H NMR (400 MHz, $CDCl_3$) δ: 4.39 (m; 1H); 3.42 (m; 1H); 2.25 (m; 1H); 2.06 (m; 4H); 1.61-1.49 (m; 2H); 1.44 (s; 9H); 1.13 (m; 2H).

Trans (4-Isopropylcarbamoyl-cyclohexyl)-carbamic acid tert-butyl ester

Isopropylamine (925 μL, 10.86 mmol) was added to a stirred solution of trans 4-tert-butoxycarbonylamino-cyclohexanecarboxylic acid (1.32 g, 5.43 mmol), HATU (2.06 g, 5.43 mmol) and diisopropylethylamine (2.79 mL, 16.3 mmol) in DMF (50 ml). The resulting mixture was stirred at ambient temperature for 72 hours. The solvent was evaporated under vacuum and the residues diluted with water and extracted into DCM. The combined organic extracts were washed with 1M sodium hydroxide, water and brine, dried with magnesium sulfate and concentrated under vacuum affording 1.37 g (89%) of trans (4-isopropylcarbamoyl-cyclohexyl)-carbamic acid tert-butyl ester as a white solid. LCMS (Method B, ESI): RT=3.07 min, m+H+ MeCN=326.3; $^{1}$H NMR (400 MHz, DMSO) δ: 7.50 (d; 1H); 6.66 (d; 1H); 3.78 (m; 1H); 3.13 (m; 1H); 1.94 (m; 1H); 1.78 (d; 2H); 1.66 (d; 2H); 1.37 (s; 9H); 1.31 (m; 2H); 1.11 (m; 2H); 1.01 (d; 6H).

Trans 4-Amino-cyclohexanecarboxylic acid isopropylamide

A mixture of trans (4-isopropylcarbamoyl-cyclohexyl)-carbamic acid tert-butyl ester (1.35 g, 4.75 mmoll) in DCM (25 ml) was treated with TFA (5 ml) at ambient temperature for 1 hour. The solvent was evaporated under vacuum and the residues diluted with water and extracted into ethyl acetate. The combined organic extracts were washed with 1M sodium hydroxide, water and brine, dried with magnesium sulfate and concentrated under vacuum affording 400 mg (46%) of trans 4-amino-cyclohexanecarboxylic acid isopropylamide as a white solid. LCMS (Method B, ESI): RT=0.43 min, m+H=185.21; $^{1}$H NMR (400 MHz, DMSO) δ: 7.50 (d; 1H); 3.81-3.75 (m; 1H); 2.55 (m, 1H); 1.94 (m; 1H); 1.79 (m; 2H); 1.69-1.58 (m; 2H); 1.35 (m; 2H); 1.01 (d; 6H) 0.99 (m; 2H).

Trans 4-(1-Benzenesulfonyl-5-nitro-1H-pyrrolo[2,3-b]pyridin-4-ylamino)-cyclohexanecarboxylic acid isopropylamide 238 mg (63%) of the title compound was made by following the procedure described for the preparation of (1-benzenesulfonyl-5-nitro-1H-pyrrolo[2,3-b]pyridin-4-yl)-((R)-1-benzyl-piperidin-3-yl)amine but using trans 4-amino-cyclohexanecarboxylic acid isopropylamide. LCMS (Method B, ESI): RT=3.89 min, m+H=486.27; $^{1}$H NMR (400 MHz, DMSO) δ: 8.89 (s; 1H); 8.79 (d; 1H); 8.13 (dd; 2H); 7.82 (d; 1H); 7.75 (m; 1H); 7.63 (m; 3H); 7.01 (d; 1H); 3.99 (m; 1H); 3.81 (m; 1H); 2.14-2.04 (m; 3H); 1.79-1.75 (m; 2H); 1.66 (m; 2H); 1.46 (m; 2H); 1.03 (d; 6H).

Trans 4-(5-Amino-1-benzenesulfonyl-1H-pyrrolo[2,3-b]pyridin-4-ylamino)-cyclohexanecarboxylic acid isopropylamide 155 mg (70%) of the title compound was made by following the procedure described for the preparation of 1-benzenesulfonyl-N*4*-((R)-1-benzyl-piperidin-3-yl)-1H-pyrrolo[2,3-b]pyridine-4,5-diamine but using trans 4-(1-benzenesulfonyl-5-nitro-1H-pyrrolo[2,3-b]pyridin-4-ylamino)-cyclohexanecarboxylic acid isopropylamide. LCMS (Method B, ESI): RT=2.50 min, m+H=456.34; $^{1}$H NMR (400 MHz, DMSO) δ: 8.01 (dd; 2H); 7.65 (m; 1H); 7.57 (m; 4H); 7.47 (d; 1H); 6.69 (d; 1H); 5.15-5.09 (br d; 1H); 4.42 (br s; 2H); 3.80 (m; 1H); 3.63 (m; 1H); 2.10 (m; 1H); 1.90 (m; 2H); 1.78-1.70 (m; 2H); 1.59-1.48 (m; 2H); 1.31-1.21 (m; 2H); 1.02 (d; 6H).

Trans 4-(6-Benzenesulfonyl-6H-1,2,3,5,6-pentaaza-as-indacen-1-yl)-cyclohexanecarboxylic acid isopropylamide Sodium nitrite (12 mg, 0.17 mmol) was added to a solution of trans 4-(5-amino-1-benzenesulfonyl-1H-pyrrolo[2,3-b]pyridin-4-ylamino)-cyclohexanecarboxylic acid isopropylamide (70 mg, 0.15 mmol) in acetic acid (1 mL) and stirred for 45 minutes. The mixture was concentrated under vacuum affording trans 4-(6-benzenesulfonyl-6H-1,2,3,5,6-pentaaza-as-indacen-1-yl)-cyclohexanecarboxylic acid isopropylamide which was used for the next step without further purification. LCMS (Method B, ESI): RT=3.58 min, m+H=467.35.

Trans 4-(6H-1,2,3,5,6-Pentaaza-as-indacen-1-yl)-cyclohexanecarboxylic acid isopropylamide 20 mg (40%) of the title compound was made by following the procedure described for the preparation of 2-[1-((R)-1-benzyl-piperidin-3-yl)-1,6-dihydro-1,2,3,5,6-tetraaza-as-indacen-2-yl]ethanol but using trans 4-(6-benzenesulfonyl-6H-1,2,3,5,6-pentaaza-as-indacen-1-yl)-cyclohexanecarboxylic acid isopropylamide. LCMS (Method A, ESI): RT=3.16 min, m+H=327.16; $^{1}$H NMR (400 MHz, DMSO) δ: 12.35 (br s; 1H); 8.99 (s; 1H); 7.68 (d; 1H); 7.60 (d; 1H); 7.02 (d; 1H); 5.02 (m; 1H); 3.86 (m; 1H); 2.24 (m; 3H); 2.09 (m; 2H); 1.90 (m; 2H); 1.85 (m; 2H); 1.07 (d; 6H).

Example 166

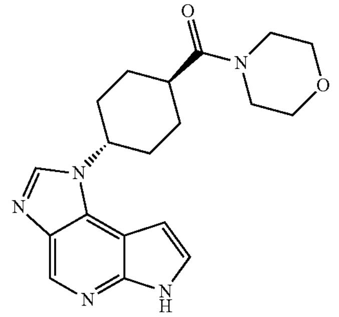 [SMILES: O=C([C@H]1CC[C@H](n2cnc3cnc4[nH]ccc4c32)CC1)N1CCOCC1]

Trans Morpholin-4-yl-[4-(6H-1,2,3,5,6-tetraaza-as-indacen-1-yl)-cyclohexyl]-methanone Trans[4-(Morpholine-4-carbonyl)-cyclohexyl]-carbamic acid tert-butyl ester 1.62 g (95%) of the title compound was made by following the procedure described for the preparation of trans (4-isopropylcarbamoyl-cyclohexyl)-carbamic acid tert-butyl ester but using morpholine. LCMS (Method B, ESI): RT=2.87 min, m+H=313.24; $^{1}$H NMR (400 MHz, DMSO) δ: 6.74 (s, 1H), 3.53-3.43 (m, 8H), 3.14 (br m, 1H), 2.48 (m; 1H); 1.77 (m, 2H), 1.64 (m, 2H), 1.37 (s, 9H), 1.35 (m; 2H); 1.23 (m, 2H).

Trans (4-Amino-cyclohexyl)-morpholin-4-yl-methanone 392 mg (37%) of the title compound was made by following the procedure described for the preparation of trans 4-amino-cyclohexanecarboxylic acid isopropylamide but using trans [4-(morpholine-4-carbonyl)-cyclohexyl]-carbamic acid tert-butyl ester. LCMS (Method B, ESI): RT=0.39 min, m+H=213.25; $^{1}$H NMR (400 MHz, DMSO) δ: 3.51-3.43 (m; 9H); 2.44 (m; 1H); 1.76 (m; 2H); 1.61 (m; 2H); 1.36 (m; 2H); 1.07 (m; 2H).

Trans[4-(1-Benzenesulfonyl-5-nitro-1H-pyrrolo[2,3-b]pyridin-4-ylamino)-cyclohexyl]-morpholin-4-yl-methanone 330 mg (84%) of the title compound was made by following the procedure described for the preparation of trans (1-benzenesulfonyl-5-nitro-1H-pyrrolo[2,3-b]pyridin-4-yl)-((R)-1-benzyl-piperidin-3-yl)amine but using trans (4-amino-cyclohexyl)-morpholin-4-yl-methanone. LCMS (Method B, ESI): RT=3.73 min, m+H=514.22; $^{1}$H NMR (400 MHz, DMSO) δ: 8.90 (s; 1H); 8.80 (d; 1H); 8.13 (m; 2H); 7.82 (d; 1H); 7.75 (m; 1H); 7.67-7.62 (m; 2H); 7.04 (d; 1H); 4.04 (m; 1H); 3.51 (m; 8H); 2.65 (m; 1H); 2.09 (d; 2H); 1.65 (m; 4H); 1.50 (m; 2H).

Trans[4-(5-Amino-1-benzenesulfonyl-1H-pyrrolo[2,3-b]pyridin-4-ylamino)-cyclohexyl]-morpholin-4-yl-methanone 191 mg (62%) of the title compound was made by following the procedure described for the preparation of 1-benzenesulfonyl-N*4*-((R)-1-benzyl-piperidin-3-yl)-1H-pyrrolo[2,3-b]pyridine-4,5-diamine but using trans[4-(1-benzenesulfonyl-5-nitro-1H-pyrrolo[2,3-b]pyridin-4-ylamino)-cyclohexyl]-morpholin-4-yl-methanone. LCMS (Method B, ESI): RT=2.29 min, m+H=484; $^{1}$H NMR (400 MHz, DMSO) δ: 8.01 (m; 2H); 7.66 (m; 1H); 7.56 (m; 3H); 7.46 (d; 1H); 6.69 (d; 1H); 5.14-5.09 (d; 1H); 4.36 (br s; 2H); 3.65 (m; 1H); 3.59-3.40 (m; 8H); 2.55 (m; 1H); 2.02-1.92 (m; 2H); 1.71 (m; 2H); 1.60-1.51 (m; 2H); 1.38-1.27 (m; 2H).

Trans[4-(6-Benzenesulfonyl-6H-1,2,3,5,6-tetraaza-as-indacen-1-yl)-cyclohexyl]-morpholin-4-yl-methanone A stirred solution of trans[4-(5-amino-1-benzenesulfonyl-1H-pyrrolo[2,3-b]pyridin-4-ylamino)-cyclohexyl]-morpholin-4-yl-methanone (100 mg, 207 μmol) and triethyl orthoformate (86.2 μL, 518 μmol) in acetic acid (1 mL) was heated to 105° C. for 3 hours. After cooling, the solvent was removed in vacuo to provide trans[4-(6-benzenesulfonyl-6H-1,2,3,5,6-tetraaza-as-indacen-1-yl)-cyclohexyl]-morpholin-4-yl-methanone as an orange residue which was used without purification. LCMS (Method B, ESI): RT=3.01 min, m+H=494.35.

Morpholin-4-yl-[4-(6H-1,2,3,5,6-tetraaza-as-indacen-1-yl)-cyclohexyl]-methanone 44 mg (60%) of the title compound was made by following the procedure described for the preparation of 2-[1-((R)-1-benzyl-piperidin-3-yl)-1,6-dihydro-1,2,3,5,6-tetraaza-as-indacen-2-yl]ethanol but using trans[4-(6-benzenesulfonyl-6H-1,2,3,5,6-tetraaza-as-indacen-1-yl)-cyclohexyl]-morpholin-4-yl-methanone. LCMS (Method A, ESI): RT=2.13 min, m+H=354.16; $^{1}$H NMR (400 MHz, DMSO) δ: 11.83 (s; 1H); 8.57 (s; 1H); 8.24 (s; 1H); 7.46 (t; 1H); 6.79 (dd; 1H); 4.66-4.57 (m; 1H); 3.57-3.43 (m; 8H); 2.84-2.76 (m; 1H); 2.21 (d; 2H); 2.02 (m; 2H); 1.85-1.75 (m; 4H).

Example 167

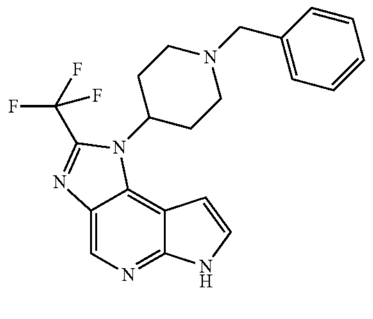 [SMILES: FC(F)(F)c1nc2cnc3[nH]ccc3c2n1C1CCN(Cc2ccccc2)CC1]

1-(1-Benzyl-piperidin-4-yl)-2-trifluoromethyl-1,6-dihydro-1,2,3,5,6-tetraaza-as-indacene N-[1-Benzenesulfonyl-4-(1-benzyl-piperidin-4-ylamino)-1H-pyrrolo[2,3-b]pyridine-5-yl]-2,2,2-trifluoro-acetamide 1-Benzenesulfonyl-N*4*-(1-benzyl-piperidin-4-yl)-1H-pyrrolo[2,3-b]pyridine-4,5-diamine (500 mg, 1.08 mmol) in TFA (5 mL) was heated to reflux for 5 hours. After cooling the mixture was concentrated under vacuum affording N-[1-benzenesulfonyl-4-(1-benzyl-piperidin-4-ylamino)-1H-pyrrolo[2,3-b]pyridine-5-yl]-2,2,2-trifluoro-acetamide as an orange residue which was used for the next step without further purification. LCMS (Method B, ESI): RT=2.68 min, m+H=558.35.

6-Benzenesulfonyl-1-(1-benzyl-piperidin-4-yl)-2-trifluoromethyl-1,6-dihydro-1,2,3,5,6-tetraaza-as-indacene A mixture of N-[1-benzenesulfonyl-4-(1-benzyl-piperidin-4-ylamino)-1H-pyrrolo[2,3-b]pyridine-5-yl]-2,2,2-trifluoro-acetamide (582 mg, 1.08 mmol) and p-toluenesulfonic acid monohydrate (catalytic) in toluene (10 ml) was heated to reflux for 1.5 hours. After cooling the mixture was concentrated under vacuum affording 6-benzenesulfonyl-1-(1-benzyl-piperidin-4-yl)-2-trifluoromethyl-1,6-dihydro-1,2,3,5,6-tetraaza-as-indacene as an orange residue which was used for the next step without further purification. LCMS (Method B, ESI): RT=2.87 min, m+H=540.28.

1-(1-Benzyl-piperidin-4-yl)-2-trifluoromethyl-1,6-dihydro-1,2,3,5,6-tetraaza-as-indacene 240 mg (56%) of the title compound was made by following the procedure described for the preparation of 2-[1-((R)-1-benzyl-piperidin-3-yl)-1,6-dihydro-1,2,3,5,6-tetraaza-as-indacen-2-yl]ethanol but using 6-benzenesulfonyl-1-(1-benzyl-piperidin-4-yl)-2-trifluoromethyl-1,6-dihydro-1,2,3,5,6-tetraaza-as-indacene. LCMS (Method A, ESI): RT=2.81 min, m+H=400.07; $^{1}$H NMR (400 MHz, DMSO) δ: 12.26 (s; 1H); 8.78 (s; 1H); 7.70 (t; 1H); 7.41 (m; 4H); 7.29 (t; 1H); 7.14 (s; 1H); 4.58 (m; 1H); 3.63 (s; 2H); 3.08 (d; 2H); 2.68 (m; 2H); 2.24 (t; 2H); 1.95-1.92 (m; 2H).

Example 168

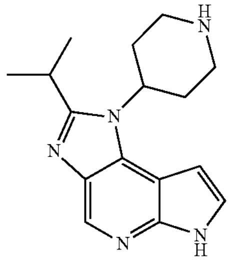 [SMILES: CC(C)c1nc2cnc3[nH]ccc3c2n1C1CCNCC1]

2-Isopropyl-1-piperidin-4-yl-1,6-dihydro-1,2,3,5,6-tetraaza-as-indacene 4-(1-Benzenesulfonyl-5-isobutyrylamino-1H-pyrrolo[2,3-b]pyridine-4-ylamino)-piperidine-1-carboxylic acid tert-butyl ester 4-(5-Amino-1-benzenesulfonyl 1H-pyrrolo[2,3-b]pyridine-4-ylamino)-piperidine-1-carboxylic acid tert-butyl ester (1.00 g, 2.12 mmol), isobutyryl chloride (225 mg, 2.12 mmol) and triethylamine (590 μL, 4.24 mmol) in DCM (15 mL) were stirred at ambient temperature for 2 hours. The mixture was diluted with DCM, washed with a saturated sodium hydrogen carbonate solution, water and brine, dried through a phase separator and concentrated under vacuum affording 4-(1-benzenesulfonyl-5-isobutyrylamino-1H-pyrrolo[2,3-b]pyridine-4-ylamino)-piperidine-1-carboxylic acid tert-butyl ester as a brown residue which was used for the next step without further purification. LCMS (Method B, ESI): RT=3.77 min, m+H=542.36.

4-(6-Benzenesulfonyl-2-isopropyl-6H-1,2,3,5,6-tetraaza-as-indacen-1-yl)-piperidine-1-carboxylic acid tert-butyl ester A mixture of 4-(1-benzenesulfonyl-5-isobutyrylamino-1H-pyrrolo[2,3-b]pyridine-4-ylamino)-piperidine-1-carboxylic acid tert-butyl ester (1.15 g, 2.12 mmol) and p-toluenesulfonic acid monohydrate (catalytic) in toluene (20 ml) was heated to reflux for 4 hours, then 120° C. for 36 hours and finally 130° C. After cooling the mixture was concentrated under vacuum. Purification by column chromatography on silica gel (gradient: 0 to 100% ethyl acetate in cyclohexane) afforded 130 mg (12%) of 4-(6-benzenesulfonyl-2-isopropyl-6H-1,2,3,5,6-tetraaza-as-indacen-1-yl)-piperidine-1-carboxylic acid tert-butyl ester.

4-(2-Isopropyl-6H-1,2,3,5,6-tetraaza-as-indacen-1-yl)-piperidine-1-carboxylic acid tert-butyl ester 80 mg (85%) of the title compound was made by following the procedure described for the preparation of 2-[1-((R)-1-benzyl-piperidin-3-yl)-1,6-dihydro-1,2,3,5,6-tetraaza-as-indacen-2-yl]ethanol but using 4-(6-benzenesulfonyl-2-isopropyl-6H-1,2,3,5,6-tetraaza-as-indacen-1-yl)-piperidine-1-carboxylic acid tert-butyl ester. LCMS (Method B, ESI) RT=2.71 min, m+H=384.4.

2-Isopropyl-1-piperidin-4-yl-1,6-dihydro-1,2,3,5,6-tetraaza-as-indacene 6.6 mg (12%) of the title compound was made by following the procedure described for the preparation of 1-azetidin-3-yl-1,6-dihydro-1,2,3,5,6-tetraaza-as-indacene but using 4-(2-isopropyl-6H-1,2,3,5,6-tetraaza-as-indacen-1-yl)-piperidine-1-carboxylic acid tert-butyl ester. Further purification by HPLC (gradient: 0 to 65% acetonitrile in water) affording 2-isopropyl-1-piperidin-4-yl-1,6-dihydro-1,2,3,5,6-tetraaza-as-indacene as a white solid. LCMS (Method A, ESI): RT=1.12 min, m+H=284.27; $^1$H NMR (400 MHz, DMSO) δ: 11.74 (s; 1H); 8.50 (s; 1H); 7.43 (t; 1H); 7.01 (s; 1H); 4.53 (m; 1H); 3.44 (br s; 1H); 3.17 (m; 3H); 2.73 (t; 2H); 2.54 (m; 2H); 1.75 (s; 2H); 1.35 (d; 6H).

Example 169

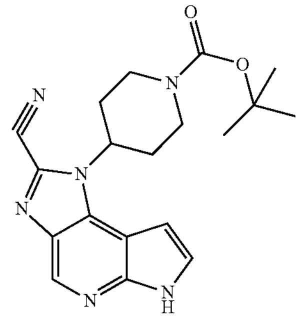 [SMILES: CC(C)(C)OC(=O)N1CCC(n2c(C#N)nc3cnc4[nH]ccc4c32)CC1]

4-(2-Cyano-6H-1,2,3,5,6-tetraaza-as-indacen-1-yl)-piperidine-1-carboxylic acid tert-butyl ester 4-(2-Acetoxymethyl-6-benzenesulfonyl-6H-1,2,3,5,6-tetraaza-as-indacen-1-yl)-piperidine-1-carboxylic acid tert-butyl ester A mixture of 4-(5-amino-1-benzenesulfonyl-1H-pyrrolo[2,3-b]pyridine-4-ylamino)-piperidine-1-carboxylic acid tert-butyl ester (1.50 g, 3.18 mmol) and triethylamine (660 μl, 4.77 mmol) in DCM (40 ml) was treated dropwise with acetoxyacetyl chloride (410 μl, 3.82 mmol) and stirred at ambient temperature for 1 hour. The mixture was washed with water and brine, dried with sodium sulphate and concentrated under vacuum. The residues were taken up in toluene (20 mL), treated with toluenesulfonic acid monohydrate (60 gm, 0.318 mmol) and heated at 100° C. for 3 hours, then further at 120° C. for 18 hours. After cooling the residue was partitioned between ethyl acetate and a saturated sodium hydrogen carbonate solution. The organic phase was washed with water and brine, dried with sodium sulfate and concentrated under vacuum. Purification by column chromatography on silica gel (gradient: 0 to 100% ethyl acetate in DCM) afforded 1.30 g (74%) of 4-(2-acetoxymethyl-6-benzenesulfonyl-6H-1,2,3,5,6-tetraaza-as-indacen-1-yl)-piperidine-1-carboxylic acid tert-butyl ester. LCMS (Method B, ESI): RT=3.97 min, m+H=554.37; $^1$H NMR (400 MHz, $CDCl_3$) δ: 8.91 (s, 1H), 8.22 (m, 2H), 7.80 (d, 1H), 7.60-7.53 (m, 1H), 7.51-7.44 (m, 2H), 6.73 (d, 1H), 5.43 (s, 2H), 4.61 (br m, 1H), 4.41 (br m, 2H), 2.92 (br m, 2H), 2.43 (br m, 2H), 2.12 (s, 3H), 1.88 (br m, 2H), 1.58 (s, 9H).

4-(6-Benzenesulfonyl-2-hydroxymethyl-6H-1,2,3,5,6-tetraaza-as-indacen-1-yl)-piperidine-1-carboxylic acid tert-butyl ester 1.08 g (91%) of the title compound was made by following the procedure described for the preparation of [6-benzenesulfonyl-1-(1-benzyl-piperidin-4-yl)-1,6-dihydro-1,2,3,5,6-tetraaza-as-indacen-2-yl]methanol but using 4-(2-Acetoxymethyl-6-benzenesulfonyl-6H-1,2,3,5,6-tetraaza-as-indacen-1-yl)-piperidine-1-carboxylic acid tert-butyl ester. LCMS (Method B, ESI): RT=3.55 min, m+H=512.31; $^1$H NMR (400 MHz, DMSO) δ: 8.70 (s, 1H), 8.15 (m, 2H), 7.95 (d, 1H), 7.70 (m, 1H), 7.61 (m, 2H), 6.74 (br m, 1H), 5.76 (t, 1H), 4.95 (br m, 1H), 4.81 (d, 2H), 4.16 (br m, 2H), 3.00 (br m, 2H), 2.18 (m, 2H), 1.93 (m, 2H), 1.52 (s, 9H).

4-(6-Benzenesulfonyl-2-formyl-6H-1,2,3,5,6-tetraaza-as-indacen-1-yl)-piperidine-1-carboxylic acid tert-butyl ester 558 mg (52%) of the title compound was made by following the procedure described for the preparation of [6-benzenesulfonyl-1-(1-benzyl-piperidin-4-yl)-1,6-dihydro-1,2,3,5,6-tetraaza-as-indacene-2-carbaldehyde but using 4-(6-benzenesulfonyl-2-hydroxymethyl-6H-1,2,3,5,6-tetraaza-as-indacen-1-yl)-piperidine-1-carboxylic acid tert-butyl ester. $^1$H NMR (400 MHz, $CDCl_3$) δ: 10.08 (s, 1H), 9.05 (s, 1H), 8.25 (dd, 2H), 7.85 (d, 1H), 7.59 (m, 1H), 7.52 (m, 2H), 6.81 (d, 1H), 5.91 (br m, 1H), 4.38 (br m, 2H), 2.96 (br m, 2H), 2.44 (br m, 2H), 1.90 (br m, 2H), 1.58 (s, 9H).

4-(6-Benzenesulfonyl-2-(hydroxyimino-methyl)-6H-1,2,3,5,6-tetraaza-as-indacen-1-yl)-piperidine-1-carboxylic acid tert-butyl ester 410 mg (72%) of the title compound was made by following the procedure described for the preparation of 6-benzenesulfonyl-1-(1-benzyl-piperidin-4-yl)-1,6-dihydro-1,2,3,5,6-tetraaza-as-indacene-2-carbaldehyde oxime but using 4-(6-benzenesulfonyl-2-formyl-6H-1,2,3,5,6-tetraaza-as-indacen-1-yl)-piperidine-1-carboxylic acid tert-butyl ester. LCMS (Method B, ESI): RT=3.82 min, m+H=525.26; $^1$H NMR (400 MHz, DMSO) δ: 12.24 (s; 1H); 8.79 (s; 1H); 8.43 (s; 1H); 8.17 (dd; 2H); 7.98 (d; 1H); 7.73-7.68 (m; 1H); 7.63 (m; 2H); 6.77 (br s, 1H); 5.50 (m; 1H); 4.22-4.13 (m; 2H); 2.94 (m; 2H); 2.20 (m; 1H); 1.97-1.89 (m; 3H); 1.52 (s; 9H).

4-(6-Benzenesulfonyl-2-cyano-6H-1,2,3,5,6-tetraaza-as-indacen-1-yl)-piperidine-1-carboxylic acid tert-butyl ester A solution of 4-(6-benzenesulfonyl-2-(hydroxyimino-methyl)-6H-1,2,3,5,6-tetraaza-as-indacen-1-yl)-piperidine-1-carboxylic acid tert-butyl ester (400 mg, 0.76 mmol), TFAA (169 μL, 1.22 mmol) and triethylamine (315 μL, 2.28 mmol) were heated at reflux for 1 hour. Ethyl acetate was added to the cooled reaction, the organics were washed with sodium hydrogen carbonate (sat. aq.), water and brine, dried with sodium sulfate and concentrated under vacuum. Purification by column chromatography on silica gel (gradient: 0 to 50% ethyl acetate in cyclohexane) afforded 332 mg (86%) of 4-(6-benzenesulfonyl-2-cyano-6H-1,2,3,5,6-tetraaza-as-indacen-1-yl)-piperidine-1-carboxylic acid tert-butyl ester as a yellow solid. LCMS (Method B, ESI): RT=4.05 min, m+H=507.20; $^1$H NMR (400 MHz, DMSO) δ: 8.93 (s; 1H); 8.15 (m; 3H); 7.73-7.68 (m; 1H); 7.65-7.60 (m; 2H); 7.29 (m; 1H); 5.06 (m; 1H); 4.17-4.08 (m; 2H); 3.14 (br s; 2H); 2.15 (m; 4H); 1.47 (s; 9H).

4-(2-Cyano-6H-1,2,3,5,6-tetraaza-as-indacen-1-yl)-piperidine-1-carboxylic acid tert-butyl ester tetra-Butyl ammonium fluoride (1M, 296 μL, 0.30 mmol) was added to a solution of 4-(6-benzenesulfonyl-2-cyano-6H-1,2,3,5,6-tetraaza-as-indacen-1-yl)-piperidine-1-carboxylic acid tert-butyl ester in THF (2 mL) in sealed tube and heated to reflux for 1 hour. Ethyl acetate was added to the cooled reaction, the organics were washed with water and brine, dried with sodium sulfate and concentrated under vacuum. Purification by column chromatography on silica gel (gradient: 0 to 100% ethyl acetate in cyclohexane) afforded 24 mg (66%) of 4-(2-cyano-6H-1,2,3,5,6-tetraaza-as-indacen-1-yl)-piperidine-1-carboxylic acid tert-butyl ester as a white solid. LCMS (Method A, ESI): RT=4.31 min, m+H=367.21; $^1$H NMR (400 MHz, DMSO) δ: 12.32 (s; 1H); 8.76 (s; 1H); 7.59 (t; 1H); 6.77 (s; 1H); 5.08-4.97 (m; 1H); 4.16 (s; 2H); 3.14 (s; 2H); 2.35-2.21 (m; 2H); 2.13 (d; 2H); 1.49 (s; 9H).

Example 170

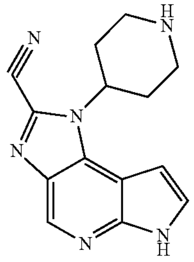 [SMILES: N#Cc1nc2cnc3[nH]ccc3c2n1C1CCNCC1]

1-Piperidin-4-yl-1,6-dihydro-1,2,3,5,6-tetraaza-as-indacene-2-carbonitrile 48 mg (37%) of the title compound was made by following the procedure described for the preparation of 1-azetidin-3-yl-1,6-dihydro-1,2,3,5,6-tetraaza-as-indacene but using 4-(2-cyano-6H-1,2,3,5,6-tetraaza-as-indacen-1-yl)-piperidine-1-carboxylic acid tert-butyl ester. LCMS (Method A, ESI): RT=1.67 min, m+H=267.21; $^1$H NMR (400 MHz, DMSO) δ: 12.23 (s; 1H); 8.70 (s; 1H); 7.57 (s; 1H); 7.00 (d; 1H); 4.77-4.67 (m; 1H); 3.13 (d; 2H); 2.71 (t; 2H); 2.28 (m; 2H); 1.98 (d; 2H).

Example 171

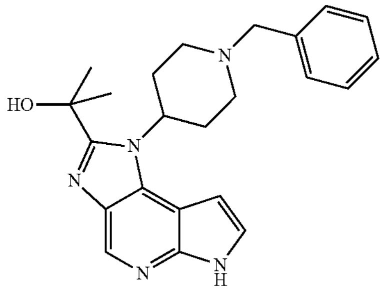 [SMILES: CC(C)(O)c1nc2cnc3[nH]ccc3c2n1C1CCN(Cc2ccccc2)CC1]

2-[1-(1-Benzyl-piperidin-4-yl)-1,6-dihydro-1,2,3,5,6-tetraaza-as-indacen-2-yl]-propan-2-ol 2-[6-Benzenesulfonyl-1-(1-benzyl-piperidin-4-yl)-1,6-dihydro-1,2,3,5,6-tetraaza-as-indacen-2-yl]-propan-2-ol Methyl magnesium bromide (3.0 M, 340 μL, 1.02 mmol) was slowly added to a solution of 6-benzenesulfonyl-1-(1-benzyl-piperidin-4-yl)-1,6-dihydro-1,2,3,5,6-tetraaza-as-indacene-2-carbaldehyde (403 mg, 0.78 mmol) in THF (5 ml), under argon, was stirred at ambient temperature for 18 hours. The reaction was partitioned between water and ethyl acetate. The organics were washed with water and brine, dried with sodium sulfate and concentrated under vacuum. Purification by column chromatography on silica gel (gradient: 0 to 100% ethyl acetate in DCM) afforded 307 mg (74%) 2-[6-benzenesulfonyl-1-(1-benzyl-piperidin-4-yl)-1,6-dihydro-1,2,3,5,6-tetraaza-as-indacen-2-yl]-propan-2-ol as a white solid. LCMS (Method A, ESI): RT=2.54 min, m+H=530.33; $^1$H NMR (400 MHz, $CDCl_3$) δ: 8.86 (s, 1H), 8.22 (d, 2H), 7.87 (d, 1H), 7.47 (m, 9H), 5.28-5.17 (m, 1H), 3.61 (s, 2H), 3.17-3.07 (m, 2H), 2.71-2.59 (m, 3H), 2.22-2.16 (m, 2H), 1.92-1.83 (m, 2H), 1.80 (s, 6H).

2-[1-(1-Benzyl-piperidin-4-yl)-1,6-dihydro-1,2,3,5,6-tetraaza-as-indacen-2-yl]-propan-2-ol 158 mg (72%) of the title compound was made by following the procedure described for the preparation of 2-[1-((R)-1-benzyl-piperidin-3-yl)-1,6-dihydro-1,2,3,5,6-tetraaza-as-indacen-2-yl]ethanol but using 2-[6-benzenesulfonyl-1-(1-benzyl-piperidin-4-yl)-1,6-dihydro-1,2,3,5,6-tetraaza-as-indacen-2-yl]-propan-2-ol. LCMS (Method A, ESI): RT=2.16 min, m+H=390.31; $^1$H NMR (400 MHz, DMSO) δ: 11.82 (s, 1H), 8.53 (s, 1H), 7.54 (t, 1H), 7.41 (m, 4H), 7.29 (m, 1H), 7.11 (s, 1H), 5.47 (s, 1H), 5.31 (m, 1H), 3.62 (s, 2H), 3.08 (d, 2H), 2.67 (m, 2H), 2.16 (t, 2H), 1.87 (m, 2H), 1.67 (s, 6H).

Example 172

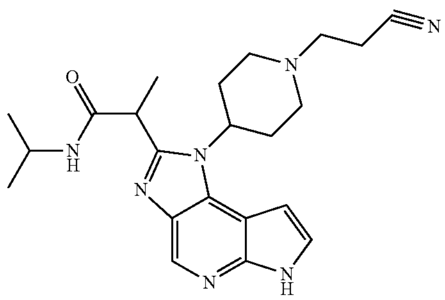 [SMILES: CC(C)NC(=O)C(C)c1nc2cnc3[nH]ccc3c2n1C1CCN(CCC#N)CC1]

Racemic 2-{1-[1-(2-Cyano-ethyl)-piperidin-4-yl]-1,6-dihydro-1,2,3,5,6-tetraaza-as-indacene-2-yl}-N-isopropyl-propionamide 4-(1-Benzenesulfonyl-5-nitro-1H-pyrrolo[2,3-b]pyridine-4-ylamino)-piperidine-1-carboxylic acid benzyl ester 21.3 g (100%) of the title compound was made by following the procedure described for the preparation of (1-benzenesulfonyl-5-nitro-1H-pyrrolo[2,3-b]pyridin-4-yl)-(1-benzyl-piperidin-4-yl)amine. $^1$H NMR (400 MHz, $CDCl_3$) δ: 9.11 (s, 2H), 8.19 (m, 2H), 7.62 (m, 2H), 7.54-7.49 (m, 2H), 7.35 (m, 4H), 6.68 (d, 1H), 5.15 (s, 2H), 4.20-4.04 (m, 2H), 3.20 (t, 2H), 2.17-2.07 (m, 3H), 1.62 (m, 3H).

4-(5-Amino-1-benzenesulfonyl-1H-pyrrolo[2,3-b]pyridine-4-ylamino)-piperidine-1-carboxylic acid benzyl ester Zinc (24 g) was added to a solution of 4-(1-benzenesulfonyl-5-nitro-1H-pyrrolo[2,3-b]pyridine-4-ylamino)-piperidine-1-carboxylic acid benzyl ester (21.3 g, 40 mmol) in acetic acid (150 mL) and heated to 60° C. for 30 minutes. After cooling the mixture was filtered and the filtrate concentrated to dryness under vacuum. The resulting residue was partitioned between ethyl acetate and sodium hydrogen carbonate (sat. aq.), the organics layer dried with sodium sulphate and concentrated under vacuum. Purification by column chromatography on silica gel (gradient: 100% ethyl acetate) afforded 14.7 g (75%) of 4-(5-amino-1-benzenesulfonyl-1H-pyrrolo[2,3-b]pyridine-4-ylamino)-piperidine-1-carboxylic acid benzyl ester as a purple residue. $^1$H NMR (400 MHz, $CDCl_3$) δ: 8.16-8.11 (m, 2H), 7.87 (s, 1H), 7.58-7.41 (m, 4H), 7.35 (m, 5H), 6.52 (d, 1H), 5.13 (s, 2H), 4.89 (br s, 1H), 4.11 (m, 2H), 3.95-3.84 (m, 1H), 3.10-2.96 (m, 2H), 2.10-2.05 (m, 1H), 1.54-1.40 (m, 2H).

4-(6-Benzenesulfonyl-2-ethoxycarbonylmethyl-6H-1,2,3,5,6-tetraaza-as-indacen-1-yl)-piperidine-1-carboxylic acid benzyl ester Ethoxycarbonimidoyl-acetic acid ethyl ester hydrochloride salt (16.8 g) was added to a solution of 4-(5-amino-1-benzenesulfonyl-1H-pyrrolo[2,3-b]pyridine-4-ylamino)-piperidine-1-carboxylic acid benzyl ester (14.5 g) in ethanol (100 mL) and heated to reflux for 18 hours. After cooling the mixture concentrated to dryness under vacuum, the residue partitioned between ethyl acetate and sodium hydrogen carbonate (sat. aq.), the organics layer dried with sodium sulphate and concentrated under vacuum. Purification by column chromatography on silica gel (gradient: 5 to 15% acetone in DCM) afforded 14.29 g (85%) of 4-(6-benzenesulfonyl-2-ethoxycarbonylmethyl-6H-1,2,3,5,6-tetraaza-as-indacen-1-yl)-piperidine-1-carboxylic acid benzyl ester as a yellow residue. $^1$H NMR (400 MHz, $CDCl_3$) δ: 8.85 (s, 1H), 8.21 (m, 2H), 7.68 (d, 1H), 7.55 (m, 1H), 7.50-7.40 (m, 7H), 6.60 (d, 1H), 5.26 (br m, 2H), 4.50 (br m, 3H), 4.19 (q, 2H), 4.11 (s, 2H), 2.98 (s, 2H), 2.44 (s, 2H), 1.98 (s, 2H), 1.27 (t, 3H).

Racemic 4-[6-Benzenesulfonyl-2-(1-ethoxycarbonyl-ethyl)-6H-1,2,3,5,6-tetraaza-as-indacen-1-yl]-piperidine-1-carboxylic acid benzyl ester n-Butyl lithium (2.5M, 0.33 mL, 0.83 mmol) was added to a solution of diisopropylamine (117 μL, 0.83 mmol) in THF (15 mL) at −78° C. and stirred for 10 minutes before warming to 0° C. for minutes. The reaction was re-cooled to −78° C. and 4-(6-benzenesulfonyl-2-ethoxycarbonylmethyl-6H-1,2,3,5,6-tetraaza-as-indacen-1-yl)-piperidine-1-carboxylic acid benzyl ester (500 mg, 0.83 mmol) added, stirred for 20 minutes then warmed to 0° C. for a further 30 minutes. Methyl iodide (51.9 μL, 0.83 mL) was added at 0° C. before warming to ambient temperature for 18 hours. The reaction was partitioned between ammonium chloride (sat. aq.) and ethyl acetate, the organics separated, washed with sodium hydrogen carbonate (sat. aq.) and brine, dried with sodium sulphate and concentrated under vacuum. Purification by column chromatography on silica gel (gradient: 0 to 50% ethyl acetate in DCM) afforded 405 mg (79%) of racemic 4-[6-benzenesulfonyl-2-(1-ethoxycarbonyl-ethyl)-6H-1,2,3,5,6-tetraaza-as-indacen-1-yl]-piperidine-1-carboxylic acid benzyl ester. LCMS (Method B, ESI): RT=4.06 min, m+H=616.30; $^1$H NMR (400 MHz, $CDCl_3$) δ: 8.90 (s, 1H), 8.20 (m, 2H), 7.66 (d, 1H), 7.55 (m, 1H), 7.44 (m, 7H), 6.58 (m, 1H), 5.26 (br m, 2H), 4.51 (br m, 3H), 4.18 (m, 3H), 2.97 (m, 2H), 2.47 (m, 2H), 1.89 (m, 2H), 1.78 (d, 3H), 1.20 (t, 3H).

Racemic Lithium, 2-[6-Benzenesulfonyl-1-(1-benzyloxycarbonyl-piperidin-4-yl)-1,6-dihydro-1,2,3,5,6-tetraaza-as-indacen-2-yl]-propionic acid The title compound was made by following the procedure described for the preparation of lithium, [6-benzenesulfonyl- 1-(1-benzyl-piperidin-4-yl)-1,6-dihydro-1,2,3,5,6-tetraaza-as-indacen-2-yl]acetate but using racemic 4-[6-benzene-sulfonyl-2-(1-ethoxycarbonyl-ethyl)-6H-1,2,3,5,6-tetraaza-as-indacen-1-yl]-piperidine-1-carboxylic acid benzyl ester. The residue was used for the next step without further purification or analysis.

Racemic 4-[Benzenesulfonyl-2-(1-isopropylcarbamoyl-ethyl)-6H-1,2,3,5,6-tetraaza-as-indacen-1-yl]-piperidine-1-carboxylic acid benzyl ester 204 mg (62%) of the title compound was made by following the procedure described for the preparation of 2-[6-benzene-sulfonyl-1-(1-benzyl-piperidin-4-yl)-1,6-dihydro-1,2,3,5,6-tetraaza-as-indacen-2-yl]-1-morpholin-4-yl-ethanone but using racemic lithium, 2-[6-benzenesulfonyl-1-(1-benzyloxycarbonyl-piperidin-4-yl)-1,6-dihydro-1,2,3,5,6-tetraaza-as-indacen-2-yl]-propionic acid and isopropylamine. LCMS (Method B, ESI): RT=3.75 min, m+H=629.41; $^1$H NMR (400 MHz, DMSO) δ: 8.70 (s, 1H), 8.11 (m, 3H), 7.87 (m, 1H), 7.70 (m, 1H), 7.62 (m, 2H), 7.45 (m, 5H), 6.55 (m, 1H), 5.23 (br s, 2H), 4.72 (m, 1H), 4.26 (m, 2H), 4.16 (m, 1H), 3.80 (m, 1H), 3.10-2.98 (br m, 2H), 2.17 (m, 2H), 1.93 (m, 1H), 1.78 (m, 1H), 1.58 (d, 3H), 1.05 (m, 6H).

Racemic 4-[2-(1-isopropylcarbamoyl-ethyl)-6H-1,2,3,5,6-tetraaza-as-indacen-1-yl]-piperidine-1-carboxylic acid benzyl ester 96 mg (63%) of the title compound was made by following the procedure described for the preparation of 2-[1-((R)-1-benzyl-piperidin-3-yl)-1,6-dihydro-1,2,3,5,6-tetraaza-as-indacen-2-yl]ethanol but using racemic 4-[benzenesulfonyl-2-(1-isopropylcarbamoyl-ethyl)-6H-1,2,3,5,6-tetraaza-as-indacen-1-yl]-piperidine-1-carboxylic acid benzyl ester. LCMS (Method A, ESI): RT=3.54 min, m+H=489.23; $^1$H NMR (400 MHz, DMSO) δ: 11.80 (m, 1H), 8.51 (s, 1H), 8.10 (d, 1H), 7.34 (m, 6H), 6.28 (br m, 1H), 5.16 (br s, 2H), 4.66 (m, 1H), 4.24 (m, 2H), 4.10 (m, 1H), 3.78 (m, 1H), 3.09-2.85 (br m, 2H), 2.32 (br m, 2H), 1.85 (m, 1H), 1.72 (m, 1H), 1.56 (d, 3H), 1.03 (d, 6H).

Racemic N-Isopropyl-2-(1-piperidin-4-yl-1,6-dihydro-1,2,3,5,6-tetraaza-as-indacen-2-yl)-propionamide 4-[2-(1-Isopropylcarbamoyl-ethyl)-6H-1,2,3,5,6-tetraaza-as-indacen-1-yl]-piperidine-1-carboxylic acid benzyl ester (85 mg, 0.17 mmol) in water (0.15 ml) was treated with TFA (1.5 ml) at 65° C. for 3 hours. The solvent was removed under vacuum and the residue purified using an Isolute® SCX-2 column (gradient: methanol to 2M $NH_3$ in methanol) affording 54 mg (87%) of racemic N-isopropyl-2-(1-piperidin-4-yl-1,6-dihydro-1,2,3,5,6-tetraaza-as-indacen-2-yl)-propionamide as a beige solid. LCMS (Method B, ESI): RT=0.52 min, m+H=355.26; $^1$H NMR (400 MHz, DMSO) δ: 11.78 (s br, 1H), 8.54 (s, 1H), 8.19 (d, 1H), 7.45 (t, 1H), 7.00 (s br, 1H), 4.45 (m, 1H), 4.10 (q, 1H), 3.84 (m, 1H), 3.18 (m, 2H), 2.67 (t, 1H), 2.58 (t, 1H), 2.44-2.38 (m, 2H), 1.76 (m, 1H), 1.60 (m, 1H) 1.62 (d, 3H), 1.11 (dd, 6H).

Racemic 2-{1-[1-(2-Cyano-ethyl)-piperidin-4-yl]-1,6-dihydro-1,2,3,5,6-tetraaza-as-indacen-2-yl}-N-isopropyl-propionamide A solution of racemic N-isopropyl-2-(1-piperidin-4-yl-1,6-dihydro-1,2,3,5,6-tetraaza-as-indacen-2-yl)-propionamide (50 mg, 0.14 mmol), acrylonitrile (37.4 mg, 0.71 mmol) and ethanol (1.5 mL) was heated to 80° C. for 3 hours. After cooling the mixture was concentrated under vacuum and the residues purified by column chromatography on silica gel (gradient: 0 to 20% (2M $NH_3$ in MeOH) in DCM) then further purified by HPLC (gradient: 5 to 50% acetonitrile in water with 0.1% ammonium hydroxide) afforded 7.6 mg (13%) of racemic 2-{1-[1-(2-cyano-ethyl)-piperidin-4-yl]-1,6-dihydro-1,2,3,5,6-tetraaza-as-indacen-2-yl}-N-isopropyl-propionamide as a white solid. LCMS (Method A, ESI): RT=1.92 min, m+H=408.33; $^1$H NMR (400 MHz, DMSO) δ: 11.79 (s br, 1H), 8.55 (s, 1H), 8.17 (d, 1H), 7.39 (t, 1H), 6.98 (s br, 1H), 4.45 (m, 1H), 4.11 (m, 1H), 3.84 (m, 1H), 3.15 (d, 2H), 2.78 (t, 2H), 2.69 (t, 2H), 2.57 (m, 2H), 2.22 (t, 1H), 2.16 (t, 1H), 1.87 (d, 1H), 1.73 (d, 1H), 1.62 (d, 3H), 1.11 (dd, 6H).

Example 173

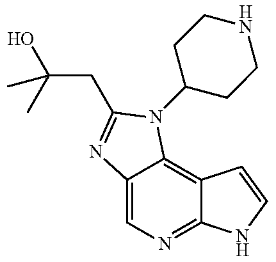 [SMILES: CC(C)(O)Cc1nc2cnc3[nH]ccc3c2n1C1CCNCC1]

2-Methyl-1-(1-piperidin-4-yl-1,6-dihydro-1,2,3,5,6-tetraaza-as-indacen-2-yl)-propan-2-ol 3-Hydroxy-3-methyl-butyrimidic acid ethyl ester HCl (g) was bubbled through a solution of 3-hydroxy-3-methylbutyronitrile (5.0 g, 50.4 mmol) in diethyl ether (20 mL) and IMS (3.48 g, 75.6 mmol) at 0° C. for 30 minutes before leaving to stand at −5° C. over night. The solution was concentrated under vacuum affording 6.48 g (72%) of 3-hydroxy-3-methyl-butyrimidic acid ethyl ester. $^1$H NMR (400 MHz, $CDCl_3$) δ: 11.36 (m br, 1H), 4.66 (q, 2H), 2.89 (s, 2H), 1.51 (t, 3H), 1.36 (s, 6H).

4,4,4-Triethoxy-2-methyl-butan-2-ol

A solution of 3-hydroxy-3-methyl-butyrimidic acid ethyl ester (4.40 g) in ethanol (50 mL) was left to stand for 72 hours. The mixture was filtered and the filtrate concentrated to dryness under vacuum affording 4,4,4-triethoxy-2-methyl-butan-2-ol which was used for the next step without further purification or analysis.

4-[6-Benzenesulfonyl-2-(2-hydroxy-2-methyl-propyl)-6H-1,2,3,5,6-tetraaza-as-indacen-1-yl]-piperidine-1-carboxylic acid tert-butyl ester A mixture of 4-(5-amino-1-benzenesulfonyl-1H-pyrrolo[2,3-b]pyridine-4-ylamino)-piperidine-1-carboxylic acid tert-butyl ester (300 mg, 0.64 mmol), 4,4,4-triethoxy-2-methyl-butan-2-ol (423 mg, 1.92 mmol) and p-toluenesulfonic acid monohydrate (catalytic) in toluene (10 ml) was heated to reflux for 6 hours before further addition of 4,4,4-triethoxy-2-methyl-butan-2-ol (1 eq) and refluxing for 1 hour. After cooling ethyl acetate was added, the organics washed with water and brine, dried with sodium sulfate and concentrated under vacuum. Purification by column chromatography on silica gel (gradient: 5% (2M $NH_3$ in MeOH) in toluene) affording 4-[6-benzenesulfonyl-2-(2-hydroxy-2-methyl-propyl)-6H-1,2,3,5,6-tetraaza-as-indacen-1-yl]-piperidine-1-carboxylic acid tert-butyl ester which was used for the next step without further purification. LCMS (Method B, ESI): RT=3.61 min, m+H=554.45; $^1$H NMR (400 MHz, $CDCl_3$) δ: 8.86 (s, 1H), 8.22 (m, 2H), 7.79 (d, 1H), 7.56 (m, 1H), 7.48 (m, 2H), 6.73 (d, 1H), 4.62 (m, 1H), 4.39 (br m, 2H), 3.11 (s, 2H), 2.92 (br m, 2H), 2.44 (br m, 2H), 1.86 (br m, 2H), 1.58 (s, 9H), 1.39 (s, 6H).

4-[2-(2-Hydroxy-2-methyl-propyl)-6H-1,2,3,5,6-tetraaza-as-indacen-1-yl]-piperidine-1-carboxylic acid tert-butyl ester 150 mg (20%) of the title compound was made by following the procedure described for the preparation of 4-(2-cyano-6H-1,2,3,5,6-tetraaza-as-indacen-1-yl)-piperidine-1-carboxylic acid tert-butyl ester but using 4-[6-benzenesulfonyl-2-(2-hydroxy-2-methyl-propyl)-6H-1,2,3,5,6-tetraaza-as-indacen-1-yl]-piperidine-1-carboxylic acid tert-butyl ester. LCMS (Method B, ESI): RT=2.50 min, m+H=414.38; $^1$H NMR (400 MHz, DMSO) δ: 11.84 (s, 1H), 8.53 (s, 1H), 7.38 (t, 1H), 6.41 (s, 1H), 4.96 (m, 1H), 4.87 (s br, 1H), 4.17 (m, 2H), 3.10 (s, 2H), 2.98 (m, 2H), 2.38 (m, 2H), 1.88 (m, 2H), 1.52 (s, 9H), 1.26 (s, 6H).

2-Methyl-1-(1-piperidin-4-yl-1,6-dihydro-1,2,3,5,6-tetraaza-as-indacen-2-yl)-propan-2-ol 4-[2-(2-Hydroxy-2-methyl-propyl)-6H-1,2,3,5,6-tetraaza-as-indacen-1-yl]-piperidine-1-carboxylic acid tert-butyl ester (120 mg, 0.29 mmol) in DCM (5 ml) was treated with TFA (3 ml) at ambient temperature for 1 hour. The solvent was evaporated under vacuum and the residues purified by column chromatography on silica gel (gradient: 0 to 15% (2M $NH_3$ in MeOH) in toluene) affording 48 mg (53%) of 2-methyl-1-(1-piperidin-4-yl-1,6-dihydro-1,2,3,5,6-tetraaza-as-indacen-2-yl)-propan-2-ol as a beige solid. LCMS (Method A, ESI): RT=1.22 min, m+H=314.26; $^1$H NMR (400 MHz, DMSO) δ: 11.86 (s, 1H), 8.53 (s, 1H), 7.51 (t, 1H), 7.13 (dd, 1H), 4.98 (m br, 1H), 4.86 (m, 1H), 3.56 (d, 2H), 3.28-3.15 (m, 2H), 3.14 (s, 2H), 2.63-2.59 (m, 2H), 2.08 (d, 2H), 1.26 (s, 6H).

Example 174

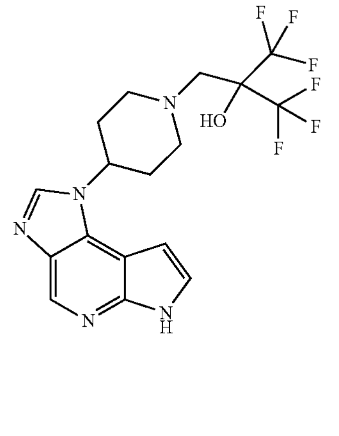 [SMILES: OC(CN1CCC(n2cnc3cnc4[nH]ccc4c32)CC1)(C(F)(F)F)C(F)(F)F]

1,1,1,3,3,3-Hexafluoro-2-[4-(6H-1,2,3,5,6-tetraaza-as-indacen-1-yl)-piperidin-1-ylmethyl]-propan-2-ol A 5 ml microwave vial was charged with 1-piperidin-4-yl-1,6-dihydro-1,2,3,5,6-tetraaza-as-indacene (95 mg, 0.39 mmol), 3,3,3-trifluoro-2-(trifluoromethyl)-1,2-propenoxide (88 mg, 0.49 mmol) and potassium carbonate (108 mg, 0.78 mmol) in DMF (2 mL). The mixture was heated in a microwave reactor at 150° C. for 1 hour. The solvent was removed under vacuum and the isolated residue purified by column chromatography on silica gel (gradient: 0 to 20% (2M $NH_3$ in MeOH) in DCM) then further purified by HPLC (gradient: 5 to 75% acetonitrile in water with 0.1% ammonium hydroxide) affording 22 mg (13%) of 1,1,1,3,3,3-hexafluoro-2-[4-(6H-1,2,3,5,6-tetraaza-as-indacen-1-yl)-piperidin-1-ylmethyl]-propan-2-ol as a beige solid. LCMS (Method A, ESI): RT=3.57 min, m+H=422.16; $^1$H NMR (400 MHz, DMSO) δ: 11.85 (s, 1H), 8.58 (s, 1H), 8.29 (s, 1H), 7.66 (s, 1H), 7.48 (t, 1H), 6.77 (dd, 1H), 4.60 (m, 1H), 3.08 (d, 2H), 3.02 (s, 2H), 2.71 (t, 2H), 2.24 (m, 2H), 2.06 (m, 2H).

Example 175

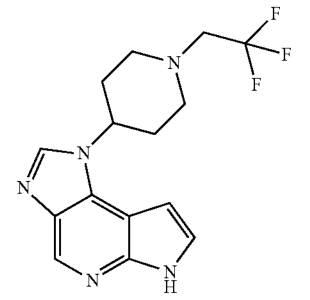 [SMILES: FC(F)(F)CN1CCC(n2cnc3cnc4[nH]ccc4c32)CC1]

1-[1-(2,2,2-Trifluoro-ethyl)-piperidin-4-yl]-1,6-dihydro-1,2,3,5,6-tetraaza-as-indacene 2,2,2-Trifluoroethyl trifluoromethane sulfonate (113 μL, 0.784 mmol) was added to a stirred suspension of 1-piperidin-4-yl-1,6-dihydro-1,2,3,5,6-tetraaza-as-indacene (94.6 mg, 392 μmol) and triethylamine (218 μL, 1.57 mmol) in DCM (2 mL) at ambient temperature. After 18 hours, LCMS indicated no reaction, DMF (2 mL) was added and the solution was stirred at ambient temperature for 4 hours. The mixture was concentrated under vacuum and the residue purified by column chromatography on silica gel (gradient: 0 to 10% (2M $NH_3$ in MeOH) in DCM) to give 58 mg (46%) of 1-[1-(2,2,2-trifluoro-ethyl)-piperidin-4-yl]-1,6-dihydro-1,2,3,5,6-tetraaza-as-indacene as a pale yellow solid. LCMS (Method A, ESI): RT=2.74 min, m+H=324.21; $^1$H NMR (400 MHz, DMSO) δ: 11.85 (s, 1H), 8.58 (s, 1H), 8.33 (s, 1H), 7.48 (t, 1H), 6.77 (dd, 1H), 4.61 (m, 1H), 3.30 (m, 2H), 3.12 (d, 2H), 2.75 (t, 2H), 2.20 (m, 2H), 2.15-2.05 (m, 2H).

Example 176

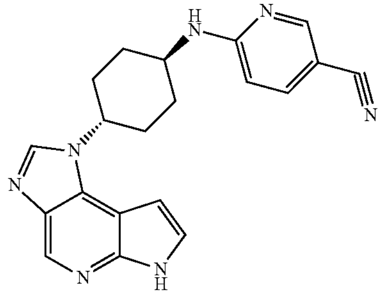 [SMILES: N#Cc1ccc(N[C@H]2CC[C@H](n3cnc4cnc5[nH]ccc5c43)CC2)nc1]

Trans 6-[4-(6H-1,2,3,5,6-Tetraaza-as-indacen-1-yl)-cyclohexylamino]-nicotinonitrile 7 mg (12%) of the title compound was made by following the procedure described for the preparation of (R)-1-(3,4,5,6-tetrahydro-2H-[1,4]bipyridinyl-3-yl)-1,6-dihydro-1,2,3,5,6-tetraaza-as-indacene but using trans 4-(6H-1,2,3,5,6-tetraaza-as-indacen-1-yl)-cyclohexylamine and 2-chloro-4-cyanopyridine. Further purification by HPLC (gradient: 5-65% acetonitrile in water with 0.1% ammonium hydroxide) affording trans 6-[4-(6H-1,2,3,5,6-tetraaza-as-indacen-1-yl)-cyclohexylamino]-nicotinonitrile. LCMS (Method A, ESI): RT=2.56 min, m+H=358.20; $^1$H NMR (400 MHz, DMSO) δ: 11.80 (m; 1H); 8.53 (s; 1H); 8.38 (d; 1H); 8.27 (s; 1H); 7.62 (m; 2H); 7.44 (t; 1H); 6.73 (m; 1H); 6.55 (d; 1H); 4.64-4.57 (m; 1H); 3.95 (br s; 1H); 2.11 (m; 6H); 1.58-1.49 (m; 2H).

Example 177

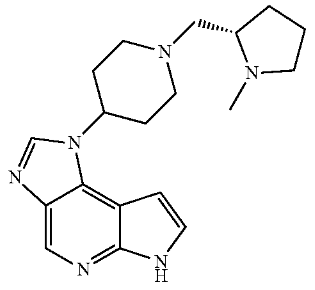 [SMILES: CN1CCC[C@H]1CN1CCC(n2cnc3cnc4[nH]ccc4c32)CC1]

1-[1-((S)-1-Methyl-pyrrolidin-2-ylmethyl)-piperidin-4-yl]-1,6-dihydro-1,2,3,5,6-tetraaza-as-indacene A mixture of 1-piperidin-4-yl-1,6-dihydro-1,2,3,5,6-tetraaza-as-indacene (100 mg, 0.41 mmol), (S)-2-chloromethyl-1-methyl-pyrrolidine hydrochloride (72 mg, 0.41 mmol), triethylamine (143 μL, 1.03 mmol) and sodium iodide (12 mg, 0.08 mmol) in MeCN (2 mL) and DMF (1 mL) was heated to 100° C. for 1.5 hours. Potassium carbonate (141 mg, 1.03 mmol) was added and the mixture heated at 100° C. for 16 hours. 1M aqueous HCl (2.2 mL) was added and the mixture concentrated under vacuum. The resulting residue was partitioned between water and DCM, the organic layer dried over sodium sulfate and concentrated under vacuum. The resulting residue was purified by column chromatography on silica gel (gradient: 0 to 10% methanol in DCM to DMAW 90). The residue was further purified by Isolute® SCX-2 column (gradient: methanol to 2M $NH_3$ in methanol) to afford 46 mg (33%) of 1-[1-((S)-1-methyl-pyrrolidin-2-ylmethyl)-piperidin-4-yl]-1,6-dihydro-1,2,3,5,6-tetraaza-as-indacene. LCMS (Method A, ESI): RT=1.24 min, m+H=339.3; $^1$H NMR (400 MHz, DMSO) δ: 11.85 (s, 1H), 8.58 (s, 1H), 8.31 (s, 1H), 7.47 (t, 1H), 6.74 (dd, 1H), 4.55 (m, 1H), 3.16-3.01 (m, 2H), 2.94 (m, 1H), 2.33 (s, 3H), 2.28 (m, 4H), 2.22-2.02 (m, 6H), 1.94 (m, 1H), 1.63 (m, 3H).

Example 178

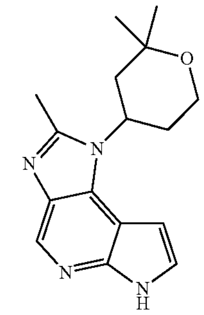

racemic 1-(2,2-Dimethyl-tetrahydro-pyran-4-yl)-2-methyl-1,6-dihydro-1,2,3,5,6-tetraaza-as-indacene A mixture of 1-benzenesulfonyl-4-chloro-5-nitro-1H-pyrrolo[2,3-b]pyridine (250 mg, 0.74 mmol), 2,2-Dimethyl-tetrahydro-pyran-4-ylamine (105 mg, 0.81 mmol), diisopropylethylamine (335 μl, 1.92 mmol) in propan-2-ol (2.5 ml) was heated in a glass vial at 80° C. for 12 hours. The mixture was concentrated, diluted with potassium bisulfate solution (1N, 3 mL), and applied to a Varian Chemelut™ column. The product was eluted with dichloromethane and concentrated to yield a yellow solid (LCMS (Method F, ESI): RT=1.12 min, m+H=431.2). The solid was dissolved in ethanol (20 mL), palladium (10% on carbon, 40 mg, 0.037 mmol) was added, and the mixture was hydrogenated under one atmosphere of hydrogen at room temperature overnight. The mixture was filtered through CELITE®, thoroughly washing the filter cake with ethanol. The filtrate and washings were combined and concentrated under vacuum to yield a brown solid (LCMS (Method F, ESI): RT=0.71 min, m+H=401.3). The solid was dissolved in acetic acid (3 mL) and triethyl orthoacetate (1.5 mL). The mixture was heated at 115° C. for 10 minutes. The mixture was concentrated to yield a brown solid (LCMS (Method F, ESI): RT=0.85 min, m+H=425.3). The solid was dissolved in ethanol (5 mL) and sodium hydroxide (5 ml) and the mixture was stirred at room temperature overnight. The reaction was quenched with acetic acid (0.5 mL) and the mixture was concentrated under vacuum to leave a brown residue. Purification by column chromatography on silica gel (eluting with 10% methanol in ethyl acetate) afforded 110.0 mg (52% over four steps) of 1-(2,2-Dimethyl-tetrahydro-pyran-4-yl)-2-methyl-1,6-dihydro-1,2,3,5,6-tetraaza-as-indacene. LCMS (Method C, ESI): RT=2.95 min, m+H=285.1; $^1$H NMR (400 MHz, DMSO) δ 11.81 (s, 1H), 8.47 (s, 1H), 7.48 (t, J=3.0 Hz, 1H), 6.69 (dd, J=3.1, 1.9 Hz, 1H), 4.87 (s, 1H), 3.88 (d, J=7.9 Hz, 2H), 2.65 (s, 3H), 2.48-2.39 (m, 1H), 2.33 (t, J=12.7 Hz, 1H), 1.82 (dd, J=12.5, 4.6 Hz, 2H), 1.37 (s, 3H), 1.26 (s, J=9.0 Hz, 3H).

Example 179

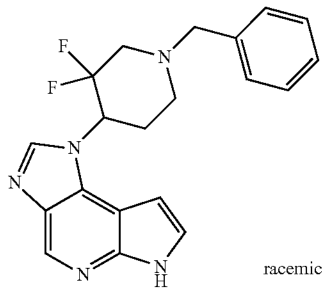 [SMILES: FC1(F)CN(Cc2ccccc2)CCC1n1cnc2cnc3[nH]ccc3c21]

racemic 1-(1-Benzyl-3,3-difluoro-piperidin-4-yl)-1,6-dihydro-1,2,3,5,6-tetraaza-as-indacene 1-Benzenesulfonyl-N*4*-(1-benzyl-3,3-difluoro-piperidin-4-yl)-1H-pyrrolo[2,3-b]pyridine-4,5-diamine A mixture of 1-benzenesulfonyl-4-chloro-5-nitro-1H-pyrrolo[2,3-b]pyridine (4.6 g, 14 mmol), 1-benzyl-3,3-difluoropiperidin-4-amine (prepared according to EP2123651 A1, 3.08 g, 13.6 mmol), diisopropylethylamine (6 mL, 34 mmol) in propan-2-ol (100 mL) was heated at 80° C. for 12 hours. The mixture was concentrated, suspended in potassium bisulfate solution (1N, 100 mL), and filtered to yield 7.06 g of a yellow solid (LCMS (Method F, ESI): RT=1.28 min, m+H=528.3). The solid was suspended in ethanol (90 mL) and water (30 mL), iron powder (2.3 g, 41 mmol) and ammonium chloride (3.6 g, 68 mmol) was added, and the mixture was refluxed for 4 hours. The mixture was filtered through CELITE®, thoroughly washing the filter cake with ethanol and ethyl acetate. The filtrate and washings were combined and concentrated under vacuum. The resulting residue was partitioned between ethyl acetate and water, and the organic layer dried with sodium sulfate and concentrated under vacuum. Purification by column chromatography on silica gel (gradient: 0 to 50% (20% methanol in ethyl acetate) in heptanes) affording 4.6 g (68%) of 1-Benzenesulfonyl-N*4*-(1-benzyl-3,3-difluoro-piperidin-4-yl)-1H-pyrrolo[2,3-b]pyridine-4,5-diamine as a purple solid (LCMS (Method F, ESI): RT=0.83 min, m+H=490.3). $^1$H NMR (400 MHz, DMSO) δ 8.02 (d, J=7.9 Hz, 2H), 7.72-7.62 (m, 2H), 7.57 (t, J=7.7 Hz, 2H), 7.50 (d, J=4.2 Hz, 1H), 7.40-7.22 (m, 5H), 6.82 (d, J=4.2 Hz, 1H), 5.17 (d, J=9.9 Hz, 1H), 4.46 (s, 2H), 4.27-4.08 (m, J=16.0, 13.3, 8.1 Hz, 1H), 3.69-3.52 (m, 2H), 3.04 (dd, J=16.5, 10.6 Hz, 1H), 2.80 (d, J=11.5 Hz, 1H), 2.60-2.42 (m, J=11.9 Hz, 1H), 2.31 (t, J=11.0 Hz, 1H), 1.91 (d, J=13.0 Hz, 1H), 1.85-1.69 (m, 1H).

6-Benzenesulfonyl-1-(1-benzyl-3,3-difluoro-piperidin-4-yl)-1,6-dihydro-1,2,3,5,6-tetraaza-as-indacene 1-Benzenesulfonyl-N*4*-(1-benzyl-3,3-difluoro-piperidin-4-yl)-1H-pyrrolo[2,3-b]pyridine-4,5-diamine (522 mg, 1.05 mmol) was dissolved in acetic acid (6 mL) and triethyl orthoacetate (3 mL). The mixture was heated at 115° C. for 10 minutes. The mixture was concentrated to yield a brown solid. Purification by column chromatography on silica gel (gradient: 0 to 100% ethyl acetate in heptanes) afforded 442.0 mg (83%) of 6-Benzenesulfonyl-1-(1-benzyl-3,3-difluoro-piperidin-4-yl)-1,6-dihydro-1,2,3,5,6-tetraaza-as-indacene. LCMS (Method F, ESI): RT=1.05 min, m+H=508.3; $^1$H NMR (400 MHz, DMSO) δ 8.75 (s, 1H), 8.59 (s, 1H), 8.12 (d, J=7.9 Hz, 2H), 7.96 (d, J=3.9 Hz, 1H), 7.69 (t, J=7.4 Hz, 1H), 7.60 (t, J=7.7 Hz, 2H), 7.45-7.34 (m, 5H), 7.31 (d, J=4.2 Hz, 1H), 5.37-5.11 (m, 1H), 3.72 (s, 2H), 3.20 (t, J=10.9 Hz, 1H), 3.01 (d, J=11.4 Hz, 1H), 2.89 (dd, J=30.3, 12.1 Hz, 1H), 2.67 (dd, J=24.1, 14.3 Hz, 1H), 2.57 (d, J=11.5 Hz, 1H), 2.19 (d, J=10.3 Hz, 1H).

1-(1-Benzyl-3,3-difluoro-piperidin-4-yl)-1,6-dihydro-1,2,3,5,6-tetraaza-as-indacene 6-Benzenesulfonyl-1-(1-benzyl-3,3-difluoro-piperidin-4-yl)-1,6-dihydro-1,2,3,5,6-tetraaza-as-indacene (142.0 mg, 280.0 μmol) was treated with sodium hydroxide (1N, 4 mL, 4 mmol) in ethanol (5 ml) and the mixture was stirred at room temperature overnight. The reaction was quenched with acetic acid (0.5 mL) and the mixture was concentrated under vacuum to leave a white residue. Purification by column chromatography on silica gel (eluting with 20% methanol in ethyl acetate) afforded 66.0 mg (64%) of 1-(1-Benzyl-3,3-difluoro-piperidin-4-yl)-1,6-dihydro-1,2,3,5,6-tetraaza-as-indacene. LCMS (Method C, ESI): RT=3.25 min, m+H=368.1; $^1$H NMR (400 MHz, DMSO) δ 11.78 (s, 1H), 8.58 (s, 1H), 8.38 (d, J=1.8 Hz, 1H), 7.43 (t, J=2.9 Hz, 1H), 7.41-7.35 (m, J=4.4 Hz, 4H), 7.34-7.27 (m, 1H), 6.91 (s, 1H), 5.19 (dd, J=23.5, 12.2 Hz, 1H), 3.81-3.64 (m, 2H), 3.25-3.16 (m, 1H), 3.03 (d, J=10.6 Hz, 1H), 2.86 (dd, J=29.8, 12.1 Hz, 1H), 2.74-2.53 (m, 2H), 2.20 (d, J=12.5 Hz, 1H).

Example 180

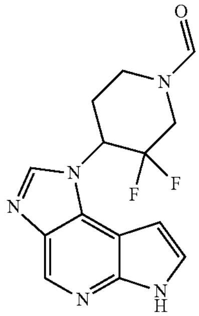

racemic 3,3-Difluoro-4-(6H-1,2,3,5,6-tetraaza-as-indacen-1-yl)-piperidine-1-carbaldehyde A mixture of 1-(1-Benzyl-3,3-difluoro-piperidin-4-yl)-1,6-dihydro-1,2,3,5,6-tetraaza-as-indacene (60 mg, 0.16 mmol), palladium hydroxide (20 wt % on carbon, 12.0 mg, 16.0 μmol) and ammonium formate (103 mg, 1.6 mmol) in ethanol (5 mL) was heated to reflux for 1½ hours. After cooling the mixture was filtered through Celite®, washing the filter cake with ethanol, and concentrated under vacuum. Purification by preparative HPLC afforded 15.0 mg (30%) of 3,3-Difluoro-4-(6H-1,2,3,5,6-tetraaza-as-indacen-1-yl)-piperidine-1-carbaldehyde. LCMS (Method C, ESI): RT=2.46 min, m+H=306.0; $^1$H NMR (400 MHz, DMSO) δ 11.82 (s, 2H), 8.59 (s, 2H), 8.36 (dd, J=10.8, 2.0 Hz, 2H), 8.27 (t, J=6.8 Hz, 1H), 8.15 (s, 1H), 7.50-7.40 (m, 2H), 7.01 (s, 2H), 5.62-5.40 (m, 2H), 4.62 (t, J=12.7 Hz, 1H), 4.44 (d, J=11.3 Hz, 1H), 4.29 (t, J=12.7 Hz, 1H), 3.99 (dd, J=31.8, 13.9 Hz, 2H), 3.70-3.52 (m, 2H), 3.21-3.10 (m, 2H), 2.74-2.54 (m, 1H), 2.46 (d, J=4.5 Hz, 1H), 2.33 (t, J=16.9 Hz, 2H).

Example 181

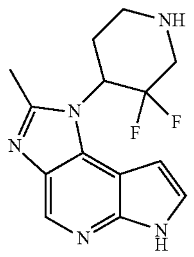
racemic 1-(3,3-Difluoro-piperidin-4-yl)-2-methyl-1,6-dihydro-1,2,3,5,6-tetraaza-as-indacene A solution of 1-(1-Benzyl-3,3-difluoro-piperidin-4-yl)-2-methyl-1,6-dihydro-1,2,3,5,6-tetraaza-as-indacene (69 mg, 0.18 mmol) in THF (6 mL) was hydrogenated on a ThalesNano H-Cube® Continuous-flow Hydrogenation Reactor using a 20% Pd(OH)2/C Catcart® (1 ml/min, full hydrogen pressure, 80° C.). Purification by preparative HPLC afforded 25.0 mg (47%) of 1-(3,3-Difluoro-piperidin-4-yl)-2-methyl-1,6-dihydro-1,2,3,5,6-tetraaza-as-indacene. LCMS (Method C, ESI): RT=1.98 min, m+H=292.0;

Example 182 and 182a

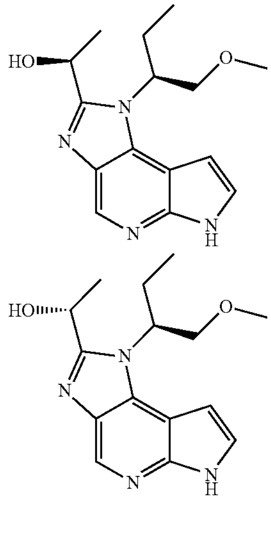

1-[1-(1-Methoxymethyl-propyl)-1,6-dihydro-1,2,3,5,6-tetraaza-as-indacen-2-yl]-ethanol 6-Benzenesulfonyl-1-(1-methoxymethyl-propyl)-1,6-dihydro-1,2,3,5,6-tetraaza-as-indacene (synthesized according to Example 179, 240 mg, 0.62 mmol) was dissolved in THF (6 mL). A solution of 2,2,6,6-tetramethylpiperidinylmagnesium chloride lithium chloride (1M in Tetrahydrofuran, 0.81 mL, 0.81 mmol) was added at 0° C. The reaction was stirred at 0° C. for 1.5 hours. A solution of acetaldehyde in tetrahydrofuran (0.85 M, 1.6 mL, 1.36 mmol) was added. The reaction was stirred at 0° C. for 2 hours. The reaction was quenched with ammonium chloride solution. The mixture was applied to a Varian Chem Elut cartridge and eluted with ethyl acetate. The mixture was concentrated. The crude product was purified using preparative HPLC and dissolved in ethanol (3 mL) and sodium hydroxide solution (1N in water, 0.27 mL) and the mixture was stirred at room temperature overnight. The reaction was quenched with acetic acid (0.1 mL) and concentrated under vacuum. The crude product was purified using preparative HPLC to yield two isomers. First eluting isomer of 1-[1-(1-Methoxymethyl-propyl)-1,6-dihydro-1,2,3,5,6-tetraaza-as-indacen-2-yl]-ethanol (12 mg, 47%) LCMS (Method A, ESI): RT=2.93 min, m+H=289.1; $^1$H NMR (400 MHz, DMSO) δ 11.82 (s, 1H), 8.55 (s, 1H), 7.44 (s, 1H), 6.58 (s, 1H), 5.55 (d, J=5.9 Hz, 1H), 5.17-4.96 (m, 2H), 3.95 (p, J=9.7 Hz, 2H), 3.23 (s, 3H), 2.27-2.00 (m, 2H), 1.64 (d, J=6.5 Hz, 3H), 0.71 (t, J=7.3 Hz, 3H). Second eluting isomer of 1-[1-(1-Methoxymethyl-propyl)-1,6-dihydro-1,2,3,5,6-tetraaza-as-indacen-2-yl]-ethanol (15 mg, 70%) LCMS (Method C, ESI): RT=2.86 min, m+H=289.1; $^1$H NMR (400 MHz, DMSO) δ 11.81 (s, 1H), 8.56 (s, 1H), 7.43 (s, 1H), 6.57 (s, 1H), 5.55 (d, J=6.9 Hz, 1H), 5.22-4.69 (m, 2H), 4.00 (t, J=9.8 Hz, 1H), 3.83 (dd, J=10.2, 4.3 Hz, 1H), 3.13 (s, 3H), 2.33-1.76 (m, 2H), 1.65 (d, J=6.4 Hz, 3H), 0.79 (t, J=7.3 Hz, 3H).

Example 183

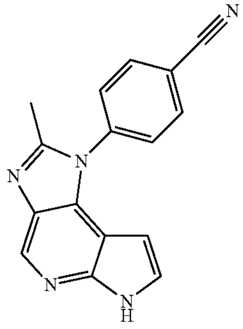 [SMILES: Cc1nc2cnc3[nH]ccc3c2n1-c1ccc(C#N)cc1]

4-(2-Methyl-6H-1,2,3,5,6-tetraaza-as-indacen-1-yl)-benzonitrile

A mixture of 1-benzenesulfonyl-4-chloro-5-nitro-1H-pyrrolo[2,3-b]pyridine (500 mg, 1.48 mmol), 4-amino-benzonitrile, (192.4 mg, 1.628 mmol), tris(dibenzylideneacetone)dipalladium(0) chloroform adduct (0.038 g, 0.037 mmol), 2-(dicyclohexylphosphino)-2',4',6'-triisopropyl-1,1'-biphenyl (0.042 g, 0.088 mmol), and cesium carbonate (1.45 g, 4.44 mmol) were suspended in 1,4-Dioxane (3.0 mL, 38 mmol). The sample was irradiated in a microwave oven at 120° C. for 30 minutes. The mixture was filtered through CELITE®, washing the filter cake with ethanol and ethyl acetate. The mixture was concentrated to give a red solid (LCMS (Method F, ESI): RT=1.12 min, m+H=420.2). The intermediate was dissolved in ethanol (30 mL), palladium (10% on carbon, 157 mg, 0.15 mmol) was added, and the mixture was hydrogenated under one atmosphere of hydrogen at room temperature overnight. The mixture was filtered through CELITE®, washing the filter cake with ethanol. The filtrate and washings were combined and concentrated under vacuum to yield 969 mg of a brown solid (LCMS (Method F, ESI): RT=0.94 min, m+H=390.2). A fraction of the solid (307 mg) was dissolved in acetic acid (6 mL) and triethyl orthoacetate (3 mL). The mixture was heated at 115° C. for 10 minutes. The mixture was concentrated to yield a brown solid (LCMS (Method F, ESI): RT=0.94 min, m+H=414.2). The solid was dissolved in ethanol (5 mL) and sodium hydroxide (5 ml) and the mixture was stirred at room temperature overnight. The reaction was quenched with acetic acid (0.5 mL) and the mixture was concentrated under vacuum to leave a brown residue. Purification by preparative HPLC afforded 8 mg (6% over four steps) of 4-(2-Methyl-6H-1,2,3,5,6-tetraaza-as-indacen-1-yl)-benzonitrile. LCMS (Method C, ESI): RT=3.03 min, m+H=274.0; $^1$H NMR (400 MHz, DMSO) δ 11.82 (s, 1H), 8.57 (s, 1H), 8.19 (d, J=8.2 Hz, 2H), 7.91 (d, J=8.1 Hz, 2H), 7.31 (s, 1H), 5.79 (d, J=1.6 Hz, 1H), 2.48 (s, 3H).

Example 184

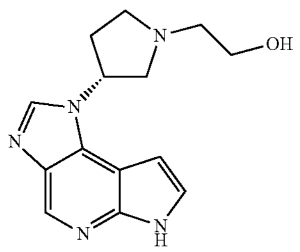 [SMILES: OCCN1CC[C@@H](n2cnc3cnc4[nH]ccc4c32)C1]

2-[(R)-3-(6H-1,2,3,5,6-Tetraaza-as-indacen-1-yl)-pyrrolidin-1-yl]-ethanol (1-Benzenesulfonyl-5-nitro-1H-pyrrolo[2,3-b]pyridin-4-yl)-((R)-1-benzyl-pyrrolidin-3-yl)-amine A mixture of 1-benzenesulfonyl-4-chloro-5-nitro-1H-pyrrolo[2,3-b]pyridine (2 g, 5.9 mmol), (R)-1-Benzyl-pyrrolidin-3-ylamine (2.4 g, 15.3 mmol), and diisopropylethylamine (6 mL, 35.4 mmol) in propan-2-ol (50 mL) was heated to reflux for 4 hours. Volatile components were removed under vacuum and the residue was purified by column chromatography on silica gel (gradient: 0 to 5% methanol in dichloromethane), gave 2.48 g (88%) of (R)—N-(1-benzylpyrrolidin-3-yl)-5-nitro-1-(phenylsulfonyl)-1H-pyrrolo[2,3-b]pyridin-4-amine. LCMS (Method J, ESI): RT=0.98 min, M+H$^+$=478.1; $^1$H NMR (400 MHz, $CDCl_3$) δ: 9.29-9.27 (s, 1H), 9.10 (s, 1H), 8.20-8.17 (m, 2H), 7.63-7.57 (m, 2H), 7.53-7.49 (m, 2H), 7.36-7.25 (m, 6H), 6.77-6.76 (d, J=4.4, 1H), 4.55-4.54 (m, 1H), 3.73-3.63 (m, 1H), 2.94-2.91 (m, 1H), 2.78-2.77 (m, 2H), 2.49-2.41 (m, 4H), 1.90-1.88 (m, 1H).

(1-Benzenesulfonyl-5-amino-1H-pyrrolo[2,3-b]pyridin-4-yl)-((R)-1-benzyl-pyrrolidin-3-yl)-amine A mixture of (1-Benzenesulfonyl-5-nitro-1H-pyrrolo[2,3-b]pyridin-4-yl)-((R)-1-benzyl-pyrrolidin-3-yl)-amine (2.48 g, 5.2 mmol) and Raney Ni (5.5 g) in ethyl acetate (50 mL) was hydrogenated at 25° C. for 2.5 hours. The mixture was filtered through Celite, thoroughly washing the filter cake with methanol. The filtrate and washings were combined and concentrated under vacuum, gave 2.2 g (96%) of (1-Benzenesulfonyl-5-amino-1H-pyrrolo[2,3-b]pyridin-4-yl)-((R)-1-benzyl-pyrrolidin-3-yl)-amine, which was used in the next step without further purification. LCMS (Method J, ESI): RT=0.81 min, M+H$^+$=447.9; $^1$H NMR (400 MHz, $CDCl_3$) δ: 8.07-8.05 (d, J=6.8 Hz, 2H), 7.74 (s, 1H), 7.46-7.44 (m, 2H), 7.39-7.35 (m, 3H), 7.25-7.18 (m, 6H), 6.52-6.50 (d, J=4.4 Hz, 1H), 4.30-4.40 (m, 1H), 3.56 (s, 2H), 2.79-2.76 (m, 2H), 2.69-2.59 (m, 1H), 2.36-2.25 (m, 2H), 1.60-1.70 (m, 1H).

6-Benzenesulfonyl-1-((R)-1-benzyl-pyrrolidin-3-yl)-1,6-dihydro-1,2,3,5,6-tetraaza-as-indacene A mixture of (1-Benzenesulfonyl-5-amino-1H-pyrrolo[2,3-b]pyridin-4-yl)-((R)-1-benzyl-pyrrolidin-3-yl)-amine (2.2 g, 5.0 mmol), triethyl orthoformate (1.2 g, 8.3 mol), and p-toluenesulfonic acid monohydrate (95 mg, 0.5 mmol, catalytic) in toluene (50 mL) was heated to reflux for 16 hours. Volatile components were removed under vacuum, the residue was taken up in ethyl acetate and the mixture was washed with water and brine, dried with sodium sulfate and concentrated under vacuum. Purification by column chromatography on silica gel (gradient: 10 to 15% methanol in DCM) gave 1.9 g (83%) of 6-Benzenesulfonyl-14R)-1-benzyl-pyrrolidin-3-yl)-1,6-dihydro-1,2,3,5,6-tetraaza-as-indacene. LCMS (Method K, ESI): RT=0.90 min, M+H$^+$=458.1; $^1$H NMR (400 MHz, $CDCl_3$) δ: 8.86 (s, 1H), 8.40-8.20 (m, 1H), 8.21-8.19 (d, J=8.0, 2H), 7.77-7.54 (m, 1H), 7.54 (s, 1H), 7.47-7.43 (m, 2H), 7.39-7.36 (m, 5H), 6.98 (s, 1H), 5.40-5.10 (m, 1H), 3.90-3.60 (m, 2H), 3.40-3.10 (m, 2H), 2.70-2.50 (m, 2H), 2.30-2.10 (m, 2H).

1-((R)-1-Benzyl-pyrrolidin-3-yl)-1,6-dihydro-1,2,3,5,6-tetraaza-as-indacene

6-Benzenesulfonyl-1-((R)-1-benzyl-pyrrolidin-3-yl)-1,6-dihydro-1,2,3,5,6-tetraaza-as-indacene (1.7 g, 3.7 mmol) in methanol (10 ml) was treated with 1M aqueous sodium hydroxide (11 ml, 11.1 mmol) and heated to 40° C. for 40 minutes. The mixture was partially concentrated under vacuum and the resulting suspension was extracted with ethyl acetate (2×50 ml), washed with water and brine. The combined organic extracts were dried with sodium sulfate and concentrated under vacuum to gave 1.1 g (94%) of 1-((R)-1-Benzyl-pyrrolidin-3-yl)-1,6-dihydro-1,2,3,5,6-tetraaza-as-indacene as a yellow solid. LCMS (Method K, ESI): RT=0.83 min, M+H$^+$=318.0; $^1$H NMR (400 MHz, $CDCl_3$) δ: 10.70 (s, 1H), 8.82 (s, 1H), 8.25 (s, 1H), 7.41-7.31 (m, 5H), 7.28-7.26 (m, 1H), 6.80 (s, 1H), 5.50-5.30 (m, 1H), 3.82-3.69 (m, 2H), 3.21-3.19 (m, 2H), 2.91-2.86 (m, 1H), 2.55-2.53 (m, 2H), 2.17 (m, 1H).

(R)-1-Pyrrolidin-3-yl-1,6-dihydro-1,2,3,5,6-tetraaza-as-indacene

To 1-((R)-1-Benzyl-pyrrolidin-3-yl)-1,6-dihydro-1,2,3,5,6-tetraaza-as-indacene (1.6 g, 5 mmol) in MeOH (50 mL) was added ammonium formate (2.2 g, 35 mmol) and 10% $Pd(OH)_2$ (2.5 g, 50% $H_2O$, 0.83 mmol). The mixture was refluxed under nitrogen atmosphere for 24 hours. The mixture was filtered through celite, thoroughly washing the filter cake with methanol. The filtrate and washings were combined and concentrated under vacuum to leave a residue. Purification by column chromatography on silica gel (eluting with 10 to 20% methanol in DCM) afforded 960 mg (85%) of (R)-1-Pyrrolidin-3-yl-1,6-dihydro-1,2,3,5,6-tetraaza-as-indacene. LCMS (Method K, ESI): RT=0.67 min, $M+H^+$=228.0; $^1$H NMR (400 MHz, methanol-$d_4$) δ: 8.58 (s, 1H), 8.34 (s, 1H), 7.47-7.46 (d, J=3.6, 1H), 6.88-6.87 (d, J=3.6, 1H), 5.48-5.38 (m, 1H), 3.49-3.48 (m, 1H), 3.34-3.31 (m, 2H), 3.31-3.30 (m, 1H), 2.68-2.51 (m, 1H), 2.42-2.35 (m, 1H).

1-{(R)-1-[2-(tert-Butyl-dimethyl-silanyloxy)-ethyl]-pyrrolidin-3-yl}-1,6-dihydro-1,2,3,5,6-tetraaza-as-indacene To (R)-1-Pyrrolidin-3-yl-1,6-dihydro-1,2,3,5,6-tetraaza-as-indacene (100 mg, 0.44 mmol) in acetonitrile (50 mL) was added triethylamine (0.3 mL, 2.16 mmol) and (2-Bromo-ethoxy)-tert-butyl-dimethyl-silane (250 mg, 1.05 mmol). The mixture was heated to 70° C. for 5 h and concentrated under vacuum to leave a residue. Purification by column chromatography on silica gel (eluting with 10 to 15% methanol in DCM) afforded 100 mg (60%) of 1-{(R)-1-[2-(tert-Butyl-dimethyl-silanyloxy)-ethyl]-pyrrolidin-3-yl}-1,6-dihydro-1,2,3,5,6-tetraaza-as-indacene. LCMS (Method J, ESI): RT=0.84 min, $M+H^+$=386.2; $^1$H NMR (400 MHz, $CDCl_3$) δ: 8.73 (s, 1H), 8.21 (s, 1H), 7.33-7.31 (d, J=3.6, 1H), 6.77-6.76 (d, J=3.6, 1H), 5.40-5.20 (m, 1H), 3.81-3.79 (t, J=6.8, 2H), 3.30-3.20 (m, 2H), 3.07-3.03 (t, J=6.8, 2H), 2.90-2.70 (m, 2H), 2.55-2.65 (m, 1H), 2.30-2.10 (m, 1H), 0.82-0.81 (s, 9H), 0.03-0.00 (d, 6H).

2-[(R)-3-(6H-1,2,3,5,6-Tetraaza-as-indacen-1-yl)-pyrrolidin-1-yl]-ethanol

To 1-{(R)-1-[2-(tert-Butyl-dimethyl-silanyloxy)-ethyl]-pyrrolidin-3-yl}-1,6-dihydro-1,2,3,5,6-tetraaza-as-indacene (100 mg, 0.24 mmol) in ethyl acetate (5 mL) was added 4N HCl in ethyl acetate (3 mL) and the mixture was allowed to stir at about 15° C. for overnight. The resulting white solid was filtered off, and washed with ethyl acetate (5 mL×3), to afford 50 mg (77%) 2-[(R)-3-(6H-1,2,3,5,6-Tetraaza-as-indacen-1-yl)-pyrrolidin-1-yl]-ethanol as the HCl salt. MS: 272.3 [$M+H^+$], 542.8 [$2M+H^+$]; $^1$H NMR (400 MHz, DMSO-$d_6$) δ: 12.67 (s, 1H), 11.1-11.4 (m, 1H), 9.57-9.30 (m, 1H), 7.75 (s, 1H), 7.13-7.11 (m, 1H), 5.88-5.85 (m, 1H), 5.72 (m, 1H), 4.04-3.97 (m, 2H), 3.93 (m, 2H), 3.40-3.31 (m, 2H), 2.90-2.63 (m, 2H).

Example 185

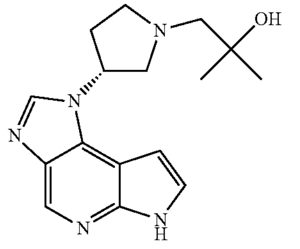 [SMILES: CC(C)(O)CN1CC[C@@H](n2cnc3cnc4[nH]ccc4c32)C1]

2-Methyl-1-[(R)-3-(6H-1,2,3,5,6-tetraaza-as-indacen-1-yl)-pyrrolidin-1-yl]-propan-2-ol To (R)-1-Pyrrolidin-3-yl-1,6-dihydro-1,2,3,5,6-tetraaza-as-indacene (80 mg, 0.35 mmol) in acetonitrile (15 mL) was added triethylamine (0.2 mL, 4.1 mmol) and excess isobutylene oxide (3 mL). The mixture was heated at 70° C. overnight and concentrated under vacuum to leave a residue. Purification by column chromatography on silica gel (eluting with 10 to 15% methanol in DCM) afforded 50 mg (63%) of 2-Methyl-1-[(R)-3-(6H-1,2,3,5,6-tetraaza-as-indacen-1-yl)-pyrrolidin-1-yl]-propan-2-ol. MS: 300 [$M+H^+$], 599 [$2M+H^+$]; $^1$H NMR (400 MHz, DMSO-$d_6$) δ: 11.83 (s, 1H), 8.56 (s, 1H), 8.32 (s, 1H), 7.45-7.43 (d, J=3.2, 1H), 6.92-6.91 (d, J=3.2, 1H), 5.30-5.29 (m, 1H), 3.29-3.16 (m, 3H), 2.89-2.85 (m, 1H), 2.53-2.42 (m, 3H), 2.20-2.10 (m, 1H), 1.13 (s, 3H), 1.11 (s, 3H).

Example 186

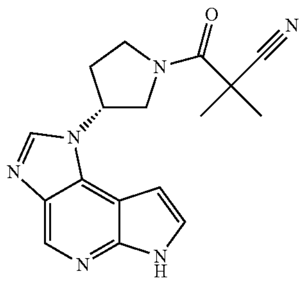 [SMILES: CC(C)(C#N)C(=O)N1CC[C@@H](n2cnc3cnc4[nH]ccc4c32)C1]

2,2-Dimethyl-3-oxo-3-[(R)-3-(6H-1,2,3,5,6-tetraaza-as-indacen-1-yl)-pyrrolidin-1-yl]-propionitrile To (R)-1-Pyrrolidin-3-yl-1,6-dihydro-1,2,3,5,6-tetraaza-as-indacene (100 mg, 0.44 mmol) in anhydrous DCM (5 mL) was added triethylamine (0.2 mL, 1.44 mmol), 2-cyano-2-methylpropanoic acid (100 mg, 0.88 mmol) and HATU (334 mg, 0.88 mmol). The mixture was allowed to stir at about 10° C. for 1.5 h and concentrated under vacuum to leave a residue. Purification by preparative HPLC afforded 65 mg (46%) of 2,2-Dimethyl-3-oxo-3-[(R)-3-(6H-1,2,3,5,6-tetraaza-as-indacen-1-yl)-pyrrolidin-1-yl]-propionitrile as the HCOOH salt. LCMS (Method K, ESI): RT=0.89 min, $M+H^+$=323.1; $^1$H NMR (400 MHz, DMSO-$d_6$) δ: 11.93 (s, 1H), 8.59 (s, 1H), 8.29-8.26 (m, 1H), 7.49 (s, 1H), 6.83-6.78 (m, 1H), 5.60-5.40 (m, 1H), 3.93-3.92 (m, 2H), 3.80-3.60 (m, 2H), 2.67-2.63 (m, 2H), 1.56-1.36 (m, 6H).

Example 187

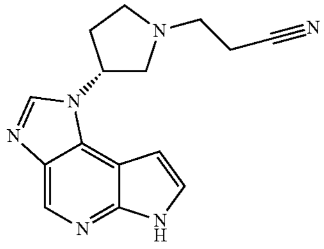 [SMILES: N#CCCN1CC[C@@H](n2cnc3cnc4[nH]ccc4c32)C1]

3-[(R)-3-(6H-1,2,3,5,6-Tetraaza-as-indacen-1-yl)-pyrrolidin-1-yl]-propionitrile

To (R)-1-Pyrrolidin-3-yl-1,6-dihydro-1,2,3,5,6-tetraaza-as-indacene (80 mg, 0.35 mmol) in anhydrous acetonitrile (5 mL) was added triethylene diamine hexahydrate (154 mg, 0.7 mmol) and acrylonitrile (22 mg, 0.42 mmol). The mixture was heated to 80° C. for 2 h and concentrated under vacuum to leave a residue. Purification by preparative HPLC afforded 35 mg (36%) of 3-[(R)-3-(6H-1,2,3,5,6-Tetraaza-as-indacen-1-yl)-pyrrolidin-1-yl]-propionitrile. LCMS (Method L, ESI): RT=0.83 min, M-41'=380.9; $^1$H NMR (400 MHz, DMSO-$d_6$) δ: 11.78 (s, 1H), 8.52 (s, 1H), 8.27 (s, 1H), 7.39-7.3 (d, J=3.2, 1H), 6.88-6.87 (d, J=3.2, 1H), 5.40-5.20 (m, 1H), 3.22-3.13 (m, 2H), 2.84-2.80 (m, 1H), 2.77-2.70 (m, 4H), 2.46-2.44 (m, 2H), 2.10-2.00 (m, 1H)

Example 188

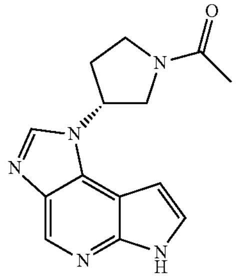 [SMILES: CC(=O)N1CC[C@@H](n2cnc3cnc4[nH]ccc4c32)C1]

1-[(R)-3-(6H-1,2,3,5,6-Tetraaza-as-indacen-1-yl)-pyrrolidin-1-yl]-ethanone

To (R)-1-Pyrrolidin-3-yl-1,6-dihydro-1,2,3,5,6-tetraaza-as-indacene (83.5 mg, 0.37 mmol) in anhydrous N,N-Dimethylformamide (2 mL) cooled to 0° C. was added triethylamine (0.2 mL, 1.48 mmol) and acetyl chloride (46 mg, 0.58 mmol, dropwise addition). The mixture was allowed to stir at about 10° C. for 30 min, then methanol (5 mL) was added and the mixture was concentrated to leave a residue. Purification by preparative HPLC afforded 30 mg (20%) of 1-[(R)-3-(6H-1,2,3,5,6-Tetraaza-as-indacen-1-yl)-pyrrolidin-1-yl]-ethanone. LCMS (Method L, ESI): RT=0.92 min, M+H$^+$=269.7; $^1$H NMR (400 MHz, DMSO-$d_6$) δ: 11.91 (s, 1H), 8.59-8.58 (s, 1H), 8.28-8.21 (m, 1H), 7.48 (s, 1H), 6.80-6.74 (m, 1H), 5.40 (m, 1H), 4.09-3.87 (m, 2H), 3.81-3.71 (m, 2H), 3.56-3.52 (m, 1H), 2.57-2.56 (m, 1H), 2.49-2.46 (m, 1H), 2.00-1.96 (m, 3H)

Example 189

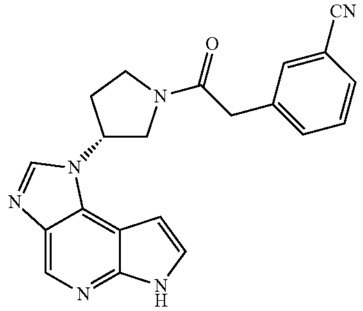 [SMILES: N#Cc1cccc(CC(=O)N2CC[C@@H](n3cnc4cnc5[nH]ccc5c43)C2)c1]

3-{2-oxo-2-[(R)-3-(6H-1,2,3,5,6-tetraaza-as-indacen-1-yl)-pyrrolidin-1-yl]-ethyl}-benzonitrile To (R)-1-Pyrrolidin-3-yl-1,6-dihydro-1,2,3,5,6-tetraaza-as-indacene (110 mg, 0.48 mmol) in anhydrous DCM (10 mL) was added triethylamine (0.2 mL, 1.44 mmol), (3-Cyano-phenyl)-acetic acid (85 mg, 0.53 mmol) and HATU (201 mg, 0.53 mmol). The mixture was allowed to stir at about 10° C. for 0.5 h and then concentrated to leave a residue. Purification by preparative HPLC afforded 29.6 mg (17%) of 3-{2-oxo-2-[(R)-3-(6H-1,2,3,5,6-tetraaza-as-indacen-1-yl)-pyrrolidin-1-yl]-ethyl}-benzonitrile. LCMS (Method K, ESI): RT=0.96 min, M+H'=371.0; $^1$H NMR (400 MHz, DMSO-$d_6$) δ: 11.88 (s, 1H), 8.58-8.57 (s, 1H), 8.27-8.20 (m, 1H), 7.71-7.69 (m, 1H), 7.65-7.64 (m, 1H), 7.58-7.45 (m, 3H), 6.76-6.75 (m, 1H), 5.60-5.40 (m, 1H), 3.85-3.80 (m, 2H), 3.76-3.74 (m, 3H), 3.59 (m, 1H), 2.49-2.47 (m, 2H).

Example 190

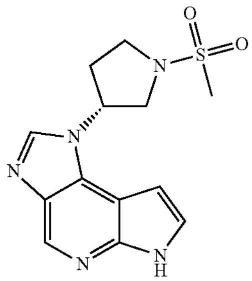 [SMILES: CS(=O)(=O)N1CC[C@@H](n2cnc3cnc4[nH]ccc4c32)C1]

1-((R)-1-Methanesulfonyl-pyrrolidin-3-yl)-1,6-dihydro-1,2,3,5,6-tetraaza-as-indacene To (R)-1-Pyrrolidin-3-yl-1,6-dihydro-1,2,3,5,6-tetraaza-as-indacene (100 mg, 0.44 mmol) in anhydrous DCM (10 ml) was added triethylamine (0.25 mL, 1.8 mmol), and methanesulfonyl chloride (150 mg, 0.79 mmol). The mixture was allowed to stir at about 10° C. for 1.5 h, then methanol was added, and mixture was concentrated to leave a residue. Purification by preparative HPLC afforded 18.5 mg (17%) of 1-((R)-1-Methanesulfonyl-pyrrolidin-3-yl)-1,6-dihydro-1,2,3,5,6-tetraaza-as-indacene. LCMS (Method L, ESI): RT=1.03 min, M+H'=305.8; $^1$H NMR (400 MHz, DMSO-$d_6$) δ: 11.98 (s, 1H), 8.67 (s, 1H), 8.38 (s, 1H), 7.58-7.56 (m, J=3.2, 1H), 6.89-6.88 (m, J=3.2, 1H), 5.55 (m, 1H), 4.00-3.95 (m, 1H), 3.75-3.64 (m, 3H), 3.05 (s, 3H), 2.67-2.61 (m, 2H).

Example 191

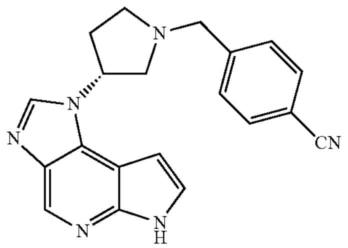 [SMILES: N#Cc1ccc(CN2CC[C@@H](n3cnc4cnc5[nH]ccc5c43)C2)cc1]

4-[(R)-3-(6H-1,2,3,5,6-Tetraaza-as-indacen-1-yl)-pyrrolidin-1-ylmethyl]-benzonitrile To (R)-1-Pyrrolidin-3-yl-1,6-dihydro-1,2,3,5,6-tetraaza-as-indacene (120 mg, 0.53 mmol) in anhydrous DCM (10 mL) was added triethylamine (0.2 mL, 1.44 mmol), and 4-bromomethyl-benzonitrile (103 mg, 0.53 mmol). The mixture was allowed to stir at about 10° C. for 1.5 hours, and concentrated to leave a residue. Purification by preparative HPLC afforded 20 mg (17%) of 4-[(R)-3-(6H-1,2,3,5,6-Tetraaza-as-indacen-1-yl)-pyrrolidin-1-ylmethyl]-benzonitrile. LCMS (Method K, ESI): RT=0.98 min, $M+H^+$=343.0; $^1$H NMR (400 MHz, DMSO-$d_6$) δ: 11.89 (s, 1H), 8.57 (s, 1H), 8.42 (s, 1H), 8.11 (s, HCOOH, 1H), 7.84-7.82 (d, J=6.8, 2H), 7.66-7.64 (d, J=6.8, 2H), 7.46 (s, 1H), 6.87 (s, 1H), 5.49 (m, 1H), 4.18 (m, 2H), 3.37 (m, 2H), 3.13 (m, 1H), 2.96 (m, 1H), 2.65 (m, 1H), 2.38 (m, 1H).

Example 192

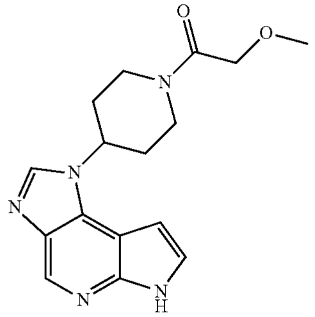 [SMILES: COCC(=O)N1CCC(n2cnc3cnc4[nH]ccc4c32)CC1]

2-Methoxy-1-[4-(6H-1,2,3,5,6-tetraaza-as-indacen-1-yl)-piperidin-1-yl]-ethanone

To 1-Piperidin-4-yl-1,6-dihydro-1,2,3,5,6-tetraaza-as-indacene (240 mg, 1 mmol) was added anhydrous DCM and $Et_3N$ (0.28 mL, 5 mmol). The mixture was cooled to 0° C., then 2-methoxyacetyl chloride (129 mg, 1.2 eq) was added dropwise. The mixture was allowed to stir at about 10° C. for 2 hours, then MeOH was added, and the mixture concentrated. 3 mL of DMF was added to the residue, the insoluble solids were removed by filtration, then the filtrate was concentrated and purified by preparative HPLC. 21.3 mg of the title compound was obtained (isolated yield: 6.8%). LCMS (Method K, ESI): RT=0.82 min, $M+H^+$=313.7; $^1$H NMR (400 MHz, MeOD) δ: 9.10 (s, 1H), 8.80 (s, 1H), 7.68 (d, 1H), 7.07 (d, 1H); 5.06-5.12 (m, 1H), 4.30-4.40 (m, 1H), 4.19-4.23 (m, 2H), 4.11-4.14 (m, 1H), 3.35-3.39 (m, 1H); 3.25 (s, 3H) 2.91-2.98 (m, 1H), 2.32-2.35 (m, 2H), 2.20-2.00 (m, 2H).

Example 193

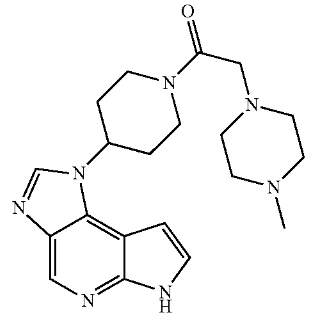 [SMILES: CN1CCN(CC(=O)N2CCC(n3cnc4cnc5[nH]ccc5c43)CC2)CC1]

2-(4-Methyl-piperazin-1-yl)-1-[4-(6H-1,2,3,5,6-tetraaza-as-indacen-1-yl)-piperidin-1-yl]-ethanone 2-Bromo-1-[4-(6H-1,2,3,5,6-tetraaza-as-indacen-1-yl)-piperidin-1-yl]-ethanone 1-Piperidin-4-yl-1,6-dihydro-1,2,3,5,6-tetraaza-as-indacene (120 mg, 0.49 mmol) was dissolved in DCM (10 mL), and cooled to 0° C. TEA (251 mg, 2.49 mmol) was added, followed by 2-bromoacetyl bromide (130 mg, 0.647 mmol, dropwise addition). The mixture was stirred for 1 h. The reaction mixture was quenched by addition of 10 mL methanol and the resulting solution was concentrated and used in next step without further purification.

2-(4-Methyl-piperazin-1-yl)-1-[4-(6H-1,2,3,5,6-tetraaza-as-indacen-1-yl)-piperidin-1-yl]-ethanone A solution of 2-Bromo-1-[4-(6H-1,2,3,5,6-tetraaza-as-indacen-1-yl)-piperidin-1-yl]-ethanone (100 mg, 0.277 mmol) was added dropwise to a stirred solution of 1-methylpiperazine (55.4 mg, 0.554 mmol) in $CH_3CN$ (10 mL). The resulting mixture was allowed to stand for 3 h, then the mixture was concentrated and purified via HPLC. 10.8 mg desired product was obtained (isolated yield: 5.7%). LCMS (Method L, ESI): RT=0.83 min, $M+H^+$=382.0; $^1$H NMR (400 MHz, DMSO) δ: 11.80 (s, 1H), 9.44 (s, 1H), 8.91 (s, 1H), 7.78-7.80 (s, 1H), 7.18-7.20 (m, 1H), 5.17-5.19 (m, 1H), 4.46-4.57 (m, 2H), 3.52-3.77 (m, 12H), 2.77-2.82 (s, 3H), 2.05-2.49 (m, 4H).

Example 194

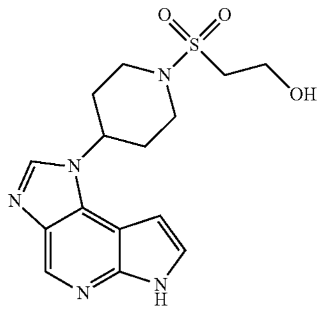 [SMILES: O=S(=O)(CCO)N1CCC(n2cnc3cnc4[nH]ccc4c32)CC1]

2-[4-(6H-1,2,3,5,6-Tetraaza-as-indacen-1-yl)-piperidine-1-sulfonyl]-ethanol

[4-(6H-1,2,3,5,6-Tetraaza-as-indacen-1-yl)-piperidine-1-sulfonyl]-acetic acid methyl ester 1-Piperidin-4-yl-1,6-dihydro-1,2,3,5,6-tetraaza-as-indacene (120 mg, 0.5 mmol) was added to anhydrous DCM, followed by methyl 2-(chlorosulfonyl)acetate (90 mg, 0.52 mmol, 1.05 eq) and $Et_3N$ (0.2 mL, 1.44 mmol, 2.8 eq). The mixture was warmed to 0° C. slowly over 1 hour. LCMS showed there was 51% of desired product. The solvent was removed in vacuum, the residue was purified by column separation, affording 130 mg of desired product was obtained (isolated yield: 68.9%).

$^1$H NMR (400 MHz, DMSO) δ: 11.85 (s, 1H), 8.56 (s, 1H), 8.30 (s, 1H), 7.46 (d, J=2.8 Hz, 1H), 6.78 (d, J=2.8 Hz, 1H), 4.70-4.90 (m, 1H), 4.36 (m, 2H), 3.83-3.79 (m, 2H), 3.72 (s, 3H), 3.21-3.26 (m, 2H), 2.10-2.21 (m, 4H).

2-[4-(6H-1,2,3,5,6-Tetraaza-as-indacen-1-yl)-piperidine-1-sulfonyl]-ethanol

[4-(6H-1,2,3,5,6-Tetraaza-as-indacen-1-yl)-piperidine-1-sulfonyl]-acetic acid methyl ester (60 mg, 0.16 mmol) was dissolved in anhydrous MeOH. $LiBH_4$ (35 mg, 1.6 mmol, 10 eq) was added every hour for five hours (16 mmol, 50 eq total), then water was added to quench the reaction. The residue was concentrated and the residue was purified by column chromatography. 6.0 mg of the desired product was obtained (isolated yield: 9.9%). LCMS (Method K, ESI): RT=0.84 min, M+H=349.9; $^1$H NMR (400 MHz, DMSO) δ: 11.87 (s, 1H), 8.57 (s, 1H), 8.32 (s, 1H), 7.47 (d, 1H), 6.79 (d, 1H), 5.11-5.12 (m, 1H), 4.75-4.76 (m, 1H), 4.10-4.12 (m, 1H), 3.80-3.76 (m, 4H), 3.14-3.16 (m, 3H), 2.12-2.18 (m, 4H).

Example 195

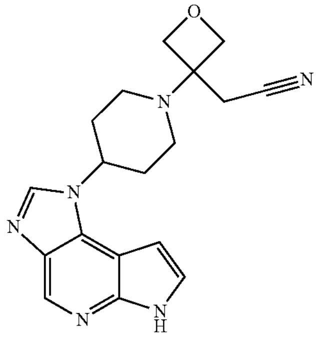 [SMILES: N#CCC1(N2CCC(n3cnc4cnc5[nH]ccc5c43)CC2)COC1]

{3-[4-(6H-1,2,3,5,6-Tetraaza-as-indacen-1-yl)-piperidin-1-yl]-oxetan-3-yl}-acetonitrile 1-Piperidin-4-yl-1,6-dihydro-1,2,3,5,6-tetraaza-as-indacene (70 mg, 0.29 mmol) was dissolved in DMF, then 2-(oxetan-3-ylidene)acetonitrile (55 mg, 0.58 mmol, 2 eq) and NaOH (50 mg, 1.25 mmol, 4.3 eq) dissolved in 0.5 mL $H_2O$ were added. The mixture was heated to 80° C. overnight. The crude product was purified by column chromatography, eluting with 15%-20% MeOH in DCM, to give 20 mg of crude product. Further purification by HPLC, afforded 5.1 mg of desired product (isolated yield: 5.2%). LCMS (Method L, ESI): RT=1.29 min, M+Na$^+$=358.8; $^1$H NMR (400 MHz, DMSO) δ: 11.83 (s, 1H), 8.55 (s, 1H), 8.28 (s, 1H), 7.45 (s, 1H), 6.74 6.76 (m, 1H), 4.55-4.61 (m, 1H), 4.48-4.51 (m, 2H), 4.38-4.40 (m, 2H) 3.04 (s, 2H), 2.76-2.80 (m, 2H), 2.43-2.51 (m, 2H), 2.06-2.15 (m, 4H).

Example 196 and 196a

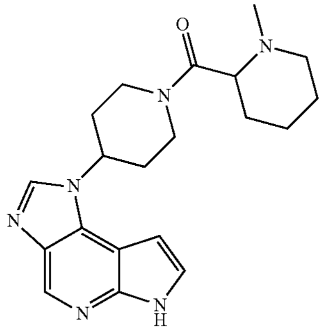

Single enantiomers (1-Methyl-piperidin-2-yl)-[4-(6H-1,2,3,5,6-tetraaza-as-indacen-1-yl)-piperidin-1-yl]-methanone 1-Piperidin-4-yl-1,6-dihydro-1,2,3,5,6-tetraaza-as-indacene (200 mg, 0.828 mmol) and 1-methylpiperidine-2-carboxylic acid (153 mg, 1.076 mmol) were dissolved in 20 mL of DCM, then DIPEA (409 mg, 4.14 mmol) and HATU (534 mg, 1.076 mmol) were added. The resulting mixture was allowed to stir at room temperature for 2 h. The reaction mixture was concentrated and triturated with methanol. The solid was isolated by filtration, then dissolved in 5 mL of DMSO and purified via HPLC and chiral SFC. 14.0 mg and 16.4 mg of the isomerically pure desired products were obtained respectively. The absolute stereochemistry for the isomers were not determined.

LCMS (Method L, ESI): RT=0.89 min, $M+H^+$=367.1; $^1H$ NMR (400 MHz, DMSO) δ: 11.86 (s, 1H), 8.56 (s, 1H), 8.30 (s, 1H), 7.46 (s, 1H), 6.76 (s, 1H), 4.85 (s, 2H), 4.34 (s, 1H), 3.32 (s, 1H), 2.86 (d, 3H), 2.15 (d, 5H), 1.94-1.97 (m, 3H), 1.51-1.67 (m, 5H), 1.33 (s, 1H).

Example 197 and 197a

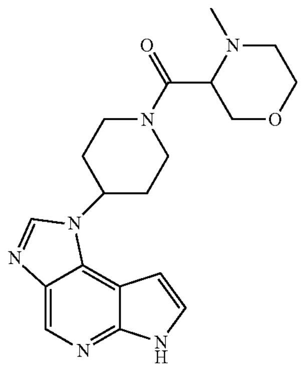

Single enantiomers (4-Methyl-morpholin-3-yl)-[4-(6H-1,2,3,5,6-tetraaza-as-indacen-1-yl)-piperidin-1-yl]-methanone morpholine-3-carboxylic acid 4-(tert-butoxycarbonyl)morpholine-3-carboxylic acid (180 mg, 0.78 mmol) was dissolved in EtOAc and stirred at room temperature. 5 mL of 4N HCl in EtOAc was added and the mixture was stirred at room temperature for 3 hours. The volatile components were removed in vacuum, affording the title compound as the HCl salt, which was adjusted to pH-8 with aqueous ammonia solution before the next step.

$^1H$ NMR (DMSO-$d_6$, 400 MHz): δ 10.00-9.50 (m, 1H), 4.21-4.18 (m, 1H), 4.07 (s, 1H), 3.85-3.78 (m, 2H), 3.74-3.72 (m, 1H), 3.20-3.19 (m, 1H), 3.10-3.04 (m, 1H)

4-methylmorpholine-3-carboxylic acid

To the above prepared solution of morpholine-3-carboxylic acid (140 mg, 0.86 mmol, 1 eq) was added aqueous formaldehyde (0.1 g, 1 mmol, 37%, 1.2 equiv), and the solution was stirred under hydrogen atmosphere at room temperature for 24 h in the presence of 10% palladium on carbon (150 mg, 50% water). After completion of the reaction, the catalyst was filtered off and the filtrate was concentrated under vacuum to give 120 mg of the desired 4-methylmorpholine-3-carboxylic acid. The crude material was used in the next step without further purification. $^1H$ NMR ($CD_3OD$, 400 MHz): δ 4.24-4.22 (m, 1H), 4.00-3.99 (m, 1H), 3.74-3.64 (m, 3H), 3.42-3.38 (m, 1H), 3.20-3.19 (m, 1H), 2.95 (s, 3H)

(4-Methyl-morpholin-3-yl)-[4-(6H-1,2,3,5,6-tetraaza-as-indacen-1-yl)-piperidin-1-yl]-methanone 1-Piperidin-4-yl-1,6-dihydro-1,2,3,5,6-tetraaza-as-indacene (100 mg, 0.41 mmol) was added to 5 mL of anhydrous DCM, then 4-methylmorpholine-3-carboxylic acid (100 mg, 0.7 mmol, 1.7 eq), HATU (266 mg, 0.7 mmol, 1.68 eq) and DIPEA (0.2 mL, 1.2 mmol, 3 eq) were added and the mixture was stirred at room temperature for 5 hours. The crude reaction mixture was purified by preparative HPLC to afford the racemic title compound, which was further purified by chiral SFC to give both enantiomers of (4-Methyl-morpholin-3-yl)-[4-(6H-1,2,3,5,6-tetraaza-as-indacen-1-yl)-piperidin-1-yl]-methanone in chirally pure form (6.8 and 6.4 mg). $^1H$ NMR: ($CDCl_3$, 400 MHz): δ 10.36 (s, 1H), 8.85 (s, 1H), 7.95 (s, 1H), 7.43-7.42 (m, 1H), 6.63-6.62 (m, 1H), 5.10-4.90 (m, 1H), 4.80-4.70 (m, 1H), 3.89-3.75 (m, 4H), 3.33-3.30 (m, 2H), 2.87-2.84 (m, 2H), 2.43-2.39 (m, 2H), 2.34 (s, 3H), 2.10-1.80 (m, 4H), 1.73 (m, 2H).

Example 198

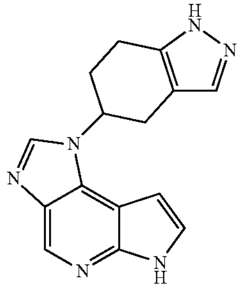

Racemic 1-(4,5,6,7-Tetrahydro-1H-indazol-5-yl)-1,6-dihydro-1,2,3,5,6-tetraaza-as-indacene 1-(4,5,6,7-Tetrahydro-1H-indazol-5-yl)-1,6-dihydro-1,2,3,5,6-tetraaza-as-indacene was synthesized using experimental methods similar to those of example 1, using 4,5,6,7-Tetrahydro-1H-indazol-5-ylamine (synthesized according to US2009/111800) instead of (R)-1-benzyl-3-aminopiperidine. LCMS (ESI): $M+H^+$=279; $^1H$ NMR ($CDCl_3$, 400 MHz) δ: 12.25 (br, 1H), 11.81 (br, 1H), 8.53 (s, 1H), 8.18 (s, 1H), 7.39-7.37 (m, 2H), 6.63 (d, J=3.6 Hz, 1H), 5.00-4.93 (m, 1H), 3.15-3.03 (m, 2H), 2.92-2.84 (m, 1H), 2.72-2.67 (m, 1H), 2.42-2.34 (m, 2H).

Example 199

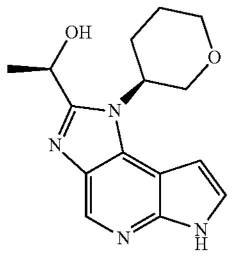 [SMILES: C[C@@H](O)c1nc2cnc3[nH]ccc3c2n1[C@H]1CCCOC1]

(R)-1-[(S)-1-(Tetrahydro-pyran-3-yl)-1,6-dihydro-1,2,3,5,6-tetraaza-as-indacen-2-yl]-ethanol 5-nitro-1-(phenylsulfonyl)-N-(tetrahydro-2H-pyran-3-yl)-1H-pyrrolo[2,3-b]pyridin-4-amine A stirred suspension of 4-chloro-5-nitro-1-(phenyl sulfonyl)-1H-pyrrolo[2,3-b]pyridine (11.10 g, 33.0 mmol) in isopropanol (IPA) (100 ml) was treated with tetrahydro-2H-pyran-3-amine hydrochloride (5.0 g, 36.0 mmol) and N,N-diisopropylethylamine (15.0 mL, 84.0 mmol), and stirred at 82° C. for four hours. The mixture was then cooled and left to stand at 5° C. for 2 h. The resulting precipitate was collected by filtration and washed with IPA. Trituration (water) afforded 11.7 g (89%) of 5-nitro-1-(phenylsulfonyl)-N-(tetrahydro-2H-pyran-3-yl)-1H-pyrrolo[2,3-b]pyridin-4-amine. LCMS (Method E, ESI): RT=1.65 min, m+H=403.2; $^{1}$H NMR (400 MHz, $CDCl_3$) δ 9.22 (d, J=7.6 Hz, 1H), 9.11 (s, 1H), 8.20 (d, J=8.0 Hz, 2H), 7.69-7.56 (m, 2H), 7.60-7.42 (m, 2H), 6.76 (d, J=4.2 Hz, 1H), 4.14 (ddt, J=10.7, 7.1, 3.5 Hz, 1H), 3.98 (dd, J=11.5, 2.7 Hz, 1H), 3.85-3.62 (m, 2H), 3.58 (dd, J=11.5, 6.4 Hz, 1H), 2.27-2.06 (m, 1H), 1.86 (tdt, J=11.8, 7.5, 3.9 Hz, 2H), 1.79-1.63 (m, 1H).

1-(phenylsulfonyl)-N4-(tetrahydro-2H-pyran-3-yl)-1H-pyrrolo[2,3-b]pyridine-4,5-diamine To a solution of 5-nitro-1-(phenylsulfonyl)-N-(tetrahydro-2H-pyran-3-yl)-1H-pyrrolo[2,3-b]pyridin-4-amine (11.7 g, 29.1 mmol) in ethyl acetate (400 mL) was added 10% palladium on carbon (3.0 g, 3.0 mmol). The mixture was stirred at ambient temperature under an atmosphere of hydrogen for 16 h. Filtration and concentration afforded 10.2 g (94.2%) of 1-(phenylsulfonyl)-N4-(tetrahydro-2H-pyran-3-yl)-1H-pyrrolo[2,3-b]pyridine-4,5-diamine. LCMS (Method E, ESI): RT=1.16 min, m+H=373.3; $^{1}$H NMR (400 MHz, $CDCl_3$) δ 8.25-7.99 (m, 2H), 7.84 (s, 1H), 7.61-7.35 (m, 4H), 6.58 (d, J=4.2 Hz, 1H), 5.04 (t, J=12.8 Hz, 1H), 4.02-3.82 (m, 2H), 3.80-3.55 (m, 2H), 3.47 (dd, J=11.1, 6.1 Hz, 1H), 2.86 (s, 2H), 2.11-1.93 (m, 1H), 1.80 (dtd, J=14.6, 7.2, 3.7 Hz, 1H), 1.74-1.51 (m, 3H).

(2R)-1-oxo-1-(1-(phenylsulfonyl)-4-(tetrahydro-2H-pyran-3-ylamino)-1H-pyrrolo[2,3-b]pyridin-5-ylamino)propan-2-yl acetate A solution of 1-(phenylsulfonyl)-N4-(tetrahydro-2H-pyran-3-yl)-1H-pyrrolo[2,3-b]pyridine-4,5-diamine (1.1 g, 3.0 mmol) in dichloromethane (DCM) (18 mL) was treated with acetyl-D-lactic acid (530 mg, 4.0 mmol), 2-(3H-[1,2,3]triazolo[4,5-b]pyridin-3-yl)-1,1,3,3-tetramethylisouronium hexafluorophosphate(V) (HATU) (1.24 g, 3.25 mmol) and N,N-diisopropylethylamine (1.13 mL, 6.5 mmol) at room temperature for 20 h. The mixture was then washed with 10% $NaHCO_3$ in water, dried with $MgSO_4$, filtered and concentrated. Purification by flash chromatography (40 to 100% Ethyl acetate in Heptane) afforded 830 mg (58%) of (2R)-1-oxo-1-(1-(phenylsulfonyl)-4-(tetrahydro-2H-pyran-3-ylamino)-1H-pyrrolo[2,3-b]pyridin-5-ylamino)propan-2-yl acetate. LCMS (Method E, ESI): RT=1.37 min, m+H=487.2; $^{1}$H NMR (400 MHz, $CDCl_3$) δ 8.13 (d, J=7.8 Hz, 2H), 7.92 (d, J=34.9 Hz, 1H), 7.66-7.38 (m, 5H), 6.61 (t, J=14.7 Hz, 1H), 5.13 (p, J=6.9 Hz, 1H), 4.94 (t, J=7.6 Hz, 1H), 3.93 (d, J=11.5 Hz, 2H), 3.71 (dt, J=13.3, 6.5 Hz, 3H), 3.57 (s, 1H), 3.50-3.29 (m, 1H), 3.17 (q, J=7.4 Hz, 2H), 2.17 (t, J=14.0 Hz, 3H), 1.61 (t, J=13.7 Hz, 5H).

(1R)-1-(6-(phenylsulfonyl)-1-(tetrahydro-2H-pyran-3-yl)-1,6-dihydroimidazo[4,5-d]pyrrolo[2,3-b]pyridin-2-yl)ethyl acetate A solution of (2R)-1-oxo-1-(1-(phenylsulfonyl)-4-(tetrahydro-2H-pyran-3-ylamino)-1H-pyrrolo[2,3-b]pyridin-5-ylamino)propan-2-yl acetate (830 mg, 1.7 mmol) in acetic acid (10 mL) was stirred at 105° C. for 5 h, then the reaction was cooled down and concentrated. Purification by flash chromatography (40 to 100% ethyl acetate in heptane) afforded 525 mg (66%) of (1R)-1-(6-(phenylsulfonyl)-1-(tetrahydro-2H-pyran-3-yl)-1,6-dihydroimidazo[4,5-d]pyrrolo[2,3-b]pyridin-2-yl)ethyl acetate. LCMS (Method E, ESI): RT=1.49 min, m+H=469.2; $^{1}$H NMR (400 MHz, $CDCl_3$) δ 8.25-7.99 (m, 2H), 7.84 (s, 1H), 7.61-7.35 (m, 4H), 6.58 (d, J=4.2 Hz, 1H), 5.04 (t, J=12.8 Hz, 1H), 4.02-3.82 (m, 2H), 3.80-3.55 (m, 2H), 3.47 (dd, J=11.1, 6.1 Hz, 1H), 2.86 (s, 2H), 2.11-1.93 (m, 1H), 2.17 (s, 3H), 1.80 (dtd, J=14.6, 7.2, 3.7 Hz, 1H), 1.74-1.51 (m, 3H).

(R)-1-[1-(Tetrahydro-pyran-3-yl)-1,6-dihydro-1,2,3,5,6-tetraaza-as-indacen-2-yl]-ethanol A solution of (1R)-1-(6-(phenylsulfonyl)-1-(tetrahydro-2H-pyran-3-yl)-1,6-dihydroimidazo[4,5-d]pyrrolo[2,3-b]pyridin-2-yl)ethyl acetate (300 mg, 0.6 mmol) in ethanol (5 mL) was treated with 1N sodium hydroxide (3.0 mL, 3.0 mmol) at 60° C. for 5 h. The reaction mixture was then concentrated and the crude material was purified and separated from the epimeric product (Example 456, (R)-1-[(R)-1-(Tetrahydro-pyran-3-yl)-1,6-dihydro-1,2,3,5,6-tetraaza-as-indacen-2-yl]-ethanol) by preparative chiral SFC (*See below for conditions) to afford 65 mg (27%) of (R)-1-[(S)-1-(Tetrahydro-pyran-3-yl)-1,6-dihydro-1,2,3,5,6-tetraaza-as-indacen-2-yl]-ethanol. LCMS (Method C, ESI): RT=2.69 min, m+H=287.0; Chiral SFC (Method A1): RT=0.73 min, $^{1}$H NMR (400 MHz, DMSO) δ 11.88 (s, 1H), 8.55 (s, 1H), 7.49 (d, J=3.3 Hz, 1H), 6.85 (d, J=3.4 Hz, 1H), 5.74 (s, 1H), 5.14 (q, J=6.4 Hz, 1H), 5.09-4.95 (m, 1H), 4.11 (t, J=11.0 Hz, 1H), 3.97 (dd, J=10.5, 5.8 Hz, 2H), 3.69 (t, J=11.2 Hz, 1H), 2.66-2.54 (m, 1H), 2.08 (d, J=9.9 Hz, 1H), 2.00-1.74 (m, 2H), 1.64 (d, J=6.5 Hz, 3H).

*Preparative Chiral SFC Conditions:

Instrument: Mettler-Toledo MGII

Column: Chiral Technologies Chiralpak AD, 21.2×250 mm, 5 um

Detection: UV 230 nm

Mobile Phase: 35% MeOH, 65% CO2

Flowrate: 60 g/min

Runtime: 5 minutes

Back pressure setting: 100 bar

Temperature: 40° C.

Example 199a

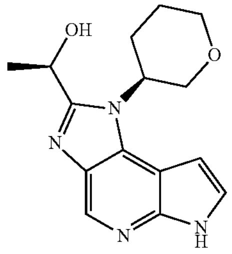 [SMILES: C[C@@H](O)c1nc2cnc3[nH]ccc3c2n1[C@H]1CCCOC1]

(R)-1-[(S)-1-(Tetrahydro-pyran-3-yl)-1,6-dihydro-1,2,3,5,6-tetraaza-as-indacen-2-yl]-ethanol (1-Benzenesulfonyl-5-nitro-1H-pyrrolo[2,3-b]pyridin-4-yl)-(S)-tetrahydro-pyran-3-yl-amine (S)-(Tetrahydro-pyran-3-yl)amine hydrochloride (40.7 g, 296.09 mmol) and N,N-diisopropylethylamine (130 mL, 760 mmol) were added to a solution of 1-Benzenesulfonyl-4-chloro-5-nitro-1H-pyrrolo[2,3-b]pyridine (100.0 g, 296.09 mmol) in ispropanol (1.0 L). The mixture was stirred at an internal temperature of 75° C. for 4 hours. The mixture was then allowed to cool down slowly and left still overnight. The resulting solid was collected by filtration and washed with cold isopropanol. The solid was then dried in a vacuum oven for 24 h to afford 114.0 g (95.7%) of (1-Benzenesulfonyl-5-nitro-1H-pyrrolo[2,3-b]pyridin-4-yl)-(S)-tetrahydro-pyran-3-yl-amine as a yellow solid. LCMS (Method D, ESI): RT=1.63 min, m+H=403.2; $^1$H NMR (400 MHz, DMSO) δ 9.21 (d, J=8.1 Hz, 1H), 8.92 (s, 1H), 8.13 (d, J=7.8 Hz, 2H), 7.77 (dt, J=25.1, 10.9 Hz, 2H), 7.66 (t, J=7.7 Hz, 2H), 7.02 (d, J=4.1 Hz, 1H), 4.28 (s, 1H), 3.88-3.65 (m, 3H), 3.56 (t, J=8.9 Hz, 1H), 2.00 (t, J=11.5 Hz, 1H), 1.93-1.63 (m, 2H), 1.53 (dd, J=9.4, 4.2 Hz, 1H), 1.28 (t, J=6.9 Hz, 1H).

1-Benzenesulfonyl-N-4-(S)-tetrahydro-pyran-3-yl-1H-pyrrolo[2,3-b]pyridine-4,5-diamine (1-Benzenesulfonyl-5-nitro-1H-pyrrolo[2,3-b]pyridin-4-yl)-(S)-tetrahydro-pyran-3-yl-amine (115.0 g, 285.8 mmol) was dissolved in ethyl acetate (2.5 L) and 10% palladium on carbon (30.0 g, 28.19 mmol) was added. The mixture was stirred at room temperature under an atmosphere of hydrogen for 48 h. The mixture was then filtered over a bed of celite and washed with 1 L of 10% methanol in dichloromethane. The filtrate was concentrated to afford 106.0 g (99.6%) 1-Benzenesulfonyl-N-4-(S)-tetrahydro-pyran-3-yl-1H-pyrrolo[2,3-b]pyridine-4,5-diamine. LCMS (Method D, ESI): RT=1.13 min, m+H=373.2; $^1$H NMR (400 MHz, $CDCl_3$) δ 8.13 (d, J=7.6 Hz, 2H), 7.84 (s, 1H), 7.62-7.38 (m, 4H), 6.58 (d, J=4.2 Hz, 1H), 5.02 (d, J=8.7 Hz, 1H), 3.92 (m, 2H), 3.80-3.55 (m, 2H), 3.47 (qd, 6.0 Hz, 1H), 2.84 (s, 2H), 2.00 (m, 1H), 1.80 (m, 1H), 1.73-1.56 (m, 3H).

(R)-1-((S)-6-Benzenesulfonyl-1-tetrahydro-pyran-3-yl-1,6-dihydro-1,2,3,5,6-tetraaza-as-indacen-2-yl)-ethanol (R)-(+)-lactamide (33.5 g, 376.0 mmol) was added to a suspension of triethyloxonium tetrafluoroborate (73.6 g, 376.0 mmol) in tetrahydrofuran (800 mL) and the mixture was stirred for an hour while the suspension turned to a clear solution. This solution was then added to a solution of 1-Benzenesulfonyl-N-4-(S)-tetrahydro-pyran-3-yl-1H-pyrrolo[2,3-b]pyridine-4,5-diamine (70.0 g, 188.0 mmol) in ethanol (1.5 L) and the solution was stirred at an internal temperature of 67° C. for 2 hours. The solution was then cooled down and 500 mL of ethyl acetate was added. The mixture was left still overnight. The resulting solid was collected by filtration and washed with cold ethyl acetate. Dried under vacuum overnight to afford 60.9 g (80.2%) of (R)-1-((S)-6-Benzenesulfonyl-1-tetrahydro-pyran-3-yl-1,6-dihydro-1,2,3,5,6-tetraaza-as-indacen-2-yl)-ethanol. LCMS (Method D, ESI): RT=1.34 min, m+H=427.2;

(R)-1-[(S)-1-(Tetrahydro-pyran-3-yl)-1,6-dihydro-1,2,3,5,6-tetraaza-as-indacen-2-yl]-ethanol (R)-1-((S)-6-Benzenesulfonyl-1-tetrahydro-pyran-3-yl-1,6-dihydro-1,2,3,5,6-tetraaza-as-indacen-2-yl)-ethanol (40.0 g, 93.8 mmol) was suspended in ethanol (50 mL) and 9N sodium hydroxide solution (30 mL, 281.4 mmol) was added. The mixture was stirred at 60° C. for 1 h. The mixture was then concentrated to remove ethanol. The aqueous solution was cooled down to 0° C. and neutralized with concentrated aqueous hydrochloric acid. The resulting solid was removed by filtration. The filtrate was concentrated. The residue was taken up in 200 mL of a 1:1 mixture of ethanol and ethyl acetate. The resulting solid was removed by filtration and washed with ethyl acetate. The filtrate was concentrated and the residue was dissolved in 150 mL of methanol and treated with MP-carbonate resin (30 g) to remove the remainder phenylsulfonic acid (monitored by $^1$H NMR). The resin was removed by filtration and washed with methanol. The filtrate was concentrated. The residue was recrystallized in hot acetonitrile (20v). The solid was collected by filtration and washed with cold acetonitrile. The solid was taken up in 15 mL of water and concentrated to afford 10.6 g (39.5%) of (R)-1-[(S)-1-(Tetrahydro-pyran-3-yl)-1,6-dihydro-1,2,3,5,6-tetraaza-as-indacen-2-yl]-ethanol. LCMS (Method A, ESI): RT=3.60 min, m+H=287.00; $^1$H NMR (400 MHz, DMSO) δ 11.88 (s, 1H), 8.55 (s, 1H), 7.49 (d, J=3.3 Hz, 1H), 6.85 (d, J=3.4 Hz, 1H), 5.74 (s, 1H), 5.14 (q, J=6.4 Hz, 1H), 5.09-4.95 (m, 1H), 4.11 (t, J=11.0 Hz, 1H), 3.97 (dd, J=10.5, 5.8 Hz, 2H), 3.69 (t, J=11.2 Hz, 1H), 2.66-2.54 (m, 1H), 2.08 (d, J=9.9 Hz, 1H), 2.00-1.74 (m, 2H), 1.64 (d, J=6.5 Hz, 3H).

Example 200

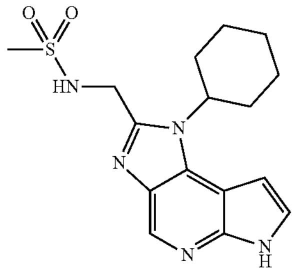 [SMILES: CS(=O)(=O)NCc1nc2cnc3[nH]ccc3c2n1C1CCCCC1]

N-(1-Cyclohexyl-1,6-dihydro-1,2,3,5,6-tetraaza-as-indacen-2-ylmethyl)-methanesulfonamide 6-Benzenesulfonyl-2-chloromethyl-1-cyclohexyl-1,6-dihydro-1,2,3,5,6-tetraaza-as-indacene A stirred suspension of 1-benzenesulfonyl-N*4*-cyclohexyl-1H-pyrrolo[2,3-b]pyridine-4,5-diamine (2.00 g, 5.4 mmol) and 2-chloro-1,1,1-triethyoxyethane (3.18 g, 16.2 mmol) in acetic acid (6 ml) was heated at 125° C. for 20 min. The mixture was cooled, diluted with DCM and stirred over aqueous sodium bicarbonate solution. The organic layer separated, washed with water, brine, and dried with sodium sulfate and concentrated in vacuo to give crude product. Trituration (heptane/ethyl acetate) afforded 1.60 g (69%) of 6-benzenesulfonyl-2-chloromethyl-1-cyclohexyl-1,6-dihydro-1,2,3,5,6-tetraaza-as-indacene: LCMS (Method F, ESI): RT=1.17 min, m+H=429.2; 1H NMR (500 MHz, $CDCl_3$) δ 8.86 (s, 1H), 8.23 (d, J=8.0 Hz, 2H), 7.84 (d, J=3.9 Hz, 1H), 7.51 (m, 3H), 6.96 (s, 1H), 4.87 (s, 2H), 4.48 (s, 1H), 2.37-2.16 (m, 2H), 2.12-1.95 (m, 4H), 1.91 (d, J=12.4 Hz, 1H), 1.59-1.37 (m, 2H), 1.37-1.16 (m, 1H).

N-(6-Benzenesulfonyl-1-cyclohexyl-1,6-dihydro-1,2,3,5,6-tetraaza-as-indacen-2-ylmethyl)-methanesulfonamide To a solution of 6-benzenesulfonyl-2-chloromethyl-1-cyclohexyl-1,6-dihydro-1,2,3,5,6-tetraaza-as-indacene (1.35 g, 3.15 mmol) dissolved in DMF (10 ml) was added N-(tert-butoxycarbonyl)methylsulfonamide (0.92 g, 4.7 mmol) and potassium carbonate (0.87 g, 6.3 mmol). The mixture was stirred at 50° C. for 20 h, cooled and diluted with water. The solid was collected by filtration while washing with water. The solid was then dissolved in DCM and washed with water, brine, dried over sodium sulphate and concentrated. Trituaration (heptane/ethyl acetate) afforded (1.4 g, 76%) of N-(6-benzenesulfonyl-1-cyclohexyl-1,6-dihydro-1,2,3,5,6-tetraaza-as-indacen-2-ylmethyl)-N-(tert-butoxycarbonyl) methanesulfonamide: LCMS (Method F, ESI): RT=1.28 min, M+1=588.3. This solid was suspended in a mixture of 48% HBr (0.54 mL) and acetic acid (10 mL) and heated at 60° C. for 2 h. Cooled and diluted with water and the solid was collected by filtration, washed with water and dried to afford N-(6-benzenesulfonyl 1-cyclohexyl-1,6-dihydro-1,2,3,5,6-tetraaza-as-indacen-2-ylmethyl)-methanesulfonamide (1.0 g, 86.2%): LCMS (method F, ESI):RT=1.00, M+1=488.3. $^{1}$H NMR (400 MHz, $CDCl_3$) δ 8.76 (s, 1H), 8.23 (d, J=7.8 Hz, 2H), 7.84 (d, J=4.0 Hz, 1H), 7.66-7.36 (m, 2H), 6.96 (s, 1H), 5.56 (s, 1H), 4.64 (d, J=5.5 Hz, 2H), 4.57-4.37 (m, 1H), 3.04 (s, 3H), 2.31-1.76 (m, 5H), 1.56-1.32 (m, 4H).

N-(1-Cyclohexyl-1,6-dihydro-1,2,3,5,6-tetraaza-as-indacen-2-ylmethyl)-methanesulfonamide N-(6-Benzenesulfonyl)-cyclohexyl-1,6-dihydro-1,2,3,5,6-tetraaza-as-indacen-2-ylmethyl)-methanesulfonamide (1.0 g) was suspended in isopropanol (5 mL) and 1N NaOH (4.8 mL) and heated at 50 deg for 20 h. The reaction mixture was cooled and 1N HCl 4.8 mL) was added and the mixture was concentrated in vacuo. Purification of the residue by reverse phase HPLC afforded N-(1-cyclohexyl-1,6-dihydro-1,2,3,5,6-tetraaza-as-indacen-2-ylmethyl)-methanesulfonamide (0.61 g, 86%): LCMS (Method C, ESI): RT=8.18 min, m+H=348.1.

Example 201

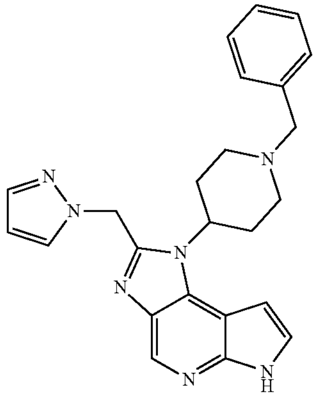 [SMILES: c1ccc(CN2CCC(n3c(Cn4cccn4)nc4cnc5[nH]ccc5c43)CC2)cc1]

1-(1-Benzyl-piperidin-4-yl)-2-pyrazol-1-ylmethyl-1,6-dihydro-1,2,3,5,6-tetraaza-as-indacene To an ice-cold mixture of 1-benzenesulfonyl-N*4*-(1-benzyl-piperidin-4-yl)-1H-pyrrolo[2,3-b]pyridine-4,5-diamine 1.30 g, 2.80 mmol) and triethylamine (0.59 mL, 4.20 mmol) in DCM (50 mL) was added chloroacetyl chloride (0.25 mL, 3.10 mmol) and the mixture was stirred 2 h. The reaction mixture was diluted with DCM, washed with water, brine, and dried over sodium sulphate. The residue was purified by flash (silica gel. 0-5% MeOH/DCM) to afford N-[1-Benzenesulfonyl-4-(1-benzyl-piperidin-4-ylamino)-1H-pyrrolo[2,3-b]pyridin-5-yl]-2-chloro-acetamide (1.10 g, 72%): LCMS (method E, ESI): RT=1.2 min; m+1=538.2.

6-Benzenesulfonyl-1-(1-benzyl-piperidin-4-yl)-2-chloromethyl-1,6-dihydro-1,2,3,5,6-tetraaza-as-indacene A mixture of N-[1-benzenesulfonyl-4-(1-benzyl-piperidin-4-ylamino)-1H-pyrrolo[2,3-b]pyridin-5-yl]-2-chloro-acetamide (1.2 g, 2.2 mmol) in acetic acid (5 mL) was heated at 100° C. for 20 h. Cooled, diluted with EtOAc, stirred over aqueous sodium bicarbonate solution. The organic layer separated washed with water, brine, dried over sodium sulphate and concentrated in vacuo. The residue was purified by flash (silica gel, 80% EtOAc/heptane) to afford 6-benzenesulfonyl-1-(1-benzyl-piperidin-4-yl)-2-chloromethyl-1,6-dihydro-1,2,3,5,6-tetraaza-as-indacene (0.50 g, 40%): LCMS (method E, ESI): RT=1.23 min, m+1=521.

1-(1-Benzyl-piperidin-4-yl)-2-pyrazol-1-ylmethyl-1,6-dihydro-1,2,3,5,6-tetraaza-as-indacene To an ice-cold solution of 6-benzenesulfonyl-1-(1-benzyl-piperidin-4-yl)-2-chloromethyl-1,6-dihydro-1,2,3,5,6-tetraaza-as-indacene (0.17 g, 0.33 mmol) and pyrazole (0.044 g, 0.65 mmol) in DMF (3 mL) was added 60% NaH dispersion (0.026 mg, 0.65 mmol) and the mixture was stirred for 2 h. The reaction mixture was quenched with water (1 mL) and stirred for 2 h. The reaction mixture was diluted with water, extracted with ethyl acetate. The organic layer washed with water, brine, dried over sodium sulphate and concentrated in vacuo. Purification by reverse phase HPLC afforded 1-(1-benzyl-piperidin-4-yl)-2-pyrazol-1-ylmethyl-1,6-dihydro-1,2,3,5,6-tetraaza-as-indacene (0.047 g, 35%): LCMS (Method C, ESI) RT=2.99 min, m+1=412.2; $^1$H NMR (400 MHz, DMSO) δ 8.57 (s, 1H), 7.83 (d, J=2.2 Hz, 1H), 7.64-7.17 (m, 7H), 6.96 (s, 1H), 6.29 (t, J=2.0 Hz, 1H), 5.80 (s, 2H), 4.88-4.49 (m, 1H), 3.59 (s, 2H), 2.99 (m, 2H), 2.58-2.33 (m, 2H), 2.10 (m, 2H), 1.58 (m, 2H).

Example 202

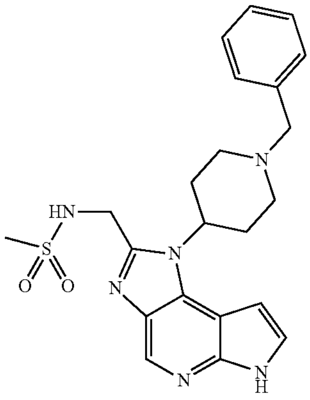 [SMILES: CS(=O)(=O)NCc1nc2cnc3[nH]ccc3c2n1C1CCN(Cc2ccccc2)CC1]

N-[1-(1-Benzyl-piperidin-4-yl)-1,6-dihydro-1,2,3,5,6-tetraaza-as-indacen-2-ylmethyl]-methanesulfonamide N-[6-Benzenesulfonyl-1-(1-benzyl-piperidin-4-yl)-1,6-dihydro-1,2,3,5,6-tetraaza-as-indacen-2-ylmethyl]-N-(tert-butoxycarbonyl)methanesulfonamide A mixture of 6-benzenesulfonyl-1-(1-benzyl-piperidin-4-yl)-2-chloromethyl-1,6-dihydro-1,2,3,5,6-tetraaza-as-indacene (0.4 g, 0.08 mmol), N-(tert-butoxycarbony)methane sulfonamide (0.27 g, 2.40 mmol) and potassium carbonate (0.21 g, 1.50 mmol) in acetonitrile (10 mL) was heated at 80° C. for 20 h. The reaction mixture was cooled, diluted with ethyl acetate, washed with water, brine, dried over sodium sulphate and concentrated in vacuo. The residue was purified by flash chromatography (silica gel, 20-40% EtOAc/heptane) to obtain N-[6-benzenesulfonyl-1-(1-benzyl-piperidin-4-yl)-1,6-dihydro-1,2,3,5,6-tetraaza-as-indacen-2-ylmethyl]-N-tert-(butoxycarbonyl)methanesulfonamide (0.25 g, 50%): LCMS (method E, ESI): RT=0.88 min; m+1=579.3

N-[1-(1-Benzyl-piperidin-4-yl)-1,6-dihydro-1,2,3,5,6-tetraaza-as-indacen-2-ylmethyl]-methanesulfonamide A mixture N-[6-benzenesulfonyl-1-(1-benzyl-piperidin-4-yl)-1,6-dihydro-1,2,3,5,6-tetraaza-as-indacen-2-ylmethyl]-N-tert-(butoxycarbonyl)methanesulfonamide (0.25 g, 0.37 mmol) in TFA/DCM (0.3 mL/4 mL) was stirred at ambient for 20 h. The reaction mixture was concentrated and to the residue was added methanol (5 mL), water (1 mL) and sodium hydroxide (0.75 mg, 1.8 mmol) and the mixture was heated at 50° C. for 20 h. The reaction mixture was concentrated to dryness and the residue was purified by flash chromatography (silica gel, 0-10% MeOH/DCM) to obtain N-[1-(1-benzyl-piperidin-4-yl)-1,6-dihydro-1,2,3,5,6-tetraaza-as-indacen-2-ylmethyl]-methanesulfonamide (0.06 g, 20%): LCMS (method C, ESI): RT=2.59 min; m+1=439.2; $^1$H NMR (400 MHz, $CDCl_3$) δ 10.09 (s, 1H), 8.66 (s, 1H), 7.55-7.27 (m, 6H), 7.02 (d, J=21.8 Hz, 1H), 6.86 (s, 1H), 4.68 (s, 2H), 4.49 (s, 1H), 3.62 (s, 2H), 3.10 (s, 5H), 2.60 (d, J=9.6 Hz, 2H), 2.39-1.53 (m, 6H).

Example 203

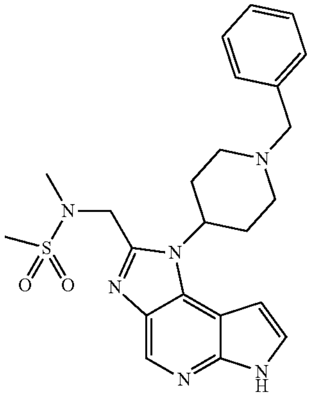 [SMILES: CN(Cc1nc2cnc3[nH]ccc3c2n1C1CCN(Cc2ccccc2)CC1)S(C)(=O)=O]

N-[1-(1-Benzyl-piperidin-4-yl)-1,6-dihydro-1,2,3,5,6-tetraaza-as-indacen-2-ylmethyl]-N-methyl-methanesulfonamide N-[1-(1-benzyl-piperidin-4-yl)-1,6-dihydro-1,2,3,5,6-tetraaza-as-indacen-2-ylmethyl]-N-methyl-methanesulfonamide (0.04 g, 20%) was isolated from the above reaction: LCMS (method C, ESI): RT=2.79 min, m+1=453.2; $^1$H NMR (400 MHz, $CDCl_3$) δ 10.24 (s, 1H), 8.74 (s, 1H), 7.63-7.09

(m, 8H), 4.89 (s, 1H), 4.71 (s, 2H), 3.62 (s, 2H), 3.12 (m, 2H), 2.95 (s, 3H), 2.87-2.65 (m, 5H), 2.40-2.20 (m, 2H), 1.89 (m, 2H).

Example 204

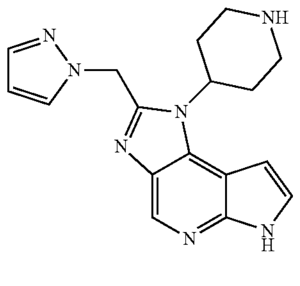 [SMILES: c1cnn(Cc2nc3cnc4[nH]ccc4c3n2C2CCNCC2)c1]

1-Piperidin-4-yl-2-pyrazol-1-ylmethyl-1,6-dihydro-1,2,3,5,6-tetraaza-as-indacene 4-(6-Benzenesulfonyl-2-chloromethyl-6H-1,2,3,5,6-tetraaza-as-indacen-1-yl)-piperidine-1-carboxylic acid tert-butyl ester A mixture of 4-(5-amino-1-benzenesulfonyl-1H-pyrrolo[2,3-b]pyridin-4-ylamino)-piperidine-1-carboxylic acid tert-butyl ester (1.00 g, 2.10 mmol) and 2-chloro-1,1,1-triethyoxyethane (2 mL, 10 mmol) in acetic acid (5 mL) was heated at 120° C. for 20 min. The reaction mixture was cooled, diluted with ethyl acetate, stirred over aqueous sodium bicarbonate solution. Organic layer separated, washed with water, brine dried over sodium sulfate and concentrated in vacuo. Trituration (heptane/ethyl acetate) afforded 4-(6-benzenesulfonyl-2-chloromethyl-6H-1,2,3,5,6-tetraaza-as-indacen-1-yl)-piperidine-1-carboxylic acid tert-butyl ester (1.00 g, 80%): LCMS (method E, ESI): RT=1.76 min, m+1=531.3.

1-Piperidin-4-yl-2-pyrazol-1-ylmethyl-1,6-dihydro-1,2,3,5,6-tetraaza-as-indacene To an ice-cold mixture of 4-(6-benzenesulfonyl-2-chloromethyl-6H-1,2,3,5,6-tetraaza-as-indacen-1-yl)-piperidine-1-carboxylic acid tert-butyl ester (0.80 g, 2.00 mmol) and pyrazole (0.20 g, 3.00 mmol) in DMF (5 mL) was added 60% NaH dispersion (0.09 g, 2.30 mmol) and the mixture was stirred for 20 h. The mixture was diluted with water and the solid was collected by filtration to afford 4-(6-benzenesulfonyl-2-pyrazol-1-ylmethyl-6H-1,2,3,5,6-tetraaza-as-indacen-1-yl)-piperidine-1-carboxylic acid tert-butyl ester (0.15 g, 20%). The filtrate was concentrated in vacuo to afford crude 4-(2-pyrazol-1-ylmethyl-6H-1,2,3,5,6-tetraaza-as-indacen-1-yl)-piperidine-1-carboxylic acid tert-butyl ester (0.2 g, 30%). This intermediate was treated with 4N HCl/dioxane (5 mL) for 1 h. The solid was collected by filtration and was purified by reverse phase HPLC to afford 1-piperidin-4-yl-2-pyrazol-1-ylmethyl-1,6-dihydro-1,2,3,5,6-tetraaza-as-indacene (68 mg, 68%): LCMS (Method C, ESI): RT=2.31 min, m+1=322.1; $^{1}$H NMR (400 MHz, DMSO) δ 11.87 (s, 1H), 8.54 (s, 1H), 7.84 (d, J=2.2 Hz, 1H), 7.47 (dd, J=7.1, 2.2 Hz, 2H), 6.98 (s, 1H), 6.30 (t, J=2.1 Hz, 1H), 5.80 (s, 2H), 4.82-4.55 (m, 2H), 3.23-2.91 (m, 2H), 2.74-2.22 (m, 4H), 1.48 (s, 2H).

Example 205

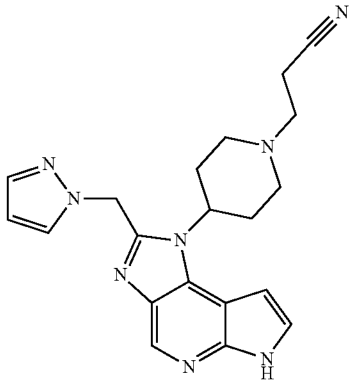 [SMILES: N#CCCN1CCC(n2c(Cn3cccn3)nc3cnc4[nH]ccc4c32)CC1]

3-[4-(2-Pyrazol-1-ylmethyl-6H-1,2,3,5,6-tetraaza-as-indacen-1-yl)-piperidin-1-yl]-propionitrile 4-(6-Benzenesulfonyl-2-pyrazol-1-ylmethyl-6H-1,2,3,5,6-tetraaza-as-indacen-1-yl)-piperidine-1-carboxylic acid tert-butyl ester (0.12 g, 0.21 mmol) was treated with 4N HCl/dioxane for 2 h. The solvent was removed in vacuo and the residue was suspended in DCM (3 mL) and triethylamine (0.30 ml, 3.00 mmol) and acrylonitrile (0.10 mL, 2.00 mmol) were added and heated at 50° C. for 20 h. The reaction mixture was concentrated in vacuo and purified by flash chromatography (silica gel, 0-5% MeOH/DCM) to obtain 3-[4-(6-benzenesulfonyl-2-pyrazol-1-ylmethyl-6H-1,2,3,5,6-tetraaza-as-indacen-1-yl)-piperidin-1-yl]-propionitrile (0.06 g, 58%): LCMS (Method E, ESI): RT=1.16 in, m+1=515.2.

The above residue was dissolved in ethanol (2 mL) and 1N NaOH (1 mL) was added and heated at 50° C. for 2 h. Cooled, concentrated and purification by reverse phase HPLC provided 3-[4-(2-pyrazol-1-ylmethyl-6H-1,2,3,5,6-tetraaza-as-indacen-1-yl)-piperidin-1-yl]-propionitrile (0.02 g, 20%): LCMS (Method C, ESI): RT=2.44 min; m+1=375.1; $^{1}$H NMR (400 MHz, DMSO) δ 8.58 (s, 1H), 7.85 (d, J=2.2 Hz, 1H), 7.48 (d, J=1.6 Hz, 1H), 7.42 (d, J=3.4 Hz, 1H), 6.94 (d, J=3.4 Hz, 1H), 6.30 (t, J=2.0 Hz, 1H), 5.92-5.68 (m, 2H), 4.79-4.56 (m, 1H), 3.16-3.00 (m, 2H), 2.76 (t, J=6.4 Hz, 2H), 2.67 (t, J=6.4 Hz, 2H), 2.58-2.38 (m, 2H), 2.23-2.10 (m, 2H), 1.65-1.54 (m, 2H).

Example 206

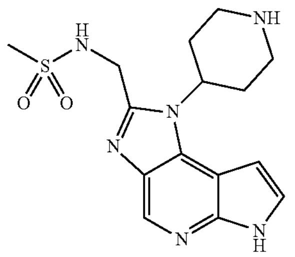 [SMILES: CS(=O)(=O)NCc1nc2cnc3[nH]ccc3c2n1C1CCNCC1]

N-(1-Piperidin-4-yl-1,6-dihydro-1,2,3,5,6-tetraaza-as-indacen-2-ylmethyl)-methanesulfonamide N-(1-Piperidin-4-yl-1,6-dihydro-1,2,3,5,6-tetraaza-as-indacen-2-ylmethyl)-methanesulfonamide A mixture of 4-(6-benzenesulfonyl-2-chloromethyl-6H-1,2,3,5,6-tetraaza-as-indacen-1-yl)-piperidine-1-carboxylic acid tert-butyl ester (1.0 g, 2.8 mmol), N-(tert-butoxycarbony)methanesulfonamide (0.55 g, 11 mmol) and potassium carbonate (0.78 g, 5.60 mmol) in acetonitrile (10 mL) was heated at 90° C. for 20 h. The reaction mixture was cooled, diluted with water, extracted with ethyl acetate. The organic layer washed with water, brine, dried over sodium sulfate and concentrated in vacuo and purified by flash chromatography (silica gel, 30-100% EtOAc/heptane) to afford tert-butyl 4-(2-4N-(tert-butoxycarbonyl)methylsulfonamido)methyl)-6-(phenylsulfonyl)imidazo[4,5-d]pyrrolo[2,3-b]pyridin-1(6H)-yl)piperidine-1-carboxylate (0.53 g, 53%): LCMS (Method E, ESI): RT=2.03 min, m+1=689.1

A mixture of tert-butyl 4-(2-4N-(tert-butoxycarbonyl)methylsulfonamido)methyl)-6-(phenylsulfonyl)imidazo[4,5-d]pyrrolo[2,3-b]pyridin-1(6H)-yl)piperidine-1-carboxylate (0.50 g, 0.72 mmol) in 4N HCl/dioxane (5 mL) was stirred at ambient temperature for 20 h. The solid was collected by filtration washed with ethyl acetate and suspended (0.10 g) in ethanol (3 mL) and 1N NaOH (4 mL) was added and heated at 60° C. for 2 h. Cooled and concentrated in vacuo. Purification by reverse phase HPLC afforded N-(1-piperidin-4-yl-1,6-dihydro-1,2,3,5,6-tetraaza-as-indacen-2-ylmethyl)-methanesulfonamide (0.012 mg, 25%): LCMS (method C, ESI): RT=1.35 min; m+1=349.1; $^1$H NMR (400 MHz, DMSO) δ 11.83 (d, J=20.3 Hz, 1H), 8.54 (d, J=5.1 Hz, 1H), 7.79 (s, 1H), 7.44 (d, J=27.0 Hz, 1H), 7.01 (d, J=2.9 Hz, 1H), 4.76-4.45 (m, 3H), 3.16 (d, J=11.3 Hz, 2H), 2.96 (s, 3H), 2.76-2.56 (m, 2H), 2.46-2.24 (m, 3H), 1.92-1.64 (m, 2H).

Example 207

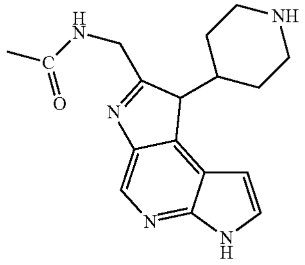 [SMILES: CC(=O)NCC1=Nc2cnc3[nH]ccc3c2C1C1CCNCC1]

N-(1-Piperidin-4-yl-1,6-dihydro-1,2,3,5,6-tetraaza-as-indacen-2-ylmethyl)-acetamide 4-[2-(Acetylamino-methyl)-6-benzenesulfonyl-6H-1,2,3,5,6-tetraaza-as-indacen-1-yl]-piperidine-1-carboxylic acid tert-butyl ester A mixture of 4-(5-amino-1-benzene sulfonyl-1H-pyrrolo[2,3-b]pyridin-4-ylamino)-piperidine-1-carboxylic acid tert-butyl ester (1.00 g, 2.12 mmol), N-acetylglycine (0.30 g, 2.5 mmol), HBTU (1.0 g, 2.8 mmol) and DIEA (1.1 mL, 6.4 mmol) in DMF (5 mL) was stirred at ambient temperature for 20 h. Diluted with water and the solid was collected by filtration, washed with water and dried in vacuum oven at 50° C. for 20 h to afford 4-[5-(2-Acetylamino-acetylamino)-1-benzenesulfonyl-1H-pyrrolo[2,3-b]pyridin-4-ylamino]-piperidine-1-carboxylic acid tert-butyl ester (1.20 g, 99%). This intermediate was suspended in acetic acid (6 mL) and heated at 100° C. for 7 h. Cooled, diluted with DCM and stirred over aqueous sodium bicarbonate solution. Organic layer separated, washed with water, brine dried over sodium sulfate and concentrated in vacuo. The residue was purified by flash chromatography (silica gel, 0-10% MeOH/DCM) to afford 4-[2-(acetylamino-methyl)-6-benzenesulfonyl-6H-1,2,3,5,6-tetraaza-as-indacen-1-yl]-piperidine-1-carboxylic acid tert-butyl ester (0.26 g, 24%): LCMS (Method E, ESI): RT=1.53 min, m+1=553.2.

N-(1-Piperidin-4-yl-1,6-dihydro-1,2,3,5,6-tetraaza-as-indacen-2-ylmethyl)-acetamide 4-[2-(Acetylamino-methyl)-6-benzenesulfonyl-6H-1,2,3,5,6-tetraaza-as-indacen-1-yl]-piperidine-1-carboxylic acid tert-butyl ester (0.10 g, 0.18 mmol) was treated with 4N HCl/dioxane (3 mL) at ambient temperature for 20 h. The solvent was removed and the residue was dissolved in ethanol (3 ml) and 1N NAOH (1 mL) was added and heated at 50° C. for 3 h. Cooled and concentrated. Purification by reverse phase HPLC afforded N-(1-piperidin-4-yl-1,6-dihydro-1,2,3,5,6-tetraaza-as-indacen-2-ylmethyl)-acetamide (10 mg, 18%): LCMS (method C, ESI): RT=1.40 min, m+1=313.1; $^1$H NMR (400 MHz, DMSO) δ 11.84 (s, 1H), 8.67-8.39 (m, 2H), 7.58-7.34 (m, 1H), 6.98 (s, 1H), 4.74-4.59 (m, 2H), 4.53

(s, 1H), 3.23-3.11 (m, 2H), 2.74-2.55 (m, 2H), 2.36 (m, 3H), 1.88 (s, 3H), 1.81-1.63 (m, 2H).

Example 208

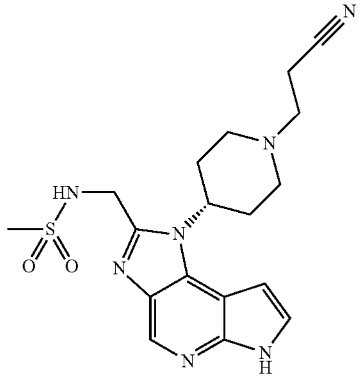

N-{1-[1-(2-Cyano-ethyl)-piperidin-4-yl]-1,6-dihydro-1,2,3,5,6-tetraaza-as-indacen-2-ylmethyl}-methanesulfonamide A mixture of N-(6-benzenesulfonyl-1-piperidin-4-yl-1,6-dihydro-1,2,3,5,6-tetraaza-as-indacen-2-ylmethyl)-methanesulfonamide (0.30 g, 0.5 mmol), acrylonitrile (0.3 mL, 4.5 mmol) and triethyl amine (50 μL) in ethanol (3 ml) was heated at 60° C. for 20 h. Cooled, concentrated and the residue was dissolved in ethanol (5 mL) and 1N NAOH was added and heated at 50° C. for 2 hrs. Cooled, concentrated. Purification by reverse phase HPLC provided N-{1-[1-(2-cyano-ethyl)-piperidin-4-yl]-1,6-dihydro-1,2,3,5,6-tetraaza-as-indacen-2-ylmethyl}-methanesulfonamide (0.10, 50%): LCMS (method C, ESI): RT=2.15 min, m+1=402.1; $^1$H NMR (400 MHz, DMSO) δ 8.54 (s, 1H), 7.41 (d, J=3.3 Hz, 1H), 6.97 (d, J=3.4 Hz, 1H), 4.76 (m, 1H), 4.48 (s, 2H), 3.22-3.03 (m, 3H), 2.85-2.64 (m, 7H), 2.66-2.52 (m, 2H), 2.23 (m, 2H)

Example 209

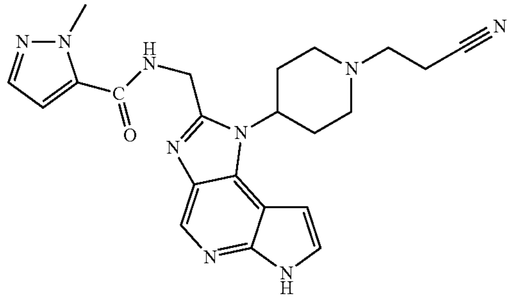 [SMILES: Cn1nccc1C(=O)NCc1nc2cnc3[nH]ccc3c2n1C1CCN(CCC#N)CC1]

2-Methyl-2H-pyrazole-3-carboxylic acid {1-[1-(2-cyano-ethyl)-piperidin-4-yl]-1,6-dihydro-1,2,3,5,6-tetraaza-as-indacen-2-ylmethyl}-amide 3-[4-(6-Benzenesulfonyl-2-chloromethyl-6H-1,2,3,5,6-tetraaza-as-indacen-1-yl)-piperidin-1-yl]-propionitrile A mixture of 3-[4-(5-amino-1-benzenesulfonyl-1H-pyrrolo[2,3-b]pyridin-4-ylamino)-piperidin-1-yl]-propionitrile (5.0 g, 10.00 mmol) and 2-chloro-1,1,1-triethyoxyethane (13 mL, 71.00 mmol) in acetic acid (30 mL) was lowered into a bath at 120° C. and heated for 20 min. Cooled, diluted with DCM, stirred over aqueous sodium bicarbonate solution. Organic layer washed with water, brine, dried over sodium sulfate and concentrated in vacuo. Trituration (EtOAc/heptane) afforded 3-[4-(6-benzenesulfonyl-2-chloromethyl-6H-1,2,3,5,6-tetraaza-as-indacen-1-yl)-piperidin-1-yl]-propionitrile (3.8 g, 63.3%): LCMS (method F, ESI): RT=0.67 min, m+1=483.2.

3-[4-(2-Aminomethyl-6-benzenesulfonyl-6H-1,2,3,5,6-tetraaza-as-indacen-1-yl)-piperidin-1-yl]-propionitrile A mixture of 3-[4-(6-benzenesulfonyl-2-chloromethyl-6H-1,2,3,5,6-tetraaza-as-indacen-1-yl)-piperidin-1-yl]-propionitrile (3.8 g, 7.90 mmol), sodium azide (2.60 g, 39.00 mmol) in DMF (10 mL) was stirred at ambient temperature for 20 h. Water was added and the solid was collected by filtration and washed well with water. The solid was dissolved in DCM, washed with brine, dried over sodium sulfate, concentrated and the residue purified by flash chromatography (silica gel, 80-100% EtOAc/heptane) to afford 3-[4-(2-azidomethyl-6-benzenesulfonyl-6H-1,2,3,5,6-tetraaza-as-indacen-1-yl)-piperidin-1-yl]-propionitrile (3.00 g, 79%): LCMS (method F, ESI): RT=0.65 min; m+1=490.3. This intermediate was dissolved in ethanol (60 mL) and 10% Pd—C (0.5 g) was added and the mixture was stirred under 1 atm $H_2$ pressure at ambient temperature for 20 h. The catalyst was removed by filtration through Celite® and concentrated in vacuo. The residue was purified by flash chromatography (0-10% 2N ammonia-methanol/DCM) to afford (1.60 g, 44%): LCMS (Method F, ESI): RT=0.49 min; m+1=464.3.

To a solution 3-[4-(2-aminomethyl-6-benzenesulfonyl-6H-1,2,3,5,6-tetraaza-as-indacen-1-yl)-piperidin-1-yl]-propionitrile (0.10 g, 0.22 mmol) in DCM (2 mL) was added TEA (0.09 mL, 0.65 mmol) and 2-methyl-2H-pyrazole-3-carbonyl chloride (0.06 mg, 0.40 mmol) and the mixture was stirred for 2 hrs. The reaction mixture was stirred over sodium bicarbonate solution (2 mL), the organic layer separated and concentrated. To the residue was added 1N NaOH (1 mL) and the mixture was heated at 50° C. for 20 h. To this was added 1N HCl (1 mL) and the mixture was concentrated in vacuo. Purification by reverse phase HPLC afforded 2-methyl-2H-pyrazole-3-carboxylic acid {1-[1-(2-cyano-ethyl)-piperidin-4-yl]-1,6-dihydro-1,2,3,5,6-tetraaza-as-indacen-2-ylmethyl}-amide (58.7 mg, 61.7%): LCMS (method C, ESI): RT=2.41 min; m+1=432.2; $^1$H NMR (400 MHz, DMSO) δ 11.82 (s, 1H), 9.16 (t, J=5.4 Hz, 1H), 9.16 (t, J=5.4 Hz, 1H), 8.55 (s, 1H), 7.45 (d, J=2.0 Hz, 1H), 7.42 (t, J=2.9 Hz, 1H), 6.95 (s, 1H), 6.92 (d, J=2.0 Hz, 1H), 4.86 (d, J=5.6 Hz, 2H), 4.72-4.60 (m, 1H), 4.09 (s, 3H), 3.18-3.04 (m, 2H), 2.81-2.71 (m, 2H), 2.72-2.63 (m, 2H), 2.63-2.54 (m, 2H), 2.26-2.10 (m, 2H), 1.93-1.73 (m, 2H).

Example 210

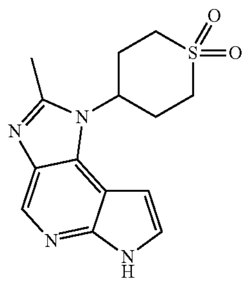 [SMILES: Cc1nc2cnc3[nH]ccc3c2n1C1CCS(=O)(=O)CC1]

1-(1,1-Dioxo-hexahydro-1-thiopyran-4-yl)-2-methyl-1,6-dihydro-1,2,3,5,6-tetraaza-as-indacene (1-Benzenesulfonyl-5-nitro-1H-pyrrolo[2,3-b]pyridin-4-yl)-(tetrahydro-thiopyran-4-yl)-amine A mixture 1-benzenesulfonyl-4-chloro-5-nitro-1H-pyrrolo[2,3-b]pyridine (0.50 g, 1.50 mmol) and tetrahydro-thiopyran-4-ylamine (0.19 g, 1.60 mmol) and DIEA (0.52 mL, 3.00 mmol) in IPA (4 mL) was heated in a microwave reactor at 120° C. for 10 minutes. The mixture was diluted with EtOAc, washed with water, brine, dried over sodium sulfate and then purified by column chromatography on silica gel (gradient: 0 to 30% ethyl acetate/heptane) to afford (1-benzenesulfonyl-5-nitro-1H-pyrrolo[2,3-b]pyridin-4-yl)-(tetrahydro-thiopyran-4-yl)-amine (0.53 g, 86%). $^1$H NMR (400 MHz, $CDCl_3$) δ 9.18-9.03 (m, 2H), 8.26-8.12 (m, 2H), 7.70-7.46 (m, 4H), 6.65 (d, J=4.2 Hz, 1H), 4.07-3.91 (m, 1H), 2.88-2.70 (m, 4H), 2.49-2.34 (m, 2H), 2.05-1.76 (m, 2H).

6-Benzenesulfonyl-2-methyl-1-(tetrahydro-thiopyran-4-yl)-1,6-dihydro-1,2,3,5,6-tetraaza-as-indacene To a vigorously mixture of (1-benzenesulfonyl-5-nitro-1H-pyrrolo[2,3-b]pyridin-4-yl)-(tetrahydro-thiopyran-4-yl)-amine (0.25 g, 0.60 mmol) and zinc dust (0.50 g, 8.00 mmol) in DCM (5 mL) was added acetic acid (0.50 ml). After 15 min of stirring, the solids were removed by filtration through Celite® and concentrated. The residue was dissolved in acetic acid (3 mL) and trimethylorthoacetate (0.50 mL, 4.00 mmol) was added and the mixture was heated at 120° C. for 20 min. Cooled, concentrated, and treated with oxone (1.10 g) in methanol/water. The solid was collected by filtration and washed with water and carried onto next step.

1-(1,1-Dioxo-hexahydro-1-thiopyran-4-yl)-2-methyl-1,6-dihydro-1,2,3,5,6-tetraaza-as-indacene The above solid was suspended in ethanol (5 mL) and 1N NaOH (2 mL) was added and heated at 50° C. for 20 h. The reaction was cooled and concentrated in vacuo and the residue was purified by reverse phase HPLC afforded 6-benzenesulfonyl-1-(1,1-dioxo-thiopyran-4-yl)-2-methyl-1,6-dihydro-1,2,3,5,6-tetraaza-as-indacene (0.05 g, 30%): LCMS (Method C, ESI): RT=2.5 min; m+1=305. $^1$H NMR (400 MHz, DMSO) δ 11.82 (s, 1H), 8.47 (s, 1H), 8.39-8.36 (m, 1H), 7.50 (t, J=2.9 Hz, 1H), 7.08 (s, 1H), 5.00-4.84 (m, 1H), 3.70-3.54 (m, 2H), 3.13-2.91 (m, 3H), 2.66 (m, 3H), 2.24 (s, 3H).

Example 211

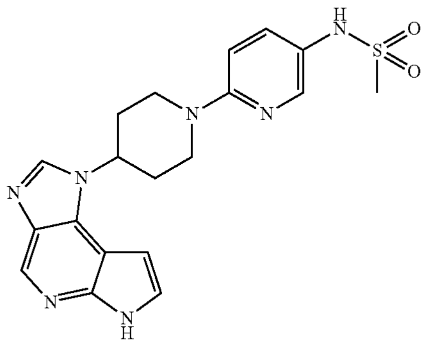 [SMILES: CS(=O)(=O)Nc1ccc(N2CCC(n3cnc4cnc5[nH]ccc5c43)CC2)nc1]

N-[4-(6H-1,2,3,5,6-Tetraaza-as-indacen-1-yl)-3,4,5,6-tetrahydro-2H-[1,2]bipyridinyl-5'-yl]-methanesulfonamide 4-(6-Benzenesulfonyl-6H-1,2,3,5,6-tetraaza-as-indacen-1-yl)-piperidine-1-carboxylic acid tert-butyl ester A mixture of 4-(5-Amino-1-benzenesulfonyl-1H-pyrrolo[2,3-b]pyridin-4-ylamino)-piperidine-1-carboxylic acid tert-butyl ester (1.00 g, 2.1 mmol) and triethylorthoformate (1.76 ml; 10.6 mmol) in acetic acid (5 mL) was heated at 120° for 20 min. The reaction mixture was cooled, diluted with ethyl acetate, stirred over sodium bicarbonate solution. The organic layer separated, washed with water, brine, dried over sodium sulfate and concentrated in vacuo. Trituration (EtOAc/heptanes) afforded 4-(6-benzenesulfonyl-6H-1,2,3,5,6-tetraaza-as-indacen-1-yl)-piperidine-1-carboxylic acid tert-butyl ester (1.0 g, 100%): LCMS (Method E, ESI): RT=1.6 min; m+1=482.2

6-Benzenesulfonyl-1-piperidin-4-yl-1,6-dihydro-1,2,3,5,6-tetraaza-as-indacene

To a solution of 4-(6-benzenesulfonyl-6H-1,2,3,5,6-tetraaza-as-indacen-1-yl)-piperidine-1-carboxylic acid tert-butyl ester (1.00 g, 2.1 mmol) in DCM was added 4N HCl/dioxane (10 mL, 400 mmol) and stirred at ambient temperature for 20 h. The solid was collected by filtration to obtain 6-benzenesulfonyl-1-piperidin-4-yl-1,6-dihydro-1,2,3,5,6-tetraaza-as-indacene.HCl salt (0.72 g, 82%): LCMS (Method F, ESI): RT=0.54 min, m+1=382.2.

N-[4-(6H-1,2,3,5,6-Tetraaza-as-indacen-1-yl)-3,4,5,6-tetrahydro-2H-[1,2]bipyridinyl-5'-yl]-methanesulfonamide A mixture of 6-benzene sulfonyl-1-piperidin-4-yl-1,6-dihydro-1,2,3,5,6-tetraaza-as-indacene.HCl salt (0.25 g, 0.60 mmol) and 2-chloro-5-nitro-pyridine (0.095 g, 0.6 mmol) and DIEA (0.15 g, 1.2 mmol) in IPA (5 ml) was heated in a microwave reactor at 120° C. for 10 minutes. The reaction mixture was diluted with ethyl acetate and the solid was collected by filtration. The solid was dissolved in DCM (5 mL), and zinc dust (0.39 g, 6.00 mmol) and acetic acid were added. The mixture was stirred vigorously for 15 min and the solids were removed by filtration. The filtrate stirred over sodium bicarbonate solution, washed with water, brine, dried over sodium sulfate and concentrated in vacuo. The residue was dissolved in DCM and pyridine (1 mL) and methanesulfonyl chloride (0.10 mL) was added and the mixture stirred for 20 h at ambient temperature. The reaction mixture was washed with water, brine, dried over sodium sulfate and concentrated. The residue was dissolved in ethanol (2 mL) and 1N NaOH (0.5 mL) added and the mixture was heated at 50° C. for 20 h. Cooled, concentrated and after reverse phase HPLC purification N-[4-(6H-1,2,3,5,6-tetraaza-as-indacen-1-yl)-3,4,5,6-tetrahydro-2H-[1,2]bipyridinyl-5'-yl]-methanesulfonamide (0.019 g, 8%): LCMS (Method C, ESI): 2.56 min, m+1=412.1; $^1$H NMR (400 MHz, DMSO) δ 11.84 (s, 1H), 8.58 (d, J=2.4 Hz, 1H), 8.30 (d, J=6.7 Hz, 1H), 8.04 (d, J=2.6 Hz, 1H), 7.50-7.40 (m, 2H), 6.99 (d, J=9.1 Hz, 1H), 6.68-6.62 (m, 1H), 4.97-4.85 (m, 1H), 4.51 (d, J=13.6 Hz, 2H), 3.24-3.13 (m, 2H), 2.93 (s, 3H), 2.25-1.97 (m, 6H).

Example 212

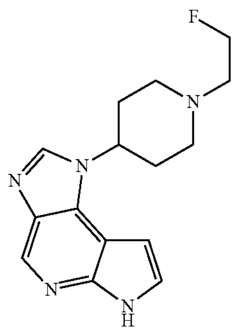 [SMILES: FCCN1CCC(n2cnc3cnc4[nH]ccc4c32)CC1]

1-[1-(2-Fluoro-ethyl)-piperidin-4-yl]-1,6-dihydro-1,2,3,5,6-tetraaza-as-indacene 1-(2-Fluoro-ethyl)-piperidin-4-ylamine.HCl A mixture of piperidin-4-yl-carbamic acid tert-butyl ester (2.00 g, 10.00 mmol), bromofluoroethane (1.5 g, 12.00 mmol) and potassium carbonate (2.80 g, 20.00 mmol) in acetonitrile (50 mL) was heated at 80° C. for 20 h. Cooled, diluted with ethyl acetate, washed with water, brine, dried over sodium sulfate and concentrated. The residue was dissolved in DCM (10 mL) and 4N HCl/dioxane (12 mL, 50.00 mmol) was added and the suspension was stirred for 20 h at ambient temperature. The solid was collected by filtration, washed well with ethyl acetate and dried in a vacuum oven to afford 1-(2-fluoro-ethyl)-piperidin-4-ylamine.HCl salt (1.70 g, 93%): $^1$H NMR (400 MHz, DMSO) δ 8.43 (s, 3H), 5.02-4.90 (m, 1H), 4.89-4.77 (m, 1H), 3.56-3.50 (m, 2H), 3.46 (d, J=3.7 Hz, 1H), 3.38 (d, J=3.8 Hz, 1H), 3.26 (d, J=4.9 Hz, 1H), 3.18-3.02 (m, 2H), 2.20-2.09 (m, 2H), 2.07-1.89 (m, 2H).

1-[1-(2-Fluoro-ethyl)-piperidin-4-yl]-1,6-dihydro-1,2,3,5,6-tetraaza-as-indacene 1-[1-(2-fluoro-ethyl)-piperidin-4-yl]-1,6-dihydro-1,2,3,5,6-tetraaza-as-indacene was obtained using the method described for Example 110: LCMS (Method C, ESI): RT=1.27 min; 288.1; $^1$H NMR (400 MHz, DMSO) δ 11.84 (s, 1H), 8.58 (s, 1H), 8.31 (s, 1H), 7.47 (s, 1H), 6.75 (d, J=3.0 Hz, 1H), 4.65 (t, J=4.9 Hz, 1H), 4.64-4.48 (m, 2H), 3.16-3.02 (m, 2H), 2.78 (t, J=4.9 Hz, 1H), 2.76-2.65 (m, 1H), 2.46-2.34 (m, 2H), 2.24-2.03 (m, 4H).

Example 213

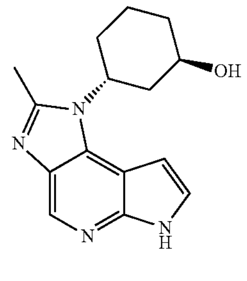 [SMILES: Cc1nc2cnc3[nH]ccc3c2n1[C@@H]1CCC[C@@H](O)C1]

(1R,3R)-3-(2-Methyl-6H-1,2,3,5,6-tetraaza-as-indacen-1-yl)-cyclohexanol 3-(1-Benzenesulfonyl-5-nitro-1H-pyrrolo[2,3-b]pyridin-4-ylamino)-cyclohexanol A stirred suspension of 1-Benzenesulfonyl-4-chloro-5-nitro-1H-pyrrolo[2,3-b]pyridine (40.00 g, 118.4 mmol) and 3-amino-cyclohexanol (13.99 g, 121.5 mmol, mixture of four stereoisomers) in isopropyl alcohol (150 ml) was treated with N,N-diisopropylethylamine (30.94 ml, 117.65 mmol) and heated at about 82° C. overnight. The reaction mixture was concentrated under reduced pressure to give the crude product, which was purified in four batches by ISCO column chromatography (0-100% Ethyl acetate in heptane), to afford 8.84 g of the trans racemic product as a yellow solid (16.2% yield), and 27.97 g of the cis racemic product as a yellow solid (52.5% yield). In addition 8.66 g of a mixture of cis and trans racemic products (42% trans, 58% cis) was obtained as a yellow solid. Trans (racemic) 3-(1-Benzenesulfonyl-5-nitro-1H-pyrrolo[2,3-b]pyridin-4-ylamino)-cyclohexanol. LCMS (Method M, ESI): RT=2.61 min, m+H=417.2; $^1$H NMR (400 MHz, DMSO) δ 8.88 (d, J=11.4 Hz, 1H), 8.12 (d, J=8.0 Hz, 1H), 7.83 (d, J=4.1 Hz, 1H), 7.76 (t, J=7.3 Hz, 1H), 7.65 (t, J=7.7 Hz, 1H), 7.18 (d, J=4.2 Hz, 1H), 4.77 (d, J=3.5 Hz, 1H), 4.36 (s, 1H), 3.99 (d, J=8.4 Hz, 1H), 1.99 (s, 1H), 1.90 (s, 1H), 1.77 (s, 1H), 1.66 (t, J=10.8 Hz, 1H), 1.59-1.46 (m, 2H), 1.25 (s, 1H), 0.85 (d, J=7.0 Hz, 1H). Cis (racemic) 3-(1-Benzenesulfonyl-5-nitro-1H-pyrrolo[2,3-b]pyridin-4-ylamino)-cyclohexanol. LCMS (Method M): RT=2.47 min, m+H=417.3; $^1$H NMR (400 MHz, DMSO) δ 8.89 (s, 1H), 8.12 (d, J=7.8 Hz, 2H), 7.85-7.72 (m, 2H), 7.65 (t, J=7.8 Hz, 2H), 6.99 (d, J=4.2 Hz, 1H), 4.89 (d, J=3.8 Hz, 1H), 4.26-4.14 (m, 1H), 3.77 (d, J=3.6 Hz, 1H), 2.05 (d, J=12.4 Hz, 1H), 1.84 (s, 1H), 1.74 (d, J=13.0 Hz, 2H), 1.60-1.28 (m, 5H).

Acetic acid 3-(1-benzenesulfonyl-5-nitro-1H-pyrrolo[2,3-b]pyridin-4-ylamino)-cyclohexyl ester To a solution of Trans (racemic) 3-(1-Benzenesulfonyl-5-nitro-1H-pyrrolo[2,3-b]pyridin-4-ylamino)-cyclohexanol (8.84 g, 21.2 mmol) dissolved in DCM (5 ml) was added N,N-diisopropylethylamine (3.88 ml, 22.28 mmol), followed by 4-Dimethylamino pyridine (420.3 mg, 3.44 mmol) at room temperature. To this was added Acetyl chloride (6.04 ml, 84.90 mmol) dropwise with stirring at room temperature. The mixture was stirred for 4 hours at room temperature and concentrated under reduced pressure to give an oil, which was used, as is, for the next step. LCMS (Method M, ESI): RT=3.07 min, m+H=459.3.

Acetic acid 3-(5-amino-1-benzenesulfonyl-1H-pyrrolo[2,3-b]pyridin-4-ylamino)-cyclohexyl ester A mixture of Acetic acid 3-(1-benzenesulfonyl-5-nitro-1H-pyrrolo[2,3-b]pyridin-4-ylamino)-cyclohexyl ester (trans racemic) (9.72 g, 21.2 mmol), ammonium chloride (2.26 g, 42.40 mmol), iron powder (5.92 g, 106 mmol), and water (15.0 mL) in ethanol (150 ml) was heated at 80° C. overnight. The reaction was followed by LC/MS to completion. On completion, the reaction mixture was used as is for the next step without any workup. LCMS (Method M, ESI): RT=1.90 min, m+H=428.9.

Acetic acid 3-(6-benzenesulfonyl-2-methyl-6H-1,2,3,5,6-tetraaza-as-indacen-1-yl)-cyclohexyl ester To the above reaction mixture at 80° C. was added triethyl orthoacetate (62 ml, 2.31 mmol) and acetic acid (11 ml, 193 mmol). The reaction mixture was heated at 90° C. for 5 days, then cooled to room temperature and filtered through CELITE®. The black filtrate was concentrated under reduced pressure to obtain a black oil, which was dissolved in 75 ml of dichloromethane and filtered through CELITE®. The filtrate was concentrated to give a black oil, which was then purified by silica column chromatography (ISCO, 0-10% methanol in dichloromethane) to give 7.48 g (64.7%) of Acetic acid 3-(6-benzenesulfonyl-2-methyl-6H-1,2,3,5,6-tetraaza-as-indacen-1-yl)-cyclohexyl ester (trans racemic) as a black foamy solid. LCMS (Method M, ESI): RT=1.61 min, m+H=453.4.

(1R,3R)-3-(2-Methyl-6H-1,2,3,5,6-tetraaza-as-indacen-1-yl)-cyclohexanol

Acetic acid 3-(6-benzenesulfonyl-2-methyl-6H-1,2,3,5,6-tetraaza-as-indacen-1-yl)-cyclohexyl ester (mixture of cis and trans racemic products) (545.7 mg, 1.20 mmol) was dissolved in methanol (5.0 mL). Solid sodium hydroxide (483 mg, 12.0 mmol) was added, the reaction mixture was stirred overnight at room temperature, then concentrated under reduced pressure and purified by reverse phase HPLC and preparative chiral SFC* (*see below for method) to give 8.9 mg (2.7%) of (1R,3R)-3-(2-Methyl-6H-1,2,3,5,6-tetraaza-as-indacen-1-yl)-cyclohexanol. LCMS (Method C, ESI): RT=2.709 min, m+H=271.1; Chiral SFC (Method A3): RT=0.99 minutes; $^1$H NMR (400 MHz, DMSO) δ 11.77 (s, 1H), 8.44 (s, 1H), 7.43 (d, J=3.3 Hz, 1H), 6.67 (s, 1H), 4.79 (s, 2H), 4.21 (s, 1H), 2.29 (d, J=30.8 Hz, 2H), 2.06-1.84 (m, 3H), 1.78 (d, J=12.2 Hz, 1H), 1.69 (d, J=13.4 Hz, 2H). Also isolated was (1S,3S)-3-(2-Methyl-6H-1,2,3,5,6-tetraaza-as-indacen-1-yl)-cyclohexanol, as well as the two cis-isomers, Examples 544 and 545.

*Preparative Chiral SFC Method

Instrument: Mettler-Toledo MGII

Column: Phenomenex Lux Cellulose-2, 21.2×250 mm, 5 um

Detection: UV 220 nm

Mobile Phase: 30% EtOH containing 0.1% TEA, 70% CO2

Flowrate: 50 g/min

Runtime: 5.2 minutes

Back pressure setting: 100 bar

Example 213a

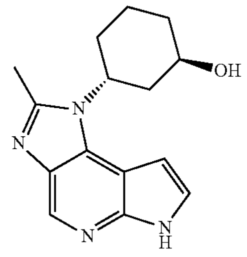 [SMILES: Cc1nc2cnc3[nH]ccc3c2n1[C@@H]1CCC[C@@H](O)C1]

(1R,3R)-3-(2-Methyl-6H-1,2,3,5,6-tetraaza-as-indacen-1-yl)-cyclohexanol (1R,3R)-3-(5-Amino-1-benzenesulfonyl-1H-pyrrolo[2,3-b]pyridin-4-ylamino)-cyclohexanol A stirred suspension of 1-Benzenesulfonyl-4-chloro-5-nitro-1H-pyrrolo[2,3-b]pyridine (24.5 g, 72.6 mmol) in methanol (120 ml) was treated with (1R,3R)-3-Amino-cyclohexanol* (8.9 g, 76.3 mmol) and N,N-diisopropylethylamine (13.3 mL, 76.3 mmol), and stirred at 65° C. for three hours. The mixture was then cooled and 10% palladium on carbon (7.6 g, 3.6 mmol) was added. The mixture was pressurized to 100 psi with hydrogen and stirred at 50° C. for 18 h. Filtration and concentration afforded the desired product which was carried on directly into the next step. LCMS (Method P, ESI): RT=2.17 min, m+H=387.1.

*Prepared following the procedures described in: P. Bernardelli et al./Tetrahedron: Asymmetry 15 (2004) 1451-1455

(1R,3R)-3-(6-Benzenesulfonyl-2-methyl-6H-1,2,3,5,6-tetraaza-as-indacen-1-yl)-cyclohexanol A slurry of acetamide (7.1 g, 120 mmol) in tetrahydrofuran (THF) (124 mL) was treated with triethyloxonium tetrafluoroborate (22.8 g, 116 mmol) and stirred at room temperature for one hour. A solution of (1R,3R)-3-(5-Amino-1-benzenesulfonyl-1H-pyrrolo[2,3-b]pyridin-4-ylamino)-cyclohexanol (31.0 g, 80.2 mmol) in ethanol (EtOH) (217 mL) was added to the above mixture and stirred at 70° C. for 2 h. Water (150 mL) was added and the mixture was extracted with 2-methyltetrahydrofuran (meTHF) (2×250 mL). The organic layer was separated and concentrated to dryness. EtOH (200 mL) was added and after dissolving the crude solids with heat, the solution was seeded (0.1 g) to afford 24.0 g (72.9%) of the desired product as a crystalline solid. LCMS (Method P, ESI): RT=2.52 min, m+H=411.1; $^1$H NMR (400 MHz, $CDCl_3$) δ 8.79 (s, 1H), 8.22 (d, J=8.2 Hz, 2H), 7.78 (d, J=4.0 Hz, 1H), 7.58-7.41 (m, 4H), 6.90 (s, 1H), 4.48-4.42 (m, 1H), 3.99-3.85 (m, 1H), 2.68 (s, 3H), 2.41-1.48 (m, 8H).

(1R,3R)-3-(2-Methyl-6H-1,2,3,5,6-tetraaza-as-indacen-1-yl)-cyclohexanol

A slurry of (1R,3R)-3-(6-Benzenesulfonyl-2-methyl-6H-1,2,3,5,6-tetraaza-as-indacen-1-yl)-cyclohexanol (24.0 g, 58.5 mmol) in ethanol (240 mL) was treated with 1N sodium hydroxide (168 mL, 168.0 mmol) and stirred at 50° C. for 18 h. The reaction mixture was then concentrated to remove the ethanol and extracted with methyl ethyl ketone (MEK) (250 mL). After separating the layers, the aqueous layer was extracted again with MEK (250 mL). The organic layers were combined and washed with brine (100 mL), dried with MgSO4 and filtered. This solution was concentrated to dryness and the resulting solid was slurried in isopropyl alcohol (IPA) (50 mL) for 24 h. The solids were filtered off and dried under vacuum for 18 h to afford the desired product. LCMS (Method C, ESI): RT=2.709 min, m+H=271.1; Chiral SFC (Method A3): RT=0.99 minutes; $^1$H NMR (400 MHz, DMSO) δ 11.77 (s, 1H), 8.44 (s, 1H), 7.43 (d, J=3.3 Hz, 1H), 6.67 (s, 1H), 4.79 (s, 2H), 4.21 (s, 1H), 2.29 (d, J=30.8 Hz, 2H), 2.06-1.84 (m, 3H), 1.78 (d, J=12.2 Hz, 1H), 1.69 (d, J=13.4 Hz, 2H).

Example 214

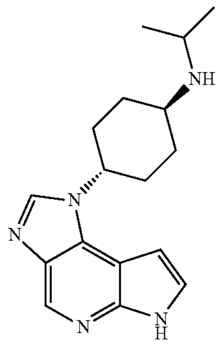 [SMILES: CC(C)N[C@H]1CC[C@H](n2cnc3cnc4[nH]ccc4c32)CC1]

Trans Isopropyl-[4-(6H-1,2,3,5,6-tetraaza-as-indacen-1-yl)-cyclohexyl]-amine

[4-(6-Benzenesulfonyl-6H-1,2,3,5,6-tetraaza-as-indacen-1-yl)-cyclohexyl]-carbamic acid tert-butyl ester To a stirred suspension of [4-(5-Amino-1-benzenesulfonyl-1H-pyrrolo[2,3-b]pyridin-4-ylamino)-cyclohexyl]-carbamic acid tert-butyl ester (5.0 g, 110.3 mmol) in ethanol (50 ml) was added triethyl orthoformate (6.85 ml, 41.19 mmol) and refluxed at 82° C. overnight. The reaction was cooled to room temperature and concentrated under reduced pressure to give 5.12 g (93.36%) of the [4-(6-Benzenesulfonyl-6H-1,2,3,5,6-tetraaza-as-indacen-1-yl)-cyclohexyl]-carbamic acid tert-butyl ester as a white solid. LCMS (Method M, ESI): RT=2.37 min, m+H=496.4.

4-(6-Benzenesulfonyl-6H-1,2,3,5,6-tetraaza-as-indacen-1-yl)-cyclohexylamine

To solid [4-(6-Benzenesulfonyl-6H-1,2,3,5,6-tetraaza-as-indacen-1-yl)-cyclohexyl]-carbamic acid tert-butyl ester (4.70 g, 9.48 mmol) was added 4 M HCl in dioxane (11.85 ml, 50 mmol) and stirred at room temperature overnight. The reaction was concentrated under reduced pressure and the residue treated with saturated sodium bicarbonate solution (75 ml), followed by water (50 ml). The mixture was sonicated for 10 minutes and filtered. The solid was washed with water (2×20 mL) and dried under vacuum to give 4.054 g (88.72%) of 4-(6-Benzenesulfonyl-6H-1,2,3,5,6-tetraaza-as-indacen-1-yl)-cyclohexylamine as a white solid. LCMS (Method M, ESI): RT=1.38 min, m+H=396.3.

[4-(6-Benzenesulfonyl-6H-1,2,3,5,6-tetraaza-as-indacen-1-yl)-cyclohexyl]-isopropyl-amine To a solution of 4-(6-Benzenesulfonyl-6H-1,2,3,5,6-tetraaza-as-indacen-1-yl)-cyclohexylamine (51 mg, 0.129 mmol) in methanol (2.0 ml) was added acetone (7.49 mg, 0.129 mmol), followed by sodium triacetoxyborohydride (43.7 mg, 0.20 mmol) and acetic acid (7.75 mg, 0.129 mmol), and the mixture was stirred overnight. The reaction mixture used without workup for the next step. LCMS (Method M, ESI): RT=0.64 min, m+H=438.3.

Isopropyl-[4-(6H-1,2,3,5,6-tetraaza-as-indacen-1-yl)-cyclohexyl]-amine

To the reaction containing [4-(6-Benzenesulfonyl-6H-1,2,3,5,6-tetraaza-as-indacen-1-yl)-cyclohexyl]-isopropyl-amine (0.129 mmol) in methanol was added solid sodium hydroxide (16.4 mg, 0.41 mmol) at room temperature. The reaction was then stirred overnight. The reaction was followed by LC/MS to completion. The reaction was then concentrated under reduced pressure and purified by HPLC to give 24.6 mg of isopropyl-[4-(6H-1,2,3,5,6-tetraaza-as-indacen-1-yl)-cyclohexyl]-amine as a white solid. LCMS (Method C, ESI): RT=2.369 min, m+H=298.1. $^1$H NMR (400 MHz, DMSO) δ 11.84 (s, 1H), 8.56 (d, J=7.0 Hz, 1H), 8.27 (s, 1H), 7.46 (d, J=3.3 Hz, 1H), 6.71 (d, J=3.3 Hz, 1H), 4.59-4.51 (m, 1H), 2.93 (dd, J=12.1, 6.1 Hz, 1H), 2.67 (s, 1H), 2.15 (d, J=12.3 Hz, 2H), 2.08-1.90 (m, 4H), 1.42-1.29 (m, 2H), 1.21 (s, 1H), 1.00 (d, J=6.2 Hz, 7H).

Example 215

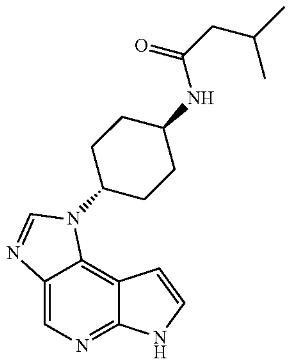 [SMILES: CC(C)CC(=O)N[C@H]1CC[C@H](n2cnc3cnc4[nH]ccc4c32)CC1]

Trans 3-Methyl-N-[4-(6H-1,2,3,5,6-tetraaza-as-indacen-1-yl)-cyclohexyl]-butyramide N-[4-(6-Benzenesulfonyl-6H-1,2,3,5,6-tetraaza-as-indacen-1-yl)-cyclohexyl]-3-methyl-butyramide To a solution of 4-(6-Benzenesulfonyl-6H-1,2,3,5,6-tetraaza-as-indacen-1-yl)-cyclohexylamine (100 mg, 0.253 mmol) in dichloromethane (3.0 ml) was added N,N-diisopropylethylamine (0.050 ml, 0.29 mmol), followed by 4-dimethylaminopyridine (3.0 mg, 0.025 mmol). To this was added isovaleryl chloride (30.49 mg, 0.253 mmol) in dichloromethane (0.5 mL) dropwise with stirring. This was then stirred overnight. The reaction was followed by LC/MS to completion. Reaction concentrated under reduced pressure and the residue used as is for the next step. LCMS (Method M, ESI): RT=2.05 min, m+H=480.4.

3-Methyl-N-[4-(6H-1,2,3,5,6-tetraaza-as-indacen-1-yl)-cyclohexyl]-butyramide

N-[4-(6-Benzenesulfonyl-6H-1,2,3,5,6-tetraaza-as-indacen-1-yl)-cyclohexyl]-3-methyl-butyramide (0.253 mmol) in methanol (3.0) was added solid sodium hydroxide (345 mg, 8.626 mmol) at room temperature. The reaction was then stirred overnight. The reaction was followed by LC/MS to completion. The reaction was then concentrated under reduced pressure and purified by HPLC to give 20.0 mg of 3-Methyl-N-[4-(6H-1,2,3,5,6-tetraaza-as-indacen-1-yl)-cyclohexyl]-butyramide as a white solid. LCMS (Method C, ESI): RT=3.149 min, m+H=340.1. $^1$H NMR (400 MHz, DMSO) δ 11.87 (s, 1H), 8.57 (s, 1H), 8.30 (s, 1H), 7.81 (d, J=7.5 Hz, 1H), 7.48 (t, J=3.0 Hz, 1H), 6.72 (dd, J=3.3, 1.9 Hz, 1H), 4.58 (t, J=11.8 Hz, 1H), 3.73 (d, J=7.8 Hz, 1H), 2.17 (d, J=11.4 Hz, 2H), 2.07-1.94 (m, 7H), 1.55 (dd, J=24.7, 9.4 Hz, 2H), 0.89 (d, J=6.2 Hz, 6H).

Example 216 and 216a

Trans, Single Enantiomers

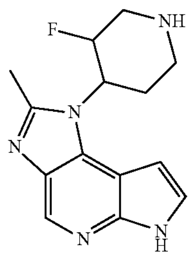 [SMILES: Cc1nc2cnc3[nH]ccc3c2n1C1CCNCC1F]

1-(3-Fluoro-piperidin-4-yl)-2-methyl-1,6-dihydro-1,2,3,5,6-tetraaza-as-indacene

Cis and trans 4-Benzylamino-3-fluoro-piperidine-1-carboxylic acid tert-butyl ester A stirred solution of 3-Fluoro-4-oxo-piperidine-1-carboxylic acid tert-butyl ester (2.00 g, 9.21 mmol) in methanol (20 ml) and acetic acid (1 ml) was treated with benzyl amine (1.106 ml, 10.013 mmol) and stirred at ambient temperature for three hours. The mixture was then treated with sodium cyanoborohydride (0.8678 g, 13.81 mmol) and left to stand overnight. The reaction was quenched with a saturated solution of sodium bicarbonate (20 ml) and extracted with three portions of dichloromethane (50 ml). Combined organic layers were dried with magnesium sulfate and concentrated under vacuum to give crude product. Purification by column chromatography on silica gel (gradient: 0 to 60% ethyl acetate in heptane) gave 734 mg (26%) of trans-4-benzylamino-3-fluoro-piperidine-1-carboxylic acid tert-butyl ester and 653 mg (23%) of cis-4-benzylamino-3-fluoro-piperidine-1-carboxylic acid tert-butyl ester.

Trans Data: LCMS (Method F): RT=0.67 min, m+H=309.2; $^1$H NMR (500 MHz, DMSO) 6=7.33 (s, 5H), 4.44-4.31 (m, 1H), 3.84-3.65 (m, 3H), 3.53-3.41 (m, 1H), 3.17-3.07 (m, 1H), 2.80-2.68 (m, 1H), 2.34-2.28 (m, 1H), 1.85-1.74 (m, 1H), 1.39 (s, 9H), 1.36-1.30 (m, 1H)

Cis Data: LCMS (Method F): RT=0.63 min, m+H=309.2; $^1$H NMR (500 MHz, DMSO) δ=7.32 (dd, J=18.4, 7.3, 5H), 4.84-4.69 (m, 1H), 4.21-4.06 (m, 1H), 3.97-3.86 (m, 1H), 3.77 (s, 2H), 3.09-2.88 (m, 2H), 2.85-2.69 (m, 1H), 2.65-2.55 (m, 1H), 2.07-1.97 (m, 1H), 1.72-1.61 (m, 1H), 1.48-1.42 (m, 1H), 1.38 (s, 9H).

trans-4-Amino-3-fluoro-piperidine-1-carboxylic acid tert-butyl ester

A stirred solution of trans-4-benzylamino-3-fluoro-piperidine-1-carboxylic acid tert-butyl ester (0.170 g, 0.551 mmol) in methanol (2 ml) and was treated with ammonium formate (0.139 g, 2.20 mmol) and 10% palladium on activated carbon (0.059 g, 0.055 mmol) and stirred at 50° C. for one hour. The mixture was then filtered through Celite, washed with copious methanol and concentrated under vacuum to give 118 mg (100%) of trans-4-amino-3-fluoro-piperidine-1-carboxylic acid tert-butyl ester that was used without further purification. LCMS (Method F): RT=0.14 min, m+H=219.0; $^1$H NMR (400 MHz, DMSO) δ 4.22-4.01 (m, 1H), 3.96-3.68 (m, 2H), 3.62-3.52 (m, 1H), 3.22-2.94 (m, 2H), 2.89-2.77 (m, 1H), 1.81-1.63 (m, 2H), 1.39 (s, 10H), 1.28-1.16 (m, 1H).

trans-4-(1-Benzenesulfonyl-5-nitro-1H-pyrrolo[2,3-b]pyridin-4-ylamino)-3-fluoro-piperidine-1-carboxylic acid tert-butyl ester A stirred solution of 1-benzenesulfonyl-4-chloro-5-nitro-1H-pyrrolo[2,3-b]pyridine (173 mg, 0.513 mmol), trans-4-Amino-3-fluoro-piperidine-1-carboxylic acid tert-butyl ester (112 mg, 0.513 mmol), diisopropylethylamine (211 μl, 1.16 mmol) in propan-2-ol (2 ml) were stirred at 82° C. overnight then cooled to room temperature. The precipitated solid was then collected by filtration to yield 231 mg (87%) of trans-4-(1-benzenesulfonyl-5-nitro-1H-pyrrolo[2,3-b]pyridin-4-ylamino)-3-fluoro-piperidine-1-carboxylic acid tert-butyl ester that was used without further purification. LCMS (Method F): RT=1.22 min, m+H=520.0; $^1$H NMR (400 MHz, DMSO) 6=8.91 (s, 2H), 8.13 (d, J=7.4, 2H), 7.86-7.83 (m, 1H), 7.81-7.72 (m, 1H), 7.65 (s, 2H), 7.20-7.15 (m, 1H), 4.88-4.69 (m, 1H), 4.57-4.41 (m, 1H), 4.33 (d, J=4.2, 1H), 4.23-4.02 (m, 1H), 3.26-3.02 (m, 2H), 2.08-1.96 (m, 1H), 1.81-1.69 (m, 1H), 1.42 (s, 9H).

trans-4-(5-Amino-1-benzenesulfonyl-1H-pyrrolo[2,3-b]pyridin-4-ylamino)-3-fluoro-piperidine-1-carboxylic acid tert-butyl ester A stirred solution of trans-4-(1-benzenesulfonyl-5-nitro-1H-pyrrolo[2,3-b]pyridin-4-ylamino)-3-fluoro-piperidine-1-carboxylic acid tert-butyl ester (0.231 g, 0.445 mmol) in ethyl acetate (5 ml) was treated with 10% palladium on activated carbon (0.025 g, 0.023 mmol) and stirred at 50° C. overnight. The mixture was then filtered through Celite, washed with copious methanol and concentrated under vacuum to give 201 mg (92%) of trans-4-(5-amino-1-benzenesulfonyl-1H-pyrrolo[2,3-b]pyridin-4-ylamino)-3-fluoro-piperidine-1-carboxylic acid tert-butyl ester that was used without further purification. LCMS (Method F): RT=0.88 min, m+H=490.0; $^1$H NMR (400 MHz, DMSO) δ=8.06-7.99 (m, 2H), 7.72-7.64 (m, 1H), 7.60 (s, 3H), 7.54-7.46 (m, 1H), 6.87-6.79 (m, 1H), 5.33-5.22 (m, 1H), 4.60-4.33 (m, 3H), 4.13-4.07 (m, 1H), 3.80-3.66 (m, 1H), 3.26-3.03 (m, 2H), 1.96-1.87 (m, 1H), 1.41 (s, 9H), 1.37-1.32 (m, 1H).

trans-4-(6-Benzenesulfonyl-2-methyl-6H-1,2,3,5,6-tetraaza-as-indacen-1-yl)-3-fluoro-piperidine-1-carboxylic acid tert-butyl ester A solution of trans-4-(5-amino-1-benzenesulfonyl-1H-pyrrolo[2,3-b]pyridin-4-ylamino)-3-fluoro-piperidine-1-carboxylic acid tert-butyl ester (0.540 g, 1.10 mmol) and triethylorthoacetate (1.01 ml, 5.52 mmol) in acetic acid (5 ml) was heated at 120° C. for ten minutes. The mixture was then concentrated under vacuum to give crude product. Purification by column chromatography on silica gel (gradient: 0 to 100% (20% methanol: ethyl acetate) in heptane) gave 476 mg (84%) of trans-4-(6-benzenesulfonyl-2-methyl-6H-1,2,3,5,6-tetraaza-as-indacen-1-yl)-3-fluoro-piperidine-1-carboxylic acid tert-butyl ester. LCMS (Method F): RT=1.07 min, m+H=514.0; $^1$H NMR (400 MHz, DMSO) δ 8.66 (s, 1H), 8.16 (d, J=7.3, 2H), 7.94 (d, J=3.7, 1H), 7.71 (s, 1H), 7.62 (d, J=7.7, 2H), 6.55-6.44 (m, 1H), 5.21-4.88 (m, 3H), 4.48-4.35 (m, 1H), 4.19-4.07 (m, 1H), 3.22-3.05 (m, 2H), 2.80-2.66 (m, 1H), 2.63 (s, 3H), 2.31-2.19 (m, 1H), 2.19-2.08 (m, 1H), 1.49 (m, 9H).

trans-3-Fluoro-4-(2-methyl-6H-1,2,3,5,6-tetraaza-as-indacen-1-yl)-piperidine-1-carboxylic acid tert-butyl ester A solution of trans-4-(6-benzenesulfonyl-2-methyl-6H-1,2,3,5,6-tetraaza-as-indacen-1-yl)-3-fluoro-piperidine-1-carboxylic acid tert-butyl ester (0.476 g, 0.927 mmol) in ethanol (5 ml), 1 M aqueous sodium hydroxide (5 ml), and tetrahydrofuran (8 ml) was heated at 50° C. for two hours. The mixture was then concentrated under vacuum to give crude product. Purification by column chromatography on silica gel (gradient: 0 to 100% (20% methanol: ethyl acetate) in heptane) gave 238 mg (69%) of trans3-Fluoro-4-(2-methyl-6H-1,2,3,5,6-tetraaza-as-indacen-1-yl)-piperidine-1-carboxylic acid tert-butyl ester. LCMS (Method F): RT=0.14 min, m+H=374.0; $^1$H NMR (400 MHz, DMSO) δ 8.66 (s, 1H), 8.16 (d, J=7.3, 2H), 7.94 (d, J=3.7, 1H), 7.71 (s, 1H), 7.62 (d, J=7.7, 2H), 6.55-6.44 (m, 1H), 5.21-4.88 (m, 3H), 4.48-4.35 (m, 1H), 4.19-4.07 (m, 1H), 3.22-3.05 (m, 2H), 2.80-2.66 (m, 1H), 2.63 (s, 3H), 2.31-2.19 (m, 1H), 2.19-2.08 (m, 1H), 1.49 (m, 9H).

trans-1-(3-Fluoro-piperidin-4-yl)-2-methyl-1,6-dihydro-1,2,3,5,6-tetraaza-as-indacene A solution of 4-(2-methyl-6H-1,2,3,5,6-tetraaza-as-indacen-1-yl)-piperidine-1-carboxylic acid tert-butyl ester (238 mg, 0.758 mmol) in dioxane (5 ml) was charged with 4M hydrogen chloride in dioxane (1 ml) and left to stand at room temperature for two hours. Concentrate reaction mixture under vacuum to give crude product. Purification by chiral SFC (*see below for method) afforded two enantiopure trans products: 56.9 mg (28%) and 65.9 mg (32%).

*Preparative Chiral SFC Method

| | |
|---|---|
| System | Mettler-Toledo MGII |
| Mobile phase A | Methanol with 0.1% Diethylamine |
| Mobile phase B | Super-critical carbon dioxide |
| Column | Chiral Technologies Chiralpak IC, 21.2 × 250 mm, 5 uM |
| Column temperature | 40 degree C. |
| LC gradient | Isocratic 30% B, 8 min |
| LC Flowrate | 50 g/min |
| UV wavelength | 230 nm |

First eluting enantiomer: LCMS (Method™, D): RT=3.70 min, m+H=274.0; Analytical chiral SFC (Method A2): RT=0.89 $^1$H NMR (400 MHz, DMSO) δ 11.83 (s, 1H), 8.49 (s, 1H), 7.47 (s, 1H), 6.86 (s, 1H), 5.40-5.24 (m, 1H), 5.24-5.11 (m, 1H), 4.71-4.52 (m, 1H), 3.59-3.41 (m, 1H), 3.15-3.02 (m, 1H), 2.71 (d, J=10.8, 3H), 2.60 (s, 3H), 2.07-1.93 (m, 1H).

Second eluting enantiomer: LCMS (Method™, D): RT=3.77 min, m+H=274.0; Analytical chiral SFC (Method A2): RT=1.26 $^1$H NMR (400 MHz, DMSO) δ 11.83 (s, 1H), 8.49 (s, 1H), 7.47 (s, 1H), 6.86 (s, 1H), 5.40-5.24 (m, 1H), 5.24-5.11 (m, 1H), 4.71-4.52 (m, 1H), 3.59-3.41 (m, 1H), 3.15-3.02 (m, 1H), 2.71 (d, J=10.8, 3H), 2.60 (s, 3H), 2.07-1.93 (m, 1H).

Examples 217-578 shown in Table 2 were prepared generally following the above-described Examples and making non-critical variations where necessary. The general synthetic method used for each compound is indicated.

TABLE 2

| Ex | Structure | Name | Synthetic Method | LCMS RT (min)/Method | LCMS (ESI) m/z |
|---|---|---|---|---|---|
| 217 | 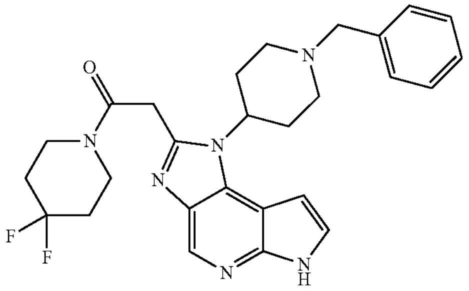 [SMILES: O=C(Cc1nc2cnc3[nH]ccc3c2n1C1CCN(Cc2ccccc2)CC1)N1CCC(F)(F)CC1] | 2-[1-(1-Benzyl-piperidin-4-yl)-1,6-dihydro-1,3,5,6-tetraaza-as-indacen-2-yl)-1-(4,4-difluoro-piperidin-1-yl)-ethanone | 23 | 2.57/A | 493.1 |

TABLE 2-continued

| Ex | Structure | Name | Synthetic Method | LCMS RT (min)/Method | LCMS (ESI) m/z |
|---|---|---|---|---|---|
| 218 | 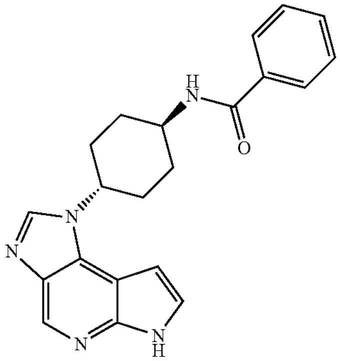 [SMILES: O=C(N[C@H]1CC[C@H](n2cnc3cnc4[nH]ccc4c32)CC1)c1ccccc1] | Trans N-[4-(6H-1,3,5,6-Tetraaza-as-indacen-1-yl)-cyclohexyl]-benzamide | 6 | 2.73/A | 360.1 |
| 219 | 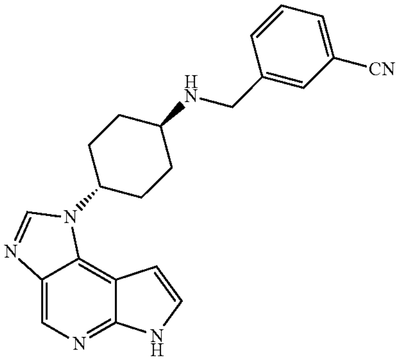 [SMILES: N#Cc1cccc(CN[C@H]2CC[C@H](n3cnc4cnc5[nH]ccc5c43)CC2)c1] | Trans 3-{[4-(6H-1,3,5,6-Tetraaza-as-indacen-1-yl)-cyclohexylamino]-methyl}-benzonitrile | 8 | 1.86/A | 371.1 |
| 220 | 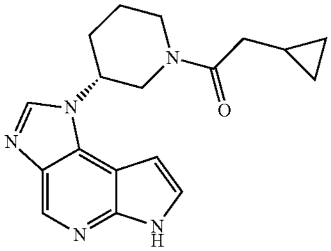 [SMILES: O=C(CC1CC1)N1CCC[C@@H](n2cnc3cnc4[nH]ccc4c32)C1] | 2-Cyclopropyl-1-[(R)-3-(6H-1,3,5,6-tetraaza-as-indacen-1-yl)-piperidin-1-yl]-ethanone | 5 | 2.52/A | 324.1 |
| 221 | 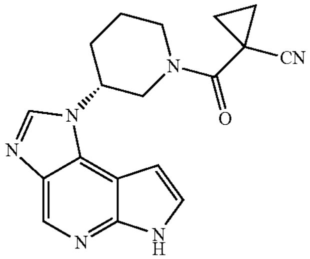 [SMILES: N#CC1(C(=O)N2CCC[C@@H](n3cnc4cnc5[nH]ccc5c43)C2)CC1] | 1-[(R)-3-(6H-1,3,5,6-Tetraaza-as-indacen-1-yl)-piperidine-1-carbonyl]-cyclopropanecarbonitrile | 5 | 2.37/A | 335.1 |
| 222 | 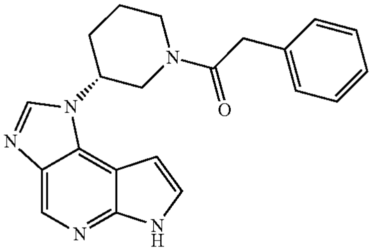 [SMILES: O=C(Cc1ccccc1)N1CCC[C@@H](n2cnc3cnc4[nH]ccc4c32)C1] | 2-Phenyl-1-[(R)-3-(6H-1,3,5,6-tetraaza-as-indacen-1-yl)-piperidin-1-yl]-ethanone | 6 | 2.85/A | 360.2 |

TABLE 2-continued

| Ex | Structure | Name | Synthetic Method | LCMS RT (min)/Method | LCMS (ESI) m/z |
|---|---|---|---|---|---|
| 223 | 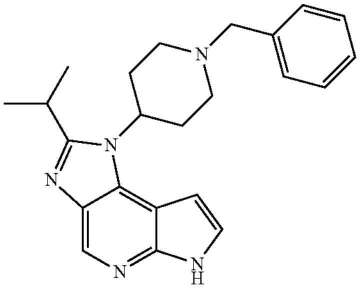 [SMILES: CC(C)c1nc2cnc3[nH]ccc3c2n1C1CCN(Cc2ccccc2)CC1] | 1-(1-Benzyl-piperidin-4-yl)-2-isopropyl-1,6-dihydro-1,3,5,6-tetraaza-as-indacene | 154 | 2.20/A | 374.1 |
| 224 | 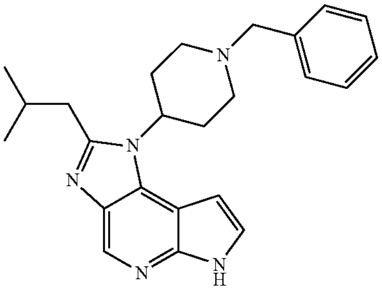 [SMILES: CC(C)Cc1nc2cnc3[nH]ccc3c2n1C1CCN(Cc2ccccc2)CC1] | 1-(1-Benzyl-piperidin-4-yl)-2-isobutyl-1,6-dihydro-1,3,5,6-tetraaza-as-indacene | 154 | 2.40/A | 388.1 |
| 225 | 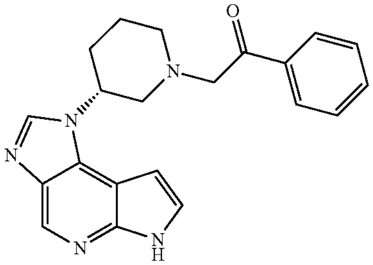 [SMILES: O=C(CN1CCC[C@@H](n2cnc3cnc4[nH]ccc4c32)C1)c1ccccc1] | 1-Phenyl-2-[(R)-3-(6H-1,3,5,6-tetraaza-as-indacen-1-yl)-piperidin-1-yl]-ethanone | 11 | 2.18/A | 360.1 |
| 226 | 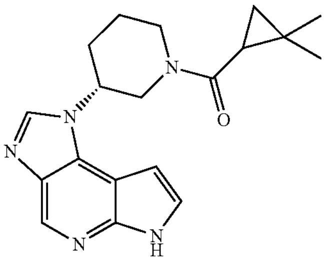 [SMILES: CC1(C)CC1C(=O)N1CCC[C@@H](n2cnc3cnc4[nH]ccc4c32)C1] | (2,2-Dimethyl-cyclopropyl)-[(R)-3-(6H-1,3,5,6-tetraaza-as-indacen-1-yl)-piperidin-1-yl]-methanone | 5 | 2.83 and 2.87/A | 338.1 |
| 227 | 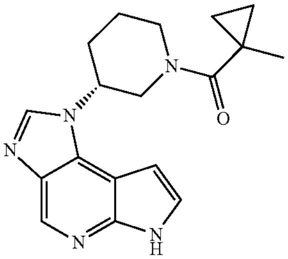 [SMILES: CC1(C(=O)N2CCC[C@@H](n3cnc4cnc5[nH]ccc5c43)C2)CC1] | (1-Methyl-cyclopropyl)-[(R)-3-(6H-1,3,5,6-tetraaza-as-indacen-1-yl)-piperidin-1-yl]-methanone | 5 | 2.49/A | 324.1 |

TABLE 2-continued

| Ex | Structure | Name | Synthetic Method | LCMS RT (min)/Method | LCMS (ESI) m/z |
|---|---|---|---|---|---|
| 228 | 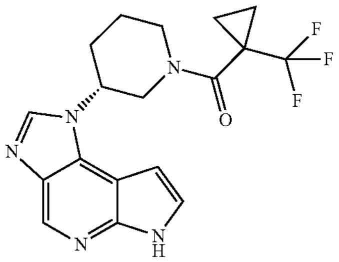 [SMILES: O=C(N1CCC[C@@H](n2cnc3cnc4[nH]ccc4c32)C1)C1(C(F)(F)F)CC1] | [(R)-3-(6H-1,3,5,6-tetraaza-as-indacen-1-yl)-piperidin-1-yl]-(1-trifluoromethyl-cyclopropyl)-methanone | 5 | 2.86/A | 378.1 |
| 229 | 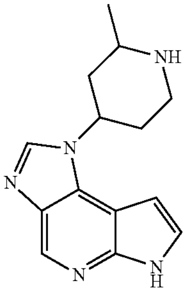 [SMILES: CC1CC(n2cnc3cnc4[nH]ccc4c32)CCN1] | racemic, cis 1-(2-Methyl-piperidin-4-yl)-1,6-dihydro-1,3,5,6-tetraaza-as-indacene | 127 & 2 | 0.83/A | 256.1 |
| 230 | 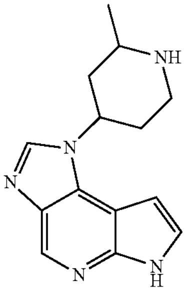 [SMILES: CC1CC(n2cnc3cnc4[nH]ccc4c32)CCN1] | racemic, trans 1-(2-Methyl-piperidin-4-yl)-1,6-dihydro-1,3,5,6-tetraaza-as-indacene | 128 & 2 | 0.82/A | 256.1 |
| 231 | 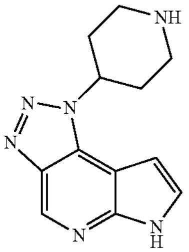 [SMILES: c1cc2c(ncc3nnn(C4CCNCC4)c32)[nH]1] | 1-Piperidin-4-yl)-1,6-dihydro-1,2,3,5,6-pentaaza-as-indacene | 18 & 2 | 1.52/A | 243.1 |
| 232 | 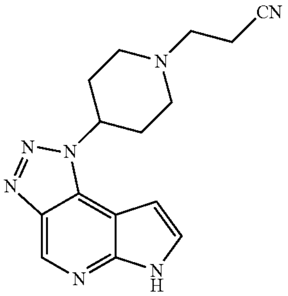 [SMILES: N#CCCN1CCC(n2nnc3cnc4[nH]ccc4c32)CC1] | 3-[4-(6H-1,2,3,5,6-Pentaaza-as-indacen-1-yl)-piperidin-1-yl]-propionitrile | 10 | 1.62/A | 296.1 |

TABLE 2-continued

| Ex | Structure | Name | Synthetic Method | LCMS RT (min)/Method | LCMS (ESI) m/z |
|---|---|---|---|---|---|
| 233 | 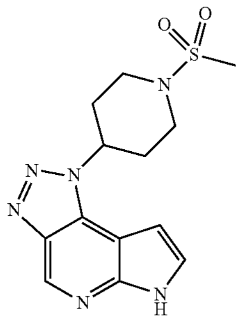 [SMILES: CS(=O)(=O)N1CCC(n2nnc3cnc4[nH]ccc4c32)CC1] | 1-(1-Methanesulfonyl-piperidin-4-yl)-1,6-dihydro-1,2,3,5,6-pentaaza-as-indacene | 9 | 2.80/A | 321.0 |
| 234 | 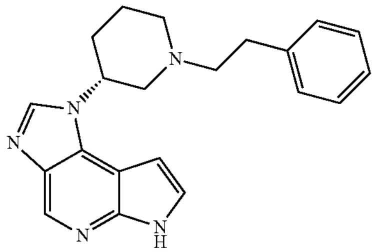 [SMILES: c1ccc(CCN2CCC[C@@H](n3cnc4cnc5[nH]ccc5c43)C2)cc1] | 1-((R)-1-Phenthyl-piperidin-3-yl)-1,6-dihydro-1,3,5,6-tetraaza-as-indacene | 8 | 2.15/A | 346.1 |
| 235 | 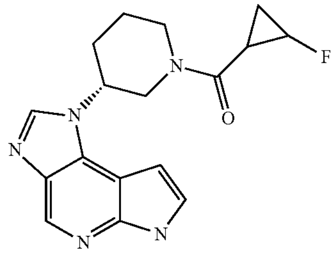 [SMILES: O=C(C1CC1F)N1CCC[C@@H](n2cnc3cnc4[nH]ccc4c32)C1] | racemic, trans (2-Fluoro-cyclopropyl)-[(R)-3-(6H-1,3,5,6-tetraaza-as-indacen-1-yl)-piperidin-1-yl]-methanone | 5 | 2.39/A | 328.1 |
| 236 | 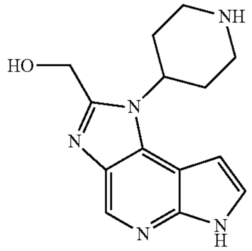 [SMILES: OCc1nc2cnc3[nH]ccc3c2n1C1CCNCC1] | (1-Piperidin-4-yl-1,6-dihydro-1,3,5,6-tetraaza-as-indacen-2-yl)-methanol | 22 & 2 | 0.70/A | 272.0 |
| 237 | 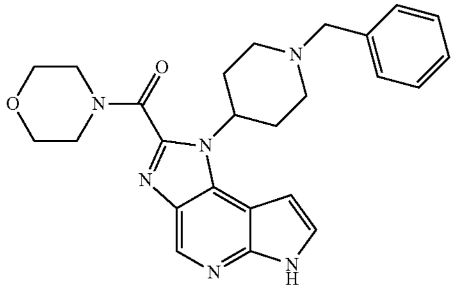 [SMILES: O=C(c1nc2cnc3[nH]ccc3c2n1C1CCN(Cc2ccccc2)CC1)N1CCOCC1] | [1-(1-Benzyl-piperidin-4-yl)-1,6-dihydro-1,3,5,6-tetraaza-as-indacen-2-yl]-morpholin-4-yl-methanone | 159 | 2.32/A | 445.0 |

TABLE 2-continued

| Ex | Structure | Name | Synthetic Method | LCMS RT (min)/Method | LCMS (ESI) m/z |
|---|---|---|---|---|---|
| 238 | 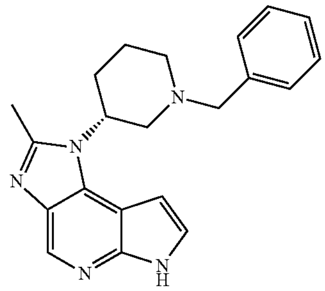 [SMILES: Cc1nc2cnc3[nH]ccc3c2n1[C@@H]1CCCN(Cc2ccccc2)C1] | (R)-1-(1-Benzyl-piperidin-3-yl)-2-methyl-1,6-dihydro-1,3,5,6-tetraaza-as-indacene | 20 | 1.89/A | 346.1 |
| 239 | 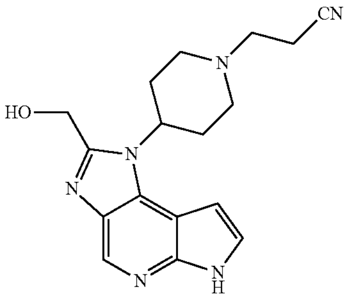 [SMILES: N#CCCN1CCC(n2c(CO)nc3cnc4[nH]ccc4c32)CC1] | 3-[4-(2-Hydroxymethyl-6H-1,3,5,6-tetraaza-as-indacen-1-yl)-piperidin-1-yl]-propionitrile | 10 | 0.92/A | 325.1 |
| 240 | 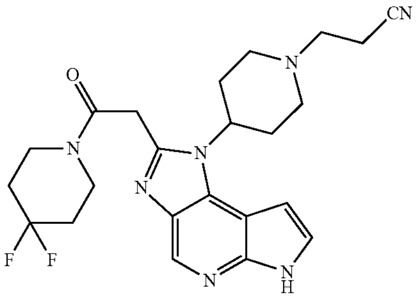 [SMILES: N#CCCN1CCC(n2c(CC(=O)N3CCC(F)(F)CC3)nc3cnc4[nH]ccc4c32)CC1] | 3-(4-{2-[2-(4,4-Difloro-piperidin-1-yl)-2-oxo-ethyl]-6H-1,3,5,6-tetraaza-as-indacen-1-yl}-piperidin-1-yl]-propionitrile | 160 | 2.11/A | 456.1 |
| 241 | 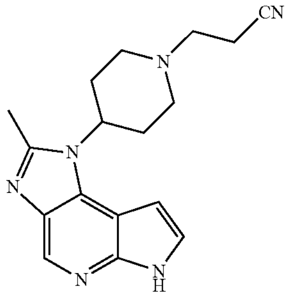 [SMILES: Cc1nc2cnc3[nH]ccc3c2n1C1CCN(CCC#N)CC1] | 3-[4-(2-Methyl-6H-1,3,5,6-tetraaza-as-indacen-1-yl)-piperidin-1-yl]-propionitrile | 2 & 10 | 1.06/A | 309.1 |
| 242 | 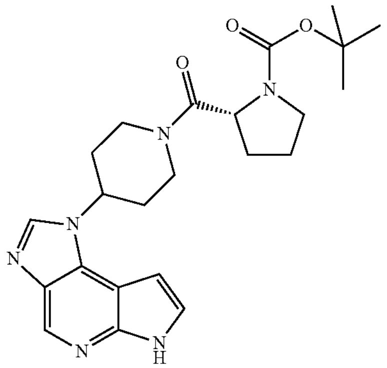 [SMILES: CC(C)(C)OC(=O)N1CCC[C@@H]1C(=O)N1CCC(n2cnc3cnc4[nH]ccc4c32)CC1] | (R)-2-[4-(6H-1,3,5,6-Tetraaza-as-indacen-1-yl)-piperidine-1-carbonyl]-pyrrolidine-1-carboxylic acid tert-butyl ester | 144 | 2.88/A | 439.1 |

TABLE 2-continued

| Ex | Structure | Name | Synthetic Method | LCMS RT (min)/Method | LCMS (ESI) m/z |
|---|---|---|---|---|---|
| 243 | 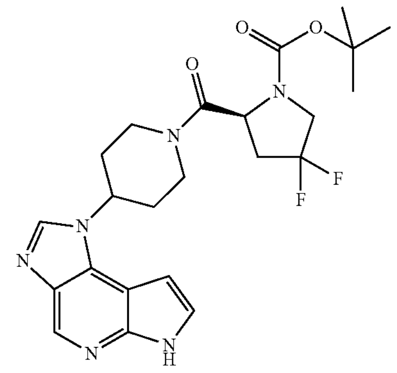 [SMILES: CC(C)(C)OC(=O)N1CC(F)(F)C[C@H]1C(=O)N1CCC(n2cnc3cnc4[nH]ccc4c32)CC1] | (S)-4,4-Difluoro-2-[4-(6H-1,3,5,6-tetraaza-as-indacen-1-yl)-piperidine-1-carbonyl]-pyrrolidine-1 carboxylic acid tert-butyl ester | 144 | 3.20/A | 475.1 |
| 244 | 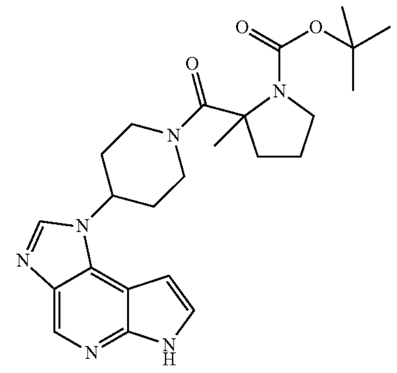 [SMILES: CC(C)(C)OC(=O)N1CCCC1(C)C(=O)N1CCC(n2cnc3cnc4[nH]ccc4c32)CC1] | racemic 2-Methyl-2-[4-(6H-1,3,5,6-tetraaza-as-indacen-1-yl)-piperidine-1-carbonyl]-pyrrolidine-1 carboxylic acid tert-butyl ester | 144 | 3.09/A | 453.1 |
| 245 | 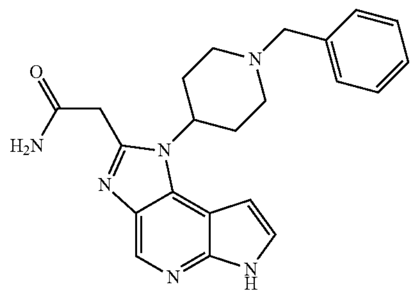 [SMILES: NC(=O)Cc1nc2cnc3[nH]ccc3c2n1C1CCN(Cc2ccccc2)CC1] | 2-[1-(1-Benzyl-piperidin-4-yl)-1,6-dihydro-1,3,5,6-tetraaza-as-indacen-2-yl]-acetamide | 23 | 1.76/A | 389.1 |
| 246 | 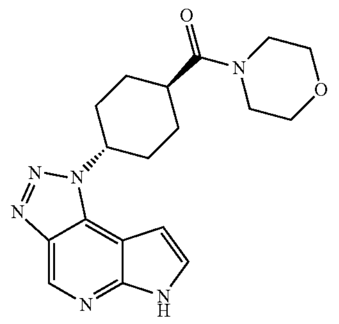 [SMILES: O=C([C@H]1CC[C@H](n2nnc3cnc4[nH]ccc4c32)CC1)N1CCOCC1] | Trans Morpholin-4-yl-[4-(6H-1,2,3,5,6-pentaaza-as-indacen-1-yl)-cyclohexyl]-methanone | 165 | 2.87/A | 355.1 |

TABLE 2-continued

| Ex | Structure | Name | Synthetic Method | LCMS RT (min)/Method | LCMS (ESI) m/z |
|---|---|---|---|---|---|
| 247 | 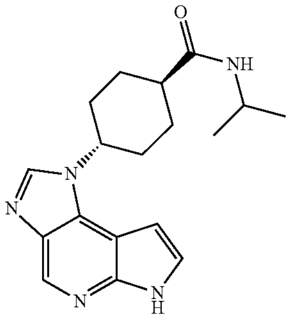 [SMILES: CC(C)NC(=O)[C@H]1CC[C@H](n2cnc3cnc4[nH]ccc4c32)CC1] | Trans 4-(6H-1,3,5,6-Tetraaza-as-indacen-1-yl)-cyclohexanecarboxylic acid isopropylamide | 166 | 2.35/A | 326.2 |
| 248 | 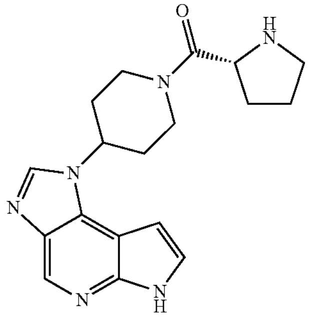 [SMILES: O=C([C@H]1CCCN1)N1CCC(n2cnc3cnc4[nH]ccc4c32)CC1] | (R)-Pyrrolidin-2-yl-[4-(6H-1,3,5,6-tetraaza-as-indacen-1-yl)-piperidin-1-yl]-methanone | 144 & 4 | 1.20/A | 339.1 |
| 249 | 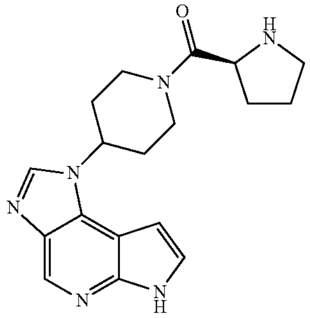 [SMILES: O=C([C@@H]1CCCN1)N1CCC(n2cnc3cnc4[nH]ccc4c32)CC1] | (S)-Pyrrolidin-2-yl-[4-(6H-1,3,5,6-tetraaza-as-indacen-1-yl)-piperidin-1-yl]-methanone | 144 & 4 | 1.18/A | 339.2 |
| 250 | 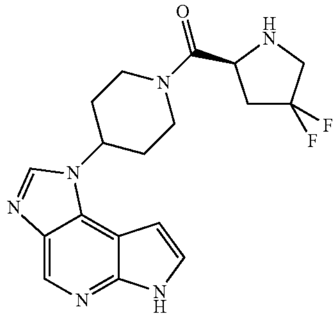 [SMILES: O=C([C@@H]1CC(F)(F)CN1)N1CCC(n2cnc3cnc4[nH]ccc4c32)CC1] | ((S)-4,4-Difluoro-pyrrolidin-2-yl)-[4-(6H-1,3,5,6-tetraaza-as-indacen-1-yl)-piperidin-1-yl]-methanone | 144 & 4 | 1.51/A | 375.1 |

TABLE 2-continued

| Ex | Structure | Name | Synthetic Method | LCMS RT (min)/Method | LCMS (ESI) m/z |
|---|---|---|---|---|---|
| 251 | 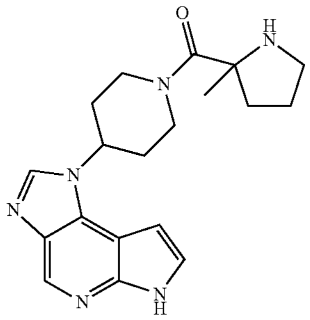 [SMILES: CC1(C(=O)N2CCC(n3cnc4cnc5[nH]ccc5c43)CC2)CCCN1] | racemic 2-Methyl-pyrrolidin-2-yl)-[4-(6H-1,3,5,6-tetraaza-as-indacen-1-yl)-piperidin-1-yl]-methanone | 144 & 4 | 1.36/A | 353.1 |
| 252 | 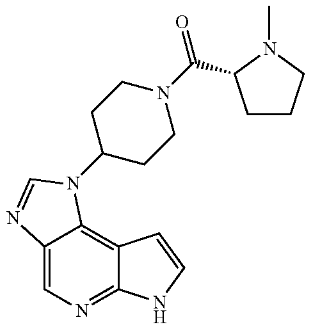 [SMILES: CN1CCC[C@@H]1C(=O)N1CCC(n2cnc3cnc4[nH]ccc4c32)CC1] | ((R)-1-Methyl-pyrrolidin-2-yl)-[4-(6H-1,3,5,6-tetraaza-as-indacen-1-yl)-piperidin-1-yl]-methanone | 145 | 1.10/A | 353.2 |
| 253 | 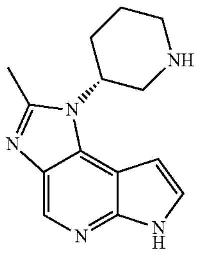 [SMILES: Cc1nc2cnc3[nH]ccc3c2n1[C@@H]1CCCNC1] | 2-Methyl-1-(R)-piperidin-3-yl-1,6-dihydro-1,3,5,6-tetraaza-as-indacene | 20 & 2 | 0.90/A | 256.1 |
| 254 | 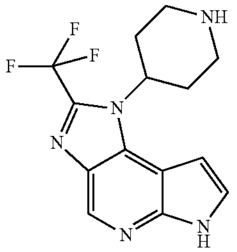 [SMILES: FC(F)(F)c1nc2cnc3[nH]ccc3c2n1C1CCNCC1] | 1-Piperidin-4-yl-2-trifluoromethyl-1,6-dihydro-1,3,5,6-tetraaza-as-indacene | 167 & 2 | 1.98/A | 310.1 |
| 255 | 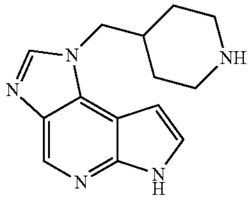 [SMILES: c1cc2c(ncc3ncn(CC4CCNCC4)c32)[nH]1] | 1-Piperidin-4-ylmethyl-1,6-dihydro-1,3,5,6-tetraaza-as-indacene | 3 & 4 | 0.84/A | 256.1 |

TABLE 2-continued

| Ex | Structure | Name | Synthetic Method | LCMS RT (min)/Method | LCMS (ESI) m/z |
|---|---|---|---|---|---|
| 256 | 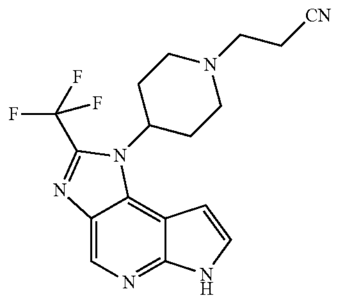 [SMILES: N#CCCN1CCC(n2c(C(F)(F)F)nc3cnc4[nH]ccc4c32)CC1] | 3-[4-(-2-Trifluoromethyl-6H-1,3,5,6-tetraaza-as-indacen-1-yl)-piperidin-1-yl]-propionitrile | 10 | 2.47/A | 363.1 |
| 257 | 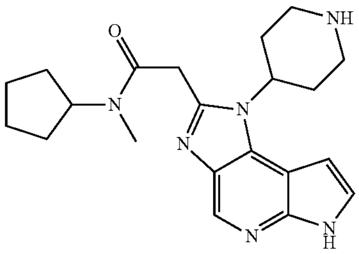 [SMILES: CN(C(=O)Cc1nc2cnc3[nH]ccc3c2n1C1CCNCC1)C1CCCC1] | N-Cyclopentyl-N-methyl-2-(1-piperidin-4-yl-1,6-dihydro-1,3,5,6-tetraaza-as-indacen-2-yl)-acetamide | 23 & 160 | 2.02/A | 381.1 |
| 258 | 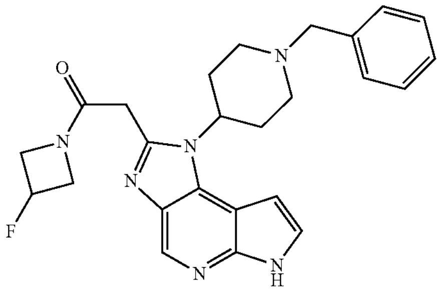 [SMILES: O=C(Cc1nc2cnc3[nH]ccc3c2n1C1CCN(Cc2ccccc2)CC1)N1CC(F)C1] | 2-[1-(1-Benzyl-piperidin-4-yl)-1,6-dihydro-1,3,5,6-tetraaza-as-indacen-2-yl)-1-(3-fluoro-azetidin-1-yl)-ethanone | 23 | 2.14/A | 447.2 |
| 259 | 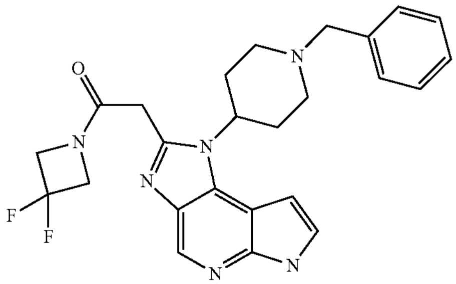 [SMILES: O=C(Cc1nc2cnc3[nH]ccc3c2n1C1CCN(Cc2ccccc2)CC1)N1CC(F)(F)C1] | 2-[1-(1-Benzyl-piperidin-4-yl)-1,6-dihydro-1,3,5,6-tetraaza-as-indacen-2-yl)-1-(3,3-difluoro-azetidin-1-yl)-ethanone | 23 | 2.33/A | 465.2 |
| 260 | 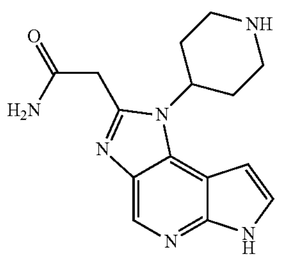 [SMILES: NC(=O)Cc1nc2cnc3[nH]ccc3c2n1C1CCNCC1] | 2-(1-Piperidin-4-yl-1,6-dihydro-1,3,5,6-tetraaza-as-indacen-2-yl)-acetamide | 160 | 0.66/A | 299.1 |

TABLE 2-continued

| Ex | Structure | Name | Synthetic Method | LCMS RT (min)/Method | LCMS (ESI) m/z |
|---|---|---|---|---|---|
| 261 | 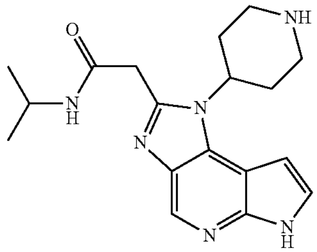 [SMILES: CC(C)NC(=O)Cc1nc2cnc3[nH]ccc3c2n1C1CCNCC1] | N-Isopropyl-2-(1-piperidin-4-yl-1,6-dihydro-1,3,5,6-tetraaza-as-indacen-2-yl)-acetamide | 160 | 1.50/A | 341.1 |
| 262 | 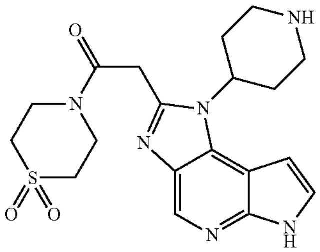 [SMILES: O=C(Cc1nc2cnc3[nH]ccc3c2n1C1CCNCC1)N1CCS(=O)(=O)CC1] | 1-(1,1-Dioxo-1lambda*6*-thiomorpholin-4-yl)-2-(1-piperidin-4-yl-1,6-dihydro-1,3,5,6-tetraaza-as-indacen-2-yl)-ethanone | 160 | 0.95/A | 417.1 |
| 263 | 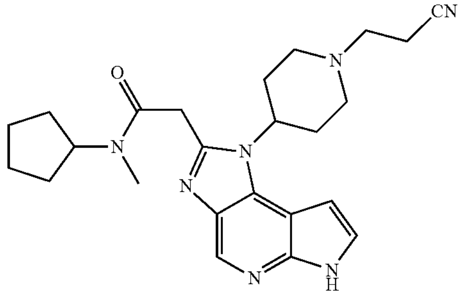 [SMILES: CN(C(=O)Cc1nc2cnc3[nH]ccc3c2n1C1CCN(CCC#N)CC1)C1CCCC1] | 2-{1-[1-(2-Cyano-ethyl)-piperidin-4-yl]-1,6-dihydro-1,3,5,6-tetraaza-as-indacen-2-yl}-N-cyclopentyl-N-methyl-acetamide | 160 | 2.29/A | 434.3 |
| 264 | 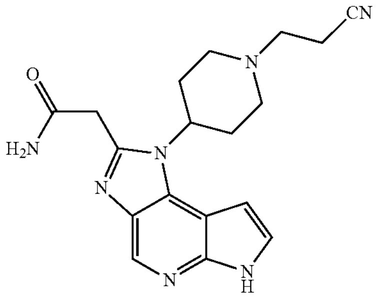 [SMILES: N#CCCN1CCC(n2c(CC(N)=O)nc3cnc4[nH]ccc4c32)CC1] | 2-{1-[1-(2-Cyano-ethy)-piperidin-4-yl]-1,6-dihydro-1,3,5,6-tetraaza-as-indacen-2-yl}-acetamide | 160 | 0.85/A | 352.1 |
| 265 | 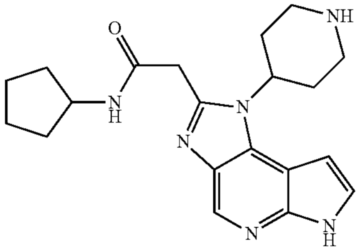 [SMILES: O=C(Cc1nc2cnc3[nH]ccc3c2n1C1CCNCC1)NC1CCCC1] | N-Cyclopentyl-2-(1-piperidin-4-yl-1,6-dihydro-1,3,5,6-tetraaza-as-indacen-2-yl)-acetamide | 160 | 1.81/A | 367.2 |

TABLE 2-continued

| Ex | Structure | Name | Synthetic Method | LCMS RT (min)/Method | LCMS (ESI) m/z |
|---|---|---|---|---|---|
| 266 | 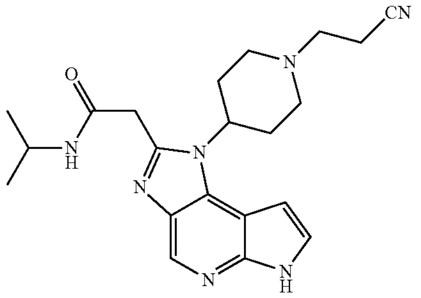 [SMILES: CC(C)NC(=O)Cc1nc2cnc3[nH]ccc3c2n1C1CCN(CCC#N)CC1] | 2-{1-[1-(2-Cyano-ethyl)-piperidin-4-yl]-1,6-dihydro-1,3,5,6-tetraaza-as-indacen-2-yl}-N-isopropyl-acetamide | 160 | 1.76/A | 394.2 |
| 267 | 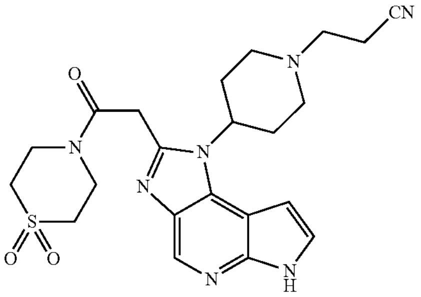 [SMILES: N#CCCN1CCC(n2c(CC(=O)N3CCS(=O)(=O)CC3)nc3cnc4[nH]ccc4c32)CC1] | 3-(4-{2-[2-(1,1-Dioxo-1lambda*6*-thiomorpholin-4-yl)-2-oxo-ethyl]-6H-1,3,5,6-tetraaza-as-indacen-1-yl}-piperidin-1-yl)-propionitrile | 160 | 1.54/A | 470.2 |
| 268 | 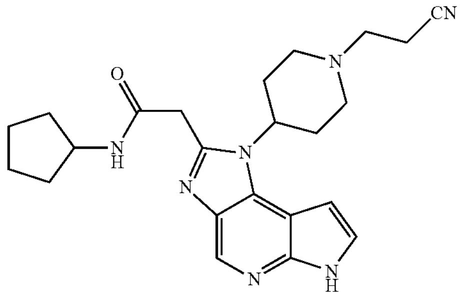 [SMILES: N#CCCN1CCC(n2c(CC(=O)NC3CCCC3)nc3cnc4[nH]ccc4c32)CC1] | 2-{1-[1-(2-Cyano-ethyl)-piperidin-4-yl]-1,6-dihydro-1,3,5,6-tetraaza-as-indacen-2-yl}-N-cyclopentyl-acetamide | 160 | 2.12/A | 420.2 |
| 269 | 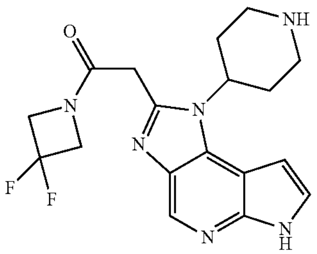 [SMILES: O=C(Cc1nc2cnc3[nH]ccc3c2n1C1CCNCC1)N1CC(F)(F)C1] | 1-(3,3-Difluoro-azetidin-1-yl)-2-(1-piperidin-4-yl-1,6-dihydro-1,3,5,6-tetraaza-as-indacen-2-yl)-ethanone | 160 | 1.50/A | 375.1 |
| 270 | 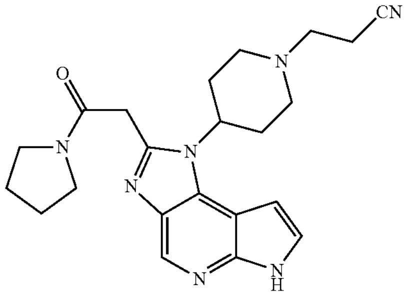 [SMILES: N#CCCN1CCC(n2c(CC(=O)N3CCCC3)nc3cnc4[nH]ccc4c32)CC1] | 3-{4-[2-(2-Oxo-2-pyrrolidin-1-yl-ethyl)-6H-1,3,5,6-tetraaza-as-indacen-1-yl]-piperidin-1-yl}-propionitrile | 160 | 1.72/A | 406.2 |

TABLE 2-continued

| Ex | Structure | Name | Synthetic Method | LCMS RT (min)/Method | LCMS (ESI) m/z |
|---|---|---|---|---|---|
| 271 | 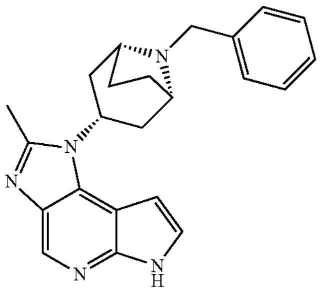 [SMILES: Cc1nc2cnc3[nH]ccc3c2n1[C@@H]1C[C@H]2CC[C@@H](C1)N2Cc1ccccc1] | 1-(8-Benzyl-8-aza-bicyclo[3.2.1]oct-3-yl)-2-methyl-1,6-dihydro-1,3,5,6-tetraaza-as-indacene | 20 | 2.01/A | 372.1 |
| 272 | 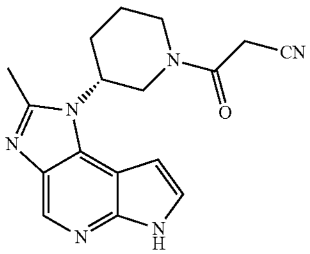 [SMILES: Cc1nc2cnc3[nH]ccc3c2n1[C@@H]1CCCN(C(=O)CC#N)C1] | 3-[(R)-3-(2-Methyl-6H-1,3,5,6-tetraaza-as-indacen-1-yl)-piperidin-3-yl]-3-oxo-propionitrile | 20, 2 & 5 | 1.95/A | 323.1 |
| 273 | 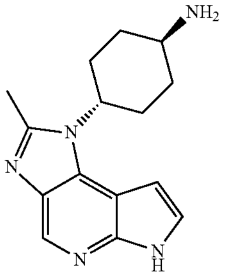 [SMILES: Cc1nc2cnc3[nH]ccc3c2n1[C@H]1CC[C@H](N)CC1] | Trans 4-(2-Methyl-6H-1,3,5,6-tetraaza-as-indacen-1-yl)-cyclohexylamine | 20 & 4 | 0.76/A | 270.1 |
| 274 | 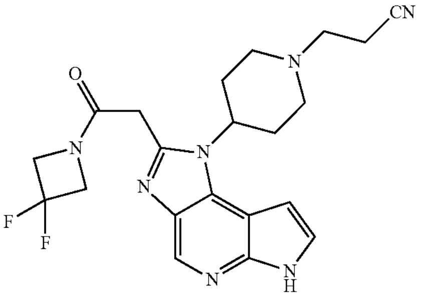 [SMILES: N#CCCN1CCC(n2c(CC(=O)N3CC(F)(F)C3)nc3cnc4[nH]ccc4c32)CC1] | 3-(4-{2-[2-(3,3-Difluoro-azetidin-1-yl)-2-oxo-ethyl]-6H-1,3,5,6-tetraaza-as-indacen-1-yl]-piperidin-1-yl}-propionitrile | 160 | 3.41/A | 428.2 |
| 275 | 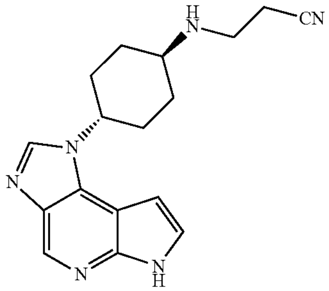 [SMILES: N#CCCN[C@H]1CC[C@H](n2cnc3cnc4[nH]ccc4c32)CC1] | Trans 3-[4-(6H-1,3,5,6-Tetraaza-as-indacen-1-yl)-cyclohexylamino]-propionitrile | 3, 4 & 10 | 1.22/A | 309.2 |

TABLE 2-continued

| Ex | Structure | Name | Synthetic Method | LCMS RT (min)/Method | LCMS (ESI) m/z |
|---|---|---|---|---|---|
| 276 | 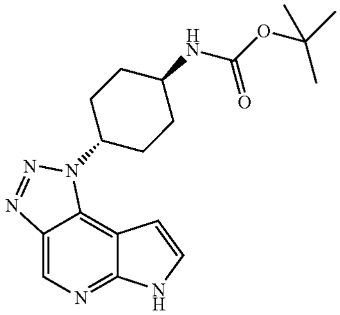 [SMILES: CC(C)(C)OC(=O)N[C@H]1CC[C@H](n2nnc3cnc4[nH]ccc4c32)CC1] | Trans [4-(6H-1,2,3,5,6-Pentaaza-as-indacen-1-yl)-cyclohexyl]-carbamic acid tert-butyl ester | 18 | 8.80/A | 357.2 |
| 277 | 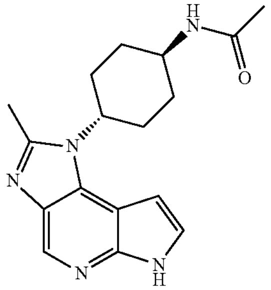 [SMILES: CC(=O)N[C@H]1CC[C@H](n2c(C)nc3cnc4[nH]ccc4c32)CC1] | Trans N-[4-(2-Methyl-6H-1,3,5,6-tetraaza-as-indacen-1-yl)-cyclohexyl]-acetamide | 6 | 1.89/A | 312.1 |
| 278 | 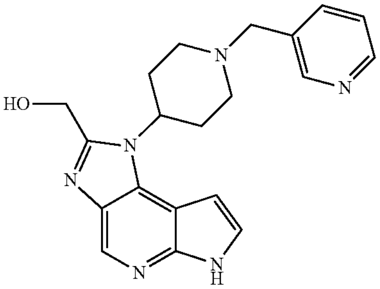 | [1-(1-Pyridin-3-ylmethyl-piperidin-4-yl)-1,6-dihydro-1,3,5,6-tetraaza-as-indacen-2-yl]-methanol | 22, 2 & 8 | 0.83/A | 363.2 |
| 279 | 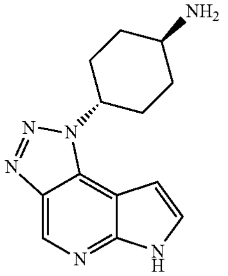 [SMILES: N[C@H]1CC[C@H](n2nnc3cnc4[nH]ccc4c32)CC1] | Trans 4-(6H-1,2,3,5,6-Pentaaza-as-indacen-1-yl)-cyclohexylamine | 18 & 4 | 1.63/A | 255 (ES-) |
| 280 | 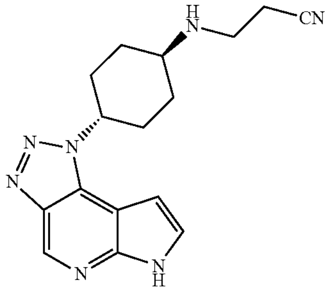 [SMILES: N#CCCN[C@H]1CC[C@H](n2nnc3cnc4[nH]ccc4c32)CC1] | Trans 3-[4-(6H-1,2,3,5,6-Pentaaza-as-indacen-1-yl)-cyclohexylamino]-propionitrile | 10 | 1.77/A | 310.2 |

TABLE 2-continued

| Ex | Structure | Name | Synthetic Method | LCMS RT (min)/Method | LCMS (ESI) m/z |
|---|---|---|---|---|---|
| 281 | 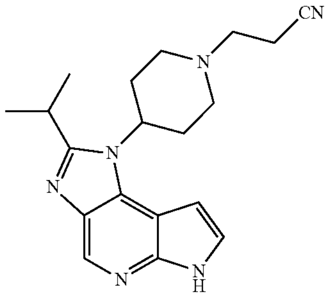 [SMILES: CC(C)c1nc2cnc3[nH]ccc3c2n1C1CCN(CCC#N)CC1] | 3-[4-(2-Isopropyl-6H-1,3,5,6-tetraaza-as-indacen-1-yl)-piperidin-1-yl]-propionitrile | 168 & 10 | 1.79/A | 337.3 |
| 282 | 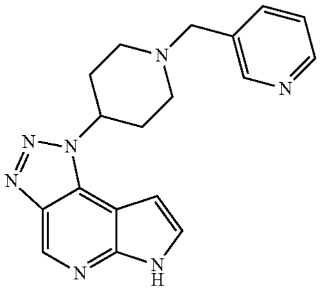 [SMILES: c1cncc(CN2CCC(n3nnc4cnc5[nH]ccc5c43)CC2)c1] | 1-(1-Pyridin-3-ylmethyl-piperidin4-yl)-1,6-dihydro-1,2,3,5,6-pentaaza-as-indacene | 18, 19 & 8 | 1.68/A | 334.2 |
| 283 | 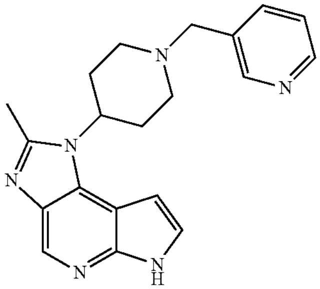 [SMILES: Cc1nc2cnc3[nH]ccc3c2n1C1CCN(Cc2cccnc2)CC1] | 2-Methyl-1-(1-pyridin-3-ylmethyl-piperidin-4-yl)-1,6-dihydro-1,3,5,6-tetraaza-as-indacene | 20, 2 & 8 | 1.07/A | 347.2 |
| 284 | 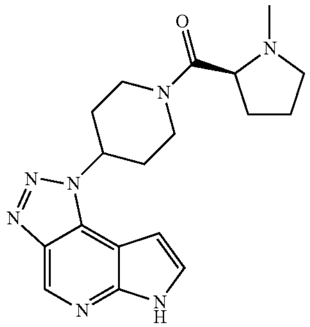 [SMILES: CN1CCC[C@H]1C(=O)N1CCC(n2nnc3cnc4[nH]ccc4c32)CC1] | ((S)-1-Methyl-pyrrolidin-2-yl)-[4-(6H-1,2,3,5,6-pentaaza-as-indacen-1-yl)-piperidin-1-yl]-methanone | 145 | 1.89/A | 354.3 |
| 285 | 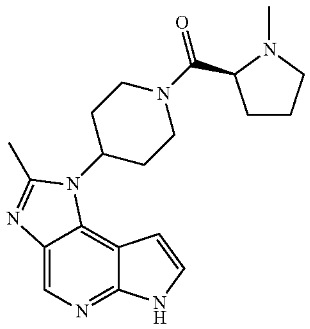 [SMILES: Cc1nc2cnc3[nH]ccc3c2n1C1CCN(C(=O)[C@@H]2CCCN2C)CC1] | ((S)-1-Methyl-pyrrolidin-2-yl-[4-(2-methyl-6H-1,3,5,6-tetraaza-as-indacen-1-yl)-piperidin-1-yl]-methanone | 145 | 0.98/A | 367.3 |

TABLE 2-continued

| Ex | Structure | Name | Synthetic Method | LCMS RT (min)/Method | LCMS (ESI) m/z |
|---|---|---|---|---|---|
| 286 | 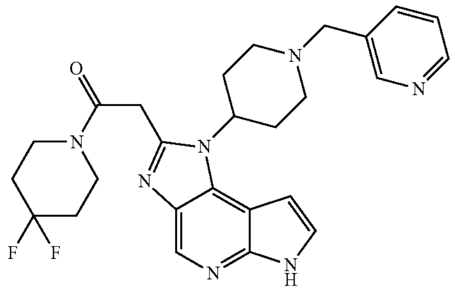 [SMILES: O=C(Cc1nc2cnc3[nH]ccc3c2n1C1CCN(Cc2cccnc2)CC1)N1CCC(F)(F)CC1] | 1-(4,4-Difluoro-piperidin-yl)-2-[1-(1-pyridin-3-ylmethyl-piperidin-4-yl)-1,6-dihydro-1,3,5,6-tetraaza-as-indacen-2-yl]-ethanone | 160 & 8 | 2.02/A | 494.3 |
| 287 | 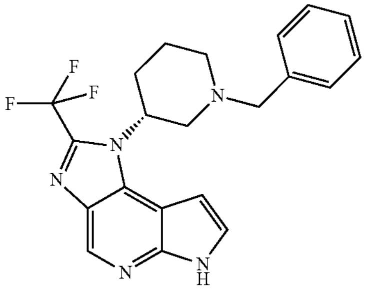 [SMILES: FC(F)(F)c1nc2cnc3[nH]ccc3c2n1[C@@H]1CCCN(Cc2ccccc2)C1] | 1-((R)-1-Benzyl-piperidin-3-yl)-1,6-dihydro-1,3,5,6-tetraaza-as-indacene | 167 | 2.77/A | 400.2 |
| 288 | 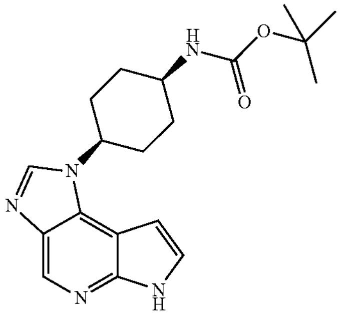 [SMILES: CC(C)(C)OC(=O)N[C@H]1CC[C@@H](n2cnc3cnc4[nH]ccc4c32)CC1] | Cis [4-(6H-1,3,5,6-Tetraaza-as-indacen-1-yl)-cyclohexyl]-carbamic acid tert-butyl ester | 3 | 3.10/A | 356.2 |
| 289 | 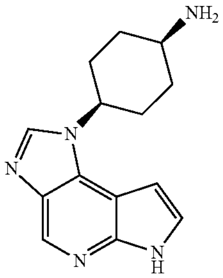 [SMILES: N[C@H]1CC[C@@H](n2cnc3cnc4[nH]ccc4c32)CC1] | Cis 4-(6H-1,3,5,6-Tetraaza-as-indacen-1-yl)-cyclohexylamine | 4 | 1.04/A | 256.2 |
| 290 | 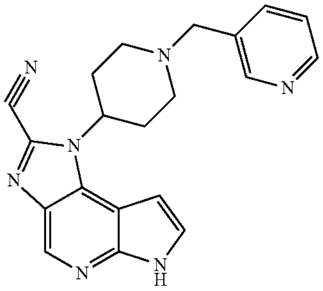 [SMILES: N#Cc1nc2cnc3[nH]ccc3c2n1C1CCN(Cc2cccnc2)CC1] | 1-(1-Pyridin-3-ylmethyl-piperidin-4-yl)-1,6-dihydro-1,3,5,6-tetraaza-as-indacene-2-carbonitrile | 170 & 8 | 1.90/A | 358.2 |

TABLE 2-continued

| Ex | Structure | Name | Synthetic Method | LCMS RT (min)/Method | LCMS (ESI) m/z |
|---|---|---|---|---|---|
| 291 | 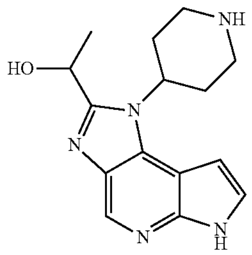 [SMILES: CC(O)c1nc2cnc3[nH]ccc3c2n1C1CCNCC1] | Racemic 1-(1-Piperidin-4-yl)-1,6-dihydro-1,3,5,6-tetraaza-as-indacen-2-yl)-ethanol | 156 | 1.00/A | 286.2 |
| 292 | 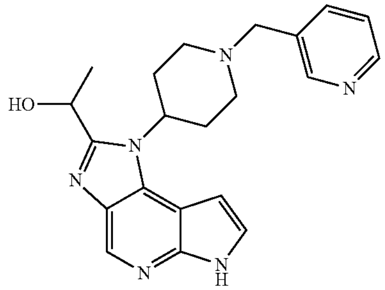 [SMILES: CC(O)c1nc2cnc3[nH]ccc3c2n1C1CCN(Cc2cccnc2)CC1] | Racemic 1-[1-(1-Pyridin-3-ylmethyl-piperidin-4-yl)-1,6-dihydro-1,3,5,6-tetraaza-as-indacen-2-yl]-ethanol | 156 | 1.49/A | 377.2 |
| 293 | 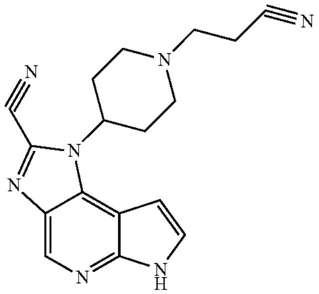 [SMILES: N#CCCN1CCC(n2c(C#N)nc3cnc4[nH]ccc4c32)CC1] | 1-[1-(2-Cyano-ethyl)-piperidin-4-yl]-1,6-dihydro-1,3,5,6-tetraaza-as-indacene-2-carbonitrile | 170 & 10 | 1.94/A | 320.2 |
| 294 | 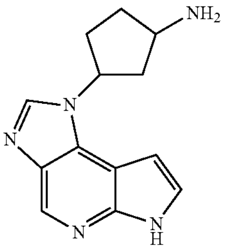 [SMILES: NC1CCC(n2cnc3cnc4[nH]ccc4c32)C1] | racemic, trans 3-(6H-1,3,5,6-Tetraaza-as-indacen-1-yl)-cyclopentylamine | 137 & 4 | 0.88/A | 242.2 |
| 295 | 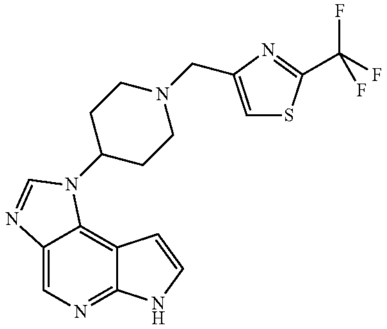 [SMILES: FC(F)(F)c1nc(CN2CCC(n3cnc4cnc5[nH]ccc5c43)CC2)cs1] | 1-[1-(2-Trifluoromethyl-thiazol-4-ylmethyl)-piperidin-4-yl]-1,6-dihydro-1,3,5,6-tetraaza-as-indacene | 8 | 2.18/A | 407.2 |

TABLE 2-continued

| Ex | Structure | Name | Synthetic Method | LCMS RT (min)/Method | LCMS (ESI) m/z |
|---|---|---|---|---|---|
| 296 | 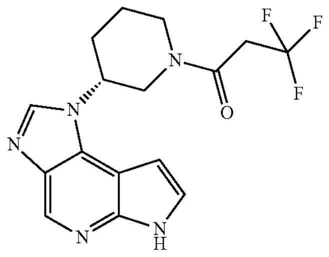 [SMILES: O=C(CC(F)(F)F)N1CCC[C@@H](n2cnc3cnc4[nH]ccc4c32)C1] | 3,3,3-Trifluoro-1-[(R)-3-(6H-1,3,5,6-tetraaza-as-indacen-1-yl]-propan-1-one | 5 | 2.48/A | 352.3 |
| 297) | 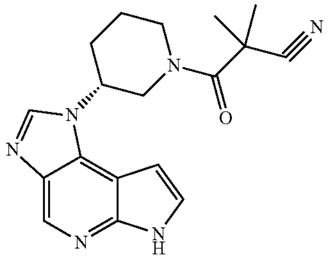 [SMILES: CC(C)(C#N)C(=O)N1CCC[C@@H](n2cnc3cnc4[nH]ccc4c32)C1] | 2,2-Dimethyl-3-oxo-3-[(R)-3-(6H-1,3,5,6-tetraaza-as-indacen-1-yl)-piperidin-1-yl]-propionitrile | 5 | 2.55/A | 337.3 |
| 298 | 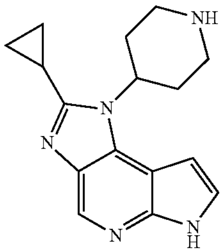 [SMILES: c1cc2c(ncc3nc(C4CC4)n(C4CCNCC4)c32)[nH]1] | 2-Cyclopropyl-1-piperidin-4-yl-1,6-dihydro-1,3,5,6-tetraaza-as-indacene | 153 | 1.49/A | 282.2 |
| 299 | 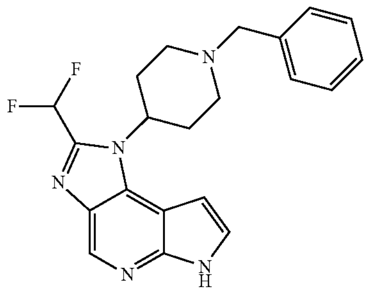 [SMILES: FC(F)c1nc2cnc3[nH]ccc3c2n1C1CCN(Cc2ccccc2)CC1] | 1-(1-Benzyl-piperidin-4-yl)-2-difluoromethyl-1,6-dihydro-1,3,5,6-tetraaza-as-indacene | 154 | 2.52/A | 382.2 |
| 300 | 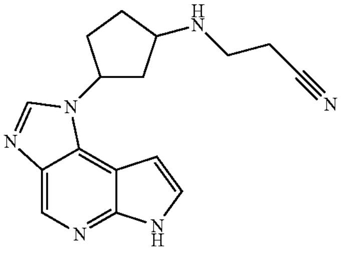 [SMILES: N#CCCNC1CCC(n2cnc3cnc4[nH]ccc4c32)C1] | racemic, trans 3-[3-(6H-1,3,5,6-Tetraaza-as-indacen-1-yl)-cyclopentylamino]-propionitrile | 10 | 1.03/A | 295.2 |

TABLE 2-continued

| Ex | Structure | Name | Synthetic Method | LCMS RT (min)/Method | LCMS (ESI) m/z |
|---|---|---|---|---|---|
| 301 | 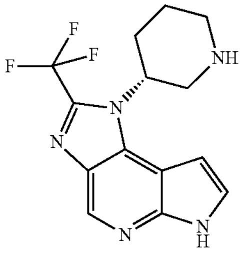 [SMILES: FC(F)(F)c1nc2cnc3[nH]ccc3c2n1[C@@H]1CCCNC1] | 1-(R)-Piperidin-3-yl-2-trifluoromethyl-1,6-dihydro-1,3,5,6-tetraaza-as-indacene | 167 & 2 | 2.09/A | 310.1 |
| 302 | 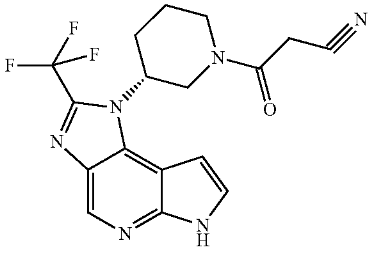 [SMILES: N#CCC(=O)N1CCC[C@@H](n2c(C(F)(F)F)nc3cnc4[nH]ccc4c32)C1] | 3-Oxo-3-[(R)-3-(2-trifluoromethyl-6H-1,3,5,6-tetraaza-as-indacen-1-yl)-piperidin-1-yl]-propionitrile | 5 | 3.28 | 377.1 |
| 303 | 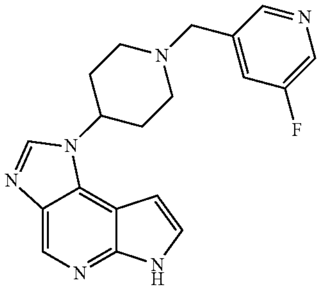 [SMILES: Fc1cncc(CN2CCC(n3cnc4cnc5[nH]ccc5c43)CC2)c1] | 1-[1-(5-Fluoro-pyridin-3-ylmethyl)-piperidin-4-yl]-1,6-dihydro-1,3,5,6-tetraaza-as-indacene | 8 | 1.52/A | 351.2 |
| 304 | 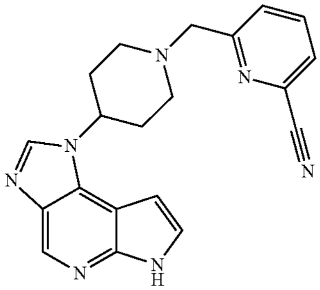 [SMILES: N#Cc1cccc(CN2CCC(n3cnc4cnc5[nH]ccc5c43)CC2)n1] | 6-[4-(6H-1,3,5,6-Tetraaza-as-indacen-1-yl)-piperidin-1-ylmethyl]-pyridine-2-carbonitrile | 8 | 1.62/A | 358.2 |
| 305 | 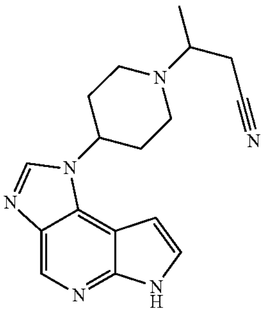 [SMILES: CC(CC#N)N1CCC(n2cnc3cnc4[nH]ccc4c32)CC1] | racemic 3-[4-(6H-1,3,5,6-Tetraaza-as-indacen-1-yl)-piperidin-1-yl]-butyronitrile | 10 | 1.03/A | 309.2 |

TABLE 2-continued

| Ex | Structure | Name | Synthetic Method | LCMS RT (min)/Method | LCMS (ESI) m/z |
|---|---|---|---|---|---|
| 306 | 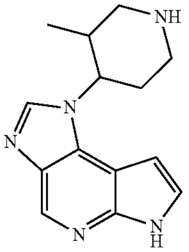 [SMILES: CC1CNCCC1n1cnc2cnc3[nH]ccc3c21] | racemic, cis 1-(3-Methyl-piperidin-4-yl)-1,6-dihydro-1,3,5,6-tetraaza-as-indacene | 149 & 2 | 0.87/A | 256.2 |
| 307 | 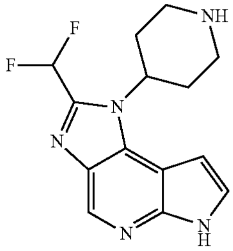 [SMILES: FC(F)c1nc2cnc3[nH]ccc3c2n1C1CCNCC1] | 2-Difluoromethyl-1-piperidin-4-yl-1,6-dihydro-1,3,5,6-tetraaza-as-indacene | 2 | 1.63/A | 292.2 |
| 308 | 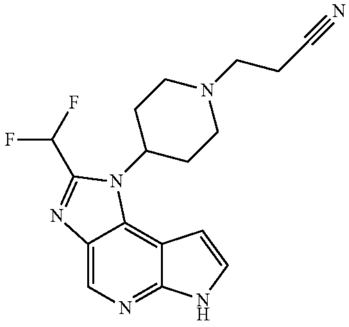 [SMILES: N#CCCN1CCC(n2c(C(F)F)nc3cnc4[nH]ccc4c32)CC1] | 3-[4-(2-Difluoromethyl-6H-1,3,5,6-tetraaza-as-indacen-1-yl)-piperidin-1-yl]-propionitrile | 10 | 1.99/A | 345.2 |
| 309 | 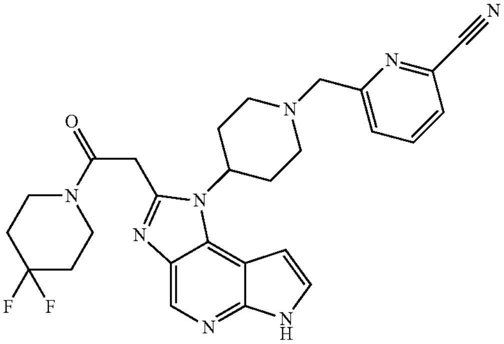 [SMILES: N#Cc1cccc(CN2CCC(n3c(CC(=O)N4CCC(F)(F)CC4)nc4cnc5[nH]ccc5c43)CC2)n1] | 6-(4-{2-(4,4-Difluoro-piperidin-1-yl)-2-oxo-ethyl]-6H-1,3,5,6-tetraaza-as-indacen-1-yl}-piperidin-1-yl methyl)-pyridine-2-carbonitrile | 160 & 8 | 2.4/A | 519.2 |
| 310 | 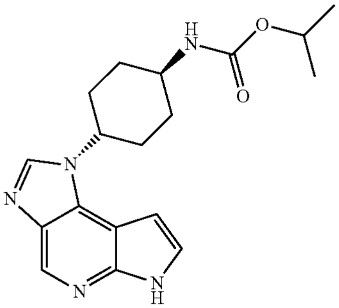 | Trans [(R)-4-(6H-1,3,5,6-Tetraaza-as-indacen-1-yl)-cyclohexyl]-carbamic acid isopropyl ester | 140 | 2.76/A | 342.3 |

TABLE 2-continued

| Ex | Structure | Name | Synthetic Method | LCMS RT (min)/Method | LCMS (ESI) m/z |
|---|---|---|---|---|---|
| 311 | 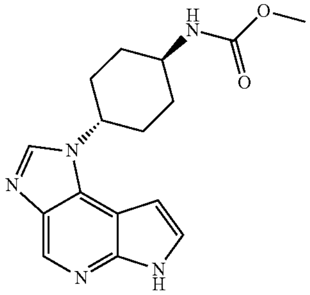 [SMILES: COC(=O)N[C@H]1CC[C@H](n2cnc3cnc4[nH]ccc4c32)CC1] | Trans [4-(6H-1,3,5,6-Tetraaza-as-indacen-1-yl)-cyclohexyl]-carbamic acid methyl ester | 143 | 2.21/A | 314.2 |
| 312 | 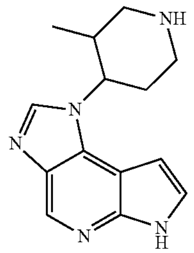 [SMILES: CC1CNCCC1n1cnc2cnc3[nH]ccc3c21] | racemic, trans 1-(3-Methyl-piperidin-4-yl)-1,6-dihydro-1,3,5,6-tetraaza-as-indacene | 150 & 2 | 0.84/A | 256.2 |
| 313 | 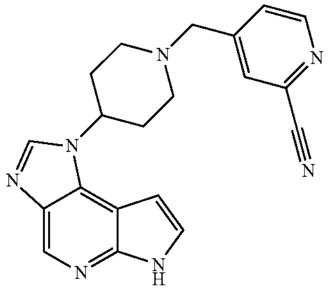 [SMILES: N#Cc1cc(CN2CCC(n3cnc4cnc5[nH]ccc5c43)CC2)ccn1] | 4-[4-(6H-1,3,5,6-Tetraaza-as-indacen-1-yl)-piperidin-1-ylmethyl]-pyridine-2-carbonitrile | 8 | 1.72/A | 358.2 |
| 314 | 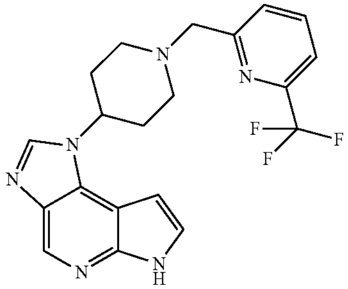 [SMILES: FC(F)(F)c1cccc(CN2CCC(n3cnc4cnc5[nH]ccc5c43)CC2)n1] | 1-[1-(6Trifluoromethyl-pyridin-2-ylmethyl)-piperidin-4-yl]-1,6-dihydro-1,3,5,6-tetraaza-as-indacene | 8 | 2.15/A | 401.2 |
| 315 | 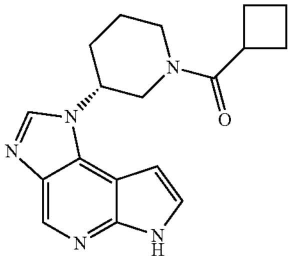 [SMILES: O=C(C1CCC1)N1CCC[C@@H](n2cnc3cnc4[nH]ccc4c32)C1] | Cyclobutyl-[(R)-3-(6H-1,3,5,6-tetraaza-as-indacen-1-yl)-piperidin1-yl]-methanone | 6 | 2.64/A | 324.3 |

TABLE 2-continued

| Ex | Structure | Name | Synthetic Method | LCMS RT (min)/Method | LCMS (ESI) m/z |
|---|---|---|---|---|---|
| 316 | 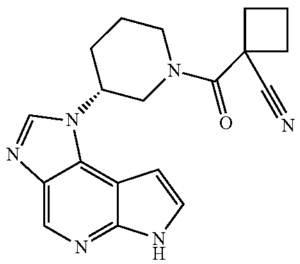 [SMILES: N#CC1(C(=O)N2CCC[C@@H](n3cnc4cnc5[nH]ccc5c43)C2)CCC1] | 1-[(R)-3-(6H-1,3,5,6-Tetraaza-as-indacen-1-yl)-piperidine-carbonyl]-cyclobutanecarbonitrile | 5 | 2.66/A | 349.3 |
| 317 | 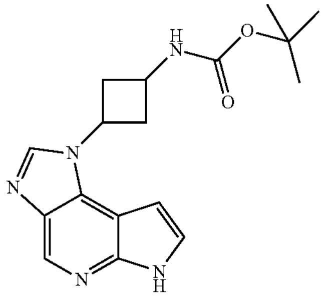 [SMILES: CC(C)(C)OC(=O)NC1CC(n2cnc3cnc4[nH]ccc4c32)C1] | [3-(6H-1,3,5,6-Tetraaza-as-indacen-1-yl)-cyclobutyl]-carbamic acid tert-butyl ester | 3 | 2.85/A | 328.2 |
| 318 | 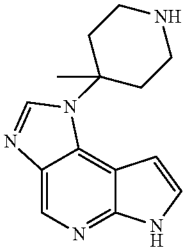 [SMILES: CC1(n2cnc3cnc4[nH]ccc4c32)CCNCC1] | 1-(4-Methyl-piperidin-4-yl)-1,6-dihydro-1,3,5,6-tetraaza-as-indacene | 132 & 4 | 1.21/A | 278.2 |
| 319 | 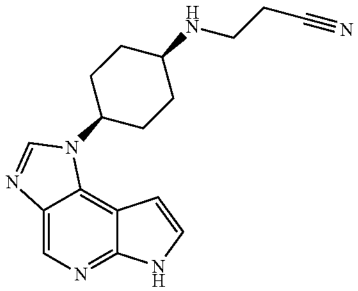 [SMILES: N#CCCN[C@H]1CC[C@@H](n2cnc3cnc4[nH]ccc4c32)CC1] | Cis 3-[4-(6H-1,3,5,6-Tetraaza-as-indacen-1-yl)-cyclohexylamino]-propionitrile | 10 | 0.98/A | 309.2 |
| 320 | 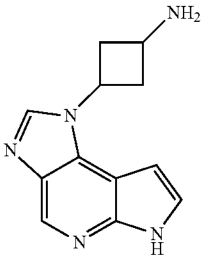 [SMILES: NC1CC(n2cnc3cnc4[nH]ccc4c32)C1] | 3-(6H-1,3,5,6-Tetraaza-as-indacen-1-yl)-cyclobutylamine | 4 | | |

TABLE 2-continued

| Ex | Structure | Name | Synthetic Method | LCMS RT (min)/Method | LCMS (ESI) m/z |
|---|---|---|---|---|---|
| 321 | 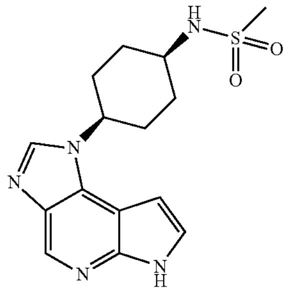 [SMILES: CS(=O)(=O)N[C@H]1CC[C@@H](n2cnc3cnc4[nH]ccc4c32)CC1] | Cis N-[4-(6H-1,3,5,6-Tetraaza-as-indacen-1-yl)-cyclohexyl]-methanesulfonamide | 9 | 2.10/A | 334.2 |
| 322 | 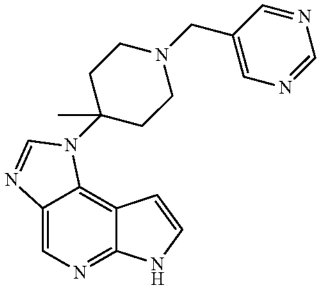 [SMILES: CC1(n2cnc3cnc4[nH]ccc4c32)CCN(Cc2cncnc2)CC1] | 1-(4-Methyl-1-pyrimidin-5-ylmethyl-piperidin-4-yl)-1,6-dihydro-1,3,5,6-tetraaza-as-indacene | 8 | 1.45/A | 348.2 |
| 323 | 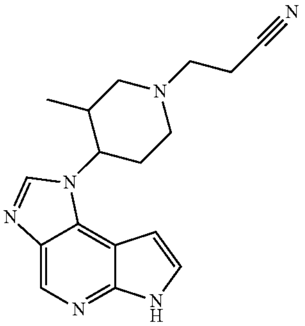 [SMILES: CC1CN(CCC#N)CCC1n1cnc2cnc3[nH]ccc3c21] | Racemic trans 3-[3-Methyl-4-(6H-1,3,5,6-tetraaza-as-indacen-1-yl)-piperidin-1-yl]-propionitrile | 10 | 1.20/A | 309.2 |
| 324 | 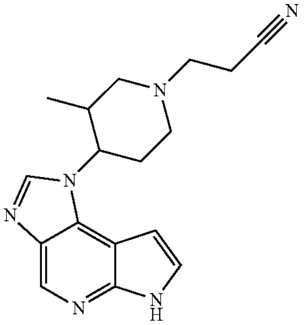 [SMILES: CC1CN(CCC#N)CCC1n1cnc2cnc3[nH]ccc3c21] | Racemic cis 3-[3-Methyl-4-(6H-1,3,5,6-tetraaza-as-indacen-1-yl)-piperidin-1-yl]-propionitrile | 10 | 1.17/A | 309.2 |
| 325 | 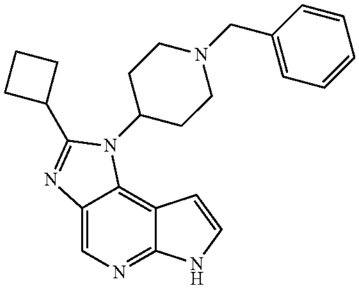 [SMILES: c1ccc(CN2CCC(n3c(C4CCC4)nc4cnc5[nH]ccc5c43)CC2)cc1] | 1-(1-Benzyl-piperidin-4-yl)-2-cyclobutyl-1,6-dihydro-1,3,5,6-tetraaza-as-indacene | 154 | 2.29/A | 386.3 |

TABLE 2-continued

| Ex | Structure | Name | Synthetic Method | LCMS RT (min)/Method | LCMS (ESI) m/z |
|---|---|---|---|---|---|
| 326 | 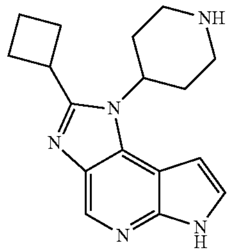 [SMILES: c1cc2c(ncc3nc(C4CCC4)n(C4CCNCC4)c32)[nH]1] | 2-Cyclobutyl-1-piperidin-4-yl-1,6-dihydro-1,3,5,6-tetraaza-as-indacene | 2 | 1.55/A | 296.4 |
| 327 | 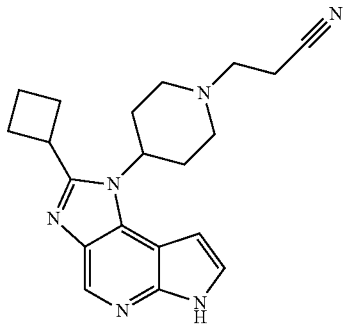 [SMILES: N#CCCN1CCC(n2c(C3CCC3)nc3cnc4[nH]ccc4c32)CC1] | 3-[4-(2-Cyclobutyl-6H-1,3,5,6-tetraaza-as-indacen-1-yl)-piperidin-1-yl]-propionitrile | 10 | 1.92/A | 349.3 |
| 328 | 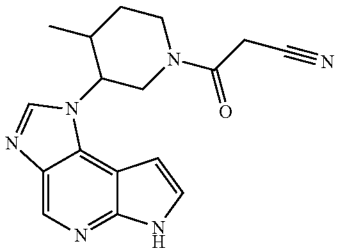 [SMILES: CC1CCN(C(=O)CC#N)CC1n1cnc2cnc3[nH]ccc3c21] | Racemic cis 3-[4-Methyl-3-(6H-1,3,5,6-tetraaza-as-indacen-1-yl)-piperidin-1-yl]-3-oxo-propionitrile | 131, 2 & 5 | 2.14/A | 323.2 |
| 329 | 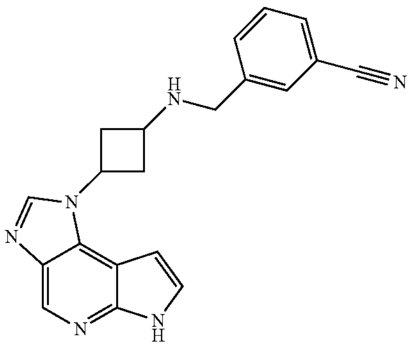 [SMILES: N#Cc1cccc(CNC2CC(n3cnc4cnc5[nH]ccc5c43)C2)c1] | 3-{[3-(6H-1,3,5,6-Tetraaza-as-indacen-1-yl)-cyclobutylamino]-methyl}-benzonitrile | 8 | 1.72/A | 343.2 |
| 330 | 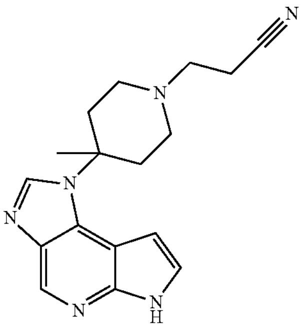 [SMILES: CC1(n2cnc3cnc4[nH]ccc4c32)CCN(CCC#N)CC1] | 3-[4-Methyl-4-(6H-1,3,5,6-tetraaza-as-indacen-1-yl)-piperidin-1-yl]-propionitrile | 10 | 1.31/A | 309.2 |

TABLE 2-continued

| Ex | Structure | Name | Synthetic Method | LCMS RT (min)/Method | LCMS (ESI) m/z |
|---|---|---|---|---|---|
| 331 | 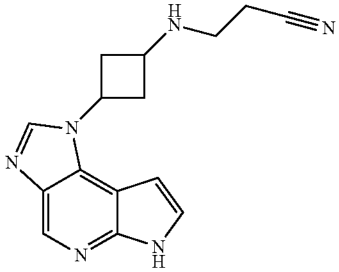 [SMILES: N#CCCNC1CC(n2cnc3cnc4[nH]ccc4c32)C1] | 3-[3-(6H-1,3,5,6-Tetraaza-as-indacen-1-yl)-cyclobutylamino]-propionitrile | 10 | 0.87/A | 281.3 |
| 332 | 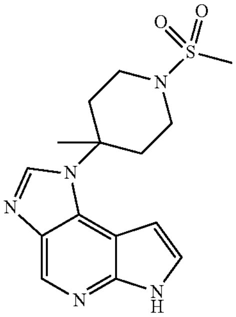 [SMILES: CC1(n2cnc3cnc4[nH]ccc4c32)CCN(S(C)(=O)=O)CC1] | 1-(1-Methanesulfonyl-4-methyl-piperidin-4-yl)-1,6-dihydro-1,3,5,6-tetraaza-as-indacene | 9 | 2.19/A | 334.3 |
| 333 | 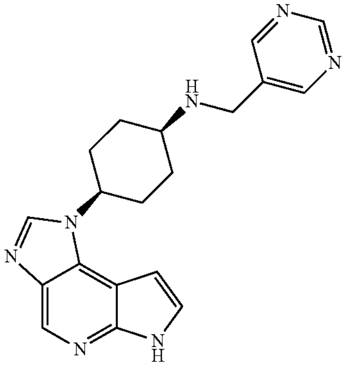 [SMILES: c1ncc(CN[C@H]2CC[C@@H](n3cnc4cnc5[nH]ccc5c43)CC2)cn1] | Cis Pyrimidin-5-ylmethyl-[4-(6H-1,3,5,6-tetraaza-as-indacen-1-yl)-cyclohexyl]-amine | 8 | 1.52/A | 348.3 |
| 334 | 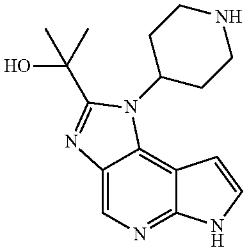 [SMILES: CC(C)(O)c1nc2cnc3[nH]ccc3c2n1C1CCNCC1] | 2-(1-Piperidin-4-yl-1,6-dihydro-1,3,5,6-tetraaza-as-indacen-2-yl)-propan-2-ol | 171 & 2 | 1.54/A | 300.2 |
| 335 | 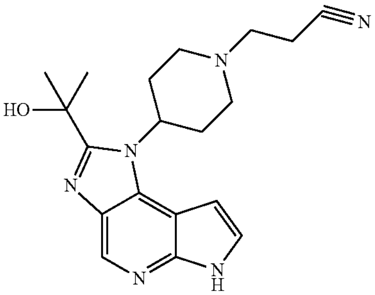 [SMILES: CC(C)(O)c1nc2cnc3[nH]ccc3c2n1C1CCN(CCC#N)CC1] | 3-{4-[2-(1-Hydroxy-1-methyl-ethyl)-6H-1,3,5,6-tetraaza-as-indacen-1-yl]-piperidin-1-yl}-propionitrile | 10 | 1.70/A | 353.3 |

TABLE 2-continued
| Ex | Structure | Name | Synthetic Method | LCMS RT (min)/Method | LCMS (ESI) m/z |
|---|---|---|---|---|---|
| 336 | 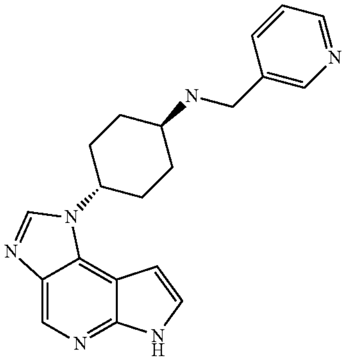 [SMILES: c1cncc(CN[C@H]2CC[C@H](n3cnc4cnc5[nH]ccc5c43)CC2)c1] | Trans Pyridin-3-ylmethyl-[4-(6H-1,3,5,6-tetraaza-as-indacen-1-yl)-cyclohexyl]-amine | 8 | 1.17/A | 347.3 |
| 337 | 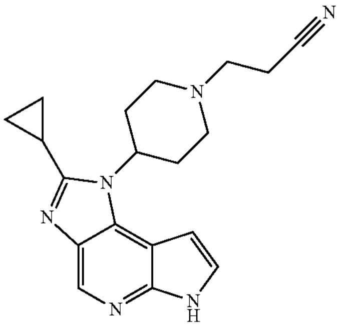 [SMILES: N#CCCN1CCC(n2c(C3CC3)nc3cnc4[nH]ccc4c32)CC1] | 3-[4-(2-Cyclopropyl-6H-1,3,5,6-tetraaza-as-indacen-1-yl)-piperidin-1-yl]-propionitrile | 10 | 1.61/A | 335.3 |
| 338 | 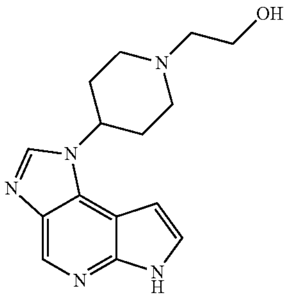 | 2-[4-(6H-1,3,5,6-Tetraaza-as-indacen-1-yl)-piperidin-1-yl]-ethanol | 174 | 0.79/A | 286.2 |
| 339 | 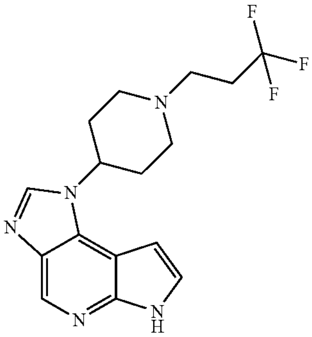 [SMILES: FC(F)(F)CCN1CCC(n2cnc3cnc4[nH]ccc4c32)CC1] | 1-[1-(3,3,3-Trifluoro-propyl)-piperidin-4-yl]-1,6-dihydro-1,3,5,6-tetraaza-as-indacene | 11 | 1.49/A | 338.2 |

TABLE 2-continued

| Ex | Structure | Name | Synthetic Method | LCMS RT (min)/Method | LCMS (ESI) m/z |
|---|---|---|---|---|---|
| 340 | 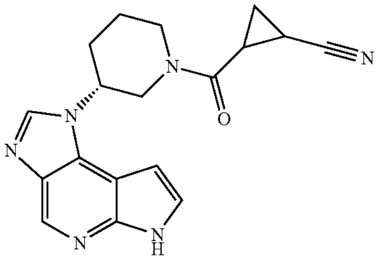 [SMILES: N#CC1CC1C(=O)N1CCC[C@@H](n2cnc3cnc4[nH]ccc4c32)C1] | (1R,2S)-2-[(R)-3-(6H-1,3,5,6-Tetraaza-as-indacen-1-yl)-piperidine-1-carbonyl]-cyclopropanecarbonitrile | 5 | 2.06 and 2.09/A | 335.2 |
| 341 | 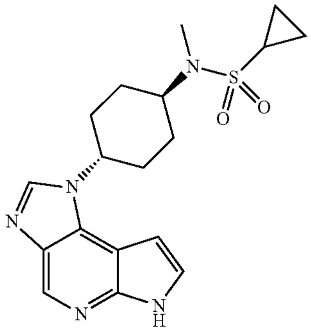 [SMILES: CN([C@H]1CC[C@H](n2cnc3cnc4[nH]ccc4c32)CC1)S(=O)(=O)C1CC1] | Trans Cyclopropanesulfonic acid methyl-[4-(6H-1,3,5,6-tetraaza-as-indacen1-yl)-cyclohexyl]-amide | 142 | 2.63/A | 374.3 |
| 342 | 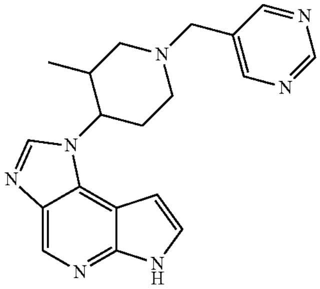 [SMILES: CC1CN(Cc2cncnc2)CCC1n1cnc2cnc3[nH]ccc3c21] | racemic, cis 1-(3-Methyl-1-pyrimidin-5-ylmethyl-piperidin-4-yl)-1,6-dihydro-1,3,5,6-tetraaza-as-indacene | 8 | 1.45/A | 348.2 |
| 343 | 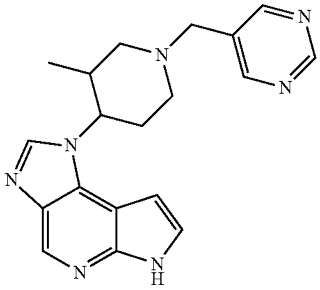 [SMILES: CC1CN(Cc2cncnc2)CCC1n1cnc2cnc3[nH]ccc3c21] | racemic, trans 1-(3-Methyl-1-pyrimidin-5-ylmethyl-piperidin-4-yl)-1,6-dihydro-1,3,5,6-tetraaza-as-indacene | 8 | 1.35/A | 348.2 |
| 344 | 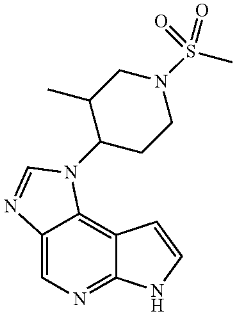 [SMILES: CC1CN(S(C)(=O)=O)CCC1n1cnc2cnc3[nH]ccc3c21] | racemic, trans 1-(1-Methanesulfonyl-3-methyl-piperidin-4-yl)-1,6-dihydro-1,3,5,6-tetraaza-as-indacene | 9 | 2.20/A | 334.2 |

TABLE 2-continued

| Ex | Structure | Name | Synthetic Method | LCMS RT (min)/Method | LCMS (ESI) m/z |
|---|---|---|---|---|---|
| 345 | 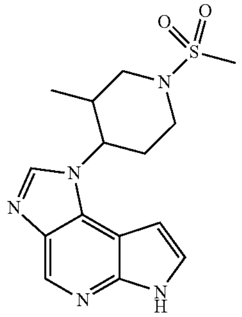 [SMILES: CC1CN(S(C)(=O)=O)CCC1n1cnc2cnc3[nH]ccc3c21] | racemic, cis 1-(1-Methanesulfonyl-3-methyl-piperidin-4-yl)-1,6-dihydro-1,3,5,6-tetraaza-as-indacene | 9 | 2.16/A | 334.2 |
| 346 | 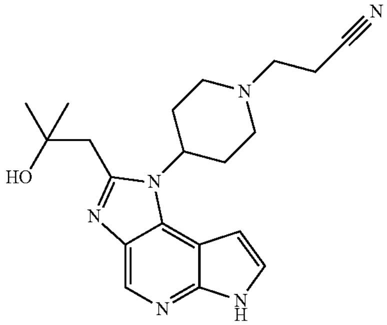 [SMILES: CC(C)(O)Cc1nc2cnc3[nH]ccc3c2n1C1CCN(CCC#N)CC1] | 3-{4-[2-(2-Hydroxy-2-methyl-propyl)-6H-1,3,5,6-tetraaza-as-indacen-1-yl)-piperidin-1-yl}-propionitrile | 173 & 10 | 1.61/A | 367.3 |
| 347 | 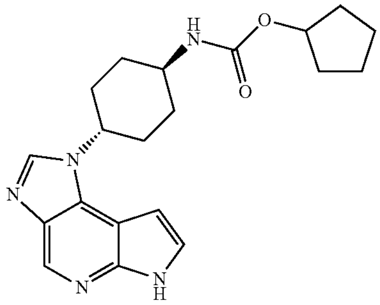 [SMILES: O=C(N[C@H]1CC[C@H](n2cnc3cnc4[nH]ccc4c32)CC1)OC1CCCC1] | Trans [4-(6H-1,3,5,6-Tetraaza-as-indacen-1-yl)-cyclohexyl]-carbamic acid cyclopentyl ester | 140 | 3.14/A | 368.3 |
| 348 | 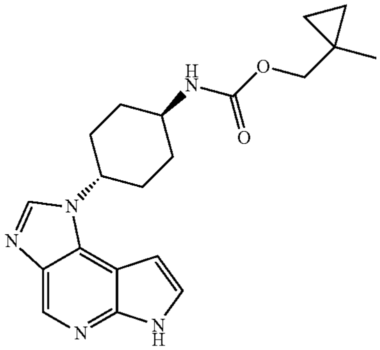 [SMILES: CC1(COC(=O)N[C@H]2CC[C@H](n3cnc4cnc5[nH]ccc5c43)CC2)CC1] | Trans [4-(6H-1,3,5,6-Tetraaza-as-indacen-1-yl)-cyclohexyl]-carbamic acid 1-methyl-cyclopropylmethyl ester | 140 | 3.14/A | 368.3 |
| 349 | 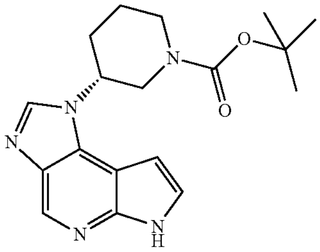 [SMILES: CC(C)(C)OC(=O)N1CCC[C@@H](n2cnc3cnc4[nH]ccc4c32)C1] | (R)-3-(6H-1,3,5,6-Tetraaza-as-indacen-1-yl)-piperidine-1-carboxylic acid tert-butyl ester | 124 | 3.11/A | 342.3 |

TABLE 2-continued

| Ex | Structure | Name | Synthetic Method | LCMS RT (min)/Method | LCMS (ESI) m/z |
|---|---|---|---|---|---|
| 350 | 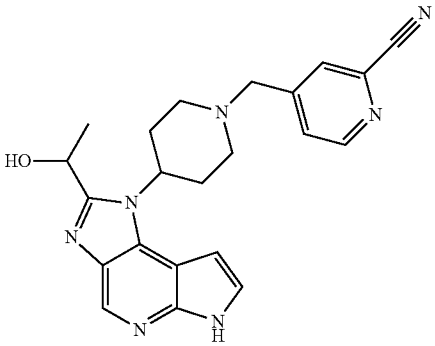 [SMILES: CC(O)c1nc2cnc3[nH]ccc3c2n1C1CCN(Cc2ccnc(C#N)c2)CC1] | racemic 4-{4-[2-(1-Hydroxy-ethyl)-6H-1,3,5,6-tetraaza-as-indacen-1-yl]-piperidin-1-ylmethyl}-pyridine-2-carbonitrile | 156 | 2.02/A | 402.2 |
| 351 | 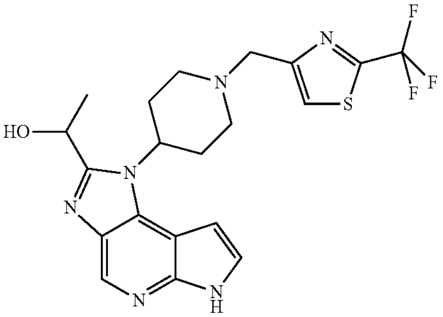 [SMILES: CC(O)c1nc2cnc3[nH]ccc3c2n1C1CCN(Cc2csc(C(F)(F)F)n2)CC1] | racemic 1-{1-[1-(2-Trifluoromethyl-thiazol-4-ylmethyl)-piperidin-4-yl]-1,6-dihydro-1,3,5,6-tetraaza-as-indacen-2-yl}-ethanol | 156 | 2.28/A | 451.2 |
| 352 | 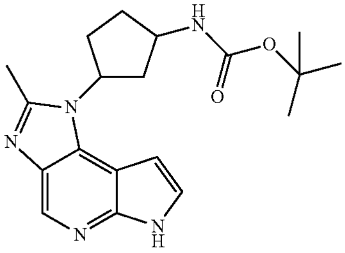 [SMILES: Cc1nc2cnc3[nH]ccc3c2n1C1CCC(NC(=O)OC(C)(C)C)C1] | racemic, trans [(1S,3S)-3-(2-Methyl-6H-1,3,5,6-tetraaza-as-indacen-1-yl)-cyclopentyl]-carbamic acid tert-butyl ester | 20 | 2.88/A | 356.3 |
| 353 | 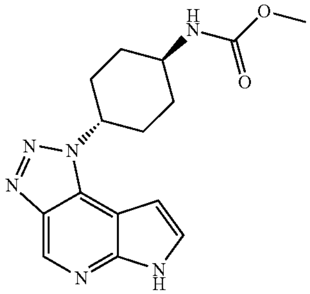 [SMILES: COC(=O)N[C@H]1CC[C@H](n2nnc3cnc4[nH]ccc4c32)CC1] | Trans [4-(6H-1,2,3,5,6-Pentaaza-as-indacen-1-yl)-cyclohexyl]-carbamic acid methyl ester | 143 | 3.00/A | 315.2 |
| 354 | 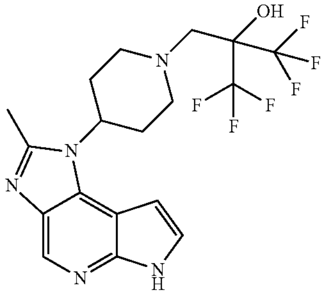 [SMILES: Cc1nc2cnc3[nH]ccc3c2n1C1CCN(CC(O)(C(F)(F)F)C(F)(F)F)CC1] | 1,1,1,3,3,3-Hexafluoro-2-[4-(2-methyl-6H-1,3,5,6-tetraaza-as-indacen-1-yl)-piperidin-1-ylmethyl]-propan-2-ol | 174 | 3.35/A | 436.2 |

TABLE 2-continued

| Ex | Structure | Name | Synthetic Method | LCMS RT (min)/Method | LCMS (ESI) m/z |
|---|---|---|---|---|---|
| 355 | 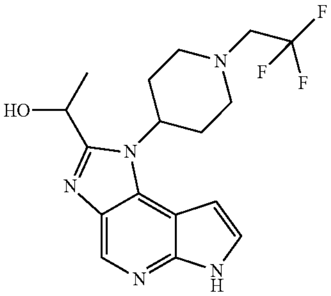 [SMILES: CC(O)c1nc2cnc3[nH]ccc3c2n1C1CCN(CC(F)(F)F)CC1] | Racemic 1-{1-[1-(2,2,2-Trifluoro-ethyl)-piperidin-4-yl]-1,6-dihydro-1,3,5,6-tetraaza-as-indacen-2-yl}-ethanol | 156 & 175 | 3.02/A | 368.3 |
| 356 | 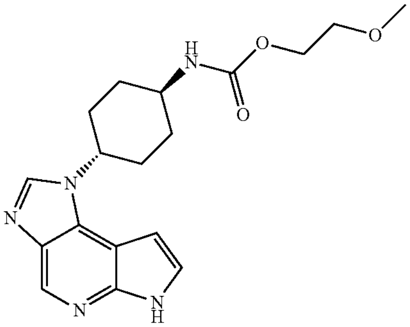 [SMILES: COCCOC(=O)N[C@H]1CC[C@H](n2cnc3cnc4[nH]ccc4c32)CC1] | Trans [4-(6H-1,3,5,6-Tetraaza-as-indacen-1-yl)-cyclohexyl]-carbamic acid 2-methoxy-ethyl ester | 140 | 2.28/A | 358.3 |
| 357 | 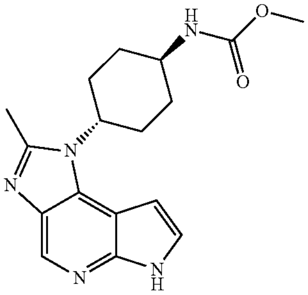 | Trans [4-(2-Methyl-6H-1,3,5,6-tetraaza-as-indacen-1-yl)-cyclohexyl]-carbamic acid methyl ester | 140 | 2.18/A | 328.3 |
| 358 | 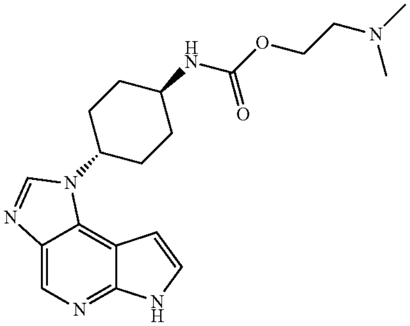 [SMILES: CN(C)CCOC(=O)N[C@H]1CC[C@H](n2cnc3cnc4[nH]ccc4c32)CC1] | Trans [4-(6H-1,3,5,6-Tetraaza-as-indacen-1-yl)-cyclohexyl]-carbamic acid 2-dimethylamino-ethyl ester | 140 | 1.74/A | 371.3 |

TABLE 2-continued

| Ex | Structure | Name | Synthetic Method | LCMS RT (min)/Method | LCMS (ESI) m/z |
|---|---|---|---|---|---|
| 359 | 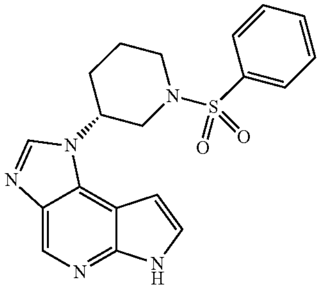 [SMILES: O=S(=O)(c1ccccc1)N1CCC[C@@H](n2cnc3cnc4[nH]ccc4c32)C1] | 1-((R)-1-Benzenesulfonyl-piperidin-3-yl)-1,6-dihydro-1,3,5,6-tetraaza-as-indacene | 9 | 3.12/A | 382.1 |
| 360 | 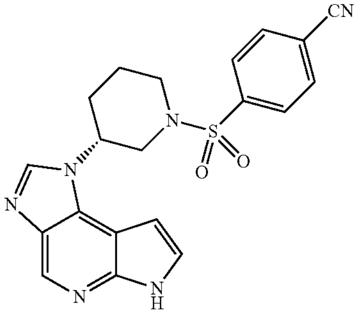 [SMILES: N#Cc1ccc(S(=O)(=O)N2CCC[C@@H](n3cnc4cnc5[nH]ccc5c43)C2)cc1] | 4-[(R)-3-(6H-1,3,5,6-Tetraaza-as-indacen-1-yl)-piperidine-1-sulfonyl]-benzonitrile | 9 | 3.15/A | 407.1 |
| 361 | 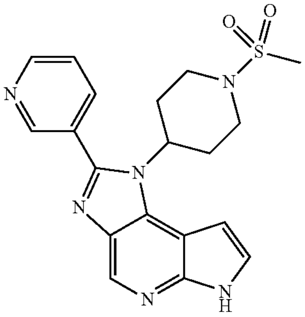 [SMILES: CS(=O)(=O)N1CCC(n2c(-c3cccnc3)nc3cnc4[nH]ccc4c32)CC1] | 1-(1-Methanesulfonyl-piperidin-4-yl)-2-pyridin-3-yl-1,6-dihydro-1,3,5,6-tetraaza-as-indacene | 153 & 9 | 2.37/A | 397.0 |
| 362 | 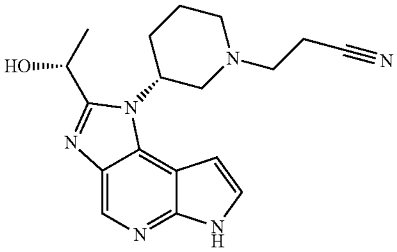 [SMILES: C[C@@H](O)c1nc2cnc3[nH]ccc3c2n1[C@@H]1CCCN(CCC#N)C1] | 3-{(R)-3-[2-((R)-1-Hydroxy-ethyl)-6H-1,3,5,6-tetraaza-as-indacen-1-yl] -piperidin-1-yl}-propionitrile | 10, 199 | 2.241/C | 339.1 |
| 363 | 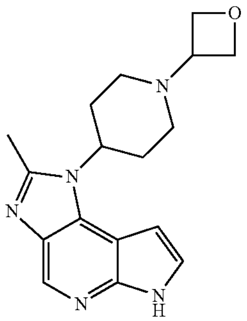 [SMILES: Cc1nc2cnc3[nH]ccc3c2n1C1CCN(C2COC2)CC1] | 2-Methyl-1-(1-oxetan-3-yl-piperidin-4-yl)-1,6-dihydro-1,3,5,6-tetraaza-as-indacene | 8, 20 | 3.474/D | 312.1 |

TABLE 2-continued

| Ex | Structure | Name | Synthetic Method | LCMS RT (min)/Method | LCMS (ESI) m/z |
|---|---|---|---|---|---|
| 364 | 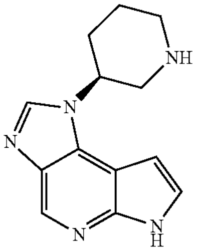 [SMILES: c1cc2c(ncc3ncn([C@H]4CCCNC4)c32)[nH]1] | (S)-1-Piperidin-3-yl-1,6-dihydro-1,3,5,6-tetraaza-as-indacene | 2 | 1.77/C | 242.1 |
| 365 | 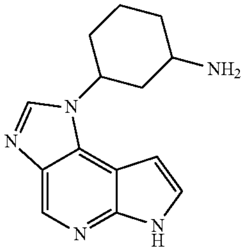 [SMILES: NC1CCCC(n2cnc3cnc4[nH]ccc4c32)C1] single enantiomer, absolute stereochemistry unknown | 3-(6H-1,3,5,6-Tetraaza-as-indacen-1-yl)-cyclohexylamine | 3 and 4 | 2.22/C | 256.1 |
| 366 | 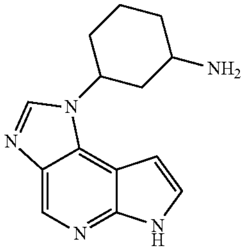 [SMILES: NC1CCCC(n2cnc3cnc4[nH]ccc4c32)C1] single enantiomer, absolute stereochemistry unknown | 3-(6H-1,3,5,6-Tetraaza-as-indacen-1-yl)-cyclohexylamine | 3 and 4 | 2.20/C | 256.1 |
| 367 | 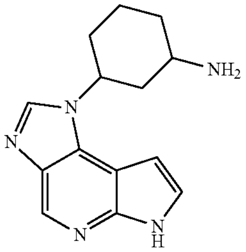 [SMILES: NC1CCCC(n2cnc3cnc4[nH]ccc4c32)C1] single enantiomer, absolute stereochemistry unknown | 3-(6H-1,3,5,6-Tetraaza-as-indacen-1-yl)-cyclohexylamine | 3 and 4 | 2.16/C | 256.1 |
| 368 | 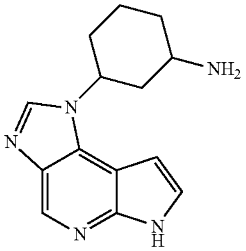 [SMILES: NC1CCCC(n2cnc3cnc4[nH]ccc4c32)C1] single enantiomer, absolute stereochemistry unknown | 3-(6H-1,3,5,6-Tetraaza-as-indacen-1-yl)-cyclohexylamine | 3 and 4 | 2.14/C | 256.1 |

TABLE 2-continued

| Ex | Structure | Name | Synthetic Method | LCMS RT (min)/Method | LCMS (ESI) m/z |
|---|---|---|---|---|---|
| 369 | 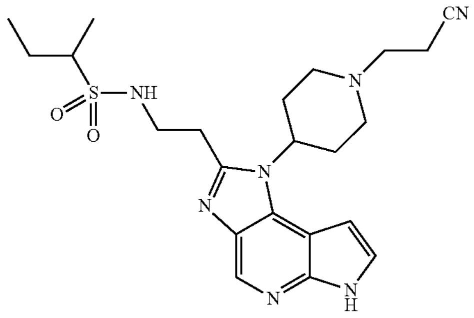 [SMILES: CCC(C)S(=O)(=O)NCCc1nc2cnc3[nH]ccc3c2n1C1CCN(CCC#N)CC1] racemic | Butane-2- sulfonic acid (2-{1-[1-(2-cyano-ethyl)-piperidin-4-yl]-1,6-dihydro-1,3,5,6-tetraaza-as-indacen-2-yl}-ethyl)-amide | 118 | 2.73/C | 458.2 |
| 370 | 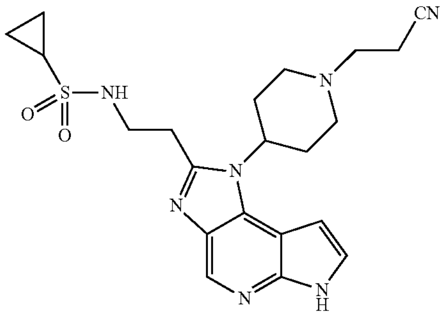 [SMILES: N#CCCN1CCC(n2c(CCNS(=O)(=O)C3CC3)nc3cnc4[nH]ccc4c32)CC1] | Cyclopropanesulfonic acid (2-{1-[1-(2-cyano-ethyl)-piperidin-4-yl]-1,6-dihydro-1,3,5,6-tetraaza-as-indacen-2-yl}-ethyl)-amide | 118 | 2.44/C | 442.1 |
| 371 | 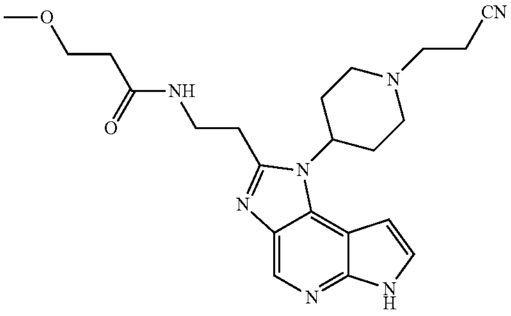 [SMILES: COCCC(=O)NCCc1nc2cnc3[nH]ccc3c2n1C1CCN(CCC#N)CC1] | N-(2-{1-[1-(2-Cyano-ethyl)-piperidin-4-yl]-1,6-dihydro-1,3,5,6-tetraaza-as-indacen-2-yl}-ethyl)-3-methoxy-propionamide | 118 | 2.25/C | 424.2 |
| 372 | 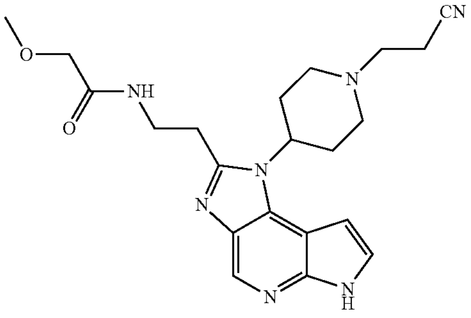 [SMILES: COCC(=O)NCCc1nc2cnc3[nH]ccc3c2n1C1CCN(CCC#N)CC1] | N-(2-{1-[1-(2-Cyano-ethyl)-piperidin-4-yl]-1,6-dihydro-1,3,5,6-tetraaza-as-indacen-2-yl}-ethyl)-2-methoxy-acetamide | 118 | 2.26/C | 410.2 |

TABLE 2-continued

| Ex | Structure | Name | Synthetic Method | LCMS RT (min)/Method | LCMS (ESI) m/z |
|---|---|---|---|---|---|
| 373 | 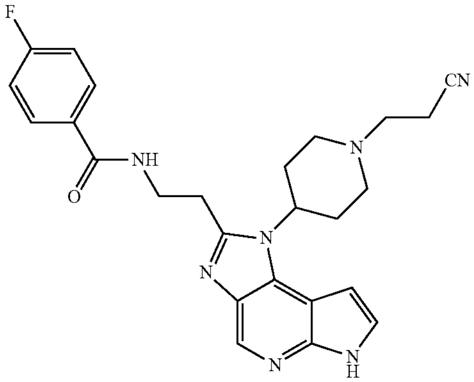 [SMILES: N#CCCN1CCC(n2c(CCNC(=O)c3ccc(F)cc3)nc3cnc4[nH]ccc4c32)CC1] | N-(2-{1-[1-(2-Cyano-ethyl)-piperidin-4-yl]-1,6-dihydro-1,3,5,6-tetraaza-as-indacen-2-yl}-ethyl)-4-fluoro-benzamide | 118 | 2.85/C | 460.2 |
| 374 | 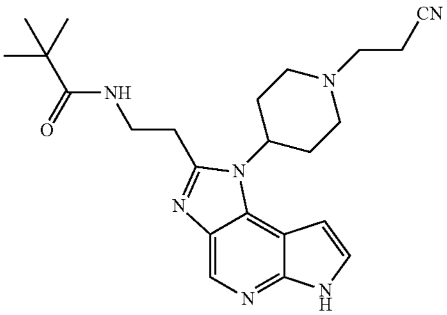 [SMILES: CC(C)(C)C(=O)NCCc1nc2cnc3[nH]ccc3c2n1C1CCN(CCC#N)CC1] | N-(2-{l-[l-(2-Cyano-ethyl)-piperidin-4-yl]-1,6-dihydro-1,3,5,6-tetraaza-as-indacen-2-yl}-ethyl)-2,2-dimethyl-propionamide | 118 | 2.62/C | 422.2 |
| 375 | 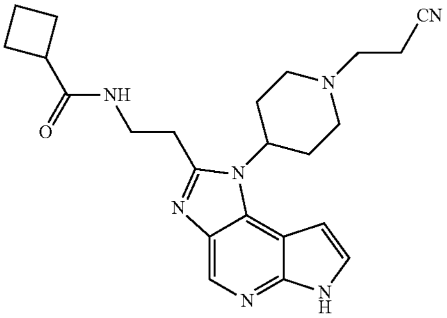 [SMILES: N#CCCN1CCC(n2c(CCNC(=O)C3CCC3)nc3cnc4[nH]ccc4c32)CC1] | Cyclobutanecarboxylic acid (2-{1-[1-(2-cyano-ethyl)-piperidin-4-yl]-1,6-dihydro-1,3,5,6-tetraaza-as-indacen-2-yl}-ethyl)-amide | 118 | 2.52/C | 420.2 |
| 376 | 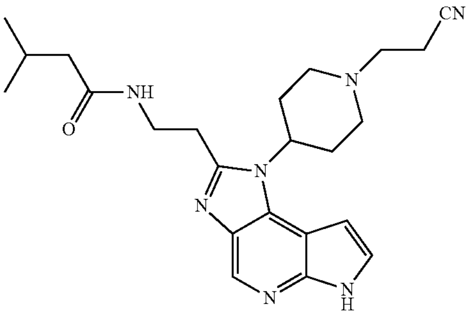 [SMILES: CC(C)CC(=O)NCCc1nc2cnc3[nH]ccc3c2n1C1CCN(CCC#N)CC1] | N-(2-{1-[1-(2-Cyano-ethyl)-piperidin-4-yl]-1,6-dihydro-1,3,5,6-tetraaza-as-indacen-2-yl}-ethyl)-3-methyl-butyramide | 118 | 2.63/C | 422.2 |

TABLE 2-continued

| Ex | Structure | Name | Synthetic Method | LCMS RT (min)/Method | LCMS (ESI) m/z |
|---|---|---|---|---|---|
| 377 | 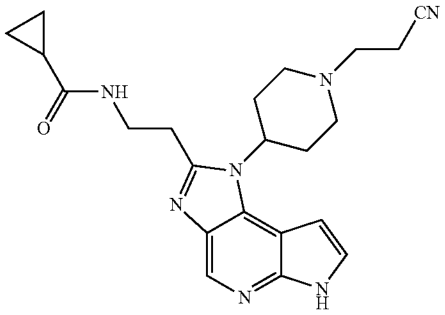 [SMILES: N#CCCN1CCC(n2c(CCNC(=O)C3CC3)nc3cnc4[nH]ccc4c32)CC1] | Cyclopropanecarboxylic acid (2-{1-[1-(2-cyano-ethyl)-piperidin-4-yl]-1,6-dihydro-1,3,5,6-tetraaza-as-indacen-2-yl}-ethyl)-amide | 118 | 2.37/C | 406.2 |
| 378 | 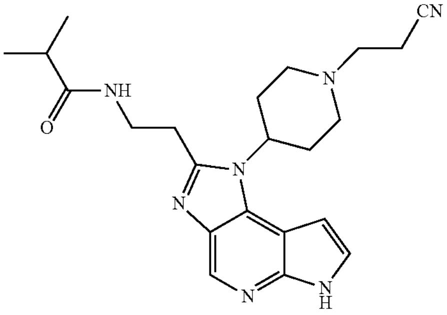 [SMILES: CC(C)C(=O)NCCc1nc2cnc3[nH]ccc3c2n1C1CCN(CCC#N)CC1] | N-(2-{1-[1-(2-Cyano-ethyl)-piperidin-4-yl]-1,6-dihydro-1,3,5,6-tetraaza-as-indacen-2-yl}-ethyl)-isobutyramide | 118 | 2.42/C | 408.2 |
| 379 | 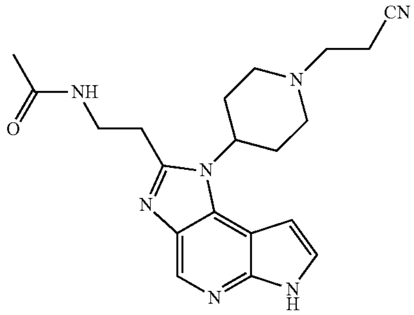 [SMILES: CC(=O)NCCc1nc2cnc3[nH]ccc3c2n1C1CCN(CCC#N)CC1] | N-(2-{1-[1-(2-Cyano-ethyl)-piperidin-4-yl]-1,6-dihydro-1,3,5,6-tetraaza-as-indacen-2-yl}-ethyl)-acetamide | 118 | 2.13/C | 380.2 |
| 380 | 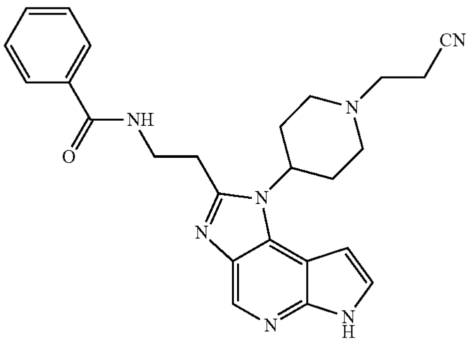 [SMILES: N#CCCN1CCC(n2c(CCNC(=O)c3ccccc3)nc3cnc4[nH]ccc4c32)CC1] | N-(2-{1-[1-(2-Cyano-ethyl)-piperidin-4-yl]-1,6-dihydro-1,3,5,6-tetraaza-as-indacen-2-yl}-ethyl)-benzamide | 118 | 2.76/C | 442.2 |

TABLE 2-continued

| Ex | Structure | Name | Synthetic Method | LCMS RT (min)/Method | LCMS (ESI) m/z |
|---|---|---|---|---|---|
| 381 | 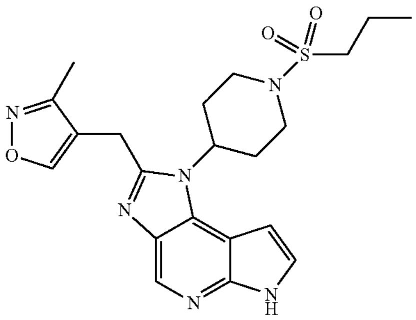 [SMILES: CCCS(=O)(=O)N1CCC(n2c(Cc3conc3C)nc3cnc4[nH]ccc4c32)CC1] | 2-(3-Methyl-isoxazol-4-ylmethyl)-1-[1-(propane-1-sulfonyl)-piperidin-4-yl]-1,6-dihydro-1,3,5,6-tetraaza-as-indacene | 119 | 2.79/C | 403.1 |
| 382 | 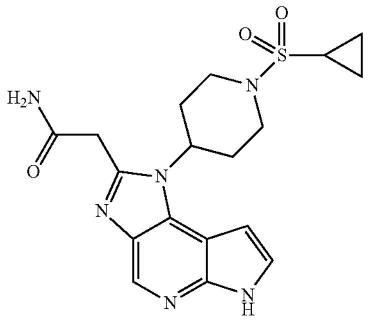 [SMILES: NC(=O)Cc1nc2cnc3[nH]ccc3c2n1C1CCN(S(=O)(=O)C2CC2)CC1] | 2-[1-(1-Cyclopropanesulfonyl-piperidin-4-yl)-1,6-dihydro-1,3,5,6-tetraaza-as-indacen-2-yl]-acetamide | 117 | 2.79/C | 403.1 |
| 383 | 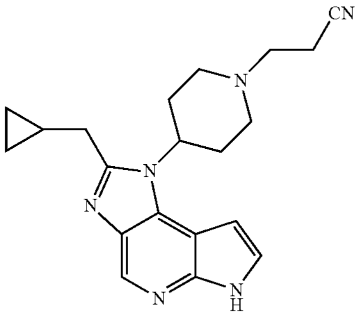 [SMILES: N#CCCN1CCC(n2c(CC3CC3)nc3cnc4[nH]ccc4c32)CC1] | 3-[4-(2-Cyclopropylmethyl-6H-1,3,5,6-tetraaza-as-indacen-1-yl)-piperidin-1-yl]-propionitrile | 120 | 2.50/C | 349.1 |
| 384 | 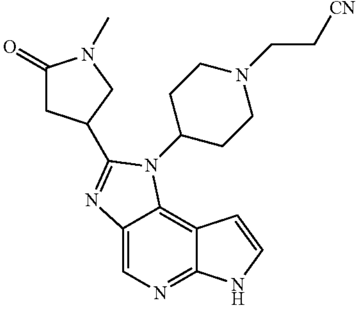 [SMILES: CN1CC(c2nc3cnc4[nH]ccc4c3n2C2CCN(CCC#N)CC2)CC1=O] racemic | 3-{4-[2-(1-Methyl-5-oxo-pyrrolidin-3-yl)-6H-1,3,5,6-tetraaza-as-indacen-1-yl]-piperidin-1-yl}-propionitrile | 120 | 2.22/C | 392.2 |

TABLE 2-continued

| Ex | Structure | Name | Synthetic Method | LCMS RT (min)/Method | LCMS (ESI) m/z |
|---|---|---|---|---|---|
| 385 | 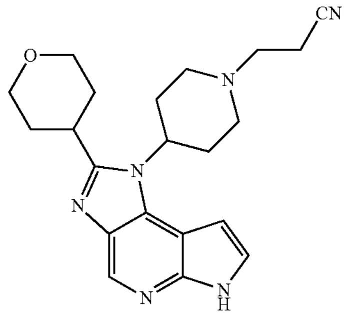 [SMILES: N#CCCN1CCC(n2c(C3CCOCC3)nc3cnc4[nH]ccc4c32)CC1] | 3-{4-[2-(Tetrahydro-pyran-4-yl)-6H-1,3,5,6-tetraaza-as-indacen-1-yl]-piperidin-1-yl}-propionitrile | 120 | 2.40/C | 379.2 |
| 386 | 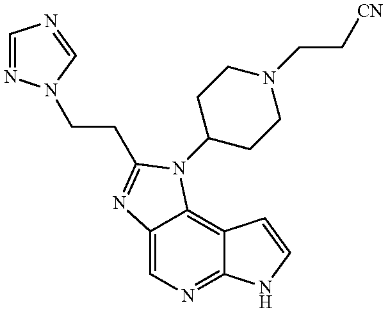 [SMILES: N#CCCN1CCC(n2c(CCn3cncn3)nc3cnc4[nH]ccc4c32)CC1] | 3-{4-[2-(2-[1,2,4]Triazol-1-yl-ethyl)-6H-1,3,5,6-tetraaza-as-indacen-1-yl]-piperidin-1-yl}-propionitrile | 120 | 2.17/C | 390.2 |
| 387 | 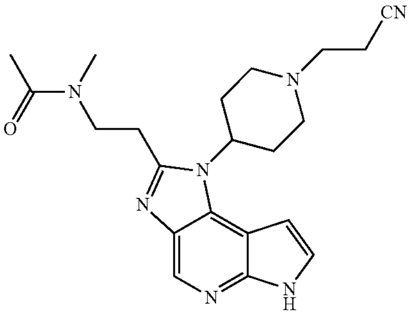 [SMILES: CC(=O)N(C)CCc1nc2cnc3[nH]ccc3c2n1C1CCN(CCC#N)CC1] | N-(2-{1-[1-(2-Cyano-ethyl)-piperidin-4-yl]-1,6-dihydro-1,3,5,6-tetraaza-as-indacen-2-yl}-ethyl)-N-methyl-acetamide | 120 | 2.26/C | 394.2 |
| 388 | 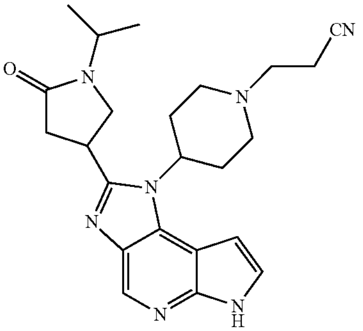 [SMILES: CC(C)N1CC(c2nc3cnc4[nH]ccc4c3n2C2CCN(CCC#N)CC2)CC1=O] racemic | 3-{4-[2-(1-Isopropyl-5-oxo-pyrrolidin-3-yl)-6H-1,3,5,6-tetraaza-as-indacen-1-yl]-piperidin-1-yl}-propionitrile | 120 | 2.58/C | 420.2 |

TABLE 2-continued

| Ex | Structure | Name | Synthetic Method | LCMS RT (min)/Method | LCMS (ESI) m/z |
|---|---|---|---|---|---|
| 389 | 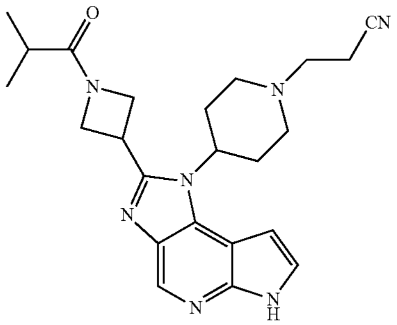 [SMILES: CC(C)C(=O)N1CC(c2nc3cnc4[nH]ccc4c3n2C2CCN(CCC#N)CC2)C1] | 3-{4-[2-(1-Isobutyryl-azetidin-3-yl)-6H-1,3,5,6-tetraaza-as-indacen-1-yl]-piperidin-1-yl}-propionitrile | 120 | 2.59/C | 420.2 |
| 390 | 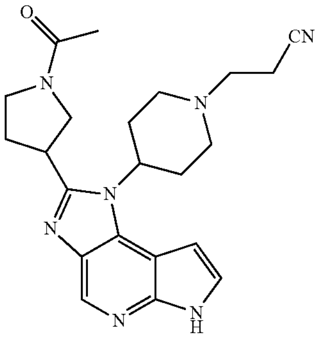 [SMILES: CC(=O)N1CCC(c2nc3cnc4[nH]ccc4c3n2C2CCN(CCC#N)CC2)C1] racemic | 3-{4-[2-(1-Acetyl-pyrrolidin-3-yl)-6H-1,3,5,6-tetraaza-as-indacen-1-yl]-piperidin-1-yl}-propionitrile | 120 | 2.35/C | 406.2 |
| 391 | 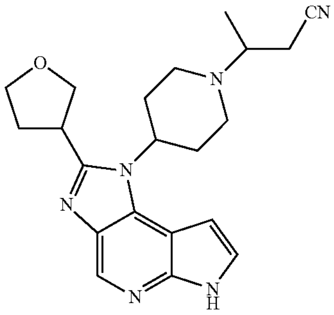 [SMILES: CC(CC#N)N1CCC(n2c(C3CCOC3)nc3cnc4[nH]ccc4c32)CC1] mix of racemic diasteromers | 3-{4-[2-(Tetrahydro-furan-3-yl)-6H-1,3,5,6-tetraaza-as-indacen-1-yl]-piperidin-1-yl}-butyronitrile | 123 | 2.45/C | 379.2 |
| 392 | 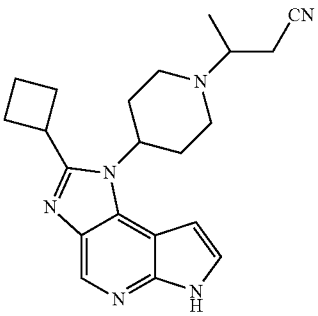 [SMILES: CC(CC#N)N1CCC(n2c(C3CCC3)nc3cnc4[nH]ccc4c32)CC1] racemic | 3-[4-(2-Cyclobutyl-6H-1,3,5,6-tetraaza-as-indacen-1-yl)-piperidin-1-yl]-butyronitrile | 123 | 2.69/C | 363.2 |

TABLE 2-continued

| Ex | Structure | Name | Synthetic Method | LCMS RT (min)/Method | LCMS (ESI) m/z |
|---|---|---|---|---|---|
| 393 | 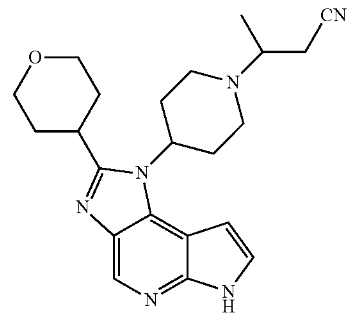 [SMILES: CC(CC#N)N1CCC(n2c(C3CCOCC3)nc3cnc4[nH]ccc4c32)CC1] racemic | 3-{4-[2-(Tetrahydro-pyran-4-yl)-6H-1,3,5,6-tetraaza-as-indacen-1-yl]-piperidin-1-yl}-butyronitrile | 123 | 2.53/C | 393.2 |
| 394 | 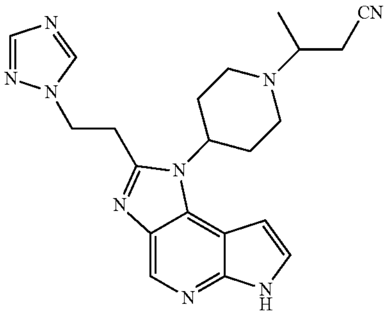 [SMILES: CC(CC#N)N1CCC(n2c(CCn3cncn3)nc3cnc4[nH]ccc4c32)CC1] racemic | 3-{4-[2-(2-[1,2,4]Triazol-1-yl-ethyl)-6H-1,3,5,6-tetraaza-as-indacen-1-yl]-piperidin-1-yl}-butyronitrile | 123 | 2.34/C | 404.2 |
| 395 | 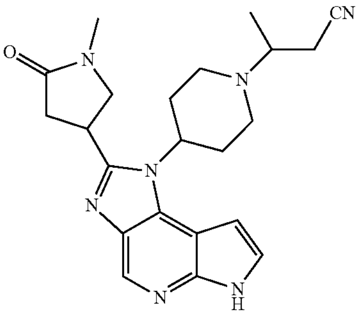 [SMILES: CC(CC#N)N1CCC(n2c(C3CC(=O)N(C)C3)nc3cnc4[nH]ccc4c32)CC1] mix of racemic diastereomers | 3-{4-[2-(1-Methyl-5-oxo-pyrrolidin-3-yl)-6H-1,3,5,6-tetraaza-as-indacen-1-yl]-piperidin-1-yl}-butyronitrile | 123 | 2.37/C | 406.2 |
| 396 | 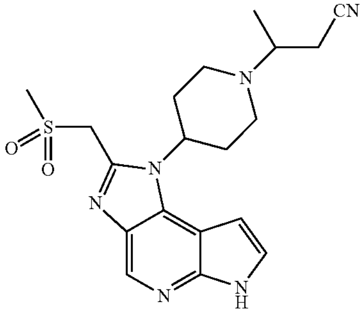 [SMILES: CC(CC#N)N1CCC(n2c(CS(C)(=O)=O)nc3cnc4[nH]ccc4c32)CC1] racemic | 3-[4-(2-Methanesulfonylmethyl-6H-1,3,5,6-tetraaza-as-indacen-1-yl)-piperidin-1-yl]-butyronitrile | 123 | 2.27/C | 401.1 |

TABLE 2-continued

| Ex | Structure | Name | Synthetic Method | LCMS RT (min)/Method | LCMS (ESI) m/z |
|---|---|---|---|---|---|
| 397 | 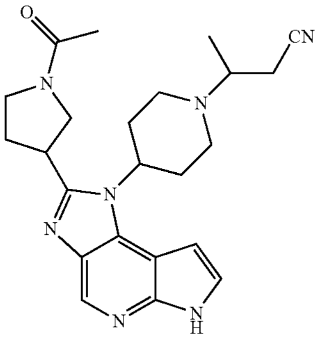 [SMILES: CC(=O)N1CCC(c2nc3cnc4[nH]ccc4c3n2C2CCN(C(C)CC#N)CC2)C1] mix of racemic diastereomers | 3-{4-[2-(1-Acetyl-pyrrolidin-3-yl)-6H-1,3,5,6-tetraaza-as-indacen-1-yl]-piperidin-1-yl}-butyronitrile | 123 | 2.45/C | 420.2 |
| 398 | 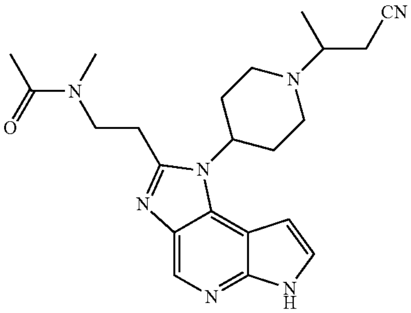 [SMILES: CC(=O)N(C)CCc1nc2cnc3[nH]ccc3c2n1C1CCN(C(C)CC#N)CC1] racemic | N-(2-{1-[1-(2-Cyano-1-methyl-ethyl)-piperidin-4-yl]-1,6-dihydro-1,3,5,6-tetraaza-as-indacen-2-yl}-ethyl)-N-methyl-acetamide | 123 | 2.39/C | 408.2 |
| 399 | 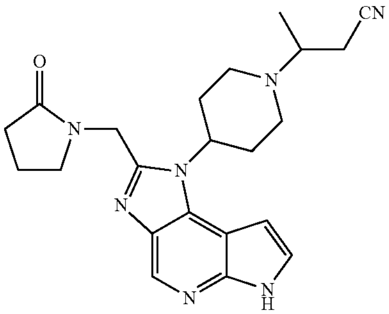 [SMILES: CC(CC#N)N1CCC(n2c(CN3CCCC3=O)nc3cnc4[nH]ccc4c32)CC1] racemic | 3-{4-[2-(2-Oxo-pyrrolidin-1-ylmethyl)-6H-1,3,5,6-tetraaza-as-indacen-1-yl]-piperidin-1-yl}-butyronitrile | 123 | 2.41/C | 406.2 |
| 400 | 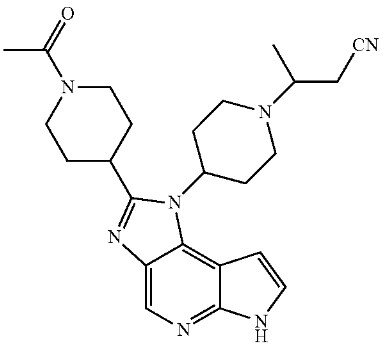 [SMILES: CC(=O)N1CCC(c2nc3cnc4[nH]ccc4c3n2C2CCN(C(C)CC#N)CC2)CC1] racemic | 3-{4-[2-(1-Acetyl-piperidin-4-yl)-6H-1,3,5,6-tetraaza-as-indacen-1-yl]-piperidin-1-yl}-butyronitrile | 123 | 2.53/C | 434.2 |

TABLE 2-continued

| Ex | Structure | Name | Synthetic Method | LCMS RT (min)/Method | LCMS (ESI) m/z |
|---|---|---|---|---|---|
| 401 | 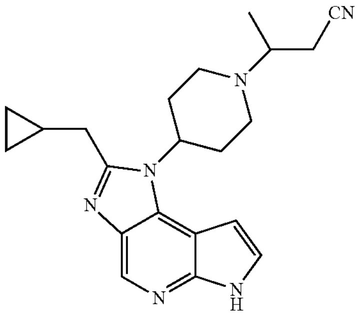 [SMILES: CC(CC#N)N1CCC(n2c(CC3CC3)nc3cnc4[nH]ccc4c32)CC1] racemic | 3-[4-(2-Cyclopropylmethyl-6H-1,3,5,6-tetraaza-as-indacen-1-yl)-piperidin-1-yl]-butyronitrile | 123 | 2.65/C | 363.2 |
| 402 | 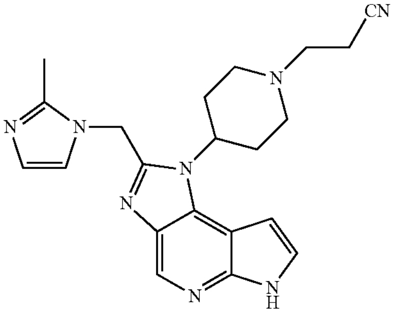 [SMILES: Cc1nccn1Cc1nc2cnc3[nH]ccc3c2n1C1CCN(CCC#N)CC1] | 3-{4-[2-(2-Methyl-imidazol-1-ylmethyl)-6H-1,3,5,6-tetraaza-as-indacen-1-yl]-piperidin-1-yl}-propionitrile | 120 | 1.42/C | 389.1 |
| 403 | 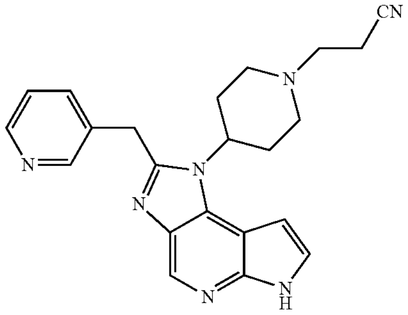 [SMILES: N#CCCN1CCC(n2c(Cc3cccnc3)nc3cnc4[nH]ccc4c32)CC1] | 3-[4-(2-Pyridin-3-ylmethyl-6H-1,3,5,6-tetraaza-as-indacen-1-yl)-piperidin-1-yl]-propionitrile | 120 | 2.26/C | 386.2 |
| 404 | 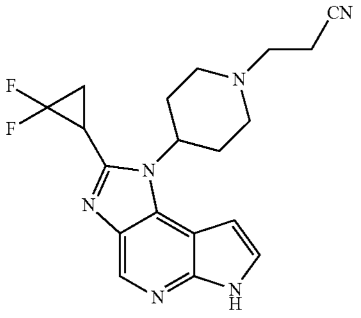 [SMILES: N#CCCN1CCC(n2c(C3CC3(F)F)nc3cnc4[nH]ccc4c32)CC1] racemic | 3-{4-[2-(2,2-Difluoro-cyclopropyl)-6H-1,3,5,6-tetraaza-as-indacen-1-yl]-piperidin-1-yl}-propionitrile | 120 | 2.56/C | 371.1 |

TABLE 2-continued

| Ex | Structure | Name | Synthetic Method | LCMS RT (min)/Method | LCMS (ESI) m/z |
|---|---|---|---|---|---|
| 405 | 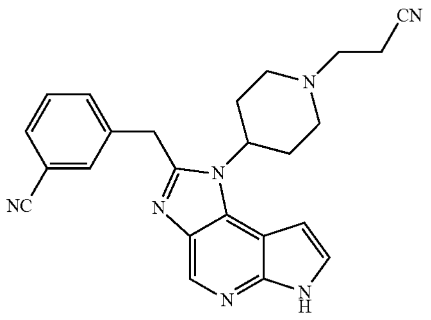 [SMILES: N#CCCN1CCC(n2c(Cc3cccc(C#N)c3)nc3cnc4[nH]ccc4c32)CC1] | 3-{1-[1-(2-Cyano-ethyl)-piperidin-4-yl]-1,6-dihydro-1,3,5,6-tetraaza-as-indacen-2-ylmethyl}-benzonitrile | 120 | 2.82/C | 410.1 |
| 406 | 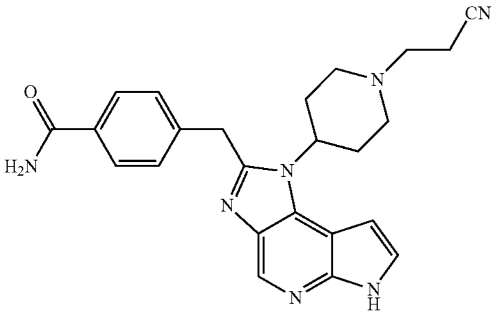 [SMILES: N#CCCN1CCC(n2c(Cc3ccc(C(N)=O)cc3)nc3cnc4[nH]ccc4c32)CC1] | 4-{1-[1-(2-Cyano-ethyl)-piperidin-4-yl]-1,6-dihydro-1,3,5,6-tetraaza-as-indacen-2-ylmethyl}-benzamide | 120 | 2.37/C | 428.2 |
| 407 | 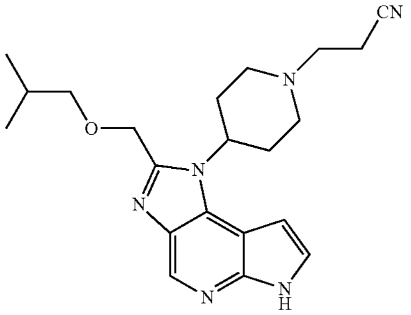 [SMILES: CC(C)COCc1nc2cnc3[nH]ccc3c2n1C1CCN(CCC#N)CC1] | 3-[4-(2-Isobutoxymethyl-6H-1,3,5,6-tetraaza-as-indacen-1-yl)-piperidin-1-yl]-propionitrile | 120 | 2.96/C | 381.2 |
| 408 | 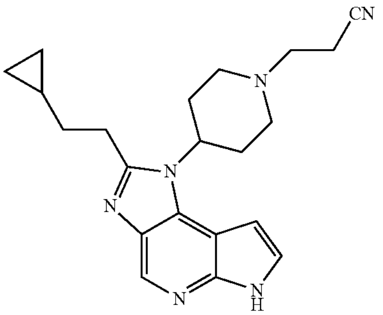 [SMILES: N#CCCN1CCC(n2c(CCC3CC3)nc3cnc4[nH]ccc4c32)CC1] | 3-{4-[2-(2-Cyclopropyl-ethyl)-6H-1,3,5,6-tetraaza-as-indacen-1-yl]-piperidin-1-yl}-propionitrile | 120 | 2.73/C | 363.2 |

TABLE 2-continued

| Ex | Structure | Name | Synthetic Method | LCMS RT (min)/Method | LCMS (ESI) m/z |
|---|---|---|---|---|---|
| 409 | 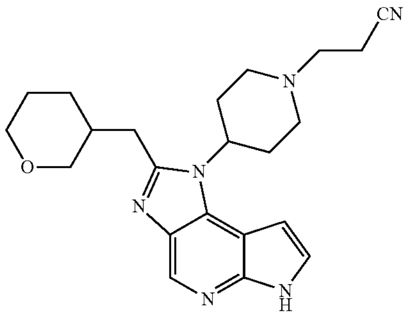 [SMILES: N#CCCN1CCC(n2c(CC3CCCOC3)nc3cnc4[nH]ccc4c32)CC1] racemic | 3-{4-[2-(Tetrahydro-pyran-3-ylmethyl)-6H-1,3,5,6-tetraaza-as-indacen-1-yl]-piperidin-1-yl}-propionitrile | 120 | 2.55/C | 393.2 |
| 410 | 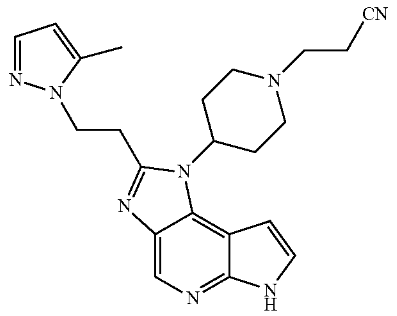 [SMILES: Cc1ccnn1CCc1nc2cnc3[nH]ccc3c2n1C1CCN(CCC#N)CC1] | 3-(4-{2-[2-(5-Methyl-pyrazol-1-yl)-ethyl]-6H-1,3,5,6-tetraaza-as-indacen-1-yl}-piperidin-1-yl)-propionitrile | 120 | 2.62/C | 403.2 |
| 411 | 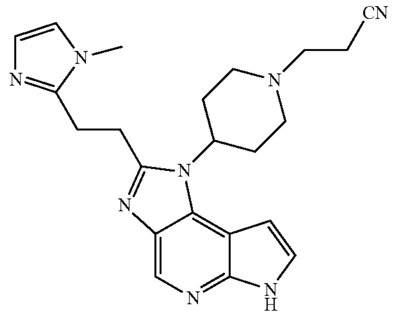 [SMILES: Cn1ccnc1CCc1nc2cnc3[nH]ccc3c2n1C1CCN(CCC#N)CC1] | 3-(4-{2-[2-(1-Methyl-1H-imidazol-2-yl)-ethyl]-6H-1,3,5,6-tetraaza-as-indacen-1-yl}-piperidin-1-yl)-propionitrile | 120 | 2.11/C | 403.2 |
| 412 | 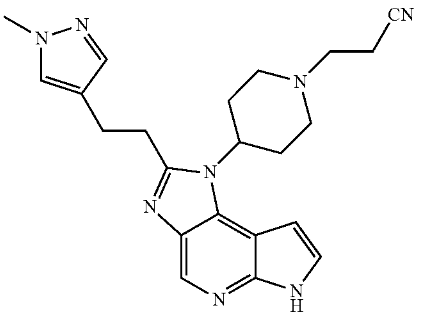 [SMILES: Cn1cc(CCc2nc3cnc4[nH]ccc4c3n2C2CCN(CCC#N)CC2)cn1] | 3-(4-{2-[2-(1-Methyl-1H-pyrazol-4-yl)-ethyl]-6H-1,3,5,6-tetraaza-as-indacen-1-yl}-piperidin-1-yl)-propionitrile | 120 | 2.44/C | 403.2 |

TABLE 2-continued

| Ex | Structure | Name | Synthetic Method | LCMS RT (min)/Method | LCMS (ESI) m/z |
|---|---|---|---|---|---|
| 413 | 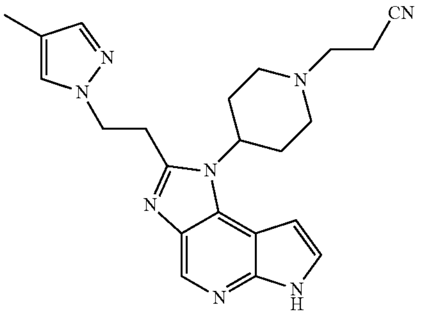 [SMILES: Cc1cnn(CCc2nc3cnc4[nH]ccc4c3n2C2CCN(CCC#N)CC2)c1] | 3-(4-{2-[2-(4-Methyl-pyrazol-1-yl)-ethyl]-6H-1,3,5,6-tetraaza-as-indacen-1-yl}-piperidin-1-yl)-propionitrile | 120 | 2.64/C | 403.2 |
| 414 | 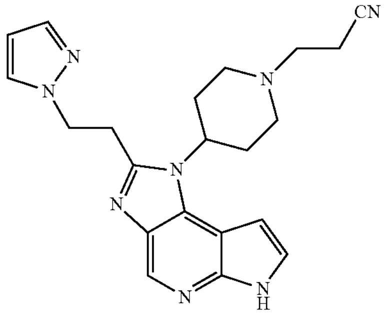 [SMILES: N#CCCN1CCC(n2c(CCn3cccn3)nc3cnc4[nH]ccc4c32)CC1] | 3-{4-[2-(2-Pyrazol-1-yl-ethyl)-6H-1,3,5,6-tetraaza-as-indacen-1-yl]-piperidin-1-yl}-propionitrile | 120 | 2.49/C | 389.2 |
| 415 | 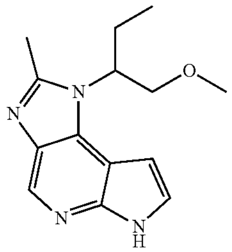 [SMILES: CCC(COC)n1c(C)nc2cnc3[nH]ccc3c21] racemic | 1-(1-Methoxymethyl-propyl)-2-methyl-1,6-dihydro-1,3,5,6-tetraaza-as-indacene | 178 | 2.88/C | 259.1 |
| 416 | 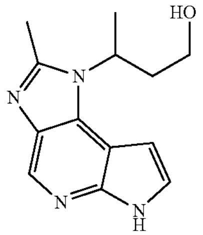 [SMILES: Cc1nc2cnc3[nH]ccc3c2n1C(C)CCO] racemic | 3-(2-Methyl-6H-1,3,5,6-tetraaza-as-indacen-1-yl)-butan-1-ol | 178 | 2.44/C | 245.1 |
| 417 | 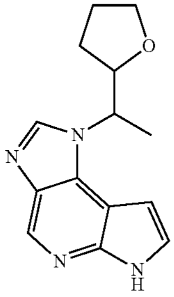 [SMILES: CC(C1CCCO1)n1cnc2cnc3[nH]ccc3c21] Single diastereomer, racemic, relative stereochemistry unknown | 1-[1-(Tetrahydro-furan-2-yl)-ethyl]-1,6-dihydro-1,3,5,6-tetraaza-as-indacene | 1 | 2.70/C | 257.1 |

TABLE 2-continued

| Ex | Structure | Name | Synthetic Method | LCMS RT (min)/Method | LCMS (ESI) m/z |
|---|---|---|---|---|---|
| 418 | 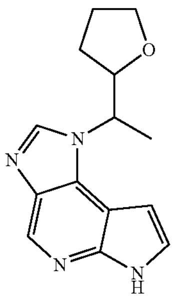 [SMILES: CC(C1CCCO1)n1cnc2cnc3[nH]ccc3c21] Single diastereomer, racemic, relative stereochemistry unknown | 1-[1-(Tetrahydro-furan-2-yl)-ethyl]-1,6-dihydro-1,3,5,6-tetraaza-as-indacene | 1 | 2.85/C | 257.1 |
| 419 | 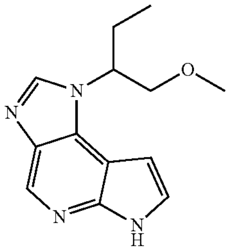 [SMILES: CCC(COC)n1cnc2cnc3[nH]ccc3c21] racemic | 1-(1-Methoxymethyl-propyl)-1,6-dihydro-1,3,5,6-tetraaza-as-indacene | 1 | 2.75/C | 245.1 |
| 420 | 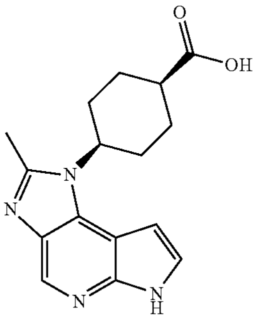 [SMILES: Cc1nc2cnc3[nH]ccc3c2n1[C@H]1CC[C@@H](C(=O)O)CC1] | cis 4-(2-Methyl-6H-1,3,5,6-tetraaza-as-indacen-1-yl)-cyclohexanecarboxylic acid | 1 | 2.80/C | 299.1 |
| 421 | 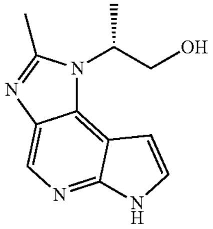 [SMILES: Cc1nc2cnc3[nH]ccc3c2n1[C@H](C)CO] | (R)-2-(2-Methyl-6H-1,3,5,6-tetraaza-as-indacen-1-yl)-propan-1-ol | 1 | 2.33/C | 231.0 |
| 422 | 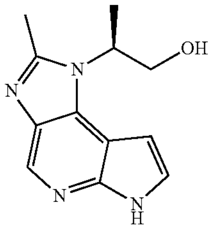 [SMILES: Cc1nc2cnc3[nH]ccc3c2n1[C@@H](C)CO] | (S)-2-(2-Methyl-6H-1,3,5,6-tetraaza-as-indacen-1-yl)-propan-1-ol | 1 | 2.33/C | 231.0 |

TABLE 2-continued

| Ex | Structure | Name | Synthetic Method | LCMS RT (min)/Method | LCMS (ESI) m/z |
|---|---|---|---|---|---|
| 423 | 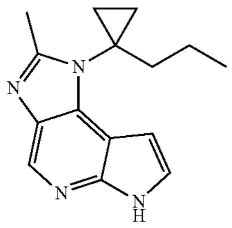 [SMILES: CCCC1(n2c(C)nc3cnc4[nH]ccc4c32)CC1] | 2-Methyl-1-(1-propyl-cyclopropyl)-1,6-dihydro-1,3,5,6-tetraaza-as-indacene | 1 | 3.34/C | 255.1 |
| 424 | 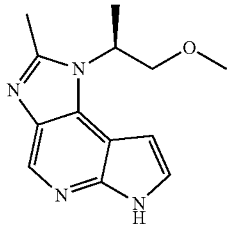 [SMILES: COC[C@H](C)n1c(C)nc2cnc3[nH]ccc3c21] | 1-((S)-2-Methoxy-1-methyl-ethyl)-2-methyl-1,6-dihydro-1,3,5,6-tetraaza-as-indacene | 1 | 2.69/C | 245.0 |
| 425 | 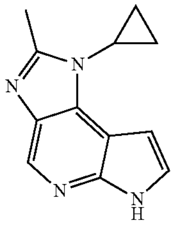 [SMILES: Cc1nc2cnc3[nH]ccc3c2n1C1CC1] | 1-Cyclopropyl-2-methyl-1,6-dihydro-1,3,5,6-tetraaza-as-indacene | 1 | 2.61/C | 213.1 |
| 426 | 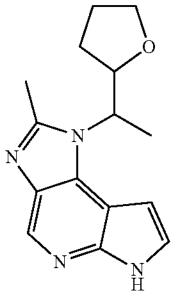 [SMILES: Cc1nc2cnc3[nH]ccc3c2n1C(C)C1CCCO1] Single diastereomer, racemic, relative stereochemistry unknown | 2-Methyl-1-[1-(tetrahydro-furan-2-yl)-ethyl]-1,6-dihydro-1,3,5,6-tetraaza-as-indacene | 1 | 2.92/C | 271.0 |
| 427 | 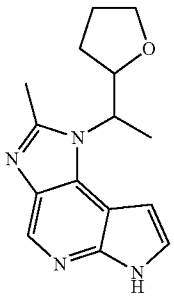 [SMILES: Cc1nc2cnc3[nH]ccc3c2n1C(C)C1CCCO1] Single diastereomer, racemic, relative stereochemistry unknown | 2-Methyl-1-[1-(tetrahydro-furan-2-yl)-ethyl]-1,6-dihydro-1,3,5,6-tetraaza-as-indacene | 1 | 2.88/C | 271.0 |

TABLE 2-continued

| Ex | Structure | Name | Synthetic Method | LCMS RT (min)/Method | LCMS (ESI) m/z |
|---|---|---|---|---|---|
| 428 | 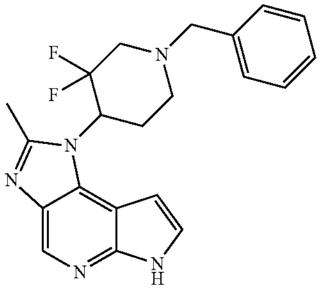 [SMILES: Cc1nc2cnc3[nH]ccc3c2n1C1CCN(Cc2ccccc2)CC1(F)F] racemic | 1-(1-Benzyl-3,3-difluoro-piperidin-4-yl)-2-methyl-1,6-dihydro-1,3,5,6-tetraaza-as-indacene | 179 | 3.54/C | 382.1 |
| 429 | 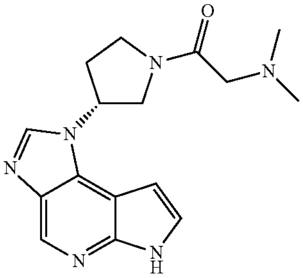 [SMILES: CN(C)CC(=O)N1CC[C@@H](n2cnc3cnc4[nH]ccc4c32)C1] | 2-Dimethylamino-1-[(R)-3-(6H-1,3,5,6-tetraaza-as-indacen-1-yl)-pyrrolidin-1-yl]-ethanone | 188 | 0.76/L | 312.9 |
| 430 | 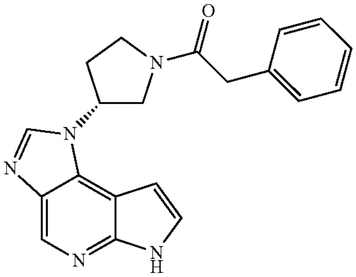 [SMILES: O=C(Cc1ccccc1)N1CC[C@@H](n2cnc3cnc4[nH]ccc4c32)C1] | 2-Phenyl-1-[(R)-3-(6H-1,3,5,6-tetraaza-as-indacen-1-yl)-pyrrolidin-1-yl]-ethanone | 188 | 0.96/K | 345.7 |
| 431 | 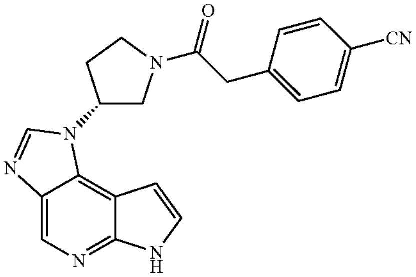 [SMILES: N#Cc1ccc(CC(=O)N2CC[C@@H](n3cnc4cnc5[nH]ccc5c43)C2)cc1] | 4-{2-Oxo-2-[(R)-3-(6H-1,3,5,6-tetraaza-as-indacen-1-yl)-pyrrolidin-1-yl]-ethyl}-benzonitrile | 189 | 0.96/K | 371.0 |
| 432 | 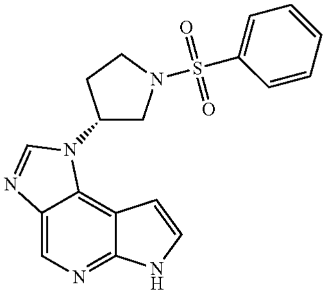 [SMILES: O=S(=O)(c1ccccc1)N1CC[C@@H](n2cnc3cnc4[nH]ccc4c32)C1] | 1-((R)-1-Benzenesulfonyl-pyrrolidin-3-yl)-1,6-dihydro-1,3,5,6-tetraaza-as-indacene | 190 | 1.01/K | 367.7 |

TABLE 2-continued

| Ex | Structure | Name | Synthetic Method | LCMS RT (min)/Method | LCMS (ESI) m/z |
|---|---|---|---|---|---|
| 433 | 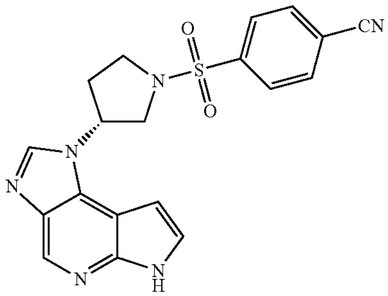 [SMILES: N#Cc1ccc(S(=O)(=O)N2CC[C@@H](n3cnc4cnc5[nH]ccc5c43)C2)cc1] | 4-[(R)-3-(6H-1,3,5,6-Tetraaza-as-indacen-1-yl)-pyrrolidine-1-sulfonyl]-benzonitrile | 190 | 1.00/K | 393.0 |
| 434 | 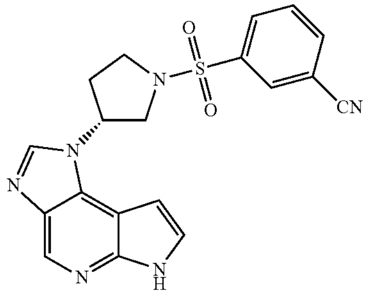 [SMILES: N#Cc1cccc(S(=O)(=O)N2CC[C@@H](n3cnc4cnc5[nH]ccc5c43)C2)c1] | 3-[(R)-3-(6H-1,3,5,6-Tetraaza-as-indacen-1-yl)-pyrrolidine-1-sulfonyl]-benzonitrile | 190 | 1.06/K | 392.8 |
| 435 | 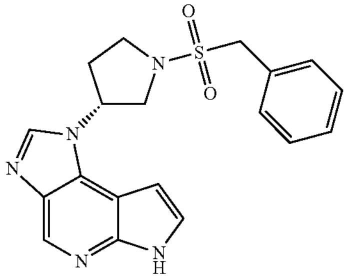 [SMILES: O=S(=O)(Cc1ccccc1)N1CC[C@@H](n2cnc3cnc4[nH]ccc4c32)C1] | 1-((R)-1-Phenylmethanesulfonyl-pyrrolidin-3-yl)-1,6-dihydro-1,3,5,6 -tetraaza-as-indacene | 190 | 1.03/K | 382.1 |
| 436 | 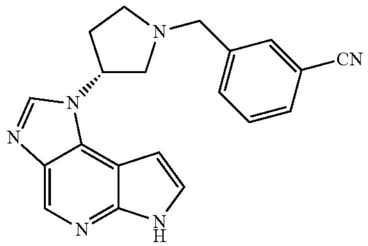 [SMILES: N#Cc1cccc(CN2CC[C@@H](n3cnc4cnc5[nH]ccc5c43)C2)c1] | 3-[(R)-3-(6H-1,3,5,6-Tetraaza-as-indacen-1-yl)-pyrrolidin-1-ylmethyl]-benzonitrile | 191 | 0.98/K | 343.0 |
| 437 | 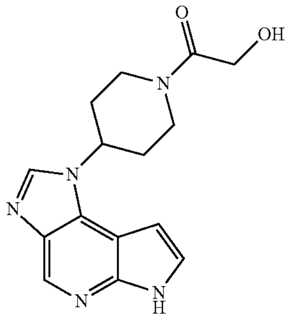 [SMILES: O=C(CO)N1CCC(n2cnc3cnc4[nH]ccc4c32)CC1] | 2-Hydroxy-1-[4-(6H-1,3,5,6-tetraaza-as-indacen-1-yl)-piperidin-1-yl]-ethanone | 7 | 0.88/L | 300.1 |

TABLE 2-continued
| Ex | Structure | Name | Synthetic Method | LCMS RT (min)/Method | LCMS (ESI) m/z |
| --- | --- | --- | --- | --- | --- |
| 438 | 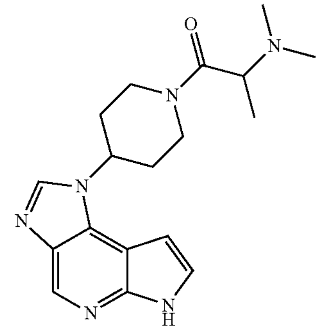 [SMILES: CC(C(=O)N1CCC(n2cnc3cnc4[nH]ccc4c32)CC1)N(C)C] Racemic | 2-Dimethylamino-1-[4-(6H-1,3,5,6-tetraaza-as-indacen-1-yl)-piperidin-1-yl]-propan-1-one | 7 | 0.83/L | 341.1 |
| 439 | 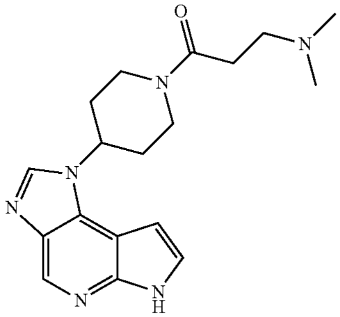 [SMILES: CN(C)CCC(=O)N1CCC(n2cnc3cnc4[nH]ccc4c32)CC1] | 3-Dimethylamino-1-[4-(6H-1,3,5,6-tetraaza-as-indacen-1-yl)-piperidin-1-yl]-propan-1-one | 7 | 0.81/L | 341.0 |
| 440 | 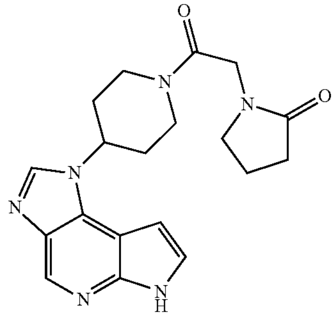 [SMILES: O=C(CN1CCCC1=O)N1CCC(n2cnc3cnc4[nH]ccc4c32)CC1] | 1-{2-Oxo-2-[4-(6H-1,3,5,6-tetraaza-as-indacen-1-yl)-piperidin-1-yl]-ethyl}-pyrrolidin-2-one | 7 | 1.02/L | 367.1 |
| 441 | 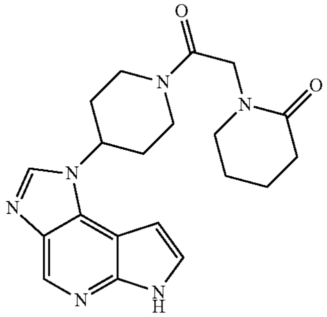 [SMILES: O=C(CN1CCCCC1=O)N1CCC(n2cnc3cnc4[nH]ccc4c32)CC1] | 1-{2-Oxo-2-[4-(6H-1,3,5,6-tetraaza-as-indacen-1-yl)-piperidin-1-yl]-ethyl}-piperidin-2-one | 7 | 0.68/J | 381.1 |

TABLE 2-continued

| Ex | Structure | Name | Synthetic Method | LCMS RT (min)/Method | LCMS (ESI) m/z |
|---|---|---|---|---|---|
| 442 | 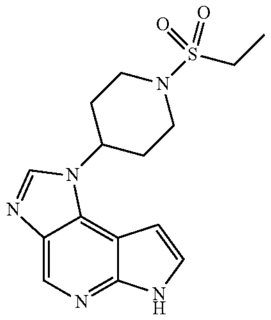 [SMILES: CCS(=O)(=O)N1CCC(n2cnc3cnc4[nH]ccc4c32)CC1] | 1-(1-Ethanesulfonyl-piperidin-4-yl)-1,6-dihydro-1,3,5,6-tetraaza-as-indacene | 9 | 1.16/L | 333.7 |
| 443 | 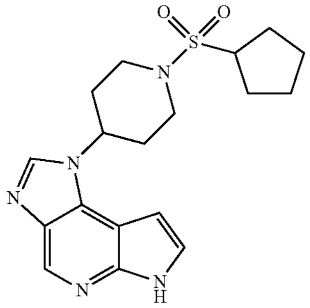 [SMILES: O=S(=O)(C1CCCC1)N1CCC(n2cnc3cnc4[nH]ccc4c32)CC1] | 1-(1-Cyclopentanesulfonyl-piperidin-4-yl)-1,6-dihydro-1,3,5,6-tetraaza-as-indacene | 9 | 1.316/L | 374.0 |
| 444 | 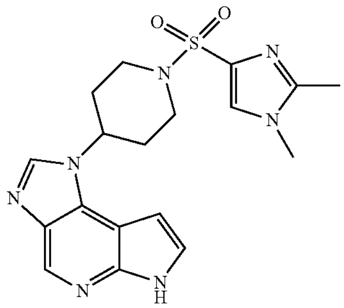 [SMILES: Cc1nc(S(=O)(=O)N2CCC(n3cnc4cnc5[nH]ccc5c43)CC2)cn1C] | 1-[1-(1,2-Dimethyl-1H-imidazole-4-sulfonyl)-piperidin-4-yl]-1,6-dihydro-1,3,5,6-tetraaza-as-indacene | 9 | 0.95/K | 399.9 |
| 445 | 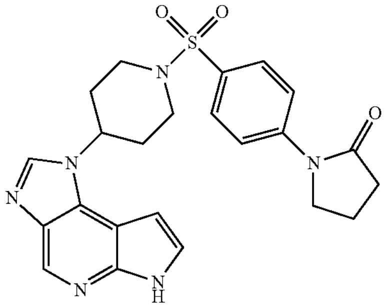 [SMILES: O=C1CCCN1c1ccc(S(=O)(=O)N2CCC(n3cnc4cnc5[nH]ccc5c43)CC2)cc1] | 1-{4-[4-(6H-1,3,5,6-Tetraaza-as-indacen-1-yl)-piperidine-1-sulfonyl]-phenyl}-pyrrolidin-2-one | 9 | 1.09/K | 464.9 |
| 446 | 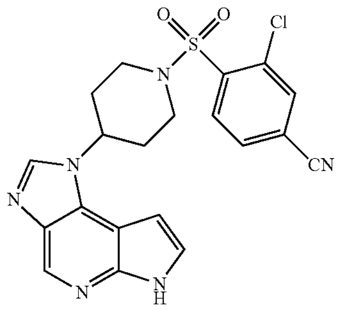 [SMILES: N#Cc1ccc(S(=O)(=O)N2CCC(n3cnc4cnc5[nH]ccc5c43)CC2)c(Cl)c1] | 3-Chloro-4-[4-(6H-1,3,5,6-tetraaza-as-indacen-1-yl)-piperidine-1-sulfonyl]-benzonitrile | 9 | 0.89/J | 441.0 |

TABLE 2-continued

| Ex | Structure | Name | Synthetic Method | LCMS RT (min)/Method | LCMS (ESI) m/z |
|---|---|---|---|---|---|
| 447 | 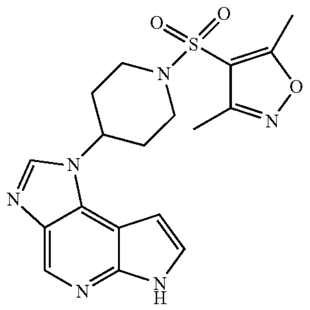 [SMILES: Cc1noc(C)c1S(=O)(=O)N1CCC(n2cnc3cnc4[nH]ccc4c32)CC1] | 1-[1-(3,5-Dimethyl-isoxazole-4-sulfonyl)-piperidin-4-yl]-1,6-dihydro-1,3,5,6-tetraaza-as-indacene | 9 | 1.10/K | 400.8 |
| 448 | 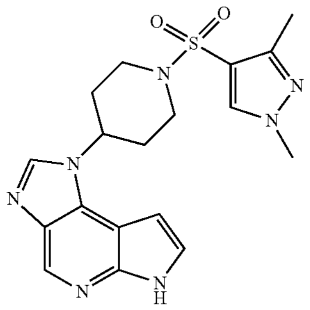 [SMILES: Cc1nn(C)cc1S(=O)(=O)N1CCC(n2cnc3cnc4[nH]ccc4c32)CC1] | 1-[1-(1,3-Dimethyl-1H-pyrazole-4-sulfonyl)-piperidin-4-yl]-1,6-dihydro-1,3,5,6-tetraaza-as-indacene | 9 | 1.02/K | 399.8 |
| 449 | 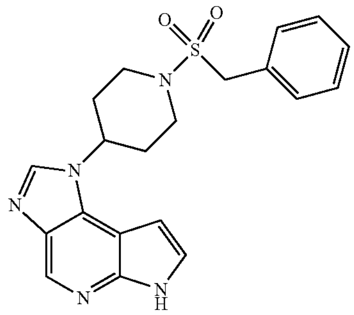 [SMILES: O=S(=O)(Cc1ccccc1)N1CCC(n2cnc3cnc4[nH]ccc4c32)CC1] | 1-(1-Phenylmethanesulfonyl-piperidin-4-yl)-1,6-dihydro-1,3,5,6-tetraaza-as-indacene | 9 | 1.05/K | 396.0 |
| 450 | 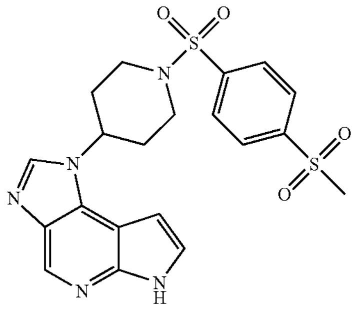 [SMILES: CS(=O)(=O)c1ccc(S(=O)(=O)N2CCC(n3cnc4cnc5[nH]ccc5c43)CC2)cc1] | 1-(1-(4-(methylsulfonyl)phenylsulfonyl)piperidin-4-yl)-1,6-dihydroimidazo[4,5-d]pyrrolo[2,3-b]pyridine | 9 | 1.05/K | 459.9 |

TABLE 2-continued

| Ex | Structure | Name | Synthetic Method | LCMS RT (min)/Method | LCMS (ESI) m/z |
|---|---|---|---|---|---|
| 451 | 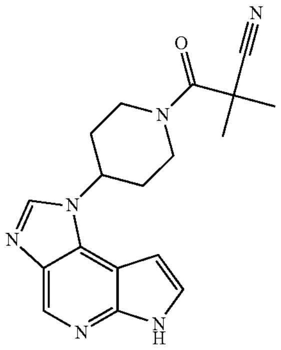 [SMILES: CC(C)(C#N)C(=O)N1CCC(n2cnc3cnc4[nH]ccc4c32)CC1] | 2,2-Dimethyl-3-oxo-3-[4-(6H-1,3,5,6-tetraaza-as-indacen-1-yl)-piperidin-1-yl]-propionitrile | 7 | 1.21/L | 337.1 |
| 452 | 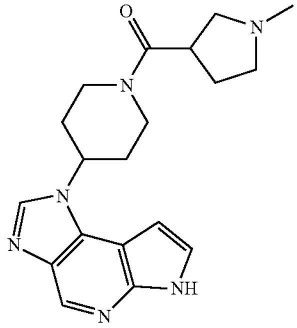 [SMILES: CN1CCC(C(=O)N2CCC(n3cnc4cnc5[nH]ccc5c43)CC2)C1] Racemic | (1-Methyl-pyrrolidin-3-yl)-[4-(6H-1,3,5,6-tetraaza-as-indacen-1-yl)-piperidin-1-yl]-methanone | 7 | 0.70/K | 353.1 |
| 453 | 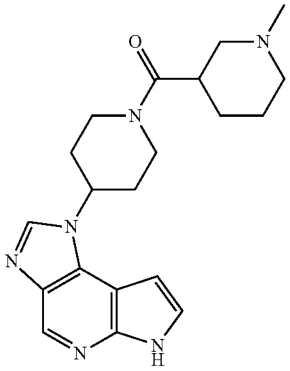 [SMILES: CN1CCCC(C(=O)N2CCC(n3cnc4cnc5[nH]ccc5c43)CC2)C1] Single enantiomer, absolute stereochemistry unknown | (1-Methyl-piperidin-3-yl)-[4-(6H-1,3,5,6-tetraaza-as-indacen-1-yl)-piperidin-1-yl]-methanone | 197 | 0.90/K | 367.0 |
| 454 | 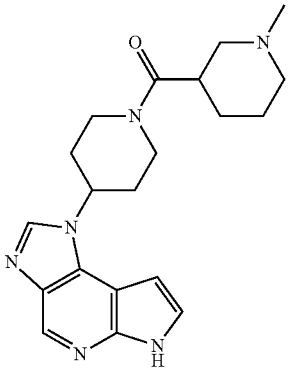 [SMILES: CN1CCCC(C(=O)N2CCC(n3cnc4cnc5[nH]ccc5c43)CC2)C1] Single enantiomer, absolute stereochemistry unknown | (1-Methyl-piperidin-3-yl)-[4-(6H-1,3,5,6-tetraaza-as-indacen-1-yl)-piperidin-1-yl]-methanone | 197 | 0.90/K | 367.0 |

TABLE 2-continued

| Ex | Structure | Name | Synthetic Method | LCMS RT (min)/Method | LCMS (ESI) m/z |
|---|---|---|---|---|---|
| 455 | 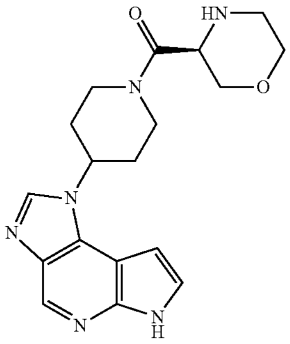 [SMILES: O=C([C@@H]1COCCN1)N1CCC(n2cnc3cnc4[nH]ccc4c32)CC1] | (S)-Morpholin-3-yl-[4-(6H-1,3,5,6-tetraaza-as-indacen-1-yl)-piperidin-1-yl]-methanone | 7 | 0.76/K | 355.1 |
| 456 | 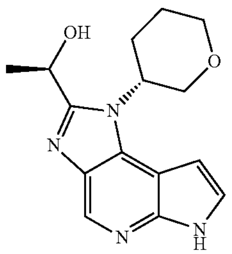 [SMILES: C[C@@H](O)c1nc2cnc3[nH]ccc3c2n1[C@@H]1CCCOC1] | (R)-1-[(R)-1-(Tetrahydro-pyran-3-yl)-1,6-dihydro-1,3,5,6-tetraaza-as-indacen-2-yl]-ethanol | 199 | 2.71/C 0.81/A1 | 287.1 |
| 457 | 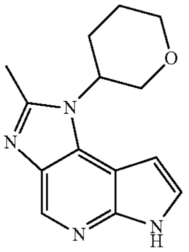 [SMILES: Cc1nc2cnc3[nH]ccc3c2n1C1CCCOC1] Single isomer, absolute stereochemistry unknown. | 2-Methyl-1-(tetrahydro-pyran-3-yl)-1,6-dihydro-1,3,5,6-tetraaza-as-indacene | 20 | 2.63/C | 257.1 |
| 458 | 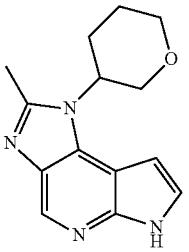 [SMILES: Cc1nc2cnc3[nH]ccc3c2n1C1CCCOC1] Single isomer, absolute stereochemistry unknown. | 2-Methyl-1-(tetrahydro-pyran-3-yl)-1,6-dihydro-1,3,5,6-tetraaza-as-indacene | 20 | 2.64/C | 257.1 |
| 459 | 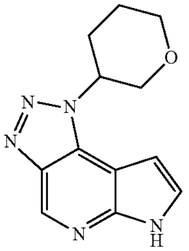 [SMILES: c1cc2c(ncc3nnn(C4CCCOC4)c32)[nH]1] Single isomer, absolute stereochemistry unknown. | 1-(Tetrahydro-pyran-3-yl)-1,6-dihydro-1,2,3,5,6-pentaaza-as-indacene | 18 | 3.34/C | 244.1 |

TABLE 2-continued

| Ex | Structure | Name | Synthetic Method | LCMS RT (min)/Method | LCMS (ESI) m/z |
|---|---|---|---|---|---|
| 460 | 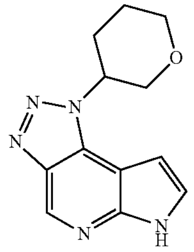 [SMILES: c1cc2c(ncc3nnn(C4CCCOC4)c32)[nH]1] Single isomer, absolute stereochemistry unknown. | 1-(Tetrahydro-pyran-3-yl)-1,6-dihydro-1,2,3,5,6-pentaaza-as-indacene | 18 | 3.34/C | 244.1 |
| 461 | 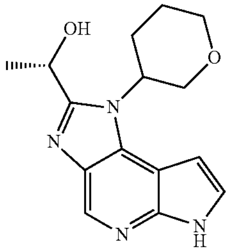 [SMILES: C[C@H](O)c1nc2cnc3[nH]ccc3c2n1C1CCCOC1] Single isomer, absolute stereochemistry unknown. | (S)-1-[1-(Tetrahydro-pyran-3-yl)-1,6-dihydro-1,3.5,6-tetraaza-as-indacen-2-yl]-ethanol | 199 | 2.72/C | 287.1 |
| 462 | 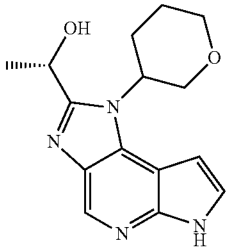 [SMILES: C[C@H](O)c1nc2cnc3[nH]ccc3c2n1C1CCCOC1] Single isomer, absolute stereochemistry unknown. | (S)-1-[1-(Tetrahydro-pyran-3-yl)-1,6-dihydro-1,3,5,6-tetraaza-as-indacen-2-yl]-ethanol | 199 | 2.71/C | 287.1 |
| 463 | 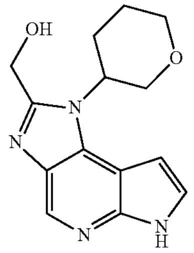 [SMILES: OCc1nc2cnc3[nH]ccc3c2n1C1CCCOC1] Single isomer, absolute stereochemistry unknown. | [1-(Tetrahydro-pyran-3-yl)-1,6-dihydro-1,3,5,6-tetraaza-as-indacen-2-yl]-methanol | 22 | 2.54/C | 273.1 |
| 464 | 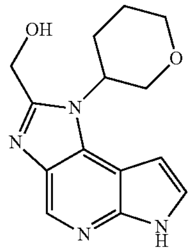 [SMILES: OCc1nc2cnc3[nH]ccc3c2n1C1CCCOC1] Single isomer, absolute stereochemistry unknown. | [1-(Tetrahydro-pyran-3-yl)-1,6-dihydro-1,3,5,6-tetraaza-as-indacen-2-yl]-methanol | 22 | 2.56/C | 273.1 |

TABLE 2-continued

| Ex | Structure | Name | Synthetic Method | LCMS RT (min)/Method | LCMS (ESI) m/z |
|---|---|---|---|---|---|
| 465 | 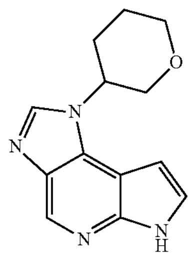 [SMILES: c1cc2c(ncc3ncn(C4CCCOC4)c32)[nH]1] Single isomer, absolute stereochemistry unknown. | 1-(Tetrahydro-pyran-3-yl)-1,6-dihydro-1,3,5,6-tetraaza-as-indacene | 1 | 2.53/C | 243.1 |
| 466 | 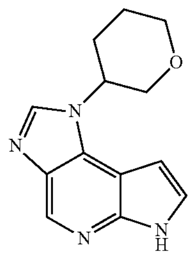 [SMILES: c1cc2c(ncc3ncn(C4CCCOC4)c32)[nH]1] Single isomer, absolute stereochemistry unknown. | 1-(Tetrahydro-pyran-3-yl)-1,6-dihydro-1,3,5,6-tetraaza-as-indacene | 1 | 2.63/C | 243.1 |
| 467 | 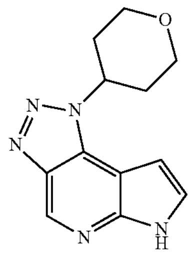 [SMILES: c1cc2c(ncc3nnn(C4CCOCC4)c32)[nH]1] | 1-(Tetrahydro-pyran-4-yl)-1,6-dihydro-1,2,3,5,6-pentaaza-as-indacene | 18 | 3.17/C | 244.1 |
| 468 | 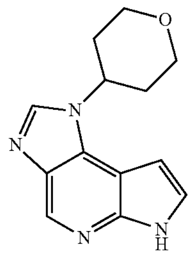 [SMILES: c1cc2c(ncc3ncn(C4CCOCC4)c32)[nH]1] | 1-(Tetrahydro-pyran-4-yl)-1,6-dihydro-1,3,5,6-tetraaza-as-indacene | 1 | 2.50/C | 243.1 |
| 469 | 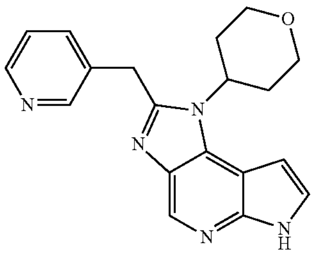 [SMILES: c1cncc(Cc2nc3cnc4[nH]ccc4c3n2C2CCOCC2)c1] | 2-Pyridin-3-ylmethyl-1-(tetrahydro-pyran-4-yl)-1,6-dihydro-1,3,5,6-tetraaza-as-indacene | 119 | 2.40/C | 334.1 |

TABLE 2-continued

| Ex | Structure | Name | Synthetic Method | LCMS RT (min)/Method | LCMS (ESI) m/z |
|---|---|---|---|---|---|
| 470 | 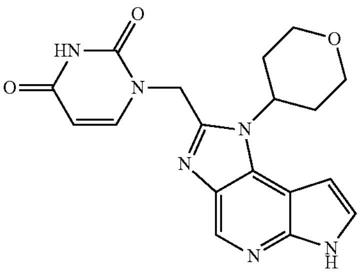 [SMILES: O=c1ccn(Cc2nc3cnc4[nH]ccc4c3n2C2CCOCC2)c(=O)[nH]1] | 1-[1-(Tetrahydro-pyran-4-yl)-1,6-dihydro-1,3,5,6-tetraaza-as-indacen-2-ylmethyl]-1H-pyrimidine-2,4-dione | 119 | 2.44/C | 385.1 |
| 471 | 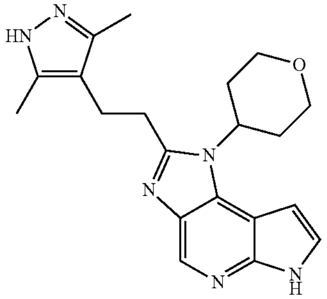 [SMILES: Cc1n[nH]c(C)c1CCc1nc2cnc3[nH]ccc3c2n1C1CCOCC1] | 2-[2-(3,5-Dimethyl-1H-pyrazol-4-yl)-ethyl]-1-(tetrahydro-pyran-4-yl)-1,6-dihydro-1,3,5,6-tetraaza-as-indacene | 119 | 2.88/C | 365.1 |
| 472 | 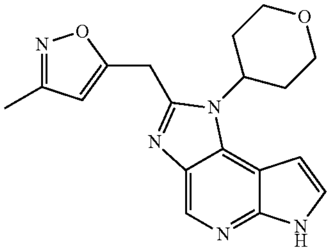 [SMILES: Cc1cc(Cc2nc3cnc4[nH]ccc4c3n2C2CCOCC2)on1] | 2-(3-Methyl-isoxazol-5-ylmethyl)-1-(tetrahydro-pyran-4-yl)-1,6-dihydro-1,3,5,6-tetraaza-as-indacene | 119 | 2.94/C | 338.1 |
| 473 | 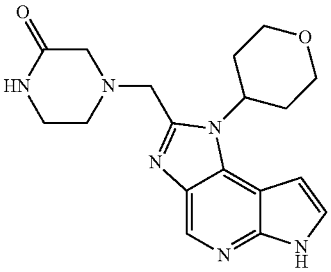 [SMILES: O=C1CN(Cc2nc3cnc4[nH]ccc4c3n2C2CCOCC2)CCN1] | 4-[1-(Tetrahydro-pyran-4-yl)-1,6-dihydro-1,3,5,6-tetraaza-as-indacen-2-ylmethyl]-piperazin-2-one | 119 | 2.53/C | 355.1 |
| 474 | 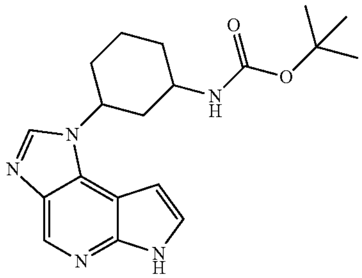 [SMILES: CC(C)(C)OC(=O)NC1CCCC(n2cnc3cnc4[nH]ccc4c32)C1] Single isomer, absolute stereochemistry unknown. | [3-(6H-1,3,5,6-Tetraaza-as-indacen-1-yl)-cyclohexyl]-carbamic acid tert-butyl ester | 1 | 3.55/C | 356.1 |

TABLE 2-continued

| Ex | Structure | Name | Synthetic Method | LCMS RT (min)/Method | LCMS (ESI) m/z |
|---|---|---|---|---|---|
| 475 | 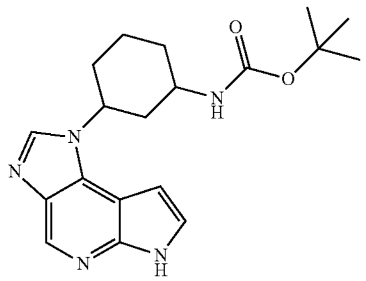 [SMILES: CC(C)(C)OC(=O)NC1CCCC(n2cnc3cnc4[nH]ccc4c32)C1] Single isomer, absolute stereochemistry unknown. | [3-(6H-1,3,5,6-Tetraaza-as-indacen-1-yl)-cyclohexyl]-carbamic acid tert-butyl ester | 1 | 3.56/C | 356.1 |
| 476 | 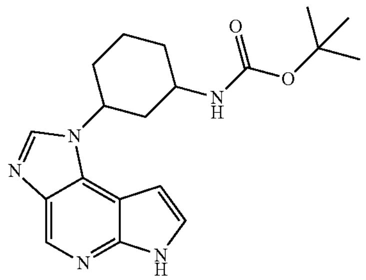 [SMILES: CC(C)(C)OC(=O)NC1CCCC(n2cnc3cnc4[nH]ccc4c32)C1] Single isomer, absolute stereochemistry unknown. | [3-(6H-1,3,5,6-Tetraaza-as-indacen-1-yl)-cyclohexyl]-carbamic acid tert-butyl ester | 1 | 3.51/C | 356.2 |
| 477 | 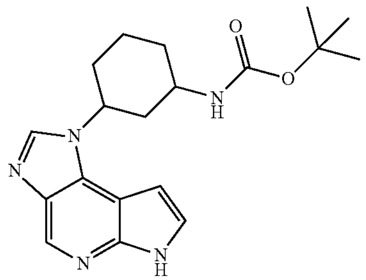 [SMILES: CC(C)(C)OC(=O)NC1CCCC(n2cnc3cnc4[nH]ccc4c32)C1] Single isomer, absolute stereochemistry unknown. | [3-(6H-1,3,5,6-Tetraaza-as-indacen-1-yl)-cyclohexyl]-carbamic acid tert-butyl ester | 1 | 3.51/C | 356.2 |
| 478 | 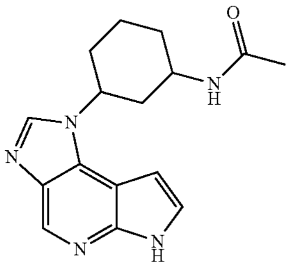 [SMILES: CC(=O)NC1CCCC(n2cnc3cnc4[nH]ccc4c32)C1] Single isomer, absolute stereochemistry unknown. | N-[3-(6H-1,3,5,6-Tetraaza-as-indacen-1-yl)-cyclohexyl]-acetamide | 1 | 2.60/C | 298.1 |
| 479 | 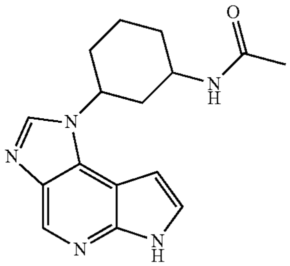 [SMILES: CC(=O)NC1CCCC(n2cnc3cnc4[nH]ccc4c32)C1] Single isomer, absolute stereochemistry unknown. | N-[3-(6H-1,3,5,6-Tetraaza-as-indacen-1-yl)-cyclohexyl]-acetamide | 1 | 2.62/C | 298.1 |

TABLE 2-continued

| Ex | Structure | Name | Synthetic Method | LCMS RT (min)/Method | LCMS (ESI) m/z |
|---|---|---|---|---|---|
| 480 | 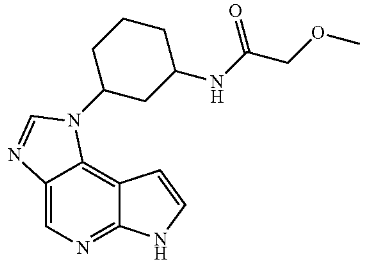 [SMILES: COCC(=O)NC1CCCC(n2cnc3cnc4[nH]ccc4c32)C1] Single isomer, absolute stereochemistry unknown. | 2-Methoxy-N-[3-(6H-1,3,5,6-tetraaza-as-indacen-1-yl)-cyclohexyl]-acetamide | 1 | 2.76/C | 328.1 |
| 481 | 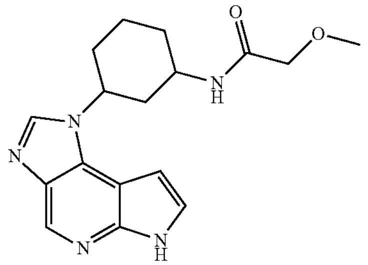 [SMILES: COCC(=O)NC1CCCC(n2cnc3cnc4[nH]ccc4c32)C1] Single isomer, absolute stereochemistry unknown. | 2-Methoxy-N-[3-(6H-1,3,5,6-tetraaza-as-indacen-1-yl)-cyclohexyl]-acetamide | 1 | 2.75/C | 328.1 |
| 482 | 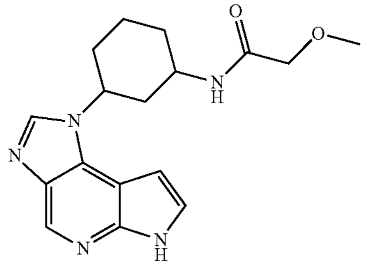 [SMILES: COCC(=O)NC1CCCC(n2cnc3cnc4[nH]ccc4c32)C1] Single isomer, absolute stereochemistry unknown. | 2-Methoxy-N-[3-(6H-1,3,5,6-tetraaza-as-indacen-1-yl)-cyclohexyl]-acetamide | 1 | 2.77/C | 328.1 |
| 483 | 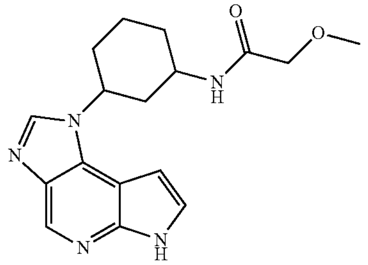 [SMILES: COCC(=O)NC1CCCC(n2cnc3cnc4[nH]ccc4c32)C1] Single isomer, absolute stereochemistry unknown. | 2-Methoxy-N-[3-(6H-1,3,5,6-tetraaza-as-indacen-1-yl)-cyclohexyl]-acetamide | 1 | 2.76/C | 328.1 |
| 484 | 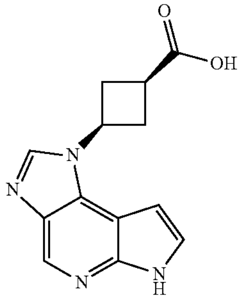 [SMILES: O=C(O)[C@H]1C[C@@H](n2cnc3cnc4[nH]ccc4c32)C1] Single isomer | Cis 3-(6H-1,3,5,6-Tetraaza-as-indacen-1-yl)-cyclobutanecarboxylic acid | 1 | 2.42/C | 257.0 |

TABLE 2-continued

| Ex | Structure | Name | Synthetic Method | LCMS RT (min)/Method | LCMS (ESI) m/z |
|---|---|---|---|---|---|
| 485 | 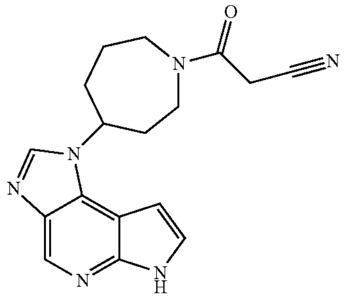 [SMILES: N#CCC(=O)N1CCCC(n2cnc3cnc4[nH]ccc4c32)CC1] racemic | 3-Oxo-3-[4-(6H-1,3,5,6-tetraaza-as-indacen-1-yl)-azepan-1-yl]-propionitrile | 3, 4, 5 | 2.5/C | 323.1 |
| 486 | 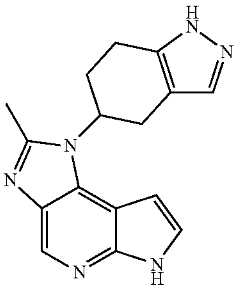 [SMILES: Cc1nc2cnc3[nH]ccc3c2n1C1CCc2[nH]ncc2C1] racemic | 2-Methyl-1-(4,5,6,7-tetrahydro-1H-indazol-5-yl)-1,6-dihydro-1,3,5,6-tetraaza-as-indacene | 109 | 2.41/C | 293.1 |
| 487 | 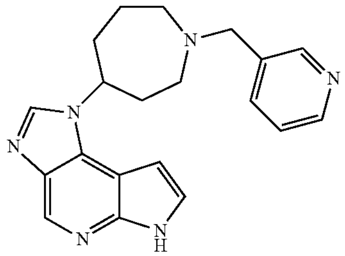 [SMILES: c1cncc(CN2CCCC(n3cnc4cnc5[nH]ccc5c43)CC2)c1] racemic | 1-(1-Pyridin-3-ylmethyl-azepan-4-yl)-1,6-dihydro-1,3,5,6-tetraaza-as-indacene | 4, 5 | 2.14/C | 347.2 |
| 488 | 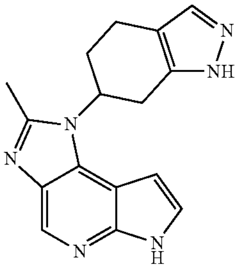 [SMILES: Cc1nc2cnc3[nH]ccc3c2n1C1CCc2cn[nH]c2C1] racemic | 1-(4,5,6,7-Tetrahydro-1H-indazol-6-yl)-1,6-dihydro-1,3,5,6-tetraaza-as-indacene | 109 | 2.66/C | 293.1 |
| 489 | 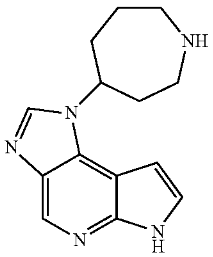 [SMILES: c1cc2c(ncc3ncn(C4CCCNCC4)c32)[nH]1] racemic | 1-Azepan-4-yl-1,6-dihydro-1,3,5,6-tetraaza-as-indacene | 110 | 1.72/C | 256.1 |

TABLE 2-continued

| Ex | Structure | Name | Synthetic Method | LCMS RT (min)/Method | LCMS (ESI) m/z |
|---|---|---|---|---|---|
| 490 | 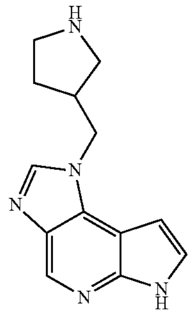 [SMILES: c1cc2c(ncc3ncn(CC4CCNC4)c32)[nH]1] racemic | 1-Pyrrolidin-3-ylmethyl-1,6-dihydro-1,3,5,6-tetraaza-as-indacene | 109 | 1.06/C | 242.1 |
| 491 | 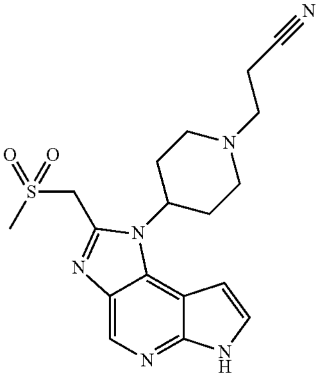 [SMILES: CS(=O)(=O)Cc1nc2cnc3[nH]ccc3c2n1C1CCN(CCC#N)CC1] | 3-[4-(2-Methanesulfonylmethyl-6H-1,3,5,6-tetraaza-as-indacen-1-yl)-piperidin-1-yl]-propionitrile | 116 | 2.28/C | 387.1 |
| 492 | 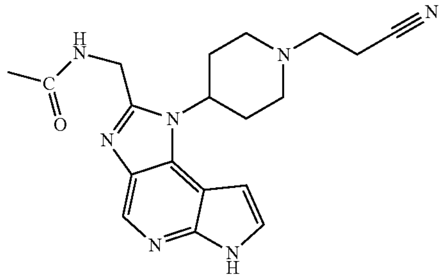 [SMILES: CC(=O)NCc1nc2cnc3[nH]ccc3c2n1C1CCN(CCC#N)CC1] | N-{1-[1-(2-Cyano-ethyl)-piperidin-4-yl]-1,6-dihydro-1,3,5,6-tetraaza-as-indacen-2-ylmethyl}-acetamide | 209 | 2.0/C | 366.1 |
| 493 | 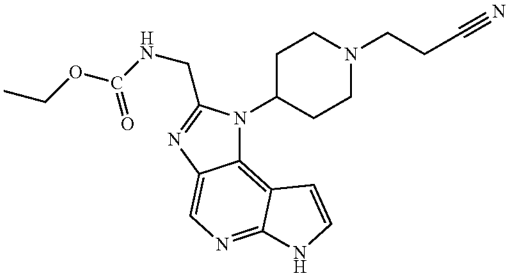 [SMILES: CCOC(=O)NCc1nc2cnc3[nH]ccc3c2n1C1CCN(CCC#N)CC1] | {1-[1-(2-Cyano-ethyl)-piperidin-4-yl]-1,6-dihydro-1,3,5,6-tetraaza-as-indacen-2-ylmethyl}-carbamic acid ethyl ester | 209 | 2.44/C | 396.2 |
| 494 | 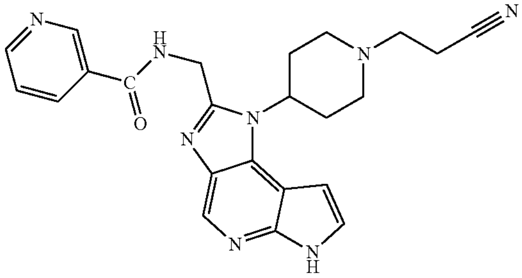 [SMILES: N#CCCN1CCC(n2c(CNC(=O)c3cccnc3)nc3cnc4[nH]ccc4c32)CC1] | N-{1-[1-(2-Cyano-ethyl)-piperidin-4-yl]-1,6-dihydro-1,3,5,6-tetraaza-as-indacen-2-ylmethyl}-nicotinamide | 209 | 2.20/C | 429.2 |

TABLE 2-continued

| Ex | Structure | Name | Synthetic Method | LCMS RT (min)/Method | LCMS (ESI) m/z |
|---|---|---|---|---|---|
| 495 | 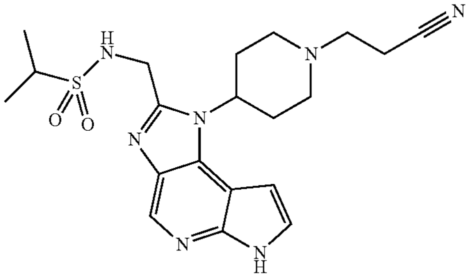 [SMILES: CC(C)S(=O)(=O)NCc1nc2cnc3[nH]ccc3c2n1C1CCN(CCC#N)CC1] | Propane-2-sulfonic acid {1-[1-(2-cyano-ethyl)-piperidin-4-yl]-1,6-dihydro-1,3,5,6-tetraaza-as-indacen-2-ylmethyl}-amide | 209 | 2.48/C | 430.2 |
| 496 | 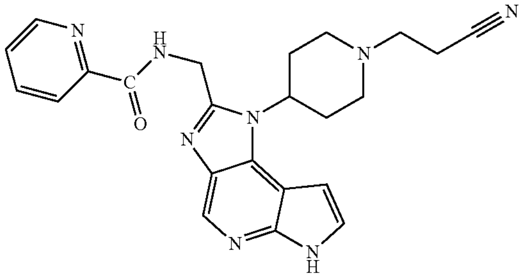 [SMILES: N#CCCN1CCC(n2c(CNC(=O)c3ccccn3)nc3cnc4[nH]ccc4c32)CC1] | Pyridine-2-carboxylic acid {1-[1-(2-cyano-ethyl)-piperidin-4-yl]-1,6-dihydro-1,3,5,6-tetraaza-as-indacen-2-ylmethyl}-amide | 209 | 2.57/C | 429.2 |
| 497 | 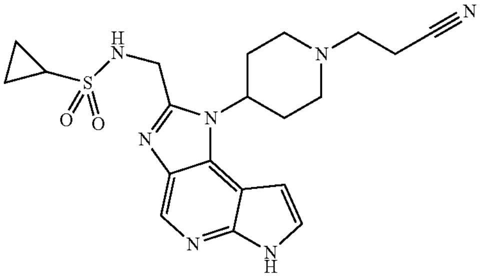 [SMILES: N#CCCN1CCC(n2c(CNS(=O)(=O)C3CC3)nc3cnc4[nH]ccc4c32)CC1] | Cyclopropanesulfonic acid {1-[1-(2-cyano-ethyl)-piperidin-4-yl]-1,6-dihydro-1,3,5,6-tetraaza-as-indacen-2-ylmethyl}-amide | 209 | 2.41/C | 428.1 |
| 498 | 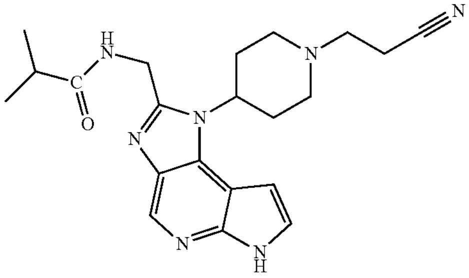 [SMILES: CC(C)C(=O)NCc1nc2cnc3[nH]ccc3c2n1C1CCN(CCC#N)CC1] | N-{1-[1-(2-Cyano-ethyl)-piperidin-4-yl]-1,6-dihydro-1,3,5,6-tetraaza-as-indacen-2-ylmethyl}-isobutyramide | 209 | 2.33/C | 394.2 |
| 499 | 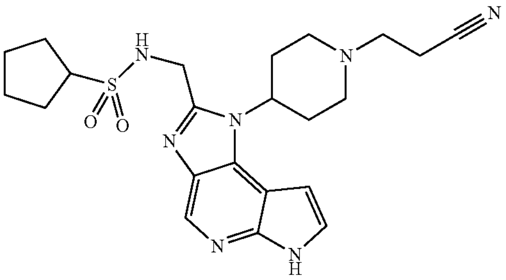 [SMILES: N#CCCN1CCC(n2c(CNS(=O)(=O)C3CCCC3)nc3cnc4[nH]ccc4c32)CC1] | Cyclopentanesulfonic acid {1-[1-(2-cyano-ethyl)-piperidin-4-yl]-1,6-dihydro-1,3,5,6-tetraaza-as-indacen-2-ylmethyl}-amide | 209 | 2.76/C | 456.2 |

TABLE 2-continued

| Ex | Structure | Name | Synthetic Method | LCMS RT (min)/Method | LCMS (ESI) m/z |
|---|---|---|---|---|---|
| 500 | 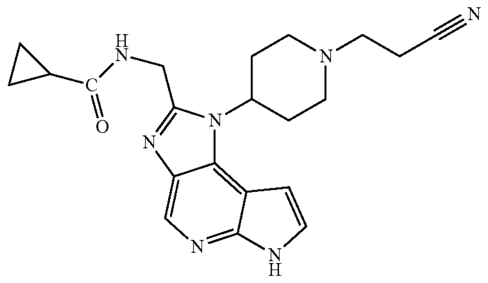 [SMILES: N#CCCN1CCC(n2c(CNC(=O)C3CC3)nc3cnc4[nH]ccc4c32)CC1] | Cyclopropanecarboxylic acid {1-[1-(2-cyano-ethyl)-piperidin-4-yl]-1,6-dihydro-1,3,5,6-tetraaza-as-indacen-2-ylmethyl}-amide | 209 | 2.27/C | 392.2 |
| 501 | 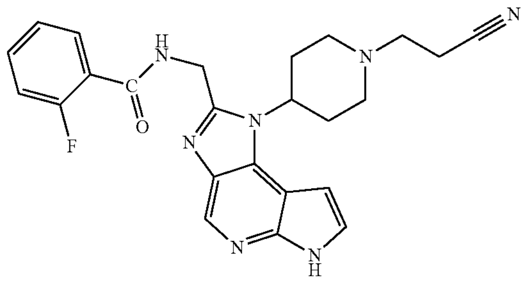 [SMILES: N#CCCN1CCC(n2c(CNC(=O)c3ccccc3F)nc3cnc4[nH]ccc4c32)CC1] | N-{1-[1-(2-Cyano-ethyl)-piperidin-4-yl]-1,6-dihydro-1,3,5,6-tetraaza-as-indacen-2-ylmethyl}-2-fluoro-benzamide | 209 | 2.75/C | 446.2 |
| 502 | 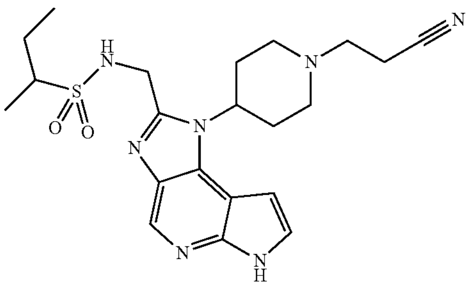 [SMILES: CCC(C)S(=O)(=O)NCc1nc2cnc3[nH]ccc3c2n1C1CCN(CCC#N)CC1] racemic | Butane-2-sulfonic acid {1-[1-(2-cyano-ethyl)-piperidin-4-yl]-1,6-dihydro-1,3,5,6-tetraaza-as-indacen-2-ylmethyl}-amide | 209 | 2.70/C | 444.2 |
| 503 | 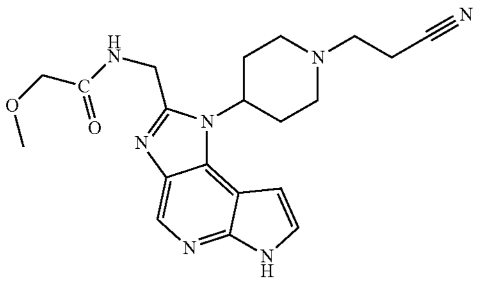 [SMILES: COCC(=O)NCc1nc2cnc3[nH]ccc3c2n1C1CCN(CCC#N)CC1] | N-{1-[1-(2-Cyano-ethyl)-piperidin-4-yl]-1,6-dihydro-1,3,5,6-tetraaza-as-indacen-2-ylmethyl}-2-methoxy-acetamide | 209 | 2.21/C | 396.1 |
| 504 | 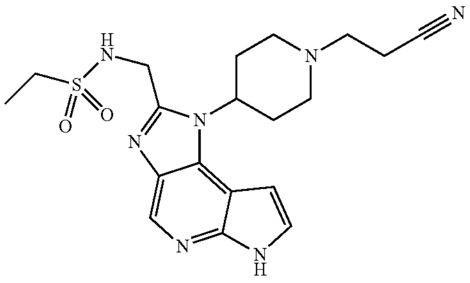 [SMILES: CCS(=O)(=O)NCc1nc2cnc3[nH]ccc3c2n1C1CCN(CCC#N)CC1] | 3Butane-2-sulfonic acid {1-[1-(2-cyano-ethyl)-piperidin-4-yl]-1,6-dihydro-1,3,5,6-tetraaza-as-indacen-2-ylmethyl}-amide | 209 | 2.30/C | 416.1 |

TABLE 2-continued

| Ex | Structure | Name | Synthetic Method | LCMS RT (min)/Method | LCMS (ESI) m/z |
|---|---|---|---|---|---|
| 505 | 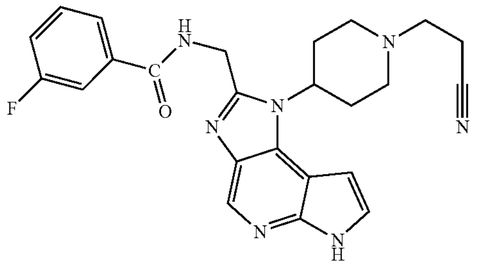 [SMILES: N#CCCN1CCC(n2c(CNC(=O)c3cccc(F)c3)nc3cnc4[nH]ccc4c32)CC1] | N-{1-[1-(2-Cyano-ethyl)-piperidin-4-yl]-1,6-dihydro-1,3,5,6-tetraaza-as-indacen-2-ylmethyl}-3-fluoro-benzamide | 209 | 2.85/C | 446.1 |
| 506 | 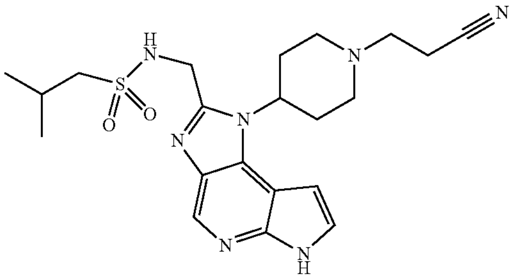 [SMILES: CC(C)CS(=O)(=O)NCc1nc2cnc3[nH]ccc3c2n1C1CCN(CCC#N)CC1] | 2-Methyl-propane-1-sulfonic acid {1-[1-(2-cyano-ethyl)-piperidin-4-yl]-1,6-dihydro-1,3,5,6-tetraaza-as-indacen-2-ylmethyl}-amide | 209 | 2.74/C | 444.2 |
| 507 | 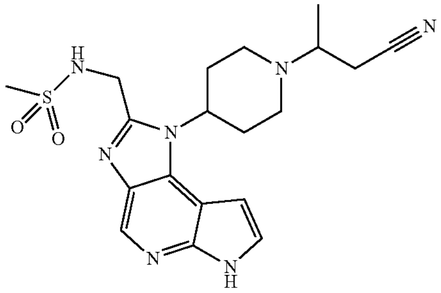 [SMILES: CC(CC#N)N1CCC(n2c(CNS(C)(=O)=O)nc3cnc4[nH]ccc4c32)CC1] racemic | N-{1-[1-(2-Cyano-1-methyl-ethyl)-piperidin-4-yl]-1,6-dihydro-1,3,5,6-tetraaza-as-indacen-2-ylmethyl}-methanesulfonamide | 209 | 2.29/C | 416.1 |
| 508 | 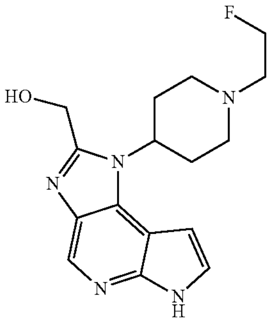 [SMILES: OCc1nc2cnc3[nH]ccc3c2n1C1CCN(CCF)CC1] | {1-[1-(2-Fluoro-ethyl)-piperidin-4-yl]-1,6-dihydro-1,3,5,6-tetraaza-as-indacen-2-yl}-methanol | 22 | 1.86/C | 318.1 |
| 509 | 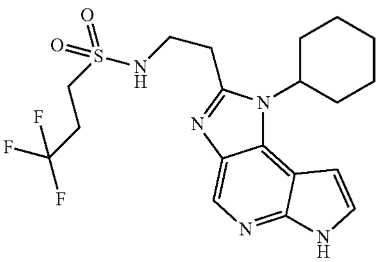 [SMILES: O=S(=O)(CCC(F)(F)F)NCCc1nc2cnc3[nH]ccc3c2n1C1CCCCC1] | 3,3,3-Trifluoro-propane-1-sulfonic acid [2-(1-cyclohexyl-1,6-dihydro-1,3,5,6-tetraaza-as-indacen-2-yl)-ethyl]-amide | 113 and 118 | 3.91/C | 444.1 |

TABLE 2-continued

| Ex | Structure | Name | Synthetic Method | LCMS RT (min)/Method | LCMS (ESI) m/z |
|---|---|---|---|---|---|
| 510 | 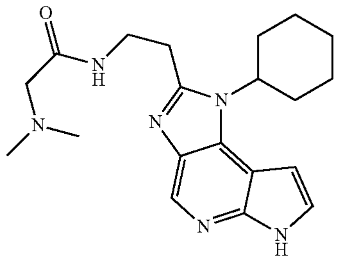 [SMILES: CN(C)CC(=O)NCCc1nc2cnc3[nH]ccc3c2n1C1CCCCC1] | N-[2-(1-Cyclohexyl-1,6-dihydro-1,3,5,6-tetraaza-as-indacen-2-yl)-ethyl]-2-dimethylamino-acetamide | 113 and 118 | 2.89/C | 369.2 |
| 511 | 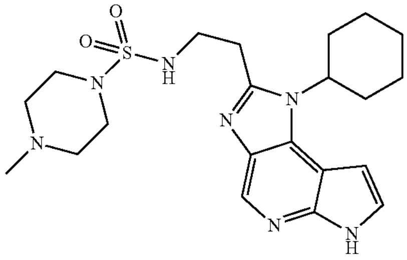 [SMILES: CN1CCN(S(=O)(=O)NCCc2nc3cnc4[nH]ccc4c3n2C2CCCCC2)CC1] | 4-Methyl-piperazine-1-sulfonic acid [2-(1-cyclohexyl-1,6-dihydro-1,3,5,6-tetraaza-as-indacen-2-yl)-ethyl]-amide | 113 and 118 | 2.96/C | 424.2 |
| 512 | 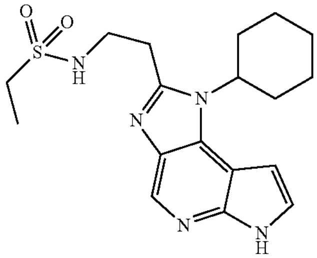 [SMILES: CCS(=O)(=O)NCCc1nc2cnc3[nH]ccc3c2n1C1CCCCC1] | Ethanesulfonic acid [2-(1-cyclohexyl-1,6-dihydro-1,3,5,6-tetraaza-as-indacen-2-yl)-ethyl]-amide | 113 and 118 | 3.47/C | 376.1 |
| 513 | 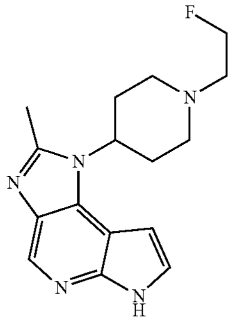 [SMILES: Cc1nc2cnc3[nH]ccc3c2n1C1CCN(CCF)CC1] | 1-[1-(2-Fluoro-ethyl)-piperidin-4-yl]-2-methyl-1,6-dihydro-1,3,5,6-tetraaza-as-indacene | 109 | 2.04/C | 302.1 |
| 514 | 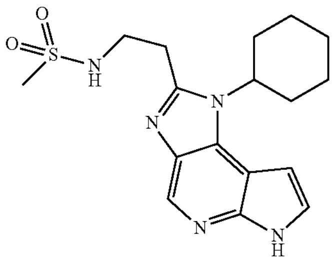 [SMILES: CS(=O)(=O)NCCc1nc2cnc3[nH]ccc3c2n1C1CCCCC1] | N-[2-(1-Cyclohexyl-1,6-dihydro-1,3,5,6-tetraaza-as-indacen-2-yl)-ethyl]-methanesulfonamide | 113 and 118 | 3.33/C | 362.1 |

TABLE 2-continued

| Ex | Structure | Name | Synthetic Method | LCMS RT (min)/Method | LCMS (ESI) m/z |
|---|---|---|---|---|---|
| 515 | 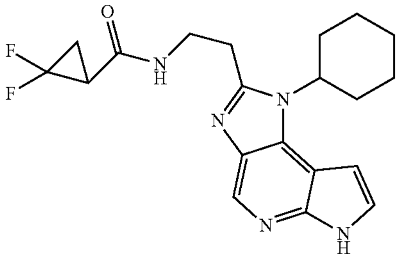 [SMILES: O=C(NCCc1nc2cnc3[nH]ccc3c2n1C1CCCCC1)C1CC1(F)F] racemic | 2,2-Difluoro-cyclopropanecarboxylic acid [2-(1-cyclohexyl-1,6-dihydro-1,3,5,6-tetraaza-as-indacen-2-yl)-ethyl]-amide | 113 and 118 | 3.56/C | 388.1 |
| 516 | 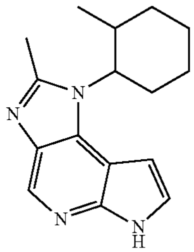 [SMILES: Cc1nc2cnc3[nH]ccc3c2n1C1CCCCC1C] Mixture of four stereoisomers | 2-Methyl-1-(2-methyl-cyclohexyl)-1,6-dihydro-1,3,5,6-tetraaza-as-indacene | 110 | 3.51/C | 269.1 |
| 517 | 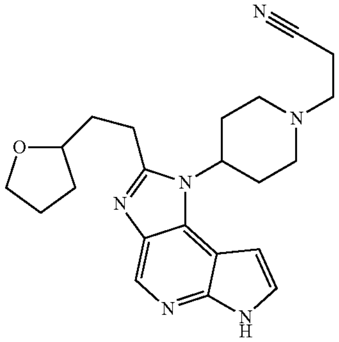 [SMILES: N#CCCN1CCC(n2c(CCC3CCCO3)nc3cnc4[nH]ccc4c32)CC1] racemic | 3-(4-{2-[2-(Tetrahydro-furan-2-yl)-ethyl]-6H-1,3,5,6-tetraaza-as-indacen-1-yl}-piperidin-1-yl)-propionitrile | 116 | 2.61/C | 393.2 |
| 518 | 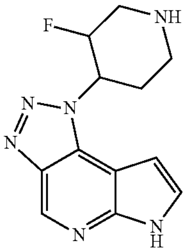 [SMILES: FC1CNCCC1n1nnc2cnc3[nH]ccc3c21] Racemic, cis | 1-(3-Fluoro-piperidin-4-yl)-1,6-dihydro-1,2,3,5,6-pentaaza-as-indacene | 18 | 1.78/C | 261.1 |
| 519 | 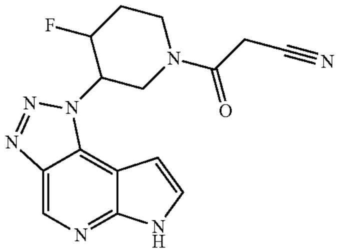 [SMILES: N#CCC(=O)N1CCC(F)C(n2nnc3cnc4[nH]ccc4c32)C1] Racemic, cis | 3-[4-Fluoro-3-(6H-1,2,3,5,6-pentaaza-as-indacen-1-yl)-piperidin-1-yl]-3-oxo-propionitrile | 19 | 1.20/D | 328.1 |

TABLE 2-continued

| Ex | Structure | Name | Synthetic Method | LCMS RT (min)/Method | LCMS (ESI) m/z |
|---|---|---|---|---|---|
| 520 | 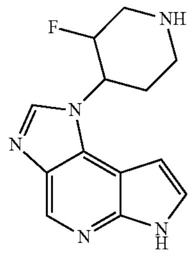 Racemic, cis | 1-(3-Fluoro-piperidin-4-yl)-1,6-dihydro-1,3,5,6-tetraaza-as-indacene | 3 | 0.67, C | 260.1 |
| 521 | 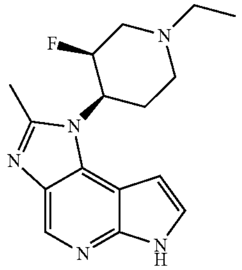 [SMILES: CCN1CC[C@@H](n2c(C)nc3cnc4[nH]ccc4c32)[C@@H](F)C1] | 1-((3S,4R)-1-Ethyl-3-fluoro-piperidin-4-yl)-2-methyl-1,6-dihydro-1,3,5,6-tetraaza-as-indacene | 178 | 1.94, C | 302.1 |
| 522 | 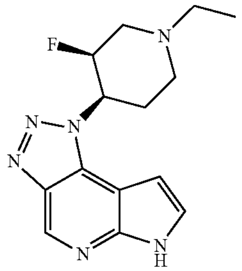 [SMILES: CCN1CC[C@@H](n2nnc3cnc4[nH]ccc4c32)[C@@H](F)C1] | 1-((3S,4R)-1-Ethyl-3-fluoro-piperidin-4-yl)-1,6-dihydro-1,2,3,5,6-pentaaza-as-indacene | 18 | 2.28, C | 289.1 |
| 523 | 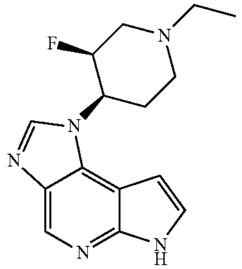 [SMILES: CCN1CC[C@@H](n2cnc3cnc4[nH]ccc4c32)[C@@H](F)C1] | 1-((3S,4R)-1-Ethyl-3-fluoro-piperidin-4-yl)-1,6-dihydro-1,3,5,6-tetraaza-as-indacene | 3 | 3.03, C | 288.1 |
| 524 | 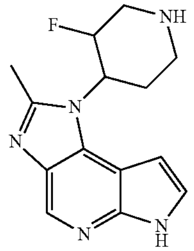 [SMILES: Cc1nc2cnc3[nH]ccc3c2n1C1CCNCC1F] Cis, single enantiomer, absolute stereochemistry unknown | 1-(3-Fluoro-piperidin-4-yl)-2-methyl-1,6-dihydro-1,3,5,6-tetraaza-as-indacene | 216 | 1.33, C | 274.1 |

TABLE 2-continued

| Ex | Structure | Name | Synthetic Method | LCMS RT (min)/Method | LCMS (ESI) m/z |
|---|---|---|---|---|---|
| 525 | 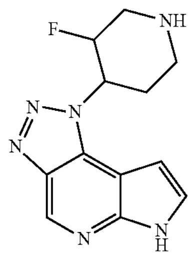 [SMILES: FC1CNCCC1n1nnc2cnc3[nH]ccc3c21] Racemic, trans | 1-(3-Fluoro-piperidin-4-yl)-l,6-dihydro-1,2,3,5,6-pentaaza-as-indacene | 18 | 2.31, C | 261.1 |
| 526 | 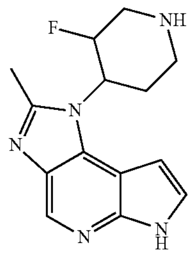 [SMILES: Cc1nc2cnc3[nH]ccc3c2n1C1CCNCC1F] Cis, single enantiomer, absolute stereochemistry unknown | l-(3-Fluoro-piperidin-4-yl)-2-methyl-1,6-dihydro-1,3,5,6-tetraaza-as-indacene | 216 | 0.75, C | 274.1 |
| 527 | 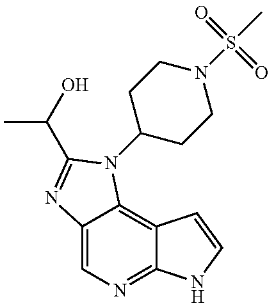 [SMILES: CC(O)c1nc2cnc3[nH]ccc3c2n1C1CCN(S(C)(=O)=O)CC1] Racemic | 1-[1-(1-Methanesulfonyl-piperidin-4-yl)-1,6-dihydro-1,3,5,6-tetraaza-as-indacen-2-yl]-ethanol | 182, 4 and 9 | 2.69, C | 364.1 |
| 528 | 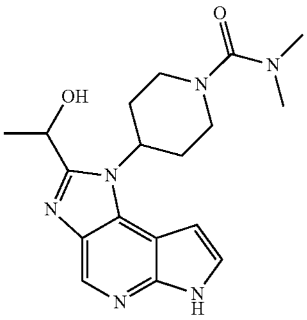 [SMILES: CC(O)c1nc2cnc3[nH]ccc3c2n1C1CCN(C(=O)N(C)C)CC1] Racemic | 4-[2-(1-Hydroxy-ethyl)-6H-1,3,5,6-tetraaza-as-indacen-1-yl]-piperidine-1-carboxylic acid dimethylamide | 182, 4 and 9 | 2.83, C | 357.1 |

TABLE 2-continued

| Ex | Structure | Name | Synthetic Method | LCMS RT (min)/Method | LCMS (ESI) m/z |
|---|---|---|---|---|---|
| 529 | 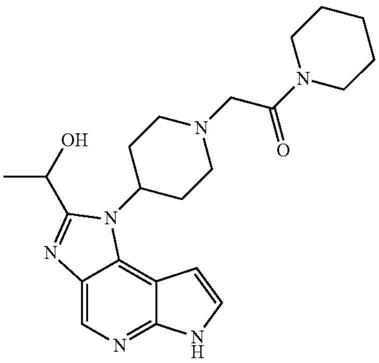 [SMILES: CC(O)c1nc2cnc3[nH]ccc3c2n1C1CCN(CC(=O)N2CCCCC2)CC1] Racemic | 2-{4-[2-(1-Hydroxy-ethyl)-6H-1,3,5,6-tetraaza-as-indacen-1-yl]-piperidin-1-yl}-1-piperidin-1-yl-ethanone | 182, 4 and 11 | 2.62, C | 411.2 |
| 530 | 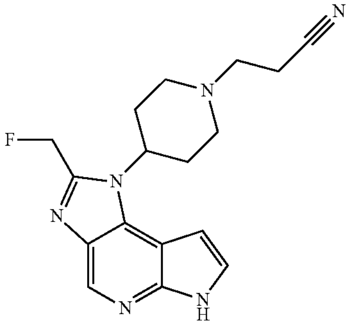 [SMILES: N#CCCN1CCC(n2c(CF)nc3cnc4[nH]ccc4c32)CC1] | 3-[4-(2-Fluoromethyl-6H-1,3,5,6-tetraaza-as-indacen-1-yl)-piperidin-1-yl]-propionitrile | 2 | 2.20, C | 327.1 |
| 531 | 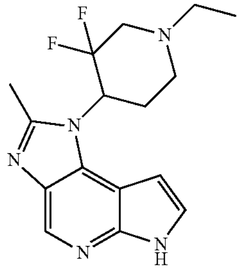 [SMILES: CCN1CCC(n2c(C)nc3cnc4[nH]ccc4c32)C(F)(F)C1] Racemic | 1-(1-Ethyl-3,3-difluoro-piperidin-4-yl)-2-methyl-1,6-dihydro-1,3,5,6-tetraaza-as-indacene | 178 | 2.33, C | 320.1 |
| 532 | 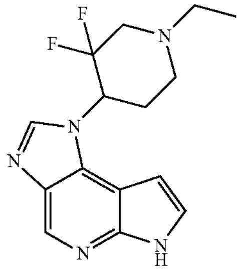 [SMILES: CCN1CCC(n2cnc3cnc4[nH]ccc4c32)C(F)(F)C1] Racemic | 1-(1-Ethyl-3,3-difluoro-piperidin-4-yl)-1,6-dihydro-1,3,5,6-tetraaza-as-indacene | 3 | 2.21, C | 306.1 |

TABLE 2-continued

| Ex | Structure | Name | Synthetic Method | LCMS RT (min)/Method | LCMS (ESI) m/z |
|---|---|---|---|---|---|
| 533 | 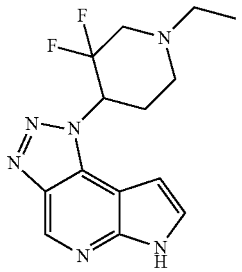 [SMILES: CCN1CCC(n2nnc3cnc4[nH]ccc4c32)C(F)(F)C1] Racemic | 1-(1-Ethyl-3,3-difluoro-piperidin-4-yl)-1,6-dihydro-1,2,3,5,6-pentaaza-as-indacene | 18 | 2.53, C | 307.0 |
| 534 | 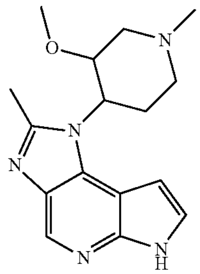 Racemic, cis | 1-(3-Methoxy-1-methyl-piperidin-4-yl)-2-methyl-1,6-dihydro-1,3,5,6-tetraaza-as-indacene | 178 (3 THF:1 H2O:1 MeOHas solvent for sulfonyl benzyl deprotection) | 1.87, C | 300.1 |
| 535 | 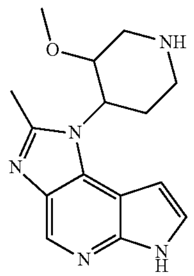 [SMILES: COC1CNCCC1n1c(C)nc2cnc3[nH]ccc3c21] Racemic, cis | 1-(3-Methoxy-piperidin-4-yl)-2-methyl-1,6-dihydro-1,3,5,6-tetraaza-as-indacene | 178 | 1.87, C | 286.1 |
| 536 | 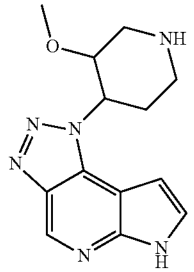 [SMILES: COC1CNCCC1n1nnc2cnc3[nH]ccc3c21] Racemic, cis | 1-(3-Methoxy-piperidin-4-yl)-1,6-dihydro-1,2,3,5,6-pentaaza-as-indacene | 18 | 2.27, C | 273.0 |
| 537 | 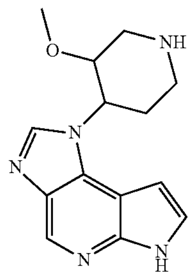 [SMILES: COC1CNCCC1n1cnc2cnc3[nH]ccc3c21] Racemic cis | 1-(3-Methoxy-piperidin-4-yl)-1,6-dihydro-1,3,5,6-tetraaza-as-indacene | 3 | 3.21, D | 272.1 |

TABLE 2-continued

| Ex | Structure | Name | Synthetic Method | LCMS RT (min)/Method | LCMS (ESI) m/z |
|---|---|---|---|---|---|
| 538 | 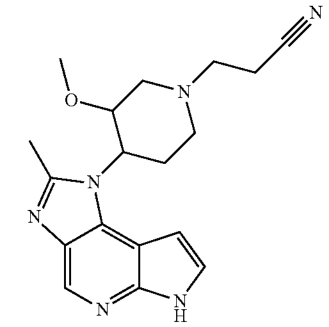 [SMILES: COC1CN(CCC#N)CCC1n1c(C)nc2cnc3[nH]ccc3c21] Racemic, cis | 3-[3-Methoxy-4-(2-methyl-6H-1,3,5,6-tetraaza-as-indacen-1-yl)-piperidin-1-yl]-propionitrile | 178 and 10 | 2.09, C | 339.1 |
| 539 | 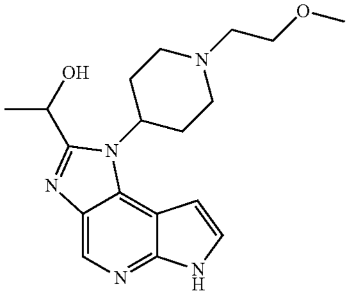 [SMILES: COCCN1CCC(n2c(C(C)O)nc3cnc4[nH]ccc4c32)CC1] Racemic | 1-{1-[1-(2-Methoxy-ethyl)-piperidin-4-yl]-1,6-dihydro-1,3,5,6-tetraaza-as-indacen-2-yl}-ethanol | 182, 4 and 11 | 2.29, C | 344.1 |
| 540 | 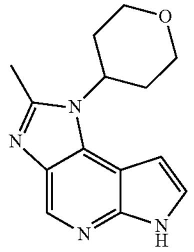 [SMILES: Cc1nc2cnc3[nH]ccc3c2n1C1CCOCC1] | 2-Methyl-1-(tetrahydro-pyran-4-yl)-1,6-dihydro-1,3,5,6-tetraaza-as-indacene | 20, 199 | 2.55/C | 257.2 |
| 541 | 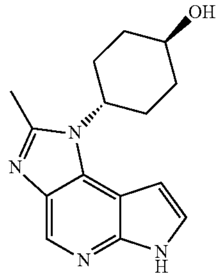 [SMILES: Cc1nc2cnc3[nH]ccc3c2n1[C@H]1CC[C@H](O)CC1] | trans 4-(2-Methyl-6H-1,3,5,6-tetraaza-as-indacen-1-yl)-cyclohexanol | 20, 213 | 2.42/C | 271.1 |
| 542 | 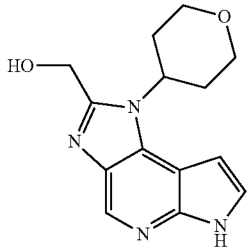 [SMILES: OCc1nc2cnc3[nH]ccc3c2n1C1CCOCC1] | [1-(Tetrahydro-pyran-4-yl)-1,6-dihydro-1,3,5,6-tetraaza-as-indacen-2-yl]-methanol | 22, 199 | 2.47/C | 273.1 |

TABLE 2-continued

| Ex | Structure | Name | Synthetic Method | LCMS RT (min)/Method | LCMS (ESI) m/z |
|---|---|---|---|---|---|
| 543 | 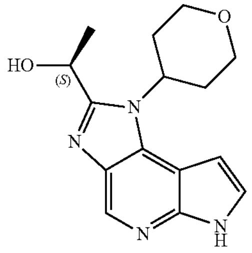 | (S)-1-[1-(Tetrahydro-pyran-4-yl)-1,6-dihydro-1,3,5,6-tetraaza-as-indacen-2-yl]-ethanol | 199 | 2.62/C | 287.1 |
| 544 | 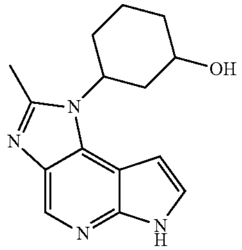 [SMILES: Cc1nc2cnc3[nH]ccc3c2n1C1CCCC(O)C1] Cis, single enatiomer, absolute stereochemistry unknown | 3-(2-Methyl-6H-1,3,5,6-tetraaza-as-indacen-1-yl)-cyclohexanol | 213 | 2.63/C | 271.1 |
| 545 | 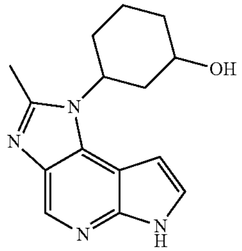 [SMILES: Cc1nc2cnc3[nH]ccc3c2n1C1CCCC(O)C1] Cis, single enatiomer, absolute stereochemistry unknown | 3-(2-Methyl-6H-1,3,5,6-tetraaza-as-indacen-1-yl)-cyclohexanol | 213 | 2.64/C | 271.1 |
| 546 | 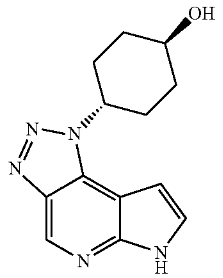 [SMILES: O[C@H]1CC[C@H](n2nnc3cnc4[nH]ccc4c32)CC1] | trans 4-(6H-1,2,3,5,6-Pentaaza-as-indacen-1-yl)-cyclohexanol | 18, 213 | 2.94/C | 258.1 |
| 547 | 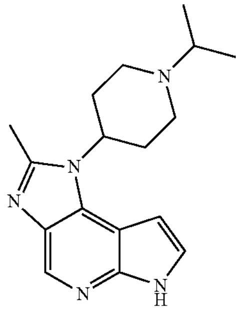 [SMILES: Cc1nc2cnc3[nH]ccc3c2n1C1CCN(C(C)C)CC1] | 1-(1-Isopropyl-piperidin-4-yl)-2-methyl-1,6-dihydro-1,3,5,6-tetraaza-as-indacene | 20, 156 | 2.21/C | 298.1 |

TABLE 2-continued

| Ex | Structure | Name | Synthetic Method | LCMS RT (min)/Method | LCMS (ESI) m/z |
|---|---|---|---|---|---|
| 548 | 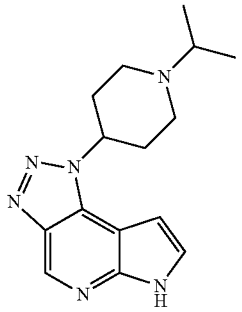 [SMILES: CC(C)N1CCC(n2nnc3cnc4[nH]ccc4c32)CC1] | 1-(1-Isopropyl-piperidin-4-yl)-1,6-dihydro-1,2,3,5,6-pentaaza-as-indacene | 18, 156 | 2.56/C | 285.1 |
| 549 | 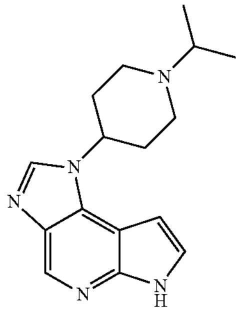 [SMILES: CC(C)N1CCC(n2cnc3cnc4[nH]ccc4c32)CC1] | 1-(1-Isopropyl-piperidin-4-yl)-1,6-dihydro-1,3,5,6-tetraaza-as-indacene | 1, 156 | 2.14/C | 284.1 |
| 550 | 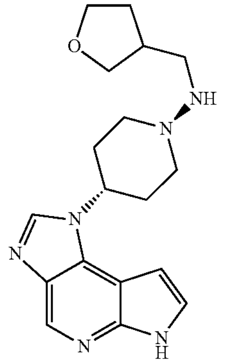 | Trans [4-(6H-1,3,5,6-Tetraaza-as-indacen-1-yl)-cyclohexyl]-(tetrahydro-furan-3-ylmethyl)-amine | 214 | 2.36/C | 240.2 |
| 551 | 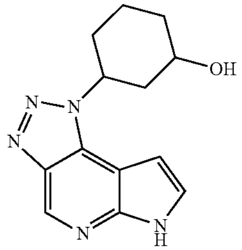 [SMILES: OC1CCCC(n2nnc3cnc4[nH]ccc4c32)C1] Cis, single enatiomer, absolute stereochemistry unknown | 3-(6H-1,2,3,5,6-Pentaaza-as-indacen-1-yl)-cyclohexanol | 18, 213 | 3.07/C | 258.0 |
| 552 | 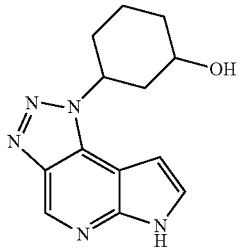 [SMILES: OC1CCCC(n2nnc3cnc4[nH]ccc4c32)C1] Trans, single enatiomer, absolute stereochemistry unknown | 3-(6H-1,2,3,5,6-Pentaaza-as-indacen-1-yl)-cyclohexanol | 18, 213 | 3.17/C | 258.0 |

TABLE 2-continued

| Ex | Structure | Name | Synthetic Method | LCMS RT (min)/Method | LCMS (ESI) m/z |
|---|---|---|---|---|---|
| 553 | 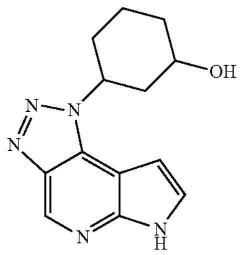 [SMILES: OC1CCCC(n2nnc3cnc4[nH]ccc4c32)C1] Trans, single enatiomer, absolute stereochemistry unknown | 3-(6H-1,2,3,5,6-Pentaaza-as-indacen-1-yl)-cyclohexanol | 18, 213 | 3.17/C | 258.0 |
| 554 | 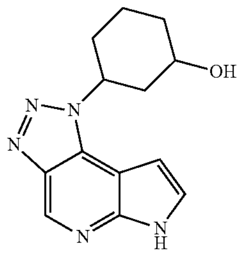 [SMILES: OC1CCCC(n2nnc3cnc4[nH]ccc4c32)C1] Cis, single enatiomer, absolute stereochemistry unknown | 3-(6H-1,2,3,5,6-Pentaaza-as-indacen-1-yl)-cyclohexanol | 18, 213 | 3.07/C | 258.0 |
| 555 | 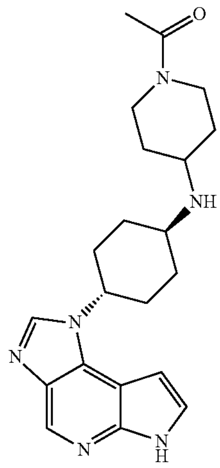 [SMILES: CC(=O)N1CCC(N[C@H]2CC[C@H](n3cnc4cnc5[nH]ccc5c43)CC2)CC1] | trans 1-{4-[4-(6H-1,3,5,6-Tetraaza-as-indacen-1-yl)-cyclohexylamino]-piperidin-1-yl}-ethanone | 214 | 2.32/C | 381.2 |
| 556 | 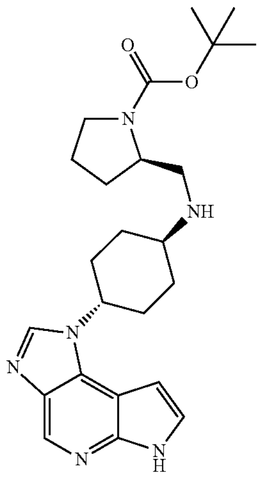 [SMILES: CC(C)(C)OC(=O)N1CCC[C@@H]1CN[C@H]1CC[C@H](n2cnc3cnc4[nH]ccc4c32)CC1] | trans (R)-2-{[4-(6H-1,3,5,6-Tetraaza-as-indacen-1-yl)-cyclohexylamino]-methyl}-pyrrolidine-1-carboxylic acid tert-butyl ester | 214 | 3.27/C | 439.2 |

TABLE 2-continued

| Ex | Structure | Name | Synthetic Method | LCMS RT (min)/Method | LCMS (ESI) m/z |
|---|---|---|---|---|---|
| 557 | 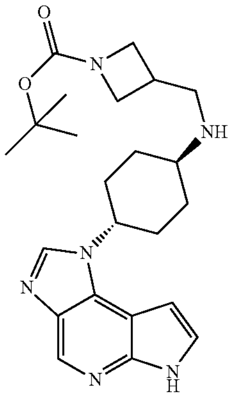 [SMILES: CC(C)(C)OC(=O)N1CC(CN[C@H]2CC[C@H](n3cnc4cnc5[nH]ccc5c43)CC2)C1] | trans 3-{[4-(6H-1,3,5,6-Tetraaza-as-indacen-1-yl)-cyclohexylamino]-methyl}-azetidine-1-carboxylic acid tert-butyl ester | 214 | 3.06/C | 425.2 |
| 558 | 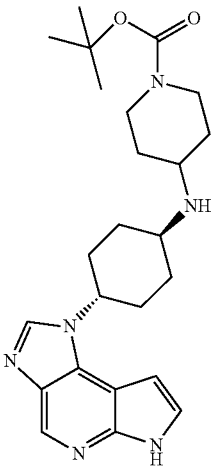 [SMILES: CC(C)(C)OC(=O)N1CCC(N[C@H]2CC[C@H](n3cnc4cnc5[nH]ccc5c43)CC2)CC1] | trans 4-[4-(6H-1,3,5,6-Tetraaza-as-indacen-1-yl)-cyclohexylamino]-piperidine-1-carboxylic acid tert-butyl ester | 214 | 2.99/C | 439.2 |
| 559 | 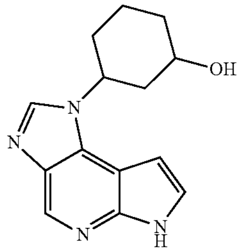 [SMILES: OC1CCCC(n2cnc3cnc4[nH]ccc4c32)C1] Cis, single enatiomer, absolute stereochemistry unknown | 3-(6H-1,3,5,6-Tetraaza-as-indacen-1-yl)-cyclohexanol | 213 | 2.56/C | 257.1 |
| 560 | 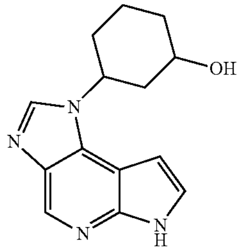 [SMILES: OC1CCCC(n2cnc3cnc4[nH]ccc4c32)C1] Cis, single enatiomer, absolute stereochemistry unknown | 3-(6H-1,3,5,6-Tetraaza-as-indacen-1-yl)-cyclohexanol | 213 | 2.55/C | 257.1 |

TABLE 2-continued

| Ex | Structure | Name | Synthetic Method | LCMS RT (min)/Method | LCMS (ESI) m/z |
|---|---|---|---|---|---|
| 561 | 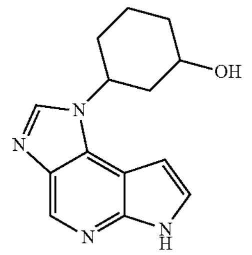 [SMILES: OC1CCCC(n2cnc3cnc4[nH]ccc4c32)C1] Trans, single enatiomer, absolute stereochemistry unknown | 3-(6H-1,3,5,6-Tetraaza-as-indacen-1-yl)-cyclohexanol | 213 | 2.61/C | 257.1 |
| 562 | 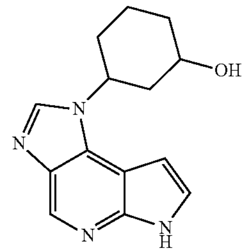 [SMILES: OC1CCCC(n2cnc3cnc4[nH]ccc4c32)C1] Trans, single enatiomer, absolute stereochemistry unknown | 3-(6H-1,3,5,6-Tetraaza-as-indacen-1-yl)-cyclohexanol | 213 | 2.63/C | 257.1 |
| 563 | 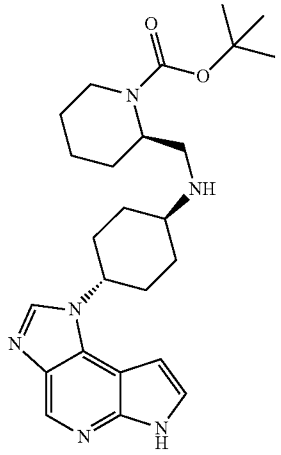 [SMILES: CC(C)(C)OC(=O)N1CCCC[C@@H]1CN[C@H]1CC[C@H](n2cnc3cnc4[nH]ccc4c32)CC1] | trans (R)-2-{[4-(6H-1,3,5,6-Tetraaza-as-indacen-1-yl)-cyclohexylamino]-methyl}-piperidine-1-carboxylic acid tert-butyl ester | 214 | 3.48/C | 453.3 |
| 564 | 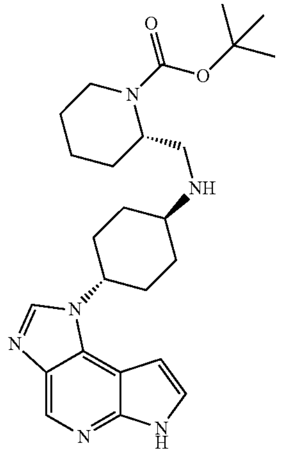 [SMILES: CC(C)(C)OC(=O)N1CCCC[C@H]1CN[C@H]1CC[C@H](n2cnc3cnc4[nH]ccc4c32)CC1] | trans (S)-2-{[4-(6H-1,3,5,6-Tetraaza-as-indacen-1-yl)-cyclohexylamino]-methyl}-piperidine-1-carboxylic acid tert-butyl ester | 214 | 3.29/C | 453.2 |

TABLE 2-continued

| Ex | Structure | Name | Synthetic Method | LCMS RT (min)/Method | LCMS (ESI) m/z |
|---|---|---|---|---|---|
| 565 | 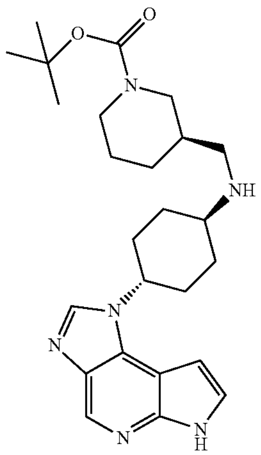 [SMILES: CC(C)(C)OC(=O)N1CCC[C@H](CN[C@H]2CC[C@H](n3cnc4cnc5[nH]ccc5c43)CC2)C1] | trans (R)-3-{[4-(6H-1,3,5,6-Tetraaza-as-indacen-1-yl)-cyclohexylamino]-methyl}-piperidine-1-carboxylic acid tert-butyl ester | 214 | 3.25/C | 453.3 |
| 566 | 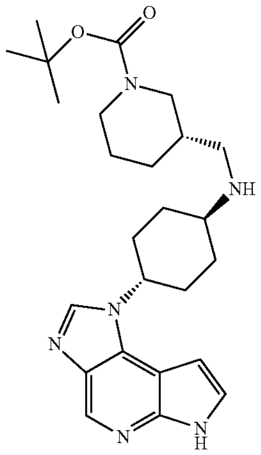 [SMILES: CC(C)(C)OC(=O)N1CCC[C@@H](CN[C@H]2CC[C@H](n3cnc4cnc5[nH]ccc5c43)CC2)C1] | trans (S)-3-{[4-(6H-1,3,5,6-Tetraaza-as-indacen-1-yl)-cyclohexylamino]-methyl}-piperidine-1-carboxylic acid tert-butyl ester | 214 | 3.28/C | 453.3 |
| 567 | 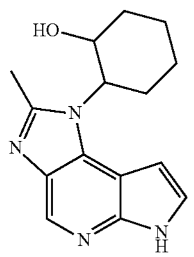 [SMILES: Cc1nc2cnc3[nH]ccc3c2n1C1CCCCC1O] Trans, single enatiomer, absolute stereochemistry unknown | 2-(2-Methyl-6H-1,3,5,6-tetraaza-as-indacen-1-yl)-cyclohexanol | 213 | 2.87/C | 271.0 |

TABLE 2-continued
| Ex | Structure | Name | Synthetic Method | LCMS RT (min)/Method | LCMS (ESI) m/z |
|---|---|---|---|---|---|
| 568 | 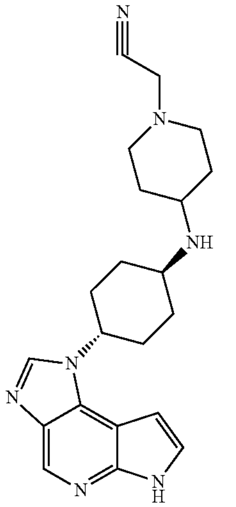 [SMILES: N#CCN1CCC(N[C@H]2CC[C@H](n3cnc4cnc5[nH]ccc5c43)CC2)CC1] | trans {4-[4-(6H-1,3,5,6-Tetraaza-as-indacen-1-yl)-cyclohexylamino]-piperidin-1-yl}-acetonitrile | 214 | 2.44/C | 378.2 |
| 569 | 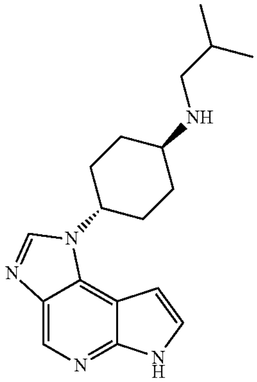 [SMILES: CC(C)CN[C@H]1CC[C@H](n2cnc3cnc4[nH]ccc4c32)CC1] | trans Isobutyl-[4-(6H-1,3,5,6-tetraaza-as-indacen-1-yl)-cyclohexyl]-amine | 214 | 2.53/C | 312.1 |
| 570 | 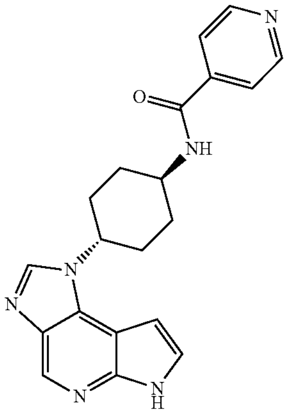 [SMILES: O=C(N[C@H]1CC[C@H](n2cnc3cnc4[nH]ccc4c32)CC1)c1ccncc1] | trans N-[4-(6H-1,3,5,6-Tetraaza-as-indacen-1-yl)-cyclohexyl]-isonicotinamide | 215 | 2.54/C | 361.1 |

TABLE 2-continued

| Ex | Structure | Name | Synthetic Method | LCMS RT (min)/Method | LCMS (ESI) m/z |
|---|---|---|---|---|---|
| 571 | 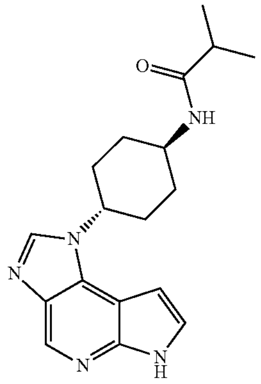 [SMILES: CC(C)C(=O)N[C@H]1CC[C@H](n2cnc3cnc4[nH]ccc4c32)CC1] | trans N-[4-(6H-1,3,5,6-Tetraaza-as-indacen-1-yl)-cyclohexyl]-isobutyramide | 215 | 2.92/C | 326.1 |
| 572 | 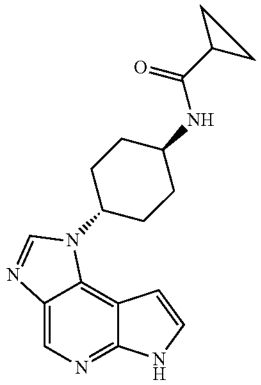 [SMILES: O=C(N[C@H]1CC[C@H](n2cnc3cnc4[nH]ccc4c32)CC1)C1CC1] | trans Cyclopropanecarboxylic acid [4-(6H-1,3,5,6-tetraaza-as-indacen-1-yl)-cyclohexyl]-amide | 215 | 2.86/C | 324.1 |
| 573 | 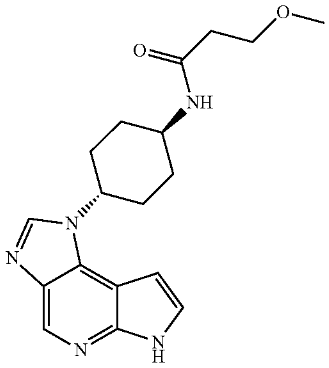 [SMILES: COCCC(=O)N[C@H]1CC[C@H](n2cnc3cnc4[nH]ccc4c32)CC1] | trans 3-Methoxy-N-[4-(6H-1,3,5,6-tetraaza-as-indacen-1-yl)-cyclohexyl]-propionamide | 215 | 2.69/C | 342.1 |
| 574 | 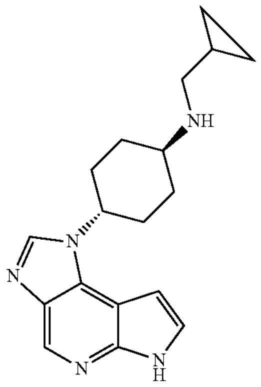 [SMILES: c1cc2c(ncc3ncn([C@H]4CC[C@H](NCC5CC5)CC4)c32)[nH]1] | trans Cyclopropylmethyl-[4-(6H-1,3,5,6-tetraaza-as-indacen-1-yl)-cyclohexyl]-amine | 214 | 2.42/C | 310.1 |

TABLE 2-continued

| Ex | Structure | Name | Synthetic Method | LCMS RT (min)/Method | LCMS (ESI) m/z |
|---|---|---|---|---|---|
| 575 | 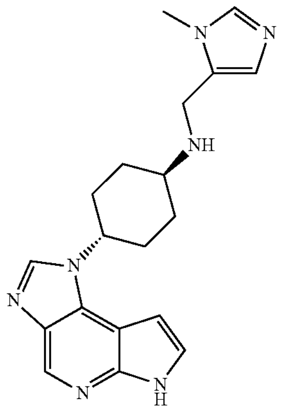 [SMILES: Cn1cncc1CN[C@H]1CC[C@H](n2cnc3cnc4[nH]ccc4c32)CC1] | trans (3-Methyl-3H-imidazol-4-ylmethyl)-[4-(6H-1,3,5,6-tetraaza-as-indacen-1-yl)-cyclohexyl]-amine | 214 | 2.41/C | 350.1 |
| 576 | 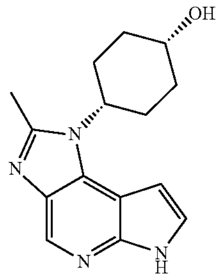 [SMILES: Cc1nc2cnc3[nH]ccc3c2n1[C@H]1CC[C@@H](O)CC1] | Cis 4-(2-Methyl-6H-1,3,5,6-tetraaza-as-indacen-1-yl)-cyclohexanoll | 213 | 2.54/C | 271.1 |
| 577 | 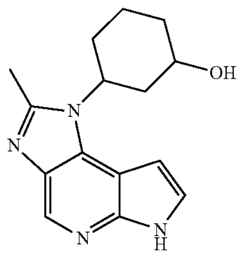 [SMILES: Cc1nc2cnc3[nH]ccc3c2n1C1CCCC(O)C1] Trans, single enatiomer, absolute stereochemistry unknown | 3-(2-Methyl-6H-1,3,5,6-tetraaza-as-indacen-1-yl)-cyclohexanol | 213 | 2.70/C 0.89/A3 | 271.1 |
| 578 | 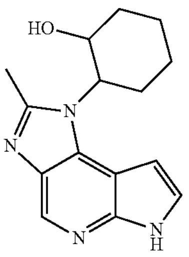 [SMILES: Cc1nc2cnc3[nH]ccc3c2n1C1CCCCC1O] Trans, single enatiomer, absolute stereochemistry unknown | 2-(2-Methyl-6H-1,3,5,6-tetraaza-as-indacen-1-yl)-cyclohexanol | 213 | 2.88/C | 271.1 |

Example 579

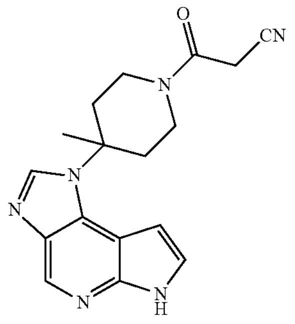 [SMILES: CC1(n2cnc3cnc4[nH]ccc4c32)CCN(C(=O)CC#N)CC1]

3-[4-Methyl-4-(6H-1,2,3,5,6-tetraaza-as-indacen-1-yl)-piperidin-1-yl]-3-oxo-propionitrile 1-(4-Methyl-piperidin-4-yl)-1,6-dihydro-1,2,3,5,6-tetraaza-as-indacene 4-Methyl-4-(6H-1,2,3,5,6-tetraaza-as-indacen-1-yl)-piperidine-1-carboxylic acid tert-butyl ester (1.07 g, 3.01 mmol) was dissolved in DCM/TFA was stirred for 30 min. The solvent was evaporated under vacuum and the resulting residue purified by column chromatography (SCX-2, gradient: 0 to 50% [2M ammonia in methanol] in DCM) to afford 0.70 g (100%) of 1-(4-methyl-piperidin-4-yl)-1,6-dihydro-1,2,3,5,6-pentaaza-as-indacene. LCMS (Method I, ESI): RT=0.28 min, m+H=256; $^{1}$H NMR (400 MHz, DMSO): δ 11.89 (s, 1H), 8.63 (s, 1H), 8.34 (s, 1H), 7.49 (t, 1H), 7.02 (s, 1H), 4.12 (s, 1H), 2.87 (d, 4H), 2.5 (m, 2H), 1.97 (d, 2H), 1.83 (s, 3H).

3-[4-Methyl-4-(6H-1,2,3,5,6-tetraaza-as-indacen-1-yl)-piperidin-1-yl]-3-oxo-propionitrile A mixture of 1-(4-methyl-piperidin-4-yl)-1,6-dihydro-1,2,3,5,6-pentaaza-as-indacene (95.0 mg, 0.37 mmol), cyanoacetic acid (35.0 mg, 0.41 mmol), N-(3-dimethyl-laminopropyl)-N'-ethyl carbodiimide hydrochloride (89.0 mg, 0.46 mmol) and HOBt (102 mg, 0.74 mmol) in DCM was stirred for 16 hours. The solvent was evaporated under vacuum and the resulting residue purified by column chromatography on silica gel (gradient: 0 to 8% [2M $NH_3$ in methanol] in DCM) to afford 20.0 mg (17%) of 3-[4-methyl-4-(6H-1,2,3,5,6-tetraaza-as-indacen-1-yl)-piperidin-1-yl]-3-oxo-propionitrile. LCMS (Method A, ESI): RT=2.00 min, m+H=323.3; $^{1}$H NMR (400 MHz, DMSO): δ 11.94 (s, 1H), 8.63 (s, 1H), 8.35 (s, 1H), 7.50 (t, 1H), 6.66 (dd, 1H), 4.10 (s, 2H), 3.72 (d, 1H), 3.52-3.49 (m, 3H), 2.5 (m, 2H), 2.25-2.19 (m, 2H), 1.82 (s, 3H).

Example 580

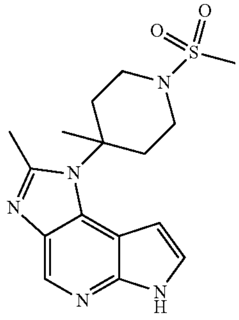

1-(1-Methanesulfonyl-4-methyl-piperidin-4-yl)-2-methyl-1,6-dihydro-1,2,3,5,6-tetraaza-as-indacene 4-(6-Benzenesulfonyl-2-methyl-6H-1,2,3,5,6-tetraaza-as-indacen-1-yl)-4-methyl-piperidine-1-carboxylic acid tert-butyl ester A mixture of 4-(5-amino-1-benzene sulfonyl-1H-pyrrolo[2,3-b]pyridin-4-ylamino)-4-methyl-piperidine-1-carboxylic acid tert-butyl ester (28.0 g, 57.7 mmol), triethyl orthoacetate (15.8 mL, 86.5 mmol) and acetic acid (150 mL) was heated at reflux for 1 hour. After cooling, the mixture was concentrated in vacuo and taken up into ethyl acetate. The mixture was washed with saturated sodium hydrogencarbonate solution and brine, and concentrated to dryness. The residue was triturated (diethyl ether), filtered and air dried to afford 25.7 g (87%) of 4-(6-benzenesulfonyl-2-methyl-6H-1,2,3,5,6-tetraaza-as-indacen-1-yl)-4-methyl-piperidine-1-carboxylic acid tert-butyl ester as a grey solid. LCMS (Method Q, ESI): RT=3.70 min, m+Na=532.1; $^{1}$H NMR (400 MHz, DMSO) δ: 8.61 (s, 1H), 8.15 (m, 2H), 7.90 (d, 1H), 7.71 (m, 1H), 7.61 (m, 2H), 6.95 (d, 1H), 3.98 (m, 2H), 3.18 (m, 2H), 2.80 (s, 3H), 2.28 (m, 4H), 1.88 (s, 3H), 1.45 (s, 9H).

6-Benzenesulfonyl-2-methyl-1-(4-methyl-piperidin-4-yl)-1,6-dihydro-1,2,3,5,6-tetraaza-as-indacene To a slurry of 4-(6-benzenesulfonyl-2-methyl-6H-1,2,3,5,6-tetraaza-as-indacen-1-yl)-4-methyl-piperidine-1-carboxylic acid tert-butyl ester (25.6 g, 50.2 mmol) and water (10 mL), trifluoroacetic acid (170 mL) was added at 0° C. The mixture was stirred at room temperature for 2 hours. The solvent was removed in vacuo and the residue azeotroped with DCM to provide a foam. The crude material was partitioned between 2% diisopropylethylamine in DCM and saturated sodium hydrogencarbonate solution and the organic phase separated. The aqueous layer was extracted with 2% diisopropylethylamine in DCM. The combined organic phases were concentrated to give crude 6-benzenesulfonyl-2-methyl-1-(4-methyl-piperidin-4-yl)-1,6-dihydro-1,2,3,5,6-tetraaza-as-indacene which was used for the next step without purification. LCMS (Method Q, ESI): RT=2.20 min, m+Na=432.3.

6-Benzenesulfonyl-1-(1-methanesulfonyl-4-methyl-piperidin-4-yl)-2-methyl-1,6-dihydro-1,2,3,5,6-tetraaza-as-indacene To a stirred solution of crude 6-benzenesulfonyl-2-methyl-1-(4-methyl-piperidin-4-yl)-1,6-dihydro-1,2,3,5,6-tetraaza-as-indacene (assumed to be 50.2 mmol) and methane sulfonyl chloride (3.89 mL, 50.2 mmol) in DCM (250 mL), triethylamine (13.9 mL, 100 mmol) was added dropwise at 0° C. Stirring was continued at room temperature for an additional 18 hours. Methane sulfonyl chloride (0.2 eq) and triethylamine (0.4 eq) were added and stirring was continued for 1 hour. The mixture was concentrated in vacuo, the resulting residue triturated (water) and re-triturated (diethyl ether) and air dried to provide 23.3 g (95%) of 6-benzenesulfonyl-1-(1-methanesulfonyl-4-methyl-piperidin-4-yl)-2-methyl-1,6-dihydro-1,2,3,5,6-tetraaza-as-indacene as a beige solid. LCMS (Method Q, ESI): RT=3.02 min, m+H=488.3; $^1$H NMR (400 MHz, DMSO) δ: 8.62 (s, 1H), 8.15 (m, 2H), 8.00 (d, 1H), 7.70 (m, 1H), 7.62 (m, 2H), 7.21 (d, 1H), 3.60 (m, 2H), 3.19 (m, 2H), 2.98 (s, 3H), 2.82 (s, 3H), 2.53 (m, 2H, partially obscured by DMSO), 2.34 (m, 2H), 1.90 (s, 3H).

1-(1-Methanesulfonyl-4-methyl-piperidin-4-yl)-2-methyl-1,6-dihydro-1,2,3,5,6-tetraaza-as-indacene Sodium hydroxide solution (239 mL, 239 mmol, 1M) was added to a stirred suspension of 6-benzenesulfonyl-1-(1-methanesulfonyl-4-methyl-piperidin-4-yl)-2-methyl-1,6-dihydro-1,2,3,5,6-tetraaza-as-indacene (23.3 g, 47.8 mmol) in methanol (350 mL) and THF (350 mL). The mixture was stirred at room temperature for 7 hours and then concentrated in vacuo. The resulting solid was triturated (water) and re-triturated (diethyl ether), air dried and then suspended in acetonitrile at reflux for 3 hours. The mixture was allowed to cool to room temperature over 18 hours and then filtered. The isolated solid was washed with cold acetonitrile and diethyl ether, and air dried to provide 13.3 g (80%) 1-(1-methanesulfonyl-4-methyl-piperidin-4-yl)-2-methyl-1,6-dihydro-1,2,3,5,6-tetraaza-as-indacene as a beige powder. LCMS (Method A, ESI): RT=2.06 min, m+H=348.1; $^1$H NMR (400 MHz, DMSO) δ: 11.82 (s, 1H), 8.48 (s, 1H), 7.48 (t, 1H), 6.81 (dd, 1H), 3.62 (m, 2H), 3.20 (m, 2H), 2.98 (s, 3H), 2.81 (s, 3H), 2.67 (m, 2H), 2.39 (m, 2H), 1.95 (s, 3H).

Example 581

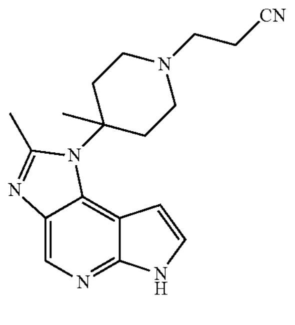 [SMILES: Cc1nc2cnc3[nH]ccc3c2n1C1(C)CCN(CCC#N)CC1]

3-[4-Methyl-4-(2-methyl-6H-1,2,3,5,6-tetraaza-as-indacen-1-yl)-piperidin-1-yl]-propionitrile 4-Methyl-4-(2-methyl-6H-1,2,3,5,6-tetraaza-as-indacen-1-yl)-piperidine-1-carboxylic acid tert butyl ester A mixture of 4-(6-benzenesulfonyl-2-methyl-6H-1,2,3,5,6-tetraaza-as-indacen-1-yl)-4-methyl-piperidine-1-carboxylic acid tert-butyl ester (330 mg, 0.65 mmol) in THF/methanol containing aqueous sodium hydroxide (3.25 mmol) was stirred for 16 hours. The solvent was evaporated under vacuum to a small volume, the residue dissolved in DCM, washed with saturated sodium bicarbonate solution and brine, dried over sodium sulfate and concentrated under vacuum to afford 230 mg (90%) of 4-methyl-4-(2-methyl-6H-1,2,3,5,6-tetraaza-as-indacen-1-yl)-piperidine-1-carboxylic acid tert butyl ester. LCMS (Method I, ESI): RT=2.28 min, m+H=370.2; $^1$H NMR (400 MHz, DMSO) δ: 11.83 (s, 1H), 8.48 (s, 1H), 7.39 (t, 1H), 6.55 (m, 1H), 4.03 (m, 2H), 3.18 (m, 2H), 2.80 (s, 3H), 2.47 (m, 2H), 2.27 (m, 2H), 1.94 (s, 3H), 1.45 (s, 9H).

2-Methyl-1-(4-methyl-piperidin-4-yl)-1,6-dihydro-1,2,3,5,6-tetraaza-as-indacene

A mixture of 4-methyl-4-(2-methyl-6H-1,2,3,5,6-tetraaza-as-indacen-1-yl)-piperidine-1-carboxylic acid tert butyl ester (210 mg, 0.57 mmol) in DCM/TFA was stirred for 1.5 hours. The solvent was evaporated under vacuum and the resulting residue purified by column chromatography (SCX-2, gradient: 0 to 50% [2M ammonia in methanol] in DCM) to afford 150 mg (98%) of 2-methyl-1-(4-methyl-piperidin-4-yl)-1,6-dihydro-1,2,3,5,6-tetraaza-as-indacene. LCMS (Method I, ESI): RT=0.32 min, m+H=270.4; $^1$H NMR (400 MHz, DMSO) δ: 8.46 (s, 1H), 7.42 (t, 1H), 7.26 (m, 1H), 2.98 (m, 2H), 2.88 (m, 2H), 2.79 (s, 3H), 2.59 (m, 2H), 2.07 (m, 2H), 1.93 (s, 3H).

3-[4-Methyl-4-(2-methyl-6H-1,2,3,5,6-tetraaza-as-indacen-1-yl)-piperidin-1-yl]-propionitrile A mixture of 2-methyl-1-(4-methyl-piperidin-4-yl)-1,6-dihydro-1,2,3,5,6-tetraaza-as-indacene (60.0 mg, 0.222 mmol) and acrylonitrile (75.0 μL, 1.11 mmol) in ethanol was stirred at 80° C. for 3 hours. The solvent was evaporated under vacuum and the residue purified by column chromatography on silica gel (gradient: 0 to 5% [2M $NH_3$ in methanol] in DCM) to afford 54.0 mg (76%) of 3-[4-methyl-4-(2-methyl-6H-1,2,3,5,6-tetraaza-as-indacen-1-yl)-piperidin-1-yl]-propionitrile. LCMS (Method A, ESI): RT=1.39 min, m+H=323.3; $^1$H NMR (400 MHz, DMSO) δ: 11.70 (s, 1H), 8.46 (s, 1H), 7.40 (t, 1H), 7.33 (t, 1H), 2.94 (m, 2H), 2.85 (t, 2H), 2.80 (s, 3H), 2.77 (t, 2H), 2.67 (m, 2H), 2.44 (m, 2H), 2.03 (m, 2H), 1.92 (s, 3H).

Example 582

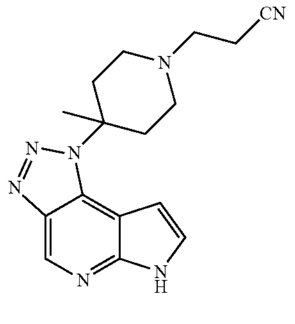 [SMILES: CC1(n2nnc3cnc4[nH]ccc4c32)CCN(CCC#N)CC1]

3-[4-Methyl-4-(6H-1,2,3,5,6-pentaaza-as-indacen-1-yl)-piperidin-1-yl]-propionitrile 4-(6-Benzenesulfonyl-2-methyl-6H-1,2,3,5,6-pentaaza-as-indacen-1-yl)-4-methyl-piperidine-1-carboxylic acid tert-butyl ester A mixture of 4-(5-amino-1-benzenesulfonyl-1H-pyrrolo[2,3-b]pyridin-4-ylamino)-4-methyl-piperidine-1-carboxylic acid tert-butyl ester (485 mg, 1.00 mmol) was dissolved in glacial acetic acid. Sodium nitrite (76.0 mg, 1.10 mmol) was added in one portion and the reaction mixture stirred for 1 hour. The reaction mixture was reduced in volume under vacuum diluted with ethyl acetate, washed with saturated sodium bicarbonate solution and brine, dried over sodium sulfate and concentrated under vacuum. The resulting residue was purified by column chromatography on silica gel (gradient: 0 to 10% ethyl acetate in DCM) to afford 370 mg (80%) of 4-(6-benzenesulfonyl-2-methyl-6H-1,2,3,5,6-pentaaza-as-indacen-1-yl)-4-methyl-piperidine-1-carboxylic acid tert-butyl ester. LCMS (Method H, ESI): RT=4.05 min, m+H=497.2; $^{1}$H NMR (400 MHz, DMSO) δ: 9.27 (d, 1H), 8.21 (m, 2H), 8.16 (d, 1H), 7.75 (m, 1H), 7.65 (m, 2H), 7.28 (d, 1H), 3.59 (m, 2H), 3.26 (m, 2H), 2.59 (m, 2H), 2.15 (m, 2H), 1.78 (s, 3H), 1.41 (s, 9H).

4-Methyl-4-(6H-1,2,3,5,6-pentaaza-as-indacen-1-yl)-piperidine-1-carboxylic acid tert butyl ester A mixture of 4-(6-benzenesulfonyl-2-methyl-6H-1,2,3,5,6-pentaaza-as-indacen-1-yl)-4-methyl-piperidine-1-carboxylic acid tert-butyl ester (0.37 g, 0.75 mmol) in THF/methanol containing aqueous sodium hydroxide (3.75 mmol) was stirred for 16 hours. The solvent was evaporated under vacuum to a small volume, the residue dissolved in DCM, washed with saturated sodium bicarbonate solution and brine, dried over sodium sulfate and concentrated under vacuum to afford 240 mg (90%) of 4-methyl-4-(6H-1,2,3,5,6-pentaaza-as-indacen-1-yl)-piperidine-1-carboxylic acid tert butyl ester. LCMS (Method I, ESI): RT=3.20 min, m+H=357.3; $^{1}$H NMR (400 MHz, DMSO) δ: 12.46 (s, 1H), 9.06 (s, 1H), 7.63 (t, 1H), 6.86 (m, 1H), 3.62 (m, 2H), 3.33 (m, 2H), 2.71 (m, 2H), 2.12 (m, 2H), 1.85 (s, 3H), 1.43 (s, 9H).

1-(4-Methyl-piperidin-4-yl)-1,6-dihydro-1,2,3,5,6-pentaaza-as-indacene

A mixture of 4-methyl-4-(6H-1,2,3,5,6-pentaaza-as-indacen-1-yl)-piperidine-1-carboxylic acid tert butyl ester (200 mg, 0.56 mmol) in DCM/TFA was stirred for 1.5 hours. The solvent was evaporated under vacuum and the resulting residue purified by column chromatography using an Isolute® SCX-2 column (gradient: 0 to 50% [2M $NH_3$ in methanol] in DCM) to afford 145 mg (100%) of 1-(4-methyl-piperidin-4-yl)-1,6-dihydro-1,2,3,5,6-pentaaza-as-indacene. LCMS (Method I, ESI): RT=0.32 & 1.58 min, m+H=257.3; $^{1}$H NMR (400 MHz, DMSO) δ: 12.41 (s, 1H), 9.04 (s, 1H), 7.62 (d, 1H), 7.04 (m, 1H), 2.90 (m, 2H), 2.79 (m, 2H), 2.70 (m, 2H), 2.05 (m, 2H), 1.84 (s, 3H).

3-[4-Methyl-4-(6H-1,2,3,5,6-pentaaza-as-indacen-1-yl)-piperidin-1-yl]-propionitrile A mixture of 1-(4-methyl-piperidin-4-yl)-1,6-dihydro-1,2,3,5,6-pentaaza-as-indacene (75.0 mg, 0.29 mmol) and acrylonitrile (95.5 μL, 1.45 mmol) in ethanol was stirred at 80° C. for 5 hours. The solvent was evaporated under vacuum and the residue purified by column chromatography on silica gel (gradient: 0 to 4.5% [2M $NH_3$ in methanol] in DCM) to afford 64.0 mg (71%) of 3-[4-methyl-4-(6H-1,2,3,5,6-pentaaza-as-indacen-1-yl)-piperidin-1-yl]-propionitrile. LCMS (Method A, ESI): RT=1.91 min, m+H=310.3; $^{1}$H NMR (400 MHz, DMSO) δ: 12.41 (s, 1H), 9.04 (s, 1H), 7.59 (t, 1H), 7.08 (m, 1H), 2.85 (m, 2H), 2.66 (m, 4H), 2.58 (m, 2H), 2.49 (m, 2H), 2.11 (m, 2H), 1.85 (s, 3H).

Example 583

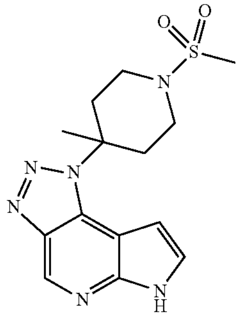 [SMILES: CC1(n2nnc3cnc4[nH]ccc4c32)CCN(S(C)(=O)=O)CC1]

1-(1-Methanesulfonyl-4-methyl-piperidine-4-yl)-1,6-dihydro-1,2,3,5,6-pentaaza-as-indacen-1-yl To a mixture of 1-(4-methyl-piperidin-4-yl)-1,6-dihydro-1,2,3,5,6-pentaaza-as-indacene (70.0 mg, 0.27 mmol) and triethylamine (42.0 μL, 0.30 mmol) in DCM was added methanesulfonyl chloride (23.0 μL, 0.30 mmol) and the reaction mixture stirred for 2 hours. The reaction mixture was diluted with DCM, washed with saturated sodium bicarbonate solution and brine, dried over sodium sulfate and concentrated under vacuum. The residue was purified by column chromatography on silica gel (gradient: 0 to 5% [2M $NH_3$ in methanol] in DCM) to afford 70.0 mg (78%) of 1-(1-methanesulfonyl-4-methyl-piperidine-4-yl)-1,6-dihydro-1,2,3,5,6-pentaaza-as-indacen-1-yl. LCMS (Method A, ESI): RT=3.09 min, m+H=335.2; $^{1}$H NMR (400 MHz, DMSO) δ: 12.46 (s, 1H), 9.07 (s, 1H), 7.66 (t, 1H), 6.93 (d, 1H), 3.45 (m, 2H), 3.06 (m, 2H), 2.92 (m, 2H), 2.84 (s, 3H), 2.29 (m, 2H), 1.84 (s, 3H).

Example 584

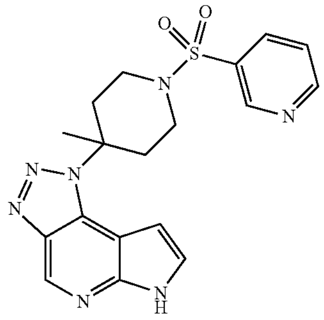 [SMILES: CC1(n2nnc3cnc4[nH]ccc4c32)CCN(S(=O)(=O)c2cccnc2)CC1]

1-[4-Methyl-1-(pyridine-3-sulfonyl)-piperidin-4-yl]-1,6-dihydro-1,2,3,5,6-pentaaza-as-indacene 6-Benzenesulfonyl-1-(4-methyl-piperidine-4-yl)1,6-dihydro-1,2,3,5,6-pentaaza-as-indacene A mixture of 4-(6-benzenesulfonyl-2-methyl-6H-1,2,3,5,6-pentaaza-as-indacen-1-yl)-4-methyl-piperidine-1-carboxylic acid tert-butyl ester (280 mg, 0.56 mmol)) in DCM/TFA was stirred for 1 hr. The solvent was evaporated under vacuum and the resulting residue purified by column chromatography (SCX-2, gradient: 0 to 50% [2M $NH_3$ in methanol] in DCM) to afford 205 mg (93%) of 6-benzenesulfonyl-1-(4-methyl-piperidine-4-yl)1,6-dihydro-1,2,3,5,6-pentaaza-as-indacene. $^1$H NMR (400 MHz, DMSO): δ 9.25 (s, 1H), 8.19-8.17 (m, 3H), 7.76-7.72 (m, 1H), 7.65 (t, 2H), 7.48 (d, 1H), 2.83-2.80 (m, 4H), 2.55 (m, 2H), 2.00 (d, 2H), 1.82 (s, 3H).

6-benzenesulfonyl-1-[4-methyl-1-(pyridine-3-sulfonyl)-piperidin-4-yl]-1,6-dihydro-1,2,3,5,6-pentaaza-as-indacene A mixture of 6-benzenesulfonyl-1-(4-methyl-piperidine-4-yl)1,6-dihydro-1,2,3,5,6-pentaaza-as-indacene (60.0 mg, 0.15 mmol) was dissolved in DCM, triethylamine (28.0 μL, 0.20 mmol) was added followed by pyridine-3-sulfonyl chloride (32.0 mg, 0.18 mmol) and the reaction stirred at room temperature for 16 hr. The reaction mixture was diluted with DCM, washed with saturated sodium bicarbonate solution and brine, dried over sodium sulfate and concentrated under vacuum to afford 74 mg (91%) of 6-benzenesulfonyl-1-[4-methyl-1-(pyridine-3-sulfonyl)-piperidin-4-yl]-1,6-dihydro-1,2,3,5,6-pentaaza-as-indacene. LCMS (Method H, ESI): RT=3.52 min, m+H=538.3; $^1$H NMR (400 MHz, DMSO): δ 9.21 (s, 1H), 8.84 (m, 2H), 8.19 (m, 3H), 8.10 (m, 1H), 7.74 (d, 1H), 7.62 (m, 3H), 7.31 (d, 1H), 3.45 (d, 2H), 2.82-2.67 (m, 4H), 2.33 (m, 2H), 1.69 (s, 3H).

1-[4-Methyl-1-(pyridine-3-sulfonyl)-piperidin-4-yl]-1,6-dihydro-1,2,3,5,6-pentaaza-as-indacene A mixture of 6-benzenesulfonyl-1-[4-methyl-1-(pyridine-3-sulfonyl)-piperidin-4-yl]-1,6-dihydro-1,2,3,5,6-pentaaza-as-indacene (74.0 mg, 0.14 mmol) in THF/methanol containing aqueous sodium hydroxide (0.53 mmol) was stirred for 64 hr. The solvent was evaporated under vacuum to a small volume, the residue dissolved in DCM, washed with saturated sodium bicarbonate solution and brine, dried over sodium sulfate and concentrated under vacuum and the resulting residue purified by column chromatography on silica gel (gradient: 0 to 5% [2M $NH_3$ in methanol] in DCM) to afford 15.0 mg (27%) of 1-[4-methyl-1-(pyridine-3-sulfonyl)-piperidin-4-yl]-1,6-dihydro-1,2,3,5,6-pentaaza-as-indacene. LCMS (Method A, ESI): RT=3.42 min, m+H=398.2; $^1$H NMR (400 MHz, DMSO): δ 12.45 (s, 1H), 8.99 (s, 1H), 8.86 (m, 2H), 8.13 (ddd, 1H), 7.65 (m, 2H), 6.91 (dd, 1H), 3.49 (m, 2H), 2.90 (m, 2H), 2.75 (m, 2H), 2.31 (m, 2H), 1.75 (s, 3H).

Example 585

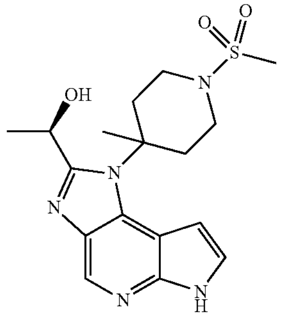 [SMILES: C[C@@H](O)c1nc2cnc3[nH]ccc3c2n1C1(C)CCN(S(C)(=O)=O)CC1]

(R)-1-[1-(1-Methanesulfonyl-4-methyl-piperidinyl)-1,6-dihydro-1,2,3,5,6-tetraaza-as-indacen-2-yl]-ethanol 4-[6-Benzenesulfonyl-2-((R)-1-hydroxy-ethyl)-6H-1,2,3,5,6-tetraaza-as-indacen-1-yl]-4-methyl-piperidine-1-carboxylic acid tert-butyl ester A mixture of triethyloxonium tetrafluoroborate (855 mg, 4.50 mmol) and (R)-(+)-lactamide (481 mg, 5.40 mol) in dry THF was stirred for 2 hr. The reaction mixture was evaporated under vacuum (100 mbar, 40° C.) to a thin, clear oil. To this was added 4-(5-amino-1-benzenesulfonyl-1H-pyrrolo[2,3-b]pyridin-4-ylamino)-4-methyl-piperidine-1-carboxylic acid tert-butyl ester (728 mg, 1.50 mmol), in ethanol and the reaction stirred at 45° C. for 20 hr. The reaction was concentrated under vacuum, dissolved in DCM, washed with saturated sodium bicarbonate solution and brine, dried over sodium sulfate and concentrated under vacuum to an oil. The resulting residue was purified by column chromatography on silica gel (gradient: 0 to 4% MeOH in DCM) to afford 0.75 g (93%) of 4-[6-benzenesulfonyl-2-((R)-1-hydroxy-ethyl)-6H-1,2,3,5,6-tetraaza-as-indacen-1-yl]-4-methyl-piperidine-1-carboxylic acid tert-butyl ester. LCMS (Method H, ESI): RT=3.48 min, m+H=540.2; $^1$H NMR (400 MHz, DMSO) δ: 8.73 (s, 1H), 8.15-8.13 (m, 2H), 7.93 (d, 1H), 7.70-7.69 (m, 1H), 7.67-7.55 (m, 2H), 6.99 (d, 1H), 5.51 (d, 1H), 5.20 (m, 1H), 4.39-4.31 (m, 1H), 4.10-3.70 (m, 2H), 3.38-3.37 (m, 4H), 2.36 (d, 1H), 1.94 (s, 3H), 1.66 (d, 3H), 1.43 (s, 9H).

(R)-1-[6-Benzenesulfonyl-1-(4-methyl-piperidin-4-yl)-1,6-dihydro-1,2,3,5,6-tetraaza-as-indacen-2-yl]-ethanol A mixture of 4-[6-benzenesulfonyl-2-((R)-1-hydroxy-ethyl)-6H-1,2,3,5,6-tetraaza-as-indacen-1-yl]-4-methyl-piperidine-1-carboxylic acid tert-butyl ester (750 mg, 1.39 mmol) in DCM/TFA was stirred for 1.5 hr. The solvent was evaporated under vacuum and the resulting residue purified by column chromatography (SCX-2, gradient: 0 to 80% [2M ammonia in methanol] in DCM) to afford 410 mg (67%) of (R)-1-[6-benzenesulfonyl-1-(4-methyl-piperidin-4-yl)-1,6-dihydro-1,2,3,5,6-tetraaza-as-indacen-2-yl]-ethanol. LCMS (Method B, ESI): RT=1.95 min, m+H=440.1

(R)-1-[6-Benzenesulfonyl-1-(1-methanesulfonyl-4-methyl-piperidin-4-yl)-1,6-dihydro-1,2,3,5,6-tetraaza-as-indacen-2-yl]-ethanol (R)-1-[6-Benzenesulfonyl-1-(4-methyl-piperidin-4-yl)-1,6-dihydro-1,2,3,5,6-tetraaza-as-indacen-2-yl]-ethanol (320 mg, 0.73 mmol), was dissolved in THF, triethylamine (142 μL, 1.02 mmol) was added followed by methanesulfonyl chloride (68.0 μL, 0.874 mmol) and the reaction stirred at room temperature for 1 hr. The reaction mixture was reduced to a small volume under vacuum, diluted with ethyl acetate, the solid recovered by filtration and dried. The resulting residue was purified by column chromatography on silica gel (gradient: 0 to 4% methanol in DCM) to afford 323 mg (67%) of (R)-1-[6-benzenesulfonyl-1-(1-methanesulfonyl-4-methyl-piperidin-4-yl)-1,6-dihydro-1,2,3,5,6-tetraaza-as-indacen-2-yl]-ethanol. LCMS (Method H, ESI): RT=2.84 min, m+H=518.2; $^1$H NMR (400 MHz, DMSO) δ: 8.75 (s, 1H), 8.17-8.13 (m, 2H), 8.02 (d, 1H), 7.71-7.71 (m, 1H), 7.63-7.62 (m, 2H), 7.22 (d, 1H), 5.56 (d, 1H), 5.22 (t, 1H), 3.58 (d, 1H), 3.48 (d, 1H), 3.27-3.19 (m, 2H), 2.80-2.60 (m, 2H), 2.5 (m, 2H), 2.97 (s, 3H), 1.99-1.98 (m, 3H), 1.68 (d, 3H).

(R)-1-[1-(1-Methanesulfonyl-4-methyl-piperidinyl)-1,6-dihydro-1,2,3,5,6-tetraaza-as-indacen-2-yl]-ethanol A mixture of (R)-1-[6-benzenesulfonyl-1-(1-methanesulfonyl-4-methyl-piperidin-4-yl)-1,6-dihydro-1,2,3,5,6-tetraaza-as-indacen-2-yl]-ethanol (323 mg, 0.62 mmol) in THF/methanol containing aqueous sodium hydroxide (3.12 mmol) was stirred for 16 hr. The solvent was evaporated under vacuum to a small volume, the residue dissolved in DCM, washed with saturated sodium bicarbonate solution and brine, dried over sodium sulfate and concentrated under vacuum to afford 207 mg (88%) of (R)-1-[1-(1-methanesulfonyl-4-methyl-piperidinyl)-1,6-dihydro-1,2,3,5,6-tetraaza-as-indacen-2-yl]-ethanol as an off-white solid. LCMS (Method A, ESI): RT=2.13 min, m+H=378.1; $^1$H NMR (400

MHz, DMSO) δ: 11.82 (s, 1H), 8.54 (s, 1H), 7.44 (t, 1H), 6.76 (dd, 1H), 5.42 (d, 1H), 5.16 (t, 1H), 3.55 (d, 1H), 3.46 (d, 1H), 3.18-3.15 (m, 2H), 2.92 (s, 3H), 2.83 (td, 1H), 2.74-2.71 (m, 1H), 2.51 (d, 2H), 1.99 (s, 3H), 1.65 (d, 3H).

Example 586

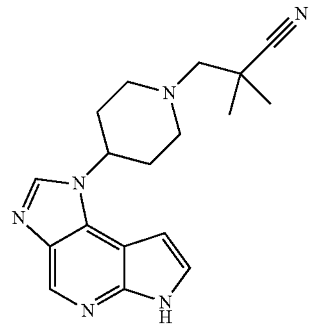 [SMILES: CC(C)(C#N)CN1CCC(n2cnc3cnc4[nH]ccc4c32)CC1]

2,2-Dimethyl-3-[4-(6H-1,2,3,5,6-tetraaza-as-indacen-1-yl)-piperidin-1-yl]-propionitrile 2,2-Dimethyl-3-oxo-propionitrile 3-Hydroxy-2,2-dimethyl-propionitrile (278 mg, 2.90 mmol) was added to a solution of pyridinium chlorochromate (753 mg, 3.50 mmol) in DCM (15.0 mL). The mixture was stirred for 18 hours, the supernatant poured into $Et_2O$ (50.0 mL), and the suspension so formed passed through silica gel, eluting with $Et_2O$. Evaporation of the eluant at 500 mbar afforded a colourless oil (292 mg) which was determined by nmr to be a 1:2:1 mixture of desired product, starting alcohol, and an unidentified component. Used without further purification $^1$H NMR (400 MHz, $CDCl_3$) δ: 9.53 (s, 1H), 1.54 (s, 6H).

2,2-Dimethyl-3-[4-(6H-1,2,3,5,6-tetraaza-as-indacen-1-yl)-piperidin-1-yl]-propionitrile A mixture of 1-piperidin-4-yl-1,6-dihydro-1,2,3,5,6-tetraaza-as-indacene (120 mg, 0.50 mmol), the product from the previous step (280 mg, approx. 0.70 mmol), and acetic acid (60.0 mg, 1.00 mmol) in MeOH (5 mL) was sonicated for 1 min, followed by addition of powdered 4 Å molecular sieve and stirring for a further 3 hours. Sodium triacetoxyborohydride (159 mg, 0.75 mmol) was added and stirring continued overnight. Following dilution with methanol, the mixture was passed through an SCX-2 cartridge (gradient elution: MeOH to 2M $NH_3$ in MeOH). The relevant fractions were collected to leave a gum, which was further purified by column chromatography on silica gel (gradient: 0 to 10% MeOH in DCM) to afford 53.0 mg of 2,2-dimethyl-3-[4-(6H-1,2,3,5,6-tetraaza-as-indacen-1-yl)-piperidin-1-yl]-propionitrile as a white solid. LCMS (Method A, ESI): RT=1.98 min, m+H=323.2; NMR (400 MHz, $CDCl_3$): δ 10.40 (br s, 1H), 8.82 (s, 1H), 8.08 (s, 1H), 7.45 (d, 1H), 6.77 (d, 1H), 4.57-4.47 (m, 1H), 3.28 (d, 2H), 2.71-2.62 (m, 2H), 2.57 (s, 2H), 2.38-2.24 (m, 4H), 1.40 (s, 6H).

Example 587

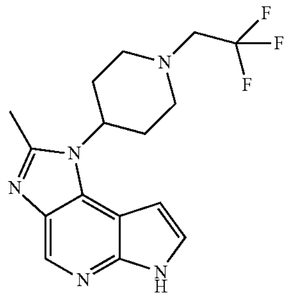 [SMILES: Cc1nc2cnc3[nH]ccc3c2n1C1CCN(CC(F)(F)F)CC1]

2-Methyl-1-[1-(2,2,2-trifluoro-ethyl)-piperidin-4-yl]-1,6-dihydro-1,2,3,5,6-tetraaza-as-indacene To a stirred mixture of 2-methyl-1-piperidin-4-yl-1,6-dihydro-1,2,3,5,6-tetraaza-as-indacene (100 mg, 392 μmol) and triethylamine (218 μL, 1.57 mmol) in DCM/DMF (4 mL, 1:1), 2,2,2-trifluoroethyl trifluoromethane sulfonate (113 μL, 784 μmol) was added at room temperature. Stirring was continued until consumption of the starting material had ceased. The solvent was removed in vacuo and the residue purified by column chromatography on silica gel (gradient: DCM to 10% [2M $NH_3$ in MeOH] in DCM) to afford 36.0 mg of 2-methyl-1-[1-(2,2,2-trifluoro-ethyl)-piperidin-4-yl]-1,6-dihydro-1,2,3,5,6-tetraaza-as-indacene as a white solid. LCMS (Method A, ESI): RT=2.90 min, m+H=338.2; $^1$H NMR (400 MHz, DMSO) δ: 11.77 (s, 1H), 8.45 (s, 1H), 7.47 (t, 1H), 6.85 (m, 1H), 4.49 (m, 1H), 3.35 (m, 2H, partially obscured by water), 3.15 (m, 2H), 2.73-2.52 (m, 7H), 1.88 (m, 2H).

Example 588

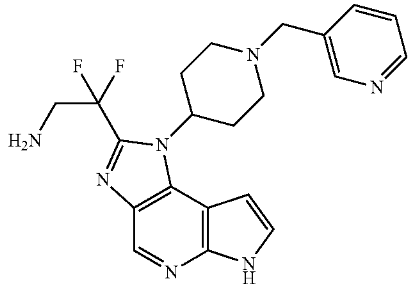 [SMILES: NCC(F)(F)c1nc2cnc3[nH]ccc3c2n1C1CCN(Cc2cccnc2)CC1]

2,2-Difluoro-2-[1-(1-pyridin-3-ylmethyl-piperidin-4-yl)-1,6-dihydro-1,2,3,5,6-tetraaza-as-indacen-2-yl]-ethylamine {2,2-Difluoro-2-[1-(1-pyridin-3-ylmethyl-piperidin-4-yl)-1,6-dihydro-1,2,3,5,6-tetraaza-as-indacen-2-yl]-ethyl}-carbamic acid benzyl ester A solution of 4-[1-benzenesulfonyl-5-(3-benzyloxycarbonylamino-2,2-difluoro-propionylamino)-1H-pyrrolo[2,3-b]pyridin-4-ylamino]-piperidine-1-carboxylic acid tert-butyl ester (1.20 g) in acetic acid (10 mL) was stirred at 100° C. for 2 hours. The cooled reaction mixture was concentrated under vacuum then purified by column chromatography on silica gel (gradient: 0 to 10% methanol in DCM then 10% 2M $NH_3$ in methanol solution in DCM). The resulting residue was further purified by Isolute® SCX-2 column (gradient: methanol to 2M $NH_3$ in methanol solution) and again by column chromatography on silica gel (gradient: 0 to 5% methanol in 1:1 ethyl acetate: cyclohexane then 5-10% [2M $NH_3$ in methanol] in 1:1 ethyl acetate: cyclohexane) to afford 220 mg of crude {2-[1-(1-acetyl-piperidin-4-yl)-6-benzenesulfonyl-1,6-dihydro-1,2,3,5,6-tetraaza-as-indacen-2-yl]-2,2-difluoro-ethyl}-carbamic acid benzyl ester as a white semi-solid. A suspension of the crude material (220 mg, 370 μmol) in methanol (3 mL) and 1,2-dichloroethane (1 mL) was treated with 3-pyridine carboxaldehyde (44.0 mg, 470 μmol) and sodium triacetoxyborohydride (166 mg, 740 μmol) at 0° C. under an argon atmosphere. After 1 hour the mixture was allowed to warm to ambient temperature and a further portion of sodium triacetoxyborohydride (160 mg) was added and the mixture stirred for 18 hours. Additional 3-pyridine carboxaldehyde (120 mg) and sodium triacetoxyborohydride (320 mg) were added and after a further 24 hours the solvent was removed under vacuum. The resulting residue was purified by column chromatography on silica gel (gradient: 0 to 10% methanol in DCM) to afford 150 mg of crude {2-[6-benzenesulfonyl-1-(1-pyridin-3-ylmethyl-piperidin-4-yl)-1,6-dihydro-1,2,3,5,6-tetraaza-as-indacen-2-yl]-2,2-di fluoro-ethyl}-carbamic acid benzyl ester. A mixture of crude {2-[6-benzenesulfonyl-1-(1-pyridin-3-ylmethyl-piperidin-4-yl)-1,6-dihydro-1,2,3,5,6-tetraaza-as-indacen-2-yl]-2,2-difluoro-ethyl}-carbamic acid benzyl ester (150 mg, 210 μmol) in methanol (2 mL) and THF (2 mL) was treated with a 1M sodium hydroxide solution (4 mL) and stirred at ambient temperature for 18 hours. The mixture was concentrated under vacuum, acidified with dilute HCl and re-concentrated. Purification by reverse phase HPLC (gradient: 5 to 98% MeCN in water+0.1% $NH_4OH$) gave 15.0 mg (13%) of {2,2-difluoro-2-[1-(1-pyridin-3-ylmethyl-piperidin-4-yl)-1,6-dihydro-1,2,3,5,6-tetraaza-as-indacen-2-yl]-ethyl}-carbamic acid benzyl ester as a white solid. LCMS (Method B, ESI): RT=2.47 min, m+H=546.4.

2,2-Difluoro-2-[1-(1-pyridin-3-ylmethyl-piperidin-4-yl)-1,6-dihydro-1,2,3,5,6-tetraaza-as-indacen-2-yl]-ethylamine A solution of {2,2-difluoro-2-[1-(1-pyridin-3-ylmethyl-piperidin-4-yl)-1,6-dihydro-1,2,3,5,6-tetraaza-as-indacen-2-yl]-ethyl}-carbamic acid benzyl ester (15.0 mg, 27.0 μmol) in TFA (2 mL) was heated at 80° C. for 1 hour. The cooled mixture was concentrated under vacuum and the residue treated with a 1M lithium hydroxide solution (250 μL). Purification by reverse phase HPLC (gradient: 5 to 75% MeCN in water+0.1% $NH_4OH$) gave 4.2 mg (38%) of 2,2-difluoro-2-[1-(1-pyridin-3-ylmethyl-piperidin-4-yl)-1,6-dihydro-1,2,3,5,6-tetraaza-as-indacen-2-yl]-ethylamine as a white solid. LCMS (Method A, ESI): RT=1.44 min, m+H=412.27; $^1$H NMR (400 MHz, DMSO): δ 12.12 (s, 1H), 8.70 (s, 1H), 8.63 (d, 1H), 8.51 (dd, 1H), 7.83 (m, 1H), 7.64 (m, 1H), 7.43 (m, 1H), 7.09 (m, 1H), 4.86 (m, 1H), 3.67 (s, 2H), 3.54 (m, 2H), 3.08 (m, 2H), 2.69 (m, 2H), 2.24 (m, 2H), 1.90 (m, 4H).

Example 589

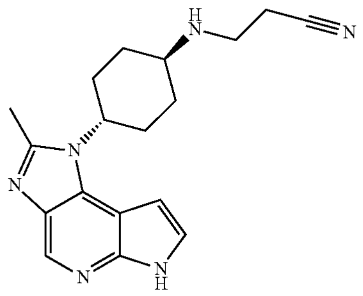 [SMILES: Cc1nc2cnc3[nH]ccc3c2n1[C@H]1CC[C@H](NCCC#N)CC1]

Trans 3-[4-(2-methyl-6H-1,2,3,5,6-tetraaza-as-indacen-1-yl)-cyclohexylamino]-propionitrile Trans[4-(6-benzenesulfonyl-2-methyl-6H-1,2,3,5,6-tetraaza-as-indacen-1-yl)-cyclohexyl]-carbamic acid tert-butyl ester A mixture of trans[4-(5-amino-1-benzenesulfonyl-1H-pyrrolo[2,3-b]pyridin-4-ylamino)-cyclohexyl]-carbamic acid tert-butyl ester (10.0 g, 20.6 mmol), triethyl orthoacetate (15.0 mL, 82.4 mmol) and acetic acid (120 mL) was heated to reflux for 20 minutes. After cooling the solvent was removed in vacuo. The residue was diluted with ethyl acetate, washed with saturated sodium hydrogen carbonate solution (3×) and brine, and concentrated to dryness. Purification by column chromatography on silica gel (gradient: DCM to neat ethyl acetate to 5% methanol in ethyl acetate) and trituration (diethyl ether) provided 8.30 g (79%) of trans[4-(6-benzenesulfonyl-2-methyl-6H-1,2,3,5,6-tetraaza-as-indacen-1-yl)-cyclohexyl]-carbamic acid tert-butyl ester as a grey solid. LCMS (Method H, ESI): RT=3.29 min, m+H=510.2; $^1$H NMR (400 MHz, DMSO) δ: 8.59 (s, 1H), 8.13 (m, 2H), 8.01 (d, 1H), 7.70 (m, 1H), 7.61 (m, 2H), 7.03 (d, 1H), 6.92 (m, 1H), 4.43 (m, 1H), 3.53 (m, 1H), 2.64 (s, 3H), 2.17 (m, 2H), 2.02-1.88 (m, 4H), 1.50 (m, 2H), 1.42 (s, 9H).

Trans[4-(2-methyl-6H-1,2,3,5,6-tetraaza-as-indacen-1-yl)-cyclohexyl]-carbamic acid tert-butyl ester A solution of trans[4-(6-benzenesulfonyl-2-methyl-6H-1,2,3,5,6-tetraaza-as-indacen-1-yl)-cyclohexyl]-carbamic acid tert-butyl ester (6.00 g, 11.8 mmol) and sodium hydroxide solution (29.4 mL, 58.8 mmol, 2M) in methanol (150 mL) and THF (150 mL) was stirred at room temperature for 5 hours. The mixture was partitioned between DCM and brine and then separated. The organic extracts were concentrated in vacuo and the resulting residue triturated (DCM) and air dried to afford 3.08 g (71%) of trans[4-(2-methyl-6H-1,2,3,5,6-tetraaza-as-indacen-1-yl)-cyclohexyl]-carbamic acid tert-butyl ester as a pale yellow solid. LCMS (Method H, ESI): RT=2.18 min, m+H=370.0; $^1$H NMR (400 MHz, DMSO) δ: 11.79 (s, 1H), 8.45 (s, 1H), 7.49 (m, 1H), 6.94 (br d, 1H), 6.64 (m, 1H), 4.42 (m, 1H), 3.56 (m, 1H), 2.62 (s, 3H), 2.34 (m, 2H), 2.05-1.88 (m, 4H), 1.51 (m, 2H), 1.42 (s, 9H).

Trans 4-(2-methyl-6H-1,2,3,5,6-tetraaza-as-indacen-1-yl)-cyclohexylamine

To a slurry of trans[4-(2-methyl-6H-1,2,3,5,6-tetraaza-as-indacen-1-yl)-cyclohexyl]-carbamic acid tert-butyl ester (3.08 g, 8.34 mmol) and water (150 μL), trifluoroacetic acid (25 mL) was added at room temperature. The mixture was stirred for 2 hours and then concentrated in vacuo. Purification by flash chromatography (SCX-2, gradient: methanol to 2M $NH_3$ in methanol) afforded of trans 4-(2-methyl-6H-1,2,3,5,6-tetraaza-as-indacen-1-yl)-cyclohexylamine as a colourless oil which was used without further purification. LCMS (Method Q, ESI): RT=0.55 and 0.67 min, m+H=270.1.

Trans 3-[4-(2-methyl-6H-1,2,3,5,6-tetraaza-as-indacen-1-yl)-cyclohexylamino]-propionitrile A mixture of trans 4-(2-methyl-6H-1,2,3,5,6-tetraaza-as-indacen-1-yl)-cyclohexylamine (assumed to be 8.34 mmol) and acrylonitrile (2.75 mL, 41.7 mmol) in ethanol (100 mL, IMS grade) was heated to 80° C. for 2 hours. After cooling the solvent was removed in vacuo, the residue triturated (diethyl ether), washed with ethyl acetate and air dried to give a solid. Purification by column chromatography on silica gel (gradient: DCM to 20% [2M $NH_3$ in methanol] in DCM) and trituration (acetonitrile) afforded 750 mg of trans 3-[4-(2-methyl-6H-1,2,3,5,6-tetraaza-as-indacen-1-yl)-cyclohexylamino]-propionitrile. LCMS (Method A, ESI): RT=1.24 min, m+H=323.2; $^1$H NMR (400 MHz, DMSO) δ: 11.77 (s, 1H), 8.44 (s, 1H), 7.44 (t, 1H), 6.69 (m, 1H), 4.46 (br s, 1H), 2.86 (t, 2H), 2.77 (m, 1H), 2.62 (m, 5H), 2.33 (br m, 2H), 2.08 (m, 2H), 1.99 (m, 3H), 1.35 (m, 2H).

Example 590

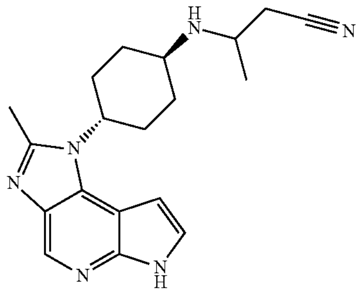 [SMILES: Cc1nc2cnc3[nH]ccc3c2n1[C@H]1CC[C@H](NC(C)CC#N)CC1]

Trans 3-[4-(2-methyl-6H-1,2,3,5,6-tetraaza-as-indacen-1-yl)-cyclohexylamino]-butyronitrile A mixture of trans 4-(2-methyl-6H-1,2,3,5,6-tetraaza-as-indacen-1-yl)-cyclohexylamine (120 mg, 445 μmol) and crotononitrile (182 μL, 2.23 mmol) in ethanol (5 mL, IMS grade) was stirred at 80° C. for 24 hours. Additional crotononitrile (182 μL, 2.23 mmol) was added and heating was continued for 24 hours. The solvent was removed in vacuo and the residue purified by column chromatography on silica gel (gradient: DCM to 10%[2M $NH_3$ in methanol] in DCM) to afford 55.0 mg (37%) of trans 3-[4-(2-methyl-6H-1,2,3,5,6-tetraaza-as-indacen-1-yl)-cyclohexylamino]-butyronitrile as a pale yellow solid. LCMS (Method A, ESI): RT=1.55 min, m+H=337.3; $^1$H NMR (400 MHz, DMSO) δ: 11.77 (s, 1H), 8.45 (s, 1H), 7.44 (t, 1H), 6.71 (dd, 1H), 4.45 (br s, 1H), 3.13

(m, 1H), 2.84 (m, 1H), 2.67-2.55 (m, 5H), 2.34 (br m, 2H), 2.06 (m, 2H), 1.89 (m, 2H), 1.65 (br s, 1H), 1.34 (m, 2H), 1.15 (d, 3H).

Example 591

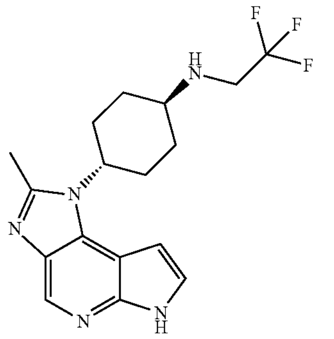 [SMILES: Cc1nc2cnc3[nH]ccc3c2n1[C@H]1CC[C@H](NCC(F)(F)F)CC1]

Trans[4-(2-methyl-6H-1,2,3,5,6-tetraaza-as-indacen-1-yl)-cyclohexyl]-(2,2,2-trifluoro-ethyl)-amine To a stirred solution of trans 4-(2-methyl-6H-1,2,3,5,6-tetraaza-as-indacen-1-yl)-cyclohexylamine (106 mg, 392 μmol) and triethylamine (218 μL, 1.57 mmol) in DCM/DMF (4 mL, 1:1), 2,2,2-trifluoroethyl trifluoromethane sulfonate (113 μL, 784 μmol) was added. Stirring was continued for 18 hours at room temperature and the mixture concentrated in vacuo. Purification by column chromatography on silica gel (gradient: DCM to 10% [2M $NH_3$ in methanol] in DCM) followed by reverse phase HPLC (5 to 60% acetonitrile in water+0.1% $NH_4OH$) afforded 21.0 mg (15%) of trans[4-(2-methyl-6H-1,2,3,5,6-tetraaza-as-indacen-1-yl)-cyclohexyl]-(2,2,2-trifluoro-ethyl)-amine. LCMS (Method A, ESI): RT=1.78 min, m+H=352.3; $^1$H NMR (400 MHz, DMSO) δ: 11.77 (s, 1H), 8.45 (s, 1H), 7.45 (t, 1H), 6.65 (br s, 1H), 4.45 (m, 1H), 3.35 (m, 2H, partially obscured by water), 2.80 (m, 1H), 2.62 (s, 3H), 2.42-2.24 (m, 3H), 2.10 (d, 2H), 1.91 (m, 2H), 1.37 (q, 2H).

Example 592

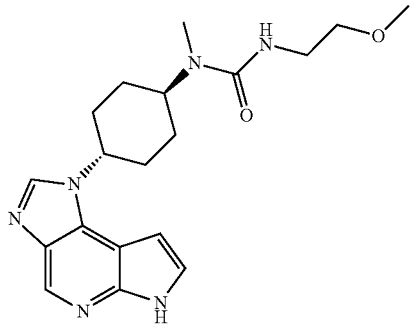 [SMILES: COCCNC(=O)N(C)[C@H]1CC[C@H](n2cnc3cnc4[nH]ccc4c32)CC1]

Trans 3-(2-Methoxy-ethyl)-1-methyl-1-[4-(6H-1,2,3,5,6-tetraaza-as-indacen-1-yl)-cyclohexyl]-urea Trans 1-[4-(6-Benzenesulfonyl-6H-1,2,3,5,6-tetraaza-as-indacen-1-yl)-cyclohexyl]-3-(2-methoxy-ethyl)-1-methyl-urea A solution of triphosgene (32.0 mg, 0.11 mmol) in dichloromethane (DCM) (1 mL) was treated dropwise with a solution of trans 4-(6-benzenesulfonyl-6H-1,2,3,5,6-tetraaza-as-indacen-1-yl)-cyclohexyl]-methyl-amine (89.0 mg, 0.22 mmol) and triethylamine (30 μL, 0.22 mmol) in DCM (1 mL). The reaction mixture was stirred at ambient temperature for 40 minutes then a solution of 2-methoxyethylamine (23 μl, 0.26 mmol) and triethylamine (30 μL, 0.22 mmol) in DCM (1 mL) was added dropwise. The reaction mixture was stirred at ambient temperature overnight. Additional 2-methoxyethylamine (46 μL, 0.52 mmol) was added and the reaction mixture was heated to reflux for 3.25 hours. After cooling, the mixture was diluted with saturated sodium hydrogen carbonate solution and the phases were separated. The aqueous layer was extracted with DCM (2×) and the combined organic layers were washed with water, saturated sodium hydrogen carbonate solution, and brine, dried with sodium sulfate and concentrated under vacuum to give crude product. Purification by column chromatography on silica gel (gradient: 0 to 8% methanol in DCM) afforded 35.0 mg (32%) of trans 1-[4-(6-benzenesulfonyl-6H-1,2,3,5,6-tetraaza-as-indacen-1-yl)-cyclohexyl]-3-(2-methoxy-ethyl)-1-methyl-urea as a white solid. LCMS (Method B, ESI): RT=3.06 min, m+H=511.3; $^1$H NMR (400 MHz, $CDCl_3$) δ: 8.93 (s, 1H), 8.23 (d, 2H), 8.09 (br s, 1H), 7.83 (d, 1H), 7.56 (t, 1H), 7.48 (t, 2H), 6.79 (d, 1H), 4.81 (t, 1H), 4.40 (m, 2H), 3.53-3.43 (m, 4H), 3.38 (s, 3H), 2.83 (s, 3H), 2.42-2.32 (m, 2H), 2.08-1.86 (m, 4H), 1.84-1.71 (m, 2H).

Trans 3-(2-Methoxy-ethyl)-1-methyl-1-[4-(6H-1,2,3,5,6-tetraaza-as-indacen-1-yl)-cyclohexyl]-urea A suspension of trans 1-[4-(6-benzenesulfonyl-6H-1,2,3,5,6-tetraaza-as-indacen-1-yl)-cyclohexyl]-3-(2-methoxy-ethyl)-1-methyl-urea (31.0 mg, 61.0 μmol) in methanol (1 mL) was treated with 2 M aqueous sodium hydroxide (0.15 mL, 0.30 mmol) and stirred at ambient temperature overnight. The mixture was concentrated under vacuum and the resulting residue partitioned between DCM and water. The phases were separated and the aqueous layer was extracted with DCM (×2). The combined organic phases were washed with saturated sodium hydrogen carbonate solution and brine, dried (sodium sulfate) and concentrated to dryness. The crude product was triturated (ether) and the isolated solid washed with ether and dried under vacuum to afford 17.0 mg (77%) of trans 3-(2-methoxy-ethyl)-1-methyl-1-[4-(6H-1,2,3,5,6-tetraaza-as-indacen-1-yl)-cyclohexyl]-urea as an off-white solid. LCMS (Method A): RT=2.35 min, m+H=371.3; $^1$H NMR (400 MHz, $CDCl_3$) δ: 10.19 (br s, 1H), 8.83 (s, 1H), 8.01 (s, 1H), 7.42 (d, 1H), 6.72 (d, 1H), 4.85 (t, 1H), 4.55-4.38

(m, 2H), 3.55-3.45 (m, 4H), 3.39 (s, 3H), 2.84 (s, 3H), 2.49-2.40 (m, 2H), 2.15-1.96 (m, 4H), 1.87-1.73 (m, 2H).

Example 593

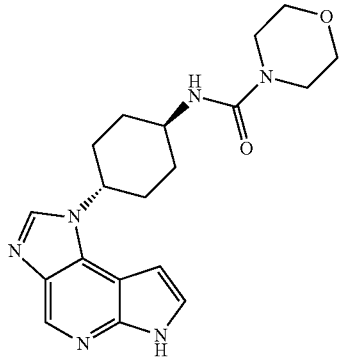 [SMILES: O=C(N[C@H]1CC[C@H](n2cnc3cnc4[nH]ccc4c32)CC1)N1CCOCC1]

Trans Morpholine-4-carboxylic acid [4-(6H-1,2,3,5,6-tetraaza-as-indacen-1-yl)-cyclohexyl]-amide Trans Morpholine-4-carboxylic acid [4-(6-benzenesulfonyl-6H-1,2,3,5,6-tetraaza-as-indacen-1-yl)-cyclohexyl]-amide A solution of trans 4-(6-benzenesulfonyl-6H-1,2,3,5,6-tetraaza-as-indacen-1-yl)-cyclohexylamine (200 mg, 0.51 mmol) in DCM (5.1 mL) was treated with diisopropylethylamine (0.13 mL, 0.76 mmol) followed by morpholine-4-carbonyl chloride (71.0 μL, 0.61 mmol). The reaction mixture was stirred at ambient temperature for 21 hours then morpholine-4-carbonyl chloride (71 μL, 0.61 mmol) and diisopropylethylamine (0.13 mL, 0.76 mmol) were added and the mixture was stirred for another 24 hours. The mixture was diluted with water and the phases were separated. The aqueous layer was extracted with DCM (×2) and the combined organic layers were washed with saturated sodium hydrogen carbonate solution, and brine, dried with sodium sulfate and concentrated under vacuum. Purification by column chromatography on silica gel (gradient: 0 to 12% methanol in DCM) followed by trituration (ethyl acetate) afforded 169 mg (66%) of trans morpholine-4-carboxylic acid [4-(6-benzenesulfonyl-6H-1,2,3,5,6-tetraaza-as-indacen-1-yl)-cyclohexyl]-amide as a white solid. LCMS (Method B, ESI): RT=2.96 min, m+H=509.4; $^1$H NMR (400 MHz, $CDCl_3$) δ: 8.94 (s, 1H), 8.24 (d, 2H), 8.10 (s, 1H), 7.83 (d, 1H), 7.56 (t, 1H), 7.48 (t, 2H), 6.74 (d, 1H), 4.49-4.38 (m, 1H), 4.33 (d, 1H), 3.93-3.81 (m, 1H), 3.71 (t, 4H), 3.36 (t, 4H), 2.34 (d, 4H), 2.08-1.95 (m, 2H), 1.55-1.41 (m, 2H).

Trans Morpholine-4-carboxylic acid [4-(6H-1,2,3,5,6-tetraaza-as-indacen-1-yl)-cyclohexyl]-amide A suspension of trans morpholine-4-carboxylic acid [4-(6-benzenesulfonyl-6H-1,2,3,5,6-tetraaza-as-indacen-1-yl)-cyclohexyl]-amide (165 mg, 0.32 mmol) in methanol (3.2 mL) was treated with 2 M aqueous sodium hydroxide (0.81 mL, 1.62 mmol) and the mixture was stirred at ambient temperature overnight. The mixture was concentrated under vacuum and the residue was partitioned between DCM (containing a few drops of methanol) and water and the phases were separated. The aqueous layer was extracted with DCM (containing a few drops of methanol) (×2) and the combined organic phases were washed with saturated sodium hydrogen carbonate solution, and brine, dried with sodium sulfate and concentrated under vacuum. The first aqueous layer was extracted with 10% MeOH/DCM (×4) and the combined extracts were dried with sodium sulfate and concentrated under vacuum to give a second batch of crude product. The two batches of crude product were combined and purified by triturated (ethyl acetate) to afford 53.0 mg (44%) of trans morpholine-4-carboxylic acid [4-(6H-1,2,3,5,6-tetraaza-as-indacen-1-yl)-cyclohexyl]-amide as a white solid. LCMS (Method A, ESI): RT=2.11 min, m+H=369.3; $^1$H NMR (400 MHz, $CDCl_3$) δ: 10.47 (br s, 1H), 8.84 (s, 1H), 7.99 (s, 1H), 7.42 (d, 1H), 6.67 (d, 1H), 4.58-4.48 (m, 1H), 4.35 (d, 1H), 3.97-3.86 (m, 1H), 3.72 (t, 4H), 3.37 (t, 4H), 2.47-2.30 (m, 4H), 2.14-2.01 (m, 2H), 1.58-1.45 (m, 2H).

Example 594

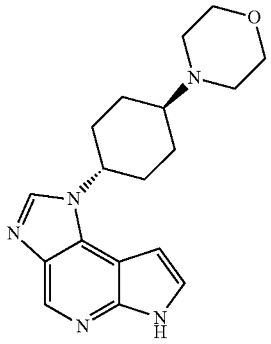 [SMILES: c1cc2c(ncc3ncn([C@H]4CC[C@H](N5CCOCC5)CC4)c32)[nH]1]

Trans 1-(4-Morpholin-4-yl-cyclohexyl)-1,6-dihydro-1,2,3,5,6-tetraaza-as-indacene Trans 4-(6-benzenesulfonyl-6H-1,2,3,5,6-tetraaza-as-indacen-1-yl)-cyclohexanol Trans 4-(5-amino-1-benzenesulfonyl-1H-pyrrolo[2,3-b]pyridin-4-ylamino)-cyclohexanol (19.0 g, 49.2 mmol) was dissolved in acetic acid (150 mL) and triethyl orthoformate (32.7 mL, 197 mmol) was added. The mixture was stirred at 110° C. for 15 min, then cooled to rt and stood for 16 h. The solid precipitate was collected by filtration, washed on the filter sequentially with acetic acid and diethyl ether then dried under vacuum. The resulting solid was stirred briefly in 2 M ammonia in methanol, then concentrated under vacuum. Trituration with methanol gave 13.0 g (67%) of trans 4-(6-benzenesulfonyl-6H-1,2,3,5,6-tetraaza-as-indacen-1-yl)-cyclohexanol. The mother liquors from the original filtration were concentrated, then the residue was dissolved in dichloromethane. The resulting solution was washed with saturated aqueous $NaHCO_3$, then dried ($Na_2SO_4$) and concentrated under vacuum. Treatment with 2 M ammonia in methanol and trituration with methanol as before gave a further 3.0 g of trans 4-(6-benzenesulfonyl-6H-1,2,3,5,6-tetraaza-as-indacen-1-yl)-cyclohexanol. NMR (400 MHz, $CDCl_3$) δ: 8.93 (s, 1H), 8.24 (m, 2H), 8.05 (s, 1H), 7.84 (d, 1H), 7.56 (m, 1H), 7.48 (m, 2H), 6.77 (d, 1H), 4.45 (m, 1H), 3.85 (m, 1H), 2.34 (m, 2H), 2.25 (m, 2H), 1.93 (m, 2H), 1.63 (m, 2H).

4-(6-Benzenesulfonyl-6H-1,2,3,5,6-tetraaza-as-indacen-1-yl)-cyclohexanone

A solution of trans 4-(6-benzenesulfonyl-6H-1,2,3,5,6-tetraaza-as-indacen-1-yl)-cyclohexanol (354 mg, 0.89 mmol) in DCM (9 mL) at 0° C. was treated with Dess-Martin periodinane (417 µL, 0.98 mmol). The reaction mixture was stirred at 0° C. for 1 hour then at ambient temperature for 80 hours. The mixture was diluted with 10% methanol in DCM and saturated sodium hydrogen carbonate solution and the phases were separated. The aqueous layer was extracted with 10% methanol in DCM (×2) and the combined organic layers were washed with water, and brine, dried with sodium sulfate and concentrated under vacuum. Purification by crystallisation (ethyl acetate) gave 201 mg (57%) of 4-(6-benzenesulfonyl-6H-1,2,3,5,6-tetraaza-as-indacen-1-yl)-cyclohexanone as a fawn solid after drying. A second crop of product, 113 mg (32%) was obtained by concentration of the mother liquors and trituration (diethyl ether) of the resulting solid. LCMS (Method B, ESI): RT=3.10 min, m+H=395.2; $^1$H NMR (400 MHz, DMSO) δ: 8.75 (s, 1H), 8.50 (s, 1H), 8.13 (d, 2H), 8.03 (d, 1H), 7.70 (t, 1H), 7.61 (t, 2H), 7.42 (d, 1H), 5.26-5.17 (m, 1H), 2.94-2.82 (m, 2H), 2.41-2.30 (m, 6H).

Cis and Trans 6-Benzenesulfonyl-1-(4-morpholin-4-yl-cyclohexyl)-1,6-dihydro-1,2,3,5,6-tetraaza-as-indacene A suspension of 4-(6-benzenesulfonyl-6H-1,2,3,5,6-tetraaza-as-indacen-1-yl)-cyclohexanone (163 mg, 0.41 mmol) in THF (4 mL) was treated with morpholine (40 µL, 0.46 mmol) followed by sodium triacetoxyborohydride (132 mg, 0.62 mmol) then acetic acid (24 µL, 0.41 mmol). The reaction mixture was stirred at ambient temperature for 20 hours. The mixture was diluted with ethyl acetate, water and saturated sodium hydrogen carbonate solution and the phases were separated. The aqueous layer was extracted with ethyl acetate (×2) and the combined organic layers were washed with water, saturated sodium hydrogen carbonate solution, and brine, dried with sodium sulfate and concentrated under vacuum. The crude product was purified by column chromatography on silica gel (gradient: 0 to 10% methanol in DCM) to give 45.0 mg (23%) of cis 6-benzenesulfonyl-1-(4-morpholin-4-yl-cyclohexyl)-1,6-dihydro-1,2,3,5,6-tetraaza-as-indacene as a fawn glass (first eluting isomer) and 36 mg (19%) of trans 6-benzenesulfonyl-1-(4-morpholin-4-yl-cyclohexyl)-1,6-dihydro-1,2,3,5,6-tetraaza-as-indacene as a fawn glass (second eluting isomer).

Cis isomer: LCMS (Method B, ESI): RT=2.24 & 2.35 min, m+H=466.3; $^1$H NMR (400 MHz, DMSO, 80° C.) δ: 8.69 (s, 1H), 8.28 (br s, 1H), 8.13 (d, 2H), 7.92 (d, 1H), 7.66 (t, 2H), 7.57 (t, 2H), 4.70 (br s, 1H), 3.75 (br s, 4H), 2.36-2.20 (m, 3H), 2.15-2.04 (m, 2H), 1.86-1.56 (m, 4H), plus 4H obscured by solvent peak.

Trans isomer: LCMS (Method B, ESI): RT=2.21 & 2.31 min, m+H=466.3; $^1$H NMR (400 MHz, $CDCl_3$) δ: 8.91 (s, 1H), 8.24 (d, 2H), 7.98 (s, 1H), 7.82 (d, 1H), 7.55 (t, 1H), 7.47 (t, 2H), 6.75 (m, 1H), 4.45-4.35 (m, 1H), 3.80 (br s, 4H), 2.67 (br s, 4H), 2.53-2.36 (m, 3H), 2.31-2.19 (m, 2H), 1.95-1.83 (m, 2H) plus 2H obscured by water peak.

Trans 1-(4-Morpholin-4-yl-cyclohexyl)-1,6-dihydro-1,2,3,5,6-tetraaza-as-indacene A solution of trans 6-benzenesulfonyl-1-(4-morpholin-4-yl-cyclohexyl)-1,6-dihydro-1,2,3,5,6-tetraaza-as-indacene (30.0 mg, 65.0 µmol) in methanol (1 mL) was treated with 2 M aqueous sodium hydroxide (0.16 mL, 0.32 mmol) and the mixture was stirred at ambient temperature overnight. The mixture was concentrated under vacuum and the residue was partitioned between DCM (containing a few drops of methanol) and saturated sodium hydrogen carbonate solution and the phases were separated. The aqueous layer was extracted with DCM (×2) and the combined organic phases were washed with saturated sodium hydrogen carbonate solution, and brine, dried with sodium sulfate and concentrated under vacuum. Purification by trituration (diethyl ether) gave 14.0 mg (67%) of trans 1-(4-morpholin-4-yl-cyclohexyl)-1,6-dihydro-1,2,3,5,6-tetraaza-as-indacene as an off-white solid. LCMS (Method A, ESI): RT=1.44 min, m+H=326.0; $^1$H NMR (400 MHz, $CDCl_3$) δ: 10.01 (br s, 1H), 8.84 (s, 1H), 7.97 (s, 1H), 7.40 (t, 1H), 6.67 (m, 1H), 4.57-4.47 (m, 1H), 3.81 (t, 4H), 2.76-2.65 (m, 4H), 2.54-2.44 (m, 3H), 2.32-2.23 (m, 2H), 2.01-1.89 (m, 2H), 1.73-1.59 (m, 2H).

Example 595

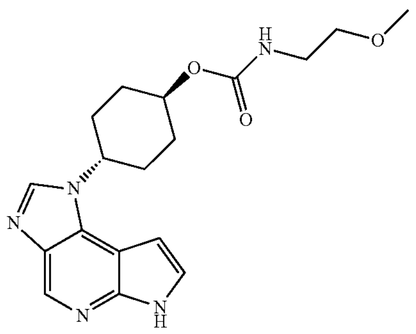 [SMILES: COCCNC(=O)O[C@H]1CC[C@H](n2cnc3cnc4[nH]ccc4c32)CC1]

Trans (2-methoxy-ethyl)-carbamic acid 4-(6H-1,2,3,5,6-tetraaza-as-indacen-1-yl)-cyclohexyl ester Trans (2-methoxy-ethyl)-carbamic acid 4-(6-benzenesulfonyl-6H-1,2,3,5,6-tetraaza-as-indacen-1-yl)-cyclohexyl ester A suspension of trans 4-(6-benzenesulfonyl-6H-1,2,3,5,6-tetraaza-as-indacen-1-yl)-cyclohexanol (100 mg, 0.25 mmol) in DCM (1.5 mL) was treated with triethylamine (39 µL, 0.28 mmol) followed by a solution of 1-isocyanato-2-methoxyethane (28.0 mg, 0.28 mmol) in DCM (1 mL). The mixture was stirred at ambient temperature for 21 hours, then THF (0.5 mL), 1-isocyanato-2-methoxyethane (25 mg, 0.25 mmol) in THF (0.5 mL) and DMAP (3.10 mg, 25.0 µmol) were added. The mixture was heated at 50° C. for 2 hours. Additional 1-isocyanato-2-methoxyethane (25 mg, 0.25 mmol) in THF (0.1 mL) was added followed by NaH (60% dispersion in mineral oil, 11.0 mg, 0.28 mmol) and the mixture was stirred at 50° C. for 40 minutes, then at ambient temperature for 88 hours. The mixture was diluted with saturated ammonium chloride solution and DCM and the phases were separated. The aqueous layer was extracted with DCM (2×) and the combined organic layers were washed with water, saturated sodium hydrogen carbonate solution, and brine, dried with sodium sulfate and concentrated under vacuum to give the crude product. Purification by column chromatography on silica gel (gradient: 0 to 8% methanol in DCM) then further purification by reverse phase HPLC (gradient: 5 to 95% MeCN in water+0.1% $HCO_2H$) afforded 60.0 mg (48%) of trans (2-methoxy-ethyl)-carbamic acid 4-(6-benzenesulfonyl-6H-1,2,3,5,6-tetraaza-as-indacen-1-yl)-cyclohexyl ester as a white solid. LCMS (Method B, ESI): RT=3.24 min, m+H=498.3; $^1$H NMR (400 MHz, $CDCl_3$) δ: 8.93 (s, 1H), 8.24 (d, 2H), 8.04 (s, 1H), 7.84 (d, 1H), 7.56 (t, 1H), 7.48 (t, 2H), 6.76 (d, 1H), 5.03 (br t, 1H), 4.82-4.72 (m, 1H), 4.50-4.40 (m, 1H), 3.48 (t, 2H), 3.42-3.35 (m, 5H), 2.33 (br t, 4H), 2.05-1.91 (m, 2H), 1.72-1.59 (m, 2H).

Trans (2-methoxy-ethyl)-carbamic acid 4-(6H-1,2,3,5,6-tetraaza-as-indacen-1-yl)-cyclohexyl ester A suspension of trans (2-methoxy-ethyl)-carbamic acid 4-(6-benzenesulfonyl-6H-1,2,3,5,6-tetraaza-as-indacen-1-yl)-cyclohexyl ester (53.0 mg, 0.11 mmol) in methanol (0.5 mL) and THF (0.5 mL) was treated with 2 M aqueous sodium hydroxide (0.27 mL, 0.53 mmol) and the mixture was stirred at 50° C. for 1 hour then concentrated under vacuum. The residue was partitioned between DCM and water and separated. The aqueous layer was extracted with DCM (×2) and the combined organic phases were washed with saturated sodium hydrogen carbonate solution, and brine, dried with sodium sulfate and concentrated under vacuum. The crude product was triturated (ethyl acetate), filtered and washed with ethyl acetate, then dried under vacuum to afford 21.0 mg (55%) of trans (2-methoxy-ethyl)-carbamic acid 4-(6H-1,2,3,5,6-tetraaza-as-indacen-1-yl)-cyclohexyl ester as an off-white solid. LCMS (Method A, ESI): RT=2.39 min, m+H=358.3; $^1$H NMR (400 MHz, $CDCl_3$) δ: 10.02 (br s, 1H), 8.82 (s, 1H), 8.00 (s, 1H), 7.42 (d, 1H), 6.70 (d, 1H), 5.08 (br t, 1H), 4.87-4.76 (m, 1H), 4.60-4.50 (m, 1H), 3.49 (t, 2H), 3.44-3.35 (m, 5H), 2.43 (br d, 2H), 2.34 (br d, 2H), 2.11-1.98 (m, 2H), 1.77-1.63 (m, 2H).

Example 596

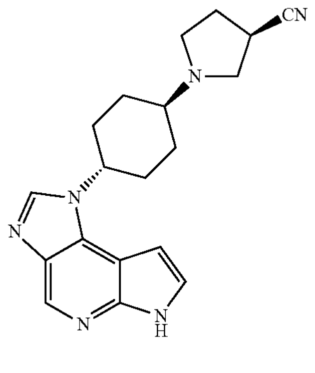 [SMILES: N#C[C@@H]1CCN([C@H]2CC[C@H](n3cnc4cnc5[nH]ccc5c43)CC2)C1]

Trans (R)-1-[4-(6H-1,2,3,5,6-tetraaza-as-indacen-1-yl)-cyclohexyl]-pyrrolidine-3-carbonitrile (R)-Pyrrolidine-3-carbonitrile A solution of (R)-1-N-Boc-3-cyano-pyrrolidine (475 mg, 2.40 mmol) in DCM (14 mL) was treated with trifluoroacetic acid (14 mL) and the mixture stirred at ambient temperature for 40 minutes then concentrated under vacuum. The residue was azeotroped with toluene, then purified by column chromatography using Isolute® SCX-2 cartridge (gradient: MeOH to 2M $NH_3$ in MeOH) to afford 240 mg (quant) of (R)-pyrrolidine-3-carbonitrile as an orange-pink oil that was used without further purification. $^1$H NMR (400 MHz, $CDCl_3$) δ: 3.26-3.08 (m, 5H), 3.02-2.86 (m, 3H).

Trans (R)-1-[4-(6-benzenesulfonyl-6H-1,2,3,5,6-tetraaza-as-indacen-1-yl)-cyclohexyl]-pyrrolidine-3-carbonitrile A mixture of 4-(6-benzenesulfonyl-6H-1,2,3,5,6-tetraaza-as-indacen-1-yl)-cyclohexanone (300 mg, 0.76 mmol), (R)-pyrrolidine-3-carbonitrile (88.0 mg, 0.91 mmol) and titanium tetraisopropoxide (0.41 mL, 1.37 mmol) was heated at 80° C. for 2 hours. The mixture was cooled to 0° C. and treated with MeOH (8 mL) followed by sodium borohydride (29.0 mg, 0.76 mmol) and stirred at ambient temperature overnight. Additional sodium borohydride (29.0 mg, 0.76 mmol) was added and the mixture was stirred at ambient temperature for 1 hour then concentrated under vacuum. The residue was partitioned between MeOH/DCM and water and the insoluble solid was removed by filtration. The phases were separated and the aqueous layer was extracted with DCM (×2). The combined organic phases were washed with saturated sodium hydrogen carbonate solution, and brine, dried with sodium sulfate and concentrated under vacuum. Purification by column chromatography on silica gel (gradient: 0 to 11% methanol in DCM) to gave 153 mg (42%) of trans (R)-1-[4-(6-benzenesulfonyl-6H-1,2,3,5,6-tetraaza-as-indacen-1-yl)-cyclohexyl]-pyrrolidine-3-carbonitrile as a golden gum. LCMS (Method B, ESI): RT=2.33 min, m+H=475.5; $^1$H NMR (400 MHz, $CDCl_3$) δ: 8.92 (s, 1H), 8.24 (d, 2H), 7.97 (s, 1H), 7.83 (d, 1H), 7.56 (t, 1H), 7.47 (t, 2H), 6.74 (d, 1H), 4.47-4.37 (m, 1H), 3.08 (br s, 2H), 2.93-2.74 (m, 3H), 2.43-2.11 (m, 7H), 1.96-1.82 (m, 2H) plus 2H obscured by water peak.

Trans (R)-1-[4-(6H-1,2,3,5,6-tetraaza-as-indacen-1-yl)-cyclohexyl]-pyrrolidine-3-carbonitrile A solution of trans (R)-1-[4-(6-benzenesulfonyl-6H-1,2,3,5,6-tetraaza-as-indacen-1-yl)-cyclohexyl]-pyrrolidine-3-carbonitrile (139 mg, 0.29 mmol) in methanol (3 mL) was treated with 2 M aqueous sodium hydroxide (0.73 mL, 1.5 mmol) with stirring at ambient temperature for 40 hours. The solvent was removed under vacuum and the residue was partitioned between DCM (containing a few drops of MeOH) and water and the phases were separated. The aqueous layer was extracted with 10% MeOH in DCM (×2) and the combined organic extracts were washed with saturated sodium hydrogen carbonate solution, and brine, dried with sodium sulfate and concentrated under vacuum. The crude product was triturated (ethyl acetate), filtered, washed with ethyl acetate and dried under vacuum to afford 68.0 mg (69%) of trans (R)-1-[4-(6H-1,2,3,5,6-tetraaza-as-indacen-1-yl)-cyclohexyl]-pyrrolidine-3-carbonitrile as a white solid. LCMS (Method A, ESI): RT=1.44 min, m+H=335.3; $^1$H NMR (400 MHz, DMSO) δ: 11.84 (br s, 1H), 8.57 (s, 1H), 8.27 (s, 1H), 7.46 (t, 1H), 6.77 (dd, 1H), 4.63-4.53 (m, 1H), 3.30-3.21 (m, 1H), 2.87-2.76 (m, 3H), 2.61-2.53 (m, 1H), 2.35-2.25 (m, 1H), 2.23-2.15 (m, 3H), 2.11 (br d, 2H), 2.02-1.89 (m, 3H), 1.65-1.53 (m, 2H).

Example 597

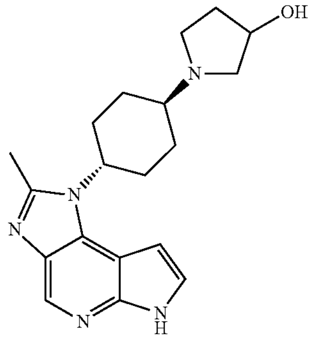 [SMILES: Cc1nc2cnc3[nH]ccc3c2n1[C@H]1CC[C@H](N2CCC(O)C2)CC1]

Racemic trans 1-[4-(2-Methyl-6H-1,2,3,5,6-tetraaza-as-indacen-1-yl)-cyclohexyl]-pyrrolidin-3-ol 4-(6-benzenesulfonyl-2-methyl-6H-1,2,3,5,6-tetraaza-as-indacen-1-yl)-cyclohexanone A suspension of 4-(6-benzenesulfonyl-2-methyl-6H-1,2,3,5,6-tetraaza-as-indacen-1-yl)-cyclohexanol (2.20 g, 5.40 mmol) DMSO (22 mL) was treated with triethylamine (3.00 ml, 21.5 mmol) followed by sulphur trioxide pyridine complex (2.56 g, 16.1 mmol) and the mixture was stirred at ambient temperature for 24 hours. Triethylamine (0.75 mL, 5.40 mmol) and sulphur trioxide pyridine complex (0.43 g, 2.70 mmol) were added and the mixture was stirred at ambient temperature for 1.5 hours then the mixture was diluted with water and DCM. The phases were separated and the aqueous layer was extracted with DCM (×2) and the combined organic phases were washed with water, and brine, dried with sodium sulfate and concentrated under vacuum to give crude product. Trituration (ethyl acetate) gave 2.05 g (94%) of 4-(6-benzenesulfonyl-2-methyl-6H-1,2,3,5,6-tetraaza-as-indacen-1-yl)-cyclohexanone as a white solid. LCMS (Method B, ESI): RT=2.93 min, m+H=409.4; $^1$H NMR (400 MHz, DMSO) δ: 8.61 (s, 1H), 8.13 (d, 2H), 7.98 (d, 1H), 7.70 (t, 1H), 7.61 (t, 2H), 7.27-6.97 (br s, 1H), 5.20-5.06 (m, 1H), 2.92-2.78 (m, 2H), 2.70 (s, 3H), 2.59-2.45 (m, 2H), 2.42-2.33 (m, 2H), 2.25-2.16 (m, 2H).

Racemic trans 1-[4-(6-Benzenesulfonyl-2-methyl-6H-1,2,3,5,6-tetraaza-as-indacen-1-yl)-cyclohexyl]-pyrrolidin-3-ol A suspension of 4-(6-benzenesulfonyl-2-methyl-6H-1,2,3,5,6-tetraaza-as-indacen-1-yl)-cyclohexanone (300 mg, 0.74 mmol) in dry THF (3.5 mL) under nitrogen was treated with titanium tetraisopropoxide (0.33 mL) followed by a solution of DL-pyrrolidin-3-ol (59.0 μL, 0.74 mmol) in dry THF (140 μL) and the mixture was stirred at ambient temperature for 1 hour. MeOH (3.5 mL) was added followed by sodium borohydride (56.0 mg, 1.47 mmol) in two portions. The mixture was stirred at ambient temperature overnight then concentrated under vacuum. The residue was treated with DCM and water and the insoluble solid was removed by filtration. The phases were separated and the aqueous layer was extracted with DCM (×2). The combined organic phases were washed with saturated sodium hydrogen carbonate solution, and brine, dried with sodium sulfate and concentrated under vacuum. The crude product was purified by column chromatography on silica gel (gradient: 0 to 20% [2N $NH_3$ in methanol] in DCM) to give 77.0 mg (22%) of racemic trans 1-[4-(6-benzenesulfonyl-2-methyl-6H-1,2,3,5,6-tetraaza-as-indacen-1-yl)-cyclohexyl]-pyrrolidin-3-ol as a white solid. LCMS (Method B, ESI): RT=2.28 min, m+H=480.5; $^1$H NMR (400 MHz, $CDCl_3$) δ: 8.79 (s, 1H), 8.22 (d, 2H), 7.81 (d, 1H), 7.55 (t, 1H), 7.47 (t, 2H), 6.84 (d, 1H), 4.50-4.30 (m, 2H), 3.08 (q, 1H), 2.90 (br d, 1H), 2.82-2.73 (m, 1H), 2.67 (s, 3H), 2.62-2.51 (m, 1H), 2.48-2.18 (m, 6H), 2.16-1.93 (m, 3H), 1.90-1.79 (m, 1H), 1.67-1.53 (m, 2H).

Racemic trans 1-[4-(2-Methyl-6H-1,2,3,5,6-tetraaza-as-indacen-1-yl)-cyclohexyl]-pyrrolidin-3-ol A solution of racemic trans 1-[4-(6-benzenesulfonyl-2-methyl-6H-1,2,3,5,6-tetraaza-as-indacen-1-yl)-cyclohexyl]-pyrrolidin-3-ol (72.0 mg, 0.15 mmol) in methanol (0.5 mL) and THF (1.1 mL) was treated with 2 M aqueous sodium hydroxide (0.38 mL, 0.75 mmol) and the mixture was stirred at ambient temperature for 72 hours then concentrated under vacuum. The residue was triturated with water and the solid filtered off, washed with water, ethyl acetate and ether. Further purification by column chromatography on silica gel (gradient: 0 to 20% [2N $NH_3$ in methanol] in DCM) gave a white solid that was suspended in ether, filtered off, washed with ether and dried under vacuum to afford 19.0 mg (37%) of racemic trans 1-[4-(2-methyl-6H-1,2,3,5,6-tetraaza-as-indacen-1-yl)-cyclohexyl]-pyrrolidin-3-ol as a white solid. LCMS (Method A, ESI): RT=1.45 min, m+H=340.3; $^1$H NMR (400 MHz, DMSO) δ: 11.78 (br s, 1H), 8.45 (s, 1H), 7.46 (t, 1H), 6.68 (br s, 1H), 4.69 (m, 1H), 4.46 (br s, 1H), 4.25-4.16 (m, 1H), 2.91-2.81 (m, 1H), 2.80-2.69 (m, 1H), 2.61-2.54 (m, 1H), 2.48-2.45 (m, 1H), 2.43-2.24 (m, 3H), 2.14 (br d, 2H), 2.03-1.87 (m, 3H), 1.63-1.41 (m, 3H).

Example 598

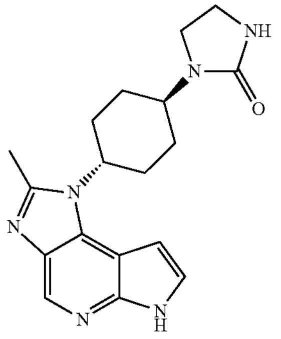 [SMILES: Cc1nc2cnc3[nH]ccc3c2n1[C@H]1CC[C@H](N2CCNC2=O)CC1]

Trans 1-[4-(2-methyl-6H-1,2,3,5,6-tetraaza-as-indacen-1-yl)-cyclohexyl]-imidazolidin-2-one formic acid salt Trans {2-[4-(6-benzenesulfonyl-2-methyl-6H-1,2,3,5,6-tetraaza-as-indacen-1-yl)-cyclohexylamino]-ethyl}-carbamic acid tert-butyl ester Trans 4-(6-benzenesulfonyl-2-methyl-6H-1,2,3,5,6-tetraaza-as-indacen-1-yl)-cyclohexyl amine (313 mg, 0.77 mmol) was treated with a solution of N-Boc-2-aminoacetaldehyde (122 mg, 0.77 mmol) in THF (7.7 mL), acetic acid (44.0 μL, 0.77 mmol) and sodium triacetoxyborohydride (243 mg, 1.20 mmol). The mixture was stirred at ambient temperature for 18 hours. A solution of N-Boc-2-aminoacetaldehyde (37.0 mg, 0.23 mmol) in THF (1 mL), and sodium triacetoxyborohydride (81.0 mg, 0.38 mmol) were added and the mixture was stirred at ambient temperature for 4.5 hours then concentrated under vacuum. The residue was partitioned between DCM and saturated sodium hydrogen carbonate solution and the phases were separated. The aqueous layer was extracted with DCM (×2) and the combined organic phases washed with saturated sodium hydrogen carbonate solution, and brine, dried with sodium sulfate and concentrated under vacuum to give crude product. Purification by column chromatography on silica gel (gradient: 0 to 11% [2M $NH_3$ in methanol] in DCM) gave 266 mg (63%) of trans {2-[4-(6-benzenesulfonyl-2-methyl-6H-1,2,3,5,6-tetraaza-as-indacen-1-yl)-cyclohexylamino]-ethyl}-carbamic acid tert-butyl ester as a white foam. LCMS (Method B, ESI): RT=2.65 min, m+H=553.5; $^1$H NMR (400 MHz, $CDCl_3$) δ: 8.80 (s, 1H), 8.23 (d, 2H), 7.81 (d, 1H), 7.55 (t, 1H), 7.47 (t, 2H), 6.84 (d, 1H), 4.94 (br s, 1H), 4.37 (br s, 1H), 3.33-3.24 (m, 1H), 2.90-2.73 (m, 3H), 2.67 (m, 4H), 2.41-2.17 (m, 4H), 2.04-1.91 (m, 2H), 1.53-1.34 (m, 11H).

Trans N*1*-[4-(6-benzenesulfonyl-2-methyl-6H-1,2,3,5,6-tetraaza-as-indacen-1-yl)-cyclohexyl]-ethane-1,2-diamine A solution of trans {2-[4-(6-benzenesulfonyl-2-methyl-6H-1,2,3,5,6-tetraaza-as-indacen-1-yl)-cyclohexylamino]-ethyl}-carbamic acid tert-butyl ester (260 mg, 0.47 mmol) in DCM (2.5 mL) was treated with trifluoroacetic acid (2.5 mL) and the mixture was stirred at ambient temperature for 1 hour. The solvents were removed under vacuum and the residue azeotroped with toluene. Purification by column chromatography using Isolute® SCX-2 cartridge (gradient: methanol then 2M $NH_3$ in methanol) and subsequent trituration (diethyl ether) gave 200 mg (94%) of trans N*1*-[4-(6-benzenesulfonyl-2-methyl-6H-1,2,3,5,6-tetraaza-as-indacen-1-yl)-cyclohexyl]-ethane-1,2-diamine as a pale yellow solid. LCMS (Method B, ESI): RT=1.99 min, m+H=453.4; $^1$H NMR (400 MHz, $CDCl_3$) δ: 8.80 (s, 1H), 8.23 (d, 2H), 7.81 (d, 1H), 7.55 (t, 1H), 7.47 (t, 2H), 6.84 (d, 1H), 4.38 (br s, 1H), 2.89 (t, 2H), 2.84-2.72 (m, 3H), 2.67 (s, 3H), 2.43-2.18 (m, 4H), 2.05-1.91 (m, 2H), 1.49-1.35 (m, 2H).

Trans 1-[4-(6-benzenesulfonyl-2-methyl-6H-1,2,3,5,6-tetraaza-as-indacen-1-yl)-cyclohexyl]-imidazolidin-2-one A suspension of trans N*1*-[4-(6-benzenesulfonyl-2-methyl-6H-1,2,3,5,6-tetraaza-as-indacen-1-yl)-cyclohexyl]-ethane-1,2-diamine (195 mg, 0.43 mmol) in THF (4.3 mL) was treated with carbonyl diimidazole (105 mg, 0.65 mmol) at reflux for 6 hours. The mixture was concentrated under vacuum and partitioned between DCM (containing a bit of MeOH) and saturated sodium hydrogen carbonate solution and the phases were separated. The aqueous phase was extracted with DCM (×2) and the combined organic phases washed with brine, dried with sodium sulfate and concentrated under vacuum. Purification by column chromatography on silica gel (gradient: 0 to 9% methanol in DCM) gave 99.0 mg (48%) of trans 1-[4-(6-benzenesulfonyl-2-methyl-6H-1,2,3,5,6-tetraaza-as-indacen-1-yl)-cyclohexyl]-imidazolidin-2-one as a white solid. LCMS (Method B, ESI): RT=2.75 min, m+H=479.4; $^1$H NMR (400 MHz, DMSO) δ: 8.60 (s, 1H), 8.13 (d, 2H), 8.03 (d, 1H), 7.70 (t, 1H), 7.61 (t, 2H), 7.22-6.99 (br s, 1H), 6.30 (s, 1H), 4.52 (br s, 1H), 3.87-3.74 (m, 1H), 3.37 (t, 2H), 3.25 (t, 2H), 2.66 (s, 3H), 2.29-2.15 (m, 2H), 2.03-1.93 (m, 2H), 1.91-1.72 (m, 4H).

Trans 1-[4-(2-methyl-6H-1,2,3,5,6-tetraaza-as-indacen-1-yl)-cyclohexyl]-imidazolidin-2-one formic acid salt A suspension of trans 1-[4-(6-benzenesulfonyl-2-methyl-6H-1,2,3,5,6-tetraaza-as-indacen-1-yl)-cyclohexyl]-imidazolidin-2-one (94.0 mg, 0.20 mmol) in methanol (1 mL) was treated with 2 M aqueous sodium hydroxide (0.49 mL, 0.98 mmol) and THF (0.5 mL) at ambient temperature for 20 hours. The solvents were evaporated under vacuum and the resulting suspension was diluted with water. The suspension was filtered and the solid washed with water and ethyl acetate. The solid was mostly taken up in acetonitrile and water containing 0.1% formic acid and filtered to remove any insoluble material. The solution was lyophilised to afford 44.0 mg (67%) of trans 1-[4-(2-methyl-6H-1,2,3,5,6-tetraaza-as-indacen-1-yl)-cyclohexyl]-imidazolidin-2-one formic acid salt as a white solid. LCMS (Method A, ESI): RT=2.03 min, m+H=339.3; $^1$H NMR (400 MHz, DMSO) δ: 11.80 (br s, 1H), 8.46 (s, 1H), 7.50 (s, 1H), 6.70 (s, 1H), 6.32 (s, 1H), 4.50 (br s, 1H), 3.89-3.78 (m, 1H), 3.42-3.22 (m, 4H), 2.64 (s, 3H), 2.47-2.30 (m, 2H), 2.04-1.93 (m, 2H), 1.91-1.75 (m, 4H).

Example 599

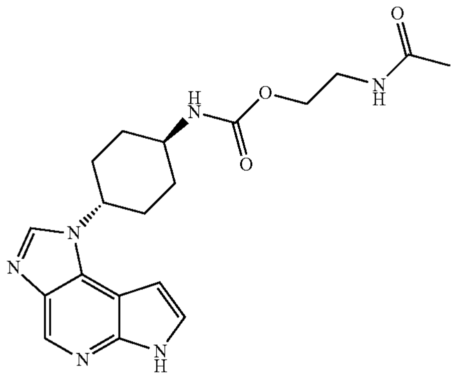 [SMILES: CC(=O)NCCOC(=O)N[C@H]1CC[C@H](n2cnc3cnc4[nH]ccc4c32)CC1]

Trans[4-(6H-1,2,3,5,6-tetraaza-as-indacen-1-yl)-cyclohexyl]-carbamic acid 2-acetylamino-ethyl ester Trans[4-(6-benzenesulfonyl-6H-1,2,3,5,6-tetraaza-as-indacen-1-yl)-cyclohexyl]-carbamic acid 2-acetylamino-ethyl ester Trans [4-(6-benzenesulfonyl-6H-1,2,3,5,6-tetraaza-as-indacen-1-yl)-cyclohexyl]-carbamic acid 4-nitro-phenyl ester (140 mg) was suspended in THF (0.25 mL) and triethylamine (104 μL, 0.75 mmol) was added. N-Acetylethanolamine (230 μL, 2.5 mmol) was added and the mixture was stirred at 65° C. for 90 min. 1 M Aqueous HCl (1.5 mL) was added and the resulting mixture purified by Isolute® SCX-2 column (gradient: methanol to 2 M $NH_3$ in methanol) to give a white solid. Further purification by column chromatography on silica gel (gradient: DCM to 8% methanol in DCM) gave 74 mg (56%)

of trans[4-(6-benzenesulfonyl-6H-1,2,3,5,6-tetraaza-as-indacen-1-yl)-cyclohexyl]-carbamic acid 2-acetylamino-ethyl ester. LCMS (Method B, ESI): RT=2.86 min, m+H=525.3.

Trans[4-(6H-1,2,3,5,6-tetraaza-as-indacen-1-yl)-cyclohexyl]-carbamic acid 2-acetylamino-ethyl ester Trans [4-(6-benzenesulfonyl-6H-1,2,3,5,6-tetraaza-as-indacen-1-yl)-cyclohexyl]-carbamic acid 2-acetylamino-ethyl ester (74 mg, 0.14 mmol) was dissolved in THF (1 mL) and methanol (1 mL). 2 M Aqueous NaOH (1 mL) was added and the mixture was stirred at room temperature for 16 h. 1 M Aqueous HCl (2 mL) was added and the mixture was concentrated. Purification by column chromatography on silica gel (gradient: DCM to 12% (2 M $NH_3$ in methanol) in DCM) and subsequent trituration with ethyl acetate gave 38 mg (70%) of trans[4-(6H-1,2,3,5,6-tetraaza-as-indacen-1-yl)-cyclohexyl]-carbamic acid 2-acetylamino-ethyl ester. LCMS (Method A, ESI): RT=2.00 min, m+H=385.3; NMR (400 MHz, DMSO) δ: 11.84 (s, 1H), 8.57 (s, 1H), 8.28 (s, 1H), 7.47 (t, 1H), 7.33 (d, 1H), 6.70 (dd, 1H), 4.54 (m, 1H), 4.08 (t, 2H), 3.51 (m, 3H), 3.27 (s, 3H), 2.19 (m, 2H), 2.01 (m, 4H), 1.57 (m, 2H).

Example 600

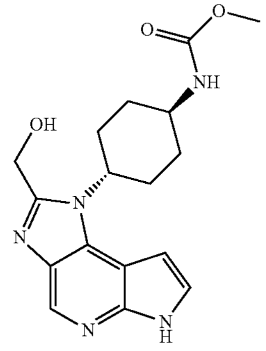 [SMILES: COC(=O)N[C@H]1CC[C@H](n2c(CO)nc3cnc4[nH]ccc4c32)CC1]

Trans[4-(2-hydroxymethyl-6H-1,2,3,5,6-tetraaza-as-indacen-1-yl)-cyclohexyl]-carbamic acid methyl ester Trans acetic acid 1-(4-amino-cyclohexyl)-6-benzene-sulfonyl-1,6-dihydro-1,2,3,5,6-tetraaza-as-indacen-2-ylmethyl ester Trans [4-(5-amino-1-benzenesulfonyl-1H-pyrrolo[2,3-b]pyridin-4-ylamino)-cyclohexyl]-carbamic acid tert-butyl ester (2.00 g, 4.12 mmol) was dissolved in DCM (20 mL) and triethylamine (750 μL, 5.36 mmol) was added, followed by acetoxyacetyl chloride (490 μL, 4.53 mmol). The mixture was stirred at room temperature for 30 min, then concentrated under vacuum. The residue was dissolved in acetic acid (20 mL) and stirred at 110° C. for 3 h, then concentrated under vacuum. Purification by column chromatography on silica gel (gradient: 1:1 DCM:pentane to neat DCM to 20% [2 M $NH_3$ in methanol] in DCM) gave 1.33 g (69%) of trans acetic acid 1-(4-amino-cyclohexyl)-6-benzenesulfonyl-1,6-dihydro-1,2,3,5,6-tetraaza-as-indacen-2-ylmethyl ester. LCMS (Method B, ESI): RT=2.30 min, m+H=468.4.

Trans[4-(6-benzenesulfonyl-2-hydroxymethyl-6H-1,2,3,5,6-tetraaza-as-indacen-1-yl)-cyclohexyl]-carbamic acid methyl ester Trans acetic acid 1-(4-amino-cyclohexyl)-6-benzenesulfonyl-1,6-dihydro-1,2,3,5,6-tetraaza-as-indacen-2-ylmethyl ester (338 mg, 0.72 mmol) was dissolved in DCM (5 mL) and DIPEA (246 μL, 1.44 mmol) was added, followed by methyl chloroformate (84 μL, 1.08 mmol). The mixture was stirred for 16 h, then concentrated under vacuum. Purification by column chromatography on silica gel (gradient: DCM to 6% methanol in DCM) gave 290 mg (83%) of trans[4-(6-benzenesulfonyl-2-hydroxymethyl-6H-1,2,3,5,6-tetraaza-as-indacen-1-yl)-cyclohexyl]-carbamic acid methyl ester. LCMS (Method B, ESI): RT=2.98 min, m+H=484.4.

Trans[4-(2-hydroxymethyl-6H-1,2,3,5,6-tetraaza-as-indacen-1-yl)-cyclohexyl]-carbamic acid methyl ester Trans [4-(6-benzenesulfonyl-2-hydroxymethyl-6H-1,2,3,5,6-tetraaza-as-indacen-1-yl)-cyclohexyl]-carbamic acid methyl ester (290 mg, 0.60 mmol) was dissolved in methanol (1 mL) and THF (1 mL). 2 M Aqueous NaOH (2 mL) was added and the mixture was stirred at 50° C. for 1 h. 1 M Aqueous HCl (4 mL) was added and the mixture was concentrated under vacuum. Purification by column chromatography on silica gel (gradient: DCM to 12% (2 M ammonia in methanol) in DCM) and sequential trituration with ethyl acetate and acetonitrile gave 33 mg (17%) of trans[4-(2-hydroxymethyl-6H-1,2,3,5,6-tetraaza-as-indacen-1-yl)-cyclohexyl]-carbamic acid methyl ester. LCMS (Method A, ESI): RT=2.16 min, m+H=344.3; NMR (400 MHz, DMSO) δ: 11.89 (s, 1H), 8.53 (s, 1H), 7.52 (t, 1H), 7.26 (d, 1H), 6.67 (s, 1H), 5.69 (t, 1H), 4.79 (d, 2H), 4.67 (m, 1H), 3.56 (m, 4H), 2.40 (m, 2H), 2.00 (dd, 4H), 1.55-1.42 (m, 2H).

Example 601

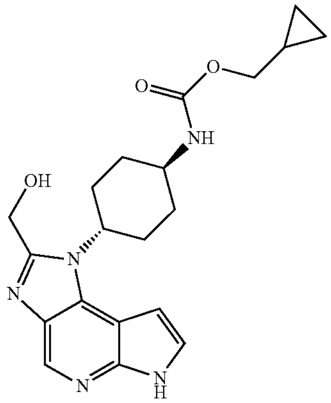 [SMILES: O=C(N[C@H]1CC[C@H](n2c(CO)nc3cnc4[nH]ccc4c32)CC1)OCC1CC1]

Trans[4-(2-hydroxymethyl-6H-1,2,3,5,6-tetraaza-as-indacen-1-yl)-cyclohexyl]-carbamic acid cyclopropylmethyl ester Trans acetic acid 6-benzenesulfonyl-1-[4-(4-nitro-phenoxycarbonylamino)-cyclohexyl]-1,6-dihydro-1,2,3,5,6-tetraaza-as-indacen-2-yl methyl ester Trans acetic acid 1-(4-amino-cyclohexyl)-6-benzenesulfonyl-1,6-dihydro-1,2,3,5,6-tetraaza-as-indacen-2-ylmethyl ester (617 mg, 1.32 mmol) was dissolved in DCM (5 mL) and pyridine (5 mL). The mixture was cooled to 0° C. and 4-nitrophenyl chloroformate (319 mg, 1.58 mmol) was added. The mixture was stirred at 0° C. for 90 min, then further 4-nitrophenyl chloroformate (319 mg, 1.58 mmol) was added. The mixture was stirred for 1 h (allowed to warm to room temperature), then diluted with water. The mixture was extracted into DCM (×3). The combined organic extracts were washed with brine, then dried ($Na_2SO_4$) and concentrated. Purification by column chromatography on silica gel (gradient: 9:1 cyclohexane:ethyl acetate to neat ethyl acetate) gave 385 mg (46%) of trans acetic acid 6-benzenesulfonyl-1-[4-(4-nitro-phenoxycarbonylamino)-cyclohexyl]-1,6-dihydro-1,2,3,5,6-tetraaza-as-indacen-2-yl methyl ester. LCMS (Method B, ESI): RT=3.86 min, m+H=633.4.

Trans acetic acid 6-benzenesulfonyl-1-(4-cyclopropylmethoxycarbonylamino-cyclohexyl)-1,6-dihydro-1,2,3,5,6-tetraaza-as-indacen-2-ylmethyl ester Trans acetic acid 6-benzenesulfonyl-1-[4-(4-nitro-phenoxycarbonylamino)-cyclohexyl]-1,6-dihydro-1,2,3,5,6-tetraaza-as-indacen-2-yl methyl ester (204 mg, 0.32 mmol) was suspended in cyclopropylmethanol (1 mL) and triethylamine (135 μL, 0.96 mmol) was added. The mixture was stirred at 65° C. for 30 min, then cooled to room temperature. 1 M Aqueous HCl (1 mL) was added and the resultant mixture was purified by Isolute® SCX column (gradient: methanol to 2 M $NH_3$ in methanol) to give 127 mg (70%) of crude trans acetic acid 6-benzenesulfonyl-1-(4-cyclopropylmethoxy-carbonylamino-cyclohexyl)-1,6-dihydro-1,2,3,5,6-tetraaza-as-indacen-2-ylmethyl ester, which was used directly without further purification. LCMS (Method B, ESI): RT=3.72 min, m+H=566.4.

Trans[4-(2-hydroxymethyl-6H-1,2,3,5,6-tetraaza-as-indacen-1-yl)-cyclohexyl]-carbamic acid cyclopropylmethyl ester Trans acetic acid 6-benzenesulfonyl-1-(4-cyclopropylmethoxy-carbonylamino-cyclohexyl)-1,6-dihydro-1,2,3,5,6-tetraaza-as-indacen-2-ylmethyl ester (127 mg, 0.22 mmol) was dissolved in THF (1 mL) and methanol (1 mL). 2 M Aqueous NaOH (1 mL) was added and the mixture was stirred for 16 h. 1 M Aqueous HCl (2 mL) was added and the mixture was concentrated under vacuum. Purification by column chromatography on silica gel (gradient: DCM to 6% (2 M $NH_3$ in methanol) in DCM) followed by sequential trituration with ethyl acetate and acetonitrile gave 53 mg (62%) of trans[4-(2-hydroxymethyl-6H-1,2,3,5,6-tetraaza-as-indacen-1-yl)-cyclohexyl]-carbamic acid cyclopropylmethyl ester. LCMS (Method A, ESI): RT=2.77 min, m+H=384.3; NMR (400 MHz, DMSO) δ: 11.87 (s, 1H), 8.52 (s, 1H), 7.51 (t, 1H), 7.28 (d, 1H), 6.66 (s, 1H), 5.68 (m, 1H), 4.78 (s, 2H), 4.66 (m, 1H), 3.80 (d, 2H), 3.60 (m, 1H), 2.36 (q, 2H), 1.99 (dd, 4H), 1.57-1.42 (m, 2H), 1.07 (m, 1H), 0.50-0.49 (m, 2H), 0.25 (d, 2H).

Example 602

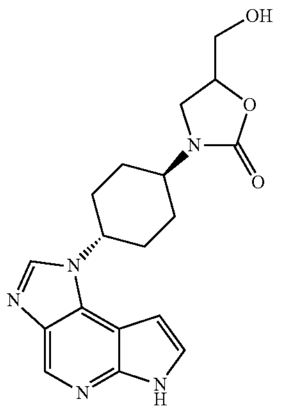 [SMILES: O=C1OC(CO)CN1[C@H]1CC[C@H](n2cnc3cnc4[nH]ccc4c32)CC1]

Trans 5-hydroxymethyl-3-[4-(6H-1,2,3,5,6-tetraaza-as-indacen-1-yl)-cyclohexyl]-oxazolidin-2-one Trans [4-(6-benzenesulfonyl-6H-1,2,3,5,6-tetraaza-as-indacen-1-yl)-cyclohexyl]-carbamic acid 4-nitro-phenyl ester (200 mg, 0.36 mmol) was suspended in acetonitrile (0.8 mL) and 3-oxetanol (200 mg, 2.68 mmol) was added, followed by sodium hydride (54 mg, 60% dispersion in mineral oil, 1.42 mmol). The mixture was heated using microwave irradiation at 120° C. for 15 min, then cooled to room temperature. 1 M Aqueous HCl (1.5 mL) was added and the mixture purified by Isolute® SCX column (gradient: methanol to 2 M $NH_3$ in methanol) to give a brown residue. Further purification by column chromatography on silica gel (gradient: DCM to 10% (2 M $NH_3$ in methanol) in DCM) followed by sequential trituration with ethyl acetate and acetonitrile gave 25 mg (20%) of trans 5-hydroxymethyl-3-[4-(6H-1,2,3,5,6-tetraaza-as-indacen-1-yl)-cyclohexyl]-oxazolidin-2-one. LCMS (Method A, ESI): RT=1.92 min, m+H=356.3; NMR (400 MHz, DMSO) δ: 11.84 (s, 1H), 8.57 (s, 1H), 8.29 (s, 1H), 7.47 (t, 1H), 6.83 (dd, 1H), 5.13 (t, 1H), 4.63 (m, 1H), 4.54 (m, 1H), 3.72 (m, 1H), 3.63-3.48 (m, 3H), 3.40 (dd, 1H), 2.22 (d, 2H), 2.14-1.80 (m, 6H).

Example 603

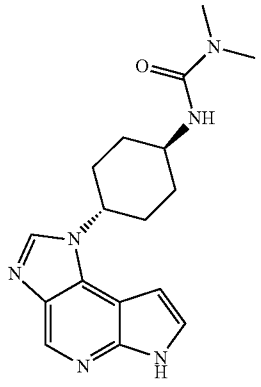

Trans 1,1-dimethyl-3-[4-(6H-1,2,3,5,6-tetraaza-as-indacen-1-yl)-cyclohexyl]-urea Trans 3-[4-(6-benzenesulfonyl-6H-1,2,3,5,6-tetraaza-as-indacen-1-yl)-cyclohexyl]-1,1-dimethyl-urea Trans [4-(6-benzenesulfonyl-6H-1,2,3,5,6-tetraaza-as-indacen-1-yl)-cyclohexyl]-carbamic acid 4-nitro-phenyl ester (200 mg, 0.36 mmol) was suspended in a solution of dimethylamine (approx. 2 M) in THF (1.5 mL). The mixture was heated at 65° C. for 30 min, then concentrated under vacuum. The residue was taken up in methanol and acidified (1 M aqueous HCl), then purified by Isolute® SCX column (gradient: methanol to 2 M $NH_3$ in methanol) to give trans 3-[4-(6-benzenesulfonyl-6H-1,2,3,5,6-tetraaza-as-indacen-1-yl)-cyclohexyl]-1,1-dimethyl-urea (168 mg, quantitative), which was used directly without further purification. LCMS (Method B, ESI): RT=3.02 min, m+H=467.4.

Trans 1,1-dimethyl-3-[4-(6H-1,2,3,5,6-tetraaza-as-indacen-1-yl)-cyclohexyl]-urea Trans 3-[4-(6-benzene sulfonyl-6H-1,2,3,5,6-tetraaza-as-indacen-1-yl)-cyclohexyl]-1,1-dimethyl-urea (168 mg) was dissolved in methanol (1.5 mL) and THF (1.5 mL). 2 M Aqueous NaOH (1.5 mL) was added and the mixture was stirred 90 min at room temperature, then concentrated under vacuum. The residue was neutralised with 1 M aqueous HCl (3 mL), then concentrated. Purification by column chromatography on silica gel (gradient: DCM to 6% (2 M $NH_3$ in methanol) in DCM) followed by trituration with acetonitrile gave 85 mg (71%) of trans 1,1-dimethyl-3-[4-(6H-1,2,3,5,6-tetraaza-as-indacen-1-yl)-cyclohexyl]-urea. LCMS (Method A, ESI): RT=2.13 min, m+H=327.3; NMR (400 MHz, DMSO) δ: 11.86 (s, 1H), 8.57 (s, 1H), 8.30 (s, 1H), 7.48 (t, 1H), 6.65 (dd, 1H), 6.03 (d, 1H), 4.52 (m, 1H), 3.62 (m, 1H), 2.80 (s, 6H), 2.17 (m, 2H), 2.10-1.90 (m, 4H), 1.70-1.55 (m, 2H).

Example 604

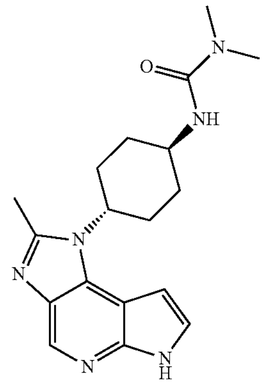

Trans 1,1-dimethyl-3-[4-(2-methyl-6H-1,2,3,5,6-tetraaza-as-indacen-1-yl)-cyclohexyl]-urea Trans 4-(6-benzenesulfonyl-2-methyl-6H-1,2,3,5,6-tetraaza-as-indacen-1-yl)-cyclohexylamine Trans [4-(6-benzenesulfonyl-2-methyl-6H-1,2,3,5,6-tetraaza-as-indacen-1-yl)-cyclohexyl]-carbamic acid tert-butyl ester (540 mg, 1.08 mmol) was suspended in water (0.5 mL) and trifluoroacetic acid (5 mL) was added. The mixture was stirred at room temperature for 1 h, then concentrated under vacuum. The residue was taken up in methanol and purified by Isolute® SCX-2 column (gradient: methanol to 2 M $NH_3$ in methanol) to give 440 mg (99%) of trans 4-(6-benzenesulfonyl-2-methyl-6H-1,2,3,5,6-tetraaza-as-indacen-1-yl)-cyclohexylamine, which was used directly without further purification. LCMS (Method B, ESI): RT=2.06 min, m+H=410.3.

Trans[4-(6-benzenesulfonyl-2-methyl-6H-1,2,3,5,6-tetraaza-as-indacen-1-yl)-cyclohexyl]-carbamic acid 4-nitro-phenyl ester Trans 4-(6-benzenesulfonyl-2-methyl-6H-1,2,3,5,6-tetraaza-as-indacen-1-yl)-cyclohexyl amine (1.00 g, 2.44 mmol) was dissolved in DCM (8 mL) and pyridine (8 mL). The mixture was cooled to 0° C. and 4-nitrophenyl chloroformate (986 mg, 4.88 mmol) was added. The mixture was allowed to return to room temperature and stirred for 1 h, then further 4-nitrophenyl chloroformate (986 mg, 4.88 mmol) was added. The mixture was stirred 1 h, then diluted with water and extracted into DCM (×3). The combined organic extracts were washed with brine then dried ($Na_2SO_4$) and concentrated. Purification by column chromatography on silica gel (gradient: 9:1 cyclohexane:ethyl acetate to neat ethyl acetate to 2:3 acetone:ethyl acetate) gave 880 mg (63%) of trans[4-(6-benzenesulfonyl-2-methyl-6H-1,2,3,5,6-tetraaza-as-indacen-1-yl)-cyclohexyl]-carbamic acid 4-nitrophenyl ester. LCMS (Method B, ESI): RT=3.60 min, m+H=575.4.

Trans 3-[4-(6-benzenesulfonyl-2-methyl-6H-1,2,3,5,6-tetraaza-as-indacen-1-yl)-cyclohexyl]-1,1-dimethyl-urea Trans [4-(6-benzenesulfonyl-2-methyl-6H-1,2,3,5,6-tetraaza-as-indacen-1-yl)-cyclohexyl]-carbamic acid 4-nitrophenyl ester (198 mg, 0.35 mmol) was suspended in a solution of dimethylamine (approx. 2 M) in THF (1.5 ml). The mixture was heated at 60° C. for 30 min, then concentrated under vacuum. The residue was dissolved in methanol and acidified with 1 M aqueous HCl, then purified by Isolute® SCX column (gradient: methanol to 2 M $NH_3$ in methanol) to give 135 mg (81%) trans 3-[4-(6-benzenesulfonyl-2-methyl-6H-1,2,3,5,6-tetraaza-as-indacen-1-yl)-cyclohexyl]-1,1-dimethyl-urea, which was used directly without further purification. LCMS (Method B, ESI): RT=2.83 min, m+H=481.5.

Trans 1,1-dimethyl-3-[4-(2-methyl-6H-1,2,3,5,6-tetraaza-as-indacen-1-yl)-cyclohexyl]-urea Trans 3-[4-(6-benzenesulfonyl-2-methyl-6H-1,2,3,5,6-tetraaza-as-indacen-1-yl)-cyclohexyl]-1,1-dimethyl-urea (135 mg, 0.28 mmol) was dissolved in methanol (1.5 mL) and THF (1.5 mL). 2 M Aqueous NaOH (1.5 mL) was added and the mixture was stirred at rt for 2 h, then concentrated. The residue was neutralised with 1 N HCl (3 mL), then concentrated. Purification by column chromatography on silica gel (gradient: DCM to 6% (2 M $NH_3$ in methanol) in DCM) and subsequent trituration with acetonitrile gave 51 mg (55%) of trans 1,1-dimethyl-3-[4-(2-methyl-6H-1,2,3,5,6-tetraaza-as-indacen-1-yl)-cyclohexyl]-urea. LCMS (Method A, ESI): RT=2.13 min, m+H=341.3; NMR (400 MHz, DMSO) δ: 11.80 (s, 1H), 8.46 (s, 1H), 7.49 (t, 1H), 6.65 (dd, 1H), 6.06 (d, 1H), 4.43 (s, 1H), 3.75 (m, 1H), 2.81 (s, 6H), 2.64 (s, 3H), 2.36 (m, 2H), 2.08-1.90 (m, 4H), 1.66-1.51 (m, 2H).

Example 605

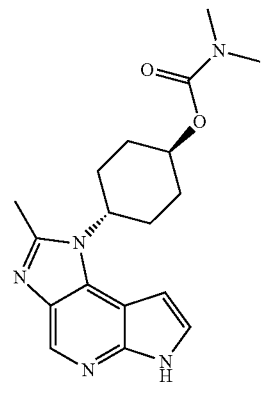

Trans dimethyl-carbamic acid 4-(2-methyl-6H-1,2,3,5,6-tetraaza-as-indacen-1-yl)-cyclohexyl ester Trans 4-(1-benzenesulfonyl-5-nitro-1H-pyrrolo[2,3-b]pyridin-4-ylamino)-cyclohexanol 1-Benzenesulfonyl-4-chloro-5-nitro-1H-pyrrolo[2,3-b]pyridine (50.0 g, 148 mmol) was suspended in isopropanol (400 mL) and DIPEA (35.0 mL, 207 mmol) was added, followed by trans-4-aminocyclohexanol (18.7 g, 163 mmol). The mixture was heated at reflux for 2 hours, then cooled and concentrated under vacuum. The residue was dissolved in dichloromethane and washed with water (added 1 N HCl to bring pH to 6-7). The organic layer was dried ($Na_2SO_4$) and concentrated under vacuum. The residual foam was taken up in ethanol and the resulting precipitate collected to give 65.0 g (quant) of crude trans 4-(1-benzenesulfonyl-5-nitro-1H-pyrrolo[2,3-b]pyridin-4-ylamino)-cyclohexanol. NMR (400 MHz, $CDCl_3$) δ: 9.10 (s, 1H), 9.03 (d, 1H), 8.19 (dd, 2H), 7.62 (m, 2H), 7.52 (m, 2H), 6.71 (d, 1H), 3.95 (m, 1H), 3.79 (m, 1H), 3.78-3.67 (m, 2H), 2.22 (m, 2H), 2.08 (m, 2H), 1.59 (m, 1H), 1.54 (m, 4H).

Trans 4-(5-amino-1-benzenesulfonyl-1H-pyrrolo[2,3-b]pyridin-4-ylamino)-cyclohexanol Crude trans 4-(1-benzenesulfonyl-5-nitro-1H-pyrrolo[2,3-b]pyridin-4-ylamino)-cyclohexanol (65.0 g, approx. 148 mmol) was suspended in ethanol (1000 mL, IMS grade) and water (300 mL). Ammonium chloride (47.5 g, 888 mmol) was added, and the mixture was stirred at 50° C. Powdered iron (33.0 g, 592 mmol) was added slowly and the resulting mixture was stirred at reflux for 2 h, then cooled to room temperature. The mixture was filtered and the filter cake washed with further ethanol, then the combined filtrate was concentrated under vacuum. The residue was suspended in water and extracted with dichloromethane (×2) and the combined organic extracts were dried ($Na_2SO_4$) and concentrated under vacuum. The residue was triturated with methanol then water to give 19.0 g (33%) of trans 4-(5-amino-1-benzenesulfonyl-1H-pyrrolo[2,3-b]pyridin-4-ylamino)-cyclohexanol. The methanol mother liquor was concentrated and the resulting residue triturated with acetonitrile to give a further 11.0 g (19%) of trans 4-(5-amino-1-benzenesulfonyl-1H-pyrrolo[2,3-b]pyridin-4-ylamino)-cyclohexanol. NMR (400 MHz, DMSO) δ: 8.04 (m, 2H), 7.68 (m, 2H), 7.59 (m, 3H), 6.76 (d, 1H), 5.68 (br s, 1H), 3.71 (br s, 1H), 1.91 (m, 2H), 1.84 (m, 2H), 1.34 (m, 4H), further signals partially obscured residual water peak.

Trans 4-(6-benzenesulfonyl-2-methyl-6H-1,2,3,5,6-tetraaza-as-indacen-1-yl)-cyclohexanol Trans 4-(5-amino-1-benzenesulfonyl-1H-pyrrolo[2,3-b]pyridin-4-ylamino)-cyclohexanol (10 g, 26 mmol) was dissolved in acetic acid (100 mL) and triethyl orthoacetate (18.9 mL, 100 mmol) was added. The mixture was stirred at 120° C. for 15 min, after cooling the mixture was concentrated under vacuum. The residue was suspended in saturated aqueous $NaHCO_3$ and the mixture was extracted with DCM (×3). The combined organic extracts were washed sequentially with saturated aqueous $NaHCO_3$ and brine, then dried ($Na_2SO_4$) and concentrated to give 10.5 g (98%) of trans 4-(6-benzenesulfonyl-2-methyl-6H-1,2,3,5,6-tetraaza-as-indacen-1-yl)-cyclohexanol. LCMS (Method B, ESI): RT=2.71 min, m+H=411.1; NMR (400 MHz, $CDCl_3$) δ: 8.81 (s, 1H), 8.23 (d, 2H), 7.82 (d, 1H), 7.56 (t, 1H), 7.47 (t, 2H), 6.81 (d, 1H), 4.39 (br s, 1H), 3.97 (br s, 1H), 2.69 (s, 3H), 2.26 (m, 2H), 1.98 (m, 2H), 1.76 (m, 2H), 1.61 (m, 2H).

Trans carbonic acid 4-(6-benzenesulfonyl-2-methyl-6H-1,2,3,5,6-tetraaza-as-indacen-1-yl)-cyclohexyl ester 4-nitro-phenyl ester Trans 4-(6-benzenesulfonyl-2-methyl-6H-1,2,3,5,6-tetraaza-as-indacen-1-yl)-cyclohexanol (600 mg, 1.46 mmol) was dissolved in pyridine (5 mL) and DCM (5 mL). The mixture was cooled to 0° C. and 4-nitrophenyl chloroformate (472 mg, 2.34 mmol) was added. After stirring for 1 h, further 4-nitrophenyl chloroformate (443 mg, 2.19 mmol) was added and the mixture was allowed to return to room temperature and stirred for 1 h. Water was added and the mixture extracted with DCM (×3). The combined organic extracts were washed with brine then dried ($Na_2SO_4$) and concentrated under vacuum. Purification by column chromatography on silica gel (gradient: 9:1 cyclohexane:ethyl acetate to neat ethyl acetate to 1:4 ethyl acetate: acetone) gave 334 mg (40%) of trans carbonic acid 4-(6-benzenesulfonyl-2-methyl-6H-1,2,3,5,6-tetraaza-as-indacen-1-yl)-cyclohexyl ester 4-nitro-phenyl ester, which was used directly without further purification. LCMS (Method B, ESI): RT=3.87 min, m+H=576.3.

Trans dimethyl-carbamic acid 4-(6-benzenesulfonyl-2-methyl-6H-1,2,3,5,6-tetraaza-as-indacen-1-yl)-cyclohexyl ester Trans carbonic acid 4-(6-benzenesulfonyl-2-methyl-6H-1,2,3,5,6-tetraaza-as-indacen-1-yl)-cyclohexyl ester 4-nitro-phenyl ester (160 mg, 0.28 mmol) was dissolved in THF (1.5 mL) containing dimethylamine (approx. 2 M). The mixture was heated at 50° C. for 20 min, then concentrated under vacuum. The residue was dissolved in methanol and acidified with 1 M aqueous HCl, then the resulting mixture was purified by Isolute® SCX column (gradient: methanol to 2 M $NH_3$ in methanol) to give 125 mg (93%) of trans dimethyl-carbamic acid 4-(6-benzenesulfonyl-2-methyl-6H-1,2,3,5,6-tetraaza-as-indacen-1-yl)-cyclohexyl ester, which was used directly without further purification. LCMS (Method B, ESI): RT=3.27 min, m+H=382.4.

Trans dimethyl-carbamic acid 4-(2-methyl-6H-1,2,3,5,6-tetraaza-as-indacen-1-yl)-cyclohexyl ester Trans dimethyl-carbamic acid 4-(6-benzenesulfonyl-2-methyl-6H-1,2,3,5,6-tetraaza-as-indacen-1-yl)-cyclohexyl ester (125 mg, 0.26 mmol) was dissolved in THF (1.5 mL) and methanol (1.5 mL). 2 M Aqueous NaOH (1 mL) was added and the mixture was stirred at 50° C. for 45 min. 1 M Aqueous HCl (2 mL) was added and the mixture was concentrated. Purification by column chromatography on silica gel (gradient: DCM to 4% (2 M $NH_3$ in methanol) in DCM) and subsequent trituration with acetonitrile gave 60 mg (67%) of trans dimethyl-carbamic acid 4-(2-methyl-6H-1,2,3,5,6-tetraaza-as-indacen-1-yl)-cyclohexyl ester. LCMS (Method A, ESI): RT=2.60 min, m+H=342.3; NMR (400 MHz, DMSO) δ: 11.80 (s, 1H), 8.45 (s, 1H), 7.48 (t, 1H), 6.68 (s, 1H), 4.79

(m, 1H), 4.57 (s, 1H), 2.86 (s, 6H), 2.64 (s, 3H), 2.38 (m, 2H), 2.15 (m, 2H), 1.97 (m, 2H), 1.74 (m, 2H).

Example 606

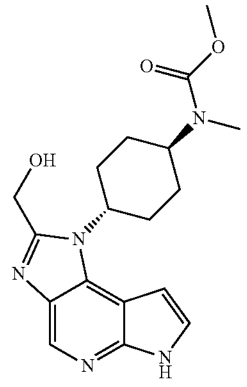 [SMILES: COC(=O)N(C)[C@H]1CC[C@H](n2c(CO)nc3cnc4[nH]ccc4c32)CC1]

Trans[4-(2-hydroxymethyl-6H-1,2,3,5,6-tetraaza-as-indacen-1-yl)-cyclohexyl]-methyl-carbamic acid methyl ester Trans acetic acid 6-benzenesulfonyl-1-(4-formylamino-cyclohexyl)-1,6-dihydro-1,2,3,5,6-tetraaza-as-indacen-2-ylmethyl ester Acetic anhydride (370 μL, 3.9 mmol) was added to formic acid (740 μL, 19.5 mmol) at 0° C. The mixture was stirred at 50° C. for 10 min, then cooled to 0° C. A solution of trans acetic acid 1-(4-amino-cyclohexyl)-6-benzenesulfonyl-1,6-dihydro-1,2,3,5,6-tetraaza-as-indacen-2-ylmethyl ester (367 mg, 0.79 mmol) in THF (4 mL) was added. The mixture was stirred for 1 h (allowed to return to room temperature). A further portion of acetic anhydride (370 μL, 3.9 mmol) and formic acid (740 μL, 19.5 mmol) premixed at 50° C. as before was added and the mixture stirred 30 min. Saturated aqueous $NaHCO_3$ was added and the mixture extracted with DCM (×3). The combined organic extracts were washed with brine then dried ($Na_2SO_4$) and concentrated under vacuum to give 346 mg (89%) of crude trans acetic acid 6-benzenesulfonyl-1-(4-formylamino-cyclohexyl)-1,6-dihydro-1,2,3,5,6-tetraaza-as-indacen-2-ylmethyl ester, which was used directly without further purification. LCMS (Method B, ESI): RT=2.97 min, m+H=482.3.

Trans[6-benzenesulfonyl-1-(4-methylamino-cyclohexyl)-1,6-dihydro-1,2,3,5,6-tetraaza-as-indacen-2-yl]-methanol Trans acetic acid 6-benzenesulfonyl-1-(4-formylamino-cyclohexyl)-1,6-dihydro-1,2,3,5,6-tetraaza-as-indacen-2-ylmethyl ester (315 mg, 0.64 mmol) was dissolved in a 1 M solution of borane in THF (3.8 mL, 3.8 mmol). The mixture was stirred for 1 h, then methanol was added carefully and the mixture was concentrated under vacuum. The residue was suspended in water (10 mL) and 37% concentrated HCl (2 mL) was added. The mixture was heated at 100° C. for 20 min, then cooled and purified by Isolute® SCX column (gradient: methanol to 2 M $NH_3$ in methanol) to give 196 mg (70%) of crude trans[6-benzenesulfonyl-1-(4-methylamino-cyclohexyl)-1,6-dihydro-1,2,3,5,6-tetraaza-as-indacen-2-yl]-methanol, which was used directly without further purification. LCMS (Method B, ESI): RT=2.26 min, m+H=440.3.

Trans[4-(6-benzenesulfonyl-2-hydroxymethyl-6H-1,2,3,5,6-tetraaza-as-indacen-1-yl)-cyclohexyl]-methyl-carbamic acid methyl ester Trans [6-benzenesulfonyl-1-(4-methylamino-cyclohexyl)-1,6-dihydro-1,2,3,5,6-tetraaza-as-indacen-2-yl]-methanol (196 mg, 0.45 mmol) was suspended in DCM (4 mL) and DIPEA (230 μL, 1.35 mmol) was added, followed by methyl chloroformate (87 μL, 1.12 mmol). The mixture was stirred at room temperature for 45 min, then concentrated under vacuum. The residue was suspended in methanol and acidified with 1 M aqueous HCl, then the mixture was purified by Isolute® SCX column (gradient: methanol to 2 M $NH_3$ in methanol) to give 256 mg (over quantitative) of crude trans [4-(6-benzenesulfonyl-2-hydroxymethyl-6H-1,2,3,5,6-tetraaza-as-indacen-1-yl)-cyclohexyl]-methyl-carbamic acid methyl ester, which was used directly without further purification. LCMS (Method B, ESI): RT=3.15 min, m+H=498.4.

Trans[4-(2-hydroxymethyl-6H-1,2,3,5,6-tetraaza-as-indacen-1-yl)-cyclohexyl]-methyl-carbamic acid methyl ester Trans [4-(6-benzenesulfonyl-2-hydroxymethyl-6H-1,2,3,5,6-tetraaza-as-indacen-1-yl)-cyclohexyl]-methyl-carbamic acid methyl ester (256 mg crude, assumed to be 0.45 mmol) was dissolved in THF (2 mL) and methanol (2 mL). 2 M Aqueous NaOH (2 mL) was added and the mixture was stirred for 45 min at 50° C. The mixture was concentrated under vacuum, then neutralised with 1 M aqueous HCl (4 mL) and concentrated. Purification by two rounds of column chromatography on silica gel (gradient: DCM to 10% (2 M $NH_3$ in methanol) in DCM, then DCM to 6% (2 M $NH_3$ in methanol) in DCM) followed by trituration with acetonitrile gave 44 mg (26%) of trans [4-(2-hydroxymethyl-6H-1,2,3,5,6-tetraaza-as-indacen-1-yl)-cyclohexyl]-methyl-carbamic acid methyl ester. LCMS (Method A, ESI): RT=2.45 min, m+H=358.3; NMR (400 MHz, DMSO) δ: 11.89 (s, 1H), 8.54 (s, 1H), 7.53 (s, 1H), 6.72 (s, 1H), 5.68 (t, 1H), 4.65 (d, 2H), 4.61 (m, 1H), 4.10 (s, 1H), 3.65 (s, 3H), 2.82 (s, 3H), 2.43 (m, 2H), 2.07 (m, 2H), 1.88-1.64 (m, 4H).

Example 607

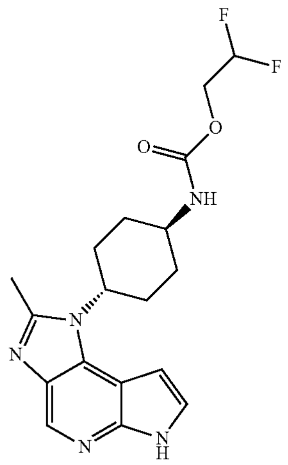 [SMILES: Cc1nc2cnc3[nH]ccc3c2n1[C@H]1CC[C@H](NC(=O)OCC(F)F)CC1]

Trans[4-(2-methyl-6H-1,2,3,5,6-tetraaza-as-indacen-1-yl)-cyclohexyl]-carbamic acid 2,2-difluoro-ethyl ester Trans[4-(6-benzenesulfonyl-2-methyl-6H-1,2,3,5,6-tetraaza-as-indacen-1-yl)-cyclohexyl]-carbamic acid 2,2-difluoro-ethyl ester Trans [4-(6-benzenesulfonyl-2-methyl-6H-1,2,3,5,6-tetraaza-as-indacen-1-yl)-cyclohexyl]-carbamic acid 4-nitrophenyl ester (250 mg, 0.44 mmol) was dissolved in 2,2-difluoroethanol (750 μL) and triethylamine (182 μL, 1.32 mmol) was added. The mixture was stirred at 60° C. for 20 min, then concentrated. Purification by column chromatography on silica gel (gradient: DCM to 6% methanol in DCM) gave 203 mg (89%) of trans [4-(6-benzenesulfonyl-2-methyl-6H-1,2,3,5,6-tetraaza-as-indacen-1-yl)-cyclohexyl]-carbamic acid 2,2-difluoro-ethyl ester. LCMS (Method B, ESI): RT=3.27 min, m+H=518.4.

Trans[4-(2-methyl-6H-1,2,3,5,6-tetraaza-as-indacen-1-yl)-cyclohexyl]-carbamic acid 2,2-difluoro-ethyl ester Trans [4-(6-benzenesulfonyl-2-methyl-6H-1,2,3,5,6-tetraaza-as-indacen-1-yl)-cyclohexyl]-carbamic acid 2,2-difluoro-ethyl ester (180 mg, 0.35 mmol) was dissolved in tetrahydrofuran (1.5 mL) and methanol (1.5 mL), and 2 M aqueous NaOH (1.5 mL) was added. The mixture was stirred at room temperature for 2.5 h, then neutralised with 1 N aqueous HCl (3 mL) and concentrated. Purification by column chromatography on silica gel (gradient: DCM to 6% (2 M $NH_3$ in methanol) in DCM) and further purification by reverse phase HPLC (gradient: 5% to 80% acetonitrile in water, 0.1% $NH_4OH$) gave 53 mg (39%) of trans [4-(2-methyl-6H-1,2,3,5,6-tetraaza-as-indacen-1-yl)-cyclohexyl]-carbamic acid 2,2-difluoro-ethyl ester. LCMS (Method A, ESI): RT=2.57 min, m+H=378.3; NMR (400 MHz, DMSO) δ: 11.78 (s, 1H), 8.44 (s, 1H), 7.63 (d, 1H), 7.47 (t, 1H), 6.63

(s, 1H), 6.23 (tt, 1H), 4.47 (m, 1H), 4.26 (t, 2H), 3.61 (m, 1H), 2.62 (s, 3H), 2.34 (m, 2H), 2.21-1.79 (m, 4H), 1.57 (m, 2H).

Example 608

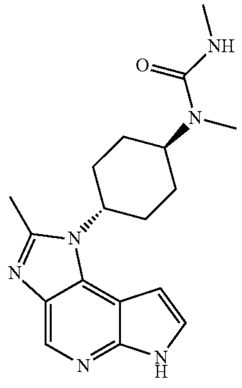

Trans 1,3-dimethyl-1-[4-(2-methyl-6H-1,2,3,5,6-tetraaza-as-indacen-1-yl)-cyclohexyl]-urea Trans N-[4-(6-benzenesulfonyl-2-methyl-6H-1,2,3,5,6-tetraaza-as-indacen-1-yl)-cyclohexyl]-formamide Acetic anhydride (342 μL, 3.6 mmol) was dissolved in formic acid (680 μL, 18 mmol) at 0° C. The mixture was stirred for 5 min, then stirred at 50° C. for 10 min, then cooled to 0° C. A solution of trans 4-(6-benzenesulfonyl-2-methyl-6H-1,2,3,5,6-tetraaza-as-indacen-1-yl)-cyclohexylamine (370 mg, 0.90 mmol) in THF (1 mL) was added and the mixture was stirred for 1.75 h at 0° C. Further acetic anhydride (86 μL, 0.90 mmol) and formic acid (170 μL, 4.5 mmol), premixed as described above, were added and the mixture was stirred a further 30 min at 0° C. Saturated aqueous $NaHCO_3$ was added and the mixture extracted with DCM (×3). The combined organic extracts were washed with brine then dried ($Na_2SO_4$) and concentrated under vacuum to give 390 mg (99%) of trans N-[4-(6-benzenesulfonyl-2-methyl-6H-1,2,3,5,6-tetraaza-as-indacen-1-yl)-cyclohexyl]-formamide which was used without further purification. LCMS (Method B, ESI): RT=2.66 min, m+H=438.3.

Trans[4-(6-benzenesulfonyl-2-methyl-6H-1,2,3,5,6-tetraaza-as-indacen-1-yl)-cyclohexyl]-methyl-amine Trans N-[4-(6-benzenesulfonyl-2-methyl-6H-1,2,3,5,6-tetraaza-as-indacen-1-yl)-cyclohexyl]-formamide (380 mg, 0.87 mmol) was dissolved in 1 M borane in THF (5 mL) and the mixture was stirred at room temperature for 2 h. A further 1 mL of 1 M borane in THF was added and the mixture stirred for 1 h. Methanol was added slowly dropwise, then the mixture was concentrated under vacuum. The residue was suspended in water (10 mL) and 37% aqueous HCl (2 mL), and the mixture was heated at 100° C. for 30 min, then cooled. Purification by Isolute® SCX column (gradient: methanol to 2 M $NH_3$ in methanol) gave 400 mg (109%) of crude trans [4-(6-benzenesulfonyl-2-methyl-6H-1,2,3,5,6-tetraaza-as-indacen-1-yl)-cyclohexyl]-methyl-amine, which was used directly without further purification. LCMS (Method B, ESI): RT=2.11 min, m+H=424.3.

Trans 1-[4-(6-benzenesulfonyl-2-methyl-6H-1,2,3,5,6-tetraaza-as-indacen-1-yl)-cyclohexyl]-1,3-dimethyl-urea Trans [4-(6-benzenesulfonyl-2-methyl-6H-1,2,3,5,6-tetraaza-as-indacen-1-yl)-cyclohexyl]-methyl-amine (204 mg, 0.48 mmol) was dissolved in acetonitrile (2 mL) and DIPEA (124 μL, 0.62 mmol) was added. N-succinimidyl-N-methylcarbamate (124 mg, 0.72 mmol) was added and the mixture was stirred at 50° C. for 30 min, then concentrated. Purification by column chromatography on silica gel (gradient: DCM to 8% methanol in DCM) gave 134 mg (58%) of trans 1-[4-(6-benzenesulfonyl-2-methyl-6H-1,2,3,5,6-tetraaza-as-indacen-1-yl)-cyclohexyl]-1,3-dimethyl-urea. LCMS (Method B, ESI): RT=2.80 min, m+H=481.4.

Trans 1,3-dimethyl-1-[4-(2-methyl-6H-1,2,3,5,6-tetraaza-as-indacen-1-yl)-cyclohexyl]-urea Trans 1-[4-(6-benzenesulfonyl-2-methyl-6H-1,2,3,5,6-tetraaza-as-indacen-1-yl)-cyclohexyl]-1,3-dimethyl-urea (123 mg, 0.26 mmol) was dissolved in THF (1.5 mL) and methanol (1.5 mL). 2 M Aqueous NaOH (1 mL) was added and the mixture was stirred at room temperature for 1 h, then at 50° C. for 5 min. The mixture was concentrated, then neutralised with 1 M aqueous HCl (2 mL) and concentrated. Purification by column chromatography on silica gel (gradient: DCM to 5% (2 M $NH_3$ in methanol) in DCM) followed by sequential trituration with ethyl acetate and acetonitrile gave 55 mg (63%) of trans 1,3-dimethyl-1-[4-(2-methyl-6H-1,2,3,5,6-tetraaza-as-indacen-1-yl)-cyclohexyl]-urea. LCMS (Method A, ESI): RT=2.08 min, m+H=341.3; NMR (400 MHz, DMSO) δ: 11.80 (s, 1H), 8.45 (s, 1H), 7.49 (s, 1H), 6.79 (s, 1H), 6.28 (s, 1H), 4.49 (m, 1H), 4.26 (m, 1H), 2.73 (s, 3H), 2.62-2.61 (m, 6H), 2.41 (m, 2H), 2.02-1.77 (m, 4H), 1.71 (d, 2H).

Example 609

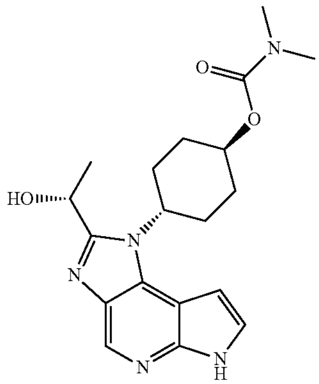 [SMILES: C[C@@H](O)c1nc2cnc3[nH]ccc3c2n1[C@H]1CC[C@H](OC(=O)N(C)C)CC1]

Trans dimethyl-carbamic acid 4-[2-((R)-1-hydroxy-ethyl)-6H-1,2,3,5,6-tetraaza-as-indacen-1-yl]-cyclohexyl ester Trans 1-benzenesulfonyl-N*4*-[4-(tert-butyl-dimethyl-silanyloxy)-cyclohexyl]-1H-pyrrolo[2,3-b]pyridine-4,5-diamine Trans 4-(5-amino-1-benzenesulfonyl-1H-pyrrolo[2,3-b]pyridin-4-ylamino)-cyclohexanol (5.00 g, 13.0 mmol) was dissolved in DCM (50 mL) and 2,6-lutidine (6.0 mL, 51.8 mmol) was added. The mixture was cooled to 0° C. and tert-butyldimethylsilyl triflate (8.90 mL, 38.9 mmol) was added dropwise. The mixture was allowed to return to room temperature and stirred for 16 h. The mixture was concentrated under vacuum, then the residue was dissolved in methanol (10 mL). This mixture was stirred at room temperature for 90 min, then concentrated. The residue was suspended in water and extracted with DCM (×3). The combined organic extracts were washed sequentially with 10% aqueous citric acid, saturated aqueous $NaHCO_3$ and brine, then dried ($Na_2SO_4$) and concentrated under vacuum. Purification by column chromatography on silica gel (gradient: DCM to 25% ethyl acetate in DCM) gave 3.09 g (48%) of trans 1-benzenesulfonyl-N*4*-[4-(tert-butyl-dimethyl-silanyloxy)-cyclohexyl]-1H-pyrrolo[2,3-b]pyridine-4,5-diamine. LCMS (Method B, ESI): RT=3.99 min, m+H=501.1; NMR (400 MHz, $CDCl_3$) δ: 8.14 (d, 2H), 7.84 (s, 1H), 7.54 (m, 1H), 7.45 (m, 3H), 6.55 (d, 1H), 3.70 (m, 2H), 2.35-1.85 (m, 6H), 1.46 (m, 2H), 1.30 (m, 2H), 0.89 (s, 9H), 0.06 (s, 6H).

Trans (R)-1-{6-benzenesulfonyl-1-[4-(tert-butyl-dimethyl-silanyloxy)-cyclohexyl]-1,6-dihydro-1,2,3,5,6-tetraaza-as-indacen-2-yl}-ethanol (R)-Lactamide (1.65 g, 18.5 mmol) was dissolved in THF (28 mL) and triethyloxonium tetrafluoroborate (3.52 g, 18.5 mmol) was added. The mixture was stirred for 3 h at room temperature, then concentrated under vacuum. The residue was dissolved in ethanol (14 mL, IMS grade) and added to a suspension of trans 1-benzenesulfonyl-N*4*-[4-(tert-butyl-dimethyl-silanyloxy)-cyclohexyl]-1H-pyrrolo[2,3-b]pyridine-4,5-diamine (3.09 g) in ethanol (42 mL, IMS grade). The mixture was stirred at 75° C. for 3 h, then cooled and concentrated under vacuum. The residue was dissolved in absolute ethanol (42 mL), and a further portion of (R)-Lactamide (1.65 g, 18.5 mmol) and triethyloxonium tetrafluoroborate (3.52 g, 18.5 mmol) premixed as above was added as a solution in absolute ethanol (14 mL). The resulting mixture was stirred at 75° C. for 45 min, then cooled to rt. Saturated aqueous $NaHCO_3$ was added and the mixture extracted with ethyl acetate (×3). The combined organic extracts were washed with brine then dried ($Na_2SO_4$) and concentrated under vacuum. Purification by column chromatography on silica gel (gradient: 3:1 cyclohexane: [1:1 DCM: ethyl acetate] to 1:4 cyclohexane: [1:1 DCM: ethyl acetate] to 1:1 DCM: ethyl acetate) gave 3.31 g (97%) of trans (R)-1-{6-benzenesulfonyl-1-[4-(tert-butyl-dimethyl-silanyloxy)-cyclohexyl]-1,6-dihydro-1,2,3,5,6-tetraaza-as-indacen-2-yl}-ethanol, which was used directly without further purification. LCMS (Method B, ESI): RT=4.70 min, m+H=555.3.

Trans 2-((R)-1-allyloxy-ethyl)-6-benzenesulfonyl-1-[4-(tert-butyl-dimethyl-silanyloxy)-cyclohexyl]-1,6-dihydro-1,2,3,5,6-tetraaza-as-indacene Trans (R)-1-{6-benzene sulfonyl-1-[4-(tert-butyl-dimethyl-silanyloxy)-cyclohexyl]-1,6-dihydro-1,2,3,5,6-tetraaza-as-indacen-2-yl}-ethanol (1 g, 1.81 mmol) was dissolved in THF (10 mL) and allyl t-butyl carbonate (1.42 g, 8.05 mmol) was added. The mixture was evacuated and purged with nitrogen (×3). Palladium tetrakistriphenylphosphine (105 mg, 0.081 mmol) was added and the mixture heated at 85° C. under nitrogen for 1 h. The mixture was concentrated, then purification by silica gel chromatography (gradient: cyclohexane to 1:2 ethyl acetate: cyclohexane) gave 715 mg (66%) of trans 2-((R)-1-allyloxy-ethyl)-6-benzenesulfonyl-1-[4-(tert-butyl-dimethyl-silanyloxy)-cyclohexyl]-1,6-dihydro-1,2,3,5,6-tetraaza-as-indacene. LCMS (Method B, ESI): RT=5.36 min, m+H=595.44.

Trans 4-[2-((R)-1-allyloxy-ethyl)-6-benzenesulfonyl-6H-1,2,3,5,6-tetraaza-as-indacen-1-yl]-cyclohexanol Trans 2-((R)-1-allyloxy-ethyl)-6-benzenesulfonyl-1-[4-(tert-butyl-dimethyl-silanyloxy)-cyclohexyl]-1,6-dihydro-1,2,3,5,6-tetraaza-as-indacene (710 mg) was dissolved in ethanol (10 mL, IMS grade) and 37% aqueous HCl (100 μL) was added, The mixture was stirred at room temperature for 1 h, then a further 100 μL of HCl was added. The mixture was stirred a further 90 min, then concentrated under vacuum. The residue was triturated with cyclohexane then dried under vacuum to give 490 mg (85%) of trans 4-[2-((R)-1-allyloxy-ethyl)-6-benzenesulfonyl-6H-1,2,3,5,6-tetraaza-as-indacen-1-yl]-cyclohexanol. LCMS (Method B, ESI): RT=3.31 min, m+H=481.4; NMR (400 MHz, DMSO) δ: 8.88 (s, 1H), 8.23 (m, 2H), 7.84 (d, 1H), 7.56 (t, 1H), 7.48 (t, 2H), 6.85 (d, 1H), 5.87 (m, 1H), 5.28 (m, 1H), 5.19 (m, 1H), 5.11-4.91 (m, 1H), 4.06-3.89 (m, 3H), 3.42 (m, 2H), 2.45-2.17 (m, 4H), 2.03-1.82 (m, 2H), 1.72 (d, 3H), Trans dimethyl-carbamic acid 4-[2-((R)-1-allyloxy-ethyl)-6-benzenesulfonyl-6H-1,2,3,5,6-tetraaza-as-indacen-1-yl]-cyclohexyl ester Trans 4-[2-((R)-1-allyloxy-ethyl)-6-benzenesulfonyl-6H-1,2,3,5,6-tetraaza-as-indacen-1-yl]-cyclohexanol (200 mg, 0.42 mmol) was dissolved in THF (2.5 mL) and carbonyl diimidazole (135 mg, 0.84 mmol) was added. The mixture was stirred at room temperature for 90 min. A solution of dimethylamine in THF (2.5 mL, approx. 2 M) was added and the mixture was stirred 30 min, then concentrated under vacuum. The residue was suspended in saturated aqueous $NaHCO_3$ and extracted with DCM (×3). The combined organic extracts were dried ($Na_2SO_4$) and concentrated. Purification by column chromatography on silica gel (gradient: 4:1 cyclohexane: ethyl acetate to 2:3) gave 170 mg (74%) of trans dimethyl-carbamic acid 4-[2-((R)-1-allyloxy-ethyl)-6-benzenesulfonyl-6H-1,2,3,5,6-tetraaza-as-indacen-1-yl]-cyclohexyl ester. LCMS (Method B, ESI): RT=3.99 min, m+H=552.5.

Trans dimethyl-carbamic acid 4-[6-benzenesulfonyl-2-((R)-1-hydroxy-ethyl)-6H-1,2,3,5,6-tetraaza-as-indacen-1-yl]-cyclohexyl ester Trans dimethyl-carbamic acid 4-[2-((R)-1-allyloxy-ethyl)-6-benzenesulfonyl-6H-1,2,3,5,6-tetraaza-as-indacen-1-yl]-cyclohexyl ester (100 mg, 0.18 mmol) was dissolved in THF (2 mL). The solution was evacuated and purged with nitrogen (×3). 1,3-dimethylbarbituric acid (142 mg, 0.90 mmol) was added, then tetrakis(triphenylphosphinyl)palladium (0) (21 mg, 0.018 mmol). The mixture was stirred under nitrogen at 90° C. for 2.5 h then concentrated under vacuum. The residue was purified by Isolute® SCX column (gradient: methanol to 2 M $NH_3$ in methanol) to give 105 mg (114%) of crude trans dimethyl-carbamic acid 4-[6-benzenesulfonyl-2-((R)-1-hydroxy-ethyl)-6H-1,2,3,5,6-tetraaza-as-indacen-1-yl]-cyclohexyl ester, which was used directly without further purification. LCMS (Method B, ESI): RT=3.30 min, m+H=512.4.

Trans dimethyl-carbamic acid 4-[2-((R)-1-hydroxy-ethyl)-6H-1,2,3,5,6-tetraaza-as-indacen-1-yl]-cyclohexyl ester Trans dimethyl-carbamic acid 4-[6-benzenesulfonyl-2-(R)-1-hydroxy-ethyl)-6H-1,2,3,5,6-tetraaza-as-indacen-1-yl]- cyclohexyl ester (105 mg, approx. 0.18 mmol) was dissolved in THF (1 mL) and methanol (1 mL). 2 M Aqueous NaOH (1 mL) was added and the mixture was stirred at room temperature for 1 h, then at 40° C. for 30 min. The mixture was cooled to room temperature and neutralised with 1 M aqueous HCl (2 mL), then concentrated. Purification by column chromatography on silica gel (gradient: DCM to 6% (2 M $NH_3$ in methanol) in DCM) and subsequent trituration with acetonitrile gave 27 mg (36% over two steps) of trans dimethyl-carb amic acid 4-[2-((R)-1-hydroxy-ethyl)-6H-1,2,3,5,6-tetraaza-as-indacen-1-yl]-cyclohexyl ester. LCMS (Method A, ESI): RT=2.68 min, m+H=372.4; NMR (400 MHz, DMSO) δ: 11.87 (s, 1H), 8.55 (s, 1H), 7.51 (t, 1H), 6.67 (s, 1H), 5.67 (d, 1H), 5.14 (m, 1H), 4.85 (m, 2H), 2.86 (s, 6H), 2.45 (m, 2H), 2.17 (m, 2H), 1.98 (m, 2H), 1.64 (d, 3H).

Example 610

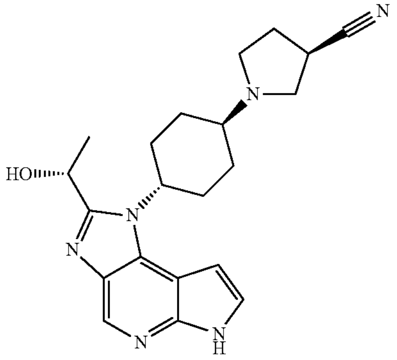 [SMILES: C[C@@H](O)c1nc2cnc3[nH]ccc3c2n1[C@H]1CC[C@H](N2CC[C@@H](C#N)C2)CC1]

Trans (R)-1-{4-[2-((R)-1-hydroxy-ethyl)-6H-1,2,3,5,6-tetraaza-as-indacen-1-yl]-cyclohexyl}-pyrrolidine-3-carbonitrile 4-[2-((R)-1-Allyloxy-ethyl)-6-benzenesulfonyl-6H-1,2,3,5,6-tetraaza-as-indacen-1-yl]-cyclohexanone Trans 4-[2-((R)-1-allyloxy-ethyl)-6-benzenesulfonyl-6H-1,2,3,5,6-tetraaza-as-indacen-1-yl]-cyclohexanol (271 mg, 0.56 mmol) was dissolved in DMSO (4 mL) and triethylamine (390 μL, 2.80 mmol) was added. The mixture was cooled to 0° C. and sulfur trioxide pyridine complex (356 mg, 2.24 mmol) was added. The mixture was allowed to return to room temperature and stirred for 2 h. Water was added and the mixture was extracted with DCM (×2). The combined organic extracts were washed sequentially with water and brine, then dried ($Na_2SO_4$) and concentrated under vacuum. The residue was triturated with diethyl ether to give 204 mg (76%) of 4-[2-((R)-1-allyloxy-ethyl)-6-benzenesulfonyl-6H-1,2,3,5,6-tetraaza-as-indacen-1-yl]-cyclohexanone. LCMS (Method B, ESI): RT=3.61 min, m+H=479.4; $^1$H-NMR (400 MHz, DMSO) δ: 8.74 (s, 1H), 8.13 (m, 2H), 8.02 (d, 1H), 7.71 (t, 1H), 7.62 (t, 2H), 7.17 (t, 1H), 5.90 (m, 1H), 5.28 (m, 2H), 5.21 (q, 1H), 5.13 (d, 1H), 4.03 (m, 2H), 2.80 (m, 2H), 2.60 (m, 2H), 2.41 (m, 2H), 2.16 (m, 2H), 1.68 (d, 3H).

Trans (R)-1-{4-[2-((R)-1-allyloxy-ethyl)-6-benzenesulfonyl-6H-1,2,3,5,6-tetraaza-as-indacen-1-yl]-cyclohexyl}-pyrrolidine-3-carbonitrile 4-[2-((R)-1-Allyloxy-ethyl)-6-benzenesulfonyl-6H-1,2,3,5,6-tetraaza-as-indacen-1-yl]-cyclohexanone (186 mg, 0.39 mmol) was dissolved in methanol (0.75 mL) and (R)-3-cyanopyrrolidine (71 mg, 0.74 mmol) was added, followed by titanium isopropoxide (209 μL, 0.70 mmol). The mixture was stirred at room temperature for 30 min, then at 80° C. for 2 h. After cooling to room temperature, THF (1 mL) was added and the mixture was cooled to −78° C. A suspension of lithium borohydride (9 mg, 0.39 mmol) in THF (0.75 mL) was added, and the mixture was stirred for 64 h (allowed to return to room temperature). The mixture was concentrated in vacuo, then suspended in water and DCM. The mixture was filtered through Celite®, then the layers were separated and the aqueous layer extracted with DCM (×3). The combined organic extracts were dried ($Na_2SO_4$) and concentrated. Purification by column chromatography on silica gel (gradient: 9:1 cyclohexane:ethyl acetate to neat ethyl acetate to 2% methanol in ethyl acetate) gave 45 mg (21%) of trans (R)-1-{4-[2-((R)-1-allyloxy-ethyl)-6-benzenesulfonyl-6H-1,2,3,5,6-tetraaza-as-indacen-1-yl]-cyclohexyl}-pyrrolidine-3-carbonitrile. LCMS (Method B, ESI): RT=2.79 min, m+H=559.5; NMR (400 MHz, DMSO) δ: 8.72 (s, 1H), 8.15-8.11 (m, 2H), 8.00 (d, 1H), 7.72-7.67 (m, 1H), 7.61 (t, 2H), 7.10 (d, 1H), 5.88 (m, 1H), 5.25 (dd, 1H), 5.13-5.12 (m, 2H), 4.72 (m, 1H), 3.99 (d, 2H), 3.27 (m, 1H), 2.92-2.78 (m, 3H), 2.61 (m, 1H), 2.18 (m, 3H), 1.95 (m, 3H), 1.63 (d, 3H), 1.46 (m, 2H).

Trans (R)-1-{4-[6-benzenesulfonyl-2-((R)-1-hydroxy-ethyl)-6H-1,2,3,5,6-tetraaza-as-indacen-1-yl]-cyclohexyl}-pyrrolidine-3-carbonitrile Trans (R)-1-{4-[2-((R)-1-allyloxy-ethyl)-6-benzenesulfonyl-6H-1,2,3,5,6-tetraaza-as-indacen-1-yl]-cyclohexyl}-pyrrolidine-3-carbonitrile (40.0 mg, 72.0 μmol) was dissolved in THF (2 mL) and 1,3-dimethylbarbituric acid (56.0 mg, 0.36 mmol) was added. The mixture was evacuated and purged with nitrogen (×3). Tetrakis(triphenylphosphinyl)palladium (7.20 μmol) was added and the mixture was stirred at 90° C. for 4 h. The mixture was cooled to room temperature and concentrated under vacuum. The residue was taken up in methanol and water and purified by Isolute® SCX column (gradient: methanol to 2 M $NH_3$ in methanol) to give 40 mg (quantitative) of crude trans (R)-1-{-4-[6-benzenesulfonyl-2-((R)-1-hydroxy-ethyl)-6H-1,2,3,5,6-tetraaza-as-indacen-1-yl]-cyclohexyl}-pyrrolidine-3-carbonitrile, which was used directly without further purification. LCMS (Method B, ESI): RT=2.44 min, m+H=519.5.

Trans (R)-1-{4-[2-((R)-1-hydroxy-ethyl)-6H-1,2,3,5,6-tetraaza-as-indacen-1-yl]-cyclohexyl}-pyrrolidine-3-carbonitrile Trans (R)-1-{4-[6-benzenesulfonyl-2-((R)-1-hydroxy-ethyl)-6H-1,2,3,5,6-tetraaza-as-indacen-1-yl]-cyclohexyl}-pyrrolidine-3-carbonitrile (40.0 mg, assumed to be 72.0 μmol) was dissolved in THF (0.5 mL) and methanol (0.5 mL). 2 M Aqueous NaOH (0.5 mL) was added and the mixture was stirred at room temperature for 3 h. 1 M Aqueous HCl (1 mL) was added and the mixture was concentrated. Purification by column chromatography on silica gel (gradient: DCM to 6% (2 M $NH_3$ in methanol) in DCM) followed by trituration with acetonitrile gave 11 mg (38%) of trans (R)-1-{4-[2-((R)-1-hydroxy-ethyl)-6H-1,2,3,5,6-tetraaza-as-indacen-1-yl]-cyclohexyl}-pyrrolidine-3-carbonitrile. LCMS (Method A, ESI): RT=1.50 min, m+H=379.1; NMR (400 MHz, DMSO) δ: 11.85 (s, 1H), 8.55 (s, 1H), 7.47 (t, 1H), 6.71 (s, 1H), 5.66 (d, 1H), 5.12 (m, 1H), 4.83 (m, 1H), 3.26-3.25 (m, 1H), 2.86-2.85 (m, 3H), 2.64-2.63 (m, 1H), 2.40 (m, 3H), 2.17 (m, 3H), 1.94 (m, 3H), 1.63 (d, 3H), 1.46 (m, 2H).

Example 611

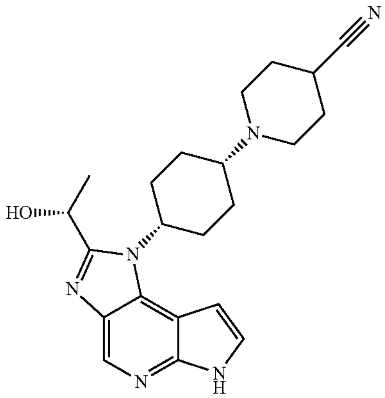 [SMILES: C[C@@H](O)c1nc2cnc3[nH]ccc3c2n1[C@H]1CC[C@@H](N2CCC(C#N)CC2)CC1]

Cis 1-{4-[2-(1-hydroxy-ethyl)-6H-1,2,3,5,6-tetraaza-as-indacen-1-yl]-cyclohexyl}-piperidine-4-carbonitrile Cis 1-{4-[2-((R)-1-allyloxy-ethyl)-6-benzenesulfonyl-6H-1,2,3,5,6-tetraaza-as-indacen-1-yl]-cyclohexyl}-piperidine-4-carbonitrile 4-[2-((R)-1-Allyloxy-ethyl)-6-benzenesulfonyl-6H-1,2,3,5,6-tetraaza-as-indacen-1-yl]-cyclohexanone (140 mg, 0.29 mmol) was suspended in toluene (2 mL) and 4-cyanopiperidine (130 μL, 1.08 mmol) was added, followed by dried 4 Å powdered molecular sieves (250 mg). The mixture was stirred at 125° C. for 16 h, then cooled. Solid was removed by decanting and the mixture was concentrated under vacuum. The residue was dissolved in THF (4 mL) and sodium triacetoxyborohydride (74 mg, 0.35 mmol) was added. The mixture was stirred for 30 min, then a further 31 mg sodium triacetoxyborohydride was added and the mixture stirred a further 1.5 h. Saturated aqueous $Na_2CO_3$ was added and the mixture was extracted with DCM (×3). The combined organic extracts were washed with brine then dried ($Na_2SO_4$) and concentrated. Purification by column chromatography on silica gel (gradient: 9:1 cyclohexane:ethyl acetate to 3:2 cyclohexane:ethyl acetate) gave 53 mg (32%) of cis 1-{4-[2-((R)-1-allyloxy-ethyl)-6-benzenesulfonyl-6H-1,2,3,5,6-tetraaza-as-indacen-1-yl]-cyclohexyl}-piperidine-4-carbonitrile, which was used directly without further purification. LCMS (Method B, ESI): RT=3.34 min, m+H=573.5.

Cis 1-{4-[2-(1-hydroxy-ethyl)-6H-1,2,3,5,6-tetraaza-as-indacen-1-yl]-cyclohexyl}-piperidine-4-carbonitrile Cis 1-{4-[2-((R)-1-allyloxy-ethyl)-6-benzenesulfonyl-6H-1,2,3,5,6-tetraaza-as-indacen-1-yl]-cyclohexyl}-piperidine-4-carbonitrile (70.0 mg, 0.12 mmol) was dissolved in THF (2 mL) and 1,3-dimethylbarbituric acid (94.0 mg, 0.60 mmol) was added. The mixture was evacuated and purged with nitrogen (×3). Tetrakis(triphenylphosphinyl)palladium (14 mg, 12.0 μmol) was added and the mixture was stirred at 90° C. for 3 h. The mixture was cooled then diluted with methanol and water and purified by Isolute® SCX column (gradient: methanol to 2 M $NH_3$ in methanol) to give 65 mg of crude cis 1-{-4-[6-benzenesulfonyl-2-((R)-1-hydroxy-ethyl)-6H-1,2,3,5,6-tetraaza-as-indacen-1-yl]-cyclohexyl}-piperidine-4-carbonitrile. LCMS (Method B, ESI): RT=2.59, m+H=533.5. This was dissolved in THF (0.5 mL) and methanol (0.5 mL) and 2 M aqueous NaOH (0.5 mL) was added. The mixture was stirred at room temperature for 3 h, then at 50° C. for 1 h. 1 M Aqueous HCl (1 mL) was added and the mixture was concentrated. Purification by column chromatography on silica gel (gradient: DCM to 5% (2 M $NH_3$ in methanol) in DCM) followed by sequential trituration with acetonitrile and methanol gave 12 mg (25%) of cis 1-{4-[2-(1-hydroxy-ethyl)-6H-1,2,3,5,6-tetraaza-as-indacen-1-yl]-cyclohexyl}-piperidine-4-carbonitrile. LCMS (Method A, ESI): RT=1.86 min, m+H=393.1; NMR (400 MHz, DMSO) δ: 11.74 (s, 1H), 8.53 (s, 1H), 7.91 (s, 1H), 7.38 (s, 1H), 5.65 (d, 1H), 5.12 (m, 1H), 4.89 (m, 1H), 3.08 (m, 1H), 2.69 (m, 2H), 2.54 (m, 2H), 2.24 (m, 3H), 2.09 (m, 2H), 1.95 (m, 2H), 1.63 (m, 7H), plus two signals obscured by the solvent peak.

Example 612

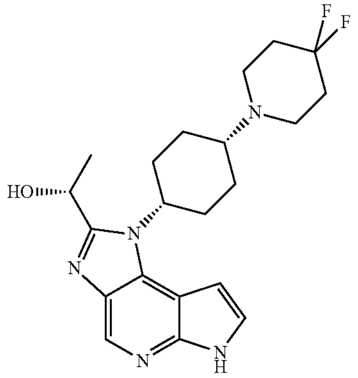 [SMILES: C[C@@H](O)c1nc2cnc3[nH]ccc3c2n1[C@H]1CC[C@@H](N2CCC(F)(F)CC2)CC1]

Cis (R)-1-{1-[4-(4,4-difluoro-piperidin-1-yl)-cyclohexyl]-1,6-dihydro-1,2,3,5,6-tetraaza-as-indacen-2-yl}-ethanol Cis 2-((R)-1-allyloxy-ethyl)-6-benzenesulfonyl-1-[4-(4,4-difluoro-piperidin-1-yl)-cyclohexyl]-1,6-dihydro-1,2,3,5,6-tetraaza-as-indacene 4-[2-((R)-1-Allyloxy-ethyl)-6-benzenesulfonyl-6H-1,2,3,5,6-tetraaza-as-indacen-1-yl]-cyclohexanone (305 mg, 0.64 mmol) was suspended in toluene (3 mL) and DIPEA (437 μL, 2.56 mmol) was added, followed by 4-difluoropiperidine hydrochloride (403 mg, 2.56 mmol). Dried 4 Å powdered molecular sieves (500 mg) were then added and the mixture was stirred at 120° C. for 16 h, then allowed to cool. The suspension was decanted to remove solid then concentrated. The residue was dissolved in THF (6 mL) and cooled to 0° C. Sodium triacetoxyborohydride (271 mg, 1.28 mmol) was added and the mixture was stirred at 0° C. for 1 h. Saturated aqueous $Na_2CO_3$ was added and the mixture extracted with DCM (×3). The combined organic extracts were washed with brine then dried ($Na_2SO_4$) and concentrated. Purification by column chromatography on silica gel (gradient: 9:1 cyclohexane:ethyl acetate to 1:1 cyclohexane:ethyl acetate) gave 93 mg (34%) of cis 2-((R)-1-allyloxy-ethyl)-6-benzenesulfonyl-1-[4-(4,4-difluoro-piperidin-1-yl)-cyclohexyl]-1,6-dihydro-1,2,3,5,6-tetraaza-as-indacene. LCMS (Method B, ESI): RT=4.33 min, m+H=584.4.

Cis (R)-1-{1-[4-(4,4-difluoro-piperidin-1-yl)-cyclohexyl]-1,6-dihydro-1,2,3,5,6-tetraaza-as-indacen-2-yl}-ethanol Following the procedure for cis 1-{4-[2-(1-hydroxy-ethyl)-6H-1,2,3,5,6-tetraaza-as-indacen-1-yl]-cyclohexyl}-piperidine-4-carbonitrile, the title compound was prepared from 93 mg (0.16 mmol) of cis 2-((R)-1-allyloxy-ethyl)-6-benzenesulfonyl-1-[4-(4,4-difluoro-piperidin-1-yl)-cyclohexyl]-1,6-dihydro-1,2,3,5,6-tetraaza-as-indacene, with further purification by column chromatography on silica gel (gradient: DCM to 5% (2 M $NH_3$ in methanol) in DCM). Subsequent trituration with acetonitrile then methanol gave 10 mg (16%) of cis (R)-1-{1-[4-(4,4-difluoro-piperidin-1-yl)-cyclohexyl]-1,6-dihydro-1,2,3,5,6-tetraaza-as-indacen-2-yl}-ethanol. LCMS (Method A, ESI): RT=2.51 min, m+H=404.1; NMR (400 MHz, DMSO) δ: 11.76 (s, 1H), 8.53 (s, 1H), 7.85 (s, 1H), 7.29 (t, 1H), 5.67 (d, 1H), 5.13 (m, 1H), 4.90 (m, 1H), 2.71 (m, 4H), 2.55 (s, 2H), 2.38 (s, 1H), 2.30-2.10 (m, 6H), 1.63 (d, 7H).

Example 613

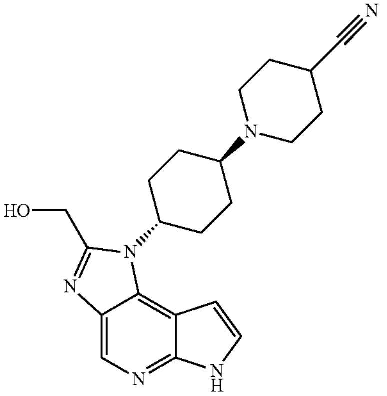 [SMILES: N#CC1CCN([C@H]2CC[C@H](n3c(CO)nc4cnc5[nH]ccc5c43)CC2)CC1]

Trans 1-[4-(2-hydroxymethyl-6H-1,2,3,5,6-tetraaza-as-indacen-1-yl)-cyclohexyl]-piperidine-4-carbonitrile 4-(2-Allyloxymethyl-6-benzenesulfonyl-6H-1,2,3,5,6-tetraaza-as-indacen-1-yl)-cyclohexanone Trans 4-(2-allyloxymethyl-6-benzenesulfonyl-6H-1,2,3,5,6-tetraaza-as-indacen-1-yl)-cyclohexanol (1.11 g, 2.38 mmol) was dissolved in DMSO (20 mL) and triethylamine (2.48 mL, 17.9 mmol) was added, followed by sulfur trioxide pyridine complex (2.27 g, 14.3 mmol). The mixture was stirred at room temperature for 16 h. Water was added and the mixture was extracted with DCM (×2). The combined organic extracts were washed with water then brine, then dried ($Na_2SO_4$) and concentrated. Purification by column chromatography on silica gel (gradient: 9:1 cyclohexane:ethyl acetate to 1:4 cyclohexane:ethyl acetate) gave 792 mg (70%) of 4-(2-allyloxymethyl-6-benzenesulfonyl-6H-1,2,3,5,6-tetraaza-as-indacen-1-yl)-cyclohexanone. LCMS (Method B, ESI:) RT=3.53 min, m+H=465.4; NMR (400 MHz, $CDCl_3$) δ: 8.90 (s, 1H), 8.25 (m, 2H), 7.85 (d, 1H), 7.57 (t, 1H), 7.49 (t, 2H), 6.68 (d, 1H), 5.87 (m, 1H), 5.33-5.15 (m, 3H), 4.92 (s, 2H), 4.03 (m, 2H), 2.80-2.60 (m, 6H), 2.36-2.28 (m, 2H).

Trans 1-[4-(2-allyloxymethyl-6-benzenesulfonyl-6H-1,2,3,5,6-tetraaza-as-indacen-1-yl)-cyclohexyl]-piperidine-4-carbonitrile 4-(2-allyloxymethyl-6-benzenesulfonyl-6H-1,2,3,5,6-tetraaza-as-indacen-1-yl)-cyclohexanone (250 mg, 0.54 mmol) was suspended in toluene (3 mL) and 4-cyanopiperidine (302 μL, 2.70 mmol) was added, followed by dried 4 Å powdered molecular sieves (500 mg). The mixture was stirred at 120° C. for 16 h, then decanted to remove solids and concentrated. The residue was taken up in acetic acid (3 mL) and sodium borohydride (22 mg, 0.60 mmol) was added. The mixture was stirred for 45 min, then saturated aqueous $Na_2CO_3$ was added. The mixture was extracted with DCM (×3), and the combined organics were dried ($Na_2SO_4$) and concentrated. Purification by column chromatography on silica gel (gradient: 9:1 cyclohexane:ethyl acetate to neat ethyl acetate to 10% methanol in ethyl acetate) gave 40 mg (13%) of trans 1-[4-(2-allyloxymethyl-6-benzenesulfonyl-6H-1,2,3,5,6-tetraaza-as-indacen-1-yl)-cyclohexyl]-piperidine-4-carbonitrile. LCMS (Method B, ESI): RT=2.68 min, m+H=559.4.

Trans 1-[4-(2-hydroxymethyl-6H-1,2,3,5,6-tetraaza-as-indacen-1-yl)-cyclohexyl]-piperidine-4-carbonitrile Following the procedure for cis 1-{4-[2-(1-hydroxy-ethyl)-6H-1,2,3,5,6-tetraaza-as-indacen-1-yl]-cyclohexyl}-piperidine-4-carbonitrile, the title compound was prepared from 40 mg (0.072 mmol) of trans 1-[4-(2-allyloxymethyl-6-benzenesulfonyl-6H-1,2,3,5,6-tetraaza-as-indacen-1-yl)-cyclohexyl]-piperidine-4-carbonitrile, with further purification by column chromatography on silica gel (gradient: DCM to 6% (2 M $NH_3$ in methanol) in DCM) and subsequent trituration with acetonitrile to give 13 mg (48%) of trans 1-[4-(2-hydroxymethyl-6H-1,2,3,5,6-tetraaza-as-indacen-1-yl)-cyclohexyl]-piperidine-4-carbonitrile. LCMS (Method A, ESI): RT=1.59 min, m+H=379.1; NMR (400 MHz, DMSO) δ: 11.85 (s, 1H), 8.52 (s, 1H), 7.46 (t, 1H), 6.74 (s, 1H), 5.64 (t, 1H), 4.77 (d, 2H), 4.65 (s, 1H), 2.87 (m, 1H), 2.74 (m, 3H), 2.36 (m, 3H), 2.85-1.82 (m, 6H), 2.56 (m, 1H), 1.71 (m, 2H), 1.57 (m, 2H).

Example 614

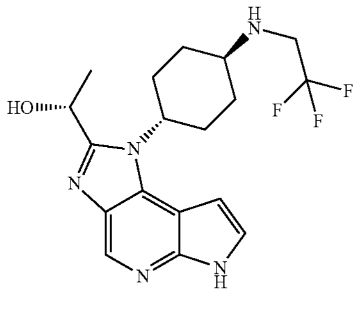 [SMILES: C[C@@H](O)c1nc2cnc3[nH]ccc3c2n1[C@H]1CC[C@H](NCC(F)(F)F)CC1]

Trans (R)-1-{1-[4-(2,2,2-trifluoro-ethylamino)-cyclohexyl]-1,6-dihydro-1,2,3,5,6-tetraaza-as-indacen-2-yl}-ethanol

Trans {-4-[6-benzenesulfonyl-2-((R)-1-hydroxy-ethyl)-6H-1,2,3,5,6-tetraaza-as-indacen-1-yl]-cyclohexyl}-carbamic acid tert-butyl ester (R)-lactamide (1.65 g, 3.60 mmol) was dissolved in THF (25 mL) and triethyloxonium tetrafluoroborate (3.42 g, 18.0 mmol) was added. The mixture was stirred at room temperature for 2 h, then concentrated. The residue was taken up in absolute ethanol (12 mL) and added to a suspension of [4-(5-amino-1-benzenesulfonyl-1H-pyrrolo[2,3-b]pyridin-4-ylamino)-cyclohexyl]-carbamic acid tert-butyl ester (2.50 g, 5.15 mmol) in absolute ethanol (35 mL). The resulting mixture was stirred at 75° C. for 2 h, then concentrated under vacuum. Purification by column chromatography on silica gel (gradient: 3:1 cyclohexane:ethyl acetate to neat ethyl acetate to 7.5% methanol in ethyl acetate) gave 3.00 g (108%) crude trans {-4-[6-benzenesulfonyl-2-((R)-1-hydroxy-ethyl)-6H-1,2,3,5,6-tetraaza-as-indacen-1-yl]-cyclohexyl}-carbamic acid tert-butyl ester, which was used directly without further purification. LCMS (Method I, ESI): RT=3.19 min, m+H=540.4.

Trans (R)-1-[1-(4-amino-cyclohexyl)-6-benzenesulfonyl-1,6-dihydro-1,2,3,5,6-tetraaza-as-indacen-2-yl]-ethanol Trans {4-[6-benzenesulfonyl-2-((R)-1-hydroxy-ethyl)-6H-1,2,3,5,6-tetraaza-as-indacen-1-yl]-cyclohexyl}-carbamic acid tert-butyl ester (2 g, 3.71 mmol) was dissolved in a mixture of trifluoroacetic acid (10 mL) and water (1 mL). The mixture was stirred at room temperature for 1 h, then concentrated under vacuum. The residue was taken up in methanol and purified by Isolute® SCX column (gradient: methanol to 2 M NH₃ in methanol) to give 1.59 g (98%) of trans (R)-1-[1-(4-amino-cyclohexyl)-6-benzenesulfonyl-1,6-dihydro-1,2,3,5,6-tetraaza-as-indacen-2-yl]-ethanol. LCMS (Method I, ESI): RT=1.81 min, m+H=440.34; NMR (400 MHz, CDCl₃) δ: 8.85 (s, 1H), 8.22 (m, 2H), 7.82 (d, 1H), 7.55 (t, 1H), 7.47 (t, 2H), 6.87 (d, 1H), 5.16 (q, 1H), 4.65 (m, 1H), 3.07 (m, 1H), 2.46-2.28 (m, 2H), 2.15-2.06 (m, 2H), 2.02-1.87 (m, 2H), 1.73 (d, 3H), 1.44 (d, 2H).

Trans (R)-1-{1-[4-(2,2,2-trifluoro-ethylamino)-cyclohexyl]-1,6-dihydro-1,2,3,5,6-tetraaza-as-indacen-2-yl}-ethanol Trans (R)-1-[1-(4-amino-cyclohexyl)-6-benzenesulfonyl-1,6-dihydro-1,2,3,5,6-tetraaza-as-indacen-2-yl]-ethanol (200 mg, 0.46 mmol) was dissolved in dichoromethane (2 mL) and DMF (2 mL). Triethylamine (254 µL, 1.84 mmol) was added, followed by trifluoroethyl triflate (131 µL, 0.91 mmol). The mixture was stirred for 16 h at room temperature. Water was added and the mixture was extracted with DCM (×3), and the combined organic extracts were dried (Na₂SO₄) and concentrated under vacuum. The residue was dissolved in methanol (2 mL) and THF (2 mL), and 2 M aqueous NaOH (2 mL) was added. This mixture was stirred at room temperature for 2 h, then concentrated under vacuum. 1 M Aqueous HCl (4 mL) was added and the mixture was concentrated under vacuum. Purification by column chromatography on silica gel (gradient: DCM to 8% (2 M NH₃ in methanol) in DCM) followed by trituration with acetonitrile gave 77 mg (44%) of trans (R)-1-{1-[4-(2,2,2-trifluoro-ethylamino)-cyclohexyl]-1,6-dihydro-1,2,3,5,6-tetraaza-as-indacen-2-yl}-ethanol. LCMS (Method A, ESI): RT=1.85 min, m+H=382.2; NMR (400 MHz, DMSO) δ: ¹H NMR (400 MHz, DMSO-d): δ 11.84 (s, 1H), 8.54 (s, 1H), 7.47 (t, 1H), 6.67 (m, 1H), 5.66 (d, 1H), 5.12 (m, 1H), 4.83 (m, 1H), 3.38 (m, 2H), 2.83 (br s, 1H), 2.36 (m, 3H), 2.12 (d, 2H), 1.91 (m, 2H), 1.63 (d, 3H), 1.31 (s, 2H).

Example 615

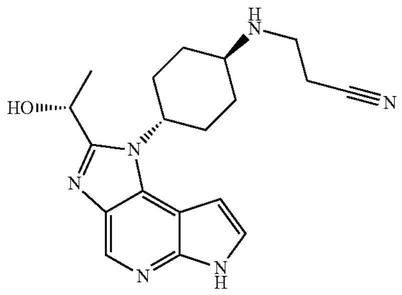 [SMILES: C[C@@H](O)c1nc2cnc3[nH]ccc3c2n1[C@H]1CC[C@H](NCCC#N)CC1]

Trans 3-{4-[2-((R)-1-hydroxy-ethyl)-6H-1,2,3,5,6-tetraaza-as-indacen-1-yl]-cyclohexylamino}-propionitrile Trans (R)-1-[1-(4-amino-cyclohexyl)-6-benzenesulfonyl-1,6-dihydro-1,2,3,5,6-tetraaza-as-indacen-2-yl]-ethanol (202 mg, 0.46 mmol) was suspended in ethanol (2 mL, IMS grade) and acrylonitrile (120 µL, 1.84 mmol) was added. The mixture was stirred at 80° C. for 4 h. Further acrylonitrile (30 µL, 0.46 mmol) was added and the mixture was stirred at 80° C. for 30 min, then cooled to room temperature. The mixture was concentrated under vacuum, then triturated with diethyl ether to give a white foam. This was dissolved in THF (1.5 mL) and methanol (1.5 mL) and 2 M aqueous NaOH (1.5 mL) was added. This mixture was stirred for 45 min at 45° C., then 1 M aqueous HCl (3 mL) was added and the mixture was concentrated. Purification by column chromatography on silica gel (gradient: DCM to 8% (2 M NH₃ in DCM) followed by trituration with acetonitrile gave 64 mg (40%) of trans 3-{4-[2-((R)-1-hydroxy-ethyl)-6H-1,2,3,5,6-tetraaza-as-indacen-1-yl]-cyclohexylamino}-propionitrile. LCMS (Method A, ESI): RT=1.61 min, m+H=353.4; NMR (400 MHz, DMSO) δ: 11.83 (s, 1H), 8.54 (s, 1H), 7.46 (t, 1H), 6.72 (dd, 1H), 5.66

(d, 1H), 5.12 (m, 1H), 4.83 (m, 1H), 2.87 (t, 2H), 2.80 (s, 1H), 2.62 (t, 2H), 2.38-2.37 (m, 2H), 2.11 (m, 2H), 1.91 (m, 2H), 1.63 (d, 3H), 1.29 (m, 2H).

Example 616

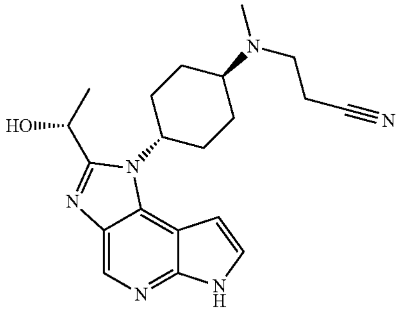 [SMILES: C[C@@H](O)c1nc2cnc3[nH]ccc3c2n1[C@H]1CC[C@H](N(C)CCC#N)CC1]

Trans 3-({4-[2-((R)-1-hydroxy-ethyl)-6H-1,2,3,5,6-tetraaza-as-indacen-1-yl]-cyclohexyl}-methyl-amino)-propionitrile Trans N-{-4-[6-benzenesulfonyl-2-((R)-1-hydroxy-ethyl)-6H-1,2,3,5,6-tetraaza-as-indacen-1-yl]-cyclohexyl-formamide Following the procedure for trans acetic acid 6-benzenesulfonyl-1-(4-formylamino-cyclohexyl)-1,6-dihydro-1,2,3,5,6-tetraaza-as-indacen-2-ylmethyl ester, the title compound was prepared from trans (R)-1-[1-(4-amino-cyclohexyl)-6-benzenesulfonyl-1,6-dihydro-1,2,3,5,6-tetraaza-as-indacen-2-yl]-ethanol (600 mg, 1.37 mmol), giving 501 mg (74%) of trans N-{-4-[6-benzenesulfonyl-2-((R)-1-hydroxy-ethyl)-6H-1,2,3,5,6-tetraaza-as-indacen-1-yl]-cyclohexyl}-formamide. LCMS (method H, ESI): RT=2.83 min, m+H=496.1.

Trans (R)-1-[6-benzenesulfonyl-1-(4-methylamino-cyclohexyl)-1,6-dihydro-1,2,3,5,6-tetraaza-as-indacen-2-yl]-ethanol Following the procedure for trans [6-benzenesulfonyl-1-(4-methylamino-cyclohexyl)-1,6-dihydro-1,2,3,5,6-tetraaza-as-indacen-2-yl]-methanol, the title compound was prepared from trans N-{4-[6-benzenesulfonyl-2-((R)-1-hydroxy-ethyl)-6H-1,2,3,5,6-tetraaza-as-indacen-1-yl]-cyclohexyl}-formamide (497 mg, 1.00 mmol). Further purification by trituration with ethyl acetate gave 403 mg (83%) of trans (R)-1-[6-benzenesulfonyl-1-(4-methylamino-cyclohexyl)-1,6-dihydro-1,2,3,5,6-tetraaza-as-indacen-2-yl]-ethanol. LCMS (Method I, ESI): RT=1.99 min, m+H=454.1.

Trans 3-({4-[2-((R)-1-hydroxy-ethyl)-6H-1,2,3,5,6-tetraaza-as-indacen-1-yl]-cyclohexyl}-methyl-amino)-propionitrile Trans (R)-1-[6-benzenesulfonyl-1-(4-methylamino-cyclohexyl)-1,6-dihydro-1,2,3,5,6-tetraaza-as-indacen-2-yl]-ethanol (178 mg, 0.39 mmol) was dissolved in ethanol (2 mL, IMS grade) and acrylonitrile (103 μL, 1.56 mmol) was added. The mixture was stirred at 80° C. for 4 h, then further acrylonitrile (25 μL, 0.39 mmol) was added. The mixture was stirred at 80° C. for 30 min, then cooled to room temperature and concentrated under vacuum. The residue was triturated with diethyl ether to give a white foam. This was dissolved in THF (1.5 mL) and methanol (1.5 mL), and 2 M aqueous NaOH (1.5 mL) was added. The mixture was stirred at 45° C. for 1 h then cooled to room temperature. 1 M Aqueous HCl (3 mL) was added and the mixture was concentrated under vacuum. Purification by column chromatography on silica gel (gradient: DCM to 7% (2 M $NH_3$ in methanol) in DCM) and sequential trituration with DCM and ethyl acetate gave 45 mg (28%) of trans 3-({4-[2-((R)-1-hydroxy-ethyl)-6H-1,2,3,5,6-tetraaza-as-indacen-1-yl]-cyclohexyl}-methyl-amino)-propionitrile. LCMS (Method A, ESI): RT=1.62 min, m+H=367.2; NMR (400 MHz, DMSO) δ: 11.83 (s, 1H), 8.54 (s, 1H), 7.46 (t, 1H), 6.76 (s, 1H), 5.66 (d, 1H), 5.12 (m, 1H), 4.81 (m, 1H), 2.83 (m, 1H), 2.76 (t, 2H), 2.66 (t, 2H), 2.40 (m, 2H), 2.30 (s, 3H), 1.96 (m, 4H), 1.63 (d, 3H), 1.56 (m, 2H).

Example 617

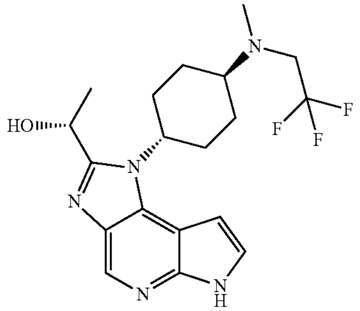 [SMILES: C[C@@H](O)c1nc2cnc3[nH]ccc3c2n1[C@H]1CC[C@H](N(C)CC(F)(F)F)CC1]

Trans (R)-1-(1-{4-[methyl-(2,2,2-trifluoro-ethyl)-amino]-cyclohexyl}-1,6-dihydro-1,2,3,5,6-tetraaza-as-indacen-2-yl)-ethanol Trans (R)-1-[6-benzenesulfonyl-1-(4-methylamino-cyclohexyl)-1,6-dihydro-1,2,3,5,6-tetraaza-as-indacen-2-yl]-ethanol (175 mg, 0.39 mmol) was dissolved in DCM (2 mL) and DMF (2 mL). 2,2,2-Trifluoroethyl triflate (112 μL, 0.78 mmol) was added, followed by triethylamine (217 μL, 1.56 mmol). The mixture was stirred for 16 h. 2,2,2-Trifluoroethyl triflate (168 μL, 1.17 mmol) was added, then triethylamine (162 μL, 1.17 mmol), and the mixture was stirred a further 24 h. 2,2,2-Trifluoroethyl triflate (168 μL, 1.17 mmol) was added, then triethylamine (162 μL, 1.17 mmol), and the mixture stirred for an additional 3 days and then allowed to stand a further 14 days. Water was added and the mixture extracted with DCM (×3). The combined organic extracts were dried ($Na_2SO_4$) and concentrated under vacuum. The residue was dissolved in THF (2 mL) and methanol (2 mL), then 2 M aqueous NaOH (2 mL) was added. This mixture was stirred at room temperature for 2 h. 1 M Aqueous HCl (4 mL) was added and the mixture was concentrated. Purification by column chromatography on silica gel (gradient: DCM to 6% (2 M $NH_3$ in methanol) in DCM) followed by trituration with acetonitrile gave a white residue which was crystallised from DCM/methanol to give a white crystalline solid. Further purification by reverse phase HPLC (gradient 5% to 98% acetonitrile in water, +0.1% $NH_4OH$) gave 19 mg (12%) of trans (R)-1-(1-{4-[methyl-(2,2,2-trifluoro-ethyl)-amino]-cyclohexyl}-1,6-dihydro-1,2,3,5,6-tetraaza-as-indacen-2-yl)-ethanol. LCMS (Method A, ESI): RT=2.72 min, m+H=396.2; NMR (400 MHz, DMSO) δ: 11.83 (s, 1H), 8.54 (s, 1H), 7.46 (t, 1H), 6.74 (s, 1H), 5.64 (d, 1H), 5.12 (m, 1H), 4.82 (m, 1H), 3.28-3.23 (m, 2H), 2.89 (m, 1H), 2.45 (s, 3H), 2.43-2.33 (m, 2H), 1.95 (m, 4H), 1.63 (d, 3H), 1.62-1.50 (m, 2H).

Example 618

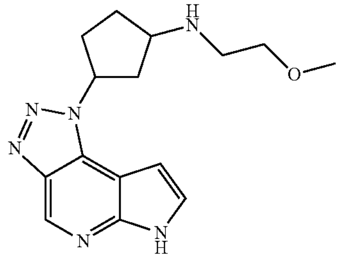 [SMILES: COCCNC1CCC(n2nnc3cnc4[nH]ccc4c32)C1]

Racemic trans (2-methoxy-ethyl)-[3-(6H-1,2,3,5,6-pentaaza-as-indacen-1-yl)-cyclopentyl]-amine hydrochloride Racemic trans [3-(1-benzenesulfonyl-5-nitro-1H-pyrrolo[2,3-b]pyridin-4-ylamino)-cyclopentyl]-carbamic acid tert-butyl ester A mixture of 1-benzenesulfonyl-4-chloro-5-nitro-1H-pyrrolo[2,3-b]pyridine (16.9 g, 49.9 mmol), racemic trans (3-amino-cyclopentyl)-carbamic acid tert-butyl ester (10.0 g, 49.9 mmol: Prepared according to J. Org. Chem. 2004, 69(13), 4538; Tetrahedron 1997, 53(9), 3347; WO94/17090 and Org. Lett. 2000, 2, 4169) and diisopropylethylamine (12.0 mL, 69.9 mmol) in propan-2-ol (175 mL) was heated at reflux for 4 hours. After cooling, the mixture was concentrated in vacuo and the residue triturated (water) to give 23.7 g (94%) of racemic trans [3-(1-benzenesulfonyl-5-nitro-1H-pyrrolo[2,3-b]pyridin-4-ylamino)-cyclopentyl]-carbamic acid tert-butyl ester as a yellow solid. LCMS (Method B, ESI): RT=4.25 min, m+H=502.3; $^1$H NMR (400 MHz, DMSO) δ: 8.89 (s, 1H), 8.87 (d, 1H), 8.12 (d, 2H), 7.83 (d, 1H), 7.76 (m, 1H), 7.65 (t, 2H), 7.17 (d, 1H), 7.06 (br d, 1H), 4.62 (m, 1H), 3.99 (m, 1H), 2.24 (m, 1H), 1.97 (m, 3H), 1.56 (m, 2H), 1.38 (s, 9H).

Racemic trans [3-(5-amino-1-benzenesulfonyl-1H-pyrrolo[2,3-b]pyridin-4-ylamino)-cyclopentyl]-carbamic acid tert-butyl ester A mixture of racemic trans [3-(1-benzenesulfonyl-5-nitro-1H-pyrrolo[2,3-b]pyridin-4-ylamino)-cyclopentyl]-carbamic acid tert-butyl ester (23.7 g, 47.2 mmol) and palladium hydroxide (2.44 g, 20%) in acetic acid (285 mL) was stirred under an atmosphere of hydrogen at 50° C. for 3 hours and then room temperature for 18 hours. The mixture was filtered through Celite® and then concentrated in vacuo. The residue was dissolved in DCM, then washed (saturated sodium hydrogen carbonate solution (3×) and brine) and concentrated to dryness. Purification by column chromatography on silica gel (gradient: DCM to ethyl acetate) afforded 11.6 g (52%) of racemic trans [3-(5-amino-1-benzenesulfonyl-1H-pyrrolo[2,3-b]pyridin-4-ylamino)-cyclopentyl]-carbamic acid tert-butyl ester as a purple solid. LCMS (Method B, ESI): RT=2.85 min, m+H=472.4; $^1$H NMR (400 MHz, DMSO) δ: 8.00 (d, 2H), 7.66 (t, 1H), 7.57 (t, 2H), 7.52 (s, 1H), 7.45 (d, 1H), 6.97 (d, 1H), 6.82 (d, 1H), 5.21 (d, 1H), 4.35 (m, 3H), 3.95 (m, 1H), 2.13-1.91 (m, 2H), 1.79 (m, 2H), 1.44 (m, 2H), 1.37 (s, 9H).

Racemic trans [3-(6-benzenesulfonyl-6H-1,2,3,5,6-pentaaza-as-indacen-1-yl)-cyclopentyl]-carbamic acid tert-butyl ester Sodium nitrite (612 mg, 8.87 mmol) was added to a stirred solution of racemic trans [3-(5-amino-1-benzenesulfonyl-1H-pyrrolo[2,3-b]pyridin-4-yl amino)-cyclopentyl]-carbamic acid tert-butyl ester (3.80 g, 8.06 mmol) in acetic acid (50 mL). Stirring was continued for 45 minutes at room temperature and then the solvent removed in vacuo. The residue was dissolved in ethyl acetate, washed (saturated sodium hydrogen carbonate (3×) and brine) and concentrated to dryness. Purification by column chromatography on silica gel (gradient: DCM to ethyl acetate) gave 3.39 g (87%) of racemic trans [3-(6-benzenesulfonyl-6H-1,2,3,5,6-pentaaza-as-indacen-1-yl)-cyclopentyl]-carbamic acid tert-butyl ester as a beige solid. LCMS (Method B, ESI): RT=4.00 min, m+H=483.3; $^1$H NMR (400 MHz, DMSO) δ: 9.20 (s, 1H), 8.15 (m, 3H), 7.73 (t, 1H), 7.63 (t, 2H), 7.45 (d, 1H), 7.15 (d, 1H), 5.65 (m, 1H), 4.21 (m, 1H), 2.44 (m, 2H, partially obscured by DMSO), 2.16 (m, 3H), 1.65 (m, 1H), 1.40 (s, 9H).

Racemic trans [3-(6H-1,2,3,5,6-pentaaza-as-indacen-1-yl)-cyclopentyl]-carbamic acid tert-butyl ester A mixture of racemic trans [3-(6-benzenesulfonyl-6H-1,2,3,5,6-pentaaza-as-indacen-1-yl)-cyclopentyl]-carbamic acid tert-butyl ester (2.00 g, 4.14 mmol), aqueous sodium hydroxide solution (10.4 mL, 20.7 mmol, 2M), methanol (30 mL) and THF (50 mL) was stirred at ambient temperature for 45 minutes. DCM was added and the solution washed (water and brine) and concentrated to dryness. Purification by column chromatography on silica gel (gradient: DCM to ethyl acetate) afforded 902 mg (64%) of racemic trans [3-(6H-1,2,3,5,6-pentaaza-as-indacen-1-yl)-cyclopentyl]-carbamic acid tert-butyl ester as an off white solid. LCMS (Method B, ESI): RT=3.21 min, m+H=343.3; $^1$H NMR (400 MHz, DMSO) δ: 12.34 (s, 1H), 8.99 (s, 1H), 7.60 (d, 1H), 7.18 (d, 1H), 7.03 (d, 1H), 5.64 (m, 1H), 4.23 (m, 1H), 2.47 (m, 2H, partially obscured by DMSO), 2.20 (m, 3H), 1.70 (m, 1H), 1.40 (s, 9H).

Racemic trans 3-(6H-1,2,3,5,6-pentaaza-as-indacen-1-yl)-cyclopentylamine

A mixture of racemic trans [3-(6H-1,2,3,5,6-pentaaza-as-indacen-1-yl)-cyclopentyl]-carbamic acid tert-butyl ester (900 mg, 2.63 mmol), trifluoroacetic acid (5 mL), water (50.0 μL) and DCM (10 mL) was stirred at ambient temperature for 5 hours. The solvents were removed in vacuo and the resulting residue purified by column chromatography (SCX-2, gradient: methanol to 2M $NH_3$ in methanol) to give 586 mg (92%) of racemic trans 3-(6H-1,2,3,5,6-pentaaza-as-indacen-1-yl)-cyclopentylamine as a white foam solid. LCMS (Method B, ESI): RT=0.36 & 1.05 min, m+H=243.3; $^1$H NMR (400 MHz, DMSO) δ: 12.35 (br s, 1H), 8.98 (s, 1H), 7.59 (d, 1H), 6.98 (d, 1H), 5.67 (m, 1H), 3.67 (m, 1H), 2.52 (m, 1H, partially obscured by DMSO), 2.40 (m, 1H), 2.25-2.03 (m, 3H), 1.54 (m, 1H).

Racemic trans (2-methoxy-ethyl)-[3-(6H-1,2,3,5,6-pentaaza-as-indacen-1-yl)-cyclopentyl]-amine hydrochloride A mixture of racemic trans 3-(6H-1,2,3,5,6-pentaaza-as-indacen-1-yl)-cyclopentylamine (95.0 mg, 392 μmol), 2-bromoethyl methyl ether (59.9 mg, 431 μmol), potassium carbonate (108 mg, 780 μmol) and DMF (2 mL) was heated to 135° C. for 15 minutes using microwave irradiation. The mixture was filtered, concentrated in vacuo and purified by column chromatography on silica gel (gradient: DCM to 10% [2M $NH_3$ in methanol] in DCM) followed by reverse phase HPLC (5 to 50% acetonitrile in water, +0.1% $NH_4OH$). The colourless residue was treated with 1.25 M HCl in methanol (2 eq) in DCM and concentrated to afford 17.6 mg of racemic trans (2-methoxy-ethyl)-[3-(6H-1,2,3,5,6-pentaaza-as-indacen-1-yl)-cyclopentyl]-amine hydrochloride was isolated as a beige gum. LCMS (Method A, ESI): RT=1.92 min, m+H=301.3; $^1$H NMR (400 MHz, DMSO) δ: 12.35 (s, 1H), 8.99 (s, 1H), 7.60 (t, 1H), 7.00 (dd, 1H), 5.65 (m, 1H), 3.59 (m, 1H), 3.47 (t, 2H), 3.28 (s, 3H), 2.83 (t, 2H), 2.47 (m, 2H, partially obscured by DMSO), 2.29-2.17 (m, 3H), 1.72 (m, 1H).

Example 619

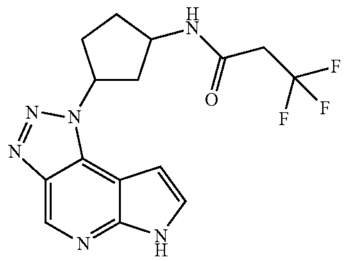 [SMILES: O=C(CC(F)(F)F)NC1CCC(n2nnc3cnc4[nH]ccc4c32)C1]

Racemic trans 3,3,3-trifluoro-N-[3-(6H-1,2,3,5,6-pentaaza-as-indacen-1-yl)-cyclopentyl]-propionamide To a stirred solution of racemic trans 3-(6H-1,2,3,5,6-pentaaza-as-indacen-1-yl)-cyclopentylamine (120 mg, 0.49 mmol) in DMF (3 mL), 3,3,3-trifluoropropionic acid (53.0 μL, 0.60 mmol), DMAP (103 mg, 0.84 mmol), HOBt (100 mg, 0.74 mmol) and EDCI (161 mg, 0.84 mmol) were added. Stirring was continued for 18 hours at ambient temperature. The mixture was diluted with water and purified by column chromatography (SCX-2, gradient: methanol to 2M $NH_3$ in methanol). The isolated product was triturated (DCM), washed with water and dried in vacuo at 40° C. for 18 hours affording 79.8 mg (45%) of racemic trans 3,3,3-trifluoro-N-[3-(6H-1,2,3,5,6-pentaaza-as-indacen-1-yl)-cyclopentyl]-propionamide as a grey powder. LCMS (Method A, ESI): RT=3.14 min, m+H=353.3; $^1$H NMR (400 MHz, DMSO) δ: 12.37 (s, 1H), 9.00 (s, 1H), 8.53 (d, 1H), 7.61 (t, 1H), 7.00 (dd, 1H), 5.67 (m, 1H), 4.48 (m, 1H), 3.26 (q, 2H), 2.55 (m, 2H), 2.33-2.18 (m, 3H), 1.71 (m, 1H).

Example 620

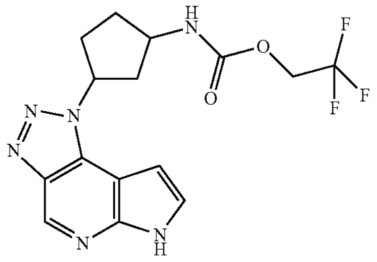 [SMILES: O=C(NC1CCC(n2nnc3cnc4[nH]ccc4c32)C1)OCC(F)(F)F]

Racemic trans [3-(6H-1,2,3,5,6-Pentaaza-as-indacen-1-yl)-cyclopentyl]-carbamic acid 2,2,2-trifluoro-ethyl ester A suspension of 3-(6H-1,2,3,5,6-pentaaza-as-indacen-1-yl)-cyclopentyl amine (100 mg, 410 μmol) and diisopropylethylamine (284 μL, 1.65 mmol) in DCM (3.0 mL) was treated with 2,2,2-trifluoromethyl chloroformate (101 μL, 870 μmol) and stirred under an argon atmosphere for 4 hours. The mixture was concentrated under vacuum and the residue purified by column chromatography on silica gel (gradient: 20 to 100% ethyl acetate in cyclohexane followed by 5-10% methanol in ethyl acetate). Further purification by column chromatography on silica gel (gradient: 0 to 100% ethyl acetate in cyclohexane). The product obtained was triturated with a diethyl ether/pentane mixture and purified further by reverse phase HPLC (gradient: 5 to 85% acetonitrile in water with 0.1% $NH_4OH$) to afford 19 mg (9%) of racemic trans [3-(6H-1,2,3,5,6-pentaaza-as-indacen-1-yl)-cyclopentyl]-carbamic acid 2,2,2-trifluoro-ethyl ester as a white solid. LCMS (Method A, ESI): RT=3.74 min, m+H=369.25; $^1$H NMR (400 MHz, DMSO) δ: 12.35 (s, 1H), 9.00 (s, 1H), 8.03 (d, 1H), 7.60 (d, 1H), 7.03 (d, 1H), 5.67 (m, 1H), 4.67 (q, 2H), 4.31 (m, 1H), 2.52 (m, 2H), 2.24 (m, 3H), 1.75 (m, 1H).

Example 621

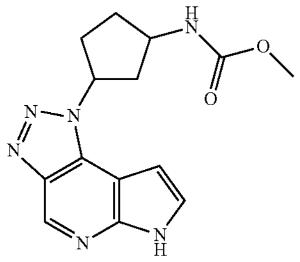 [SMILES: COC(=O)NC1CCC(n2nnc3cnc4[nH]ccc4c32)C1]

Racemic trans [3-(6H-1,2,3,5,6-Pentaaza-as-indacen-1-yl)-cyclopentyl]-carbamic acid methyl ester Racemic trans 3-(6-benzenesulfonyl-6H-1,2,3,5,6-pentaaza-as-indacen-1-yl)-cyclopentylamine A mixture of racemic trans [3-(6-benzenesulfonyl-6H-1,2,3,5,6-pentaaza-as-indacen-1-yl)-cyclopentyl]-carbamic acid tert-butyl ester (1.00 g, 2.07 mmol) and trifluoroacetic acid (4 mL) was stirred at ambient temperature for 90 minutes. The mixture was purified by column chromatography (SCX-2, gradient: methanol to 2M $NH_3$ in methanol) to afford 600 mg (76%) of racemic trans 3-(6-benzenesulfonyl-6H-1,2,3,5,6-pentaaza-as-indacen-1-yl)-cyclopentylamine as an off white foam. LCMS (Method B, ESI): RT=2.40 min, m+H=383.

Racemic trans [3-(6-Benzenesulfonyl-6H-1,2,3,5,6-pentaaza-as-indacen-1-yl)-cyclopentyl]-carbamic acid methyl ester Methyl chloroformate (31.0 μL, 0.40 mmol) was added to a stirred mixture of racemic trans 3-(6-benzenesulfonyl-6H-1,2,3,5,6-pentaaza-as-indacen-1-yl)-cyclopentylamine (150 mg, 390 μmol) and diisopropylethylamine (135 μL, 790 μmol) in DCM (3 mL) at ambient temperature. Stirring was continued for 4 hours. The mixture was concentrated under vacuum and the residue obtained purified by column chromatography on silica gel (gradient: 0 to 100% ethyl acetate in pentane) to afford 171 mg (98%) of racemic trans [3-(6-benzenesulfonyl-6H-1,2,3,5,6-pentaaza-as-indacen-1-yl)-cyclopentyl]-carbamic acid methyl ester as a colourless foam. LCMS (Method B, ESI): RT=3.48 min, m+H=441.3.

Racemic trans [3-(6H-1,2,3,5,6-Pentaaza-as-indacen-1-yl)-cyclopentyl]-carbamic acid methyl ester A solution of racemic trans [3-(6-benzenesulfonyl-6H-1,2,3,5,6-pentaaza-as-indacen-1-yl)-cyclopentyl]-carbamic acid methyl ester (171 mg, 380 μmol) in methanol (2 mL) and THF (1 mL) was treated with a 1M sodium hydroxide solution (2 mL) and stirred at ambient temperature for 1.5 hours. Dilute HCl was added and the mixture purified by Isolute® SCX-2 column (gradient: methanol to 2M $NH_3$ in methanol solution). The residue obtained was purified further by column chromatography on silica gel (gradient: 50% ethyl acetate in cyclohexane then 0-10% methanol in ethyl acetate). The product was further purified by a diethyl ether/cyclohexane trituration to afford 48 mg (41%) of racemic trans [3-(6H-1,2,3,5,6-pentaaza-as-indacen-1-yl)-cyclopentyl]-carbamic acid methyl ester as a white solid. LCMS (Method A, ESI): RT=2.92 min, m+H=301.3; $^1$H NMR (400 MHz, DMSO) δ: 12.35 (s, 1H), 8.99 (s, 1H), 7.60 (d, 1H), 7.47 (d, 1H), 7.03 (d, 1H), 5.66 (m, 1H), 4.28 (m, 1H), 3.55 (s, 3H), 2.50 (m, 2H), 2.23 (m, 3H), 1.73 (m, 1H).

Example 622

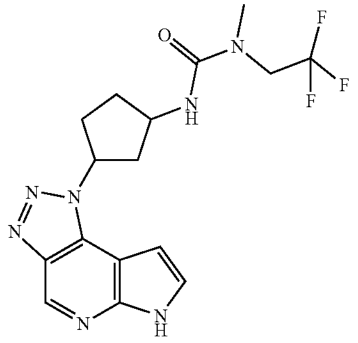 [SMILES: CN(CC(F)(F)F)C(=O)NC1CCC(n2nnc3cnc4[nH]ccc4c32)C1]

Racemic trans 1-Methyl-3-[3-(6H-1,2,3,5,6-pentaaza-as-indacen-1-yl)-cyclopentyl]-1-(2,2,2-trifluoro-ethyl)-urea Racemic trans 3-[3-(6-Benzenesulfonyl-6H-1,2,3,5,6-pentaaza-as-indacen-1-yl)-cyclopentyl]-1-methyl-1-(2,2,2-trifluoro-ethyl)-urea A mixture of 3-(6-benzene sulfonyl-6H-1,2,3,5,6-pentaaza-as-indacen-1-yl)cyclopentylamine (200 mg, 520 μmol) and triethylamine (333 μL, 2.39 mmol) in DCM (3 mL) was added dropwise to a stirred solution of triphosgene (121 mg, 400 μmol) in DCM (3 mL) and stirred at ambient temperature for 1 hour. A solution of the free base of methyl (2,2,2-trifluoroethyl) amine hydrochloride (240 mg, 1.60 mmol) in DCM (2 mL) was added dropwise and after 1 hour the reaction was quenched with a saturated solution of sodium bicarbonate. After standing for 2 days and organic phase was dried using a phase separator cartridge and purified by column chromatography on silica gel (gradient: 0 to 100% ethyl acetate in cyclohexane) to afford 80 mg (29%) of racemic trans 3-[3-(6-benzenesulfonyl-6H-1,2,3,5,6-pentaaza-as-indacen-1-yl)-cyclopentyl]-1-methyl-1-(2,2,2-trifluoro-ethyl)-urea as a gum. LCMS (Method B, ESI): RT=3.70 min, m+H=522.4.

Racemic trans 1-Methyl-3-[3-(6H-1,2,3,5,6-pentaaza-as-indacen-1-yl)-cyclopentyl]-1-(2,2,2-trifluoro-ethyl)-urea A solution of racemic trans 3-[3-(6-benzenesulfonyl-6H-1,2,3,5,6-pentaaza-as-indacen-1-yl)-cyclopentyl]-1-methyl-1-(2,2,2-trifluoro-ethyl)-urea (80.0 mg, 150 μmol) and sodium hydroxide solution (1.5 mL, 1N) in methanol (1 mL) and THF (1 mL) was stirred at ambient temperature for 30 minutes. Dilute HCl was added and the mixture purified by Isolute® SCX-2 column (gradient: methanol to 2M $NH_3$ in methanol solution). The residue obtained was purified further by trituration with DCM/diethyl ether to afford 30 mg (51%) of racemic trans 1-methyl-3-[3-(6H-1,2,3,5,6-pentaaza-as-indacen-1-yl)-cyclopentyl]-1-(2,2,2-trifluoro-ethyl)-urea as a white solid. LCMS (Method A, ESI): RT=3.40 min, m+H=382.10; $^1$H NMR (400 MHz, DMSO) δ: 12.36 (s, 1H), 9.00 (s, 1H), 7.61 (t, 1H), 7.00 (dd, 1H), 6.67 (d, 1H), 5.66 (m, 1H), 4.41 (m, 1H), 4.09 (q, 2H), 2.97 (s, 3H), 2.50 (m, 2H), 2.27 (m, 3H), 1.79 (m, 1H).

Example 623

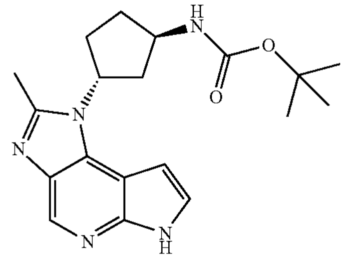 [SMILES: Cc1nc2cnc3[nH]ccc3c2n1[C@@H]1CC[C@@H](NC(=O)OC(C)(C)C)C1]

[(1R,3R)-3-(2-Methyl-6H-1,2,3,5,6-tetraaza-as-indacen-1-yl)-cyclopentyl]-carbamic acid tert-butyl ester

[(1R,3R)-3-(6-Benzenesulfonyl-2-methyl-6H-1,2,3,5,6-tetraaza-as-indacen-1-yl)-cyclopentyl]-carbamic acid tert-butyl ester A mixture of [(1R,3R)-3-(5-amino-1-benzenesulfonyl-1H-pyrrolo[2,3-b]pyridin-4-ylamino)-cyclopentyl]-carbamic acid tert-butyl ester (230 mg, 0.48 mmol) and triethyl orthoacetate (355 μL, 1.94 mmol) in acetic acid (4 mL) was heated to 80° C. for 15 minutes. The solvent was removed in vacuo and the residue partitioned between aqueous sodium hydrogen carbanate solution and DCM. The chlorinated extracts were washed (water and brine), dried (magnesium sulfate) and concentrated to dryness. Purification by column chromatography on silica gel (gradient: DCM to 2% methanol in DCM) gave 230 mg of [(1R,3R)-3-(6-benzenesulfonyl-2-methyl-6H-1,2,3,5,6-tetraaza-as-indacen-1-yl)-cyclopentyl]-carbamic acid tert-butyl ester as an off white foam. LCMS (Method B, ESI): RT=3.45 min, m+H=496.1.

[(1R,3R)-3-(2-Methyl-6H-1,2,3,5,6-tetraaza-as-indacen-1-yl)-cyclopentyl]-carbamic acid tert-butyl ester A mixture of [(1R,3R)-3-(6-benzenesulfonyl-2-methyl-6H-1,2,3,5,6-tetraaza-as-indacen-1-yl)-cyclopentyl]-carbamic acid tert-butyl ester (30.0 mg, 60.0 μmol), aqueous sodium hydroxide solution (2 mL, 1N), methanol (1 mL) and THF (1 mL) was stirred at ambient temperature for 18 hours. The solvent was removed in vacuo, the residue treated with aqueous HCl solution (2 mL, 1N) and concentrated to dryness. Purification by reverse phase HPLC (5-98% acetonitrile in water, +0.1% $NH_4OH$) afforded 5.70 mg of [(1R,3R)-3-(2-Methyl-6H-1,2,3,5,6-tetraaza-as-indacen-1-yl)-cyclopentyl]-carbamic acid tert-butyl ester. LCMS (Method A, ESI): RT=2.91 min, m+H=356.30; $^1$H NMR (400 MHz, DMSO) δ: 11.79 (s, 1H), 8.45 (s, 1H), 7.45 (d, 1H), 7.25 (m, 1H), 6.55 (d, 1H), 5.20 (m, 1H), 4.30 (m, 1H), 2.63 (s, 3H), 2.50 (m, 1H), 2.38 (m, 1H), 2.20 (m, 2H), 1.99 (m, 1H), 1.74 (m, 1H), 1.41 (s, 9H).

Example 624

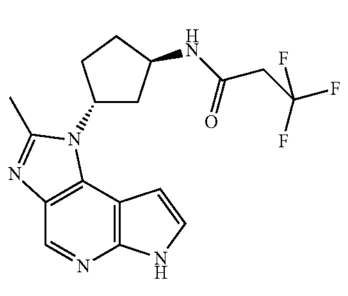 [SMILES: Cc1nc2cnc3[nH]ccc3c2n1[C@@H]1CC[C@@H](NC(=O)CC(F)(F)F)C1]

3,3,3-Trifluoro-N-[(1R,3R)-3-(2-methyl-6H-1,2,3,5,6-tetraaza-as-indacen-1-yl)-cyclopentyl]-propionamide (1R,3R)-3-(6-Benzenesulfonyl-2-methyl-6H-1,2,3,5,6-tetraaza-as-indacen-1-yl)-cyclopentylamine A mixture of [(1R,3R)-3-(6-benzenesulfonyl-2-methyl-6H-1,2,3,5,6-tetraaza-as-indacen-1-yl)-cyclopentyl]-carbamic acid tert-butyl ester (3.15 g, 6.36 mmol) in DCM (26 mL) was treated with trifluoroacetic acid (11 mL) at ambient temperature for 20 minutes. The mixture was concentrated in vacuo and the residue purified by column chromatography (SCX-2, gradient: methanol to 2M $NH_3$ in methanol) to afford 2.18 g (87%) of (1R,3R)-3-(6-benzenesulfonyl-2-methyl-6H-1,2,3,5,6-tetraaza-as-indacen-1-yl)-cyclopentylamine as a pale brown solid. LCMS (Method Q, ESI): RT=2.11 min, m+H=396.1. $^1$H NMR (400 MHz, DMSO) δ: 8.76 (s, 1H), 8.16 (d, 2H), 8.10 (br s, 2H), 8.07 (d, 1H), 7.72 (t, 1H), 7.63 (t, 2H), 7.11 (d, 1H), 5.36 (m, 1H), 4.09 (m, 1H), 2.76 (s, 3H), 2.47 (m, 2H), 2.26 (m, 3H), 1.83 (m, 1H).

(1R,3R)-3-(2-Methyl-6H-1,2,3,5,6-tetraaza-as-indacen-1-yl)-cyclopentylamine

To a stirred mixture of (1R,3R)-3-(6-benzenesulfonyl-2-methyl-6H-1,2,3,5,6-tetraaza-as-indacen-1-yl)-cyclopentylamine (600 mg, 1.52 mmol) in methanol (9 mL) and THF (9 mL), aqueous sodium hydroxide solution (3.80 mL, 7.60 mmol) was added at ambient temperature. After 18 hours, the solvents were removed in vacuo and the residue purified by column chromatography (SCX-2, gradient: methanol to 2M $NH_3$ in methanol) to give a yellow syrup. Trituration (diethyl ether) afforded 383 mg (99%) of (1R,3R)-3-(2-methyl-6H-1,2,3,5,6-tetraaza-as-indacen-1-yl)-cyclopentylamine as gray solid. $^1$H NMR (400 MHz, $CDCl_3$) δ: 10.77 (s, 1H), 8.73 (s, 1H), 7.39 (d, 1H), 6.57 (d, 1H), 5.31 (m, 1H), 4.02 (m, 1H), 2.71 (s, 3H), 2.66 (m, 1H), 2.53-2.30 (m, 3H), 1.93 (m, 1H), 1.69 (m, 1H).

3,3,3-Trifluoro-N-[(1R,3R)-3-(2-methyl-6H-1,2,3,5,6-tetraaza-as-indacen-1-yl)-cyclopentyl]-propionamide To a stirred solution of (1R,3R)-3-(2-methyl-6H-1,2,3,5,6-tetraaza-as-indacen-1-yl)-cyclopentylamine (100 mg, 0.40 mmol) in DMF (3 mL), 3,3,3-trifluoropropionic acid (42.4 μL, 0.48 mmol), DMAP (78.0 mg, 0.64 mmol), HOBt (86.5 mg, 0.64 mmol) and EDCI (123 mg, 0.64 mmol) were added. Stirring was continued for 18 hours at ambient temperature. The mixture was diluted with DCM, washed (water) and concentrated in vacuo. Purification by column chromatography on silica gel (gradient: DCM to 10% methanol in DCM) and subsequent crystallisation (acetonitrile) of the isolated product, afforded 71.5 mg (49%) of 3,3,3-trifluoro-N-[(1R,3R)-3-(2-methyl-6H-1,2,3,5,6-tetraaza-as-indacen-1-yl)-cyclopentyl]-propionamide as a white solid. LCMS (Method A, ESI): RT=2.31 min, m+H=366.2; $^1$H NMR (400 MHz, DMSO) δ: 11.81 (s, 1H), 8.57 (d, 1H), 8.46 (s, 1H), 7.46 (t, 1H), 6.56 (dd, 1H), 5.18 (m, 1H), 4.55 (m, 1H), 3.28 (q, 2H), 2.63 (s, 3H), 2.56 (m, 1H), 2.44 (m, 1H), 2.25 (m, 2H), 2.01 (m, 1H), 1.73 (m, 1H).

Example 625

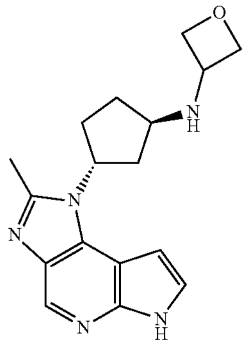 [SMILES: Cc1nc2cnc3[nH]ccc3c2n1[C@@H]1CC[C@@H](NC2COC2)C1]

[(1R,3R)-3-(2-Methyl-6H-1,2,3,5,6-tetraaza-as-indacen-1-yl)-cyclopentyl]-oxetan-3-yl-amine

[(1R,3R)-3-(6-Benzenesulfonyl-2-methyl-6H-1,2,3,5,6-tetraaza-as-indacen-1-yl)-cyclopentyl]-oxetan-3-yl-amine A solution of (1R,3R)-3-(6-benzenesulfonyl-2-methyl-6H-1,2,3,5,6-tetraaza-as-indacen-1-yl)-cyclopentylamine (200 mg, 505 μmol) in methanol (5.0 mL) was treated with zinc chloride (275 mg, 2.02 mmol) and 3-oxetanone (44.0 μL, 757 μmol) and cooled in an ice bath. Sodium cyanoborohydride (95.0 mg, 1.51 mmol) was added and the mixture was stirred at 40° C. for 5 days. A further portion of 3-oxetanone (90.0 μL) was added and after a further 24 hours at 40° C. the reaction was quenched by pouring onto an ammonium chloride/ice mixture. The aqueous phase was extracted with ethyl acetate (3×). The combined extracts were dried over sodium sulfate and concentrated under vacuum. The residue was purified by column chromatography on silica gel (gradient: 0 to 10% methanol in DCM) to afford 40.0 mg (18%) of [(1R,3R)-3-(6-benzenesulfonyl-2-methyl-6H-1,2,3,5,6-tetraaza-as-indacen-1-yl)-cyclopentyl]-oxetan-3-yl-amine as a white solid. LCMS (Method Q, ESI): RT=2.24 min, m+H=452; $^{1}$H NMR (400 MHz, $CDCl_3$) δ: 8.85 (s, 1H), 8.28 (d, 2H), 7.84 (d, 1H), 7.59-7.58 (m, 1H), 7.52 (t, 2H), 6.69 (d, 1H), 5.20 (m, 1H), 4.93 (td, 2H), 4.53 (td, 2H), 4.09 (t, 1H), 3.65 (s, 1H), 2.72 (s, 3H), 2.45-2.44 (m, 2H), 2.33 (t, 2H), 2.00 (d, 1H), 1.73 (dd, 1H).

[(1R,3R)-3-(2-Methyl-6H-1,2,3,5,6-tetraaza-as-indacen-1-yl)-cyclopentyl]-oxetan-3-yl-amine A solution of [(1R,3R)-3-(6-benzenesulfonyl-2-methyl-6H-1,2,3,5,6-tetraaza-as-indacen-1-yl)-cyclopentyl]-oxetan-3-yl-amine (62.0 mg, 1.37 mmol) in methanol (300 μL) and THF (1.0 mL) was treated with a 2M sodium hydroxide solution (0.5 mL, 7.55 mmol) and stirred at ambient temperature for 8 hours. The reaction mixture was concentrated under vacuum and the resulting residue was purified by Isolute® SCX-2 column (gradient: methanol to 2M $NH_3$ in methanol solution). The product was purified further by acetonitrile trituration to afford 15.0 mg (6%) of [(1R,3R)-3-(2-methyl-6H-1,2,3,5,6-tetraaza-as-indacen-1-yl)-cyclopentyl]-oxetan-3-yl-amine as a white solid. LCMS (Method A, ESI): RT=1.15 min, m+H=312.19; $^{1}$H NMR (400 MHz, DMSO) δ: 11.80 (s, 1H), 8.48 (s, 1H), 7.46 (t, 1H), 6.53 (dd, 1H), 5.21-5.18 (m, 1H), 4.69 (t, 2H), 4.42 (td, 2H), 3.99 (t, 1H), 3.51 (d, 1H), 2.64 (s, 3H), 2.35-2.32 (m, 2H), 2.28-2.16 (m, 3H), 1.98-1.89 (m, 1H), 1.64-1.62 (m, 1H).

Example 626

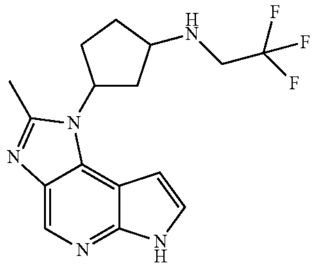 [SMILES: Cc1nc2cnc3[nH]ccc3c2n1C1CCC(NCC(F)(F)F)C1]

Racemic trans [3-(2-Methyl-6H-1,2,3,5,6-tetraaza-as-indacen-1-yl)-cyclopentyl]-(2,2,2-trifluoro-ethyl)-amine Racemic trans [3-(6-benzenesulfonyl-2-methyl-6H-1,2,3,5,6-tetraaza-as-indacen-1-yl)-cyclopentyl]-carbamic acid tert-butyl ester A mixture of racemic trans [3-(5-amino-1-benzenesulfonyl-1H-pyrrolo[2,3-b]pyridin-4-ylamino)-cyclopentyl]-carbamic acid tert-butyl ester (2.50 g, 5.30 mmol), triethyl orthoacetate (3.45 g, 21.2 mmol) in acetic acid (30 mL) was heated to 120° C. for 20 minutes. After cooling the mixture was concentrated in vacuo. The residue was dissolved in ethyl acetate, washed (saturated sodium hydrogen carbonate (3×) and brine) and concentrated to dryness. Purification by column chromatography on silica gel (gradient: DCM to ethyl acetate) afforded 1.38 g (52%) of racemic trans [3-(6-benzenesulfonyl-2-methyl-6H-1,2,3,5,6-tetraaza-as-indacen-1-yl)-cyclopentyl]-carbamic acid tert-butyl ester as a pale yellow foam. LCMS (Method B, ESI): RT=3.50 min, m+H=496.3; $^{1}$H NMR (400 MHz, DMSO) δ: 8.59 (s, 1H), 8.12 (d, 2H), 7.96 (d, 1H), 7.69 (m, 1H), 7.60 (t, 2H), 7.25 (d, 1H), 7.01 (d, 1H), 5.21 (m, 1H), 4.27 (m, 1H), 2.64 (s, 3H), 2.35 (m, 2H), 2.20 (m, 1H), 2.01 (m, 2H), 1.72 (m, 1H), 1.41 (s, 9H).

Racemic trans 3-(6-benzenesulfonyl-2-methyl-6H-1,2,3,5,6-tetraaza-as-indacen-1-yl)-cyclopentylamine A mixture of racemic trans [3-(6-benzenesulfonyl-2-methyl-6H-1,2,3,5,6-tetraaza-as-indacen-1-yl)-cyclopentyl]-carbamic acid tert-butyl ester (1.38 g, 2.78 mmol), trifluoroacetic acid (5 mL) and DCM (10 mL) was stirred at ambient temperature for 2 hours. The solvents were removed in vacuo and the resulting residue purified by column chromatography (SCX-2, gradient: methanol to 2M $NH_3$ in methanol) to give 1.01 g (92%) of racemic trans 3-(6-benzenesulfonyl-2-methyl-6H-1,2,3,5,6-tetraaza-as-indacen-1-yl)-cyclopentylamine as a orange foam solid. LCMS (Method B, ESI): RT=2.19 min, m+H=396.3; $^{1}$H NMR (400 MHz, DMSO) δ: 8.60 (s, 1H), 8.12 (m, 2H), 7.95 (d, 1H), 7.69 (m, 1H), 7.61

(m, 2H), 6.91 (d, 1H), 5.30 (m, 1H), 3.73 (m, 1H), 2.63 (m, 3H), 2.34-2.18 (m, 3H), 2.03 (m, 1H), 1.87 (m, 1H), 1.55 (m, 1H).

Racemic trans [3-(6-benzenesulfonyl-2-methyl-6H-1,2,3,5,6-tetraaza-as-indacen-1-yl)-cyclopentyl]-(2,2,2-trifluoro-ethyl)-amine To a stirred solution of racemic trans 3-(6-benzenesulfonyl-2-methyl-6H-1,2,3,5,6-tetraaza-as-indacen-1-yl)-cyclopentylamine (155 mg, 392 μmol) and triethylamine (218 μL, 1.57 mmol) in DCM/DMF (4 mL, 1:1), 2,2,2-trifluoroethyl trifluoromethane sulfonate (113 μL, 784 μmol) was added. Stirring was continued for 18 hours at room temperature and the mixture concentrated in vacuo. Purification by column chromatography on silica gel (gradient: DCM to 10% methanol in DCM) afforded 157 mg (84%) of racemic trans [3-(6-benzenesulfonyl-2-methyl-6H-1,2,3,5,6-tetraaza-as-indacen-1-yl)-cyclopentyl]-(2,2,2-trifluoro-ethyl)-amine as a pale yellow foam. LCMS (Method B, ESI): RT=2.79 min, m+H=478.4; $^{1}$H NMR (400 MHz, DMSO) δ: 8.60 (s, 1H), 8.12 (m, 2H), 7.95 (d, 1H), 7.69 (m, 1H), 7.61 (m, 2H), 6.92 (d, 1H), 5.21 (m, 1H), 3.59 (m, 1H), 3.21 (m, 2H, partially obscured by water), 2.69-2.60 (m, 4H), 2.34-2.16 (m, 3H), 2.05 (m, 2H), 1.65 (m, 1H).

Racemic trans [3-(2-methyl-6H-1,2,3,5,6-tetraaza-as-indacen-1-yl)-cyclopentyl]-(2,2,2-trifluoro-ethyl)-amine A mixture of racemic trans [3-(6-benzenesulfonyl-2-methyl-6H-1,2,3,5,6-tetraaza-as-indacen-1-yl)-cyclopentyl]-(2,2,2-trifluoro-ethyl)-amine (155 mg, 324 μmol), aqueous sodium hydroxide solution (0.81 mL, 1.62 mmol, 2M), methanol (3 mL) and THF (3 mL) was stirred at ambient temperature for 2 hours. The mixture was partitioned between DCM and water, the organics separated and washed with brine, then concentrated to dryness. Purification by column chromatography on silica gel (gradient: DCM to 10% [2M $NH_3$ in methanol] in DCM) followed by reverse phase HPLC (5 to 50% acetonitrile in water, +0.1% $NH_4OH$) afforded 25.1 mg of racemic trans [3-(2-methyl-6H-1,2,3,5,6-tetraaza-as-indacen-1-yl)-cyclopentyl]-(2,2,2-trifluoro-ethyl)-amine as a white residue. LCMS (Method A, ESI): RT=1.95 min, m+H=338.3; $^{1}$H NMR (400 MHz, DMSO) δ: 11.79 (s, 1H), 8.45 (s, 1H), 7.44 (t, 1H), 6.51 (dd, 1H), 5.21 (m, 1H), 3.62 (m, 1H), 3.28 (m, 2H), 2.65 (m, 1H), 2.61 (s, 3H), 2.34 (m, 2H), 2.21 (m, 2H), 2.05 (m, 1H), 1.67 (m, 1H).

Example 627

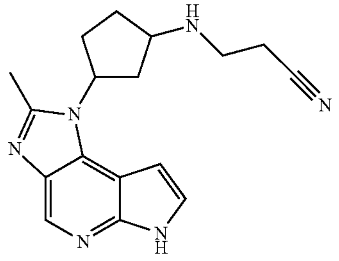 [SMILES: Cc1nc2cnc3[nH]ccc3c2n1C1CCC(NCCC#N)C1]

Racemic trans 3-[3-(2-methyl-6H-1,2,3,5,6-tetraaza-as-indacen-1-yl)-cyclopentylamino]-propionitrile Racemic trans 3-[3-(6-benzenesulfonyl-2-methyl-6H-1,2,3,5,6-tetraaza-as-indacen-1-yl)-cyclopentylamino]-propionitrile A mixture of racemic trans 3-(6-benzenesulfonyl-2-methyl-6H-1,2,3,5,6-tetraaza-as-indacen-1-yl)-cyclopentylamine (176 mg, 445 μmol) and acrylonitrile (147 μL, 2.23 mmol) in ethanol (5 mL, IMS grade) was heated to 80° C. for 2 hours. After cooling, the mixture was concentrated in vacuo to give 195 mg (98%) of racemic trans 3-[3-(6-benzenesulfonyl-2-methyl-6H-1,2,3,5,6-tetraaza-as-indacen-1-yl)-cyclopentylamino]-propionitrile as a cream coloured foam. LCMS (Method B, ESI): RT=2.32 min, m+H=449.4.

Racemic trans 3-[3-(2-methyl-6H-1,2,3,5,6-tetraaza-as-indacen-1-yl)-cyclopentylamino]-propionitrile A mixture of racemic trans 3-[3-(6-benzenesulfonyl-2-methyl-6H-1,2,3,5,6-tetraaza-as-indacen-1-yl)-cyclopentylamino]-propionitrile (192 mg, 428 μmol) and tetrabutylammonium fluoride solution (1.28 mL, 1.28 mmol, 1M in THF) in THF (3.72 mL) was heated to 60° C. for 18 hours. After cooling, ethyl acetate was added and the mixture extracted with water (3×). The combined aqueous extracts were extracted with DCM/MeOH (10:1) and the organic layer separated and concentrated in vacuo. Purification by column chromatography on silica gel (gradient: chloroform to 10% [2M $NH_3$ in methanol] in chloroform) to afford 38.0 mg (29%) of racemic trans 3-[3-(2-methyl-6H-1,2,3,5,6-tetraaza-as-indacen-1-yl)-cyclopentylamino]-propionitrile as a pale yellow foam. LCMS (Method A, ESI): RT=1.17 min, m+H=309.3; $^{1}$H NMR (400 MHz, DMSO) δ: 11.78 (s, 1H), 8.45 (s, 1H), 7.43 (t, 1H), 6.52 (dd, 1H), 5.19 (m, 1H), 3.56 (m, 1H), 2.79 (m, 2H), 2.61 (m, 5H), 2.42-2.15 (m, 5H), 2.01 (m, 1H), 1.63 (m, 1H).

Example 628

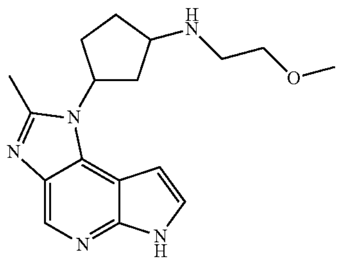

Racemic trans (2-methoxy-ethyl)-[3-(2-methyl-6H-1,2,3,5,6-tetraaza-as-indacen-1-yl)-cyclopentyl]-amine Racemic trans [3-(6-benzenesulfonyl-2-methyl-6H-1,2,3,5,6-tetraaza-as-indacen-1-yl)-cyclopentyl]-(2-methoxy-ethyl)-amine A mixture of racemic trans 3-(6-benzenesulfonyl-2-methyl-6H-1,2,3,5,6-tetraaza-as-indacen-1-yl)-cyclopentylamine (155 mg, 392 μmol), 2-bromoethyl methyl ether (59.9 mg, 431 μmol), potassium carbonate (108 mg, 780 μmol) and DMF (2 mL) was heated to 135° C. for 15 minutes using microwave irradiation. The mixture was filtered, concentrated in vacuo and purified by column chromatography on silica gel (gradient: DCM to 10% methanol in DCM) to give 88.0 mg (49%) of racemic trans [3-(6-benzenesulfonyl-2-methyl-6H-1,2,3,5,6-tetraaza-as-indacen-1-yl)-cyclopentyl]-(2-methoxy-ethyl)-amine as a beige foam. LCMS (Method B, ESI): RT=2.29 min, m+H=454.4; $^1$H NMR (400 MHz, DMSO) δ: 8.60 (s, 1H), 8.13 (m, 2H), 7.95 (d, 1H), 7.70 (m, 1H), 7.61 (m, 2H), 6.92 (d, 1H), 5.18 (m, 1H), 3.51 (m, 1H), 3.41 (t, 2H), 3.26 (s, 3H), 2.69 (t, 2H), 2.64 (s, 3H), 2.32-2.14 (m, 3H), 2.04 (m, 2H), 1.61 (m, 1H).

Racemic trans (2-methoxy-ethyl)-[3-(2-methyl-6H-1,2,3,5,6-tetraaza-as-indacen-1-yl)-cyclopentyl]-amine A mixture of racemic trans [3-(6-benzenesulfonyl-2-methyl-6H-1,2,3,5,6-tetraaza-as-indacen-1-yl)-cyclopentyl]-(2-methoxy-ethyl)-amine (86.0 mg, 190 umol), aqueous sodium hydroxide solution (0.48 mL, 950 μmol, 2M), methanol (3 mL) and THF (3 mL) was stirred at ambient temperature for 2 hours. The mixture was partitioned between DCM and water, the organics separated and washed with brine, then concentrated to dryness. Purification by column chromatography on silica gel (gradient: DCM to 10% [2M $NH_3$ in methanol] in DCM) followed by reverse phase HPLC (5 to 50% acetonitrile in water, +0.1% $NH_4OH$) afforded 17.6 mg of racemic trans (2-methoxy-ethyl)-[3-(2-methyl-6H-1,2,3,5,6-tetraaza-as-indacen-1-yl)-cyclopentyl]-amine as a colourless gum. LCMS (Method A, ESI): RT=1.57 min, m+H=314.3; $^1$H NMR (400 MHz, DMSO) δ: 11.78 (s, 1H), 8.45 (s, 1H), 7.43 (t, 1H), 6.51 (dd, 1H), 5.17 (m, 1H), 3.53 (m, 1H), 3.42 (t, 2H), 3.26 (s, 3H), 2.70 (t, 2H), 2.61 (s, 3H), 2.42-2.15 (m, 4H), 2.01 (m, 1H), 1.82 (br s, 1H), 1.63 (m, 1H).

Example 629

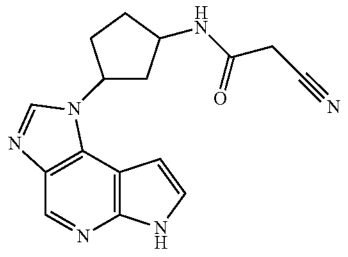 [SMILES: N#CCC(=O)NC1CCC(n2cnc3cnc4[nH]ccc4c32)C1]

Racemic trans 2-cyano-N-[3-(6H-1,2,3,5,6-tetraaza-as-indacen-1-yl)-cyclopentyl]-acetamide Racemic trans 3-(6-benzenesulfonyl-6H-1,2,3,5,6-tetraaza-as-indacen-1-yl)-cyclopentylamine Racemic trans [3-(6-benzenesulfonyl-6H-1,2,3,5,6-tetraaza-as-indacen-1-yl)-cyclopentyl]-carbamic acid tert-butyl ester (2.12 mmol, Prepared analogously to [(1R,3R)-3-(6-benzenesulfonyl-6H-1,2,3,5,6-tetraaza-as-indacen-1-yl)-cyclopentyl]-carbamic acid tert-butyl ester) was treated with trifluoroacetic acid (5 mL) at ambient temperature for 1 hour. The mixture was purified by column chromatography (SCX-2, gradient: methanol to 2M $NH_3$ in methanol) to give 695 mg (86%) of racemic trans 3-(6-benzenesulfonyl-6H-1,2,3,5,6-tetraaza-as-indacen-1-yl)-cyclopentylamine as a beige foam. LCMS (Method B, ESI): RT=2.18 min, m+H=382.0.

Racemic trans 3-(6H-1,2,3,5,6-tetraaza-as-indacen-1-yl)-cyclopentylamine

To a stirred solution of racemic trans 3-(6-benzenesulfonyl-6H-1,2,3,5,6-tetraaza-as-indacen-1-yl)-cyclopentylamine (230 mg, 600 μmol) in methanol (3 mL) and THF (3 mL), aqueous sodium hydroxide solution (3 mL, 1 N) was added. After 3 hours, the reaction was neutralised by the addition of aqueous HCl solution (ca. 2 mL, 1N) and concentrated in vacuo. Purification by column chromatography (SCX-2, gradient: methanol to 2M $NH_3$ in methanol) gave 150 mg (100%) of racemic trans 3-(6H-1,2,3,5,6-tetraaza-as-indacen-1-yl)-cyclopentylamine as a beige foam. LCMS (Method B, ESI): RT=0.34 min, m+H=242.0.

Racemic trans 2-cyano-N-[3-(6H-1,2,3,5,6-tetraaza-as-indacen-1-yl)-cyclopentyl]-acetamide To a stirred mixture of racemic trans 3-(6H-1,2,3,5,6-tetraaza-as-indacen-1-yl)-cyclopentylamine (100 mg, 0.41 mmol) in acetonitrile (3 mL) and DCM (3 mL), cyano acetic acid (42.0 mg, 0.50 mmol), EDCI (127 mg, 0.66 mmol), DMAP (81.0 mg, 0.66 mmol) and HOBt (79.0 mg, 0.58 mmol) were added. Stirring was continued for 18 hours. The solvent was removed in vacuo and the residue purified by column chromatography on silica gel (gradient: DCM to 10% methanol in DCM, then 5 to 10% [2M $NH_3$ in methanol] in DCM) to give 47.0 mg (37%) of racemic trans 2-cyano-N-[3-(6H-1,2,3,5,6-tetraaza-as-indacen-1-yl)-cyclopentyl]-acetamide as a white solid. LCMS (Method A, ESI): RT=1.87 min, m+H=309.28; $^1$H NMR (400 MHz, DMSO) δ: 11.85 (s, 1H), 8.57 (s, 1H), 8.52 (d, 1H), 8.32 (s, 1H), 7.48 (t, 1H), 6.80 (dd, 1H), 5.25 (m, 1H), 4.36 (m, 1H), 3.65 (s, 2H), 2.26 (m, 5H), 1.69 (m, 1H).

Example 630

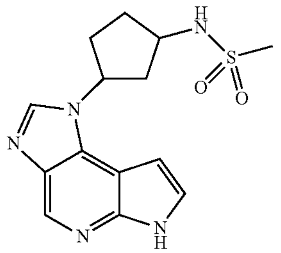 [SMILES: CS(=O)(=O)NC1CCC(n2cnc3cnc4[nH]ccc4c32)C1]

Racemic trans N-[3-(6H-1,2,3,5,6-tetraaza-as-indacen-1-yl)-cyclopentyl]-methanesulfonamide To a stirred solution of racemic trans 3-(6H-1,2,3,5,6-tetraaza-as-indacen-1-yl)-cyclopentylamine (94.6 mg, 392 μmol) and triethylamine (109 μL, 784 μmol) in DCM (2 mL), methanesulfonyl chloride (30.3 μL, 392 μmol) was added. The mixture was then stirred at ambient temperature and then filtered. The solid was washed with DCM and water, then air dried. The solid was purified by flash chromatography on silica gel (gradient: chloroform to 10% [2M $NH_3$ in methanol] in chloroform) to afford 20.7 mg (17%) of racemic trans N-[3-(6H-1,2,3,5,6-tetraaza-as-indacen-1-yl)-cyclopentyl]- methanesulfonamide as a beige solid. LCMS (Method A, ESI): RT=1.89 min, m+H=320.2; $^1$H NMR (400 MHz, DMSO) δ: 11.84 (s, 1H), 8.56 (s, 1H), 8.32 (s, 1H), 7.47 (t, 1H), 7.40 (br d, 1H), 6.83 (dd, 1H), 5.25 (m, 1H), 4.04 (m, 1H), 2.95 (s, 3H), 2.44-2.24 (m, 4H), 2.05 (m, 1H), 1.76 (m, 1H).

Example 631

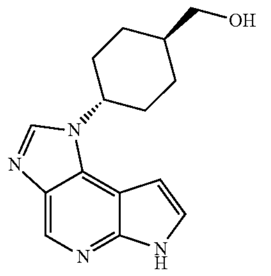 [SMILES: OC[C@H]1CC[C@H](n2cnc3cnc4[nH]ccc4c32)CC1]

trans [4-(6H-1,2,3,5,6-Tetraaza-as-indacen-1-yl)-cyclohexyl]-methanol trans [4-(6-Benzenesulfonyl-6H-1,2,3,5,6-tetraaza-as-indacen-1-yl)-cyclohexyl]-methanol A solution of trans 4-(6-benzenesulfonyl-6H-1,2,3,5,6-tetraaza-as-indacen-1-yl)-cyclohexanecarboxylic acid ethyl ester (750 mg, 1.66 mmol) and sodium borohydride (75.0 mg, 2.00 mmol) in THF (20 mL) and MeOH (0.5 mL) was stirred at reflux for 8 hours. The suspension was filtered, the filtrate evaporated, and the residue partitioned between aq. $NH_4Cl$ (25 mL) and ethyl acetate (2×25 mL). The organic layers were dried ($MgSO_4$), evaporated, and the residue purified by column chromatography on silica gel (gradient: 0 to 10% MeOH in DCM) to afford 143 mg of a gum which was determined to be a 3:1 mixture of the desired product and desulfonylated starting ester. LCMS (ESI) m+H=410.0; NMR (400 MHz, $CDCl_3$): δ 8.92 (s, 1H), 8.24-8.20 (m, 2H), 8.01 (s, 1H), 7.81 (d, 1H), 7.5-7.51 (m, 1H), 7.49-7.44 (m, 2H), 6.77 (d, 1H), 4.45-4.35 (m, 1H), 3.61 (d, 2H), 2.52-2.44 (m, 1H), 2.39-2.30 (m, 2H), 2.15-2.07 (m, 2H), 1.89-1.86 (m, 2H), 1.42-1.28 (m, 2H).

trans [4-(6H-1,2,3,5,6-Tetraaza-as-indacen-1-yl)-cyclohexyl]-methanol

1M TBAF in THF (0.25 mL, 0.25 mmol) was added to crude trans [4-(6-benzenesulfonyl-6H-1,2,3,5,6-tetraaza-as-indacen-1-yl)-cyclohexyl]-methanol (35.0 mg, approx 0.09 mmol) in THF (5 mL) and the solution stirred at reflux for 3 hours, evaporated, and the residue passed through an SCX-2 cartridge (gradient elution: MeOH, to 2M $NH_3$ in MeOH). The relevant fractions were evaporated and the resulting residue purified by column chromatography on silica gel (gradient: 0 to 10% MeOH in DCM) followed by crystallisation from absolute ethanol to give 6.0 mg of trans [4-(6H-1,2,3,5,6-tetraaza-as-indacen-1-yl)-cyclohexyl]-methanol as a white solid. LCMS (Method A, ESI) RT=2.00 min, m+H=271.2; NMR (400 MHz, MeOD): δ 8.58 (s, 1H), 8.30 (s, 1H), 7.46 (d, 1H), 6.79 (d, 1H), 4.62 (dt, 1H), 3.51 (d, 2H), 2.43-2.32 (m, 2H), 2.14-2.05 (m, 2H), 2.08-1.94 (m, 2H), 1.76-1.65 (m, 1H), 1.47-1.34 (m, 2H).

Example 632

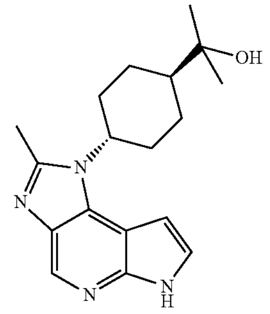 [SMILES: Cc1nc2cnc3[nH]ccc3c2n1[C@H]1CC[C@H](C(C)(C)O)CC1]

2-[4-(2-Methyl-6H-1,2,3,5,6-tetraaza-as-indacen-1-yl)-cyclohexyl]-propan-2-ol

Trans 4-amino-cyclohexanecarboxylic acid methyl ester

A solution of trans 4-amino-cyclohexanecarboxylic acid (12.5 g, 87.0 mmol) in methanol (400 mL) and conc. sulphuric acid (9.0 mL) was stirred at room temperature for one week. The mixture was then neutralised with sodium bicarbonate and the solvent was concentrated under vacuum. The residue was taken into water and continuously extracted with DCM for 18 hours. The organic phase was dried over sodium sulphate and concentrated under vacuum to afford 9.20 g (67%) of trans 4-amino-cyclohexanecarboxylic acid methyl ester as an oil. $^1$H NMR (400 MHz, $CDCl_3$): δ 3.67 (s, 3H), 2.67 (tt, 1H), 2.24 (tt, 1H), 2.02-1.90 (m, 4H), 1.55-1.41 (m, 2H), 1.19-1.10 (m, 2H).

Trans 4-(5-amino-1-benzenesulfonyl-1H-pyrrolo[2,3-b]pyridin-4-ylamino)-cyclohexanecarboxylic acid methyl ester

&

Trans 4-(5-acetylamino-1-benzenesulfonyl-1H-pyrrolo[2,3-b]pyridin-4-ylamino)-cyclohexanecarboxylic acid methyl ester A mixture of 1-benzenesulfonyl-4-chloro-5-nitro-1H-pyrrolol[2,3-b]pyridine (13.1 g, 38.8 mmol), trans 4-amino-cyclohexanecarboxylic acid methyl ester (6.70 g, 42.7 mmol), propan-2-ol (130 mL) and diisopropylethylamine (9.30 mL, 54.3 mmol) was stirred and heated at reflux for 1.5 hours. The mixture was cooled and concentrated under vacuum. The residue was partitioned between water and dichloromethane. The organic phase was dried over sodium sulfate and concentrated under vacuum to afford 17.7 g (99%) of crude 4-(1-benzenesulfonyl-5-nitro-1H-pyrrolo[2,3-b]pyridine-4-ylamino)-cyclohexanecarboxylic acid methyl ester as a yellow solid. $^1$H NMR (400 MHz, $CDCl_3$): δ 9.10 (s, 1H), 9.0 (d, 1H), 8.23-8.16 (m, 2H), 7.65-7.59 (m, 2H), 7.52 (t, 2H), 6.69 (d, 1H), 3.96-3.84 (m, 1H), 3.71 (s, 3H), 2.41 (tt, 1H), 2.30-2.22 (m, 2H), 2.19-2.11 (m, 2H), 1.73-1.60 (m, 2H), 1.53-1.40 (m, 2H).

This material was suspended in acetic acid (150 mL). Palladium hydroxide on carbon (2.50 g, 20% catalyst loading) was added and the inert atmosphere replaced with hydrogen. The mixture was heated at 50° C. for 6.5 hours then stirred at room temperature for 18 hours whilst maintaining a hydrogen atmosphere. The reaction mixture was filtered through a pad of Celite®. The pad was washed with DCM and the combined filtrate was concentrated under vacuum. The residue was partitioned between DCM and saturated aqueous sodium bicarbonate and then separated. The organic phase was dried over sodium sulfate, concentrated under vacuum and the residue was purified by chromatography on silica gel (eluting with 0-100% ethyl acetate in DCM) to afford 12.0 g (72%) of trans 4-(5-amino-1-benzenesulfonyl-1H-pyrrolo[2,3-b]pyridine-4-ylamino)-cyclohexanecarboxylic acid methyl ester as a purple solid. LCMS (Method I, ESI): RT=2.44 min, m+H=429.2; $^1$H NMR (400 MHz, DMSO): δ 8.01-7.96 (m, 2H), 7.66 (t, 1H), 7.60-7.52 (m, 3H), 7.45 (d, 1H), 6.71 (d, 1H), 5.09 (d, 1H), 4.33 (s, 2H), 3.73-3.61 (m, 1H), 3.59 (s, 3H), 2.30 (tt, 1H), 2.00-1.87 (m, 4H), 1.60-1.47 (m, 2H), 1.35-1.21 (m, 2H).

Also isolated was 2.20 g (5%) of trans 4-(5-acetylamino-1-benzenesulfonyl-1H-pyrrolo[2,3-b]pyridine-4-ylamino)-cyclohexanecarboxylic acid methyl ester as a brown solid. LCMS (Method I, ESI): RT=2.81 min, m+H=471.2; $^1$H NMR (400 MHz, DMSO): δ 9.04 (s, 1H), 8.08-8.02 (m, 2H), 7.71-7.65 (m, 2H), 7.61-7.53 (m, 3H), 6.84 (d, 1H), 5.52 (d, 1H), 3.79-3.65 (m, 1H), 3.59 (s, 3H), 2.29 (tt, 1H), 2.01 (s, 3H), 1.96-1.86 (m, 4H), 1.61-1.45 (m, 2H), 1.39-1.24 (m, 2H).

Trans 4-(6-benzenesulfonyl-2-methyl-6H-1,2,3,5,6-tetraaza-as-indacen-1-yl)-cyclohexanecarboxylic acid methyl ester A mixture of trans 4-(5-acetylamino-1-benzenesulfonyl-1H-pyrrolo[2,3-b]pyridine-4-ylamino)-cyclohexanecarboxylic acid methyl ester (2.20 g, 4.68 mmol) and p-toluenesulfonic acid monohydrate (89.0 mg, 0.47 mmol) in toluene (30 mL) was heated at reflux for 64 hours. The cooled mixture was partitioned between ethyl acetate and saturated aqueous sodium bicarbonate. The organic phase was washed with water then concentrated under vacuum (some fine solid was suspended in the organic phase). The residue was triturated with ether and acetonitrile to afford 1.67 g (79%) of trans 4-(6-benzenesulfonyl-2-methyl-6H-1,2,3,5,6-tetraaza-as-indacen-1-yl)-cyclohexanecarboxylic acid methyl ester as a green solid. LCMS (Method I, ESI): RT=3.00 min, m+H=453.2; $^1$H NMR (400 MHz, DMSO): δ 8.60 (s, 1H), 8.13 (d, 2H), 7.93 (d, 1H), 7.70 (t, 1H), 7.61 (t, 2H), 7.19 (br s, 1H), 4.60-4.45 (m, 1H), 3.66 (s, 3H), 2.80-2.60 (m, 4H), 2.23-2.06 (m, 4H), 2.00-1.90 (m, 2H), 1.81-1.65 (m, 2H).

Trans 2-[4-(6-benzenesulfonyl-2-methyl-6H-1,2,3,5,6-tetraaza-as-indacen-1-yl)-cyclohexyl]-propan-2-ol To a solution of trans 4-(6-benzenesulfonyl-2-methyl-6H-1,2,3,5,6-tetraaza-as-indacen-1-yl)-cyclohexanecarboxylic acid methyl ester (200 mg, 0.44 mmol) in THF (4 mL) at 0° C. was added methyl magnesium bromide (737 μL of a 3.0 M solution in ether, 2.21 mmol). The mixture was stirred and allowed to warm to ambient temperature. The reaction mixture was then treated with saturated aqueous ammonium chloride and extracted with DCM. The organic phase was dried over sodium sulfate and concentrated under vacuum to afford crude trans 2-[4-(6-benzenesulfonyl-2-methyl-6H-1,2,3,5,6-tetraaza-as-indacen-1-yl)-cyclohexyl]-propan-2-ol as an orange semi-solid, which was used without purification. LCMS (Method I, ESI): RT=2.75 min, m+H=453.3; $^1$H NMR (400 MHz, DMSO): δ 8.58 (s, 1H), 8.11 (d, 2H), 7.97 (d, 1H), 7.68 (t, 1H), 7.60 (t, 2H), 7.05 (br s, 1H), 4.51-4.36 (m, 1H), 4.19 (s, 1H), 2.63 (s, 3H), 2.16-1.85 (m, 6H), 1.58-1.46 (m, 1H), 1.41-1.30 (m, 2H), 1.11 (s, 6H).

Trans 2-[4-(Methyl-6H-1,2,3,5,6-tetraaza-as-indacen-1-yl)-cyclohexyl]-propan-2-ol Crude trans 2-[4-(6-benzenesulfonyl-2-methyl-6H-1,2,3,5,6-tetraaza-as-indacen-1-yl)-cyclohexyl]-propan-2-ol (assumed to be 0.44 mmol) was dissolved in a 1M solution of tetrabutylammonium fluoride in THF (10 mL, 10.0 mmol). The mixture was heated at reflux for 1 hour. The cooled mixture was concentrated under vacuum and the residue was diluted with water. Purification by reverse phase column chromatography using an Isolute® C18 cartridge (eluting with 10 to 100% acetonitrile in water) then by reverse phase HPLC (5 to 95% acetonitrile in water) gave 55.0 mg (40%) of trans 2-[4-(methyl-6H-1,2,3,5,6-tetraaza-as-indacen-1-yl)-cyclohexyl]-propan-2-ol as a white solid. LCMS (Method A, ESI): RT=2.39 min, m+H=313.3; $^1$H NMR (400 MHz, DMSO): δ 11.78 (s, 1H), 8.45 (s, 1H), 7.46 (t, 1H), 6.68 (s, 1H), 4.53-4.32 (m, 1H), 4.20 (s, 1H), 2.62 (s, 3H), 2.40-2.20 (m, 2H), 2.09-1.88 (m, 4H), 1.63-1.50 (m, 1H), 1.43-1.29 (m, 2H), 1.13 (s, 6H).

Example 633

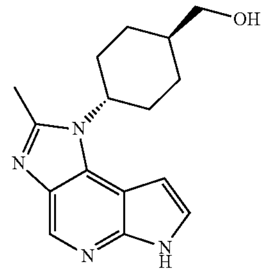 [SMILES: Cc1nc2cnc3[nH]ccc3c2n1[C@H]1CC[C@H](CO)CC1]

Trans[4-(2-methyl-6H-1,2,3,5,6-tetraaza-as-indacen-1-yl)-cyclohexyl]-methanol

Trans 2-[4-(6-benzenesulfonyl-2-methyl-6H-1,2,3,5,6-tetraaza-as-indacen-1-yl)-cyclohexyl]-methanol A cold (0° C.) solution of trans 4-(6-benzenesulfonyl-2-methyl-6H-1,2,3,5,6-tetraaza-as-indacen-1-yl)-cyclohexanecarboxylic acid methyl ester (200 mg, 0.44 mmol) in DCM (4 mL) was treated with diisobutylaluminium hydride (906 μL of a 1.0M solution in toluene, 0.91 mmol). The mixture was stirred cold for 1 hour then treated with 10% aqueous potassium sodium tartrate (2 mL). The mixture was stirred without cooling for 2 hours then partitioned between water and DCM. The organic phase was dried over sodium sulfate and concentrated under vacuum. The residue was purified by column chromatography on silica gel (eluting with 0-10% methanol in DCM) to afford crude trans 2-[4-(6-benzenesulfonyl-2-methyl-6H-1,2,3,5,6-tetraaza-as-indacen-1-yl)-cyclohexyl]-methanol as a green oil that solidified on standing. LCMS (Method I, ESI): RT=2.53 min, m+H=425.3.

Trans[4-(2-methyl-6H-1,2,3,5,6-tetraaza-as-indacen-1-yl)-cyclohexyl]-methanol

A solution of crude trans 2-[4-(6-benzenesulfonyl-2-methyl-6H-1,2,3,5,6-tetraaza-as-indacen-1-yl)-cyclohexyl]-methanol (assumed to be 0.44 mmol) in THF (10 mL) was treated with tetrabutyl ammonium fluoride (880 μL of a 1M solution in THF, 0.88 mmol). The mixture was heated at reflux for 18 hours. The cooled mixture was purified by column chromatography using Isolute® SCX-2 cartridge (gradient: methanol to 2M $NH_3$ in methanol). The resulting residue was purified by reverse phase HPLC (5 to 95% MeCN in water) to afford 52.0 mg (41%) of trans [4-(2-methyl-6H-1,2,3,5,6-tetraaza-as-indacen-1-yl)-cyclohexyl]-methanol as a white solid. LCMS (Method A, ESI): RT=2.02 min, m+H=285.3; $^1$H NMR (400 MHz, DMSO): δ 11.77 (s, 1H), 8.45 (s, 1H), 7.45 (t, 1H), 6.67 (s, 1H), 4.60-4.33 (m, 2H), 2.62 (s, 3H), 2.38-2.20 (m, 2H), 2.04-1.87 (m, 4H), 1.77-1.61 (m, 1H), 1.35-1.20 (m, 2H).

With addition of deuterated TFA: $^1$H NMR (400 MHz, DMSO): δ 8.81 (s, 1H), 7.79 (d, 1H), 6.90 (s, 1H), 4.81-4.58m, 1H), 3.36 (d, 2H), 2.94 (s, 3H), 2.44-2.21 (m, 2H), 2.16-1.95 (m, 4H), 1.85-1.65 (m, 1H), 1.41-1.22 (m, 2H); two mobile protons absent.

Example 634

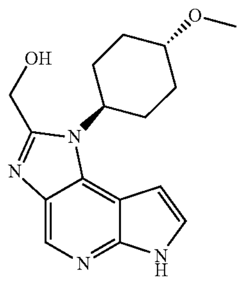 [SMILES: CO[C@H]1CC[C@H](n2c(CO)nc3cnc4[nH]ccc4c32)CC1]

Trans[1-(4-Methoxy-cyclohexyl)-1,6-dihydro-1,2,3,5,6-tetraaza-as-indacen-2-yl]-methanol trans {6-Benzenesulfonyl-1-[4-(tert-butyl-dimethyl-silanyloxy)-cyclohexyl]-1,6-dihydro-1,2,3,5,6-tetraaza-as-indacen-2-yl}-methanol A solution of glycolamide (1.88 g, 25.0 mmol) in dry THF (30 ml) under nitrogen was treated with triethyloxonium tetrafluoroborate (4.45 g, 23.4 mmol) and the mixture was stirred at ambient temperature for 2 hours then concentrated under vacuum. The residue was treated with absolute ethanol (15 mL) and added to a suspension of trans 1-benzenesulfonyl-N*4*-[4-(tert-butyl-dimethyl-silanyloxy)-cyclohexyl]-1H-pyrrolo[2,3-b]pyridine-4,5-diamine (3.90 g, 7.80 mmol) in absolute ethanol (40 mL) under nitrogen. The mixture was heated to 75° C. for 1.5 hour then concentrated under vacuum. The residue was partitioned between DCM and saturated sodium hydrogen carbonate solution and the phases were separated. The aqueous phase was extracted with DCM (×2) and the combined organic phase was washed with brine, dried with sodium sulfate and concentrated under vacuum to gave brown oil. Crude product was purified by column chromatography on silica gel (eluting with 0-5% MeOH in DCM) to give 2.50 g (60%) of trans-{6-benzenesulfonyl-1-[4-(tert-butyl-dimethyl-silanyloxy)-cyclohexyl]-1,6-dihydro-1,2,3,5,6-tetraaza-as-indacen-2-yl}-methanol contaminated with some aliphatic impurities as an off-white foam. LCMS (Method I, ESI): RT=4.35 min, m+H=541.4; $^1$H NMR (300 MHz, $CDCl_3$) δ: 8.84 (s, 1H), 8.26-8.18 (m, 2H), 7.89 (d, 1H), 7.62-7.44 (m, 3H), 6.83 (d, 1H), 5.00 (s, 2H), 4.67-4.52 (m, 1H), 3.93-3.78 (m, 1H), 3.20-2.50 (m, 2H) 2.38-1.96 (m, 6H), 0.93 (s, 9H), 0.14 (s, 6H).

Trans 2-Allyloxymethyl-6-benzenesulfonyl-1-[4-(tert-butyl-dimethyl-silanyloxy)-cyclohexyl]-1,6-dihydro-1,2,3,5,6-tetraaza-as-indacene Trans {6-benzenesulfonyl-1-[4-(tert-butyl-dimethyl-silanyloxy)-cyclohexyl]-1,6-dihydro-1,2,3,5,6-tetraaza-as-indacen-2-yl}-methanol (2.30 g, 4.26 mmol), carbonic acid allyl ester tert-butyl ester (3.40 g, 21.3 mmol) was taken in dry THF (20 mL) and mixture degassed with vacuum/argon (×3). Tetrakis(triphenylphosphine)palladium(0) (0.25 g, 0.22 mmol) was added and mixture was heated at 70° C. for 1 hour. The mixture was concentrated under vacuum to give an orange solid which was purified by column chromatography on silica gel (eluting with 0-30% ethyl acetate in DCM). This gave trans 2-allyloxymethyl-6-benzenesulfonyl-1-[4-(tert-butyl-dimethyl-silanyloxy)-cyclohexyl]-1,6-dihydro-1,2,3,5,6-tetraaza-as-indacene 2.30 g (93%) as an off-white solid. LCMS (Method I, ESI): RT=5.03 min, m+H=581.1; $^1$H NMR (300 MHz, $CDCl_3$) δ: 8.87 (s, 1H), 8.27-8.20 (m, 2H), 7.86 (d, 1H), 7.60-7.43 (m, 3H), 6.83 (d, 1H), 5.95-5.80 (m, 1H), 5.34-5.17 (m, 2H), 4.83 (s, 2H), 4.70-4.56 (m, 1H), 4.01 (dt, 2H), 3.92-3.78 (m, 1H), 2.42-2.21 (m, 2H), 2.17-2.06 (m, 2H), 2.01-1.89 (m, 2H), 1.70-1.50 (m, 2H), 0.93 (s, 9H), 0.13 (s, 6H).

Trans 4-(2-Allyloxymethyl-6-benzenesulfonyl-6H-1,2,3,5,6-tetraaza-as-indacen-1-yl)-cyclohexanol A mixture of trans 2-allyloxymethyl-6-benzenesulfonyl-1-[4-(tert-butyl-dimethyl-silanyloxy)-cyclohexyl]-1,6-dihydro-1,2,3,5,6-tetraaza-as-indacene (2.30 g, 3.96 mmol), ethanol (50 mL, IMS grade), conc.HCl (1.3 mL) was stirred at room temperature for 30 minutes. The reaction mixture was concentrated under vacuum to a small volume and the residue was partitioned between DCM and saturated sodium hydrogen carbonate solution. The phases were separated. The aqueous phase was extracted with DCM (×2) and the combined organic phases were washed with brine, dried with sodium sulfate and concentrated under vacuum to give 1.89 g (100%) of trans 4-(2-allyloxymethyl-6-benzenesulfonyl-6H-1,2,3,5,6-tetraaza-as-indacen-1-yl)-cyclohexanol as an off-white foam that was used without further purification. $^1$H NMR (400 MHz, $CDCl_3$) δ: 8.88 (s, 1H), 8.29-8.20 (m, 2H), 7.85 (d, 1H), 7.60-7.44 (m, 3H), 6.85 (d, 1H), 5.95-5.80 (m, 1H), 5.34-5.18 (m, 2H), 4.85 (s, 2H), 4.74-4.60 (m, 1H), 4.05-3.91 (m, 3H), 2.47-2.19 (m, 4H), 2.05-1.94 (m, 2H), 1.70-1.50 (m, 2H).

Trans 2-Allyloxymethyl-6-benzenesulfonyl-1-(4-methoxy-cyclohexyl)-1,6-dihydro-1,2,3,5,6-tetraaza-as-indacene A mixture of trans 4-(2-Allyloxymethyl-6-benzenesulfonyl-6H-1,2,3,5,6-tetraaza-as-indacen-1-yl)-cyclohexanol (0.30 g, 0.64 mmol), 2,6-di-tert-butyl-4-methyl-pyridine (0.46 g, 2.25 mmol), silver triflate (0.52 g, 1.99 mmol) in dry DCM (5 mL) was cooled to 0° C. under nitrogen, then iodomethane (0.13 mL, 2.09 mmol) was added. The mixture was stirred for 4 hours at 0° C. and allowed to stir at room temperature overnight. A pale green solid precipitated and the mixture was diluted with DCM and filtered. The filtrate was washed with 10% aqueous citric acid solution, saturated sodium hydrogen carbonate solution, and brine, dried with sodium sulphate and concentrated under vacuum. The crude product was purified by column chromatography on silica gel (gradient: 0 to 100% ethyl acetate in DCM) afforded 0.12 g (39%) of trans 2-allyloxymethyl-6-benzenesulfonyl-1-(4-methoxy-cyclohexyl)-1,6-dihydro-1,2,3,5,6-tetraaza-as-indacene as an off-white solid. LCMS (Method H, ESI): RT=3.45 min, m+H=481.1.

Trans[6-Benzenesulfonyl-1-(4-methoxy-cyclohexyl)-1,6-dihydro-1,2,3,5,6-tetraaza-as-indacen-2-yl]-methanol A mixture of trans 2-allyloxymethyl-6-benzenesulfonyl-1-(4-methoxy-cyclohexyl)-1,6-dihydro-1,2,3,5,6-tetraaza-as-indacene (0.12 g, 0.25 mmol), 1,3-dimethyl barbituric acid (0.20 g, 1.25 mmol) and tetrakis(triphenylphosphine)palladium(0) (60.0 mg, 0.05 mmol) in DCM (5 mL) was stirred at 70° C. for 4 hours then concentrated under vacuum. The resulting residue was purified by Isolute® SCX-2 column (gradient: DCM to 5 to 60% [2M $NH_3$ in methanol] solution in DCM) to afford 72.0 mg (65%) of trans [6-benzenesulfonyl-1-(4-methoxy-cyclohexyl)-1,6-dihydro-1,2,3,5,6-tetraaza-as-indacen-2-yl]-methanol. LCMS (Method I, ESI): RT=2.57 min, m+H=441.1; $^1$H NMR (300 MHz, DMSO) δ: 8.68 (s, 1H), 8.17-8.10 (m, 2H), 7.98 (d, 1H), 7.75-7.57 (m, 3H), 7.12 (d, 1H), 5.73 (t, 1H), 4.79 (d, 2H), 4.76-4.63 (m, 1H), 3.59-3.44 (m, 1H), 3.34 (s, 3H), 2.29-2.13 (m, 4H) 2.02-1.89 (m, 2H), 1.50-1.31 (m, 2H).

Trans[1-(4-Methoxy-cyclohexyl)-1,6-dihydro-1,2,3,5,6-tetraaza-as-indacen-2-yl]-methanol A suspension of trans [6-benzenesulfonyl-1-(4-methoxy-cyclohexyl)-1,6-dihydro-1,2,3,5,6-tetraaza-as-indacen-2-yl]-methanol (70.0 mg, 0.16 mmol) in methanol (3 mL) and THF (2 mL) was treated with an aqueous 1M sodium hydroxide solution (0.79 mL, 0.79 mmol) and the mixture was stirred at ambient temperature overnight. the solvent was evaporated under vacuum and the aqueous residue was extracted with DCM (×3). The combined organic phases were washed with brine, dried with sodium sulfate and concentrated under vacuum to give crude product. Purification by column chromatography on silica gel (gradient: 0 to 10% [2M $NH_3$ in MeOH] in DCM) gave 49.0 mg (98%) of trans [1-(4-methoxy-cyclohexyl)-1,6-dihydro-1,2,3,5,6-tetraaza-as-indacen-2-yl]-methanol as a white solid. LCMS (Method A): RT=2.20 min, m+H=301.2; $^1$H NMR (400 MHz, DMSO): δ 11.87 (s, 1H), 8.54 (s, 1H), 7.48 (t, 1H), 6.70 (dd, 1H), 5.66 (t, 1H), 4.78 (d, 2H), 4.74-4.64 (m, 1H), 3.56-3.46 (m, 1H), 3.34 (s, 3H), 2.43-2.30 (m, 2H), 2.27-2.19 (m, 2H), 1.99-1.91 (m, 2H), 1.48-1.34 (m, 2H).

Example 635

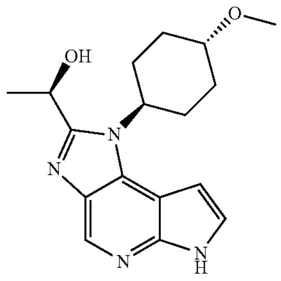 [SMILES: CO[C@H]1CC[C@H](n2c([C@@H](C)O)nc3cnc4[nH]ccc4c32)CC1]

Trans (R)-1-[1-(4-methoxy-cyclohexyl)-1,6-dihydro-1,2,3,5,6-tetraaza-as-indacen-2-yl]-ethanol Trans 2-((R-1-allyloxy-ethyl)-6-benzenesulfonyl-1-(4-methoxy-cyclohexyl]-1,6-dihydro-1,2,3,5,6-tetraaza-as-indacene A mixture of trans 4-[2-((R)-1-allyloxy-ethyl)-6-benzenesulfonyl-6H-1,2,3,5,6-tetraaza-as-indacen-1-yl]-cyclohexanol (240 mg, 0.50 mmol), 2,6-di-tert-butyl-4-methyl piperidine (360 mg, 1.75 mmol) and silver trifluoromethane sulfonate (400 mg, 1.55 mmol) in dry DCM was cooled to 0° C. Iodomethane (102 μl, 1.63 mmol) was added and the reaction mixture stirred for 3 hours at 0° C. followed by 16 hours at room temperature. The reaction was diluted with DCM, washed with aqueous citric acid, aqueous sodium bicarbonate, brine, dried over sodium sulfate, filtered and the filtrate evaporated under vacuum. The residue was purified by column chromatography on silica gel (gradient: 0 to 70% ethyl acetate in DCM) to afford 140 mg (57%) of trans 2-((R-1-allyloxy-ethyl)-6-benzenesulfonyl-1-(4-methoxy-cyclohexyl]-1,6-dihydro-1,2,3,5,6-tetraaza-as-indacene as a white foam. LCMS (Method H, ESI): RT=3.65 min, m+H=495.3; $^1$H NMR (400 MHz, $CDCl_3$): δ 8.88 (s, 1H), 8.23 (m, 2H), 7.85 (d, 1H), 7.55 (m, 1H), 7.47 (m, 2H), 6.86 (d, 1H), 5.85 (m, 1H), 5.26 (m, 1H), 5.18 (m, 1H), 5.01 (m, 2H), 3.96 (m, 2H), 3.46 (m, 4H), 2.35 (m, 4H), 1.95 (m, 2H), 1.71 (d, 3H), 1.48 (m, 2H).

Trans (R)-1-[-6-benzenesulfonyl-1-(4-methoxy-cyclohexyl]-1,6-dihydro-1,2,3,5,6-tetraaza-as-indacene-2-yl]-ethanol A mixture of trans 2-((R-1-allyloxy-ethyl)-6-benzenesulfonyl-1-(4-methoxy-cyclohexyl]-1,6-dihydro-1,2,3,5,6-tetraaza-as-indacene (120 mg, 0.24 mmol) and 1,3-dimethylbarbituric acid (190 mg, 1.21 mmol) were dissolved in dry THF under argon. Tetrakistriphenylphosphine palladium (0) (28.0 mg, 0.024 mmol) was added and the reaction heated at 70° C. for 2 hours. The solvent was concentrated under vacuum and the resulting residue purified by column chromatography on silica gel (gradient: 0 to 5% MeOH in DCM) to afford 88.0 mg of trans (R)-1-[-6-benzenesulfonyl-1-(4-methoxy-cyclohexyl]-1,6-dihydro-1,2,3,5,6-tetraaza-as-indacene-2-yl]-ethanol. LCMS (Method B, ESI): RT=2.88 min, m+H=455.2; $^1$H NMR (400 MHz, DMSO): δ 8.70 (s, 1H), 8.13 (m, 2H), 7.97 (d, 1H), 7.70 (m, 1H), 7.61 (m, 2H), 7.10 (d, 1H), 5.75 (m, 1H), 5.14 (m, 1H), 4.84 (m, 1H), 3.54 (m, 1H), 2.21 (m, 4H), 1.94 (m, 2H), 1.61 (d, 3H), 1.39 (m, 2H).

Trans (R)-1-[1-(4-methoxy-cyclohexyl)-1,6-dihydro-1,2,3,5,6-tetraaza-as-indacen-2-yl]-ethanol A mixture of trans (R)-1-[-6-benzenesulfonyl-1-(4-methoxy-cyclohexyl]-1,6-dihydro-1,2,3,5,6-tetraaza-as-indacene-2-yl]-ethanol (88.0 mg, 0.19 mmol) in THF/methanol containing aqueous sodium hydroxide (0.95 mmol) was stirred for 64 hours. The solvent was evaporated under vacuum to a small volume, the residue dissolved in DCM, washed with saturated sodium bicarbonate solution and brine, dried over sodium sulfate and concentrated under vacuum to afford 58.0 mg (97%) of trans (R)-1-[1-(4-methoxy-cyclohexyl)-1,6-dihydro-1,2,3,5,6-tetraaza-as-indacen-2-yl]-ethanol. LCMS (Method A, ESI): RT=2.34 min, m+H=315.5; $^1$H NMR (400 MHz, DMSO): δ 11.85 (s, 1H), 8.54 (s, 1H), 7.47 (t, 1H), 6.69 (m, 1H), 5.66 (d, 1H), 5.12 (m, 1H), 4.84 (m, 1H), 3.54 (m, 4H), 2.39 (m, 2H), 2.24 (m, 2H), 1.94 (m, 2H), 1.63 (d, 3H), 1.40 (m, 2H).

Example 636

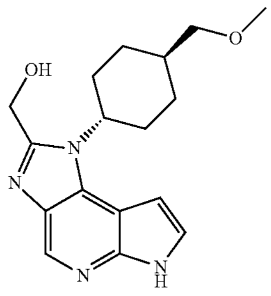 [SMILES: COC[C@H]1CC[C@H](n2c(CO)nc3cnc4[nH]ccc4c32)CC1]

Trans[1-(4-methoxymethyl-cyclohexyl)-1,6-dihydro-1,2,3,5,6-tetraaza-as-indacen-2-yl]-methanol Trans (4-methoxymethyl-cyclohexyl)-carbamic acid tert-butyl ester A solution of sodium methoxide in methanol (6.0 mL of a 25% solution, ~27.0 mmol) was added to a solution of trans methanesulfonic acid 4-tert-butoxycarbonylamino-cyclohexylmethyl ester (1.50 g, 4.88 mmol) in THF (15 mL) and methanol (15 mL). The mixture was heated at reflux for 6.75 hours. The cold mixture was concentrated under vacuum to remove most of the solvent then diluted with water (10 mL). The mixture was then cautiously neutralised with 1M hydrochloric acid then extracted with DCM (3×20 mL). The combined organic phase was dried over magnesium sulphate and concentrated under vacuum. The residue was purified by chromatography on silica gel (eluting with 9:1 cyclohexane: ethyl acetate) to afford 1.07 g (90%) of trans (4-methoxymethyl-cyclohexyl)-carbamic acid tert-butyl ester as a white solid. $^1$H NMR (400 MHz, $CDCl_3$): δ 4.36 (br s, 1H), 3.37 (br s, 1H), 3.32 (s, 3H), 3.18 (d, 2H), 2.07-1.97 (m, 2H), 1.84-1.75 (m, 2H), 1.56-1.45 (m, 1H), 1.44 (s, 9H), 1.16-0.96 (m, 4H).

Trans 4-methoxymethyl-cyclohexylamine trifluoroacetic acid salt

A solution of trans (4-methoxymethyl-cyclohexyl)-carbamic acid tert-butyl ester (1.41 g, 5.80 mmol) in DCM (12 mL) was treated with trifluoroacetic acid (4 mL). The mixture was stirred for 1 hour then concentrated under vacuum. The residue was taken into ether and concentrated under vacuum a total of five times to afford 1.88 g of crude trans 4-methoxymethyl-cyclohexylamine trifluoroacetic acid salt as a colourless residue. This was not purified further. $^1$H NMR (400 MHz, $CDCl_3$): δ 7.48 (br s, 3H), 3.34 (s, 3H), 3.22 (d, 2H), 3.15-3.00 (m, 1H), 2.11-2.00 (m, 2H), 1.94-1.83 (m, 2H), 1.65-1.50 (m, 1H), 1.46-1.31 (m, 2H), 1.13-0.96 (m, 2H).

Trans (1-benzenesulfonyl-5-nitro-1H-pyrrolo[2,3-b]pyridin-4-yl)-(4-methoxymethyl-cyclohexyl)-amine A mixture of crude trans 4-methoxymethyl-cyclohexylamine trifluoroacetic acid salt (1.88 g, ~5.80 mmol), 1-benzene-sulfonyl-4-chloro-5-nitro-1H-pyrrolol[2,3-b]pyridine (1.80 g, 5.30 mmol), propan-2-ol (55 mL) and diisopropylethylamine (4.33 mL, 25.4 mmol) was stirred and heated at reflux. After 4 hours, the mixture was cooled and a yellow solid precipitated. This was collected by filtration, washed with propan-2-ol (2×5 mL) and dried under vacuum to afford 1.92 g (75%) of trans (1-benzenesulfonyl-5-nitro-1H-pyrrolo[2,3-b]pyridin-4-yl)-(4-methoxymethyl-cyclohexyl)-amine as a yellow solid. LCMS (Method I, ESI): RT=4.12 min, m+H=445.1; $^1$H NMR (400 MHz, DMSO): δ 8.89 (s, 1H), 8.81 (d, 1H), 8.12 (d, 2H), 7.80 (d, 1H), 7.75 (t, 1H), 7.65 (t, 2H), 6.97 (d, 1H), 4.02-3.90 (m, 1H), 3.23 (s, 3H), 3.17 (d, 2H) 2.10-2.00 (m, 2H), 1.80-1.70 (m, 2H), 1.65-1.51 (m, 1H), 1.50-1.35 (m, 2H), 1.28-1.14 (m, 2H).

Trans 1-benzenesulfonyl-N*4*-(4-methoxymethyl-cyclohexyl)-1H-pyrrolo[2,3-b]pyridine-4,5-diamine A mixture of trans (1-benzenesulfonyl-5-nitro-1H-pyrrolo[2,3-b]pyridin-4-yl)-(4-methoxymethyl-cyclohexyl)-amine (1.92 g, 4.32 mmol), iron powder (0.96 g, 17.3 mmol) ammonium chloride (1.39 g, 26.0 mmol) and methanol/water (90 mL, 3:1) was stirred and heated at reflux for 1 hour. The cooled mixture was filtered through a pad of Celite® washing the filter cake with methanol. The combined filtrate was concentrated to dryness and the residue dissolved in DCM then purified by column chromatography on silica gel (eluting with 20%-50% ethyl acetate in DCM) affording 1.79 g (99%) of trans 1-benzenesulfonyl-N*4*-(4-methoxymethyl-cyclohexyl)-1H-pyrrolo[2,3-b]pyridine-4,5-diamine as a grey solid. LCMS (Method I, ESI): RT=2.49 min, m+H=415.2; $^1$H NMR (300 MHz, $CDCl_3$): δ 8.14 (d, 2H), 7.81 (s, 1H), 7.57-7.39 (m, 4H), 6.55 (d, 1H), 4.70 (br s, 1H), 3.72-3.55 (m, 1H), 3.35 (s, 3H), 3.24 (d, 2H), 2.22-2.11 (m, 2H), 1.95-1.85 (m, 2H), 1.76-1.50 (m, 3H), 1.33-1.07 (m, 4H).

Trans[6-benzenesulfonyl-1-(4-methoxymethyl-cyclohexyl)-1,6-dihydro-1,2,3,5,6-tetraaza-as-indacen-2-yl]-methanol Triethyloxonium tetrafluoroborate (2.47 g, 13.0 mmol) was added to a solution of glycolamide (1.00 g, 13.9 mmol) in THF (20 mL). The mixture was stirred for 2 hours then concentrated under vacuum. The residue was taken into absolute ethanol (20 mL) and added to a suspension of trans 1-benzenesulfonyl-N*4*-(4-methoxymethyl-cyclohexyl)-1H-pyrrolo[2,3-b]pyridine-4,5-diamine (1.79 g, 4.30 mmol)

in absolute ethanol (20 mL). The mixture was heated at 75° C. for 1 hour. The mixture was cooled and concentrated under vacuum. The residue taken into a mixture of DCM and saturated aqueous sodium bicarbonate solution, a precipitate formed and was collected by filtration and washed with acetonitrile. Addition of ether to the solvent mixture precipitated more solid. This was also collected by filtration and washed with acetonitrile. The combined solid was dried under vacuum to afford 1.72 g (87%) of trans [6-benzenesulfonyl-1-(4-methoxymethyl-cyclohexyl)-1,6-dihydro-1,2,3,5,6-tetraaza-as-indacen-2-yl]-methanol as a white solid. $^1$H NMR (400 MHz, DMSO): δ 8.67 (s, 1H), 8.13 (d, 2H), 7.96 (d, 1H), 7.69 (t, 1H), 7.60 (t, 2H), 7.10 (d, 1H), 5.7 (br s, 1H), 4.77 (s, 2H), 4.72-4.60 (m, 1H), 3.28 (s, 3H), 3.24 (d, 2H), 2.23-2.09 (m, 2H), 1.96-1.82 (m, 5H), 1.32-1.18 (m, 2H).

Trans[1-(4-methoxymethyl-cyclohexyl)-1,6-dihydro-1,2,3,5,6-tetraaza-as-indacen-2-yl]-methanol Aqueous sodium hydroxide (1.50 mL of a 1.0M solution, 1.50 mmol) was added to a suspension of trans [6-benzenesulfonyl-1-(4-methoxymethyl-cyclohexyl)-1,6-dihydro-1,2,3,5,6-tetraaza-as-indacen-2-yl]-methanol (150 mg, 0.33 mmol) in THF (3 mL) and methanol (3 mL). The mixture was stirred at ambient temperature for 3 days. The resultant solution was treated with saturated aqueous ammonium chloride solution (1.5 mL) and the organic solvents were removed under vacuum. The resulting suspension was filtered and the residue washed with water and ether, then dried under vacuum to afford 83.0 mg (80%) of trans [1-(4-methoxymethyl-cyclohexyl)-1,6-dihydro-1,2,3,5,6-tetraaza-as-indacen-2-yl]-methanol as a white solid. LCMS (Method A, ESI): RT=2.53 min, m+H=315.2; $^1$H NMR (400 MHz, DMSO): δ 11.84 (s, 1H), 8.52 (s, 1H), 7.46 (t, 1H), 6.70 (dd, 1H), 5.64 (t, 1H), 4.77 (d, 2H), 4.70-4.61 (m, 1H), 3.29 (s, 3H), 3.26 (d, 2H) 2.40-2.26 (m, 2H), 2.00-1.82 (m, 5H), 1.35-1.20 (m, 2H).

Example 637

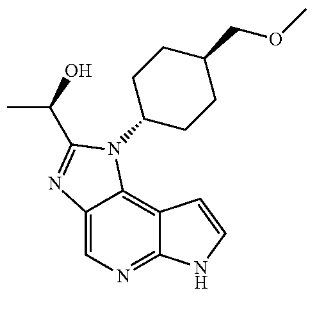 [SMILES: COC[C@H]1CC[C@H](n2c([C@@H](C)O)nc3cnc4[nH]ccc4c32)CC1]

Trans (R)-1-[1-(4-methoxymethyl-cyclohexyl)-1,6-dihydro-1,2,3,5,6-tetraaza-as-indacen-2-yl]-ethanol Trans 4-[6-benzenesulfonyl-2-((R)-1-hydroxy-ethyl)-6H-1,2,3,5,6-tetraaza-as-indacen-1-yl]-cyclohexanecarboxylic acid methyl ester Triethyloxonium tetrafluoroborate (4.32 g, 22.5 mmol) was added to a solution of (R)-lactamide (2.25 g, 25.2 mmol) in THF (30 mL). The mixture was stirred at room temperature for 2 hours then concentrated under vacuum. The residue was taken into absolute ethanol (60 mL) and after minutes trans 4-(5-amino-1-benzenesulfonyl-1H-pyrrolo[2,3-b]pyridin-4-ylamino)-cyclohexanecarboxylic acid methyl ester (3.21 g, 7.50 mmol) was added. The mixture was heated at 75° C. for 2 hours. As the mixture cooled a precipitate formed, the suspension was chilled with ice/water and the precipitate was recovered by filtration. The solid residue was washed with water then acetonitrile then dried under vacuum. The ethanolic filtrate was then concentrated under vacuum. The resulting residue was diluted with ethyl acetate (30 mL), combined with the water and acetonitrile washings of the original solid and the mixture was then washed with saturated aqueous sodium bicarbonate solution (30 mL). The phases were separated and the aqueous phase was extracted with ethyl acetate (30 mL). A solid began to precipitate in the combined organic phase which was concentrated under vacuum to approximately a 10 mL volume. The solid was recovered by filtration, washed with acetonitrile (10 mL) and dried under vacuum. The two crops of solid were each dissolved in THF (100 mL) and filtered. The combined filtrate was concentrated under vacuum. The resulting residue was washed with acetonitrile (5 mL) and dried under vacuum to afford 2.84 g (77%) of trans 4-[6-benzenesulfonyl-2-((R)-1-hydroxy-ethyl)-6H-1,2,3,5,6-tetraaza-as-indacen-1-yl]-cyclohexanecarboxylic acid methyl ester as a white solid. LCMS (Method I, ESI): RT=3.06 min, m+H=483.2; $^1$H NMR (400 MHz, DMSO): δ 8.69 (s, 1H), 8.14-8.10 (m, 2H), 7.93 (d, 1H), 7.72-7.66 (m, 1H), 7.64-7.57 (m, 2H), 7.18 (d, 1H), 5.74 (d, 1H), 5.18-5.09 (m, 1H), 4.89-4.77 (m, 1H), 3.65 (s, 3H), 2.87-2.72 (m, 1H), 2.26-2.07 (m, 4H) 1.99-1.88 (m, 2H), 1.71-1.57 (m+d, signal overlap, 5H).

Trans 4-{6-benzenesulfonyl-2-[(R)-1-(tert-butyl-dimethyl-silanyloxy)-ethyl]-6H-1,2,3,5,6-tetraaza-as-indacen-1-yl}-cyclohexanecarboxylic acid methyl ester Tert-butyldimethylchlorosilane (1.01 g, 6.7 mmol) was added to a suspension of trans 4-[6-benzenesulfonyl-2-((R)-1-hydroxy-ethyl)-6H-1,2,3,5,6-tetraaza-as-indacen-1-yl]-cyclohexanecarboxylic acid methyl ester (2.80 g, 5.80 mmol) and imidazole (0.60 g 8.44 mmol) in DMF (5.6 mL). After stirring for 16 hours further imidazole (0.60 g, 8.44 mmol) and tert-butyldimethylchlorosilane (1.01 g, 6.70 mmol) were added. The mixture was stirred for a further 4 hours then water (15 mL) was added and extracted with ethyl acetate (2×20 mL). The combined organic extracts were washed with saturated brine (2×10 mL), dried over magnesium sulphate and concentrated under vacuum. The residual gum was triturated with cyclohexane, dried under vacuum to afford 2.83 g (82%) of trans 4-{6-benzenesulfonyl-2-[(R)-1-(tert-butyl-dimethyl-silanyloxy)-ethyl]-6H-1,2,3,5,6-tetraaza-as-indacen-1-yl}-cyclohexanecarboxylic acid methyl ester as a white solid. LCMS (Method I, ESI): RT=4.64 min, m+H=597.4; $^1$H NMR (400 MHz, $CDCl_3$): δ 8.84 (s, 1H), 8.24 (dd, 2H), 7.83 (d, 1H), 7.460-7.52 (m, 1H), 7.51-7.45 (m, 2H), 6.86 (d, 1H), 5.39 (q, 1H), 5.21-4.09 (m, 1H), 3.75 (s, 3H), 2.66-2.56 (m, 1H), 2.41-2.23 (m, 4H), 2.07-1.98 (m, 2H), 1.82-1.63 (m, 2H), 1.61 (d, 3H), 0.89 (s, 9H), 0.12 (s, 3H), −0.01 (s, 3H).

Trans (4-{6-benzenesulfonyl-2-[(R)-1-(tert-butyl-dimethyl-silanyloxy)-ethyl]-6H-1,2,3,5,6-tetraaza-as-indacen-1-yl}-cyclohexyl)-methanol A solution of trans 4-{6-benzenesulfonyl-2-[(R)-1-(tert-butyl-dimethyl-silanyloxy)-ethyl]-6H-1,2,3,5,6-tetraaza-as-indacen-1-yl}-cyclohexanecarboxylic acid methyl ester (597 mg, 1.00 mmol) in DCM (20 mL) at 0° C. was treated with diisobutylaluminium hydride (2.5 mL of a 1.0M solution in toluene, 2.50 mmol). The mixture was stirred cold for 1 hour then treated with saturated aqueous ammonium chloride solution (2.0 mL). After 5 minutes, water (20 mL) was added and the phases separated. The aqueous phase was extracted with DCM (3×15 mL) and the combined organic extracts dried over magnesium sulphate and concentrated under vacuum. Purification by column chromatography on silica gel (eluting with 1:1 ether:cyclohexane to ether) gave 210 mg (37%) of trans (4-{6-benzenesulfonyl-2-[(R)-1-(tert-butyl-dimethyl-silanyloxy)-ethyl]-6H-1,2,3,5,6-tetraaza-as-indacen-1-yl}-cyclohexyl)-methanol as a white solid. LCMS (Method H, ESI): RT=4.23 min, m+H=569.4; $^1$H NMR (400 MHz, $CDCl_3$): δ 8.85 (s, 1H), 8.26-8.21 (m, 2H), 7.82 (d, 1H), 7.59-7.53 (m, 1H), 7.50-7.44 (m, 2H), 6.94 (d, 1H), 5.45-5.35 (m, 1H), 5.18-5.06 (m, 1H), 3.61 (d, 2H), 2.43-2.26 (m, 2H), 2.17-2.06 (m, 2H), 2.05-1.95 (m, 2H), 1.91-1.79 (m, 1H), 1.62 (d, 3H), 1.35-1.16 (m, 2H), 0.89 (s, 9H), 0.13 (s, 3H), −0.01 (s, 3H).

Trans 6-benzenesulfonyl-2-[(R)-1-(tert-butyl-dimethyl-silanyloxy)-ethyl]-1-(4-methoxymethyl-cyclohexyl)-1,6-dihydro-1,2,3,5,6-tetraaza-as-indacene A mixture of trans (4-{6-benzenesulfonyl-2-[(R)-1-(tert-butyl-dimethyl-silanyloxy)-ethyl]-6H-1,2,3,5,6-tetraaza-as-indacen-1-yl}-cyclohexyl)-methanol (250 mg, 0.36 mmol), silver trifluoromethylsulfonate (287 mg, 1.12 mmol) and 2,6-di-tert-butyl-4-methylpyridine (260 mg, 1.26 mmol) in DCM (5.4 mL) was sonicated and the resultant slurry was cooled to 0° C. The mixture was treated with iodomethane (156 mg, 73.0 μL, 1.17 mmol) and stirred cold for 3 hours. The mixture was allowed to warm to room temperature and then treated with 0.1M hydrochloric acid (15 mL, 1.50 mmol). The mixture was extracted with DCM (2×15 mL) and the combined organic extracts filtered to remove suspended solids, washed with saturated aqueous sodium bicarbonate solution, dried over magnesium sulfate. The solvent was removed under vacuum and the resultant product purified by column chromatography on silica gel (eluting with 1:1 cyclohexane:ether) to afford 145 mg (67%) of trans 6-benzenesulfonyl-2-[(R)-1-(tert-butyl-dimethyl-silanyloxy)-ethyl]-1-(4-methoxymethyl-cyclohexyl)-1,6-dihydro-1,2,3,5,6-tetraaza-as-indacene a white foam. LCMS (Method I, ESI): RT=4.99 min, m+H=583.3; $^1$H NMR (400 MHz, $CDCl_3$): δ 8.83 (s, 1H), 8.2-8.21 (m, 2H), 7.80 (d, 1H), 7.58-7.52 (m, 1H), 7.50-7.44 (m, 2H), 6.93 (d, 1H), 5.38 (q, 1H), 5.16-5.04 (m, 1H) 3.41 (s, 3H), 3.32 (d, 2H), 2.41-2.24 (m, 2H), 2.15-2.03 (m, 2H), 2.02-1.84 (m, 3H), 1.61 (d, 3H) 1.35-1.15 (m, 2H), 0.89 (s, 9H), 0.12 (s, 3H), −0.01 (s, 3H).

Trans (R)-1-[1-(4-methoxymethyl-cyclohexyl)-1,6-dihydro-1,2,3,5,6-tetraaza-as-indacen-2-yl]-ethanol Sodium hydroxide (1.5 mL of a 1.0M aqueous solution, 1.50 mmol) was added to a solution of trans 6-benzenesulfonyl-2-[(R)-1-(tert-butyl-dimethyl-silanyloxy)-ethyl]-1-(4-methoxymethyl-cyclohexyl)-1,6-dihydro-1,2,3,5,6-tetraaza-as-indacene (145 mg, 0.25 mmol) in THF (3 mL) and methanol (3 mL). The mixture was stirred for 18 hours, then hydrochloric acid (5.0 mL of a 1.0M aqueous solution, 5.0 mmol) added and stirring continued for 24 hours. The mixture was neutralised with saturated aqueous sodium hydrogencarbonate solution and then concentrated under reduced pressure to provide a residual aqueous phase that was extracted with DCM (3×10 mL). The combined organic extracts were dried over magnesium sulphate and concentrated under vacuum.

The gummy residue obtained solidified upon trituration (cyclohexane) and was dried under vacuum to afford 70.0 mg (85%) of trans (R)-1-[1-(4-methoxymethyl-cyclohexyl)-1,6-dihydro-1,2,3,5,6-tetraaza-as-indacen-2-yl]-ethanol a fawn solid. LCMS (Method A, ESI): RT=2.67 min, m+H=329.1; $^1$H NMR (400 MHz, DMSO): δ 11.82 (s, 1H), 8.54 (s, 1H), 7.46 (t, 1H), 6.71 (dd, 1H), 5.66 (d, 1H), 5.16-5.07 (m, 1H), 4.89-4.76 (m, 1H), 3.30 (s, 3H), 3.27 (d, 2H), 2.43-2.29 (m, 2H), 2.03-1.85 (m, 5H), 1.63 (d, 3H), 1.34-1.19 (m, 2H).

Example 638

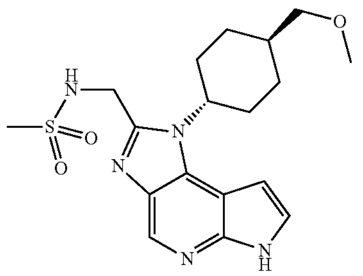

Trans N-[1-(4-methoxymethyl-cyclohexyl)-1,6-dihydro-1,2,3,5,6-tetraaza-as-indacen-2-ylmethyl]-methanesulfonamide Trans {N-6-benzenesulfonyl-1-(4-methoxymethyl-cyclohexyl)-1,6-dihydro-1,2,3,5,6-tetraaza-as-indacen-2-ylmethyl]-methanesulfonamide}-carbamic acid tert-butyl ester Trans [6-benzenesulfonyl-1-(4-methoxymethyl-cyclohexyl)-1,6-dihydro-1,2,3,5,6-tetraaza-as-indacen-2-yl]-methanol (200 mg, 0.44 mmol) was dissolved in THF (5 mL) and N-Boc-methanesulfonamide (189 mg, 0.97 mmol) was added, followed by triphenylphosphine (231 mg, 0.88 mmol). Diisopropylazodicarboxylate (173 μL, 0.88 mmol) was added and the mixture was stirred for 64 h at room temperature. Water was added and the mixture extracted with ethyl acetate (×3). The combined organic extracts were washed with brine then dried ($Na_2SO_4$) and concentrated. Purification by column chromatography on silica gel (gradient: 9:1 cyclohexane:ethyl acetate to 3:1 cyclohexane:ethyl acetate) gave 383 mg (138%) of crude trans {N-6-benzenesulfonyl-1-(4-methoxymethyl-cyclohexyl)-1,6-dihydro-1,2,3,5,6-tetraaza-as-indacen-2-ylmethyl]-methanesulfonamide}-carbamic acid tert-butyl ester, which was used directly without further purification. LCMS (Method Q, ESI): RT=4.43 min, m+H=632.2.

Trans N-[6-benzenesulfonyl-1-(4-methoxymethyl-cyclohexyl)-1,6-dihydro-1,2,3,5,6-tetraaza-as-indacen-2-ylmethyl]-methanesulfonamide Trans {N-6-benzenesulfonyl-1-(4-methoxymethyl-cyclohexyl)-1,6-dihydro-1,2,3,5,6-tetraaza-as-indacen-2-ylmethyl]-methanesulfonamide}-carbamic acid tert-butyl ester (278 mg, 0.44 mmol) was dissolved in DCM (3 mL) and trifluoroacetic acid (3 mL) was added. The mixture was stirred at room temperature for 1.5 h, then concentrated under vacuum. The residue was dissolved in methanol and purified by Isolute® SCX-2 column (gradient: methanol to 2 M $NH_3$ in methanol), giving 182 mg (78%) of trans N-[6-benzenesulfonyl-1-(4-methoxymethyl-cyclohexyl)-1,6-dihydro-1,2,3,5,6-tetraaza-as-indacen-2-ylmethyl]-methanesulfonamide. LCMS (Method Q, ESI): RT=3.57 min, m+H=532.2; NMR (400 MHz, DMSO) δ: 8.70 (s, 1H), 8.14 (m, 2H), 7.98 (d, 1H), 7.71 (t, 1H), 7.61 (t, 2H), 7.11 (d, 1H), 4.63 (m, 1H), 4.58 (s, 2H), 3.29 (s, 3H), 3.25 (d, 2H), 2.97 (s, 3H), 2.15 (m, 2H), 1.94 (m, 5H), 1.27 (m, 2H).

Trans N-[1-(4-methoxymethyl-cyclohexyl)-1,6-dihydro-1,2,3,5,6-tetraaza-as-indacen-2-ylmethyl]-methanesulfonamide Trans N-[6-benzenesulfonyl-1-(4-methoxymethyl-cyclohexyl)-1,6-dihydro-1,2,3,5,6-tetraaza-as-indacen-2-ylmethyl]-methanesulfonamide (182 mg, 0.34 mmol) was dissolved in THF (1.5 mL) and methanol (1.5 mL). 2 M Aqueous NaOH (1.5 mL) was added and the mixture was stirred at 45° C. for 1 h. 1 M Aqueous HCl (3 mL) was added and the mixture was concentrated. Purification by column chromatography on silica gel (gradient: DCM to 6% (2 M $NH_3$ in methanol) in DCM) and subsequent trituration with acetonitrile gave 54 mg (41%) of trans N-[1-(4-methoxymethyl-cyclohexyl)-1,6-dihydro-1,2,3,5,6-tetraaza-as-indacen-2-yl-methyl]methanesulfonamide. LCMS (Method A, ESI): RT=2.79 min, m+H=392.1; NMR (400 MHz, DMSO) δ: 11.88 (s, 1H), 8.55 (s, 1H), 7.77 (s, 1H), 7.48 (t, 1H), 6.71 (s, 1H), 4.62 (m, 1H), 4.56 (s, 2H), 3.29 (s, 3H), 3.25 (d, 2H), 2.97 (s, 3H), 2.34 (m, 2H), 1.96 (m, 5H), 1.28 (m, 2H).

Example 639

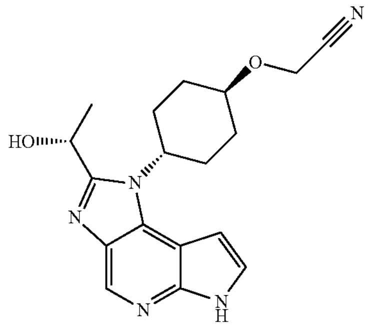 [SMILES: C[C@@H](O)c1nc2cnc3[nH]ccc3c2n1[C@H]1CC[C@H](OCC#N)CC1]

Trans {4-[2-((R)-1-hydroxy-ethyl)-6H-1,2,3,5,6-tetraaza-as-indacen-1-yl]-cyclohexyloxy}-acetonitrile Trans (4-tert-butoxycarbonylamino-cyclohexyloxy)-acetic acid ethyl ester A suspension of trans (4-hydroxy-cyclohexyl)-carbamic acid tert-butyl ester (1.03 g, 4.80 mmol) in dry toluene (38 mL) under an nitrogen atmosphere was treated with rhodium acetate (110 mg, 200 μmol) and heated at reflux. A solution of ethyl diazoacetate (600 μL, 5.70 mmol) in dry toluene (9 mL) was added dropwise over 1.5 hours. The mixture was then stirred at reflux for a further 30 minutes and allowed to cool to ambient temperature overnight. The reaction was treated with a further portion of rhodium acetate (50 mg) and re-heated to reflux. Further ethyl diazoacetate (300 μL) in dry toluene (5 mL) was added dropwise over 1 hour. Heating was continued for 30 minutes and then the cooled mixture was concentrated under vacuum. The residue was purified by column chromatography on silica gel (gradient: 0-35% ethyl acetate in cyclohexane) to afford 720 mg (50%) of trans (4-tert-butoxycarbonylamino-cyclohexyloxy)-acetic acid ethyl ester as a white solid. LCMS (Method Q, ESI): RT=3.63 min, m+H=324.0; $^1$H NMR (400 MHz, $CDCl_3$) δ: 4.35 (br s, 1H), 4.21 (q, 2H), 4.09 (s, 2H), 3.44 (br s, 1H), 3.32 (m, 1H), 2.04 (m, 4H), 1.44 (m, 11H), 1.28 (t, 3H), 1.13 (m, 2H).

Trans (4-tert-butoxycarbonylamino-cyclohexyloxy)-acetic acid

A solution of trans (4-tert-butoxycarbonylamino-cyclohexyloxy)-acetic acid ethyl ester (720 mg, 2.40 mmol) in methanol (18 mL) and water (6 mL) as treated with lithium hydroxide monohydrate (210 mg, 5.00 mmol) and stirred at ambient temperature for 2.25 hours. Methanol was removed under vacuum and the residue partitioned between ethyl acetate and 1M HCl. The phases were separated and the aqueous phase extracted into ethyl acetate (2×). The combined organic extracts were washed with brine, dried over sodium sulfate and concentrated under vacuum to afford 600 mg (92%) of trans (4-tert-butoxycarbonylamino-cyclohexyloxy)-acetic acid as a white solid. LCMS (Method Q, ESI): RT=2.96 min, m+H=296.0; $^1$H NMR (400 MHz, $CDCl_3$) δ: 4.38 (br s, 1H), 4.12 (s, 2H), 3.41 (m, 2H), 2.04 (m, 4H), 1.44 (m, 11H), 1.15 (m, 2H).

Trans (4-carbamoylmethoxy-cyclohexyl)-carbamic acid tert-butyl ester

A solution of trans (4-tert-butoxycarbonylamino-cyclohexyloxy)-acetic acid (600 mg, 2.20 mmol) and triethylamine (400 μL, 2.90 mmol) in THF (22 mL) at 0° C. was treated dropwise with ethyl chloroformate (250 μL, 2.60 mmol). After 30 minutes ammonium hydroxide (2.20 mL, 170 mmol) was added dropwise. The golden solution was stirred at ambient temperature for 30 minutes and then concentrated under vacuum. The residue was partitioned between ethyl acetate and water. The aqueous phase was extracted with ethyl acetate (2×). The combined organic extracts were washed with 1M HCl, a saturated sodium bicarbonate solution and brine, dried over sodium sulfate and concentrated under vacuum to afford 550 mg (92%) of trans (4-carbamoylmethoxy-cyclohexyl)-carbamic acid tert-butyl ester as a white solid. LCMS (Method Q, ESI): RT=2.82 min, m+H=295.0; $^1$H NMR (400 MHz, $CDCl_3$) δ: 6.52 (s, 1H), 5.55 (s, 1H), 4.38 (s, 1H), 3.96 (s, 2H), 3.44 (s, 1H), 3.30 (m, 1H), 2.03 (d, 4H), 1.44 (s, 9H), 1.38 (m, 2H), 1.16 (m, 2H).

Trans (4-cyanomethoxy-cyclohexyl)-carbamic acid tert-butyl ester

A suspension of trans (4-carbamoylmethoxy-cyclohexyl)-carbamic acid tert-butyl ester (500 mg, 1.80 mmol) and triethylamine (510 μL, 3.70 mmol) in DCM (9 mL) at 0° C. was treated dropwise with a solution of 2,2,2-trichloroacetyl chloride (310 μL, 2.80 mmol) in DCM (1 mL). After the addition the mixture was stirred at ambient temperature for 45 minutes. The reaction mixture was diluted with water and the phases separated. The aqueous phase was extracted with DCM (2×) and the combined organic phases washed with a 10% citric acid solution, a saturated sodium bicarbonate solution and brine, dried over sodium sulfate and concentrated under vacuum. Purification by column chromatography on silica gel (gradient: 0-40% ethyl acetate in cyclohexane) to afford 280 mg (60%) of trans (4-cyanomethoxy-cyclohexyl)-carbamic acid tert-butyl ester as a white solid. LCMS (Method Q, ESI): RT=3.53 min, m+H=255.0; $^{1}$H NMR (400 MHz, $CDCl_3$) δ: 4.37 (s, 1H), 4.27 (s, 2H), 3.47 (m, 1H), 2.05 (d, 4H), 1.44 (s, 9H), 1.38 (m, 2H), 1.18 (m, 2H).

Trans (4-amino-cyclohexyloxy)-acetonitrile trifluoroacetic acid salt

A solution of trans (4-cyanomethoxy-cyclohexyl)-carbamic acid tert-butyl ester (280 mg, 1.10 mmol) in DCM (22 mL) was treated with trifluoroacetic acid (22 mL) and stirred at ambient temperature for 30 minutes. The mixture was diluted with toluene and concentrated under vacuum. The residue was azeotroped with toluene to afford 450 mg (quantitative yield) of trans (4-amino-cyclohexyloxy)-acetonitrile trifluoroacetic acid salt as a colourless oil. LCMS (Method Q, ESI): RT=0.59 min, m+H=154.0; $^{1}$H NMR (400 MHz, DMSO) δ: 7.75 (br s, 2H), 4.43 (s, 2H), 3.35 (m, 1H), 2.95 (d, 1H), 1.99 (d, 2H), 1.90 (s, 2H), 1.25 (m, 4H).

Trans[4-(1-benzenesulfonyl-5-nitro-1H-pyrrolo[2,3-b]pyridin-4-ylamino)-cyclohexyloxy]-acetonitrile A suspension of 1-benzenesulfonyl-4-chloro-5-nitro-1H-pyrrolo[2,3-b]pyridine (340 mg, 1.00 mmol) and diisopropylethylamine (440 μL, 2.50 mmol) in propan-2-ol was treated with trans (4-mino-cyclohexyloxy)-acetonitrile trifluoroacetic acid salt (300 mg, 1.10 mmol) and heated at 120° C. for 2×10 minutes using microwave irradiation. The reaction mixture was diluted with DCM then concentrated under vacuum. The residue obtained was partitioned between DCM and water and the phases separated. The aqueous phase was extracted with DCM (2×). The combined extracts were washed with a 10% citric acid solution, a saturated sodium bicarbonate solution and brine, dried over sodium sulfate and concentrated under vacuum. Purification by column chromatography on silica gel (gradient: 0-50% ethyl acetate in cyclohexane) to afford 350 mg (76%) of trans [4-(1-benzenesulfonyl-5-nitro-1H-pyrrolo[2,3-b]pyridin-4-ylamino)-cyclohexyloxy]-acetonitrile as a yellow gum. LCMS (Method Q, ESI): RT=4.22 min, m+H=456.1; $^{1}$H NMR (400 MHz, $CDCl_3$) δ: 9.11 (s, 1H), 9.08 (m, 1H), 8.20 (d, 2H), 7.62 (m, 2H), 7.52 (m, 2H), 6.69 (d, 1H), 4.31 (s, 2H), 4.00 (m, 1H), 3.64 (m, 1H), 2.19 (m, 4H), 1.57 (m, 4H), 1.26 (t, 3H).

Trans[4-(5-amino-1-benzenesulfonyl-1H-pyrrolo[2,3-b]pyridin-4-ylamino)-cyclohexyloxy]-acetonitrile A suspension of trans [4-(1-benzenesulfonyl-5-nitro-1H-pyrrolo[2,3-b]pyridin-4-ylamino)-cyclohexyloxy]-acetonitrile (350 mg, 770 μmol) in a mixture of ethanol (2.5 mL) and water (800 μL) was treated with ammonium chloride (250 mg, 4.60 mmol) and iron powder (170 mg, 3.10 mmol) and heated at 80° C. for 90 minutes. The reaction mixture was hot filtered through Celite® washing several times with ethanol/water. The filtrate was concentrated under vacuum, the residue diluted with water and extracted in to DCM (3×). The combined organic extracts were dried over sodium sulfate and concentrated under vacuum. The iron filter cake was stirred in 20% methanol in DCM, filtered and repeated until no further product was extracted. The combined filtrates were washed with water and the phases separated. The aqueous phase was extracted with DCM (2×). The combined organic extracts were washed with brine, dried over sodium sulfate, concentrated under vacuum and combined with the material isolated above to afford 300 mg (91%) of trans [4-(5-amino-1-benzenesulfonyl-1H-pyrrolo[2,3-b]pyridin-4-ylamino)-cyclohexyloxy]-acetonitrile as a yellow solid. LCMS (Method Q, ESI): RT=2.76 min, m+H=426.1; $^{1}$H NMR (400 MHz, $CDCl_3$) δ: 8.14 (m, 2H), 7.83 (s, 1H), 7.53 (t, 1H), 7.49 (d, 1H), 7.45 (t, 2H), 6.52 (d, 1H), 4.72 (d, 1H), 4.30 (s, 2H), 3.73 (m, 1H), 3.58 (m, 1H), 2.80 (br s, 2H), 2.16 (m, 4H), 1.48 (m, 2H), 1.33 (m, 2H).

Trans{-4-[6-benzenesulfonyl-2-((R)-1-hydroxy-ethyl)-6H-1,2,3,5,6-tetraaza-as-indacen-1-yl]-cyclohexyloxy}-acetonitrile A suspension of triethyloxonium tetrafluoroborate (400 mg, 2.10 mmol) in dry DCM (3.2 mL) under a nitrogen atmosphere was treated with R-(+)-lactamide (200 mg, 2.30 mmol) and stirred at ambient temperature for 2 hours. The reaction mixture was concentrated under vacuum and the residue stirred in absolute ethanol (1.5 mL) before being treated with a suspension of trans [4-(5-amino-1-benzenesulfonyl-1H-pyrrolo[2,3-b]pyridin-4-ylamino)-cyclohexyloxy]-acetonitrile (300 mg, 710 μmol) in absolute ethanol (5.3 mL). The mixture was heated at 75° C. for 2 hours, cooled, and concentrated under vacuum. The residue obtained was partitioned between ethyl acetate and a saturated sodium bicarbonate solution and the aqueous phase extracted with ethyl acetate (2×). The combined organic extracts were washed with brine, dried over sodium sulfate and concentrated under vacuum. Purification by column chromatography on silica gel (gradient: 0-7% 2M $NH_3$/methanol solution in DCM) to afford 280 mg (82%) of trans {4-[6-benzenesulfonyl-2-((R)-1-hydroxy-ethyl)-6H-1,2,3,5,6-tetraaza-as-indacen-1-yl]-cyclohexyloxy}-acetonitrile as a white foam. LCMS (Method Q, ESI): RT=3.35 min, m+H=480.1; $^{1}$H NMR (400 MHz, $CDCl_3$) δ: 8.86 (s, 1H), 8.22 (m, 2H), 7.86 (d, 1H), 7.55 (t, 1H), 7.47 (t, 2H), 6.80 (d, 1H), 5.16 (t, 1H), 4.72-4.61 (m, 1H), 4.38 (s, 2H), 3.80 (m, 1H), 2.76 (d, 1H), 2.36 (m, 4H), 2.04 (m, 3H), 1.75 (d, 3H), 1.61 (m, 2H).

Trans {4-[2-((R)-1-hydroxy-ethyl)-6H-1,2,3,5,6-tetraaza-as-indacen-1-yl]-cyclohexyloxy}-acetonitrile A solution of trans {-4-[6-benzenesulfonyl-2-((R)-1-hydroxy-ethyl)-6H-1,2,3,5,6-tetraaza-as-indacen-1-yl]-cyclohexyloxy}-acetonitrile (280 mg, 580 μmol) in methanol (3 mL) was treated with a 2M sodium hydroxide solution (1.5 mL, 3.00 mmol) and stirred at ambient temperature for 1 hour. The methanol was removed under vacuum, the aqueous phase diluted with water and extracted into ethyl acetate (2×). The combined organic extracts were washed with brine, dried over sodium sulfate and concentrated under vacuum. Purification by column chromatography on silica gel (gradient: 0-15% [2M $NH_3$ in methanol] in DCM). Further purification by trituration (acetonitrile) gave 48.0 mg (24%) of trans {4-[2-((R)-1-hydroxy-ethyl)-6H-1,2,3,5,6-tetraaza-as-indacen-1-yl]-cyclohexyloxy}-acetonitrile as a white solid. LCMS (Method A, ESI): RT=2.41 min, m+H=340.1; $^{1}$H NMR (400 MHz, DMSO) δ: 11.87 (s, 1H), 8.55 (s, 1H), 7.49 (s, 1H), 6.69

(s, 1H), 5.67 (d, 1H), 5.14 (t, 1H), 4.85 (m, 1H), 4.59 (s, 2H), 3.87 (br s, 1H), 2.41 (m, 2H), 2.27 (m, 2H), 1.97 (m, 2H), 1.63 (d, 3H), 1.50 (m, 2H).

Example 640

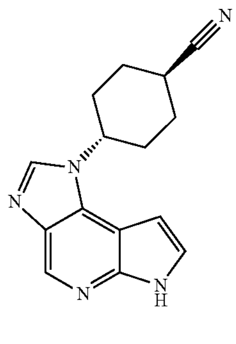 [SMILES: N#C[C@H]1CC[C@H](n2cnc3cnc4[nH]ccc4c32)CC1]

trans 4-(6H-1,2,3,5,6-Tetraaza-as-indacen-1-yl)-cyclohexanecarbonitrile trans 4-(6-Benzenesulfonyl-6H-1,2,3,5,6-tetraaza-as-indacen-1-yl)-cyclohexanecarboxylic acid amide A suspension of trans 4-(6-benzenesulfonyl-6H-1,2,3,5,6-tetraaza-as-indacen-1-yl)-cyclohexanecarboxylic acid ethyl ester (226 mg, 0.50 mmol) in methanolic $NH_3$ (7M; 5 mL) was heated using microwave irradiation at 120° C. for 1 hour. Additional $NH_3$ in MeOH (7M, 5 mL) was added and heating at 150° C. resumed for 6 hours. The residue on evaporation was subjected to column chromatography on silica gel (gradient 0 to 10% MeOH in DCM) to afford 30.0 mg (14%) of trans 4-(6-benzenesulfonyl-6H-1,2,3,5,6-tetraaza-as-indacen-1-yl)-cyclohexanecarboxylic acid amide as a pale yellow solid. LCMS (ESI) m+H=424.0; NMR (400 MHz, $CDCl_3$): δ 8.89 (s, 1H), 8.21-8.18 (m, 2H), 7.95 (s, 1H), 7.79 (d, 1H), 7.56-7.50 (m, 1H), 7.48-7.42 (m, 2H), 6.73 (d, 1H), 5.78 (br s, 2H), 4.47-4.38 (m, 1H), 2.40-2.26 (m, 3H), 2.22-2.14 (m, 1H), 2.02 (br s, 1H), 1.92-1.74 (m, 4H).

Trans 4-(6-Benzenesulfonyl-6H-1,2,3,5,6-tetraaza-as-indacen-1-yl)-cyclohexanecarbonitrile Phosphorus oxychloride (130 mg, 0.84 mmol) was added to a stirred solution of trans 4-(6-benzenesulfonyl-6H-1,2,3,5,6-tetraaza-as-indacen-1-yl)-cyclohexanecarboxylic acid amide (50.0 mg, 0.12 mmol) and imidazole (25.0 mg, 0.37 mmol) in pyridine (2 mL) with cooling from an ice-MeOH bath. The mixture was allowed to warm to room temperature over 2 hours, evaporated, and the residue partitioned between aq. $NH_4Cl$ (10 mL) and ethyl acetate (3×10 mL). The organic layers were dried ($MgSO_4$) and evaporated to afford 52.0 mg of crude trans 4-(6-benzenesulfonyl-6H-1,2,3,5,6-tetraaza-as-indacen-1-yl)-cyclohexanecarbonitrile as a gum. LCMS (ESI) m+H=406.0; NMR (400 MHz, MeOD): δ 8.69 (s, 1H), 8.35 (s, 1H), 8.17-8.13 (m, 2H), 7.93 (d, 1H), 7.62 (t, 1H), 7.52 (t, 2H), 7.12 (d, 1H), 4.75-4.62 (m, 1H), 2.88-2.75 (m, 1H), 2.40-2.21 (m, 4H), 2.06-1.90 (m, 4H).

trans 4-(6H-1,2,3,5,6-Tetraaza-as-indacen-1-yl)-cyclohexanecarbonitrile

To a solution of trans 4-(6-benzenesulfonyl-6H-1,2,3,5,6-tetraaza-as-indacen-1-yl)-cyclohexanecarbonitrile (50.0 mg, 0.12 mmol) in THF (5 mL) was added 1M TBAF in THF (1 mL, 1.00 mmol) and the mixture stirred at reflux for 1.5 hours. The residue left on evaporation was passed through an Isolute® SCX-2 cartridge (gradient elution: MeOH, to 2M $NH_3$ in MeOH). The relevant fractions were evaporated, the resulting residue purified by column chromatography on silica gel (gradient: 0 to 10% MeOH in DCM) and crystallised from propan-2-ol to afford 10.3 mg of trans 4-(6H-1,2,3,5,6-tetraaza-as-indacen-1-yl)-cyclohexanecarbonitrile as white crystals. LCMS (Method A, ESI): RT=2.23 min, m+H=266.2; NMR (400 MHz, MeOD) δ: 8.58 (s, 1H), 8.27 (s, 1H), 7.47 (d, 1H), 6.85 (d, 1H), 4.80-4.68 (m, 1H), 2.92-2.79 (m, 1H), 2.46-2.30 (m, 4H), 2.1-1.95 (m, 4H).

Example 641

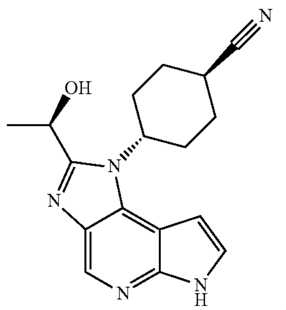 [SMILES: C[C@@H](O)c1nc2cnc3[nH]ccc3c2n1[C@H]1CC[C@H](C#N)CC1]

trans 4-[2-((R)-1-Hydroxy-ethyl)-6H-1,2,3,5,6-tetraaza-as-indacen-1-yl]-cyclohexanecarbonitrile trans 4-Amino-cyclohexanecarbonitrile trifluoroacetic acid salt Following the procedure outlined in WO2009/145719 the title compound was prepared from trans-4-(t-butoxycarbonylamino)-cyclohexane carboxylic acid in three steps with isolation of the TFA salt of trans 4-amino-cyclohexanecarbonitrile via diethyl ether trituration and filtration to afford a white solid in 63% overall yield. $^1H$ NMR (400 MHz, DMSO) δ: 7.93 (s, 3H), 3.03 (m, 1H), 2.66 (m, 1H), 2.05 (m, 2H), 1.92 (dd, 2H), 1.58 (m, 2H), 1.31 (m, 2H).

trans 4-(1-Benzenesulfonyl-5-nitro-1H-pyrrolo[2,3-b]pyridin-4-ylamino)-cyclohexanecarbonitrile A mixture of trans 4-amino-cyclohexanecarbonitrile trifluoroacetic acid salt (6.36 g, 26.7 mmol), 1-benzenesulfonyl-4-chloro-5-nitro-1H-pyrrolo[2,3-b]pyridine (8.21 g, 24.3 mmol) and diisopropylethylamine (12.5 mL, 73.0 mmol) in propan-2-ol (200 mL) was heated at reflux for 3 hours. The cooled mixture was filtered and the precipitate washed with propan-2-ol to afford 9.04 g (87%) of trans 4-(1-benzenesulfonyl-5-nitro-1H-pyrrolo[2,3-b]pyridin-4-ylamino)-cyclohexanecarbonitrile as a bright yellow solid. LCMS (Method Q, ESI): RT=4.15 min, m+H=426.0; $^1H$ NMR (400 MHz, $CDCl_3$) δ: 9.11 (s, 1H), 9.07 (d, 1H), 8.20 (m, 2H), 7.63 (m, 2H), 7.53 (m, 2H), 6.67 (d, 1H), 4.06 (m, 1H), 2.66 (m, 1H), 2.24 (m, 4H), 1.83 (m, 2H), 1.58 (m, 2H).

trans 4-(5-Amino-1-benzenesulfonyl-1H-pyrrolo[2,3-b]pyridin-4-ylamino)-cyclohexanecarbonitrile A suspension of trans 4-(1-benzenesulfonyl-5-nitro-1H-pyrrolo[2,3-b]pyridin-4-ylamino)-cyclohexanecarbonitrile (5.00 g, 11.8 mmol), iron powder (−325 mesh, 2.59 g, 47.0 mmol) and ammonium chloride (3.74 g, 70.5 mmol) in a mixture of ethanol and water (3:1, 400 mL) was mechanically stirred at reflux for 4 hours. The cooled mixture was filtered through Celite®. The filtrate was concentrated under vacuum to low volume and the residue extracted into DCM (3×). The combined extracts were washed with water and brine, dried over sodium sulphate and concentrated under vacuum. Purification by diethyl ether trituration afforded 4.51 g (97%) of trans 4-(5-amino-1-benzenesulfonyl-1H-pyrrolo[2,3-b]pyridin-4-ylamino)-cyclohexanecarbonitrile as a light grey solid. LCMS (Method Q, ESI): RT=2.69 min, m+H=396.1; $^1$H NMR (400 MHz, DMSO) δ: 8.02 (dd, 2H), 7.65 (m, 1H), 7.57 (m, 3H), 7.47 (d, 1H), 6.76 (d, 1H), 5.09 (d, 2H), 4.36 (s, 2H), 3.76 (m, 2H), 2.70 (m, 1H), 2.04 (dd, 2H), 1.94 (m, 2H), 1.72 (m, 2H), 1.29 (m, 2H).

trans 4-[6-Benzenesulfonyl-2-((R)-1-hydroxy-ethyl)-6H-1,2,3,5,6-tetraaza-as-indacen-1-yl]cyclohexanecarbonitrile A suspension of triethyloxonium tetrafluoroborate (5.36 g, 28.2 mmol) and R-(+)-lactamide (2.85 g, 32.0 mmol) in dry THF (40 mL) was stirred at ambient temperature under a nitrogen atmosphere for 2 hours. The mixture was concentrated under vacuum, stirred in absolute ethanol (70 mL) for 10 minutes, treated with trans 4-(5-amino-1-benzenesulfonyl-1H-pyrrolo[2,3-b]pyridin-4-ylamino)-cyclohexanecarbonitrile (4.00 g, 10.1 mmol) and heated at reflux for 2 hours. The cooled mixture was concentrated under vacuum and the residue triturated with ethyl acetate to afford 5.25 g of trans 4-[6-benzenesulfonyl-2-((R)-1-hydroxy-ethyl)-6H-1,2,3,5,6-tetraaza-as-indacen-1-yl]cyclohexanecarbonitrile as an off-white solid. Used without further purification. LCMS (Method Q, ESI): RT=3.33 min, m+H=450.3; $^1$H NMR (400 MHz, DMSO) δ: 8.71 (s, 1H), 8.13 (m, 2H), 7.94 (d, 1H), 7.69 (m, 1H), 7.61 (m, 2H), 7.25 (m, 1H), 5.74 (d, 1H), 5.14 (m, 1H), 4.85 (m, 1H), 3.23 (m, 1H), 2.20 (m, 4H), 1.85 (m, 4H), 1.62 (d, 3H).

trans 4-[2-((R)-1-Hydroxy-ethyl)-6H-1,2,3,5,6-tetraaza-as-indacen-1-yl]-cyclohexanecarbonitrile A solution of trans 4-[6-benzenesulfonyl-2-((R)-1-hydroxy-ethyl)-6H-1,2,3,5,6-tetraaza-as-indacen-1-yl]cyclohexanecarbonitrile (1.20 g, 2.67 mmol) in methanol/THF (1:1, 150 mL) was treated with a 1M sodium hydroxide solution (20 mL) and stirred at room temperature for 3 hours. The organic solvent was removed under vacuum and the aqueous residue extracted into ethyl acetate (3×). The combined organic extracts were washed with water and brine, dried over sodium sulphate and concentrated under vacuum. Purification by column chromatography on silica gel (gradient: 0 to 10% [2M $NH_3$ in methanol] in ethyl acetate) with further purification by reverse phase HPLC (gradient: 5 to 75% acetonitrile in water+0.1% $NH_4OH$) afforded 149 mg (18%) of trans 4-[2-((R)-1-hydroxy-ethyl)-6H-1,2,3,5,6-tetraaza-as-indacen-1-yl]-cyclohexanecarbonitrile as a white solid.

LCMS (Method A, ESI): RT=2.30 min, m+H=310.10; $^1$H NMR (400 MHz, DMSO) δ: 11.85 (s, 1H), 8.54 (s, 1H), 7.45 (m, 1H), 6.79 (m, 1H), 5.65 (d, 1H), 5.13 (m, 1H), 4.85 (m, 1H), 3.17 (m, 1H), 2.32 (m, 4H), 1.95 (m, 2H), 1.81 (m, 2H), 1.64 (d, 3H).

Example 642

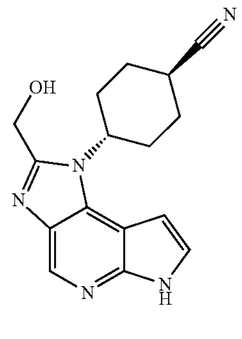 [SMILES: N#C[C@H]1CC[C@H](n2c(CO)nc3cnc4[nH]ccc4c32)CC1]

Trans 4-(2-hydroxymethyl-6H-1,2,3,5,6-tetraaza-as-indacen-1-yl)cyclohexane carbonitrile Trans 4-(6-benzenesulfonyl-2-hydroxymethyl-6H-1,2,3,5,6-tetraaza-as-indacen-1-yl)-cyclohexanecarboxylic acid methyl ester Triethyloxonium tetrafluoroborate (3.26 g, 17.2 mmol) was added to a solution of glycolamide (1.37 g, 18.3 mmol) in THF (25 mL). The mixture was stirred for 2 hours then concentrated under vacuum. The residue was taken up in absolute ethanol (50 mL) and trans 4-(5-amino-1-benzenesulfonyl-1H-pyrrolo[2,3-b]pyridine-4-ylamino)-cyclohex anecarboxylic acid methyl ester (2.45 g, 5.73 mmol) was added. The mixture was then heated at 75° C. for 1.25 hours. The cold mixture was concentrated under vacuum and the residue was partitioned between DCM and saturated aqueous sodium bicarbonate solution. The aqueous phase was then extracted with 10% methanol in DCM. The combined organic extracts were dried over sodium sulfate and concentrated under vacuum to leave a solid. Some precipitated solid remained in the aqueous phase and was recovered by filtration. The combined solids were triturated (acetonitrile) to afford 2.46 g (92%) of trans 4-(6-benzenesulfonyl-2-hydroxymethyl-6H-1,2,3,5,6-tetraaza-as-indacen-1-yl)-cyclohexanecarboxylic acid methyl ester as a pale grey solid. LCMS (Method I, ESI): RT=2.95 min, m+H=469.2; $^1$H NMR (400 MHz, DMSO): δ 8.67 (s, 1H), 8.15-8.11 (m, 2H), 7.94 (d, 1H), 7.69 (tt, 1H), 7.63-7.58 (m, 2H), 7.19 (d, 1H), 5.73 (s, 1H), 4.78 (s, 2H), 4.74-4.64 (m, 1H), 3.65 (s, 3H), 2.80-2.69 (m, 1H), 2.25-2.07 (m, 4H), 2.00-1.92 (m, 2H), 1.73-1.59 (m, 2H).

Trans 4-[6-benzenesulfonyl-2-(tert-butyl-dimethylsilanoxymethyl)-6H-1,2,3,5,6-tetraaza-as-indacen-1-yl]-cyclohexanecarboxylic acid methyl ester Tert-butyldimethylsilyl chloride (2.50 g, 2.17 mL, 9.44 mmol) and 2,6-lutidine (1.52 g, 1.64 mL, 14.2 mmol) were added to a suspension of trans 4-(6-benzenesulfonyl-2-hydroxymethyl-6H-1,2,3,5,6-tetraaza-as-indacen-1-yl)-cyclohexanecarboxylic acid methyl ester (2.21 g, 4.72 mmol) in DCM (50 mL). The mixture was stirred for 1.5 hours then diluted with aqueous citric acid (100 mL). The phases were separated and the aqueous phase was extracted with DCM.

The combined chlorinated extracts were dried over sodium sulphate and concentrated under vacuum. The residue was taken into ether and concentrated under vacuum to yield a foam. This was triturated (cyclohexane) to afford 2.65 g (96%) of trans 4-[6-benzenesulfonyl-2-(tert-butyl-dimethyl-silanoxymethyl)-6H-1,2,3,5,6-tetraaza-as-indacen-1-yl]-cyclohexanecarboxylic acid methyl ester as an off-white solid. LCMS (Method I, ESI): RT=4.56 min, m+H=583.3; $^{1}$H NMR (400 MHz, $CDCl_3$): δ 8.89 (s, 1H), 8.24 (d, 2H), 7.85 (d, 1H), 7.59-7.53 (m, 1H), 7.51-7.45 (m, 2H), 6.84 (d, 1H), 5.00 (s, 2H), 4.79-4.66 (m, 1H), 3.75 (s, 3H), 2.64-2.52 (m, 1H), 2.40-2.25 (m, 4H), 2.11-2.02 (m, 2H), 1.79-1.66 (m, 2H), 0.88 (s, 9H), 0.10 (s, 6H).

Trans-4-[6-benzenesulfonyl-2-(tert-butyl-dimethyl-silanoxymethyl)-6H-1,2,3,5,6-tetraaza-as-indacen-1-yl]-cyclohexylcarbaldehyde A solution of diisobutylaluminum hydride (1.12 mL of a 1.0 M solution in toluene, 1.12 mmol) was added dropwise over 15 minutes to solution of trans 4-[6-benzenesulfonyl-2-(tert-butyl-dimethyl-silanoxymethyl)-6H-1,2,3,5,6-tetraaza-as-indacen-1-yl]-cyclohexanecarboxylic acid methyl ester (435 mg, 0.75 mmol) in DCM (15 mL) maintained at −78° C. The mixture was stirred at −78° C. during 7 hours then saturated aqueous ammonium chloride solution (2 mL) was added. The mixture was then allowed to warm slowly to ambient temperature. The mixture was diluted with water and the phases were separated. The aqueous phase was extracted with DCM and the combined organic extracts were dried over sodium sulfate and concentrated under vacuum. The residue was purified by chromatography on silica gel (eluting with 10-95% ether in pentane) to afford 155 mg (38%) of trans-4-[6-benzenesulfonyl-2-(tert-butyl-dimethyl-silanoxymethyl)-6H-1,2,3,5,6-tetraaza-as-indacen-1-yl]-cyclohexylcarbaldehyde. $^{1}$H NMR (400 MHz, $CDCl_3$): δ 9.76 (s, 1H), 8.89 (s, 1H), 8.24 (d, 2H), 7.85 (d, 1H), 7.55 (t, 1H), 7.49 (t, 2H), 6.83 (d, 1H), 5.00 (s, 2H), 4.77-4.65 (m, 1H), 2.59-2.48 (m, 1H), 2.42-2.25 (m, 4H), 2.17-2.08 (m, 2H), 1.62-1.49 (m, 2H), 0.88 (s, 9H), 0.10 (s, 6H).

Trans 4-(2-hydroxymethyl-6H-1,2,3,5,6,-tetraaza-as-indacen-1-yl)-cyclohexanecarbonitrile A mixture of trans-4-[6-benzenesulfonyl-2-(tert-butylsilanoxymethyl)-6H-1,2,3,5,6-tetraaza-as-indacen-1-yl]-cyclohexylcarbaldehyde (155 mg, 0.28 mmol) and hydroxylamine hydrochloride (23.0 mg, 0.34 mmol) in formic acid (3 mL) was heated at reflux for 1 hour. The mixture was concentrated under vacuum. The residue (a mixture of O-formylated and unformylated products) was taken into THF (2 mL), methanol (2 mL) and aqueous 1.0M sodium hydroxide solution (1 mL). The mixture was stirred at ambient temperature for 1 day then at 40° C. for 6 hours. The cooled mixture was treated with saturated aqueous ammonium chloride solution (1 mL) then diluted with water. The mixture was lyophilised and the resulting residue purified by reverse phase HPLC (5-95% MeCN in water) to afford 55.0 mg (67%) of trans 4-(2-hydroxymethyl-6H-1,2,3,5,6,-tetraaza-as-indacen-1-yl)-cyclohexanecarbonitrile as a white solid. LCMS (Method A, ESI): RT=2.16 min, m+H=296.3; $^{1}$H NMR (400 MHz, DMSO): δ 11.86 (s, 1H), 8.52 (s, 1H), 7.46 (t, 1H), 6.80 (s, 1H), 5.65 (t, 1H), 4.78 (d, 2H), 4.76-4.65 (m, 1H), 3.21-3.08 (m, 1H), 2.42.39-2.21 (m, 4H), 2.02-1.92 (m, 2H), 1.91-1.75 (m, 2H).

Example 643

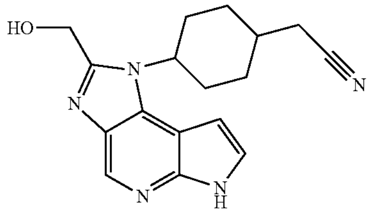 [SMILES: N#CCC1CCC(n2c(CO)nc3cnc4[nH]ccc4c32)CC1]

[4-(2-Hydroxymethyl-6H-1,2,3,5,6-tetraaza-as-indacen-1-yl)-cyclohexyl]-acetonitrile

[4-(2-Allyloxymethyl-6-benzenesulfonyl-6H-1,2,3,5,6-tetraaza-as-indacen-1-yl)-cyclohexylidene]-acetonitrile A suspension of potassium tert-butoxide (87.3 mg, 0.78 mmol) in dry THF (8 mL) at 0° C. was treated slowly with diethyl cyanomethyl phosphonate (0.13 mL, 0.78 mmol) and the mixture was stirred at 0° C. for 1 hour. A solution of 4-(2-allyloxymethyl-6-benzenesulfonyl-6H-1,2,3,5,6-tetraaza-as-indacen-1-yl)-cyclohexanone (0.30 g, 0.65 mmol) in dry THF (4 mL) was added slowly over ~15 mins, then the cooling bath was removed, and the mixture was stirred at ambient temperature for 3 hours. DCM and water were added and the phases separated. The aqueous phase was extracted with DCM (×2) and the combined organic extracts were washed with 10% aqueous citric acid solution, saturated sodium hydrogen carbonate solution and brine, dried with sodium sulphate and concentrated under vacuum to give 0.42 g (100%) of [4-(2-allyloxymethyl-6-benzenesulfonyl-6H-1,2,3,5,6-tetraaza-as-indacen-1-yl)-cyclohexylidene]-acetonitrile as a golden oil which crystallized almost immediately and was used in the next step without further purification. LCMS (Method I, ESI): RT=3.52 min, m+H=488.1; $^{1}$H NMR (300 MHz, $CDCl_3$) δ: 8.90 (s, 1H), 8.27-8.20 (m, 2H), 7.87 (d, 1H), 7.61-7.45 (m, 3H), 6.66 (d, 1H), 5.94-5.80 (m, 1H), 5.40-5.18 (m, 3H), 5.00-4.83 (m, 3H), 4.02 (d, 2H), 3.28-3.17 (m, 1H), 2.74-2.63 (m, 1H), 2.58-2.32 (m, 4H), 2.29-2.11 (m, 2H).

[4-(6-Benzenesulfonyl-2-hydroxymethyl-6H-1,2,3,5,6-tetraaza-as-indacen-1-yl)-cyclohexylidene]-acetonitrile The titled compound was prepared by an analogous procedure to that used for trans [6-benzenesulfonyl-1-(4-methoxy-cyclohexyl)-1,6-dihydro-1,2,3,5,6-tetraaza-as-indacen-2-yl]-methanol, afforded 74.0 mg (68%) of [4-(6-benzenesulfonyl-2-hydroxymethyl-6H-1,2,3,5,6-tetraaza-as-indacen-1-yl)-cyclohexylidene]-acetonitrile as an off-white solid. LCMS (Method I, ESI): RT=3.01 min, m+H=447.1. $^{1}$H NMR (300 MHz, DMSO) δ: 8.71 (s, 1H), 8.18-8.09 (m, 2H), 8.06 (d, 1H), 7.77-7.55 (m, 3H), 6.86 (br s, 1H), 5.79 (t, 1H), 5.70 (s, 1H), 5.10-4.94 (m, 1H), 4.83 (d, 2H), 2.98-2.87 (m, 1H), 2.74-2.52 (m, 3H), 2.33-2.07 (m, 4H).

[4-(6-Benzenesulfonyl-2-hydroxymethyl-6H-1,2,3,5,6-tetraaza-as-indacen-1-yl)-cyclohexyl]-acetonitrile A mixture of [4-(6-benzenesulfonyl-2-hydroxymethyl-6H-1,2,3,5,6-tetraaza-as-indacen-1-yl)-cyclohexylidene]-acetonitrile (50.0 mg, 0.120 mmol) in DMF/THF (3:1 ml) under nitrogen, was treated with 10% palladium/carbon (25.0 mg, 0.024 mmol palladium). The mixture was purged with hydrogen gas and stirred under an atmosphere of hydrogen (balloon) for 24 hours. The catalyst was filtered off through Celite® and the filter cake washed with DMF. The filtrate was concentrated under vacuum to give 50.0 mg (50%) of [4-(6-benzenesulfonyl-2-hydroxymethyl-6H-1,2,3,5,6-tetraaza-as-indacen-1-yl)-cyclohexyl]-acetonitrile as a off-white semi-solid. LCMS (Method H, ESI): RT=2.99 min, m+H=450.1.

[4-(2-Hydroxymethyl-6H-1,2,3,5,6-tetraaza-as-indacen-1-yl)-cyclohexyl]-acetonitrile The titled compound was prepared by an analogous procedure to that used for trans 3-{4-[2-((R)-1-hydroxy-ethyl)-6H-1,2,3,5,6-tetraaza-as-indacen-1-yl]-cyclohexyl}-propionitrile affording 25.0 mg (72%) of [4-(2-hydroxymethyl-6H-1,2,3,5,6-tetraaza-as-indacen-1-yl)-cyclohexyl]-acetonitrile of as an off-white solid. LCMS (Method A, ESI): RT=2.33 min, m+H=310.1. $^1$H NMR (400 MHz, DMSO) δ: 11.86 (s, 1H), 8.54-8.50 (m, 1H), 7.50-7.44 (m, 1H), 6.80-6.65 (m, 1H), 5.77-5.65 (m, 1H), 4.84-4.75 (m, 2H), 4.75-4.62 (m, 1H), 2.82 (d) and 2.60 (d, together 2H), 2.43-1.34 remaining signals mix of cis and trans geometries.

Example 644

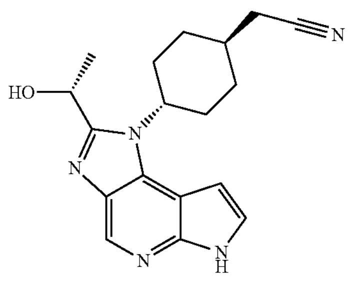 [SMILES: C[C@@H](O)c1nc2cnc3[nH]ccc3c2n1[C@H]1CC[C@H](CC#N)CC1]

Trans {4-[2-((R)-1-Hydroxy-ethyl)-6H-1,2,3,5,6-tetraaza-as-indacen-1-yl]-cyclohexyl}-acetonitrile Trans Methanesulfonic acid 4-tert-butoxycarbonylamino-cyclohexylmethyl ester Trans (4-hydroxymethyl-cyclohexyl)-carbamic acid tert-butyl ester (3.49 g, 15.0 mmol) in DCM (50 mL) was treated with pyridine (4.98 mL, 60.8 mmol). The mixture was cooled to 0° C. and methanesulfonyl chloride (2.36 mL, 30.4 mmol) was added dropwise over 5 minutes. The mixture was stirred at room temperature for 5 hours. The mixture was then concentrated under vacuum. The residue was partitioned between ethyl acetate and water and the aqueous phase was extracted with ethyl acetate (×2). The combined organic extracts were washed with brine, dried with sodium sulfate and concentrated under vacuum. The residue was triturated with cyclohexane then dried under vacuum to give a white solid. Further purification by column chromatography on silica gel (eluting with 1:1 cyclohexane/ethyl acetate) gave 4.17 g (90%) of trans methanesulfonic acid 4-tert-butoxycarbonylamino-cyclohexylmethyl ester as a white solid. $^1$H NMR (400 MHz, $CDCl_3$) δ: 4.37 (br s, 1H), 4.02 (d, 2H), 3.39 (br s, 1H), 3.00 (s, 3H), 2.11-2.00 (m, 2H), 1.91-1.81 (m, 2H), 1.77-1.64 (m, 1H), 1.43 (s, 9H), 1.18-1.05 (m, 4H).

Trans (4-Cyanomethyl-cyclohexyl)-carbamic acid tert-butyl ester

A mixture of trans methanesulfonic acid 4-tert-butoxycarbonylamino-cyclohexylmethyl ester (0.93 mg, 3.00 mmol) and sodium cyanide (0.44 g, 9.00 mmol) in DMSO (10 mL) was stirred at 90° C. for 4 hours. After cooling the mixture was partitioned between ethyl acetate and brine and the aqueous phase was extracted with ethyl acetate (×2). The combined organic extracts were washed with water, brine, dried with sodium sulfate and concentrated under vacuum to give 0.72 g (100%) of trans (4-cyanomethyl-cyclohexyl)-carbamic acid tert-butyl ester as a white solid. $^1$H NMR (400 MHz, $CDCl_3$) δ: 4.38 (br s, 1H), 3.45-3.33 (m, 1H), 2.26 (d, 2H), 2.10-2.02 (m, 2H), 1.96-1.87 (m, 2H), 1.71-1.57 (m, 1H), 1.45 (s, 9H), 1.26-1.03 (m, 4H).

Trans (4-Amino-cyclohexyl)-acetonitrile

A solution of trans (4-cyanomethyl-cyclohexyl)-carbamic acid tert-butyl ester (0.71 g, 3.00 mmol) in DCM (15 mL) was treated with trifluoroacetic acid (2 mL) and the mixture was stirred at ambient temperature for 2.5 hours, then concentrated under vacuum. The residue was purified by column chromatography using Isolute SCX-2 cartridge (eluting with MeOH then 2M $NH_3$ in MeOH). The relevant fractions were combined and concentrated under vacuum to afford 0.40 g (97%) of trans (4-amino-cyclohexyl)-acetonitrile that was used without further purification. $^1$H NMR (400 MHz, $CDCl_3$) δ: 3.52-3.42 (m, 2H), 2.69-2.60 (m, 1H), 2.26 (d, 2H), 1.94-1.83 (m, 4H), 1.70-1.57 (m, 1H), 1.24-1.06 (m, 4H).

Trans {4-[2-((R)-1-Hydroxy-ethyl)-6H-1,2,3,5,6-tetraaza-as-indacen-1-yl]-cyclohexyl}-acetonitrile The titled compound was prepared following an analogous route to that used to prepare trans 3-{4-[2-((R)-1-hydroxy-ethyl)-6H-1,2,3,5,6-tetraaza-as-indacen-1-yl]-cyclohexyl}-propionitrile, except using trans (4-amino-cyclohexyl)-acetonitrile, to afford 0.19 g (40%) of trans {4-[2-((R)-1-hydroxy-ethyl)-6H-1,2,3,5,6-tetraaza-as-indacen-1-yl]-cyclohexyl}-acetonitrile as a white solid. LCMS (Method A, ESI): RT=2.42 min, m+H=324.2; $^1$H NMR (400 MHz, $CDCl_3$) δ: 10.13 (s, 1H), 8.80 (s, 1H), 7.46-7.40 (m, 1H), 6.74

(dd, 1H), 5.29-5.21 (m, 1H), 4.76-4.65 (m, 1H), 3.50 (br s, 1H), 2.69-2.49 (m, 2H), 2.46, (d, 2H), 2.26-2.02 (m, 5H), 1.82 (d, 3H), 1.60-1.1.46 (m, 2H).

Example 645

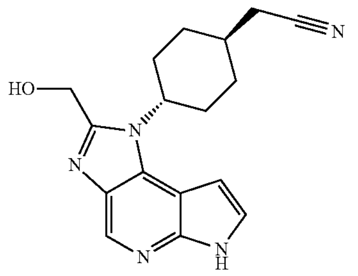 [SMILES: N#CC[C@H]1CC[C@H](n2c(CO)nc3cnc4[nH]ccc4c32)CC1]

Trans[4-(2-hydroxymethyl-6H-1,2,3,5,6-tetraaza-as-indacen-1-yl)-cyclohexyl]-acetonitrile The titled compound was prepared following an analogous route to that used to prepare trans 3-{4-[2-((R)-1-hydroxy-ethyl)-6H-1,2,3,5,6-tetraaza-as-indacen-1-yl]-cyclohexyl}-propionitrile, except using trans (4-amino-cyclohexyl)-acetonitrile and utilising glycolamide (instead of (R)-(+)-lactamide) to afford 55.0 mg (35%) of trans [4-(2-hydroxymethyl-6H-1,2,3,5,6-tetraaza-as-indacen-1-yl)-cyclohexyl]-acetonitrile as a white solid. LCMS (Method A, ESI): RT=2.28 min, m+H=310.2; $^{1}H$ NMR (400 MHz, DMSO) δ: 11.84 (s, 1H), 8.51 (s, 1H), 7.45 (t, 1H), 6.73-6.69 (m, 1H), 5.65 (t, 1H), 4.78 (d, 2H), 4.73-4.62 (m, 1H), 2.59 (d, 2H) 2.44-2.29 (m, 2H), 2.09-1.91 (m, 5H), 1.52-1.34 (m, 2H).

Example 646

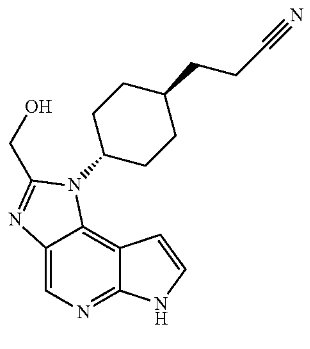 [SMILES: N#CCC[C@H]1CC[C@H](n2c(CO)nc3cnc4[nH]ccc4c32)CC1]

3-[4-(2-hydroxymethyl-6H-1,2,3,5,6-tetraaza-as-indacen-1-yl)-cyclohexyl]-propionitrile Trans 3-{4-[6-benzenesulfonyl-2-(tert-butyl-dimethyl-silanoxymethyl)-6H-1,2,3,5,6-tetraaza-as-indacen-1-yl]-cyclohexyl}-acrylonitrile A mixture of potassium tert-butoxide (49.0 mg, 0.44 mmol) and THF (1.0 mL) was cooled to 0° C. and diethyl cyanomethylphosphonate (78.0 mg, 71 μL, 0.44 mmol) was added. The mixture was stirred cold for 1 hour then a suspension of trans-4-[6-benzenesulfonyl-2-(tert-butyl-dimethyl-silanoxymethyl)-6H-1,2,3,5,6-tetraaza-as-indacen-1-yl]-cyclohexylcarbaldehyde (226 mg, 0.40 mmol) in THF (4 mL) was added. The mixture was stirred for 1 hour then partitioned between brine and dichloromethane. The organic phase was dried over sodium sulphate and concentrated under vacuum to afford the crude product. This was purified by chromatography on silica gel (eluting with 1:1 ether:pentane to ether) affording 190 mg (82%) of trans 3-{-4-[6-benzenesulfonyl-2-(tert-butyl-dimethyl-silanoxymethyl)-6H-1,2,3,5,6-tetraaza-as-indacen-1-yl]-cyclohexyl}-acrylonitrile as a colourless oil. LCMS (Method I, ESI): RT=4.56 min, m+H=576.2.

Trans 3-{4-[6-benzenesulfonyl-2-(tert-butyl-dimethyl-silanoxymethyl)-6H-1,2,3,5,6-tetraaza-as-indacen-1-yl]-cyclohexyl}-propionitrile 10% Palladium on carbon (33.0 mg) was added to a solution of trans 3-{-4-[6-benzenesulfonyl-2-(tert-butyl-dimethyl-silanoxymethyl)-6H-1,2,3,5,6-tetraaza-as-indacen-1-yl]-cyclohexyl}-acrylonitrile (190 mg, 0.33 mmol) in ethyl acetate (10 mL). The mixture was stirred under a hydrogen atmosphere for 24 hours. The mixture was then filtered through a pad of Celite® under an inert atmosphere, washing with ethyl acetate. The filtrate was concentrated under vacuum to afford 176 mg (92%) of trans 3-{-4-[6-benzenesulfonyl-2-(tert-butyl-dimethyl-silanoxymethyl)-6H-1,2,3,5,6-tetraaza-as-indacen-1-yl]-cyclohexyl}-propionitrile as a colourless oil. LCMS (Method I, ESI): RT=4.49 min, m+H=578.3; $^{1}H$ NMR (400 MHz, $CDCl_3$): δ 8.87 (s, 1H), 8.24 (d, 2H), 7.84 (d, 1H), 7.56 (t, 1H), 7.48 (t, 2H), 6.89 (d, 1H), 4.97 (s, 2H), 4.75-4.62 (m, 1H), 2.48 (t, 2H), 2.41-2.25 (m, 2H), 2.13-1.94 (m, 4H), 1.82-1.66 (m, 3H), 1.33-1.18 (m, 2H), 0.89 (s, 9H), 0.10 (s, 6H).

Trans 3-[4-(2-hydroxymethyl-6H-1,2,3,5,6-tetraaza-as-indacen-1-yl)-cyclohexyl]-propionitrile Aqueous sodium hydroxide (1.5 mL of a 1.0M solution, 1.50 mmol) was added to a solution of trans 3-{-4-[6-benzenesulfonyl-2-(tert-butyl-dimethyl-silanoxymethyl)-6H-1,2,3,5,6-tetraaza-as-indacen-1-yl]-cyclohexyl}-propionitrile (176 mg, 0.30 mmol) in THF (3 mL) and methanol (3 mL). The solution was stirred for 18 hours then treated with saturated aqueous ammonium chloride solution (1 mL). The mixture was concentrated under vacuum to give a suspension. The solid was collected by filtration and was purified by column chromatography on an Isolute®$NH_2$ cartridge (eluting with 10% methanol in DCM) to afford 59.0 mg (61%) of trans 3-[4-(2-hydroxymethyl-6H-1,2,3,5,6-tetraaza-as-indacen-1-yl)-cyclohexyl]-propionitrile as a white solid. LCMS (Method A, ESI): RT=2.50 min, m+H=324.2; $^{1}H$ NMR (400 MHz, DMSO): δ 11.86 (s, 1H), 8.53 (s, 1H), 7.48 (t, 1H), 6.68 (s, 1H), 5.65 (t, 1H), 4.77 (d, 2H), 4.72-4.60 (m, 1H), 2.61 (t, 2H), 2.41-2.25 (m, 2H), 2.03-1.87 (m, 4H), 1.74-1.54 (m, 3H), 1.32-1.18 (m, 2H).

Example 647

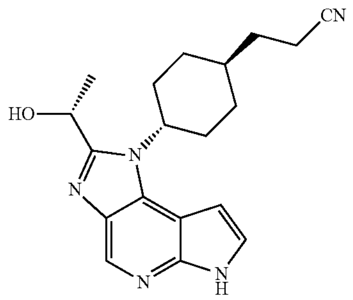 [SMILES: C[C@@H](O)c1nc2cnc3[nH]ccc3c2n1[C@H]1CC[C@H](CCC#N)CC1]

Trans 3-{4-[2-((R)-1-Hydroxy-ethyl)-6H-1,2,3,5,6-tetraaza-as-indacen-1-yl]-cyclohexyl}-propionitrile Trans (4-Formyl-cyclohexyl)-carbamic acid tert-butyl ester A mixture of trans (4-hydroxymethyl-cyclohexyl)-carbamic acid tert-butyl ester (10.0 g, 43.7 mmol) in DCM (225 mL) was treated with dimethylsulfoxide (DMSO) (75 mL) and then cooled to 0° C. Diisopropylethylamine (30.4 mL, 0.17 mol) was added followed by dropwise addition of a fine suspension of sulphur trioxide pyridine complex (27.8 g, 0.17 mol) in DMSO (75 mL). The mixture was stirred at ambient temperature for 10 minutes and then diluted with diethyl ether and 1N aqueous hydrochloric acid with cooling in an ice bath. The phases were separated and the aqueous layer was extracted with ether (×2) and the combined organic phases were washed with 1N aqueous hydrochloric acid, and brine, dried with sodium sulfate and concentrated under vacuum. Trituration with pentane gave 9.36 g (94%) of trans (4-formyl-cyclohexyl)-carbamic acid tert-butyl ester as a white solid which was used without further purification. $^1$H NMR (400 MHz, $CDCl_3$) δ: 9.62 (d, 1H), 4.40 (br s, 1H), 3.51-3.28 (m, 1H), 2.20-1.99 (m, 4H), 1.44 (s, 9H), 1.38 (m, 2H), 1.16 (m, 2H).

Trans E- and Z-[4-(2-cyano-vinyl)-cyclohexyl]-carbamic acid tert-butyl ester

To a suspension of potassium tert-butoxide (5.54 g, 49.5 mmol) in dry THF (110 mL) at 0° C., diethyl cyanomethyl phosphonate (8.00 mL, 49.5 mmol) was added slowly dropwise and the mixture was stirred at 0° C. for 1 hour. A solution of trans (4-formyl-cyclohexyl)-carbamic acid tert-butyl ester (9.36 g, 41.2 mmol) in dry THF (290 mL) was added slowly over ~15 mins, then the cooling bath was removed and the mixture was stirred at ambient temperature for 1 hour. Ethyl acetate and water were added and the phases were separated. The aqueous phase was extracted with ethyl acetate (×2) and the combined organic phase was washed with 10% aqueous citric acid solution, saturated sodium hydrogen carbonate solution, and brine, dried with sodium sulfate and concentrated under vacuum to give 12.6 g (>quant) of trans [4-(2-cyano-vinyl)-cyclohexyl]-carbamic acid tert-butyl ester as a~1:2 mixture of E- and Z-isomers which was contaminated with some phosphonate residues. The golden oil crystallized almost immediately and was used in the next step without further purification.

E-isomer: $^1$H NMR (400 MHz, $CDCl_3$) δ: 6.64 (dd, 1H), 5.29 (dd, 1H), 4.39 (m, 1H), 4.26 (m, 1H), 3.52-3.28 (m, 1H), 2.08 (m, 2H), 1.83 (m, 2H), 1.44 (s, 9H), 1.35-1.10 (m, 4H).

Z-isomer: $^1$H NMR (400 MHz, $CDCl_3$) δ: 6.28 (dd, 1H), 5.25 (dd, 1H), 4.39 (m, 1H), 4.26 (m, 1H), 3.52-3.28 (m, 1H), 2.08 (m, 2H), 1.83 (m, 2H), 1.44 (s, 9H), 1.35-1.10 (m, 4H).

Trans[4-(2-cyano-ethyl)-cyclohexyl]-carbamic acid tert-butyl ester

A mixture of trans E- and Z-[4-(2-cyano-vinyl)-cyclohexyl]-carbamic acid tert-butyl ester (4.00 g, 16.0 mmol) in ethanol (50 mL, IMS grade) under nitrogen was treated with 10% palladium/carbon (1.60 g, 1.50 mmol palladium). The mixture was purged with hydrogen gas and was stirred under an atmosphere of hydrogen (balloon) for 64 hours. The mixture was filtered through Celite® and the filtrate was concentrated under vacuum. Purification by column chromatography on silica gel (ethyl acetate/cyclohexane 1:3) gave 2.68 g (76% over 3 steps) of trans [4-(2-cyano-ethyl)-cyclohexyl]-carbamic acid tert-butyl ester. $^1$H NMR (400 MHz, $CDCl_3$) δ: 4.37 (br s, 1H), 3.38 (br s, 1H), 2.36 (t, 2H), 2.03 (m, 2H), 1.79 (m, 2H), 1.56 (q, 2H), 1.44 (s, 9H), 1.36 (m, 1H), 1.19-0.98 (m, 4H).

Trans 3-(4-amino-cyclohexyl)-propionitrile trifluoroacetic acid salt

A solution of trans [4-(2-cyano-ethyl)-cyclohexyl]-carbamic acid tert-butyl ester (2.68 g, 10.6 mmol) in DCM (30 mL) was treated with trifluoroacetic acid (30 mL) and the mixture was stirred at ambient temperature for 30 mins then concentrated under vacuum. The residue was azeotroped with toluene (×3) and the resulting oil was triturated (diethyl ether) to give a solid, that was washed with ether and dried to give 2.75 g (97%) of trans 3-(4-amino-cyclohexyl)-propionitrile trifluoroacetic acid salt as a white solid. $^1$H NMR (400 MHz, $CDCl_3$) δ: 7.88 (br s, 3H), 3.01 (m, 1H), 2.37 (t, 2H), 2.08 (m, 2H), 1.89 (m, 2H), 1.59 (q, 2H), 1.49-1.35 (m, 3H), 1.04 (m, 2H).

Trans 3-[4-(1-Benzenesulfonyl-5-nitro-1H-pyrrolo[2,3-b]pyridin-4-ylamino)-cyclohexyl]-propionitrile To a stirred suspension of 1-benzenesulfonyl-4-chloro-5-nitro-1H-pyrrolo[2,3-b]pyridine (3.17 g) in propan-2-ol (32 mL), trans 3-(4-amino-cyclohexyl)-propionitrile trifluoroacetic acid salt (2.75 g, 10.3 mmol) and diisopropylethylamine (4.09 mL, 23.5 mmol) were added. The mixture was stirred at reflux for 16 hours and then cooled to 0° C. The suspension was filtered, and the solid washed with propan-2-ol (×2) and ether, then air dried to afford 3.83 g (90%) of trans 3-[4-(1-benzenesulfonyl-5-nitro-1H-pyrrolo[2,3-b]pyridin-4-ylamino)-cyclohexyl]-propionitrile as a bright yellow solid. $^1$H NMR (400 MHz, $CDCl_3$) δ: 9.10 (s, 1H), 8.99 (d, 1H), 8.19 (d, 2H), 7.66-7.59 (m, 2H), 7.52 (t, 2H), 6.67 (d, 1H), 3.91-3.80 (m, 1H), 2.40 (t, 2H), 2.24 (m, 2H), 1.96 (m, 2H), 1.66 (q, 2H), 1.55-1.39 m, 3H), 1.23-1.10 (m, 2H).

Trans 3-[4-(5-Amino-1-benzenesulfonyl-1H-pyrrolo[2,3-b]pyridin-4-ylamino)-cyclohexyl]-propionitrile A suspension of trans 3-[4-(1-benzenesulfonyl-5-nitro-1H-pyrrolo[2,3-b]pyridin-4-ylamino)-cyclohexyl]-propionitrile (3.83 g, 8.50 mmol) in ethanol (28.5 mL, IMS grade) was treated with water (9.5 mL) followed by ammonium chloride (2.71 g, 50.7 mmol) and iron powder (1.89 g, 33.8 mmol) and the mixture was heated to 80° C. for 45 minutes. The solid was filtered and washed with ethanol (IMS grade). The filter cake was extracted repeatedly with DCM. The DCM extracts were washed with water and the aqueous layer was back-extracted with DCM (×2). The combined DCM extracts were washed with brine, dried with sodium sulfate and concentrated under vacuum to give 2.08 g of crude product. The filtered cake, from above, was extracted repeatedly with 2M $NH_3$ in MeOH. The washings were concentrated under vacuum and worked up to provide a further 190 mg of crude product. The remaining filter cake was stirred with DCM (35 mL) and the DCM decanted off, and then 20% [2N $NH_3$ in MeOH] in DCM. The combined chlorinated extracts were filtered through Celite® to remove traces of iron residue and concentrated under vacuum to give a third batch of crude product (0.66 g). The three batches of crude product were dissolved in DCM, combined and concentrated under vacuum to give 2.97 g (83%) of trans 3-[4-(5-amino-1-benzenesulfonyl-1H-pyrrolo[2,3-b]pyridin-4-ylamino)-cyclohexyl]-propionitrile as a pale brown solid that was used in the next step without further purification. $^1$H NMR (400 MHz, DMSO) δ: 8.01 (d, 2H), 7.66 (t, 1H), 7.57 (t, 2H), 7.54 (s, 1H), 7.46 (d, 1H), 6.66 (d, 1H), 5.10 (d, 1H), 4.33 (s, 2H), 3.68-3.56 (m, 1H), 2.01-1.91 (m, 2H), 1.81-1.72 (m, 2H), 1.50 (q, 2H), 1.38-1.19 (m, 3H), 1.17-1.04 (m, 2H) plus 2H obscured by solvent peak.

Trans 3-{4-[6-benzenesulfonyl-2-((R)-1-hydroxy-ethyl)-6H-1,2,3,5,6-tetraaza-as-indacen-1-yl]-cyclohexyl}-propionitrile To a solution of (R)-(+)-lactamide (2.00 g, 22.5 mmol) in dry THF (31 mL), triethyloxonium tetrafluoroborate (4.00 g, 21.2 mmol) was added and the mixture stirred at ambient temperature for 1.75 hours. The solvent was removed under vacuum and the residue dissolved in absolute ethanol (13 mL) and added to a suspension of trans 3-[4-(5-amino-1-benzenesulfonyl-1H-pyrrolo[2,3-b]pyridin-4-ylamino)-cyclohexyl]-propionitrile (2.97 g, 7.00 mmol) in absolute ethanol (47 mL). The mixture was heated to 75° C. for 1 hour and then concentrated under vacuum. The residue was partitioned between ethyl acetate and saturated sodium hydrogen carbonate solution and separated. The aqueous phase was extracted with ethyl acetate (×2) and the combined organic phases were washed with brine, dried with sodium sulfate and concentrated under vacuum to give a brown oil. The oil was dissolved in acetonitrile and ethyl acetate and washed with aqueous 1N sodium hydroxide solution and brine, dried with sodium sulphate and concentrated under vacuum to give crude product. Purification by column chromatography on silica gel (eluting 2 to 5% methanol in DCM) gave 2.29 g (68%) of trans 3-{-4-[6-benzenesulfonyl-2-((R)-1-hydroxy-ethyl)-6H-1,2,3,5,6-tetraaza-as-indacen-1-yl]-cyclohexyl}-propionitrile as an off-white foam. $^1$H NMR (400 MHz, DMSO) δ: 8.70 (s, 1H), 8.13 (d, 2H), 8.00 (d, 1H), 7.70 (t, 1H), 7.61 (t, 2H), 7.06 (d, 1H), 5.75 (d, 1H), 5.17-5.08 (m, 1H), 4.89-4.77 (m, 1H), 2.59 (t, 2H), 2.24-2.09 (m, 2H), 2.01-1.87 (m, 4H), 1.74-1.56 (m, 6H), 1.29-1.15 (m, 2H).

Trans 3-{4-[2-((R)-1-hydroxy-ethyl)-6H-1,2,3,5,6-tetraaza-as-indacen-1-yl]-cyclohexyl}-propionitrile To a stirred solution of trans 3-{-4-[6-benzenesulfonyl-2-((R)-1-hydroxy-ethyl)-6H-1,2,3,5,6-tetraaza-as-indacen-1-yl]-cyclohexyl}-propionitrile (2.29 g, 4.80 mmol) in methanol (24 mL), aqueous 2N sodium hydroxide solution (12 mL, 24.0 mmol) was added at ambient temperature. After 2 hours additional 2N sodium hydroxide solution (12 mL) was added and the mixture was stirred for 15 mins. The mixture was partially concentrated under vacuum and the aqueous residue was extracted with ethyl acetate (×3). The combined organic extracts were washed with brine, dried with sodium sulfate and concentrated under vacuum. Purification by column chromatography on silica gel (gradient: 0 to 12% [2N $NH_3$ in MeOH] in DCM) gave 0.80 g of trans 3-{4-[2-((R)-1-hydroxy-ethyl)-6H-1,2,3,5,6-tetraaza-as-indacen-1-yl]-cyclohexyl}-propionitrile as a white solid.

The above procedure was repeated in an identical fashion to provide a further 0.44 g of trans 3-{4-[2-((R)-1-Hydroxy-ethyl)-6H-1,2,3,5,6-tetraaza-as-indacen-1-yl]-cyclohexyl}-propionitrile as a white solid.

The two batches of product were dissolved in MeOH/DCM and concentrated under vacuum. The resulting solid was triturated (acetonitrile), washed with acetonitrile and ether and dried under vacuum to afford 1.18 g (50% over 2 steps) of trans 3-{4-[2-((R)-1-hydroxy-ethyl)-6H-1,2,3,5,6-tetraaza-as-indacen-1-yl]-cyclohexyl}-propionitrile as a white solid. LCMS (Method A, ESI): RT=2.61 min, m+H=338.2; $^1$H NMR (400 MHz, DMSO) δ: 11.85 (br s, 1H), 8.55 (s, 1H), 7.48 (t, 1H), 6.68 (t, 1H), 5.66 (d, 1H), 5.16-5.07 (m, 1H), 4.89-4.77 (m, 1H), 2.61 (t, 2H), 2.44-2.29 (m, 2H), 2.04-1.87 (m, 4H), 1.75-1.57 (m, 6H), 1.31-1.16 (m, 2H).

Example 648

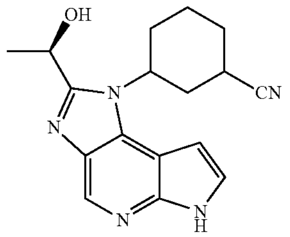 [SMILES: C[C@@H](O)c1nc2cnc3[nH]ccc3c2n1C1CCCC(C#N)C1]

Racemic cis 3-[2-((R)-1-Hydroxy-ethyl)-6H-1,2,3,5,6-tetraaza-as-indacen-1-yl]-cyclohexanecarbonitrile 3-tert-Butoxycarbonylamino-cyclohexanecarboxylic acid Prepared according to the procedure of D. C. Pryde et al, *J. Med. Chem.*, 2006, 49, 4409. $^1$H NMR (400 MHz, $CDCl_3$) δ: 4.48-4.38 (m, 1H), 3.53-3.39 (m, 1H), 2.48-2.37 (m, 1H), 2.32-2.24 (m, 1H), 2.02-1.92 (m, 2H), 1.91-1.82 (m, 1H), 1.44 (s, 9H), 1.43-1.16 (m, 3H), 1.11-0.99 (m, 1H).

(3-Carbamoyl-cyclohexyl)-carbamic acid tert-butyl ester

Isobutylchloroformate (2.06 g, 15.0 mmol) was added dropwise with cooling in an ice-methanol bath to a solution of 3-tert-butoxycarbonylamino-cyclohexanecarboxylic acid (3.15 g, 13.0 mmol) and N-methylmorpholine (1.52 g, 15.0 mmol) in THF (40 mL). After stirring for 30 mins, methanolic ammonia (7M, 5 mL) was added. The mixture was allowed to warm to room temperature, and left to stand overnight. The residue remaining on evaporation of solvent was partitioned between aq. $NH_4Cl$ (150 mL) and DCM (150 mL). The solid suspended in the organic layer was collected, the filtrate evaporated, and the combined solids crystallised from methanol to afford 2.07 (66%) of (3-carbamoyl-cyclohexyl)-carbamic acid tert-butyl ester as colourless plates. $^1$H NMR (400 MHz, MeOD) δ: 6.65-6.59 (m, 1H), 3.40-3.28 (m, 1H), 2.35-2.23, (m, 1H), 2.01-1.92 (m, 1H), 1.91-1.80 (m, 2H), 1.80-1.71 (m, 1H), 1.42 (s, 9H), 1.40-1.21 (m, 3H), 1.19-1.05 (m, 1H).

(3-Cyano-cyclohexyl)-carbamic acid tert-butyl ester

To a mixture of phosphorus oxychloride (4.60 g, 30.0 mmol) and imidazole (1.22 g, 18.0 mmol) in pyridine (40 mL) cooled in an ice-methanol bath was slowly added (3-carbamoyl-cyclohexyl)-carbamic acid tert-butyl ester (1.45 g, 6.00 mmol). The reaction was stirred for 3 hours, allowing to warm to room temperature. The suspension was filtered, the filtrate evaporated and the solids combined before partitioning between aq. $NH_4Cl$ (30 mL) and EtOAc (3×30 mL). The combined organic layers were dried ($MgSO_4$) and evaporated to give 930 mg (69%) of (3-cyano-cyclohexyl)-carbamic acid tert-butyl ester as a gum, which was used directly in the next step. $^1$H NMR (400 MHz, $CDCl_3$) δ: 4.53-4.29 (m, 1H), 3.50-3.33 (m, 1H), 2.58-2.44 (m, 1H), 2.42-2.33 (m, 1H), 2.09-1.99 (m, 1H), 1.99-1.77 (m, 3 h), 1.44 (s, 9H), 1.39-1.30 (m, 2H), 1.18-1.02 (m, 1H).

3-Amino-cyclohexanecarbonitrile (3-Cyano-cyclohexyl)-carbamic acid tert-butyl ester (0.74 g, 3.30 mmol) was dissolved in TFA/DCM and stirred for 1 hr. The solvent was evaporated to give 3-amino-cyclohexanecarbonitrile as a brown solid. The crude material was used without further purification. LCMS (Method H, ESI): RT=0.35 min, m+H=125.0.

3-(1-Benzenesulfonyl-5-nitro-1H-pyrrolo[2,3-b]pyridine-4-ylamino)-cyclohexanecarbonitrile A mixture of 1-benzenesulfonyl-4-chloro-5-nitro-1H-pyrrolo[2,3-b]pyridine (1.01 g, 3.00 mmol), 3-amino-cyclohexanecarbonitrile (3.30 mmol assumed) and diisopropylethylamine (2.60 mL, 15.0 mmol) in propan-2-ol (30 mL) were heated to reflux for 2 hours. The cooled reaction mixture was filtered and the yellow solid further purified by column chromatography on silica gel (gradient: 0 to 10% ethyl acetate in toluene) to afford 300 mg (23%) of cis 3-(1-benzenesulfonyl-5-nitro-1H-pyrrolo[2,3-b]pyridine-4-ylamino)cyclohexanecarbonitrile. $^1$H NMR (400 MHz, DMSO) δ: 8.90 (s, 1H), 8.80 (d, 1H), 8.13 (m, 2H), 7.84 (d, 1H), 7.76 (m, 1H), 7.66 (m 2H), 7.09 (d, 1H), 4.11 (m, 1H), 3.10 (m, 1H), 2.28 (m, 1H), 1.98 (m, 2H), 1.79 (m, 2H), 1.50 (m, 3H).

The filtrate was concentrated and purified by column chromatography on silica gel (gradient: 0 to 10% ethyl acetate in toluene) to afford 220 mg (17%) of trans 3-(1-benzenesulfonyl-5-nitro-1H-pyrrolo[2,3-b]pyridine-4-ylamino)cyclohexanecarbonitrile. LCMS (Method I, ESI): RT=3.76 min, m+H=426.1; $^1$H NMR (400 MHz, DMSO) δ: 8.92 (s, 1H), 8.13 (dd, 2H), 7.88 (d, 1H), 7.77 (t, 1H), 7.65 (t, 2H), 6.99 (d, 1H), 4.27 (m, 1H), 3.26 (m, 1H), 2.18 (m, 1H), 1.99 (m, 1H), 1.91 (m, 1H), 1.83-1.58 (m, 5H).

Cis 3-(5-amino-1-benzenesulfonyl-1H-pyrrolo[2,3-b]pyridine-4-ylamino)-cyclohexanecarbonitrile A mixture of cis 3-(1-benzenesulfonyl-5-nitro-1H-pyrrolo[2,3-b]pyridine-4-ylamino)cyclohexanecarbonitrile (730 mg, 1.72 mmol), ammonium chloride (552 mg, 10.3 mmol) and iron powder (384 mg, 6.88 mmol) in methanol/$H_2O$ (3:1, v/v) was heated at 85° C. for 3.5 hr. The cooled reaction mixture was filtered through celite and the filtrate concentrated under vacuum. The residue was dissolved in DCM, washed with saturated sodium bicarbonate solution and brine, dried over sodium sulfate and concentrated under vacuum to a foam. The resulting residue was purified by column chromatography on silica gel (gradient: 0 to 4% MeOH in DCM) to afford 0.55 g (81%) of cis 3-(5-amino-1-benzenesulfonyl-1H-pyrrolo[2,3-b]pyridine-4-ylamino)-cyclohexanecarbonitrile. LCMS (Method H, ESI): RT=2.45 min, m+H=396.1; $^1$H NMR (400 MHz, DMSO) δ: 8.01 (d, 2H), 7.66 (m, 1H), 7.57 (m, 3H), 7.49 (d, 1H), 6.75 (d, 1H), 5.14 (d, 1H), 4.36 (s, 2H), 3.72 (m, 1H), 2.98 (m, 1H), 2.22 (m, 1H), 2.01-1.84 (m, 2H), 1.75 (m, 1H), 1.53-1.36 (m, 3H), 1.22 (d, 1H).

Racemic cis 3-[6-benzenesulfonyl-2-4R)-1-hydroxy-ethyl]-6H-1,2,3,5,6-tetraaza-as-indecen-1-yl}-cyclohexanecarbonitrile A mixture of triethyloxonium tetrafluoroborate (800 mg, 4.20 mmol) and (R)-(+)-lactamide (450 mg, 5.04 mol) in dry THF was stirred for 2 hr. The reaction mixture was evaporated under vacuum (100 mbar, 40° C.) to a thin, clear oil. To this was added cis 3-(5-amino-1-benzenesulfonyl-1H-pyrrolo[2,3-b]pyridine-4-ylamino)-cyclo hexanecarbonitrile (550 mg, 1.40 mmol) in ethanol and the reaction stirred at 45° C. for 2 hr. The reaction was concentrated under vacuum, dissolved in DCM, washed with saturated sodium bicarbonate solution and brine, dried over sodium sulfate and concentrated under vacuum to an oil. The resulting residue was purified by column chromatography on silica gel (gradient: 0 to 4% MeOH in DCM) to afford 650 mg of racemic cis 3-[6-benzenesulfonyl-2-((R)-1-hydroxy-ethyl]-6H-1,2,3,5,6-tetraaza-as-indecen-1-yl}-cyclohexanecarbonitrile. LCMS (Method I, ESI): RT=2.94 min, m+H=450.1; $^1$H NMR (400 MHz, DMSO) isomer 1 δ: 8.71 (d, 1H), 8.14 (d, 2H), 7.99 (d, 1H), 7.69-7.69 (m, 1H), 7.62 (t, 2H), 7.20 (s, 1H), 5.78 (d, 1H), 5.14 (m, 1H), 4.86 (m, 1H), 3.02 (m, 1H), 2.28 (m, 2H), 2.11 (m, 2H), 1.90 (m, 3H), 1.62 (dd, 3H), 1.54 (m, 1H); isomer 2 δ: 8.71 (d, 1H), 8.14 (d, 2H), 7.99 (d, 1H), 7.69-7.69 (m, 1H), 7.62 (t, 2H), 7.20 (s, 1H), 5.71 (d, 1H), 5.14 (m, 1H), 4.86 (m, 1H), 3.02 (m, 1H), 2.28 (m, 2H), 2.11 (m, 2H), 1.90 (m, 3H), 1.62 (dd, 3H), 1.54 (m, 1H).

Racemic cis 3-[2-((R)-1-hydroxy-ethyl)-6H-1,2,3,5,6-tetraaza-as-indacen-1-yl]-cyclohexanecarbonitrile A mixture of cis-3-[6-benzenesulfonyl-2-4R)-1-hydroxy-ethyl]-6H-1,2,3,5,6-tetraaza-as-indecen-1-yl}-cyclohexanecarbonitrile (650 mg, 1.40 mmol assumed) in THF/methanol containing aqueous sodium hydroxide (7.00 mmol) was stirred for 16 hr. The solvent was evaporated under vacuum to a small volume, the residue dissolved in DCM, washed with saturated sodium bicarbonate solution and brine, dried over sodium sulfate and concentrated under vacuum. The resulting residue was purified by column chromatography on cation exchange silica gel (gradient: 0 to 100% [2M $NH_3$ in MeOH] in DCM) to afford 303 mg (70%) of racemic cis 3-[2-((R)-1-hydroxy-ethyl)-6H-1,2,3,5,6-tetraaza-as-indacen-1-yl]-cyclohexanecarbonitrile, as an off-white solid. LCMS (Method A, ESI): RT=2.36 & 2.40 min, m+H=310.2; $^1$H NMR (400 MHz, DMSO) isomer 1 δ: 11.90 (s, 1H), 8.56 (d, 1H), 7.50 (t, 1H), 6.75 (s, 1H), 5.70 (d, 1H), 5.13 (m, 1H), 4.87 (m, 1H), 3.11 (m, 1H), 2.45 (m, 1H), 2.30 (m, 2H), 2.14 (m, 1H), 2.05-1.73 (m, 3H), 1.64 (dd, 3H), 1.58 (m, 1H); isomer 2 δ:

11.90 (s, 1H), 8.56 (d, 1H), 7.50 (t, 1H), 6.75 (s, 1H), 5.64 (d, 1H), 5.13 (m, 1H), 4.87 (m, 1H), 3.11 (m, 1H), 2.45 (m, 1H), 2.30 (m, 2H), 2.14 (m, 1H), 2.05-1.73 (m, 3H), 1.64 (dd, 3H), 1.58 (m, 1H).

Example 649

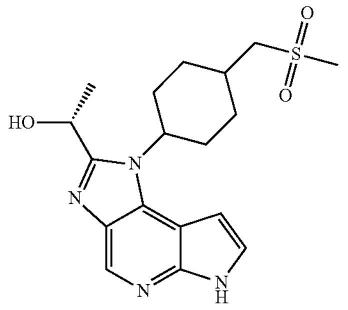 [SMILES: C[C@@H](O)c1nc2cnc3[nH]ccc3c2n1C1CCC(CS(C)(=O)=O)CC1]

(R)-1-[1-(4-Methanesulfonylmethyl-cyclohexyl)-1,6-dihydro-1,2,3,5,6-tetraaza-as-indacen-2-yl]-ethanol (4-Methanesulfonylmethyl-cyclohexyl)-carbamic acid benzyl ester 4-Methanesulfonylmethyl-cyclohexane carboxylic acid (0.50 g, 2.27 mmol), triethylamine (0.46 mL, 3.29 mmol) were dissolved in toluene (10 mL), then phosphorazidic acid diethyl ester (0.66 mL, 3.09 mmol) was added and the mixture was stirred at room temperature for 1 hour. Benzyl alcohol (1.17 mL, 11.4 mmol) was added and the mixture was stirred at 80° C. for 18 hours. The mixture was cooled to room temperature and the solvent was evaporated under vacuum to give thick oil (3.04 g). The crude product was purified by column chromatography on silica gel (gradient: 0-60% ethyl acetate in cyclohexane) affording 0.54 g (73%) of (4-methanesulfonylmethyl-cyclohexyl)-carbamic acid benzyl ester as a clear oil. LCMS (Method H, ESI): RT=2.99 min, m+Na=348.1.

4-Methanesulfonylmethyl-cyclohexylamine (4-Methanesulfonylmethyl-cyclohexyl)-carbamic acid benzyl ester (0.54 g, 1.66 mmol) in ethanol (15 mL, IMS grade) under nitrogen was treated with 10% palladium/carbon (0.18 g, 0.17 mmol). The mixture was purged with hydrogen gas and was stirred under an atmosphere of hydrogen (balloon) for 16 hours. The catalyst was filtered off through Celite® and the filter cake rinsed several times with ethanol. The filtrate was concentrated and then purified by column chromatography on Isolute® SCX-2 cartridge (eluting with MeOH then 2M $NH_3$ in MeOH). The relevant fractions were combined concentrated under vacuum to afford 0.32 g (95%) 4-methanesulfonylmethyl-cyclohexylamine as clear oil that was used without further purification. LCMS (Method I, ESI): RT=0.35 min, m+H=191.9.

(R)-1-[1-(4-Methanesulfonylmethyl-cyclohexyl)-1,6-dihydro-1,2,3,5,6-tetraaza-as-indacen-2-yl]-ethanol The titled compound was prepared following an analogous route to that used to prepare trans 3-{4-[2-((R)-1-hydroxy-ethyl)-6H-1,2,3,5,6-tetraaza-as-indacen-1-yl]-cyclohexyl}-propionitrile, except using 4-methanesulfonylmethyl-cyclohexylamine to afford 90.0 mg (54%) of mixture of cis and trans isomers of (R)-1-[1-(4-methanesulfonylmethyl-cyclohexyl)-1,6-dihydro-1,2,3,5,6-tetraaza-as-indacen-2-yl]-ethanol as an off-white solid. LCMS (Method A, ESI): RT=2.11 & 2.16 min, m+H=377.1; $^1$H NMR (400 MHz, $CDCl_3$) δ: 10.00 (s) and 9.89 (s, together 1H), 8.78-8.73 (m, 1H), 7.43-7.38 (m, 1H), 6.75 (s) and 6.59 (s, together 1H), 5.25-5.16 (m, 1H), 4.75-4.55 (m, 1H), 3.33 (d, 2H major isomer), 3.05 (d, 2H minor isomer), 3.04 (s) and 3.01 (s, together 3H), 2.80-1.85 (m, 8H), 1.82 (d) and 1.78 (d, together 3H) 1.56-1.40 (m, 2H).

Example 650

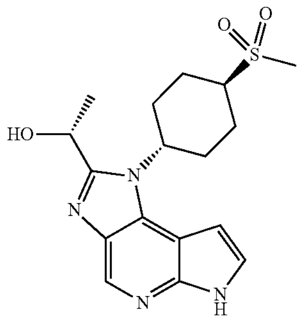 [SMILES: C[C@@H](O)c1nc2cnc3[nH]ccc3c2n1[C@H]1CC[C@H](S(C)(=O)=O)CC1]

Trans (R)-1-[1-(4-methanesulfonyl-cyclohexyl)-1,6-dihydro-1,2,3,5,6-tetraaza-as-indacen-2-yl]-ethanol Cis methanesulfonic acid 4 tert-butoxycarbonylamino-cyclohexyl ester A solution of cis (4-hydroxy-cyclohexyl)-carbamic acid tert-butyl ester (1.00 g, 4.70 mmol) in DCM (10 mL) was treated with triethylamine (1.29 mL, 9.30 mmol) and the mixture was cooled to 0° C. Methanesulfonyl chloride (0.54 mL, 7.00 mmol) was added dropwise and the mixture was stirred at 0° C. for 15 minutes. Water was added and the phases were separated. The aqueous phase was extracted with DCM (×2) and the combined organic phase was washed with saturated sodium hydrogen carbonate solution, and brine, dried with sodium sulfate and concentrated under vacuum to give 1.39 g (quant) of Cis methanesulfonic acid 4 tert-butoxycarbonylamino-cyclohexyl ester as a peach coloured solid which was used without further purification. $^1$H NMR (400 MHz, $CDCl_3$) δ: 4.89 (m, 1H), 4.46 (br s, 1H), 3.53 (br s, 1H), 3.01 (s, 3H), 2.05 (m, 2H), 1.84-(m, 2H), 1.73 (m, 2H), 1.58 (m, 2H), 1.45 (s, 9H).

Trans Thioacetic acid S-(4-tert-butoxycarbonylamino-cyclohexyl) ester

To a stirred suspension of potassium tert-butoxide (0.78 g, 7.00 mmol) and DMF (10 mL), thioacetic acid (0.50 mL, 7.0 mmol) was added at 0° C. The mixture was stirred for ~5 mins and then a solution of cis methanesulfonic acid 4 tert-butoxycarbonylamino-cyclohexyl ester (1.36 g, 4.70 mmol) in DMF (4.1 mL) was added. The mixture was heated to 80° C. for 3.75 hours and was then poured into a mixture of ethyl acetate (50 mL) and water (50 mL). The phases were separated and the aqueous phase was extracted with ethyl acetate (×2). The combined organic extracts were washed with 10% aqueous citric acid solution, saturated sodium hydrogen carbonate solution, and brine, dried with sodium sulfate and concentrated under vacuum. Purification by column chromatography on silica gel (ethyl acetate/cyclohexane, 1:6) gave 325 mg (26%) of trans thioacetic acid S-(4-tert-butoxycarbonylamino-cyclohexyl) ester as an orange solid. $^1$H NMR (400 MHz, $CDCl_3$) δ: 4.38 (br s, 1H), 3.42 (br s, 1H), 3.33 (m, 1H), 2.29 (s, 3H), 2.02 (m, 5H), 1.44 (s, 9H), 1.26-1.25 (m, 3H).

Trans (4-methylsulfanyl-cyclohexyl)-carbamic acid tert-butyl ester

A stirred solution of trans thioacetic acid S-(4-tert-butoxycarbonylamino-cyclohexyl) ester (1.31 g, 4.80 mmol) in methanol (31 mL) was treated with sodium methoxide (1.04 g, 19.2 mmol) followed by methyl iodide (0.45 mL, 7.2 mmol). The mixture was stirred at ambient temperature for 3 hours then diluted with ethyl acetate and water. The phases were separated and the aqueous phase was extracted with ethyl acetate (×2). The combined organic extracts were washed with 10% aqueous citric acid solution, saturated sodium hydrogen carbonate solution, and brine, dried with sodium sulphate and concentrated under vacuum to give crude product. Purification by column chromatography on silica gel (10% ethyl acetate in cyclohexane) gave 516 mg (44%) of trans (4-methylsulfanyl-cyclohexyl)-carbamic acid tert-butyl ester as a white solid. $^1$H NMR (400 MHz, $CDCl_3$) δ: 4.36 (br s, 1H), 3.44 (br s, 1H), 2.72-2.62 (m, 1H), 2.40 (s, 3H), 2.09 (d, 6H), 1.45 (s, 9H), 1.24-1.10 (m, 2H).

Trans (4-methanesulfonyl-cyclohexyl)-carbamic acid tert-butyl ester

A solution of trans (4-methylsulfanyl-cyclohexyl)-carbamic acid tert-butyl ester (0.51 g, 2.10 mmol) in methanol (7 mL) was cooled to 0° C. and treated with a suspension of oxone (1.28 g, 4.20 mmol) in water (3.1 mL). The mixture was stirred at ambient temperature for 20 minutes, then diluted with ethyl acetate and water. The phases were separated and the aqueous phase was extracted with ethyl acetate (×2). The combined organic extracts were washed with 10% aqueous citric acid solution, saturated sodium hydrogen carbonate solution, and brine, dried with sodium sulphate and concentrated under vacuum to give 412 mg (71%) of trans (4-methanesulfonyl-cyclohexyl)-carbamic acid tert-butyl ester as a white solid which was used without further purification. $^1$H NMR (400 MHz, $CDCl_3$) δ: 4.39 (br s, 1H), 3.43 (br s, 1H), 2.83 (s, 3H), 2.78 (m, 1H), 2.25 (m, 4H), 1.67 (m, 2H), 1.44 (s, 9H), 1.28-1.12 (m, 2H).

Trans 4-methanesulfonyl-cyclohexylamine trifluoroacetic acid salt

A suspension of trans (4-methanesulfonyl-cyclohexyl)-carbamic acid tert-butyl ester (0.40 g, 1.40 mmol) in DCM (5 mL) was treated with trifluoroacetic acid (5 mL) and the mixture was stirred at ambient temperature for 30 minutes then concentrated under vacuum. The residue was azeotroped with toluene (×2) and the resulting oil was triturated (diethyl ether) to provide a solid which was washed with ether and dried to give 386 mg (93%) of trans 4-methanesulfonyl-cyclohexylamine trifluoroacetic acid salt as a white solid. $^1$H NMR (400 MHz, DMSO) δ: 7.86 (s, 3H), 3.11-2.98 (m, 2H), 2.92 (s, 3H), 2.18-2.02 (m, 4H), 1.56-1.43 (m, 2H), 1.43-1.28 (t, 2H).

Trans (1-benzenesulfonyl-5-nitro-1H-pyrrolo[2,3-b]pyridin-4-yl)-(4-methanesulfonyl-cyclohexyl)-amine A mixture of trans 4-methanesulfonyl-cyclohexylamine trifluoroacetic acid salt (383 mg, 1.32 mmol), 1-benzenesulfonyl-4-chloro-5-nitro-1H-pyrrolo[2,3-b]pyridine (536 mg, 1.60 mmol), diisopropylethylamine (0.69 mL, 4.0 mmol) in propan-2-ol (5.5 mL), were heated at 120° C. for 10 minutes using microwave irradiation. The mixture was cooled to 0° C. and filtered, the resulting solid washed with propan-2-ol and ether, then dried under vacuum to give 588 mg (93%) of trans (1-benzenesulfonyl-5-nitro-1H-pyrrolo[2,3-b]pyridin-4-yl)-(4-methanesulfonyl-cyclohexyl)-amine as a bright yellow solid. $^1$H NMR (400 MHz, $CDCl_3$) δ: 9.11 (s, 1H), 8.99 (d, 1H), 8.20 (m, 2H), 7.64 (m, 2H), 7.53 (t, 2H), 6.66 (d, 1H), 3.95 (ddd, 1H), 2.95 (m, 1H), 2.91 (s, 3H), 2.40 (m, 4H), 1.85 (m, 2H), 1.52 (m, 2H).

Trans 1-benzenesulfonyl-N*4*-(4-methanesulfonyl-cyclohexyl)-1H-pyrrolo[2,3-b]pyridine-4,5-diamine A suspension of trans (1-benzenesulfonyl-5-nitro-1H-pyrrolo[2,3-b]pyridin-4-yl)-(4-methanesulfonyl-cyclohexyl)-amine (585 mg, 1.20 mmol) and ethanol (4 mL, IMS grade) was treated with water (1.3 mL) followed by ammonium chloride (393 mg, 7.30 mmol) and iron powder (274 mg, 4.90 mmol). The mixture was heated to 80° C. for 45 minutes. The resulting solid was isolated and washed repeatedly with ethanol/water. The filtrate was partially concentrated under vacuum and then diluted with DCM and water. The phases were separated and the aqueous phase was extracted with DCM (×2). The combined organic extracts were washed with brine, dried with sodium sulfate and concentrated under vacuum to give 505 mg (92%) of trans 1-benzenesulfonyl-N*4*-(4-methanesulfonyl-cyclohexyl)-1H-pyrrolo[2,3-b]pyridine-4,5-diamine as a pale brown solid that was used without further purification. $^1$H NMR (400 MHz, DMSO) δ: 8.01 (dd, 2H), 7.70-7.64 (m, 1H), 7.55 (m, 3H), 7.47 (d, 1H), 6.76 (d, 1H), 5.13 (d, 1H), 3.72 (br s, 1H), 3.06 (m, 1H), 2.93 (s, 3H), 2.09 (m, 4H), 1.63 (m, 2H), 1.33 (m, 2H).

Trans (R)-1-[6-benzenesulfonyl-1-(4-methanesulfonyl-cyclohexyl)-1,6-dihydro-1,2,3,5,6-tetraaza-as-indacen-2-yl]-ethanol Prepared by a similar procedure to that used for trans 3-{-4-[6-benzenesulfonyl-2-((R)-1-hydroxy-ethyl)-6H-1,2,3,5,6-tetraaza-as-indacen-1-yl]-cyclohexyl}-propionitrile but using trans 1-benzenesulfonyl-N*4*-(4-methane sulfonyl-cyclohexyl)-1H-pyrrolo[2,3b]pyridine-4,5-diamine to give 160 mg (57%) of trans (R)-1-[6-benzenesulfonyl-1-(4-methanesulfonyl-cyclohexyl)-1,6-dihydro-1,2,3,5,6-tetraaza-as-indacen-2-yl]-ethanol as an off-white solid. $^1$H NMR (400 MHz, DMSO) δ: 8.71 (s, 1H), 8.14 (dd, 2H), 7.93 (d, 1H), 7.72-7.67 (m, 1H), 7.61 (t, 2H), 7.26 (d, 1H), 5.78 (d, 1H), 5.17 (m, 1H), 4.87 (br s, 1H), 3.65 (br s, 1H), 3.02 (s, 3H), 2.32 (m, 2H), 2.26 (m, 2H), 2.05 (m, 2H), 1.73 (m, 2H), 1.61 (d, 3H).

Trans (R)-1-[1-(4-Methanesulfonyl-cyclohexyl)-1,6-dihydro-1,2,3,5,6-tetraaza-as-indacen-2-yl]-ethanol Prepared by a similar procedure to that used for trans 3-{4-[2-((R)-1-hydroxy-ethyl)-6H-1,2,3,5,6-tetraaza-as-indacen-1-yl]-cyclohexyl}-propionitrile but using trans (R)-1-[6-benzenesulfonyl-1-(4-methanesulfonyl-cyclohexyl)-1,6-dihydro-1,2,3,5,6-tetraaza-as-indacen-2-yl]-ethanol and using a mixture of methanol and THF (3:2) as the solvent to give 29.0 mg (14% over 2 steps) of trans (R)-1-[1-(4-methanesulfonyl-cyclohexyl)-1,6-dihydro-1,2,3,5,6-tetraaza-as-indacen-2-yl]-ethanol as a white solid. LCMS (Method A, ESI): RT=2.03 min, m+H=363.2; $^1$H NMR (400 MHz, DMSO) δ: 11.88 (s, 1H), 8.56 (s, 1H), 7.46 (m, 1H), 6.82 (s, 1H), 5.71 (br s, 1H), 5.17 (m, 1H), 4.87 (m, 1H), 3.61 (m, 1H), 3.04 (s, 3H), 2.40 (m, 4H), 2.06 (m, 2H), 1.75 (m, 2H), 1.64 (d, 3H).

Example 651

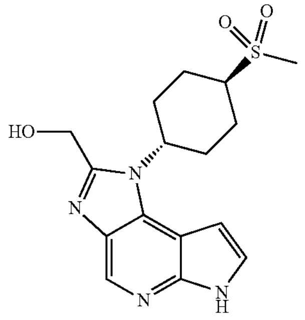 [SMILES: CS(=O)(=O)[C@H]1CC[C@H](n2c(CO)nc3cnc4[nH]ccc4c32)CC1]

Trans[1-(4-Methanesulfonyl-cyclohexyl)-1,6-dihydro-1,2,3,5,6-tetraaza-as-indacen-2-yl]-methanol Trans[6-Benzenesulfonyl-1-(4-methanesulfonyl-cyclohexyl)-1,6-dihydro-1,2,3,5,6-tetraaza-as-indacen-2-yl]-methanol Prepared by a similar procedure to trans 3-{-4-[6-benzenesulfonyl-2-((R)-1-hydroxy-ethyl)-6H-1,2,3,5,6-tetraaza-as-indacen-1-yl]-cyclohexyl}-propionitrile but using trans 1-benzene sulfonyl-N*4*-(4-methanesulfonyl-cyclohexyl)-1H-pyrrolo[2,3-b]pyridine-4,5-diamine and glycolamide instead of (R)-(+)-lactamide. There was still starting material remaining after the first treatment with the imidate (formed by the reaction of glycolamide with triethyloxonium tetrafluoroborate) so a second portion of imidate was prepared in an identical fashion and added to the reaction mixture at 75° C. This gave 111 mg (41%) of trans [6-benzenesulfonyl-1-(4-methanesulfonyl-cyclohexyl)-1,6-dihydro-1,2,3,5,6-tetraaza-as-indacen-2-yl]-methanol as a white solid. $^1$H NMR (400 MHz, DMSO) δ: 8.69 (s, 1H), 8.15 (dd, 2H), 7.94 (d, 1H), 7.71 (m, 1H), 7.63 (m, 2H), 7.27 (d, 1H), 5.76 (m, 1H), 4.81 (d, 2H), 4.74 (m, 1H), 3.62 (br s, 1H), 3.02 (s, 3H), 2.36-2.16 (m, 4H), 2.07 (m, 2H), 1.76 (m, 2H).

Trans[1-(4-Methanesulfonyl-cyclohexyl)-1,6-dihydro-1,2,3,5,6-tetraaza-as-indacen-2-yl]-methanol Prepared by a similar method to that for trans 3-{4-[2-((R)-1-hydroxy-ethyl)-6H-1,2,3,5,6-tetraaza-as-indacen-1-yl]-cyclohexyl}-propionitrile but using trans [6-benzenesulfonyl-1-(4-methanesulfonyl-cyclohexyl)-1,6-dihydro-1,2,3,5,6-tetraaza-as-indacen-2-yl]-methanol and using a mixture of MeOH and THF (3:2) as solvent and warming the mixture to 50° C. to give 47.0 mg (65%) of trans [1-(4-methanesulfonyl-cyclohexyl)-1,6-dihydro-1,2,3,5,6-tetraaza-as-indacen-2-yl]-methanol as a white solid. LCMS (Method A, ESI): RT=1.88 min, m+H=349.2; $^1$H NMR (400 MHz, DMSO) δ: 11.88 (s, 1H), 8.54 (s, 1H), 7.47 (t, 1H), 6.82 (dd, 1H), 5.68 (t, 1H), 4.80 (d, 2H), 4.73 (m, 1H), 3.59 (m, 1H), 3.04 (s, 3H), 2.47-2.29 (m, 4H), 2.08 (d, 2H), 1.78 (t, 2H).

Example 652

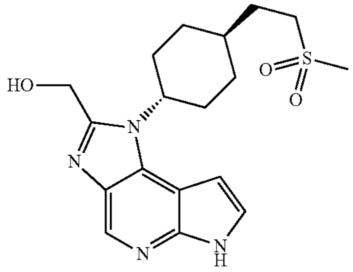 [SMILES: CS(=O)(=O)CC[C@H]1CC[C@H](n2c(CO)nc3cnc4[nH]ccc4c32)CC1]

Trans {1-[4-(2-methanesulfonyl-ethyl)-cyclohexyl]-1,6-dihydro-1,2,3,5,6-tetraaza-as-indacen-2-yl}-methanol Trans[4-(2-methanesulfonyl-vinyl)-cyclohexyl]-carbamic acid tert-butyl ester A solution of diethyl methanesylfonylmethyl phosphonate (900 mg, 3.90 mmol) in THF (20 mL) was treated with sodium hydride (160 mg of a 60% dispersion in mineral oil, 4.00 mmol). The mixture was stirred for 1 hour to give a thick slurry. Trans (4-formyl-cyclohexyl) carbamic acid tert butyl ester (975 mg, 4.30 mmol) was added and the slurry thinned. The mixture was stirred for 2 hours. A few drops of methanol were added and after 5 minutes the solvent was removed under vacuum. The residue was partitioned between water (25 mL) and DCM (25 mL). The aqueous phase was washed with DCM (2×10 mL). The combined organic phase was dried over magnesium sulfate and concentrated under vacuum to afford 1.30 g (100%) of crude trans [4-(2-methanesulfonyl-vinyl)-cyclohexyl]-carbamic acid tert-butyl ester as a white solid ($^1$H NMR showed ~4:1 mixture of double bond geometries). Major isomer $^1$H NMR (400 MHz, $CDCl_3$): δ 6.88 (dd, 1H), 6.32 (dd, 1H), 4.39 (br s, 1H), 3.40 (br s, 1H), 2.93 (s, 3H), 2.21-1.98 (m, 3H), 1.91-1.78 (m, 2H), 1.44 (s, 9H), 1.35-1.09 (m, 4H).

For the minor isomer the following signals were clearly discernable δ 6.20 (d, 1H), 6.12 (t, 1H) and 2.96 (s, 3H). Other signals were either coincident with those for the major isomer or ill-defined.

Trans[4-(2-methanesulfonyl-ethyl)-cyclohexyl]-carbamic acid tert-butyl ester

Trans [4-(2-methanesulfonyl-vinyl)-cyclohexyl]-carbamic acid tert-butyl ester (1.00 g, 3.30 mmol) was dissolved in ethanol (15 mL, IMS grade) and 10% palladium on carbon (100 mg) was added, followed by ammonium formate (1.25 g, 19.8 mmol). The mixture was heated at 90° C. for 45 min, then cooled to room temperature. A further 100 mg palladium on carbon was added and the mixture was heated at 95° C. for 16 h. The mixture was cooled to room temperature then filtered and concentrated under vacuum. The residue was taken up in water and extracted with ethyl acetate (×3). The combined organic extracts were washed with brine then dried ($Na_2SO_4$) and concentrated under vacuum to give 928 mg (92%) of trans [4-(2-methanesulfonyl-ethyl)-cyclohexyl]- carbamic acid tert-butyl ester. LCMS (method Q, ESI): RT=3.35 min, m+H=204.1; NMR (400 MHz, $CDCl_3$) δ: 4.36 (br s, 1H), 3.38 (br s, 1H), 3.01 (m, 2H), 2.89 (s, 3H), 2.07-1.98 (m, 2H), 1.82-1.72 (m, 4H), 1.44 (s, 9H), 1.36-1.08 (m, 5H).

Trans 4-(2-methanesulfonyl-ethyl)-cyclohexylamine

Trans [4-(2-methanesulfonyl-ethyl)-cyclohexyl]-carbamic acid tert-butyl ester (900 mg, 2.95 mmol) was dissolved in DCM (7 mL) and trifluoroacetic acid (7 mL) was added. The mixture was stirred at room temperature for 1 h, then concentrated. The residue was taken up in methanol and purified by Isolute® SCX-2 column (gradient: methanol to 2 M $NH_3$ in methanol) to give 594 mg (98%) of trans 4-(2-methanesulfonyl-ethyl)-cyclohexylamine. LCMS (method Q, ESI): RT=0.48 min, m+H=206.1; NMR (400 MHz, DMSO) δ: 3.09 (m, 2H), 2.93 (s, 3H), 2.48-2.41 (m, 1H), 1.78-1.64 (m, 4H), 1.58-1.51 (m, 2H), 1.30-1.18 (m, 1H), 1.03-0.82 (m, 4H).

Trans (1-benzenesulfonyl-5-nitro-1H-pyrrolo[2,3-b]pyridin-4-yl)-[4-(2-methanesulfonyl-ethyl)-cyclohexyl]-amine Trans 4-(2-methanesulfonyl-ethyl)-cyclohexylamine (563 mg, 2.75 mmol) was dissolved in propan-2-ol (10 mL) and trans 1-benzenesulfonyl-4-chloro-5-nitro-1H-pyrrolo[2,3-b]pyridine (805 mg, 2.39 mmol) was added, followed by DIPEA (623 μL, 3.60 mmol). The mixture was heated at 110° C. for 90 min, then cooled. The solid precipitate was collected by filtration, washed with propan-2-ol and dried under vacuum to give 1.05 g (87%) of trans (1-benzenesulfonyl-5-nitro-1H-pyrrolo[2,3-b]pyridin-4-yl)-[4-(2-methanesulfonyl-ethyl)-cyclohexyl]-amine. LCMS (Method Q, ESI): RT=4.04 min, m+H=507.1; NMR (400 MHz, DMSO) δ: 8.90 (s, 1H), 8.81 (d, 1H), 8.13 (d, 2H), 7.82 (d, 1H), 7.76 (t, 1H), 7.66 (t, 2H), 6.99 (d, 1H), 3.98 (m, 1H), 3.14 (m, 2H), 2.96 (s, 3H), 2.06 (m, 2H), 1.80 (m, 2H), 1.63 (m, 2H), 1.43 (m, 3H), 1.23 (m, 2H).

Trans 1-benzenesulfonyl-N*4*-[4-(2-methanesulfonyl-ethyl)-cyclohexyl]-1H-pyrrolo[2,3-b]pyridine-4,5-diamine Trans (1-benzenesulfonyl-5-nitro-1H-pyrrolo[2,3-b]pyridin-4-yl)-[4-(2-methanesulfonyl-ethyl)-cyclohexyl]-amine (1.04 g, 2.05 mmol) was suspended in a mixture of ethanol (10 mL, IMS grade) and water (3.3 mL). Ammonium chloride (658 mg, 12.3 mmol) was added, followed by iron (dust, 460 mg, 8.20 mmol), and the mixture was heated at 100° C. for 2 h. The mixture was cooled to room temperature, then diluted with a 4:1 mixture of DCM: 2 M ammonia in methanol and filtered through Celite®. The filter cake was washed with further 4:1 DCM: 2 M ammonia in methanol and the combined filtrate was concentrated under vacuum. The residue was suspended in water and extracted with DCM (×3). The combined organic extracts were washed with brine then dried ($Na_2SO_4$) and concentrated to give 1.04 g (quant) of crude trans 1-benzenesulfonyl-N*4*-[4-(2-methanesulfonyl-ethyl)-cyclohexyl]-1H-pyrrolo[2,3-b]pyridine-4,5-diamine, which was used directly without further purification. LCMS (Method Q, ESI): RT=2.62 min, m+H=477.1.

Trans {6-benzenesulfonyl-1-[4-(2-methanesulfonyl-ethyl)-cyclohexyl]-1,6-dihydro-1,2,3,5,6-tetraaza-as-indacen-2-yl}-methanol Glycolamide (173 mg, 2.31 mmol) was dissolved in THF (6 mL) and triethyloxonium tetrafluoroborate (399 mg, 2.10 mmol) was added. The mixture was stirred 1.75 h at room temperature, then concentrated. The residue was dissolved in absolute ethanol (3 mL) and added to a solution of trans 1-benzenesulfonyl-N*4*-[4-(2-methanesulfonyl-ethyl)-cyclohexyl]-1H-pyrrolo[2,3-b]pyridine-4,5-diamine (500 mg, 1.05 mmol) in absolute ethanol (9 mL). The resulting mixture was stirred at 80° C. for 90 min, then cooled to room temperature and allowed to stand for 16 h. The mixture was concentrated under vacuum, then the residue suspended in saturated aqueous $NaHCO_3$ and extracted with DCM (×3). The combined organic extracts were washed with brine then dried ($Na_2SO_4$) and concentrated under vacuum. Purification by column chromatography on silica gel (gradient: 1:1 DCM: pentane to DCM to 5% methanol in DCM) gave 465 mg (86%) of trans {6-benzenesulfonyl-1-[4-(2-methanesulfonyl-ethyl)-cyclohexyl]-1,6-dihydro-1,2,3,5,6-tetraaza-as-indacen-2-yl}-methanol. LCMS (Method Q, ESI): RT=3.10 min, m+H=517.1; NMR (400 MHz, DMSO) δ: 8.68 (s, 1H), 8.13-8.12 (m, 2H), 7.98 (d, 1H), 7.70-7.69 (m, 1H), 7.62-7.61 (m, 2H), 7.09 (d, 1H), 5.73 (t, 1H), 4.78 (d, 2H), 4.68 (s, 1H), 3.21 (m, 2H), 2.99 (s, 3H), 2.16 (d, 2H), 1.95 (m, 2H), 1.70 (m, 2H), 1.51 (m, 3H), 1.27 (m, 2H).

Trans {1-[4-(2-methanesulfonyl-ethyl)-cyclohexyl]-1,6-dihydro-1,2,3,5,6-tetraaza-as-indacen-2-yl}-methanol Trans {6-benzenesulfonyl-1-[4-(2-methanesulfonyl-ethyl)-cyclohexyl]-1,6-dihydro-1,2,3,5,6-tetraaza-as-indacen-2-yl}-methanol (258 mg, 0.50 mmol) was dissolved in THF (2.5 mL) and methanol (2.5 mL). 2 M Aqueous NaOH (2.5 mL) was added and the mixture was stirred at 50° C. for 45 min. The mixture was cooled and 1 M aqueous HCl (5 mL) was added, then the mixture was concentrated. Purification by column chromatography on silica gel (gradient: DCM to 7% (2 M $NH_3$ in methanol) in DCM) gave 73 mg (39%) of trans {1-[4-(2-methanesulfonyl-ethyl)-cyclohexyl]-1,6-dihydro-1,2,3,5,6-tetraaza-as-indacen-2-yl}-methanol. LCMS (method A, ESI): RT=2.16 min, m+H=377.1; NMR (400 MHz, DMSO) δ: 11.86 (s, 1H), 8.53 (s, 1H), 7.47 (t, 1H), 6.71 (dd, 1H), 5.65 (t, 1H), 4.78 (d, 2H), 4.68 (m, 1H), 3.24 (m, 2H), 2.99 (s, 3H), 2.38 (m, 2H), 1.97 (m, 4H), 1.72 (m, 3H), 1.27 (d, 2H).

Example 653

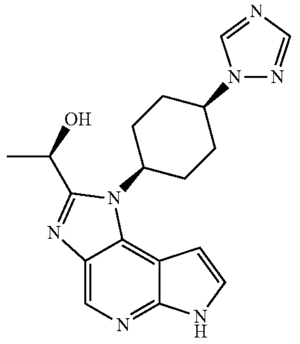 [SMILES: C[C@@H](O)c1nc2cnc3[nH]ccc3c2n1[C@H]1CC[C@@H](n2cncn2)CC1]

Cis (R)-1-[1-(4-[1,2,4]triazol-1-yl-cyclohexyl)-1,6-dihydro-1,2,3,5,6-tetraaza-as-indacen-2-yl]-ethanol Trans methanesulfonic acid 4-tert-butoxycarbonylamino-cyclohexyl ester Methanesulfonyl chloride (1.37 g, 929 μL, 12 mmol) was added dropwise to a stirred suspension of trans (4-hydroxycyclohexyl)-carbamic acid tert-butyl ester (2.15 g, 10.0 mmol) in DCM (25 mL) and triethylamine (1.42 g, 1.95 mL, 14.0 mmol). After 2.5 hours saturated aqueous sodium hydrogen carbonate solution (25 mL) was added and the phases were separated. The aqueous phase was extracted with DCM (2×20 mL). The combined organic extracts were washed with brine (50 mL), dried over sodium sulfate and concentrated under vacuum to afford 3.13 g (100%) of trans methanesulfonic acid 4-tert-butoxycarbonylamino-cyclohexyl ester an off white solid. $^1$H NMR (400 MHz, $CDCl_3$): δ 4.66-4.56 (m, 1H), 4.37 (br s, 1H), 3.46 (br s, 1H), 3.00 (s, 3H), 2.18-2.02 (m, 4H), 1.74-1.61 (m, 2H), 1.43 (s, 9H), 1.31-1.19 (m, 2H).

Cis (4-[1,2,4]triazol-1-yl-cyclohexyl)-carbamic acid tert-butyl ester

Sodium hydride (104 mg of a 60% dispersion in mineral oil, 2.60 mmol) was added portionwise to a solution of 1,2,4-triazole (194 mg, 2.80 mmol) in DMF (5 mL). After 5 minutes trans methanesulfonic acid 4-tert-butoxycarbonylamino-cyclohexyl ester (587 mg, 2.00 mmol) was added. The reaction mixture was then heated at 65° C. for 3 days. The cooled mix was poured into ice-cold water (75 mL) which was then extracted with ethyl acetate (2×25 mL). The combined organic extracts were washed with brine (75 mL), dried over sodium sulfate and concentrated under vacuum to give the crude product. This was purified by chromatography on silica gel (eluting with 0-5% methanol in ethyl acetate) to afford 260 mg (49%) of cis (4-[1,2,4]triazol-1-yl-cyclohexyl)-carbamic acid tert-butyl ester a white solid. LCMS (Method H, ESI): RT=2.60 min M+H=267.0; $^1$H NMR (400 MHz, DMSO): δ 8.55 (s, 1H), 7.95 (s, 1H), 6.89 (br s, 1H), 4.32-4.22 (m, 1H), 3.58 (br s, 1H), 2.20-2.07 (m, 2H), 1.88-1.77 (m, 2H), 1.69-1.56 (m, 4H), 1.39 (s, 9H).

Cis (1-benzenesulfonyl-5-nitro-1H-pyrrolo[2,3b]pyridin-4-yl)-(4-[1,2,4]triazol-1-yl-cyclohexyl)-amine A solution of cis (4-[1,2,4]triazol-1-yl-cyclohexyl)-carbamic acid tert-butyl ester (250 mg, 0.94 mmol) in DCM (2 mL) was treated with trifluoroacetic acid (660 mg, 430 µL, 5.70 mmol). The mixture was stirred for 1 hour then concentrated under vacuum to give the crude amine trifluoroacetate salt. This was taken into propan-2-ol (10 mL) and treated with diisopropylethylamine (853 mg, 1.15 mL, 6.60 mmol). 1-Benzenesulfonyl-4-chloro-5-nitro-1H-pyrrolo[2,3-b]pyridine (886 mg, 2.62 mmol) was added and the mixture was heated at 75° C. for 2 hours. The cooled mixture was concentrated under vacuum to give the crude product which was purified by chromatography on silica gel (eluting with 0-10% ethyl acetate in DCM). Providing 0.40 g (86%) of cis (1-benzenesulfonyl-5-nitro-1H-pyrrolo[2,3b]pyridin-4-yl)-(4-[1,2,4]triazol-1-yl-cyclohexyl)-amine a yellow solid. LCMS (Method H, ESI): RT=3.40 min M+H=468.0; $^1$H NMR (300 MHz, $CDCl_3$): δ 9.42 (d, 1H), 9.14 (s, 1H), 8.26-8.11 (m, 2H), 8.14 (s, 1H), 7.96 (s, 1H), 7.69-7.59 (m, 2H), 7.54 (t, 2H), 6.74 (d, 1H), 4.44-4.31 (m, 2H), 2.26-2.09 (m, 6H), 2.09-1.92 (m, 2H).

Cis 1-benzenesulfonyl-N*4*-(4-[1,2,4]triazol-1-yl-cyclohexyl)-1H-pyrrolo[2,3-b]pyridine-4,5-diamine A solution of ammonium chloride (276 mg, 5.14 mmol) in water (7.5 mL), was added to a suspension of cis (1-benzenesulfonyl-5-nitro-1H-pyrrolo[2,3b]pyridin-4-yl)-(4-[1,2,4]triazol-1-yl-cyclohexyl)-amine (400 mg, 0.86 mmol) in methanol (22.5 mL). Powdered iron (193 mg, 3.43 mmol) was added and the mixture was heated at 85° C. for 3.5 hours. The cooled mixture was filtered through a pad of Celite® washing the filter cake with DCM. The combined filtrate was concentrated under vacuum and the residue was partitioned between saturated aqueous sodium hydrogen carbonate solution (20 mL) and DCM (3×20 mL). The combined organic extracts were washed with brine (20 mL), dried over sodium sulfate and concentrated under vacuum to afford the crude product 410 mg (ca. 100%) of cis 1-benzenesulfonyl-N*4*-(4-[1,2,4]triazol-1-yl-cyclohexyl)-1H-pyrrolo[2,3-b]pyridine-4,5-diamine a red solid. $^1$H NMR (300 MHz, $CDCl_3$): δ 8.19-8.09 (m, 3H), 7.96 (s, 1H), 7.87 (s, 1H), 7.59-7.41 (m, 4H), 6.57 (d, 1H), 5.11 (d, 1H), 4.39-4.27 (m, 1H), 4.20-4.08 (m, 1H), 2.87 (s, 2H), 2.29-1.84 (m, 8H).

Cis (R)-1-[1-(4-[1,2,4]triazol-1-yl-cyclohexyl)-1,6-dihydro-1,2,3,5,6-tetraaza-as-indacen-2-yl]-ethanol Triethyloxonium tetrafluoroborate (550 mg, 2.81 mmol) was added to a solution of (R)-lactamide (274 mg, 3.00 mmol) in THF (10 mL). The mixture was stirred for 3 hours then concentrated under vacuum. The residue was taken into absolute ethanol (10 mL) and added to a mixture of crude cis 1-benzenesulfonyl-N*4*-(4-[1,2,4]triazol-1-yl-cyclohexyl)-1H-pyrrolo[2,3-b]pyridine-4,5-diamine (410 mg, 0.86 mmol) in absolute ethanol (10 mL). The resultant mixture was heated at 75° C. for 1.5 hours. The cooled mixture was concentrated under vacuum and the residue was partitioned between saturated aqueous sodium hydrogencarbonate (25 mL) solution and DCM (3×25 mL). The combined organic extracts were washed with brine (25 mL), dried over sodium sulfate and concentrated under vacuum to afford 460 mg of crude cis (R)-1-[6-benzenesulfonyl-1-(4-[1,2,4]triazol-1-yl-cyclohexyl)-1,6-dihydro-1,2,3,5,6-tetraaza-as-indacen-2-yl]-ethanol. LCMS (method I, ESI): RT=2.59 min, M+H=492.1.

Crude cis (R)-1-[6-benzenesulfonyl-1-(4-[1,2,4]triazol-1-yl-cyclohexyl)-1,6-dihydro-1,2,3,5,6-tetraaza-as-indacen-2-yl]-ethanol was dissolved in methanol (10 mL) and aqueous potassium carbonate (3.10 mL of a 2M solution, 6.20 mmol) was added. The mixture was heated at 70° C. for 1.5 hours. The cooled mixture was concentrated under vacuum and the residue was partitioned between water (25 mL) and ethyl acetate (3×25 mL). The combined organic extracts were washed with 1M aqueous sodium hydroxide solution (25 mL), water (25 mL) and brine (25 mL), dried over sodium sulfate and concentrated under vacuum to give the crude product. Purification by column chromatography on silica gel (eluting with 0-10% 2M $NH_3$ in methanol in DCM) to afford 24.0 mg (8%) of cis (R)-1-[1-(4-[1,2,4]triazol-1-yl-cyclohexyl)-1,6-dihydro-1,2,3,5,6-tetraaza-as-indacen-2-yl]-ethanol an off-white solid. LCMS (Method A, ESI): RT=2.11 min, M+H=352.1. $^1$H NMR (400 MHz, DMSO): δ 11.69 (s, 1H), 8.91 (s, 1H), 8.50 (s, 1H), 8.22 (s, 1H), 7.15 (s, 1H), 5.67 (d, 1H), 5.46 (br s, 1H), 5.20-5.11 (m, 1H), 5.01-4.90 (m, 1H), 4.63-4.58 (m, 1H), 2.83-2.7 (m, 2H), 2.45-2.32 (m, 2H), 2.23-2.08 (m, 2H) 1.87-1.77 (m, 2H), 1.64 (d, 3H).

Example 654

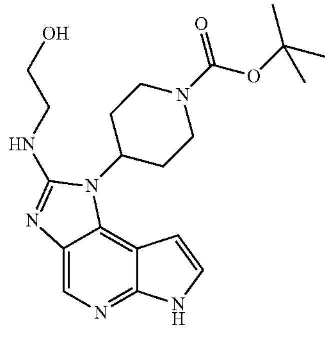 [SMILES: CC(C)(C)OC(=O)N1CCC(n2c(NCCO)nc3cnc4[nH]ccc4c32)CC1]

4-[(2-Hydroxy-ethylamino)-6H-1,2,3,5,6-tetraaza-as-indacen-1-yl]-piperidine-1-carboxylic acid tert-butyl ester 4-(6-Benzenesulfonyl-2-bromo-6H-1,2,3,5,6-tetraaza-as-indacen-1-yl)-piperidine-1-carboxylic acid tert-butyl ester A solution of 4-(6-benzenesulfonyl-6H-1,2,3,5,6-tetraaza-as-indacen-1-yl)-piperidine-1-carboxylic acid tert-butyl ester (1.92 g, 4.00 mmol) in THF (16 mL) at −78° C. was treated dropwise with a solution of 2M LDA (3.6 mL, 7.20 mmol). The mixture was stirred at −78° C. for 40 minutes then N-bromosuccinimide (1.45 g, 8.10 mmol) was added. The resultant mixture was stirred cold for 40 minutes then without external cooling for 40 minutes. A solution of sodium metabisulfite (1.00 g, 5.25 mmol) in water (20 mL) was added and the mixture was then extracted with DCM (1×15 mL then 2×10 mL). The combined organic extracts were dried over magnesium sulfate and concentrated under vacuum. The residue was purified by chromatography on silica gel (eluting with 0-20% ethyl acetate in DCM) and by trituration (acetonitrile) to afford 0.88 g (39%) of 4-(6-benzenesulfonyl-2-bromo-6H-1,2,3,5,6-tetraaza-as-indacen-1-yl)-piperidine-1-carboxylic acid tert-butyl ester as an off-white solid. LCMS (Method I, ESI): RT=3.95 min, m+H=560.3 & 562.3; $^1$H NMR (400 MHz, $CDCl_3$): δ 8.82 (s, 1H), 8.22 (d, 2H), 7.80 (d, 1H), 7.56 (t, 1H), 7.48 (t, 2H), 6.72 (d, 1H), 4.91-4.75 (m, 1H), 4.50-4.30 (m, 2H), 3.05-2.80 (m, 2H), 2.53-2.30 (m, 2H), 1.90-1.80 (m, 2H), 1.58 (s, 9H).

4-[(2-Hydroxy-ethylamino)-6H-1,2,3,5,6-tetraaza-as-indacen-1-yl]-piperidine-1-carboxylic acid tert-butyl ester A suspension of 4-(6-benzenesulfonyl-2-bromo-6H-1,2,3,5,6-tetraaza-as-indacen-1-yl)-piperidine-1-carboxylic acid tert-butyl ester (256 mg, 0.45 mmol) in ethanolamine (4 mL) was heated at 130° C. for 6 hours. The mixture was cooled and concentrated under vacuum to remove most of the excess ethanolamine. The residue was purified by chromatography on silica gel (eluting with 10% then 20% methanol in DCM). The isolated product was further purified by trituration (acetonitrile) and dried under vacuum to afford 105 mg (58%) of 4-[(2-hydroxy-ethylamino)-6H-1,2,3,5,6-tetraaza-as-indacen-1-yl]-piperidine-1-carboxylic acid tert-butyl ester as a fawn solid. LCMS (Method A, ESI): RT=2.75 min, m+H=401.3; $^1$H NMR (400 MHz, DMSO): δ 11.50 (s, 1H), 8.19 (s, 1H), 7.28 (t, 1H), 6.61 (s, 1H), 6.27 (s, 1H), 4.87 (t, 1H), 4.69-4.57 (m, 1H), 4.25-4.10 (m, 2H), 3.64 (q, 2H), 3.42 (q, 2H), 2.92 (br s, 2H), 2.39-2.23 (m, 2H), 1.78 (d, 2H), 1.50 (s, 9H).

Example 655

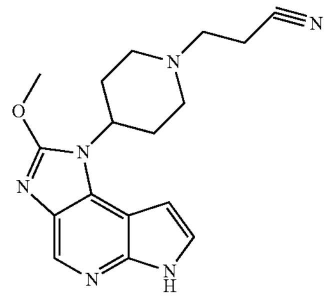 [SMILES: COc1nc2cnc3[nH]ccc3c2n1C1CCN(CCC#N)CC1]

3-[4-(2-Methoxy-6H-1,2,3,5,6-tetraaza-as-indacen-1-yl)-piperidin-1-yl]-propionitrile 2-Methoxy-1-piperidin-4-yl-1,6-dihydro-1,2,3,5,6-tetraaza-as-indacene A mixture of 4-(6-benzenesulfonyl-2-bromo-6H-1,2,3,5,6-tetraaza-as-indacen-1-yl)-piperidine-1-carboxylic acid tert-butyl ester (400 mg, 0.70 mmol) and 25% sodium methoxide in methanol (8 mL) was heated at 60° C. during 4 hours. The mixture was cooled and treated with saturated aqueous ammonium chloride solution (10 mL). The resultant mixture was concentrated under vacuum to approximately 50% of its original volume then diluted with water (10 mL). The mixture was extracted with dichloromethane (3×15 mL). The combined organic extracts were dried over magnesium sulfate and concentrated under vacuum. The residue was subjected to chromatography on silica gel (eluting with 1:1 ethyl acetate: dichloromethane to ethyl acetate). The isolated product was triturated (acetonitrile) to yield 155 mg of crude 4-(2-methoxy-6H-1,2,3,5,6-tetraaza-as indacen-1-yl)-piperidine-1-carboxylic acid tert-butyl ester as a white solid. LCMS (Method I, ESI): RT=2.37 min, m+H=372.

The crude material was suspended in DCM (3 mL) and TFA (1 mL) was added. The solution was stirred at ambient temperature for 1.5 hours then concentrated under vacuum. The residue was initially purified by column chromatography (SCX-2, gradient, methanol to 2M ammonia in methanol) and further purified by chromatography on silica gel (eluting with 0-20% [2M $NH_3$ in methanol] in DCM) finally triturated (acetonitrile) to provide 91.0 mg (47%) of 2-methoxy-1-piperidin-4-yl-1,6-dihydro-1,2,3,5,6-tetraaza-as-indacene as a fawn solid. LCMS (Method I, ESI): RT=0.67 min, m+H=272.4; $^1$H NMR (400 MHz, DMSO): δ 11.66 (s, 1H), 8.34 (s, 1H), 7.42 (t, 1H), 6.82-6.78 (m, 1H), 4.55-4.45 (m, 1H), 4.13 (s, 3H), 3.15-3.08 (m, 2H), 2.72-2.62 (m, 2H), 2.35-2.20 (m, 3H), 1.80-1.71 (m, 2H).

3-[4-(2-Methoxy-6H-1,2,3,5,6-tetraaza-as-indacen-1-yl)-piperidin-1-yl]-propionitrile A mixture of 2-methoxy-1-piperidin-4-yl-1,6-dihydro-1,2,3,5,6-tetraaza-as-indacene (65.0 mg, 0.24 mmol), acrylonitrile (64.0 mg, 79 µL, 1.50 mmol) and ethanol (5 mL, IMS grade) was heated at 80° C. for 3 hours. The reaction mixture was cooled and concentrated under vacuum. The residue was triturated (cyclohexane, then acetonitrile) then dried under vacuum to afford 62.0 mg (80%) of 3-[4-(2-methoxy-6H-1, 2,3,5,6-tetraaza-as-indacen-1-yl)-piperidin-1-yl]-propionitrile as a white solid. LCMS (Method A, ESI): RT=1.48 min, m+H=325.3; $^1$H NMR (400 MHz, DMSO): δ 11.67 (s, 1H), 8.35 (s, 1H), 7.41 (t, 1H), 6.77 (dd, 1H), 4.58-4.37 (m, 1H), 4.14 (s, 3H), 3.14-3.05 (m, 2H), 2.79-2.7 (m, 2H), 2.71-2.65 (m, 2H) 2.49-2.38 (m, 2H), 2.32-2.22 (m, 2H), 1.90-1.82 (m, 2H).

Example 656

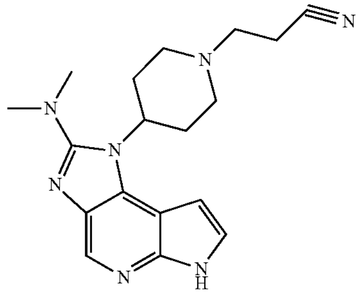 [SMILES: CN(C)c1nc2cnc3[nH]ccc3c2n1C1CCN(CCC#N)CC1]

3-[4-(2-Dimethylamino-6H-1,2,3,5,6-tetraaza-as-indacen-1-yl)-piperidin-1-yl]-propionitrile 4-(6-Benzenesulfonyl-2-dimethylamino-6H-1,2,3,5,6-tetraaza-as-indacen-1-yl)-piperidine-1-carboxylic acid tert-butyl ester Dichloromethylene-dimethylimminium chloride (200 mg, 1.25 mmol) was added to a suspension of 4-(5-amino-1-benzenesulfonyl-1H-pyrrolo[2,3-b]pyridine-4-ylamino)-piperidine-1-carboxylic acid tert butyl ester (472 mg, 1.00 mmol) in THF (8 mL). The suspension thinned and diisopropylethylamine (517 mg, 0.70 mL, 4.00 mmol) was added. The mix thickened and was stirred for 4 hours at ambient temperature then concentrated under vacuum. The residue was partitioned between water (20 mL) and DCM (20 mL). The aqueous phase was extracted with DCM (10 mL) and the combined organic extracts were dried over magnesium sulfate and concentrated under vacuum to give a yellow glass. Purification by column chromatography on silica gel (eluting with 1:1 ethyl acetate:DCM) gave 185 mg (35%) of 4-(6-benzenesulfonyl-2-dimethylamino-6H-1,2,3,5,6-tetraaza-as-indacen-1-yl)-piperidine-1-carboxylic acid tert-butyl ester as a white solid. LCMS (Method I, ESI): RT=3.33 min, m+H=525.3; $^1$H NMR (400 MHz, $CDCl_3$): δ 8.74 (s, 1H), 8.19 (d, 2H), 7.73 (d, 1H), 7.53 (t, 1H), 7.46 (t, 2H), 6.67 (d, 1H), 4.62-4.50 (m, 1H), 4.50-4.25 (m, 2H) 2.94 (s, 6H), 2.94-83 (m, 2H), 2.50-2.35 (m, 2H), 1.86-1.80 (m, 2H), 1.57 (s, 9H).

4-(2-Dimethylamino-6H-1,2,3,5,6-tetraaza-as-indacen-1-yl)-piperidine-1-carboxylic acid tert-butyl ester A solution of 4-(6-benzenesulfonyl-2-dimethylamino-6H-1,2,3,5,6-tetraaza-as-indacen-1-yl)-piperidine-1-carboxylic acid tert-butyl ester (185 mg, 0.35 mmol) in THF (3 mL), methanol (3 mL) and 1M aqueous sodium hydroxide (2 mL) was allowed to stand for 66 hours. The mixture was then concentrated under vacuum to remove most of the organic solvent then diluted with water (5 mL) and saturated aqueous ammonium chloride (1 mL). The aqueous phase was decanted from the solid crude product which was then washed with a little water. Purification by column chromatography on silica gel (eluting with 2:1 DCM:ethyl acetate to ethyl acetate, then 20% methanol in ethyl acetate) afforded a colourless glass. Trituration with acetonitrile gave a white solid which was dried under vacuum to give 115 mg (85%) of 4-(2-dimethylamino-6H-1,2,3,5,6-tetraaza-as-indacen-1-yl)-piperidine-1-carboxylic acid tert-butyl ester. LCMS (Method A, ESI): RT=3.10 min, m+H=385.3; $^1$H NMR (400 MHz, DMSO): δ 11.73 (s, 1H), 8.39 (s, 1H), 7.42-7.30 (m, 1H), 6.34 (dd, 1H), 4.71-4.60 (m, 1H), 4.14 (br s, 2H), 3.03 (br s, 2H), 2.85 (s, 6H), 2.43-2.28 (m, 2H), 1.93-1.75 (m, 2H), 1.50 (s, 9H).

Dimethyl-(1-piperidin-4-yl-1,6-dihydro-1,2,3,5,6-tetraaza-as-indacen-1-yl)-amine Trifluoroacetic acid (1 mL) was added to a solution of 4-(2-dimethylamino-6H-1,2,3,5,6-tetraaza-as-indacen-1-yl)-piperidine-1-carboxylic acid tert-butyl ester (60.0 mg, 0.15 mmol) in DCM (3 mL). The mixture was stirred for 2 hours then concentrated under vacuum. The residue was purified by column chromatography (SCX-2, eluting with 2M $NH_3$ in methanol) to afford 42.0 mg (98%) of dimethyl-(1-piperidin-4-yl-1,6-dihydro-1,2,3,5,6-tetraaza-as-indacen-1-yl)-amine as a white solid. LCMS (Method I, ESI): RT=0.64 min, m+H=285.3; $^1$H NMR (400 MHz, MeOD): δ 8.40 (s, 1H), 7.44 (d, 1H), 7.07 (d, 1H), 4.68-4.58 (m, 1H), 3.35-3.28 (br obscured by solvent presumed 2H), 2.96 (s, 6H), 2.86 (td, 2H), 2.63 (qd, 2H), 1.89 (d, 2H).

3-[4-(2-Dimethylamino-6H-1,2,3,5,6-tetraaza-as-indacen-1-yl)-piperidin-1-yl]-propionitrile A mixture of dimethyl-(1-piperidin-4-yl-1,6-dihydro-1,2,3,5,6-tetraaza-as-indacen-1-yl)-amine (42.0 mg, 0.15 mmol), acrylonitrile and ethanol (5 mL, IMS grade) was heated at reflux for 2.5 hours. The cooled mixture was concentrated under vacuum and triturated with acetonitrile. The resulting product was purified by column chromatography on silica gel (eluting with ethyl acetate then 2.5% methanol in ethyl acetate) to afford 31.0 mg (60%) of 3-[4-(2-dimethylamino-6H-1,2,3,5,6-tetraaza-as-indacen-1-yl)-piperidin-1-yl]-propionitrile as a white solid. LCMS (Method A, ESI): RT=1.61 min, m+H=338.3; $^1$H NMR (400 MHz, DMSO): δ 11.67 (s, 1H), 8.38 (s, 1H), 7.39 (t, 1H), 6.87 (dd, 1H), 4.47-4.35 (m, 1H), 3.12 (d, 2H), 2.84 (s, 6H), 2.76 (t, 2H), 2.69 (t, 2H), 2.66-2.54 (m, 2H), 2.31-2.21 (m, 2H), 1.89-1.79 (m, 2H).

Example 657

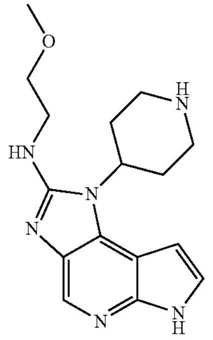 [SMILES: COCCNc1nc2cnc3[nH]ccc3c2n1C1CCNCC1]

(2-Methoxy-ethyl)-(1-piperidin-4-yl-1,6-dihydro-1,2,3,5,6-tetraaza-as-indacen-2-yl)-amine 4-[6-Benzenesulfonyl-2-(2-methoxy-ethylamino)-6H-1,2,3,5,6-tetraaza-as-indacen-1-yl]-piperidine-1-carboxylic acid tert-butyl ester 2-Methoxyethyl isothiocyanate (118 mg, 110 μL, 1.00 mmol) was added to a suspension of 4-(5-amino-1-benzenesulfonyl-1H-pyrrolo[2,3-b]pyridine-4-ylamino)-piperidine-1-carboxylic acid tert butyl ester (472 mg, 1.00 mmol) in THF (8 mL). The mix was heated at reflux for 4 hours then a second aliquot of 2-methoxyethyl isothiocyanate (59.0 mg, 55.0 μL, 0.50 mmol) was added. The mixture was heated for a further 5 hour. LCMS (Method I, ESI) (showed RT=3.56 min, m+H=589.4) was consistent with the desired thiourea intermediate. The cooled mixture was treated with 1-(3-dimethylaminopropyl)-3-ethylcarbodiimide hydrochloride (200 mg, 1.05 mmol) and stirred at ambient temperature. After 2 days a second aliquot of 1-(3-dimethylaminopropyl)-3-ethylcarbodiimide hydrochloride (200 mg, 1.05 mmol) was added and stirring was continued for 3 days. The mixture was filtered and the residue was washed with THF (10 mL). The combined filtrate was concentrated under vacuum to give the crude product. This was taken into DCM and washed with water. The water was extracted with DCM and the combined organic extracts were dried over magnesium sulfate and concentrated under vacuum. The residue was purified by column chromatography on silica gel (eluting with ethyl acetate) then by trituration with cyclohexane to afford 490 mg (88%) of 4-[6-benzenesulfonyl-2-(2-methoxy-ethylamino)-6H-1,2,3,5,6-tetraaza-as-indacen-1-yl]-piperidine-1-carboxylic acid tert-butyl ester as an off-white solid. LCMS (Method H, ESI): RT=2.83 min, m+H=555.3; $^1$H NMR (400 MHz, $CDCl_3$): δ 8.61 (s, 1H), 8.19 (d, 2H), 7.70 (d, 1H), 7.58-7.51 (m, 1H), 7.50-7.41 (m, 2H), 6.63 (d, 1H), 4.50-4.20 (m, 3H), 3.78-3.64 (m, 4H), 3.42 (s, 3H), 3.01-2.81 (m, 2H), 2.43-2.26 (m, 2H), 1.88 (br d, 2H), 1.43 (s, 9H).

4-[2-(2-Methoxy-ethylamino)-6H-1,2,3,5,6-tetraaza-as-indacen-1-yl]-piperidine-1-carboxylic acid tert-butyl ester A mixture of 4-[6-benzenesulfonyl-2-(2-methoxy-ethylamino)-6H-1,2,3,5,6-tetraaza-as-indacen-1-yl]-piperidine-1-carboxylic acid tert-butyl ester (300 mg, 0.54 mmol), 1M aqueous sodium hydroxide (2.5 mL, 2.50 mmol), THF (5 mL) and methanol (5 mL) was heated at 50° C. for 3 hours. The cooled pink solution was treated with saturated aqueous ammonium chloride (1 mL) and the colour faded. The solution was then concentrated under vacuum to leave a white slurry. This was diluted with water and the solid was recovered by filtration. The solid was washed with water (5 mL) and acetonitrile (5 mL) then dried under vacuum to afford 190 mg (85%) of 4-[2-(2-methoxy-ethylamino)-6H-1,2,3,5,6-tetraaza-as-indacen-1-yl]-piperidine-1-carboxylic acid tert-butyl ester as a white solid. LCMS (Method A, ESI): RT=2.95 min, m+H=415.4; $^1$H NMR (400 MHz, DMSO): δ 11.50 (s, 1H), 8.20 (s, 1H), 7.28 (t, 1H), 6.65 (s, 1H), 6.27 (s, 1H), 4.70-4.57 (m, 1H), 4.23-4.10 (m, 2H), 3.58-3.47 (m, 4H), 3.30 (s, 3H partially obscured by water) 3.04-2.81 (m, 2H), 2.38-2.25 (m, 2H), 1.76 (br d, 2H), 1.50 (s, 9H).

(2-Methoxy-ethyl)-(1-piperidin-4-yl-1,6-dihydro-1,2,3,5,6-tetraaza-as-indacen-2-yl)-amine 4-[2-(2-Methoxy-ethylamino)-6H-1,2,3,5,6-tetraaza-as-indacen-1-yl]-piperidine-1-carboxylic acid tert-butyl ester (150 mg, 0.36 mmol) was suspended in 4M HCl in dioxan (3 mL, 12.0 mmol). The mixture was stirred for 4 hours then concentrated under vacuum. The residue was purified by column chromatography (SCX-2, loading methanol/dichloromethane, eluting with methanol to 2M $NH_3$ in methanol) and the isolated product triturated with minimal acetonitrile, then dried under vacuum, to afford 110 mg (97%) of (2-methoxy-ethyl)-(1-piperidin-4-yl-1,6-dihydro-1,2,3,5,6-tetraaza-as-indacen-2-yl)-amine as a white solid. LCMS (Method A, ESI): RT=1.49 min, m+H=315.3; $^1$H NMR (400 MHz, DMSO): δ 11.42 (s, 1H), 8.18 (s, 1H), 7.34 (t, 1H), 6.85-6.81 (m, 1H), 6.61 (s, 1H), 4.49-4.37 (m, 1H), 3.60-3.47 (m, 4H), 3.30 (s, 3H partially obscured by water) 3.19-2.3.11 (m, 2H), 2.67 (t, 2H), 2.37 (qd, 2H) 1.67 (br d, 2H).

Example 658

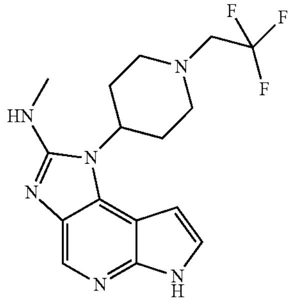 [SMILES: CNc1nc2cnc3[nH]ccc3c2n1C1CCN(CC(F)(F)F)CC1]

Methyl-{1-[1-(2,2,2-trifluoro-ethyl)-piperidin-4-yl]-1,6-dihydro-1,2,3,5,6-tetraaza-as-indacen-2-yl}-amine 4-(6-Benzenesulfonyl-2-methylamino-6H-1,2,3,5,6-tetraaza-as-indacen-1-yl)-piperidine-1-carboxylic acid tert butyl ester Following the procedure for 4-[6-benzenesulfonyl-2-(2-methoxy-ethylamino)-6H-1,2,3,5,6-tetraaza-as-indacen-1-yl]-piperidine-1-carboxylic acid tert-butyl ester the title compound was prepared using methyl isothiocyanate (220 mg, 3.00 mmol) and 4-(5-amino-1-benzenesulfonyl-1H-pyrrolo[2,3-b]pyridine-4-ylamino)-piperidine-1-carboxylic acid tert butyl ester (943 mg, 2.00 mmol) to afford 1.00 g (98%) of 4-(6-benzenesulfonyl-2-methylamino-6H-1,2,3,5,6-tetraaza-as-indacen-1-yl)-piperidine-1-carboxylic acid tert butyl ester as a white solid LCMS (Method I, ESI): RT=2.68 min m+H=511.1; $^1$H NMR (400 MHz, $CDCl_3$): δ 8.62 (s, 1H), 8.18 (d, 2H), 7.69 (d, 1H), 7.52 (t, 1H), 7.45 (t, 2H), 6.61 (d, 1H), 4.50-4.22 (m, 4H), 3.13 (d, 3H), 2.98-2.80 (m, 2H), 2.42-2.22 (m, 2H), 1.93-1.80 (m, 2H), 1.54 (s, 9H).

(6-Benzenesulfonyl-1-piperidin-4-yl-1,6-dihydro-1,2,3,5,6-tetraaza-as-indacen-2-yl)-methyl-amine A mixture of 4-(6-benzenesulfonyl-2-methylamino-6H-1,2,3,5,6-tetraaza-as-indacen-1-yl)-piperidine-1-carboxylic acid tert butyl ester (550 mg, 1.08 mmol), DCM (3.75 mL) and trifluoroacetic acid (1.25 mL) was stirred at room temperature for 2 hours. The mixture was concentrated under vacuum and purified by column chromatography using an Isolute® $NH_2$ column (eluted with 5-20% methanol in DCM) affording 440 mg (99%) of (6-benzenesulfonyl-1-piperidin-4-yl-1,6-dihydro-1,2,3,5,6-tetraaza-as-indacen-2-yl)-methyl-amine as a white solid. LCMS (Method I, ESI): RT=1.54 min, m+H=411.3; $^1$H NMR (400 MHz, DMSO): δ 8.28 (s, 1H), 8.10 (d, 2H), 7.87 (d, 1H), 7.68 (t, 1H), 7.59 (t, 2H), 7.28 (d, 1H), 6.80 (s 1H), 4.49-4.38 (m, 1H), 3.42-3.20 (m, partially obscured by water presumed 2H or 3H), 2.90 (d, 3H), 2.77 (t, 2H), 2.22 (m, 2H), 1.76 (d, 2H).

{6-Benzenesulfonyl-1-[1-(2,2,2-trifluoro-ethyl)-piperidin-4-yl]-1,6-dihydro-1,2,3,5,6-tetraaza-as-indacen-2-yl}-methyl-amine A solution of 2,2,2-trifluoroethyl trifluoromethanesulfonate (116 mg, 75 μL, 0.50 mmol) in THF (5 mL) was added in 2 portions at a 30 minute interval to a stirred. suspension of (6-benzenesulfonyl-1-piperidin-4-yl-1,6-dihydro-1,2,3,5,6-tetraaza-as-indacen-2-yl)-methyl-amine (225 mg, 0.50 mmol) in THF (40 mL) and diisopropylethylamine (129 mg, 175 μL, 1.00 mmol). The mixture was then heated at reflux for 18 hours. A further aliquot of 2,2,2-trifluoroethyl trifluoromethanesulfonate (70 μL, ~0.50 mmol) was added and heating continued for 24 hours. The mixture was then cooled and concentrated under vacuum. The residue was passed through an Isolute® $NH_2$ cartridge (eluting with 10% methanol in DCM) and the crude isolated product purified by column chromatography on silica gel (eluting with 10% methanol in DCM). Trituration with acetonitrile afforded 150 mg (60%) of {6-benzenesulfonyl-1-[1-(2,2,2-trifluoro-ethyl)-piperidin-4-yl]-1,6-dihydro-1,2,3,5,6-tetraaza-as-indacen-2-yl}-methyl-amine. LCMS (Method I, ESI): RT=2.65 min, m+H=493.0; $^1$H NMR (400 MHz, DMSO): δ 8.30 (s, 1H), 8.11 (d, 2H), 7.91 (d, 1H), 7.68 (t, 1H), 7.60 (t, 2H), 7.06 (d, 1H), 6.87-6.77 (m, 1H), 4.45-4.33 (m, 1H), 3.41-3.29 (m, partially obscured by water), 3.13 (d, 2H), 2.91 (d, 3H), 2.62-2.55 (m, 2H), 2.33 (m, 2H), 1.81-1.70 (m, 2H).

Methyl-{1-[1-(2,2,2-trifluoro-ethyl)-piperidin-4-yl]-1,6-dihydro-1,2,3,5,6-tetraaza-as-indacen-2-yl}-amine A solution of {6-benzenesulfonyl-1-[1-(2,2,2-trifluoro-ethyl)-piperidin-4-yl]-1,6-dihydro-1,2,3,5,6-tetraaza-as-indacen-2-yl}-methyl-amine (150 mg, 0.30 mmol) in THF (4 mL), methanol (4 mL) and aqueous 1M sodium hydroxide (2 mL, 2.00 mmol) was stirred for 3 days. Saturated aqueous ammonium chloride (5 mL) was added and the mixture concentrated under vacuum until a precipitate formed. The solid was recovered by filtration, the aqueous phase was extracted with DCM (3×5 mL). The combined organic extracts were concentrated under vacuum and the residue combined with the material obtained by filtration to give the crude product. This was purified by column chromatography on silica gel (eluting with 5% then 10% methanol in DCM) to afford 85.0 mg (80%) of methyl-{1-[1-(2,2,2-trifluoro-ethyl)-piperidin-4-yl]-1,6-dihydro-1,2,3,5,6-tetraaza-as-indacen-2-yl}-amine as a white solid. LCMS (Method A, ESI): RT=2.80 min, m+H=353.3; $^1$H NMR (400 MHz, DMSO): δ 11.48 (s, 1H), 8.20 (s, 1H), 7.38 (t, 1H), 6.70 (dd, 1H), 6.58 (s, 1H), 4.43-4.28 (m, 1H), 3.40-3.25 (m, partially obscured by water), 3.14 (d, 2H), 2.90 (d, 3H), 2.63-2.48 (m, partially obscured by solvent), 1.79-1.70 (m, 2H).

Examples 659 and 660

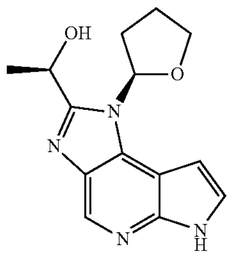

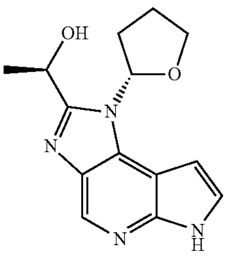

(R)-1-[(S)-1-(Tetrahydro-furan-2-yl)-1,6-dihydro-1,2,3,5,6-tetraaza-as-indacen-2-yl]-ethanol AND (R)-1-[(R)-1-(Tetrahydro-furan-2-yl)-1,6-dihydro-1,2,3,5,6-tetraaza-as-indacen-2-yl]-ethanol 1-Benzenesulfonyl-N-(tetrahydro-furan-3-yl)-1H-pyrrolo[2,3-b]pyridine-4,5-diamine 722 mg of the title compound was made by following the procedures described for the preparation of 1-Benzenesulfonyl-N-4-cyclohexyl-1H-pyrrolo[2,3-b]pyridine-4,5-diamine (Example 113) but substituting 3-aminotetrahydrofuran for cyclohexylamine.

$^1$H NMR (400 MHz, $CDCl_3$) δ 8.17-8.10 (m, 2H), 7.84 (s, 1H), 7.58-7.40 (m, 4H), 6.59 (d, J=4.2 Hz, 1H), 4.89 (d, J=7.5 Hz, 1H), 4.59-4.49 (m, 1H), 3.98-3.74 (m, 4H), 2.83 (br s, 2H), 2.37-2.24 (m, 1H), 1.99-1.88 (m, 1H).

Acetic acid (R)-1-[1-benzenesulfonyl-4-(tetrahydro-furan-3-ylamino)-1H-pyrrolo[2,3-b]pyridin-5-ylcarbamoyl]-ethyl ester (R)-2-acetoxypropanoic acid (0.306 g, 2.32 mmol) was dissolved in methylene chloride (20 mL, 200 mmol;). Triethylamine (0.42 mL, 3.0 mmol;) was added, followed by N,N,N',N'-tetramethyl-O-(7-azabenzotriazol-1-yl)uronium hexafluorophosphate (0.972 g, 2.56 mmol;) dissolved in N,N-dimethylformamide (2 mL, 20 mmol;). After 15 minutes, 1-benzenesulfonyl-N-(tetrahydro-furan-3-yl)-1H-pyrrolo[2,3-b]pyridine-4,5-diamine (0.728 g, 2.03 mmol) was added and the reaction was stirred 64 h at room temperature. The volatiles were removed under reduced pressure and the residue was dissolved in 100 ml EtOAc. This was shaken with 50 ml saturated aqueous NaHCO3. The layers were separated and the aqueous phase was extracted with EtOAc (2×50 ml). The combined organics were dried with MgSO4, filtered and concentrated. This material was then dissolved in a minimum volume of CH2Cl2 and injected onto a 40 g silica gel column which had been equilibrated with heptane. It was then eluted with a gradient of 0% to 100% ethyl acetate in heptane. The product containing fractions were combined and evaporated under reduced pressure to give the title compound as a clear oil (0.596 g, 62%). $^1$H NMR (400 MHz, CDCl3) δ 8.15 (d, J=7.6 Hz, 2H), 7.88 (s, 1H), 7.60-7.43 (m, 4H), 7.21 (d, J=7.2 Hz, 1H), 6.62 (d, J=4.1 Hz, 1H), 5.11-4.95 (m, 2H), 4.59-4.48 (m, 1H), 4.01-3.74 (m, 4H), 2.33-2.21 (m, 1H), 2.19 (d, J=3.3 Hz, 3H), 2.03-1.95 (m, 1H), 1.59 (d, J=6.9 Hz, 3H).

Acetic acid (R)-1-[6-benzenesulfonyl-1-(tetrahydro-furan-2-yl)-1,6-dihydro-1,2,3,5,6-tetraaza-as-indacen-2-yl]-ethyl ester Acetic acid (R)-1-[1-benzenesulfonyl-4-(tetrahydro-furan-3-ylamino)-1H-pyrrolo[2,3-b]pyridin-5-ylcarbamoyl]-ethyl ester (0.566 g, 1.20 mmol) was dissolved in acetic acid (10 mL, 200 mmol;) and heated to 120° C. for 4 h. The volatiles were removed under reduced pressure, and the residue was dissolved in EtOAc (50 ml). This was washed with saturated aqueous NaHCO3 (2×25 ml), dried with MgSO4, filtered and concentrated onto silica gel. This material was then subjected to silica gel chromatography using a 25 g column, with a gradient of 0% to 100% ethyl acetate in heptane. The product containing fractions were combined and evaporated under reduced pressure to give the desired material (0.24 g, 44%). $^1$H NMR (400 MHz, CDCl3) δ 8.92 (s, 1H), 8.21 (d, J=7.7 Hz, 2H), 7.80 (d, J=4.0 Hz, 1H), 7.58-7.42 (m, 3H), 7.22 (d, J=4.1 Hz, 1H), 6.31-6.19 (m, 1H), 5.50-5.35 (m, 1H), 4.47 (dd, J=17.4, 8.7 Hz, 1H), 4.29-4.06 (m, 2H), 3.96-3.82 (m, 1H), 2.60-2.32 (m, 2H), 2.10 (d, J=6.6 Hz, 3H), 1.82 (d, J=6.5 Hz, 3H).

(R)-1-[(S)-1-(Tetrahydro-furan-2-yl)-1,6-dihydro-1,2,3,5,6-tetraaza-as-indacen-2-yl]-ethanol And (R)-1-[(R)-1-(Tetrahydro-furan-2-yl)-1,6-dihydro-1,2,3,5,6-tetraaza-as-indacen-2-yl]-ethanol Acetic acid (R)-1-[6-benzenesulfonyl-1-(tetrahydro-furan-2-yl)-1,6-dihydro-1,2,3,5,6-tetraaza-as-indacen-2-yl]-ethyl ester (235 mg, 0.517 mmol) was dissolved in ethanol (2.0 mL, 34 mmol;). 1.00 M of Sodium hydroxide in Water (2.0 mL) was added and the solution was heated to 60° C. for 5 h. The volatiles were removed and purification by preparative HPLC followed by chiral SFC yielded the separated diastereomers (46.8 mg and 43.3 mg).

Peak #1 (Example 660) LC/MS (Method C): 2.549 min, M+=273.0 1H NMR (400 MHz, DMSO) δ 11.83 (s, 1H), 8.56 (s, 1H), 7.45 (t, J=2.9 Hz, 1H), 6.87-6.80 (m, 1H), 5.89-5.77 (m, 1H), 5.71 (d, J=6.6 Hz, 1H), 5.19 (dd, J=13.0, 6.5 Hz, 1H), 4.37 (t, J=8.2 Hz, 1H), 4.12 (dt, J=16.1, 9.1 Hz, 2H), 3.93-3.78 (m, 1H), 2.49-2.39 (m, 2H), 1.64 (d, J=6.5 Hz, 3H).

Peak #2 (Example 659) LC/MS (Method C): 2.484 min, M+=273.0 1H NMR (400 MHz, DMSO) δ 11.83 (s, 1H), 8.56 (s, 1H), 7.45 (t, J=2.8 Hz, 1H), 6.91-6.85 (m, 1H), 5.88-5.74 (m, 1H), 5.74-5.58 (m, 1H), 5.18 (q, J=6.1 Hz, 1H), 4.41-4.31 (m, 1H), 4.22-4.08 (m, 2H), 3.86 (dd, J=16.9, 9.0 Hz, 1H), 2.48-2.37 (m, 2H), 1.64 (d, J=6.5 Hz, 3H).

Example 661

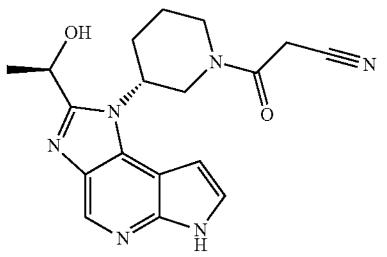 [SMILES: C[C@@H](O)c1nc2cnc3[nH]ccc3c2n1[C@@H]1CCCN(C(=O)CC#N)C1]

3-{(R)-3-[2-((R)-1-Hydroxy-ethyl)-6H-1,2,3,5,6-tetraaza-as-indacen-1-yl]-piperidin-1-yl}-3-oxo-propionitrile (R)-3-(5-Amino-1-benzenesulfonyl-1H-pyrrolo[2,3-b]pyridin-4-ylamino)-piperidine-1-carboxylic acid tert-butyl ester The title compound was made by following the procedures described for the preparation of 1-Benzenesulfonyl-N*4*-((R)-1-benzyl-piperidin-3-yl)-1H-pyrrolo[2,3-b]pyridine-4,5-diamine, substituting (R)-tert-butyl 3-aminopiperidine-1-carboxylate for (R)-1-benzyl-3-aminopiperidine. $^1$H NMR (400 MHz, DMSO) δ 8.01 (d, J=7.8 Hz, 2H), 7.66 (t, J=7.4 Hz, 1H), 7.61-7.52 (m, 3H), 7.49 (d, J=4.1 Hz, 1H), 6.76 (br s, 1H), 5.13 (d, J=8.3 Hz, 1H), 4.35 (br s, 2H), 3.80-3.63 (m, 2H), 2.93-2.77 (m, 2H), 2.03-1.92 (m, J=10.8 Hz, 1H), 1.70 (s, 1H), 1.61-1.09 (m, 12H).

(R)-3-[6-Benzenesulfonyl-2-((R)-1-hydroxy-ethyl)-6H-1,2,3,5,6-tetraaza-as-indacen-1-yl]-piperidine-1-carboxylic acid tert-butyl ester The title compound was made by following the procedures described for the preparation of (R)-1-(6-Benzenesulfonyl-1-cyclohexyl-1,6-dihydro-1,2,3,5,6-tetraaza-as-indacen-2-yl)-ethanol (Example 671) but substituting (R)-3-(5-Amino-1-benzenesulfonyl-1H-pyrrolo[2,3-b]pyridin-4-ylamino)-piperidine-1-carboxylic acid tert-butyl ester for 1-benzenesulfonyl-N-4-cyclohexyl-1H-pyrrolo[2,3-b]pyridine-4,5-diamine.

1H NMR (400 MHz, DMSO) δ 8.72 (s, 1H), 8.14 (d, J=7.6 Hz, 2H), 7.96 (d, J=3.8 Hz, 1H), 7.75-7.58 (m, 3H), 7.21 (d, J=3.7 Hz, 1H), 5.85-5.75 (m, 1H), 5.19-5.08 (m, 1H), 4.99-4.86 (m, 1H), 4.27-4.17 (m, 1H), 4.15-3.98 (m, 1H), 2.36-2.21 (m, 1H), 2.06-1.97 (m, J=16.9 Hz, 1H), 1.90 (br d, J=12.1 Hz, 1H), 1.62 (d, J=6.2 Hz, 3H), 1.51 (s, 3H), 1.38 (br s, 9H).

(R)-1-((R)-1-Piperidin-3-yl-1,6-dihydro-1,2,3,5,6-tetraaza-as-indacen-2-yl)-ethanol (R)-3-[6-Benzenesulfonyl-2-((R)-1-hydroxy-ethyl)-6H-1,2,3,5,6-tetraaza-as-indacen-1-yl]-piperidine-1-carboxylic acid tert-butyl ester (8.09 g, 15.4 mmol) was stirred in a 4.0 M solution of hydrogen chloride in 1,4-dioxane (150 mL) for 3 h. The volatiles were removed under reduced pressure and the solids were washed with Et2O (3×100 ml) and filtered. The resulting hygroscopic white powder, the hydrochloride salt of (R)-1-((R)-6-Benzenesulfonyl-1-piperidin-3-yl-1,6-dihydro-1,2,3,5,6-tetraaza-as-indacen-2-yl)-ethanol, was carried forward without further purification or characterization.

The previously prepared hydrochloride salt of (R)-1-((R)-6-Benzenesulfonyl-1-piperidin-3-yl-1,6-dihydro-1,2,3,5,6-tetraaza-as-indacen-2-yl)-ethanol was dissolved in 1.00 M of sodium hydroxide in water (100 mL) and ethanol (100 mL) and heated to 60° C. for 8 h. The crude reaction mixture was then concentrated onto silica gel. This material was then subjected to column chromatography using a 125 g column, with a gradient of 0% to 20% 2M $NH_3$ in methanol in dichloromethane. The product containing fractions were combined and evaporated under reduced pressure to give (R)-1-((R)-1-Piperidin-3-yl-1,6-dihydro-1,2,3,5,6-tetraaza-as-indacen-2-yl)-ethanol (2.695 g, 61%).

1H NMR (400 MHz, DMSO) δ 11.82 (s, 1H), 8.54 (s, 1H), 7.47 (t, J=2.9 Hz, 1H), 6.84 (s, 1H), 5.65 (d, J=6.4 Hz, 1H), 5.16-5.05 (m, 1H), 4.93-4.81 (m, 1H), 3.44-3.35 (m, 2H), 3.03 (dd, J=25.8, 10.0 Hz, 2H), 2.76 (t, J=11.7 Hz, 1H), 2.48-2.39 (m, 1H), 1.92 (dd, J=46.8, 12.2 Hz, 2H), 1.72-1.58 (m, J=10.0 Hz, 1H), 1.64 (d, J=6.5 Hz, 3H).

3-{(R)-3-[2-((R)-1-Hydroxy-ethyl)-6H-1,2,3,5,6-tetraaza-as-indacen-1-yl]-piperidin-1-yl}-3-oxo-propionitrile (R)-1-((R)-1-Piperidin-3-yl-1,6-dihydro-1,2,3,5,6-tetraaza-as-indacen-2-yl)-ethanol (60.0 mg, 0.210 mmol), 4-dimethylaminopyridine (10.0 mg, 0.0818 mmol;) and N-(3-dimethylaminopropyl)-N'-ethylcarbodiimide hydrochloride (77 mg, 0.40 mmol;) were dissolved in N,N-dimethylformamide (1.0 mL, 13 mmol;). The solution was cooled to room temperature, then added to cyanoacetic acid (0.40 mmol;). Finally, N,N-diisopropylethylamine (80.0 μL, 0.459 mmol;) was added and the solution was stirred at room temperature overnight. This material was purified by preparative HPLC (column: Gemini-NX, 5×10 cm, 10 μm; detection: UV 254 nm, mobile phase A: water w/0.1% $NH_4OH$; mobile phase B: $CH_3CN$; flowrate: 120 ml/min; gradient 5-95% B over 15 min) to afford the title compound.

LC/MS (Method C): 2.697 min, M+=353.1

1H NMR (400 MHz, DMSO) δ 11.91 (s, 1H), 8.57 (d, J=6.4 Hz, 1H), 8.32 (s, 1H), 7.49 (s, 1H), 6.80 (d, J=13.8 Hz, 1H), 5.25-5.06 (m, 1H), 5.00-4.80 (m, 1H), 4.57 (dd, J=52.5, 12.8 Hz, 1H), 4.25-4.04 (m, 2H), 3.94-3.75 (m, 2H), 3.03-2.89 (m, 1H), 2.12-1.89 (m, 2H), 1.86-1.71 (m, 1H), 1.65 (dd, J=17.5, 5.7 Hz, 4H).

Example 662

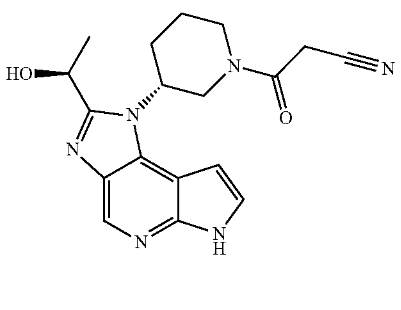 [SMILES: C[C@H](O)c1nc2cnc3[nH]ccc3c2n1[C@@H]1CCCN(C(=O)CC#N)C1]

3-{(R)-3-[2-((S)-1-Hydroxy-ethyl)-6H-1,2,3,5,6-tetraaza-as-indacen-1-yl]-piperidin-1-yl}-3-oxo-propionitrile (R)-1-((R)-1-Piperidin-3-yl-1,6-dihydro-1,2,3,5,6-tetraaza-as-indacen-2-yl)-ethanol The title compound was made by following the procedures described for the preparation of (R)-1-((R)-1-Piperidin-3-yl-1,6-dihydro-1,2,3,5,6-tetraaza-as-indacen-2-yl)-ethanol (Example 661) but substituting (S)-(−)-lactamide for (R)-(+)-lactamide.

1H NMR (400 MHz, DMSO) δ 11.83 (s, 1H), 8.54 (s, 1H), 7.48 (s, 1H), 6.84 (s, 1H), 5.66 (d, J=6.5 Hz, 1H), 5.17-5.04 (m, 1H), 4.86 (s, 1H), 3.43-3.36 (m, 1H), 3.17 (d, J=5.1 Hz, 1H), 3.02 (dd, J=24.5, 10.0 Hz, 2H), 2.75 (t, J=11.9 Hz, 1H), 2.46-2.38 (m, 1H), 2.03-1.80 (m, 2H), 1.64 (d, J=6.3 Hz, 3H), 1.70-1.57 (m, 1H).

3-{(R)-3-[2-((S)-1-Hydroxy-ethyl)-6H-1,2,3,5,6-tetraaza-as-indacen-1-yl]-piperidin-1-yl}-3-oxo-propionitrile (R)-1-((R)-1-Piperidin-3-yl-1,6-dihydro-1,2,3,5,6-tetraaza-as-indacen-2-yl)-ethanol (97.7 mg, 0.342 mmol), cyanoacetic acid (50.8 mg, 0.597 mmol;) and N,N,N',N'-tetramethyl-O-(7-azabenzotriazol-1-yl)uronium hexafluorophosphate (189.9 mg, 0.4994 mmol;) were weighed into a reaction vial. N,N-dimethylformamide (1.5 mL, 19 mmol;) was added, then N,N-diisopropylethylamine (125 uL, 0.718 mmol;). The reaction was stirred overnight at RT. The crude material was purified by preparative HPLC using a C18 column equilibrated with 5% CH3CN in aqueous NH4OH buffer. The material was eluted with a gradient of 5-50% CH3CN. Product containing fractions were concentrated in vacuo to give the desired material.

LC/MS (Method C): 2.597 min, M+=353.1

1H NMR (400 MHz, DMSO) δ 11.92 (s, 1H), 8.58 (d, J=3.9 Hz, 1H), 7.50 (s, 1H), 6.80 (d, J=8.4 Hz, 1H), 5.82-5.60 (m, 1H), 5.34-5.20 (m, 1H), 5.12-4.78 (m, 2H), 4.99-4.78 (m, 1H), 4.55 (t, J=13.8 Hz, 1H), 4.25-3.73 (m, 4H), 3.41 (t, J=11.4 Hz, 1H), 2.94 (t, J=13.1 Hz, 1H), 2.15-1.90 (m, 2H), 1.69-1.60 (m, 3H).

Example 663

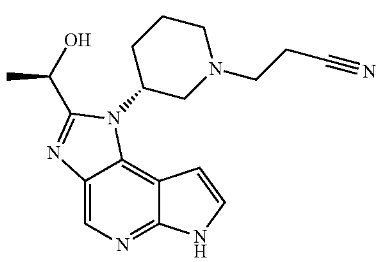 [SMILES: C[C@@H](O)c1nc2cnc3[nH]ccc3c2n1[C@@H]1CCCN(CCC#N)C1]

3-{(R)-3-[2-((R)-1-Hydroxy-ethyl)-6H-1,2,3,5,6-tetraaza-as-indacen-1-yl]-piperidin-1-yl}-propionitrile (R)-1-((R)-1-Piperidin-3-yl-1,6-dihydro-1,2,3,5,6-tetraaza-as-indacen-2-yl)-ethanol (46.5 mg, 0.163 mmol) was dissolved in 2-propenenitrile (0.5 mL, 8 mmol;) and heated to 80° C. for 2 h. The reaction was cooled to RT and the volatiles were removed under reduced pressure. The residue was purified by preparative HPLC (column: Gemini-NX, 5×10 cm, 10 um; detection: UV 254 nm, mobile phase A: water w/0.1% $NH_4OH$; mobile phase B: $CH_3CN$; flowrate: 120 ml/min; gradient 5-95% B over 15 min) to afford the title compound.

LC/MS (Method C): 2.307 min, M+=339.1

1H NMR (400 MHz, DMSO) δ 11.84 (s, 1H), 8.55 (s, 1H), 7.47 (s, 1H), 6.81 (s, 1H), 5.73-5.62 (m, 1H), 5.20-4.95 (m, 2H), 3.13-2.88 (m, 3H), 2.80-2.62 (m, 4H), 2.44-2.27 (m, 2H), 1.94 (t, J=12.5 Hz, 2H), 1.76 (t, J=12.3 Hz, 1H), 1.63 (d, J=5.5 Hz, 3H).

Example 664

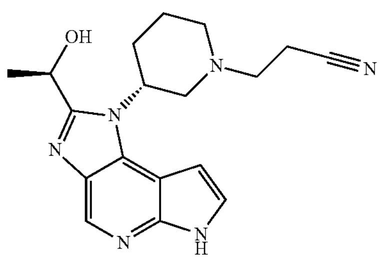 [SMILES: C[C@@H](O)c1nc2cnc3[nH]ccc3c2n1[C@@H]1CCCN(CCC#N)C1]

(R)-1-{1-[(R)-1-(2-Fluoro-ethyl)-piperidin-3-yl]-1,6-dihydro-1,2,3,5,6-tetraaza-as-indacen-2-yl}-ethanol (R)-1-((R)-1-Piperidin-3-yl-1,6-dihydro-1,2,3,5,6-tetraaza-as-indacen-2-yl)-ethanol (100.6 mg, 0.3526 mmol), 1-bromo-2-fluoroethane (0.1265 g, 0.9964 mmol;) and potassium carbonate (91.0 mg, 0.658 mmol;) were dissolved in tetrahydrofuran (3.0 mL, 37 mmol) and heated to 70° C. for 28 h. The reaction was cooled to RT and the volatiles were removed under reduced pressure. The residue was purified by preparative HPLC (column: Gemini-NX, 5×10 cm, 10 um; detection: UV 254 nm, mobile phase A: water w/0.1% $NH_4OH$; mobile phase B: $CH_3CN$; flowrate: 120 ml/min; gradient 5-95% B over 15 min) to afford the title compound.

LC/MS (Method N): 5.98 min, M+=332.2

1H NMR (500 MHz, DMSO) δ 11.87 (s, 1H), 8.55 (s, 1H), 7.48 (s, 1H), 6.82 (s, 1H), 5.69 (d, J=5.2 Hz, 1H), 5.17-5.08 (m, 1H), 5.08-4.96 (m, 1H), 4.63-4.55 (m, 1H), 4.54-4.46 (m, 1H), 3.12-2.92 (m, 3H), 2.86-2.65 (m, 2H), 2.46-2.29 (m, 2H), 1.99-1.87 (m, 2H), 1.82-1.69 (m, 1H), 1.63 (d, J=6.1 Hz, 3H).

Examples 665 and 666

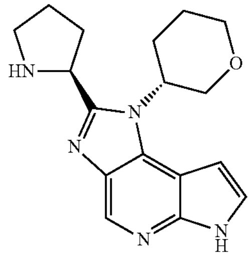

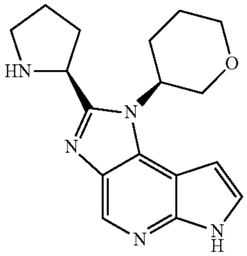

2-(S)-Pyrrolidin-2-yl-1-(S)-tetrahydro-pyran-3-yl-1,6-dihydro-1,2,3,5,6-tetraaza-as-indacene And 2-(S)-Pyrrolidin-2-yl-1-(R)-tetrahydro-pyran-3-yl-1,6-dihydro-1,2,3,5,6-tetraaza-as-indacene The title compounds were made by following the procedures described for the preparation of (R)-1-(6-Benzenesulfonyl-1-cyclohexyl-1,6-dihydro-1,2,3,5,6-tetraaza-as-indacen-2-yl)-ethanol (Example 671) but substituting 1-Boc-L-prolinamide for (R)-(+)-lactamide and substituting 1-Benzenesulfonyl-N-4-(tetrahydro-pyran-3-yl)-1H-pyrrolo[2,3-b]pyridine-4,5-diamine for 1-benzenesulfonyl-N-4-cyclohexyl-1H-pyrrolo[2,3-b]pyridine-4,5-diamine. Purification by chiral SFC yielded the separated diastereomers.

Peak #1 (Example 666) LC/MS (Method C): 2.516 min, M+=312,1

1H NMR (400 MHz, DMSO) δ 11.87 (s, 1H), 8.54 (s, 1H), 7.50 (s, 1H), 6.85 (s, 1H), 4.99-4.85 (m, 1H), 4.63 (t, J=6.9 Hz, 1H), 4.11 (t, J=11.0 Hz, 1H), 4.03-3.90 (m, 2H), 3.76-3.63 (m, J=10.7 Hz, 1H), 3.06-2.87 (m, 2H), 2.56 (d, J=11.8 Hz, 1H), 2.36-2.05 (m, 3H), 1.87 (d, J=26.6 Hz, 5H).

Peak #2 (Example 665) LC/MS (Method C): 2.600 min, M+=312.1

1H NMR (400 MHz, DMSO) δ 11.87 (s, 1H), 8.54 (s, 1H), 7.50 (s, 1H), 6.86 (s, 1H), 4.99-4.85 (m, 1H), 4.63 (t, J=6.9 Hz, 1H), 4.10 (t, J=10.6 Hz, 1H), 3.98 (d, J=11.1 Hz, 2H), 3.70 (t, J=11.1 Hz, 1H), 3.04-2.87 (m, 2H), 2.64-2.52 (m, 1H), 2.38-2.01 (m, 3H), 1.97-1.74 (m, 5H).

Examples 667 and 668

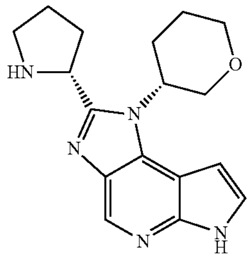

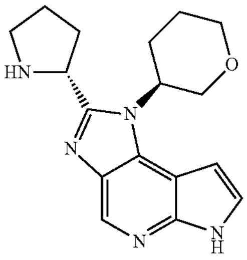

2-(R)-Pyrrolidin-2-yl-1-(S)-tetrahydro-pyran-3-yl-1,6-dihydro-1,2,3,5,6-tetraaza-as-indacene And 2-(R)-Pyrrolidin-2-yl-1-(R)-tetrahydro-pyran-3-yl-1,6-dihydro-1,2,3,5,6-tetraaza-as-indacene The title compounds were made by following the procedures described for the preparation of (R)-1-(6-Benzenesulfonyl-1-cyclohexyl-1,6-dihydro-1,2,3,5,6-tetraaza-as-indacen-2-yl)-ethanol (Example 665) but substituting 1-Boc-D-prolinamide for 1-Boc-L-prolinamide. Purification by chiral SFC yielded the separated diastereomers.

Peak #1 (Example 667) LC/MS (Method C): 2.476 min, M+=312,1

1H NMR (400 MHz, DMSO) δ 11.85 (s, 1H), 8.52 (s, 1H), 7.48 (s, 1H), 6.85 (s, 1H), 5.02-4.88 (m, 1H), 4.53 (t, J=6.9 Hz, 1H), 4.12 (t, J=11.1 Hz, 1H), 3.96 (t, J=11.2 Hz, 2H), 3.70

(t, J=10.8 Hz, 1H), 2.99-2.80 (m, 2H), 2.62-2.52 (m, 1H), 2.36-2.23 (m, 1H), 2.17-2.04 (m, 2H), 1.96-1.71 (m, 5H). Peak #2 (Example 668) LC/MS (Method C): 2.594 min, M+=312.1

1H NMR (400 MHz, DMSO) δ 11.85 (s, 1H), 8.52 (s, 1H), 7.49 (s, 1H), 6.85 (s, 1H), 5.02-4.88 (m, 1H), 4.52 (t, J=6.6 Hz, 1H), 4.09 (t, J=10.7 Hz, 1H), 4.04-3.92 (m, 2H), 3.70 (t, J=11.1 Hz, 1H), 2.95-2.80 (m, 2H), 2.63-2.53 (m, 1H), 2.41-2.28 (m, 1H), 2.17-2.00 (m, 2H), 1.98-1.70 (m, 5H).

Example 669

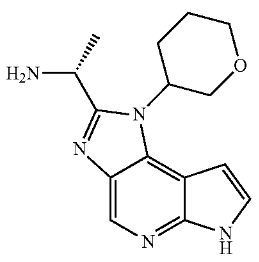 [SMILES: C[C@@H](N)c1nc2cnc3[nH]ccc3c2n1C1CCCOC1]

1-[1-(Tetrahydro-pyran-3-yl)-1,6-dihydro-1,2,3,5,6-tetraaza-as-indacen-2-yl]-ethylamine The title compound was made by following the procedures described for the preparation of (R)-1-(6-Benzenesulfonyl-1-cyclohexyl-1,6-dihydro-1,2,3,5,6-tetraaza-as-indacen-2-yl)-ethanol (Example 665) but substituting 1-Boc-D-alanine amide for 1-Boc-L-prolinamide. Purification by chiral SFC yielded only one of two diastereomers:

LC/MS (Method C): 2.414 min, M+=286.1

1H NMR (400 MHz, $CDCl_3$) δ 11.29 (s, 1H), 8.81 (s, 1H), 7.48 (d, J=26.8 Hz, 1H), 6.90 (s, 1H), 4.99-4.85 (m, 1H), 4.53-4.42 (m, J=4.9 Hz, 1H), 4.33 (dd, J=24.4, 11.3 Hz, 1H), 4.18-3.97 (m, 2H), 3.83-3.69 (m, 1H), 2.86-2.65 (m, 1H), 2.25-2.07 (m, 1H), 2.01 (s, 2H), 1.82 (s, 2H), 1.68 (d, J=4.4 Hz, 3H).

Example 670

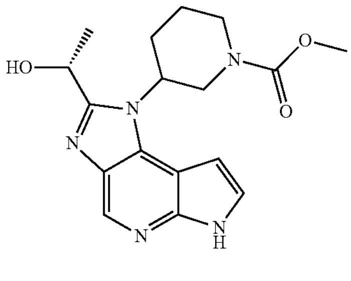 [SMILES: COC(=O)N1CCCC(n2c([C@@H](C)O)nc3cnc4[nH]ccc4c32)C1]

(R)-3-[2-((R)-1-Hydroxy-ethyl)-6H-1,2,3,5,6-tetraaza-as-indacen-1-yl]-piperidine-1-carboxylic acid methyl ester (R)-1-((R)-1-Piperidin-3-yl-1,6-dihydro-1,2,3,5,6-tetraaza-as-indacen-2-yl)-ethanol (108.0 mg, 0.3785 mmol) and N,N-diisopropylethylamine (100 uL, 0.6 mmol;) were dissolved in N,N-dimethylformamide (1.0 mL, 13 mmol;). [B] Methyl chloroformate (35.0 uL, 0.453 mmol;) was added in a single portion, and the reaction was continued overnight. The crude reaction was purified by preparative HPLC (column: Gemini-NX, 5×10 cm, 10 um; detection: UV 254 nm, mobile phase A: water w/0.1% $NH_4OH$; mobile phase B: $CH_3CN$; flowrate: 120 ml/min; gradient 5-95% B over 15 min) to afford the title compound.

LC/MS (Method C): 2.903 min, M+=344.1

1H NMR (400 MHz, DMSO) δ 11.88 (s, 1H), 8.56 (s, 1H), 7.48 (t, J=2.9 Hz, 1H), 6.78 (s, 1H), 5.71 (d, J=6.3 Hz, 1H), 5.18-5.08 (m, 1H), 5.00-4.87 (m, 1H), 4.31-4.19 (m, 1H), 4.13 (d, J=12.1 Hz, 1H), 3.62 (s, 4H), 3.12 (s, 1H), 2.09-1.89 (m, 2H), 1.63 (d, J=6.5 Hz, 4H).

Example 671

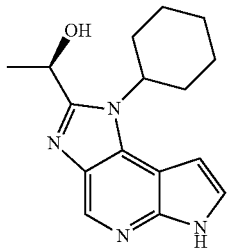 [SMILES: C[C@@H](O)c1nc2cnc3[nH]ccc3c2n1C1CCCCC1]

(R)-1-(1-Cyclohexyl-1,6-dihydro-1,2,3,5,6-tetraaza-as-indacen-2-yl)-ethanol (R)-1-(6-Benzenesulfonyl-1-cyclohexyl-1,6-dihydro-1,2,3,5,6-tetraaza-as-indacen-2-yl)-ethanol Triethyloxonium tetrafluoroborate (0.569 g, 3.00 mmol) was added to a solution of (R)-(+)-lactamide (0.267 g, 3.00 mmol) in THF (25 ml) at 25° C. The resulting suspension was stirred at 25° C. for 2 h, then was concentrated under reduced pressure to afford an oil. This material was dissolved in EtOH (10 ml) and the resulting solution was added to 1-benzenesulfonyl-N-4-cyclohexyl-1H-pyrrolo[2,3-b]pyridine-4,5-diamine (0.370 g, 1.00 mmol) in EtOH (4 ml) at 25° C. The reaction mixture was heated at 75° C. for 1 h, then was cooled to 25° C. and was partitioned between half-saturated $NaHCO_3$ (100 ml) and EtOAc (2×100 ml). The organic layers were dried over $MgSO_4$, filtered, and the filtrate was concentrated under reduced pressure. Purification of the resulting solid by column chromatography on silica gel (gradient: 0 to 8% C $H_3OH$ in $CH_2Cl_2$) afforded (R)-1-(6-benzenesulfonyl-1-cyclohexyl-1,6-dihydro-1,2,3,5,6-tetraaza-as-indacen-2-yl)-ethanol (0.20 g, 95%) as a grey solid. LCMS (Method G, ESI): RT=0.99 min, m+H=425.3. This material was used in the next step below without additional characterization.

(R)-1-(1-Cyclohexyl-1,6-dihydro-1,2,3,5,6-tetraaza-as-indacen-2-yl)-ethanol

Sodium hydroxide (1 ml of a 1.0 M solution in water, 1 mmol) was added to a solution of (R)-1-(6-benzenesulfonyl-1-cyclohexyl-1,6-dihydro-1,2,3,5,6-tetraaza-as-indacen-2-yl)-ethanol (0.20 g, 0.48 mmol) in a 1:1 mixture of THF and EtOH (10 ml) at 25° C. The reaction mixture was stirred at 50° C. for 1 h, then was cooled to 25° C. and was partitioned between half-saturated $NaHCO_3$ (100 ml) and EtOAc (2×125 ml). The combined organic layers were dried over $MgSO_4$, filtered, and the filtrate was concentrated under reduced pressure. Purification of the residue by preparative HPLC (column: Gemini-NX, 5×10 cm, 10 um; detection: UV 254 nm, mobile phase A: water w/0.1% $NH_4OH$; mobile phase B: $CH_3CN$; flowrate: 120 ml/min; gradient 5-95% B over 15 min) afforded (R)-1-(1-cyclohexyl-1,6-dihydro-1,2,3,5,6-tetraaza-as-indacen-2-yl)-ethanol (0.046 g, 34%) as an off-white solid. LCMS (Method N, ESI): RT=6.56 min, m+H=285.3; 1; $^1$H NMR (400 MHz, DMSO) δ 11.84 (s, 1H), 8.55 (s, 1H), 7.47 (s, 1H), 6.74 (s, 1H), 5.66 (d, J=6.5 Hz, 1H), 5.12 (p, J=6.4 Hz, 1H), 4.91-4.76 (m, 1H), 2.41-2.22 (m, 2H), 2.02-1.84 (m, 4H), 1.80 (s, 1H), 1.64 (d, J=6.4 Hz, 3H), 1.58-1.42 (m, 3H).

Example 672

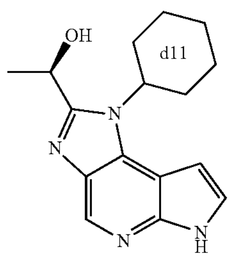 [SMILES: C[C@@H](O)c1nc2cnc3[nH]ccc3c2n1C1CCCCC1]

(R)-1-(1-Cyclohexyl-1,6-dihydro-1,2,3,5,6-tetraaza-as-indacen-2-yl)-ethanol-d11

Cyclohexylamine-d11 Hydrochloride

Cyclohexylbromide-d11 (5.0 g, 28.7 mmol) and tetrabutylammonium bromide (0.926 g, 2.87 mmol) was added sequentially to a solution of sodium azide (3.73 g, 57.4 mmol) in water (15 ml) at 25° C. The resulting biphasic mixture was heated to reflux for 5.5 h, then was cooled to 25° C. Benzene (20 ml) was added the phases were separated. The aqueous phase was extracted with benzene (20 ml) and the combined organic layers were dried over $MgSO_4$ and filtered. Triethyl phosphite (4.92 ml, 28.7 mmol) was added and the reaction mixture was heated at 35° C. for 3 h, then was stirred at 25° C. overnight. The mixture was concentrated under reduced pressure and water (28 ml) and 12 M HCl (aq., 6 ml) were added sequentially to the residue. The resulting yellow solution was heated at 95° C. for 2 h, then was cooled to 25° C. and concentrated under reduced pressure. Methanol (100 ml) was added and the mixture was again concentrated under reduced pressure. This process was repeated 4 additional times to afford impure cyclohexylamine-dl 1 hydrochloride as a white solid (9.33 g, 200%). This material was used in the next step without additional purification assuming a 75% actual yield.

(1-Benzenesulfonyl-5-nitro-1H-pyrrolo[2,3-b]pyridin-4-yl)-cyclohexyl-amine-d11

A mixture of 1-benzenesulfonyl-4-chloro-5-nitro-1H-pyrrolo[2,3-b]pyridine (7.26 g, 21.5 mmol), cyclohexylamine-d11 hydrochloride (3.15 g, 21.5 mmol), diisopropylethylamine (15 ml, 86.0 mmol) in propan-2-ol (150 ml) was heated at 80° C. for 18 h. The mixture was then cooled to 25° C. and stirred for 6 h. The resulting yellow solid was collected by vacuum filtration, washed with propan-2-ol (1×30 ml), and was air-dried to afford (1-benzenesulfonyl-5-nitro-1H-pyrrolo[2,3-b]pyridin-4-yl)-cyclohexyl-amine-d11 (7.23 g, 81%). $^1$H NMR (400 MHz, DMSO) δ 8.93 (s, 1H), 8.91 (s, 1H), 8.13 (d, J=7.6 Hz, 2H), 7.82 (d, J=4.1 Hz, 1H), 7.77 (t, J=7.4 Hz, 1H), 7.66 (t, J=7.8 Hz, 2H), 6.99 (d, J=4.2 Hz, 1H).

1-Benzenesulfonyl-N-4-cyclohexyl-1H-pyrrolo[2,3-b]pyridine-4,5-diamine-d11

A suspension of (1-benzenesulfonyl-5-nitro-1H-pyrrolo[2,3-b]pyridin-4-yl)-cyclohexyl-amine-d11 (10 g, 25.0 mmol) and palladium on carbon (1.1 g, 10%, wet, Degussa, E101 NE/W) in a 3:1 mixture of THF and ethanol (80 ml) was stirred under a hydrogen atmosphere (2-3 balloons) at 50° C. for 13 h. The reaction mixture was cooled to 25° C. then was filtered through Celite. The filtrate was concentrated under reduced pressure to afford crude 1-benzenesulfonyl-N-4-cyclohexyl-1H-pyrrolo[2,3-b]pyridine-4,5-diamine-d11 (3.96 g, 100%) as a dark purple foam. This material was used in subsequent reactions without additional purification or characterization.

(R)-1-(6-Benzenesulfonyl-1-cyclohexyl-1,6-dihydro-1,2,3,5,6-tetraaza-as-indacen-2-yl)-ethanol-d11

Triethyloxonium tetrafluoroborate (0.373 g, 1.96 mmol) was added to a solution of (R)-(+)-lactamide (0.175 g, 1.96 mmol) in THF (15 ml) at 25° C. The resulting suspension was stirred at 25° C. for 1.5 h, then was concentrated under reduced pressure to afford an oil. This material was dissolved in EtOH (15 ml) at 25° C. and 1-benzenesulfonyl-N-4-cyclohexyl-1H-pyrrolo[2,3-b]pyridine-4,5-diamine (0.300 g, 0.786 mmol) was added to the resulting solution. The reaction mixture was heated at 75° C. for 1 h, then was cooled to 25° C. and was partitioned between half-saturated $NaHCO_3$ (100 ml) and EtOAc (2×100 ml). The organic layers were dried over $MgSO_4$, filtered, and the filtrate was concentrated under reduced pressure. Purification of the resulting solid by column chromatography on silica gel (gradient: 0 to 7% $CH_3OH$ in $CH_2Cl_2$) afforded (R)-1-(6-benzenesulfonyl-1-cyclohexyl-1,6-dihydro-1,2,3,5,6-tetraaza-as-indacen-2-yl)-ethanol-d11 as a grey solid. LCMS (Method G, ESI): RT=0.99 min, m+H=436.4. This material was used in the next step below without additional characterization.

(R)-1-(1-Cyclohexyl-1,6-dihydro-1,2,3,5,6-tetraaza-as-indacen-2-yl)-ethanol-d11

Sodium hydroxide (1 ml of a 1.0 M solution in water, 1 mmol) was added to a solution of (R)-1-(6-benzenesulfonyl-1-cyclohexyl-1,6-dihydro-1,2,3,5,6-tetraaza-as-indacen-2-yl)-ethanol-d11 (0.786 mmol) in a 1:1 mixture of THF and EtOH (16 ml) at 25° C. The reaction mixture was stirred at 50° C. for 1 h, then was cooled to 25° C. and was partitioned between half-saturated $NaHCO_3$ (100 ml) and EtOAc (2×125 ml). The combined organic layers were dried over $MgSO_4$, filtered, and the filtrate was concentrated under reduced pressure. Trituration of the residue with Et2O (10 ml) produced a solid which was filtered, washed with Et2O, and air-dried to give (R)-1-(1-cyclohexyl-1,6-dihydro-1,2,3,5,6-tetraaza-as-indacen-2-yl)-ethanol-d11 (0.072 g, 31% over 2 steps) as a grey solid. LCMS (Method N, ESI): RT=3.25 min, m+H=296.2; $^1$H NMR (400 MHz, DMSO) δ 11.82 (s, 1H), 8.55 (s, 1H), 7.47 (s, 1H), 6.73 (s, 1H), 5.64 (d, J=5.5 Hz, 1H), 5.18-5.08 (m, 1H), 1.64 (d, J=6.1 Hz, 3H).

Example 673

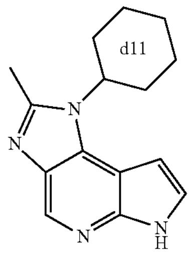 [SMILES: Cc1nc2cnc3[nH]ccc3c2n1C1CCCCC1]

1-Cyclohexyl-2-methyl-1,6-dihydro-1,2,3,5,6-tetraaza-as-indacene-d11

6-Benzenesulfonyl-1-cyclohexyl-2-methyl-1,6-dihydro-1,2,3,5,6-tetraaza-as-indacene-d11 p-Toluenesulfonic acid monohydrate (0.239 g, 1.26 mmol) was added to a solution of 1-benzenesulfonyl-N-4-cyclohexyl-1H-pyrrolo[2,3-b]pyridine-4,5-diamine-d11 (0.436 g, 1.14 mmol) and triethyl orthoacetate (0.524 ml, 2.86 mmol) in toluene (15 ml) at 25° C. The reaction mixture was heated at 105° C. for 3 h, then was cooled to 25° C. and was partitioned between half-saturated NaHCO3 (100 ml) and EtOAc (2×125 ml). The organic layers were dried over $MgSO_4$, filtered, and the filtrate was concentrated under reduced pressure. Purification of the resulting solid by column chromatography on silica gel (gradient: 0 to 7% $CH_3OH$ in $CH_2Cl_2$) afforded 6-benzenesulfonyl-1-cyclohexyl-2-methyl-1,6-dihydro-1,2,3,5,6-tetraaza-as-indacene-d11 (0.32 g, 70%) as a beige solid. LCMS (Method G, ESI): RT=1.00 min, m+H=406.4. This material was used in the next step below without additional characterization.

1-Cyclohexyl-2-methyl-1,6-dihydro-1,2,3,5,6-tetraaza-as-indacene-d11

Sodium hydroxide (3 ml of a 1.0 M solution in water, 3 mmol) was added to a solution of 6-benzenesulfonyl-1-cyclohexyl-2-methyl-1,6-dihydro-1,2,3,5,6-tetraaza-as-indacene-d11 (0.322 g, 0.794 mmol) in a 1:1 mixture of EtOH and THF (16 ml) at 25° C. The reaction mixture was stirred at 50° C. for 2 h, then was partitioned between half-saturated $NaHCO_3$ (100 ml) and EtOAc (2×200 ml). The combined organic layers were dried over $MgSO_4$, filtered, and the filtrate was concentrated under reduced pressure. The residue was triturated with EtOAc (8 ml) to give a solid which was collected by filtration, washed with $Et_2O$ (15 ml), and air-dried to give 1-cyclohexyl-2-methyl-1,6-dihydro-1,2,3,5,6-tetraaza-as-indacene-d11 (0.100 g, 47%) as an off-white solid. LCMS (Method N, ESI): RT=8.25 min, m+H=266.1; $^1H$ NMR (400 MHz, DMSO) δ 11.77 (s, 1H), 8.46 (s, 1H), 7.45 (t, J=3.0 Hz, 1H), 6.71 (dd, J=2.9, 1.8 Hz, 1H), 2.63 (s, 3H).

Example 674

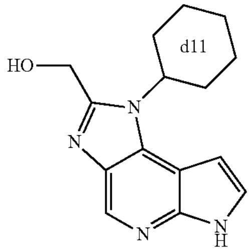 [SMILES: OCc1nc2cnc3[nH]ccc3c2n1C1CCCCC1]

(1-Cyclohexyl-1,6-dihydro-1,2,3,5,6-tetraaza-as-indacen-2-yl)-methanol-d11

(6-Benzenesulfonyl-1-cyclohexyl-1,6-dihydro-1,2,3,5,6-tetraaza-as-indacen-2-yl)-methanol-d11

Triethyloxonium tetrafluoroborate (0.256 g, 1.35 mmol) was added to a solution of 2-hydroxyacetamide (0.101 g, 1.35 mmol) in THF (15 ml) at 25° C. The resulting suspension was stirred at 25° C. for 1.5 h, then was concentrated under reduced pressure to afford an oil. This material was dissolved in EtOH (15 ml) at 25° C. and 1-benzenesulfonyl-N-4-cyclohexyl-1H-pyrrolo[2,3-b]pyridine-4,5-diamine-d11 (0.206 g, 0.540 mmol) was added to the resulting solution. The reaction mixture was heated at 75° C. for 1 h, then was cooled to 25° C. and was partitioned between half-saturated $NaHCO_3$ (100 ml) and EtOAc (2×100 ml). The organic layers were dried over $MgSO_4$, filtered, and the filtrate was concentrated under reduced pressure. Purification of the resulting solid by column chromatography on silica gel (gradient: 0 to 7% $CH_3OH$ in $CH_2Cl_2$) afforded (6-benzenesulfonyl-1-cyclohexyl-1,6-dihydro-1,2,3,5,6-tetraaza-as-indacen-2-yl)-methanol-d11 as a grey solid. LCMS (Method G, ESI): RT=1.00 min, m+H=422.4. This material was used in the next step below without additional characterization.

(1-Cyclo hexyl-1,6-dihydro-1,2,3,5,6-tetraaza-as-indacen-2-yl)-methanol-d11

Sodium hydroxide (1 ml of a 1.0 M solution in water, 1 mmol) was added to a solution of (6-benzenesulfonyl-1-cyclohexyl-1,6-dihydro-1,2,3,5,6-tetraaza-as-indacen-2-yl)-methanol-d11 (0.54 mmol) in a 1:1 mixture of EtOH and THF (10 ml) at 25° C. The reaction mixture was stirred at 50° C. for 1 h, then was partitioned between half-saturated $NaHCO_3$ (100 ml) and EtOAc (2×200 ml). The combined organic layers were dried over $MgSO_4$, filtered, and the filtrate was concentrated under reduced pressure. The residue was triturated with $Et_2O$ (10 ml) to give a solid which was collected by filtration, washed with $Et_2O$ (10 ml), and air-dried to give (1-cyclohexyl-1,6-dihydro-1,2,3,5,6-tetraaza-as-indacen-2-yl)-methanol-d11 (0.0063 g, 4% over two steps) as an off-white solid. LCMS (Method N, ESI): RT=3.21 min, m+H=282.1; $^1$H NMR (400 MHz, DMSO) δ 11.83 (s, 1H), 8.53 (s, 1H), 7.48 (s, 1H), 6.73 (s, 1H), 5.62 (s, 1H), 4.78 (d, J=4.2 Hz, 2H).

Example 675

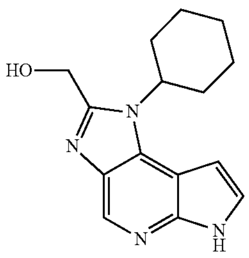 [SMILES: OCc1nc2cnc3[nH]ccc3c2n1C1CCCCC1]

(1-Cyclohexyl-1,6-dihydro-1,2,3,5,6-tetraaza-as-indacen-2-yl)-methanol (6-Benzenesulfonyl-1-cyclohexyl-1,6-dihydro-1,2,3,5,6-tetraaza-as-indacen-2-yl)-methanol Triethyloxonium tetrafluoroborate (0.256 g, 1.35 mmol) was added to a solution of 2-hydroxyacetamide (0.101 g, 1.35 mmol) in THF (15 ml) at 25° C. The resulting suspension was stirred at 25° C. for 1.5 h, then was concentrated under reduced pressure to afford an oil. This material was dissolved in EtOH (15 ml) at 25° C. and 1-benzenesulfonyl-N-4-cyclohexyl-1H-pyrrolo[2,3-b]pyridine-4,5-diamine (0.200 g, 0.540 mmol) was added to the resulting solution. The reaction mixture was heated at 75° C. for 1 h, then was cooled to 25° C. and was partitioned between half-saturated $NaHCO_3$ (100 ml) and EtOAc (2×100 ml). The organic layers were dried over $MgSO_4$, filtered, and the filtrate was concentrated under reduced pressure. Purification of the resulting solid by column chromatography on silica gel (gradient: 0 to 7% $CH_3OH$ in $CH_2Cl_2$) afforded (6-benzenesulfonyl-1-cyclohexyl-1,6-dihydro-1,2,3,5,6-tetraaza-as-indacen-2-yl)-methanol as a grey solid. LCMS (Method G, ESI): RT=0.95 min, m+H=411.3. This material was used in the next step below without additional characterization.

(1-Cyclohexyl-1,6-dihydro-1,2,3,5,6-tetraaza-as-indacen-2-yl)-methanol

Sodium hydroxide (1 ml of a 1.0 M solution in water, 1 mmol) was added to a solution of (6-benzenesulfonyl-1-cyclohexyl-1,6-dihydro-1,2,3,5,6-tetraaza-as-indacen-2-yl)-methanol (0.54 mmol) in a 1:1 mixture of EtOH and THF (10 ml) at 25° C. The reaction mixture was stirred at 50° C. for 1 h, then was partitioned between half-saturated $NaHCO_3$ (100 ml) and EtOAc (2×200 ml). The combined organic layers were dried over $MgSO_4$, filtered, and the filtrate was concentrated under reduced pressure. The residue was triturated with $Et_2O$ (10 ml) to give a solid which was collected by filtration, washed with $Et_2O$ (10 ml), and air-dried to give (1-cyclohexyl-1,6-dihydro-1,2,3,5,6-tetraaza-as-indacen-2-yl)-methanol (0.026 g, 18% over two steps) as an off-white solid. LCMS (Method N, ESI): RT=5.81 min, m+H=271.0; $^1$H NMR (400 MHz, DMSO) δ 11.83 (s, 1H), 8.53 (s, 1H), 7.47 (s, 1H), 6.74 (s, 1H), 5.67-5.55 (m, 1H), 4.78 (d, J=4.4 Hz, 2H), 4.75-4.61 (m, 1H), 2.39-2.20 (m, 2H), 2.02-1.87 (m, 4H), 1.86-1.74 (m, 1H), 1.62-1.37 (m, 3H).

Example 676

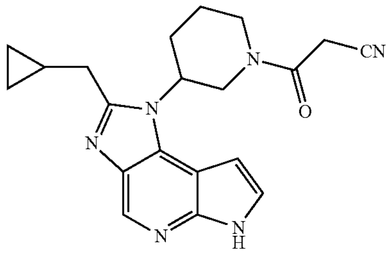 [SMILES: N#CCC(=O)N1CCCC(n2c(CC3CC3)nc3cnc4[nH]ccc4c32)C1]

3-[3-(2-Cyclopropylmethyl-6H-1,2,3,5,6-tetraaza-as-indacen-1-yl)-piperidin-1-yl]-3-oxo-propionitrile 3-(1-Benzenesulfonyl-5-nitro-1H-pyrrolo[2,3-b]pyridin-4-ylamino)-piperidine-1-carboxylic acid tert-butyl ester A suspension of 1-benzenesulfonyl-4-chloro-5-nitro-1H-pyrrolo[2,3-b]pyridine (15.3 g, 45.4 mmol), 3-amino-piperidine-1-carboxylic acid tert-butyl ester (10.00 g, 49.9 mmol), and diisopropylethylamine (25 ml, 140 mmol) in propan-2-ol (200 ml) was heated at 80° C. for 20 h. The mixture was then cooled to 25° C. and stirred for 12 h. The resulting yellow solid was collected by vacuum filtration, washed with propan-2-ol (1×30 ml), and was air-dried to afford 3-(1-benzenesulfonyl-5-nitro-1H-pyrrolo[2,3-b]pyridin-4-ylamino)-piperidine-1-carboxylic acid tert-butyl ester (19.7 g, 87%). LCMS (Method G, ESI): RT=1.25 min, m+H=502.3. This material was used in the next step below without additional purification or characterization.

(1-Benzenesulfonyl-5-nitro-1H-pyrrolo[2,3-b]pyridin-4-yl)-piperidin-3-yl-amine Hydrochloride A 4.0 M solution of HCl in 1,4-dioxane (60 ml) was added to 3-(1-benzenesulfonyl-5-nitro-1H-pyrrolo[2,3-b]pyridin-4-ylamino)-piperidine-1-carboxylic acid tert-butyl ester (6.11 g, 12.2 mmol) dissolved in 1,4-dioxane (30 ml) at 25° C. The resulting suspension mixture was stirred at 50° C. for 2 h, then was cooled to 25° C. and was concentrated under reduced pressure. Toluene (80 ml) was added to the residue and the mixture was again concentrated under reduced pressure to give crude (1-benzenesulfonyl-5-nitro-1H-pyrrolo[2,3-b]pyridin-4-yl)-piperidin-3-yl-amine hydrochloride as a yellow solid. This material was used in the next step below without additional characterization or purification.

3-(1-Benzenesulfonyl-5-nitro-1H-pyrrolo[2,3-b]pyridin-4-ylamino)-piperidine-1-carboxylic acid 9H-fluoren-9-ylmethyl ester Fmoc-Cl (3.16 g, 12.2 mmol) was added to a solution of crude (1-benzenesulfonyl-5-nitro-1H-pyrrolo[2,3-b]pyridin-4-yl)-piperidin-3-yl-amine hydrochloride (5.34 g, 12.2 mmol) and diisopropylethylamine (5.31 ml, 30.5 mmol) in $CH_2Cl_2$ (100 ml) at 0° C. The reaction mixture was warmed to 25° C. and stirred for 18 h, then was partitioned between half-saturated $NaHCO_3$ (225 ml) and $CH_2Cl_2$ (2×200 ml).

The combined organic layers were dried over $MgSO_4$, filtered, and the filtrate was concentrated under reduced pressure. The residue was purified by column chromatography on silica gel (gradient: 0 to 70% EtOAc in heptanes) to afford 3-(1-benzenesulfonyl-5-nitro-1H-pyrrolo[2,3-b]pyridin-4-ylamino)-piperidine-1-carboxylic acid 9H-fluoren-9-ylmethyl ester (7.09 g, 93%) as a yellow solid. This material was used in the next step below without additional characterization or purification.

3-(5-Amino-1-benzenesulfonyl-1H-pyrrolo[2,3-b]pyridin-4-ylamino)-piperidine-1-carboxyli c acid 9H-fluoren-9-ylmethyl ester A suspension of 3-(1-benzenesulfonyl-5-nitro-1H-pyrrolo[2,3-b]pyridin-4-ylamino)-piperidine-1-carboxylic acid 9H-fluoren-9-ylmethyl ester (7.09 g, 11.4 mmol) and palladium on carbon (2.1 g, 10%, wet, Degussa, E101 NE/W) in a 4:1 mixture of THF and EtOH (100 ml) was stirred under a hydrogen atmosphere (2 balloons) at 50° C. for 6 h. The reaction mixture was cooled to 25° C. and was filtered through Celite. The Celite was washed with THF (2×25 ml), and the combined filtrate and washings were concentrated under reduced pressure. Purification of the residue by column chromatography on silica gel (gradient: 0 to 7% $CH_3OH$ in $CH_2Cl_2$) gave 3-(5-amino-1-benzenesulfonyl-1H-pyrrolo[2,3-b]pyridin-4-ylamino)-piperidine-1-carboxylic acid 9H-fluoren-9-ylmethyl ester (5.76 g, 85%, purple foam) still containing some impurities. This material was used in the next step below without additional purification or characterization.

3-[1-Benzenesulfonyl-5-(2-cyclopropyl-acetylamino)-1H-pyrrolo[2,3-b]pyridin-4-ylamino]-piperidine-1-carboxylic acid 9H-fluoren-9-ylmethyl ester Cyclopropylacetic acid (0.300 g, 3.00 mmol), HATU (1.14 g, 3.00 mmol), and diisopropylethylamine (0.627 ml, 3.60 mmol) were added sequentially to a solution of 3-(5-amino-1-benzenesulfonyl-1H-pyrrolo[2,3-b]pyridin-4-ylamino)-piperidine-1-carboxylic acid 9H-fluoren-9-ylmethyl ester (1.78 g, 3.00 mmol) in DMF (50 ml) at 25° C. The reaction mixture was stirred for 1.5 h at 25° C., then was concentrated under reduced pressure. The residue was partitioned between half-saturated $NaHCO_3$ (125 ml) and EtOAc (2×150 ml). The combined organic layers were dried over $Mg_2SO_4$, filtered, and the filtrate was concentrated under reduced pressure to give crude 3-[1-benzenesulfonyl-5-(2-cyclopropyl-acetylamino)-1H-pyrrolo[2,3-b]pyridin-4-ylamino]-piperidine-1-carboxylic acid 9H-fluoren-9-ylmethyl ester as a brown foam. LCMS (Method G, ESI): RT=1.24 min, m+H=676.4. This material was used in the next step below without additional purification or characterization.

3-(6-Benzenesulfonyl-2-cyclopropylmethyl-6H-1,2,3,5,6-tetraaza-as-indacen-1-yl)-piperidine-1-carboxylic acid 9H-fluoren-9-ylmethyl ester A solution of crude 3-[1-benzenesulfonyl-5-(2-cyclopropyl-acetylamino)-1H-pyrrolo[2,3-b]pyridin-4-ylamino]-piperidine-1-carboxylic acid 9H-fluoren-9-ylmethyl ester prepared above (3.00 mmol) in glacial HOAc (40 ml) was heated at 95° C. for 14 h. The reaction mixture was cooled to 25° C. and was concentrated under reduced pressure. The residue was partitioned between half-saturated $NaHCO_3$ (150 ml) and EtOAc (2×225 ml). The combined organic layers were dried over $MgSO_4$, filtered, and the filtrate was concentrated under reduced pressure. Purification of the residue by column chromatography on silica gel (gradient: 0 to 7% $CH_3OH$ in $CH_2Cl_2$) afforded 3-(6-benzenesulfonyl-2-cyclopropylmethyl-6H-1,2,3,5,6-tetraaza-as-indacen-1-yl)-piperidine-1-carboxylic acid 9H-fluoren-9-ylmethyl ester (0.758 g, 38% over 3 steps) as a brown foam. LCMS (Method G, ESI): RT=1.31 min, m+H=658.4. This material was used in the next step below without additional purification or characterization.

2-Cyclopropylmethyl-1-piperidin-3-yl-1,6-dihydro-1,2,3,5,6-tetraaza-as-indacene

Sodium hydroxide (15 ml of a 1.0 M solution in water, 15 mmol) was added to a solution of 3-(6-benzene sulfonyl-2-cyclopropylmethyl-6H-1,2,3,5,6-tetraaza-as-indacen-1-yl)-piperidine-1-carboxylic acid 9H-fluoren-9-ylmethyl ester (0.758 g, 1.15 mmol) in a 1:2 mixture of EtOH and THF (30 ml) at 25° C. The reaction mixture was stirred at 60° C. for 12 h, then was cooled to 25° C. and partitioned between half-saturated $NaHCO_3$ (150 ml) and EtOAc (2×150 ml). The combined organic layers were dried over $MgSO_4$, filtered, and the filtrate was concentrated under reduced pressure. Purification of the residue by column chromatography on silica gel (6% $CH_3OH$ in $CH_2Cl_2$, then 6% $CH_3OH$ in $CH_2Cl_2$+2.0 M $NH_3$) afforded 2-cyclopropylmethyl-1-piperidin-3-yl-1,6-dihydro-1,2,3,5,6-tetraaza-as-indacene (0.117 g, 34%) as a yellow-brown solid. LCMS (Method G, ESI): RT=0.17 min, m+H=296.2.

3-[3-(2-Cyclopropylmethyl-6H-1,2,3,5,6-tetraaza-as-indacen-1-yl)-piperidin-1-yl]-3-oxo-propionitrile Cyanoacetic acid (0.034 g, 0.396 mmol), HATU (0.151 g, 0.396 mmol), and diisopropylethylamine (0.083 ml, 0.475 mmol) were added sequentially to a solution of 2-cyclopropylmethyl-1-piperidin-3-yl-1,6-dihydro-1,2,3,5,6-tetraaza-as-indacene (0.117 g, 0.396 mmol) in DMF (8 ml) at 25° C. The reaction mixture was stirred for 2 h at 25° C., then was concentrated under reduced pressure. The residue was partitioned between half-saturated $NaHCO_3$ (100 ml) and $CH_2Cl_2$ (2×100 ml). The combined organic layers were dried over $Mg_2SO_4$, filtered, and the filtrate was concentrated under reduced pressure. The residue was dissolved in DMF (2 ml) and was purified by preparative HPLC (column: Gemini-NX, 21.2×100 mm, 10 um; detection: UV 254 nm and mass, mobile phase A: water w/0.1% formic acid; mobile phase B: $CH_3CN$; flowrate: 35 ml/min; gradient 5-85% B over 9.5 min) to give 3-[3-(2-cyclopropylmethyl-6H-1,2,3,5,6-tetraaza-as-indacen-1-yl)-piperidin-1-yl]-3-oxo-propionitrile (0.022 g, 15%) as an off-white solid. LCMS (Method C, ESI): RT=3.12 min, m+H=363.1. $^1H$ NMR (400 MHz, DMSO) δ 11.86 (s, 1H), 8.53 (d, J=2.7 Hz, 1H), 7.48 (t, J=2.9 Hz, 1H), 6.78 (s, 1H), 4.68 (t, J=21.0 Hz, 1H), 4.53 (d, J=10.2 Hz, 2H), 4.18-4.06 (m, 3H), 3.94 (d, J=19.0 Hz, 1H), 3.91-3.75 (m, 2H), 3.43-3.35 (m, 1H), 3.12-2.76 (m, 4H), 2.10-1.81 (m, 3H), 1.74-1.60 (m, 1H), 1.25-1.13 (m, 1H), 0.63-0.48 (m, 2H), 0.37-0.20 (m, 2H).

Example 677

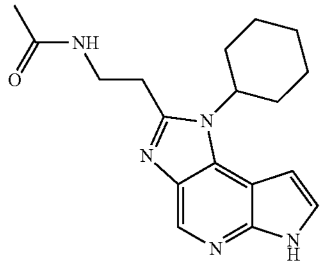 [SMILES: CC(=O)NCCc1nc2cnc3[nH]ccc3c2n1C1CCCCC1]

N-[2-(1-Cyclohexyl-1,6-dihydro-1,2,3,5,6-tetraaza-as-indacen-2-yl)-ethyl]-acetamide 3-Acetylamino-N-(1-benzenesulfonyl-4-cyclohexylamino-1H-pyrrolo[2,3-b]pyridin-5-yl)-propionamide 3-Acetylaminopropionic acid (0.089 g, 0.675 mmol), HATU (0.256 g, 0.675 mmol), and diisopropylethylamine (0.141 ml, 0.840 mmol) were added sequentially to a solution of 1-benzenesulfonyl-N-4-cyclohexyl-1H-pyrrolo[2,3-b]pyridine-4,5-diamine (0.250 g, 0.675 mmol) in $CH_2Cl_2$ (15 ml) at 25° C. The reaction mixture was stirred for 18 h at 25° C., then was partitioned between half-saturated $NaHCO_3$ (100 ml) and EtOAc (2×125 ml). The combined organic layers were dried over $MgSO_4$, filtered, and the filtrate was concentrated under reduced pressure. The residue was triturated with EtOAc (10 ml) to give a solid which was collected by filtration, washed with $Et_2O$ (10 ml), and air-dried to give 3-acetylamino-N-(1-benzenesulfonyl-4-cyclohexylamino-1H-pyrrolo[2,3-b]pyridin-5-yl)-propionamide as an off-white solid (0.183 g, 56%). LCMS (Method G, ESI): RT=0.82 min, m+H=484.3. This material was used in the next step below without additional purification or characterization.

N-[2-(6-Benzenesulfonyl-1-cyclohexyl-1,6-dihydro-1,2,3,5,6-tetraaza-as-indacen-2-yl)-ethyl]-acetamide A solution of 3-acetylamino-N-(1-benzenesulfonyl-4-cyclohexylamino-1H-pyrrolo[2,3-b]pyridin-5-yl)-propionamide (0.183 g, 0.378 mmol) in glacial HOAc (6 ml) was heated at 95° C. for 16 h. The reaction mixture was cooled to 25° C. and was concentrated under reduced pressure. The residue was partitioned between half-saturated $NaHCO_3$ (100 ml) and EtOAc (2×125 ml). The combined organic layers were dried over $MgSO_4$, filtered, and the filtrate was concentrated under reduced pressure. The residue was purified by column chromatography on silica gel (gradient: 0 to 8% $CH_3OH$ in $CH_2Cl_2$) to afford N-[2-(6-benzenesulfonyl-1-cyclohexyl-1,6-dihydro-1,2,3,5,6-tetraaza-as-indacen-2-yl)-ethyl]-acetamide (0.060 g, 34%) as a white solid. LCMS (Method G, ESI): RT=0.93 min, m+H=466.3. This material was used in the next step below without additional purification or characterization.

N-[2-(1-Cyclohexyl-1,6-dihydro-1,2,3,5,6-tetraaza-as-indacen-2-yl)-ethyl]-acetamide Sodium hydroxide (1 ml of a 1.0 M solution in water, 1 mmol) was added to a solution of N-[2-(6-benzenesulfonyl-1-cyclohexyl-1,6-dihydro-1,2,3,5,6-tetraaza-as-indacen-2-yl)-ethyl]-acetamide (0.060 g, 0.13 mmol) in a 1:1 mixture of EtOH and THF (12 ml) at 25° C. The reaction mixture was stirred at 50° C. for 1.5 h, then was partitioned between half-saturated $NaHCO_3$ (100 ml) and EtOAc (2×125 ml). The combined organic layers were dried over $MgSO_4$, filtered, and the filtrate was concentrated under reduced pressure. The residue was triturated with $Et_2O$ (10 ml) to give a solid which was collected by filtration, washed with $Et_2O$ (10 ml), and air-dried to give N-[2-(1-cyclohexyl-1,6-dihydro-1,2,3,5,6-tetraaza-as-indacen-2-yl)-ethyl]-acetamide (0.020 g, 48%) as an off-white solid. LCMS (Method N, ESI): RT=7.66 min, m+H=326.1; $^1H$ NMR (400 MHz, DMSO) δ 11.80 (s, 1H), 8.51 (s, 1H), 8.08 (t, J=5.3 Hz, 1H), 7.46 (s, 1H), 6.73 (s, 1H), 4.51 (s, 1H), 3.56-3.46 (m, 2H), 3.10 (t, J=7.2 Hz, 2H), 2.39-2.20 (m, 2H), 2.00-1.84 (m, 4H), 1.82 (s, 3H), 1.64-1.42 (m, 3H).

Examples 678, 679 and 680

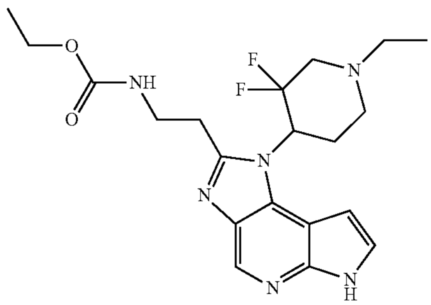 [SMILES: CCOC(=O)NCCc1nc2cnc3[nH]ccc3c2n1C1CCN(CC)CC1(F)F]

{2-[1-(1-Ethyl-3,3-difluoro-piperidin-4-yl)-1,6-dihydro-1,2,3,5,6-tetraaza-as-indacen-2-yl]-ethyl}-carbamic acid ethyl ester 1-Benzenesulfonyl-N-4-(1-ethyl-3,3-difluoro-piperidin-4-yl)-1H-pyrrolo[2,3-b]pyridine-4,5-diamine A suspension of (1-benzenesulfonyl-5-nitro-1H-pyrrolo[2,3-b]pyridin-4-yl)-(1-ethyl-3,3-difluoro-piperidin-4-yl)-amine (8.06 g, 17.3 mmol) and palladium on carbon (2.5 g, 10%, wet, Degussa, E101 NE/W) in a 3:1 mixture of THF and EtOH (200 ml) was stirred under a hydrogen atmosphere (2-3 balloons) at 50° C. for 18 h. The reaction mixture was cooled to 25° C. then was filtered through Celite. The filtrate was concentrated under reduced pressure to give 1-benzenesulfonyl-N-4-(1-ethyl-3,3-difluoro-piperidin-4-yl)-1H-pyrrolo[2,3-b]pyridine-4,5-diamine (4.39 g 58%) as a rose foam. The filter cake was stirred in DMF (100 ml) at 25° C. for 2 h and the resulting mixture was again filtered through Celite. The dark brown filtrate was concentrated under reduced pressure to give an additional 3.7 g (49%) of the title compound as a brown oil. LCMS (Method G, ESI): RT=0.48 min, m+H=436.3. This material was used in the next step below without additional purification or characterization.

{2-[1-Benzenesulfonyl-4-(1-ethyl-3,3-difluoro-piperidin-4-ylamino)-1H-pyrrolo[2,3-b]pyridin-5-ylcarbamoyl]-ethyl}-carbamic acid 9H-fluoren-9-ylmethyl ester Fmoc-beta-Alanine (2.5 g, 8.03 mmol), HATU (3.06 g, 8.05 mmol), and diisopropylethylamine (1.76 ml, 9.76 mmol) were added sequentially to a solution of 1-benzenesulfonyl-N-4-(1-ethyl-3,3-difluoro-piperidin-4-yl)-1H-pyrrolo[2,3-b]pyridine-4,5-diamine (3.5 g, 8.04 mmol) in DMF (60 ml) at 25° C. The reaction mixture was stirred for 1.5 h at 25° C., then was concentrated under reduced pressure. The residue was partitioned between half-saturated $NaHCO_3$ (150 ml) and EtOAc (2×200 ml). The combined organic layers were dried over $Mg_2SO_4$, filtered, and the filtrate was concentrated under reduced pressure. Purification of the residue by column chromatography on silica gel (gradient: 0 to 5% $CH_3OH$ in $CH_2Cl_2$) afforded {2-[1-benzenesulfonyl-4-(1-ethyl-3,3-difluoro-piperidin-4-ylamino)-1H-pyrrolo[2,3-b]pyridin-5-yl carbamoyl]-ethyl}-carbamic acid 9H-fluoren-9-ylmethyl ester (5.52 g, 94%) as a white foam. LCMS (Method G, ESI): RT=0.92 min, m+H=729.4. This material was used in the next step below without additional purification or characterization.

{2-[1-(1-Ethyl-3,3-difluoro-piperidin-4-yl)-1,6-dihydro-1,2,3,5,6-tetraaza-as-indacen-2-yl]-ethyl}-carbamic acid 9H-fluoren-9-ylmethyl ester A solution of {2-[1-benzenesulfonyl-4-(1-ethyl-3,3-di fluoro-piperidin-4-ylamino)-1H-pyrrolo[2,3-b]pyridin-5-yl carbamoyl]-ethyl}-carbamic acid 9H-fluoren-9-ylmethyl ester (5.50 g, 7.57 mmol) in glacial HOAc (60 ml) was heated at 115° C. for 23 h. The reaction mixture was cooled to 25° C. and was concentrated under reduced pressure. The residue was partitioned between half-saturated $NaHCO_3$ (150 ml) and EtOAc (2×225 ml). The combined organic layers were dried over $MgSO_4$, filtered, and the filtrate was concentrated under reduced pressure. Purification of the residue by column chromatography on silica gel (gradient: 0 to 7% $CH_3OH$ in $CH_2Cl_2$) afforded {2-[1-(1-ethyl-3,3-difluoro-piperidin-4-yl)-1,6-dihydro-1,2,3,5,6-tetraaza-as-indacen-2-yl]-ethyl}-carbamic acid 9H-fluoren-9-ylmethyl ester (1.07 g, 25%) as a white foam. LCMS (Method G, ESI): RT=0.80 min, m+H=571.4. $^1$H NMR (400 MHz, $CDCl_3$, 3:1 mix of rotamers) δ 10.76 (s, 1H), 10.39 (s, 2H), 8.75 (s, 3H), 7.73 (d, J=7.5 Hz, 6H), 7.57 (dd, J=13.8, 9.8 Hz, 6H), 7.46-7.11 (m, 18H), 6.91 (s, 2H), 6.64 (d, J=12.4 Hz, 1H), 6.19 (s, 1H), 6.04 (s, 2H), 5.52 (d, J=6.5 Hz, 1H), 5.29 (s, 3H), 5.04 (d, J=25.3 Hz, 1H), 4.70-4.50 (m, 2H), 4.48-4.37 (m, 4H), 4.36-4.28 (m, 3H), 4.21 (t, J=6.9 Hz, 3H), 3.95-3.76 (m, 6H), 3.49-3.09 (m, 14H), 2.71-2.56 (m, 6H), 2.57-2.39 (m, 3H), 2.31 (t, J=10.5 Hz, 3H), 1.92 (s, 2H), 1.17 (q, J=7.2 Hz, 8H).

2-[1-(1-Ethyl-3,3-difluoro-piperidin-4-yl)-1,6-dihydro-1,2,3,5,6-tetraaza-as-indacen-2-yl]-ethylamine Piperidine (1.11 ml, 11.2 mmol) was added to a solution of {2-[1-(1-ethyl-3,3-difluoro-piperidin-4-yl)-1,6-dihydro-1,2,3,5,6-tetraaza-as-indacen-2-yl]-ethyl}-carbamic acid 9H-fluoren-9-ylmethyl ester (1.07 g, 1.88 mmol) in DMF (40 ml) at 25° C. The reaction mixture was stirred at 25° C. for 30 min, then was concentrated under reduced pressure. Purification of the residue by column chromatography on silica gel (8% $CH_3OH$ in $CH_2Cl_2$, then 9% $CH_3OH$ in $CH_2Cl_2$+2.0 M $NH_3$) afforded 2-[1-(1-ethyl-3,3-difluoro-piperidin-4-yl)-1,6-dihydro-1,2,3,5,6-tetraaza-as-indacen-2-yl]-ethylamine (0.46 g, 70%) as a white foam. LCMS (Method G, ESI): RT=0.19 min, m+H=349.3. This material was used in the next step below without additional purification or characterization.

{2-[1-(1-Ethyl-3,3-difluoro-piperidin-4-yl)-1,6-dihydro-1,2,3,5,6-tetraaza-as-indacen-2-yl]-ethyl}-carbamic acid ethyl ester Diisopropylethylamine (0.048 ml, 0.28 mmol) and ethyl chloroformate (0.020 ml, 0.21 mmol) were added sequentially to a solution of 2-[1-(1-ethyl-3,3-difluoro-piperidin-4-yl)-1,6-dihydro-1,2,3,5,6-tetraaza-as-indacen-2-yl]-ethylamine (0.060, 0.17 mmol) in $CH_2Cl_2$ (3 ml) at 25° C. The reaction mixture was stirred for 30 min at 25° C., then saturated $NaHCO_3$ (0.50 ml) was added. After stirring for an additional 30 min at 25° C., the reaction mixture was concentrated under reduced pressure. The solid thus obtained was suspended in DMF (2 ml) and the resulting mixture was filtered through a 0.45 um syringe filter. The filtrate was purified by preparative HPLC (column: Gemini-NX, 21.2×100 mm, 10 um; detection: UV 254 nm and mass, mobile phase A: water w/0.1% formic acid; mobile phase B: $CH_3CN$; flowrate: 35 ml/min; gradient 5-85% B over 9.5 min) to give {2-[1-(1-ethyl-3,3-difluoro-piperidin-4-yl)-1,6-dihydro-1,2,3,5,6-tetraaza-as-indacen-2-yl]-ethyl}-carbamic acid ethyl ester (0.031 g, 42%) as an off-white solid. LCMS (Method C, ESI): RT=2.71 min, m+H=421.2; $^1$H NMR (400 MHz, DMSO) δ 11.71 (s, 1H), 8.52 (s, 1H), 7.41 (t, J=2.8 Hz, 1H), 7.24 (t, J=5.7 Hz, 1H), 6.67 (s, 1H), 5.09-4.92 (m, 1H), 3.98 (q, J=7.0 Hz, 2H), 3.58-3.46 (m, 1H), 3.24-3.08 (m, 3H), 3.02 (t, J=11.6 Hz, 2H), 2.66-2.54 (m, 2H), 2.46-2.36 (m, 1H), 2.06-1.96 (m, 1H), 1.20-1.06 (m, 6H). Purification of a portion of this material by chiral SFC (column: Phenomenex Lux Cellulose-1, 21.2×250 mm, 5 um; detection: UV 230 nm, mobile phase: 1:3 $CH_3OH:CO_2$; flowrate: 60 g/min; runtime: 6 min) afforded separate pure enantiomers of the title compound (faster isomer=Example 679; slower isomer=Example 680; absolute configuration unknown).

Example 681

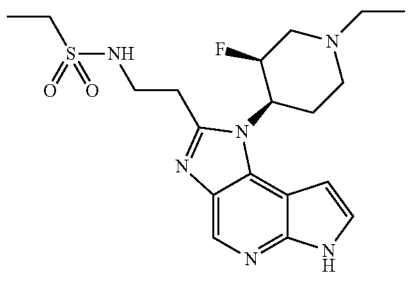 [SMILES: CCN1CC[C@@H](n2c(CCNS(=O)(=O)CC)nc3cnc4[nH]ccc4c32)[C@@H](F)C1]

Ethanesulfonic acid {2-[1-((3S,4R)-1-ethyl-3-fluoro-piperidin-4-yl)-1,6-dihydro-1,2,3,5,6-tetraaza-as-indacen-2-yl]-ethyl}-amide (1-Benzenesulfonyl-5-nitro-1H-pyrrolo[2,3-b]pyridin-4-yl)-((3S,4R)-1-ethyl-3-fluoro-piperidin-4-yl)-amine A mixture of 1-benzenesulfonyl-4-chloro-5-nitro-1H-pyrrolo[2,3-b]pyridine (15.35 g, 45.5 mmol), (3S,4R)-1-ethyl-3- fluoro-piperidin-4-ylamine (dihydrochloride salt) (6.30 g, 29.0 mmol), diisopropylethylamine (21.0 ml, 120 mmol) in propan-2-ol (200 ml) was heated at 80° C. for 14 h. The mixture was cooled to 25° C. and was stirred at that temperature for 4 h. The resulting yellow precipitate was collected by vacuum filtration, washed with Et2O (1×30 ml), and air-dried to give (1-benzenesulfonyl-5-nitro-1H-pyrrolo[2,3-b]pyridin-4-yl)-((3S,4R)-1-ethyl-3-fluoro-piperidin-4-yl)-amine (11.5 g, 90% over 3 steps) as a yellow solid. LCMS (Method G, ESI): RT=0.69 min, m+H=448.3; $^1$H NMR (400 MHz, $CDCl_3$) δ 9.35 (d, J=8.4 Hz, 1H), 9.12 (s, 1H), 8.29-8.11 (m, 2H), 7.69-7.59 (m, 2H), 7.52 (t, J=7.8 Hz, 2H), 7.26 (s, 1H), 6.65 (d, J=4.2 Hz, 1H), 4.86 (d, J=48.6 Hz, 1H), 4.28-4.05 (m, 1H), 3.27-3.13 (m, 1H), 2.97-2.87 (m, 1H), 2.52 (q, J=7.2 Hz, 2H), 2.49-2.37 (m, 1H), 2.29 (t, J=10.0 Hz, 1H), 2.15-1.98 (m, 2H), 1.12 (t, J=7.2 Hz, 3H).

1-Benzenesulfonyl-N-4-((3S,4R)-1-ethyl-3-fluoro-piperidin-4-yl)-1H-pyrrolo[2,3-b]pyridine-4,5-diamine A suspension of (1-benzenesulfonyl-5-nitro-1H-pyrrolo[2,3-b]pyridin-4-yl)-((3S,4R)-1-ethyl-3-fluoro-piperidin-4-yl)-amine (11.5 g, 25.7 mmol) and palladium on carbon (2.8 g, 10%, wet, Degussa, E101 NE/W) in a 3:1 mixture of THF and EtOH (120 ml) was stirred under a hydrogen atmosphere (2-3 balloons) at 50° C. for 14 h. The reaction mixture was cooled to 25° C. then was filtered through Celite. The Celite was washed with THF (2×30 ml) and the combined filtrate and washings were concentrated under reduced pressure to afford 1-benzenesulfonyl-N-4-((3S,4R)-1-ethyl-3-fluoro-piperidin-4-yl)-1H-pyrrolo[2,3-b]pyridine-4,5-diamine (11.3 g 103%) as a tan foam. LCMS (Method G, ESI): RT=0.47 min, m+H=418.3. This material was used in the next step below without additional purification or characterization.

{2-[1-Benzenesulfonyl-4-((3S,4R)-1-ethyl-3-fluoro-piperidin-4-ylamino)-1H-pyrrolo[2,3-b]pyridin-5-ylcarbamoyl]-ethyl}-carbamic acid 9H-fluoren-9-ylmethyl ester Fmoc-beta-Alanine (3.4 g, 11.0 mmol), HATU (4.10 g, 11.0 mmol), and diisopropylethylamine (2.20 ml, 13.0 mmol) were added sequentially to a solution of 1-benzenesulfonyl-N-4-((3S,4R)-1-ethyl-3-fluoro-piperidin-4-yl)-1H-pyrrolo[2,3-b]pyridine-4,5-diamine (4.5 g, 11.0 mmol) in DMF (100 ml) at 25° C. The reaction mixture was stirred for 2 h at 25° C., then was concentrated under reduced pressure. The residue was partitioned between half-saturated $NaHCO_3$ (150 ml) and EtOAc (2×200 ml). The combined organic layers were dried over $Mg_2SO_4$, filtered, and the filtrate was concentrated under reduced pressure to give crude {2-[1-benzenesulfonyl-4-((3 S,4R)-1-ethyl-3-fluoro-piperidin-4-ylamino)-1H-pyrrolo[2,3-b]pyridin-5-ylcarbamoyl]-ethyl}-carbamic acid 9H-fluoren-9-ylmethyl ester as a tan foam. LCMS (Method G, ESI): RT=0.87 min, m+H=711.4. This material was used in the next step below without additional purification or characterization.

{2-[6-Benzenesulfonyl-1-((3S,4R)-1-ethyl-3-fluoro-piperidin-4-yl)-1,6-dihydro-1,2,3,5,6-tetraaza-as-indacen-2-yl]-ethyl}-carbamic acid 9H-fluoren-9-ylmethyl ester A solution of crude {2-[1-benzenesulfonyl-4-((3S,4R)-1-ethyl-3-fluoro-piperidin-4-ylamino)-1H-pyrrolo[2,3-b]pyridin-5-ylcarbamoyl]-ethyl}-carbamic acid 9H-fluoren-9-ylmethyl ester (11.0 mmol) in glacial HOAc (80 ml) was heated at 95° C. for 14 h. The reaction mixture was cooled to 25° C. and was concentrated under reduced pressure. The residue was partitioned between half-saturated $NaHCO_3$ (150 ml) and EtOAc (2×225 ml). The combined organic layers were dried over $MgSO_4$, filtered, and the filtrate was concentrated under reduced pressure. Purification of the residue by column chromatography on silica gel (gradient: 0 to 6% $CH_3OH$ in $CH_2Cl_2$) afforded {2-[6-benzenesulfonyl-1-((3S,4R)-1-ethyl-3-fluoro-piperidin-4-yl)-1,6-dihydro-1,2,3,5,6-tetraaza-as-indacen-2-yl]-ethyl}-carbamic acid 9H-fluoren-9-ylmethyl ester (1.55 g, 20% over 2 steps) as a beige foam. LCMS (Method G, ESI): RT=0.88 min, m+H=693.4. This material was used in the next step below without additional purification or characterization.

2-[6-Benzenesulfonyl-1-((3S,4R)-1-ethyl-3-fluoro-piperidin-4-yl)-1,6-dihydro-1,2,3,5,6-tetraaza-as-indacen-2-yl]-ethylamine Piperidine (1.11 ml, 11.2 mmol) was added to a solution of {2-[6-benzenesulfonyl-1-((3S,4R)-1-ethyl-3-fluoro-piperidin-4-yl)-1,6-dihydro-1,2,3,5,6-tetraaza-as-indacen-2-yl]-ethyl}-carbamic acid 9H-fluoren-9-ylmethyl ester (1.55 g, 2.24 mmol) in DMF (30 ml) at 25° C. The reaction mixture was stirred at 25° C. for 1 h, then was concentrated under reduced pressure. Purification of the residue by column chromatography on silica gel (9% $CH_3OH$ in $CH_2Cl_2$, then 9% $CH_3OH$ in $CH_2Cl_2$+2.0 M $NH_3$) afforded 2-[6-benzenesulfonyl-1-((3S,4R)-1-ethyl-3-fluoro-piperidin-4-yl)-1,6-dihydro-1,2,3,5,6-tetraaza-as-indacen-2-yl]-ethylamine (0.409 g, 40%) as a white foam. LCMS (Method G, ESI): RT=0.47 min, m+H=471.3. $^1$H NMR (400 MHz, $CDCl_3$) δ 8.82 (s, 1H), 8.20 (d, J=7.5 Hz, 2H), 7.76 (d, J=3.9 Hz, 1H), 7.58-7.39 (m, 3H), 7.26 (s, 1H), 4.86 (d, J=49.6 Hz, 1H), 4.68-4.43 (m, 1H), 3.55-3.36 (m, 2H), 3.36-3.20 (m, 3H), 3.18-2.95 (m, 3H), 2.65-2.51 (m, 2H), 2.39 (dd, J=38.0, 13.3 Hz, 1H), 2.23 (t, J=11.2 Hz, 1H), 2.00-1.81 (m, 1H), 1.24-1.09 (m, 4H).

Ethanesulfonic acid {2-[6-benzenesulfonyl-1-((3S,4R)-1-ethyl-3-fluoro-piperidin-4-yl)-1,6-dihydro-1,2,3,5,6-tetraaza-as-indacen-2-yl]-ethyl}-amide Diisopropylethylamine (0.065 ml, 0.375 mmol) and ethanesulfonyl chloride (0.029 ml, 0.306 mmol) were added sequentially to a solution of 2-[6-benzenesulfonyl-1-((3S,4R)-1-ethyl-3-fluoro-piperidin-4-yl)-1,6-dihydro-1,2,3,5,6-tetraaza-as-indacen-2-yl]-ethylamine (0.080, 0.17 mmol) in $CH_2Cl_2$ (2 ml) at 25° C. The reaction mixture was stirred for 2 h at 25° C., then was partitioned between half-saturated $NaHCO_3$ (4 ml) and $CH_2Cl_2$ (6 ml). The phases were separated using a phase separation column (Biotage) and the organic layer was concentrated under reduced pressure to give crude {2-[6-benzenesulfonyl-1-((3S,4R)-1-ethyl-3-fluoro-piperidin-4-yl)-1,6-dihydro-1,2,3,5,6-tetraaza-as-indacen-2-yl]-ethyl}-amide. This material was used in the next step below without additional purification or characterization.

Ethanesulfonic acid {2-[1-((3S,4R)-1-ethyl-3-fluoro-piperidin-4-yl)-1,6-dihydro-1,2,3,5,6-tetraaza-as-indacen-2-yl]-ethyl}-amide Sodium hydroxide (1 ml of a 1.0 M solution in water, 1 mmol) was added to a solution of crude {2-[6-benzenesulfonyl-1-((3S,4R)-1-ethyl-3-fluoro-piperidin-4-yl)-1,6-dihydro-1,2,3,5,6-tetraaza-as-indacen-2-yl]-ethyl}-amide (0.17 mmol) in EtOH (3 ml) at 25° C. The reaction mixture was stirred at 50° C. for 2 h, then was cooled to 25° C. 1.0 M HCl (1 ml) and saturated $NaHCO_3$ (0.5 ml) were added sequentially. After stirring for an additional 30 min at 25° C., the reaction mixture was concentrated under reduced pressure. The solid thus obtained was suspended in DMF (2 ml) and the resulting mixture was filtered through a 0.45 um syringe filter. The filtrate was purified by preparative HPLC (column: Gemini-NX, 21.2×100 mm, 10 um; detection: UV 254 nm and mass, mobile phase A: water w/0.1% formic acid; mobile phase B: $CH_3CN$; flowrate: 35 ml/min; gradient 5-85% B over 9.5 min) to give ethanesulfonic acid {2-[1-((3S,4R)-1-ethyl-3-fluoro-piperidin-4-yl)-1,6-dihydro-1,2,3,5,6-tetraaza-as-indacen-2-yl]-ethyl}-amide (0.029 g, 40% over 2 steps) as an off-white solid. LCMS (Method C, ESI): RT=2.33 min, m+H=423.1; $^1$H NMR (400 MHz, DMSO) δ 11.70 (s, 2H), 8.50 (s, 2H), 7.40 (s, 1H), 7.19 (t, J=5.9 Hz, 1H), 6.78 (s, 1H), 4.88-4.67 (m, 2H), 3.59-3.39 (m, 3H), 3.29-3.12 (m, 4H), 3.07 (d, J=7.3 Hz, 2H), 3.03-2.94 (m, 1H), 2.37-2.26 (m, 2H), 1.96-1.88 (m, 1H), 1.19 (t, J=7.3 Hz, 3H), 1.08 (t, J=7.1 Hz, 3H).

Example 682

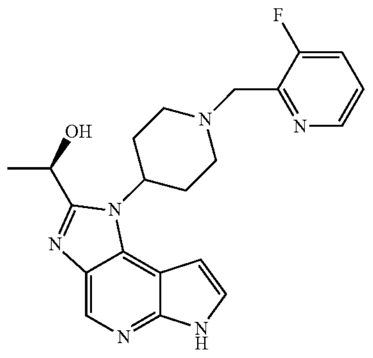 [SMILES: C[C@@H](O)c1nc2cnc3[nH]ccc3c2n1C1CCN(Cc2ncccc2F)CC1]

(R)-1-{1-[1-(3-Fluoro-pyridin-2-ylmethyl)-piperidin-4-yl]-1,6-dihydro-1,2,3,5,6-tetraaza-as-indacen-2-yl}-ethanol 4-[6-Benzenesulfonyl-2-((R)-1-hydroxy-ethyl)-6H-1,2,3,5,6-tetraaza-as-indacen-1-yl]-piperidine-1-carboxylic acid tert-butyl ester Triethyloxonium tetrafluoroborate (6.04 g, 31.8 mmol) was added to a solution of (R)-(+)-lactamide (2.83 g, 31.8 mmol) in THF (100 ml) at 25° C. The resulting suspension was stirred at 25° C. for 1.5 h, then was concentrated under reduced pressure to afford an oil. This material was dissolved in EtOH (90 ml) at 25° C. and 4-(5-amino-1-benzenesulfonyl-1H-pyrrolo[2,3-b]pyridin-4-ylamino)-piperidine-1-carboxylic acid tert-butyl ester (6.00 g, 12.7 mmol) was added. The reaction mixture was heated at 75° C. for 2 h, then was cooled to 25° C. and concentrated under reduced pressure. The residue was dissolved in EtOAc (225 ml) and washed with half-saturated $NaHCO_3$ (2×150 ml). The organic layer was dried over $MgSO_4$, filtered, and the filtrate was concentrated under reduced pressure. Purification of the resulting solid by column chromatography on silica gel (gradient: 0 to 7% $CH_3OH$ in $CH_2Cl_2$) afforded 4-[6-benzenesulfonyl-2-((R)-1-hydroxy-ethyl)-6H-1,2,3,5,6-tetraaza-as-indacen-1-yl]-piperidine-1-carboxylic acid tert-butyl ester (10.25 g, 150%) still contaminated with unknown impurities. This material was used in the next step below without additional purification or characterization.

(R)-1-(6-Benzenesulfonyl-1-piperidin-4-yl-1,6-dihydro-1,2,3,5,6-tetraaza-as-indacen-2-yl)-ethanol A 4.0 M solution of HCl in 1,4-dioxane (35 ml) was added to a portion of the 4-[6-benzenesulfonyl-2-((R)-1-hydroxy-ethyl)-6H-1,2,3,5,6-tetraaza-as-indacen-1-yl]-piperidine-1-carboxylic acid tert-butyl ester prepared above (6.68 g) dissolved in 1,4-dioxane (30 ml) at 25° C. The resulting white suspension mixture was stirred at 25° C. for 4 h, then was filtered through a medium frit. The collected white solid was washed with $Et_2O$ (2×25 ml) and air-dried (5.95 g isolated). A portion of this solid (3.10 g) was partitioned between half-saturated $NaHCO_3$ (150 ml) and EtOAc (2×250 ml). The combined organic layers were dried over $MgSO_4$, filtered, and the filtrate was concentrated under reduced pressure. The residue was triturated with $Et_2O$ (20 ml) and the resulting solid was collected by filtration, washed with $Et_2O$ (2×20 ml) and air-dried overnight to give (R)-1-(6-benzenesulfonyl-1-piperidin-4-yl-1,6-dihydro-1,2,3,5,6-tetraaza-as-indacen-2-yl)-ethanol (1.83 g) as a white solid. $^1$H NMR (400 MHz, DMSO) δ 8.70 (s, 1H), 8.18-8.10 (m, 2H), 8.01 (d, J=4.1 Hz, 1H), 7.74-7.66 (m, 1H), 7.66-7.57 (m, 2H), 7.43 (d, J=4.1 Hz, 1H), 5.75 (d, J=6.6 Hz, 1H), 5.14 (p, J=6.5 Hz, 1H), 5.00-4.82 (m, 1H), 3.17 (d, J=11.9 Hz, 2H), 2.65 (t, J=12.1 Hz, 2H), 2.35-2.14 (m, 2H), 1.82 (d, J=10.5 Hz, 2H), 1.61 (d, J=6.5 Hz, 3H).

(R)-1-{6-Benzenesulfonyl-1-[1-(3-fluoro-pyridin-2-ylmethyl)-piperidin-4-yl]-1,6-dihydro-1,2,3,5,6-tetraaza-as-indacen-2-yl}-ethanol A solution of (R)-1-(6-benzenesulfonyl-1-piperidin-4-yl-1,6-dihydro-1,2,3,5,6-tetraaza-as-indacen-2-yl)-ethanol (0.15 g, 0.35 mmol) and 3-fluoro-pyridine-2-carbaldehyde (0.064 ml, 0.635 mmol) in 1,2-dichloroethane (6 ml) was heated at 65° C. for 5 min, then was allowed to cool to 45° C. Sodium triacetoxyborohydride (0.187 g, 0.882 mmol) was added and the reaction mixture was allowed to cool to 25° C. After stirring for 2 h at 25° C., the mixture was partitioned between half-saturated $NaHCO_3$ (7 ml) and 1,2-dichloroethane (2 ml). The phases were separated using a phase separation column (Biotage) and the organic layer was concentrated under reduced pressure to give crude (R)-1-{6-benzenesulfonyl-1-[1-(3-fluoro-pyridin-2-ylmethyl)-piperidin-4-yl]-1,6-dihydro-1,2,3,5,6-tetraaza-as-indacen-2-yl}-ethanol as a tan oil LCMS (Method G, ESI): RT=0.64 min, m+H=535.3. This material was used in the next step below without additional purification or characterization.

(R)-1-{1-[1-(3-Fluoro-pyridin-2-ylmethyl)-piperidin-4-yl]-1,6-dihydro-1,2,3,5,6-tetraaza-as-indacen-2-yl}-ethanol Sodium hydroxide (1 ml of a 1.0 M solution in water, 1 mmol) was added to a solution of crude (R)-1-{6-benzene sulfonyl-1-[1-(3-fluoro-pyridin-2-ylmethyl)-piperidin-4-yl]-1,6-dihydro-1,2,3,5,6-tetraaza-as-indacen-2-yl}-ethanol (0.35 mmol) in a 1:1 mixture of THF and EtOH (4 ml) at 25° C. The reaction mixture was stirred at 50° C. for 4 h, then was cooled to 25° C. 1.0 M HCl (1 ml) and saturated $NaHCO_3$ (0.5 ml) were added sequentially. After stirring for an additional 10 min at 25° C., the reaction mixture was concentrated under reduced pressure. The solid thus obtained was suspended in DMF (2 ml) and the resulting mixture was filtered through a 0.45 um syringe filter. The filtrate was purified by preparative HPLC (column: Gemini-NX, 21.2×100 mm, 10 um; detection: UV 254 nm and mass, mobile phase A: water w/0.1% formic acid; mobile phase B: $CH_3CN$; flowrate: 35 ml/min; gradient 5-85% B over 9.5 min) to give (R)-1-{1-[1-(3-fluoro-pyridin-2-ylmethyl)-piperidin-4-yl]-1,6-dihydro-1,2,3,5,6-tetraaza-as-indacen-2-yl}-ethanol (0.055 g, 40% over 2 steps) as an off-white solid. LCMS (Method C, ESI): RT=2.47 min, m+H=395.1; $^1$H NMR (400 MHz, DMSO) δ 11.79 (s, 1H), 8.53 (s, 1H), 8.44 (s, 1H), 7.76 (t, J=9.3 Hz, 1H), 7.50-7.42 (m, 2H), 6.91 (s, 1H), 5.64 (d, J=6.1 Hz, 1H), 5.14-5.07 (m, 1H), 4.87-4.77 (m, 1H), 3.85 (s, 2H), 3.11 (d, J=9.5 Hz, 2H), 2.66-2.54 (m, 2H), 2.31 (t, J=11.2 Hz, 2H), 1.86 (d, J=10.8 Hz, 2H), 1.61 (d, J=6.0 Hz, 3H).

Example 683

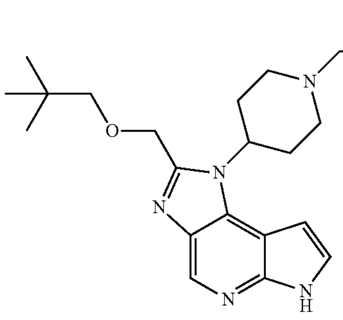

3-{4-[2-(2,2-Dimethyl-propoxymethyl)-6H-1,2,3,5,6-tetraaza-as-indacen-1-yl]-piperidin-1-yl}-propionitrile 3-[4-(6-Benzenesulfonyl-2-chloromethyl-6H-1,2,3,5,6-tetraaza-as-indacen-1-yl)-piperidin-1-yl]-propionitrile 2-Chloro-1,1,1-triethyoxyethane (7.06 ml, 37.0 mmol) was added to a solution of 3-[4-(5-amino-1-benzenesulfonyl-1H-pyrrolo[2,3-b]pyridin-4-ylamino)-piperidin-1-yl]-propionitrile (3.14 g, 7.40 mmol) in glacial HOAc (50 ml) at 25° C. The mixture was heated at 125° C. for 30 min, then was cooled to 25° C. and was concentrated under reduced pressure. The residue was partitioned between half-saturated $NaHCO_3$ (150 ml) and EtOAc (2×225 ml). The combined organic layers were dried over $MgSO_4$, filtered, and the filtrate was concentrated under reduced pressure. The residue was triturated with $CH_2Cl_2$ (20 ml) to give a solid. This material was collected by filtration, washed with $Et_2O$ (2×20 ml), and air-dried to give {3-[4-(6-benzenesulfonyl-2-chloromethyl-6H-1,2,3,5,6-tetraaza-as-indacen-1-yl)-piperidin-1-yl]-propionitrile (2.24 g, 63%) as a beige solid. LCMS (Method G, ESI): RT=0.69 min, m+H=483.3; $^1$H NMR (400 MHz, DMSO) δ 8.75 (s, 1H), 8.15 (d, J=7.9 Hz, 2H), 7.92 (d, J=4.1 Hz, 1H), 7.71 (t, J=7.4 Hz, 1H), 7.62 (t, J=7.7 Hz, 2H), 7.48 (d, J=4.0 Hz, 1H), 5.22 (s, 2H), 4.76-4.66 (m, 1H), 3.14 (d, J=10.8 Hz, 2H), 2.81 (t, J=6.4 Hz, 2H), 2.71 (t, J=6.4 Hz, 2H), 2.48-2.36 (m, 2H), 2.30 (t, J=11.2 Hz, 2H), 2.02-1.92 (m, 2H).

3-{4-[2-(2,2-Dimethyl-propoxymethyl)-6H-1,2,3,5,6-tetraaza-as-indacen-1-yl]-piperidin-1-yl}-propionitrile Sodium bis(trimethylsilyl)amide (1.90 ml of a 1.0 M solution in THF, 1.9 mmol) was added to a solution of 2,2-dimethyl-1-propanol (0.182 g, 2.07 mmol) in THF (3 ml) at 25° C. The resulting solution was stirred at 25° C. for 5 min, then a solution of {3-[4-(6-benzenesulfonyl-2-chloromethyl-6H-1,2,3,5,6-tetraaza-as-indacen-1-yl)-piperidin-1-yl]-propionitrile (0.250 g, 0.518 mmol) in THF (8 ml) was added. The reaction mixture was heated to 50° C. for 20 min, then was cooled to 25° C. 1.0 M HCl (2 ml) and saturated $NaHCO_3$ (0.5 ml) were added sequentially. After stirring for an additional 10 min at 25° C., the reaction mixture was concentrated under reduced pressure. The solid thus obtained was suspended in DMF (2 ml) and the resulting mixture was filtered through a 0.45 um syringe filter. The filtrate was purified by preparative HPLC (column: Gemini-NX, 21.2×100 mm, 10 um; detection: UV 254 nm and mass, mobile phase A: water w/0.1% formic acid; mobile phase B: $CH_3CN$; flowrate: 35 ml/min; gradient 5-85% B over 9.5 min) to give 3-{4-[2-(2,2-dimethyl-propoxymethyl)-6H-1,2,3,5,6-tetraaza-as-indacen-1-yl]-piperidin-1-yl}-propionitrile (0.086 g, 42%) as an off-white solid. LCMS (Method C, ESI): RT=3.21 min, m+H=395.2; $^1$H NMR (400 MHz, DMSO) δ 11.87 (s, 1H), 8.56 (s, 1H), 7.44 (t, J=2.9 Hz, 1H), 6.97 (s, 1H), 4.81 (s, 2H), 4.69-4.57 (m, 1H), 3.18 (s, 3H), 3.16-3.11 (m, 1H), 2.78 (t, J=6.6 Hz, 2H), 2.69 (t, J=6.6 Hz, 2H), 2.66-2.55 (m, 2H), 2.24 (t, J=11.0 Hz, 2H), 1.94-1.86 (m, 2H), 0.89 (s, 9H).

Example 684

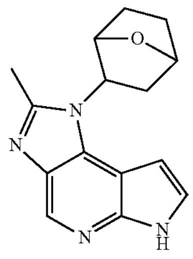 [SMILES: Cc1nc2cnc3[nH]ccc3c2n1C1CC2CCC1O2]

Endo-2-Methyl-1-(7-oxa-bicyclo[2.2.1]hept-2-yl)-1,6-dihydro-1,2,3,5,6-tetraaza-as-indacene Endo-(7-Oxa-bicyclo[2.2.1]hept-5-en-2-yl)-carbamic acid benzyl ester Ethyl chloroformate (3.22 ml, 33.7 mmol) was added to a solution of endo-7-oxa-bicyclo[2.2.1]hept-5-ene-2-carboxylic acid (2.36 g, 1.68 mmol) and triethylamine (7.04 ml, 50.5 mmol) in THF (110 ml) at 0° C. The resulting suspension was stirred at 0° C. for 45 min, then a solution of sodium azide (3.28 g, 50.5 mmol) in water (15 ml) was added dropwise via addition funnel over 15 min. The reaction mixture was warmed to 25° C. and stirred for 1.5 h, then was partitioned between water (200 ml) and EtOAc (2×225 ml). The combined organic layers were dried over $MgSO_4$, filtered, and the filtrate was concentrated under reduced pressure to give a pale yellow liquid. This material was dissolved in benzene (50 ml) at 25° C. and the resulting solution was refluxed for 2 h. After cooling to 25° C., the reaction mixture was concentrated under reduced pressure to afford a yellow oil. This material was dissolved in $CH_2Cl_2$ (45 ml) at 25° C. and triethylamine (4.68 ml, 33.6 mmol) and benzyl alcohol (1.91 ml, 18.5 mmol) were added sequentially. The mixture was refluxed for 18 h, then was cooled to 25° C. and concentrated under reduced pressure. Purification of the residue by column chromatography on silica gel (gradient: 0 to 60% EtOAc in heptanes) afforded endo-(7-oxa-bicyclo[2.2.1]hept-5-en-2-yl)-carbamic acid benzyl ester (1.20 g, 29%) as a white solid. LCMS (Method G, ESI): RT=0.74 min, m+H=246.1. $^1H$ NMR (400 MHz, $CDCl_3$) δ 7.46-7.28 (m, 5H), 6.54 (dd, J=5.9, 1.6 Hz, 1H), 6.31 (d, J=5.8 Hz, 1H), 5.26-4.88 (m, 4H), 4.49-4.24 (m, 2H), 2.50-2.26 (m, 1H), 0.86 (dd, J=11.8, 2.9 Hz, 1H).

Endo-7-Oxa-bicyclo[2.2.1]hept-2-ylamine

A suspension of endo-(7-oxa-bicyclo[2.2.1]hept-5-en-2-yl)-carbamic acid benzyl ester (1.10 g, 4.48 mmol) and palladium on carbon (0.30 g, 10%, wet, Degussa, E101 NE/W) in THF (30 ml) was stirred under a hydrogen atmosphere (2 balloons) at 25° C. for 3.5 h. The reaction mixture was filtered through Celite, and the Celite was washed with THF (2×20 ml). The combined filtrate and washings were concentrated under reduced pressure to afford crude endo-7-oxa-bicyclo[2.2.1]hept-2-ylamine as a colorless oil. This material was used in the next step below without additional purification or characterization.

Endo-(1-Benzenesulfonyl-5-nitro-1H-pyrrolo[2,3-b]pyridin-4-yl)-(7-oxa-bicyclo[2.2.1]hept-2-yl)-amine A suspension of 1-benzenesulfonyl-4-chloro-5-nitro-1H-pyrrolo[2,3-b]pyridine (1.44 g, 4.26 mmol), crude endo-7-oxa-bicyclo[2.2.1]hept-2-ylamine (4.48 mmol), diisopropylethylamine (0.89 ml, 5.11 mmol) in propan-2-ol (25 ml) was heated at 85° C. for 18 h. The mixture was then cooled to 25° C. and stirred for 4 h. The resulting yellow solid was collected by vacuum filtration, washed with propan-2-ol (1×20 ml), and was air-dried to afford endo-(1-benzenesulfonyl-5-nitro-1H-pyrrolo[2,3-b]pyridin-4-yl)-(7-oxa-bicyclo[2.2.1]hept-2-yl)-amine (1.54 g, 87% over 2 steps). LCMS (Method G, ESI): RT=1.08 min, m+H=415.2. This material was used in the next step below without additional purification or characterization.

Endo-1-Benzenesulfonyl-N-4-(7-oxa-bicyclo[2.2.1]hept-2-yl)-1H-pyrrolo[2,3-b]pyridine-4,5-diamine A suspension of endo-(1-benzenesulfonyl-5-nitro-1H-pyrrolo[2,3-b]pyridin-4-yl)-(7-oxa-bicyclo[2.2.1]hept-2-yl)-amine (1.54 g, 3.72 mmol) and palladium on carbon (0.40 g, 10%, wet, Degussa, E101 NE/W) in DMF (160 ml) was stirred under a hydrogen atmosphere (2 balloons) at 50° C. for 13 h. The reaction mixture was cooled to 25° C. and was filtered through Celite. The Celite was washed with DMF (1×20 ml), and the combined filtrate and washings were concentrated under reduced pressure. Purification of the residue by column chromatography on silica gel (gradient: 2 to 9% $CH_3OH$ in $CH_2Cl_2$) afforded endo-1-benzenesulfonyl-N-4-(7-oxa-bicyclo[2.2.1]hept-2-yl)-1H-pyrrolo[2,3-b]pyridine-4,5-diamine (1.50 g, 104%) as a black foam. A portion of this material was used in the next step below without additional purification or characterization.

Endo-6-Benzenesulfonyl-2-methyl-1-(7-oxa-bicyclo[2.2.1]hept-2-yl)-1,6-dihydro-1,2,3,5,6-tetraaza-as-indacene p-Toluenesulfonic acid monohydrate (0.209 g, 1.10 mmol) was added to a solution of endo-1-benzenesulfonyl-N-4-(7-oxa-bicyclo[2.2.1]hept-2-yl)-1H-pyrrolo[2,3-b]pyridine-4,5-diamine (0.384 g, 1.00 mmol) and triethyl orthoacetate (0.458 ml, 2.50 mmol) in toluene (15 ml) at 25° C. The reaction mixture was heated at 105° C. for 2 h, then was cooled to 25° C. and was partitioned between half-saturated $NaHCO_3$ (100 ml) and EtOAc (2×125 ml). The organic layers were dried over $MgSO_4$, filtered, and the filtrate was concentrated under reduced pressure. Purification of the resulting solid by column chromatography on silica gel (gradient: 0 to 8% $CH_3OH$ in $CH_2Cl_2$) afforded endo-6-benzenesulfonyl-2-methyl-1-(7-oxa-bicyclo[2.2.1]hept-2-yl)-1,6-dihydro-1,2,3,5,6-tetraaza-as-indacene as an off-white foam. LCMS (Method G, ESI): RT=0.82 min, m+H=409.3. This material was used in the next step below without additional characterization.

Endo-2-Methyl-1-(7-oxa-bicyclo[2.2.1]hept-2-yl)-1,6-dihydro-1,2,3,5,6-tetraaza-as-indacene Sodium hydroxide (3 ml of a 1.0 M solution in water, 3 mmol) was added to a solution of endo-6-benzenesulfonyl-2-methyl-1-(7-oxa-bicyclo[2.2.1]hept-2-yl)-1,6-dihydro-1,2,3,5,6-tetraaza-as-indacene (1.00 mmol) in a 1:1 mixture of EtOH and THF (12 ml) at 25° C. The reaction mixture was stirred at 50° C. for 2 h, then was partitioned between half-saturated $NaHCO_3$ (100 ml) and EtOAc (2×125 ml). The combined organic layers were dried over $MgSO_4$, filtered, and the filtrate was concentrated under reduced pressure. The residue was triturated with DMF (3 ml) to give a solid which was collected by filtration, washed with $Et_2O$ (15 ml), and air-dried to give endo-2-methyl-1-(7-oxa-bicyclo[2.2.1]hept-2-yl)-1,6-dihydro-1,2,3,5,6-tetraaza-as-indacene (0.023 g, 9% over 3 steps) as grey solid. LCMS (Method N, ESI): RT=5.76 min, m+H=269.0; $^1H$ NMR (400 MHz, DMSO) δ 11.84 (s, 1H), 8.48 (s, 1H), 7.48 (t, J=2.7 Hz, 1H), 6.65 (s, 1H), 5.24-5.13 (m, 1H), 4.82 (t, J=4.9 Hz, 2H), 2.73 (s, 3H), 2.47 (d, J=5.6 Hz, 1H), 2.43-2.31 (m, 1H), 1.96-1.84 (m, 1H), 1.82-1.68 (m, 1H), 1.58-1.45 (m, 1H), 1.42-1.31 (m, 1H).

Example 685

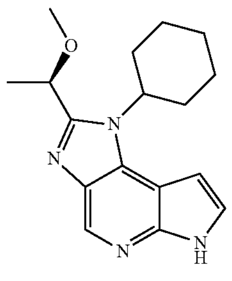 [SMILES: CO[C@H](C)c1nc2cnc3[nH]ccc3c2n1C1CCCCC1]

1-Cyclohexyl-2-((R)-1-methoxy-ethyl)-1,6-dihydro-1,2,3,5,6-tetraaza-as-indacene (R)-2-Methoxy-propionamide Oxalyl chloride (5.28 ml of a 2.0 M solution in $CH_2Cl_2$, 10.6 mmol) was added to a solution of (R)-2-methoxy-propionic acid (1.0 g, 9.60 mmol) and DMF (1 drop) in $CH_2Cl_2$ (20 ml) at 25° C. The reaction mixture was stirred at 25° C. for 1.5 h, then ammonia (86.4 ml of a 0.5 M solution in 1,4-dioxane, 43.2 mmol) was added. After stirring for 4 h at 25° C., the mixture was filtered and the collected solid was washed with $CH_2Cl_2$ (1×25 ml). The filtrate was concentrated under reduced pressure to approximately 30 ml volume whereupon a white precipitate appeared. Heptanes (70 ml) were added and the resulting solid was collected by filtration and air-dried to give (R)-2-methoxy-propionamide (0.611 g 62%) as a white solid. $^1$H NMR (400 MHz, $CDCl_3$) δ 6.53 (s, 1H), 6.18 (s, 1H), 3.74 (q, J=6.8 Hz, 1H), 3.41 (s, 3H), 1.40 (d, J=6.8 Hz, 3H).

6-Benzenesulfonyl-1-cyclohexyl-2-((R)-1-methoxy-ethyl)-1,6-dihydro-1,2,3,5,6-tetraaza-as-indacene Triethyloxonium tetrafluoroborate (0.333 g, 1.75 mmol) was added to a solution of (R)-2-methoxy-propionamide (0.181 g, 1.75 mmol) in THF (25 ml) at 25° C. The resulting suspension was stirred at 25° C. for 1.5 h, then was concentrated under reduced pressure to afford an oil. This material was dissolved in EtOH (15 ml) and the resulting solution was added to 1-benzenesulfonyl-N-4-cyclohexyl-1H-pyrrolo[2,3-b]pyridine-4,5-diamine (0.260 g, 0.702 mmol) in EtOH (4 ml) at 25° C. The reaction mixture was heated at 75° C. for 1 h, then was cooled to 25° C. and was concentrated under reduced pressure. The residue was partitioned between half-saturated $NaHCO_3$ (100 ml) and EtOAc (2×100 ml). The organic layers were dried over $MgSO_4$, filtered, and the filtrate was concentrated under reduced pressure. Purification of the resulting solid by column chromatography on silica gel (gradient: 0 to 7% $CH_3OH$ in $CH_2Cl_2$) afforded 6-benzenesulfonyl-1-cyclohexyl-2-((R)-1-methoxy-ethyl)-1,6-dihydro-1,2,3,5,6-tetraaza-as-indacene as a greenish solid. LCMS (Method G, ESI): RT=1.15 min, m+H=439.3. This material was used in the next step below without additional characterization.

1-Cyclohexyl-2-((R)-1-methoxy-ethyl)-1,6-dihydro-1,2,3,5,6-tetraaza-as-indacene

Sodium hydroxide (1 ml of a 1.0 M solution in water, 1 mmol) was added to a solution of 6-benzenesulfonyl-1-cyclohexyl-2-((R)-1-methoxy-ethyl)-1,6-dihydro-1,2,3,5,6-tetraaza-as-indacene (0.702 mmol) in a 1:1 mixture of THF and EtOH (16 ml) at 25° C. The reaction mixture was stirred at 50° C. for 1 h, then was cooled to 25° C. and was partitioned between half-saturated $NaHCO_3$ (100 ml) and EtOAc (2×125 ml). The combined organic layers were dried over $MgSO_4$, filtered, and the filtrate was concentrated under reduced pressure. Trituration of the residue with EtOAc (15 ml) produced a solid which was filtered, washed with $Et_2O$ (10 ml) and air-dried to give 1-cyclo hexyl-2-((R)-1-methoxy-ethyl)-1,6-dihydro-1,2,3,5,6-tetraaza-as-indacene (0.091 g, 42% over 2 steps) as a grey solid. LCMS (Method N, ESI): RT=3.67 min, m+H=299.1; 1; $^1$H NMR (500 MHz, DMSO) δ 11.90 (s, 1H), 8.58 (s, 1H), 7.50 (s, 1H), 6.76 (s, 1H), 5.00-4.94 (m, 1H), 4.75-4.63 (m, 1H), 3.26 (s, 3H), 2.45-2.26 (m, 2H), 2.04-1.93 (m, 2H), 1.87 (s, 2H), 1.80 (s, 1H), 1.63 (d, J=6.3 Hz, 3H), 1.57-1.45 (m, 3H).

Example 686

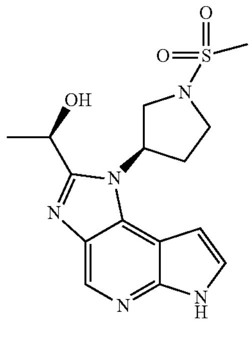 [SMILES: C[C@@H](O)c1nc2cnc3[nH]ccc3c2n1[C@@H]1CCN(S(C)(=O)=O)C1]

(R)-1-[1-((R)-1-Methanesulfonyl-pyrrolidin-3-yl)-1,6-dihydro-1,2,3,5,6-tetraaza-as-indacen-2-yl]-ethanol (R)-3-(1-Benzenesulfonyl-5-nitro-1H-pyrrolo[2,3-b]pyridin-4-ylamino)-pyrrolidine-1-carboxylic acid tert-butyl ester A suspension of 1-benzenesulfonyl-4-chloro-5-nitro-1H-pyrrolo[2,3-b]pyridine (8.16 g, 24.2 mmol), (R)-3-amino-pyrrolidine-1-carboxylic acid tert-butyl ester (5.00 g, 26.8 mmol), and diisopropylethylamine (5.14 ml, 29.5 mmol) in propan-2-ol (150 ml) was heated at 80° C. for 13 h. The mixture was then cooled to 25° C. and stirred for 4 h. The resulting yellow solid was collected by vacuum filtration, washed with heptanes (1×20 ml), and was air-dried to afford (R)-3-(1-benzenesulfonyl-5-nitro-1H-pyrrolo[2,3-b]pyridin-4-ylamino)-pyrrolidine-1-carboxylic acid tert-butyl ester (9.90 g, 88%). LCMS (Method G, ESI): RT=1.19 min, m+H=488.3. This material was used in the next step below without additional purification or characterization.

(R)-3-(5-Amino-1-benzenesulfonyl-1H-pyrrolo[2,3-b]pyridin-4-ylamino)-pyrrolidine-1-carboxylic acid tert-butyl ester A suspension of (R)-3-(1-benzenesulfonyl-5-nitro-1H-pyrrolo[2,3-b]pyridin-4-ylamino)-pyrrolidine-1-carboxylic acid tert-butyl ester (9.90 g, 20.3 mmol) and palladium on carbon (1.0 g, 10%, wet, Degussa, E101 NE/W) in a 4:1 mixture of THF and EtOH (150 ml) was stirred under a hydrogen atmosphere (2 balloons) at 50° C. for 18 h. The reaction mixture was cooled to 25° C. and was filtered through Celite. The Celite was washed with THF (1×20 ml), and the combined filtrate and washings were concentrated under reduced pressure to give (R)-3-(5-amino-1-benzenesulfonyl-1H-pyrrolo[2,3-b]pyridin-4-ylamino)-pyrrolidine-1-carboxylic acid tert-butyl ester (9.81 g, 99%) as a brown foam. LCMS (Method G, ESI): RT=0.83 min, m+H=458.3. This material was used in the next step below without additional purification or characterization.

(R)-3-[6-Benzenesulfonyl-2-((R)-1-hydroxy-ethyl)-6H-1,2,3,5,6-tetraaza-as-indacen-1-yl]-pyrrolidine-1-carboxylic acid tert-butyl ester Triethyloxonium tetrafluoroborate (6.11 g, 32.2 mmol) was added to a solution of (R)-(+)-lactamide (2.86 g, 32.2 mmol) in THF (100 ml) at 25° C. The resulting suspension was stirred at 25° C. for 1.5 h, then was concentrated under reduced pressure to afford an oil. This material was dissolved in EtOH (100 ml) at 25° C. and (R)-3-(5-amino-1-benzenesulfonyl-1H-pyrrolo[2,3-b]pyridin-4-ylamino)-pyrrolidine-1-carboxylic acid tert-butyl ester (9.81 g, 21.4 mmol) was added to the resulting solution. The reaction mixture was heated at 75° C. for 1 h, then was cooled to 25° C. and was concentrated under reduced pressure. The residue was partitioned between half-saturated $NaHCO_3$ (150 ml) and EtOAc (2×225 ml). The organic layers were dried over $MgSO_4$, filtered, and the filtrate was concentrated under reduced pressure. Purification of the residue by column chromatography on silica gel (gradient: 0 to 7% $CH_3OH$ in $CH_2Cl_2$) afforded (R)-3-[6-benzenesulfonyl-2-((R)-1-hydroxy-ethyl)-6H-1,2,3,5,6-tetraaza-as-indacen-1-yl]-pyrrolidine-1-carboxylic acid tert-butyl ester (20.6 g, 187%; dark brown oil) still containing some impurities. LCMS (Method G, ESI): RT=0.99 min, m+H=512.4. This material was used in the next step below without additional characterization or purification.

(R)-1-((R)-6-Benzenesulfonyl-1-pyrrolidin-3-yl-1,6-dihydro-1,2,3,5,6-tetraaza-as-indacen-2-yl)-ethanol A 4.0 M solution of HCl in 1,4-dioxane (20 ml) was added to (R)-3-[6-benzenesulfonyl-2-((R)-1-hydroxy-ethyl)-6H-1,2,3,5,6-tetraaza-as-indacen-1-yl]-pyrrolidine-1-carboxylic acid tert-butyl ester prepared above (20.6 g) dissolved in 1,4-dioxane (20 ml) at 25° C. The resulting brown suspension mixture was stirred at 25° C. for 3.5 h, then was concentrated under reduced pressure. The residue was partitioned between half-saturated $NaHCO_3$ (150 ml) and EtOAc (2×250 ml). The combined organic layers were dried over $MgSO_4$, filtered, and the filtrate was concentrated under reduced pressure. The residue was triturated with heptanes (20 ml) and the resulting solid was collected by filtration and air-dried overnight to give (R)-1-((R)-6-benzenesulfonyl-1-pyrrolidin-3-yl-1,6-dihydro-1,2,3,5,6-tetraaza-as-indacen-2-yl)-ethanol (1.49 g, 17% over 2 steps) as a beige solid. This material was used in the next step below without additional characterization or purification.

Example 687

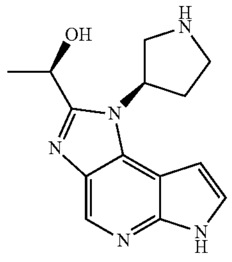 [SMILES: C[C@@H](O)c1nc2cnc3[nH]ccc3c2n1[C@@H]1CCNC1]

(R)-1-((R)-1-Pyrrolidin-3-yl-1,6-dihydro-1,2,3,5,6-tetraaza-as-indacen-2-yl)-ethanol Sodium hydroxide (1 ml of a 1.0 M solution in water, 1 mmol) was added to a solution of (R)-1-((R)-6-benzenesulfonyl-1-pyrrolidin-3-yl-1,6-dihydro-1,2,3,5,6-tetraaza-as-indacen-2-yl)-ethanol (0.200 g, 0.486 mmol) in a 1:1 mixture of THF and EtOH (4 ml) at 25° C. The reaction mixture was stirred at 50° C. for 4 h, then was cooled to 25° C. 1.0 M HCl (1 ml) and saturated $NaHCO_3$ (0.50 ml) were then added sequentially. After stirring for an additional 10 min at 25° C., the reaction mixture was concentrated under reduced pressure. The solid thus obtained was suspended in DMF (2 ml) and the resulting mixture was filtered through a 0.45 um syringe filter. The filtrate was purified by preparative HPLC (column: Gemini-NX, 21.2×100 mm, 10 um; detection: UV 254 nm and mass, mobile phase A: water w/0.1% formic acid; mobile phase B: $CH_3CN$; flowrate: 35 ml/min; gradient 5-85% B over 9.5 min) to give (R)-1-((R)-1-pyrrolidin-3-yl-1,6-dihydro-1,2,3,5,6-tetraaza-as-indacen-2-yl)-ethanol (0.026 g, 20%) as an off-white solid. LCMS (Method C, ESI): RT=1.18 min, m+H=272.0.

(R)-1-[6-Benzenesulfonyl-1-((R)-1-methanesulfonyl-pyrrolidin-3-yl)-1,6-dihydro-1,2,3,5,6-tetraaza-as-indacen-2-yl]-ethanol Methanesulfonyl chloride (0.062 ml, 0.802 mmol) was added to a solution of (R)-1-((R)-6-benzenesulfonyl-1-pyrrolidin-3-yl-1,6-dihydro-1,2,3,5,6-tetraaza-as-indacen-2-yl)-ethanol (0.300 g, 0.729 mmol) and diisopropylethylamine (0.254 ml, 1.46 mmol) in $CH_2Cl_2$ (8 ml) at 25° C. The reaction mixture was stirred for 4 h at 25° C., then was partitioned between half-saturated $NaHCO_3$ (5 ml) and $CH_2Cl_2$ (2 ml). The phases were separated using a phase separation column (Biotage) and the organic layer was concentrated under reduced pressure to give crude (R)-1-[6-benzenesulfonyl-1-((R)-1-methanesulfonyl-pyrrolidin-3-yl)-1,6-dihydro-1,2,3,5,6-tetraaza-as-indacen-2-yl]-ethanol. This material was used in the next step below without additional purification or characterization.

(R)-1-[1-((R)-1-Methanesulfonyl-pyrrolidin-3-yl)-1,6-dihydro-1,2,3,5,6-tetraaza-as-indacen-2-yl]-ethanol Sodium hydroxide (1 ml of a 1.0 M solution in water, 1 mmol) was added to a solution of crude (R)-1-[6-benzenesulfonyl-1-((R)-1-methanesulfonyl-pyrrolidin-3-yl)-1,6-dihydro-1,2,3,5,6-tetraaza-as-indacen-2-yl]-ethanol (0.729 mmol) in a 1:1 mixture of THF and EtOH (4 ml) at 25° C. The reaction mixture was stirred at 50° C. for 4 h, then was cooled to 25° C. 1.0 M HCl (1 ml) and saturated $NaHCO_3$ (0.50 ml) were then added sequentially. After stirring for an additional 10 min at 25° C., the reaction mixture was concentrated under reduced pressure. The solid thus obtained was suspended in DMF (2 ml) and the resulting mixture was filtered through a 0.45 um syringe filter. The filtrate was purified by preparative HPLC (column: Gemini-NX, 21.2×100 mm, 10 um; detection: UV 254 nm and mass, mobile phase A: water w/0.1% formic acid; mobile phase B: $CH_3CN$; flowrate: 35 ml/min; gradient 5-85% B over 9.5 min) to give (R)-1-[1-((R)-1-methanesulfonyl-pyrrolidin-3-yl)-1,6-dihydro-1,2,3,5,6-tetraaza-as-indacen-2-yl]-ethanol (0.062 g, 24% over 2 steps) as an off-white solid. LCMS (Method C, ESI): RT=1.77 min, m+H=350.2; $^1H$ NMR (400 MHz, DMSO) δ 11.90 (s, 1H), 8.58 (s, 1H), 7.51 (t, J=2.9 Hz, 1H), 6.73 (s, 1H), 5.82 (dd, J=19.5, 9.7 Hz, 1H), 5.75 (d, J=6.5 Hz, 1H), 5.18 (p, J=6.4 Hz, 1H), 3.92-3.78 (m, 2H), 3.73-3.65 (m, 1H), 3.48 (td, J=10.2, 6.5 Hz, 1H), 3.08 (s, 3H), 2.76-2.60 (m, 1H), 2.44 (dd, J=12.5, 6.7 Hz, 1H), 1.65 (d, J=6.5 Hz, 3H).

Example 688

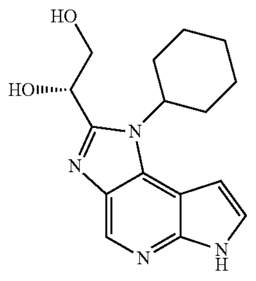 [SMILES: OC[C@@H](O)c1nc2cnc3[nH]ccc3c2n1C1CCCCC1]

(S)-1-(1-Cyclohexyl-1,6-dihydro-1,2,3,5,6-tetraaza-as-indacen-2-yl)-ethane-1,2-diol 6-Benzenesulfonyl-1-cyclohexyl-1,6-dihydro-1,2,3,5,6-tetraaza-as-indacene A suspension of 1-(benzenesulfonyl)-N-4-cyclohexyl-pyrrolo[2,3-b]pyridine-4,5-diamine (7.80 g, 21 mmol) in triethyl orthoformate (48 ml) was heated at 82° C. overnight. LC/MS shows reaction complete. Reaction cooled to room temperature and concentrated under reduced pressure to give a purple blackish solid which was then purified by flash column chromatography (silica, 120 g, ISCO, 60 mL/min, 0-100% Ethyl acetate in heptane in 24 mins, 100% Ethyl acetate for 25 mins) to give 5.34 g (67.6%) of 6-Benzenesulfonyl-1-cyclohexyl-1,6-dihydro-1,2,3,5,6-tetraaza-as-indacene as a white solid. LCMS (Method M, ESI): RT=2.27 min, m+H=381.3.

1-(6-Benzenesulfonyl-1-cyclohexyl-1,6-dihydro-1,2,3,5,6-tetraaza-as-indacen-2-yl)-2-benzyloxy-ethanol 6-Benzenesulfonyl-1-cyclohexyl-1,6-dihydro-1,2,3,5,6-tetraaza-as-indacene (5.34 g, 14.0 mmol) was dissolved in anhydrous tetrahydrofuran (100 ml) under a nitrogen atmosphere. The reaction mixture was cooled to 0° C., and then a 1 M solution of 2,2,6,6-tetramethylpiperidinemagnesiumchloride lithium chloride complex solution in tetrahydrofuran (16.8 mL, 16.8 mmol) was added and stirred at 0° C. for 1 hour under nitrogen. The cold reaction mixture was then added to a solution of Benzyloxyacetaldehyde (3.95 mL, 28.07 mmol) in tetrahydrofuran (35 mL) at 0° C. and stirring was continued overnight, warming to room temperature in the process. LC/MS shows reaction complete. Reaction quenched by adding 50 mL sat. ammonium chloride solution and extracting with ethyl acetate (3×75 mL). The combined ethyl acetate layers were dried with solid anhydrous magnesium sulfate, filtered and concentrated to give a brownish foamy solid. The residue was then purified by flash column chromatography (silica, ISCO, 120 g, 60 mL/min, 0-100% Ethyl acetate in heptane in 24 mins, 100% Ethyl acetate for 25 mins) to give 6.56 g (87.9%) of 1-(6-Benzenesulfonyl-1-cyclohexyl-1,6-dihydro-1,2,3,5,6-tetraaza-as-indacen-2-yl)-2-benzyloxy-ethanol (racemic mixture) as a foamy off white solid. LCMS (Method M, ESI): RT=2.71 min, m+H=531.3.

(S)-2-Benzyloxy-1-(1-cyclohexyl-1,6-dihydro-1,2,3,5,6-tetraaza-as-indacen-2-yl)-ethanol and (R)-2-Benzyloxy-1-(1-cyclohexyl-1,6-dihydro-1,2,3,5,6-tetraaza-as-indacen-2-yl)-ethanol To a solution of 1-(6-Benzenesulfonyl-1-cyclohexyl-1,6-dihydro-1,2,3,5,6-tetraaza-as-indacen-2-yl)-2-benzyloxy-ethanol (racemic mixture) (6.56 g, 12.4 mmol) in ethyl alcohol (50.0 ml) was added 1N sodium hydroxide solution in water (24.72 mL, 24.72 mmol), and stirred at room temperature overnight. The reaction mixture was concentrated under reduced pressure and the residue obtained was neutralized with 1 N HCl, then concentrated under reduced pressure and the residue azeotroped with ethyl alcohol (2×50 mL). The residue was then treated with 100 mL of ethyl alcohol and filtered, and the filtrate was concentrated to give a foamy off white solid, which was then purified by chiral SFC using the conditions below to afford the indicated amounts of title compounds.

Mobile Phase A: $CO2$

Mobile phase B: Methanol with 0.1% dimethylamine

Isocratic conditions with 30% Mobile phase B

Flow Rate: 200 mL/min

Column: Lux Cellulose-1, 3×25 cm, 5 um

Outlet pressure: 100 Bar

Temperature: 40 degrees C.

System: Thar 350

Uv: 230 nm

Runtime: 5.2 minutes 2.12 g (43.9%) of (S)-1-(S)-2-Benzyloxy-1-(1-cyclohexyl-1,6-dihydro-1,2,3,5,6-tetraaza-as-indacen-2-yl)-ethanol. LCMS (Method N, ESI): RT=10.69 min, m+H=391.1. $^1$H NMR (400 MHz, DMSO) δ 11.82 (s, 1H), 8.53 (s, 1H), 8.18 (s, 1H), 7.60 (dd, J=7.5, 1.9 Hz, 1H), 7.46 (t, J=2.9 Hz, 1H), 7.40-7.24 (m, 7H), 6.73 (s, 1H), 5.92 (d, J=6.5 Hz, 1H), 5.17 (dd, J=11.6, 6.8 Hz, 1H), 4.79 (t, J=12.2 Hz, 1H), 4.66-4.56 (m, 2H), 4.05 (dd, J=10.1, 4.6 Hz, 1H), 3.93 (dd, J=10.0, 7.4 Hz, 1H), 2.31 (d, J=12.7 Hz, 3H), 1.86 (dd, J=37.8, 21.4 Hz, 6H), 1.47 (d, J=7.7 Hz, 4H) and 1.53 g (31.7%) of (R)-2-Benzyloxy-1-(1-cyclohexyl-1,6-dihydro-1,2,3,5,6-tetraaza-as-indacen-2-yl)-ethanol. LCMS (Method N, ESI): RT=10.65 min, m+H=391.1. $^1$H NMR (400 MHz, DMSO) δ 11.82 (s, 1H), 8.53 (s, 1H), 7.46 (t, J=2.9 Hz, 1H), 7.38-7.25 (m, 6H), 6.73 (s, 1H), 5.92 (d, J=6.4 Hz, 1H), 5.17 (dd, J=11.5, 6.6 Hz, 1H), 4.79 (t, J=12.3 Hz, 1H), 4.59 (d, J=12.6 Hz, 2H), 4.05 (dd, J=10.1, 4.6 Hz, 1H), 3.93 (dd, J=10.1, 7.4 Hz, 1H), 2.31 (d, J=12.5 Hz, 3H), 1.86 (dd, J=36.9, 21.4 Hz, 6H), 1.47 (d, J=7.6 Hz, 4H).

(S)-1-(1-Cyclohexyl-1,6-dihydro-1,2,3,5,6-tetraaza-as-indacen-2-yl)-ethane-1,2-diol (S)-2-Benzyloxy-1-(1-cyclohexyl-1,6-dihydro-1,2,3,5,6-tetraaza-as-indacen-2-yl)-ethanol (2.064 g, 5.288 mmol) was dissolved in a mixture of ethanol (25 mL) and methanol (25 mL) by sonication for 20 minutes in a Parr bottle (500 mL). To the reaction mixture was then added 20% Palladium hydroxide in carbon (371.2 mg), followed by pressurization with hydrogen gas to 50 psi in a Parr reactor. The reaction mixture was shaken for 2 days in the Parr reactor. LC/MS shows reaction complete. Reaction filtered through celite 545 and concentrated under reduced pressure. The residue was then purified by reverse phase HPLC and SFC to give 253.1 mg (16.9%) of (S)-1-(1-Cyclohexyl-1,6-dihydro-1,2,3,5,6-tetraaza-as-indacen-2-yl)-ethane-1,2-diol. LCMS (Method N, ESI): RT=5.07 min, m+H=301.1. $^1$H NMR (400 MHz, DMSO) δ 11.82 (s, 1H), 8.54 (s, 1H), 8.18 (s, 1H), 7.46 (t, J=2.9 Hz, 1H), 6.74 (s, 1H), 5.77 (s, 1H), 4.94 (t, J=5.9 Hz, 1H), 4.83 (t, J=12.3 Hz, 2H), 3.90 (ddd, J=17.8, 11.1, 6.1 Hz, 3H), 2.31 (d, J=10.1 Hz, 3H), 1.94 (s, 5H), 1.80 (s, 1H), 1.50 (s, 4H).

Example 689

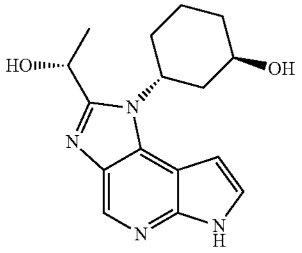 [SMILES: C[C@@H](O)c1nc2cnc3[nH]ccc3c2n1[C@@H]1CCC[C@@H](O)C1]

(1R,3R)-3-[2-((R)-1-Hydroxy-ethyl)-6H-1,2,3,5,6-tetraaza-as-indacen-1-yl]-cyclohexanol (1R,3R)-3-(1-Benzenesulfonyl-5-nitro-1H-pyrrolo[2,3-b]pyridin-4-ylamino) cyclohexanol A stirred suspension of 1-Benzenesulfonyl-4-chloro-5-nitro-1H-pyrrolo[2,3-b]pyridine (2.92 g, 8.65 mmol) and (1R,3R)-3-Amino-cyclohexanol (1.00 g, 8.68 mmol) in isopropyl alcohol (30 ml) was treated with N,N-diisoppropylethylamine (2.27 ml, 13 mmol) and heated at 82° C. overnight. LC/MS shows reaction complete. Reaction cooled to room temperature and used as is for the next step. LCMS (Method M, ESI): RT=2.52 min, m+H=417.3; 1H).

(1R,3R)-3-(5-Amino-1-benzenesulfonyl-1H-pyrrolo[2,3-b]pyridin-4-ylamino)-cyclohexanol To the reaction mixture from the above step containing (1R,3R)-3-(1-Benzenesulfonyl-5-nitro-1H-pyrrolo[2,3-b]pyridin-4-ylamino) cyclohexanol (8.65 mmol) in isopropyl alcohol (30 mL) was added 10% Palladium on activated carbon (718 mg). The reaction mixture was then capped with a 3 way glass valve with a hydrogen gas balloon. The flask was opened to vacuum for two minutes, followed by opening to hydrogen. This purge/flush cycle was repeated 3 times before stirring under a hydrogen atmosphere at room temperature for 2 days. LC/MS showed that the reaction went to completion. The reaction mixture was then filtered through celite 545 and concentrated to give a black foamy solid, which was used as is for the next step. LCMS (Method M, ESI): RT=1.44 min, m+H=386.8.

(R)-2-Hydroxy-propionimidic acid ethyl ester

To a solution of (R)-2-Hydroxy-propionamide (1.27 g, 14.3 mmol) in anhydrous tetrahydrofuran (30 mL) under a nitrogen atmosphere was added triethyloxonium tetrafluoroborate (2.79 g, 14.3 mmol). The reaction mixture was stirred at room temperature for 2 hours until it became homogeneous, and then was used as is for the next step.

(1R,3R)-3-[6-Benzenesulfonyl-2-((R)-1-hydroxy-ethyl)-6H-1,2,3,5,6-tetraaza-as-indacen-1-yl]-cyclohexanol To the reaction mixture containing (R)-2-Hydroxy-propionimidic acid ethyl ester (14.3 mmol) in tetrahydrofuran (30 mL) was added (1R,3R)-3-(5-Amino-1-benzenesulfonyl-1H-pyrrolo[2,3-b]pyridin-4-ylamino)-cyclohexanol (8.65 mmol) in ethyl alcohol (50 ml) and heated at 75° C. for 18 hours. The reaction was followed by LC/MS to completion. The reaction mixture was cooled to room temperature and concentrated under reduced pressure. The residue was then dissolved in 50 ml of ethyl acetate and treated with 50 mL of saturated sodium bicarbonate solution. The mixture was then stirred for 2 hours, then extracted with ethyl acetate (3×50 mL) and the combined ethyl acetate layers were dried with solid anhydrous magnesium sulphate. The mixture was then filtered and the filtrate was concentrated under reduced pressure to give a black oil. The oil was treated with 1 N HCl solution (75 mL) and hexanes (25 mL), followed by stirring for 30 minutes, after which the hexane layer was decanted off and discarded. The hexane wash was repeated twice more and then the 1 N HCl layer was concentrated under reduced pressure to give a black oil, which was used as is for the next step. LCMS (Method M, ESI): RT=1.72 min, m+H=441.2.

(1R,3R)-3-[2-((R)-1-Hydroxy-ethyl)-6H-1,2,3,5,6-tetraaza-as-indacen-1-yl]-cyclohexanol To a suspension of (1R,3R)-3-[6-Benzenesulfonyl-2-((R)-1-hydroxy-ethyl)-6H-1,2,3,5,6-tetraaza-as-indacen-1-yl]-cyclohexanol (8.65 mmol) in ethyl alcohol (30.00 mL) was added 1 N sodium hydroxide solution (52 mL, 52 mmol) and heated at 40° C. for 18 hours. The reaction mixture was cooled to room temperature and neutralized with 1 N HCl solution (44 mL, 44 mmol), then concentrated under reduced pressure. The residue was treated with ethyl alcohol (25 mL), stirred and filtered. The filtrate was concentrated under reduced pressure and the residue was purified twice by preparative SFC and then by reverse phase HPLC (conditions below) to give 1.34 g (50.7%) of (1R,3R)-3-[2-((R)-1-Hydroxy-ethyl)-6H-1,2,3,5,6-tetraaza-as-indacen-1-yl]-cyclohexanol. LCMS (Method O, ESI): RT=2.69 min, m+H=301.1; $^1$H NMR (400 MHz, DMSO) δ 11.80 (s, 1H), 8.52 (s, 1H), 7.45 (s, 1H), 6.66 (s, 1H), 5.62 (s, 1H), 5.32 (dd, J=14.7, 10.6 Hz, 1H), 5.10 (d, J=6.4 Hz, 1H), 4.68 (s, 1H), 4.22 (s, 1H), 2.45 (d, J=12.6 Hz, 1H), 2.28 (dd, J=23.3, 10.8 Hz, 1H), 1.98-1.76 (m, 5H), 1.69 (s, 2H), 1.61 (d, J=6.6 Hz, 3H).

SFC Purification Method 1:
- Mobile phase A: carbon dioxide
- Mobile phase B: Methanol w/0.1% NH4OH
- Ran under isocratic conditions at 20% Mobile phase B.
- Column: Diol from Peeke Scientific, 3×15 cm, 15 um.
- Flow Rate: 300 ml/min
- Backpressure setting: 100 Bar
- Temperature: 40 degrees C.
- Uv: 230 nm
- System: Thar 350

SFC Purification Method 2:
- Mobile phase A: carbon dioxide
- Mobile phase B: Methanol
- Ran under isocratic conditions at 30% Mobile phase B.
- Column: Chiralpak IA from Chiral Technologies, 5×25 cm, 20 um.
- Flow Rate: 300 ml/min
- Backpressure setting: 100 Bar
- Temperature: 40 degrees C.
- Uv: 230 nm
- System: Thar 350

Reverse Phase HPLC Purification Method:
- Mobile phase A: H2O with 0.1% NH4OH
- Mobile phase B: ACN Ran a 5-85% gradient in 10 minutes, at 11 minutes went to 95%, held for 2 minutes, then went back the initial 5% and held for 2 minutes Column: Gemini-NX (3×10 cm), 10 um Flow rate: 60 mL/min Uv: 230 nm System: Varian prostar with Galaxie software Example 690

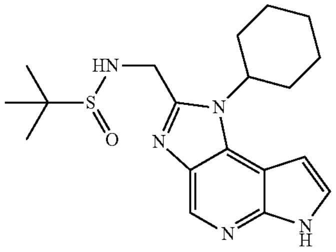 [SMILES: CC(C)(C)S(=O)NCc1nc2cnc3[nH]ccc3c2n1C1CCCCC1]

2-Methyl-propane-2-sulfinic acid (1-cyclohyl-1,6-dihydro-1,2,3,5,6-tetraaza-as-indacen-2-ylmethyl)-amide 2-Methyl-propane-2-sulfinic acid (6-benzenesulfonyl-1-cyclohyl-1,6-dihydro-1,2,3,5,6-tetraaza-as-indacen-2-ylmethyl)-amide To a solution of (6-benzenesulfonyl-1-cyclohyl-1,6-dihydro-1,2,3,5,6-tetraaza-as-indacen-2-yl)-methanol (0.320 g, 0.78 mmol) was added Dess-Martin periodinane (0.360 g, 0.86 mmol) in DCM (10 ml) at 25° C. The resulting suspension was stirred at 25° C. for 2 h, then filtered and the filtrate was concentrated under reduced pressure to afford a solid. This material was suspended in DCM (5 mL) and 2-Methyl-propane-2-sulfinic acid amide (0.200 g, 2.00 mmol), magnesium sulfate (1.00 g, 8.30 mmol) were added and the resulting suspension stirred at 25° C. for 20 h. Magnesium sulfate was removed by filtration and to the filtrate was added sodium borohydride (0.10 g, 3.00 mmol) and a few drops of methanol and stirred at 25° C. for 20 min. The reaction mixture was quenched with water, extracted with DCM (50 mL). The organic layer was dried over $Na_2SO_4$, filtered, and the filtrate was concentrated under reduced pressure. Purification of the resulting solid by column chromatography on silica gel (gradient: 0 to 20% acetone in $CH_2Cl_2$) afforded 2-Methyl-propane-2-sulfinic acid (6-benzenesulfonyl-1-cyclohyl-1,6-dihydro-1,2,3,5,6-tetraaza-as-indacen-2-ylmethyl)-amide (0.15 g, 60%). LCMS (Method G, ESI): RT=1.06 min, m+H=514.3. This material was used in the nt step below without additional characterization.

2-Methyl-propane-2-sulfinic acid (1-cyclohyl-1,6-dihydro-1,2,3,5,6-tetraaza-as-indacen-2-ylmethyl)-amide Sodium hydroxide (1 ml of a 1.0 M solution in water, 1 mmol) was added to a solution of 2-Methyl-propane-2-sulfinic acid (6-benzenesulfonyl-1-cyclohyl-1,6-dihydro-1,2,3,5,6-tetraaza-as-indacen-2-ylmethyl)-amide (0.15 g, 0.29 mmol) in EtOH (2 ml) at 25° C. The reaction mixture was stirred at 50° C. for 1 h, then was cooled to 25° C. and concentrated under reduced pressure. Purification of the residue by preparative HPLC (column: Gemini-NX, 5×10 cm, 10 um; detection: UV 254 nm, mobile phase A: water w/0.1% $NH_4OH$; mobile phase B: $CH_3CN$; flowrate: 120 ml/min; gradient 5-95% B over 15 min) afforded 2-Methyl-propane-2-sulfinic acid (6-benzenesulfonyl-1-cyclohyl-1,6-dihydro-1,2,3,5,6-tetraaza-as-indacen-2-ylmethyl)-amide (0.035 g, 32%) as an off-white solid. LCMS (Method C, ESI): RT=3.66 min, m+H=374.1; $^1$H NMR (400 MHz, DMSO) δ 11.84 (s, 1H), 8.54 (s, 1H), 7.47 (t, J=2.7 Hz, 1H), 6.73 (s, 1H), 5.91 (t, J=5.3 Hz, 1H), 4.69-4.55 (m, 1H), 4.49 (d, J=5.6 Hz, 2H), 2.38-2.20 (m, 2H), 1.93 (br s, 4H), 1.79 (br s, 1H), 1.49 (br s, 3H), 1.14 (s, 9H).

Example 691

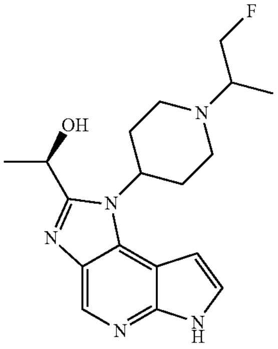 [SMILES: CC(CF)N1CCC(n2c([C@@H](C)O)nc3cnc4[nH]ccc4c32)CC1]

1-{1-[1-(2-Fluoro-1-methyl-ethyl)-piperidin-4-yl]-1,6-dihydro-1,2,3,5,6-tetraaza-as-indacen-2-yl}-ethanol Benzenesulfonyl-1-[1-(2-fluoro-1-methyl-ethyl)-piperidin-4-yl]-1,6-dihydro-1,2,3,5,6-tetraaza-as-indacen-2-yl}-ethanol To a suspension of (R)-1-(6-Benzenesulfonyl-1-piperidin-4-yl-1,6-dihydro-1,2,3,5,6-tetraaza-as-indacen-2-yl)-ethanol (0.15 g, 0.35 mmol) in acetone (2 mL) was added 2N HCl/ether (0.200 mL) and stirred for 20 min. The mixture was concentrated under reduced pressure. The residue was dissolved in methanol and fluoroacetone (0.10 g, 1.00 mmol) and sodium cyanoborohydride (0.06 g, 1.00 mmol) were added and stirred at ambient temperature for 20 h. The resulting reaction mixture was diluted with water and extracted with EtOAc (50 mL). The organic layer was washed with water, brine, dried over $Na_2SO_4$ and concentrated under pressure. Purification of the resulting solid by column chromatography on silica gel (5% MeOH in $CH_2Cl_2$) afforded (R)-1-{6-Benzenesulfonyl-1-[1-(2-fluoro-1-methyl-ethyl)-piperidin-4-yl]-1,6-dihydro-1,2,3,5,6-tetraaza-as-indacen-2-yl}-ethanol (0.06 g, 60%). LCMS (Method G, ESI): RT=0.6 min, m+H=486.3. This material was used in the nt step below without additional characterization.

1-{1-[1-(2-Fluoro-1-methyl-ethyl)-piperidin-4-yl]-1,6-dihydro-1,2,3,5,6-tetraaza-as-indacen-2-yl}-ethanol Sodium hydroxide (1 ml of a 1.0 M solution in water, 1 mmol) was added to a solution of (R)-1-{6-Benzenesulfonyl-1-[1-(2-fluoro-1-methyl-ethyl)-piperidin-4-yl]-1,6-dihydro-1,2,3,5,6-tetraaza-as-indacen-2-yl}-ethanol (0.15 g, 0.35 mmol) in EtOH (2 ml) at 25° C. The reaction mixture was stirred at 50° C. for 1 h, then was cooled to 25° C. and concentrated under reduced pressure. Purification of the resulting solid by column chromatography on silica gel (0-10% MeOH in $CH_2Cl_2$) and trituration of the residue with EtOAc/heptane afforded (0.02 g, 20%) as an off-white solid. LCMS (Method D, ESI): RT=2.4 min, m+H=345.1; 1H NMR (400 MHz, DMSO) δ 11.78 (s, 1H), 8.54 (s, 1H), 7.46 (s, 1H), 6.96 (s, 1H), 5.72-5.60 (m, 1H), 5.19-5.06 (m, 1H), 4.94-4.76 (m, 1H), 4.66-4.31 (m, 2H), 3.15-2.98 (m, 3H), 2.70-2.53 (m, 3H), 1.98-1.75 (m, 2H), 1.63 (d, J=5.8 Hz, 3H), 1.07 (d, J=6.4 Hz, 3H).

Example 692

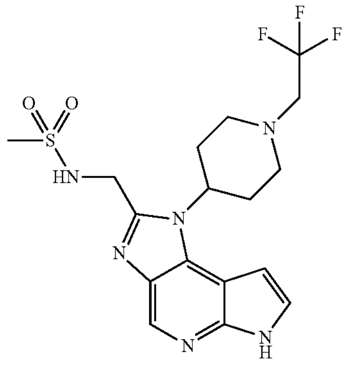 [SMILES: CS(=O)(=O)NCc1nc2cnc3[nH]ccc3c2n1C1CCN(CC(F)(F)F)CC1]

N-{1-[1-(2,2,2-Trifluoro-ethyl)-piperidin-4-yl]-1,6-dihydro-1,2,3,5,6-tetraaza-as-indacen-2-ylmethyl}-methanesulfonamide Benzenesulfonyl-2-chloromethyl-6H-1,2,3,5,6-tetraaza-as-indacen-1-yl)-piperidine-1-carboxylic acid tert-butyl ester A mixture of 4-(5-Amino-1-benzenesulfonyl-1H-pyrrolo[2,3-b]pyridin-4-ylamino)-piperidine-1-carboxylic acid tert-butyl ester (10.0 g, 21.2 mmol) and 1,1,1-triethoxychloroethane (20.0 g, 100 mmol) in acetic acid (30 mL) in 250 mL RB flask was lowered into an bath at 125° C. and heated for 20 min. The reaction mixture was cooled, diluted with DCM (200 mL) and stirred over saturated sodium bicarbonate until the bubbling stopped. The organic layer was washed with water, brine, dried over $Na_2SO_4$ and concentrated under reduced pressure. Trituration with EtOAc/heptane afforded 4-(6-benzenesulfonyl-2-chloromethyl-6H-1,2,3,5,6-tetraaza-as-indacen-1-yl)-piperidine-1-carboxylic acid tert-butyl ester (10.5 g, 93.4%) as a brown solid. M+1 (ESI)=531.3; 1H NMR (400 MHz, $CDCl_3$) δ 8.87 (s, 1H), 8.22 (d, J=7.9 Hz, 2H), 7.80 (d, J=3.9 Hz, 1H), 7.52 (m, 3H), 6.73 (d, J=3.9 Hz, 1H), 4.89 (s, 2H), 4.77-4.55 (m, 1H), 4.42 (s, 2H), 2.96 (s, 2H), 2.46 (dt, J=12.3, 8.3 Hz, 2H), 2.04 (s, 1H), 1.97 (d, J=12.5 Hz, 2H), 1.57 (s, 9H).

Benzenesulfonyl-1-piperidin-4-yl-1,6-dihydro-1,2,3,5,6-tetraaza-as-indacen-2-ylmethyl)-methanesulfonamide.HCl salt A mixture of 4-(6-benzenesulfonyl-2-chloromethyl-6H-1,2,3,5,6-tetraaza-as-indacen-1-yl)-piperidine-1-carboxylic acid tert-butyl ester (5.00 g; 9.40 mmol) and N-boc-methanesulfonamide (2.20 g, 11.0 mmol) and $K_2CO_3$ (2.60 g, 19.0 mmol) in DMF (50 mL) was heated at 50° C. for 24 h. Cooled, diluted with water and the solid was collected by filtration. The solid was dissolved in DCM (20 mL) and 4N HCl/dioxane (20 mL) was added and stirred at 25° C. for 20 h. The solid was collected by filtration, washed with ethyl acetate and dried in vav-oven at 50° C. to afford N-(6-benzenesulfonyl-1-piperidin-4-yl-1,6-dihydro-1,2,3,5,6-tetraaza-as-indacen-2-ylmethyl)-methanesulfonamide.HCl salt (3.2 g, 65%). LCMS (Method G, ESI): RT=0.58 min, m+H=489.3. This material was used in the nt step without further purification.

N-{6-Benzenesulfonyl-1-[1-(2,2,2-trifluoro-ethyl)-piperidin-4-yl]-1,6-dihydro-1,2,3,5,6-tetraaza-as-indacen-2-ylmethyl}-methanesulfonamide A mixture of 4-(6-benzenesulfonyl-1-piperidin-4-yl-1,6-dihydro-1,2,3,5,6-tetraaza-as-indacen-2-ylmethyl)-methanesulfonamide.HCl salt (0.20 g, 0.38 mmol), trifluoroethanol triflate (0.11 g, 0.46 mmol) and triethylamine (0.16 mL, 1.10 mmol) in DMF (3 mL) was heated at 50° C. for 20 h. The reaction mixture was cooled, diluted with water and extracted with DCM. The organic layer was washed with water, brine, dried over $Na_2SO_4$ and concentrated under reduced pressure. Purification of the resulting residue by column chromatography on silica gel (0-10% MeOH in $CH_2Cl_2$) afforded N-{6-Benzenesulfonyl-1-[1-(2,2,2-trifluoro-ethyl)-piperidin-4-yl]-1,6-dihydro-1,2,3,5,6-tetraaza-as-indacen-2-ylmethyl}-methanesulfonamide (0.05 g, 23%). The residue was dissolved in ethanol (1 mL) and sodium hydroxide (0.5 mL, 1M) and heated at 50° C. for 20 h. Cooled, concentrated under reduced pressure. Purification of the residue by column chromatography on silica gel (10% 2N ammonia/MeOH in DCM) afforded N-{1-[1-(2,2,2-trifluoro-ethyl)-piperidin-4-yl]-1,6-dihydro-1,2,3,5,6-tetraaza-as-indacen-2-ylmethyl}-methanesulfonamide (0.01 g, 27%). LCMS (Method D, ESI): RT=8.15 min, m+H=431.1; 1H NMR (400 MHz, $CDCl_3$) δ 9.64 (s, 1H), 8.67 (s, 1H), 7.33 (s, 1H), 6.93 (s, 1H), 6.85 (s, 1H), 4.67 (s, 2H), 4.55-4.38 (m, 1H), 3.23-3.01 (m, 5H), 2.75-2.46 (m, 3H), 1.75-1.62 (m, 2H).

Example 693

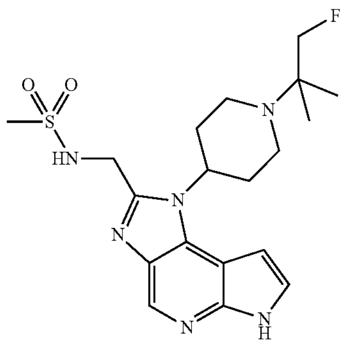 [SMILES: CC(C)(CF)N1CCC(n2c(CNS(C)(=O)=O)nc3cnc4[nH]ccc4c32)CC1]

N-{1-[1-(2-Fluoro-1,1-dimethyl-ethyl)-piperidin-4-yl]-1,6-dihydro-1,2,3,5,6-tetraaza-as-indacen-2-ylmethyl}-methanesulfonamide 2-{4-[6-benzenesulfonyl-2-(methanesulfonylamino-methyl)-6H-1,2,3,5,6-tetraaza-as-indacen-1-yl]-piperidin-1-yl}-2-methyl-propionic acid ethyl ester A mixture of 4-(6-benzenesulfonyl-1-piperidin-4-yl-1,6-dihydro-1,2,3,5,6-tetraaza-as-indacen-2-ylmethyl)-methanesulfonamide.HCl salt (0.67 g, 1.30 mmol), ethyl 2-bromoisobutyrate (0.50 g, 2.60 mmol) and $K_2CO_3$ (0.53 g; 3.8 mmol) in DMF (10 mL) was heated at 80° C. for 20 h. The reaction mixture cooled, diluted with water (50 mL) and extracted with toluene-EtOAc mixture (100 ml). The organic layer washed with brine, dried over $Na_2SO_4$ and concentrated under reduced pressure. Purification of the residue by column chromatography on silica gel (0-10% MeOH in DCM) afforded 2-{4-[6-benzenesulfonyl-2-(methanesulfonylamino-methyl)-6H-1,2,3,5,6-tetraaza-as-indacen-1-yl]-piperidin-1-yl}-2-methyl-propionic acid ethyl ester (0.42 g, 55%) as a foam. LCMS (Method G; ESI): RT+0.74 min, m+1=603.4

N-{6-Benzenesulfonyl-1-[1-(2-hydroxy-1,1-dimethyl-ethyl)-piperidin-4-yl]-1,6-dihydro-1,2,3,5,6-tetraaza-as-indacen-2-ylmethyl}-methanesulfonamide To an ice-cold solution of 2-{-4-[6-benzenesulfonyl-2-(methanesulfonylamino-methyl)-6H-1,2,3,5,6-tetraaza-as-indacen-1-yl]-piperidin-1-yl}-2-methyl-propionic acid ethyl ester (0.50 g, 0.80 mmol) in dry THF (10 mL) was added lithium aluminumhydride (0.8 mL; 2.00 mmol, 2M in THF) and stirred for 1 h. The reaction mixture was quenched with sodium hydroxide (10 mL; 1N) and extracted with EtOAc (50 mL). The organic layer separated, washed with brine, dried over $Na_2SO_4$ and concentrated under reduced pressure to obtain N-{6-benzenesulfonyl-1-[1-(2-hydroxy-1,1-dimethyl-ethyl)-piperidin-4-yl]-1,6-dihydro-1,2,3,5,6-tetraaza-as-indacen-2-ylmethyl}-methanesulfonamide (0.4 g, 80%). LCSM (Method G; ESI): RT=0.6 min; m+1=561.3. This material was used without further purification in the nt step below.

N-{6-Benzenesulfonyl-1-[1-(2-fluoro-1,1-dimethyl-ethyl)-piperidin-4-yl]-1,6-dihydro-1,2,3,5,6-tetraaza-as-indacen-2-ylmethyl}-methanesulfonamide To a solution of N-{6-benzenesulfonyl-1-[1-(2-hydroxy-1,1-dimethyl-ethyl)-piperidin-4-yl]-1,6-dihydro-1,2,3,5,6-tetraaza-as-indacen-2-ylmethyl}-methanesulfonamide (0.15 g, 0.27 mmol) in DCM (20 mL) was added DAST (0.2 mL, 2.0 mmol) and stirred for 20 min. The reaction mixture was partitioned between water and DCM and the organic layer separated, washed with brine, dried over $Na_2SO_4$ and concentrated under reduced pressure. Purification with column chromatography on silica gel (0-10% MeOH in DCM) afforded N-{6-benzenesulfonyl-1-[1-(2-fluoro-1,1-dimethyl-ethyl)-piperidin-4-yl]-1,6-dihydro-1,2,3,5,6-tetraaza-as-indacen-2-ylmethyl}-methanesulfonamide (0.10 g; 70%). LCMS (Method G; ESI): RT=0.69 min; m+1=563.4.

N-{1-[1-(2-Fluoro-1,1-dimethyl-ethyl)-piperidin-4-yl]-1,6-dihydro-1,2,3,5,6-tetraaza-as-indacen-2-ylmethyl}-methanesulfonamide N-{6-Benzenesulfonyl-1-[1-(2-fluoro-1,1-dimethyl-ethyl)-piperidin-4-yl]-1,6-dihydro-1,2,3,5,6-tetraaza-as-indacen-2-ylmethyl}-methanesulfonamide (0.10 g; 0.2 mmol) was converted to N-{1-[1-(2-Fluoro-1,1-dimethyl-ethyl)-piperidin-4-yl]-1,6-dihydro-1,2,3,5,6-tetraaza-as-indacen-2-ylmethyl}-methanesulfonamide (0.03 g, 40%) as described above using 1M sodium hydroxide. LCMS (Method D; ESI): RT=2.55 min; m+1=423.1.

Example 694

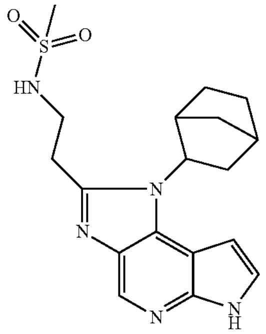 [SMILES: CS(=O)(=O)NCCc1nc2cnc3[nH]ccc3c2n1C1CC2CCC1C2]

N-[2-(1-Bicyclo[2.2.1]hept-2-yl-1,6-dihydro-1,2,3,5,6-tetraaza-as-indacen-2-yl)-ethyl]-methanesulfonamide N-[1-Benzenesulfonyl-4-(bicyclo[2.2.1]hept-2-ylamino)-1H-pyrrolo[2,3-b]pyridin-5-yl]-2-cyano-acetamide Cyanoacetic acid (0.267 g, 3.14 mmol), HATU (1.29 g, 3.40 mmol), and diisopropylethylamine (1.37 ml, 7.84 mmol) were added sequentially to a solution of 1-benzenesulfonyl-bicyclo[2.2.1]hept-2-yl-1H-pyrrolo[2,3-b]pyridine-4,5-diamine (1.00 g, 2.61 mmol) in DMF (10 ml) at 25° C. The reaction mixture was stirred for 18 h at 25° C., diluted with water and the solid was collected. The solid was dissolved in DCM (100 mL) and the organic layer was washed with water, brine, dried over $Na_2SO_4$ and concentrated under reduced pressure. Purification of the residue by column chromatography on silica gel (10-40% acetone in heptane) provided N-[1-benzenesulfonyl-4-(bicyclo[2.2.1]hept-2-ylamino)-1H-pyrrolo[2,3-b]pyridin-5-yl]-2-cyano-acetamide (0.7 g, 58%). LCMS (Method G, ESI): RT=1.02 min, m+H=450.3. This material was used in the nt step below without additional purification or characterization.

(6-Benzenesulfonyl-1-bicyclo[2.2.1]hept-2-yl-1,6-dihydro-1,2,3,5,6-tetraaza-as-indacen-2-yl)-acetonitrile N-[1-benzenesulfonyl-4-(bicyclo[2.2.1]hept-2-ylamino)-1H-pyrrolo[2,3-b]pyridin-5-yl]-2-cyano-acetamide (0.7 g, 1.5 mmol) in acetic acid (3 mL) was heated at 100° C. for 6 h. Cooled, diluted with DCM (100 mL), stirred over sodium bicarbonate solution. Organic layer washed with water, brine, dried over $Na_2SO_4$ and concentrated under reduced pressure. Purification of the residue by column chromatography on silica gel (0-10% acetone in DCM) afforded (6-benzenesulfonyl-1-bicyclo[2.2.1]hept-2-yl-1,6-dihydro-1,2,3,5,6-tetraaza-as-indacen-2-yl)-acetonitrile (0.3 g, 44%) as a foam. LCMS (Method G, ESI): RT=1.07 min, m+H=432.3; $^1$H NMR (400 MHz, $CDCl_3$) δ 8.86 (s, 1H), 8.22 (d, J=7.8 Hz, 2H), 7.82 (d, J=4.1 Hz, 1H), 7.63-7.40 (m, 3H), 6.78 (d, J=4.1 Hz, 1H), 4.66-4.47 (m, 1H), 4.19 (s, 2H), 2.78-2.56 (m, 2H), 2.35-2.08 (m, 2H), 1.92-1.67 (m, 3H), 1.56-1.35 (m, 3H).

2-(6-Benzenesulfonyl-1-bicyclo[2.2.1]hept-2-yl-1,6-dihydro-1,2,3,5,6-tetraaza-as-indacen-2-yl)-ethylamine A squirt of Raney-Ni suspension was washed with water (2.2 mL) and to this were added (6-benzenesulfonyl-1-bicyclo[2.2.1]hept-2-yl-1,6-dihydro-1,2,3,5,6-tetraaza-as-indacen-2-yl)-acetonitrile (0.25 g, 0.58 mmol), ethanol (5 mL) and stirred under a hydrogen atmosphere (balloon). The reaction mixture was filtered through Celite and the filtrate was concentrated under reduced pressure to afford crude 2-(6-benzenesulfonyl-1-bicyclo[2.2.1]hept-2-yl-1,6-dihydro-1,2,3,5,6-tetraaza-as-indacen-2-yl)-ethylamine (0.15 g, 59%) as a brown foam. This material was used in subsequent reactions without additional purification or characterization.

N-[2-(1-bicyclo[2.2.1]hept-2-yl-1,6-dihydro-1,2,3,5,6-tetraaza-as-indacen-2-yl)-ethyl]-methanesulfonamide To a solution of 2-(6-benzenesulfonyl-1-bicyclo[2.2.1]hept-2-yl-1,6-dihydro-1,2,3,5,6-tetraaza-as-indacen-2-yl)-ethylamine (0.10 g, 0.23 mmol) in DCM (3 mL) and DIEA (0.9 mL, 0.52 mmol) was added methanesulfonyl chloride (0.032 mL; 0.41 mmol) and the mixture was stirred at 25° C. for 20 h. The reaction mixture was partitioned between DCM and water. The organic layer was washed with brine, dried over $Na_2SO_4$ and concentrated under reduced pressure. To the residue was added sodium hydroxide (0.7 ml of 1M Solution, 0.7 mmol) and ethanol (3 mL) and heated at 50° C. for 20 h. The reaction mixture was cooled, concentrated. Purification by column chromatography on silica gel (0-10% MeOH in DCM) and subsequent trituration with EtOAc/heptane) afforded N-[2-(1-bicyclo[2.2.1]hept-2-yl-1,6-dihydro-1,2,3,5,6-tetraaza-as-indacen-2-yl)-ethyl]-methanesulfonamide (0.02 g; 20%) as a off-white solid: LCMS (method D; ESI): RT=8.40 min; m+1=374.1; 1H NMR (500 MHz, DMSO) δ 8.50 (s, 1H), 7.42 (s, 1H), 6.58 (s, 1H), 4.67 (s, 1H), 3.57 (dd, J=13.7, 6.9 Hz, 2H), 3.28-3.05 (m, 3H), 2.96 (s, 3H), 2.68-2.52 (m, 2H), 2.11-1.98 (m, 1H), 1.94 (d, J=10.7 Hz, 1H), 1.75-1.57 (m, 2H), 1.55-1.45 (m, 1H), 1.41-1.28 (m, 2H).

Example 695

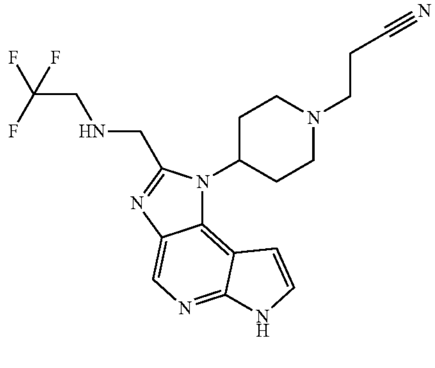 [SMILES: N#CCCN1CCC(n2c(CNCC(F)(F)F)nc3cnc4[nH]ccc4c32)CC1]

3-(4-{2-[(2,2,2-Trifluoro-ethylamino)-methyl]-6H-1,2,3,5,6-tetraaza-as-indacen-1-yl}-piperidin-1-yl)-propionitrile 3-(4-{6-Benzenesulfonyl-2-[2,2,2-trifluoro-ethylamino)-methyl]-6H-1,2,3,5,6-tetraaza-as-indacen-1-yl}-piperidin-1-yl)-propionitrile A mixture of 3-(4-{2-[(2,2,2-Trifluoro-ethylamino)-methyl]-6H-1,2,3,5,6-tetraaza-as-indacen-1-yl}-piperidin-1-yl)-propionitrile (0.29 g; 0.62 mmol), trifluoroethanol triflate (0.14 g; 0.62 mmol) and TEA (0.2 g; 2.0 mmol) in DMF (5 mL) was heated at 60° C. for 1 h. The reaction mixture cooled, partitioned between water and 1:1 mixture of EtOAc; heptane (100 mL). The organic layer was separated, washed with brine, dried over $Na_2SO_4$ and concentrated under reduced pressure. Purification of the residue by column chromatography on silica (0-10% MeOH in DCM) afforded 3-(4-{6-benzenesulfonyl-2-[(2,2,2-trifluoro-ethylamino)-methyl]-6H-1,2,3,5,6-tetraaza-as-indacen-1-yl}-piperidin-1-yl)-propionitrile (0.19 g, 56%). LCMS (Method G; ESI): RT=0.75 min; m+1=546.3.

3-(4-{2-[(2,2,2-Trifluoro-ethylamino)-methyl]-6H-1,2,3,5,6-tetraaza-as-indacen-1-yl}-piperidin-1-yl)-propionitrile 3-(4-{6-Benzenesulfonyl-2-[2,2,2-trifluoro-ethylamino)-methyl]-6H-1,2,3,5,6-tetraaza-as-indacen-1-yl}-piperidin-1-yl)-propionitrile (0.19 g, 0.34 mmol) was converted to 3-(4-{2-[(2,2,2-Trifluoro-ethylamino)-methyl]-6H-1,2,3,5,6-tetraaza-as-indacen-1-yl}-piperidin-1-yl)-propionitrile (0.07 g; 30%) as described above using sodium hydroxide. LCMS (Method: D; ESI): RT=2.61 min; m+1=406.1; $^1$H NMR (400 MHz, $CDCl_3$) δ 9.35 (s, 1H), 8.75 (s, 1H), 7.39 (s, 1H), 7.13 (s, 1H), 4.71-4.56 (m, 1H), 4.26 (d, J=5.4 Hz, 2H), 3.43-3.26 (m, 2H), 3.25-3.11 (m, 2H), 2.92-2.72 (m, 4H), 2.63 (t, J=6.8 Hz, 2H), 2.49-2.18 (m, 2H), 2.00-1.86 (m, 2H).

Example 696

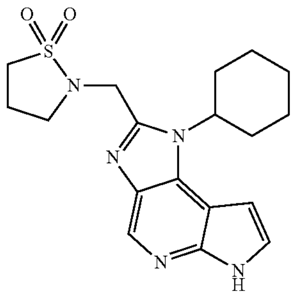 [SMILES: O=S1(=O)CCCN1Cc1nc2cnc3[nH]ccc3c2n1C1CCCCC1]

1-Cyclohyl-2-(1,1-dioxo-1,1,6-isothiazolidin-2-ylmethyl)-1,6-dihydro-1,2,3,5,6-tetraaza-as-indacene 6-Benzenesulfonyl-1-cyclohyl-2-(1,1-dioxo-isothiazolidin-2-ylmethyl)-1,6-dihydro-1,2,3,5,6-tetraaza-as-indacene 6-benzenesulfonyl-1-cyclohyl-2-(1,1-dioxo-isothiazolidin-2-ylmethyl)-1,6-dihydro-1,2,3,5,6-tetraaza-as-indacene To a solution of C-(6-Benzenesulfonyl-1-cyclohyl-1,6-dihydro-1,2,3,5,6-tetraaza-as-indacen-2-yl)-methylamine (0.30 g; 0.7 mmol) and DIEA (0.19 mL, 1.1 mmol) in DCM (10 mL) was added 3-chloropropane-1-sulfonyl chloride (0.16 g, 0.88 mmol) and stirred at 25° C. for 2 h. The reaction mixture was partitioned between water and DCM. The organic layer was washed with water, brine, dried over $Na_2SO_4$ and concentrated under reduced pressure. Purification of the residue by column chromatography on silica (0-5% MeOH in DCM) afforded 3-Chloro-propane-1-sulfonic acid (6-benzenesulfonyl-1-cyclohyl-1,6-dihydro-1,2,3, 5,6-tetraaza-as-indacen-2-ylmethyl)-amide (0.2 g, 50%). LCMS (Method G; ESI): RT=1.10 min; m+1=550.3.

1-Cyclohyl-2-(1,1-dioxo-1,1,6-isothiazolidin-2-ylmethyl)-1,6-dihydro-1,2,3,5,6-tetraaza-as-indacene A solution of 3-chloro-propane-1-sulfonic acid (6-benzenesulfonyl-1-cyclohyl-1,6-dihydro-1,2,3,5,6-tetraaza-as-indacen-2-ylmethyl)-amide (0.2 g, 0.35 mmol) in sodium hydroxide (2 mL, 1N) and ethanol (5 mL) was heated at 50° C. for 20 h. The reaction mixture was cooled and concentrated under reduced pressure. Purification by column chromatography on silica (0-10% MeOH in DCM) and subsequent trituration with heptane/EtOAc afforded 1-Cyclohyl-2-(1,1-dioxo-1$1%6&-isothiazolidin-2-ylmethyl)-1,6-dihydro-1,2,3,5,6-tetraaza-as-indacene (0.08 g; 63%). LCMS (Method D, ESI): RT=3.68 ml, m+1=374.1; 1H NMR (500 MHz, $CDCl_3$) δ 9.50 (s, 1H), 8.77 (s, 1H), 7.39 (s, 1H), 6.87 (s, 1H), 4.75-4.61 (m, 1H), 4.52 (s, 2H), 3.31-3.20 (m, 4H), 2.50-2.27 (m, 4H), 2.07-1.84 (m, 5H), 1.70-1.60 (m, 2H), 1.56-1.42 (m, 1H).

Example 697

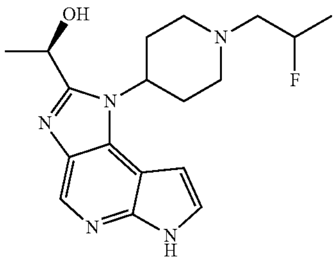 [SMILES: CC(F)CN1CCC(n2c([C@@H](C)O)nc3cnc4[nH]ccc4c32)CC1]

(R)-1-{1-[1-(2-Fluoro-propyl)-piperidin-4-yl]-1,6-dihydro-1,2,3,5,6-tetraaza-as-indacen-2-yl}-ethanol 1-(2-Fluoro-propyl)-piperidin-4-ylamine.HCl A mixture of 4-(N-Boc-amino)-piperidine (1.0 g, 5.0 mmol), 2-hydroxybromopropane (1.0 g; 7.5 mmol) and TEA (0.76 g, 7.5 mmol) in AcCN (20 mL) was heated at 60° C. for 4 days. The reaction mixture was partitioned between EtOAc and water. The organic layer was separated, washed with brine, dried over $Na_2SO_4$ concentrated under reduced pressure. Purification of the residue by column chromatography on silica (0-5% 2M ammonia-MeOH in DCM) afforded [1-(2-hydroxy-propyl)-piperidin-4-yl]-carbamic acid tert-butyl ester (0.76 g, 59%) as an oil. LCMS (Method G; ESI): RT=0.49 min, m+1=259.3.

To a cold solution of [1-(2-hydroxy-propyl)-piperidin-4-yl]-carbamic acid tert-butyl ester (0.70 g, 2.7 mmol) in DCM (30 mL) was added DAST (1.1 mL, 8.1 mmol) and the mixture was stirred at 25° C. for 20 h. The reaction mixture was washed with saturated sodium bicarbonate solution, water, brine, dried over $Na_2SO_4$ and concentrated under reduced pressure to afford [1-(2-fluoro-propyl)-piperidin-4-yl]-carbamic acid tert-butyl ester (0.5 g, 70%). LCMS (Method G; ESI): RT=0.53 min; m+1=261.3. This was used without further purification below.

[1-(2-Fluoro-propyl)-piperidin-4-yl]-carbamic acid tert-butyl ester (0.5 g, 1.9 mmol) was dissolved in DCM (10 mL) and HCl-dioxane (3.4 mL 4M; 10 mmol) was added. The resulting mixture was stirred at 25° C. for 20 h. The solid was collected by filtration and used without further purification below.

1-{1-[1-(2-Fluoro-propyl)-piperidin-4-yl]-1,6-dihydro-1,2,3,5,6-tetraaza-as-indacen-2-yl}-ethanol 1-{1-[1-(2-Fluoro-propyl)-piperidin-4-yl]-1,6-dihydro-1,2,3,5,6-tetraaza-as-indacen-2-yl}-ethanol was obtained using the method described for example 110 and 671: LCMS (Method D; ESI): RT=2.28 min; m+1=346.2; 1H NMR (400 MHz, DMSO) δ 11.80 (s, 1H), 8.54 (s, 1H), 7.47 (t, J=2.9 Hz, 1H), 6.94 (s, 1H), 5.66 (d, J=6.4 Hz, 1H), 5.18-5.06 (m, 1H), 5.04-4.78 (m, 2H), 3.19-3.07 (m, 2H), 2.76-2.52 (m, 4H), 2.37-2.20 (m, 2H), 1.92-1.77 (m, 2H), 1.63 (d, J=6.5 Hz, 3H), 1.44-1.25 (m, 3H).

Example 698

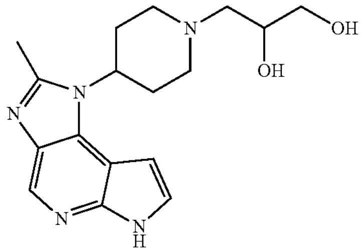 [SMILES: Cc1nc2cnc3[nH]ccc3c2n1C1CCN(CC(O)CO)CC1]

3-[4-(2-Methyl-6H-1,2,3,5,6-tetraaza-as-indacen-1-yl)-piperidin-1-yl]-propane-1,2-diol 6-benzenesulfonyl-1-[1-(2,2-dimethyl-[1,3]dioxolan-4-ylmethyl)-piperidin-4-yl]-2-methyl-1,6-dihydro-1,2,3,5,6-tetraaza-as-indacene A mixture of 6-benzenesulfonyl-2-methyl-1-piperidin-4-yl-1,6-dihydro-1,2,3,5,6-tetraaza-as-indacene (0.3 g; 0.8 mmol), 2,2-dimethyl-4-(toluene-4-sulfonylmethyl)-[1,3]dioxolane (0.26 g; 0.91 mmol), TEA (0.32 mL; 2.3 mmol) in DMF (2 mL) was heated at 80° C. for 20 h. The reaction mixture was cooled, diluted with DCM, washed with water, brine, dried over $Na_2SO_4$, concentrated under reduced pressure. Purification of the residue by column chromatography on silica (0-5% MeOH in DCM) provided 6-benzenesulfonyl-1-[1-(2,2-dimethyl-[1,3]dioxolan-4-ylmethyl)-piperidin-4-yl]-2-methyl-1,6-dihydro-1,2,3,5,6-tetraaza-as-indacene (0.15 g; 40%). LCMS (Method G; ESI): RT=0.69 min; m+1=510.4.

1-[1-(2,2-dimethyl-[1,3]dioxolan-4-ylmethyl)-piperidin-4-yl]-2-methyl-1,6-dihydro-1,2,3,5,6-tetraaza-as-indacene Sodium hydroxide (0.6 mL of 1M solution; 0.6 mmol) was added to 6-benzenesulfonyl-1-[1-(2,2-dimethyl-[1,3]dioxolan-4-ylmethyl)-piperidin-4-yl]-2-methyl-1,6-dihydro-1,2,3,5,6-tetraaza-as-indacene (0.15 g, 0.3 mmol) in IPA (3 mL) and the mixture was heated at 50° C. for 20 h. The resulting mixture was cooled and concentrated under reduced pressure. Purification of the residue by column chromatography on silica (0-10% MeOH in DCM) afforded 1-[1-(2,2-dimethyl-[1,3]dioxolan-4-ylmethyl)-piperidin-4-yl]-2-methyl-1,6-dihydro-1,2,3,5,6-tetraaza-as-indacene (0.09 g; 81%): LCMS (Method G; ESI): RT=0.41 min; m+1=370.4.

3-[4-(2-methyl-6H-1,2,3,5,6-tetraaza-as-indacen-1-yl)-piperidin-1-yl]-propane-1,2-diol 1-[1-(2,2-dimethyl-[1,3]dioxolan-4-ylmethyl)-piperidin-4-yl]-2-methyl-1,6-dihydro-1,2,3,5,6-tetraaza-as-indacene (0.09 g, 0.24 mmol) was dissolved in MeOH (2 mL) and HCl (1.5 mL of 1M; 1.0 mmol) was added. The resulting mixture was heated at 50° C. for 2 h. The resulting reaction mixture was concentrated under reduced pressure and ammonia-methanol (1 mL fo 7M solution) was added. The mixture was filtered and concentrated under reduced pressure. Purification by preparative HPLC (column: Gemini-NX, 21.2×100 mm, 10 um; detection: UV 254 nm and mass, mobile phase A: water w/0.1% formic acid; mobile phase B: $CH_3CN$; flow-rate: 35 ml/min; gradient 5-85% B over 9.5 min) gave 3-[4-(2-methyl-6H-1,2,3,5,6-tetraaza-as-indacen-1-yl)-piperidin-1-yl]-propane-1,2-diol (0.07 g, 72%). LCMS (Method C; ESI): RT=1.11 min; m+1=330.2. $^{1}$H NMR (400 MHz, DMSO) δ 11.74 (s, 1H), 8.45 (s, 1H), 7.44 (t, J=3.0 Hz, 1H), 6.87 (s, 1H), 4.65-4.51 (m, 1H), 4.51-4.39 (m, 2H), 3.77-3.61 (m, 1H), 3.44 (ddd, J=25.5, 10.7, 5.5 Hz, 2H), 3.14 (dd, J=29.6, 11.3 Hz, 2H), 2.62 (s, 3H), 2.58-2.50 (m, 3H), 2.38-2.18 (m, 3H), 1.94-1.76 (m, 2H).

Examples 699 and 700

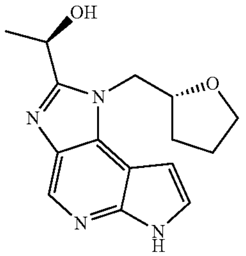

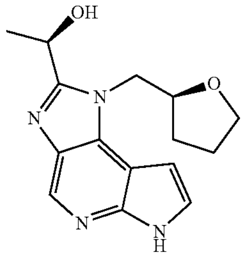

1-[1-(Tetrahydro-furan-2-ylmethyl)-1,6-dihydro-1,2,3,5,6-tetraaza-as-indacen-2-yl]-ethanol 1-[1-(Tetrahydro-furan-2-ylmethyl)-1,6-dihydro-1,2,3,5,6-tetraaza-as-indacen-2-yl]-ethanol was prepared using the method described for Examples 110 and 671 and the diastereomers were separated by column chromatography on silica (0-5% MeOH in DCM): First eluting: LCMS (Method D; ESI): RT=2.65 min; m+1=287.1; 1H NMR (400 MHz, DMSO) δ 11.73 (s, 1H), 8.52 (s, 1H), 7.41 (s, 1H), 6.72 (s, 1H), 5.54-5.41 (m, 1H), 5.25-5.05 (m, 1H), 4.72 (d, J=14.8 Hz, 1H), 4.54 (d, J=16.9 Hz, 1H), 4.41-4.25 (m, 1H), 3.77-3.49 (m, 2H), 2.14-1.92 (m, 2H), 1.88-1.70 (m, 2H), 1.63 (d, 3H). Second eluting: LCMS (Method D; ESI): RT=2.73 min; m+1=287.1; $^{1}$H NMR (400 MHz, DMSO) δ 11.74 (s, 1H), 8.52 (s, 1H), 7.41 (s, 1H), 6.70 (s, 1H), 5.58-5.44 (m, J=6.7 Hz, 1H), 5.16-5.05 (m, 1H), 4.65-4.45 (m, 2H), 4.35-4.17 (m, 1H), 3.89-3.75 (m, 1H), 3.67-3.49 (m, 1H), 2.20-1.74 (m, 4H), 1.63 (d, J=6.0 Hz, 3H).

Example 701

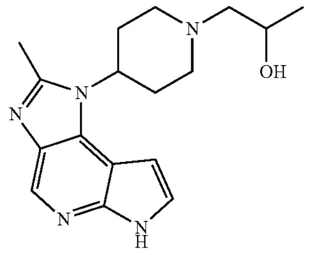 [SMILES: Cc1nc2cnc3[nH]ccc3c2n1C1CCN(CC(C)O)CC1]

1-[4-(2-Methyl-6H-1,2,3,5,6-tetraaza-as-indacen-1-yl)-piperidin-1-yl]-propan-2-ol 1-[4-(6-Benzenesulfonyl-2-methyl-6H-1,2,3,5,6-tetraaza-as-indacen-1-yl)-piperidin-1-yl]-propan-2-ol A mixture of 6-benzenesulfonyl-2-methyl-1-piperidin-4-yl-1,6-dihydro-1,2,3,5,6-tetraaza-as-indacene (0.48 g, 1.2 mmol), 2-hydroxybromoethane (0.34 g; 2.4 mmol) and TEA (0.34 mL, 2.4 mmol) in AcCN (20 mL) was heated at 70° C. for 20 h. The reaction mixture was cooled, partitioned between EtOAc and water. The organic phase separated, washed with brine, dried over $Na_2SO_4$ and concentrated under reduced pressure. Purification of the residue by column chromatography on silica (0-5% MeOH in DCM) gave 1-[4-(6-Benzenesulfonyl-2-methyl-6H-1,2,3,5,6-tetraaza-as-indacen-1-yl)-piperidin-1-yl]-propan-2-ol (0.42 g, 76%): LCMS (Method G; ESI): RT=0.61 min; m+1=454.3.

1-[4-(6-Benzenesulfonyl-2-methyl-6H-1,2,3,5,6-tetraaza-as-indacen-1-yl)-piperidin-1-yl]-propan-2-ol (0.42 g, 0.93 mmol) was deprotected using sodium hydroxide as described for example 200 to give 1-[4-(2-Methyl-6H-1,2,3,5,6-tetraaza-as-indacen-1-yl)-piperidin-1-yl]-propan-2-ol (0.21 g, 72%): LCMS (Method D; ESI): RT=1.78 min; m+1=314.2; 1H NMR (400 MHz, DMSO) δ 11.73 (s, 1H), 8.45 (s, 1H), 7.44 (t, J=2.9 Hz, 1H), 6.90 (s, 1H), 4.51-4.40 (m, 1H), 4.36 (d, J=4.1 Hz, 1H), 3.90-3.80 (m, 1H), 3.10 (d, J=11.1 Hz, 2H), 2.64 (d, J=20.1 Hz, 3H), 2.60-2.51 (m, 2H), 2.43-2.16 (m, 4H), 1.91-1.79 (m, 2H), 1.17 (d, J=6.6 Hz, 3H).

Example 702

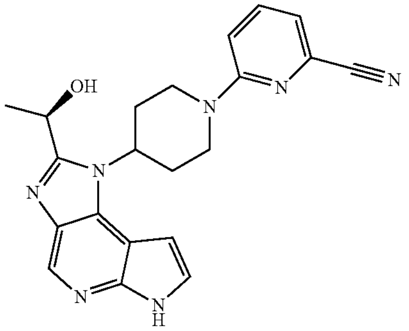 [SMILES: C[C@@H](O)c1nc2cnc3[nH]ccc3c2n1C1CCN(c2cccc(C#N)n2)CC1]

4-[2-((R)-1-Hydroxy-ethyl)-6H-1,2,3,5,6-tetraaza-as-indacen-1-yl]-3,4,5,6-tetrahydro-2H-[1,2]bipyridinyl-6'-carbonitrile (R)-1-(1-Piperidin-4-yl-1,6-dihydro-1,2,3,5,6-tetraaza-as-indacen-2-yl)-ethanol (0.08 g, 0.28 mmol) was dissolved in NMP (2 mL) and 6-chloropyridine-2-carbonitrile (0.06 g, 0.43 mmol) was added. The resulting mixture was heated at 100° C. for 20 h. The reaction mixture was cooled, diluted with DCM (10 mL) and MP-TsOH (1.5 g) was added and stirred for 30 min. Filtered and the resin was stirred over ammonia-methanol (7M in methanol 5 mL). Filtered and the filtrate was concentrated under reduced pressure. Purification of the residue by column chromatography on silica (10% MeOH in DCM) and subsequent trituration with EtOAc gave 4-[2-((R)-1-Hydroxy-ethyl)-6H-1,2,3,5,6-tetraaza-as-indacen-1-yl]-3,4,5,6-tetrahydro-2H-[1,2']bipyridinyl-6'-carbonitrile (0.02 g, 10%): LCMS (Method D; ESI): RT=3.56 min; m+1=388.1. $^{1}$H NMR (400 MHz, DMSO) δ 8.54 (s, 1H), 7.82 (t, J=7.9 Hz, 1H), 7.42 (d, J=8.6 Hz, 1H), 7.31 (d, J=7.3 Hz, 1H), 7.20 (s, 1H), 5.90 (s, 1H), 5.71 (d, J=5.7 Hz, 1H), 5.20 (s, 2H), 4.62 (s, 2H), 3.18 (s, 2H), 1.99 (s, 2H), 1.67 (d, J=5.7 Hz, 3H).

Example 703

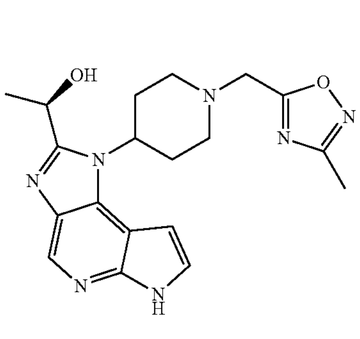 [SMILES: Cc1noc(CN2CCC(n3c([C@@H](C)O)nc4cnc5[nH]ccc5c43)CC2)n1]

(R)-1-{1-[1-(3-Methyl-[1,2,4]oxadiazol-5-ylmethyl)-piperidin-4-yl]-1,6-dihydro-1,2,3,5,6-tetraaza-as-indacen-2-yl}-ethanol (R)-1-{6-benzenesulfonyl-1-[1-(3-methyl-[1,2,4]oxadiazol-5-ylmethyl)-piperidin-4-yl]-1,6-dihydro-1,2,3,5,6-tetraaza-as-indacen-2-yl}-ethanol A mixture of (R)-1-(6-benzenesulfonyl-1-piperidin-4-yl-1,6-dihydro-1,2,3,5,6-tetraaza-as-indacen-2-yl)-ethanol (0.3 g, 0.7 mmol), 5-chloromethyl-3-methyl-[1,2,4]oxadiazole (0.11 g, 0.85 mmol) and TEA (0.20 mL, 1.4 mmol) in DMF (3 mL) was heated 50° C. for 20 h. The reaction mixture was cooled partitioned between water and 1:1 mixture of heptane.EtOAc. The organic layer was separated, washed with water, brine, dried over $Na_2SO_4$ and concentrated under reduced pressure. Purification of the residue by column chromatography on silica (0-5% MeOH in DCM) gave (R)-1-{6-benzenesulfonyl-1-[1-(3-methyl-[1,2,4]oxadiazol-5-ylmethyl)-piperidin-4-yl]-1,6-dihydro-1,2,3,5,6-tetraaza-as-indacen-2-yl}-ethanol (0.34 g, 90%): LCMS (Method G; ESI): RT=0.85 min.; m+1=522.5.

Sodium hydroxide (2.0 mL 1M solution, 2.00 mmol) was added to (R)-1-{6-benzenesulfonyl-1-[1-(3-methyl-[1,2,4]oxadiazol-5-ylmethyl)-piperidin-4-yl]-1,6-dihydro-1,2,3,5,6-tetraaza-as-indacen-2-yl}-ethanol (0.34 g, 0.65 mmol) in ethanol (2 mL) and heated at 50° C. for 4 h. Cooled, partitioned between EtOAc and water. The organic layer was washed with brine, dried over $Na_2SO_4$ and concentrated. Purification of the residue by preparative HPLC (column: Gemini-NX, 5×10 cm, 10 um; detection: UV 254 nm, mobile phase A: water w/0.1% $NH_4OH$; mobile phase B: $CH_3CN$; flowrate: 120 ml/min; gradient 5-95% B over 15 min) gave (R)-1-{1-[1-(3-Methyl-[1,2,4]oxadiazol-5-ylmethyl)-piperidin-4-yl]-1,6-dihydro-1,2,3,5,6-tetraaza-as-indacen-2-yl}-ethanol (0.13 g, 52%): LCMS (Method D; ESI): RT=2.59 min, m+1=382.2; 1H NMR (400 MHz, DMSO) δ 8.55 (s, 1H), 7.49 (t, J=2.9 Hz, 1H), 6.90 (s, 1H), 5.66 (d, J=6.6 Hz, 1H), 5.19-5.04 (m, 1H), 4.91-4.78 (m, 1H), 4.04 (s, 2H), 3.12 (d, J=10.7 Hz, 2H), 2.71-2.54 (m, 2H), 2.48-2.39 (m, 2H), 2.39 (s, 3H), 1.97-1.80 (m, 2H), 1.62 (d, J=6.5 Hz, 3H).

Example 704

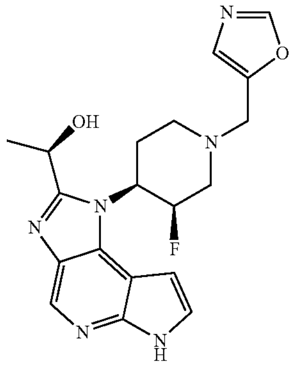 [SMILES: C[C@@H](O)c1nc2cnc3[nH]ccc3c2n1[C@H]1CCN(Cc2cnco2)C[C@H]1F]

1-[1-(3-Fluoro-1-oxazol-5-ylmethyl-piperidin-4-yl)-1,6-dihydro-1,2,3,5,6-tetraaza-as-indacen-2-yl]-ethanol (cis diastereomer)

(R)-1-[6-Benzenesulfonyl-1-(3-fluoro-piperidin-4-yl)-1,6-dihydro-1,2,3,5,6-tetraaza-as-indacen-2-yl]-ethanol To a mixture of (R)-1-[6-benzenesulfonyl-1-((3R,4 S)-3-fluoro-1-oxazol-5-ylmethyl-piperidin-4-yl)-1,6-dihydro-1,2,3,5,6-tetraaza-as-indacen-2-yl]-ethanol.HCl (0.18 g, 0.38 mmol) and 5-oxazolecarboxaldehyde (0.055 g, 0.56 mmol) im methanol (5 mL) was added sodium cyanoborohydride (0.07 g, 1.10 mmol) and stirred at 25° C. for 20 h. The reaction mixture was concentrated under reduced pressure and partitioned between EtOAc and water. The organic layer was separated, washed with brine, dried over $Na_2SO_4$ and concentrated under reduced pressure. Purification of the residue by column chromatography on silica (0-10% MeOH in DCM) gave (R)-1-[6-benzenesulfonyl-1-(3-fluoro-1-oxazol-5-ylmethyl-piperidin-4-yl)-1,6-dihydro-1,2,3,5,6-tetraaza-as-indacen-2-yl]-ethanol (0.18 g, 91%). LCMS (Method G; ESI): RT=0.69 min, m+1=525.3.

A mixture of (R)-1-[6-benzenesulfonyl-1-(3-fluoro-1-oxazol-5-ylmethyl-piperidin-4-yl)-1,6-dihydro-1,2,3,5,6-tetraaza-as-indacen-2-yl]-ethanol (0.18 g, 0.34 mmol) and $K_2CO_3$ (0.15 g, 1.1 mmol) in MeOH (5 mL) was stirred at 25° C. for 20 h. The resulting mixture was concentrated under reduced pressure and partitioned between water and EtOAc. The organic layer was separated, washed with brine, dried over $Na_2SO_4$ and concentrated under reduced pressure. Purification of the residue by column chromatography on silica (0-10% MeOH in DCM) gave 1-[1-(3-Fluoro-1-oxazol-5-ylmethyl-piperidin-4-yl)-1,6-dihydro-1,2,3,5,6-tetraaza-as-indacen-2-yl]-ethanol (0.06 g, 40%): LCMS (Method D; ESI): RT=2.19 min; m+1=385.2; $^1$H NMR (400 MHz, DMSO) δ 11.62 (s, 1H), 8.52 (d, J=5.6 Hz, 1H), 8.37 (s, 1H), 7.37 (dd, J=5.7, 2.8 Hz, 1H), 7.14 (s, 1H), 6.82 (s, 1H), 5.79-5.53 (m, 1H), 5.25-4.75 (m, 3H), 3.95-3.71 (m, 2H), 3.20-3.04 (m, 2H), 2.74-2.22 (m, J=1.5 Hz, 3H), 1.92-1.74 (m, 1H), 1.63 (d, J=6.4 Hz, 3H).

Example 705

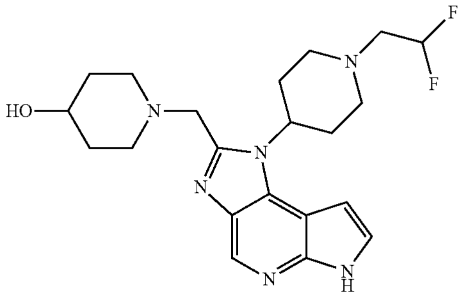 [SMILES: OC1CCN(Cc2nc3cnc4[nH]ccc4c3n2C2CCN(CC(F)F)CC2)CC1]

1-{1-[1-(2,2-Difluoro-ethyl)-piperidin-4-yl]-1,6-dihydro-1,2,3,5,6-tetraaza-as-indacen-2-ylmethyl}-piperidin-4-ol 4-[6-benzenesulfonyl-2-(4-hydroxy-piperidin-1-ylmethyl)-6H-1,2,3,5,6-tetraaza-as-indacen-1-yl]-piperidine-1-carboxylic acid tert-butyl ester 4-(6-Benzene sulfonyl-2-chloromethyl-6H-1,2,3,5,6-tetraaza-as-indacen-1-yl)-piperidine-1-carboxylic acid tert-butyl ester (0.5 g, 9.4 mmol) was dissolved in AcCN (10 mL) and 4-hydroxypiperidine (0.11 g, 1.1 mmol) and $K_2CO_3$ were added and the resulting mixture was heated at 80° C. for 20 h. The reaction mixture was cooled, partitioned between EtOAc and water. The organic layer was separated, washed with water, brine, dried over sodium sulphate and concentrated under reduced pressure. Purification by column chromatography on silica (0-5% MeOH in DCM) gave 4-[6-benzenesulfonyl-2-(4-hydroxy-piperidin-1-ylmethyl)-6H-1,2,3,5,6-tetraaza-as-indacen-1-yl]-piperidine-1-carboxylic acid tert-butyl ester (0.4 g, 76%). LCMS (Method G; ESI): RT=0.84 min; m+1=595.4.

4-[6-Benzenesulfonyl-2-(4-hydroxy-piperidin-1-ylmethyl)-6H-1,2,3,5,6-tetraaza-as-indacen-1-yl]-piperidine-1-carboxylic acid tert-butyl ester (0.2 g, 0.4 mmol) was converted to 1-{1-[1-(2,2-Difluoro-ethyl)-piperidin-4-yl]-1,6-dihydro-1,2,3,5,6-tetraaza-as-indacen-2-ylmethyl}-piperidin-4-ol (0.025 g, 10%) using the method described for Example 692. LCMS (Method D; ESI): RT=2.12 min; m+1=419.2; $^1$H NMR (400 MHz, $CDCl_3$) δ 9.41 (s, 1H), 8.75 (s, 1H), 7.38 (d, J=2.8 Hz, 1H), 7.05 (s, 1H), 6.18-5.83 (m, 1H), 4.84-4.69 (m, 1H), 3.85 (s, 2H), 3.82-3.66 (m, 1H), 3.32-3.08 (m, 2H), 2.97-2.70 (m, 5H), 2.56-2.39 (m, 2H), 2.34-2.20 (m, 2H), 1.98-1.79 (m, 3H), 1.58-1.42 (m, 3H).

Example 706

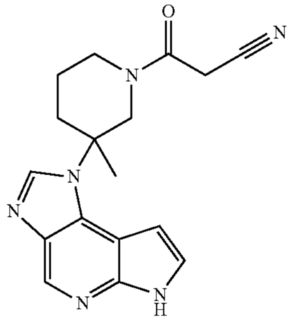 [SMILES: CC1(n2cnc3cnc4[nH]ccc4c32)CCCN(C(=O)CC#N)C1]

3-[3-Methyl-3-(6H-1,2,3,5,6-tetraaza-as-indacen-1-yl)-piperidin-1-yl]-3-oxo-propionitrile (racemic)

3-Carbamoyl-3-methyl-piperidine-1-carboxylic acid tert-butyl ester

A solution of 3-Methyl-piperidine-1,3-dicarboxylic acid 1-tert-butyl ester (1.5 g, 6.2 mmol) in tetrahydrofuran (THF) (50 mL) was cooled to −15° C. 4-Methylmorpholine (0.744 mL, 6.82 mmol) and isobutyl chloroformate (0.9 mL, 6.82 mmol) were added, and a white solid precipitated. The mixture was allowed to stir at −15° C. for 30 min. Then aqueous ammonia solution (28%, 1.3 mL, 9.3 mmol) was added to the above mixture at −15° C. The mixture was stirred for another 30 min at low temperature, then warmed to room temperature slowly for 2 h and concentrated. The residue was dissolved in ethyl acetate, washed with 1 M potassium hydrogen sulfate solution (50 mL×2), saturated sodium bicarbonate and brine. Finally crude 3-Methyl-piperidine-1,3-dicarboxylic acid 1-tert-butyl ester 1.0 g (66%) was obtained without further purification for next step. $^1$H NMR (400 MHz, DMSO-$d_6$) δ: 7.03 (s, 1H), 6.90 (m, 1H), 3.43-3.40 (m, 1H), 3.23-3.20 (m, 1H), 3.20-3.00 (m, 1H), 1.90-1.70 (m, 1H), 1.50-1.37 (m, 3H), 1.37 (m, 9H), 1.000 (s, 3H), 0.86-0.84 (m, 1H).

3-Methyl-piperidine-3-carboxylic acid amide hydrochloride

To a solution of crude 3-Methyl-piperidine-1,3-dicarboxylic acid 1-tert-butyl ester (1.0 g, 4.1 mmol) in methanol (5 mL) was added 4 N hydrochloride in ethyl acetate (20 mL), the mixture was allowed to stir at 25° C. for 2 h, then concentrated, finally about 740 mg (100%) of 3-Methyl-piperidine-3-carboxylic acid amide was obtained as hydrochloride salt without further purification.

3-Carbamoyl-3-methyl-piperidine-1-carboxylic acid benzyl ester

To a solution of 3-Methyl-piperidine-3-carboxylic acid amide hydrochloride (740 mg, 4.1 mmol) in a cosolvent of 1,4-dioxane and water (12 mL, v:v=5:1) was added sodium carbonate (1.6 g, 15 mmol). The mixture was cooled to 0° C., benzyl chloroformate (900 mg, 0.53 mmol) was added, and the mixture was allowed to stir at room temperature for 3 h. LCMS showed starting material was consumed. The volatile components were removed, and the residue was extracted with ethyl acetate, purified by column chromatography (eluting with 10% methanol in dichloromethane) to give 600 mg (53%) of 3-Carbamoyl-3-methyl-piperidine-1-carboxylic acid benzyl ester. LCMS (Method K, ESI): RT=1.18 min, m+Na=298.8; $^1$H NMR (400 MHz, $CDCl_3$) δ: 7.32-7.23 (m, 5H), 5.07-5.03 (m, 2H), 4.30-4.10 (m, 1H), 4.10-3.90 (m, 1H), 3.10-2.40 (m, 2H), 1.65-1.75 (m, 2H), 1.60-1.30 (m, 2H), 1.25-1.15 (m, 1H), 1.09 (s, 3H).

3-Amino-3-methyl-piperidine-1-carboxylic acid benzyl ester

3-Carbamoyl-3-methyl-piperidine-1-carboxylic acid benzyl ester (500 mg, 1.81 mmol) in acetonitrile (10 mL) was treated with [bis(trifluoroacetoxyl)iodo]benzene (PIFA) (800 mg, 1.86 mmol) and water (2 mL), the mixture was allowed to stir at 25° C. for 3 hours. LCMS showed starting material consumed, the mixture was heated to 70° C. for 30 min to decompose excess PIFA. The mixture was purified by column chromatography (eluting with 30~50% methanol in dichloromethane) to give 420 mg (93%) of 3-Amino-3-methyl-piperidine-1-carboxylic acid benzyl ester. LCMS (Method K, ESI): RT=0.95 min, m+H=249.0.

3-(1-Benzenesulfonyl-5-nitro-1H-pyrrolo[2,3-b]pyridin-4-ylamino)-3-methyl-piperidine-1-carboxylic acid benzyl ester To a solution of 1-Benzenesulfonyl-4-chloro-5-nitro-1H-pyrrolo[2,3-b]pyridine (580 mg, 1.7 mmol) in n-butanol (20 mL) were added diisopropylethylamine (DIPEA) (1.4 mL, 8.4 mmol) and 3-Amino-3-methyl-piperidine-1-carboxylic acid benzyl ester (420 mg, 1.7 mmol). The mixture was heated to reflux overnight, and LCMS showed 1-Benzenesulfonyl-4-chloro-5-nitro-1H-pyrrolo[2,3-b]pyridine consumed. The reaction mixture was purified by column chromatography (eluting with 30~35% ethyl acetate in hexane) to give 400 mg (43%) of 3-(1-Benzenesulfonyl-5-nitro-1H-pyrrolo[2,3-b]pyridin-4-ylamino)-3-methyl-piperidine-1-carboxylic acid benzyl ester. LCMS (Method J, ESI): RT=1.32 min, m+H=549.8; $^1$H NMR (400 MHz, $CDCl_3$) δ: 9.60 (s, 1H), 9.10 (s, 1H), 8.20 (m, 2H), 7.70-7.50 (m, 4H), 7.40-7.30 (m, 5H), 5.34 (m, 2H), 3.90-3.80 (m, 1H), 2.30-2.20 (m, 1H), 1.90-1.50 (m, 9H).

3-(5-Amino-1-benzenesulfonyl-1H-pyrrolo[2,3-b]pyridin-4-ylamino)-3-methyl-piperidine-1-carboxylic acid benzyl ester A mixture of 3-(1-Benzene sulfonyl-5-nitro-1H-pyrrolo[2,3-b]pyridin-4-ylamino)-3-methyl-piperidine-1-carboxylic acid benzyl ester (400 mg, 0.73 mmol) and Raney Ni (1.0 g) in ethyl acetate (20 mL) was hydrogenated at 25° C. for 1.5 hours. The mixture was filtered through Celite, thoroughly washing the filter cake with methanol. The filtrate and washings were combined and concentrated under vacuum to give about 380 mg (100%) of 3-(5-Amino-1-benzenesulfonyl-1H-pyrrolo[2,3-b]pyridin-4-ylamino)-3-methyl-piperidine-1-carboxyli c acid benzyl ester without further purification. LCMS (Method J, ESI): RT=1.04 min, m+H=519.8.

3-(6-Benzenesulfonyl-6H-1,2,3,5,6-tetraaza-as-indacen-1-yl)-3-methyl-piperidine-1-carboxylic acid benzyl ester A mixture of 3-(5-Amino-1-benzenesulfonyl-1H-pyrrolo[2,3-b]pyridin-4-ylamino)-3-methyl-piperidine-1-carboxylic acid benzyl ester (380 mg, 0.73 mmol), triethyl orthoformate (3 mL, excess) and acetic acid (2 mL, catalytic) in ethanol (10 mL) was heated to reflux for 2.5 hours. Volatile components were removed in vacuum, the residue was dissolved in ethyl acetate and the mixture was washed with water and brine, dried with sodium sulfate and concentrated under vacuum. Purification by column chromatography on silica gel (gradient: 10 to 15% methanol in dichloromethane) gave about 500 mg with acetic acid remained (100%) of 3-(6-Benzenesulfonyl-6H-1,2,3,5,6-tetraaza-as-indacen-1-yl)-3-methyl-piperidine-1-carboxylic acid benzyl ester. LCMS (Method J, ESI): RT=1.16 min, m+H=529.8.

3-Methyl-3-(6H-1,2,3,5,6-tetraaza-as-indacen-1-yl)-piperidine-1-carboxylic acid benzyl ester A solution of 3-(6-Benzenesulfonyl-6H-1,2,3,5,6-tetraaza-as-indacen-1-yl)-3-methyl-piperidine-1-carboxylic acid benzyl ester (crude 500 mg, 0.73 mmol) in methanol (10 mL) was treated with 1 M aqueous sodium hydroxide (6.25 mL, 6.25 mmol) at 40° C. for 30 minutes. The mixture was adjusted to pH ~7 and concentrated. Crude product was purified by column chromatography (eluting with 10% methanol in dichloromethane) to give 230 mg (81%) of 3-Methyl-3-(6H-1,2,3,5,6-tetraaza-as-indacen-1-yl)-piperidine-1-carboxyli c acid benzyl ester. LCMS (Method K, ESI): RT=1.11 min, m+H=389.8.

1-(3-Methyl-piperidin-3-yl)-1,6-dihydro-1,2,3,5,6-tetraaza-as-indacene

A mixture of 3-Methyl-3-(6H-1,2,3,5,6-tetraaza-as-indacen-1-yl)-piperidine-1-carboxylic acid benzyl ester (230 mg, 0.59 mmol) and 10% Pd/C (300 mg, 50% water) in ethanol (10 mL) was hydrogenated at 25° C. at 55 psi for 24 hours. The mixture was filtered through Celite, thoroughly washing the filter cake with methanol. The filtrate and washings were combined and concentrated under vacuum to give about 150 mg (100%) of 1-(3-Methyl-piperidin-3-yl)-1,6-dihydro-1,2, 3,5,6-tetraaza-as-indacene without further purification. LCMS (Method J, ESI): RT=0.1~1.7 min, m+H=256.0.

3-[3-Methyl-3-(6H-1,2,3,5,6-tetraaza-as-indacen-1-yl)-piperidin-1-yl]-3-oxo-propionitrile (racemic)

A mixture of 1-(3-Methyl-piperidin-3-yl)-1,6-dihydro-1,2,3,5,6-tetraaza-as-indacene (110 mg, 0.43 mmol), cyanoacetic acid (80 mg, 0.94 mmol), DIPEA (200 mg, 1.55 mmol) and HATU (300 mg, 0.79 mmol) in dichloromethane (10 mL) was stirred at room temperature for 3 hours. LCMS (Method K, ESI): RT=0.84 min, M+H=322.8. The mixture was purified by column chromatography (eluting with 10% methanol in dichloromethane) to give the crude product. Crude 3-[3-Methyl-3-(6H-1,2,3,5,6-tetraaza-as-indacen-1-yl)-piperidin-1-yl]-3-oxo-propionitrile (60 mg, 0.19 mmol) was dissolved in dichloromethane (10 mmol) and di-tert-butyl dicarbonate (52 mg, 0.24 mmol), DIPEA (0.1 mL, 0.6 mmol) and dimethylaminopyridine (2.4 mg) were added. The mixture was allowed to stir at 30° C. for 1 h. LCMS showed starting material was consumed. The mixture was purified by a reverse-phase preparatory a reverse-phase preparatory HPLC (Column: Grace C18 21.5*150 mm*Sum; Mobile phase A:$H_2O$ with 0.1% fomic acid, Mobile phase B: pure acetonitrile; from 28% to 58%; Flow rate: 22 mL/min, Gradient time: 11.2 min). 10.1 mg (7%, two steps) of 3-[3-Methyl-3-(6H-1,2,3,5,6-tetraaza-as-indacen-1-yl)-piperidin-1-yl]-3-oxo-propionitrile was obtained. LCMS (Method J, ESI): RT=0.84 min, M+H=423.2 (M-55: 367.1). $^1$H NMR (400 MHz, $CDCl_3$) δ: 8.70-8.60 (s, 1H), 8.30-8.27 (s, 1H), 7.50-7.49 (d, J=4, 1H), 7.08-7.07 (d, J=4, 1H), 4.80-4.70 (m, 1H), 4.42-4.30 (m, 1H), 4.20-4.10 (m, 1H), 3.99 (m, 1H), 3.55-3.50 (m, 2H), 2.95-2.85 (m, 1H), 2.28 (m, 1H), 1.95-1.80 (m, 1H), 1.79 (s, 3H), 1.60-1.50 (m, 1H).

Example 707

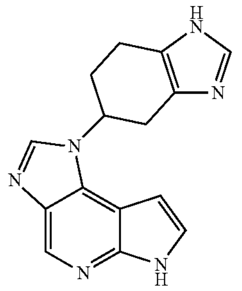 [SMILES: c1nc2c([nH]1)CCC(n1cnc3cnc4[nH]ccc4c31)C2]

1-(4,5,6,7-Tetrahydro-3H-benzoimidazol-5-yl)-1,6-dihydro-1,2,3,5,6-tetraaza-as-indacene (racemic)

3H-Benzoimidazol-5-ylamine hydrochloride

To a solution of 6-Nitro-1H-benzoimidazole (20 g, 0.123 mmol) in methanol (1 L) was added palladium on carbon (2.0 g, 10%)., the reaction mixture was stirred at 25° C. under hydrogen (50 psi) overnight. The reaction mixture was filtered through a Celite pad, rinsing with methanol. Then a solution of hydrochloride in methanol (4 N, 800 ml) was added, and the resulting solution was stirred at 20° C. for 3 h. Then the reaction mixture was concentration to afford 25 g (100%) of 3H-Benzoimidazol-5-ylamine hydrochloride. $^1$H NMR (400 MHz, DMSO-$d_6$) δ: 11.81 (br, 3H), 9.66 (s, 1H), 7.93-7.90 (m, 2H), 7.55 (d, J=8.4, 1H).

4,5,6,7-Tetrahydro-3H-benzoimidazol-5-ylamine

To a 3H-Benzoimidazol-5-ylamine hydrochloride (5.5 g, 32.5 mmol) in ethanol (100 mL) was added 10% palladium on carbon (5.6 g, 50% water), and the mixture was hydrogenated (6.5 MPa) for 72 h. Special HPLC (Mobile Phase: 0.1% TFA in water (solvent A) and 0.1% TFA in acetonitrile (solvent B), holding at 90% (solvent B) for 10 minutes at a flow rate of 1.0 ml/minutes; Column: Atlantis HILIC Silica 150*4.6 mm, 5 um) showed the reaction mixture contained 64% (RT: 3.57 min) of 3H-Benzoimidazol-5-ylamine and 22% (RT: 6.72 min) of 4,5,6,7-Tetrahydro-3H-benzoimidazol-5-ylamine. No more 4,5,6,7-Tetrahydro-3H-benzoimidazol-5-ylamine was observed by prolonging reaction time. The catalyst was filtered off and the filtrate was purified by column chromatography (eluting with 20%-25% methanol in dichloromethane) to give 2.5 g (56%) of 4,5,6,7-Tetrahydro-3H-benzoimidazol-5-ylamine. $^1$H NMR (400 MHz, Methanol-$d_4$) δ: 8.77 (s, 1H), 3.75-3.74 (m, 1H), 3.24-3.19 (m, 1H), 2.85-2.80 (m, 3H), 2.29-2.28 (m, 1H), 2.15-2.00 (m, 1H).

(1-Benzenesulfonyl-5-nitro-1H-pyrrolo[2,3-b]pyridin-4-yl)-(4,5,6,7-tetrahydro-3H-benzoimidazol-5-yl)-amine To a solution of 1-Benzenesulfonyl-4-chloro-5-nitro-1H-pyrrolo[2,3-b]pyridine (1 g, 3 mmol) and 4,5,6,7-Tetrahydro-3H-benzoimidazol-5-ylamine (450 mg, 3.3 mmol) in ethanol (50 ml) was added DIPEA (1 ml, 9.9 mmol). The mixture was heated to reflux for 1 h. Volatile components were removed, and the residue was extracted with ethyl acetate, washed with water and brine, the organic layer was purified by column chromatography (eluting with 10~20% methanol in dichloromethane) to give 0.75 g (57%) of (1-Benzenesulfonyl-5-nitro-1H-pyrrolo[2,3-b]pyridin-4-yl)-(4,5,6,7-tetrahydro-3H-benzoimidazol-5-yl)-amine. LCMS (Method J, ESI): RT=0.95, m+H=438.9; $^1$H NMR (400 MHz, $CDCl_3$+2 drops of $CD_3OD$) δ: 9.20-9.15 (m, 1H), 9.05 (s, 1H), 8.17-8.14 (m, 2H), 8.05-8.00 (s, 1H), 7.65-7.48 (m, 2H), 7.55-7.45 (m, 2H), 6.80-6.75 (m, 1H), 4.60-4.50 (m, 1H), 3.30-3.20 (m, 1H), 2.95-2.80 (m, 3H), 2.30-2.00 (m, 2H).

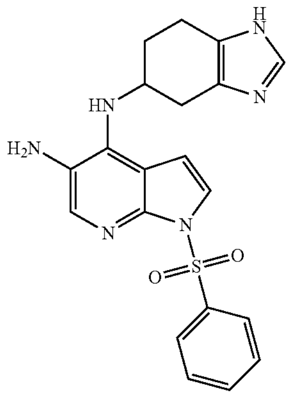 [SMILES: Nc1cnc2c(ccn2S(=O)(=O)c2ccccc2)c1NC1CCc2[nH]cnc2C1]

1-Benzenesulfonyl-N-4-(4,5,6,7-tetrahydro-3H-benzoimidazol-5-yl)-1H-pyrrolo[2,3-b]pyridine-4,5-diamine To a solution of (1-Benzenesulfonyl-5-nitro-1H-pyrrolo[2,3-b]pyridin-4-yl)-(4,5,6,7-tetrahydro-3H-benzoimidazol-5- yl)-amine (700 mg, 1.60 mmol) in methanol (20 ml) was added Raney Ni (1 g). The mixture was hydrogenated (15 psi) for 30 min and the solution became colorless. The catalyst was filtered off and the solvent was concentrated to give 500 mg (76%) of 1-Benzenesulfonyl-N-4-(4,5,6,7-tetrahydro-3H-benzoimidazol-5-yl)-1H-pyrrolo[2,3-b]pyridine-4,5-diamine, which was used in next step without further purification. LCMS (Method J, ESI): RT=0.95, m+H=408.8.

6-Benzenesulfonyl-1-(4,5,6,7-tetrahydro-1H-benzoimidazol-5-yl)-1,6-dihydro-1,2,3,5,6-tetraaza-as-indacene A mixture of 1-Benzenesulfonyl-N-4-(4,5,6,7-tetrahydro-3H-benzoimidazol-5-yl)-1H-pyrrolo[2,3-b]pyridine-4,5-diamine (500 mg, 1.23 mmol), triethyl orthoformate (1.5 ml) and acetate acid (1 ml) in ethanol (10 mL) was heated to reflux for 1.5 hours. LCMS showed starting material was consumed. Volatile components were removed under vacuum to give crude 500 mg of 6-Benzene sulfonyl-1-(4,5,6,7-tetrahydro-1H-benzoimidazol-5-yl)-1,6-dihydro-1,2,3,5,6-tetraaza-as-indacene, which was used in next step without further purification. LCMS (Method K, ESI): RT=1.05 min, m+H=418.8.

1-(4,5,6,7-Tetrahydro-3H-benzoimidazol-5-yl)-1,6-dihydro-1,2,3,5,6-tetraaza-as-indacene 6-Benzenesulfonyl-1-(4,5,6,7-tetrahydro-1H-benzoimidazol-5-yl)-1,6-dihydro-1,2,3,5,6-tetraaza-as-indacene (crude 500 mg, 1.2 mmol) in methanol (10 mL) was treated with aqueous sodium hydroxide solution (1.5 M, 3.2 mL, 3 mmol) at 30° C. for 4 hours. The solution was neutralized to pH ~8 with diluted hydrochloric acid, and concentrated. The crude product was purified by a reverse-phase preparatory HPLC (Column: XBridge 30*150 mm, 5% to 35%: acetonitrile+0.05% $NH_4OH$ in water, 10 min, 25 ml/min) to give 11.3 mg (3.4%, two steps) of 1-(4,5,6,7-Tetrahydro-3H-benzoimidazol-5-yl)-1,6-dihydro-1,2,3,5,6-tetraaza-as-indacene. LCMS (Method K, ESI): RT=1.660 min, m+H=279.1; $^1$H NMR (400 MHz, Methanol-$d_4$) δ: 8.58 (s, 1H), 8.18 (s, 1H), 7.62-7.61 (m, 1H), 7.43-7.42 (m, 1H), 6.74-6.73 (m, 1H), 5.25-5.15 (m, 1H), 3.40-3.10 (m, 2H), 3.00-2.80 (m, 1H), 2.75-2.40 (m, 3H).

Example 708

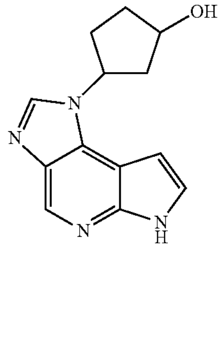 [SMILES: OC1CCC(n2cnc3cnc4[nH]ccc4c32)C1]

3-(6H-1,2,3,5,6-Tetraaza-as-indacen-1-yl)-cyclopentanol

Example 709

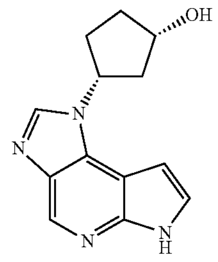 [SMILES: O[C@H]1CC[C@@H](n2cnc3cnc4[nH]ccc4c32)C1]

(1S,3R)-3-(6H-1,2,3,5,6-Tetraaza-as-indacen-1-yl)-cyclopentanol

Example 710

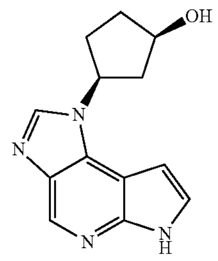 [SMILES: O[C@@H]1CC[C@H](n2cnc3cnc4[nH]ccc4c32)C1]

(1R,3S)-3-(6H-1,2,3,5,6-Tetraaza-as-indacen-1-yl)-cyclopentanol

3-Azido-cyclopentanone

To a solution of acetic acid (20 g, 0.33 mol) in dichloromethane (375 mL) was added trimethylsilyl azide (38 g, 0.33 mol), and the mixture was stirred at room temperature for 20 minutes. Then cyclopent-2-enone (9 g, 0.11 mol) was added to the reaction mixture followed by triethylamine (2.22 g, 0.022 mol), and the mixture was stirred at room temperature for 48 hours. The resulting mixture was quenched with aqueous sodium bicarbonate solution, and extracted with ethyl acetate. The organic layer was washed with brine three times and purified by column chromatography (Hexanes/ethyl acetate=1:3) to give 7.2 g of 3-Azido-cyclopentanone as a colorless liquid (TLC showed two spots), which was used for next step directly. $^1$H NMR (400 MHz, $CDCl_3$): δ: 4.31-4.26 (m, 1H), 2.46-2.08 (m, 6H).

3-Azido-cyclopentanol

To a solution of 3-Azido-cyclopentanone (about 7.2 g, 57.6 mmol) in methanol (250 mL) was added sodium borohydride (11 g, 288 mmol) in five portions at 0° C., then the reaction mixture was stirred at room temperature for 1 hour. The resulting mixture was quenched with water and extracted with ethyl acetate. The organic solution (TLC showed one spot) was concentrated and the residue was used for the next step. $^1H$ NMR (400 MHz, $CDCl_3$) δ: 4.25-4.30 (m, 1H), 3.95-3.80 (m, 6H).

3-Amino-cyclopentanol

To the solution of 3-Azido-cyclopentanol (the resulting solution of step 2) was added methanol (50 mL) and palladium on carbon (1 g, 10%). The reaction mixture was stirred under hydrogen (45 psi) overnight, the catalyst was filtered off, and the organic solution was concentrated. The residue (TLC showed one new spot) was used for next step.

3-(1-Benzenesulfonyl-5-nitro-1H-pyrrolo[2,3-b]pyridin-4-ylamino)-cyclopentanol

To a solution of 3-Amino-cyclopentanol (about 2.5 g) in ethanol (50 mL) were added 1-Benzenesulfonyl-4-chloro-5-nitro-1H-pyrrolo[2,3-b]pyridine (7 g, 20.4 mmol) and diisopropylethylamine (DIPEA) (7.2 g, 60 mmol), then the reaction mixture was stirred at 80° C. for 3 hours. The reaction mixture was purified by column chromatography (Hexanes/ethyl acetate=3:1) to give 7.4 g (76%) of 3-(1-Benzenesulfonyl-5-nitro-1H-pyrrolo[2,3-b]pyridin-4-ylamino)-cyclopentanol. $^1H$ NMR (400 MHz, $CDCl_3$) δ: 9.56 (s, 1H), 9.54 (s, 1H), 8.19-8.16 (m, 2H), 7.62-7.56 (m, 4H), 6.82-6.81 (m, 1H), 4.56-4.50 (m, 2H), 2.25-1.96 (m, 6H).

3-(5-Amino-1-benzenesulfonyl-1H-pyrrolo[2,3-b]pyridin-4-ylamino)-cyclopentanol

To a solution of 3-(1-Benzenesulfonyl-5-nitro-1H-pyrrolo[2,3-b]pyridin-4-ylamino)-cyclopentanol (6 g, 15 mmol) in methanol (250 mL) was added palladium on carbon (1 g, 10%), then the reaction mixture was stirred at room temperature under hydrogen (45 psi) for 3 hours. The catalyst was filtered off, and the organic solution was concentrated under reduce pressure to give 4.6 g (83%) of 3-(5-Amino-1-benzene sulfonyl-1H-pyrrolo[2,3-b]pyridin-4-ylamino)-cyclopentanol. $^1H$ NMR (400 MHz, $CDCl_3$) δ: 8.12-8.05 (s, 1H), 7.74 (s, 1H), 7.52-7.32 (m, 5H), 6.64-6.53 (m, 1H), 4.43-4.40 (s, 1H), 4.30-4.29 (m, 1H), 2.94-2.84 (m, 3H), 2.02-1.90 (m, 1H), 1.90-1.73 (m, 6H).

3-(6-Benzenesulfonyl-6H-1,2,3,5,6-tetraaza-as-indacen-1-yl)-cyclopentanol

To a solution of 3-(5-Amino-1-benzenesulfonyl-1H-pyrrolo[2,3-b]pyridin-4-ylamino)-cyclopentanol (2.0 g, 4.7 mmol) in ethanol (50 mL) was added triethyl orthoformate (4.7 mL, 28 mmol) and acetic acid (1 mL), then the reaction mixture was stirred at 80° C. for 3 hours. After being cooled to room temperature, the mixture was concentrated and the residue was dissolved in ethyl acetate, and washed with water and dried over sodium sulfate. The solvent was removed under reduced pressure and the residue was purified by column chromatography (Hexanes/ethyl acetate=1:1) to give 1.9 g (93%) of 3-(6-Benzenesulfonyl-6H-1,2,3,5,6-tetraaza-as-indacen-1-yl)-cyclopentanol as a solid. LCMS (Method K, ESI): RT=0.916 min, m+H=383.1.

3-(6H-1,2,3,5,6-Tetraaza-as-indacen-1-yl)-cyclopentanol

To a solution of 3-(6-Benzenesulfonyl-6H-1,2,3,5,6-tetraaza-as-indacen-1-yl)-cyclopentanol (1 g, 2.6 mmol) in methanol (10 mL) was added a solution of sodium hydroxide (260 mg, 6.5 mmol) in water (2 mL), then the reaction mixture was stirred at 60° C. for 2 hours. The reaction mixture was neutralized with diluted hydrochloride acid until pH=7. The reaction mixture was purified by a reverse-phase preparatory HPLC (Column: Waters Xbridge C18 150*30 mm*5 um, 5% to 35%: acetonitrile+0.05% $NH_4OH$ in water, 10 min, 25 mL/min) to give 250.2 mg (39%) of 3-(6H-1,2,3,5,6-Tetraaza-as-indacen-1-yl)-cyclopentanol. LCMS (Method K, ESI): RT=0.836 min, m+H=242.8.

(1S,3R)-3-(6H-1,2,3,5,6-Tetraaza-as-indacen-1-yl)-cyclopentanol & (1R,3S)-3-(6H-1,2,3,5,6-Tetraaza-as-indacen-1-yl)-cyclopentanol 3-(6H-1,2,3,5,6-Tetraaza-as-indacen-1-yl)-cyclopentanol (200 mg) was separated by SFC (Instrument: Berger Multi-Gram™ SFC, Mettler Toledo Co, Ltd; Column: AD 250 mm*20 mm, 5 um; Mobile phase: A: Supercritical $CO_2$, B: EtOH (0.05% DEA), A:B=45:55 at 40 mL/min; Column Temp: 38° C.; Nozzle Pressure: 100 Bar; Nozzle Temp: 60° C.; Evaporator Temp: 20° C.; Trimmer Temp: 25° C.; Wavelength: 220 nm) to give 15.0 mg of (1S,3R)-3-(6H-1,2,3,5,6-Tetraaza-as-indacen-1-yl)-cyclopentanol, LCMS (Method K, ESI): RT=0.861 min, m+H=243.0; and 13.8 mg of (1R,3S)-3-(6H-1,2,3,5,6-Tetraaza-as-indacen-1-yl)-cyclopentanol, LCMS (Method K, ESI): RT=0.770 min, m+H=243.1. $^1H$ NMR (400 MHz, DMSO-$d_6$) δ: 11.80 (s, 1H), 8.53 (s, 1H), 8.30 (s, 1H), 7.42-7.41 (m, 1H), 6.86-6.85 (m, 1H), 5.13-5.11 (m, 1H), 5.09 (s, 1H), 4.34-4.32 (m, 1H), 2.53-2.46 (m, 1H), 2.25-2.11 (m, 2H), 1.99-1.87 (m, 3H).

Example 711

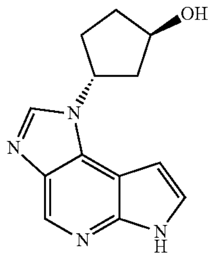 [SMILES: O[C@@H]1CC[C@@H](n2cnc3cnc4[nH]ccc4c32)C1]

(1R,3R)-3-(6H-1,2,3,5,6-Tetraaza-as-indacen-1-yl)-cyclopentanol

Example 712

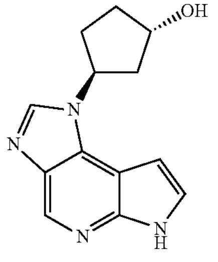 [SMILES: O[C@H]1CC[C@H](n2cnc3cnc4[nH]ccc4c32)C1]

(1S,3S)-3-(6H-1,2,3,5,6-Tetraaza-as-indacen-1-yl)-cyclopentanol

3-Amino-cyclopentanol hydrochloride

To the solution of (3-Hydroxy-cyclopentyl)-carbamic acid tert-butyl ester (1.6 g, 3.1 mmol) in ethyl acetate (5 mL) was added a solution of hydrochloric acid in ethyl acetate (4 M, 15 mL). Then the reaction mixture was stirred at room temperature for 3 hours and concentrated under reduce pressure to give 0.9 g (100%) of 3-Amino-cyclopentanol hydrochloride.

3-(1-Benzenesulfonyl-5-nitro-1H-pyrrolo[2,3-b]pyridin-4-ylamino)-cyclopentanol

A mixture of 3-Amino-cyclopentanol hydrochloride (0.9 g, 5.9 mmol), 1-Benzenesulfonyl-4-chloro-5-nitro-1H-pyrrolo[2,3-b]pyridine (2.0 g, 5.9 mmol) and diisopropylethylamine (2.3 g, 17.7 mmol) in ethanol (100 mL) was stirred at 80° C. for 3 hours. The reaction mixture was purified by column chromatography (Hexanes/ethyl acetate=3:1) to give 2.6 g (76%) of 3-(1-Benzenesulfonyl-5-nitro-1H-pyrrolo[2,3-b]pyridin-4-ylamino)-cyclopentanol; $^1$H NMR (400 MHz, $CDCl_3$) δ: 9.56 (s, 1H), 9.54 (s, 1H), 8.19-8.16 (m, 2H), 7.62-7.56 (m, 4H), 6.82-6.81 (m, 1H), 4.56-4.50 (m, 2H), 2.25-1.96 (m, 6H).

3-(5-Amino-1-benzenesulfonyl-1H-pyrrolo[2,3-b]pyridin-4-ylamino)-cyclopentanol

To a solution of 3-(1-Benzenesulfonyl-5-nitro-1H-pyrrolo[2,3-b]pyridin-4-ylamino)-cyclopentanol (2.6 g, 6.47 mmol) in ethanol (100 mL) was added palladium on carbon (10%, 1 g), then the reaction mixture was stirred at room temperature under hydrogen (45 psi) for 3 hours. The resulting mixture was concentrated under reduce pressure to give 1.7 g (83%) of 3-(5-Amino-1-benzenesulfonyl-1H-pyrrolo[2,3-b]pyridin-4-ylamino)-cyclopentanol. $^1$H NMR (400 MHz, $CDCl_3$): 8.12-8.05 (s, 1H), 7.74 (s, 1H), 7.52-7.32 (m, 5H), 6.64-6.53 (m, 1H), 4.43-4.40 (s, 1H), 4.30-4.29 (m, 1H), 2.94-2.84 (m, 3H), 2.02-1.90 (m, 1H), 1.90-1.73 (m, 6H).

3-(6-Benzenesulfonyl-6H-1,2,3,5,6-tetraaza-as-indacen-1-yl)-cyclopentanol

To a solution of 3-(5-Amino-1-benzenesulfonyl-1H-pyrrolo[2,3-b]pyridin-4-ylamino)-cyclopentanol (0.95 g, 2.55 mmol) in acetic acid (10 mL) and ethanol (30 mL) was added triethyl orthoformate (1.13 g, 7.63 mmol), then the reaction mixture was stirred at 80° C. for 3 hours. After being cooled to room temperature, the reaction mixture was concentrated and the residue was extracted with ethyl acetate. The extracts were dried over sodium sulfate and purified by column chromatography (Hexanes/ethyl acetate=1:1) to give 830 mg (93%) of 3-(6-Benzenesulfonyl-6H-1,2,3,5,6-tetraaza-as-indacen-1-yl)-cyclopentanol as a solid. LCMS (Method K, ESI): RT=0.978 min, m+H=383.0.

(1R,3R)-3-(6H-1,2,3,5,6-Tetraaza-as-indacen-1-yl)-cyclopentanol & (1S,3S)-3-(6H-1,2,3,5,6-Tetraaza-as-indacen-1-yl)-cyclopentanol To the solution of 3-(6-Benzenesulfonyl-6H-1,2,3,5,6-tetraaza-as-indacen-1-yl)-cyclopentanol (730 mg, 1.9 mmol) in methanol (25 mL) was added a solution of sodium hydroxide (191 mg, 4.7 mmol) in water (5 mL), then the reaction mixture was stirred at 60° C. for 2 hours and neutralized with diluted hydrochloride acid until pH=7. The reaction mixture was purified by a reverse-phase preparatory HPLC (Column: Waters Xbridge C18 150*30 mm*5 um, 5% to 30%: acetonitrile+0.05% $NH_4OH$ in water, 10 min, 25 mL/min) to give 260 mg (39%) of 3-(6H-1,2,3,5,6-Tetraaza-as-indacen-1-yl)-cyclopentanol. It was separated by SFC (Instrument: Berger MultiGram™ SFC, Mettler Toledo Co, Ltd; Column: AD 250 mm*20 mm, 5 um; Mobile phase: A: Supercritical $CO_2$, B: EtOH (0.05% DEA), A:B=45:55 at 40 mL/min; Column Temp: 38° C.; Nozzle Pressure: 100 Bar; Nozzle Temp: 60° C.; Evaporator Temp: 20° C.; Trimmer Temp: 25° C.; Wavelength: 220 nm) to give 37.4 mg of (1R,3R)-3-(6H-1,2,3,5,6-Tetraaza-as-indacen-1-yl)-cyclopentanol, LCMS (Method K, ESI): RT=0.730 min, m+H=243.1; $^1$H NMR (400 MHz, DMSO-$d_6$) δ: 11.85 (s, 1H), 8.56 (s, 1H), 8.29 (s, 1H), 7.46-7.45 (m, 1H), 6.7-6.69 (m, 1H), 5.29-5.25 (m, 1H), 4.88-4.87 (m, 1H), 4.42-4.41 (m, 1H), 2.41-2.38 (m, 1H), 2.22-2.14 (m, 3H), 2.02-1.99 (m, 1H), 1.72-1.67 (m, 1H); and 57.5 mg of (1S,3S)-3-(6H-1,2,3,5,6-Tetraaza-as-indacen-1-yl)-cyclopentanol, LCMS (Method K, ESI): RT=0.722 min, m+H=243.1; $^1$H NMR (400 MHz, DMSO-$d_6$) δ: 11.85 (s, 1H), 8.56 (s, 1H), 8.29 (s, 1H), 7.46-7.45 (m, 1H), 6.7-6.69 (m, 1H), 5.29-5.25 (m, 1H), 4.88-4.87 (m, 1H), 4.42-4.41 (m, 1H), 2.41-2.38 (m, 1H), 2.22-2.14 (m, 3H), 2.02-1.99 (m, 1H), 1.72-1.67 (m, 1H)

Example 713

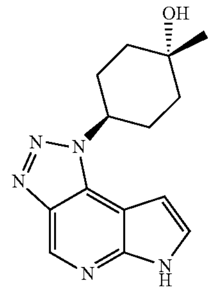 [SMILES: C[C@]1(O)CC[C@H](n2nnc3cnc4[nH]ccc4c32)CC1]

Trans-1-Methyl-4-(6H-1,2,3,5,6-pentaaza-as-indacen-1-yl)-cyclohexanol

Example 714

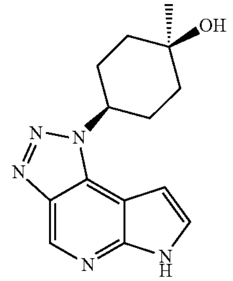 [SMILES: C[C@]1(O)CC[C@@H](n2nnc3cnc4[nH]ccc4c32)CC1]

Cis-1-Methyl-4-(6H-1,2,3,5,6-pentaaza-as-indacen-1-yl)-cyclohexanol

Acetic acid 4-(6-benzenesulfonyl-6H-1,2,3,5,6-pentaaza-as-indacen-1-yl)-cyclohexyl To a solution of 4-(1-Benzenesulfonyl-5-nitro-1H-pyrrolo[2,3-b]pyridin-4-ylamino)-cyclohexanecarboxylic acid methyl ester (2.0 g, 4.7 mmol) in acetic acid (40 mL) was added sodium nitrite (390 mg, 5.6 mmol), then the reaction mixture was stirred at room temperature for 2 hours. The resulting mixture was extracted with ethyl acetate. The organic layer was dried over sodium sulfate and purified by column chromatography (Hexanes/ethyl acetate=1:1) to give Acetic acid 4-(6-benzenesulfonyl-6H-1,2,3,5,6-pentaaza-as-indacen-1-yl)-cyclohexyl (1.8 g, yield 88%) ester as a solid. LCMS (Method J, ESI): RT=1.141 min, m+H=440.0.

4-(6-Benzenesulfonyl-6H-1,2,3,5,6-pentaaza-as-indacen-1-yl)-cyclohexanol

To a solution of Acetic acid 4-(6-benzenesulfonyl-6H-1,2,3,5,6-pentaaza-as-indacen-1-yl)-cyclohexyl (800 mg, 1.82 mmol) in water (5 mL) was added concentrated hydrochloride acid (36%, 15 mL), then the reaction mixture was stirred at 60° C. for 30 minutes. After being cooled to room temperature, the reaction mixture was basified with aqueous sodium hydroxide solution to pH ~8. Then the mixture was extracted with ethyl acetate. The extracts were dried over sodium sulfate and concentrated under reduce pressure to give 680 mg of 4-(6-Benzenesulfonyl-6H-1,2,3,5,6-pentaaza-as-indacen-1-yl)-cyclohexanol (94%) as a solid. $^1$H NMR (400 MHz, $CDCl_3$) δ: 9.20 (s, 1H), 8.25-8.23 (m, 2H), 7.91-7.90 (m, 1H), 7.59-7.57 (s, 1H), 7.52-7.48 (m, 2H), 6.89-6.88 (m, 1H), 4.79-4.75 (s, 1H), 3.94-3.89 (s, 1H), 2.32-2.24 (m, 4H), 1.71-1.58 (m, 4H).

4-(6-Benzenesulfonyl-6H-1,2,3,5,6-pentaaza-as-indacen-1-yl)-cyclohexanone

To a solution of oxalyl chloride (665.5 mg, 5.24 mmol) in anhydrous dichloromethane (40 mL) was added anhydrous dimethylsulfoxide (0.44 mL, 9.12 mmol) at −78° C. under nitrogen, followed by stirring for 15 minutes. Then the reaction temperature was warmed to −20° C. and a solution of 4-(6-Benzenesulfonyl-6H-1,2,3,5,6-pentaaza-as-indacen-1-yl)-cyclohexanol (750 mg, 1.94 mmol) in anhydrous dichloromethane (10 mL)was added dropwise. The mixture was stirred at −20° C. for 15 minutes and warmed to room temperature. Triethylamine (2.15 g, 19.4 mmol) was added and the mixture was stirred for 90 minutes. The reaction mixture was quenched with water and extracted with ethyl acetate. The extracts were dried over sodium sulfate and concentrated under reduced pressure to give the crude product, which was crystallized form ethanol to give 600 mg (78%) of 4-(6-Benzenesulfonyl-6H-1,2,3,5,6-pentaaza-as-indacen-1-yl)-cyclohexanone as a solid. $^1$H NMR (400 MHz, $CDCl_3$) δ: 9.29 (s, 1H), 8.24-8.22 (m, 3H), 7.81-7.64 (m, 4H), 5.67-5.65 (m, 1H), 2.91-2.83 (m, 2H), 2.52-2.49 (m, 6H), 4-(6-Benzenesulfonyl-6H-1,2,3,5,6-pentaaza-as-indacen-1-yl)-1-methyl-cyclohexanol To a solution of 4-(6-Benzenesulfonyl-6H-1,2,3,5,6-pentaaza-as-indacen-1-yl)-cyclohexanone (400 mg, 1.01 mmol) in anhydrous tetrahydrofuran (20 mL) was added dropwise methylmagnesium bromine (3 M in diethyl ether, 2.3 mL, 7.07 mmol), followed by stirring at 0° C. for 30 minutes under nitrogen. The reaction was warmed to room temperature and stirred for another 90 minutes. The resulting mixture was poured into water and extracted with ethyl acetate. The organic solution was used for the next step. LCMS (Method K, ESI): RT=1.318 min and 1.359, m+H=411.8.

1-Methyl-4-(6H-1,2,3,5,6-pentaaza-as-indacen-1-yl)-cyclohexanol & 1-Methyl-4-(6H-1,2,3,5,6-pentaaza-as-indacen-1-yl)-cyclohexanol To a solution of 4-(6-Benzenesulfonyl-6H-1,2,3,5,6-pentaaza-as-indacen-1-yl)-1-methyl-cyclohexanol (the resulting solution of previous step) was added a solution of sodium hydroxide (178 mg, 4.45 mmol) in water (2 mL), then the reaction mixture was stirred at 50° C. for 2 hours and neutralized with dilute hydrochloride acid until pH=7. The reaction mixture was purified by a reverse-phase preparatory HPLC (Column: Waters Xbridge C18 150*30 mm*5 um, 25% to 55%: acetonitrile+0.05% $NH_4OH$ in water, 10 min, 25 mL/min) to give 20 mg (12%) of 1-Methyl-4-(6H-1,2,3,5,6-pentaaza-as-indacen-1-yl)-cyclohexanol, LCMS (Method K, ESI): RT=0.725 min, m+H=272.1. $^1$H NMR (400 MHz, $CDCl_3$) δ: 10.00 (s, 1H), 9.10-9.09 (m, 1H), 7.45-7.44 (m, 1H), 6.82-6.80 (m, 1H), 4.97-4.93 (m, 1H), 2.39-2.34 (m, 4H), 2.06-2.00 (m, 2H), 1.82-1.74 (m, 2H), 1.44 (s, 3H); and 22 mg (14%) of 1-Methyl-4-(6H-1,2,3,5,6-pentaaza-as-indacen-1-yl)-cyclohexanol, LCMS (Method K, ESI): RT=1.023 min, m+H=272.1. $^1$H NMR (400 MHz, $CDCl_3$) δ: 10.65-10.63 (m, 1H), 9.11 (s, 1H), 7.44-7.44 (m, 1H), 7.17-7.16 (m, 1H), 5.04-4.97 (m, 1H), 2.80-2.70 (m, 2H), 2.05-1.93 (m, 4H), 1.77-1.69 (m, 2H), 1.40 (s, 3H)

Example 715

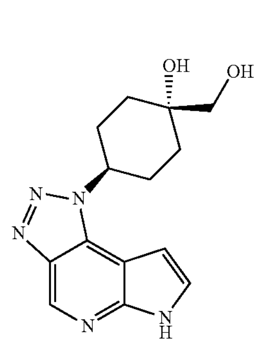 [SMILES: OC[C@]1(O)CC[C@H](n2nnc3cnc4[nH]ccc4c32)CC1]

Trans-1-Hydroxymethyl-4-(6H-1,2,3,5,6-pentaaza-as-indacen-1-yl)-cyclohexanol

Example 716

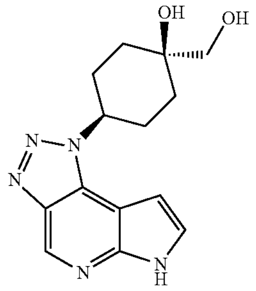 [SMILES: OC[C@]1(O)CC[C@@H](n2nnc3cnc4[nH]ccc4c32)CC1]

Cis-1-Hydroxymethyl-4-(6H-1,2,3,5,6-pentaaza-as-indacen-1-yl)-cyclohexanol

6-Benzenesulfonyl-1-(4-methylene-cyclohexyl)-1,6-dihydro-1,2,3,5,6-pentaaza-as-indacene To a solution of Methyltriphenylphosphonium iodide (1.0 g, 2.5 mmol) in tetrahydrofuran (10 mL) was added slowly n-butyllithium (2.5 M in diethyl ether, 1 mL, 2.5 mmol) at −78° C., then the reaction mixture was stirred for 1 hour under nitrogen. To the reaction mixture was added 4-(6-Benzenesulfonyl-6H-1,2,3,5,6-pentaaza-as-indacen-1-yl)-cyclohexanone (400 mg, 1.01 mmol) slowly, then the reaction mixture was stirred for 3 hours under nitrogen and quenched with saturated aqueous ammonium chloride. The mixture was extracted with ethyl acetate. The organic phase was concentrated under reduce pressure to give 200 mg (76%) of 6-Benzenesulfonyl-1-(4-methylene-cyclohexyl)-1,6-dihydro-1,2,3,5,6-pentaaza-as-indacene. $^{1}$H NMR (400 MHz, DMSO-$d_6$): δ: 9.18 (s, 1H), 8.15-8.12 (m, 3H), 7.72-7.68 (m, 1H), 7.63-7.59 (m, 2H), 7.44-7.43 (m, 1H), 5.22 (s, 1H), 4.76 (s, 2H), 2.49-2.41 (m, 4H), 2.26-2.23 (m, 2H), 2.05-2.02 (m, 2H).

4-(6-Benzenesulfonyl-6H-1,2,3,5,6-pentaaza-as-indacen-1-yl)-1-hydroxymethyl-cyclohexanol To a solution of 6-Benz ene sulfonyl-1-(4-methyl ene-cyclohexyl)-1,6-dihydro-1,2,3,5,6-pentaaza-as-indacene (200 mg, 0.51 mmol) in tetrahydrofuran (8 mL) was added water (4 mL) and pyridine (4 mL), followed by stirring for 15 min. Osmium tetroxide (30 mg, 0.12 mmol) was then added to the reaction mixture, followed by stirring at room temperature for 17 hours. The reaction mixture was quenched with aqueous sodium sulfite ($Na_2SO_3$), and extracted with ethyl acetate. The organic phase was purification by silica gel (ethyl acetate:Hexane=10:1) to give 70 mg (35%) 4-(6-Benzenesulfonyl-6H-1,2,3,5,6-pentaaza-as-indacen-1-yl)-1-hydroxymethyl-cyclohexanol. LCMS (Method K, ESI): RT=1.053 min, m+H=428.1.

1-Hydroxymethyl-4-(6H-1,2,3,5,6-pentaaza-as-indacen-1-yl)-cyclohexanol & 1-Hydroxymethyl-4-(6H-1,2,3,5,6-pentaaza-as-indacen-1-yl)-cyclohexanol To a solution of 4-(6-Benzenesulfonyl-6H-1,2,3,5,6-pentaaza-as-indacen-1-yl)-1-hydroxymethyl-cyclohexanol (200 mg, 0.47 mmol) in methanol (25 mL) was added a solution of sodium hydroxide (46.8 mg, 1.17 mmol) in water (5 mL), then the reaction mixture was stirred at 60° C. for 3 hours and neutralized with dilute hydrochloride acid until pH=7. The reaction mixture was purified by a reverse-phase preparatory HPLC (Column: Waters Xbridge C18 150*30 mm*5 um, 0% to 25%: acetonitrile+0.05% $NH_4OH$ in water, 10 min, 25 mL/min) to give 15.9 mg (39%) of 1-Hydroxymethyl-4-(6H-1,2,3,5,6-pentaaza-as-indacen-1-yl)-cyclohexanol, LCMS (Method K, ESI): RT=0.873 min, m+H=288.0; $^{1}$H NMR (400 MHz, DMSO-$d_6$) δ: 8.97 (s, 1H), 7.57 (d, 1H), 6.96 (d, 1H), 5.14-5.07 (m, 1H), 4.62-4.57 (m, 1H), 4.31-4.25 (m, 1H), 3.52 (s, 3H), 2.25-2.18 (m, 2H), 2.18-2.15 (m, 2H), 1.93-1.90 (m, 2H), 1.62-1.51 (m, 2H); and 19.3 mg (39%) of 1-Hydroxymethyl-4-(6H-1,2,3,5,6-pentaaza-as-indacen-1-yl)-cyclohexanol, LCMS (Method K, ESI): RT=0.889 min, m+H=288.1; $^{1}$H NMR (400 MHz, DMSO-$d_6$) δ: 12.32 (s, 1H), 8.96 (s, 1H), 7.57 (s, 1H), 7.17 (s, 1H), 5.01-4.98 (m, 1H), 4.67 (d, 1H), 4.38 (d, 2H), 2.54-2.46 (m, 2H), 1.88-1.63 (m, 6H).

Examples 717-1014 shown in Table 3 were prepared generally following the above-described Examples and making non-critical variations where necessary. The general synthetic method used for each compound is indicated.

TABLE 3

| Ex # | Name | Synthetic Method | LCMS RT (min)/Method | LCMS (ESI) m/z |
|---|---|---|---|---|
| 717 | Racemic trans [3-(6H-1,3,5,6-tetraaza-as-indacen-1-yl)-cyclopentyl]-(2,2,2-trifluoro-ethyl)-amine | 626 | 1.82/A | 324.3 |
| 718 | Racemic trans [3-(6H-1,2,3,5,6-Pentaaza-as-indacen-1-yl)-cyclopentyl]-(2,2,2-trifluoro-ethyl)-amine | 591 | 2.33/A | 325.3 |
| 719 | [(1R,3S)-3-(2-Methyl-6H-1,3,5,6-tetraaza-as-indacen-1-yl)-cyclopentyl]-(2,2,2-trifluoro-ethyl)-amine | 626 | 2.05/A | 338.1 |
| 720 | [(1R,3R)-3-(2-Methyl-6H-1,3,5,6-tetraaza-as-indacen-1-yl)-cyclopentyl]-(2,2,2-trifluoro-ethyl)-amine | 626 | 1.94/A | 338.2 |
| 721 | Racemic trans N-[3-(2-methyl-6H-1,3,5,6-tetraaza- | 630 | 1.96/A | 334.0 |

TABLE 3-continued

| Ex # | Name | Synthetic Method | LCMS RT (min)/Method | LCMS (ESI) m/z |
|---|---|---|---|---|
| | as-indacen-1-yl)-cyclopentyl]-methanesulfonamide | | | |
| 722 | Trans N-[4-(2-methyl-6H-1,3,5,6-tetraaza-as-indacen-1-yl)-cyclohexyl]-methanesulfonamide | 630 | 2.00/A | 348.1 |
| 723 | 3-[(1R,3S)-3-(2-Methyl-6H-1,3,5,6-tetraaza-as-indacen-1-yl)-cyclopentylamino]-propionitrile | 627 | 1.24/A | 309.3 |
| 724 | 3-[(1R,3R)-3-(2-Methyl-6H-1,3,5,6-tetraaza-as-indacen-1-yl)-cyclopentylamino]-propionitrile | 627 | 1.13/A | 309.2 |
| 725 | 3-[(1R,3R)-3-(2-Methyl-6H-1,3,5,6-tetraaza-as-indacen-1-yl)-cyclopentylamino]-butyronitrile | 627 & 590 | 1.50/A | 323.2 |
| 726 | Racemic trans (2-Methoxy-ethyl)-[3-(6H-1,3,5,6-tetraaza-as-indacen-1-yl)-cyclopentyl]-amine | 628 | 1.47/A | 300.3 |
| 727 | [(1R,3R)-3-(6H-1,2,3,5,6-Pentaaza-as-indacen-1-yl)-cyclopentyl]-carbamic acid tert-butyl ester | 623 | 3.89/A | 343.3 |
| 728 | Racemic trans 2-Cyano-N-[3-(2-methyl-6H-1,3,5,6-tetraaza-as-indacen-1-yl)-cyclopentyl]-acetamide | 624 | 2.06/A | 323.3 |
| 729 | Racemic trans 3,3,3-Trifluoro-N-[3-(6H-1,3,5,6-tetraaza-as-indacen-1-yl)-cyclopentyl]-propionamide | 629 | 2.32/A | 352.3 |
| 730 | Racemic trans 3,3,3-Trifluoro-N-[3-(2-methyl-6H-1,3,5,6-tetraaza-as-indacen-1-yl)-cyclopentyl]-propionamide | 624 | 2.33/A | 3.66.3 |
| 731 | 3,3,3-Trifluoro-N-[(1R,3S)-3-(2-methyl-6H-1,3,5,6-tetraaza-as-indacen-1-yl)-cyclopentyl]-propionamide | 624 | 2.33/A | 366.2 |
| 732 | Racemic trans 4,4,4-Trifluoro-N-[3-(6H-1,3,5,6-tetraaza-as-indacen-1-yl)-cyclopentyl]-butyramide | 629 | 2.53/A | 366.1 |
| 733 | Racemic trans [3-(6H-1,3,5,6-Tetraaza-as-indacen-1-yl)-cyclopentyl]-carbamic acid 2,2,2-trifluoro-ethyl ester | 620 | 2.82/A | 386.3 |
| 734 | Racemic trans [3-(6H-1,3,5,6-Tetraaza-as-indacen-1-yl)-cyclopentyl]-carbamic acid methyl ester | 621 | 2.10/A | 300.3 |
| 735 | [(1R,3R)-3-(2-Methyl-6H-1,3,5,6-tetraaza-as-indacen-1-yl)-cyclopentyl]-carbamic acid methyl ester | 621 | 2.15/A | 314.3 |
| 736 | Racemic trans 1-Methyl-3-[3-(2-methyl-6H-1,3,5,6-tetraaza-as-indacen-1-yl)-cyclopentyl]-1-(2,2,2-trifluoro-ethyl)-urea | 622 | 2.57/A | 395.3 |
| 737 | Racemic trans 1-Methyl-3-[3-(6H-1,3,5,6-tetraaza-as-indacen-1-yl)-cyclopentyl]-1-(2,2,2-trifluoro-ethyl)-urea | 622 | 2.60/A | 381.3 |
| 738 | Racemic trans 1-(2-Methoxy-ethyl)-1-methyl-3-[3-(2-methyl-6H-1,3,5,6-tetraaza-as-indacen-1-yl)-cyclopentyl]-urea | 622 | 2.23/A | 371.4 |
| 739 | Racemic trans 1-(2-Methoxy-ethyl)-1-methyl-3-[3-(6H-1,3,5,6-tetraaza-as-indacen-1-yl)-cyclopentyl]-urea | 622 | 2.24/A | 357.3 |
| 740 | 2-Methyl-1-[4-methyl-1-(pyridine-3-sulfonyl)-piperidinyl-4-yl]-1,6-dihydro-1,3,5,6-tetraaza-as-indacene | 580 | 2.46/A | 411.2 |

TABLE 3-continued

| Ex # | Name | Synthetic Method | LCMS RT (min)/Method | LCMS (ESI) m/z |
|---|---|---|---|---|
| 741 | 3-[4-Methyl-4-(2-methyl-6H-1,3,5,6-tetraaza-as-indacen-1-yl)-piperidin-1-yl]-3-oxo-propionitrile | 579 | 1.90/A | 337.3 |
| 742 | Racemic trans 3-[6-benzenesulfonyl-2-((R)-1-hydroxy-ethyl]-6H-1,3,5,6-tetraaza-as-indecen-1-yl}-cyclohexanecarbonitrile | 648 | 2.40 & 2.42/A | 310.2 |
| 743 | Cis & Trans mixture {4-[2-((R)-1-Hydroxy-ethyl)-6H-1,3,5,6-tetraaza-as-indacen-1-yl]cyclohexyl}acetonitrile | 643 | 2.44/A | 324.2 |
| 744 | Trans [4-(6H-1,3,5,6-tetraaza-as-indacen-1-yl)-cyclohexyl]-carbamic acid pyridin-3-ylmethyl ester | 599 | 1.93/A | 391.3 |
| 745 | Trans 1-methyl-3-[4-(6H-1,3,5,6-tetraaza-as-indacen-1-yl)-cyclohexyl]-1-(2,2,2-trifluoro-ethyl)-urea | 599 | 2.66/A | 395.3 |
| 746 | Trans azetidine-1-carboxylic acid [4-(6H-1,3,5,6-tetraaza-as-indacen-1-yl)-cyclohexyl]-amide | 603 | 2.15/A | 339.3 |
| 747 | Trans 1-(2,2-difluoro-ethyl)-1-methyl-3-[4-(6H-1,3,5,6-tetraaza-as-indacen-1-yl)-cyclohexyl]-urea | 603 | 2.46/A | 377.3 |
| 748 | Trans 3,3-difluoro-azetidine-1-carboxylic acid [4-(2-methyl-6H-1,3,5,6-tetraaza-as-indacen-1-yl)-cyclohexyl]-amide | 604 | 2.39/A | 389.3 |
| 749 | Trans 1-methyl-3-[4-(2-methyl-6H 1,3,5,6-tetraaza-as-indacen-1-yl)-cyclohexyl]-1-(2,2,2-trifluoro-ethyl)-urea | 604 | 2.66/A | 409.4 |
| 750 | Trans 1-(2,2-difluoro-ethyl)-1-methyl-3-[4-(2-methyl-6H-1,3,5,6-tetraaza-as-indacen-1-yl)-cyclohexyl]-urea | 604 | 2.44/A | 391.2 |
| 751 | Trans methyl-carbamic acid 4-(2-methyl-6H-1,3,5,6-tetraaza-as-indacen-1-yl)-cyclohexyl ester | 605 | 2.23/A | 328.3 |
| 752 | 1-[4-Methyl-1-(2,2,2-trifluoro-ethyl)-piperidin-4-yl]-1,6-dihydro-1,3,5,6-tetraaza-as-indacene | 175 | 3.04/A | 338 |
| 753 | 1-[4-Methyl-1-(pyridine-3-sulfonyl)-piperidin-4-yl]-1,6-dihydro-1,3,5,6-tetraaza-as-indacene | 580 | 2.60/A | 397 |
| 754 | 3-[4-Methyl-4-(6H-1,3,5,6-tetraaza-as-indacen-1-yl)-piperidin-1-ylmethyl]-benzonitrile | 8 | 1.98/A | 371 |
| 755 | 1-(4-Methyl-1-thiazol-5-ylmethyl-piperidin-4-yl)-1,6-dihydro-1,3,5,6-tetraaza-as-indacene | 8 | 1.57/A | 353 |
| 756 | 4-[4-Methyl-4-(6H-1,3,5,6-tetraaza-as-indacen-1-yl)-piperidin-1-ylmethyl]-pyridine-2-carbonitrile | 8 | 1.97/A | 372 |
| 757 | 1-(1-Ethanesulfonyl-4-methyl-piperidin-4-yl)-1,6-dihydro-1,3,5,6-tetraaza-as-indacene | 580 | 2.40/A | 348 |
| 758 | 4-[4-Methyl-4-(2-methyl-6H-1,3,5,6-tetraaza-as-indacen-1-yl)-piperidin-1-ylmethyl]-pyridine-2-carbonitrile | 8 | 1.61/A | 386 |
| 759 | 1-{1-[1-(3,3,3-Trifluoro-propyl)-piperidin-4-yl]-1,6-dihydro-1,3,5,6-tetraaza-as-indacen-2-yl}-ethanol | 156 & 11 | 1.74/A | 382 |
| 760 | {1-[1-(3,3,3-Trifluoro-propyl)-piperidin-4-yl]-1,6-dihydro-1,3,5,6-tetraaza-as-indacen-2-yl}-methanol | 22, 2 & 11 | 1.52/A | 368 |

TABLE 3-continued

| Ex # | Name | Synthetic Method | LCMS RT (min)/Method | LCMS (ESI) m/z |
|---|---|---|---|---|
| 761 | {1-[1-(2,2,2-Trifluoro-ethyl)-piperidin-4-yl]-1,6-dihydro-1,3,5,6-tetraaza-as-indacen-2-yl}-methanol | 22, 2 & | 2.85/A | 354 |
| 762 | 1-[1-(2,2-Difluoro-ethyl)-piperidin-4-yl]-2-methyl-1,6-dihydro-1,3,5,6-tetraaza-as-indacene | 175 | 1.83/A | 320 |
| 763 | Trans 1-(2-Methoxy-ethyl)-1-methyl-3-[4-(6H-1,3,5,6-tetraaza-as-indacen-1-yl)-cyclohexyl]-urea | 592 | 2.31/A | 371.3 |
| 764 | 4-(2-Methyl-6H-1,3,5,6-tetraaza-as-indacen-1-yl)-piperidine-1-carboxylic acid (2,2,2-trifluoro-ethyl)-amide | 592 | 2.13/A | 381.2 |
| 765 | 4-(2-Methyl-6H-1,3,5,6-tetraaza-as-indacen-1-yl)-piperidine-1-carboxylic acid (3,3,3-trifluoro-propyl)-amide | 592 | 2.31/A | 395.1 |
| 766 | Trans 1-[4-(1,1-Dioxo-thiomorpholin-4-yl)-cyclohexyl]-1,6-dihydro-1,3,5,6-tetraaza-as-indacene | 594 | 1.75/A | 374.3 |
| 767 | Trans 1-[4-(4,4-Difluoro-piperidin-1-yl)-cyclohexyl]-2-methyl-1,6-dihydro-1,3,5,6-tetraaza-as-indacene | 594 | 1.64/A | 374.5 |
| 768 | Trans 1-[4-(2-Methyl-6H-1,3,5,6-tetraaza-as-indacen-1-yl)-cyclohexyl]-piperidine-4-carbonitrile | 594 | 1.59/A | 363.3 |
| 769 | Trans Methyl-carbamic acid 4-(6H-1,3,5,6-tetraaza-as-indacen-1-yl)-cyclohexyl ester | 595 | 2.26/A | 314.3 |
| 770 | 3-{4-[2-(2-Methoxy-ethylamino)-6H-1,3,5,6-tetraaza-as-indacen-1-yl]-piperidin-1-yl}-propionitrile | 657 & 655 | 1.64/A | 368.3 |
| 771 | 3-[4-(2-Methylamino-6H-1,3,5,6 tetraaza-as indacen-1-yl)-piperidin-1-yl]-propionitrile | 657 & 655 | 1.65/A | 324.3 |
| 772 | 3-[4-(2-Methylamino-6H-1,3,56-tetraaza-as-indacen-1-yl)-piperidine-1-yl-methyl]-benzonitrile | 657 | 1.98/A | 386.3 |
| 773 | Methyl-[1-(tetrahydro-pyran-3-yl)-1,6-dihydro-1,3,5,6-tetraaza-as-indacen-2-yl]-amine | 657 | 2.06/A | 272.3 |
| 774 | [1-(1-Methanesulfonyl-piperidin-4-yl) 1,6-dihydro-1,3,5,6-tetraaza-as-indacen-1-yl]-methyl-amine | 9 | 2.02/A | 349.3 |
| 775 | Cis 1-(4-Morpholin-4-yl-cyclohexyl)-1,6-dihydro-1,3,5,6-tetraaza-as-indacene | 594 | 1.27/A | 326.3 |
| 776 | Cis 4-[2-((R)-1-Hydroxy-ethyl)-6H-1,3,5,6-tetraaza-as-indacen-1-yl]-cyclohexanecarbonitrile | 641 | 2.29/A | 310.2 |
| 777 | Cis 4-(2-Hydroxymethyl-6H-1,3,5,6-tetraaza-as-indacen-1-yl)-cyclohexanecarbonitrile | 641 | 2.14/A | 296.2 |
| 778 | Trans (R)-1-{1-[4-(2-methanesulfonyl-ethyl)-cyclohexyl]-1,6-dihydro-1,3,5,6-tetraaza-as-indacen-2-yl}-ethanol | 641 | 2.27/A | 391.1 |
| 779 | Trans (R)-1-[1-(4-[1,2,4]triazol-1-yl-cyclohexyl)-1,6-dihydro-1,3,5,6-tetraaza-as-indacen-2-yl]-ethanol | 653 | 2.08/A | 352.1 |
| 780 | Racemic 2-[1-(Tetrahydro-pyran-3-yl)-1,6-dihydro-1,3,5,6-tetraaza-as-indacen-2-yloxy]-ethanol | 655 | 2.08/A | 303.1 |
| 781 | 1-{(R)-3-[2-((S)-1-Hydroxy-ethyl)-6H-1,3,5,6-tetraaza-as-indacen-1- | 662 | 2.405/C | 394.1 |

TABLE 3-continued

| Ex # | Name | Synthetic Method | LCMS RT (min)/Method | LCMS (ESI) m/z |
|---|---|---|---|---|
| | yl]-piperidin-1-yl}-2-imidazol-1-yl-ethanone | | | |
| 782 | 3,3,3-Trifluoro-1-{(R)-3-[2-((S)-1-hydroxy-ethyl)-6H-1,3,5,6-tetraaza-as-indacen-1-yl]-piperidin-1-yl}-propan-1-one | 662 | 3.045/C | 396.1 |
| 783 | {(R)-3-[2-((R)-1-Hydroxy-ethyl)-6H-1,3,5,6-tetraaza-as-indacen-1-yl]-piperidin-1-yl}-(tetrahydro-pyran-4-yl)-methanone | 662 | 2.836/C | 398.2 |
| 784 | 1-{(R)-3-[2-((R)-1-Hydroxy-ethyl)-6H-1,3,5,6-tetraaza-as-indacen-1-yl]-piperidin-1-yl}-3-methoxy-propan-1-one | 662 | 2.796/C | 372.1 |
| 785 | 3,3,3-Trifluoro-1-{(R)-3-[2-((R)-1-hydroxy-ethyl)-6H-1,3,5,6-tetraaza-as-indacen-1-yl]-piperidin-1-yl}-propan-1-one | 662 | 3.051/ | 396.1 |
| 786 | {3-[2-(1-Hydroxy-ethyl)-6H-1,3,5,6-tetraaza-as-indacen-1-yl]-piperidin-1-yl}-(tetrahydro-furan-3-yl)-methanone | 662 | 2.796/C | 384.1 |
| 787 | 4-{3-[2-(1-Hydroxy-ethyl)-6H-1,3,5,6-tetraaza-as-indacen-1-yl]-piperidine-1-carbonyl}-1-methyl-pyrrolidin-2-one | 661 | 2.686/C | 411.2 |
| 788 | Cyclopentyl-{(R)-3-[2-((R)-1-hydroxy-ethyl)-6H-1,3,5,6-tetraaza-as-indacen-1-yl]-piperidin-1-yl}-methanone | 661 | 3.376/C | 382.2 |
| 789 | 1-{3-[2-(1-Hydroxy-ethyl)-6H-1,3,5,6-tetraaza-as-indacen-1-yl]-piperidin-1-yl}-2-(tetrahydro-furan-2-yl)-ethanone | 661 | 2.962/C | 398.2 |
| 790 | (2,2-Difluoro-cyclopropyl)-{3-[2-(1-hydroxy-ethyl)-6H-1,3,5,6-tetraaza-as-indacen-1-yl]-piperidin-1-yl}-methanone | 661 | 3.08/C | 390.1 |
| 791 | 2-Cyclopropyl-1-{(R)-3-[2-((R)-1-hydroxy-ethyl)-6H-1,3,5,6-tetraaza-as-indacen-1-yl]-piperidin-1-yl}-ethanone | 662 | 3.097/C | 368.1 |
| 792 | Cyclobutyl-{(R)-3-[2-((R)-1-hydroxy-ethyl)-6H-1,3,5,6-tetraaza-as-indacen-1-yl]-piperidin-1-yl}-methanone | 662 | 3.177/C | 368.1 |
| 793 | 1-{(R)-3-[2-((R)-1-Hydroxy-ethyl)-6H-1,3,5,6-tetraaza-as-indacen-1-yl]-piperidin-1-yl}-3-methyl-butan-1-one | 662 | 3.255/C | 370.1 |
| 794 | Cyclopropyl-{(R)-3-[2-((R)-1-hydroxy-ethyl)-6H-1,3,5,6-tetraaza-as-indacen-1-yl]-piperidin-1-yl}-methanone | 662 | 2.936/C | 354.1 |
| 795 | 1-{(R)-3-[2-((R)-1-Hydroxy-ethyl)-6H-1,3,5,6-tetraaza-as-indacen-1-yl]-piperidin-1-yl}-propan-1-one | 662 | 2.837/C | 342.1 |
| 796 | {3-[2-(1-Hydroxy-ethyl)-6H-1,3,5,6-tetraaza-as-indacen-1-yl]-piperidin-1-yl}-(2-methyl-cyclopropyl)-methanone | 662 | 3.131/C | 368.1 |
| 797 | 1-{(R)-3-[2-((R)-1-Hydroxy-ethyl)-6H-1,3,5,6-tetraaza-as-indacen-1-yl]-piperidin-1-yl}-3-imidazol-1-yl-propan-1-one | 661 | 2.553/C | 408.2 |
| 798 | 1-{(R)-3-[2-((R)-1-Hydroxy-ethyl)-6H-1,3,5,6-tetraaza-as-indacen-1-yl]-piperidin-1-yl}-2-imidazol-1-yl-ethanone | 661 | 2.467/C | 394.1 |
| 799 | {3-[2-(1-Hydroxy-ethyl)-6H-1,3,5,6-tetraaza-as-indacen-1-yl]-piperidin-1-yl}-(4-methoxy-cyclohexyl)-methanone | 661 | 3.29/C | 426.2 |
| 800 | (R)-3-[2-((R)-1-Hydroxy-ethyl)-6H-1,3,5,6-tetraaza-as-indacen-1-yl]-piperidine-1-carboxylic acid ethyl ester | 661 | 3.110/C | 358.1 |

TABLE 3-continued

| Ex # | Name | Synthetic Method | LCMS RT (min)/Method | LCMS (ESI) m/z |
|---|---|---|---|---|
| 801 | 1-[2-(1-Cyclohexyl-1,6-dihydro-1,3,5,6-tetraaza-as-indacen-2-yl)-ethyl]-pyrrolidin-2-one | 677 | 3.38/C | 352.1 |
| 802 | N-[2-(1-Cyclohexyl-1,6-dihydro-1,3,5,6-tetraaza-as-indacen-2-yl)-ethyl]-N-methyl-acetamide | 677 | 3.31/C | 340.1 |
| 803 | 3-(1-Cyclohexyl-1,6-dihydro-1,3,5,6-tetraaza-as-indacen-2-yl)-N,N-dimethyl-propionamide | 677 | 3.43/C | 340.1 |
| 804 | N-{2-[1-(1-Ethyl-3,3-difluoro-piperidin-4-yl)-1,6-dihydro-1,3,5,6-tetraaza-as-indacen-2-yl]-ethyl}-methanesulfonamide (racemic) | 678 | 2.46/C | 427.1 |
| 805 | N-{2-[1-(1-Ethyl-3,3-difluoro-piperidin-4-yl)-1,6-dihydro-1,3,5,6-tetraaza-as-indacen-2-yl]-ethyl}-methanesulfonamide (enantiomer 1) | 678 | 2.46/C | 427.1 |
| 806 | N-{2-[1-(1-Ethyl-3,3-difluoro-piperidin-4-yl)-1,6-dihydro-1,3,5,6-tetraaza-as-indacen-2-yl]-ethyl}-methanesulfonamide (enantiomer 2) | 678 | 2.46/C | 427.1 |
| 807 | N-{2-[1-(1-Ethyl-3,3-difluoro-piperidin-4-yl)-1,6-dihydro-1,3,5,6-tetraaza-as-indacen-2-yl]-ethyl}-acetamide | 678 | 2.40/C | 391.1 |
| 808 | N-{2-[1-((3S,4R)-1-Ethyl-3-fluoro-piperidin-4-yl)-1,6-dihydro-1,3,5,6-tetraaza-as-indacen-2-yl]-ethyl}-methanesulfonamide | 681 | 2.18/C | 409.1 |
| 809 | Cyclopropanesulfonic acid {2-[1-((3S,4R)-1-ethyl-3-fluoro-piperidin-4-yl)-1,6-dihydro-1,3,5,6-tetraaza-as-indacen-2-yl]-ethyl}-amide | 681 | 2.39/C | 435.1 |
| 810 | Propane-2-sulfonic acid {2-[1-((3S,4R)-1-ethyl-3-fluoro-piperidin-4-yl)-1,6-dihydro-1,3,5,6-tetraaza-as-indacen-2-yl]-ethyl}-amide | 681 | 2.50/C | 437.1 |
| 811 | N-{2-[1-((3S,4R)-1-Ethyl-3-fluoro-piperidin-4-yl)-1,6-dihydro-1,3,5,6-tetraaza-as-indacen-2-yl]-ethyl}-acetamide | 681 | 2.12/C | 373.2 |
| 812 | 3-{4-[2-(Tetrahydro-pyran-4-ylmethyl)-6H-1,3,5,6-tetraaza-as-indacen-1-yl]-piperidin-1-yl}-propionitrile | 120 | 2.46/C | 393.2 |
| 813 | 3-{4-[2-(Tetrahydro-furan-2-ylmethyl)-6H-1,3,5,6-tetraaza-as-indacen-1-yl]-piperidin-1-yl}-propionitrile | 120 | 2.51/C | 379.2 |
| 814 | 3-(4-{2-[2-(1-Methyl-1H-pyrazol-3-yl)-ethyl]-6H-1,3,5,6-tetraaza-as-indacen-1-yl}-piperidin-1-yl)-propionitrile | 120 | 2.51/C | 403.2 |
| 815 | 3-(4-{2-[2-(2-Ethyl-imidazol-1-yl)-ethyl]-6H-1,3,5,6-tetraaza-as-indacen-1-yl}-piperidin-1-yl)-propionitrile | 120 | 2.39/C | 417.2 |
| 816 | 3-(4-{2-[2-(2-Isopropyl-imidazol-1-yl)-ethyl]-6H-1,3,5,6-tetraaza-as-indacen-1-yl}-piperidin-1-yl)-propionitrile | 120 | 2.51/C | 431.2 |
| 817 | 3-{4-[2-(3,3-Difluoro-butyl)-6H-1,3,5,6-tetraaza-as-indacen-1-yl]-piperidin-1-yl}-propionitrile | 120 | 2.68/C | 387.1 |
| 818 | (R)-1-{1-[1-(1-Methyl-1H-pyrazol-4-ylmethyl)-piperidin-4-yl]-1,6-dihydro-1,3,5,6-tetraaza-as-indacen-2-yl}-ethanol | 682 | 2.33/C | 380.1 |
| 819 | (R)-1-{1-[1-(2-Methyl-2H-pyrazol-3-ylmethyl)-piperidin-4-yl]-1,6-dihydro-1,3,5,6-tetraaza-as-indacen-2-yl}-ethanol | 682 | 2.36/C | 380.2 |
| 820 | (R)-1-{1-[1-(2-Ethyl-2H-pyrazol-3-ylmethyl)-piperidin-4-yl]-1,6-dihydro-1,3,5,6-tetraaza-as-indacen-2-yl}-ethanol | 682 | 2.49/C | 394.1 |

TABLE 3-continued

| Ex # | Name | Synthetic Method | LCMS RT (min)/Method | LCMS (ESI) m/z |
|---|---|---|---|---|
| 821 | (R)-1-{1-[1-(2,5-Dimethyl-2H-pyrazol-3-ylmethyl)-piperidin-4-yl]-1,6-dihydro-1,3,5,6-tetraaza-as-indacen-2-yl}-ethanol | 682 | 2.49/C | 394.2 |
| 822 | (R)-1-{1-[1-(1-Ethyl-1H-pyrazol-4-ylmethyl)-piperidin-4-yl]-1,6-dihydro-1,3,5,6-tetraaza-as-indacen-2-yl}-ethanol | 682 | 2.46/C | 394.2 |
| 823 | (R)-1-{1-[1-(3-Methyl-3H-imidazol-4-ylmethyl)-piperidin-4-yl]-1,6-dihydro-1,3,5,6-tetraaza-as-indacen-2-yl}-ethanol | 682 | 2.20/C | 380.1 |
| 824 | (R)-1-{1-[1-(1-Isopropyl-1H-pyrazol-4-ylmethyl)-piperidin-4-yl]-1,6-dihydro-1,3,5,6-tetraaza-as-indacen-2-yl}-ethanol | 682 | 2.62/C | 408.2 |
| 825 | (R)-1-{1-[1-(1-Methyl-1H-pyrazol-3-ylmethyl)-piperidin-4-yl]-1,6-dihydro-1,3,5,6-tetraaza-as-indacen-2-yl}-ethanol | 682 | 2.40/C | 380.1 |
| 826 | (R)-1-{1-[1-(1-Methyl-1H-imidazol-2-ylmethyl)-piperidin-4-yl]-1,6-dihydro-1,3,5,6-tetraaza-as-indacen-2-yl}-ethanol | 682 | 2.48/C | 380.1 |
| 827 | (R)-1-{1-[1-(1,4,5-Trimethyl-1H-imidazol-2-ylmethyl)-piperidin-4-yl]-1,6-dihydro-1,3,5,6-tetraaza-as-indacen-2-yl}-ethanol | 682 | 2.68/C | 408.2 |
| 828 | (R)-1-{1-[1-(1,3-Dimethyl-1H-pyrazol-4-ylmethyl)-piperidin-4-yl]-1,6-dihydro-1,3,5,6-tetraaza-as-indacen-2-yl}-ethanol | 682 | 2.41/C | 394.1 |
| 829 | (R)-1-{1-[1-(1-Ethyl-3-methyl-1H-pyrazol-4-ylmethyl)-piperidin-4-yl]-1,6-dihydro-1,3,5,6-tetraaza-as-indacen-2-yl}-ethanol | 682 | 2.51/C | 408.2 |
| 830 | (R)-1-{1-[1-(2,3-Dimethyl-3H-imidazol-4-ylmethyl)-piperidin-4-yl]-1,6-dihydro-1,3,5,6-tetraaza-as-indacen-2-yl}-ethanol | 682 | 2.22/C | 394.1 |
| 831 | (R)-1-{1-[1-(1,3,5-Trimethyl-1H-pyrazol-4-ylmethyl)-piperidin-4-yl]-1,6-dihydro-1,3,5,6-tetraaza-as-indacen-2-yl}-ethanol | 682 | 2.47/C | 408.2 |
| 832 | (R)-1-[1-(1-Oxetan-3-yl-piperidin-4-yl)-1,6-dihydro-1,3,5,6-tetraaza-as-indacen-2-yl]-ethanol | 682 | 3.80/N | 342.1 |
| 833 | 3-{4-[2-(2-tert-Butylamino-ethoxymethyl)-6H-1,3,5,6-tetraaza-as-indacen-1-yl]-piperidin-1-yl}-propionitrile | 683 | 2.37/C | 424.2 |
| 834 | 3-{4-[2-(2,2,2-Trifluoro-ethoxymethyl)-6H-1,3,5,6-tetraaza-as-indacen-1-yl]-piperidin-1-yl}-propionitrile | 683 | 2.78/C | 407.1 |
| 835 | 3-{4-[2-(3,4-Difluoro-benzyloxymethyl)-6H-1,3,5,6-tetraaza-as-indacen-1-yl]-piperidin-1-yl}-propionitrile | 683 | 3.31/C | 451.2 |
| 836 | 3-{4-[2-(Tetrahydro-furan-3-ylmethoxymethyl)-6H-1,3,5,6-tetraaza-as-indacen-1-yl]-piperidin-1-yl}-propionitrile | 683 | 2.57/C | 409.2 |
| 837 | 3-{4-[2-(Tetrahydro-pyran-4-yloxymethyl)-6H-1,3,5,6-tetraaza-as-indacen-1-yl]-piperidin-1-yl}-propionitrile | 683 | 2.50/C | 409.2 |
| 838 | 3-[4-(2-Cyclopentylmethoxymethyl-6H-1,3,5,6-tetraaza-as-indacen-1-yl)-piperidin-1-yl]-propionitrile | 683 | 3.27/C | 407.2 |
| 839 | 3-[4-(2-Cyclopropylmethoxymethyl-6H-1,3,5,6-tetraaza-as-indacen-1-yl)-piperidin-1-yl]-propionitrile | 683 | 2.72/C | 379.2 |

TABLE 3-continued

| Ex # | Name | Synthetic Method | LCMS RT (min)/Method | LCMS (ESI) m/z |
|---|---|---|---|---|
| 840 | 3-[4-(2-Cyclobutylmethoxymethyl-6H-1,3,5,6-tetraaza-as-indacen-1-yl)-piperidin-1-yl]-propionitrile | 683 | 3.02/C | 393.2 |
| 841 | 3-{4-[2-(2-Methyl-cyclopropylmethoxymethyl)-6H-1,3,5,6-tetraaza-as-indacen-1-yl]-piperidin-1-yl}-propionitrile | 683 | 3.00/C | 393.2 |
| 842 | 3-[4-(2-Isopropoxymethyl-6H-1,3,5,6-tetraaza-as-indacen-1-yl)-piperidin-1-yl]-propionitrile | 683 | 2.65/C | 367.1 |
| 843 | 3-{4-[2-(2-Isopropoxy-ethoxymethyl)-6H-1,3,5,6-tetraaza-as-indacen-1-yl]-piperidin-1-yl}-propionitrile | 683 | 2.40/C | 411.2 |
| 844 | 3-[4-(2-Cyclopentyloxymethyl-6H-1,3,5,6-tetraaza-as-indacen-1-yl)-piperidin-1-yl]-propionitrile | 683 | 2.98/C | 393.2 |
| 845 | exo-2-Methyl-1-(7-oxa-bicyclo[2.2.1]hept-2-yl)-1,6-dihydro-1,3,5,6-tetraaza-as-indacene | 684 | 2.83/C | 269.0 |
| 846 | endo-1-[1-(7-Oxa-bicyclo[2.2.1]hept-2-yl)-1,6-dihydro-1,3,5,6-tetraaza-as-indacen-2-yl]-ethanol (single enantiomer, config. unknown) | 684 | 2.66/C | 299.0 |
| 847 | endo-1-[1-(7-Oxa-bicyclo[2.2.1]hept-2-yl)-1,6-dihydro-1,3,5,6-tetraaza-as-indacen-2-yl]-ethanol (single enantiomer, config. unknown) | 684 | 2.74/C | 299.0 |
| 848 | endo-1-[1-(7-Oxa-bicyclo[2.2.1]hept-2-yl)-1,6-dihydro-1,3,5,6-tetraaza-as-indacen-2-yl]-ethanol (3:1 mix of ds, config. unknown) | 684 | 2.69 + 2.75/C | 299.0 |
| 849 | endo-N-[1-(7-Oxa-bicyclo[2.2.1]hept-2-yl)-1,6-dihydro-1,3,5,6-tetraaza-as-indacen-2-ylmethyl]-methanesulfonamide (single enantiomer, config. unknown) | 684 | 2.75/C | 362.1 |
| 850 | endo-N-[1-(7-Oxa-bicyclo[2.2.1]hept-2-yl)-1,6-dihydro-1,3,5,6-tetraaza-as-indacen-2-ylmethyl]-methanesulfonamide (single enantiomer, config. unknown) | 684 | 2.75/C | 362.1 |
| 851 | endo-[1-(7-Oxa-bicyclo[2.2.1]hept-2-yl)-1,6-dihydro-1,3,5,6-tetraaza-as-indacen-2-yl]-methanol (single enantiomer, config. unknown) | 684 | 2.57/C | 285.0 |
| 852 | endo-[1-(7-Oxa-bicyclo[2.2.1]hept-2-yl)-1,6-dihydro-1,3,5,6-tetraaza-as-indacen-2-yl]-methanol (single enantiomer, config. unknown) | 684 | 2.57/C | 285.0 |
| 853 | 1-(1-Cyclohexyl-1,6-dihydro-1,3,5,6-tetraaza-as-indacen-2-yl)-ethane-1,2-diol (racemic) | 688 | 3.08/A | 301.1 |
| 854 | (S)—N-{2-[1-(Tetrahydro-pyran-3-yl)-1,6-dihydro-1,3,5,6-tetraaza-as-indacen-2-yl]-ethyl}-methanesulfonamide | 118 | 2.75/A | 364.1 |
| 855 | (S)—N-[1-(Tetrahydro-pyran-3-yl)-1,6-dihydro-1,3,5,6-tetraaza-as-indacen-2-ylmethyl]-methanesulfonamide | 209 | 2.71/A | 350.1 |
| 856 | (S)—N-{2-[1-(Tetrahydro-pyran-3-yl)-1,6-dihydro-1,3,5,6-tetraaza-as-indacen-2-yl]-ethyl}-acetamide | 118 | 2.63/A | 328.1 |
| 857 | (S)-Cyclopropanecarboxylic acid {2-[1-(tetrahydro-pyran-3-yl)-1,6-dihydro-1,3,5,6-tetraaza-as-indacen-2-yl]-ethyl}-amide | 118 | 3.06/A | 354.1 |
| 858 | (R)-1-(1-Cyclohexyl-1,6-dihydro-1,3,5,6-tetraaza-as-indacen-2-yl)-ethane-1,2-diol | 688 | 3.03/B | 301.0 |

TABLE 3-continued

| Ex # | Name | Synthetic Method | LCMS RT (min)/Method | LCMS (ESI) m/z |
|---|---|---|---|---|
| 859 | (S)-2-[1-(Tetrahydro-pyran-3-yl)-1,6-dihydro-1,3,5,6-tetraaza-as-indacen-2-yl]-ethanol | 15 | 2.55/A | 287.1 |
| 860 | 2-Methoxy-N-{2-[1-(tetrahydro-pyran-3-yl)-1,6-dihydro-1,3,5,6-tetraaza-as-indacen-2-yl]-ethyl}-acetamide (racemic) | 118 | 2.76/A | 358.1 |
| 861 | (3-{4-[2-((R)-1-Hydroxy-ethyl)-6H-1,3,5,6-tetraaza-as-indacen-1-yl]-piperidin-1-yl}-oxetan-3-yl)-acetonitrile | 195 | 2.84/A | 381.1 |
| 862 | (R)—N-{2-[1-(Tetrahydro-pyran-3-yl)-1,6-dihydro-1,3,5,6-tetraaza-as-indacen-2-yl]-ethyl}-methanesulfonamide | 118 | 2.75/A | 364.1 |
| 863 | (R)-Cyclopropanecarboxylic acid {2-[1-(tetrahydro-pyran-3-yl)-1,6-dihydro-1,3,5,6-tetraaza-as-indacen-2-yl]-ethyl}-amide | 118 | 2.89/A | 354.1 |
| 864 | (R)-2-[1-(Tetrahydro-pyran-3-yl)-1,6-dihydro-1,3,5,6-tetraaza-as-indacen-2-yl]-ethanol | 15 | 2.48/A | 287.1 |
| 865 | (R)—N-{2-[1-(Tetrahydro-pyran-3-yl)-1,6-dihydro-1,3,5,6-tetraaza-as-indacen-2-yl]-ethyl}-acetamide | 118 | 2.64/A | 328.1 |
| 866 | (R)—N-[1-(Tetrahydro-pyran-3-yl)-1,6-dihydro-1,3,5,6-tetraaza-as-indacen-2-ylmethyl]-methanesulfonamide | 209 | 2.71/A | 350.1 |
| 867 | (R)-1-(1-Cyclopentyl-1,6-dihydro-1,3,5,6-tetraaza-as-indacen-2-yl)-ethanol | 199 | 3.1/C | 271.0 |
| 868 | (R)-1-[1-((3S,4R)-1-Ethyl-3-fluoro-piperidin-4-yl)-1,6-dihydro-1,3,5,6-tetraaza-as-indacen-2-yl]-ethanol | 199 | 2.1/C | 332.1 |
| 869 | 2-(1-Bicyclo[2.2.1]hept-2-yl-1,6-dihydro-1,3,5,6-tetraaza-as-indacen-2-yl)-1-(4-hydroxy-piperidin-1-yl)-ethanone (racemic) | 160 | 3.2/C | 394.2 |
| 870 | 2-{4-[2-((R)-1-Hydroxy-ethyl)-6H-1,3,5,6-tetraaza-as-indacen-1-yl]-piperidin-1-yl}-1-morpholin-4-yl-ethanone | 199 | 2.3/C | 413.2 |
| 871 | (R)-1-[1-(1-But-3-ynyl-piperidin-4-yl)-1,6-dihydro-1,3,5,6-tetraaza-as-indacen-2-yl]-ethanol | 199 | 2.3/C | 338.1 |
| 872 | 2-{4-[2-((R)-1-Hydroxy-ethyl)-6H-1,3,5,6-tetraaza-as-indacen-1-yl]-piperidin-1-yl}-1-pyrrolidin-1-yl-ethanone | 199 | 2.5/C | 397.2 |
| 873 | (R)-1-{1-[1-(2-Fluoro-ethyl)-piperidin-4-yl]-1,6-dihydro-1,3,5,6-tetraaza-as-indacen-2-yl}-ethanol | 199 | 2.2/C | 332.1 |
| 874 | N-(1-Cyclopentyl-1,6-dihydro-1,3,5,6-tetraaza-as-indacen-2-ylmethyl)-methanesulfonamide | 200 | 3.1/C | 334.1 |
| 875 | (1-Cyclohexyl-1,6-dihydro-1,3,5,6-tetraaza-as-indacen-2-yl)-(tetrahydro-pyran-4-yl)-methanol (racemic) | 182 | 3.5/C | 355.2 |
| 876 | 1-(1-Cyclohexyl-1,6-dihydro-1,3,5,6-tetraaza-as-indacen-2-yl)-propan-1-ol | 182 | 3.5/C | 299.1 |
| 877 | (R)-1-[1-(3-Fluoro-piperidin-4-yl)-1,6-dihydro-1,3,5,6-tetraaza-as-indacen-2-yl]-ethanol (mixture of trans piperidines) | 199 | 2.2/C | 304.1 |
| 878 | (S)-1-(1-Cyclohexyl-1,6-dihydro-1,3,5,6-tetraaza-as-indacen-2-yl)-2,2,2-trifluoro-ethanol | 199 | 3.9/C | 339.1 |
| 879 | (R)-1-[1-(1-Ethyl-3,3-difluoro-piperidin-4-yl)-1,6-dihydro-1,3,5,6-tetraaza-as-indacen-2-yl]-ethanol (single isomer, unknown stereochemistry at piperidine) | 199 | 2.7/N | 350.1 |
| 880 | (R)-1-[1-(1-Ethyl-3,3-difluoro-piperidin-4-yl)-1,6-dihydro-1,3,5,6- | 199 | 3.0/N | 350.1 |

TABLE 3-continued

| Ex # | Name | Synthetic Method | LCMS RT (min)/Method | LCMS (ESI) m/z |
|---|---|---|---|---|
| | tetraaza-as-indacen-2-yl]-ethanol (single isomer, unknown stereochemistry at piperidine) | | | |
| 881 | (R)-1-[1-(Tetrahydro-pyran-4-yl)-1,6-dihydro-1,3,5,6-tetraaza-as-indacen-2-yl]-ethanol | 156 | 2.63/C | 287.1 |
| 882 | (R)-1-(1-Piperidin-1-yl-1,6-dihydro-1,3,5,6-tetraaza-as-indacen-2-yl)-ethanol | 199 | 3.22/C | 286.1 |
| 883 | 3-Methyl-N-[4-(6H-1,2,3,5,6-pentaaza-as-indacen-1-yl)-cyclohexyl]-butyramide | 18, 215 | 3.8/C | 341.2 |
| 884 | N-[4-(6H-1,3,5,6-Tetraaza-as-indacen-1-yl)-cyclohexyl]-nicotinamide | 215 | 2.59/C | 361.1 |
| 885 | (R)-3-(2-Methyl-6H-1,3,5,6-tetraaza-as-indacen-1-yl)-cyclohexanone | 213 | 2.72/C | 369.1 |
| 886 | (1S,3S)-1-Methyl-3-(2-methyl-6H-1,3,5,6-tetraaza-as-indacen-1-yl)-cyclohexanol | 213 | 2.82/C | 285.1 |
| 887 | 2-Methoxy-N-[4-(6H-1,3,5,6-tetraaza-as-indacen-1-yl)-cyclohexyl]-acetamide | 215 | 2.70/C | 328.1 |
| 888 | (1R,3S)-1-Methyl-3-(2-methyl-6H-1,3,5,6-tetraaza-as-indacen-1-yl)-cyclohexanol | 213 | 2.98/C | 285.1 |
| 889 | 1-(3-Methoxy-cyclohexyl)-2-methyl-1,6-dihydro-1,3,5,6-tetraaza-as-indacene | 213 | 2.91/C | 285.2 |
| 890 | (1S,3R)-1-Methyl-3-(2-methyl-6H-1,3,5,6-tetraaza-as-indacen-1-yl)-cyclohexanol | 213 | 2.96/C | 285.1 |
| 891 | (R)-1-(1-Morpholin-4-yl-1,6-dihydro-1,3,5,6-tetraaza-as-indacen-2-yl)-ethanol | 199 | 2.61/C | 288.1 |
| 892 | (1R,3R)-1-Methyl-3-(2-methyl-6H-1,3,5,6-tetraaza-as-indacen-1-yl)-cyclohexanol | 213 | 2.83/C | 285.1 |
| 893 | 3-{(S)-3-[2-((R)-1-Hydroxy-ethyl)-6H-1,3,5,6-tetraaza-as-indacen-1-yl]-pyrrolidin-1-yl}-propionitrile | 687, 686, 158 | 2.23/C | 325.1 |
| 894 | N-(1-Bicyclo[2.2.1]hept-2-yl-1,6-dihydro-1,3,5,6-tetraaza-as-indacen-2-ylmethyl)-methanesulfonamide | 684 | 8.41/D | 360.1 |
| 895 | 1-{1-[3-Fluoro-1-(3-methyl-isoxazol-5-ylmethyl)-piperidin-4-yl]-1,6-dihydro-1,3,5,6-tetraaza-as-indacen-2-yl}-ethanol | 703 | 3.20/C | 399.2 |
| 896 | (R)-1-{1-[1-(2H-Pyrazol-3-ylmethyl)-piperidin-4-yl]-1,6-dihydro-1,3,5,6-tetraaza-as-indacen-2-yl}-ethanol | 682 | 5.80/N | 366.0 |
| 897 | {1-[1-(2,2-Difluoro-ethyl)-piperidin-4-yl]-1,6-dihydro-1,3,5,6-tetraaza-as-indacen-2-yl}-methanol | 682 | 2.09/D | 336.1 |
| 898 | (R)-1-[1-(1-Oxazol-5-ylmethyl-piperidin-4-yl)-1,6-dihydro-1,3,5,6-tetraaza-as-indacen-2-yl]-ethanol | 682 | 2.21/C | 367.1 |
| 899 | (R)-1-{1-[1-(5-Methyl-isoxazol-3-ylmethyl)-piperidin-4-yl]-1,6-dihydro-1,3,5,6-tetraaza-as-indacen-2-yl}-ethanol | 682 | 2.54/C | 381.1 |
| 900 | (R)-1-{1-[1-(1-Ethyl-5-methyl-1H-pyrazol-4-ylmethyl)-piperidin-4-yl]-1,6-dihydro-1,3,5,6-tetraaza-as-indacen-2-yl}-ethanol | 682 | 2.57/C | 408.2 |
| 901 | (R)-1-{1-[1-(2-Methyl-imidazo[1,2-a]pyrimidin-3-ylmethyl)-piperidin-4-yl]-1,6-dihydro-1,3,5,6-tetraaza-as-indacen-2-yl}-ethanol | 682 | 2.36/C | 431.2 |
| 902 | (R)-1-{1-[1-(2-Methyl-1H-imidazol-4-ylmethyl)-piperidin-4-yl]-1,6-dihydro-1,3,5,6-tetraaza-as-indacen-2-yl}-ethanol | 682 | 5.02/N | 380.4 |
| 903 | (R)-1-{1-[1-(2,5-Dimethyl-oxazol-4-ylmethyl)-piperidin-4-yl]-1,6- | 682 | 2.58/C | 395.1 |

TABLE 3-continued

| Ex # | Name | Synthetic Method | LCMS RT (min)/Method | LCMS (ESI) m/z |
|---|---|---|---|---|
| | dihydro-1,3,5,6-tetraaza-as-indacen-2-yl}-ethanol | | | |
| 904 | (R)-1-{1-[1-(3,5-Dimethyl-1H-pyrazol-4-ylmethyl)-piperidin-4-yl]-1,6-dihydro-1,3,5,6-tetraaza-as-indacen-2-yl}-ethanol | 682 | 7.56/N | 395.3 |
| 905 | (o)-1-[1-(7-Oxa-bicyclo[2.2.1]hept-2-yl)-1,6-dihydro-1,3,5,6-tetraaza-as-indacen-2-yl]-ethanol Single diastereomer | 684 | 2.74/C | 299.1 |
| 906 | 1-[1-(7-Oxa-bicyclo[2.2.1]hept-2-yl)-1,6-dihydro-1,3,5,6-tetraaza-as-indacen-2-yl]-ethanol Single diastreomer | 684 | 2.83/C | 299.0 |
| 907 | Single unknown diastereomer of (o)-1-[1-(7-Oxa-bicyclo[2.2.1]hept-2-yl)-1,6-dihydro-1,3,5,6-tetraaza-as-indacen-2-yl]-ethanol | 684 | 2.77/C | 299.0 |
| 908 | {2-[1-(1-Ethyl-3,3-difluoro-piperidin-4-yl)-1,6-dihydro-1,3,5,6-tetraaza-as-indacen-2-yl]-ethyl}-carbamic acid methyl ester | 678 | 2.56/D | 407.1 |
| 909 | N-[1-((3S,4R)-1-Ethyl-3-fluoro-piperidin-4-yl)-1,6-dihydro-1,3,5,6-tetraaza-as-indacen-2-ylmethyl]-methanesulfonamide | 200 | 2.06/D | 395.1 |
| 910 | 2-Methyl-1-[1,4]oxazepan-6-yl-1,6-dihydro-1,3,5,6-tetraaza-as-indacene | 110 | 2.04/C | 272.0 |
| 911 | 1-{1-[3-Fluoro-1-(5-methyl-isoxazol-3-ylmethyl)-piperidin-4-yl]-1,6-dihydro-1,3,5,6-tetraaza-as-indacen-2-yl}-ethanol | 703 | 2.56/C | 399.2 |
| 912 | 1-{1-[3-Fluoro-1-(3-methyl-[1,2,4]oxadiazol-5-ylmethyl)-piperidin-4-yl]-1,6-dihydro-1,3,5,6-tetraaza-as-indacen-2-yl}-ethanol | 703 | 3.12/C | 400.2 |
| 913 | N-{1-[1-(2-Fluoro-ethyl)-piperidin-4-yl]-1,6-dihydro-1,3,5,6-tetraaza-as-indacen-2-ylmethyl}-methanesulfonamide | 692 | 3.98/D | 395.1 |
| 914 | N-{1-[1-(2,2-Difluoro-ethyl)-piperidin-4-yl]-1,6-dihydro-1,3,5,6-tetraaza-as-indacen-2-ylmethyl}-methanesulfonamide | 692 | 4.54/D | 413.1 |
| 915 | N-[1-(1-Ethyl-3,3-difluoro-piperidin-4-yl)-1,6-dihydro-1,3,5,6-tetraaza-as-indacen-2-ylmethyl]-methanesulfonamide | 200 | 2.42/D | 413.1 |
| 916 | (R)-1-{1-[1-(2,2-Difluoro-ethyl)-piperidin-4-yl]-1,6-dihydro-1,3,5,6-tetraaza-as-indacen-2-yl}-ethanol | 692 | 2.36/D | 350.1 |
| 917 | N-[1-(2-Methyl-cyclohyl)-1,6-dihydro-1,3,5,6-tetraaza-as-indacen-2-ylmethyl]-methanesulfonamide | 200 | 3.45/C | 362.1 |
| 918 | N-(1-Cyclohyl-1,6-dihydro-1,3,5,6-tetraaza-as-indacen-2-ylmethyl)-acetamide | 209 | 7.42/D | 312.1 |
| 919 | 1-[1-(8-Aza-bicyclo[3.2.1]oct-3-yl)-1,6-dihydro-1,3,5,6-tetraaza-as-indacen-2-yl]-ethanol | 682 | 2.02/C | 312.1 |
| 920 | N-{1-[1-(2,2,2-Trifluoro-ethyl)-piperidin-4-yl]-1,6-dihydro-1,3,5,6-tetraaza-as-indacen-2-ylmethyl}-acetamide | 209 and 692 | 3.19/D | 395.1 |
| 921 | N-{1-[1-(2-Fluoro-ethyl)-piperidin-4-yl]-1,6-dihydro-1,3,5,6-tetraaza-as-indacen-2-ylmethyl}-acetamide | 209 and 692 | 3.63/D | 359.1 |
| 922 | 1-Cyclohyl-2-[2-(1,1-dioxo-1-isothiazolidin-2-yl)-ethyl]-1,6-dihydro-1,3,5,6-tetraaza-as-indacene | 118 | 3.41/D | 388.1 |
| 923 | (R)-1-[1-(1-Oxazol-2-ylmethyl-piperidin-4-yl)-1,6-dihydro-1,3,5,6-tetraaza-as-indacen-2-yl]-ethanol | 682 | 2.33/C | 367.1 |
| 924 | Cyclobutanecarboxylic acid (1-cyclohyl-1,6-dihydro-1,3,5,6- | 209 | 9.33/D | 352.1 |

TABLE 3-continued

| Ex # | Name | Synthetic Method | LCMS RT (min)/Method | LCMS (ESI) m/z |
|---|---|---|---|---|
| | tetraaza-as-indacen-2-ylmethyl)-amide | | | |
| 925 | N-[1-(7-Oxa-bicyclo[2.2.1]hept-2-yl)-1,6-dihydro-1,3,5,6-tetraaza-as-indacen-2-ylmethyl]-methanesulfonamide | 200 | 2.87/C | 362.0 |
| 926 | (R)-1-((S)-1-Pyrrolidin-3-yl-1,6-dihydro-1,3,5,6-tetraaza-as-indacen-2-yl)-ethanol | 687 | 1.35/C | 272.1 |
| 927 | 4-[2-((R)-1-Hydroxy-ethyl)-6H-1,3,5,6-tetraaza-as-indacen-yl]-piperidine-1-carboxylic acid ethyl ester | 192 | 3.11/C | 358.1 |
| 928 | 1-(1-Aza-bicyclo[2.2.2]oct-3-yl)-2-methyl-1,6-dihydro-1,3,5,6-tetraaza-as-indacene | 109 | 1.64/C | 282.1 |
| 929 | 4-[2-((R)-1-Hydroxy-ethyl)-6H-1,3,5,6-tetraaza-as-indacen-1-yl]-piperidine-1-carboxylic acid methyl ester | 687 | 2.82/D | 344.1 |
| 930 | (R)-1-[1-((S)-1-Methanesulfonyl-pyrrolidin-3-yl)-1,6-dihydro-1,3,5,6-tetraaza-as-indacen-2-yl]-ethanol | 687 | 2.52/C | 350.1 |
| 931 | (S)-3-[2-((R)-1-Hydroxy-ethyl)-6H-1,3,5,6-tetraaza-as-indacen-1-yl]-pyrrolidine-1-carboxylic acid ethyl ester | 687 | 2.91/C | 344.1 |
| 932 | 1-(1-Cyclohyl-1,6-dihydro-1,3,5,6-tetraaza-as-indacen-2-ylmethyl)-piperidin-4-ol | 200, 201 | 6.48/D | 354.2 |
| 933 | 1-[1-(3-Fluoro-1-oxazol-5-ylmethyl-piperidin-4-yl)-1,6-dihydro-1,3,5,6-tetraaza-as-indacen-2-yl]-ethanol Mixture of diastereomers (trans in piperidine) | 682 | 2.74/C | 385.2 |
| 934 | 1-{4-[2-(1-Hydroxy-ethyl)-6H-1,3,5,6-tetraaza-as-indacen-1-yl]-piperidin-1-yl}-propan-2-ol | 682 | 2.00/C | 344.2 |
| 935 | (R)-1-{1-[(S)-1-(3-Methyl-[1,2,4]oxadiazol-5-ylmethyl)-pyrrolidin-3-yl]-1,6-dihydro-1,3,5,6-tetraaza-as-indacen-2-yl}-ethanol | 687 | 2.87/C | 368.2 |
| 936 | (endo)-1-[1-(7-Oxa-bicyclo[2.2.1]hept-2-yl)-1,6-dihydro-1,3,5,6-tetraaza-as-indacen-2-yl]-ethanol Single diastereomer | 684 | 2.74/C | 299.0 |
| 937 | Endo-1-[1-(7-Oxa-bicyclo[2.2.1]hept-2-yl)-1,6-dihydro-1,3,5,6-tetraaza-as-indacen-2-yl]-ethanol Single diastereomer | 684 | 2.67/C | 299.0 |
| 938 | 1-[1-(7-Oxa-bicyclo[2.2.1]hept-2-yl)-1,6-dihydro-1,3,5,6-tetraaza-as-indacen-2-yl]-ethanol | 684 | 2.67/C | 299.1 |
| 939 | (R)-1-[1-(3,3-Difluoro-piperidin-4-yl)-1,6-dihydro-1,3,5,6-tetraaza-as-indacen-2-yl]-ethanol (single enantiomer, unknown piperidine stereochemistry) | 199 | 2.43/D | 322.0 |
| 940 | (1-Cyclohexyl-1,6-dihydro-1,3,5,6-tetraaza-as-indacen-2-yl)-cyclopropyl-methanol (racemic) | 182 | 3.56/A | 311.1 |
| 941 | [1-(1-Ethyl-3,3-difluoro-piperidin-4-yl)-1,6-dihydro-1,3,5,6-tetraaza-as-indacen-2-yl]-methanol (racemic) | 22 | 2.20/A | 336.1 |
| 942 | 2-[(1-Cyclohexyl-1,6-dihydro-1,3,5,6-tetraaza-as-indacen-2-yl)-hydroxy-methyl]-cyclopropanecarboxylic acid (mixture of diastereomers, racemic) | 182 | 3.28/A | 355.1 |

TABLE 3-continued

| Ex # | Name | Synthetic Method | LCMS RT (min)/Method | LCMS (ESI) m/z |
|---|---|---|---|---|
| 943 | (R)-1-(1-Bicyclo[2.2.1]hept-2-yl-1,6-dihydro-1,3,5,6-tetraaza-as-indacen-2-yl)-ethanol (mixture of norbornyl diastereomers) | 199 | 3.34/A | 297.1 |
| 944 | (1R,5S,6S)-1-(3-Aza-bicyclo[3.1.0]hex-6-yl)-1,6-dihydro-1,3,5,6-tetraaza-as-indacene | 1 | 0.97/A | 268.0 |
| 945 | N-[1-(3,3-Difluoro-piperidin-4-yl)-1,6-dihydro-1,3,5,6-tetraaza-as-indacen-2-ylmethyl]-methanesulfonamide (racemic) | 181, 200 | 2.24/A | 385.1 |
| 946 | N-[1-(1-Benzyl-3,3-difluoro-piperidin-4-yl)-1,6-dihydro-1,3,5,6-tetraaza-as-indacen-2-ylmethyl]-methanesulfonamide (racemic) | 200 | 3.57/A | 475.1 |
| 947 | [1-(1-Benzyl-3,3-difluoro-piperidin-4-yl)-1,6-dihydro-1,3,5,6-tetraaza-as-indacen-2-yl]-methanol (racemic) | 22 | 3.37/A | 398.1 |
| 948 | [1-(3,3-Difluoro-piperidin-4-yl)-1,6-dihydro-1,3,5,6-tetraaza-as-indacen-2-yl]-methanol (racemic) | 22, 181 | 1.99/A | 308.0 |
| 949 | ((S)-1-Ethyl-piperidin-2-yl)-[4-(6H-1,3,5,6-tetraaza-as-indacen-1-yl)-piperidin-1-yl]-methanone | 197 | 0.810/K | 380.9 |
| 950 | ((S)-1-Isopropyl-piperidin-2-yl)-[4-(6H-1,3,5,6-tetraaza-as-indacen-1-yl)-piperidin-1-yl]-methanone | 197 | 0.834/K | 395.0 |
| 951 | ((S)-1-Oxetan-3-yl-piperidin-2-yl)-[4-(6H-1,3,5,6-tetraaza-as-indacen-1-yl)-piperidin-1-yl]-methanone | 197 | 0.819/K | 408.9 |
| 952 | [(S)-1-(2-Methoxy-ethyl)-piperidin-2-yl]-[4-(6H-1,3,5,6-tetraaza-as-indacen-1-yl)-piperidin-1-yl]-methanone | 197 | 0.828/K | 411.0 |
| 953 | (1-Methyl-azepan-2-yl)-[4-(6H-1,3,5,6-tetraaza-as-indacen-1-yl)-piperidin-1-yl]-methanone (racemic) | 197 | 0.838/K | 380.9 |
| 954 | 1-((S)-1-Methyl-4,5,6,7-tetrahydro-1H-indazol-5-yl)-1,6-dihydro-1,3,5,6-tetraaza-as-indacene | 198 | 0.858/K | 293.1 |
| 955 | 1-((R)-1-Methyl-4,5,6,7-tetrahydro-1H-indazol-5-yl)-1,6-dihydro-1,3,5,6-tetraaza-as-indacene | 198 | 0.857/K | 293.1 |
| 956 | 1-(2-Methyl-4,5,6,7-tetrahydro-2H-indazol-5-yl)-1,6-dihydro-1,3,5,6-tetraaza-as-indacene (racemic) | 198 | 0.860/K | 293.1 |
| 957 | Cis-2-[4-(6H-1,3,5,6-Tetraaza-as-indacen-1-yl)-cyclohexyl]-propan-2-ol | 148 | 0.923/K | 299.1 |
| 958 | Cis-2-[4-(2-Methyl-6H-1,3,5,6-tetraaza-as-indacen-1-yl)-cyclohexyl]-propan-2-ol | 148 | 0.972/K | 313.1 |
| 959 | 3-[(S)-5-(6H-1,3,5,6-Tetraaza-as-indacen-1-yl)-4,5,6,7-tetrahydro-indazol-1-yl]-propionitrile | 198 | 0.858/K | 332.1 |
| 960 | 2-[1-(Tetrahydro-pyran-3-yl)-1,6-dihydro-1,3,5,6-tetraaza-as-indacen-2-yl]-acetamide (racemic) | 23 | 0.830/K | 299.8 |
| 961 | N-Methyl-2-[1-(tetrahydro-pyran-3-yl)-1,6-dihydro-1,3,5,6-tetraaza-as-indacen-2-yl]-acetamide (racemic) | 23 | 0.870/K | 313.9 |
| 962 | N-Ethyl-2-[1-(tetrahydro-pyran-3-yl)-1,6-dihydro-1,3,5,6-tetraaza-as-indacen-2-yl]-acetamide (racemic) | 23 | 0.91/K | 328.2 |
| 963 | N-Isopropyl-2-[1-(tetrahydro-pyran-3-yl)-1,6-dihydro-1,3,5,6-tetraaza-as-indacen-2-yl]-acetamide (racemic) | 23 | 0.96/K | 341.9 |
| 964 | N-tert-Butyl-2-[1-(tetrahydro-pyran-3-yl)-1,6-dihydro-1,3,5,6-tetraaza-as-indacen-2-yl]-acetamide (racemic) | 23 | 0.96/K | 341.9 |

TABLE 3-continued

| Ex # | Name | Synthetic Method | LCMS RT (min)/Method | LCMS (ESI) m/z |
|---|---|---|---|---|
| 965 | N-Cyclobutyl-2-[1-(tetrahydro-pyran-3-yl)-1,6-dihydro-1,3,5,6-tetraaza-as-indacen-2-yl]-acetamide (racemic) | 23 | 0.98/K | 353.9 |
| 966 | N-Isobutyl-2-[1-(tetrahydro-pyran-3-yl)-1,6-dihydro-1,3,5,6-tetraaza-as-indacen-2-yl]-acetamide (racemic) | 23 | 0.967/K | 356.1 |
| 967 | 1-Azetidin-1-yl-2-[1-(tetrahydro-pyran-3-yl)-1,6-dihydro-1,3,5,6-tetraaza-as-indacen-2-yl]-ethanone (racemic) | 23 | 0.94/K | 340.0 |
| 968 | 1-Pyrrolidin-1-yl-2-[1-(tetrahydro-pyran-3-yl)-1,6-dihydro-1,3,5,6-tetraaza-as-indacen-2-yl]-ethanone (racemic) | 23 | 0.96/K | 353.9 |
| 969 | N-(2-Hydroxy-ethyl)-N-methyl-2-[1-(tetrahydro-pyran-3-yl)-1,6-dihydro-1,3,5,6-tetraaza-as-indacen-2-yl]-acetamide (racemic) | 23 | 0.89/K | 357.9 |
| 970 | N-Dimethylcarbamoylmethyl-2-[1-(tetrahydro-pyran-3-yl)-1,6-dihydro-1,3,5,6-tetraaza-as-indacen-2-yl]-acetamide (racemic) | 23 | 0.850/K | 385.1 |
| 971 | 1-(3,3-Difluoro-azetidin-1-yl)-2-[1-(tetrahydro-pyran-3-yl)-1,6-dihydro-1,3,5,6-tetraaza-as-indacen-2-yl]-ethanone (racemic) | 23 | 0.97/K | 375.9 |
| 972 | N-(4,4-Difluoro-cyclohexyl)-2-[1-(tetrahydro-pyran-3-yl)-1,6-dihydro-1,3,5,6-tetraaza-as-indacen-2-yl]-acetamide (racemic) | 23 | 1.05/K | 417.9 |
| 973 | N-(2,2-Difluoro-ethyl)-2-[1-(tetrahydro-pyran-3-yl)-1,6-dihydro-1,3,5,6-tetraaza-as-indacen-2-yl]-acetamide (racemic) | 23 | 0.870/K | 364.0 |
| 974 | N-Cyclopentyl-2-[1-(tetrahydro-pyran-3-yl)-1,6-dihydro-1,3,5,6-tetraaza-as-indacen-2-yl]-acetamide (racemic) | 23 | 1.00/K | 368.1 |
| 975 | N-(2-Imidazol-1-yl-ethyl)-2-[1-(tetrahydro-pyran-3-yl)-1,6-dihydro-1,3,5,6-tetraaza-as-indacen-2-yl]-acetamide (racemic) | 23 | 0.83/K | 393.8 |
| 976 | 1-[4-(2-Hydroxy-ethyl)-piperazin-1-yl]-2-[1-(tetrahydro-pyran-3-yl)-1,6-dihydro-1,3,5,6-tetraaza-as-indacen-2-yl]-ethanone (racemic) | 23 | 0.808/K | 412.9 |
| 977 | 1-(4-Acetyl-piperazin-1-yl)-2-[1-(tetrahydro-pyran-3-yl)-1,6-dihydro-1,3,5,6-tetraaza-as-indacen-2-yl]-ethanone (racemic) | 23 | 0.92/K | 411.0 |
| 978 | 1-(4,4-Difluoro-piperidin-1-yl)-2-[1-(tetrahydro-pyran-3-yl)-1,6-dihydro-1,3,5,6-tetraaza-as-indacen-2-yl]-ethanone (racemic) | 23 | 0.963/K | 404.1 |
| 979 | 1-(1,1-Dioxo-1$1%6&-thiomorpholin-4-yl)-2-[1-(tetrahydro-pyran-3-yl)-1,6-dihydro-1,3,5,6-tetraaza-as-indacen-2-yl]-ethanone (racemic) | 23 | 0.849/K | 418.0 |
| 980 | 1-[1,4]Oxazepan-4-yl-2-[1-(tetrahydro-pyran-3-yl)-1,6-dihydro-1,3,5,6-tetraaza-as-indacen-2-yl]-ethanone (racemic) | 23 | 0.892/K | 384.1 |
| 981 | N-(1-Methyl-piperidin-4-yl)-2-[1-(tetrahydro-pyran-3-yl)-1,6-dihydro-1,3,5,6-tetraaza-as-indacen-2-yl]-acetamide (racemic) | 23 | (MS) | 397.2 |
| 982 | 1-(3-Hydroxy-piperidin-1-yl)-2-[1-(tetrahydro-pyran-3-yl)-1,6-dihydro-1,3,5,6-tetraaza-as-indacen-2-yl]-ethanone (racemic) | 23 | 0.93/K | 384.0 |
| 983 | N-(Tetrahydro-pyran-4-yl)-2-[1-(tetrahydro-pyran-3-yl)-1,6-dihydro-1,3,5,6-tetraaza-as-indacen-2-yl]-acetamide (racemic) | 23 | 0.92/K | 383.9 |

TABLE 3-continued

| Ex # | Name | Synthetic Method | LCMS RT (min)/Method | LCMS (ESI) m/z |
|---|---|---|---|---|
| 984 | 1-(4-Hydroxymethyl-piperidin-1-yl)-2-[1-(tetrahydro-pyran-3-yl)-1,6-dihydro-1,3,5,6-tetraaza-as-indacen-2-yl]-ethanone (racemic) | 23 | 0.917/K | 397.9 |
| 985 | 2-[1-(Tetrahydro-pyran-3-yl)-1,6-dihydro-1,3,5,6-tetraaza-as-indacen-2-yl]-1-thiomorpholin-4-yl-ethanone (racemic) | 23 | 0.928/K | 386.0 |
| 986 | 1-(4-Hydroxy-piperidin-1-yl)-2-[1-(tetrahydro-pyran-3-yl)-1,6-dihydro-1,3,5,6-tetraaza-as-indacen-2-yl]-ethanone (racemic) | 23 | 0.94/K | 384.0 |
| 987 | 1-Azepan-3-yl-2-methyl-1,6-dihydro-1,3,5,6-tetraaza-as-indacene (racemic) | 2 | 0.686/K | 270.1 |
| 988 | 3-Oxo-3-[3-(6H-1,3,5,6-tetraaza-as-indacen-1-yl)-azepan-1-yl]-propionitrile (racemic) | 5 | 0.84/K | 323.1 |
| 989 | 3-[3-(6H-1,3,5,6-Tetraaza-as-indacen-1-yl)-azepan-1-yl]-propionitrile (racemic) | 10 | 0.813/K | 309.1 |
| 990 | 2-Methyl-1-(4,5,6,7-tetrahydro-3H-benzoimidazol-5-yl)-1,6-dihydro-1,3,5,6-tetraaza-as-indacene (racemic) | 707 | 1.658/K | 293.1 |
| 991 | 3-[5-(6H-1,3,5,6-Tetraaza-as-indacen-1-yl)-4,5,6,7-tetrahydro-indazol-2-yl]-propionitrile (racemic) | 198 | 0.865/K | 332.1 |
| 992 | 3-[(R)-5-(6H-1,3,5,6-Tetraaza-as-indacen-1-yl)-4,5,6,7-tetrahydro-indazol-1-yl]-propionitrile | 198 | 1.848/K | 332.1 |
| 993 | Cis-1-Methyl-4-(6H-1,3,5,6-tetraaza-as-indacen-1-yl)-cyclohexanol | 713 | 0.868/K | 271.1 |
| 994 | Trans-1-Methyl-4-(2-methyl-6H-1,3,5,6-tetraaza-as-indacen-1-yl)-cyclohexanol | 713 | 0.852/K | 285.1 |
| 995 | Trans-1-Cyclopropyl-4-(6H-1,3,5,6-tetraaza-as-indacen-1-yl)-cyclohexanol | 713 | 0.903/K | 297.1 |
| 996 | Cis-1-Cyclopropyl-4-(6H-1,3,5,6-tetraaza-as-indacen-1-yl)-cyclohexanol | 713 | 0.945/K | 297.1 |
| 997 | (1R,3S)-3-(2-Methyl-6H-1,3,5,6-tetraaza-as-indacen-1-yl)-cyclopentanol | 709 | 0.863/K | 256.9 |
| 998 | (1S,3R)-3-(2-Methyl-6H-1,3,5,6-tetraaza-as-indacen-1-yl)-cyclopentanol | 709 | 0.895/K | 256.9 |
| 999 | (1R,3R)-3-(2-Methyl-6H-1,3,5,6-tetraaza-as-indacen-1-yl)-cyclopentanol | 709 | 0.770/K | 257.1 |
| 1000 | (1S,3S)-3-(2-Methyl-6H-1,3,5,6-tetraaza-as-indacen-1-yl)-cyclopentanol | 709 | 0.770/K | 257.1 |
| 1001 | cis {4-[2-((R)-1-Hydroxy-ethyl)-6H-1,3,5,6-tetraaza-as-indacen-1-yl]-cyclohexyl}-acetonitrile | 641, 644 | 2.44/A | 324.1 |
| 1002 | trans (R)-1-{1-[4-(2,2-Difluoro-ethylamino)-cyclohexyl]-1,6-dihydro-1,3,5,6-tetraaza-as-indacen-2-yl}-ethanol | 614 | 1.64/A | 364 |
| 1003 | trans (R)-1-[1-(4-[1,2,3]Triazol-1-yl-cyclohexyl)-1,6-dihydro-1,3,5,6-tetraaza-as-indacen-2-yl]-ethanol | 653 | 2.15/A | 352.1 |
| 1004 | cis (R)-1-{1-[(1S,3R)-3-(2,2,2-Trifluoro-ethylamino)-cyclopentyl]-1,6-dihydro-1,3,5,6-tetraaza-as-indacen-2-yl}-ethanol | 614, 626 | 2.11/A | 368.1 |
| 1005 | cis (R)-1-{1-[(1S,3R)-3-(2,2-Difluoro-ethylamino)-cyclopentyl]-1,6-dihydro-1,3,5,6-tetraaza-as-indacen-2-yl}-ethanol | 614, 626 | 1.59/A | 350 |
| 1006 | trans 3-{4-[2-(1,2-Dihydroxy-ethyl)-6H-1,3,5,6-tetraaza-as- | 647, 688 | 2.35/A | 354.1 |

TABLE 3-continued

| Ex # | Name | Synthetic Method | LCMS RT (min)/Method | LCMS (ESI) m/z |
|---|---|---|---|---|
| | indacen-1-yl]-cyclohexyl}-propionitrile | | | |
| 1007 | cis 3-{4-[2-((R)-1-Hydroxy-ethyl)-6H-1,3,5,6-tetraaza-as-indacen-1-yl]-cyclohexyl}-propionitrile | 647 | 2.61/A | 338.1 |
| 1008 | trans (R)-1-{1-[(1S,3S)-3-(2,2,2-Trifluoro-ethylamino)-cyclopentyl]-1,6-dihydro-1,3,5,6-tetraaza-as-indacen-2-yl}-ethanol | 614, 626 | 1.97/A | 368 |
| 1009 | cis (R)-1-{1-[4-(2,2,2-Trifluoro-ethylamino)-cyclohexyl]-1,6-dihydro-1,3,5,6-tetraaza-as-indacen-2-yl}-ethanol | 614 | 3.03/A | 382.1 |
| 1010 | trans {4-[8-Bromo-2-((R)-1-hydroxy-ethyl)-6H-1,3,5,6-tetraaza-as-indacen-1-yl]-cyclohexyl}-acetonitrile | 644 | 3.10/A | 401.9 & 403.9 |
| 1011 | (R)-1-[1-((S)-4,4-Difluoro-tetrahydro-pyran-3-yl)-1,6-dihydro-1,3,5,6-tetraaza-as-indacen-2-yl]-ethanol | 199 | 0.92/K | 345.1 (M + Na) |
| 1012 | (R)-1-[1-((R)-4,4-Difluoro-tetrahydro-pyran-3-yl)-1,6-dihydro-1,3,5,6-tetraaza-as-indacen-2-yl]-ethanol | 199 | 0.89/K | 344.9 (M + Na) |
| 1013 | (R)-1-{1-[(S)-3,3-Difluoro-1-(2-methoxy-ethyl)-piperidin-4-yl]-1,6-dihydro-1,3,5,6-tetraaza-as-indacen-2-yl}-ethanol | 199, 179 | 2.0/L | 380.1 |
| 1014 | (R)-1-{1-[(R)-3,3-Difluoro-1-(2-methoxy-ethyl)-piperidin-4-yl]-1,6-dihydro-1,3,5,6-tetraaza-as-indacen-2-yl}-ethanol | 199, 179 | 2.0/L | 380.1 |

The corresponding JAK1, JAK2, JAK3 and TYK2 inhibitions are shown in Table 4 for representative compounds of formula I.

TABLE 4

| Example | JAK1 Ki, μM | JAK2 Ki, μM | JAK3 Ki, μM | TYK2 Ki, μM |
|---|---|---|---|---|
| 1 | 0.02351 | 0.05606 | 0.12582 | 0.24618 |
| 2 | 0.17684 | 0.51822 | 0.91338 | 1.51449 |
| 3 | 0.34838 | 0.19080 | 0.90516 | 1.64178 |
| 4 | | | | |
| 5 | 0.00046 | 0.00128 | 0.00381 | 0.00466 |
| 6 | 0.01189 | 0.02141 | 0.37287 | 0.13360 |
| 7 | 0.00860 | 0.01326 | 0.28323 | 0.06461 |
| 8 | 0.01291 | 0.04378 | 0.06888 | 0.13410 |
| 9 | 0.00748 | 0.00650 | 0.01659 | 0.03545 |
| 10 | 0.01279 | 0.02165 | 0.02121 | 0.08847 |
| 11 | 0.01733 | 0.03735 | 0.09450 | 0.17624 |
| 12 | 0.03101 | 0.03569 | 0.01716 | 0.16961 |
| 13 | 0.17873 | 0.89830 | 1.84359 | 3.47258 |
| 14 | 0.01135 | 0.01365 | 0.02653 | 0.08560 |
| 15 | 0.10166 | 0.08647 | 0.76925 | 0.44259 |
| 16 | 0.21885 | 0.67968 | 1.27134 | 0.75850 |
| 17 | 0.00404 | 0.01706 | 0.07912 | 0.02984 |
| 18 | 0.02462 | 0.04009 | 0.32294 | 0.27328 |
| 19 | 0.00149 | 0.00372 | 0.02446 | 0.02033 |
| 20 | 0.00104 | 0.00226 | 0.00587 | 0.06970 |
| 21 | 0.00993 | 0.03847 | 0.03758 | 0.62716 |
| 22 | 0.00173 | 0.00644 | 0.01076 | 0.06991 |
| 23 | 0.00622 | 0.06267 | 0.00998 | 0.61616 |
| 24 | 0.01037 | 0.06862 | 0.02923 | 0.73456 |
| 25 | 0.05445 | 0.02654 | 0.15867 | 0.04532 |
| 26 | 0.00237 | 0.00427 | 0.03397 | 0.08126 |
| 27 | 0.01071 | 0.01752 | 0.12833 | 0.07149 |
| 28 | 0.01200 | 0.02881 | 0.21668 | 0.08011 |
| 29 | | | | |
| 30 | 0.02923 | 0.04225 | 0.13886 | 0.14064 |
| 31 | 0.01317 | 0.02590 | 0.41875 | 0.15920 |

TABLE 4-continued

| Example | JAK1 Ki, μM | JAK2 Ki, μM | JAK3 Ki, μM | TYK2 Ki, μM |
|---|---|---|---|---|
| 32 | 0.18098 | 0.56842 | 1.82161 | 3.17753 |
| 33 | 0.01435 | 0.03505 | 0.16174 | 0.14328 |
| 34 | 0.03155 | 0.06310 | 1.06587 | 0.42317 |
| 35 | 0.01205 | 0.02610 | 0.69154 | 0.16490 |
| 36 | 0.03164 | 0.24240 | 1.61875 | 1.19392 |
| 37 | 0.01131 | 0.04420 | 0.14386 | 0.19774 |
| 38 | 0.41218 | 0.31547 | 0.71331 | 1.97195 |
| 39 | 0.03588 | 0.10225 | 0.18243 | 0.33017 |
| 40 | 0.00635 | 0.01777 | 0.06686 | 0.10721 |
| 41 | 0.03442 | 0.04890 | 0.15302 | 0.15928 |
| 42 | 0.01493 | 0.04102 | 0.09303 | 0.12206 |
| 43 | 0.04313 | 0.07287 | 0.17684 | 0.20442 |
| 44 | 0.10465 | 0.12074 | 0.24080 | 0.42325 |
| 45 | 0.00758 | 0.01797 | 0.02753 | 0.12885 |
| 46 | 0.07242 | 0.16028 | 0.41418 | 0.91328 |
| 47 | 0.01314 | 0.02894 | 0.05218 | 0.10081 |
| 48 | 0.00130 | 0.00267 | 0.00857 | 0.03093 |
| 49 | 0.00030 | 0.00098 | 0.02649 | 0.03569 |
| 50 | 0.00248 | 0.00484 | 0.01796 | 0.08881 |
| 51 | 0.00768 | 0.00669 | 0.13738 | 0.07658 |
| 52 | 0.00146 | 0.00315 | 0.00414 | 0.05602 |
| 53 | 0.03446 | 0.02992 | 0.19789 | 0.38175 |
| 54 | 0.00124 | 0.00299 | 0.08414 | 0.01867 |
| 55 | 0.00676 | 0.00659 | 0.33413 | 0.03105 |
| 56 | 0.00384 | 0.00997 | 0.33718 | 0.06472 |
| 57 | 0.00521 | 0.00905 | 0.01196 | 0.04580 |
| 58 | 0.00057 | 0.00100 | 0.01641 | 0.00357 |
| 59 | 0.00196 | 0.00601 | 0.02774 | 0.03052 |
| 60 | 0.13464 | 0.20087 | 0.62530 | 0.71549 |
| 61 | 0.15283 | 0.25307 | 0.21968 | 1.05198 |
| 62 | 0.02138 | 0.03971 | 0.39111 | 0.22532 |
| 63 | 0.00754 | 0.01199 | 0.09650 | 0.07386 |
| 64 | 0.03644 | 0.05135 | 0.24251 | 0.49516 |
| 65 | 0.01487 | 0.03465 | 0.28077 | 0.10727 |
| 66 | 0.00715 | 0.00986 | 0.06834 | 0.23986 |

TABLE 4-continued

| Example | JAK1 Ki, μM | JAK2 Ki, μM | JAK3 Ki, μM | TYK2 Ki, μM |
|---|---|---|---|---|
| 67 | 0.00075 | 0.00116 | 0.00948 | 0.02364 |
| 68 | 0.02098 | 0.07071 | 0.35393 | 1.15650 |
| 69 | 0.00344 | 0.00441 | 0.09334 | 0.02661 |
| 70 | 0.01252 | 0.01515 | 0.03856 | 0.06889 |
| 71 | 0.26417 | 0.37778 | 0.30655 | 1.67548 |
| 72 | 0.00426 | 0.01094 | 0.09775 | 0.05665 |
| 73 | 0.00091 | 0.00095 | 0.05766 | 0.00682 |
| 74 | 0.00125 | 0.00298 | 0.03190 | 0.01419 |
| 75 | 0.00589 | 0.00853 | 0.06065 | 0.01904 |
| 76 | 0.05166 | 0.07295 | 0.23175 | 0.53057 |
| 77 | 0.06460 | 0.18494 | 2.16347 | 1.93745 |
| 78 | 0.01527 | 0.13740 | 1.12001 | 0.43625 |
| 79 | 0.01569 | 0.02229 | 0.07709 | 0.16722 |
| 80 | 0.00561 | 0.01552 | 0.16255 | 0.10554 |
| 81 | 0.02302 | 0.01576 | 0.29710 | 0.22197 |
| 82 | 0.00350 | 0.01134 | 0.01419 | 0.19435 |
| 83 | 0.02143 | 0.05098 | 1.22742 | 0.18655 |
| 84 | 0.01161 | 0.03605 | 0.74652 | 0.15970 |
| 85 | 0.03219 | 0.06427 | 0.71599 | 0.15280 |
| 86 | 0.00753 | 0.01777 | 0.07163 | 0.04858 |
| 87 | 0.00812 | 0.14491 | 0.20092 | 0.20066 |
| 88 | 0.00898 | 0.01061 | 0.40686 | 0.06589 |
| 89 | 0.01080 | 0.01283 | 0.28309 | 0.09825 |
| 90 | 0.00681 | 0.00875 | 0.04685 | 0.06305 |
| 91 | 0.00064 | 0.00331 | 0.08214 | 0.14161 |
| 92 | 0.00364 | 0.00615 | 0.02557 | 0.10891 |
| 93 | 0.02964 | 0.10213 | 1.00195 | 0.32265 |
| 94 | 0.00073 | 0.00282 | 0.00769 | 0.02099 |
| 95 | 0.01222 | 0.03542 | 0.16124 | 0.10245 |
| 96 | 0.00583 | 0.01967 | 0.11490 | 0.08999 |
| 97 | 0.00351 | 0.00232 | 0.02957 | 0.01984 |
| 98 | 0.00204 | 0.00163 | 0.01177 | 0.00864 |
| 99 | 0.00429 | 0.01640 | 0.01081 | 0.58558 |
| 100 | 0.02207 | 0.09923 | 0.01687 | 2.10039 |
| 101 | 0.04097 | 0.19406 | 0.02766 | 3.23087 |
| 102 | 0.00578 | 0.05143 | 0.00970 | 0.44235 |
| 103 | 0.00509 | 0.01734 | 0.01156 | 0.67306 |
| 104 | 0.00090 | 0.00169 | 0.01152 | 0.02091 |
| 105 | 0.00226 | 0.00353 | 0.02312 | 0.01645 |
| 106 | 0.00550 | 0.01080 | 0.04365 | 0.03564 |
| 107 | 0.00469 | 0.02000 | 0.13225 | 0.21568 |
| 108 | 0.00486 | 0.02465 | 0.03501 | 0.07516 |
| 109 | 0.09803 | 0.24889 | 0.29558 | 0.30199 |
| 110 | 0.15445 | 0.29167 | 0.70445 | 0.64672 |
| 110a | 0.01356 | 0.08176 | 0.19357 | 0.10633 |
| 111 | 0.00487 | 0.01036 | 0.02649 | 0.02105 |
| 112 | 0.00409 | 0.01075 | 0.06339 | 0.01753 |
| 112a | 0.06438 | 0.05831 | 0.29983 | 0.63014 |
| 113 | 0.00094 | 0.00299 | 0.00398 | 0.00226 |
| 114 | 0.00974 | 0.02867 | 0.01701 | 0.01670 |
| 115 | 0.32013 | 0.74424 | 0.54738 | 0.15315 |
| 116 | 0.01969 | 0.07686 | 0.05800 | 0.32168 |
| 117 | 0.13054 | 0.78123 | 0.74643 | 1.53429 |
| 118 | 0.00194 | 0.01205 | 0.02365 | 0.06312 |
| 119 | 0.07773 | 1.30531 | 1.16169 | 1.03033 |
| 120 | 0.00556 | 0.01035 | 0.01119 | 0.08212 |
| 121 | 0.00101 | 0.00278 | 0.00931 | 0.00509 |
| 121a | 0.00032 | 0.00180 | 0.00735 | 0.00235 |
| 122 | 0.06233 | 0.28061 | 0.08338 | 1.05117 |
| 123 | 0.00355 | 0.00714 | 0.02359 | 0.03099 |
| 124 | 0.02452 | 0.03321 | 0.84457 | 0.22477 |
| 125 | 0.02452 | 0.03321 | 0.84457 | 0.22477 |
| 126 | 0.01553 | 0.01520 | 0.41783 | 0.19269 |
| 127 | 0.00260 | 0.00182 | 0.00846 | 0.02611 |
| 128 | 0.00209 | 0.00211 | 0.06084 | 0.08262 |
| 129 | 0.04384 | 0.05718 | 0.53521 | 0.31217 |
| 130 | 0.12600 | 0.38893 | 2.28038 | 0.62218 |
| 131 | 0.00678 | 0.01080 | 0.02558 | 0.08363 |
| 132 | 0.02535 | 0.19286 | 1.11720 | 0.69629 |
| 133 | 0.05418 | 0.14986 | 0.29681 | 0.79826 |
| 134 | 0.00074 | 0.00421 | 0.03276 | 0.06242 |
| 135 | 0.00145 | 0.02025 | 0.09058 | 0.16125 |
| 136 | 0.00579 | 0.01827 | 0.29058 | 0.14719 |
| 137 | 0.00173 | 0.00951 | 0.03712 | 0.11996 |
| 138 | 0.00339 | 0.02766 | 0.14340 | 0.22183 |
| 139 | 0.33929 | 0.92961 | 1.45448 | 3.47258 |
| 140 | 0.00516 | 0.01737 | 0.08811 | 0.07883 |
| 141 | 0.00844 | 0.02369 | 0.39261 | 0.33049 |
| 142 | 0.00482 | 0.00335 | 0.21052 | 0.04373 |
| 143 | 0.01041 | 0.00703 | 0.18206 | 0.05119 |
| 144 | 0.25077 | 0.38243 | 3.51594 | 3.15547 |
| 145 | 0.01487 | 0.27065 | 2.28160 | 0.42744 |
| 146 | 0.15040 | 0.18978 | 2.77023 | 1.72806 |
| 147 | 0.06526 | 0.59567 | 4.10377 | 1.52953 |
| 148 | 0.00173 | 0.00192 | 0.02378 | 0.01228 |
| 149 | 0.00098 | 0.00161 | 0.02029 | 0.01845 |
| 150 | 0.00417 | 0.01186 | 0.01774 | 0.29163 |
| 151 | 0.00178 | 0.00227 | 0.01354 | 0.03122 |
| 152 | 0.00314 | 0.00473 | 0.03969 | 0.01382 |
| 153 | 0.18128 | 0.58657 | 0.78407 | 3.47258 |
| 154 | 0.01531 | 0.02845 | 0.00924 | 3.47258 |
| 155 | 0.12003 | 0.45171 | 0.30395 | 3.47258 |
| 156 | 0.00213 | 0.01631 | 0.08459 | 0.20925 |
| 157 | 0.00359 | 0.02505 | 0.03402 | 0.20659 |
| 158 | 0.00376 | 0.02818 | 0.01822 | 0.03288 |
| 159 | 0.02058 | 0.02376 | 0.03263 | 2.33071 |
| 160 | 0.00843 | 0.07063 | 0.01070 | 0.10041 |
| 161 | 0.01156 | 0.03183 | 0.02049 | 0.38584 |
| 162 | 0.00745 | 0.02310 | 0.04684 | 0.67655 |
| 163 | 0.01117 | 0.01003 | 0.02813 | 0.60745 |
| 164 | 0.05280 | 0.12936 | 0.05713 | 3.47258 |
| 165 | 0.04887 | 0.17736 | 0.80158 | 0.55035 |
| 166 | 0.14514 | 0.15096 | 0.25481 | 1.01653 |
| 167 | 0.01045 | 0.01405 | 0.00648 | 0.81998 |
| 168 | 0.02532 | 0.31169 | 0.33027 | 1.38648 |
| 169 | 0.29207 | 0.18602 | 4.10377 | 2.92571 |
| 170 | 0.09289 | 0.33402 | 1.05337 | 0.95631 |
| 171 | 0.04989 | 0.24122 | 0.10340 | 3.47258 |
| 172 | 0.14059 | 0.25132 | 0.02262 | 2.77154 |
| 173 | 0.21524 | 3.18801 | 3.89873 | 3.47258 |
| 174 | 0.00158 | 0.00266 | 0.08742 | 0.00753 |
| 175 | 0.00276 | 0.00460 | 0.03809 | 0.01921 |
| 176 | 0.00216 | 0.00705 | 0.09579 | 0.02431 |
| 177 | 0.04200 | 0.14399 | 1.40137 | 0.51907 |
| 178 | 0.07384 | 0.02234 | 0.01619 | 0.10431 |
| 179 | 0.00058 | 0.00111 | 0.01320 | 0.02158 |
| 180 | 0.00555 | 0.01986 | 0.10146 | 0.06320 |
| 181 | 0.00153 | 0.00892 | 0.00336 | 0.01294 |
| 182 | 0.16738 | 0.43499 | 0.15434 | 0.95494 |
| 182a | 0.29136 | 0.88837 | 0.35095 | 3.17554 |
| 183 | 0.02039 | 0.04488 | 0.64952 | 0.07271 |
| 184 | 0.09469 | 0.24978 | 1.48633 | 0.64360 |
| 185 | 0.10520 | 0.16189 | 0.50211 | 0.70847 |
| 186 | 0.22043 | 0.16749 | 3.17235 | 1.50264 |
| 187 | 0.01014 | 0.02233 | 0.05762 | 0.05880 |
| 188 | 0.06854 | 0.16085 | 0.77828 | 0.67150 |
| 189 | 0.08955 | 0.36184 | 4.10377 | 1.40565 |
| 190 | 0.06271 | 0.06744 | 0.05917 | 0.11428 |
| 191 | 0.00487 | 0.01765 | 0.19215 | 0.16938 |
| 192 | 0.02453 | 0.05129 | 0.40104 | 0.38751 |
| 193 | 0.11075 | 0.69692 | 4.10377 | 3.14829 |
| 194 | 0.00391 | 0.00532 | 0.28160 | 0.03068 |
| 195 | 0.00066 | 0.00113 | 0.02763 | 0.00216 |
| 196 | 0.01017 | 0.09462 | 1.97773 | 0.29470 |
| 196a | 0.24236 | 1.33628 | 4.10377 | 3.47258 |
| 197 | 0.03250 | 0.20192 | 3.23749 | 0.66687 |
| 197a | 0.12158 | 0.21747 | 1.92642 | 2.72482 |
| 198 | 0.00638 | 0.01020 | 0.02567 | 0.04139 |
| 199 | 0.00249 | 0.06754 | 0.10970 | 0.02759 |
| 200 | 0.00253 | 0.04539 | 0.07511 | 0.01932 |
| 201 | 0.00728 | 0.02496 | 0.01217 | 0.48773 |
| 202 | 0.00481 | 0.04464 | 0.06034 | 0.83105 |
| 203 | 0.01955 | 0.14521 | 0.10386 | 0.25799 |
| 204 | 0.09191 | 1.53660 | 0.86200 | 1.47412 |
| 205 | 0.00642 | 0.02330 | 0.03260 | 0.08650 |
| 206 | 0.01729 | 0.81197 | 3.05156 | 0.56454 |
| 207 | 0.07807 | 1.86791 | 3.01394 | 1.21083 |
| 208 | 0.00884 | 0.04313 | 0.17146 | 0.15114 |
| 209 | 0.00217 | 0.01763 | 0.03056 | 0.06660 |
| 210 | 0.14657 | 0.64151 | 0.64550 | 0.51419 |
| 211 | 0.00700 | 0.02224 | 0.13338 | 0.06139 |
| 212 | 0.00217 | 0.00321 | 0.05904 | 0.01162 |
| 213 | 0.00181 | 0.01201 | 0.02117 | 0.00613 |
| 214 | 0.00564 | 0.04385 | 0.30337 | 0.08248 |

TABLE 4-continued

| Example | JAK1 Ki, μM | JAK2 Ki, μM | JAK3 Ki, μM | TYK2 Ki, μM |
|---|---|---|---|---|
| 215 | 0.00189 | 0.00788 | 0.05594 | 0.09270 |
| 216 | 0.00462 | 0.02125 | 0.01241 | 0.03441 |
| 216a | 0.00103 | 0.00564 | 0.00234 | 0.00563 |
| 217 | 0.00360 | 0.04868 | 0.00679 | 0.60826 |
| 218 | 0.00679 | 0.00607 | 0.07645 | 0.03393 |
| 219 | 0.00451 | 0.01118 | 0.08897 | 0.03733 |
| 220 | 0.00331 | 0.00743 | 0.02830 | 0.02927 |
| 221 | 0.00252 | 0.00392 | 0.00812 | 0.00937 |
| 222 | 0.01381 | 0.02909 | 0.04805 | 0.55462 |
| 223 | 0.00374 | 0.02438 | 0.00811 | 1.46721 |
| 224 | 0.01420 | 0.05917 | 0.02062 | 1.97523 |
| 225 | 0.05956 | 0.12708 | 0.11769 | 0.81651 |
| 226 | 0.01617 | 0.01810 | 0.07846 | 0.08208 |
| 227 | 0.00641 | 0.00316 | 0.08304 | 0.01254 |
| 228 | 0.01580 | 0.00599 | 0.11780 | 0.04338 |
| 229 | 0.04869 | 0.14222 | 0.41691 | 0.32977 |
| 230 | 0.04785 | 0.12333 | 0.42407 | 0.43459 |
| 231 | 0.08661 | 0.39496 | 1.14027 | 1.02620 |
| 232 | 0.00203 | 0.00335 | 0.05344 | 0.01927 |
| 233 | 0.00496 | 0.00784 | 0.24981 | 0.07714 |
| 234 | 0.06334 | 0.17942 | 0.13172 | 1.76356 |
| 235 | 0.00437 | 0.00656 | 0.04259 | 0.01791 |
| 236 | 0.00766 | 0.12593 | 0.12811 | 0.06153 |
| 237 | 0.10615 | 0.49418 | 0.04700 | 3.47258 |
| 238 | 0.02926 | 0.02604 | 0.08518 | 0.17091 |
| 239 | 0.00153 | 0.00510 | 0.01042 | 0.00739 |
| 240 | 0.00692 | 0.05598 | 0.00735 | 0.07274 |
| 241 | 0.00053 | 0.00094 | 0.00401 | 0.00403 |
| 242 | 0.21657 | 0.31119 | 4.05919 | 2.56487 |
| 243 | 0.35652 | 0.44642 | 4.10377 | 3.47258 |
| 244 | 0.19792 | 0.36342 | 3.40361 | 1.82452 |
| 245 | 0.00984 | 0.04308 | 0.01943 | 0.46755 |
| 246 | 0.16444 | 0.18261 | 0.65206 | 1.61698 |
| 247 | 0.03218 | 0.13603 | 0.24542 | 0.35816 |
| 248 | 0.21599 | 0.34179 | 1.16039 | 3.18507 |
| 249 | 0.04861 | 0.36532 | 1.17822 | 1.11056 |
| 250 | 0.02902 | 0.06469 | 0.33607 | 0.29967 |
| 251 | 0.21613 | 0.26935 | 2.04387 | 3.44700 |
| 252 | 0.03207 | 0.28545 | 1.27907 | 0.97251 |
| 253 | 0.18825 | 0.61357 | 0.57232 | 1.09400 |
| 254 | 0.06951 | 0.56806 | 0.23383 | 1.50434 |
| 255 | 0.27768 | 0.49041 | 0.47898 | 1.11909 |
| 256 | 0.00786 | 0.00921 | 0.00996 | 0.06879 |
| 257 | 0.20037 | 3.18801 | 0.39677 | 3.43426 |
| 258 | 0.02878 | 0.12464 | 0.01442 | 1.81201 |
| 259 | 0.02785 | 0.09532 | 0.01169 | 1.85112 |
| 260 | 0.04156 | 0.84709 | 0.30230 | 0.79501 |
| 261 | 0.03903 | 0.42603 | 0.10786 | 0.67813 |
| 262 | 0.02122 | 0.66309 | 0.09646 | 0.16491 |
| 263 | 0.05527 | 0.15155 | 0.01906 | 0.40150 |
| 264 | 0.00532 | 0.02673 | 0.01415 | 0.06343 |
| 265 | 0.02974 | 0.40649 | 0.06610 | 0.57014 |
| 266 | 0.00526 | 0.01722 | 0.00787 | 0.12020 |
| 267 | 0.00752 | 0.05561 | 0.00702 | 0.06317 |
| 268 | 0.00506 | 0.01608 | 0.00750 | 0.11969 |
| 269 | 0.08439 | 1.31136 | 0.24540 | 1.70423 |
| 270 | 0.03612 | 0.12103 | 0.01512 | 0.35217 |
| 271 | 0.01737 | 0.01245 | 0.06039 | 0.30204 |
| 272 | 0.00050 | 0.00135 | 0.00314 | 0.00471 |
| 273 | 0.00529 | 0.01893 | 0.01919 | 0.04839 |
| 274 | 0.03429 | 0.08884 | 0.03926 | 0.25917 |
| 275 | 0.00366 | 0.01154 | 0.04735 | 0.03644 |
| 276 | 0.01206 | 0.03232 | 0.37782 | 0.46047 |
| 277 | 0.00542 | 0.01326 | 0.03051 | 0.03764 |
| 278 | 0.00152 | 0.00519 | 0.00641 | 0.05443 |
| 279 | 0.00959 | 0.03039 | 0.23921 | 0.12288 |
| 280 | 0.00437 | 0.01369 | 0.12741 | 0.06150 |
| 281 | 0.00749 | 0.02515 | 0.01630 | 0.17133 |
| 282 | 0.00753 | 0.01211 | 0.04812 | 0.25993 |
| 283 | 0.00084 | 0.00193 | 0.00263 | 0.05023 |
| 284 | 0.09251 | 0.60383 | 2.63127 | 3.42954 |
| 285 | 0.05183 | 0.40245 | 4.10377 | 2.40876 |
| 286 | 0.00356 | 0.04776 | 0.00646 | 0.44228 |
| 287 | 0.28226 | 0.14548 | 0.82209 | 2.05485 |
| 288 | 0.00399 | 0.01187 | 0.20646 | 0.11023 |
| 289 | 0.00699 | 0.08017 | 0.07949 | 0.10671 |
| 290 | 0.00394 | 0.00488 | 0.00627 | 0.20368 |

TABLE 4-continued

| Example | JAK1 Ki, μM | JAK2 Ki, μM | JAK3 Ki, μM | TYK2 Ki, μM |
|---|---|---|---|---|
| 291 | 0.01016 | 0.85447 | 0.73104 | 0.33884 |
| 292 | 0.00292 | 0.02654 | 0.00790 | 0.21790 |
| 293 | 0.00121 | 0.00131 | 0.01400 | 0.01186 |
| 294 | 0.03757 | 0.17629 | 0.15149 | 0.37976 |
| 295 | 0.00105 | 0.00204 | 0.00986 | 0.02835 |
| 296 | 0.00330 | 0.00475 | 0.01946 | 0.01620 |
| 297 | 0.00391 | 0.00528 | 0.02099 | 0.03147 |
| 298 | 0.02778 | 0.36706 | 0.23092 | 1.28988 |
| 299 | 0.00250 | 0.00453 | 0.00453 | 0.12675 |
| 300 | 0.00781 | 0.01834 | 0.02875 | 0.06589 |
| 301 | 0.37256 | 1.30148 | 1.45268 | 2.16311 |
| 302 | 0.00945 | 0.01375 | 0.06639 | 0.07167 |
| 303 | 0.00207 | 0.00353 | 0.01455 | 0.06123 |
| 304 | 0.00332 | 0.00355 | 0.02039 | 0.05238 |
| 305 | 0.00078 | 0.00093 | 0.01703 | 0.00370 |
| 306 | 0.03488 | 0.15565 | 0.46764 | 0.44881 |
| 307 | 0.01822 | 0.22795 | 0.20177 | 0.37349 |
| 308 | 0.00150 | 0.00263 | 0.00604 | 0.01227 |
| 309 | 0.05199 | 0.29548 | 0.09343 | 1.93557 |
| 310 | 0.00901 | 0.02628 | 0.21294 | 0.19728 |
| 311 | 0.00724 | 0.01415 | 0.09157 | 0.05984 |
| 312 | 0.04765 | 0.41485 | 0.62618 | 1.05467 |
| 313 | 0.00138 | 0.00367 | 0.05957 | 0.07862 |
| 314 | 0.00446 | 0.00744 | 0.03618 | 0.12404 |
| 315 | 0.00570 | 0.00628 | 0.04129 | 0.02920 |
| 316 | 0.00277 | 0.00320 | 0.00924 | 0.01771 |
| 317 | 0.00290 | 0.00578 | 0.03736 | 0.09456 |
| 318 | 0.06148 | 1.10467 | 0.97634 | 1.89505 |
| 319 | 0.01709 | 0.03121 | 0.08288 | 0.07775 |
| 320 | 0.05596 | 0.18058 | 1.16234 | 0.60840 |
| 321 | 0.00446 | 0.00947 | 0.05605 | 0.03847 |
| 322 | 0.00500 | 0.02551 | 0.08481 | 0.42647 |
| 323 | 0.00081 | 0.00177 | 0.00677 | 0.00781 |
| 324 | 0.00063 | 0.00060 | 0.00520 | 0.00376 |
| 325 | 0.00530 | 0.02157 | 0.01949 | 1.35634 |
| 326 | 0.02758 | 0.93816 | 0.55194 | 2.63412 |
| 327 | 0.00484 | 0.01692 | 0.01996 | 0.13766 |
| 328 | 0.00054 | 0.00051 | 0.00162 | 0.00399 |
| 329 | 0.01646 | 0.04158 | 0.17342 | 0.22958 |
| 330 | 0.03828 | 0.12166 | 0.26945 | 0.27096 |
| 331 | 0.00608 | 0.01597 | 0.06445 | 0.04581 |
| 332 | 0.00126 | 0.00795 | 0.07138 | 0.03114 |
| 333 | 0.01171 | 0.02534 | 0.17000 | 0.05910 |
| 334 | 0.13714 | 2.24145 | 2.55419 | 3.47258 |
| 335 | 0.03124 | 0.12707 | 0.06757 | 0.94373 |
| 336 | 0.01596 | 0.06336 | 0.65576 | 0.07755 |
| 337 | 0.00290 | 0.00531 | 0.01068 | 0.03369 |
| 338 | 0.02114 | 0.05014 | 0.28794 | 0.15848 |
| 339 | 0.00389 | 0.00783 | 0.04054 | 0.02248 |
| 340 | 0.01717 | 0.01949 | 0.02462 | 0.10083 |
| 341 | 0.01017 | 0.00747 | 0.16898 | 0.10562 |
| 342 | 0.00200 | 0.00236 | 0.02337 | 0.02487 |
| 343 | 0.00571 | 0.01395 | 0.00320 | 0.34585 |
| 344 | 0.01570 | 0.03027 | 0.08037 | 0.32887 |
| 345 | 0.00912 | 0.00967 | 0.35410 | 0.03729 |
| 346 | 0.01387 | 0.03149 | 0.05179 | 0.13959 |
| 347 | 0.00496 | 0.01446 | 0.13555 | 0.13025 |
| 348 | 0.00560 | 0.01497 | 0.07848 | 0.14807 |
| 349 | 0.01527 | 0.01900 | 0.12034 | 0.11253 |
| 350 | 0.00644 | 0.05037 | 0.17811 | 0.26877 |
| 351 | 0.00494 | 0.02924 | 0.03141 | 0.28425 |
| 352 | 0.00103 | 0.00562 | 0.02368 | 0.04459 |
| 353 | 0.00827 | 0.01499 | 0.21585 | 0.08737 |
| 354 | 0.00250 | 0.00524 | 0.12000 | 0.01092 |
| 355 | 0.00379 | 0.04484 | 0.04122 | 0.03454 |
| 356 | 0.01060 | 0.02854 | 0.20857 | 0.19161 |
| 357 | 0.00186 | 0.00859 | 0.05792 | 0.02502 |
| 358 | 0.02219 | 0.08258 | 0.43372 | 0.14740 |
| 359 | 0.01240 | 0.01053 | 0.06711 | 0.05276 |
| 360 | 0.00843 | 0.00812 | 0.03720 | 0.04075 |
| 361 | 0.37859 | 0.24790 | 0.35443 | 0.73186 |
| 362 | 0.25979 | 0.34339 | 0.46120 | 0.55785 |
| 363 | 0.00605 | 0.01120 | 0.12287 | 0.05463 |
| 364 | 0.03693 | 0.17854 | 0.17072 | 0.20740 |
| 365 | 0.02406 | 0.11274 | 0.33086 | 0.18569 |
| 366 | 0.04593 | 0.06979 | 0.38098 | 0.29921 |
| 367 | 0.04218 | 0.09038 | 0.45271 | 0.15669 |

TABLE 4-continued

| Example | JAK1 Ki, μM | JAK2 Ki, μM | JAK3 Ki, μM | TYK2 Ki, μM |
|---|---|---|---|---|
| 368 | 0.02782 | 0.01934 | 0.41864 | 0.12985 |
| 369 | 0.00274 | 0.01437 | 0.02551 | 0.07181 |
| 370 | 0.00295 | 0.01671 | 0.02783 | 0.07791 |
| 371 | 0.00482 | 0.03550 | 0.04849 | 0.17803 |
| 372 | 0.00459 | 0.02201 | 0.02876 | 0.13457 |
| 373 | 0.00407 | 0.02699 | 0.05197 | 0.12032 |
| 374 | 0.00469 | 0.08938 | 0.10036 | 0.35011 |
| 375 | 0.00411 | 0.04297 | 0.05978 | 0.15837 |
| 376 | 0.00415 | 0.03858 | 0.06192 | 0.18843 |
| 377 | 0.00364 | 0.02946 | 0.05029 | 0.18541 |
| 378 | 0.00503 | 0.04840 | 0.06128 | 0.22552 |
| 379 | 0.00354 | 0.01800 | 0.02620 | 0.11652 |
| 380 | 0.00398 | 0.03600 | 0.06259 | 0.14250 |
| 381 | 0.08709 | 1.26551 | 1.84259 | 1.98567 |
| 382 | 0.13397 | 0.58917 | 0.53783 | 0.73290 |
| 383 | 0.00988 | 0.03556 | 0.02135 | 0.21749 |
| 384 | 0.01750 | 0.13787 | 0.04807 | 0.52649 |
| 385 | 0.05129 | 0.06846 | 0.01546 | 1.29035 |
| 386 | 0.01778 | 0.06433 | 0.07917 | 0.31876 |
| 387 | 0.01545 | 0.05406 | 0.07030 | 0.34997 |
| 388 | 0.02357 | 0.16651 | 0.07728 | 0.44619 |
| 389 | 0.01106 | 0.03432 | 0.04832 | 0.18096 |
| 390 | 0.02150 | 0.07555 | 0.04790 | 0.44589 |
| 391 | 0.00753 | 0.02714 | 0.03584 | 0.09194 |
| 392 | 0.00667 | 0.01671 | 0.03388 | 0.12811 |
| 393 | 0.04564 | 0.04468 | 0.02987 | 0.38184 |
| 394 | 0.01827 | 0.03786 | 0.15228 | 0.16953 |
| 395 | 0.01768 | 0.07303 | 0.09650 | 0.24482 |
| 396 | 0.01547 | 0.03590 | 0.01812 | 0.09498 |
| 397 | 0.02994 | 0.06244 | 0.11364 | 0.26871 |
| 398 | 0.02076 | 0.04703 | 0.17872 | 0.24138 |
| 399 | 0.03308 | 0.09709 | 0.12532 | 0.17896 |
| 400 | 0.06261 | 0.11500 | 0.28315 | 0.42821 |
| 401 | 0.00949 | 0.02278 | 0.03537 | 0.09681 |
| 402 | 0.00540 | 0.00880 | 0.06676 | 0.03566 |
| 403 | 0.01030 | 0.01918 | 0.02421 | 0.10158 |
| 404 | 0.00727 | 0.01803 | 0.02929 | 0.10005 |
| 405 | 0.03060 | 0.25179 | 0.52397 | 0.44503 |
| 406 | 0.06778 | 0.20424 | 0.61353 | 0.64775 |
| 407 | 0.08123 | 0.12223 | 0.17029 | 0.60742 |
| 408 | 0.01576 | 0.04350 | 0.05243 | 0.25538 |
| 409 | 0.02623 | 0.12493 | 0.12572 | 0.32050 |
| 410 | 0.02492 | 0.08163 | 0.24362 | 0.31470 |
| 411 | 0.01150 | 0.06445 | 0.15392 | 0.42154 |
| 412 | 0.02161 | 0.07869 | 0.12503 | 0.54460 |
| 413 | 0.02110 | 0.05982 | 0.22369 | 0.18115 |
| 414 | 0.01762 | 0.05567 | 0.15543 | 0.13715 |
| 415 | 0.11505 | 0.23280 | 0.10879 | 0.91901 |
| 416 | 0.03359 | 0.12589 | 0.04881 | 0.33872 |
| 417 | 0.08929 | 0.07412 | 0.04310 | 0.34105 |
| 418 | 0.03481 | 0.02989 | 0.03345 | 0.17315 |
| 419 | 0.14438 | 0.19795 | 0.16015 | 0.81155 |
| 420 | 0.06625 | 0.08063 | 0.03909 | 0.02863 |
| 421 | 0.25060 | 0.74663 | 0.43325 | 2.33649 |
| 422 | 0.14062 | 0.37766 | 0.30988 | 1.22510 |
| 423 | 0.00988 | 0.01406 | 0.00967 | 0.11167 |
| 424 | 0.04629 | 0.06329 | 0.03290 | 0.31702 |
| 425 | 0.08341 | 0.09783 | 0.17714 | 0.39893 |
| 426 | 0.05961 | 0.05666 | 0.02620 | 0.33463 |
| 427 | 0.201000 | 0.167500 | | |
| 428 | 0.00064 | 0.00078 | 0.00162 | 0.01273 |
| 429 | 0.21095 | 0.89377 | 4.10377 | 2.23122 |
| 430 | 0.05887 | 0.16195 | 1.23638 | 0.50667 |
| 431 | 0.03712 | 0.17471 | 3.51999 | 1.15449 |
| 432 | 0.01972 | 0.01790 | 1.27674 | 0.07316 |
| 433 | 0.02241 | 0.08761 | 4.10377 | 0.29336 |
| 434 | 0.00567 | 0.00622 | 1.20113 | 0.03250 |
| 435 | 0.03207 | 0.02813 | 0.22596 | 0.26549 |
| 436 | 0.00890 | 0.01251 | 0.20992 | 0.09770 |
| 437 | 0.00387 | 0.01122 | 0.15319 | 0.05563 |
| 438 | 0.02327 | 0.18446 | 2.38072 | 0.82274 |
| 439 | 0.08419 | 0.43654 | 1.10710 | 1.98298 |
| 440 | 0.04323 | 0.11519 | 0.84379 | 0.71318 |
| 441 | 0.05576 | 0.17859 | 1.52928 | 0.83212 |
| 442 | 0.00287 | 0.00402 | 0.10536 | 0.01885 |
| 443 | 0.00811 | 0.01393 | 0.41878 | 0.04725 |
| 444 | 0.48061 | 0.36964 | 4.10377 | 3.41834 |

TABLE 4-continued

| Example | JAK1 Ki, μM | JAK2 Ki, μM | JAK3 Ki, μM | TYK2 Ki, μM |
|---|---|---|---|---|
| 445 | 0.01194 | 0.03917 | 0.08404 | 0.09691 |
| 446 | 0.00114 | 0.00225 | 0.18897 | 0.01025 |
| 447 | 0.01639 | 0.02119 | 0.47697 | 0.08444 |
| 448 | 0.03441 | 0.03575 | 0.87321 | 0.26776 |
| 449 | 0.00350 | 0.00822 | 0.03257 | 0.05818 |
| 450 | 0.00306 | 0.01018 | 0.65898 | 0.03281 |
| 451 | 0.03664 | 0.03612 | 0.42821 | 0.32499 |
| 452 | 0.31553 | 1.17020 | 4.10377 | 3.47258 |
| 453 | 0.26302 | 1.41162 | 4.10377 | 3.47258 |
| 454 | 0.54733 | 1.30929 | 4.10377 | 3.47258 |
| 455 | 0.01853 | 0.07850 | 0.51432 | 0.26154 |
| 456 | 0.07013 | 0.35417 | 0.34624 | 0.17626 |
| 457 | 0.00873 | 0.01742 | 0.05347 | 0.04076 |
| 458 | 0.00264 | 0.00882 | 0.03873 | 0.01692 |
| 459 | 0.03405 | 0.05985 | 0.28224 | 0.12680 |
| 460 | 0.00836 | 0.01730 | 0.31336 | 0.07648 |
| 461 | 0.35377 | 1.39037 | 1.17578 | 1.57592 |
| 462 | 0.09004 | 0.53804 | 1.15790 | 1.37039 |
| 463 | 0.01222 | 0.07492 | 0.19085 | 0.05553 |
| 464 | 0.05690 | 0.22397 | 0.41189 | 0.18686 |
| 465 | 0.02345 | 0.04994 | 0.05077 | 0.07055 |
| 466 | 0.00966 | 0.02462 | 0.07556 | 0.06178 |
| 467 | 0.03226 | 0.07780 | 0.42913 | 0.23048 |
| 468 | 0.01436 | 0.04662 | 0.14951 | 0.08231 |
| 469 | 0.21479 | 1.44944 | 0.47467 | 1.77054 |
| 470 | 0.19615 | 0.55731 | 0.06484 | 0.35721 |
| 471 | 0.27782 | 0.78068 | 0.72687 | 0.79338 |
| 472 | 0.05733 | 0.69378 | 0.40537 | 0.38882 |
| 473 | 0.44724 | 1.69763 | 2.01210 | 1.70180 |
| 474 | 0.00207 | 0.00440 | 0.01958 | 0.04710 |
| 475 | 0.03242 | 0.10992 | 0.02189 | 2.25438 |
| 476 | 0.01234 | 0.02905 | 0.06842 | 0.30155 |
| 477 | 0.04068 | 0.17141 | 0.23624 | 0.79892 |
| 478 | 0.08329 | 0.12494 | 0.52713 | 0.42549 |
| 479 | 0.13003 | 0.12338 | 0.12134 | 0.41981 |
| 480 | 0.26427 | 0.17901 | 0.56317 | 1.09584 |
| 481 | 0.12724 | 0.26773 | 0.83317 | 0.79263 |
| 482 | 0.05585 | 0.09763 | 0.15044 | 0.84465 |
| 483 | 0.47220 | 0.83208 | 0.61277 | 3.47258 |
| 484 | 0.44121 | 0.18116 | 0.32281 | 1.28721 |
| 485 | 0.00107 | 0.00191 | 0.01900 | 0.00660 |
| 486 | 0.00345 | 0.00624 | 0.01012 | 0.02195 |
| 487 | 0.01655 | 0.03082 | 0.03711 | 0.23367 |
| 488 | 0.03191 | 0.03708 | 0.08700 | 0.18836 |
| 489 | 0.03405 | 0.31490 | 0.32241 | 0.59641 |
| 490 | 0.39131 | 1.10906 | 1.86636 | 3.43287 |
| 491 | 0.00970 | 0.03396 | 0.02362 | 0.09584 |
| 492 | 0.01602 | 0.08650 | 0.19999 | 0.21012 |
| 493 | 0.01126 | 0.03623 | 0.08022 | 0.12069 |
| 494 | 0.00473 | 0.02349 | 0.01856 | 0.06125 |
| 495 | 0.01620 | 0.10621 | 0.09772 | 0.41466 |
| 496 | 0.00275 | 0.00805 | 0.01309 | 0.05569 |
| 497 | 0.01297 | 0.04155 | 0.07628 | 0.16947 |
| 498 | 0.02190 | 0.06771 | 0.05996 | 0.30748 |
| 499 | 0.01380 | 0.08562 | 0.10282 | 0.41727 |
| 500 | 0.02866 | 0.05870 | 0.04099 | 0.39383 |
| 501 | 0.00393 | 0.01201 | 0.01220 | 0.05642 |
| 502 | 0.01518 | 0.09059 | 0.10471 | 0.41654 |
| 503 | 0.00254 | 0.01039 | 0.01962 | 0.05046 |
| 504 | 0.00775 | 0.02543 | 0.05357 | 0.11645 |
| 505 | 0.00518 | 0.02236 | 0.02044 | 0.09878 |
| 506 | 0.00575 | 0.05367 | 0.07402 | 0.17879 |
| 507 | 0.01110 | 0.04020 | 0.06938 | 0.10166 |
| 508 | 0.00214 | 0.01030 | 0.02316 | 0.01021 |
| 509 | 0.00255 | 0.02363 | 0.06548 | 0.02161 |
| 510 | 0.00391 | 0.05106 | 0.13173 | 0.02082 |
| 511 | 0.00530 | 0.04891 | 0.17396 | 0.03029 |
| 512 | 0.00255 | 0.02829 | 0.06170 | 0.02200 |
| 513 | 0.00084 | 0.00216 | 0.00763 | 0.00695 |
| 514 | 0.00169 | 0.02434 | 0.02823 | 0.01583 |
| 515 | 0.00241 | 0.04346 | 0.11981 | 0.02517 |
| 516 | 0.00217 | 0.00278 | 0.00535 | 0.00758 |
| 517 | 0.01033 | 0.05746 | 0.05261 | 0.29435 |
| 518 | 0.22667 | 0.85427 | 1.45084 | 1.98719 |
| 519 | 0.00174 | 0.00492 | 0.03302 | 0.02455 |
| 520 | 0.03816 | 0.12775 | 0.41238 | 0.26116 |
| 521 | 0.00348 | 0.00704 | 0.02538 | 0.04882 |

TABLE 4-continued

| Example | JAK1 Ki, μM | JAK2 Ki, μM | JAK3 Ki, μM | TYK2 Ki, μM |
|---|---|---|---|---|
| 522 | 0.03847 | 0.05693 | 0.17997 | 0.35632 |
| 523 | 0.01119 | 0.01673 | 0.30201 | 0.08565 |
| 524 | 0.01375 | 0.12121 | 0.09827 | 0.16823 |
| 525 | 0.01235 | 0.03317 | 0.08757 | 0.09676 |
| 526 | 0.00797 | 0.06142 | 0.11581 | 0.09196 |
| 527 | 0.10730 | 0.19955 | 0.18936 | 0.06520 |
| 528 | 0.15642 | 0.39583 | 0.18750 | 1.40767 |
| 529 | 0.01961 | 0.28447 | 0.56062 | 2.16949 |
| 530 | 0.00066 | 0.00145 | 0.00300 | 0.00561 |
| 531 | 0.00177 | 0.00458 | 0.00423 | 0.02116 |
| 532 | 0.00286 | 0.00600 | 0.03044 | 0.02377 |
| 533 | 0.00905 | 0.01571 | 0.04883 | 0.05975 |
| 534 | 0.00986 | 0.02444 | 0.08885 | 0.14951 |
| 535 | 0.01197 | 0.04490 | 0.22549 | 0.08823 |
| 536 | 0.03247 | 0.06123 | 1.02159 | 0.23531 |
| 537 | 0.02517 | 0.03376 | 0.32198 | 0.12173 |
| 538 | 0.00086 | 0.00089 | 0.00401 | 0.00866 |
| 539 | 0.01268 | 0.19370 | 0.09735 | 0.35158 |
| 540 | 0.01275 | 0.04128 | 0.01654 | 0.03586 |
| 541 | 0.00468 | 0.01798 | 0.02369 | 0.02410 |
| 542 | 0.01820 | 0.07656 | 0.05100 | 0.02725 |
| 543 | 0.08260 | 0.38439 | 0.17874 | 0.27378 |
| 544 | 0.00632 | 0.01526 | 0.03134 | 0.02124 |
| 545 | 0.03049 | 0.09937 | 0.04807 | 0.13249 |
| 546 | 0.00997 | 0.01961 | 0.13961 | 0.07416 |
| 547 | 0.02738 | 0.18405 | 1.41279 | 0.63763 |
| 548 | 0.22334 | 0.48449 | 4.10377 | 2.79336 |
| 549 | 0.09239 | 0.18191 | 3.49402 | 0.80892 |
| 550 | 0.01984 | 0.12885 | 0.72830 | 0.48210 |
| 551 | 0.01353 | 0.01904 | 0.12812 | 0.08857 |
| 552 | 0.00659 | 0.01024 | 0.01177 | 0.02418 |
| 553 | 0.00859 | 0.02037 | 0.04249 | 0.03352 |
| 554 | 0.01331 | 0.03164 | 0.07729 | 0.06057 |
| 555 | 0.03303 | 0.27598 | 0.49066 | 0.30230 |
| 556 | 0.06041 | 0.19022 | 0.89443 | 1.46239 |
| 557 | 0.02135 | 0.13633 | 0.31047 | 0.44285 |
| 558 | 0.00694 | 0.06087 | 0.10964 | 0.03921 |
| 559 | 0.01026 | 0.02403 | 0.05295 | 0.03851 |
| 560 | 0.00814 | 0.01325 | 0.03747 | 0.04727 |
| 561 | 0.00729 | 0.01791 | 0.01454 | 0.02449 |
| 562 | 0.00458 | 0.00755 | 0.00589 | 0.01200 |
| 563 | 0.09104 | 0.61099 | 2.36032 | 3.31963 |
| 564 | 0.11229 | 0.70988 | 2.64762 | 3.47258 |
| 565 | 0.09084 | 0.39688 | 1.04992 | 1.95314 |
| 566 | 0.02047 | 0.18644 | 0.49811 | 0.25956 |
| 567 | 0.07858 | 0.49057 | 0.25053 | 0.22063 |
| 568 | 0.00291 | 0.04860 | 0.05978 | 0.06519 |
| 569 | 0.01265 | 0.09578 | 0.44809 | 0.25406 |
| 570 | 0.01122 | 0.01000 | 0.11580 | 0.07766 |
| 571 | 0.00970 | 0.02108 | 0.19679 | 0.10125 |
| 572 | 0.01158 | 0.02702 | 0.20052 | 0.11937 |
| 573 | 0.00462 | 0.01068 | 0.06950 | 0.09149 |
| 574 | 0.00794 | 0.05462 | 0.23165 | 0.12522 |
| 575 | 0.00717 | 0.03401 | 0.20605 | 0.04470 |
| 576 | 0.00663 | 0.01775 | 0.01257 | 0.02127 |
| 577 | 0.00455 | 0.01084 | 0.02230 | 0.01492 |
| 578 | 0.17347 | 0.75730 | 0.75300 | 0.62085 |
| 579 | 0.10599 | 0.48304 | 1.35949 | 0.32949 |
| 580 | 0.00145 | 0.01277 | 0.05852 | 0.04134 |
| 581 | 0.02680 | 0.11436 | 0.27994 | 0.27473 |
| 582 | 0.10206 | 0.36434 | 0.59232 | 1.05396 |
| 583 | 0.00436 | 0.03185 | 0.36259 | 0.17267 |
| 584 | 0.03697 | 0.10545 | 1.32035 | 0.45367 |
| 585 | 0.00946 | 0.06336 | 0.08831 | 0.06732 |
| 586 | 0.00109 | 0.00160 | 0.02334 | 0.00973 |
| 587 | 0.00061 | 0.00216 | 0.00835 | 0.00802 |
| 588 | 0.00581 | 0.01332 | 0.00573 | 0.58364 |
| 589 | 0.00144 | 0.00932 | 0.01294 | 0.01905 |
| 590 | 0.00274 | 0.01352 | 0.01710 | 0.04308 |
| 591 | 0.00064 | 0.00187 | 0.01303 | 0.00251 |
| 592 | 0.01200 | 0.01553 | 0.34373 | 0.21492 |
| 593 | 0.02708 | 0.03653 | 0.31557 | 0.39781 |
| 594 | 0.00832 | 0.02272 | 0.33354 | 0.07665 |
| 595 | 0.01045 | 0.02885 | 0.09680 | 0.18484 |
| 596 | 0.00261 | 0.00551 | 0.06742 | 0.01745 |
| 597 | 0.03081 | 0.12639 | 0.82337 | 0.49700 |
| 598 | 0.00731 | 0.00834 | 0.01210 | 0.04553 |

TABLE 4-continued

| Example | JAK1 Ki, μM | JAK2 Ki, μM | JAK3 Ki, μM | TYK2 Ki, μM |
|---|---|---|---|---|
| 599 | 0.00768 | 0.02636 | 0.18580 | 0.11968 |
| 600 | 0.00273 | 0.02316 | 0.17214 | 0.02080 |
| 601 | 0.00389 | 0.05710 | 0.11134 | 0.14914 |
| 602 | 0.00167 | 0.00241 | 0.05673 | 0.01274 |
| 603 | 0.00976 | 0.02085 | 0.23653 | 0.08696 |
| 604 | 0.01635 | 0.04597 | 0.24949 | 0.24381 |
| 605 | 0.01523 | 0.04308 | 0.15223 | 0.12881 |
| 606 | 0.02875 | 0.06524 | 0.45527 | 0.11240 |
| 607 | 0.00060 | 0.00446 | 0.01118 | 0.02309 |
| 608 | 0.01778 | 0.01243 | 0.15841 | 0.18239 |
| 609 | 0.09669 | 0.64119 | 0.70060 | 0.90975 |
| 610 | 0.00725 | 0.03547 | 0.13900 | 0.01774 |
| 611 | 0.00689 | 0.14226 | 0.13896 | 0.04963 |
| 612 | 0.05293 | 0.45473 | 0.50927 | 0.22357 |
| 613 | 0.00258 | 0.01510 | 0.31797 | 0.01452 |
| 614 | 0.00076 | 0.01323 | 0.06332 | 0.00301 |
| 615 | 0.00196 | 0.05749 | 0.13693 | 0.02150 |
| 616 | 0.00449 | 0.01999 | 0.08427 | 0.01210 |
| 617 | 0.01187 | 0.03872 | 0.14688 | 0.02233 |
| 618 | 0.13757 | 0.44636 | 0.94193 | 1.44137 |
| 619 | 0.00587 | 0.01463 | 0.03114 | 0.11752 |
| 620 | 0.00164 | 0.00815 | 0.02048 | 0.09144 |
| 621 | 0.00878 | 0.02317 | 0.14774 | 0.12435 |
| 622 | 0.00900 | 0.01241 | 0.01950 | 0.23278 |
| 623 | 0.00098 | 0.00869 | 0.04266 | 0.11792 |
| 624 | 0.00223 | 0.01016 | 0.01390 | 0.06300 |
| 625 | 0.03394 | 0.09966 | 0.16857 | 0.21767 |
| 626 | 0.00204 | 0.00640 | 0.03366 | 0.00938 |
| 627 | 0.00136 | 0.00591 | 0.01396 | 0.01274 |
| 628 | 0.04309 | 0.37492 | 0.79795 | 0.97432 |
| 629 | 0.00136 | 0.00499 | 0.01103 | 0.03205 |
| 630 | 0.00259 | 0.00662 | 0.01838 | 0.02582 |
| 631 | 0.00085 | 0.00257 | 0.01935 | 0.00679 |
| 632 | 0.00291 | 0.00350 | 0.03678 | 0.01371 |
| 633 | 0.00119 | 0.00331 | 0.01212 | 0.00608 |
| 634 | 0.00380 | 0.02195 | 0.16518 | 0.00440 |
| 635 | 0.00404 | 0.07542 | 0.37066 | 0.01129 |
| 636 | 0.00382 | 0.01559 | 0.02796 | 0.00650 |
| 637 | 0.00189 | 0.03559 | 0.03696 | 0.00742 |
| 638 | 0.00956 | 0.07773 | 0.14967 | 0.07074 |
| 639 | 0.00078 | 0.01436 | 0.05812 | 0.00404 |
| 640 | 0.00393 | 0.00966 | 0.08270 | 0.02511 |
| 641 | 0.00187 | 0.06652 | 0.25422 | 0.01238 |
| 642 | 0.00206 | 0.02088 | 0.18502 | 0.00722 |
| 643 | 0.00027 | 0.00096 | 0.00526 | 0.00051 |
| 644 | 0.00012 | 0.00081 | 0.00531 | 0.00036 |
| 645 | 0.00013 | 0.00039 | 0.00356 | 0.00025 |
| 646 | 0.00053 | 0.00205 | 0.00911 | 0.00149 |
| 647 | 0.00034 | 0.00380 | 0.00771 | 0.00164 |
| 648 | 0.00606 | 0.07241 | 0.11923 | 0.02679 |
| 649 | 0.00482 | 0.03857 | 0.06863 | 0.03844 |
| 650 | 0.01047 | 0.11336 | 0.75554 | 0.05197 |
| 651 | 0.00987 | 0.04247 | 0.42960 | 0.03479 |
| 652 | 0.00081 | 0.00438 | 0.03903 | 0.00370 |
| 653 | 0.00088 | 0.02474 | 0.00131 | 0.00528 |
| 654 | 0.45294 | 0.76265 | 2.08936 | 3.47258 |
| 655 | 0.00046 | 0.00108 | 0.01591 | 0.00467 |
| 656 | 0.01463 | 0.07704 | 0.03774 | 0.41972 |
| 657 | 0.02915 | 1.28458 | 0.66844 | 3.47258 |
| 658 | 0.00351 | 0.01362 | 0.03420 | 0.06744 |
| 659 | 0.03081 | 0.39458 | 0.17200 | 0.30795 |
| 660 | 0.32740 | 1.21653 | 1.04566 | 0.64467 |
| 661 | 0.00398 | 0.06635 | 0.05543 | 0.04624 |
| 662 | 0.02624 | 0.30668 | 0.85521 | 0.87694 |
| 663 | 0.07579 | 0.07025 | 0.18794 | 0.05820 |
| 664 | 0.06378 | 0.09902 | 0.11249 | 0.05852 |
| 665 | 0.43167 | 1.80495 | 1.78196 | 3.47258 |
| 666 | 1.68518 | 3.18801 | 4.00507 | 3.47258 |
| 667 | 0.11439 | 0.46746 | 0.89465 | 0.51946 |
| 668 | 1.02288 | 2.93644 | 2.61965 | 3.24357 |
| 669 | 0.13660 | 0.91343 | 0.82306 | 0.68055 |
| 670 | 0.39654 | 1.74656 | 2.17043 | 1.51566 |
| 671 | 0.00053 | 0.01806 | 0.02245 | 0.00247 |
| 672 | 0.00081 | 0.01985 | 0.01717 | 0.00301 |
| 673 | 0.00069 | 0.00324 | 0.00396 | 0.00215 |
| 674 | 0.00113 | 0.00711 | 0.01051 | 0.00187 |
| 675 | 0.00121 | 0.00696 | 0.01144 | 0.00178 |

TABLE 4-continued

| Example | JAK1 Ki, μM | JAK2 Ki, μM | JAK3 Ki, μM | TYK2 Ki, μM |
|---|---|---|---|---|
| 676 | 0.00136 | 0.00787 | 0.04020 | 0.02215 |
| 677 | 0.00247 | 0.02946 | 0.03286 | 0.02752 |
| 678 | 0.00395 | 0.03176 | 0.02361 | 0.27636 |
| 679 | 0.00745 | 0.05555 | 0.02767 | 0.41317 |
| 680 | 0.00732 | 0.05627 | 0.02839 | 0.41245 |
| 681 | 0.00421 | 0.03261 | 0.13255 | 0.29048 |
| 682 | 0.00863 | 0.10335 | 0.03102 | 0.38706 |
| 683 | 0.16246 | 0.25867 | 0.30793 | 1.75090 |
| 684 | 0.00757 | 0.02161 | 0.01146 | 0.03780 |
| 685 | 0.03710 | 0.11503 | 0.03437 | 0.12508 |
| 686 | 0.04743 | 0.02699 | 0.01526 | 0.00417 |
| 687 | 0.16684 | 1.48110 | 0.85763 | 0.83411 |
| 688 | 0.00177 | 0.02065 | 0.01613 | 0.00470 |
| 689 | 0.00273 | 0.05239 | 0.05699 | 0.00559 |
| 690 | 0.06216 | 0.19866 | 0.22863 | 0.26991 |
| 691 | 0.06137 | 0.32004 | 0.20610 | 0.75038 |
| 692 | 0.00464 | 0.04663 | 0.06844 | 0.11752 |
| 693 | 0.01110 | 0.07208 | 0.30298 | 0.33233 |
| 694 | 0.00055 | 0.00563 | 0.02032 | 0.00758 |
| 695 | 0.02838 | 0.07767 | 0.06312 | 0.48263 |
| 696 | 0.01357 | 0.06682 | 0.05746 | 0.04961 |
| 697 | 0.00310 | 0.06485 | 0.03609 | 0.03247 |
| 698 | 0.00641 | 0.02565 | 0.06690 | 0.07440 |
| 699 | 0.23465 | 0.13063 | 0.27969 | 1.07094 |
| 700 | 0.47755 | 0.61701 | 0.54586 | 1.43427 |
| 701 | 0.01587 | 0.06064 | 0.23420 | 0.20166 |
| 702 | 0.00369 | 0.02644 | 0.04062 | 0.02368 |
| 703 | 0.00197 | 0.03007 | 0.00501 | 0.18194 |
| 704 | 0.00245 | 0.05671 | 0.01282 | 0.13818 |
| 705 | 0.04862 | 0.33994 | 0.31086 | 0.66518 |
| 706 | 0.02808 | 0.06746 | 0.02056 | 0.20746 |
| 707 | 0.07449 | 0.12252 | 0.11201 | 0.39108 |
| 708 | 0.01135 | 0.03864 | 0.07981 | 0.07748 |
| 709 | 0.00603 | 0.02405 | 0.05625 | 0.04440 |
| 710 | 0.00685 | 0.03430 | 0.04498 | 0.05059 |
| 711 | 0.01410 | 0.03686 | 0.01578 | 0.07034 |
| 712 | 0.01534 | 0.04490 | 0.02972 | 0.11360 |
| 713 | 0.00814 | 0.01504 | 0.20246 | 0.06274 |
| 714 | 0.00529 | 0.00989 | 0.10513 | 0.02857 |
| 715 | 0.01146 | 0.01687 | 0.10918 | 0.05819 |
| 716 | 0.01060 | 0.02332 | 0.16732 | 0.07426 |
| 717 | 0.00611 | 0.01329 | 0.05965 | 0.03496 |
| 718 | 0.01030 | 0.02076 | 0.14318 | 0.08305 |
| 719 | 0.00407 | 0.02323 | 0.02202 | 0.03043 |
| 720 | 0.00660 | 0.01828 | 0.08805 | 0.05454 |
| 721 | 0.00109 | 0.00404 | 0.01418 | 0.01340 |
| 722 | 0.00308 | 0.00698 | 0.04284 | 0.02436 |
| 723 | 0.00622 | 0.02966 | 0.00488 | 0.09464 |
| 724 | 0.00627 | 0.02434 | 0.01601 | 0.07885 |
| 725 | 0.02208 | 0.04951 | 0.03248 | 0.21141 |
| 726 | 0.17560 | 0.78481 | 0.75370 | 2.22103 |
| 727 | 0.00176 | 0.00773 | 0.07443 | 0.14283 |
| 728 | 0.00152 | 0.00624 | 0.00226 | 0.02240 |
| 729 | 0.00200 | 0.00979 | 0.01352 | 0.04887 |
| 730 | 0.00149 | 0.00724 | 0.00187 | 0.02111 |
| 731 | 0.00058 | 0.00554 | 0.00913 | 0.01244 |
| 732 | 0.00285 | 0.00859 | 0.01620 | 0.06474 |
| 733 | 0.00077 | 0.00483 | 0.00588 | 0.03781 |
| 734 | 0.00225 | 0.00806 | 0.05428 | 0.02850 |
| 735 | 0.00152 | 0.00567 | 0.05461 | 0.01915 |
| 736 | 0.00128 | 0.00642 | 0.00079 | 0.05718 |
| 737 | 0.00453 | 0.00844 | 0.00719 | 0.10677 |
| 738 | 0.01163 | 0.04911 | 0.08095 | 0.35123 |
| 739 | 0.02129 | 0.05380 | 0.29940 | 0.53577 |
| 740 | 0.02171 | 0.09774 | 0.40353 | 0.29557 |
| 741 | 0.10296 | 0.52808 | 1.13125 | 0.56764 |
| 742 | 0.00951 | 0.06621 | 0.03664 | 0.01112 |
| 743 | 0.00059 | 0.00368 | 0.01406 | 0.00123 |
| 744 | 0.00715 | 0.01782 | 0.08921 | 0.08600 |
| 745 | 0.00322 | 0.01157 | 0.03712 | 0.11262 |
| 746 | 0.01308 | 0.02126 | 0.18350 | 0.07543 |
| 747 | 0.00422 | 0.01168 | 0.05253 | 0.07270 |
| 748 | 0.01070 | 0.03661 | 0.14992 | 0.44449 |
| 749 | 0.00283 | 0.01581 | 0.00896 | 0.17743 |
| 750 | 0.00474 | 0.02205 | 0.01763 | 0.12963 |
| 751 | 0.00783 | 0.02787 | 0.07940 | 0.08390 |
| 752 | 0.02486 | 0.09717 | 0.23986 | 0.26353 |

TABLE 4-continued

| Example | JAK1 Ki, μM | JAK2 Ki, μM | JAK3 Ki, μM | TYK2 Ki, μM |
|---|---|---|---|---|
| 753 | 0.01843 | 0.07612 | 0.29589 | 0.28935 |
| 754 | 0.04044 | 0.28576 | 0.96147 | 2.37299 |
| 755 | 0.00715 | 0.03366 | 0.09311 | 0.21141 |
| 756 | 0.03607 | 0.25900 | 0.61651 | 1.11596 |
| 757 | 0.00206 | 0.01001 | 0.08281 | 0.03376 |
| 758 | 0.04081 | 0.20501 | 0.59808 | 1.00520 |
| 759 | 0.00713 | 0.11758 | 0.03720 | 0.10866 |
| 760 | 0.00346 | 0.02300 | 0.02169 | 0.02538 |
| 761 | 0.00159 | 0.00850 | 0.02264 | 0.01002 |
| 762 | 0.00089 | 0.00265 | 0.00551 | 0.00488 |
| 763 | 0.01251 | 0.04217 | 0.27788 | 0.22258 |
| 764 | 0.08805 | 0.44130 | 0.60872 | 0.85911 |
| 765 | 0.27461 | 0.87191 | 2.20800 | 2.83879 |
| 766 | 0.00097 | 0.00307 | 0.06847 | 0.02108 |
| 767 | 0.00281 | 0.01070 | 0.15519 | 0.03685 |
| 768 | 0.00177 | 0.00647 | 0.08589 | 0.02341 |
| 769 | 0.00960 | 0.01659 | 0.10449 | 0.06255 |
| 770 | 0.00880 | 0.03269 | 0.04266 | 0.20689 |
| 771 | 0.00206 | 0.00662 | 0.01913 | 0.02777 |
| 772 | 0.00136 | 0.00570 | 0.04354 | 0.32013 |
| 773 | 0.01217 | 0.08141 | 0.12580 | 0.14868 |
| 774 | 0.04066 | 0.08273 | 0.24234 | 0.14124 |
| 775 | 0.15882 | 0.23834 | 0.90981 | 0.84295 |
| 776 | 0.00099 | 0.01044 | 0.00188 | 0.00073 |
| 777 | 0.00130 | 0.00686 | 0.00104 | 0.00064 |
| 778 | 0.00065 | 0.01320 | 0.04244 | 0.00689 |
| 779 | 0.00487 | 0.07385 | 0.23305 | 0.03905 |
| 780 | 0.01578 | 0.04123 | 0.07417 | 0.10879 |
| 781 | 0.37961 | 1.48881 | 4.00054 | 3.47258 |
| 782 | 0.28634 | 1.46820 | 2.97204 | 3.03900 |
| 783 | 0.13709 | 1.46431 | 2.65817 | 1.79372 |
| 784 | 0.22408 | 3.18801 | 4.10377 | 3.47258 |
| 785 | 0.03193 | 0.37259 | 0.56583 | 0.27820 |
| 786 | 0.05251 | 0.59564 | 1.11697 | 0.59895 |
| 787 | 0.46428 | 3.18801 | 2.49265 | 3.47258 |
| 788 | 0.06714 | 0.79199 | 0.84376 | 0.71626 |
| 789 | 0.43808 | 3.18801 | 4.10377 | 3.47258 |
| 790 | 0.07990 | 0.73957 | 0.88375 | 0.58667 |
| 791 | 0.08238 | 1.07765 | 0.82181 | 0.81388 |
| 792 | 0.07636 | 0.26000 | 1.06088 | 0.44850 |
| 793 | 0.26735 | 2.28081 | 2.36299 | 2.01348 |
| 794 | 0.11578 | 0.88639 | 1.23306 | 0.41964 |
| 795 | 0.22070 | 0.87624 | 1.37252 | 0.69772 |
| 796 | 0.05502 | 0.74602 | 0.88410 | 0.61673 |
| 797 | 0.15919 | 1.74591 | 1.62577 | 3.47258 |
| 798 | 0.06903 | 2.63820 | 0.89684 | 3.47258 |
| 799 | 0.45580 | 3.18801 | 4.10377 | 3.47258 |
| 800 | 0.16308 | 1.45578 | 1.42103 | 1.09034 |
| 801 | 0.00774 | 0.05146 | 0.07676 | 0.06489 |
| 802 | 0.00777 | 0.04861 | 0.07946 | 0.05470 |
| 803 | 0.01609 | 0.04405 | 0.02569 | 0.07683 |
| 804 | 0.00297 | 0.02523 | 0.01355 | 0.17173 |
| 805 | 0.00280 | 0.03602 | 0.00901 | 0.15819 |
| 806 | 0.00341 | 0.02125 | 0.01788 | 0.17916 |
| 807 | 0.00378 | 0.03466 | 0.01587 | 0.25723 |
| 808 | 0.00477 | 0.03409 | 0.12828 | 0.30324 |
| 809 | 0.00567 | 0.04658 | 0.16223 | 0.38147 |
| 810 | 0.00572 | 0.04473 | 0.18053 | 0.38463 |
| 811 | 0.00678 | 0.06290 | 0.12995 | 0.51932 |
| 812 | 0.03776 | 0.21275 | 0.16778 | 0.31595 |
| 813 | 0.02107 | 0.04296 | 0.03994 | 0.36499 |
| 814 | 0.01122 | 0.08838 | 0.09073 | 0.57966 |
| 815 | 0.02346 | 0.09177 | 0.19058 | 0.25388 |
| 816 | 0.00769 | 0.01956 | 0.09082 | 0.09034 |
| 817 | 0.00858 | 0.04304 | 0.06367 | 0.20729 |
| 818 | 0.00945 | 0.38341 | 0.11661 | 1.38318 |
| 819 | 0.01091 | 0.06180 | 0.04490 | 0.16146 |
| 820 | 0.01200 | 0.06102 | 0.03577 | 0.16626 |
| 821 | 0.01767 | 0.12465 | 0.05526 | 0.47273 |
| 822 | 0.01809 | 0.89366 | 0.31131 | 2.80937 |
| 823 | 0.02219 | 0.17130 | 0.08479 | 0.17894 |
| 824 | 0.02454 | 1.21207 | 0.59961 | 3.47258 |
| 825 | 0.02596 | 0.35034 | 0.14335 | 1.96248 |
| 826 | 0.04704 | 0.41929 | 0.20857 | 1.16030 |
| 827 | 0.07386 | 1.71941 | 1.45819 | 3.47258 |
| 828 | 0.09045 | 1.66698 | 0.94873 | 3.47258 |
| 829 | 0.09431 | 0.93923 | 1.31694 | 3.47258 |

TABLE 4-continued

| Example | JAK1 Ki, μM | JAK2 Ki, μM | JAK3 Ki, μM | TYK2 Ki, μM |
|---|---|---|---|---|
| 830 | 0.10854 | 1.73157 | 0.71055 | 3.47258 |
| 831 | 0.30888 | 2.67970 | 1.00287 | 3.47258 |
| 832 | 0.05553 | 0.42819 | 0.51634 | 0.49253 |
| 833 | 0.01815 | 0.01396 | 0.10129 | 0.12463 |
| 834 | 0.03351 | 0.11683 | 0.08539 | 0.63727 |
| 835 | 0.03790 | 0.05906 | 0.02956 | 0.32034 |
| 836 | 0.03859 | 0.08902 | 0.09509 | 0.38410 |
| 837 | 0.03958 | 0.08321 | 0.11354 | 0.29769 |
| 838 | 0.05425 | 0.08548 | 0.09042 | 0.61826 |
| 839 | 0.06172 | 0.10580 | 0.07350 | 0.59468 |
| 840 | 0.06234 | 0.10204 | 0.10427 | 0.63531 |
| 841 | 0.06655 | 0.10941 | 0.14696 | 0.77056 |
| 842 | 0.08104 | 0.17141 | 0.23576 | 0.90526 |
| 843 | 0.08415 | 0.08075 | 0.16908 | 0.63088 |
| 844 | 0.09709 | 0.17667 | 0.16859 | 0.73198 |
| 845 | 0.00417 | 0.01389 | 0.05228 | 0.02882 |
| 846 | 0.09059 | 0.36897 | 0.26111 | 0.74870 |
| 847 | 0.10455 | 0.52986 | 0.38057 | 0.27921 |
| 848 | 0.11974 | 0.15565 | 0.07190 | 0.21556 |
| 849 | 0.05084 | 0.51547 | 0.59210 | 0.45921 |
| 850 | 0.06050 | 0.13422 | 0.10588 | 0.36131 |
| 851 | 0.02595 | 0.05335 | 0.02443 | 0.04987 |
| 852 | 0.02915 | 0.14019 | 0.11670 | 0.08930 |
| 853 | 0.00198 | 0.02262 | 0.02036 | 0.00529 |
| 854 | 0.00401 | 0.07712 | 0.19513 | 0.13850 |
| 855 | 0.00513 | 0.11712 | 0.49300 | 0.11173 |
| 856 | 0.00596 | 0.12082 | 0.27602 | 0.25865 |
| 857 | 0.00623 | 0.21311 | 0.52484 | 0.36428 |
| 858 | 0.00777 | 0.05222 | 0.05242 | 0.01982 |
| 859 | 0.01013 | 0.05300 | 0.10744 | 0.06838 |
| 860 | 0.02015 | 0.29647 | 0.56122 | 0.80619 |
| 861 | 0.03941 | 0.20539 | 1.66590 | 0.60172 |
| 862 | 0.04947 | 0.43710 | 0.44462 | 0.99391 |
| 863 | 0.06719 | 0.82776 | 1.23968 | 2.01617 |
| 864 | 0.07170 | 0.23545 | 0.30465 | 0.28588 |
| 865 | 0.08781 | 0.56588 | 0.71679 | 1.27258 |
| 866 | 0.08811 | 0.60386 | 1.10963 | 1.05847 |
| 867 | 0.00358 | 0.09651 | 0.11892 | 0.02658 |
| 868 | 0.00707 | 0.14805 | 0.11872 | 0.14877 |
| 869 | 0.00089 | 0.01790 | 0.00869 | 0.01011 |
| 870 | 0.26733 | 1.43995 | 1.36511 | 3.47258 |
| 871 | 0.05972 | 0.29004 | 0.17746 | 1.17366 |
| 872 | 0.16399 | 0.98286 | 0.99810 | 3.47258 |
| 873 | 0.02068 | 0.12423 | 0.07272 | 0.42188 |
| 874 | 0.00579 | 0.16195 | 0.24223 | 0.11387 |
| 875 | 0.03500 | 0.29024 | 0.09554 | 0.08622 |
| 876 | 0.00349 | 0.03066 | 0.03570 | 0.01528 |
| 877 | 0.00169 | 0.03782 | 0.01058 | 0.01092 |
| 878 | 0.00180 | 0.04373 | 0.01358 | 0.01177 |
| 879 | 0.00388 | 0.02220 | 0.02789 | 0.02651 |
| 880 | 0.00195 | 0.01945 | 0.00497 | 0.02467 |
| 881 | 0.02644 | 0.28038 | 0.09060 | 0.05974 |
| 882 | 0.00356 | 0.05164 | 0.07263 | 0.01055 |
| 883 | 0.00461 | 0.01576 | 0.08935 | 0.24368 |
| 884 | 0.00517 | 0.00639 | 0.08630 | 0.04402 |
| 885 | 0.00616 | 0.02383 | 0.04781 | 0.03296 |
| 886 | 0.01032 | 0.01669 | 0.04174 | 0.05281 |
| 887 | 0.01105 | 0.02393 | 0.19333 | 0.07905 |
| 888 | 0.01281 | 0.01769 | 0.01396 | 0.04089 |
| 889 | 0.03617 | 0.33709 | 0.33453 | 0.09649 |
| 890 | 0.03762 | 0.03815 | 0.03685 | 0.13320 |
| 891 | 0.06498 | 0.54260 | 0.23969 | 0.16461 |
| 892 | 0.08214 | 0.14504 | 0.12958 | 0.11412 |
| 893 | 0.00490 | 0.04922 | 0.06072 | 0.00949 |
| 894 | 0.00014 | 0.00618 | 0.03742 | 0.00646 |
| 895 | 0.00127 | 0.01909 | 0.00334 | 0.09908 |
| 896 | 0.00172 | 0.02138 | 0.00689 | 0.05673 |
| 897 | 0.00190 | 0.00944 | 0.01315 | 0.00442 |
| 898 | 0.00209 | 0.05437 | 0.01289 | 0.09673 |
| 899 | 0.00332 | 0.03213 | 0.00673 | 0.13966 |
| 900 | 0.01802 | 0.49405 | 0.13003 | 2.00785 |
| 901 | 0.02504 | 0.13864 | 0.07253 | 0.22289 |
| 902 | 0.02553 | 1.22994 | 0.47767 | 2.66814 |
| 903 | 0.03392 | 0.32306 | 0.08887 | 0.54171 |
| 904 | 0.21093 | 1.33831 | 1.04317 | 2.65029 |
| 905 | 0.01466 | 0.09643 | 0.12795 | 0.05707 |
| 906 | 0.05181 | 0.27093 | 0.27264 | 0.11893 |
| 907 | 0.02400 | 0.14220 | 0.19539 | 0.07693 |
| 908 | 0.00607 | 0.03709 | 0.01631 | 0.28172 |
| 909 | 0.00708 | 0.12833 | 0.21333 | 0.35200 |
| 910 | 0.05020 | 0.21222 | 0.32274 | 0.21326 |
| 911 | 0.00333 | 0.03773 | 0.00574 | 0.17979 |
| 912 | 0.00337 | 0.04277 | 0.00783 | 0.17608 |
| 913 | 0.00389 | 0.05472 | 0.06136 | 0.11563 |
| 914 | 0.00397 | 0.03543 | 0.06055 | 0.04027 |
| 915 | 0.00549 | 0.02823 | 0.02224 | 0.10104 |
| 916 | 0.00673 | 0.05279 | 0.06352 | 0.07844 |
| 917 | 0.00964 | 0.07355 | 0.06495 | 0.11216 |
| 918 | 0.01015 | 0.09389 | 0.05998 | 0.03005 |
| 919 | 0.01060 | 0.43704 | 0.47648 | 0.26428 |
| 920 | 0.01298 | 0.09304 | 0.08650 | 0.18335 |
| 921 | 0.01309 | 0.11644 | 0.07092 | 0.19060 |
| 922 | 0.01333 | 0.04984 | 0.05160 | 0.14586 |
| 923 | 0.01714 | 0.15049 | 0.03742 | 0.36350 |
| 924 | 0.01772 | 0.09566 | 0.05412 | 0.07248 |
| 925 | 0.03003 | 0.25159 | 0.55457 | 0.33765 |
| 926 | 0.03521 | 2.47096 | 1.15411 | 1.59530 |
| 927 | 0.17641 | 0.61279 | 0.38268 | 0.71136 |
| 928 | 0.12510 | 0.20581 | 0.44880 | 0.88672 |
| 929 | 0.10583 | 0.57824 | 0.18455 | 0.28102 |
| 930 | 0.08720 | 0.95038 | 0.19041 | 0.34660 |
| 931 | 0.06507 | 1.85621 | 0.90409 | 0.23192 |
| 932 | 0.04104 | 0.57935 | 1.04810 | 0.35714 |
| 933 | 0.00184 | 0.03846 | 0.01124 | 0.05454 |
| 934 | 0.01286 | 0.66949 | 0.54927 | 0.46510 |
| 935 | 0.06555 | 1.05501 | 0.39435 | 0.54228 |
| 936 | 0.07984 | 0.40300 | 0.33384 | 0.21472 |
| 937 | 0.08047 | 0.17360 | 0.07327 | 0.14361 |
| 938 | 0.08828 | 0.26278 | 0.11887 | 0.17477 |
| 939 | 0.00068 | 0.01809 | 0.00558 | 0.00720 |
| 940 | 0.00096 | 0.03131 | 0.02549 | 0.00891 |
| 941 | 0.00180 | 0.01057 | 0.00597 | 0.01467 |
| 942 | 0.00509 | 0.20044 | 0.09415 | 0.03047 |
| 943 | 0.00057 | 0.00822 | 0.01867 | 0.00292 |
| 944 | 0.22947 | 0.88643 | 2.43740 | 1.80946 |
| 945 | 0.00319 | 0.03501 | 0.02033 | 0.03248 |
| 946 | 0.00143 | 0.00965 | 0.01213 | 0.15558 |
| 947 | 0.00042 | 0.00129 | 0.00214 | 0.00563 |
| 948 | 0.00123 | 0.01362 | 0.00595 | 0.00732 |
| 949 | 0.04412 | 0.51510 | 4.10377 | 1.78787 |
| 950 | 0.25523 | 1.42380 | 4.10377 | 3.47258 |
| 951 | 0.14115 | 0.47998 | 4.10377 | 2.87808 |
| 952 | 0.14210 | 0.62773 | 4.10377 | 3.47258 |
| 953 | 0.04571 | 0.45473 | 3.47637 | 1.83212 |
| 954 | 0.03992 | 0.09760 | 0.34399 | 0.33818 |
| 955 | 0.00767 | 0.00890 | 0.10856 | 0.05362 |
| 956 | 0.05526 | 0.08976 | 0.41004 | 0.28169 |
| 957 | 0.05000 | 0.06023 | 0.21033 | 0.17392 |
| 958 | 0.00261 | 0.00513 | 0.03677 | 0.01429 |
| 959 | 0.00463 | 0.00630 | 0.08650 | 0.03802 |
| 960 | 0.03037 | 0.20754 | 0.23573 | 0.22445 |
| 961 | 0.04561 | 0.33274 | 0.31588 | 0.43765 |
| 962 | 0.03577 | 0.20819 | 0.17675 | 0.39926 |
| 963 | 0.04323 | 0.19042 | 0.11854 | 0.37345 |
| 964 | 0.07893 | 0.27426 | 0.16357 | 0.48711 |
| 965 | 0.03159 | 0.15980 | 0.10661 | 0.30601 |
| 966 | 0.03803 | 0.25648 | 0.19610 | 0.47833 |
| 967 | 0.13126 | 0.77630 | 0.48445 | 1.05657 |
| 968 | 0.13084 | 0.89127 | 0.36055 | 1.16546 |
| 969 | 0.17117 | 1.09071 | 0.51129 | 1.13611 |
| 970 | 0.03432 | 0.12372 | 0.20558 | 0.24522 |
| 971 | 0.11443 | 0.56362 | 0.35173 | 0.79872 |
| 972 | 0.02760 | 0.11327 | 0.08910 | 0.19390 |
| 973 | 0.02295 | 0.15192 | 0.12964 | 0.21537 |
| 974 | 0.02563 | 0.11004 | 0.07457 | 0.19449 |
| 975 | 0.04411 | 0.20617 | 0.21104 | 0.40637 |
| 976 | 0.03209 | 0.40508 | 0.20828 | 0.29931 |
| 977 | 0.02818 | 0.36293 | 0.19479 | 0.20968 |
| 978 | 0.01736 | 0.30461 | 0.12368 | 0.15748 |
| 979 | 0.01547 | 0.23831 | 0.12717 | 0.11332 |
| 980 | 0.07884 | 0.50612 | 0.29966 | 0.10866 |
| 981 | 0.06603 | 0.17673 | 0.16194 | 0.37640 |
| 982 | 0.03431 | 0.30690 | 0.15852 | 0.27264 |
| 983 | 0.03762 | 0.15677 | 0.10038 | 0.29954 |

TABLE 4-continued

| Example | JAK1 Ki, μM | JAK2 Ki, μM | JAK3 Ki, μM | TYK2 Ki, μM |
|---|---|---|---|---|
| 984 | 0.01769 | 0.29474 | 0.17322 | 0.25287 |
| 985 | 0.01964 | 0.36616 | 0.14609 | 0.17463 |
| 986 | 0.01754 | 0.31403 | 0.17089 | 0.18697 |
| 987 | 0.03973 | 0.20836 | 0.64258 | 0.26664 |
| 988 | 0.00419 | 0.00623 | 0.00933 | 0.02910 |
| 989 | 0.01090 | 0.01460 | 0.03941 | 0.04200 |
| 990 | 0.08456 | 0.20433 | 0.09192 | 0.32460 |
| 991 | 0.00926 | 0.01167 | 0.10944 | 0.05864 |
| 992 | 0.01780 | 0.03729 | 0.25331 | 0.10777 |
| 993 | 0.00167 | 0.00400 | 0.02407 | 0.00715 |
| 994 | 0.00291 | 0.00802 | 0.01701 | 0.02529 |
| 995 | 0.00641 | 0.01365 | 0.07410 | 0.03210 |
| 996 | 0.00201 | 0.00385 | 0.05076 | 0.00923 |
| 997 | 0.00559 | 0.03232 | 0.01695 | 0.05785 |
| 998 | 0.01393 | 0.04604 | 0.03892 | 0.10696 |
| 999 | 0.00455 | 0.02540 | 0.01093 | 0.04498 |
| 1000 | 0.00768 | 0.03904 | 0.02721 | 0.06377 |
| 1001 | 0.00115 | 0.01302 | 0.01672 | 0.00222 |
| 1002 | 0.00097 | 0.02214 | 0.11060 | 0.00476 |
| 1003 | 0.00516 | 0.06345 | 0.12915 | 0.03817 |
| 1004 | 0.00169 | 0.06297 | 0.04435 | 0.01701 |
| 1005 | 0.00236 | 0.08607 | 0.02626 | 0.01812 |
| 1006 | 0.00080 | 0.00449 | 0.01127 | 0.00352 |
| 1007 | 0.00825 | 0.01968 | 0.01854 | 0.01147 |
| 1008 | 0.00172 | 0.02395 | 0.09803 | 0.00793 |
| 1009 | 0.05949 | 0.11580 | 0.04398 | 0.07548 |
| 1010 | 0.00112 | 0.00166 | 0.00033 | 0.00220 |
| 1011 | 0.01796 | 0.13319 | 0.07928 | 0.08173 |
| 1012 | 0.00943 | 0.10275 | 0.07514 | 0.04522 |
| 1013 | 0.00215 | 0.01111 | 0.02891 | 0.01129 |
| 1014 | 0.00253 | 0.01858 | 0.00465 | 0.04552 |

Specific reference is made to U.S. Provisional Patent Application Ser. No. 61/294,404, filed Jan. 12, 2010, which is incorporated herein by reference in its entirety for all purposes. Specific reference is made to U.S. Provisional Patent Application Ser. No. 61/366,785, filed Jul. 22, 2010, which is incorporated herein by reference in its entirety for all purposes. Although the invention has been described and illustrated with a certain degree of particularity, it is understood that the present disclosure has been made only by way of example, and that numerous changes in the combination and arrangement of parts can be resorted to by those skilled in the art without departing from the spirit and scope of the invention, as defined by the claims.

What is claimed is:

1. A compound of formula I:

I

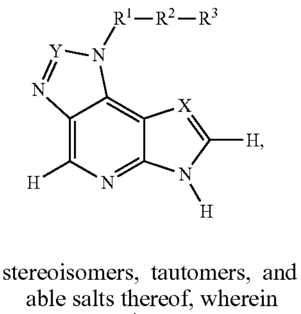

stereoisomers, tautomers, and pharmaceutically acceptable salts thereof, wherein X is N or $CR^4$;

Y is N or $CR^5$;

$R^1$ is 6-membered heterocyclyl, wherein $R^1$ is independently optionally substituted by halogen, oxo, —CN, —$OR^a$, —$SR^a$, —$NR^aR^b$, $C_{1-3}$ alkylene or $C_{1-6}$ alkyl optionally substituted by oxo, —CN or halogen;

$R^2$ is absent, $C_{1-6}$ alkyl, $C_{2-6}$ alkenyl, $C_{2-6}$ alkynyl, —($C_{1-6}$ alkylene)-, —($C_{2-6}$ alkenylene)-, —($C_{2-6}$ alkynylene)-, —($C_{0-6}$ alkylene)CN, —($C_{0-3}$ alkylene)$NR^a$($C_{0-3}$ alkylene)-, —($C_{0-3}$ alkylene)O($C_{0-3}$ alkylene)-, —($C_{0-3}$ alkylene)C(O)($C_{0-3}$ alkylene)-, —($C_{0-3}$ alkylene)$NR^a$C(O)($C_{0-3}$ alkylene)-, —($C_{0-3}$ alkylene)C(O)$NR^a$($C_{0-3}$ alkylene)-, —($C_{0-3}$ alkylene)C(O)O($C_{0-3}$ alkylene)-, —($C_{0-3}$ alkylene)OC(O)($C_{0-3}$ alkylene)-, —($C_{0-3}$ alkylene)$NR^a$C(O)$NR^b$($C_{0-3}$ alkylene)-, —($C_{0-3}$ alkylene)OC(O)$NR^a$($C_{0-3}$ alkylene)-, —($C_{0-3}$ alkylene)$NR^a$C(O)O($C_{0-3}$ alkylene)-, —($C_{0-3}$ alkylene)$S(O)_{1-2}$($C_{0-3}$ alkylene)-, —($C_{0-3}$ alkylene)$NR^aS(O)_{1-2}$($C_{0-3}$ alkylene)-, —($C_{0-3}$ alkylene)$S(O)_{1-2}NR^a$($C_{0-3}$ alkylene)- or —($C_{0-3}$ alkylene)$NR^aS(O)_{1-2}NR^b$($C_{0-3}$ alkylene)-, wherein said alkyl, alkyenyl, alkynyl, alkylene, alkenylene and alkynylene are independently optionally substituted by halogen, oxo, —CN, —$OR^c$, —$SR^c$, —$NR^cR^d$ or $C_{1-3}$ alkyl optionally substituted by halogen;

$R^3$ is absent, hydrogen, $C_{1-6}$ alkyl, $C_{2-6}$ alkenyl, $C_{2-6}$ alkynyl, $C_{3-7}$ cycloalkyl, $C_{6-14}$ aryl or 3-20 membered heterocyclyl, wherein $R^3$ is independently optionally substituted by $R^6$;

$R^4$ is hydrogen, halogen or $C_{1-3}$ alkyl;

$R^5$ is hydrogen, halogen, $C_{1-12}$ alkyl, $C_{2-12}$ alkenyl, $C_{2-12}$ alkynyl, —($C_{0-3}$ alkylene)CN, —($C_{0-3}$ alkylene)$NR^aR^b$, —($C_{0-3}$ alkylene)$OR^a$, —($C_{0-3}$ alkylene)$SR^a$, —($C_{0-3}$ alkylene)C(O)$R^a$, —($C_{0-3}$ alkylene)$NR^a$C(O)$R^b$, —($C_{0-3}$ alkylene)C(O)$NR^aR^b$, —($C_{0-3}$ alkylene)C(O)$OR^a$, —($C_{0-3}$ alkylene)OC(O)$R^a$, —($C_{0-3}$ alkylene)N-$R^a$C(O)$NR^aR^b$, —($C_{0-3}$ alkylene)OC(O)$NR^aR^b$, —($C_{0-3}$ alkylene)$NR^a$C(O)$OR^b$, —($C_{0-3}$ alkylene)$S(O)_{1-2}R^a$, —($C_{0-3}$ alkylene)$NR^aS(O)_{1-2}R^b$, —($C_{0-3}$ alkylene)$S(O)_{1-2}NR^aR^b$, —($C_{0-3}$ alkylene)$NR^aS(O)_{1-2}NR^aR^b$, —($C_{0-3}$ alkyl ene)$C_{3-12}$ cycloalkyl, —($C_{0-3}$ alkylene)$C_{6-14}$ aryl, —($C_{0-3}$ alkylene)3-12 membered heterocyclyl or —($C_{0-3}$ alkylene)C(O)3-12 membered heterocyclyl, wherein said alkyl, alkenyl, alkynyl, alkylene, cycloalkyl, aryl and heterocyclyl are independently optionally substituted by halogen, oxo, —($C_{0-3}$ alkylene)CN, —($C_{0-3}$ alkylene)$OR^c$, —($C_{0-3}$ alkylene)$NR^cR^d$, —($C_{0-3}$ alkylene)C(O)$R^c$, —($C_{0-3}$ alkylene)C(O)$OR^c$, —($C_{0-3}$ alkylene)C(O)$NR^cR^d$, —($C_{0-3}$ alkylene)$NR^c$C(O)$R^d$, —($C_{0-3}$ alkylene)OC(O)$NR^cR^d$, —($C_{0-3}$ alkylene)$NR^c$C(O)$NR^cR^d$, —($C_{0-3}$ alkylene)N-$R^c$C(O)$OR^d$, —($C_{0-3}$ alkylene)$S(O)_{0-2}R^c$, —($C_{0-3}$ alkylene)$NR^cS(O)_{1-2}R^d$, —($C_{0-3}$ alkylene)$S(O)_{1-2}NR^cR^d$, —($C_{0-3}$ alkylene)$NR^cS(O)_{1-2}NR^cR^d$ or $C_{1-6}$ alkyl optionally substituted by oxo, —CN or halogen, wherein $R^5$ is other than —OH;

$R^6$ is independently oxo, halogen, —CN, —C(O)$R^a$, —C(O)$OR^a$, —$NR^a$C(O)$R^b$, —C(O)$NR^aR^b$, —$NR^a$C(O)$NR^aR^b$, —OC(O)$NR^aR^b$, —$NR^a$C(O)$OR^b$, —$S(O)_{1-2}R^a$, —$NR^aS(O)_2R^a$, —$S(O)_2NR^aR^b$, —$OR^a$, —$SR^a$, —$NR^aR^b$, $C_{1-6}$ alkyl, $C_{3-6}$ cycloalkyl, $C_{2-6}$ alkenyl, $C_{2-6}$ alkynyl, 3-7 membered heterocycyl or $C_{6-14}$ aryl, and wherein said alkyl, alkenyl, alkynyl, cycloalkyl, heterocyclyl and aryl are independently optionally substituted by halogen, oxo, —CN, —$OR^c$, —$SR^c$, —$NR^cR^d$ or $C_{1-6}$ alkyl optionally substituted by oxo or halogen;

each $R^a$ and $R^b$ are independently hydrogen, $C_{1-6}$ alkyl, $C_{2-6}$ alkenyl, $C_{2-6}$ alkynyl, —($C_{0-3}$ alkylene)$C_{3-6}$ cycloalkyl, —($C_{0-3}$ alkylene)3-12 membered heterocyclyl, —($C_{0-3}$ alkylene)C(O)3-12 membered heterocyclyl or —($C_{0-3}$ alkylene)$C_{6-14}$ aryl, wherein said alkyl, cycloalkyl, heterocyclyl and aryl are independently optionally substituted by halogen, oxo, —CN, —$OR^e$, —$NR^eR^f$, —$C(O)R^g$, —$C(O)OR^g$, —$C(O)NR^gR^h$, —$NR^gC(O)R^h$, —$OC(O)NR^gR^h$, —$NR^gC(O)NR^gR^h$, —$NR^gC(O)OR^h$, —$S(O)_{1-2}R^g$, —$NR^gS(O)_{1-2}R^h$, —$S(O)_{1-2}NR^gR^h$, —$NR^gS(O)_{1-2}NR^gR^h$, $C_{3-6}$ cycloalkyl, 3-6 membered heterocyclyl, phenyl or $C_{1-3}$ alkyl optionally substituted by oxo or halogen, or taken together with the atom to which they are attached to form a 3-6 membered heterocyclyl optionally substituted by oxo, halogen, —$C(O)C_{1-6}$ alkyl or $C_{1-6}$ alkyl optionally substituted by oxo, halogen, $OR^g$ or $NR^gNR^h$;

each $R^c$ and $R^d$ are independently hydrogen, $C_{1-6}$ alkyl, $C_{2-6}$ alkenyl, $C_{2-6}$ alkynyl, —($C_{0-3}$ alkylene)$C_{3-6}$ cycloalkyl, —($C_{0-3}$ alkylene)3-12 membered heterocyclyl, —($C_{0-3}$ alkylene)C(O)3-12 membered heterocyclyl or —($C_{0-3}$ alkylene)$C_{6-14}$ aryl, wherein said alkyl, alkenyl, alkynyl, cycloalkyl, heterocyclyl and aryl are independently optionally substituted by halogen, oxo, —CN, —$OR^g$, —$NR^gR^h$, —$C(O)R^g$, —$C(O)OR^g$, —$C(O)NR^gR^h$, —$NR^gC(O)R^h$, —$OC(O)NR^gR^h$, —$NR^gC(O)NR^gR^h$, —$NR^gC(O)OR^h$, —$S(O)_{1-2}R^g$, —$NR^gS(O)_{1-2}R^h$, —$S(O)_{1-2}NR^gR^h$, —$NR^gS(O)_{1-2}NR^gR^h$, $C_{3-6}$ cycloalkyl, 3-6 membered heterocyclyl, phenyl or $C_{1-6}$ alkyl optionally substituted by oxo or halogen, or taken together with the atom to which they are attached to form a 3-6 membered heterocyclyl optionally substituted by oxo, halogen, —$C(O)C_{1-6}$ alkyl or $C_{1-6}$ alkyl optionally substituted by oxo or halogen; and each $R^e$, $R^f$, $R^g$, $R^h$ are independently hydrogen or $C_{1-6}$ alkyl optionally substituted by halogen or oxo.

2. The compound of claim 1, wherein X is $CR^4$ and Y is $CR^5$.

3. The compound of claim 2, wherein $R^1$ is selected from:

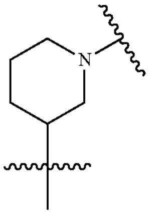
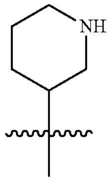
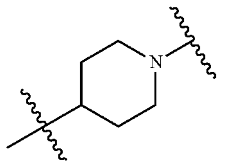
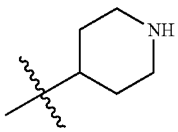
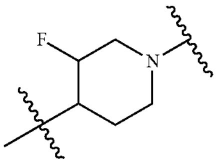
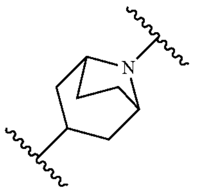
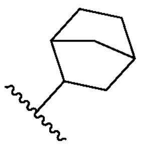
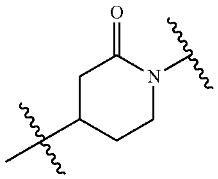
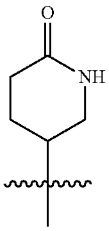

-continued

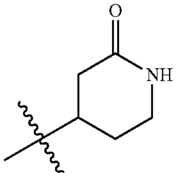
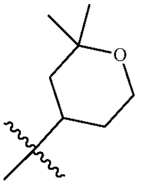
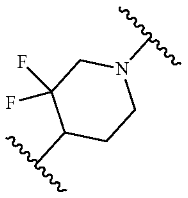
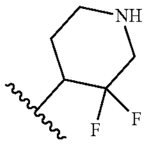
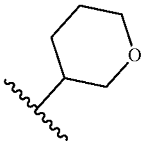
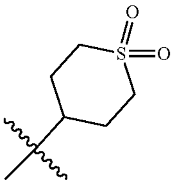
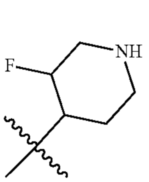
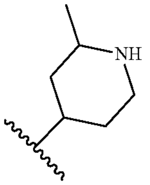
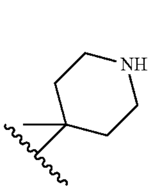
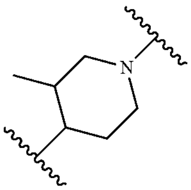
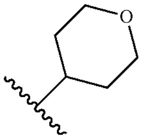
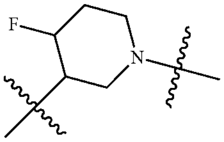
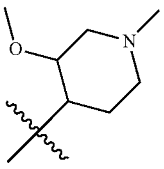
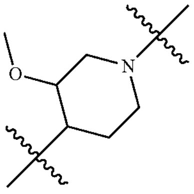
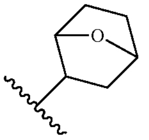
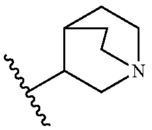
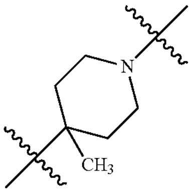
.

4. The compound of claim 1, wherein $R^1$ is 6 membered heterocyclyl, wherein $R^1$ is independently optionally substituted by halogen, oxo, —CN, —$OR^a$, —$SR^a$, —$NR^aR^b$, $C_{1-3}$ alkylene or $C_{1-6}$ alkyl optionally substituted by oxo, —CN or halogen; and $R^2$ is absent, $—NHS(O)_2—$, $—N(CH_3)S(O)_2—$, $—NHS(O)_2CH_2—$, $—C(O)CH_2S(O)_2$, —C(O)O—, —NHC(O)O—, $—N(CH_3)C(O)O—$, $—NHC(O)OCH_2—$, $—NHC(O)OCH_2CH_2—$, —C(O)NH—, $—CH_2C(O)NH—$, $—CH_2C(O)N(CH_3)—$, —NHC(O)—, $—NHC(O)CH_2—$, $—CH_2O—$, $—CH_2C(CH_2)_2O—$, $—(CH_2)_2O—$, —NH—, $—NHCH_2—$, $—NHCH_2CH_2—$, $—CH_2CN$, $—CH_2CH_2CN$, $—CH(CH_3)CN$, $—CH(CH_3)CH_2CN$, methylene, ethylene, $—C(CH_3)_2—$, $—CH_2CF_3$, $—CH_2CH_2CF_3$, $—CH_2CH_2F$, $—CH_2C(CH_3)_2OH$, $—CH_2CH_2OH$, $—CH_2CH_2OCH_3$,

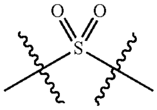 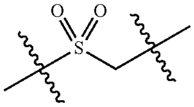

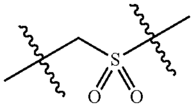 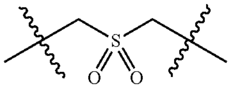

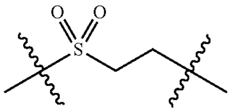 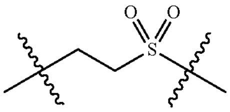

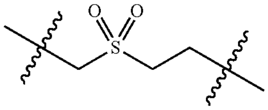

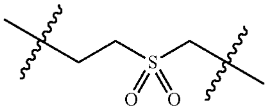

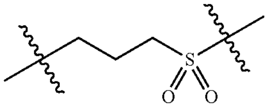

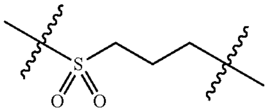 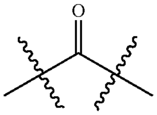

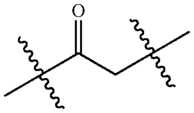 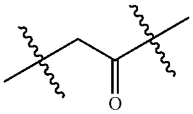

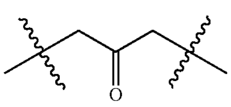 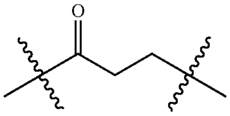

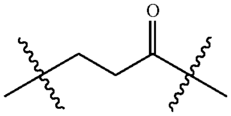 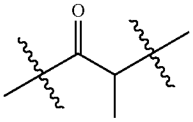

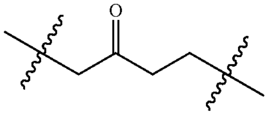

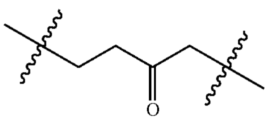

-continued

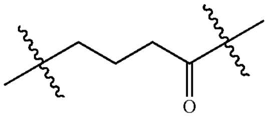

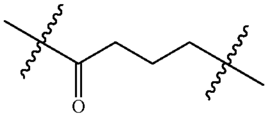 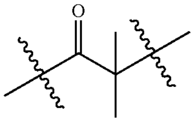

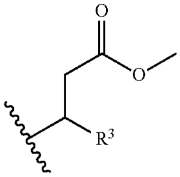 or 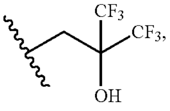

wherein the wavy line represents the point of attachment in formula I.

5. The compound of claim 1, wherein $R^2$ is absent, $—NHS(O)_2—$, $—N(CH_3)S(O)_2—$, $—NHS(O)_2CH_2—$, $—C(O)CH_2S(O)_2$, —C(O)O—, —NHC(O)O—, $—N(CH_3)C(O)O—$, $—NHC(O)OCH_2—$, $—NHC(O)OCH_2CH_2—$, —C(O)NH—, $—CH_2C(O)NH—$, $—CH_2C(O)N(CH_3)—$, —NHC(O)—, $—NHC(O)CH_2—$, $—CH_2O—$, $—CH_2C(CH_2)_2O—$, $—(CH_2)_2O—$, —NH—, $—NHCH_2—$, $—NHCH_2CH_2—$, $—CH_2CN$, $—CH_2CH_2CN$, $—CH(CH_3)CN$, $—CH(CH_3)CH_2CN$, methylene, ethylene, $—C(CH_3)_2—$, $—CH_2CF_3$, $—CH_2CH_2CF_3$, $—CH_2CH_2F$, $—CH_2C(CH_3)_2OH$, $—CH_2CH_2OH$, $—CH_2CH_2OCH_3$,

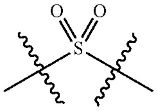 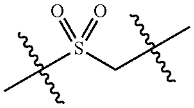

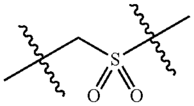 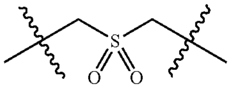

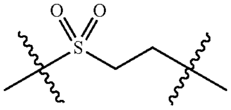 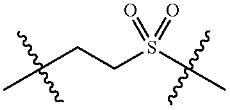

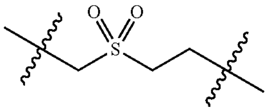

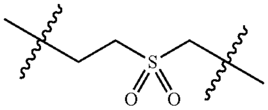

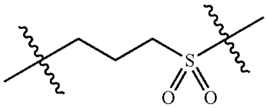

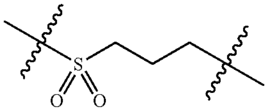 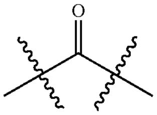

-continued

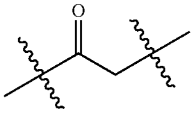 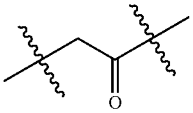

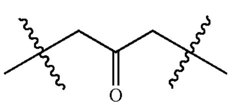 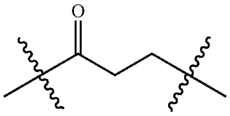

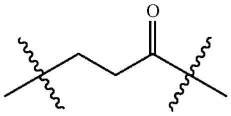 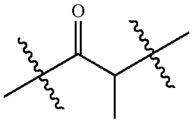

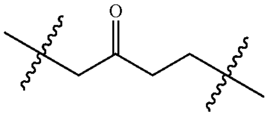

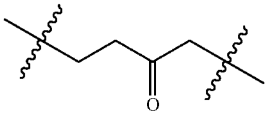

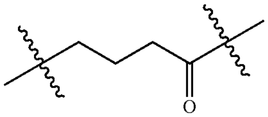

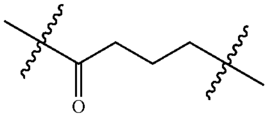 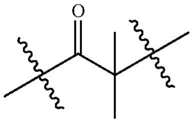

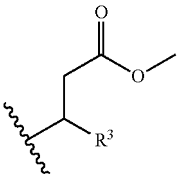 or 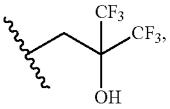

wherein the wavy line represents the point of attachment in formula I.

6. The compound of claim 1, wherein $R^1$ is 6 membered heterocyclyl, wherein $R^1$ is independently optionally substituted by halogen, oxo, —CN, —$OR^a$, —$SR^a$, —$NR^aR^b$, $C_{1-3}$ alkylene or $C_{1-6}$ alkyl optionally substituted by oxo, —CN or halogen; $R^2$ is absent, —$NHS(O)_2$—, —$N(CH_3)S(O)_2$—, —$NHS(O)_2CH_2$—, —$C(O)CH_2S(O)_2$, —C(O)O—, —NHC(O)O—, —$N(CH_3)C(O)O$—, —$NHC(O)OCH_2$—, —$NHC(O)OCH_2CH_2$—, —C(O)NH—, —$CH_2C(O)NH$—, —$CH_2C(O)N(CH_3)$—, —NHC(O)—, —$NHC(O)CH_2$—, —$CH_2O$—, —$CH_2C(CH_2)_2O$—, —$(CH_2)_2O$—, —NH—, —$NHCH_2$—, —$NHCH_2CH_2$—, —$CH_2CN$, —$CH_2CH_2CN$, —$CH(CH_3)CN$, —$CH(CH_3)CH_2CN$, methylene, ethylene, —$C(CH_3)_2$—, —$CH_2CF_3$, —$CH_2CH_2CF_3$, —$CH_2CH_2F$, —$CH_2C(CH_3)_2OH$, —$CH_2CH_2OH$, —$CH_2CH_2OCH_3$,

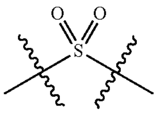 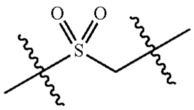

-continued

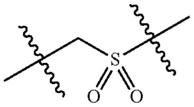 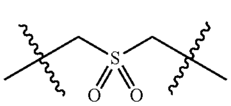

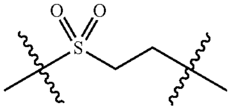 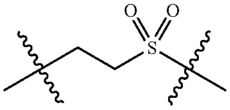

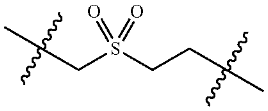

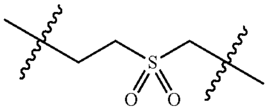

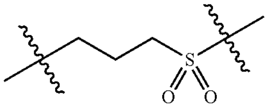

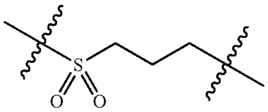 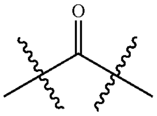

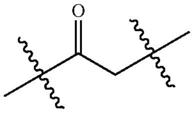 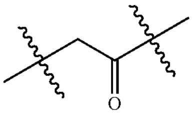

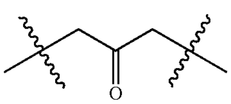 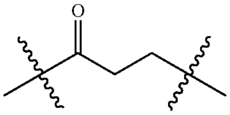

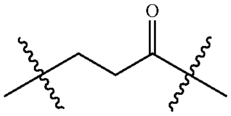 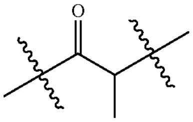

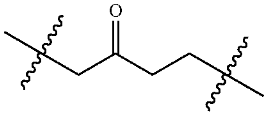

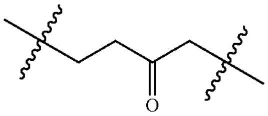

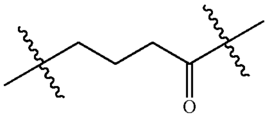

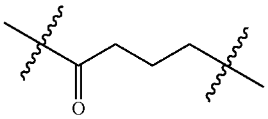 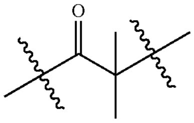

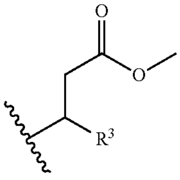 or 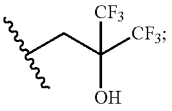

and $R^3$ is absent, hydrogen, $C_{1-6}$ alkyl, $C_{3-7}$ cycloalkyl, $C_{6-14}$ aryl or 3-12 membered heterocyclyl, wherein $R^3$ is optionally substituted by 1 to 3 $R^6$.

7. The compound of claim 1, wherein $R^3$ is absent, hydrogen, $C_{1-6}$ alkyl, $C_{3-7}$ cycloalkyl, $C_{6-14}$ aryl or 3-12 membered heterocyclyl, wherein $R^3$ is optionally substituted by 1 to 3 $R^6$.

8. The compound of claim 7, wherein $R^3$ is absent, hydrogen, methyl, ethyl, n-butyl, sec-butyl, t-butyl, $—CF_3$, $—CH_2CF_3$, $—CH_2CH_2F$, $—CH_2CH_2CF_3$, $—CH_2OCH_3$, $—CH_2CH_2OCH_3$, $—CH(CH_2CH_3)CH_2OCH_3$, $—CH(CH_3)CH_2CH_2OH$, $—CH_2C(CH_3)_2OH$, $—CH_2C(CF_3)_2OH$, $—CH_2CH_2OH$, $—C(CH_3)_2OH$, $—CH_2CN$, $—(CH_2)_2CN$, $—(CH_2)_3CN$, $—CH(CH_3)CH_2CN$, $—C(CH_3)_2CN$, $—CH(CH_3)CN$, $—CH_2NH_2$, $—CH(CH_3)N(CH_3)_2$, $—CH_2CH_2N(CH_3)_2$, cyclopropyl, 1-cyanocycloprop-1-yl, 1-trifluoromethylcycloprop-1-yl, 1-methylcycloprop-1-yl, 2-fluorocyclopyrop-1-yl, 2,2-dimethylcycloprop-1-yl, 2-cyanocyclopropyl, cyclobutyl, 4-carboxyclobutyl, 1-cyanocyclobut-1-yl, 4-aminocyclobutyl, cyclopentyl, 3-aminocyclohexyl, 4-aminocyclohexyl, 2-hydroxycyclohexyl, 3-hydroxycyclohexyl, 4-hydroxycyclohexyl, 2-hydroxycyclohexyl, 4-cyanocyclohexyl, phenyl, 2-chloro-4-cyanophenyl, 2-cyanophenyl, 3-cyanophenyl, 4-cyanophenyl, 3-methylsulfonylphenyl, 3-fluorophenyl, 4-methoxyphenyl, pyridinyl, pyridin-3-yl, 6-cyanopyridinyl, 6-trifluoromethylpyridinyl, 2-cyanopyridin-4-yl, 4-cyanopyridin-2-yl, 5-cyanopyridin-2-yl, 3-fluoropyridin-5-yl, thiazol-5-yl, pyrimidin-2-yl, pyrimidin-4-yl, pyrimidin-5-yl, pyrazin-2-yl, oxazol-2-yl, oxazol-4-yl, 1-methylpyrazol-5-yl, 1-methylpyrazol-4-yl, 1-methylimidazol-2-yl

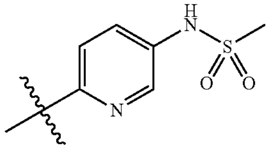
,
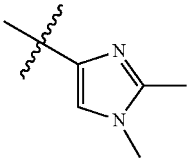
,

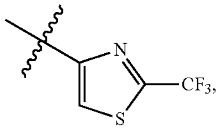
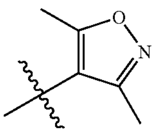
,

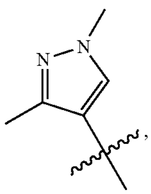
,
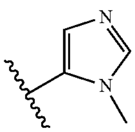
, oxetan-3-yl, piperidin-3-yl, piperidin-4-yl, N-methylpiperidin-2-yl, N-methylmorpholin-2-yl, 1-methylpyrrolidin-2-yl, pyrrolidinyl, pyrrolidinonyl, piperidinonyl, 3,3-difluoropyrrolidin-2-yl, 1-isopropylpyrrolidin-2-yl, 2-methylpyrrolidin-2-yl, 1-methylcyanopyrrolidin-2-yl, 1-cyclobutylpyrrolidin-2-yl, morpholinyl, pyran-4-yl, N-methylpiperazinyl, thiazol-5-yl, isothiazol-5-yl, N-ethylpiperidin-2-yl, N-(2-methoxyethyl)piperidin-2-yl, N-methylazepan-2-yl,

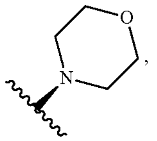
,
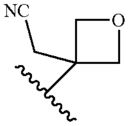
,

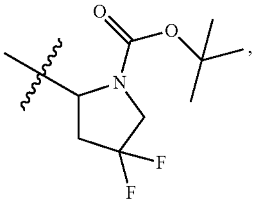
,
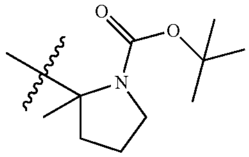
,

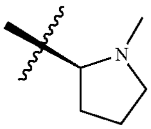
,
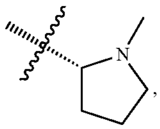
,

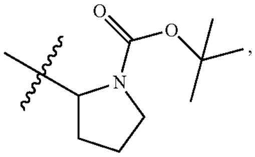
,

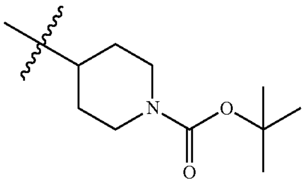
,

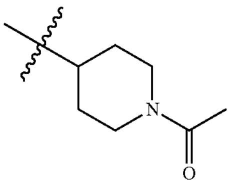
,
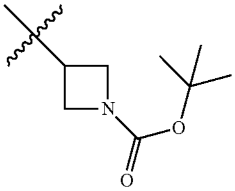
,

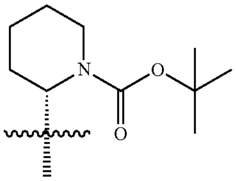
,
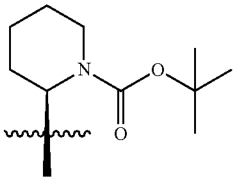
or

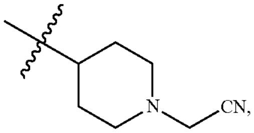

wherein the wavy line represents the point of attachment in formula I.

9. The compound of claim 1, wherein $—R^1$-$R^2$-$R^3$ taken together are:

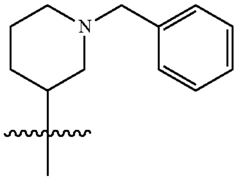
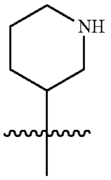

-continued
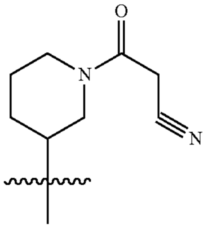
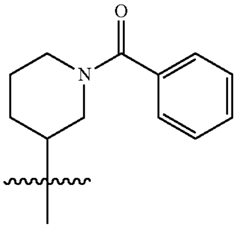
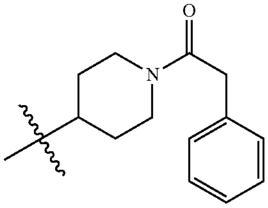
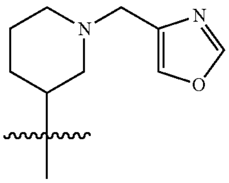
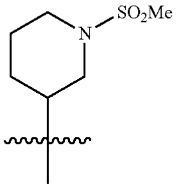
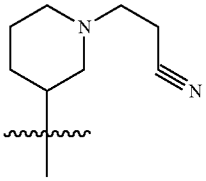
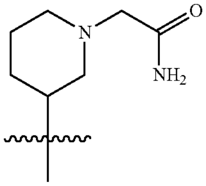
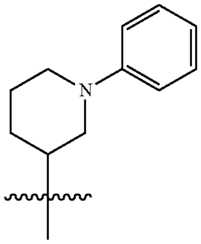
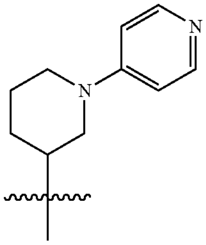
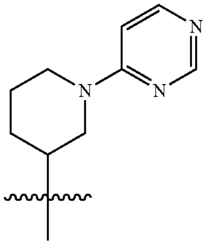
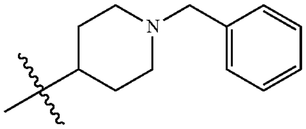
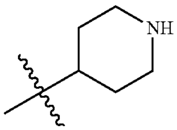
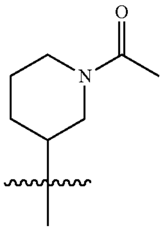
-continued
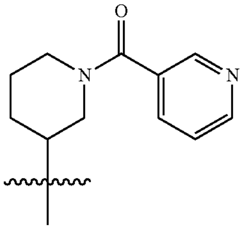
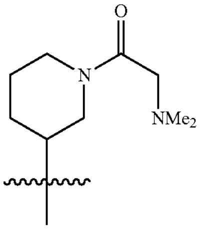
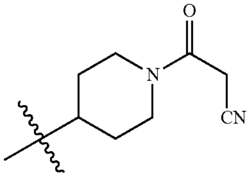
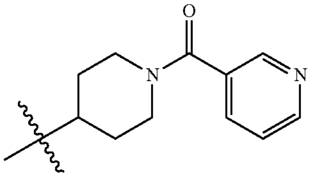
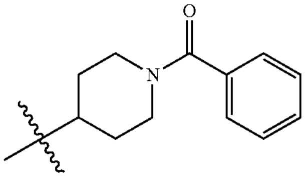
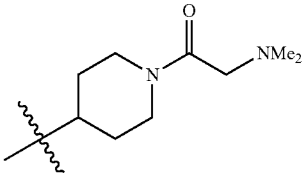
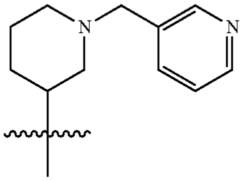
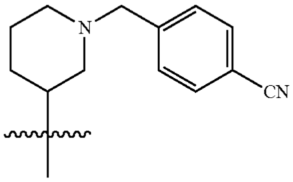
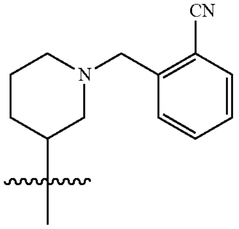
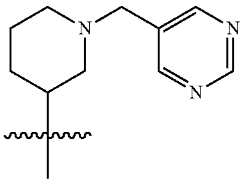

-continued
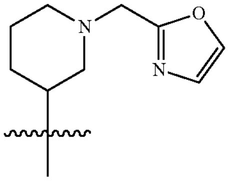
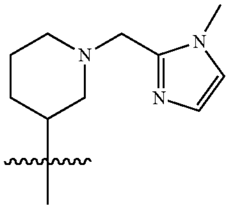
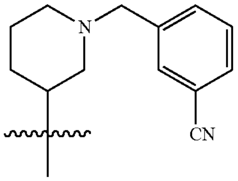
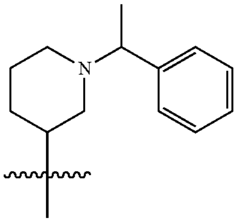
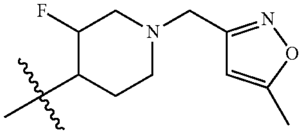
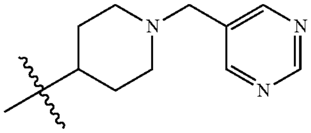
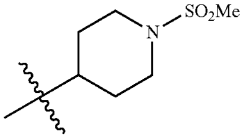
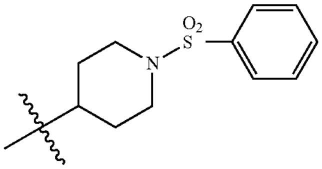
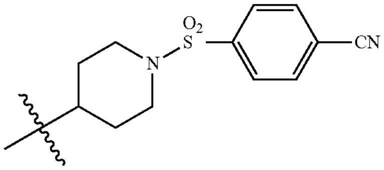
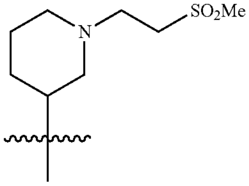
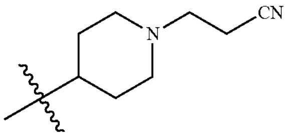
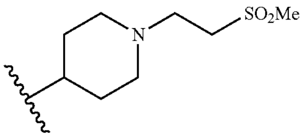
-continued
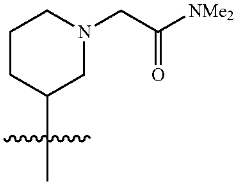
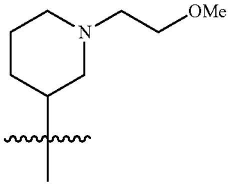
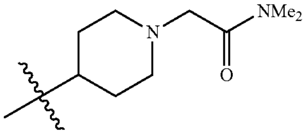
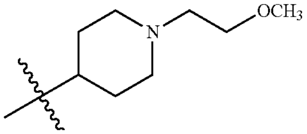
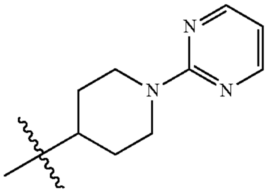
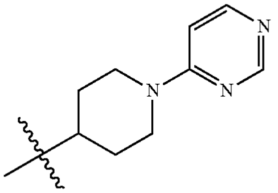
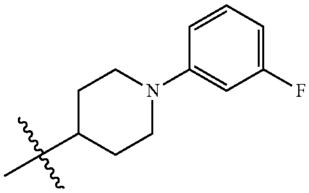
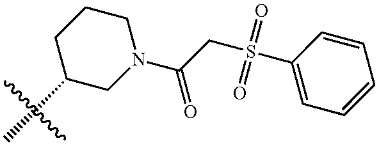
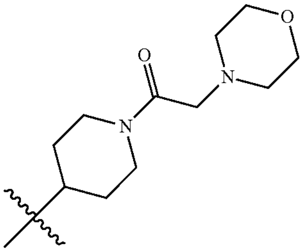
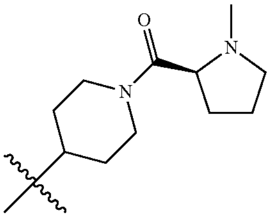

-continued
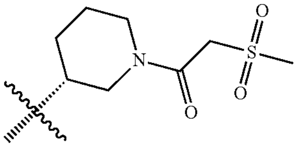
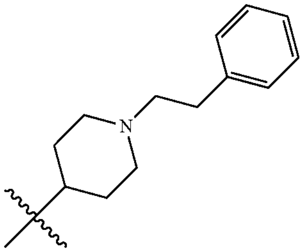
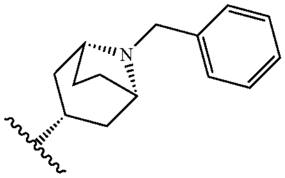
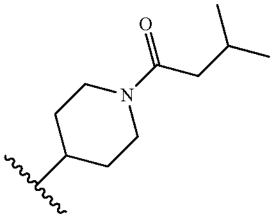
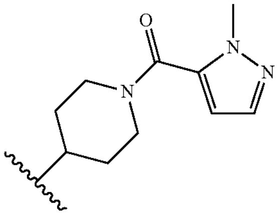
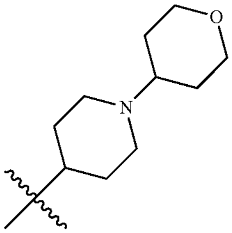
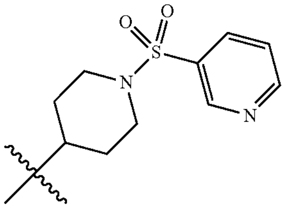
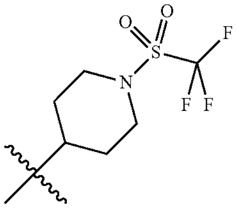
-continued
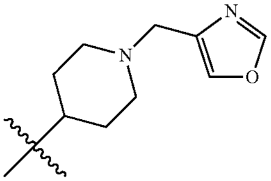
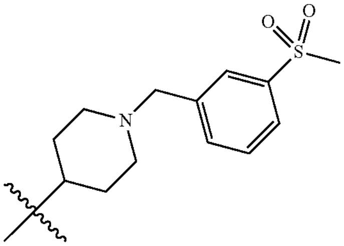
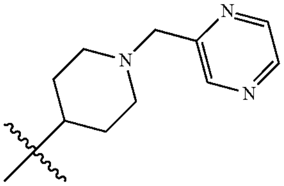
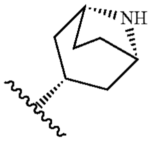
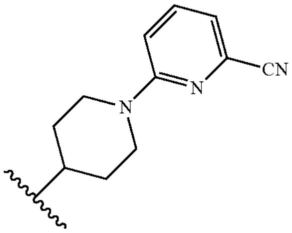
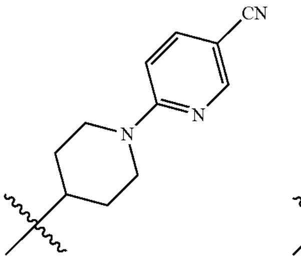
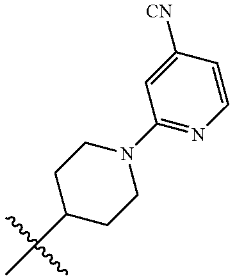
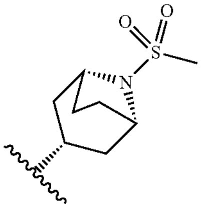
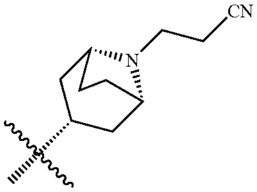
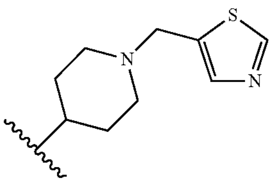
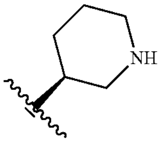

-continued
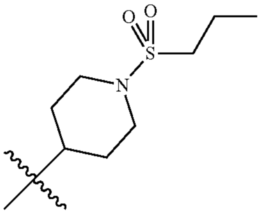
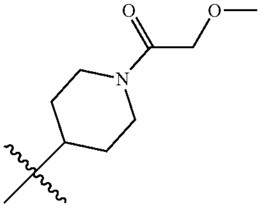
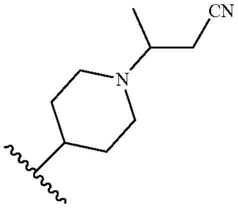
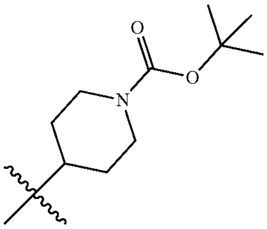
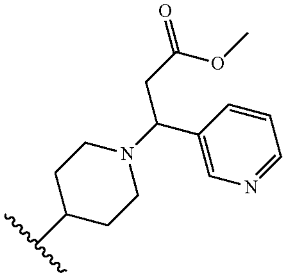
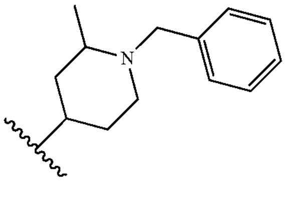
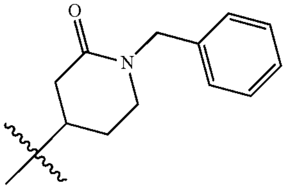
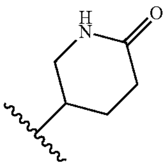
-continued
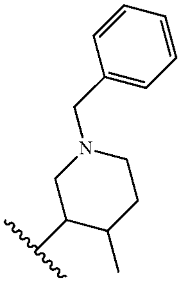
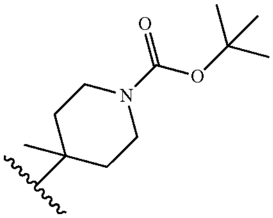
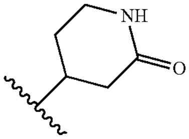
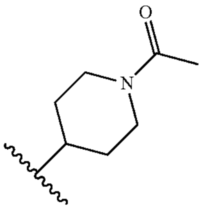
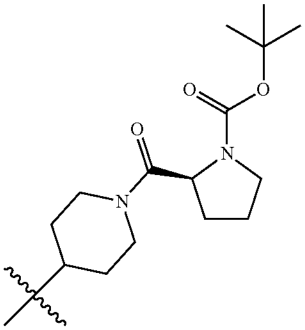
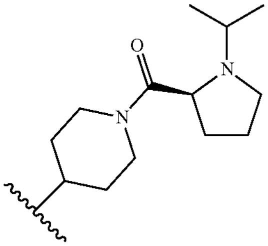
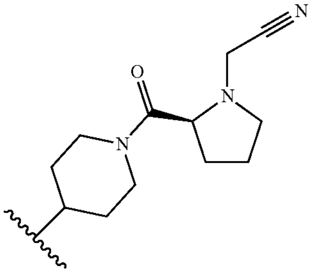

-continued
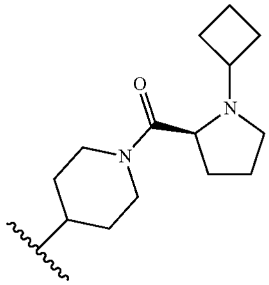
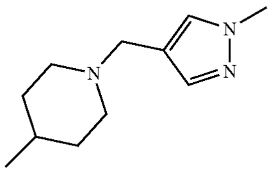
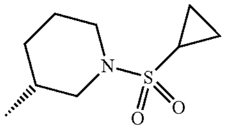
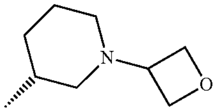
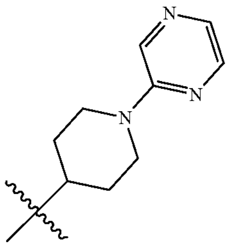
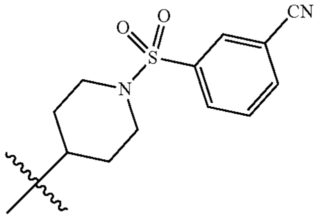
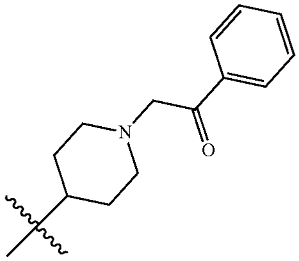
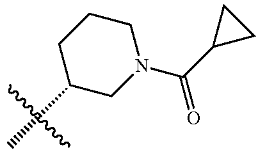
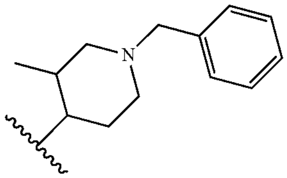
-continued
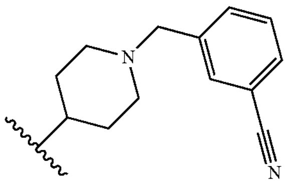
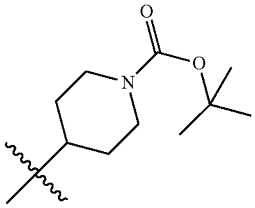
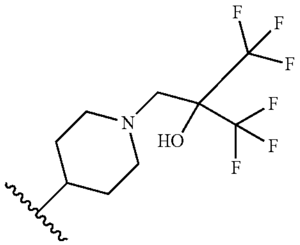
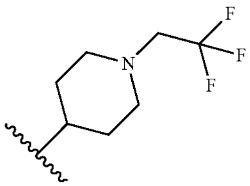
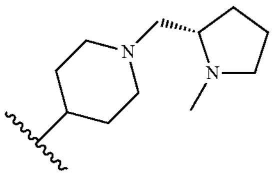
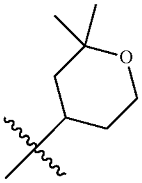
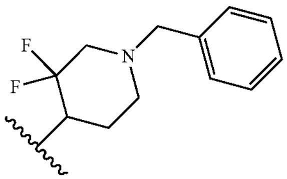
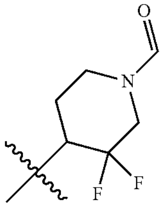
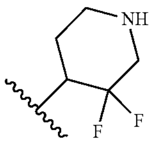
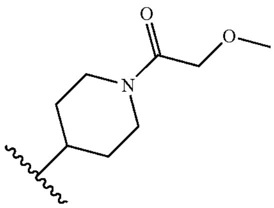 [SMILES: *C1CCN(C(=O)COC)CC1]

-continued
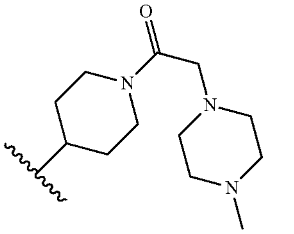
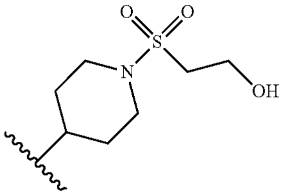
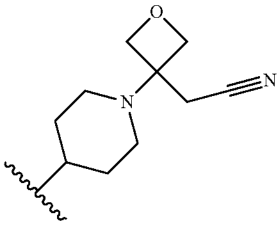
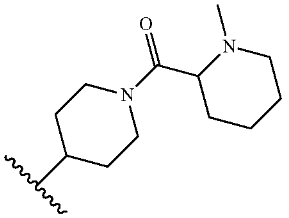
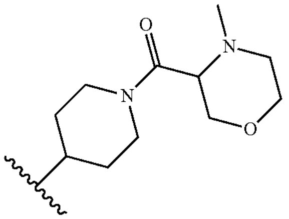
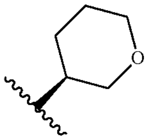
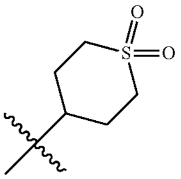
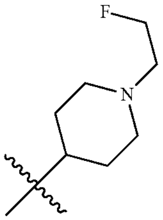
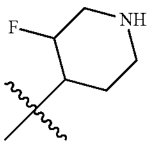
-continued
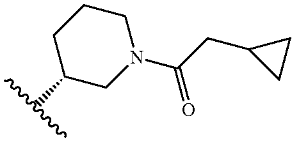
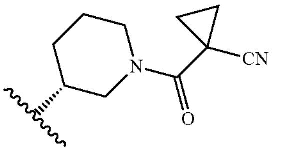
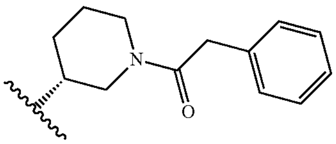
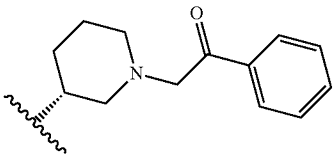
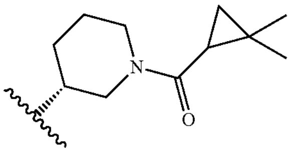
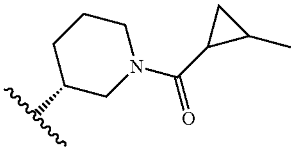
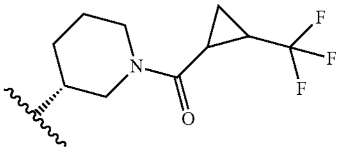
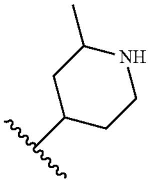
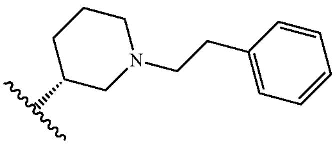
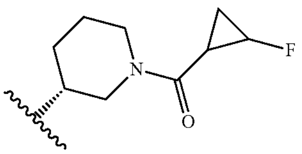
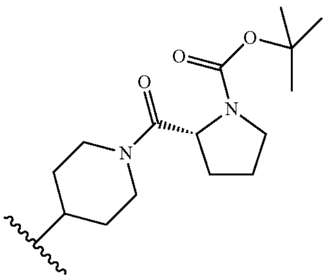

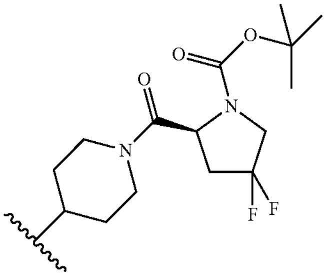
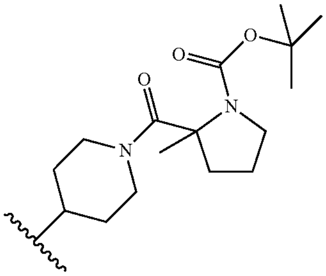
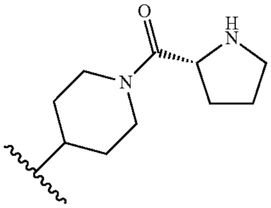
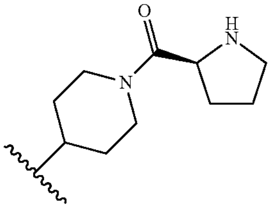
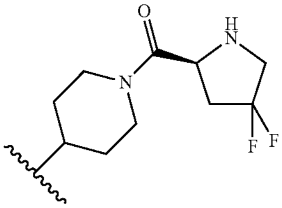
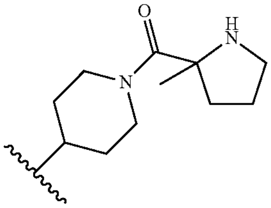
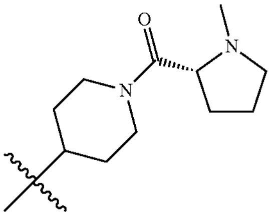
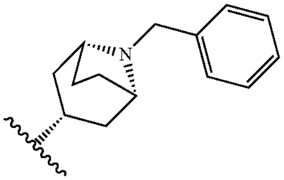
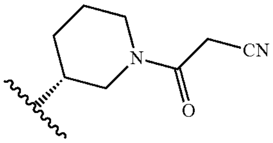
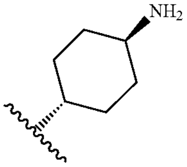
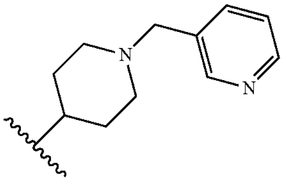
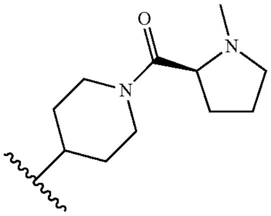
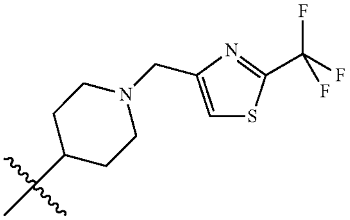
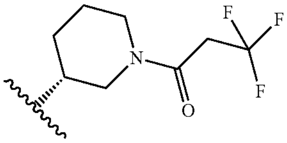
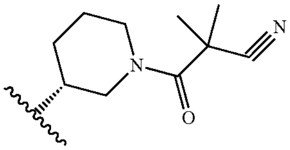
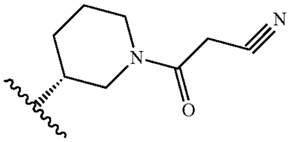
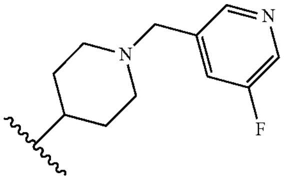

-continued
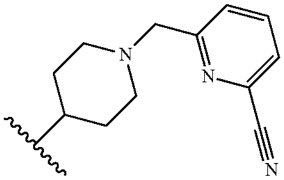
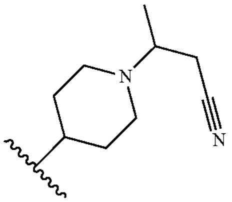
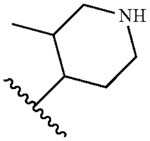
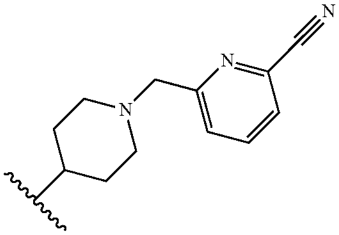
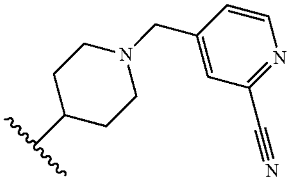
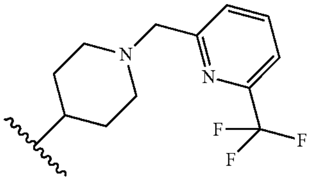
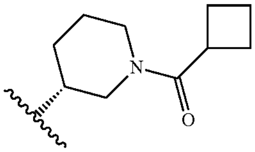
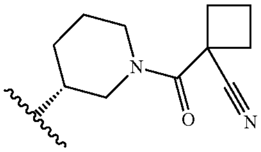
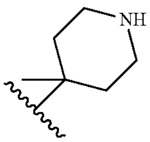
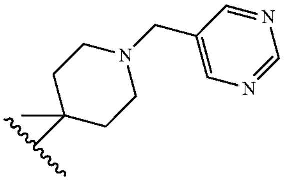
-continued
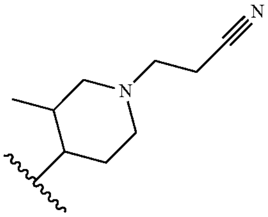
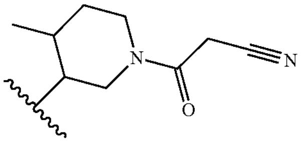
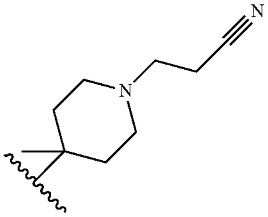
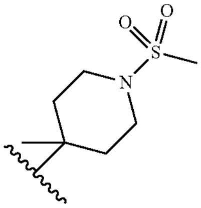
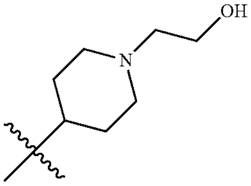
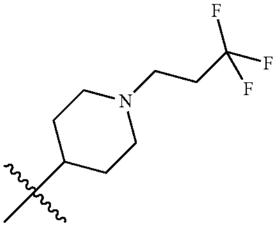
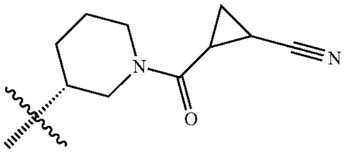
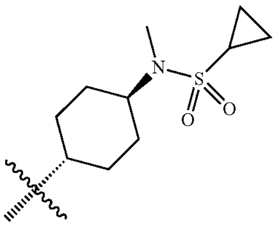

-continued
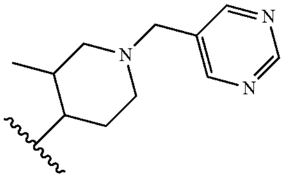
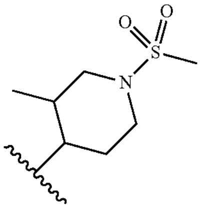
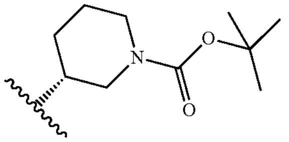
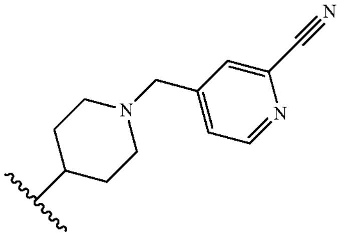
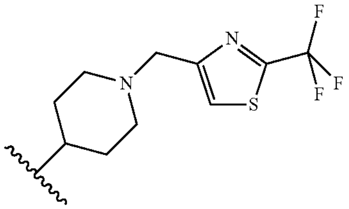
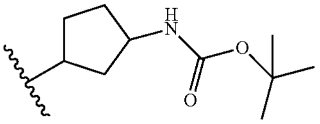
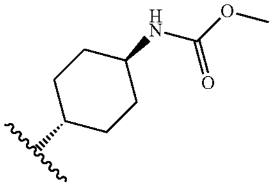
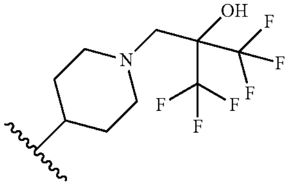
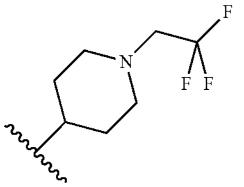
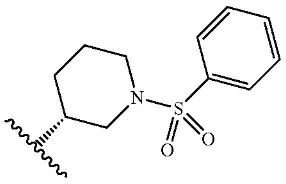
-continued
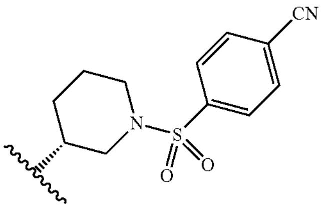
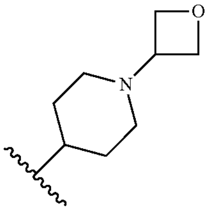
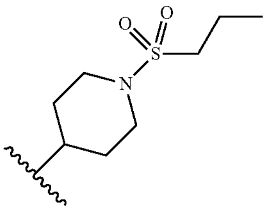
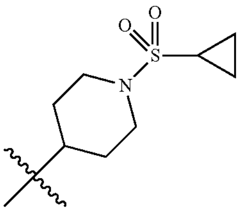
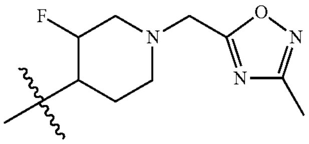
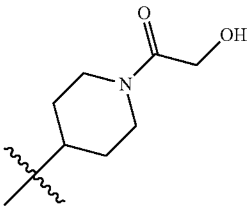
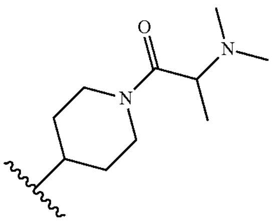
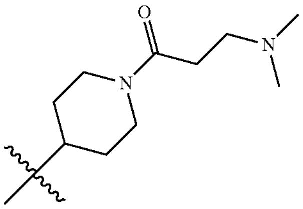

-continued
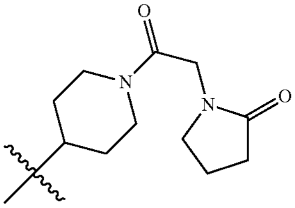
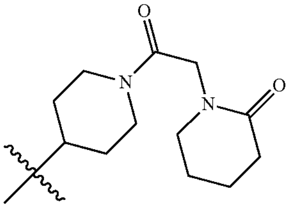
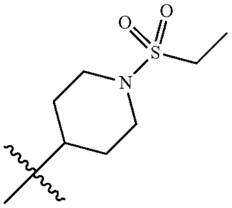
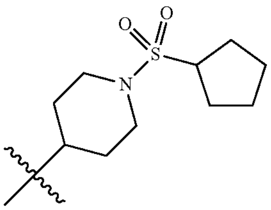
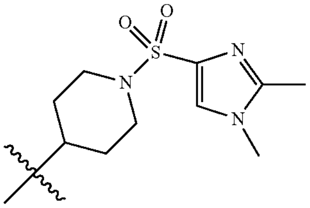
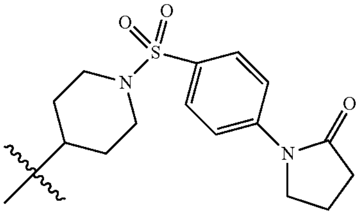
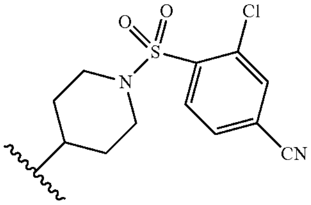
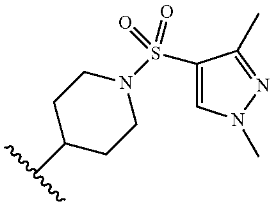
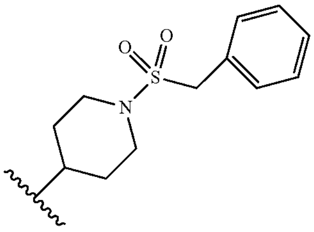
-continued
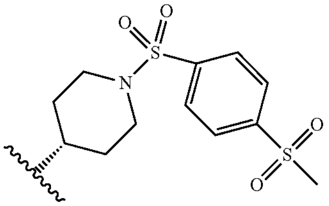
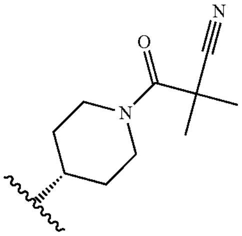
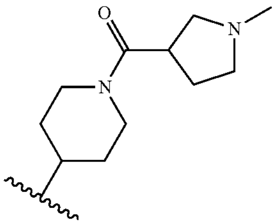
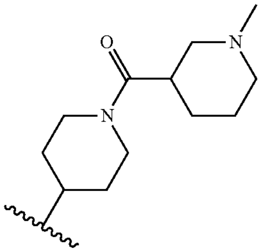
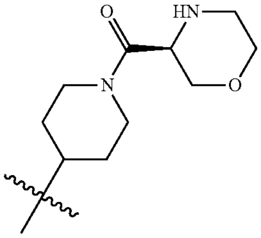
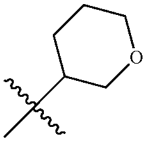
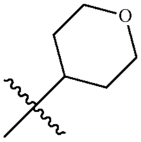
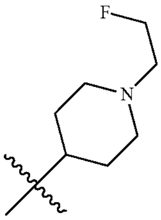
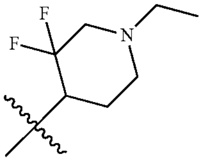

-continued
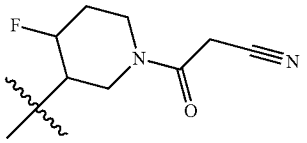
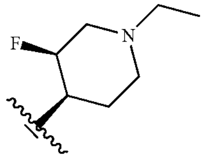
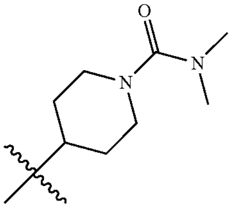
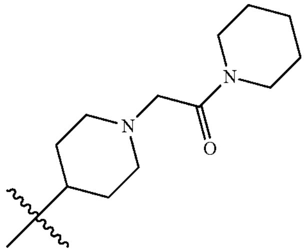
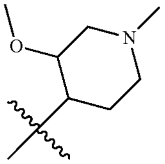
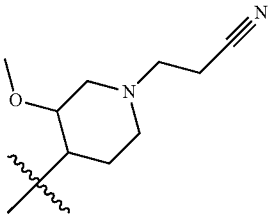
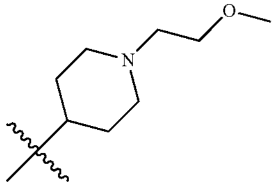
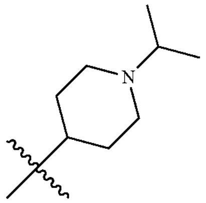
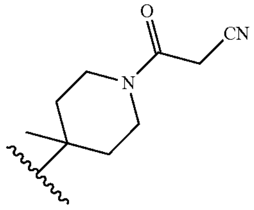
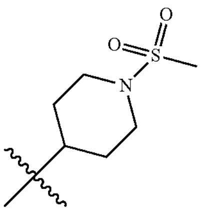
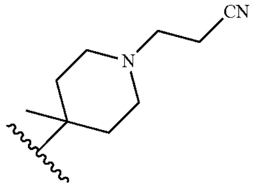
-continued
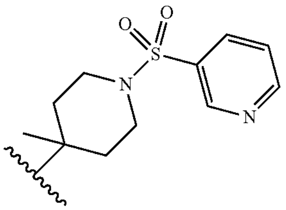
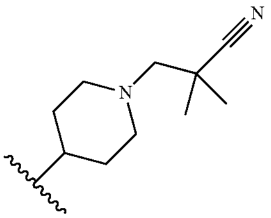
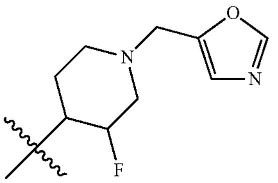 [SMILES: *C1CCN(Cc2cnco2)CC1F]
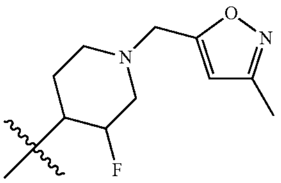 [SMILES: *C1CCN(Cc2cc(C)no2)CC1F]
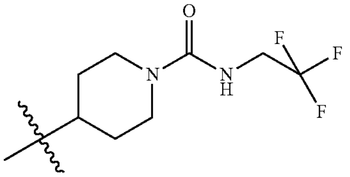 [SMILES: *C1CCN(C(=O)NCC(F)(F)F)CC1]
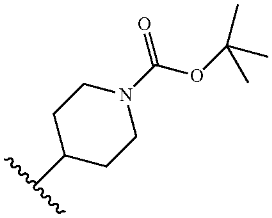 [SMILES: *C1CCN(C(=O)OC(C)(C)C)CC1]
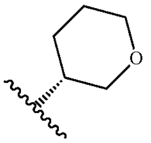
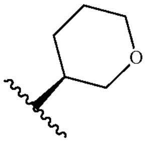
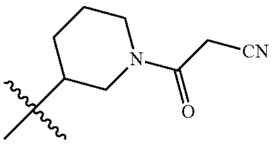
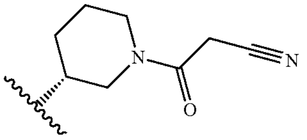

-continued
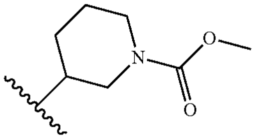
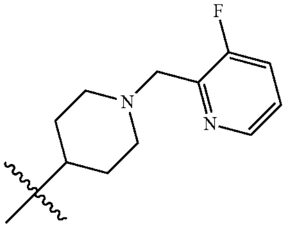
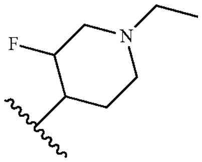
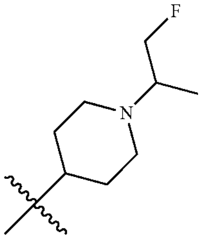
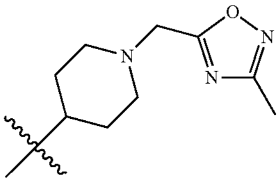
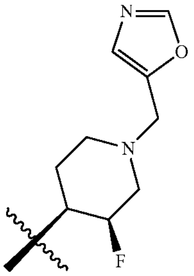
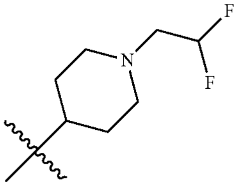
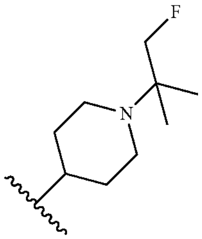
-continued
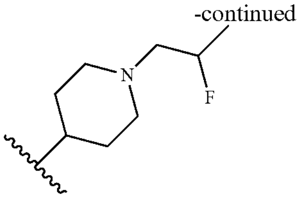
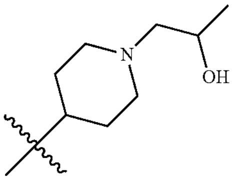
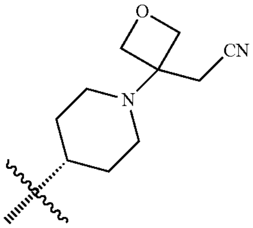
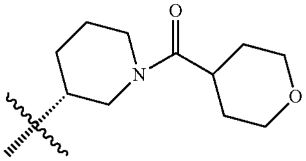
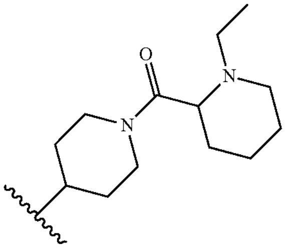
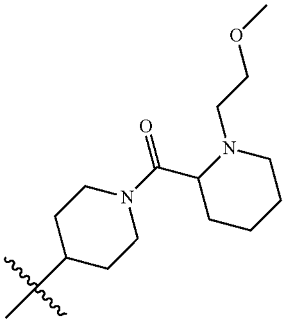
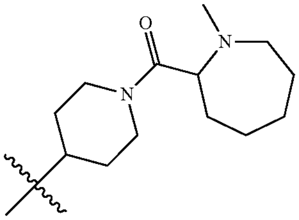
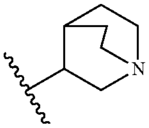
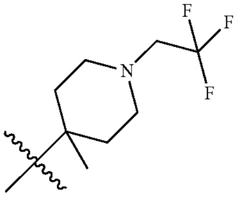

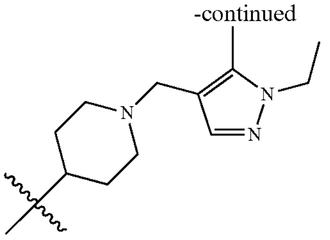
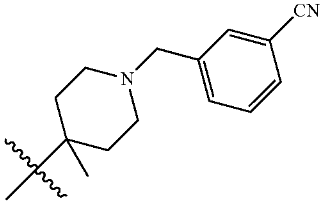
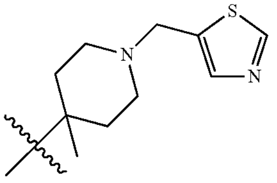
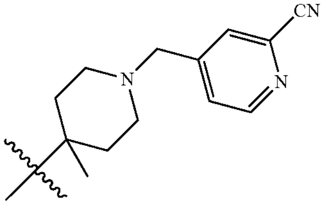
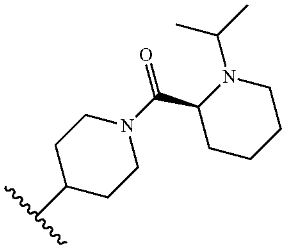
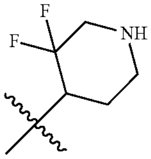
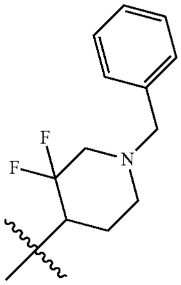
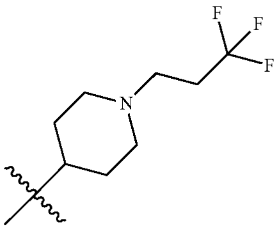
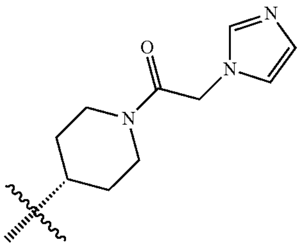
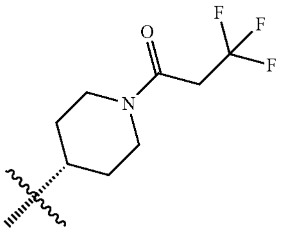
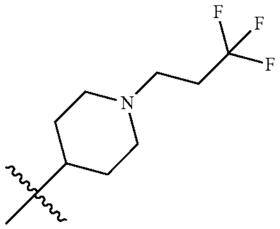
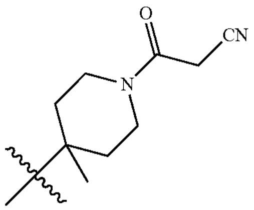
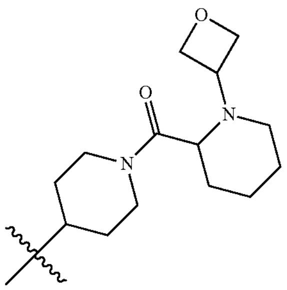
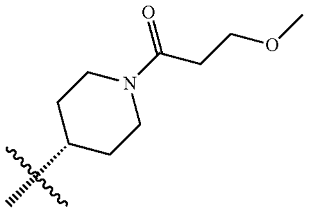
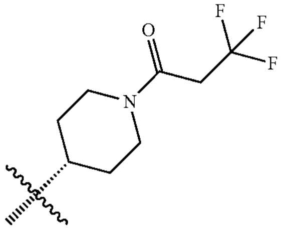

-continued
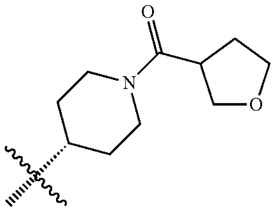
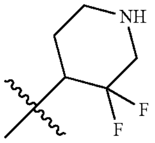
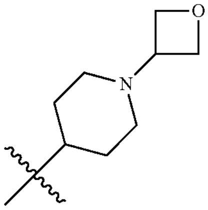
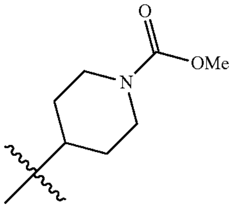
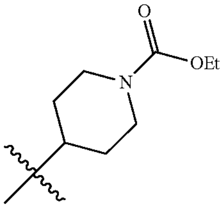
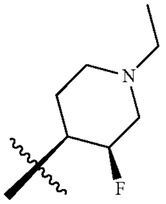
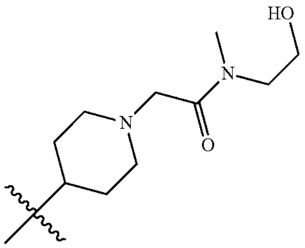
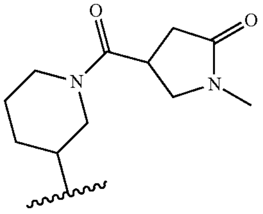
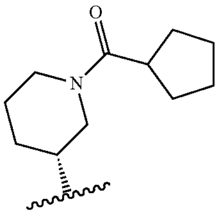
-continued
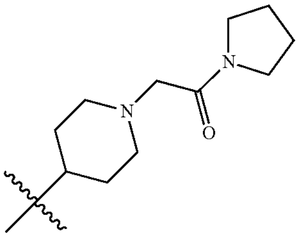
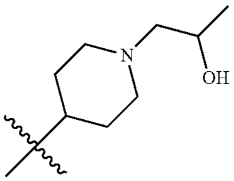
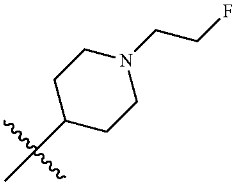
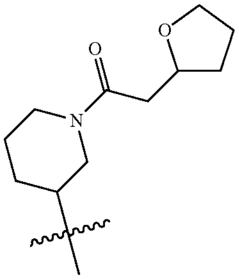
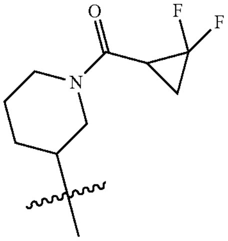
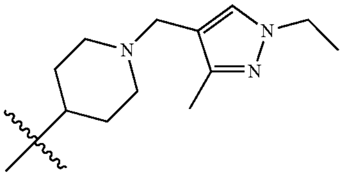
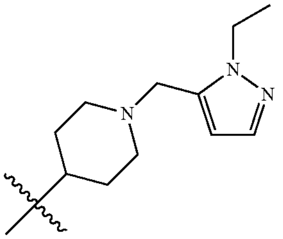
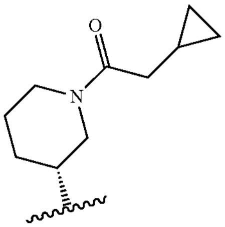
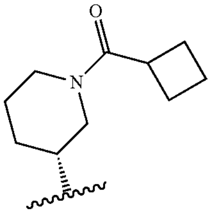
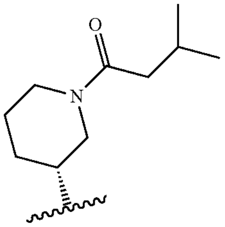
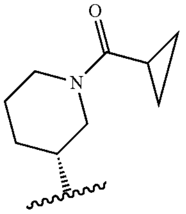

-continued
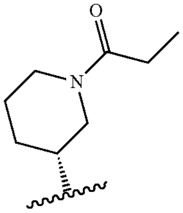
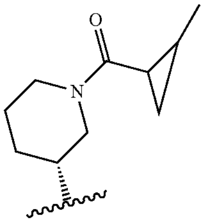
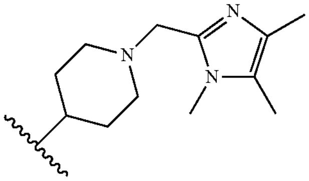
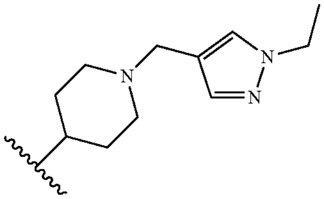
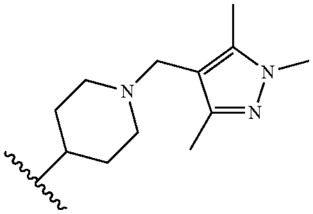
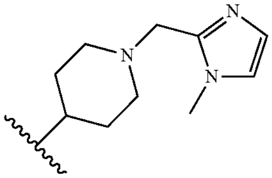
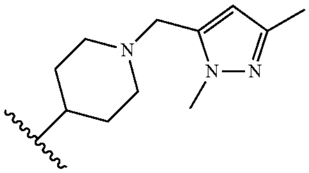
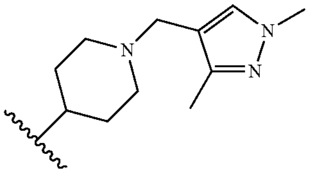
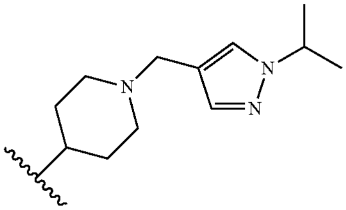
-continued
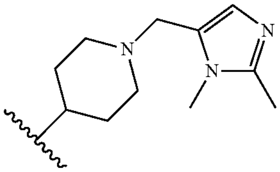
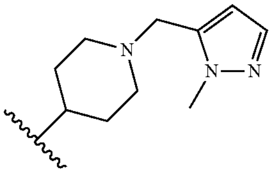
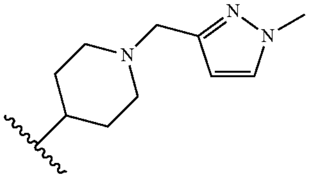
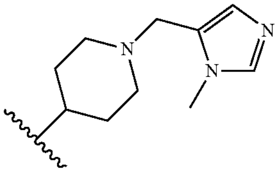
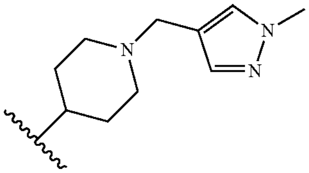
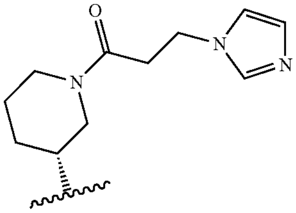
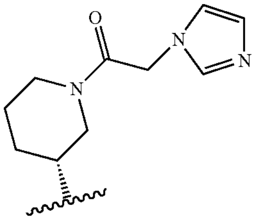
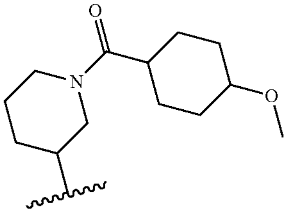
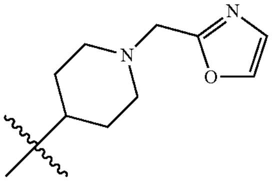

-continued

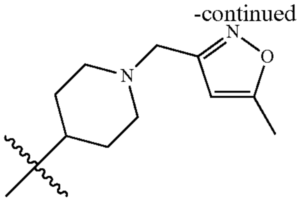

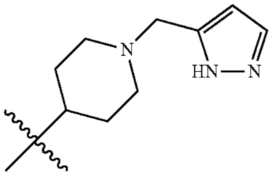

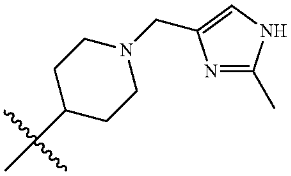

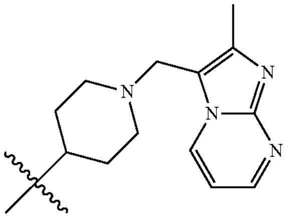

or

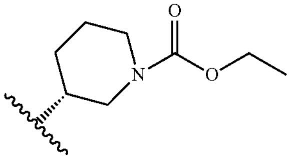

, wherein the wavy line represents the point of attachment in formula I.

10. The compound of claim 1, wherein $R^4$ is hydrogen, methyl or F.

11. The compound of claim 1, wherein $R^1$ is 6 membered heterocyclyl, wherein $R^1$ is independently optionally substituted by halogen, oxo, —CN, —$OR^a$, —$SR^a$, —$NR^aR^b$, $C_{1-3}$ alkylene or $C_{1-6}$ alkyl optionally substituted by oxo, —CN or halogen; $R^2$ is absent, —$NHS(O)_2$—, —$N(CH_3)S(O)_2$—, —$NHS(O)_2CH_2$—, —$C(O)CH_2S(O)_2$, —C(O)O—, —NHC(O)O—, —$N(CH_3)C(O)O$—, —$NHC(O)OCH_2$—, —$NHC(O)OCH_2CH_2$—, —C(O)NH—, —$CH_2C(O)NH$—, —$CH_2C(O)N(CH_3)$—, —NHC(O)—, —$NHC(O)CH_2$—, —$CH_2O$—, —$CH_2C(CH_2)_2O$—, —$(CH_2)_2O$—, —NH—, —$NHCH_2$—, —$NHCH_2CH_2$—, —$CH_2CN$, —$CH_2CH_2CN$, —$CH(CH_3)CN$, —$CH(CH_3)CH_2CN$, methylene, ethylene, —$C(CH_3)_2$—, —$CH_2CF_3$, —$CH_2CH_2CF_3$, —$CH_2CH_2F$, —$CH_2C(CH_3)_2OH$, —$CH_2CH_2OH$, —$CH_2CH_2OCH_3$,

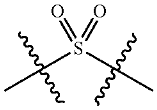 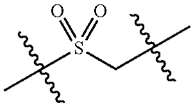

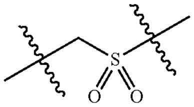 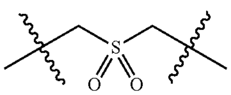

-continued

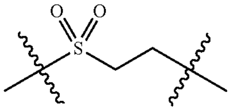 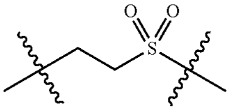

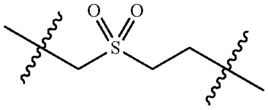

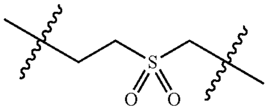

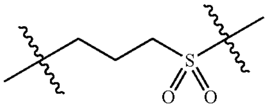

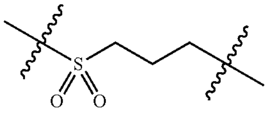 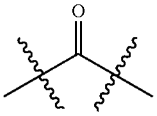

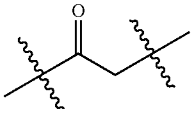 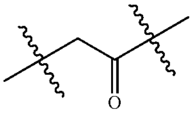

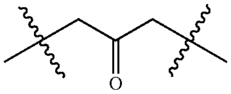 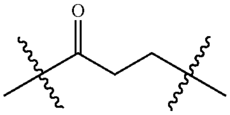

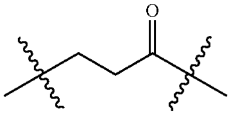 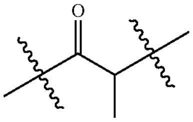

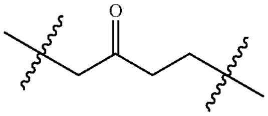

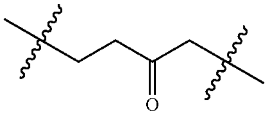

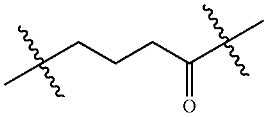

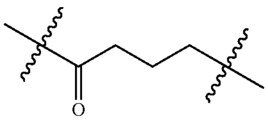 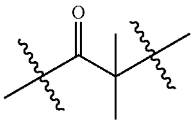

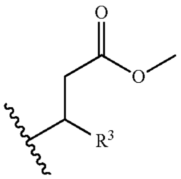 or 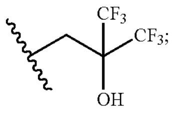

$R^3$ is absent, hydrogen, $C_{1-6}$ alkyl, $C_{3-7}$ cycloalkyl, $C_{6-14}$ aryl or 3-12 membered heterocyclyl, wherein $R^3$ is optionally substituted by 1 to 3 $R^6$; and $R^5$ is hydrogen, halogen, $C_{1-12}$ alkyl, —($C_{0-3}$ alkylene)CN, —($C_{0-3}$ alkylene)$OR^a$, —($C_{0-3}$ alkylene)$NR^aR^b$, —($C_{0-3}$ alkylene)C(O)$NR^aR^b$, —($C_{0-3}$ alkylene)$C_{3-12}$ cycloalkyl, —($C_{0-3}$ alkylene)C(O)$NR^aR^b$, —($C_{0-3}$ alkylene)$NR^aC(O)R^b$, —($C_{0-3}$ alkylene)$NR^aS(O)_{1-2}R^b$, —($C_{0-3}$ alkylene)$NR^aS(O)_{1-2}NR^aR^b$, —($C_{0-3}$ alkylene)$S(O)_{1-2}NR^aR^b$, —($C_{0-3}$ alkylene)$NR^aC(O)OR^b$, —($C_{0-3}$ alkylene)$S(O)_{1-2}R^a$, wherein $R^5$ is independently optionally substituted by halogen, oxo, —($C_{0-3}$ alkylene)CN, —($C_{0-3}$ alkylene)$OR^c$, —($C_{0-3}$ alkylene)$NR^cR^d$, —($C_{0-3}$ alkylene)$C(O)R^c$, —($C_{0-3}$ alkylene)$C(O)OR^c$, —($C_{0-3}$ alkylene)$C(O)NR^cR^d$, —($C_{0-3}$ alkylene)$NR^cC(O)R^d$, —($C_{0-3}$ alkylene)$OC(O)NR^cR^d$, —($C_{0-3}$ alkylene)$NR^cC(O)NR^cR^d$, —($C_{0-3}$ alkylene)$NR^cC(O)OR^d$, —($C_{0-3}$ alkylene)$S(O)_{0-2}R^c$, —($C_{0-3}$ alkylene)$NR^cS(O)_{1-2}R^d$, —($C_{0-3}$ alkylene)$S(O)_{1-2}NR^cR^d$, —($C_{0-3}$ alkylene)$NR^cS(O)_{1-2}NR^cR^d$ or $C_{1-6}$ alkyl optionally substituted by oxo, —CN or halogen, wherein the wavy line represents the point of attachment in formula I.

12. The compound of claim 11, wherein $R^4$ is hydrogen, methyl, chloro or bromo.

13. The compound of claim 1, wherein $R^5$ is hydrogen, halogen, $C_{1-12}$ alkyl, —($C_{0-3}$ alkylene)CN, —($C_{0-3}$ alkylene)$OR^a$, —($C_{0-3}$ alkylene)$NR^aR^b$, —($C_{0-3}$ alkylene)$C(O)NR^aR^b$, —($C_{0-3}$ alkylene)$C_{3-12}$ cycloalkyl, —($C_{0-3}$ alkylene)$C(O)NR^aR^b$, —($C_{0-3}$ alkylene)$NR^aC(O)R^b$, —($C_{0-3}$ alkylene)$NR^aS(O)_{1-2}R^b$, —($C_{0-3}$ alkylene)$NR^aS(O)_{1-2}NR^aR^b$, —($C_{0-3}$ alkylene)$S(O)_{1-2}NR^aR^b$, —($C_{0-3}$ alkylene)$NR^aC(O)OR^b$, —($C_{0-3}$ alkylene)$S(O)_{1-2}R^a$, wherein $R^5$ is independently optionally substituted by halogen, oxo, —($C_{0-3}$ alkylene)CN, —($C_{0-3}$ alkylene)$OR^c$, —($C_{0-3}$ alkylene)$NR^cR^d$, —($C_{0-3}$ alkylene)$C(O)R^c$, —($C_{0-3}$ alkylene)$C(O)OR^c$, —($C_{0-3}$ alkylene)$C(O)NR^cR^d$, —($C_{0-3}$ alkylene)$NR^cC(O)R^d$, —($C_{0-3}$ alkylene)$OC(O)NR^cR^d$, —($C_{0-3}$ alkylene)$NR^cC(O)NR^cR^d$, —($C_{0-3}$ alkylene)$NR^cC(O)OR^d$, —($C_{0-3}$ alkylene)$S(O)_{0-2}R^c$, —($C_{0-3}$ alkylene)$NR^cS(O)_{1-2}R^d$, —($C_{0-3}$ alkylene)$S(O)_{1-2}NR^cR^d$, —($C_{0-3}$ alkylene)$NR^cS(O)_{1-2}NR^cR^d$ or $C_{1-6}$ alkyl optionally substituted by oxo, —CN or halogen, wherein $R^5$ is other than —OH.

14. The compound of claim 1, wherein —$R^1$-$R^2$-$R^3$ taken together are:

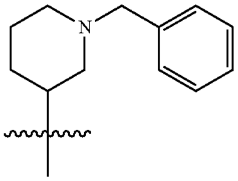
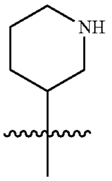
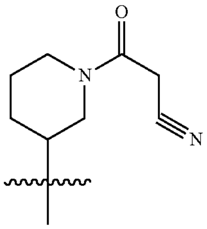
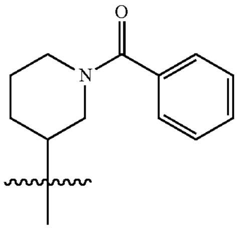
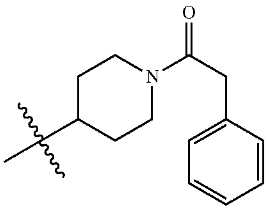
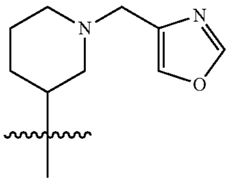

-continued

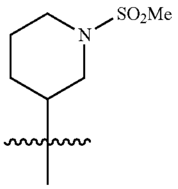
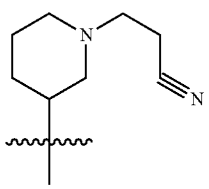
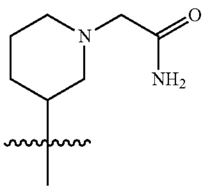
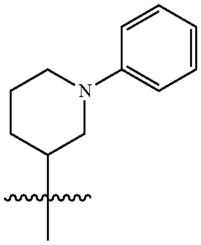
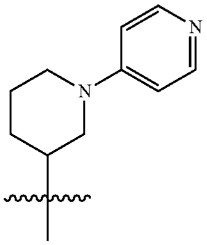
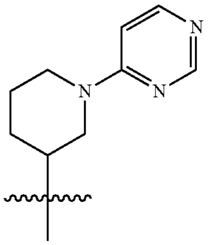
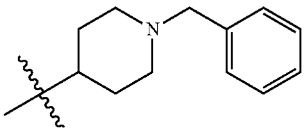
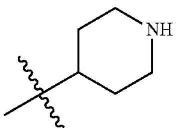
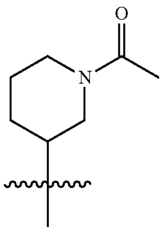
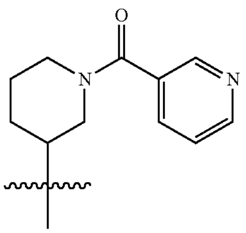
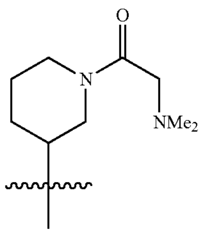
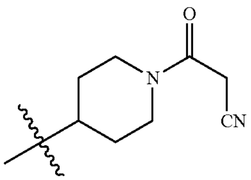

-continued
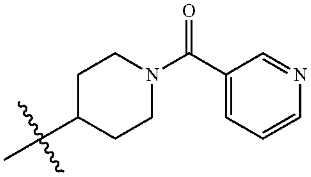
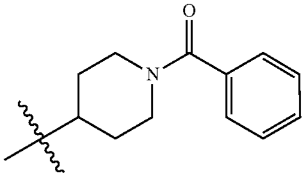
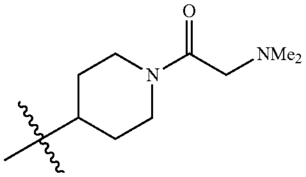
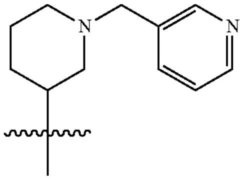
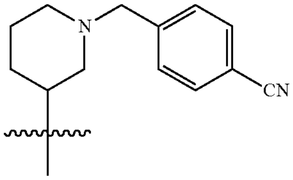
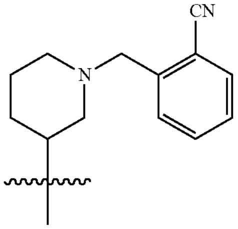
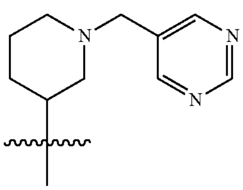
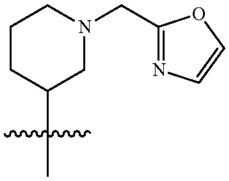
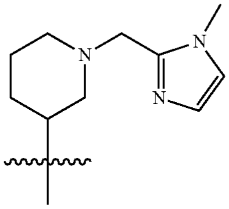
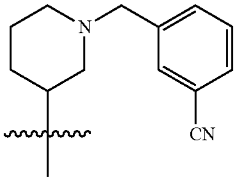
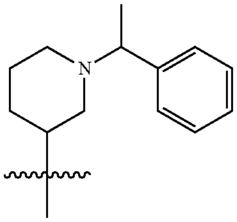
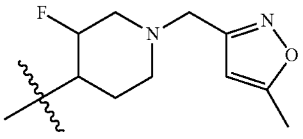
-continued
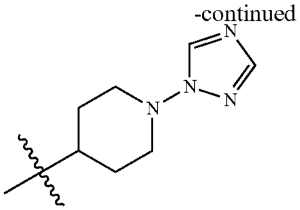
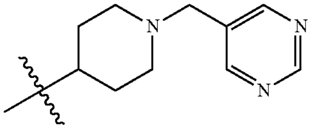
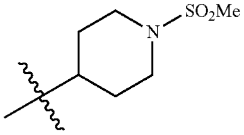
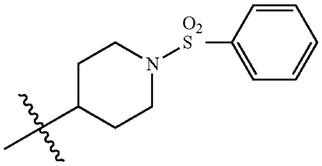
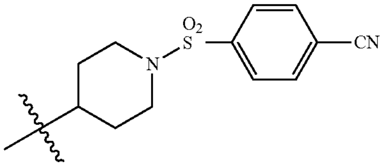
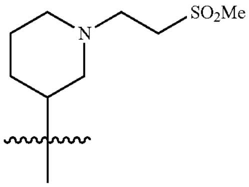
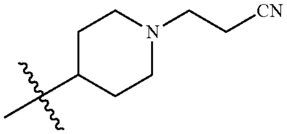
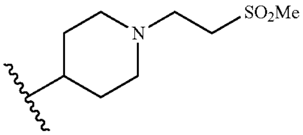
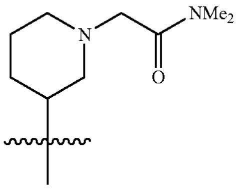
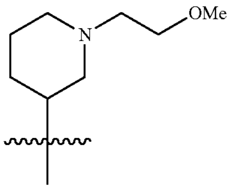
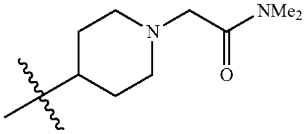
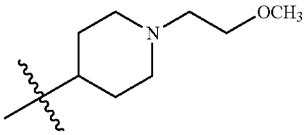

-continued
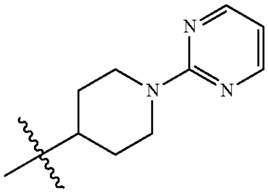
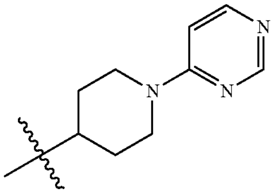
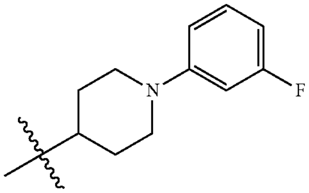
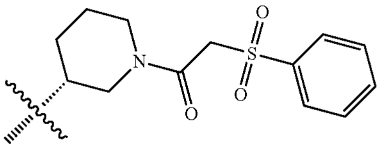
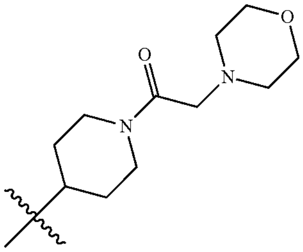
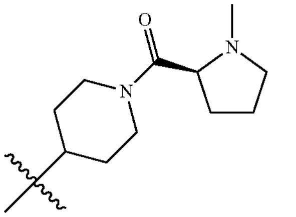
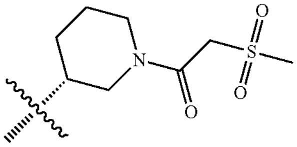
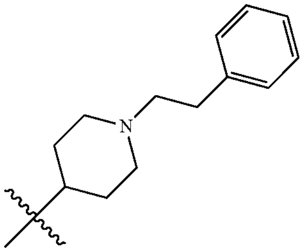
-continued
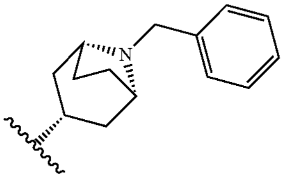
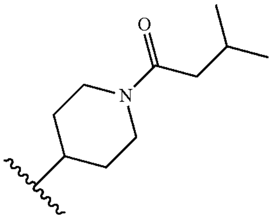
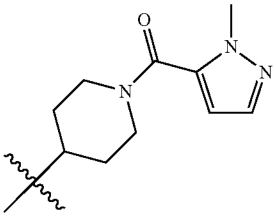
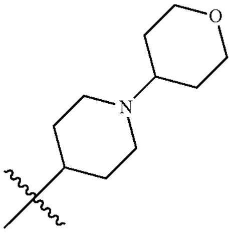
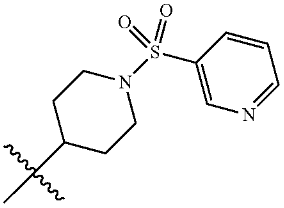
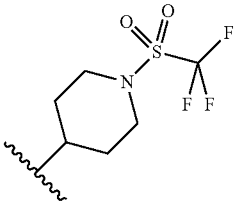
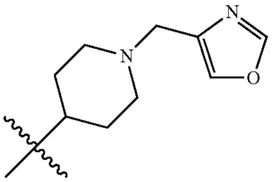
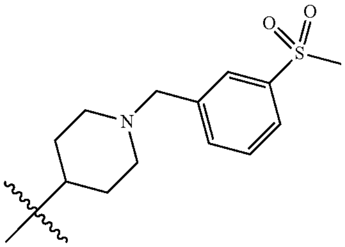
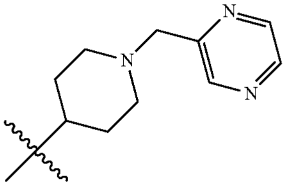
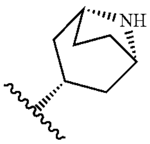

-continued
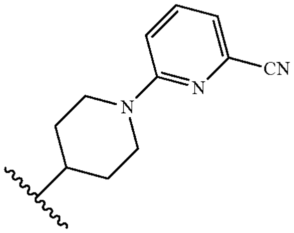
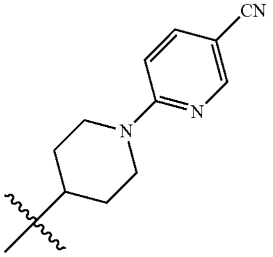
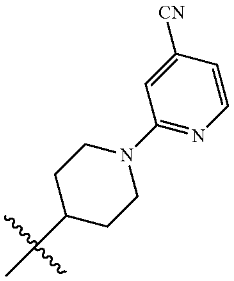
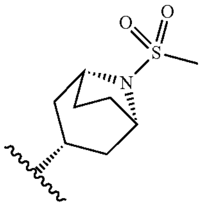
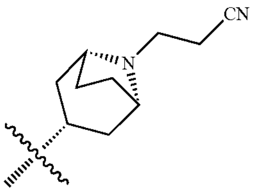
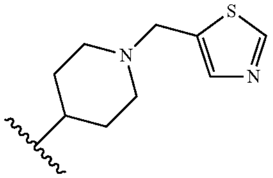
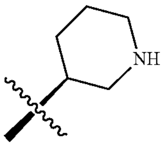
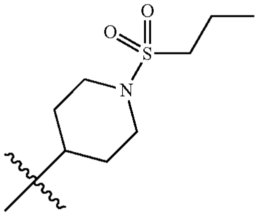
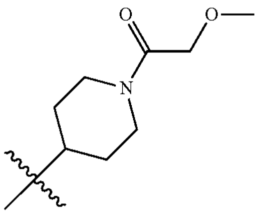
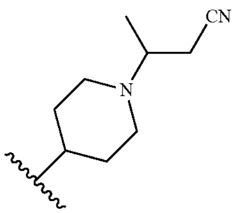
-continued
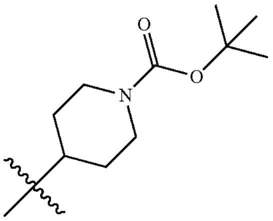
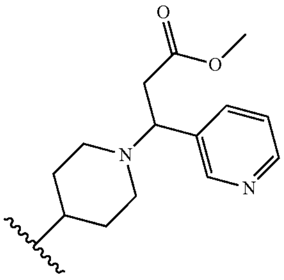
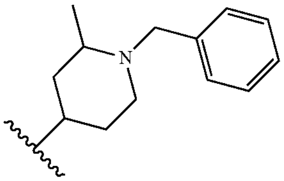
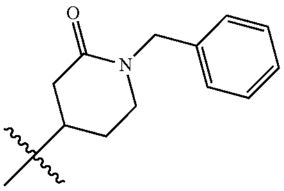
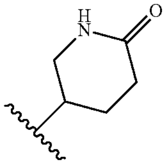
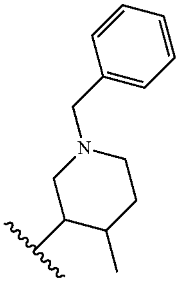
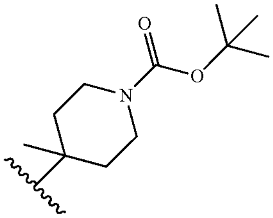
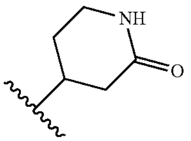 [SMILES: *C1CCNC(=O)C1]
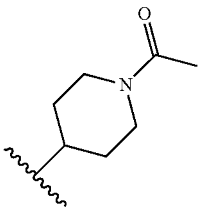

-continued
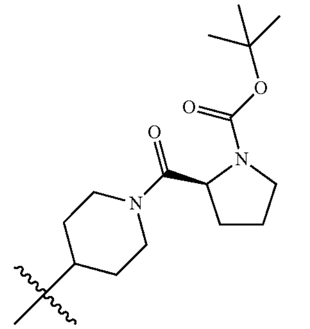
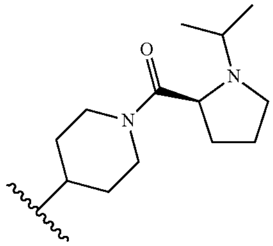
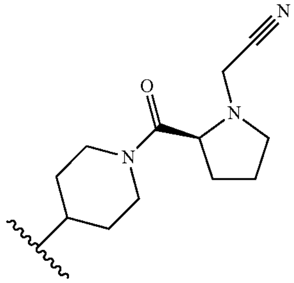
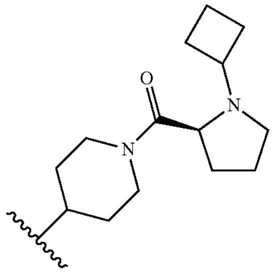
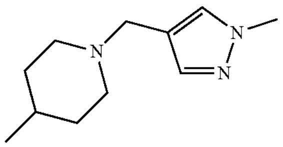
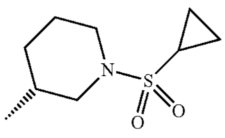
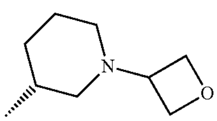
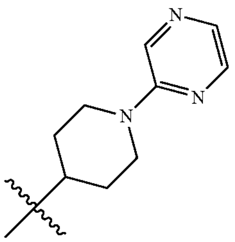
-continued
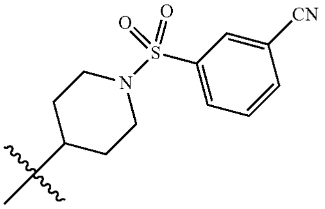
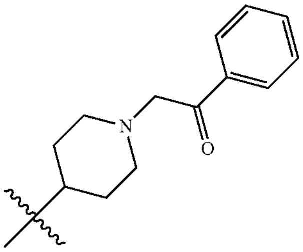
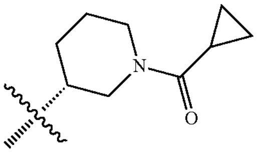
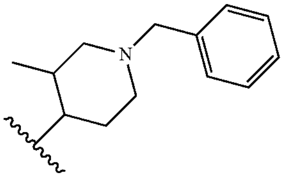
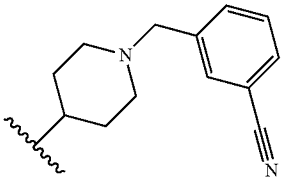
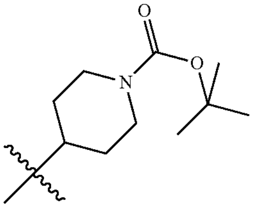
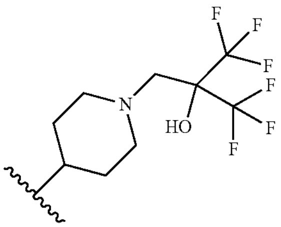
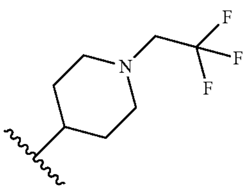

-continued
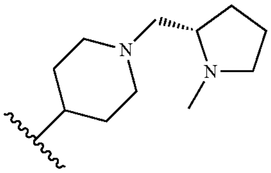
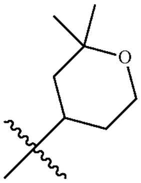
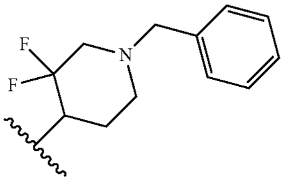
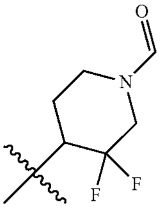
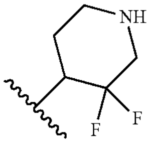
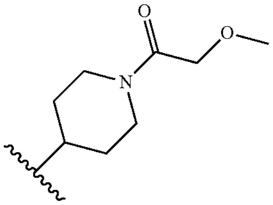
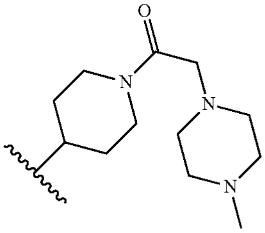
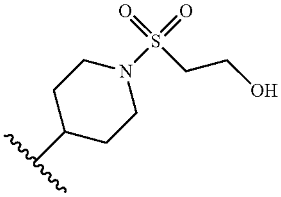
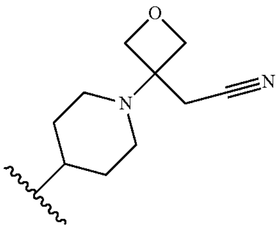
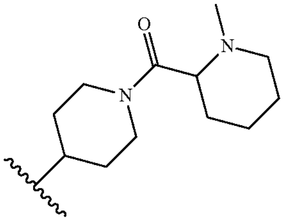
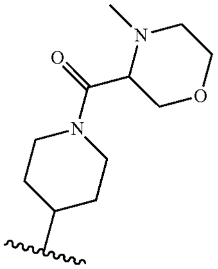
-continued
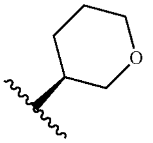
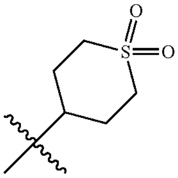
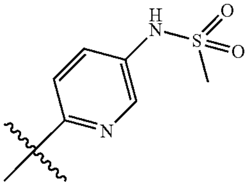
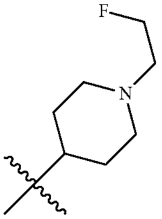
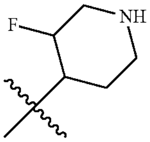
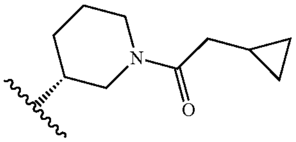
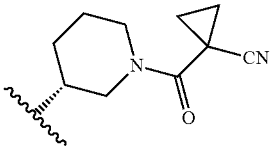
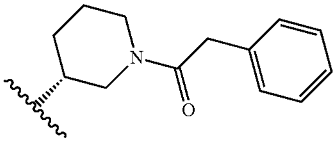
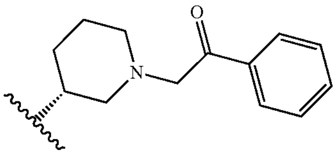
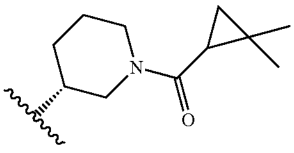
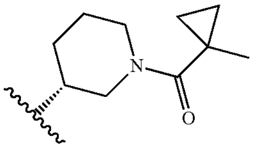

-continued
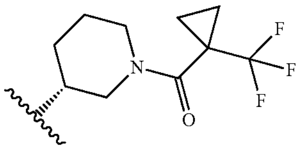
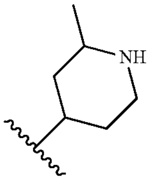
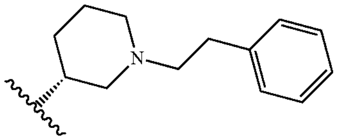
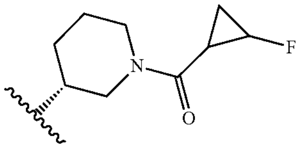
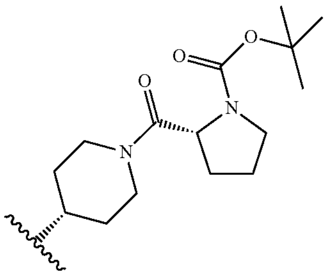
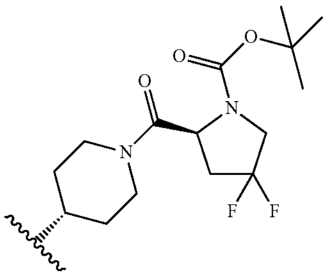
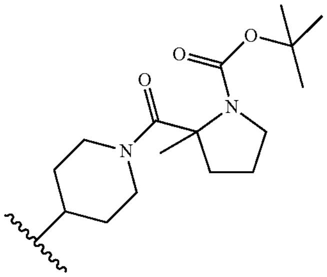
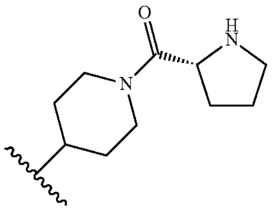
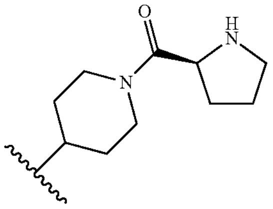
-continued
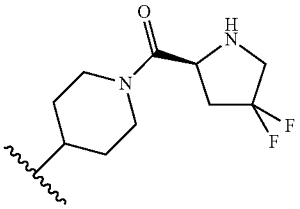
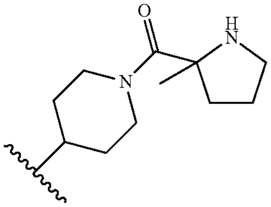
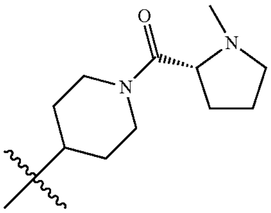
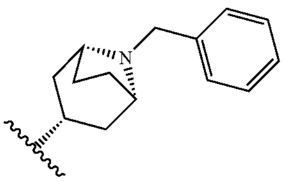
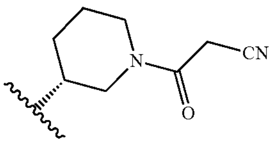
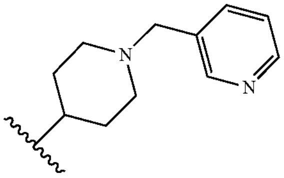
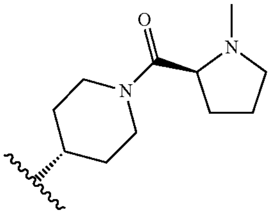
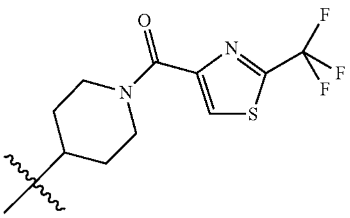
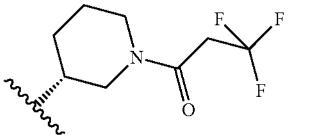

-continued
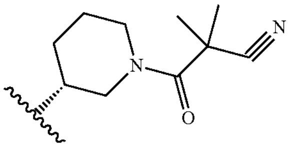
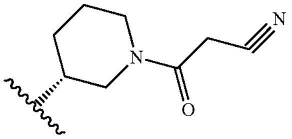
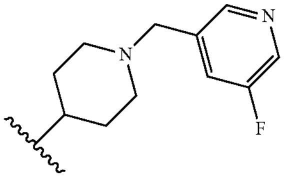
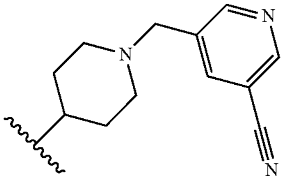
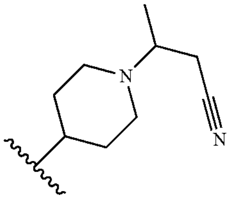
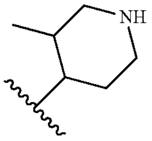
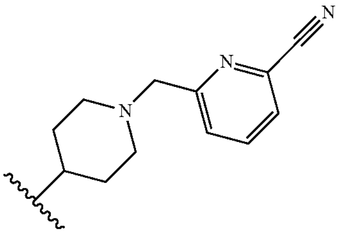
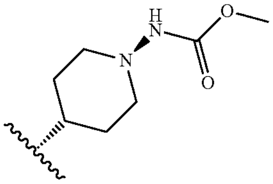
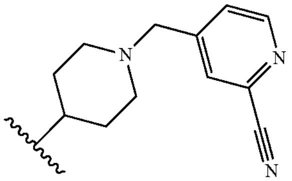
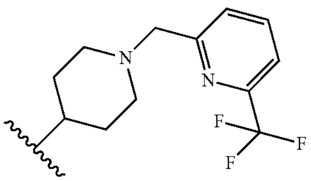
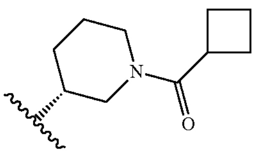
-continued
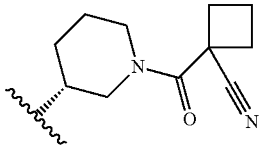
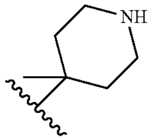
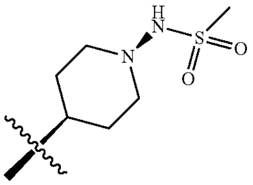
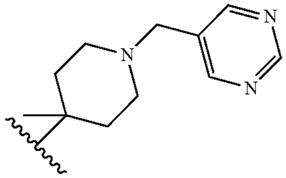
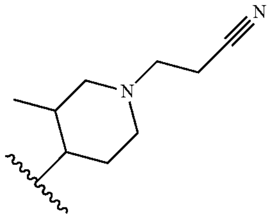
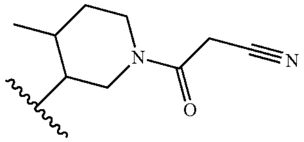
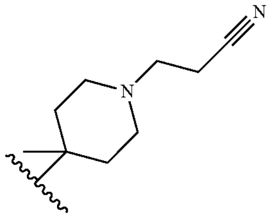
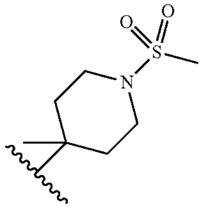
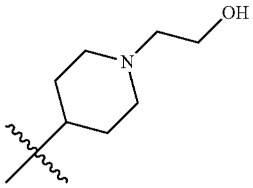

-continued
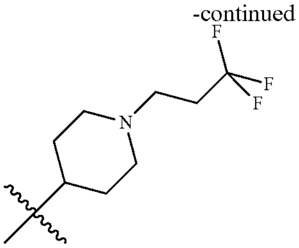
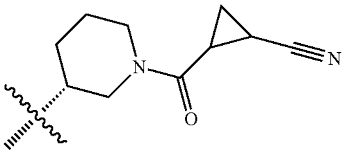
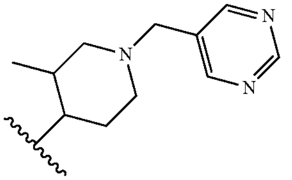
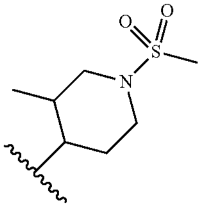
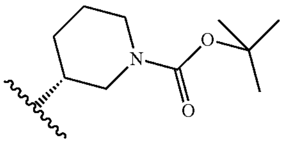
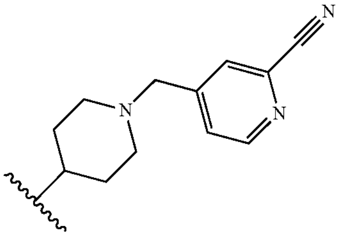
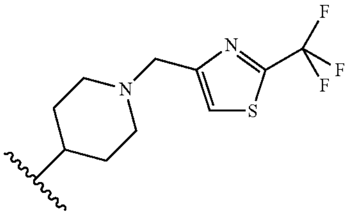
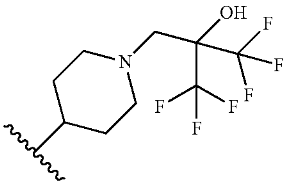
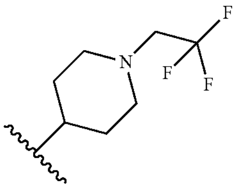
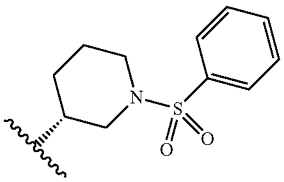
-continued
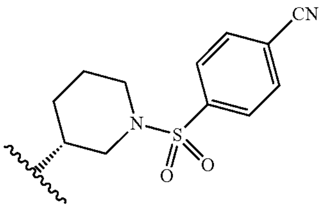
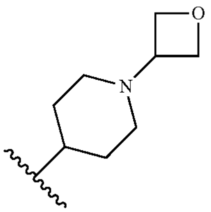
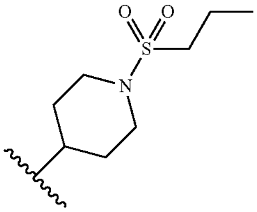
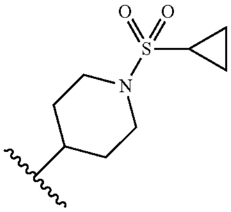
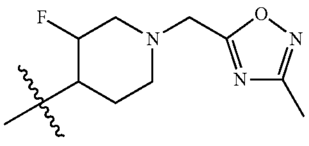
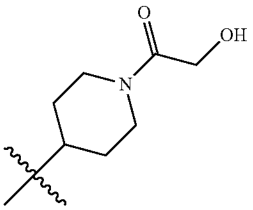 [SMILES: *C1CCN(C(=O)CO)CC1]
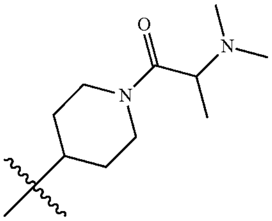
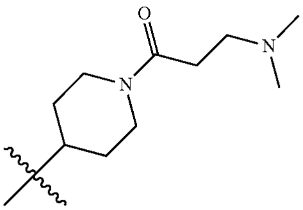
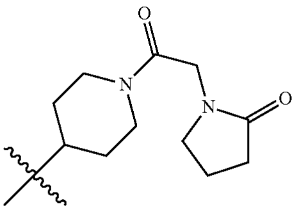

-continued
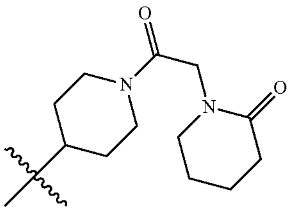
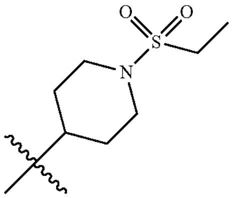
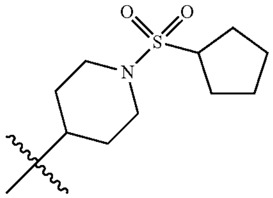
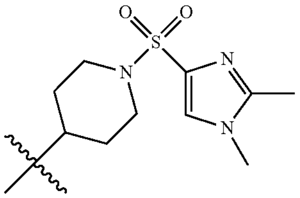
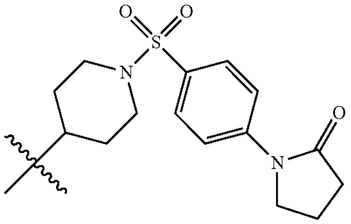
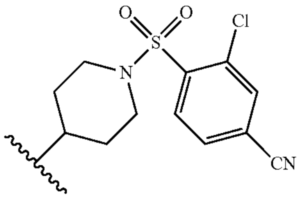
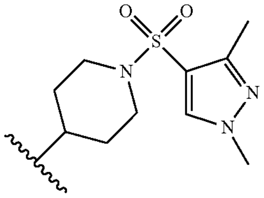
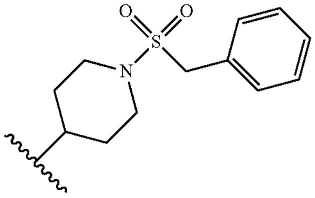
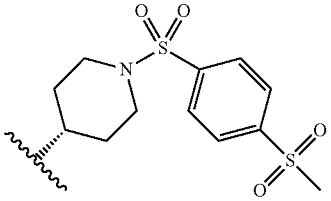
-continued
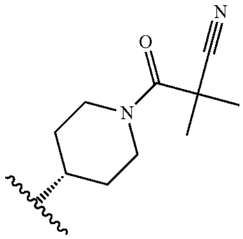
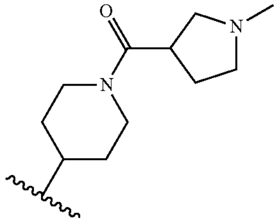
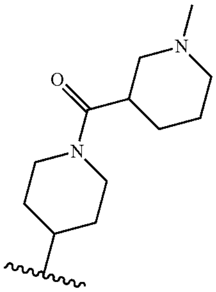
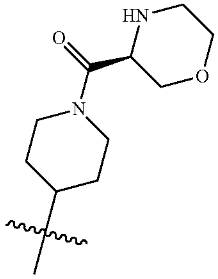
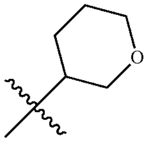
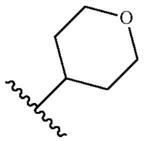
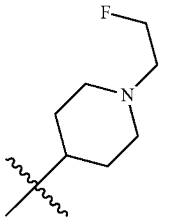
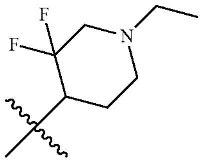
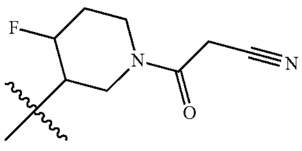
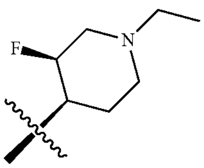
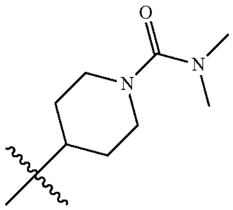

-continued
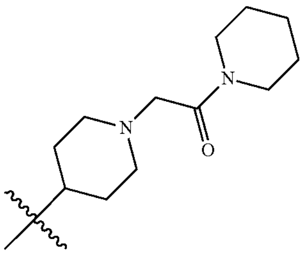
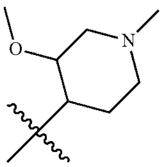
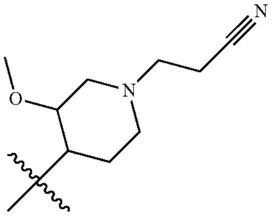
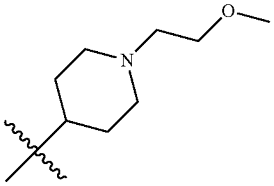
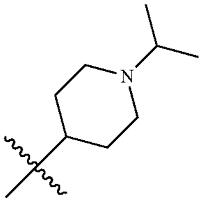
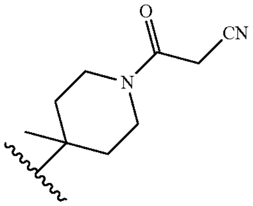
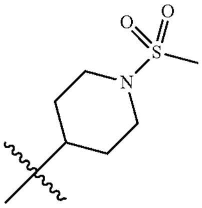
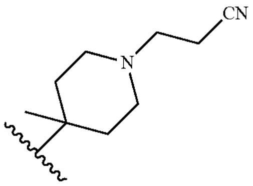
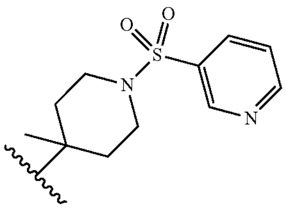
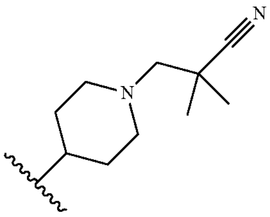
-continued
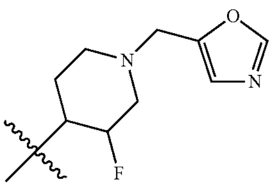
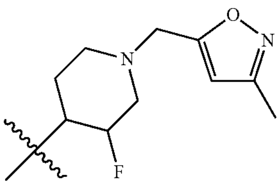
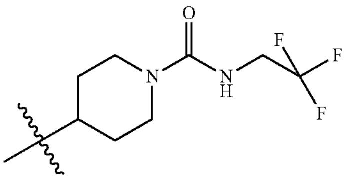 [SMILES: *C1CCN(C(=O)NCC(F)(F)F)CC1]
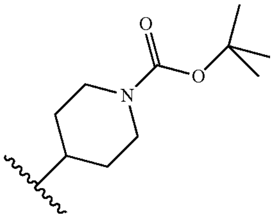 [SMILES: *C1CCN(C(=O)OC(C)(C)C)CC1]
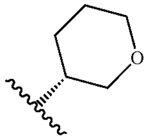
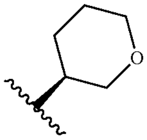
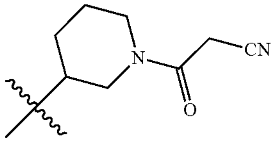
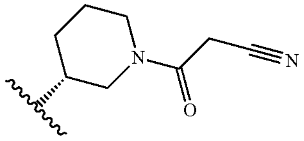
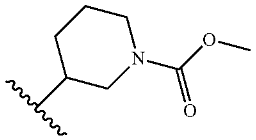
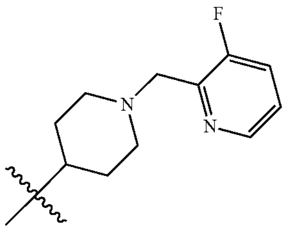

-continued
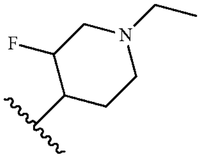
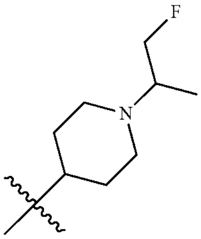
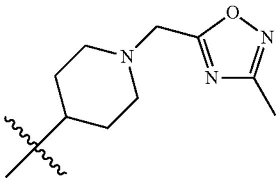
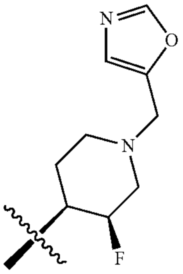
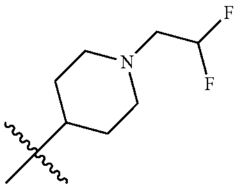
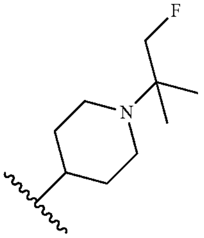
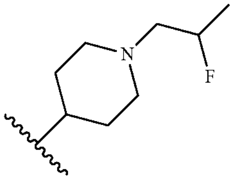
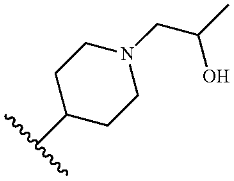
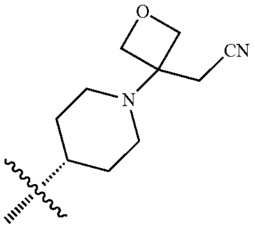
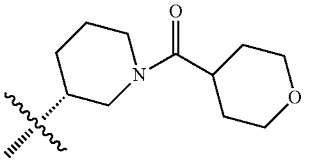
-continued
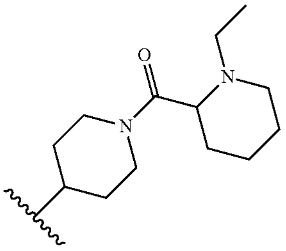
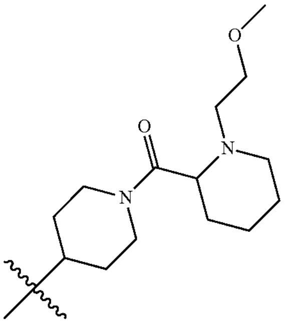
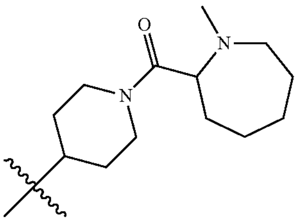
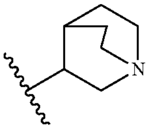
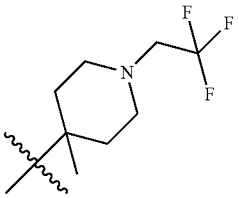
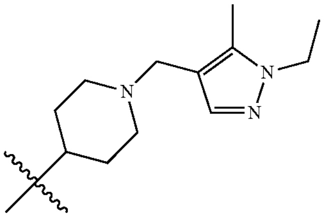
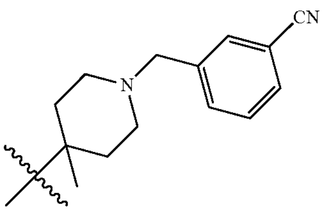
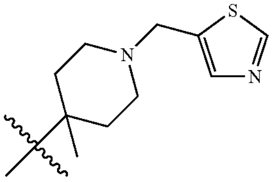

-continued
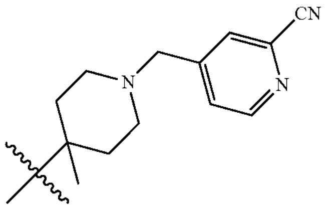
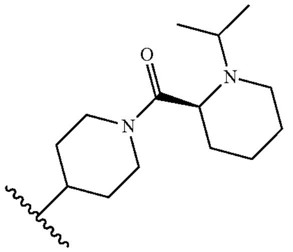
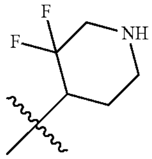
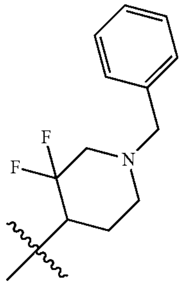
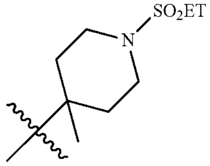
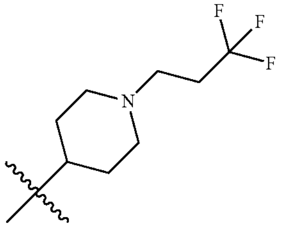
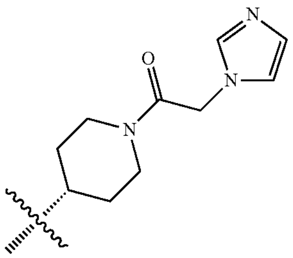
-continued
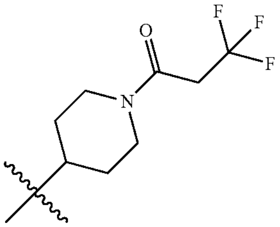
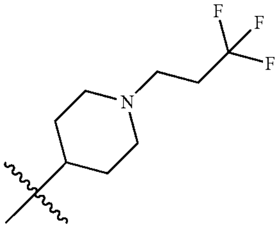
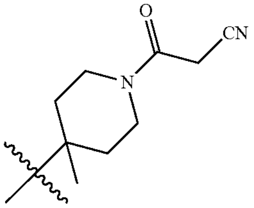
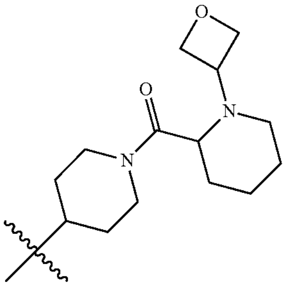
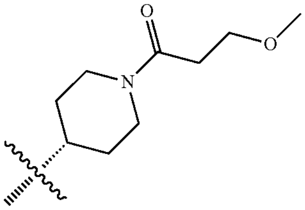
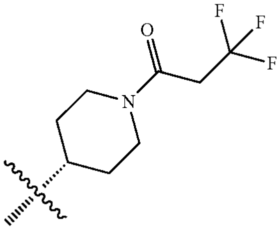
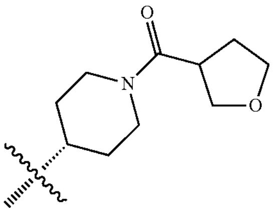

-continued
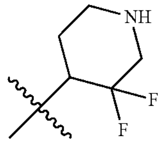
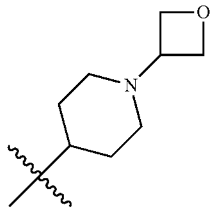
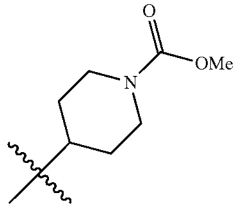
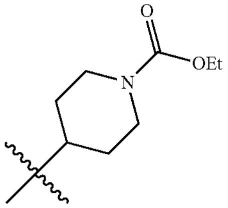
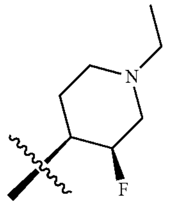
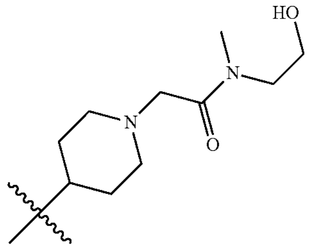
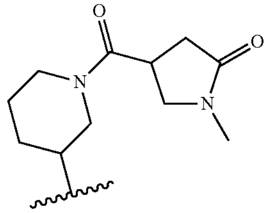
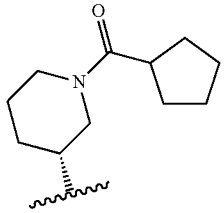
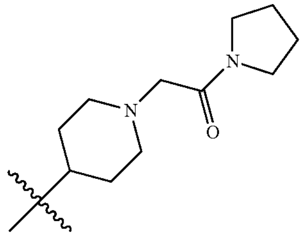
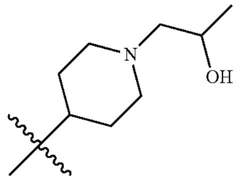
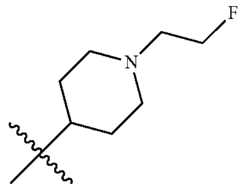
-continued
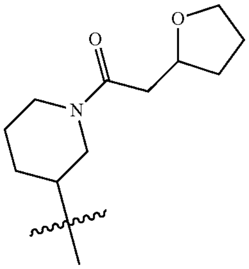
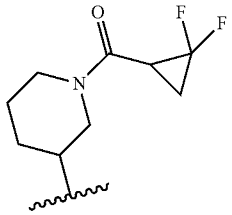
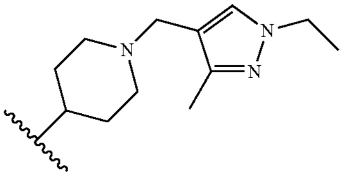
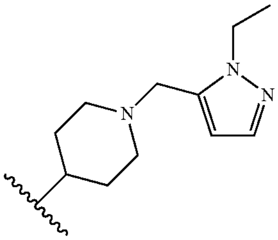
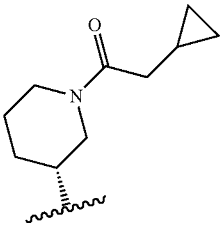
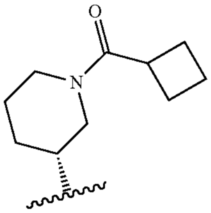
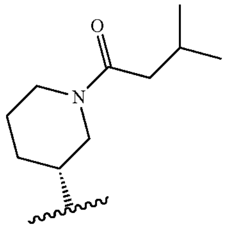
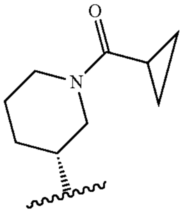
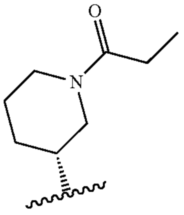
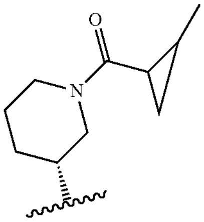
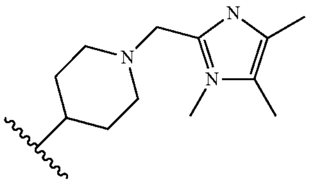
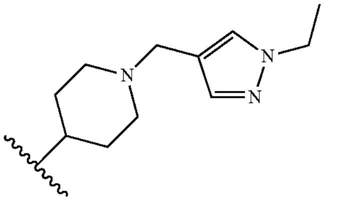

-continued
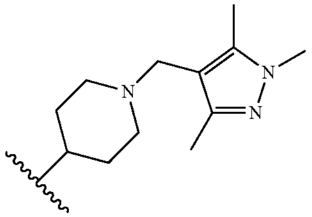
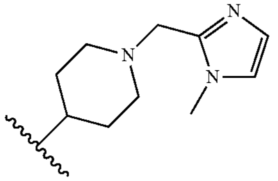
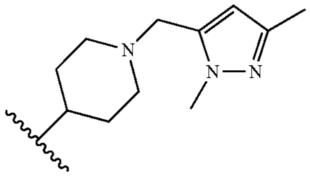
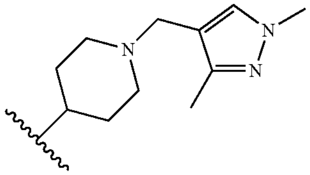
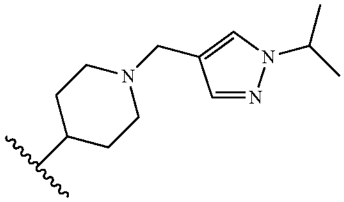
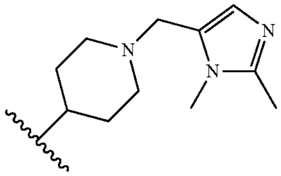
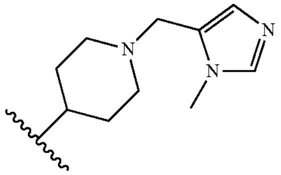
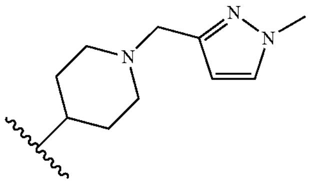
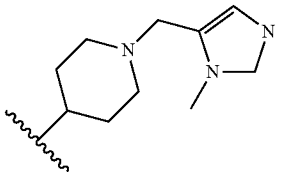
-continued
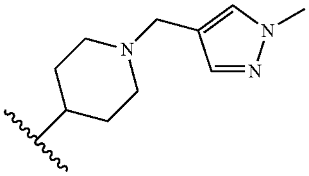
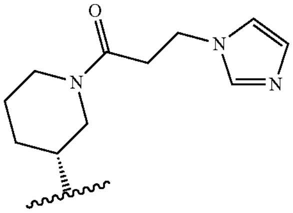
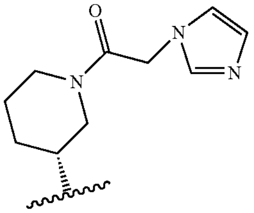
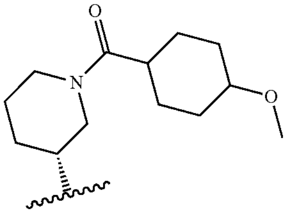
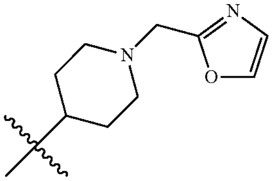
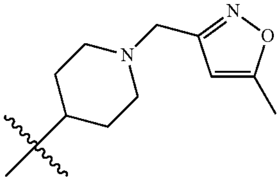
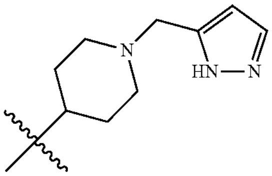
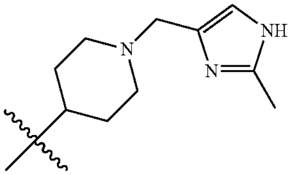

-continued

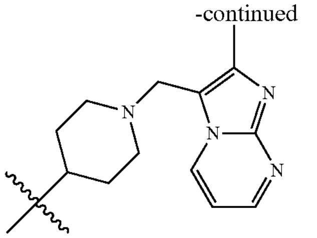

or

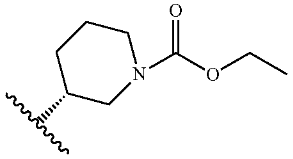

;

and $R^5$ is hydrogen, methyl, ethyl, propyl, isopropyl, cyclopropyl, cyclobutyl, cyano, 2-methylbutyl, N-(2-hydroxyethyl)amino, N-(2-methoxyethyl)amino, methylsulfonylaminomethyl, 2-(methylsulfonylamino)ethyl, cyclopropylmethyl, 2-[N-(2-propylsulfonyl)amino]ethyl, 2-[N-(cyclopropylsulfonyl)-amino]ethyl, 2-(cyclopropylcarbonylamino)ethyl, 2-(acetylamino)ethyl, 2-(methoxymethyl-carbonylamino)ethyl, cyclopentoxymethyl, cyclopropylmethoxymethyl, 2,2,2-trifluoroethoxymethyl, cyclohexyl, methylamino, 2-(N,N-dimethylaminocarbonyl) ethyl, 2-(N-acetyl-N-methylamino)ethyl, 2-(ethoxycarbonylamino)ethyl, 1-hydroxyethyl, N-acylaminomethyl, 2-amino-1,1-difluoroethyl, N,N-dimethylamino, hydroxymethyl, methoxy, N-methylamino, N,N-dimethylamino,N-(2, 2,2-trifluoroethyl)aminomethyl, (2-carboxycyclopropyl)(hydroxy)methyl, 2-hydroxyethyl, aminocarbonylmethyl, methylaminocarbonylmethyl, ethylaminocarbonylmethyl, 1-hydroxypropyl, 1,2-dihydroxyethyl, N-(2-methylpropyl) aminocarbonylmethyl, cyclopentylaminocarbonylmethyl, 2-(methoxycarbonylamino)ethyl, 2,2,2-trifluoro-1-hydroxyethyl, tert-butylaminocarbonylmethyl, cyclobutylaminocarbonylmethyl, 2-hydroxyethoxy, isopropylaminocarbonylmethyl, N—(N'N'-diemthylaminocarbonylmethyl) aminocarbonylmethyl, 4,4-difluorocyclohexylamino carbonylmethyl, 2,2-difluoroethylaminocarbonylmethyl, N-(2-hydroxyethyl)-N-methylaminocarbonylmethyl, cyclopentylmethyl, N-cyclopentyl-N-methylaminocarbonylmethyl, 2-amino-1,1-difluoroethyl, 3-pyridyl, morpholinomethyl, morpholinocarbonylmethyl, 2-cyano-2-methylethyl, trifluoromethyl, 1-hydroxy-1-methylethyl, 1-(N-isopropylaminocarbonyl)ethyl, 2-hydroxy-2-methylpropyl, N-(methylsulfonyl)-N-methylaminomethyl, difluoromethyl, 2-(2-butylsulfonylamino)ethyl, 2-(4-fluorophenylcarbonylamino) ethyl, 2-(cyclobutylcarbonylamino)ethyl, 2-(2-methylbutanoylamino)ethyl, 2-(benzoylamino)ethyl, 2,2-difluorocyclopropyl, 3-cyanobenzyl, 2-methylpropoxymethyl, 2-cyclopropylethyl, 3-pyridylmethyl, methylsulfonylmethyl, ethoxycarbonylaminomethyl, 3-pyridylcarbonylaminomethyl, isopropylsulfonylaminomethyl, 2-pyridylcarbonylaminomethyl, cyclopropylsulfonylaminomethyl, cyclopentylsulfonylaminomethyl, 2-methylpropanoylaminomethyl, cyclopropylcarbonylaminomethyl, 2-fluorobenzoylaminomethyl, 3-fluorobenzoylaminomethyl, 1-methylpropylsulfonylaminomethyl, 2-methylpropylsulfonylaminomethyl, methoxyacetylaminomethyl, ethylsylfonylaminomethyl, 2-(3,3,3-trifluoropropylsulfonylamino)ethyl, 2-(2,2-difluorocyclopropylcarbonylamino)ethyl, fluoromethyl, 2-hydroxyethylamino, 2-methoxyethylamino, 1-aminoethyl, 2-(ethylsulfonylamino)ethyl, 2,2-dimethylpropoxymethyl, 1-methoxyethyl, tert-butylsulfonylaminomethyl, 2,2,2-trifluoroethylaminomethyl,

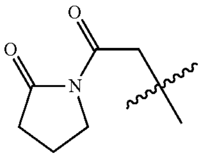
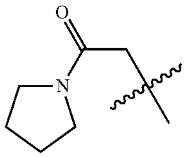
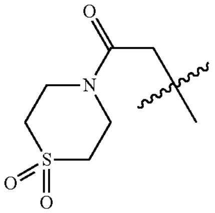
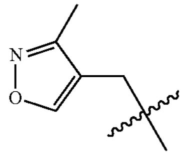
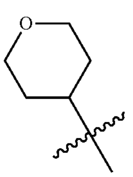
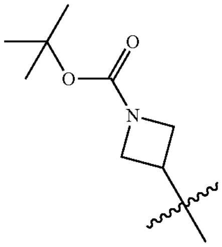
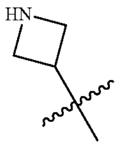
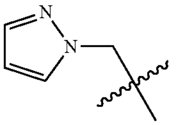
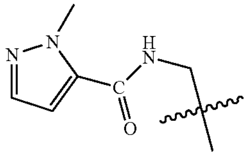
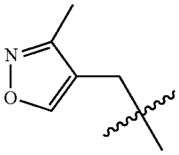
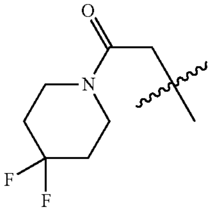
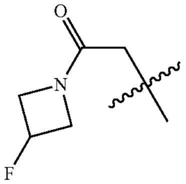
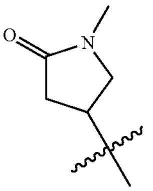
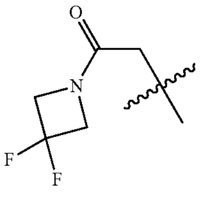
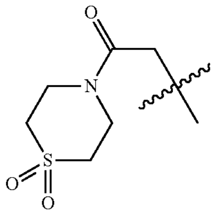

-continued
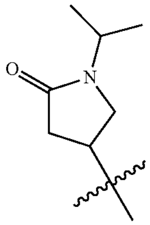
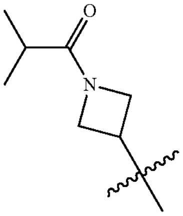
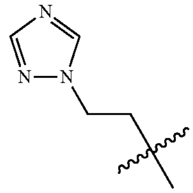
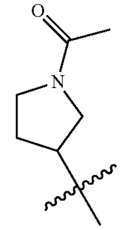
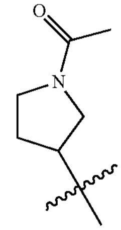
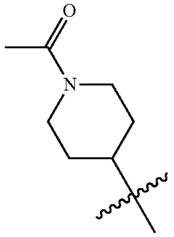
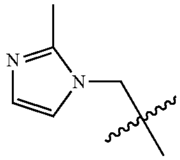
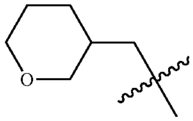
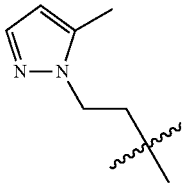
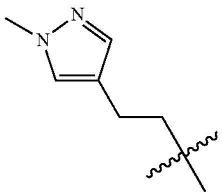
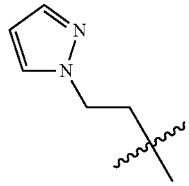
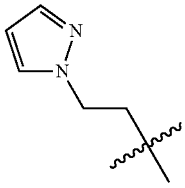
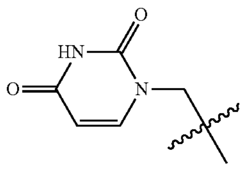
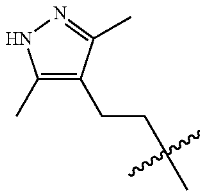
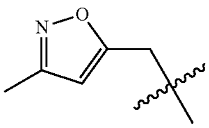
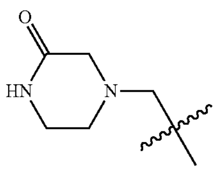
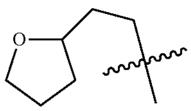
-continued
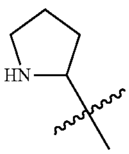
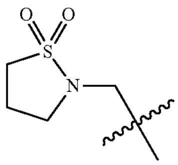
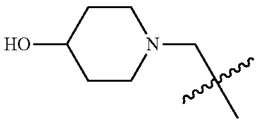
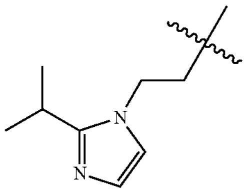
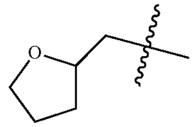
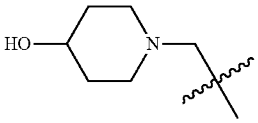
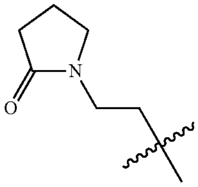
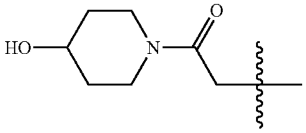
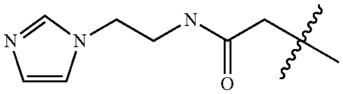
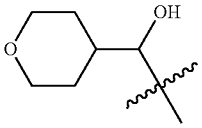
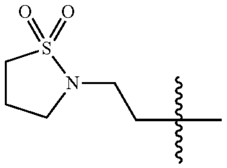
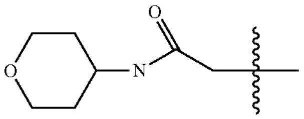
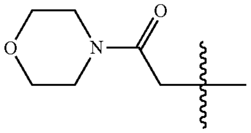
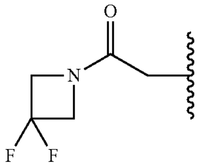
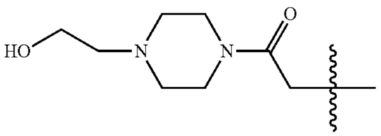
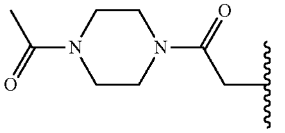
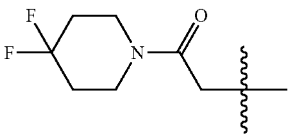

-continued

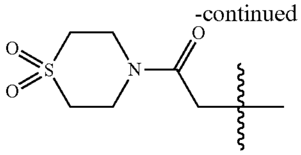

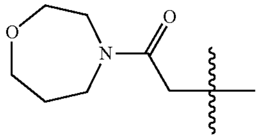

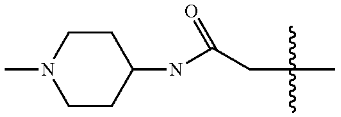

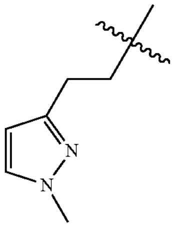

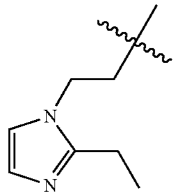

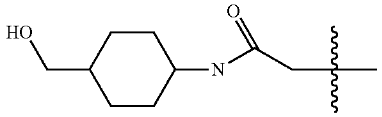

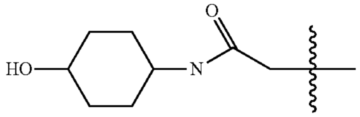

or

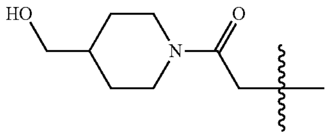

, wherein the wavy line represents the point of attachment in formula I.

15. The compound of claim 14, wherein $R^5$ is hydrogen, methyl, ethyl, propyl, isopropyl, cyclopropyl, cyclobutyl, cyano, 2-methylbutyl, N-(2-hydroxyethyl)amino, N-(2-methoxyethyl)amino, methylsulfonylaminomethyl, 2-(methylsulfonylamino)ethyl, cyclopropylmethyl, 2-[N-(2-propylsulfonyl)amino]ethyl, 2-[N-(cyclopropylsulfonyl)amino]ethyl, 2-(cyclopropylcarbonylamino)ethyl, 2-(acetylamino)ethyl, 2-(methoxymethylcarbonylamino)ethyl, cyclopentoxymethyl, cyclopropylmethoxymethyl, 2,2,2-trifluoroethoxymethyl, cyclohexyl, methylamino, 2-(N,N-dimethylaminocarbonyl)ethyl, 2-(N-acetyl-N-methylamino)ethyl, 2-(ethoxycarbonylamino)ethyl, 1-hydroxyethyl, N-acylaminomethyl, 2-amino-1,1-difluoroethyl, N,N-dimethylamino, hydroxymethyl, methoxy, N-methylamino, N,N-dimethylamino,N-(2,2,2-trifluoroethyl)aminomethyl, (2-carboxycyclopropyl)(hydroxy)methyl, 2-hydroxyethyl, aminocarbonylmethyl, methylaminocarbonylmethyl, ethylaminocarbonylmethyl, 1-hydroxypropyl, 1,2-dihydroxyethyl, N-(2-methylpropyl)aminocarbonylmethyl, cyclopentylaminocarbonylmethyl, 2-(methoxycarbonylamino)ethyl, 2,2,2-trifluoro-1-hydroxyethyl, tert-butylaminocarbonylmethyl, cyclobutylaminocarbonylmethyl, 2-hydroxyethoxy, isopropylaminocarbonylmethyl, N—(N'N'-diemthylaminocarbonylmethyl)aminocarbonylmethyl, 4,4-difluorocyclohexylaminocarbonylmethyl, 2,2-difluoroethylaminocarbonylmethyl, N-(2-hydroxyethyl)-N- methylaminocarbonylmethyl, cyclopentylmethyl, N-cyclopentyl-N-methylaminocarbonylmethyl, 2-amino-1,1-difluoroethyl, 3-pyridyl, morpholinomethyl, morpholinocarbonylmethyl, 2-cyano-2-methylethyl, trifluoromethyl, 1-hydroxy-1-methylethyl, 1-(N-isopropylaminocarbonyl)ethyl, 2-hydroxy-2-methylpropyl, N-(methylsulfonyl)-N-methylaminomethyl, difluoromethyl, 2-(2-butylsulfonylamino)ethyl, 2-(4-fluorophenylcarbonylamino)ethyl, 2-(cyclobutylcarbonylamino)ethyl, 2-(2-methylbutanoylamino)ethyl, 2-(benzoylamino)ethyl, 2,2-difluorocyclopropyl, 3-cyanobenzyl, 2-methylpropoxymethyl, 2-cyclopropylethyl, 3-pyridylmethyl, methylsulfonylmethyl, ethoxycarbonylaminomethyl, 3-pyridylcarbonylaminomethyl, isopropylsulfonylaminomethyl, 2-pyridylcarbonylaminomethyl, cyclopropylsulfonylaminomethyl, cyclopentylsulfonylaminomethyl, 2-methylpropanoylaminomethyl, cyclopropylcarbonylaminomethyl, 2-fluorobenzoylaminomethyl, 3-fluorobenzoylaminomethyl, 1-methylpropylsulfonylaminomethyl, 2-methylpropylsulfonylaminomethyl, methoxyacetylaminomethyl, ethylsylfonylaminomethyl, 2-(3,3,3-trifluoropropylsulfonylamino)ethyl, 2-(2,2-difluorocyclopropylcarbonylamino)ethyl, fluoromethyl, 2-hydroxyethylamino, 2-methoxyethylamino, 1-aminoethyl, 2-(ethylsulfonylamino)ethyl, 2,2-dimethylpropoxymethyl, 1-methoxyethyl, tert-butylsulfonylaminomethyl, 2,2,2-trifluoroethylaminomethyl,

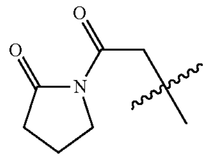

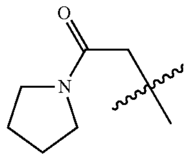

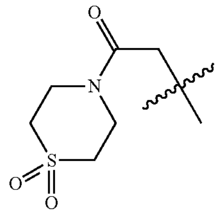

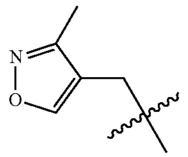

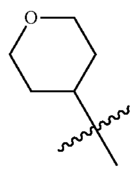

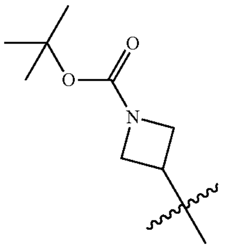

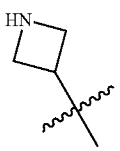

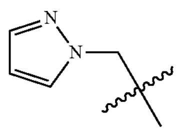

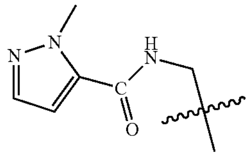

-continued
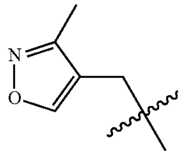
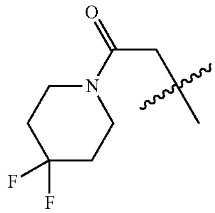
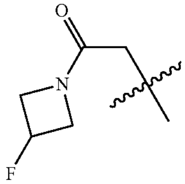
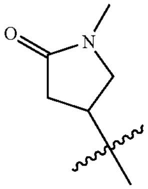
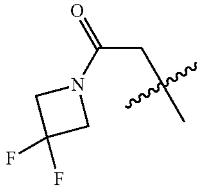
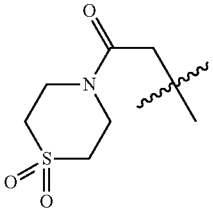
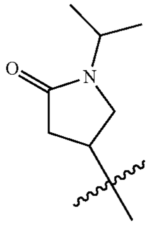
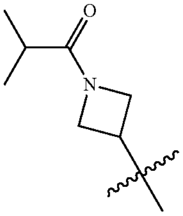
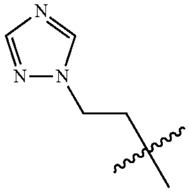
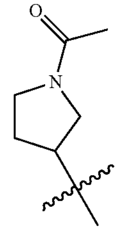
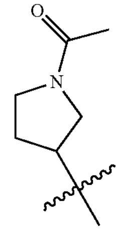
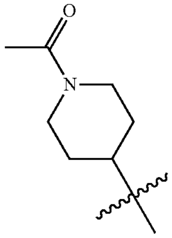
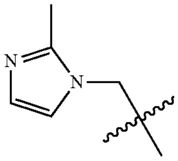
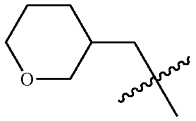
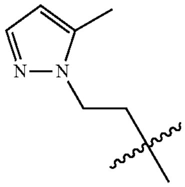
-continued
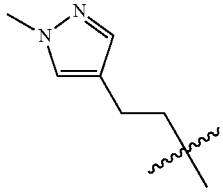
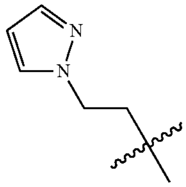
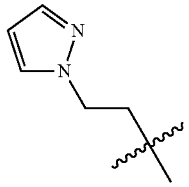
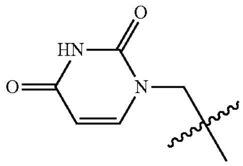
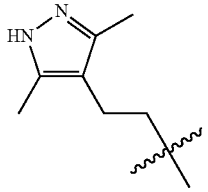
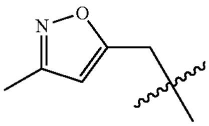
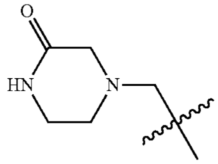
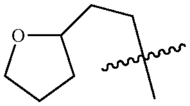
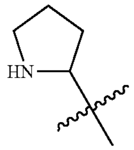
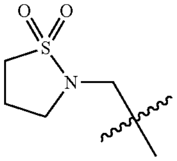
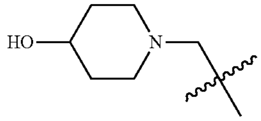
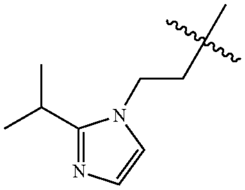
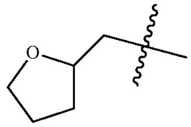
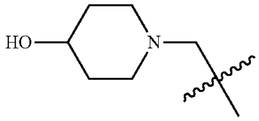
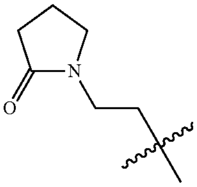
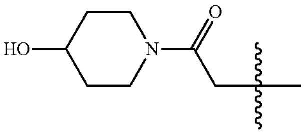
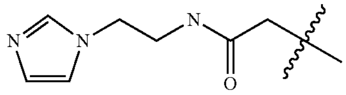
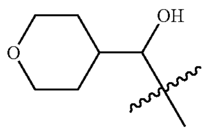
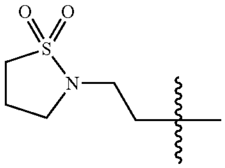

-continued

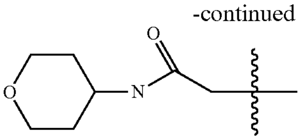

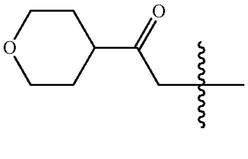

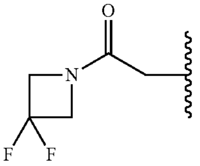

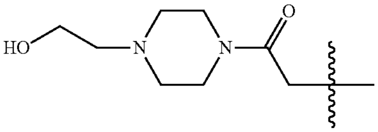

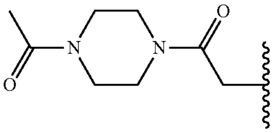

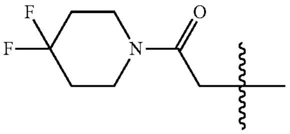

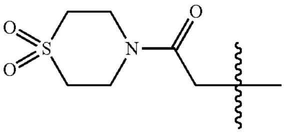

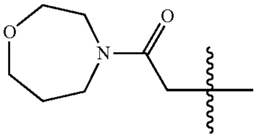

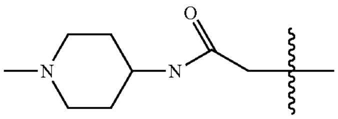

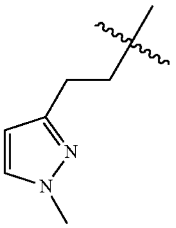

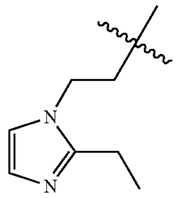

-continued

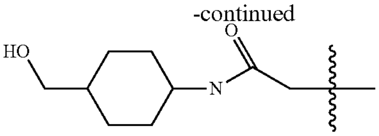

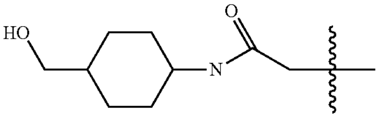

or

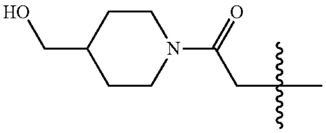

, wherein the wavy line represents the point of attachment in formula I.

16. The compound of claim 1, wherein each $R^a$ and $R^b$ are independently hydrogen, $C_{1-6}$ alkyl, $C_{2-6}$ alkenyl, $C_{2-6}$ alkynyl, —$C_{3-6}$ cycloalkyl, -3-12 membered heterocyclyl, —C(O)3-12 membered heterocyclyl or —$C_{6-14}$ aryl, wherein said alkyl, cycloalkyl, heterocyclyl and aryl are independently optionally substituted by halogen, oxo, —CN, —$OR^e$, —$NR^eR^f$, —$C(O)R^g$, —$C(O)OR^g$, —$C(O)NR^gR^h$, —$NR^gC(O)R^h$, —$OC(O)NR^gR^h$, —$NR^gC(O)NR^gR^h$, —$NR^gC(O)OR^h$, —$S(O)_{1-2}R^g$, —$NR^gS(O)_{1-2}R^h$, —$S(O)_{1-2}NR^gR^h$, —$NR^gS(O)_{1-2}NR^gR^h$, $C_{3-6}$ cycloalkyl, 3-6 membered heterocyclyl, phenyl or $C_{1-3}$ alkyl optionally substituted by oxo or halogen, or taken together with the atom to which they are attached to form a 3-6 membered heterocyclyl optionally substituted by oxo, halogen, —$C(O)C_{1-6}$ alkyl or $C_{1-6}$ alkyl optionally substituted by oxo, halogen, $OR^g$ or $NR^gNR^h$.

17. The compound of claim 1, wherein each $R^c$ and $R^d$ are independently hydrogen, $C_{1-6}$ alkyl, $C_{2-6}$ alkenyl, $C_{2-6}$ alkynyl, —$C_{3-6}$ cycloalkyl, -3-12 membered heterocyclyl, —$C(O)_{3-12}$ membered heterocyclyl or —$C_{6-14}$ aryl, wherein said alkyl, alkenyl, alkynyl, cycloalkyl, heterocyclyl and aryl are independently optionally substituted by halogen, oxo, —CN, —$OR^g$, —$NR^gR^h$, —$C(O)R^g$, —$C(O)OR^g$, —$C(O)NR^gR^h$, —$NR^gC(O)R^h$, —$OC(O)NR^gR^h$, —$NR^gC(O)NR^gR^h$, —$NR^gC(O)OR^h$, —$S(O)_{1-2}R^g$, —$NR^gS(O)_{1-2}R^h$, —$S(O)_{1-2}NR^gR^h$, —$NR^gS(O)_{1-2}NR^gR^h$, $C_{3-6}$ cycloalkyl, 3-6 membered heterocyclyl, phenyl or $C_{1-6}$ alkyl optionally substituted by oxo or halogen, or taken together with the atom to which they are attached to form a 3-6 membered heterocyclyl optionally substituted by oxo, halogen, —$C(O)C_{1-6}$ alkyl or $C_{1-6}$ alkyl optionally substituted by oxo or halogen.

18. A pharmaceutical composition comprising a compound of claim 1, a stereoisomer, tautomer or pharmaceutically acceptable salt thereof, and a pharmaceutically acceptable carrier, adjuvant or vehicle.

* * * * *